(12) United States Patent
Andrews et al.

(10) Patent No.: US 10,555,944 B2
(45) Date of Patent: Feb. 11, 2020

(54) SUBSTITUTED PYRAZOLO[1,5-A]PYRIDINE COMPOUNDS AS RET KINASE INHIBITORS

(71) Applicant: Array BioPharma, Inc., Boulder, CO (US)

(72) Inventors: Steven W. Andrews, Boulder, CO (US); Sean Aronow, Boulder, CO (US); James F. Blake, Boulder, CO (US); Barbara J. Brandhuber, Boulder, CO (US); Adam Cook, Boulder, CO (US); Julia Haas, Boulder, CO (US); Yutong Jiang, Boulder, CO (US); Gabrielle R. Kolakowski, Boulder, CO (US); Elizabeth A. McFaddin, Boulder, CO (US); Megan L. McKenney, Boulder, CO (US); Oren T. McNulty, Boulder, CO (US); Andrew T. Metcalf, Boulder, CO (US); David A. Moreno, Boulder, CO (US); Tony P. Tang, Boulder, CO (US); Li Ren, Boulder, CO (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 16/173,100

(22) Filed: Oct. 29, 2018

(65) Prior Publication Data

US 2019/0183886 A1 Jun. 20, 2019

Related U.S. Application Data

(63) Continuation of application No. 15/858,240, filed on Dec. 29, 2017, now Pat. No. 10,112,942, which is a
(Continued)

(51) Int. Cl.
*C07D 401/02* (2006.01)
*C07D 401/10* (2006.01)
*A61K 31/437* (2006.01)
*A61K 31/4353* (2006.01)
*A61K 31/496* (2006.01)
*C07D 471/04* (2006.01)
*A61P 1/12* (2006.01)
*A61P 35/04* (2006.01)
*C07D 519/00* (2006.01)
*A61P 35/02* (2006.01)
*A61P 35/00* (2006.01)
*A61K 31/444* (2006.01)
*A61K 31/4985* (2006.01)
*A61K 31/4995* (2006.01)
(Continued)

(52) U.S. Cl.
CPC .......... *A61K 31/496* (2013.01); *A61K 31/444* (2013.01); *A61K 31/4985* (2013.01); *A61K 31/4995* (2013.01); *A61K 31/506* (2013.01); *A61K 31/5377* (2013.01); *A61K 31/551* (2013.01); *A61K 45/06* (2013.01); *A61P 1/12* (2018.01); *A61P 35/00* (2018.01); *A61P 35/02* (2018.01); *A61P 35/04* (2018.01); *C07D 471/04* (2013.01); *C07D 519/00* (2013.01)

(58) Field of Classification Search
CPC .. C07D 401/02; C07D 401/10; A61K 31/437; A61K 31/4353
USPC .......................................... 514/300; 546/121
See application file for complete search history.

(56) References Cited

U.S. PATENT DOCUMENTS

| 5,844,092 A | 12/1998 | Presta et al. |
| 5,877,016 A | 3/1999 | Presta et al. |

(Continued)

FOREIGN PATENT DOCUMENTS

| CN | 105255927 A | 1/2016 |
| EP | 3037547 A1 | 6/2016 |

(Continued)

OTHER PUBLICATIONS

Albaugh et al., "Discovery of GNF-5837, a Selective TRK Inhibitor with Efficacy in Rodent Cancer Tumor Models," ACS Med Chem. Lett., Jan. 1, 2012;3(2):140-145.

(Continued)

*Primary Examiner* — Niloofar Rahmani
(74) *Attorney, Agent, or Firm* — Michael R. Asam

(57) ABSTRACT

Provided herein are compounds of the Formula I:

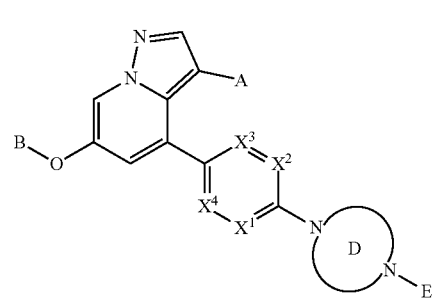

and stereoisomers and pharmaceutically acceptable salts or solvates thereof, in which A, B, $X^1$, $X^2$, $X^3$, $X^4$, Ring D, and E have the meanings given in the specification, which are inhibitors of RET kinase and are useful in the treatment and prevention of diseases which can be treated with a RET kinase inhibitor, including RET-associated diseases and disorders.

12 Claims, No Drawings

Specification includes a Sequence Listing.

Related U.S. Application Data continuation of application No. PCT/US2017/055983, filed on Oct. 10, 2017.

(60) Provisional application No. 62/566,093, filed on Sep. 29, 2017, provisional application No. 62/554,817, filed on Sep. 6, 2017, provisional application No. 62/491,164, filed on Apr. 27, 2017, provisional application No. 62/447,850, filed on Jan. 18, 2017, provisional application No. 62/406,252, filed on Oct. 10, 2016.

(51) Int. Cl.
*A61K 31/506* (2006.01)
*A61K 31/5377* (2006.01)
*A61K 45/06* (2006.01)
*A61K 31/551* (2006.01)

(56) References Cited

U.S. PATENT DOCUMENTS

| | | |
|---|---|---|
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 6,531,152 B1 | 3/2003 | Lerner et al. |
| 6,861,509 B1 | 3/2005 | Sanieola-Nadel et al. |
| 7,384,632 B2 | 6/2008 | Devaux et al. |
| 7,465,726 B2 | 12/2008 | Ahmed et al. |
| 7,504,509 B2 | 3/2009 | Ibrahim et al. |
| 7,514,446 B2 | 4/2009 | Davis-Ward et al. |
| 7,615,383 B2 | 11/2009 | Devaux et al. |
| 7,795,273 B2 | 9/2010 | Imbach et al. |
| 7,863,288 B2 | 1/2011 | Ibrahim et al. |
| 7,863,289 B2 | 1/2011 | Spevak et al. |
| 8,012,966 B2 | 9/2011 | Tang et al. |
| 8,026,247 B2 | 9/2011 | Bold et al. |
| 8,067,434 B2 | 11/2011 | Ibrahim et al. |
| 8,106,069 B2 | 1/2012 | Salom et al. |
| 8,114,989 B2 | 2/2012 | Wang et al. |
| 8,129,374 B2 | 3/2012 | Bhagwat et al. |
| 8,198,298 B2 | 6/2012 | Salom et al. |
| 8,299,057 B2 | 10/2012 | Lombardi Borgia et al. |
| 8,338,417 B2 | 12/2012 | Li et al. |
| 8,354,526 B2 | 1/2013 | Ding et al. |
| 8,399,442 B2 | 3/2013 | Berdini et al. |
| 8,450,322 B2 | 5/2013 | Andrews et al. |
| 8,461,161 B2 | 6/2013 | Burns et al. |
| 8,501,756 B2 | 8/2013 | Artman, III et al. |
| 8,513,263 B2 | 8/2013 | Haas et al. |
| 8,524,709 B2 | 9/2013 | Liang et al. |
| 8,552,002 B2 | 10/2013 | Ding et al. |
| 8,568,998 B2 | 10/2013 | Mani et al. |
| 8,629,135 B2 | 1/2014 | Gujral et al. |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,686,005 B2 | 4/2014 | Gregor |
| 8,691,221 B2 | 4/2014 | Pavone et al. |
| 8,741,849 B2 | 6/2014 | Panitch et al. |
| 8,754,209 B2 | 6/2014 | Sim et al. |
| 8,791,123 B2 | 7/2014 | Allen et al. |
| 8,815,901 B2 | 8/2014 | Furet et al. |
| 8,815,906 B2 | 8/2014 | Gregor et al. |
| 8,895,744 B2 | 11/2014 | Gambacorti Passerini et al. |
| 8,912,194 B2 | 12/2014 | Ciomei et al. |
| 8,912,204 B2 | 12/2014 | Ibrahim et al. |
| 8,933,084 B2 | 1/2015 | Andrews et al. |
| 8,933,230 B2 | 1/2015 | Yun et al. |
| 8,937,071 B2 | 1/2015 | Eidam et al. |
| 8,946,226 B2 | 2/2015 | Ciomei et al. |
| 9,006,256 B2 | 4/2015 | Matsui |
| 9,035,063 B2 | 5/2015 | Eidam et al. |
| 9,102,671 B2 | 8/2015 | Molteni et al. |
| 9,149,464 B2 | 10/2015 | Bakale et al. |
| 9,150,517 B2 | 10/2015 | Bakale et al. |
| 9,186,318 B2 | 11/2015 | Yun et al. |
| 9,216,172 B2 | 12/2015 | Kohno et al. |
| 9,242,977 B2 | 1/2016 | Takeuchi et al. |
| 9,260,437 B2 | 2/2016 | Ibrahim et al. |
| 9,273,051 B2 | 3/2016 | Chen et al. |
| 9,297,011 B2 | 3/2016 | Downing et al. |
| 9,321,772 B2 | 4/2016 | Dar et al. |
| 9,487,491 B2 | 11/2016 | Shimada et al. |
| 9,493,455 B2 | 11/2016 | Cheve et al. |
| 9,505,784 B2 | 11/2016 | Choi et al. |
| 9,522,910 B2 | 12/2016 | Chilov et al. |
| 9,550,772 B2 | 1/2017 | Cheve et al. |
| 9,604,980 B2 | 3/2017 | Menichincheri et al. |
| 9,669,028 B2 | 6/2017 | Vankayalapati et al. |
| 9,682,083 B2 | 6/2017 | Angiolini et al. |
| 9,738,660 B2 | 8/2017 | Yang et al. |
| 9,758,508 B2 | 9/2017 | Hong et al. |
| 9,789,100 B2 | 10/2017 | Eidam |
| 9,801,880 B2 | 10/2017 | Micklem |
| 2004/0185547 A1 | 9/2004 | Mohammadi et al. |
| 2005/0209195 A1 | 9/2005 | Menta et al. |
| 2005/0222171 A1 | 10/2005 | Bold et al. |
| 2006/0183900 A1 | 8/2006 | Huang et al. |
| 2007/0117800 A1 | 5/2007 | Arnold et al. |
| 2007/0149523 A1 | 6/2007 | Ehlert et al. |
| 2007/0265274 A1 | 11/2007 | Fagin et al. |
| 2008/0199426 A1 | 8/2008 | Sukhatme et al. |
| 2008/0234267 A1 | 9/2008 | Lackey |
| 2008/0234276 A1 | 9/2008 | Boyle et al. |
| 2008/0234284 A1 | 9/2008 | Imbach et al. |
| 2008/0262021 A1 | 10/2008 | Capraro et al. |
| 2008/0275054 A1 | 11/2008 | Holzer et al. |
| 2008/0287427 A1 | 11/2008 | Bold et al. |
| 2008/0312192 A1 | 12/2008 | Bold et al. |
| 2008/0319005 A1 | 12/2008 | Bold et al. |
| 2009/0012045 A1 | 1/2009 | Hitoshi et al. |
| 2009/0027556 A1 | 1/2009 | Bleau et al. |
| 2009/0048249 A1 | 2/2009 | Chiu et al. |
| 2009/0069360 A1 | 3/2009 | Batt et al. |
| 2009/0099167 A1 | 4/2009 | Bold et al. |
| 2009/0130229 A1 | 5/2009 | Lanzi et al. |
| 2009/0143399 A1 | 6/2009 | Hurley et al. |
| 2009/0152083 A1 | 6/2009 | Cheng et al. |
| 2009/0209496 A1 | 8/2009 | Chaplin et al. |
| 2009/0215761 A1 | 8/2009 | Whitten et al. |
| 2009/0227556 A1 | 9/2009 | Obaishi |
| 2009/0312321 A1 | 12/2009 | Ren et al. |
| 2010/0004239 A1 | 1/2010 | Tang et al. |
| 2010/0048540 A1 | 2/2010 | Boyle et al. |
| 2010/0069395 A1 | 3/2010 | Imbach et al. |
| 2010/0075916 A1 | 3/2010 | Gant et al. |
| 2010/0081675 A1 | 4/2010 | Hsieh et al. |
| 2010/0152219 A1 | 6/2010 | Block et al. |
| 2010/0173954 A1 | 7/2010 | Wilhelm et al. |
| 2010/0209488 A1 | 8/2010 | Wrasidlo et al. |
| 2010/0280012 A1 | 11/2010 | Lee |
| 2010/0297115 A1 | 11/2010 | Blaustein |
| 2010/0324065 A1 | 12/2010 | Ibrahim et al. |
| 2011/0046370 A1 | 2/2011 | Sim et al. |
| 2011/0053934 A1 | 3/2011 | Angell et al. |
| 2011/0133637 A1 | 6/2011 | Ota |
| 2011/0189167 A1 | 8/2011 | Flynn et al. |
| 2011/0195072 A1 | 8/2011 | Boulay et al. |
| 2011/0212053 A1 | 9/2011 | Qian et al. |
| 2011/0269739 A1 | 11/2011 | Kim et al. |
| 2011/0281841 A1 | 11/2011 | Lee et al. |
| 2011/0301157 A1 | 12/2011 | Bold et al. |
| 2012/0065233 A1 | 3/2012 | Gregor |
| 2012/0070410 A1 | 3/2012 | Apuy et al. |
| 2012/0225057 A1 | 9/2012 | Flynn et al. |
| 2012/0271048 A1 | 10/2012 | Sim et al. |
| 2012/0277247 A1 | 11/2012 | Menet et al. |
| 2012/0277424 A1 | 11/2012 | Sim et al. |
| 2012/0283261 A1 | 11/2012 | Bearss et al. |
| 2012/0302567 A1 | 11/2012 | Jung et al. |
| 2013/0012703 A1 | 1/2013 | Sim et al. |

(56) References Cited

U.S. PATENT DOCUMENTS

| | | |
|---|---|---|
| 2013/0029925 A1 | 1/2013 | Vandier et al. |
| 2013/0053370 A1 | 2/2013 | Son et al. |
| 2013/0079343 A1 | 3/2013 | Sim et al. |
| 2013/0303518 A1 | 11/2013 | Tang et al. |
| 2014/0121239 A1 | 5/2014 | Aftab |
| 2014/0137274 A1 | 5/2014 | Ishikawa |
| 2014/0272951 A1 | 9/2014 | Chakravarti et al. |
| 2014/0371219 A1 | 12/2014 | Bae et al. |
| 2015/0018336 A1 | 1/2015 | Chen et al. |
| 2015/0051222 A1 | 2/2015 | Barbugian et al. |
| 2015/0057335 A1 | 2/2015 | Kohno et al. |
| 2015/0065468 A1 | 3/2015 | Holladay et al. |
| 2015/0099721 A1 | 4/2015 | Acquaviva et al. |
| 2015/0099762 A1 | 4/2015 | Eidam et al. |
| 2015/0166564 A1 | 6/2015 | Allen et al. |
| 2015/0177246 A1 | 6/2015 | Shibata et al. |
| 2015/0238477 A1 | 8/2015 | Aftab |
| 2015/0272958 A1 | 10/2015 | Kodama et al. |
| 2015/0283132 A1 | 10/2015 | Lim et al. |
| 2015/0306086 A1 | 10/2015 | Wilcoxen |
| 2016/0000783 A1 | 1/2016 | Takeuchi et al. |
| 2016/0009709 A1 | 1/2016 | Cheve et al. |
| 2016/0046636 A1 | 2/2016 | Gray et al. |
| 2016/0137654 A1 | 5/2016 | Arrigo et al. |
| 2016/0176865 A1 | 6/2016 | Ibrahim et al. |
| 2017/0014413 A1 | 1/2017 | Downing et al. |
| 2017/0044106 A1 | 2/2017 | Aftab et al. |
| 2017/0096425 A1 | 4/2017 | Andrews et al. |
| 2017/0114032 A1 | 4/2017 | Cheng et al. |
| 2017/0121312 A1 | 5/2017 | Brubaker et al. |
| 2017/0226100 A1 | 8/2017 | Jiaang et al. |
| 2017/0267661 A1 | 9/2017 | Kim et al. |
| 2017/0281632 A1 | 10/2017 | Cox et al. |
| 2017/0283404 A1 | 10/2017 | Cheung et al. |
| 2017/0298074 A1 | 10/2017 | Cheung et al. |
| 2018/0009817 A1 | 1/2018 | Miyazaki et al. |
| 2018/0009818 A1 | 1/2018 | Miyazaki et al. |
| 2018/0133200 A1 | 5/2018 | Andrews et al. |
| 2018/0133207 A1 | 5/2018 | Andrews et al. |
| 2018/0133213 A1 | 5/2018 | Andrews et al. |
| 2018/0134703 A1 | 5/2018 | Andrews et al. |

FOREIGN PATENT DOCUMENTS

| | | |
|---|---|---|
| JP | 2015109806 A | 6/2015 |
| WO | WO8705297 | 9/1987 |
| WO | WO1997044356 | 11/1997 |
| WO | WO2001016169 | 3/2001 |
| WO | WO2001062273 | 8/2001 |
| WO | WO2003020698 | 3/2003 |
| WO | WO2005044835 | 5/2005 |
| WO | WO2005051366 | 6/2005 |
| WO | WO2005062795 | 7/2005 |
| WO | WO2005070431 | 8/2005 |
| WO | WO2006089298 | 8/2006 |
| WO | WO2006123113 | 11/2006 |
| WO | WO2006130613 | 12/2006 |
| WO | WO2006131952 | 12/2006 |
| WO | WO2007002325 | 1/2007 |
| WO | WO2007002433 | 1/2007 |
| WO | WO2007022999 | 3/2007 |
| WO | WO2007054357 | 5/2007 |
| WO | WO2007057397 | 5/2007 |
| WO | WO2007057399 | 5/2007 |
| WO | WO2007087245 | 8/2007 |
| WO | WO2007109045 | 9/2007 |
| WO | WO2007110344 | 10/2007 |
| WO | WO2007136103 | 11/2007 |
| WO | WO2008031551 | 3/2008 |
| WO | WO2008079903 | 7/2008 |
| WO | WO2008079906 | 7/2008 |
| WO | WO2008079909 | 7/2008 |
| WO | WO2008080001 | 7/2008 |
| WO | WO2008080015 | 7/2008 |
| WO | WO2009007748 | 1/2009 |
| WO | WO2009012283 | 1/2009 |
| WO | WO2009013126 | 1/2009 |
| WO | WO2009014637 | 1/2009 |
| WO | WO2009017838 | 2/2009 |
| WO | WO2009023978 | 2/2009 |
| WO | WO2009042646 | 4/2009 |
| WO | WO2009053442 | 4/2009 |
| WO | WO2009071480 | 6/2009 |
| WO | WO2009092049 | 7/2009 |
| WO | WO2009118411 | 10/2009 |
| WO | WO2009143018 | 10/2009 |
| WO | WO2009143024 | 11/2009 |
| WO | WO2009152083 | 12/2009 |
| WO | WO2010031816 | 3/2010 |
| WO | WO2010033941 | 3/2010 |
| WO | WO2010048314 | 4/2010 |
| WO | WO2010058006 | 5/2010 |
| WO | WO2010111527 | 9/2010 |
| WO | WO2010145998 | 12/2010 |
| WO | WO2011006074 | 1/2011 |
| WO | WO2011022439 | 2/2011 |
| WO | WO2011045344 | 2/2011 |
| WO | WO2011092120 | 8/2011 |
| WO | WO2011133637 | 10/2011 |
| WO | WO2011146336 | 11/2011 |
| WO | WO2012034091 | 3/2012 |
| WO | WO2012034095 | 3/2012 |
| WO | WO2012047017 | 4/2012 |
| WO | WO2012053606 | 4/2012 |
| WO | WO2012101029 | 8/2012 |
| WO | WO2012101032 | 8/2012 |
| WO | WO2012109075 | 8/2012 |
| WO | WO2012113774 | 8/2012 |
| WO | WO2012116217 | 8/2012 |
| WO | WO2012139930 | 10/2012 |
| WO | WO2012143248 | 10/2012 |
| WO | WO2012152763 | 11/2012 |
| WO | WO2012158413 | 11/2012 |
| WO | WO2012171337 | 12/2012 |
| WO | WO2013014039 | 1/2013 |
| WO | WO2013016720 | 1/2013 |
| WO | WO2013036232 | 3/2013 |
| WO | WO2013042137 | 3/2013 |
| WO | WO2013050446 | 4/2013 |
| WO | WO2013050448 | 4/2013 |
| WO | WO2013074518 | 5/2013 |
| WO | WO2013102059 | 7/2013 |
| WO | WO2013174876 | 11/2013 |
| WO | WO2013183578 | 12/2013 |
| WO | WO2014011900 | 1/2014 |
| WO | WO2014019908 | 2/2014 |
| WO | WO2014072220 | 5/2014 |
| WO | WO2014075035 | 5/2014 |
| WO | WO2014078322 | 5/2014 |
| WO | WO2014078323 | 5/2014 |
| WO | WO2014078325 | 5/2014 |
| WO | WO2014078328 | 5/2014 |
| WO | WO2014078331 | 5/2014 |
| WO | WO2014078372 | 5/2014 |
| WO | WO2014078378 | 5/2014 |
| WO | WO2014078408 | 5/2014 |
| WO | WO2014078417 | 5/2014 |
| WO | WO2014078454 | 5/2014 |
| WO | WO2014083567 | 6/2014 |
| WO | WO2014086284 | 6/2014 |
| WO | WO2014141187 | 9/2014 |
| WO | WO2014160521 | 10/2014 |
| WO | WO2014160524 | 10/2014 |
| WO | WO2014184069 | 11/2014 |
| WO | WO2014194127 | 12/2014 |
| WO | WO2015017528 | 2/2015 |
| WO | WO2015017533 | 2/2015 |
| WO | WO2015057873 | 4/2015 |
| WO | WO2015058129 | 4/2015 |
| WO | WO2015061572 | 4/2015 |
| WO | WO2015079251 | 6/2015 |
| WO | WO2015108992 | 7/2015 |
| WO | WO2015112806 | 7/2015 |
| WO | WO2015124697 | 8/2015 |

(56) References Cited

FOREIGN PATENT DOCUMENTS

| | | |
|---|---|---|
| WO | WO2015161274 | 10/2015 |
| WO | WO2015161277 | 10/2015 |
| WO | WO2015175788 | 11/2015 |
| WO | WO2015191666 | 12/2015 |
| WO | WO2015191667 | 12/2015 |
| WO | WO2016011141 | 1/2016 |
| WO | WO2016011144 | 1/2016 |
| WO | WO2016011147 | 1/2016 |
| WO | WO2016022569 | 2/2016 |
| WO | WO2016027754 | 2/2016 |
| WO | WO2016037578 | 3/2016 |
| WO | WO2016038519 | 3/2016 |
| WO | WO2016038552 | 3/2016 |
| WO | WO2016075224 | 5/2016 |
| WO | WO2016077841 | 5/2016 |
| WO | WO2016081450 | 5/2016 |
| WO | WO2016096709 | 6/2016 |
| WO | WO2016127074 | 8/2016 |
| WO | WO2016137060 | 9/2016 |
| WO | WO2016141169 | 9/2016 |
| WO | WO2016168992 | 10/2016 |
| WO | 2017011776 * | 1/2017 |
| WO | WO2017009644 | 1/2017 |
| WO | WO2017011776 | 1/2017 |
| WO | WO2017013160 | 1/2017 |
| WO | WO2017026718 | 2/2017 |
| WO | WO2017027883 | 2/2017 |
| WO | WO2017043550 | 3/2017 |
| WO | WO2017049462 | 3/2017 |
| WO | WO2017097697 | 6/2017 |
| WO | WO2017122815 | 7/2017 |
| WO | WO2017145050 | 8/2017 |
| WO | WO2017146116 | 8/2017 |
| WO | WO2017178844 | 10/2017 |
| WO | WO2017178845 | 10/2017 |

OTHER PUBLICATIONS

Amit M et al., "Upregulation of RET induces perineurial invasion of pancreatic adenocarcinoma." Oncogene Jun. 8, 2017; 36:3232-3239.
Andreucci et al., "Targeting the receptor tyrosine kinase RET in combination with aromatase inhibitors in ER positive breast cancer xenografts," Oncotarget, Dec. 6, 2016, 7(49):80543-80553.
Antonescu et al., "Molecular characterization of inflammatory myofibroblastic tumors with frequent ALK and ROS1 gene fusions and rare novel RET rearrangement," Am J Surg Pathol, Jul. 2015;39(7):957-967.
Arighi et al., "RET tyrosine kinase signaling in development and cancer," Cytokine Growth Factor Rev, Aug.-Oct. 2005;16(4-5):441-467.
Ballerini et al., "RET fusion genes are associated with chronic myelomonocytic leukemia and enhance monocytic differentiation," Leukemia, Nov. 2012;26(11):2384-2389.
Bastien et al., Journal of Molecular Diagnostics, 18(6):1027, Abstract No. S120, 2016 Annual Meeting of the Association for Molecular Pathology, Charlotte, NC, 2016.
Behrens et al., "Gö 6976 is a potent inhibitor of neurotrophin-receptor intrinsic tyrosine kinase," J Neurochem. Mar. 1999;72(3):919-924.
Bhinge et al., "EGFR mediates activation of RET in lung adenocarcinoma with neuroendocrine differentiation characterized by ASCL1 expression," Oncotarget, Apr. 18, 2017, 8(16):27155-27165.
Borecka et al., European Journal of Cancer, (Jul. 2016) vol. 61, No. 1, pp. S26, Abstract No. 162, Meeting Info: 24th Biennial Congress of the European Association for Cancer Research, EACR 2016. Manchester, United Kingdom.
Borrello et al., "RET inhibition: implications in cancer therapy," Expert Opin. Ther. Targets, Apr. 2013, 17(4):403-419.

Boulay et al., "The Ret receptor tyrosine kinase pathway functionally interacts with the ERalpha pathway in breast cancer," Cancer Res., May 15, 2008,68(10):3743-3751.
Brodeur, "Neuroblastoma: biological insights into a clinical enigma," Nat Rev Cancer., Mar. 2003, 3(3):203-216.
Butler Tjaden et al., "The developmental etiology and pathogenesis of Hirschsprung disease," Transl. Res., Jul. 2013;162(1):1-15.
Calero et al., "Sunitinib suppress neuroblastoma growth through degradation of MYCN and inhibition of angiogenesis," PLoS One. Apr. 23, 2014;9(4):e95628.
Camilleri, "Peripheral mechanisms in irritable bowel syndrome," N Engl J Med, Oct. 25, 2012, 367(17):1626-1635.
Camoratto et al., "CEP-751 inhibits TRK receptor tyrosine kinase activity in vitro exhibits anti-tumor activity," Int J Cancer. Aug. 7, 1997;72(4):673-679.
Camós et al., "Gene expression profiling of acute myeloid leukemia with translocation t(8;16)(p11;p1.3) and MYST3-CREBBP rearrangement reveals a distinctive signature with a specific pattern of HOX gene expression," Cancer Res., Jul. 15, 2006;66(14):6947-6954.
Cancer Genome Atlas Network, "Comprehensive molecular characterization of human colon and rectal cancer," Nature, Jul. 18, 2012;487(7407):330-337.
Carlomagno et al., "Identification of tyrosine 806 as a molecular determinant of RET kinase sensitivity to ZD6474," Endocr. Rel. Cancer, Mar. 2009;16(1):233-241.
Carpinelli et al., "PHA-739358, a potent inhibitor of Aurora kinases with a selective target inhibition profile relevant to cancer," Mol Cancer Ther., Dec. 2007;6(12 Pt 1):3158-68.
Cecchirini et al., "Somatic in frame deletions not involving juxtamembranous cysteine residues strongly activate the RET proto-oncogene," Oncogene, May 29, 1997;14(21):2609-2612.
Ceolin et al., "Effect of 3'UTR RET Variants on RET mRNA Secondary Structure and Disease Presentation in Medullary Thyroid Carcinoma," PLoS One, Feb. 1, 2016;11(2):e0147840. doi: 10.1371/journal.pone.0147840. eCollection 2016.
Chang et al., "EGF Induced RET Inhibitor Resistance in CCDC6-RET Lung Cancer Cells," Yonsei Med J, Jan. 2017, 58(1):9-18.
Choi et al., "(R)-2-Phenylpyrrolidine Substituted Imidazopyridazines: A New Class of Potent and Selective Pan-TRK Inhibitors," ACS Med Chem Lett., Mar. 16, 2015;6(5):562-567.
Corsello et al., Endocrine Reviews, (Jun. 2014) vol. 35, No. 3, Suppl. S, pp. SUN-0322, Meeting Info.: 96th Annual Meeting and Expo of the Endocrine-Society, Chicago, IL, USA, Jun. 21-24, 2014.
Cranston et al., "RET is constitutively activated by novel tandem mutations that alter the active site resulting in multiple endocrine neoplasia type 2B," Cancer Res., Oct. 15, 2006;66(20):10179-10187.
Croucher et al., "TrkB inhibition by GNF-4256 slows growth and enhances chemotherapeutic efficacy in neuroblastoma xenografts," Cancer Chemother Pharmacol., Jan. 2015;75(1):131-141.
Davila et al., "Comprehensive genomic profiling of a rare thyroid follicular dendritic cell sarcoma," Rare Tumors, 2017, 9(2):6834.
Dawson et al., "Altered expression of RET proto-oncogene product in prostatic intraepithelial neoplasia and prostate cancer," J Natl Cancer Inst, Apr. 1, 1998;90(7):519-523.
De Almeida et al., Endocrine Reviews, 2016, vol. 37, No. 2, Supp. Supplement 1. Abstract No. SUN-068; 93th Annual Meeting and Expo of the Endocrine Society. ENDO 2016. Boston, MA, US. Apr. 1, 2016-Apr. 4, 2016.
De Groot et al., "RET as a diagnostic and therapeutic target in sporadic and hereditary endocrine tumors," Endocrine Rev. Aug. 2006;27(5):535-560.
Demeure et al., "Whole-genome Sequencing of an Aggressive BRAF Wild-type Papillary Thyroid Cancer Identified EML4—ALK Translocation as a Therapeutic Target," World J. Surg., Jun. 2014, 38(6):1296-305.
Dinér er al., "Preparation of 3-substituted-1-isopropyl-1H-pyrazolo[3,4-d]pyrimidin-4-amines as RET kinase inhibitors," J. Med. Chem., May 24, 2012, 55(10):4872-4876.
Ding et al., "Artemin, a member of the glial cell line-derived neurotrophic factor family of ligands, is HER2-regulated and medi-

(56) References Cited

OTHER PUBLICATIONS ates acquired trastuzumab resistance by promoting cancer stem cell-like behavior in mammary carcinoma cells," J Biol Chem, Jun. 6, 2014, 289(23):16057-71.

Dogan et al., Laboratory Investigation, (Feb. 2017) vol. 97, Supp. 1, pp. 323A. Abstract No. 1298, Meeting Info: 106th Annual Meeting of the United States and Canadian Academy of Pathology, USCAP 2017. San Antonio, TX, United States.

Dogan et al., "Genomic Profiling of the Two Closely Related "cousins" Acinic Cell Carcinoma and Mammary Analog Secretory Carcinoma of Salivary Glands Reveals Novel NVOA4-RET Fusion in Mammary Analog Secretory Carcinoma," Modern Pathology, vol. 30, Supp. [2], pp. 323A-323A. MA 1298, 2017.

Drilon et al., "Phase II study of cabozantinib for patients with advanced RET-rearranged lung cancers," Journal of Clinical Oncology, May 20, 2015, 33(15S):8007-8007 [Abstract Only], 6 pages.

Esseghir et al., "A role for glial cell derived neurotrophic factor induced expression by infammatory cytokines and RET/GFR alpha 1 receptor up-regulation in breast cancer," Cancer Res, Dec. 15, 2007;67(24):11732-11741.

Fang et al., "Detection of a novel RET gene fusion in a non-small cell lung cancer patient using AMP chemistry." Journal of Thoracic Oncology, Feb. 1, 2016, 11(2):S21-S22.

Flavin et al., "RET protein expression in papillary renal cell carcinoma," Urol. Oncol., Nov.-Dec. 2012;30(6):900-905.

Fugazzola et al., "Molecular and biochemical analysis of RET/PTC4, a novel oncogenic rearrangement between RET and ELE1 genes, in a post-Chernobyl papillary thyroid cancer," Oncogene, Sep. 1996, 13(5): 1093-7.

Futami et al., "A novel somatic point mutation of the RET Proto-oncogene in tumor tissues of small cell lung cancerpatients," Jpn. J. Cancer Res., Dec. 1995, 86(12):1127-1130.

Gao et al., "Neurotrophic Factor Artemin Promotes Invasiveness and Neurotrophic Function of Pancreatic Adenocarcinoma In Vivo and In Vitro," Pancreas, Jan. 2015, 44(1):134-143.

Gattei et al., "Expression of the RET receptor tyrosine kinase and GDNFR-alpha in normal and leukemic human hematopoietic cells and stromal cells of the bone marrow microenvironment," Blood, Apr. 15, 1997;89(8):2925-2937.

Gattei, et al., "Differential expression of the RET gene in human acute myeloid leukemia," Ann. Hematol, Nov. 1998, 77(5):207-210.

Gattelli et al., "Ret inhibition decreases growth and metastatic potential of estrogen receptor positive breast cancer cells," EMBO Mol. Med., Sep. 2013;5(9):1335-1350.

Gazizova et al., Endocrine Reviews. (Jun. 2014) vol. 35, No. 3, Suppl. S, pp. SAT-0304, Meeting Info.: 96th Annual Meeting and Expo of the Endocrine-Society, Chicago, IL, USA, Jun. 21-24, 2014.

Gil et al., "Paracrine regulation of pancreatic cancer cell invasion by peripheral nerves," J. Natl. Cancer Inst., Jan. 20, 2010;102(2):107-118.

Gozgit et al., "RET fusions identified in colorectal cancer PDX models are sensitive to the potent RET inhibitor ponatinib," AACR Annual Meeting, Apr. 7, 2014, Presentation Abstract, [Abstract Only], 1 page.

Greco et al., "Molecular pathology of differentiated thyroid cancer," J. Nucl. Med. Mol. Imaging, Oct. 2009, 53:440-454.

Greene & Wuts, eds., "Protecting Groups in Organic Synthesis", 2nd ed. New York; John Wiley & Sons, Inc., 1991, Chapter One, 20 pages.

Grey et al., "The RET E616Q Variant is a Gain of Function Mutation Present in a Family with Features of Multiple Endocrine Neoplasia 2A," Endocrine Pathology, Mar. 2017, 28(1):41-48.

Grieco et al,., "PTC is a novel rearranged form of the ret proto-oncogene and is frequently detected in vivo in human thyroid papillary carcinomas," Cell, Feb. 23, 1990, 60(4):557-563.

Grubbs et al., "RET fusion as a novel driver of medullary thyroid carcinoma," J. Clin. Endocrinol. Metab., Mar. 2015;100(3):788-793.

Gura et al., "Systems for identifying new drugs are often faulty," Science, 1997, 278:1041-1042.

Halkova et al., "A novel RET/PTC variant detected in a pediatric patient with papillary thyroid cancer without ionization history," Human Pathology, Dec. 2015, 46(12):1962-1969.

Hezam et al., "Artemin promotes oncogenicity, metastasis and drug resistance in cancer cells," Rev Neurosci, Jan. 26, 2018, 29(1):93-98.

Hirshfield et al., Cancer Research, (Feb. 2017) vol. 77, No. 4, Supp. 1. Abstract No. P3-07-02. Meeting Info: 39th Annual CTRC-AACR San Antonio Breast Cancer Symposium. San Antonio, TX, United States. Dec. 6, 2016-Dec. 10, 2016.

Hoffman et al., "Activation of colonic mucosal 5-HT(4) receptors accelerates propulsive motility and inhibits visceral hypersensitivity," Gastroenterology, Apr. 2012;142(4):844-854.

Hofstra et al., "No mutations found by RET mutation scanning in sporadic and hereditary neuroblastoma," Hum Genet., Mar. 1996, 97(3):362-364.

Huang et al., "Preclinical Modeling of KIF5B-RET Fusion Lung Adenocarcinoma," Mol. Cancer Ther., Oct. 2016, 15(10):2521-2529.

Ibrahimpasic et al., "Genomic Alterations in Fatal Forms of Non-Anaplastic Thyroid Cancer: Identification of MED12 and RBM10 as Novel Thyroid Cancer Genes Associated with Tumor Virulence," Clin. Cancer Res., Oct. 2017, 23(119):5970-5980.

International Search Report and Written Opinion in International Application No. PCT/US2017/055983, dated Jan. 30, 2018, 11 pages.

Ito et al., "Expression of glial cell line-derived neurotrophic factor family members and their receptors in pancreatic cancers," Surgery, Oct. 2005, 138(4):788-794.

Iwahashi et al., "Expression of glial cell line-derived neurotrophic factor correlates with perineural invasion of bile duct carcinoma," Cancer, Jan. 1, 2002, 94(1):167-174.

Iyama et al., "Identification of Three Novel Fusion Oncogenes, SQSTM1/NTRK3, AFAP1L2/RET, and PPFIBP2/RET, in Thyroid Cancers of Young Patients in Fukushima," Thyroid, Jun. 2017, 27(6):811-818.

Iyer et al, "AZ64 inhibits TrkB and enhances the efficacy of chemotherapy and local radiation in neuroblastoma xenografts," Cancer Chemother Pharmacol., Sep. 2012;70(3):477-486.

Johnson et al., Relationships between drug, activity in NCI preclinical in vitro and in vivo models and early clinical trials, British Journal of Cancer, 84(10):1424-1431, 2001.

Joung et al., "Diffuse sclerosing variant of papillary thyroid carcinoma: major genetic alterations and prognostic implications," Histopathology, Jul. 2016, 69(1):45-53.

Jovanovic et al., "Novel RET mutations in macedonian patients with medullary thyroid carcinoma: genotype-phenotype correlations," Pril (Makedon Akad Nauk Umet Odd Med Nauki), 2015;36(1):93-107.

Ju et al., "A transforming KIF5B and RET gene fusion in lung adenocarcinoma revealed front whole-genome and transcriptome sequencing," Genome Res., Mar. 2012;22(3):436-445.

Kaneta et al., Abstract B173: Preclinical characterization and antitumor efficacy of DS-5010, a highly potent and selective RET inhibitor, Mol Cancer Ther Jan. 1, 2018 (17) (1 Supplement) B173; DOI:10.1158/1535-7163. TARG-17-B173.

Karachialiou et al., "Real-time liquid biopsies become a reality in cancer treatment," Ann. Transl. Med, Mar. 2015, 3(3):36.

Karrasch et al., "How to Assess the Clinical Relevance of Novel RET Missense Variants in the Absence of Functional Studies?" Eur. Thyroid J., Mar. 2016;5(1):73-77.

Kato et al., "Repair by Src kinase of function-impaired RET with multiple endocrine neoplasia type 2A mutation with substitutions of tyrosines in the COOH-terminal kinase domain for phenylalanine." Cancer Res., Apr. 15, 2002, 62(8):2414-2422.

Kato et al., "RET Aberrations in Diverse Cancers: Next-Generation Sequencing of 4,871 Patients," Clin. Cancer Res., Apr. 15, 2017, 23(8):1988-1997.

Keszthelyi et al., "Revisiting concepts of visceralnociception in irritable bowel syndrome," Eur. J. Pain, Nov. 2012;16(10):1444-1454.

(56) References Cited

OTHER PUBLICATIONS

Kheiroddin et al., "RET Gene Analysis in Patients with Medullary Thyroid Carcinoma," Clin. Lab., Jan. 2016, 62(5):871-876.
Kim et al., "A New Germline Ala641Thr Variant in the Transmembrane Domain of the RET Gene Associated With Medullary Thyroid Cancer," Acto Endocrinologica-Bucharest, Apr. 2015, 11(2):189-194.
Kim et al., "Mammaglobin-A is a target for breast cancer vaccination," Oncoimmunology. Feb. 26, 2016;5(2):e1069940. eCollection Feb. 2016.
Kloosterman et al., "A systematic analysis of oncogenic gene fusions in primary colon cancer," Cancer Res., Jul. 15, 2017, 77(14):3814-3822.
Klugbauer et al., "A novel type of RET rearrangement (PTC8) in childhood papillary thyroid carcinomas and characterization of the involved gene (RFG8)," Cancer Res., Dec. 15, 2000;60(24):7028-32.
Kohlmann, et al., "Next-Generation Sequencing Technology Reveals a Characteristic Pattern of Molecular Mutations in 72.8% of Chronic Myelomonocytic Leukemia by Detecting Frequent Alterations in TET2, CBL, RAS, and RUNX1," J. Clin. Oncol. Aug. 20, 2010, 28(24):3858-3865.
Kohno et al., "KIF5B-RET fusions in lung adenocarcinoma," Nature Med., Feb. 12, 2012;18(3):375-377.
Kooistra et al., "KLIFS: A structural kinaseligand interaction database," Nucleic Acids Res., Jan. 2016, 44(D1)D365-D371.
Kraft et al, Cancer Research, 2017, vol. 77, No. 13, Supp. Supplement 1. Abstract No. 4882; American Association for Cancer Research Annual Meeting 2017. Washington, DC, United States. Apr. 1, 2017-Apr. 5, 2017.
Krampitz et al., "RET gene mutations (genotype and phenotype) of multiple endocrine neoplasia type 2 and familial medullary thyroid carcinoma," Cancer, Jul. 1, 2014;120(13):1920-1931.
Kubler et al. "Self-adjuvanted mRNA vaccination in advanced prostate cancer patients: a first-in-man phase I/IIa study," J Immunother Cancer. Jun. 16, 2015, 3:26, 14 pages.
Latteyer et al., "A 6-Base Pair in Frame Germline Deletion in Exon 7 of RET Leads to Increased RET Phosphorylation, ERK Activation, and MEN2A," J. Clin Endocrinol. Metab., Mar. 2016;101(3): 1016-1022.
Le Rolle et al., "Identification and characterization of RET fusions in advanced colorectal cancer," Oncotarget, Oct. 6, 2015;6(30):28929-28937.
Lecht et al., "Angiostatic effects of K252a, a Trk inhibitor, in murine brain capillary endothelial cells," Mol Cell Biochem. Jun. 2010;339(1-2):201-213.
Lee et al., "Identification of a novel partner gene, KIAA1217, fused to RET: Functional characterization and inhibitor sensitivity of two isoforms in lung adenocarcinoma," Oncotarget, May 2, 2016, 7(24):36101-36114.
Lee et al., "Whole-exome sequencing identified mutational profiles of high-grade colon adenomas," Oncotarget, Jan. 2017, 8(4): 6579-6588.
Li et al., "Trk inhibitor attenuates the BDNF/TrkB-induced protection of neuroblastoma cells from etoposide in vitro and in vivo," Cancer Biol Ther., 2015;16(3):477-483.
Lipson et al., "Identification of new ALK and RET gene fusions from colorectal and lung cancer biopsies," Nature Med., Feb. 12, 2012;18(3):382-384.
Liu et al., "Oncogenic RET receptors display different autophosphorylation sites and substrate binding specificities," J Biol. Chem, J Biol Chem, Mar. 8, 1996;271(10):5309-5312.
Lopez-Delisle et al., "Activated ALK signals through the ERK-ETV5-RET pathway to drive neuroblastoma oncogenesis," Oncogene, Jan. 11, 2018, doi: 10.1038/s41388-017-0039-5. [Epub ahead of print].
Louis et al., "The 2016 World Health Organization Classification of Tumors of the Central Nervous System: a summary," Acta Neuropathol, Jun. 2016, 131(6):803-820.

Lu et al., "Targeted next generation sequencing identifies somatic mutations and gene fusions in papillary thyroid carcinoma," Oncotarget. Jul. 2017, 8(28):45784-45792.
Luo et al., "RET is a potential tumor suppressor gene in colorectal cancer," Oncogene, Apr. 18, 2013;32(16):2037-2047.
Mamedova et al., "Abstract #6: Construction of Baculovirial Vectors for RET Kinase Domain Mutants." Summer Undergraduate Research Programs (SURP) Student Abstracts, University of Oklahoma Health Sciences Center, 2016, p. 28 [Abstract Only].
Matsubara et al., "Identification of CCDC6-RET fusion in the human lung adenocarcinoma cell line, LC-2/ad." Journal of Thoracic Oncology, Dec. 2012;7(12):1872-1876.
McCarthy et al., "Tropomyosin receptor kinase inhibitors: a patent update 2009-2013," Expert. Opin. Ther. Pat., Jul. 2014;24(7):731-744.
Mendiola et al., "Preparation, Use, and Safety of O-Mesitylenesulfonythydroxylamine," Org. Process Res. Dev., Jan. 2009, 13(2):263-267.
Montagnoli et al., "Anti-proliferative effects of GW441756, a novel inhibitor of NGFreceptor tyrosine kinase a (TRKA), in human sarcoma," Italian Journal of Anatomy and Embryology, Nov. 11, 2010, 115(1/2):117.
Morandi et al., "GDNF-RET signaling in ER-positive breast cancers is a key determinant of response and resistance to aromatase inhibitors," Cancer Res., Jun. 15, 2013;73(12):3783-3795.
Morgensztern et al., Journal of Thoracic Oncology, (Jan. 2017) vol. 12, No. 1, Supp. 1, pp. S717-S718, Abstract No. P1.07-035, Meeting Info: 17th World Conference of the International Association for the Study of Lung Cancer, IASLC 2016. Vienna, Austria. Dec. 4, 2016.
Mulligan et al., "Investigation of the genes for RET and its ligand complex, GDNF/GFR alpha-I, in small cell lung carcinoma," Genes Chromosomes Cancer, Apr. 1998, 21(4):326-332.
Mulligan, "RET revisited: expanding the oncogenic portfolio," Nature Reviews Cancer, Mar. 2014, 14(3):173-186.
Narayanan et al., "Discovery and preclinical characterization of novel small molecule TRK and ROS1 tyrosine kinase inhibitors for the treatment of cancer and inflammation," PLoS One. Dec. 26, 2013;8(12):e83380.
Narita et al., "Functional RET G691S polymoiphism in cutaneous malignant melanoma," Oncogene, Aug. 27, 2009;28(34):3058-3068.
Nelson-Taylor et al., "Resistance to RET-Inhibition in RET-Rearranged NSCLC Is Mediated By Reactivation of RAS/MAPK Signaling," Mol. Cancer Ther., Aug. 2017, 16(8):1623-1633.
Ott et al., "An inummogenic personal neoantigen vaccine for patients with melanoma," Nature. Jul. 13, 2017, 547(7662):217-221.
Pearce et al., Failure modes in anticancer drug discovery and development, Cancer Drug Design and Discovery Edited by Stephen Neidle, Chapter 18, pp. 424-435 (2008).
Petersen and Bogenmann, "The RET and TRKA pathways collaborate to regulate neuroblastoma differentiation," Oncogene, Jan. 8, 2004;23(1):213-225.
Pirker et al., "Alectinib in RET-rearranged non-small cell lung cancer—Another progress in precision medicine?" Transl. Lung Cancer Res., Dec. 2015;4(6):797-800.
Plaza-Menacho et al., "Targeting the receptor tyrosine kinase RET sensitizes breast cancer cells to tamoxifen treatment and reveals a role for RET in endocrine resistance," Oncogene, Aug. 19, 2010;29(33):4648-4657.
Plenker et al., "Drugging the catalytically inactive state of RET kinase in RET-rearranged tumors," Sci Transl Med, Jun. 14, 2017, 9(394). pii: eaah6144. doi: 10.1126/scitranslmed.aah6144.
Plosker, "Sipuleucel-T: in metastatic castration-resistant prostate cancer," Drugs. Jan. 1, 2011;71(1):101-108.
Postow et al., "Immune Checkpoint Blockade in Cancer Therapy," Journal of Clinical Oncology, Jun. 10, 2015;33(17):1974-1982.
Qi, et al., "RET mutation p.S891A in a Chinese family with familial medullary thyroid carcinoma and associated cutaneous amyloidosis binding OSMR variant p.G513D," Oncotarget, Oct. 20, 2015;6(32):33993-4003.

(56) References Cited

OTHER PUBLICATIONS

Rausch et al., "mRNA vaccine CV9103 and CV9104 for the treatment of prostate cancer," Human Vaccin immunother, 2014;10(11):3146-3152.
Reeser et al., "Validation of a Targeted RNA Sequencing Assay for Kinase Fusion Detection in Solid Tumors," J Mol. Diagn., Sep. 2017, 19(5):682-696.
Reungwetwattana et al., "Targeted therapies in development for non-small cell lung cancer," J Carcinog., Dec. 31, 2013;12:22.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis." Acta Derma Venereol, May 2015;95(5):542-548.
Romei and Elisei, "RET/PTC Translocations and Clinico-Pathological Features in Human Papillary Thyroid Carcinoma," Front Endocrinol (Lausanne), Apr. 11, 2012, 3:54.
Romei et al., European Thyroid Journal (Aug. 2016) vol. 5, Supp. Supplement 1, pp. 75; 39th Annual Meeting of the European Thyroid Association, ETA 2016. Copenhagen, Denmark. Sep. 3, 2016-Sep. 6, 2016.
Rosenzweig et al., "A case of advanced infantile myofibromatosis harboring a novel MYH10-RET fusion," Pediatr Blood Cancer, Jul. 2017;64(7). doi: 10.1002/pbc.26377. Epub Dec. 28, 2016.
Sabari et al., "Targeting RET-rearranged lung cancers with multikinase inhibitors," Oncoscience, Mar. 2017, 4(3-4):23-24.
Sahin et al., "Personalized RNA mutanome vaccines mobilize poly-specific therapeutic immunity against cancer," Nature, Jul. 13, 2017, 547(7662):222-226.
Saito et al., "Gene aberrations for precision medicine against lung adenocarcinoma," Cancer Science, Jun. 2016;107(6):713-720.
Santoro et al., "Development of thyroid papillary carcinomas secondary to tissue-specific expression of the RET/PTC1 oncogene in transgenic mice," Oncogene, Apr. 18, 1996, 12(8):1821-1826.
Scollo et al., "A novel RET gene mutation in a patient with apparently sporadic pheochromocytoma," Endocr. J., 2016;63(1):87-91.
Silva et al., "Identification and characterization of two novel germline RET variants associated with medullary thyroid carcinoma," Endrocrine, Jun. 2015, 49(2):366-372.
Simone, Oncology: Introduction, Cecil Textbook of Medicine, 20th Edition, vol. 1, pp. 1004-101 O, 1995.
Sjoblom et al., "The consensus coding sequences of human breast and colorectal cancers," Science, Oct. 13, 2006;314(5797):268-274.
Skalova et al., "Molecular Profiling of Mammary Analog Secretory Carcinoma Revealed a Subset of Tumors Harboring a Novel ETV6-RET Translocation: Report of 10 Cases," Am. J Surg. Pathol., Feb. 2018, 42(2):234-246.
Song et al., "Potent antitumor activity of cabozantinib, a c-MET and VEGFR2 inhibitor, in a colorectal cancer patient-derived tumor explant model," International Journal of Cancer, Apr. 15, 2015;136(8):1967-1975.
Sromek et al., "Analysis of Newly Identified and Rare Synonymous Genetic Variants in the RET Gene in Patients with Medullary Thyroid Carcinoma in Polish Population," Endocr Pathol., Sep. 2017, 28(3):198-206.
Su et al., "RET/PTC Rearrangements Are Associated with Elevated Postoperative TSH Levels and Multifocal Lesions in Papillary Thyroid Cancer without Concomitant Thyroid Benign Disease," PLoS One, Nov. 1, 2016, 11(11):e0165596.
Takeuchi et al., "RET, ROS1 and ALK fusions in lung cancer," Nature Med., Feb. 12, 2012;18(3):378-381.
Tang et al., "Coexistent genetic alterations involving ALK, RET, ROS1 or MET in 15 cases of lung adenocarcinoma," Mod Pathol., Sep. 15, 2017, doi: 10.1038/modpathol.2017.109. [Epub ahead of print].
Taraviras et al., "Signalling by the RET receptor tyrosine kinase and its role in the development of the mammalian enteric nervous system," Development, Jun. 1999;126(12):2785-2797.
Thress et al., "Identification and preclinical characterization of AZ-23, a novel, selective, and orally bioavailable inhibitor of the Trk kinase pathway," Mol. Cancer Ther., Jul. 2009;8(7):1818-1827.
Van Linden et al., "KLIFS: A knowledge based structural database to navigate kinase-ligand interaction space," J Med Chem., Jan. 23, 2014, 57(2):249-277.
Vanden et al., Annals of Oncology, 2016, vol. 27, Supp. Supplement 6. Abstract No. 427PD; 4pt European Society for Medical Oncology Congress, ESMP 2016. Copenhagen, Denmark, Oct. 7, 2016-Oct. 11, 2016.
Velcheti et al., "FRMD4A/RET: A Novel RET Oncogenic Fusion Variant in Non-Small Cell Lung Carcinoma," J Thorac Oncol., Feb. 2017, 12(2):e15-e16.
Wang et al., "Identification of 4-aminopyrazolylpyrimidines as potent inhibitors of Trk kinases," J Med Chem. Aug. 14, 2008;51(15):4672-4684.
Wang et al., "Trk kinase inhibitors as new treatments for cancer and pain," Expert Opin. Ther. Pat., Mar. 2009; 19(3):305-319.
Wells and Santoro, "Targeting the RET pathway in thyroid cancer," Clin Cancer Res., Dec. 1, 2009;15(23):7119-7123.
Wells et al., "Revised American Thyroid Association guidelines for the management of medullary thyroid carcinoma," Thyroid, Jun. 2015,25(6):567-610.
Wood et al, "The genomic landscapes of human breast and colorectal cancers" Science, Nov. 16, 2007, 318(5853):1108-1113.
Yoon et al., "A Pyrazolo[3,4-d]pyrimidin-4-amine Derivative Containing an Isoxazole Moiety Is a Selective and Potent Inhibitor of RET Gatekeeper Mutants," J. Med. Chem., Jan. 14, 2016, 59(1):358-373.
Zage et al.,"The selective Trk inhibitor AZ623 inhibits brain-derived neurotrophic factor-mediated neuroblastoma cell proliferation and signaling and is synergistic with topotecan," Cancer, Mar. 15, 2011;117(6):1321-1391. doi: 10.1002/cncr.25674. Epub Oct. 19, 2010.
Zeng et al. "The relationship between overexpression of glial cell-derived neurotrophic factor and its RET receptor with progression and prognosis of human pancreatic cancer," J. Int. Med, Res., Jul.-Aug. 2008;36(4):656-664.
Zhang et al., Laboratory Investigation, (Feb. 2017) vol. 97, Supp. 1, pp. 209A. Abstract No. 840, Meeting Info: 106th Annual Meeting of the United States and Canadian Academy of Pathology, USCAP 2017. San Antonio, TX, United States.

* cited by examiner

SUBSTITUTED PYRAZOLO[1,5-A]PYRIDINE COMPOUNDS AS RET KINASE INHIBITORS

CROSS-REFERENCE TO RELATED APPLICATIONS

This application is a continuation U.S. application Ser. No. 15/858,240 filed Dec. 29, 2017, which is a continuation of International Application No. PCT/US2017/055983, filed Oct. 10, 2017, which claims priority to U.S. Provisional Application Ser. Nos. 62/566,093, filed Sep. 29, 2017; 62/554,817, filed Sep. 6, 2017; 62/491,164, filed Apr. 27, 2017; 62/447,850, filed Jan. 18, 2017; and 62/406,252, filed Oct. 10, 2016, each of which is incorporated by reference in its entirety herein.

BACKGROUND

The present disclosure relates to novel compounds which exhibit Rearranged during Transfection (RET) kinase inhibition, pharmaceutical compositions comprising the compounds, processes for making the compounds, and the use of the compounds in therapy. More particularly, it relates to substituted pyrazolo[1,5-a]pyridine compounds useful in the treatment and prevention of diseases which can be treated with a RET kinase inhibitor, including RET-associated diseases and disorders.

RET is a single-pass transmembrane receptor belonging to the tyrosine kinase superfamily that is required for normal development, maturation and maintenance of several tissues and cell types (Mulligan, L. M., *Nature Reviews Cancer*, 2014, 14, 173-186). The extracellular portion of the RET kinase contains four calcium-dependent cadherin-like repeats involved in ligand binding and a juxtamembrane cysteine-rich region necessary for the correct folding of the RET extracellular domain, while the cytoplasmic portion of the receptor includes two tyrosine kinase subdomains.

RET signaling is mediated by the binding of a group of soluble proteins of the glial cell line-derived neurotrophic factor (GDNF) family ligands (GFLs), which also includes neurturin (NTRN), artemin (ARTN) and persephin (PSPN) (Arighi et al., *Cytokine Growth Factor Rev.*, 2005, 16, 441-67). Unlike other receptor tyrosine kinases, RET does not directly bind to GFLs and requires an additional co-receptor: that is, one of four GDNF family receptor-α (GFRα) family members, which are tethered to the cell surface by a glycosylphosphatidylinositol linkage. GFLs and GFRα family members form binary complexes that in turn bind to RET and recruit it into cholesterol-rich membrane subdomains, which are known as lipid rafts, where RET signaling occurs.

Upon binding of the ligand-co-receptor complex, RET dimerization and autophosphorylation on intracellular tyrosine residues recruits adaptor and signaling proteins to stimulate multiple downstream pathways. Adaptor protein binding to these docking sites leads to activation of Ras-MAPK and PI3K-Akt/mTOR signaling pathways or to recruitment of the CBL family of ubiquitin ligases that functions in RET downregulation of the RET-mediated functions.

Aberrant RET expression and/or activity have been demonstrated in different cancers and in gastrointestinal disorders such as irritable bowel syndrome (B S).

SUMMARY OF THE INVENTION

It has now been found that substituted pyrazolo[1,5-a]pyridine compounds are inhibitors of RET kinase, and are useful for treating diseases such as proliferative diseases including cancers.

Accordingly, provided herein is a compound of the Formula I:

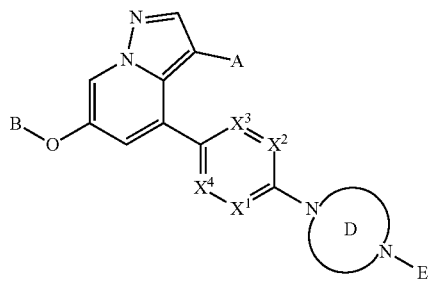

or pharmaceutically acceptable salt or solvate thereof, wherein A, B, $X^1$, $X^2$, $X^3$, $X^4$, and Ring D are as defined herein.

Also provided herein is a pharmaceutical composition comprising a compound of Formula I or a pharmaceutically acceptable salt or solvate thereof, in admixture with a pharmaceutically acceptable diluent or carrier.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein.

Also provided herein is a method of treating a RET-associated disease or disorder in a patient in need of such treatment, the method comprising administering to the patient a therapeutically effective amount of a compound of Formula I or a pharmaceutically acceptable salt or solvate thereof, or a pharmaceutical composition thereof as defined herein.

Also provided herein is a method of treating cancer and/or inhibiting metastasis associated with a particular cancer in a patient in need of such treatment, the method comprising administering to the patient a therapeutically effective amount of a compound of Formula I or a pharmaceutically acceptable salt or solvate thereof or a pharmaceutical composition thereof as defined herein.

Also provided herein is a method of treating irritable bowel syndrome (IBS) and/or pain associated with IBS in a patient in need of such treatment, the method comprising administering to the patient a therapeutically effective amount of a compound of Formula I or a pharmaceutically acceptable salt or solvate thereof or a pharmaceutical composition thereof as defined herein.

Also provided is a method of providing supportive care to a cancer patient, including preventing or minimizing gastrointestinal disorders, such as diarrhea, associated with treatment, including chemotherapeutic treatment, the method comprising administering to the patient a therapeutically effective amount of a compound of Formula I or a pharmaceutically acceptable salt or solvate thereof or a pharmaceutical composition thereof as defined herein.

Also provided herein is a compound of Formula I or a pharmaceutically acceptable salt or solvate thereof, or a pharmaceutical composition thereof as defined herein for use in therapy.

Also provided herein is a compound of Formula I or a pharmaceutically acceptable salt or solvate thereof or a pharmaceutical composition thereof as defined herein for use in the treatment of cancer and/or inhibiting metastasis associated with a particular cancer.

Also provided herein is a compound of Formula I or a pharmaceutically acceptable salt or solvate thereof or a pharmaceutical composition thereof as defined herein for use in the treatment of irritable bowel syndrome (IBS) or pain associated with IBS.

Also provided is a compound of Formula I or a pharmaceutically acceptable salt or solvate thereof or a pharmaceutical composition thereof as defined herein for use providing supportive care to a cancer patient, including preventing or minimizing gastrointestinal disorders, such as diarrhea, associated with treatment, including chemotherapeutic treatment.

Also provided herein is a compound of Formula I or a pharmaceutically acceptable salt or solvate thereof for use in the inhibition of RET kinase activity.

Also provided herein is a compound of Formula I or a pharmaceutically acceptable salt or solvate thereof or a pharmaceutical composition thereof as defined herein, for use in the treatment of a RET-associated disease or disorder.

Also provided herein is the use of a compound of Formula I or a pharmaceutically acceptable salt or solvate thereof, as defined herein in the manufacture of a medicament for the treatment of cancer and/or inhibiting metastasis associated with a particular cancer.

Also provided herein is the use of a compound of Formula I or a pharmaceutically acceptable salt or solvate thereof, as defined herein in the manufacture of a medicament for the treatment of irritable bowel syndrome (IBS) or pain associated with IBS.

Also provided herein is the use of a compound of Formula I or a pharmaceutically acceptable salt or solvate thereof, as defined herein in the manufacture of a medicament for providing supportive care to a cancer patient, including preventing or minimizing gastrointestinal disorders, such as diarrhea, associated with treatment, including chemotherapeutic treatment.

Also provided herein is a use of a compound of Formula I or a pharmaceutically acceptable salt or solvate thereof, as defined herein in the manufacture of a medicament for the inhibition of RET kinase activity.

Also provided herein is the use of a compound of Formula I or a pharmaceutically acceptable salt or solvate thereof, as defined herein, in the manufacture of a medicament for the treatment of a RET-associated disease or disorder.

Also provided herein is a method for treating cancer in a patient in need thereof, the method comprising (a) determining if the cancer is associated with a dysregulation of a RET gene, a RET kinase, or expression or activity or level of any of the same (e.g., a RET-associated cancer); and (b) if the cancer is determined to be associated with a dysregulation of a RET gene, a RET kinase, or expression or activity or level of any of the same (e.g., a RET-associated cancer), administering to the patient a therapeutically effective amount of a compound of Formula I or a pharmaceutically acceptable salt or solvate thereof, or a pharmaceutical composition thereof.

Also provided herein is a pharmaceutical combination for treating cancer (e.g., a RET-associated cancer, such as a RET-associated cancer having one or more RET inhibitor resistance mutations) in a patient in need thereof, which comprises (a) a compound of Formula I or a pharmaceutically acceptable salt or solvate thereof, (b) an additional therapeutic agent, and (c) optionally at least one pharmaceutically acceptable carrier, wherein the compound of Formula I or the pharmaceutically acceptable salt or solvate thereof and the additional therapeutic are formulated as separate compositions or dosages for simultaneous, separate or sequential use for the treatment of cancer, wherein the amounts of the compound of Formula I or a pharmaceutically acceptable salt or solvate thereof and of the additional therapeutic agent are together effective in treating the cancer. Also provided herein is a pharmaceutical composition comprising such a combination. Also provided herein is the use of such a combination for the preparation of a medicament for the treatment of cancer. Also provided herein is a commercial package or product comprising such a combination as a combined preparation for simultaneous, separate or sequential use; and to a method of treatment of cancer a patient in need thereof.

Also provided herein is a method for reversing or preventing acquired resistance to an anticancer drug, comprising administering a therapeutically effective amount of a compound of Formula I or a pharmaceutically acceptable salt or solvate thereof, to a patient at risk for developing or having acquired resistance to an anticancer drug. In some embodiments, the patient is administered a dose of the anticancer drug (e.g., at substantially the same time as a dose of a compound of Formula I or a pharmaceutically acceptable salt or solvate thereof is administered to the patient).

Also provided herein is a method of delaying and/or preventing development of cancer resistant to an anticancer drug in an individual, comprising administering to the individual an effective amount of a compound of Formula I or a pharmaceutically acceptable salt or solvate thereof, before, during, or after administration of an effective amount of the anticancer drug.

Also provided herein is a method of treating an individual with cancer who has an increased likelihood of developing resistance to an anticancer drug, comprising administering to the individual (a) an effective amount of a compound of Formula I before, during, or after administration of (b) an effective amount of the anticancer drug.

Also provided are methods of treating an individual with a RET-associated cancer that has one or more RET inhibitor resistance mutations that increase resistance of the cancer to a first RET inhibitor (e.g., a substitution at amino acid position 804, e.g., V804M, V804L, or V804E, and/or one or more RET inhibitor resistance mutations listed in Tables 3 and 4), that include administering a compound of Formula I or a pharmaceutically acceptable salt or solvate thereof, before, during, or after administration of another anticancer drug (e.g., a second RET kinase inhibitor).

Also provided are methods of treating an individual with a RET-associated cancer that include administering a compound of Formula I or a pharmaceutically acceptable salt or solvate thereof, before, during, or after administration of another anticancer drug (e.g., a first RET kinase inhibitor).

Also provided herein is a method for treating irritable bowel syndrome (IBS) in a patient in need thereof, the method comprising (a) determining if the IBS is associated with a dysregulation of a RET gene, a RET kinase, or expression or activity or level of any of the same; and (b) if the IBS is determined to be associated with a dysregulation of a RET gene, a RET kinase, or expression or activity or level of any of the same, administering to the patient a therapeutically effective amount of a compound of Formula I or a pharmaceutically acceptable salt or solvate thereof, or a pharmaceutical composition thereof.

Also provided herein is a pharmaceutical combination for treating irritable bowel syndrome (IBS) in a patient in need thereof, which comprises administering (a) a compound of General Formula I or a pharmaceutically acceptable salt or solvate thereof, (b) an additional therapeutic agent, and (c) optionally at least one pharmaceutically acceptable carrier, for simultaneous, separate or sequential use for the treatment of IBS, wherein the amounts of the compound of Formula I or a pharmaceutically acceptable salt or solvate thereof and of the additional therapeutic agent are together effective in treating the IBS. Also provided herein is a pharmaceutical composition comprising such a combination. Also provided herein is the use of such a combination for the preparation of a medicament for the treatment of the IBS. Also provided herein is a commercial package or product comprising such a combination as a combined preparation for simultaneous, separate or sequential use; and to a method of treatment of the IBS a patient in need thereof.

Also provided herein is a process for preparing a compound of Formula I or a pharmaceutically acceptable salt or solvate thereof.

Also provided herein is a compound of Formula I or a pharmaceutically acceptable salt or solvate thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Provided herein is a compound of the Formula I:

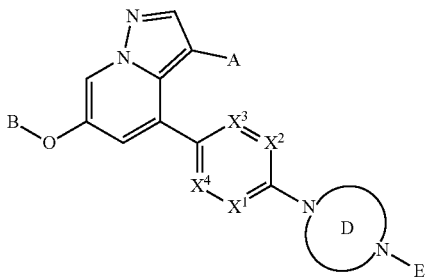

I and pharmaceutically acceptable salts and solvates thereof, wherein:

$X^1$, $X^2$, $X^3$ and $X^4$ are independently CH, CF, CCH$_3$ or N, wherein zero, one or two of $X^1$, $X^2$, $X^3$ and $X^4$ is N;

A is H, CN, Cl, CH$_3$—, CH$_3$CH$_2$—, cyclopropyl, —CH$_2$CN or —CH(CN)CH$_3$;

B is
(a) hydrogen,
(b) C1-C6 alkyl optionally substituted with 1-3 fluoros,
(c) hydroxyC2-C6 alkyl-, wherein the alkyl portion is optionally substituted with 1-3 fluoros or a C3-C6 cycloalkylidene ring,
(d) dihydroxyC3-C6 alkyl-, wherein the alkyl portion is optionally substituted with a C3-C6 cycloalkylidene ring,
(e) (C1-C6 alkoxy)C1-C6 alkyl- optionally substituted with 1-3 fluoros,
(f) ($R^1R^2N$)C1-C6 alkyl- wherein said alkyl portion is optionally substituted with OH and wherein $R^1$ and $R^2$ are independently H or C1-C6 alkyl (optionally substituted with 1-3 fluoros);
(g) hetAr$^1$C1-C3 alkyl-, wherein hetAr$^1$ is a 5-6 membered heteroaryl ring having 1-3 ring heteroatoms independently selected from N, O and S and is optionally substituted with one or more independently selected C1-C6 alkyl substituents;
(h) (C3-C6 cycloalkyl)C1-C3 alkyl-, wherein said cycloalkyl is optionally substituted with OH,
(i) (hetCyc$^a$)C1-C3 alkyl-,
(j) hetCyc$^a$-,
(k) C3-C6 cycloalkyl-, wherein said cycloalkyl is optionally substituted with OH,
(l) (C1-C4 alkyl)C(═O)O—C1-C6 alkyl-, wherein each of the C1-C4 alkyl and C1-C6 alkyl portions is optionally and independently substituted with 1-3 fluoros, or
(m) ($R^1R^2N$)C(═O)C1-C6 alkyl-, wherein $R^1$ and $R^2$ are independently H or C1-C6 alkyl (optionally substituted with 1-3 fluoros);

hetCyc$^a$- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(═O)—, (C1-C6 alkoxy)C1-C6 alkyl-, and fluoro, or wherein hetCyc$^a$ is substituted with oxo;

Ring D is (i) a saturated 4-7 membered heterocyclic ring having two ring nitrogen atoms, (ii) a saturated 7-8 membered bridged heterocyclic ring having two ring nitrogen atoms and optionally having a third ring heteroatom which is oxygen, (iii) a saturated 7-11 membered heterospirocyclic ring having two ring nitrogen atoms, or (iv) a saturated 9-10 membered bicyclic fused heterocyclic ring having two ring nitrogen atoms, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;

E is
(a) hydrogen,
(b) C1-C6 alkyl optionally substituted with 1-3 fluoros,
(c) (C1-C6 alkoxy)C1-C6 alkyl- optionally substituted with 1-3 fluoros,
(d) (C1-C6 alkyl)C(═O)—, wherein said alkyl portion is optionally substituted with 1-3 fluoros or with a $R^gR^hN$— substituent wherein $R^g$ and $R^h$ are independently H or C1-C6 alkyl,
(e) (hydroxyC2-C6 alkyl)C(═O)— optionally substituted with 1-3 fluoros,
(f) (C1-C6 alkoxy)C(═O)—,
(g) (C3-C6 cycloalkyl)C(═O)—, wherein said cycloalkyl is optionally substituted with one or more substituents independently selected from C1-C6 alkyl, C1-C6 alkoxy, OH, and (C1-C6 alkoxy)C1-C6 alkyl-, or said cycloalkyl is substituted with a 5-6 membered heteroaryl ring having 1-3 ring heteroatoms independently selected from N and O,
(h) Ar$^1$C1-C6 alkyl-,
(i) Ar$^1$(C1-C6 alkyl)C(═O)—, wherein said alkyl portion is optionally substituted with OH, hydroxyC1-C6 alkyl-, C1-C6 alkoxy, R'''R''N— or R'''R''N—CH$_2$—, wherein each R''' and R'' is independently H or C1-C6 alkyl, (j) hetAr$^2$C1-C6 alkyl-, wherein said alkyl portion is optionally substituted with 1-3 fluoros, (k) hetAr$^2$(C1-C6 alkyl)C(=O)— wherein said alkyl portion is optionally substituted with OH, hydroxyC1-C6 alkyl- or C1-C6 alkoxy, (l) hetAr$^2$C(=O)—, (m) hetCyc$^1$C(=O)—, (n) hetCyc$^1$C1-C6 alkyl-, (o) R$^3$R$^4$NC(=O)—, (p) Ar$^1$N(R$^3$)C(=O)—, (q) hetAr$^2$N(R$^3$)C(=O)—, (r) (C1-C6 alkyl)SO$_2$—, wherein the alkyl portion is optionally substituted with 1-3 fluoros, (s) Ar$^1$SO$_2$—, (t) hetAr$^2$SO$_2$—, (u) N—(C1-C6 alkyl)pyridinonyl, (v) Ar$^1$C(=O)—;

(w) Ar$^1$O—C(=O)—, (x) (C3-C6 cycloalkyl)(C1-C6 alkyl)C(=O)—, (y) (C3-C6 cycloalkyl)(C1-C6 alkyl)SO$_2$—, wherein the alkyl portion is optionally substituted with 1-3 fluoros, (z) Ar$^1$(C1-C6 alkyl)SO$_2$—, (aa) hetCyc$^1$-O—C(=O)—, (bb) hetCyc$^1$CH$_2$C(=O)—, (cc) hetAr$^2$, or (dd) C3-C6 cycloalkyl;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), R$^e$R$^f$N— wherein R$^e$ and R$^f$ are independently H, C1-C6 alkyl, (R$^p$R$^q$N)C1-C6 alkoxy- wherein R$^p$ and R$^q$ are independently H or C1-C6 alkyl, and (hetAr$^a$)C1-C6 alkyl- wherein hetAr$^a$ is a 5-6 membered heteroaryl ring having 1-2 ring nitrogen atoms, or Ar$^1$ is a phenyl ring fused to a 5-6 membered heterocyclic ring having 1-2 ring heteroatoms independently selected from N and 0;

hetAr$^2$ is a 5-6 membered heteroaryl ring having 1-3 ring heteroatoms independently selected from N, O and S or a 9-10 membered bicyclic heteroaryl ring having 1-3 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), R$^e$R$^f$N— wherein R$^e$ and R$^f$ are independently H or C1-C6 alkyl, OH, (C1-C6 alkoxy)C1-C6 alkoxy- and C3-C6 cycloalkyl;

hetCyc$^1$ is a 4-6 membered saturated heterocyclic ring having 1-2 ring heteroatoms independently selected from N, O and S wherein said heterocyclic ring is optionally substituted with one or more substituents independently selected from C1-C6 alkoxy and halogen;

R$^3$ is H or C1-C6 alkyl; and

R$^4$ is C1-C6 alkyl.

For complex chemical names employed herein, the substituent group is named before the group to which it attaches. For example, methoxyethyl comprises an ethyl backbone with a methoxy substituent.

The term "halogen" means —F (sometimes referred to herein as "fluoro" or "fluoros"), —Cl, —Br and —I.

The terms "C1-C3 alkyl", "C1-C6 alkyl", "C2-C6 alkyl" and "C3-C6 alkyl" as used herein refer to saturated linear or branched-chain monovalent hydrocarbon radicals of one to three, one to six, two to six, or three to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "C1-C6 alkoxy" as used herein refers to a saturated linear or branched-chain monovalent alkoxy radical of one to six carbon atoms, wherein the radical is on the oxygen atom. Examples include methoxy, ethoxy, propoxy, isopropoxy, butoxy and tert-butoxy.

The terms "(C1-C6 alkoxy)C1-C6 alkyl-" and "(C1-C6 alkoxy)C2-C6 alkyl-" as used herein refers to saturated linear or branched-chain monovalent radicals of one to six carbon atoms or two to six carbon atoms, respectively, wherein one of the carbon atoms is substituted with a (C1-C6 alkoxy) group as defined herein. Examples include methoxymethyl (CH$_3$OCH$_2$—) and methoxyethyl (CH$_3$OCH$_2$CH$_2$—).

The terms "hydroxyC1-C6 alkyl-" and "hydroxyC2-C6 alkyl-" as used herein refer to a saturated linear or branched-chain monovalent alkyl radicals of one to six or two to six carbon atoms, respectively, wherein one of the carbon atoms is substituted with a hydroxy group.

The term "dihydroxyC3-C6 alkyl-" as used herein refers to a saturated linear or branched-chain monovalent alkyl radical of three to six carbon atoms, wherein two of the carbon atoms are substituted with a hydroxy group.

The terms "(R$^1$R$^2$N)C1-C6 alkyl-" and "(R$^1$R$^2$N)C2-C6 alkyl-" as used herein refers to a C1-C6 alkyl or C2-C6 radical, respectively, as defined herein, wherein one of the carbon atoms is substituted with a R$^1$R$^2$N— group, wherein R$^1$ and R$^2$ are as defined herein.

The term "hetAr$^1$C1-C6 alkyl-" as used herein refers to a C1-C6 alkyl radical as defined herein, wherein one of the carbon atoms is substituted with a hetAr$^1$ group, wherein hetAr$^1$ is as defined herein.

The term "C3-C6 cycloalkyl" as used herein refers to cyclopropyl, cyclobutyl, cyclopentyl or cyclohexyl.

The terms "(C3-C6 cycloalkyl)C1-C3 alkyl-" and "(C3-C6 cycloalkyl)C1-C6 alkyl- as used herein refers to a C1-C3 alkyl radical or C1-C6 radical, respectively, as defined herein, wherein one of the carbon atoms is substituted with a C3-C6 cycloalkyl ring as defined herein.

The term "C3-C6 cycloalkylidene ring" as used herein refers to a divalent carbocyclic ring of three to six carbons. The suffix "ylidine" refers to bivalent radical derived from a saturated hydrocarbon by removal of two hydrogen atoms from the same carbon atom The term "(hetCyc$^a$)C1-C3 alkyl-" as used herein refers to a C1-C3 alkyl radical as defined herein, wherein one of the carbon atoms is substituted with a hetCyc$^a$ group, wherein hetCyc$^a$ is as defined herein.

The term "Ar$^1$C1-C6 alkyl-" as used herein refers to a C1-C6 alkyl radical as defined herein, wherein one of the carbon atoms is substituted with an Ar$^1$ group, wherein Ar$^1$ is as defined herein.

The terms "hetAr$^2$C1-C6 alkyl-" as used herein refers to a C1-C6 alkyl radical as defined herein, wherein one of the carbon atoms is substituted with an hetAr$^2$ group, wherein hetAr$^2$ is as defined herein.

The term "hetCyc$^1$C1-C6 alkyl-" as used herein refers to a C1-C6 alkyl radical as defined herein, wherein one of the carbon atoms is substituted with a hetCyc$^1$ group, wherein hetCyc$^1$ is as defined herein.

The term "N—(C1-C6 alkyl)pyridinonyl" as used herein refers to a pyridin-2(1H)-one ring wherein the ring nitrogen atom is substituted with a C1-C6 alkyl substituent, and wherein the radical may be on any of the ring carbon atoms other than the carbon bearing the oxo group. Examples include the structures:

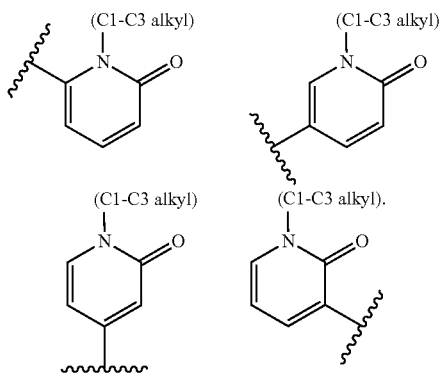

The term "heterospirocyclic" as used herein refers to a group having two rings joined by a spirocyclic linkage through a carbon atom, wherein each ring has 4 to 6 ring atoms (with one ring carbon atom being common to both rings), and wherein two of the ring atoms are nitrogen atoms.

The term "oxo" or "oxo group" as used herein means an oxygen that is double bonded to a carbon atom, i.e., =O. For example, in one embodiment when referring to Ring D, a saturated 6 membered heterocyclic ring having two ring nitrogen atoms may be, for example, a piperazinyl ring that is substituted with an oxo group (e.g., a piperazinonyl ring), which may be represented by the structure:

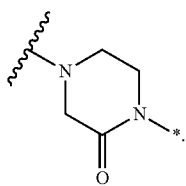

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer. Exemplary tautomerizations include, but are not limited to, keto-to-enol; amide-to-imide; lactam-to-lactim; enamine-to-imine; and enamine-to-(a different) enamine tautomerizations. A specific example of phenol-keto tautomerization is the interconversion of pyridin-2-ol and pyridin-2(1H)-one tautomers, for example:

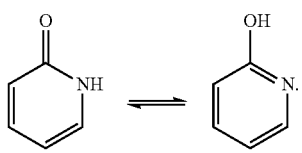 [SMILES: O=c1cccc[nH]1 ; Oc1ccccn1]

It will be appreciated that certain compounds provided herein may contain one or more centers of asymmetry and may therefore be prepared and isolated in a mixture of isomers such as a racemic mixture, or in an enantiomerically pure form.

In certain embodiments of Formula I, $X^1$, $X^2$, $X^3$ and $X^4$ are independently CH, CF or $CCH_3$. In certain embodiments, each of $X^1$, $X^2$, $X^3$ and $X^4$ is CH.

In certain embodiments of Formula I, $X^1$, $X^2$, $X^3$ and $X^4$ are independently CH, CF or $CCH_3$ or N, wherein one of $X^1$, $X^2$, $X^3$ and $X^4$ is N and the remainder are independently CH, CF or $CCH_3$. In certain embodiments of Formula I, $X^1$ is N, and $X^2$, $X^3$ and $X^4$ are independently CH or CF. In certain embodiments, $X^1$ is N, and $X^2$, $X^3$ and $X^4$ are CH. In certain embodiments, $X^1$ is N, $X^2$ is CF, and $X^3$ and $X^4$ are CH.

In certain embodiments of Formula I, $X^1$, $X^2$, $X^3$ and $X^4$ are independently CH, CF or $CCH_3$ or N, wherein two of $X^1$, $X^2$, $X^3$ and $X^4$ are N. In certain embodiments of Formula I, $X^1$ and $X^3$ are N and $X^2$ and $X^4$ are independently CH, CF or $CCH_3$. In one embodiment, $X^1$ and $X^3$ are N and $X^2$ and $X^4$ are CH. In certain embodiments of Formula I, $X^1$ and $X^2$ are N and $X^1$ and $X^4$ are independently CH or CF. In certain embodiments of Formula I, $X^1$ and $X^2$ are N and $X^1$ and $X^4$ are CH.

In certain embodiments of Formula I, A is H.
In certain embodiments of Formula I, A is Cl.
In certain embodiments of Formula I, A is CN.
In certain embodiments of Formula I, A is $CH_3$—.
In certain embodiments of Formula I, A is $CH_3CH_2$—.
In certain embodiments of Formula I, A is cyclopropyl.
In certain embodiments of Formula I, A is —$CH_2CN$.
In certain embodiments of Formula I, A is —CH(CN)$CH_3$.

In certain embodiments of Formula I, B is hydrogen.
In certain embodiments of Formula I, B is C1-C6 alkyl optionally substituted with 1-3 fluoros. Non-limiting examples include methyl, ethyl, propyl, isopropyl, isobutyl, 2-methylbutyl, 2-ethylbutyl, 2,2-dimethylpropyl, difluoromethyl, 2,2-difluoroethyl, and 2,2,2-trifluoroethyl.

In certain embodiments of Formula I, B is hydroxyC2-C6 alkyl-, wherein the alkyl portion is optionally substituted with 1-3 fluoros or a C3-C6 cycloalkylidene ring. In certain embodiments of Formula I, B is hydroxyC2-C6 alkyl-, wherein the alkyl portion is unsubstituted. Non-limiting examples include the structures:

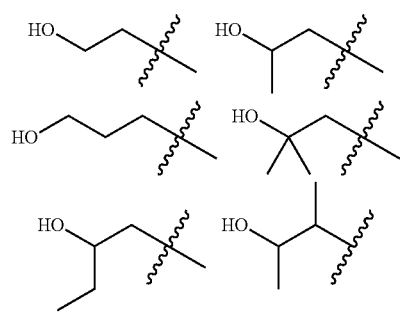

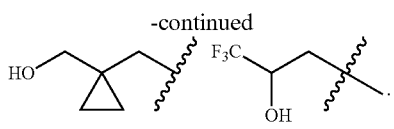

In certain embodiments of Formula I, B is dihydroxyC3-C6 alkyl-, wherein the alkyl portion is optionally substituted with a C3-C6 cycloalkylidene ring. In certain embodiments of Formula I, B is dihydroxyC3-C6 alkyl-. A non-limiting example includes 2,3-dihydroxypropyl.

In certain embodiments of Formula I, B is (C1-C6 alkoxy)C1-C6 alkyl- optionally substituted with 1-3 fluoros. In certain embodiments of Formula I, B is (C1-C6 alkoxy)C2-C6 alkyl- optionally substituted with 1-3 fluoros. Non-limiting examples include the structures:

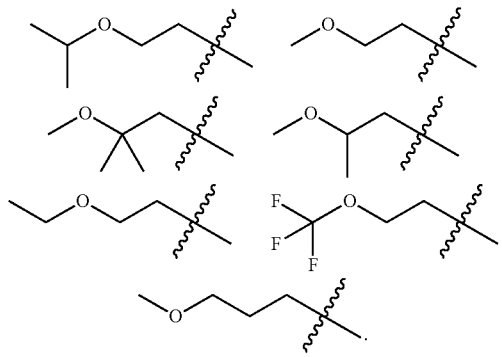

In certain embodiments of Formula I, B is (R$^1$R$^2$N)C1-C6 alkyl-, wherein said alkyl portion is optionally substituted with OH and R$^1$ and R$^2$ are independently H or C1-C6 alkyl (optionally substituted with 1-3 fluoros). In certain embodiments of Formula I, B is (R$^1$R$^2$N)C1-C6 alkyl-, wherein said alkyl portion is optionally substituted with OH and R$^1$ and R$^2$ are independently H or C2-C6 alkyl (optionally substituted with 1-3 fluoros). In certain embodiments of Formula I, B is (R$^1$R$^2$N)C1-C6 alkyl- wherein said alkyl portion is optionally substituted with OH and R$^1$ and R$^2$ are independently selected from C1-C6 alkyl substituents. Non-limiting examples when B is (R$^1$R$^2$N)C1-C6 alkyl- include the structures

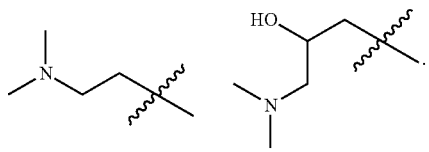

In certain embodiments of Formula I, B is hetAr$^1$C1-C3 alkyl-, wherein hetAr$^1$ is a 5-6 membered heteroaryl ring having 1-3 ring heteroatoms independently selected from N, O and S and is optionally substituted with one or more independently selected C1-C6 alkyl substituents. In certain embodiments, hetAr$^1$ is a 5-6 membered heteroaryl ring having 1-3 ring heteroatoms independently selected from N and O and is optionally substituted with C1-C6 alkyl. Non-limiting examples of hetAr$^1$C1-C3 alkyl- include the structures:

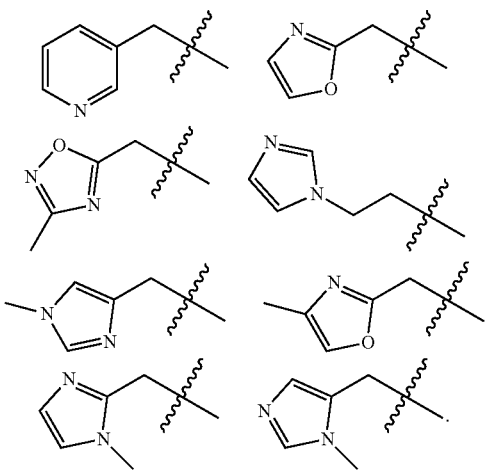

In certain embodiments of Formula I, B is (C3-C6 cycloalkyl)C1-C3 alkyl- wherein said cycloalkyl is optionally substituted with OH. Non-limiting examples include the structures:

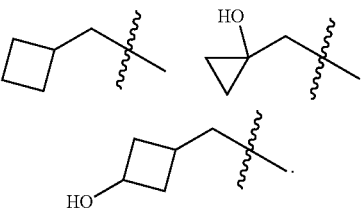

In certain embodiments of Formula I, B is (hetCyc$^a$)C1-C3 alkyl-, wherein hetCyc$^a$ is a 4-6 membered heterocyclic ring having 1-2 ring heteroatoms independently selected from N and O and is optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-C6 alkoxy)C1-C6 alkyl- and fluoro, or wherein hetCyc$^a$ is substituted with oxo. Non-limiting examples include the structures:

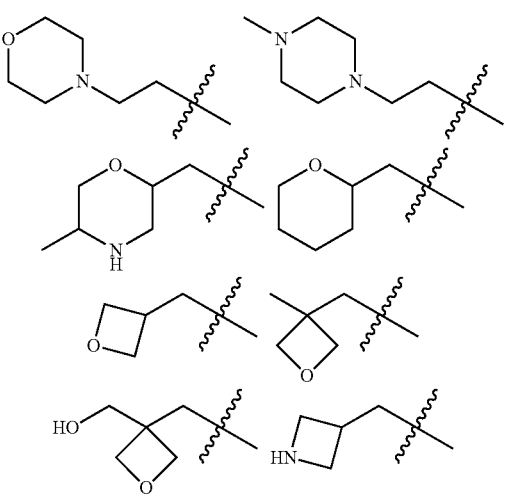

-continued

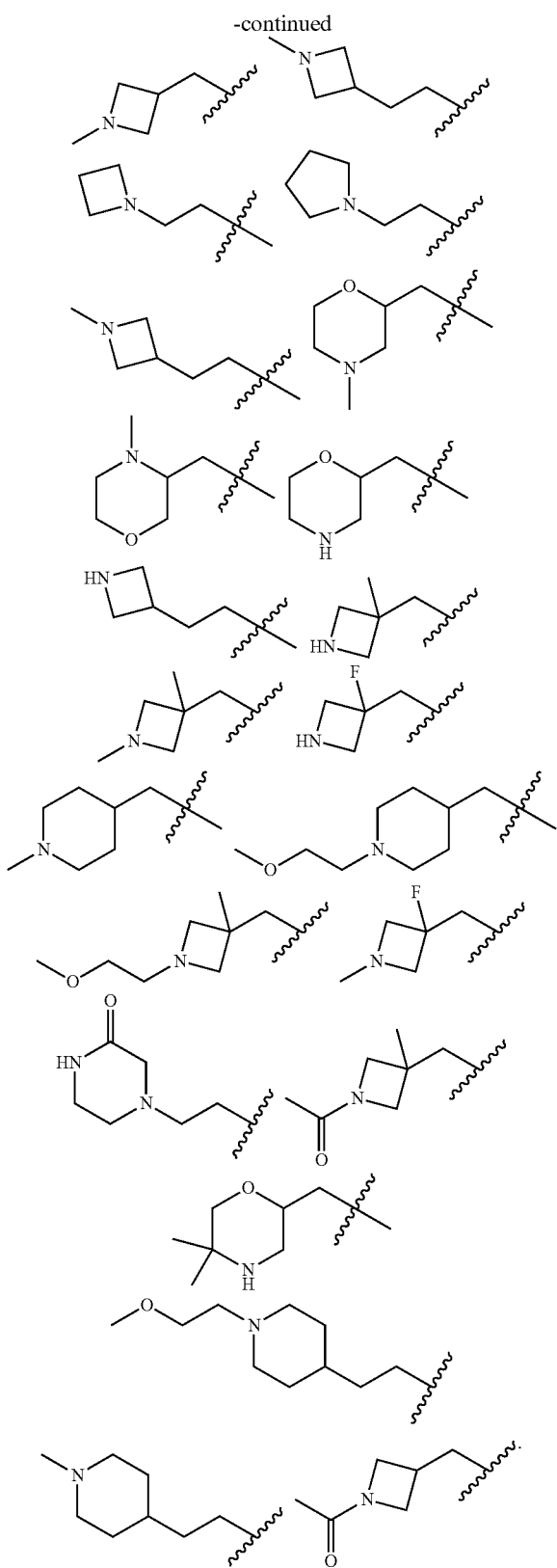

In certain embodiments of Formula I, B is hetCyc$^a$, wherein hetCyc$^a$ is a 4-6 membered heterocyclic ring having 1-2 ring heteroatoms independently selected from N and O and is optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-C6 alkoxy)C1-C6 alkyl- and fluoro, or wherein hetCyc$^a$ is substituted with oxo. In certain embodiments, hetCyc$^a$ is optionally substituted with OH or C1-C6 alkyl (optionally substituted with 1-3 fluoros). Non-limiting examples include the structures:

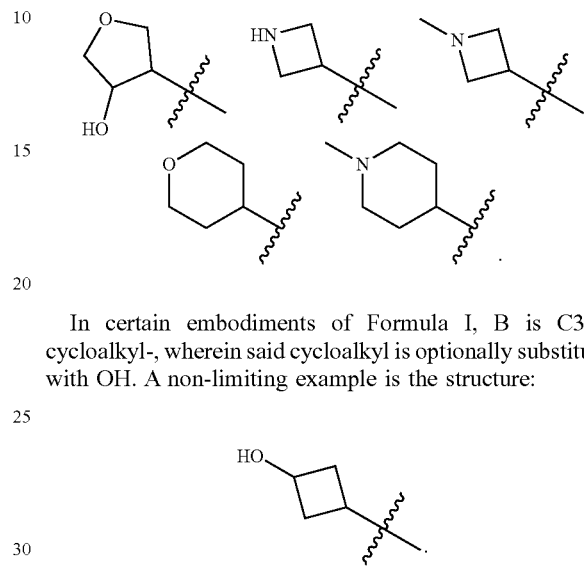

In certain embodiments of Formula I, B is C3-C6 cycloalkyl-, wherein said cycloalkyl is optionally substituted with OH. A non-limiting example is the structure:

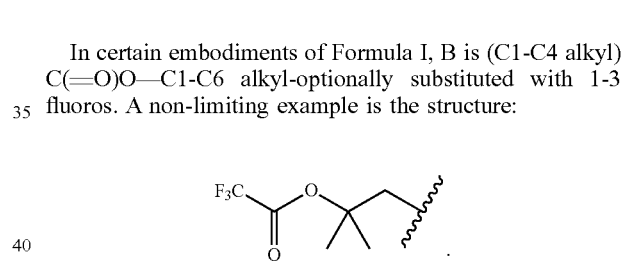

In certain embodiments of Formula I, B is (C1-C4 alkyl)C(=O)O—C1-C6 alkyl-optionally substituted with 1-3 fluoros. A non-limiting example is the structure:

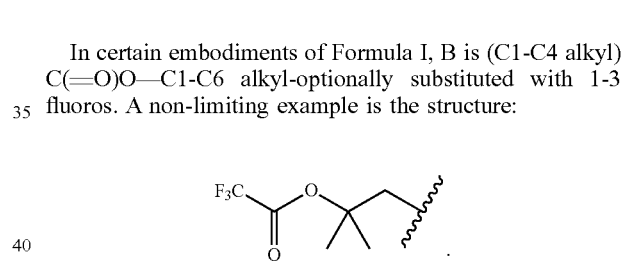

In certain embodiments of Formula I, B is (R$^1$R$^2$N)C(=O)C1-C6 alkyl- wherein R$^1$ and R$^2$ are independently H or C1-C6 alkyl (optionally substituted with 1-3 fluoros). Non-limiting examples include the structures:

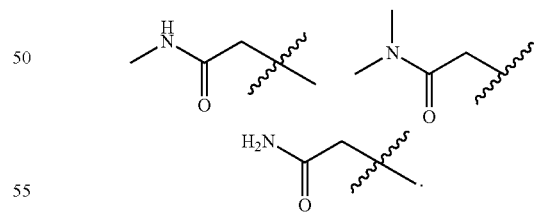

In one embodiment of Formula I, Ring D is a (i) saturated 4-7 membered heterocyclic ring having two ring nitrogen atoms, (ii) a saturated 7-8 membered bridged heterocyclic ring having two ring nitrogen atoms and optionally having a third ring heteroatom which is oxygen, (iii) a saturated 7-11 membered heterospirocyclic ring having two ring nitrogen atoms, or (iv) a saturated 9-10 membered bicyclic fused heterocyclic ring having two ring nitrogen atoms, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group.

As used herein, the phrase "having two ring nitrogen atoms" when referring to Ring D means that the two ring nitrogen atoms of Ring D are the two ring nitrogen atoms shown in Formula I, wherein one of the ring nitrogen atoms is bonded the ring comprising $X^1$, $X^2$, $X^3$ and $X^4$, and the other ring nitrogen atom is bonded to the E group.

In one embodiment, Ring D is a (i) saturated 4-7 membered heterocyclic ring having two ring nitrogen atoms, (ii) a saturated 7-8 membered bridged heterocyclic ring having two ring nitrogen atoms and optionally having a third ring heteroatom which is oxygen, (iii) a saturated 7-11 membered heterospirocyclic ring having two ring nitrogen atoms, or (iv) a saturated 9-10 membered bicyclic fused heterocyclic ring having two ring nitrogen atoms, wherein each of said rings is unsubstituted.

In one embodiment, Ring D is a saturated 4-7 membered heterocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. As used herein, the phrase "having two ring nitrogen atoms" when Ring D is a saturated monocyclic 4-7 membered heterocyclic ring means that said ring nitrogen atoms are the two nitrogen atoms shown in Ring D of Formula I, that is, Ring D may be represented by the structures:

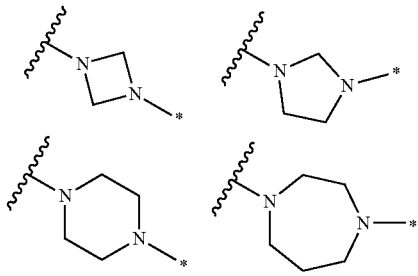

wherein the wavy line indicates the point of attachment to the ring comprising $X^1$, $X^2$, $X^3$ and $X^4$, and the asterisk indicates the point of attachment to the E group, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment, Ring D is an unsubstituted saturated 6 membered heterocyclic ring having two ring nitrogen atoms. In one embodiment, Ring D is a saturated 6 membered heterocyclic ring having two ring nitrogen atoms wherein said ring is substituted with oxo. In one embodiment, Ring D is a saturated 6 membered heterocyclic ring having two ring nitrogen atoms wherein said ring is substituted with a C3-C6 cycloalkylidene ring. In one embodiment, Ring D is a saturated 6 membered heterocyclic ring having two ring nitrogen atoms wherein said ring is substituted with a C3-C6 cyclopropylidine ring. In one embodiment, Ring D is a saturated 6 membered heterocyclic ring having two ring nitrogen atoms wherein said ring is substituted with (a) one to four groups independently selected from halogen, OH, C1-C3 alkyl which is optionally substituted with 1-3 fluoros, or C1-C3 alkoxy which is optionally substituted with 1-3 fluoros. In one embodiment, Ring D is a saturated 6 membered heterocyclic ring having two ring nitrogen atoms wherein said ring is substituted with C1-C3 alkyl which is optionally substituted with 1-3 fluoros. In one embodiment, Ring D is a saturated 7 membered heterocyclic ring having two ring nitrogen atoms, wherein said ring is unsubstituted.

In one embodiment when Ring D is a saturated 6-7 membered heterocyclic ring having two ring nitrogen atoms, Ring D and E portion of Formula I, that is,

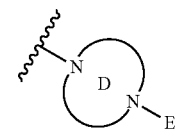

may be represented by the structures:

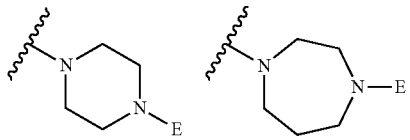

wherein the wavy line indicates the point of attachment to the ring comprising $X^1$, $X^2$, $X^3$ and $X^4$, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment, Ring D is unsubstituted. In one embodiment, Ring D is substituted with oxo. In one embodiment, Ring D is substituted with a C3-C6 cyclopropylidine ring. In one embodiment, Ring D is substituted with oxo. In one embodiment, Ring D is substituted with one to four groups independently selected from halogen, OH, C1-C3 alkyl which is optionally substituted with 1-3 fluoros, or C1-C3 alkoxy which is optionally substituted with 1-3 fluoros. In one embodiment, Ring D is a saturated 6 membered heterocyclic ring having two ring nitrogen atoms wherein said ring is substituted with one to four C1-C3 alkyl groups which are optionally substituted with 1-3 fluoros. In one embodiment, Ring D is unsubstituted, or ring D is substituted with one to four independently selected C1-C3 alkyl groups (each of which is optionally substituted with 1-fluoros), or Ring D is substituted with a C3-C6 cyclopropylidine ring, or Ring D is substituted with oxo. In one embodiment, Ring D is a saturated 7 membered heterocyclic ring having two ring nitrogen atoms, wherein said ring is unsubstituted. Examples of saturated 6 and 7 membered heterocyclic D rings include the structures:

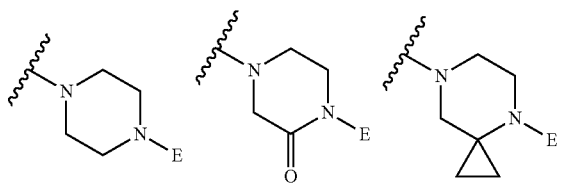

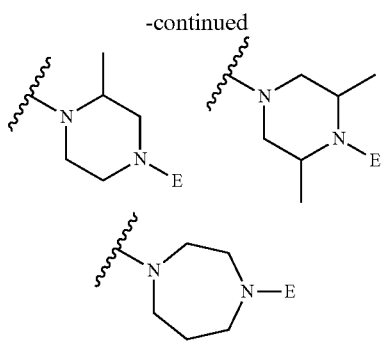

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is as defined for Formula I. In one embodiment, Ring D is a saturated 6-7 membered heterocyclic ring having two ring nitrogen atoms. In one embodiment, Ring D is a saturated 6 membered heterocyclic ring having two ring nitrogen atoms. In one embodiment, Ring D is unsubstituted. In one embodiment, Ring D is substituted with oxo. In one embodiment, Ring D is substituted with a cyclopropylidine ring. In one embodiment, Ring D is substituted with one or two C1-C3 alkyl groups, for example one or two methyl groups.

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (a) hydrogen, (c) (C1-C6 alkoxy)C1-C6 alkyl-optionally substituted with 1-3 fluoros, (d) (C1-C6 alkyl)C(=O)— optionally substituted with 1-3 fluoros, (e) (hydroxy C2-C6 alkyl)C(=O)— optionally substituted with 1-3 fluoros, (f) (C1-C6 alkoxy)C(=O)—, (g) (C3-C6 cycloalkyl)C(=O)— wherein said cycloalkyl is optionally substituted with (C1-C6 alkoxy)C1-C6 alkyl- or a 5-6 membered heteroaryl ring having 1-3 ring heteroatoms independently selected from N and O, (h) Ar$^1$C1-C6 alkyl-, (i) Ar$^1$(C1-C6 alkyl)C(=O)— wherein said alkyl portion is optionally substituted with OH, hydroxyC1-C6 alkyl- or C1-C6 alkoxy, (j) hetAr$^2$C1-C6 alkyl-, wherein the alkyl portion is optionally substituted with 1-3 fluoros, (k) hetAr$^2$(C1-C6 alkyl)C(=O)— wherein said alkyl portion is optionally substituted with OH, hydroxyC1-C6 alkyl- or C1-C6 alkoxy, (l) hetAr$^2$C(=O)—, (m) hetCyc$^1$C(=O)—, (n) hetCyc$^1$C1-C6 alkyl- (o) R$^3$R$^4$NC(=O)—, or (cc) hetAr$^2$, wherein Ar$^1$, hetAr$^2$, hetCyc$^1$, R$^3$ and R$^4$ are as defined for Formula I. In one embodiment, Ring D is a saturated 6-7 membered heterocyclic ring having two ring nitrogen atoms. In one embodiment, Ring D is a saturated 6 membered heterocyclic ring having two ring nitrogen atoms. In one embodiment, Ring D is a saturated 7 membered heterocyclic ring having two ring nitrogen atoms. In one embodiment, Ring D a saturated 6-7 membered heterocyclic ring, wherein Ring D is unsubstituted. In one embodiment, Ring D is a saturated 6 membered ring. In one embodiment, Ring D is substituted with oxo. In one embodiment, Ring D is substituted with a cyclopropylidine ring. In one embodiment, Ring D is substituted with one or two C1-C3 alkyl groups, for example one or two methyl groups.

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hydrogen. In one embodiment, Ring D is a saturated 6 membered heterocyclic ring having two ring nitrogen atoms. In one embodiment, Ring D is unsubstituted. A non-limiting example is the structure:

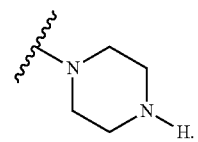

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkoxy)C1-C6 alkyl- optionally substituted with 1-3 fluoros. In one embodiment, Ring D is a saturated 6 membered heterocyclic ring having two ring nitrogen atoms. In one embodiment, Ring D is unsubstituted. A non-limiting example is the structure:

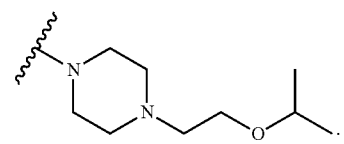 [SMILES: *N1CCN(CCOC(C)C)CC1]

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkyl)C(=O)— optionally substituted with 1-3 fluoros. In one embodiment, Ring D is a saturated 6 membered heterocyclic ring having two ring nitrogen atoms. In one embodiment, Ring D is unsubstituted. A non-limiting example is the structure:

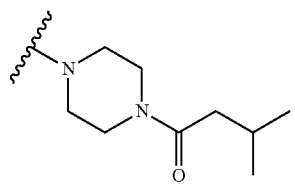

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (hydroxy C2-C6 alkyl)C(=O)— optionally substituted with 1-3 fluoros. In one embodiment, Ring D is a saturated 6 membered heterocyclic ring having two ring nitrogen atoms. In one embodiment, Ring D is unsubstituted. A non-limiting example is the structure:

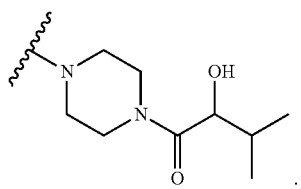 [SMILES: *N1CCN(C(=O)C(O)C(C)C)CC1 ; "."]

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkoxy)C(=O)—. In one embodiment, Ring D is a saturated 6 membered heterocyclic ring having two ring nitrogen atoms. In one embodiment, Ring D is unsubstituted. A non-limiting example is the structure:

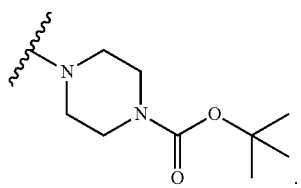 [SMILES: *N1CCN(C(=O)OC(C)(C)C)CC1 ; "."]

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C3-C6 cycloalkyl)C(=O)— wherein said cycloalkyl is optionally substituted with (C1-C6 alkoxy)C1-C6 alkyl- or a 5-6 membered heteroaryl ring having 1-3 ring heteroatoms independently selected from N and O, for example pyridinyl. In one embodiment, Ring D is a saturated 6 membered heterocyclic ring having two ring nitrogen atoms. In one embodiment, Ring D is unsubstituted. Non-limiting examples include the structures:

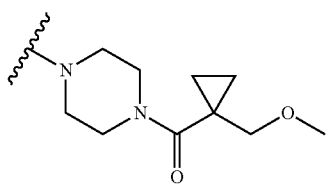

-continued

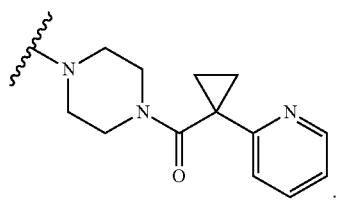

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is Ar¹C1-C6 alkyl-, wherein Ar¹ is as defined for Formula I. In one embodiment, Ring D is a saturated 6 membered heterocyclic ring having two ring nitrogen atoms. In one embodiment, Ring D is unsubstituted. In one embodiment, Ring D is substituted with oxo. In one embodiment, Ar¹ is unsubstituted. Non-limiting examples include the structures:

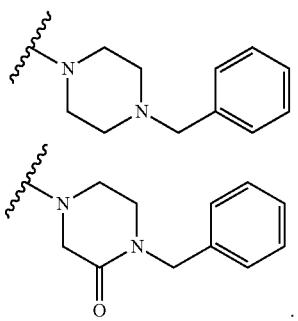

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is Ar¹(C1-C6 alkyl)C(=O)— wherein said alkyl portion is optionally substituted with OH, hydroxyC1-C6 alkyl, C1-C6 alkoxy, R'''R''N— or R'''R''N—CH$_2$—, wherein each R''' and R'' is independently H or C1-C6 alkyl, and Ar¹ is as defined for Formula I. In one embodiment, Ring D is a saturated 6 membered heterocyclic ring having two ring nitrogen atoms. In one embodiment, Ring D is unsubstituted. In one embodiment, Ar¹ is unsubstituted or substituted with one or more halogens. Non-limiting examples include the structures:

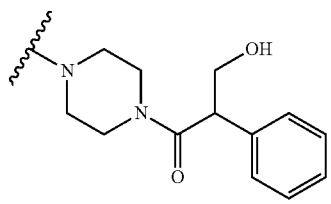

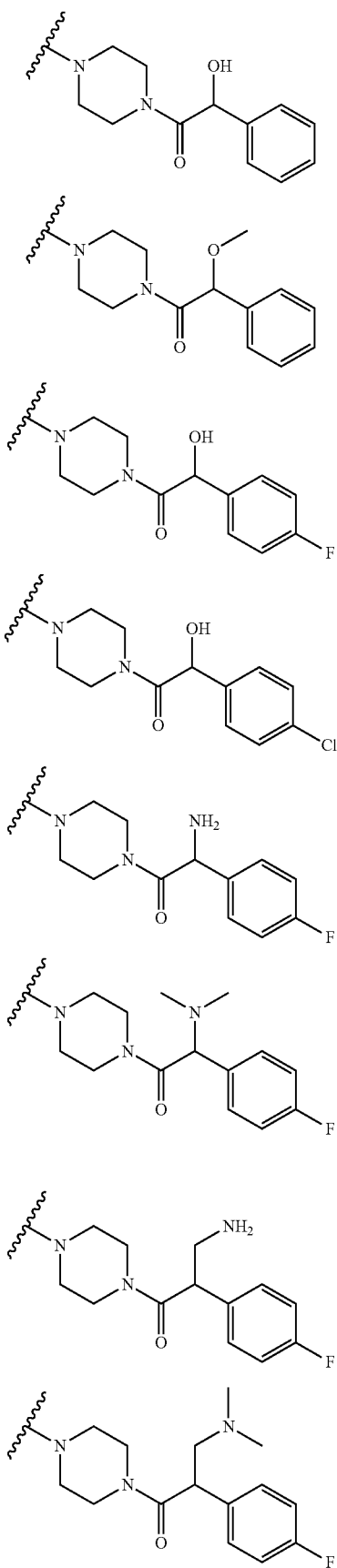

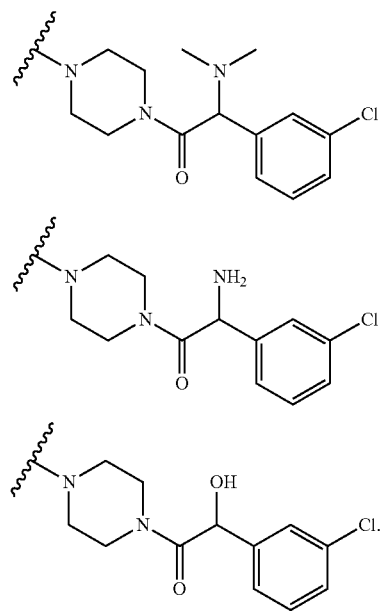

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr$^2$C1-C6 alkyl-, wherein the alkyl portion is optionally substituted with 1-3 fluoros, and wherein hetAr$^2$ is as defined for Formula I. In one embodiment, Ring D is a saturated 6-7 membered heterocyclic ring having two ring nitrogen atoms. In one embodiment, Ring D is unsubstituted. In one embodiment, Ring D is substituted with a cyclopropylidine ring. In one embodiment, hetAr$^2$ is a 5-6 membered heterocyclic ring having 1-2 ring nitrogen atoms. In one embodiment, hetAr$^2$ is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, hetAr$^2$ is a 6 membered heteroaryl ring having 1-2 ring nitrogen atoms and is optionally substituted with one or more substituents independently selected from the group consisting of halogen, C1-C6 alkyl (optionally substituted with 1-3 fluoros), and C1-C6 alkoxy (optionally substituted with 1-3 fluoros). Non-limiting examples include the structures:

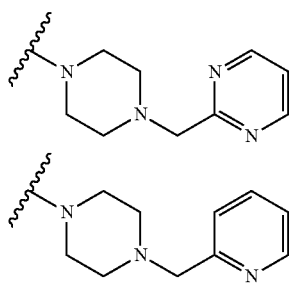

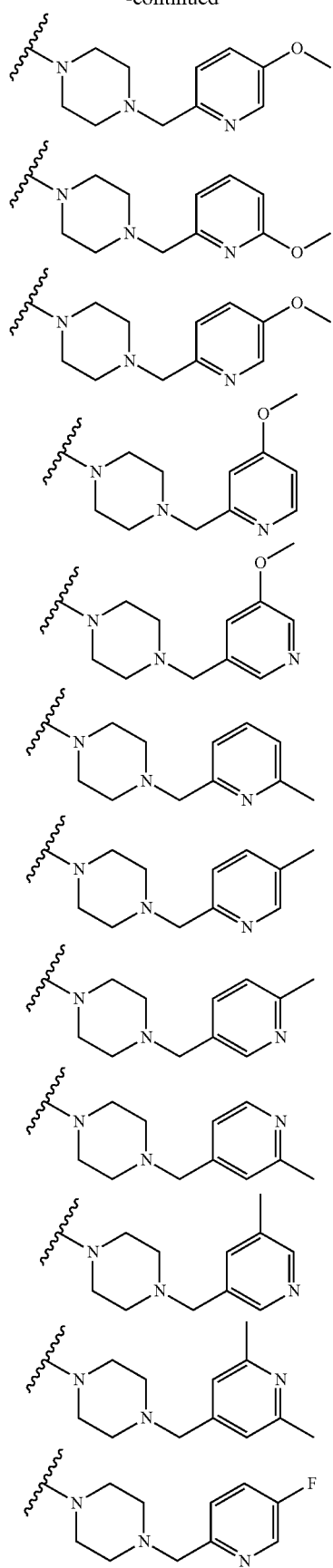
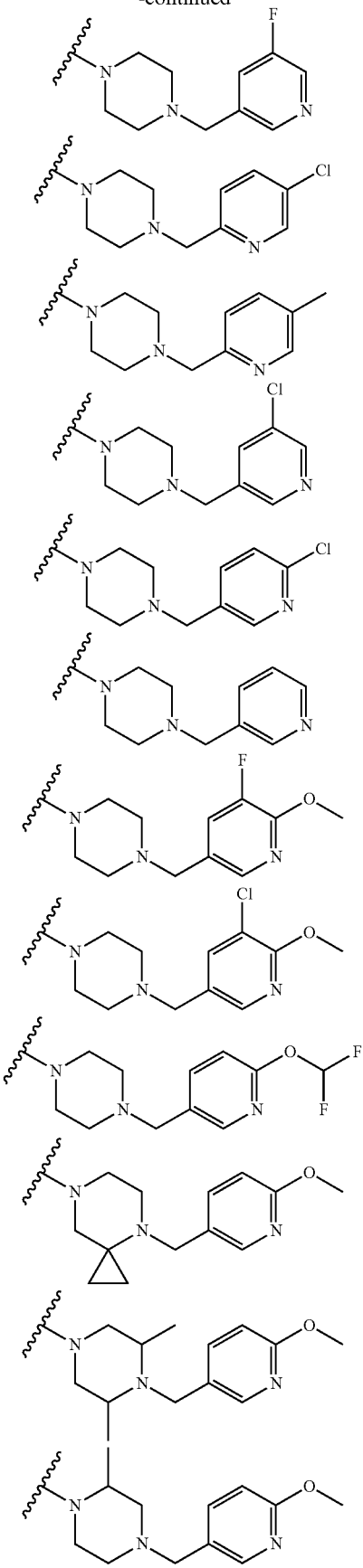

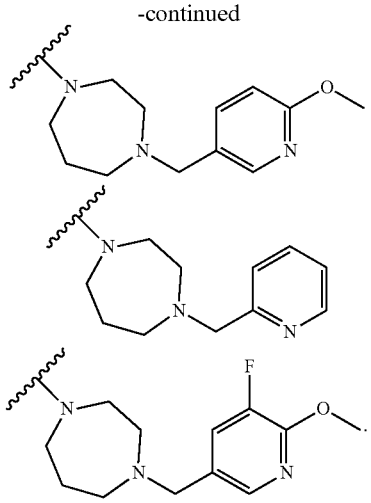

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr²(C1-C6 alkyl)C(=O)— wherein said alkyl portion is optionally substituted with OH, hydroxyC1-C6 alkyl or C1-C6 alkoxy, and wherein hetAr² is as defined for Formula I. In one embodiment, Ring D is a saturated 6 membered heterocyclic ring having two ring nitrogen atoms. In one embodiment, Ring D is unsubstituted. In one embodiment, the alkyl portion of hetAr²(C1-C6 alkyl)C(=O)— is unsubstituted. In one embodiment, hetAr² is a 5-6 membered heterocyclic ring having 1-2 ring nitrogen atoms. In one embodiment, hetAr² is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, hetAr² is a 6 membered ring having 1-2 ring nitrogen atoms and is optionally substituted with one or more halogens. A non-limiting example includes the structure:

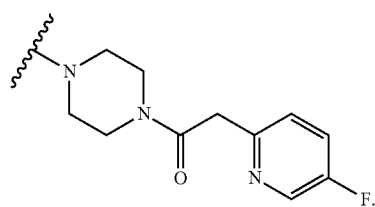 [SMILES: *N1CCN(C(=O)Cc2ccc(F)cn2)CC1]

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr²C(=O)— wherein hetAr² is as defined for Formula I. In one embodiment, Ring D is a saturated 6-7 membered heterocyclic ring having two ring nitrogen atoms, wherein Ring D is unsubstituted. In one embodiment, Ring D is a saturated 7 membered heterocyclic ring having two ring nitrogen atoms, wherein Ring D is unsubstituted. In one embodiment, hetAr² is a 5-6 membered heterocyclic ring having 1-2 ring nitrogen atoms. In one embodiment, hetAr² is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, hetAr² is a 6 membered ring having 1-2 ring nitrogen atoms and is optionally substituted with C1-C6 alkoxy. Non-limiting examples includes the structures:

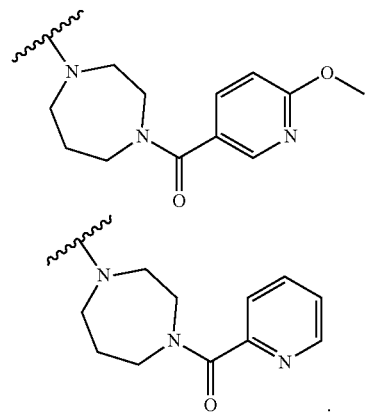

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetCyc¹C(=O)— wherein hetCyc¹ is as defined for Formula I. In one embodiment, Ring D is a saturated 6 membered heterocyclic ring having two ring nitrogen atoms. In one embodiment, Ring D is unsubstituted. In one embodiment hetCyc¹ is a 4-6 membered saturated heterocyclic ring having a ring nitrogen atom, wherein said heterocyclic ring is optionally substituted with one or more independently selected C1-C6 alkoxy substituents. A non-limiting example includes the structure:

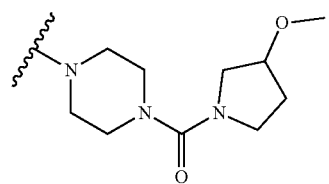

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetCyc¹C1-C6 alkyl- wherein hetCyc¹ is as defined for Formula I. In one embodiment, Ring D is a saturated 6 membered heterocyclic ring having two ring nitrogen atoms. In one embodiment, Ring D is unsubstituted. In one embodiment hetCyc¹ is a 4-6 membered saturated heterocyclic ring having a ring oxygen atom. In one embodiment, hetCyc¹ is unsubstituted. A non-limiting example includes the structure:

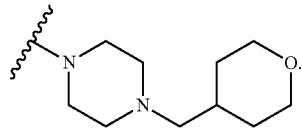 [SMILES: *N1CCN(CC2CCOCC2)CC1]

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is $R^3R^4NC(=O)$— wherein $R^3$ and $R^4$ are as defined for Formula I. In one embodiment, Ring D is a saturated 6 membered heterocyclic ring having two ring nitrogen atoms. In one embodiment, said Ring D is unsubstituted. A non-limiting example includes the structure:

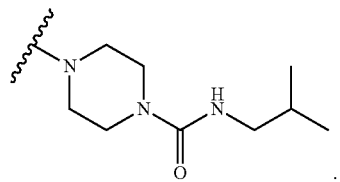 [SMILES: *N1CCN(C(=O)NCC(C)C)CC1 ; "."]

In one embodiment, Ring D is a saturated 4-7 membered heterocyclic ring having two ring nitrogen atoms, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr², wherein hetAr² is as defined for Formula I. In one embodiment, Ring D is a saturated 6 membered heterocyclic ring having two ring nitrogen atoms, wherein Ring D is unsubstituted. In one embodiment, hetAr² is a 5-6 membered heterocyclic ring having 1-2 ring nitrogen atoms. In one embodiment, hetAr² is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, hetAr² is a 6 membered ring having 1-2 ring nitrogen atoms and is optionally substituted with C1-C6 alkoxy. A non-limiting example includes the structure:

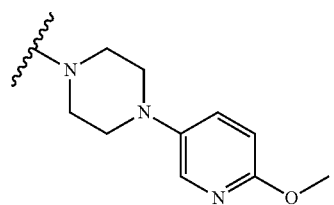 [SMILES: *N1CCN(c2ccc(OC)nc2)CC1]

In one embodiment of Formula I, Ring D is a saturated 7-8 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. As used herein, the phrase "having two ring nitrogen atoms" when Ring D is a saturated 7-8 membered bridged heterocyclic ring means that said ring nitrogen atoms are the two nitrogen atoms shown in Ring D of Formula I, wherein one of the ring nitrogen atoms is bonded the ring comprising $X^1$, $X^2$, $X^3$ and $X^4$, and the other ring nitrogen atom is bonded to the E group as shown in Formula I. Non-limiting examples when Ring D is a saturated 7-9 membered bridged heterocyclic ring having two ring nitrogen atoms and optionally having a third ring heteroatom which is oxygen include the following structures:

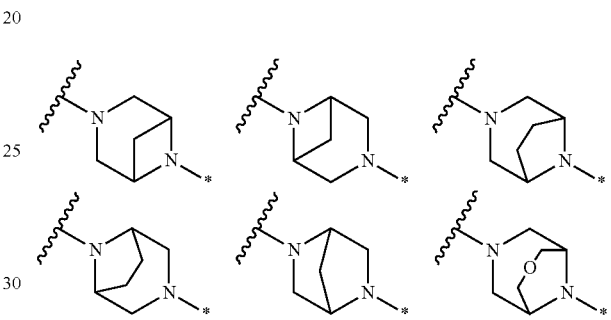

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment, Ring D is unsubstituted.

In one embodiment when Ring D is a saturated 7-9 membered bridged heterocyclic ring having 2-3 ring heteroatoms independently selected from N and O, Ring D and E portion of Formula I, that is

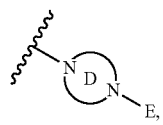

may be represented by the non-limiting structures:

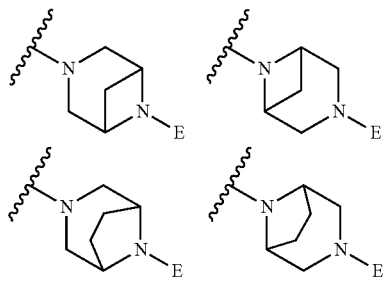

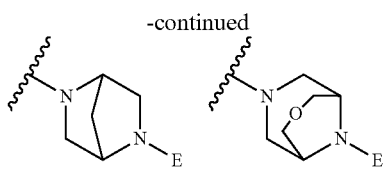

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment, Ring D is unsubstituted.

In one embodiment, Ring D is a saturated 7 membered bridged heterocyclic ring having two ring nitrogen atoms represented by the structure:

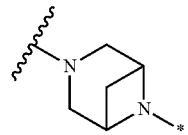

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment, Ring D is unsubstituted.

In one embodiment, Ring D is a saturated 7-8 membered bridged heterocyclic ring having two ring nitrogen atoms and optionally having a third ring heteroatom which is oxygen, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is as defined for Formula I. In one embodiment, Ring D is a saturated 7-8 membered bridged heterocyclic ring having two ring nitrogen atoms. In one embodiment, Ring D is unsubstituted.

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is selected from the group consisting of (a) hydrogen, (b) C1-C6 alkyl, (c) (C1-C6 alkoxy)C1-C6 alkyl-, (d) (C1-C6 alkyl)C(=O)—, (e) (hydroxyC2-C6 alkyl)C(=O)—, (f) (C1-C6 alkoxy)C(=O)—, (g) (C3-C6 cycloalkyl)C(=O)—, (h) $Ar^1$C1-C6 alkyl-, (i) $Ar^1$(C1-C6 alkyl)C(=O)— wherein said alkyl portion is optionally substituted with OH, hydroxyC1-C6 alkyl or C1-C6 alkoxy, (j) $hetAr^2$C1-C6 alkyl-, wherein the alkyl portion is optionally substituted with 1-3 fluoros, (k) $hetAr^2$(C1-C6 alkyl)C(=O)— wherein said alkyl portion is optionally substituted with OH, hydroxyC1-C6 alkyl- or C1-C6 alkoxy, (l) $hetAr^2$C(=O)—, (m) $hetCyc^1$C(=O)—, (o) $R^3R^4$NC(=O)—, (p) $Ar^1R^3$NC(=O)—, (q) $hetAr^2$N($R^3$)C(=O)—, (r) (C1-C6 alkyl)$SO_2$—, (t) $hetAr^2SO_2$—. (u) N—(C1-C6 alkyl)pyridinonyl, (v) $Ar^1$C(=O)—, (w) $Ar^1$O—C(=O)—, (x) (C3-C6 cycloalkyl)$CH_2$C(=O)—, (y) (C3-C6 cycloalkyl)(C1-C6 alkyl)$SO_2$—, (z) $Ar^1$(C1-C6 alkyl)$SO_2$—, (aa) $hetCyc^1$-O—C(=O)—, (bb) $hetCyc^1$-$CH_2$—C(=O)—, and (cc) $hetAr^2$, wherein $Ar^1$, $hetAr^2$, $R^3$ and $hetCyc^1$ are as defined for Formula I. In one embodiment, Ring D is selected from the structures

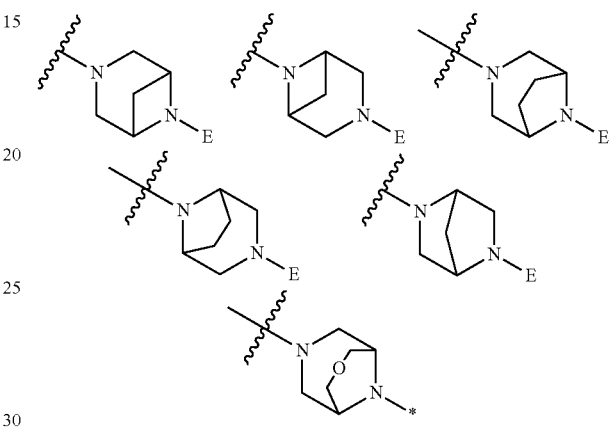

wherein the wavy line indicates the point of attachment of Ring D to the ring comprising $X^1$, $X^2$, $X^3$ and $X^4$, and the asterisk indicates the point of attachment to E.

In one embodiment, Ring D is a saturated 7-8 membered bridged heterocyclic ring having two ring nitrogen atoms represented by the structure:

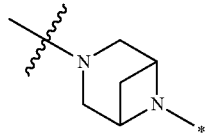 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E, and E is selected from the group consisting of (a) hydrogen, (b) C1-C6 alkyl, (c) (C1-C6 alkoxy)C1-C6 alkyl-, (d) (C1-C6 alkyl)C(=O)—, (e) (hydroxyC2-C6 alkyl)C(=O)—, (f) (C1-C6 alkoxy)C(=O)—, (g) (C3-C6 cycloalkyl)C(=O)—, (h) $Ar^1$C1-C6 alkyl-, (i) $Ar^1$(C1-C6 alkyl)C(=O)— wherein said alkyl portion is optionally substituted with OH, hydroxyC1-C6 alkyl or C1-C6 alkoxy, (j) $hetAr^2$C1-C6 alkyl-, wherein the alkyl portion is optionally substituted with 1-3 fluoros, (k) $hetAr^2$(C1-C6 alkyl)C(=O)— wherein said alkyl portion is optionally substituted with OH, hydroxyC1-C6 alkyl- or C1-C6 alkoxy, (l) $hetAr^2$C(=O)—, (m) $hetCyc^1$C(=O)—, (o) $R^3R^4$NC(=O)—, (p) $Ar^1$N($R^3$)C(=O)—, (q) $hetAr^2$N($R^3$)C(=O)—, (r) (C1-C6 alkyl)$SO_2$—, (t) $hetAr^2SO_2$—, (u) N—(C1-C6 alkyl)pyridinonyl, (v) $Ar^1$C(=O)—, (w) $Ar^1$O—C(=O)—, (x) (C3-C6 cycloalkyl)$CH_2$C(=O)—, (y) (C3-C6 cycloalkyl)(C1-C6 alkyl)$SO_2$—, (z) $Ar^1$(C1-C6 alkyl)$SO_2$—, (aa) $hetCyc^1$-O—C(=O)—, (bb) $hetCyc^1$-

CH₂—C(=O)—, and (cc) hetAr², wherein Ar¹, hetAr², R³ and hetCyc¹ are as defined for Formula I. In one embodiment, said Ring D is unsubstituted.

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is H. In one embodiment, Ring D is a saturated 7-8 membered bridged heterocyclic ring having two ring nitrogen atoms. In one embodiment, Ring D is represented by the structure:

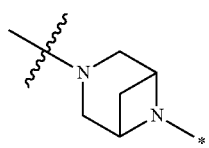 [SMILES: *N1CC2CC(C1)N2C]

wherein the wavy line indicates the point of attachment of Ring D to the ring comprising X¹, X², X³ and X⁴, and the asterisk indicates the point of attachment to E. In one embodiment, Ring D is unsubstituted. Non-limiting examples include the structures:

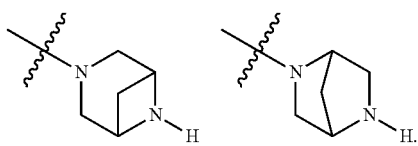

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is C1-C6 alkyl optionally substituted with 1-3 fluoros. In one embodiment, Ring D is a saturated 7-8 membered bridged heterocyclic ring having two ring nitrogen atoms. In one embodiment, Ring D is represented by the structure:

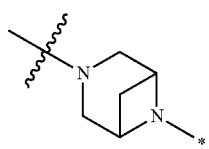 [SMILES: *N1CC2CC(C1)N2C]

wherein the wavy line indicates the point of attachment of Ring D to the ring comprising X¹, X², X³ and X⁴, and the asterisk indicates the point of attachment to E. In one embodiment, Ring D is unsubstituted. Non-limiting examples include the structures:

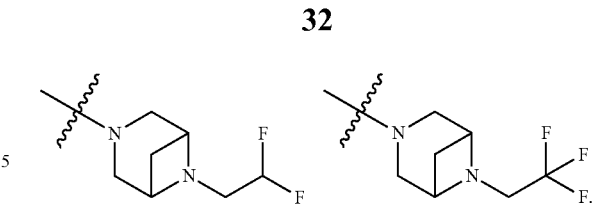

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkoxy)C1-C6 alkyl- optionally substituted with 1-3 fluoros. In one embodiment, Ring D is a saturated 7-8 membered bridged heterocyclic ring having two ring nitrogen atoms. In one embodiment, Ring D is represented by the structure:

wherein the wavy line indicates the point of attachment of Ring D to the ring comprising X¹, X², X³ and X⁴, and the asterisk indicates the point of attachment to E. In one embodiment, Ring D is unsubstituted. A non-limiting example includes the structure:

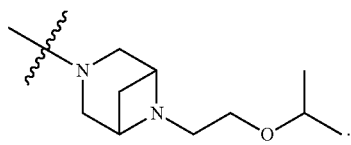 [SMILES: *N1CC2CC(C1)N2CCOC(C)C]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkyl)C(=O)— wherein said alkyl portion is optionally substituted with 1-3 fluoros or with a R^g R^h N— substituent wherein R^g and R^h are independently H or C1-C6 alkyl. In one embodiment, Ring D is a saturated 7-8 membered bridged heterocyclic ring having two ring nitrogen atoms. In one embodiment, Ring D is represented by the structure:

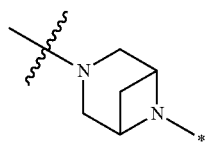 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

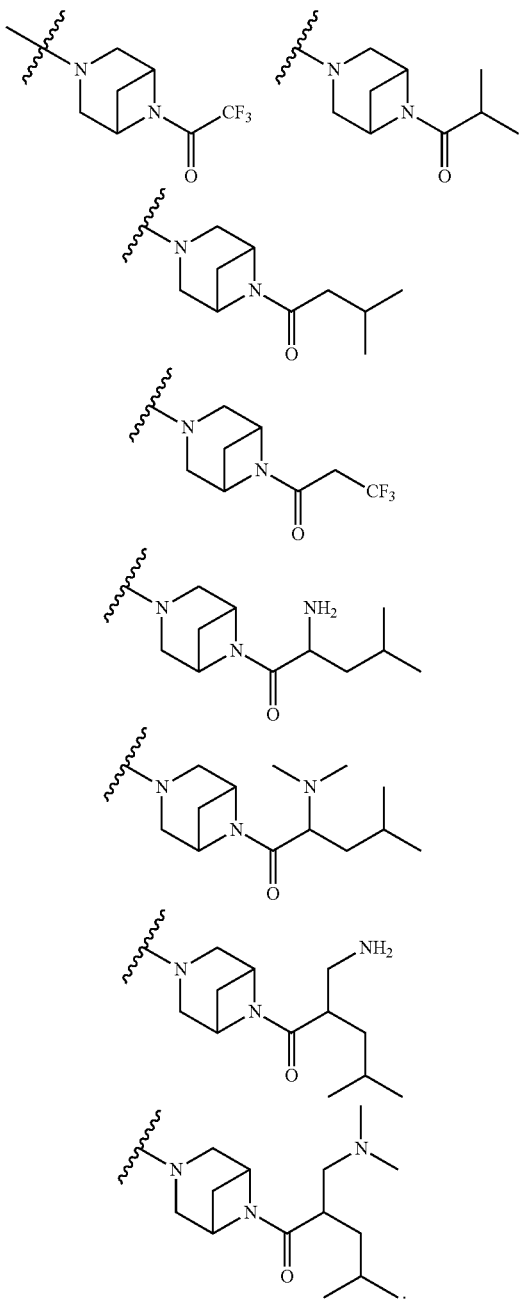

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (hydroxyC2-C6 alkyl)C(=O)— optionally substituted with 1-3 fluoros. In one embodiment, Ring D is a saturated 7-8 membered bridged heterocyclic ring having two ring nitrogen atoms. In one embodiment, Ring D is represented by the structure:

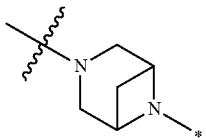 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example includes the structure:

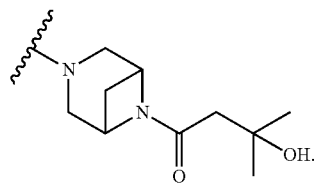 [SMILES: *N1CC2CC(C1)N2C(=O)CC(C)(C)O]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b a C3-C6 cycloalkylidene ring, or (c) an oxo group, and E is (C1-C6 alkoxy)C(=O)—. In one embodiment, Ring D is a saturated 7-8 membered bridged heterocyclic ring having two ring nitrogen atoms. In one embodiment, Ring D is represented by the structures:

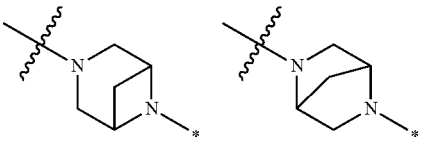

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

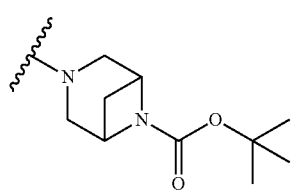

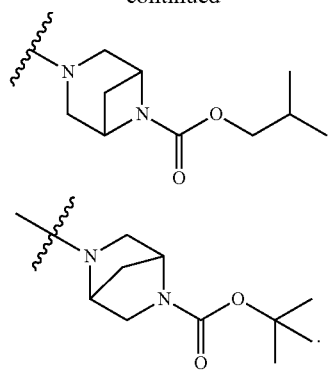

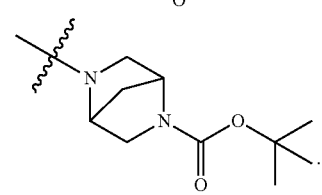

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is C3-C6 cycloalkyl)C(=O)— wherein said cycloalkyl is optionally substituted with one or more substituents independently selected from C1-C6 alkyl, C1-C6 alkoxy, OH, and (C1-C6 alkoxy)C1-C6 alkyl-, or said cycloalkyl is substituted with a 5-6 membered heteroaryl ring having 1-3 ring heteroatoms independently selected from N and O. In one embodiment, E is C3-C6 cycloalkyl)C(=O)— wherein said cycloalkyl is optionally substituted with one or more substituents independently selected from C1-C6 alkyl, C1-C6 alkoxy, OH, and (C1-C6 alkoxy)C1-C6 alkyl-. In one embodiment, Ring D is a saturated 7-8 membered bridged heterocyclic ring having two ring nitrogen atoms. In one embodiment, Ring D is represented by the structure:

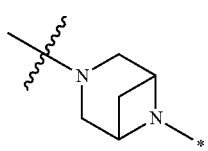 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

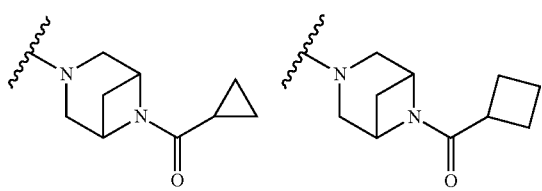
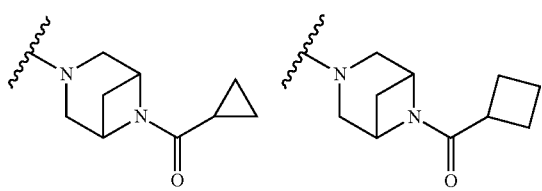

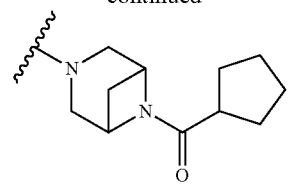

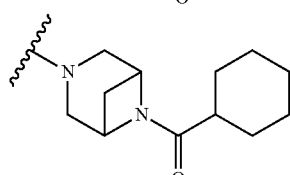

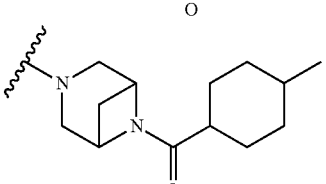

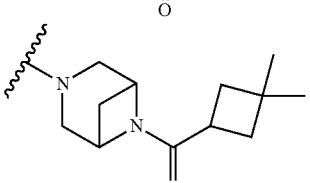

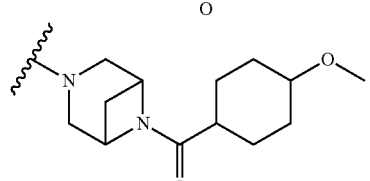

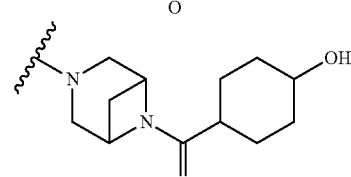

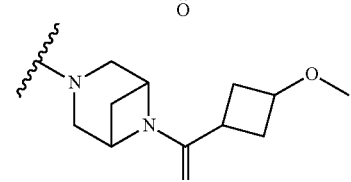

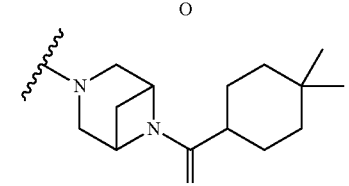

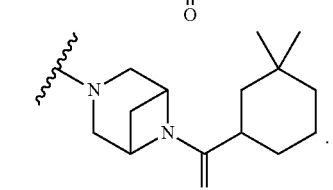

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is Ar¹C1-C6 alkyl-, wherein Ar¹ is as defined for Formula I. In one embodiment, E is Ar¹C1-C6 alkyl- wherein Ar¹ is phenyl optionally substituted with one or more substituents independently selected from the group consisting of halogen, C1-C6 alkyl (optionally substituted with 1-3 fluoros), C1-C6 alkoxy (optionally substituted with 1-3 fluoros), (R$^p$R$^q$N)C1-C6 alkoxy- wherein R$^p$ and R$^q$ are independently H or C1-C6 alkyl, and (hetAr$^a$)C1-C6 alkyl- wherein hetAr$^a$ is a 5-6 membered heteroaryl ring having 1-2 ring nitrogen atoms. In one embodiment, Ring D is a saturated 7-8 membered bridged heterocyclic ring having two ring nitrogen atoms. In one embodiment, Ring D is represented by the structure:

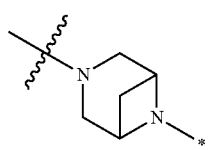 [SMILES: *N1CC2CC(C1)N2C]

wherein the wavy line indicates the point of attachment of Ring D to the ring comprising X¹, X², X³ and X⁴, and the asterisk indicates the point of attachment to E. In one embodiment, Ring D is unsubstituted. Nonlimiting examples include the structures:

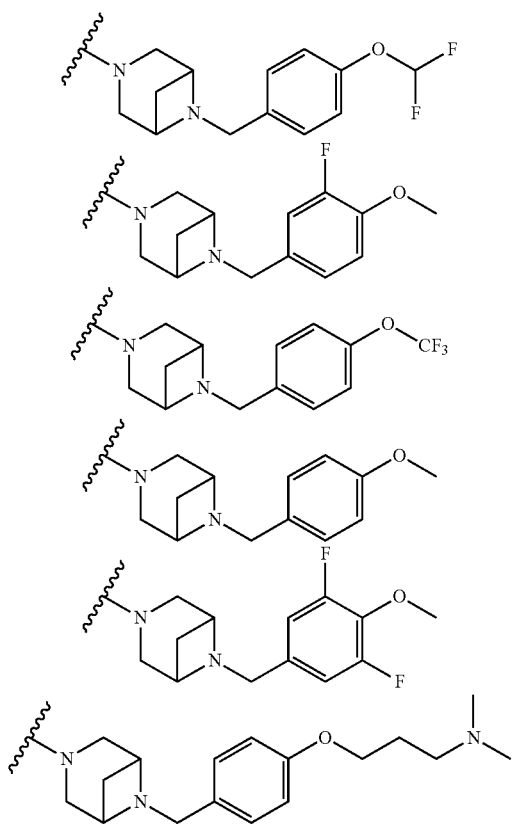

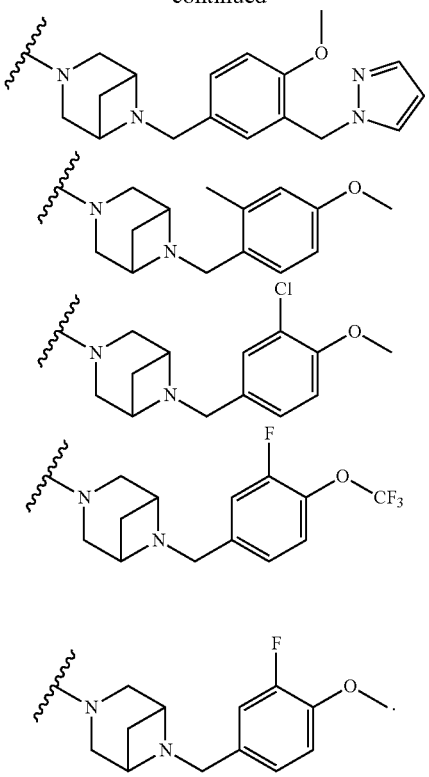

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is Ar¹(C1-C6 alkyl)C (=O)— wherein said alkyl portion is optionally substituted with OH, hydroxyC1-C6 alkyl, C1-C6 alkoxy, R'''R''N— or R'''R''N—CH₂—, wherein each R''' and R'' is independently H or C1-C6 alkyl, and Ar¹ is as defined for Formula I. In one embodiment, Ar¹ is phenyl which is unsubstituted or substituted with one or more halogens. In one embodiment, Ring D is a saturated 7-8 membered bridged heterocyclic ring having two ring nitrogen atoms. In one embodiment, Ring D is represented by the structure:

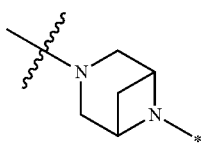

wherein the wavy line indicates the point of attachment of Ring D to the ring comprising X¹, X², X³ and X⁴, and the asterisk indicates the point of attachment to E. In one embodiment, Ring D is unsubstituted. Non-limiting examples include the structures:

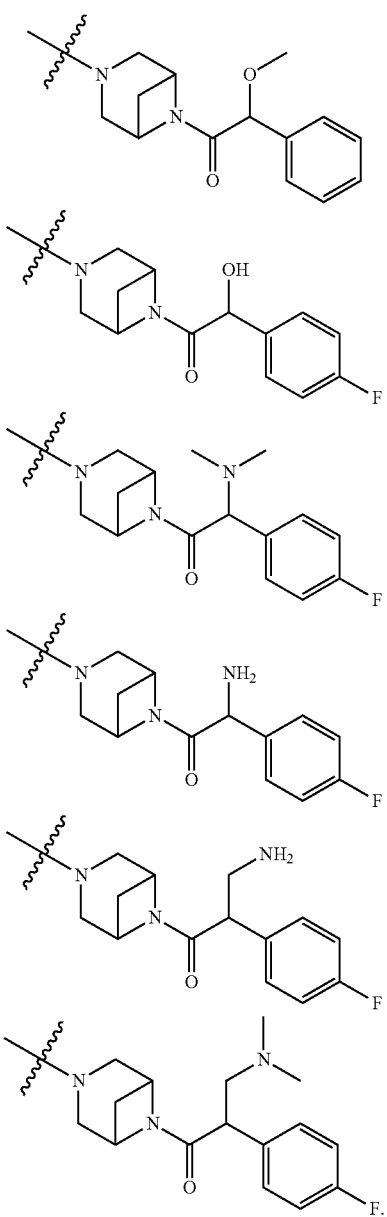

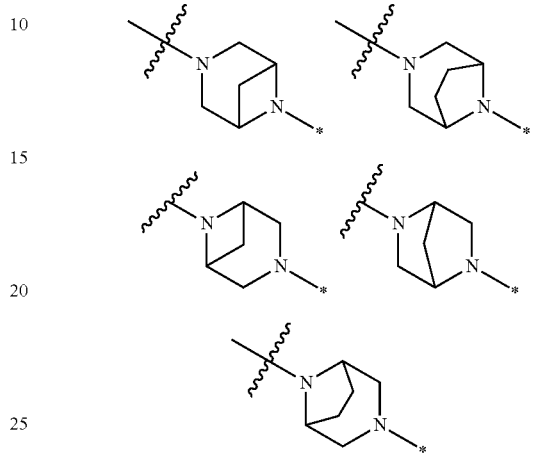

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

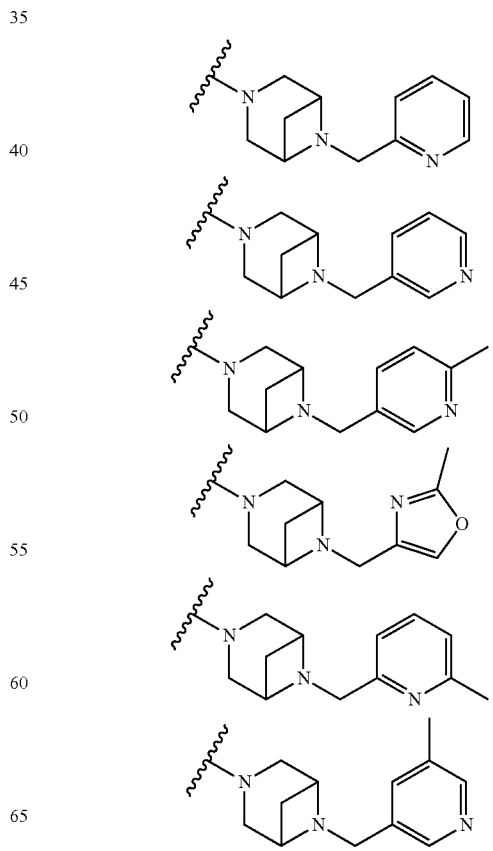

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr²C1-C6 alkyl-, wherein said alkyl portion is optionally substituted with 1-3 fluoros and hetAr² is as defined for Formula I. In one embodiment, hetAr² is a 5-6 membered heteroaryl ring having 1-3 ring heteroatoms independently selected from N, O and S, or a 9-10 membered bicyclic heteroaryl ring having 1-3 ring nitrogen atoms, wherein hetAr² is optionally substituted with one or more substituents independently selected from the group consisting of halogen, CN, C1-C6 alkyl (optionally substituted with 1-3 fluoros), C1-C6 alkoxy (optionally substituted with 1-3 fluoros), OH, C3-C6 cycloalkyl, and $R^e R^f N$— wherein $R^e$ and $R^f$ are independently H or C1-C6 alkyl. In one embodiment, Ring D is a saturated 7-8 membered bridged heterocyclic ring having two ring nitrogen atoms. In one embodiment, Ring D is represented by the structures:

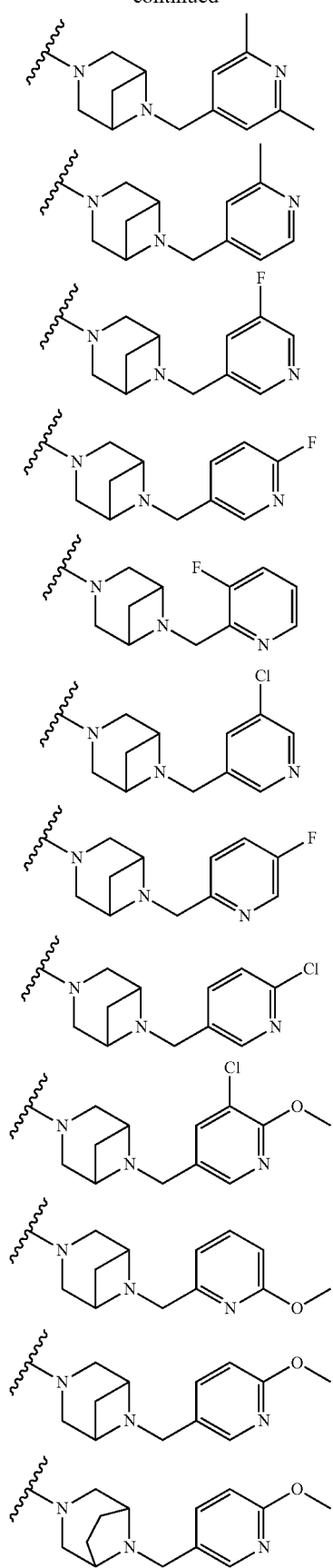
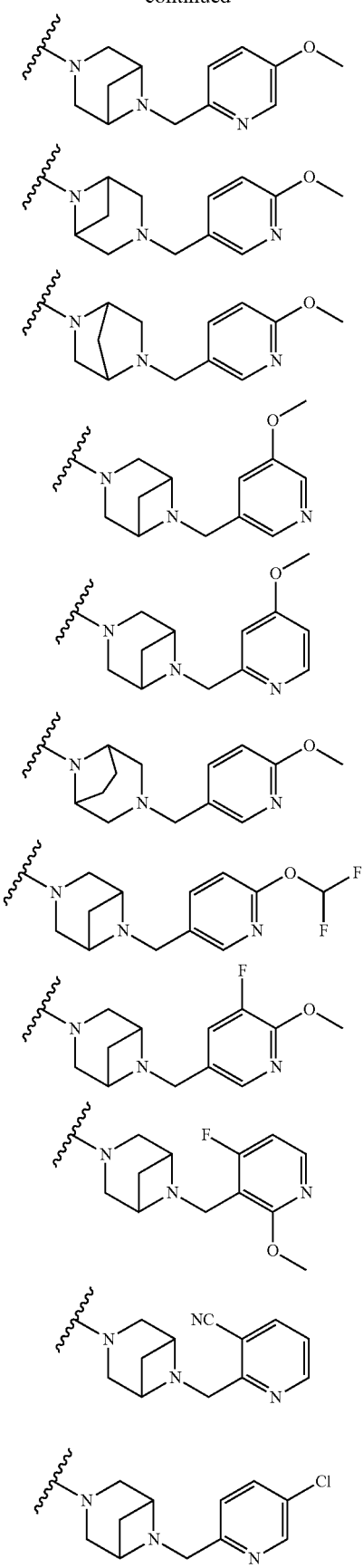

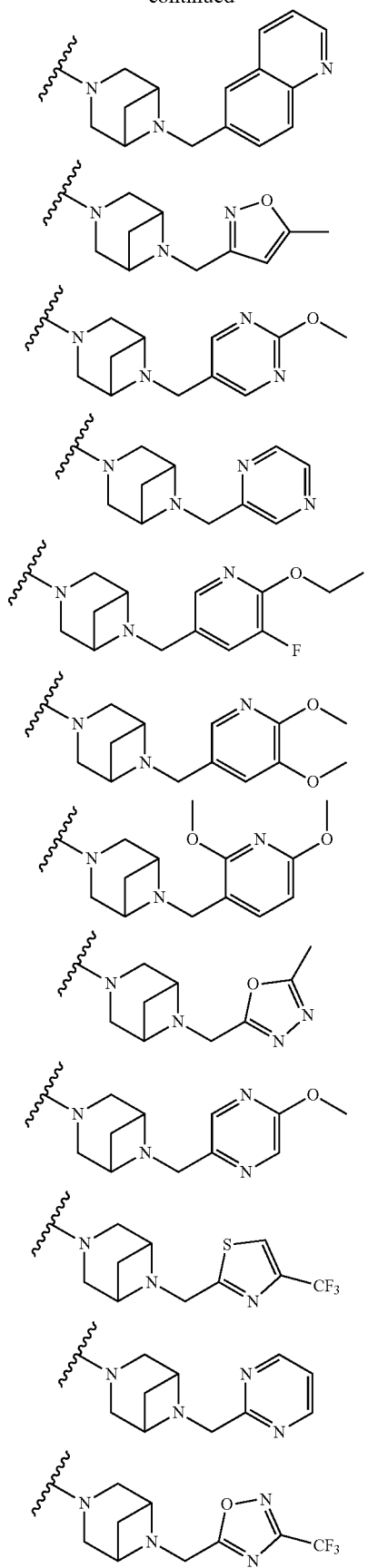
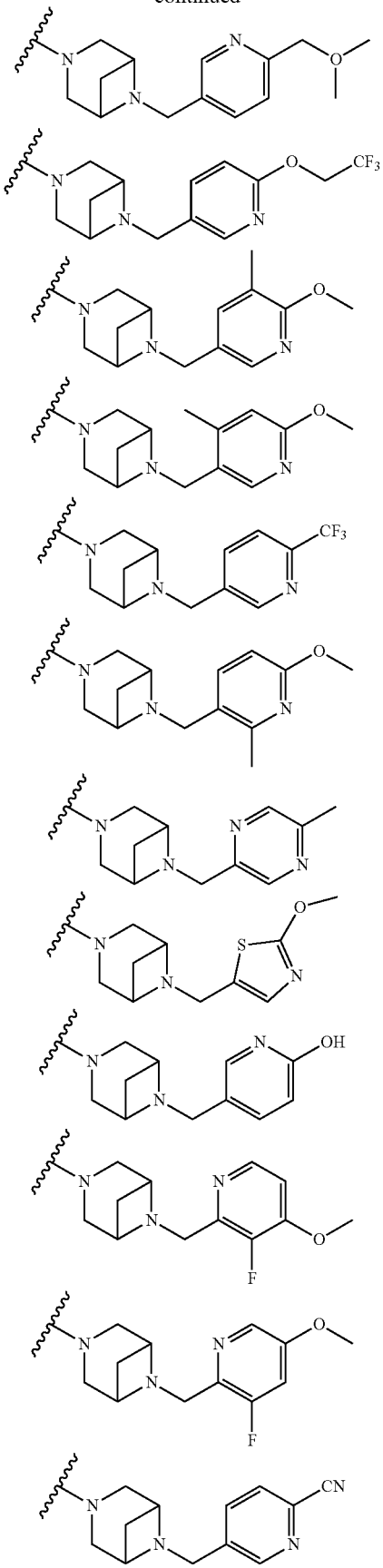

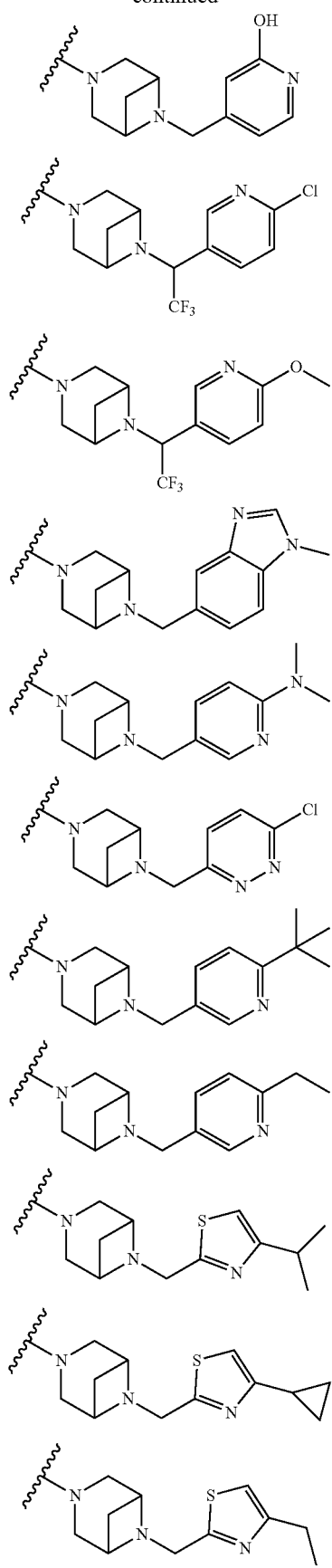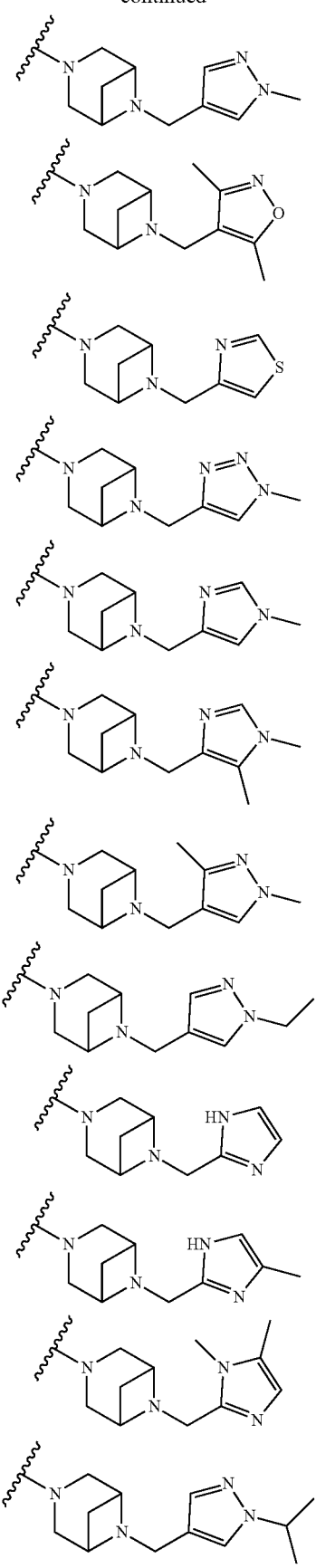

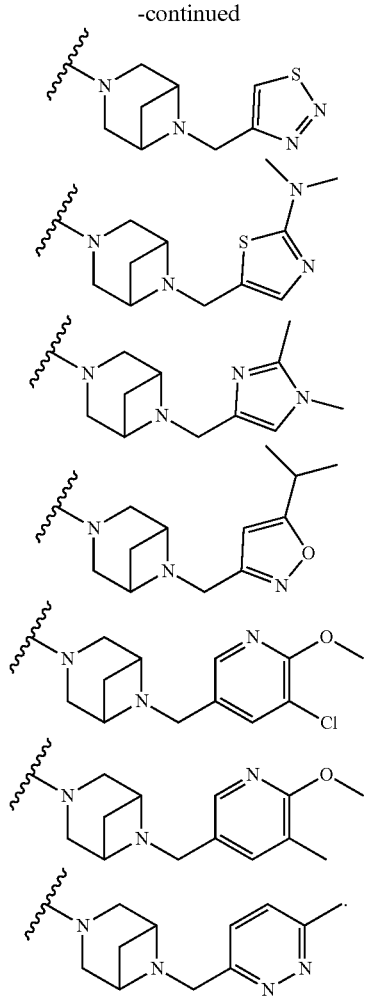

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr²(C1-C6 alkyl)C (=O)— wherein said alkyl portion is optionally substituted with OH, hydroxyC1-C6 alkyl- or C1-C6 alkoxy and hetAr² is as defined for Formula I. In one embodiment the alkyl portion is unsubstituted. In one embodiment hetAr² is a 5-6 membered heteroaryl ring having 1-2 ring nitrogen atoms and is optionally substituted with one or more halogens. In one embodiment, Ring D is unsubstituted. In one embodiment, Ring D is a saturated 7-8 membered bridged heterocyclic ring having two ring nitrogen atoms. In one embodiment, Ring D is represented by the structure:

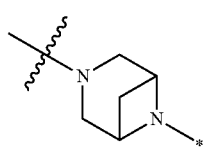

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example is the structure:

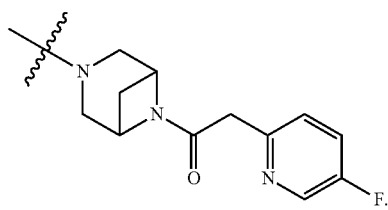 [SMILES: *N1CC2CC(C1)N2C(=O)Cc1ccc(F)cn1]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr²C(=O)— wherein hetAr² is as defined for Formula I. In one embodiment hetAr² is a 6-membered heteroaryl ring having 1-2 ring nitrogen atoms and is optionally substituted with one or more substituents independently selected from halogen, C1-C6 alkoxy (optionally substituted with 1-3 fluoros) and (C1-C6 alkoxy)C1-C6 alkoxy-. In one embodiment, Ring D is represented by the structures:

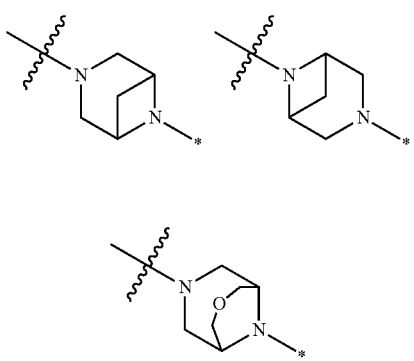

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

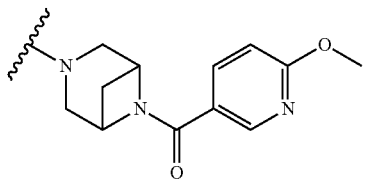

-continued
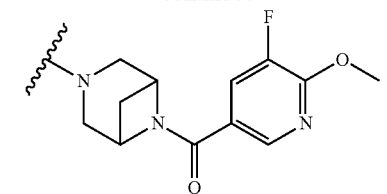
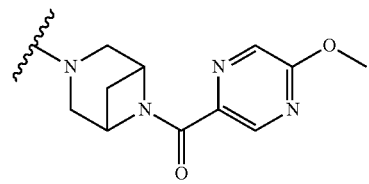
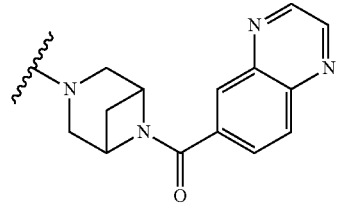
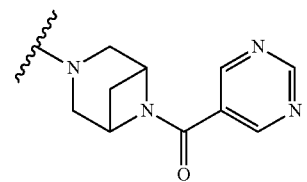
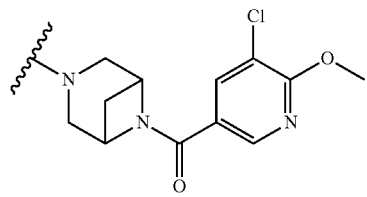
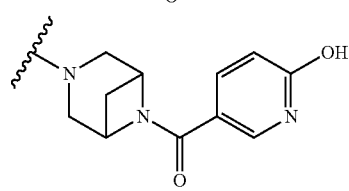
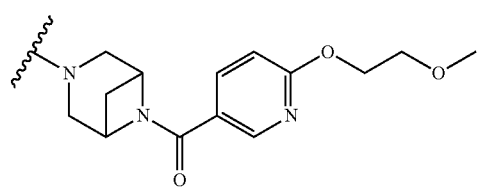
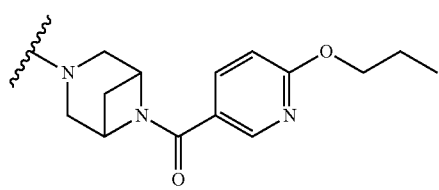
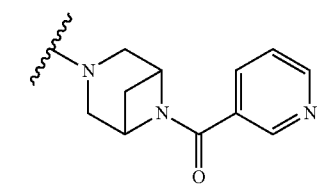
-continued
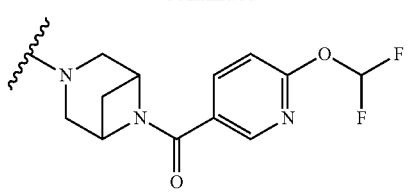
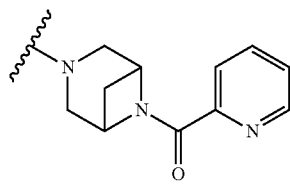
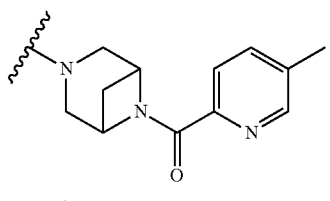
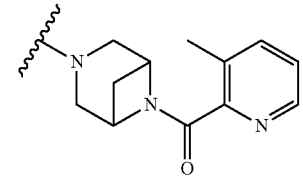
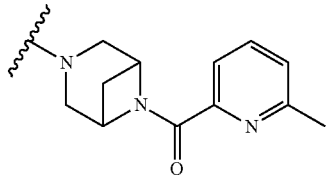
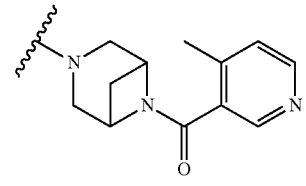
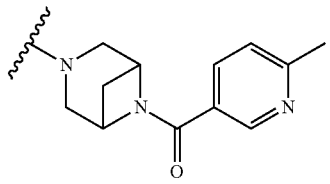
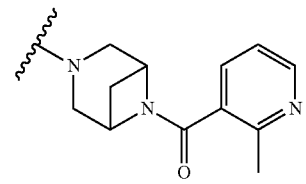
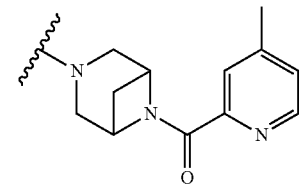

-continued

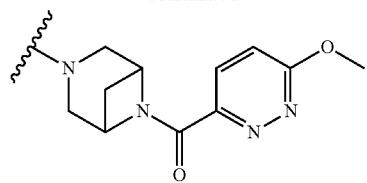
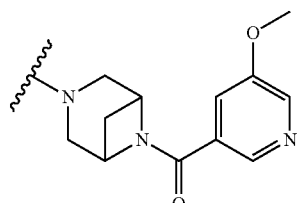
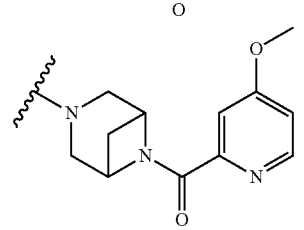
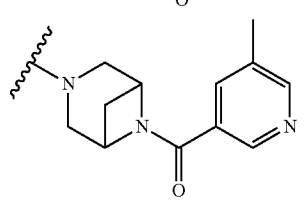
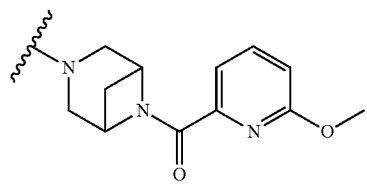
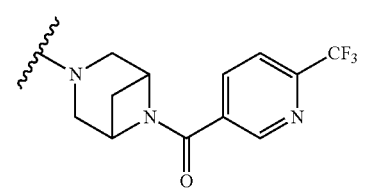
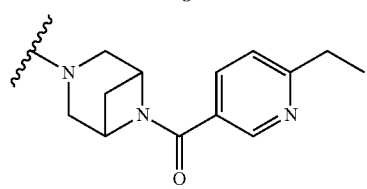
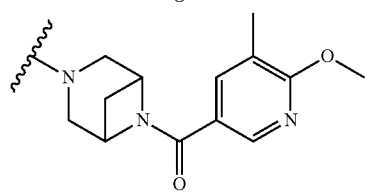
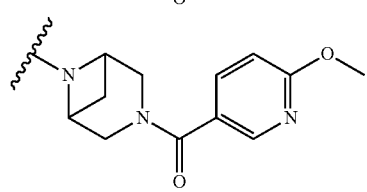

-continued

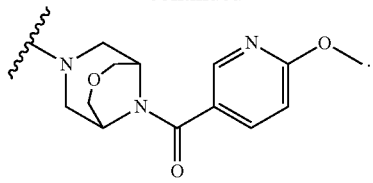

In one embodiment of Formula I, Ring D is a saturated 7-8 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetCyc$^1$C(=O)—, wherein hetCyc$^1$ is as defined for Formula I. In one embodiment, Ring D is a saturated 7-8 membered bridged heterocyclic ring having two ring nitrogen atoms. In one embodiment, Ring D is represented by the structure:

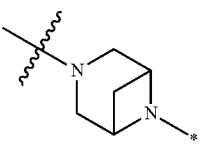 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

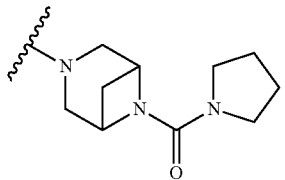
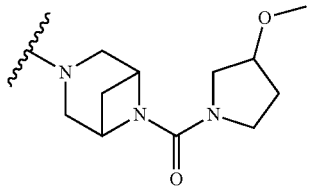
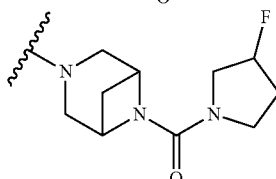
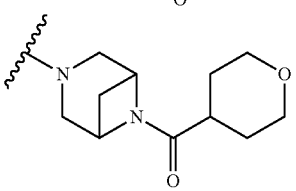

-continued

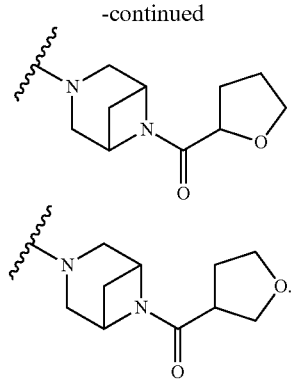

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is $R^3R^4NC(=O)—$, wherein $R^3$ is H or C1-C6 alkyl and $R^4$ is C1-C6 alkyl. In one embodiment, Ring D is a saturated 7-8 membered bridged heterocyclic ring having two ring nitrogen atoms. In one embodiment, Ring D is represented by the structure:

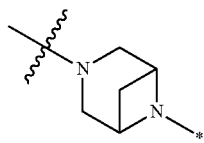

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example includes the structure:

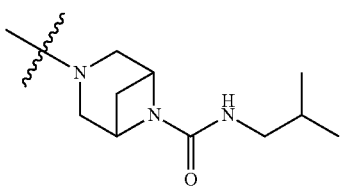

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is $Ar^1N(R^3)C(=O)—$ wherein $Ar^1$ and $R^3$ are as defined for Formula I. In one embodiment, $Ar^1$ is unsubstituted or substituted with C1-C6 alkoxy (optionally substituted with 1-3 fluoros). In one embodiment, Ring D is unsubstituted. In one embodiment, Ring D is a saturated 7-8 membered bridged heterocyclic ring having two ring nitrogen atoms. In one embodiment, Ring D is represented by the structure:

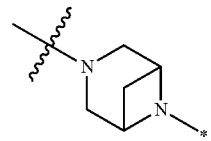

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

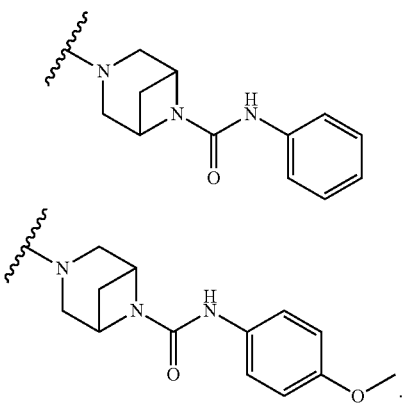

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is $hetAr^2N(R^3)C(=O)—$, wherein $hetAr^2$ and $R^3$ are as defined for Formula I. In one embodiment, $hetAr^2$ is unsubstituted or substituted with C1-C6 alkoxy (optionally substituted with 1-3 fluoros). In one embodiment, Ring D is a saturated 7-8 membered bridged heterocyclic ring having two ring nitrogen atoms. In one embodiment, Ring D is represented by the structure:

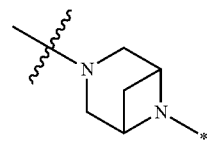 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example is the structure:

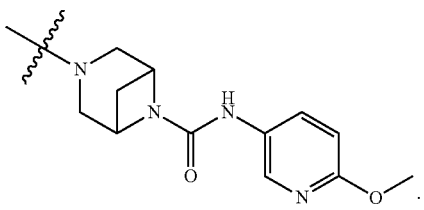 [SMILES: *N1CC2CC(C1)N2C(=O)Nc1ccc(OC)nc1]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkyl)SO$_2$— wherein the alkyl portion is optionally substituted with 1-3 fluoros. In one embodiment, Ring D is a saturated 7-8 membered bridged heterocyclic ring having two ring nitrogen atoms. In one embodiment, Ring D is unsubstituted. In one embodiment, Ring D is represented by the structure:

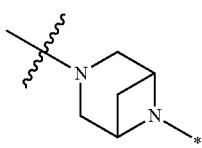 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

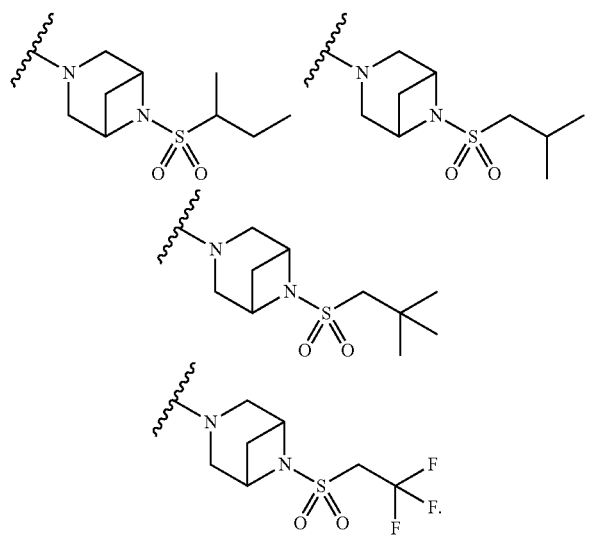

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr$^2$SO$_2$— wherein hetAr$^2$ is as defined for Formula I. In one embodiment, hetAr$^2$ is unsubstituted or substituted with C1-C6 alkoxy (optionally substituted with 1-3 fluoros). In one embodiment, Ring D is a saturated 7-8 membered bridged heterocyclic ring having two ring nitrogen atoms. In one embodiment, Ring D is represented by the structure:

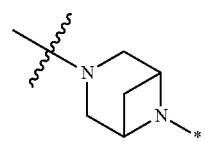 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example is the structure:

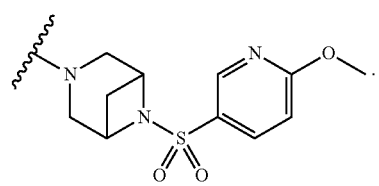 [SMILES: *N1CC2CC(C1)N2S(=O)(=O)c1ccc(OC)nc1]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is N—(C1-C6 alkyl)pyridinonyl. In one embodiment, Ring D is a saturated 7-8 membered bridged heterocyclic ring having two ring nitrogen atoms. In one embodiment, Ring D is represented by the structure:

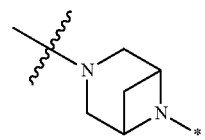

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

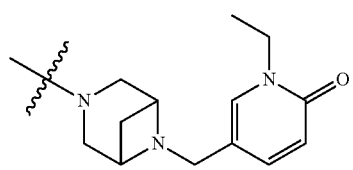

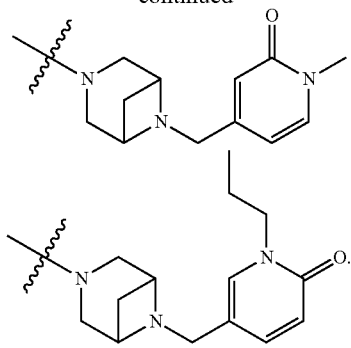

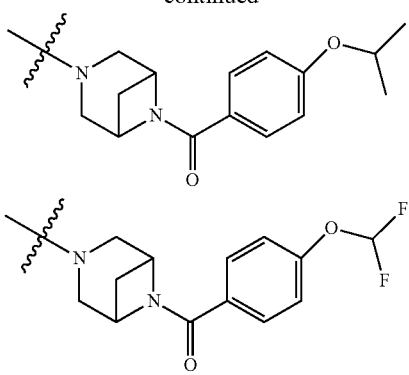

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is $Ar^1C(=O)-$ wherein $Ar^1$ is as defined for Formula I. In one embodiment, $Ar^1$ is phenyl optionally substituted with one or more substituents independently selected from the group consisting of halogen, C1-C6 alkyl (optionally substituted with 1-3 fluoros), and C1-C6 alkoxy (optionally substituted with 1-3 fluoros), or $Ar^1$ is a phenyl ring fused to a 5-6 membered heterocyclic ring having two ring oxygen atoms. In one embodiment, Ring D is a saturated 7-8 membered bridged heterocyclic ring having two ring nitrogen atoms. In one embodiment, Ring D is represented by the structure:

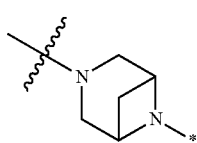 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

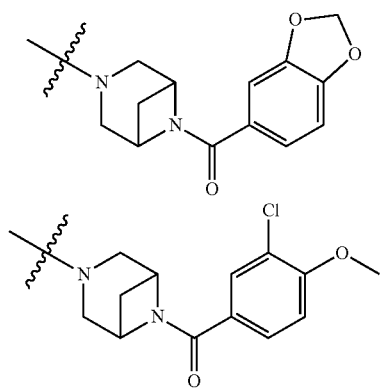

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is $Ar^1O-C(=O)-$ wherein $Ar^1$ is as defined for Formula I. In one embodiment, $Ar^1$ is unsubstituted. In one embodiment, Ring D is unsubstituted. In one embodiment, Ring D is a saturated 7-8 membered bridged heterocyclic ring having two ring nitrogen atoms. In one embodiment, Ring D is represented by the structure:

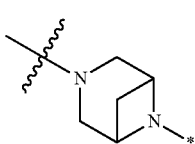 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E. A non-limiting example includes the structure:

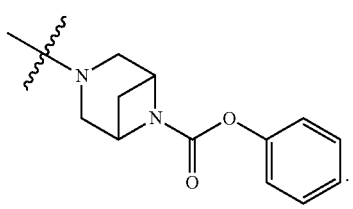 [SMILES: *N1CC2CC(C1)N2C(=O)Oc1ccccc1]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is C3-C6 cycloalkyl)CH$_2$C(=O)—, wherein the alkyl portion is optionally substituted with 1-3 fluoros. In one embodiment, Ring D is a saturated 7-8 membered bridged heterocyclic ring having two ring nitrogen atoms. In one embodiment, Ring D is represented by the structure:

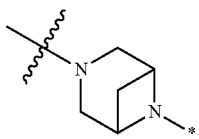 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example includes the structure:

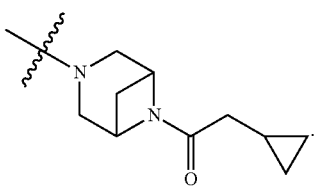 [SMILES: *N1CC2CC(C1)N2C(=O)CC1CC1]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C3-C6 cycloalkyl)(C1-C3 alkyl)SO$_2$—, wherein the alkyl portion is optionally substituted with 1-3 fluoros. In one embodiment, Ring D is a saturated 7-8 membered bridged heterocyclic ring having two ring nitrogen atoms. In one embodiment, Ring D is represented by the structure:

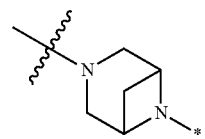 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example includes the structure:

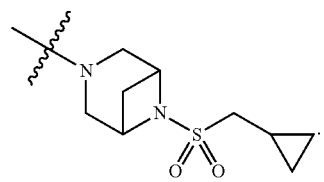 [SMILES: *N1CC2CC(C1)N2S(=O)(=O)CC1CC1]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is Ar$^1$(C1-C6 alkyl)SO$_2$— wherein Ar$^1$ is as defined for Formula I. In one embodiment, Ar$^1$ is unsubstituted. In one embodiment, Ring D is a saturated 7-8 membered bridged heterocyclic ring having two ring nitrogen atoms. In one embodiment, Ring D is represented by the structure

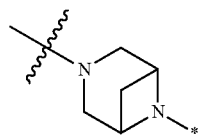 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example includes the structure:

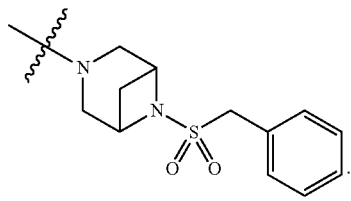 [SMILES: *N1CC2CC(C1)N2S(=O)(=O)Cc1ccccc1]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetCyc¹-O—C(=O)—, wherein hetCyc¹ is as defined for Formula I. In one embodiment, Ring D is a saturated 7-8 membered bridged heterocyclic ring having two ring nitrogen atoms. In one embodiment, Ring D is represented by the structure:

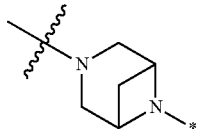

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

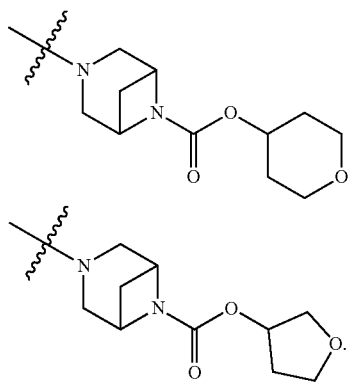

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetCyc¹-CH₂—C(=O)—, wherein hetCyc¹ is as defined for Formula I. In one embodiment, Ring D is a saturated 7-8 membered bridged heterocyclic ring having two ring nitrogen atoms. In one embodiment, Ring D is represented by the structure:

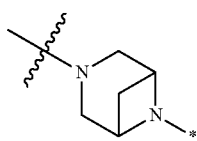 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A non-limiting example includes the structure:

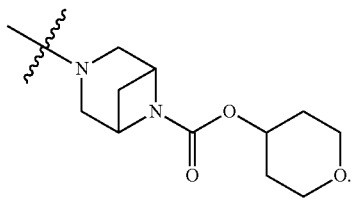 [SMILES: *N1CC2CC(C1)N2C(=O)OC1CCOCC1]

In one embodiment of Formula I, Ring D is a saturated 7-9 membered bridged heterocyclic ring having two ring nitrogen atoms and optionally having a third ring heteroatom which is oxygen, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr², wherein hetAr² is as defined for Formula I. In one embodiment, hetAr² is a 6 membered ring having 1-2 ring nitrogen atoms and is optionally substituted with C1-C6 alkoxy. In one embodiment, Ring D is a saturated 7-8 membered bridged heterocyclic ring having two ring nitrogen atoms. In one embodiment, Ring D is represented by the structures:

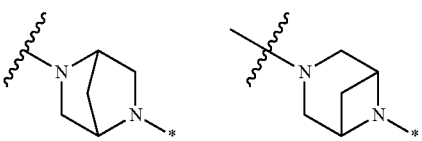 [SMILES: *N1CC2CC1CN2* ; *N1CC2CC(C1)N2*]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. Non-limiting examples include the structures:

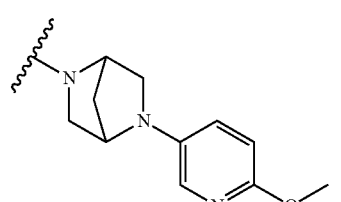

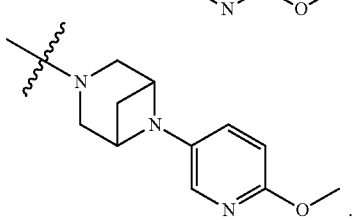

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. As used herein, the phrase "having two ring nitrogen atoms" when Ring D is a saturated 7-11 membered heterospirocyclic ring means that said ring nitrogen atoms are the two nitrogen atoms shown in Ring D of Formula I, wherein one of the ring nitrogen atoms is bonded the ring comprising $X^1$, $X^2$, $X^3$ and $X^4$, and the other ring nitrogen atom is bonded to the E group as shown in Formula I. Non-limiting examples when Ring D is a saturated 7-11 membered heterospirocyclic ring having two ring nitrogen atoms include the structures:

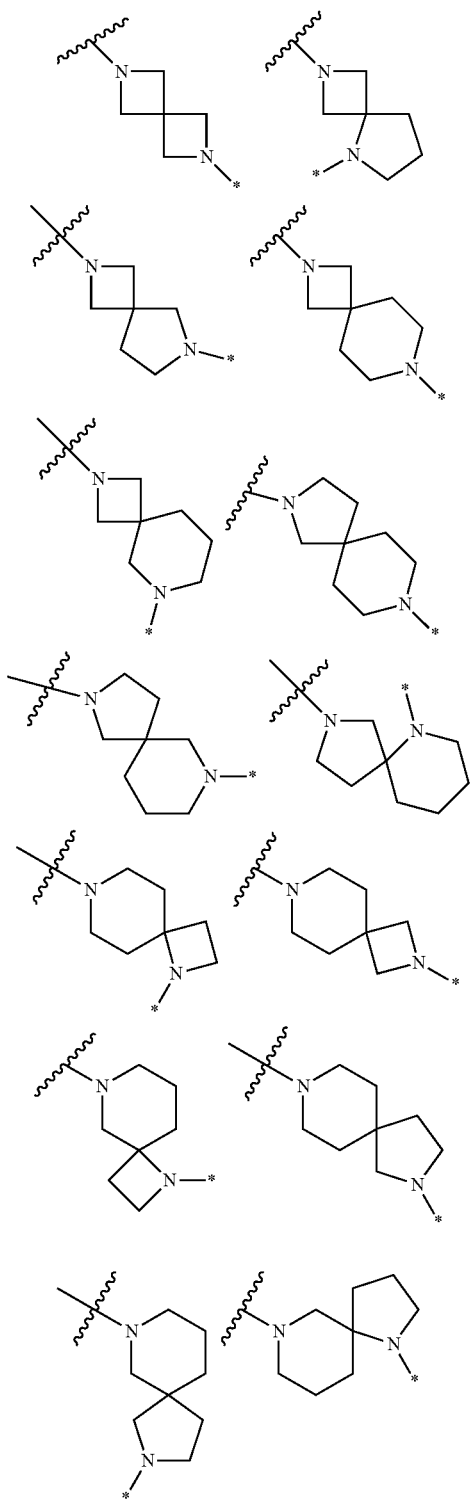

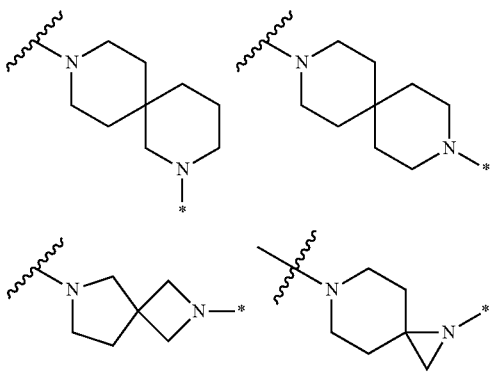

wherein the wavy line indicates the point of attachment of Ring D to the ring comprising $X^1$, $X^2$, $X^3$ and $X^4$, and the asterisk indicates the point of attachment to E, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment, Ring D is unsubstituted.

In one embodiment when Ring D is a saturated 7-11 membered heterospirocyclic ring having two ring nitrogen atoms, Ring D and E portion of Formula I, that is

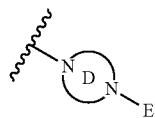

may be represented by the non-limiting structures:

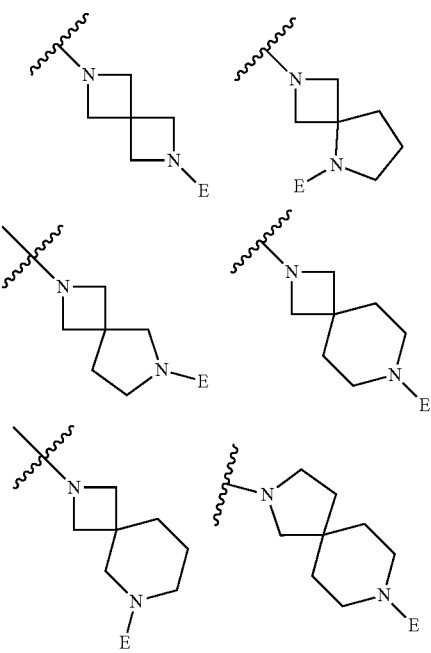

-continued

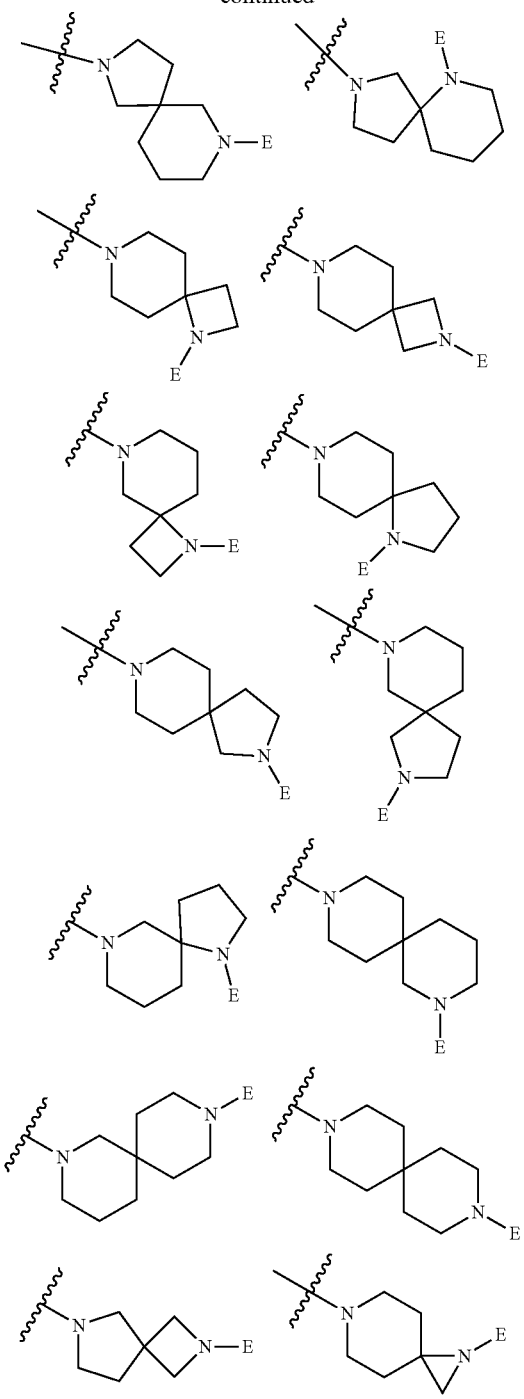

wherein the wavy line indicates the point of attachment of Ring D to the ring containing $X^1$, $X^2$, $X^3$ and $X^4$, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is as defined for Formula I. In one embodiment, Ring D is unsubstituted.

In one embodiment, Ring D is represented by the structure:

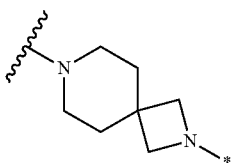 [SMILES: *N1CCC2(CC1)CN(*)C2]

wherein the wavy line indicates the point of attachment of Ring D to the ring comprising $X^1$, $X^2$, $X^3$ and $X^4$, and the asterisk indicates the point of attachment to E, wherein optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment, said Ring D is unsubstituted.

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is selected from the group consisting of (a) hydrogen, (b) C1-C6 alkyl optionally substituted with 1-3 fluoros, (d) (C1-C6 alkyl)C(=O)— wherein said alkyl portion is optionally substituted with 1-3 fluoros or with a $R^gR^hN$— substituent wherein $R^g$ and $R^h$ are independently H or C1-C6 alkyl, (f) (C1-C6 alkoxy)C(=O)—, (l) hetAr$^2$C(=O)—, (o) $R^3R^4$NC(=O)—, (s) Ar$^1$SO$_2$—, (t) hetAr$^2$SO$_2$—, (v) Ar$^1$C(=O)—, (cc) hetAr$^2$, and (dd) C3-C6 cycloalkyl, wherein hetAr$^2$, Ar$^1$, $R^3$ and $R^4$ are as defined for Formula I. In one embodiment, said Ring D is unsubstituted.

In one embodiment, Ring D is a saturated 9 membered heterospirocyclic ring having two ring nitrogen atoms represented by the structure:

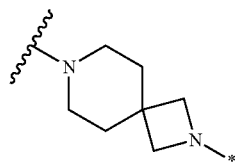 [SMILES: *N1CCC2(CC1)CN(*)C2]

wherein the wavy line indicates the point of attachment of Ring D to the ring comprising $X^1$, $X^2$, $X^3$ and $X^4$, and the asterisk indicates the point of attachment to E, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is selected from the group consisting of (a) hydrogen, (d) (C1-C6 alkoxy)C(=O)— and (o) $R^3R^4$NC(=O)—. In one embodiment, said Ring D is unsubstituted In one embodiment, In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hydrogen. In one embodiment, said Ring D is represented by the structures:

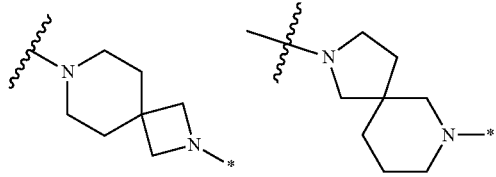 [SMILES: *N1CCC2(CC1)CN(*)C2 ; *N1CCCC2(CCN(*)C2)C1]

wherein the wavy line indicates the point of attachment of Ring D to the ring comprising $X^1$, $X^2$, $X^3$ and $X^4$, and the asterisk indicates the point of attachment to E. In one embodiment, said Ring D is unsubstituted. Non-limiting examples includes the structures:

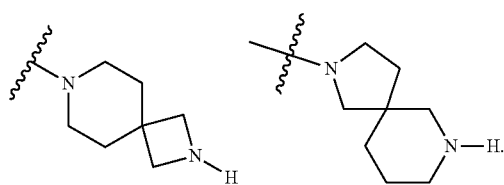

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (b) C1-C6 alkyl optionally substituted with 1-3 fluoros. In one embodiment, said Ring D is represented by the structure:

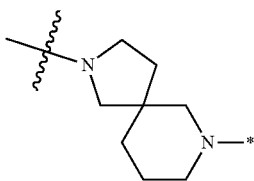 [SMILES: *N1CCCC2(CCN(*)C2)C1]

wherein the wavy line indicates the point of attachment of Ring D to the ring comprising $X^1$, $X^2$, $X^3$ and $X^4$, and the asterisk indicates the point of attachment to E. In one embodiment, said Ring D is unsubstituted. Non-limiting examples includes the structures:

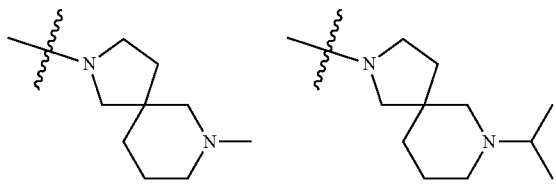

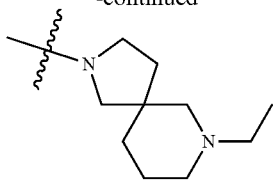

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkyl)C(=O)—, wherein said alkyl portion is optionally substituted with 1-3 fluoros or with a $R^gR^hN$— substituent wherein $R^g$ and $R^h$ are independently H or C1-C6 alkyl. In one embodiment, said Ring D is represented by the structures:

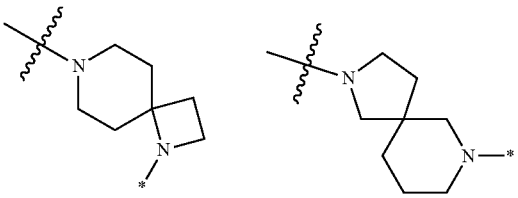 [SMILES: *N1CCC2(CC1)CCN2* ; *N1CCCC2(CCN(*)C2)C1]

wherein the wavy line indicates the point of attachment of Ring D to the ring comprising $X^1$, $X^2$, $X^3$ and $X^4$, and the asterisk indicates the point of attachment to E. In one embodiment, said Ring D is unsubstituted. Non-limiting examples includes the structures:

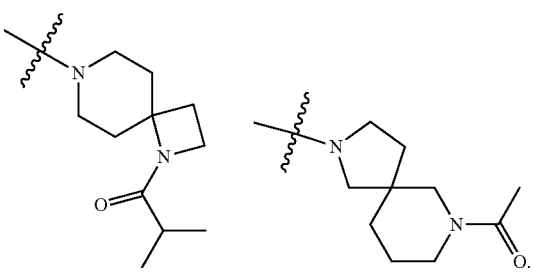 [SMILES: *N1CCC2(CC1)CCN2C(=O)C(C)C ; *N1CCC2(CCCN(C(C)=O)C2)C1]

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkoxy)C(=O)—. In one embodiment, said Ring D is represented by the structures:

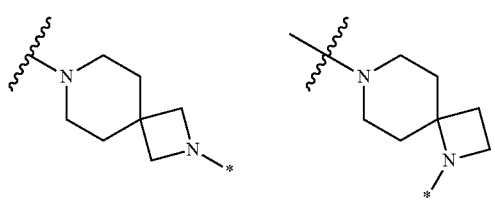

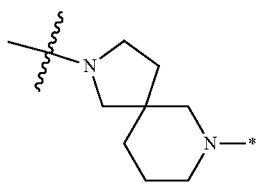

wherein the wavy line indicates the point of attachment of Ring D to the ring comprising $X^1$, $X^2$, $X^3$ and $X^4$, and the asterisk indicates the point of attachment to E. In one embodiment, said Ring D is unsubstituted. Non-limiting examples include the structures:

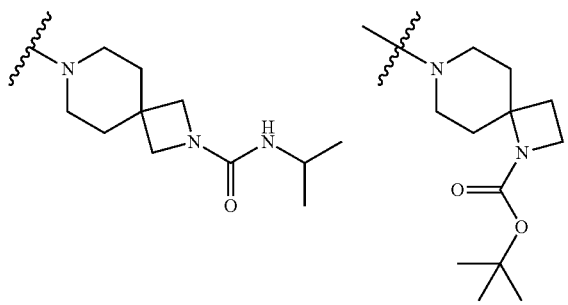

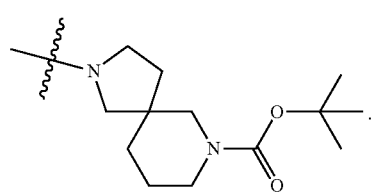

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr²C(=O)—, wherein hetAr² is as defined for Formula I. In one embodiment, hetAr² is a 5-6 membered heterocyclic ring having 1-2 ring nitrogen atoms. In one embodiment, hetAr² is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, hetAr² is a 6 membered ring having 1-2 ring nitrogen atoms and is optionally substituted with C1-C6 alkoxy. In one embodiment, Ring D is unsubstituted. In one embodiment, Ring D is represented by the structure:

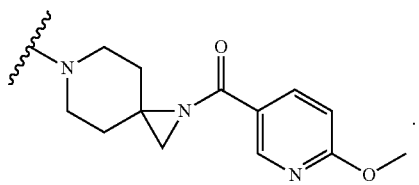 [SMILES: *N1CCC2(CC1)CN2C(=O)c1ccc(OC)nc1]

wherein the wavy line indicates the point of attachment of Ring D to the ring comprising $X^1$, $X^2$, $X^3$ and $X^4$, and the asterisk indicates the point of attachment to E. A non-limiting example includes the structure:

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is $R^3R^4NC(=O)$— wherein $R^3$ and $R^4$ are as defined for Formula I. In one embodiment, $R^3$ is H and $R^4$ is C1-C6 alkyl. In one embodiment, said Ring D is represented by the structure:

wherein the wavy line indicates the point of attachment of Ring D to the ring comprising $X^1$, $X^2$, $X^3$ and $X^4$, and the asterisk indicates the point of attachment to E. In one embodiment, said Ring D is unsubstituted. A non-limiting example includes the structure:

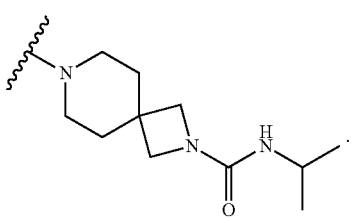 [SMILES: *N1CCC2(CC1)CN(C(=O)NC(C)C)C2]

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is $Ar^1SO_2$—, wherein $Ar^1$ is as defined for Formula I. In one embodiment, Ar¹ is phenyl optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, said Ring D is unsubstituted. In one embodiment, said Ring D is represented by the structure

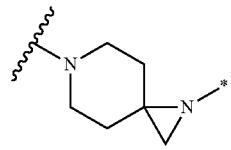 [SMILES: *N1CCC2(CC1)CN2*]

wherein the wavy line indicates the point of attachment of Ring D to the ring comprising X¹, X², X³ and X⁴, and the asterisk indicates the point of attachment to E. Non-limiting examples include the structures:

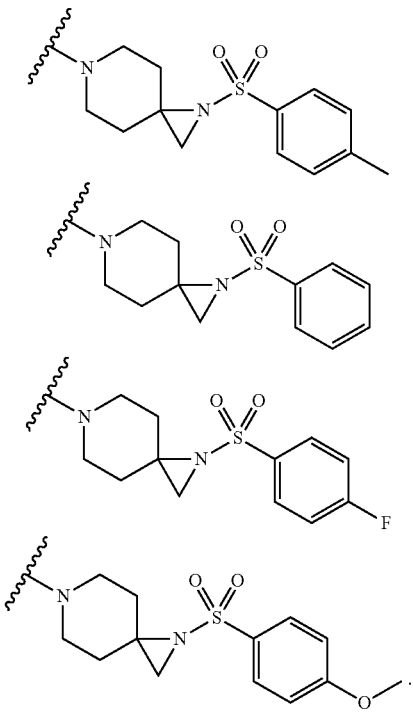

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr²SO₂—, wherein hetAr² is as defined for Formula I. In one embodiment, hetAr² is a 5-6 membered heterocyclic ring having 1-2 ring nitrogen atoms. In one embodiment, hetAr² is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, hetAr² is a 6 membered ring having 1-2 ring nitrogen atoms and is optionally substituted with C1-C6 alkoxy. In one embodiment, said Ring D is unsubstituted. In one embodiment, said Ring D is represented by the structure:

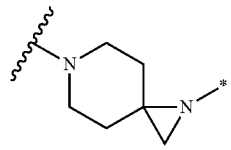

wherein the wavy line indicates the point of attachment of Ring D to the ring comprising X¹, X², X³ and X⁴, and the asterisk indicates the point of attachment to E. A non-limiting example includes the structure:

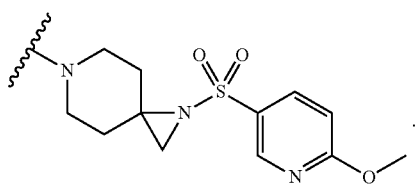 [SMILES: *N1CCC2(CC1)CN2S(=O)(=O)c1ccc(OC)nc1]

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is Ar¹C(═O)—, wherein Ar¹ is as defined for Formula I. In one embodiment, Ar¹ is phenyl optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, said Ring D is unsubstituted. In one embodiment, said Ring D is represented by the structure:

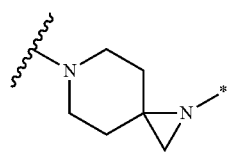 [SMILES: *N1CCC2(CC1)CN2*]

wherein the wavy line indicates the point of attachment of Ring D to the ring comprising X¹, X², X³ and X⁴, and the asterisk indicates the point of attachment to E. Non-limiting examples include the structures:

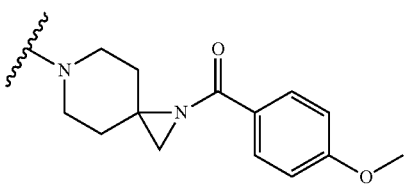

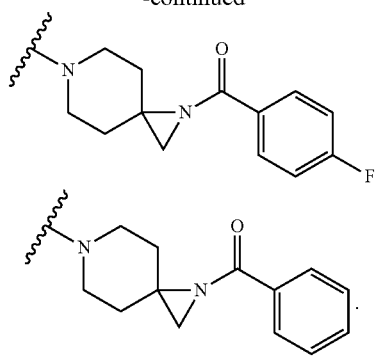

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hetAr$^2$, wherein hetAr$^2$ is as defined for Formula I. In one embodiment, hetAr$^2$ is a 5-6 membered heterocyclic ring having 1-2 ring nitrogen atoms. In one embodiment, hetAr$^2$ is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, hetAr$^2$ is a 6 membered ring having 1-2 ring nitrogen atoms and is optionally substituted with C1-C6 alkoxy. In one embodiment, said Ring D is unsubstituted. In one embodiment, said Ring D is represented by the structure:

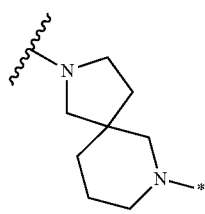 [SMILES: *N1CCCC2(CCN(*)C2)C1]

wherein the wavy line indicates the point of attachment of Ring D to the ring comprising X$^1$, X$^2$, X$^3$ and X$^4$, and the asterisk indicates the point of attachment to E. A non-limiting example includes the structure:

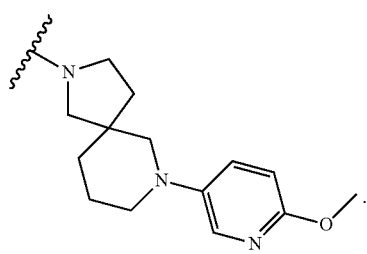 [SMILES: *N1CCC2(CCCN(c3ccc(OC)nc3)C2)C1]

In one embodiment, Ring D is a saturated 7-11 membered heterospirocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is C3-C6 cycloalkyl. In one embodiment, said Ring D is unsubstituted. In one embodiment, said Ring D is represented by the structure:

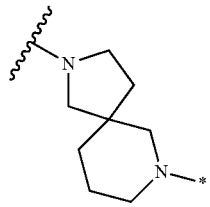 [SMILES: *N1CCCC2(CCN(*)C2)C1]

wherein the wavy line indicates the point of attachment of Ring D to the ring comprising X$^1$, X$^2$, X$^3$ and X$^4$, and the asterisk indicates the point of attachment to E. A non-limiting example includes the structure:

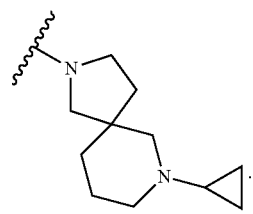 [SMILES: *N1CCC2(CCCN(C3CC3)C2)C1]

In one embodiment, Ring D is a saturated 9-10 membered bicyclic fused heterocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. As used herein, the phrase "having two ring nitrogen atoms" when Ring D is a saturated 9-10 membered bicyclic fused heterocyclic ring means that said ring nitrogen atoms are the two nitrogen atoms shown in Ring D of Formula I, wherein one of the ring nitrogen atoms is bonded the ring comprising X$^1$, X$^2$, X$^3$ and X$^4$, and the other ring nitrogen atom is bonded to the E group as shown in Formula I. Fused ring include 5,5, 5,6, 6,5 and 6,6 fused ring systems. In one embodiment, said Ring D is represented by the structure:

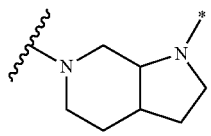 [SMILES: *N1CCC2CCN(*)C2C1]

wherein the wavy line indicates the point of attachment of Ring D to the ring comprising X$^1$, X$^2$, X$^3$ and X$^4$, and the asterisk indicates the point of attachment to E, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment, said Ring D is unsubstituted.

In one embodiment, Ring D is a saturated 9-10 membered bicyclic fused heterocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is as defined for Formula I.

In one embodiment, Ring D is a saturated 9-10 membered bicyclic fused heterocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hydrogen or (C1-C6 alkoxy)C(=O)—. In one embodiment, Ring D is represented by the structure:

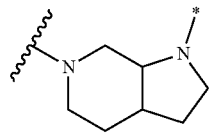 [SMILES: *N1CCC2CCN(*)C2C1]

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted.

In one embodiment, Ring D is a saturated 9-10 membered bicyclic fused heterocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is hydrogen. In one embodiment, Ring D is represented by the structure:

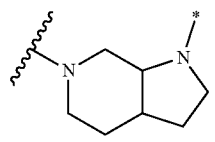

wherein the wavy line indicates the point of attachment of Ring D to the ring comprising $X^1$, $X^2$, $X^3$ and $X^4$, and the asterisk indicates the point of attachment to E. In one embodiment, Ring D is unsubstituted. A nonlimiting example is the structure:

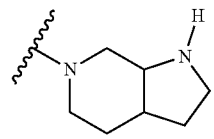 [SMILES: *N1CCC2CCN(*)C2C1]

In one embodiment, Ring D is a saturated 9-10 membered bicyclic fused heterocyclic ring having two ring nitrogen atoms, wherein said ring is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group, and E is (C1-C6 alkoxy)C(=O)—. In one embodiment, Ring D is represented by the structure:

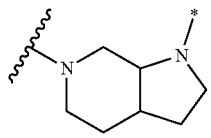

wherein the wavy line indicates the point of attachment of Ring D to the ring comprising $X^1$, $X^2$, $X^3$ and $X^4$, and the asterisk indicates the point of attachment to E. In one embodiment, said Ring D is unsubstituted. A nonlimiting example is the structure:

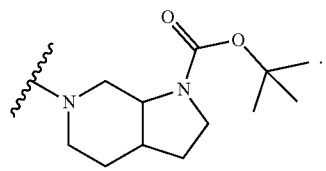 [SMILES: *N1CCC2CCN(C(=O)OC(C)(C)C)C2C1]

In one embodiment, Formula I includes compounds of Formula I-A, wherein:

$X^1$, $X^2$, $X^3$ and $X^4$ are independently CH, CF or N, wherein zero, one or two of $X^1$, $X^2$, $X^3$ and $X^4$ is N;

A is H, CN, Cl, $CH_3$—, $CH_3CH_2$—, cyclopropyl, —$CH_2CN$ or —CH(CN)$CH_3$;

B is
(a) hydrogen,
(b) C1-C6 alkyl optionally substituted with 1-3 fluoros,
(c) hydroxyC2-C6 alkyl-, wherein the alkyl portion is optionally substituted with 1-3 fluoros or a C3-C6 cycloalkylidene ring,
(d) dihydroxyC3-C6 alkyl-, wherein the alkyl portion is optionally substituted with a C3-C6 cycloalkylidene ring,
(e) (C1-C6 alkoxy)C1-C6 alkyl- optionally substituted with 1-3 fluoros,
(f) ($R^1R^2N$)C1-C6 alkyl- wherein said alkyl portion is optionally substituted with OH and wherein $R^1$ and $R^2$ are independently H or C1-C6 alkyl (optionally substituted with 1-3 fluoros);
(g) hetAr$^1$C1-C3 alkyl-, wherein hetAr$^1$ is a 5-6 membered heteroaryl ring having 1-3 ring heteroatoms independently selected from N, O and S and is optionally substituted with one or more independently selected C1-C6 alkyl substituents;
(h) (C3-C6 cycloalkyl)C1-C3 alkyl-, wherein said cycloalkyl is optionally substituted with OH,
(i) (hetCyc$^a$)C1-C3 alkyl-,
(j) hetCyc$^a$-,
(k) C3-C6 cycloalkyl-, wherein said cycloalkyl is optionally substituted with OH,
(l) (C1-C4 alkyl)C(=O)O—C1-C6 alkyl-, wherein each of the C1-C4 alkyl and C1-C6 alkyl portions is optionally and independently substituted with 1-3 fluoros, or
(m) ($R^1R^2N$)C(=O)C1-C6 alkyl-, wherein $R^1$ and $R^2$ are independently H or C1-C6 alkyl (optionally substituted with 1-3 fluoros);

hetCyc$^a$- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-C6 alkoxy)C1-C6 alkyl-, and fluoro, or wherein hetCyc$^a$ is substituted with oxo;

Ring D is

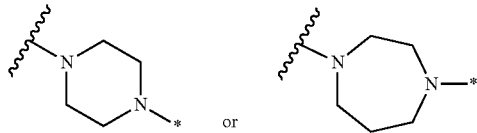 [SMILES: *N1CCN(*)CC1 ; *N1CCCN(*)CC1]

or wherein the wavy line indicates the point of attachment to the ring comprising $X^1$, $X^2$, $X^3$ and $X^4$, and the asterisk indicates the point of attachment to the E group, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;

E is
(a) hydrogen,
(c) (C1-C6 alkoxy)C1-C6 alkyl- optionally substituted with 1-3 fluoros,
(d) (C1-C6 alkyl)C(=O)— wherein said alkyl portion is optionally substituted with 1-3 fluoros or with a $R^g R^h N$— substituent wherein $R^g$ and $R^h$ are independently H or C1-C6 alkyl,
(e) (hydroxy C2-C6 alkyl)C(=O)— optionally substituted with 1-3 fluoros,
(f) (C1-C6 alkoxy)C(=O)—,
(g) (C3-C6 cycloalkyl)C(=O)— wherein said cycloalkyl is optionally substituted with one or more substituents independently selected from C1-C6 alkyl, C1-C6 alkoxy, OH, and (C1-C6 alkoxy)C1-C6 alkyl-, or said cycloalkyl is substituted with a 5-6 membered heteroaryl ring having 1-3 ring heteroatoms independently selected from N and O,
(h) Ar$^1$C1-C6 alkyl-,
(i) Ar$^1$(C1-C6 alkyl)C(=O)— wherein said alkyl portion is optionally substituted with OH, hydroxyC1-C6 alkyl-, C1-C6 alkoxy, $R'''R''N$— or $R'''R''N$—CH$_2$—, wherein each $R'''$ and $R''$ is independently H or C1-C6 alkyl,
(j) hetAr$^2$C1-C6 alkyl- wherein said alkyl portion is optionally substituted with 1-3 fluoros,
(k) hetAr$^2$(C1-C6 alkyl)C(=O)— wherein said alkyl portion is optionally substituted with OH, hydroxyC1-C6 alkyl or C1-C6 alkoxy,
(l) hetAr$^2$C(=O)—,
(m) hetCyc$^1$C(=O)—,
(n) hetCyc$^1$C1-C6 alkyl-,
(o) $R^3R^4$NC(=O)—, or
(cc) hetAr$^2$;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), $R^e R^f N$— wherein $R^e$ and $R^f$ are independently H or C1-C6 alkyl, ($R^p R^q N$)C1-C6 alkoxy- wherein $R^p$ and $R^q$ are independently H or C1-C6 alkyl, and (hetAr$^a$)C1-C6 alkyl- wherein hetAr$^a$ is a 5-6 membered heteroaryl ring having 1-2 ring nitrogen atoms, or Ar$^1$ is a phenyl ring fused to a 5-6 membered heterocyclic ring having 1-2 ring heteroatoms independently selected from N and 0;

hetAr$^2$ is a 5-6 membered heteroaryl ring having 1-3 ring heteroatoms independently selected from N, O and S or a 9-10 membered bicyclic heteroaryl ring having 1-3 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), $R^e R^f N$— wherein $R^e$ and $R^f$ are independently H or C1-C6 alkyl, OH, (C1-C6 alkoxy)C1-C6 alkoxy- and C3-C6 cycloalkyl;

hetCyc$^1$ is a 4-6 membered saturated heterocyclic ring having 1-2 ring heteroatoms independently selected from N, O and S wherein said heterocyclic ring is optionally substituted with one or more substituents independently selected from C1-C6 alkoxy and halogen; and R$^4$ is C1-C6 alkyl.

In one embodiment of Formula I-A, Ring D is unsubstituted.

In one embodiment of Formula I-A, $X^1$ is N; $X^2$, $X^3$ and $X^4$ are CH.

In one embodiment of Formula I-A, A is CN.

In one embodiment of Formula I-A, Ring D is unsubstituted; $X^1$ is N; $X^2$, $X^3$ and $X^4$ are CH; and A is CN.

In one embodiment of Formula I-A, B is C1-C6 alkyl optionally substituted with 1-3 fluoros.

In one embodiment of Formula I-A, B is (C1-C6 alkoxy) C1-C6 alkyl- optionally substituted with 1-3 fluoros, or hydroxyC2-C6 alkyl- wherein the alkyl portion is optionally substituted with a C3-C6 cycloalkylidene ring.

In one embodiment of Formula I-A, B is (C1-C6 alkoxy) C1-C6 alkyl- optionally substituted with 1-3 fluoros. In one embodiment of Formula I-A, B is (C1-C6 alkoxy)C2-C6 alkyl-optionally substituted with 1-3 fluoros.

In one embodiment of Formula I-A, B is hydroxyC2-C6 alkyl- wherein the alkyl portion is optionally substituted with a C3-C6 cycloalkylidene ring. In one embodiment, the alkyl portion is unsubstituted.

In one embodiment of Formula I-A, Ring D is unsubstituted; $X^1$ is N; $X^2$, $X^3$ and $X^4$ are CH; A is CN; and B is (C1-C6 alkoxy)C1-C6 alkyl- optionally substituted with 1-3 fluoros, or hydroxyC2-C6 alkyl- wherein the alkyl portion is optionally substituted with a C3-C6 cycloalkylidene ring.

In one embodiment of Formula I-A, Ring D is unsubstituted; $X^1$ is N; $X^2$, $X^3$ and $X^4$ are CH; A is CN; and B is (C1-C6 alkoxy)C1-C6 alkyl- optionally substituted with 1-3 fluoros. In one embodiment, B is (C1-C6 alkoxy)C2-C6 alkyl- optionally substituted with 1-3 fluoros.

In one embodiment of Formula I-A, Ring D is unsubstituted; $X^1$ is N; $X^2$, $X^3$ and $X^4$ are CH; A is CN; and B is hydroxyC2-C6 alkyl- wherein the alkyl portion is optionally substituted with a C3-C6 cycloalkylidene ring. In one embodiment, the alkyl portion of the B group is unsubstituted.

In one embodiment of Formula I-A, E is Ar$^1$C1-C6 alkyl-, hetAr$^2$C1-C6 alkyl- wherein the alkyl portion is optionally substituted with 1-3 fluoros, or Ar$^1$(C1-C6 alkyl)C(=O)—, wherein Ar$^1$ and hetAr$^2$ are as defined for Formula I-A.

In one embodiment of Formula I-A, E is Ar$^1$C1-C6 alkyl-, hetAr$^2$C1-C6 alkyl- wherein the alkyl portion is optionally substituted with 1-3 fluoros, or Ar$^1$(C1-C6 alkyl)C(=O)—, wherein Ar$^1$ is an unsubstituted phenyl and hetAr$^2$ is a 5-6 membered heterocyclic ring having 1-2 ring nitrogen atoms and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment of Formula I-A, hetAr$^2$ is a 6 membered heterocyclic ring having 1-2 ring nitrogen atoms and is optionally substituted with one or more substituents independently selected from the group consisting of halogen, C1-C6 alkyl (optionally substituted with 1-3 fluoros), and C1-C6 alkoxy (optionally substituted with 1-3 fluoros).

In one embodiment of Formula I-A, Ring D is unsubstituted; $X^1$ is N; $X^2$, $X^3$ and $X^4$ are CH; A is CN; B is (C1-C6 alkoxy)C1-C6 alkyl- optionally substituted with 1-3 fluoros or hydroxyC2-C6 alkyl- wherein the alkyl portion is optionally substituted with a C3-C6 cycloalkylidene ring; and E is $Ar^1$C1-C6 alkyl-, $hetAr^2$C1-C6 alkyl- wherein the alkyl portion is optionally substituted with 1-3 fluoros, or $Ar^1$(C1-C6 alkyl)C(=O)—, wherein $Ar^1$ and $hetAr^2$ are as defined for Formula I-A.

In one embodiment of Formula I-A, Ring D is unsubstituted; $X^1$ is N; $X^2$, $X^3$ and $X^4$ are CH; A is CN; B is (C1-C6 alkoxy)C1-C6 alkyl- optionally substituted with 1-3 fluoros; and E is $Ar^1$C1-C6 alkyl-, $hetAr^2$C1-C6 alkyl- wherein the alkyl portion is optionally substituted with 1-3 fluoros, or $Ar^1$(C1-C6 alkyl)C(=O)—, wherein $Ar^1$ and $hetAr^2$ are as defined for Formula I-A.

In one embodiment of Formula I-A, Ring D is unsubstituted; $X^1$ is N; $X^2$, $X^3$ and $X^4$ are CH; A is CN; B is (C1-C6 alkoxy)C1-C6 alkyl- optionally substituted with 1-3 fluoros; and E is $Ar^1$C1-C6 alkyl- wherein $Ar^1$ is as defined for Formula I-A.

In one embodiment of Formula I-A, Ring D is unsubstituted; $X^1$ is N; $X^2$, $X^3$ and $X^4$ are CH; A is CN; B is (C1-C6 alkoxy)C1-C6 alkyl- optionally substituted with 1-3 fluoros; and E is $hetAr^2$C1-C6 alkyl-, wherein the alkyl portion is optionally substituted with 1-3 fluoros and $hetAr^2$ is as defined for Formula I-A.

In one embodiment of Formula I-A, Ring D is unsubstituted; $X^1$ is N; $X^2$, $X^3$ and $X^4$ are CH; A is CN; B is (C1-C6 alkoxy)C1-C6 alkyl- optionally substituted with 1-3 fluoros; or E is $Ar^1$(C1-C6 alkyl)C(=O)— wherein said alkyl portion is optionally substituted with OH, hydroxyC1-C6 alkyl- or C1-C6 alkoxy and $Ar^1$ is as defined for Formula I-A.

In one embodiment of Formula I-A, Ring D is unsubstituted; $X^1$ is N; $X^2$, $X^3$ and $X^4$ are CH; A is CN; B is hydroxyC2-C6 alkyl- wherein the alkyl portion is optionally substituted with a C3-C6 cycloalkylidene ring; and E is $Ar^1$C1-C6 alkyl-, $hetAr^2$C1-C6 alkyl- wherein the alkyl portion is optionally substituted with 1-3 fluoros, or $Ar^1$(C1-C6 alkyl)C(=O)—, wherein $Ar^1$ and $hetAr^2$ are as defined for Formula I-A. In one embodiment, the alkyl portion of the B group is unsubstituted.

In one embodiment of Formula I-A, Ring D is unsubstituted; $X^1$ is N; $X^2$, $X^3$ and $X^4$ are CH; A is CN; B is hydroxyC2-C6 alkyl- wherein the alkyl portion is optionally substituted with a C3-C6 cycloalkylidene ring; and E is $Ar^1$C1-C6 alkyl- wherein $Ar^1$ is as defined for Formula I-A. In one embodiment, the alkyl portion of the B group is unsubstituted.

In one embodiment of Formula I-A, Ring D is unsubstituted; $X^1$ is N; $X^2$, $X^3$ and $X^4$ are CH; A is CN; B is hydroxyC2-C6 alkyl- wherein the alkyl portion is optionally substituted with a C3-C6 cycloalkylidene ring; and E is $hetAr^2$C1-C6 alkyl-, wherein the alkyl portion is optionally substituted with 1-3 fluoros and $hetAr^2$ is as defined for Formula I-A. In one embodiment, the alkyl portion of the B group is unsubstituted.

In one embodiment of Formula I-A, Ring D is unsubstituted; $X^1$ is N; $X^2$, $X^3$ and $X^4$ are CH; A is CN; B is hydroxyC2-C6 alkyl- wherein the alkyl portion is optionally substituted with a C3-C6 cycloalkylidene ring; and E is $Ar^1$(C1-C6 alkyl)C(=O)— wherein said alkyl portion is optionally substituted with OH, hydroxyC1-C6 alkyl- or C1-C6 alkoxy and $Ar^1$ is as defined for Formula I-A. In one embodiment, $Ar^1$ is an unsubstituted phenyl. In one embodiment, B is hydroxyC2-C6 alkyl- wherein the alkyl portion is unsubstituted.

In one embodiment of Formula I-A, Ring D is unsubstituted; $X^2$ is N; $X^1$, $X^3$ and $X^4$ are CH; A is CN; B is C1-C6 alkyl optionally substituted with 1-3 fluoros, (C1-C6 alkoxy)C1-C6 alkyl- optionally substituted with 1-3 fluoros, or $(hetCyc^a)$C1-C3 alkyl-; and E is $Ar^1$C1-C6 alkyl- or $Ar^1$(C1-C6 alkyl)C(=O)—, wherein the alkyl portion is optionally substituted with OH, hydroxyC1-C6 alkyl- or C1-C6 alkoxy and $hetCyc^a$ and $Ar^1$ are as defined for Formula I-A.

In one embodiment of Formula I-A, Ring D is unsubstituted; $X^2$ is N; $X^1$, $X^3$ and $X^4$ are CH; A is CN; B is C1-C6 alkyl optionally substituted with 1-3 fluoros; and E is $Ar^1$(C1-C6 alkyl)C(=O)—, wherein the alkyl portion is optionally substituted with OH, hydroxyC1-C6 alkyl- or C1-C6 alkoxy and $Ar^1$ is as defined for Formula I-A.

In one embodiment of Formula I-A, Ring D is unsubstituted; $X^2$ is N; $X^1$, $X^3$ and $X^4$ are CH; A is CN; B is (C1-C6 alkoxy)C1-C6 alkyl- optionally substituted with 1-3 fluoros; and E is $Ar^1$C1-C6 alkyl- and $Ar^1$ is as defined for Formula I-A.

In one embodiment of Formula I-A, Ring D is unsubstituted; $X^2$ is N; $X^1$, $X^3$ and $X^4$ are CH; A is CN; B is $(hetCyc^a)$C1-C3 alkyl-; and E is $Ar^1$C1-C6 alkyl- and $hetCyc^a$ and $Ar^1$ are as defined for Formula I-A.

In one embodiment, Formula I includes compounds of Formula I-B, wherein:

$X^1$, $X^2$, $X^3$ and $X^4$ are independently CH, CF or N, wherein zero, one or two of $X^1$, $X^2$, $X^3$ and $X^4$ is N;

A is H, CN, Cl, $CH_3$—, $CH_3CH_2$—, cyclopropyl, —$CH_2CN$ or —$CH(CN)CH_3$;

B is (a) hydrogen, (b) C1-C6 alkyl optionally substituted with 1-3 fluoros, (c) hydroxyC2-C6 alkyl-, wherein the alkyl portion is optionally substituted with 1-3 fluoros or a C3-C6 cycloalkylidene ring, (d) dihydroxyC3-C6 alkyl-, wherein the alkyl portion is optionally substituted with a C3-C6 cycloalkylidene ring, (e) (C1-C6 alkoxy)C1-C6 alkyl- optionally substituted with 1-3 fluoros, (f) $(R^1R^2N)$C1-C6 alkyl- wherein said alkyl portion is optionally substituted with OH and wherein $R^1$ and $R^2$ are independently H or C1-C6 alkyl (optionally substituted with 1-3 fluoros);

(g) $hetAr^1$C1-C3 alkyl-, wherein $hetAr^1$ is a 5-6 membered heteroaryl ring having 1-3 ring heteroatoms independently selected from N, O and S and is optionally substituted with one or more independently selected C1-C6 alkyl substituents;

(h) (C3-C6 cycloalkyl)C1-C3 alkyl-, wherein said cycloalkyl is optionally substituted with OH, (i) $(hetCyc^a)$C1-C3 alkyl-, (j) $hetCyc^a$-, (k) C3-C6 cycloalkyl-, wherein said cycloalkyl is optionally substituted with OH, (l) (C1-C4 alkyl)C(=O)O—C1-C6 alkyl-, wherein each of the C1-C4 alkyl and C1-C6 alkyl portions is optionally and independently substituted with 1-3 fluoros, or (m) $(R^1R^2N)C(=O)$C1-C6 alkyl-, wherein $R^1$ and $R^2$ are independently H or C1-C6 alkyl (optionally substituted with 1-3 fluoros);

$hetCyc^a$- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-C6 alkoxy)C1-C6 alkyl-, and fluoro, or wherein hetCyc$^a$ is substituted with oxo;

Ring D is

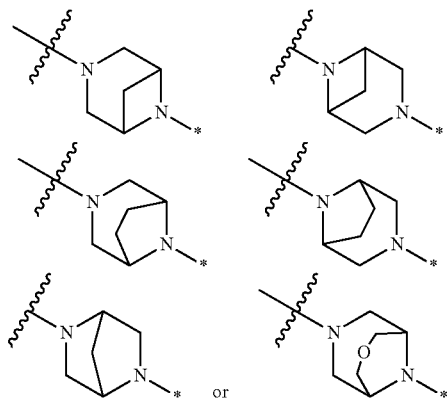

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;

E is
(a) hydrogen,
(b) C1-C6 alkyl,
(c) (C1-C6 alkoxy)C1-C6 alkyl-,
(d) (C1-C6 alkyl)C(=O)—,
(e) (hydroxyC2-C6 alkyl)C(=O)—,
(f) (C1-C6 alkoxy)C(=O)—,
(g) (C3-C6 cycloalkyl)C(=O)—,
(h) Ar$^1$C1-C6 alkyl-,
(i) Ar$^1$(C1-C6 alkyl)C(=O)— wherein said alkyl portion is optionally substituted with OH, hydroxyC1-C6 alkyl-, C1-C6 alkoxy, R′′′R″N— or R′′′R″N—CH$_2$—, wherein each R′′′ and R″ is independently H or C1-C6 alkyl,
(j) hetAr$^2$C1-C6 alkyl- wherein said alkyl portion is optionally substituted with 1-3 fluoros,
(k) hetAr$^2$(C1-C6 alkyl)C(=O)— wherein said alkyl portion is optionally substituted with OH, hydroxyC1-C6 alkyl- or C1-C6 alkoxy,
(l) hetAr$^2$C(=O)—,
(m) hetCyc$^1$C(=O)—,
(o) R$^3$R$^4$NC(=O)—,
(p) Ar$^1$R$^3$NC(=O)—,
(q) hetAr$^2$N(R$^3$)C(=O)—,
(r) (C1-C6 alkyl)SO$_2$— wherein the alkyl portion is optionally substituted with 1-3 fluoros,
(t) hetAr$^2$SO$_2$—,
(u) N—(C1-C6 alkyl)pyridinonyl,
(v) Ar$^1$C(=O)—,
(w) Ar$^1$O—C(=O)—,
(x) (C3-C6 cycloalkyl)CH$_2$C(=O)—,
(y) (C3-C6 cycloalkyl)(C1-C6 alkyl)SO$_2$—,
(z) Ar$^1$(C1-C6 alkyl)SO$_2$—,
(aa) hetCyc$^1$-O—C(=O)—,
(bb) hetCyc$^1$-CH$_2$—C(=O)—, or
(cc) hetAr$^2$;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), R$^e$R$^f$N— wherein R$^e$ and R$^f$ are independently H or C1-C6 alkyl, (R$^p$R$^q$N)C1-C6 alkoxy- wherein R$^p$ and R$^q$ are independently H or C1-C6 alkyl, and (hetAr$^a$)C1-C6 alkyl- wherein hetAr$^a$ is a 5-6 membered heteroaryl ring having 1-2 ring nitrogen atoms, or Ar$^1$ is a phenyl ring fused to a 5-6 membered heterocyclic ring having 1-2 ring heteroatoms independently selected from N and O;

hetAr$^2$ is a 5-6 membered heteroaryl ring having 1-3 ring heteroatoms independently selected from N, O and S or a 9-10 membered bicyclic heteroaryl ring having 1-3 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), R$^e$R$^f$N— wherein R$^e$ and R$^f$ are independently H or C1-C6 alkyl, OH, (C1-C6 alkoxy)C1-C6 alkoxy- and C3-C6 cycloalkyl;

hetCyc$^1$ is a 4-6 membered saturated heterocyclic ring having 1-2 ring heteroatoms independently selected from N, O and S wherein said heterocyclic ring is optionally substituted with one or more substituents independently selected from C1-C6 alkoxy and halogen;

R$^3$ is H or C1-C6 alkyl; and
R$^4$ is C1-C6 alkyl.

In one embodiment of Formula I-B, $X^1$ is N; $X^2$, $X^3$ and $X^4$ are CH.

In one embodiment of Formula I-B, $X^1$ and $X^3$ are N; and $X^2$ and $X^4$ are CH.

In one embodiment of Formula I-B, A is CN.

In one embodiment of Formula I-B, Ring D is

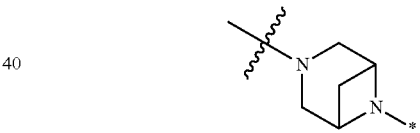

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group.

In one embodiment of Formula I-B, Ring D is

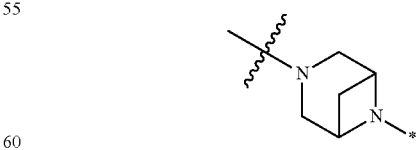

wherein the wavy line indicates the point of attachment of Ring D to the ring comprising $X^1$, $X^2$, $X^3$ and $X^4$, and the asterisk indicates the point of attachment to E, wherein Ring D is unsubstituted.

In one embodiment of Formula I-B, B is C1-C6 alkyl optionally substituted with 1-3 fluoros; (C1-C6 alkoxy)C1-

C6 alkyl- optionally substituted with 1-3 fluoros; hydroxyC2-C6 alkyl wherein the alkyl portion is optionally substituted with a C3-C6 cycloalkylidene ring; hetAr¹C1-C3 alkyl-; or (hetCyc^a)C1-C3 alkyl-; wherein hetAr¹ and hetCyc^a are as defined for Formula I-B.

In one embodiment of Formula I-B, B is C1-C6 alkyl optionally substituted with 1-3 fluoros. In one embodiment of Formula I-B, B is C1-C6 alkyl.

In one embodiment of Formula I-B, B is (C1-C6 alkoxy)C1-C6 alkyl- optionally substituted with 1-3 fluoros, or hydroxyC2-C6 alkyl wherein the alkyl portion is optionally substituted with a C3-C6 cycloalkylidene ring.

In one embodiment of Formula I-B, B is (C1-C6 alkoxy)C1-C6 alkyl- optionally substituted with 1-3 fluoros. In one embodiment of Formula I-B, B is (C1-C6 alkoxy)C2-C6 alkyl-optionally substituted with 1-3 fluoros.

In one embodiment of Formula I-B, B is hydroxyC2-C6 alkyl- wherein the alkyl portion is optionally substituted with a C3-C6 cycloalkylidene ring. In one embodiment, the alkyl portion of the B group is unsubstituted.

In one embodiment of Formula I-B, B is hetAr¹C1-C3 alkyl-, wherein hetAr¹ is as defined for Formula I-B.

In one embodiment of Formula I-B, B is (hetCyc^a)C1-C3 alkyl-; wherein hetCyc^a is as defined for Formula I-B.

In one embodiment of Formula I-B, X¹ is N; X², X³ and X⁴ are CH, or X¹ and X³ are N; and X² and X⁴ are CH; A is CN; and B is C1-C6 alkyl optionally substituted with 1-3 fluoros. In one embodiment of Formula I-B, B is C1-C6 alkyl.

In one embodiment of Formula I-B, X¹ is N; X², X³ and X⁴ are CH, or X¹ and X³ are N; and X² and X⁴ are CH; A is CN; and B is (C1-C6 alkoxy)C1-C6 alkyl- optionally substituted with 1-3 fluoros, or hydroxyC2-C6 alkyl- wherein the alkyl portion is optionally substituted with a C3-C6 cycloalkylidene ring. In one embodiment, X¹ is N; X², X³ and X⁴ are CH. In one embodiment, X¹ and X³ are N; and X² and X⁴ are CH.

In one embodiment of Formula I-B, X¹ is N; X², X³ and X⁴ are CH, or X¹ and X³ are N; and X² and X⁴ are CH; A is CN; and B is (C1-C6 alkoxy)C1-C6 alkyl- optionally substituted with 1-3 fluoros. In one embodiment, X¹ is N; X², X³ and X⁴ are CH. In one embodiment, X¹ and X³ are N; and X² and X⁴ are CH.

In one embodiment of Formula I-B, X¹ is N; X², X³ and X⁴ are CH, or X¹ and X³ are N; and X² and X⁴ are CH; A is CN; and B is hydroxyC2-C6 alkyl- wherein the alkyl portion is optionally substituted with a C3-C6 cycloalkylidene ring. In one embodiment, the alkyl portion of the B group is unsubstituted. In one embodiment, X¹ is N; X², X³ and X⁴ are CH. In one embodiment, X¹ and X³ are N; and X² and X⁴ are CH.

In one embodiment of Formula I-B, X¹ is N; X², X³ and X⁴ are CH, or X¹ and X³ are N; and X² and X⁴ are CH; A is CN; and B is hetAr¹C1-C3 alkyl-, wherein hetAr¹ is as defined for Formula I-B. In one embodiment, X¹ is N; X², X³ and X⁴ are CH. In one embodiment, X¹ and X³ are N; and X² and X⁴ are CH In one embodiment of Formula I-B, X¹ is N; X², X³ and X⁴ are CH, or X¹ and X³ are N; and X² and X⁴ are CH; A is CN; and B is (hetCyc^a)C1-C3 alkyl-; wherein hetCyc^a is as defined for Formula I-B. In one embodiment, X¹ is N; X², X³ and X⁴ are CH. In one embodiment, X¹ and X³ are N; and X² and X⁴ are CH.

In one embodiment of Formula I-B, X¹ is N; X², X³ and X⁴ are CH, or X¹ and X³ are N; and X² and X⁴ are CH; A is CN; B is C1-C6 alkyl optionally substituted with 1-3 fluoros; and Ring D is

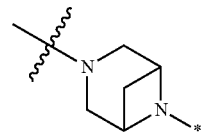 [SMILES: *N1CC2CC(C1)N2*]

wherein the wavy line indicates the point of attachment of Ring D to the ring comprising X¹, X², X³ and X⁴, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment of Formula I-B, said Ring D is unsubstituted. In one embodiment, X¹ is N; X², X³ and X⁴ are CH. In one embodiment, X¹ and X³ are N; and X² and X⁴ are CH.

In one embodiment of Formula I-B, X¹ is N; X², X³ and X⁴ are CH, or X¹ and X³ are N; and X² and X⁴ are CH; A is CN; B is (C1-C6 alkoxy)C1-C6 alkyl- optionally substituted with 1-3 fluoros or hydroxyC2-C6 alkyl- wherein the alkyl portion is optionally substituted with a C3-C6 cycloalkylidene ring; and Ring D is

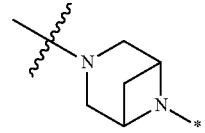 [SMILES: *N1CC2CC(C1)N2*]

wherein the wavy line indicates the point of attachment of Ring D to the ring comprising X¹, X², X³ and X⁴, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment of Formula I-B, said Ring D is unsubstituted. In one embodiment, X¹ is N; X², X³ and X⁴ are CH. In one embodiment, X¹ and X³ are N; and X² and X⁴ are CH.

In one embodiment of Formula I-B, X¹ is N; X², X³ and X⁴ are CH, or X¹ and X³ are N; and X² and X⁴ are CH; A is CN; B is hydroxyC2-C6 alkyl- wherein the alkyl portion is optionally substituted with a C3-C6 cycloalkylidene ring; and Ring D is

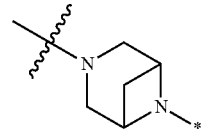 [SMILES: *N1CC2CC(C1)N2*]

wherein the wavy line indicates the point of attachment of Ring D to the ring comprising X¹, X², X³ and X⁴, and the asterisk indicates the point of attachment to E, wherein Ring D is unsubstituted. In one embodiment, X¹ is N; and X², X³ and X⁴ are CH. In one embodiment, X¹ and X³ are N; and X² and X⁴ are CH.

In one embodiment of Formula I-B, X¹ is N, and X², X³ and X⁴ are CH; or X¹ and X³ are N, and X² and X⁴ are CH;

A is CN; B is hetAr$^1$C1-C3 alkyl-, wherein hetAr$^1$ is as defined for Formula I-B; and Ring D is

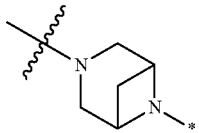 [SMILES: *N1CC2CC(C1)N2*]

wherein the wavy line indicates the point of attachment of Ring D to the ring comprising X$^1$, X$^2$, X$^3$ and X$^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment of Formula I-B, Ring D is unsubstituted. In one embodiment, X$^1$ is N; and X$^2$, X$^3$ and X$^4$ are CH. In one embodiment, X$^1$ and X$^3$ are N; and X$^2$ and X$^4$ are CH.

In one embodiment of Formula I-B, X$^1$ is N, and X$^2$, X$^3$ and X$^4$ are CH; or X$^1$ and X$^3$ are N, and X$^2$ and X$^4$ are CH; A is CN; B is (hetCyc$^a$)C1-C3 alkyl-; wherein hetCyc$^a$ is as defined for Formula I-B; and Ring D is

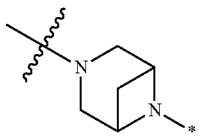

wherein the wavy line indicates the point of attachment of Ring D to the ring comprising X$^1$, X$^2$, X$^3$ and X$^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group. In one embodiment of Formula I-B, Ring D is unsubstituted. In one embodiment, X$^1$ is N; and X$^2$, X$^3$ and X$^4$ are CH. In one embodiment, X$^1$ and X$^3$ are N; and X$^2$ and X$^4$ are CH.

In one embodiment of Formula I-B, E is hetAr$^2$C1-C6 alkyl wherein the alkyl portion is optionally substituted with 1-3 fluoros, hetAr$^2$C(=O)—, Ar$^1$R$^3$NC(=O)—, or (C1-C6 alkyl)SO$_2$—, wherein hetAr$^2$, Ar$^1$, and R$^3$ are as defined for Formula I-B. In one embodiment, hetAr$^2$ is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros).

In one embodiment of Formula I-B, X$^1$ is N; X$^2$, X$^3$ and X$^4$ are CH, or X$^1$ and X$^3$ are N; and X$^2$ and X$^4$ are CH; A is CN; B is C1-C6 alkyl optionally substituted with 1-3 fluoros; Ring D is

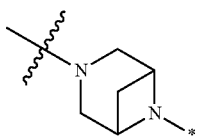

wherein the wavy line indicates the point of attachment of Ring D to the ring comprising X$^1$, X$^2$, X$^3$ and X$^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr$^2$C1-C6 alkyl wherein the alkyl portion is optionally substituted with 1-3 fluoros, hetAr$^2$C(=O)—, Ar$^1$R$^3$NC(=O)— or (C1-C6 alkyl)SO$_2$— wherein hetAr$^2$, Ar$^1$ and R$^3$ are as defined for Formula I-B. In one embodiment of Formula I-B, said Ring D is unsubstituted. In one embodiment, X$^1$ is N; X$^2$, X$^3$ and X$^4$ are CH. In one embodiment, X$^1$ and X$^3$ are N; and X$^2$ and X$^4$ are CH.

In one embodiment of Formula I-B, X$^1$ is N; X$^2$, X$^3$ and X$^4$ are CH, or X$^1$ and X$^3$ are N; and X$^2$ and X$^4$ are CH; A is CN; B is C1-C6 alkyl optionally substituted with 1-3 fluoros; Ring D is

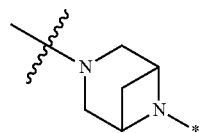

wherein the wavy line indicates the point of attachment of Ring D to the ring comprising X$^1$, X$^2$, X$^3$ and X$^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr$^2$C1-C6 alkyl wherein the alkyl portion is optionally substituted with 1-3 fluoros. In one embodiment of Formula I-B, said Ring D is unsubstituted. In one embodiment, X$^1$ is N; X$^2$, X$^3$ and X$^4$ are CH. In one embodiment, X$^1$ and X$^3$ are N; and X$^2$ and X$^4$ are CH.

In one embodiment of Formula I-B, X$^1$ is N; X$^2$, X$^3$ and X$^4$ are CH, or X$^1$ and X$^3$ are N; and X$^2$ and X$^4$ are CH; A is CN; B is C1-C6 alkyl optionally substituted with 1-3 fluoros; Ring D is

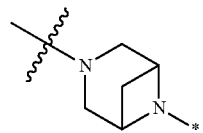

wherein the wavy line indicates the point of attachment of Ring D to the ring comprising X$^1$, X$^2$, X$^3$ and X$^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr$^2$C(=O)—, wherein hetAr$^2$ is as defined for Formula I-B. In one embodiment of Formula I-B, said Ring D is unsubstituted. In one embodiment, X$^1$ is N; X$^2$, X$^3$ and X$^4$ are CH. In one embodiment, X$^1$ and X$^3$ are N; and X$^2$ and X$^4$ are CH.

In one embodiment of Formula I-B, $X^1$ is N; $X^2$, $X^3$ and $X^4$ are CH, or $X^1$ and $X^3$ are N; and $X^2$ and $X^4$ are CH; A is CN; B is C1-C6 alkyl optionally substituted with 1-3 fluoros; Ring D is

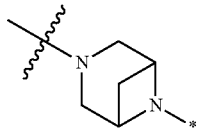 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $Ar^1R^3NC(=O)-$ wherein $Ar^1$ is as defined for Formula I-B. In one embodiment of Formula I-B, said Ring D is unsubstituted. In one embodiment, $X^1$ is N; $X^2$, $X^3$ and $X^4$ are CH. In one embodiment, $X^1$ and $X^3$ are N; and $X^2$ and $X^4$ are CH.

In one embodiment of Formula I-B, $X^1$ is N; $X^2$, $X^3$ and $X^4$ are CH, or $X^1$ and $X^3$ are N; and $X^2$ and $X^4$ are CH; A is CN; B is C1-C6 alkyl optionally substituted with 1-3 fluoros; Ring D is

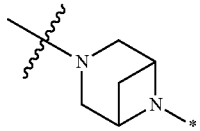 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is (C1-C6 alkyl)$SO_2-$. In one embodiment of Formula I-B, said Ring D is unsubstituted. In one embodiment, $X^1$ is N; $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (C1-C6 alkoxy)C1-C6 alkyl- optionally substituted with 1-3 fluoros or hydroxyC2-C6 alkyl- wherein the alkyl portion is optionally substituted with a C3-C6 cycloalkylidene ring; Ring D is

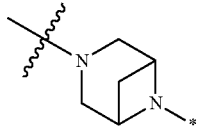 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $hetAr^2$C1-C6 alkyl wherein the alkyl portion is optionally substituted with 1-3 fluoros, $hetAr^2C(=O)-$, $Ar^1R^3NC(=O)-$ or (C1-C6 alkyl)$SO_2-$ wherein $hetAr^2$, $Ar^1$ and $R^3$ are as defined for Formula I-B. In one embodiment, Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (C1-C6 alkoxy)C1-C6 alkyl- optionally substituted with 1-3 fluoros; Ring D is

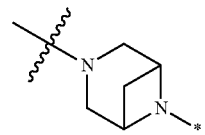

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $hetAr^2$C1-C6 alkyl wherein the alkyl portion is optionally substituted with 1-3 fluoros, $hetAr^2C(=O)-$, $Ar^1R^3NC(=O)-$ or (C1-C6 alkyl)$SO_2-$ wherein $hetAr^2$, $Ar^1$ and $R^3$ and are as defined for Formula I-B. In one embodiment said Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

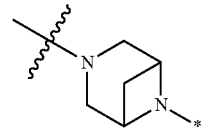 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $hetAr^2$C1-C6 alkyl wherein the alkyl portion is optionally substituted with 1-3 fluoros, $hetAr^2C(=O)-$, $Ar^1R^3NC(=O)-$ or (C1-C6 alkyl)$SO_2-$ wherein $hetAr^2$, $Ar^1$ and $R^3$ and are as defined for Formula I-B. In one embodiment said Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hetAr$^1$C1-C3 alkyl-, wherein hetAr$^1$ is as defined for Formula I-B; Ring D is

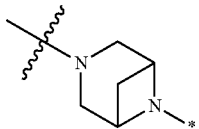 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr$^2$C1-C6 alkyl wherein the alkyl portion is optionally substituted with 1-3 fluoros, hetAr$^2$C(=O)—, Ar$^1$R$^3$NC(=O)— or (C1-C6 alkyl)SO$_2$— wherein hetAr$^2$, Ar$^1$ and R$^3$ and are as defined for Formula I-B. In one embodiment said Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (hetCyc$^a$)C1-C3 alkyl-, wherein hetCyc$^a$ is as defined for Formula I-B; Ring D is

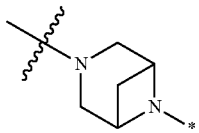

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr$^2$C1-C6 alkyl wherein the alkyl portion is optionally substituted with 1-3 fluoros, hetAr$^2$C(=O)—, Ar$^1$R$^3$NC(=O)— or (C1-C6 alkyl)SO$_2$— wherein hetAr$^2$, Ar$^1$ and R$^3$ and are as defined for Formula I-B. In one embodiment said Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

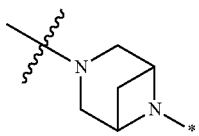 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr$^2$C1-C6 alkyl, wherein the alkyl portion is optionally substituted with 1-3 fluoros and hetAr$^2$ is as defined for Formula I-B. In one embodiment said Ring D is unsubstituted. In one embodiment, hetAr$^2$ is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

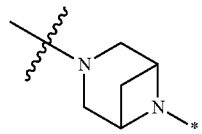 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr$^2$C(=O)—, wherein hetAr$^2$ is as defined for Formula I-B. In one embodiment said Ring D is unsubstituted. In one embodiment, hetAr$^2$ is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

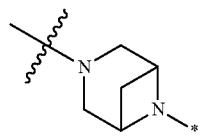

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $Ar^1R^3NC(=O)$— wherein $Ar^1$ and $R^3$ are as defined for Formula I-B. In one embodiment, Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

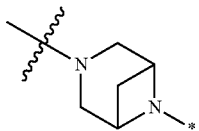 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is (C1-C6 alkyl)$SO_2$—. In one embodiment said Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (C1-C6 alkoxy)C1-C6 alkyl- optionally substituted with 1-3 fluoros; Ring D is

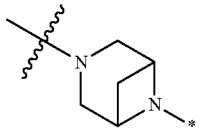

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $hetAr^2$C1-C6 alkyl wherein the alkyl portion is optionally substituted with 1-3 fluoros, $hetAr^2C(=O)$—, $Ar^1R^3NC(=O)$— or (C1-C6 alkyl)$SO_2$— wherein $hetAr^2$, $Ar^1$ and $R^3$ are as defined for Formula I-B. In one embodiment said Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (C1-C6 alkoxy)C1-C6 alkyl- optionally substituted with 1-3 fluoros; Ring D is

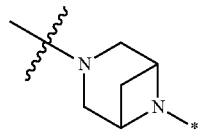

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $hetAr^2$C1-C6 alkyl, wherein the alkyl portion is optionally substituted with 1-3 fluoros and $hetAr^2$ is as defined for Formula I-B. In one embodiment said Ring D is unsubstituted. In one embodiment, $hetAr^2$ is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (C1-C6 alkoxy)C1-C6 alkyl- optionally substituted with 1-3 fluoros; Ring D is

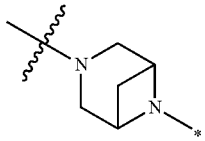 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $hetAr^2C(=O)$—, wherein $hetAr^2$ is as defined for Formula I-B. In one embodiment said Ring D is unsubstituted. In one embodiment, $hetAr^2$ is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (C1-C6 alkoxy)C1-C6 alkyl- optionally substituted with 1-3 fluoros; Ring D is

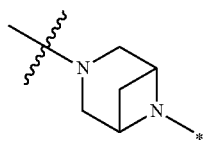 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is $Ar^1R^3NC(=O)$— wherein $Ar^1$ and $R^3$ are as defined for Formula I-B. In one embodiment, Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (C1-C6 alkoxy)C1-C6 alkyl- optionally substituted with 1-3 fluoros; Ring D is

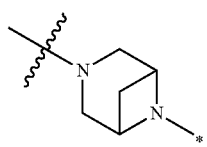 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is (C1-C6 alkyl)$SO_2$—. In one embodiment Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl-; Ring D is

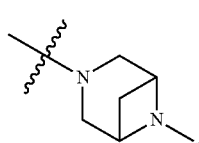

wherein the wavy line indicates the point of attachment of Ring D to the ring comprising $X^1$, $X^2$, $X^3$ and $X^4$, and the asterisk indicates the point of attachment to E; and E is hetAr$^2$C1-C6 alkyl wherein the alkyl portion is optionally substituted with 1-3 fluoros, or hetAr$^2$C(=O), wherein hetAr$^2$ is optionally substituted with one or more substituents independently selected from the group consisting of halogen and C1-C6 alkoxy (optionally substituted with 1-3 fluoros) and hetAr$^2$ is as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl-; Ring D is

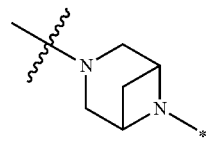

wherein the wavy line indicates the point of attachment of Ring D to the ring comprising $X^1$, $X^2$, $X^3$ and $X^4$, and the asterisk indicates the point of attachment to E; and E is hetAr$^2$C1-C6 alkyl wherein the alkyl portion is optionally substituted with 1-3 fluoros, wherein hetAr$^2$ is optionally substituted with one or more substituents independently selected from the group consisting of halogen and C1-C6 alkoxy (optionally substituted with 1-3 fluoros) and hetAr$^2$ is as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl-; Ring D is

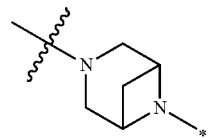

wherein the wavy line indicates the point of attachment of Ring D to the ring comprising $X^1$, $X^2$, $X^3$ and $X^4$, and the asterisk indicates the point of attachment to E; and E is hetAr$^2$C(=O), wherein hetAr$^2$ is optionally substituted with one or more substituents independently selected from the group consisting of halogen and C1-C6 alkoxy (optionally substituted with 1-3 fluoros) and hetAr$^2$ is as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

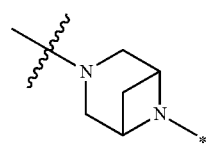 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E; and E is $Ar^1N(R^3)C(=O)$ and $Ar^1$ and $R^3$ are as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

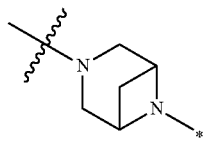 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E; and E is hetAr²C1-C6 alkyl- wherein the alkyl portion is optionally substituted with 1-3 fluoros, or hetAr²C(=O)—, and hetAr² is as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

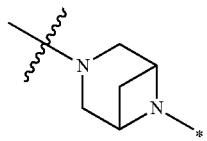

wherein the wavy line indicates the point of attachment of Ring D to the ring comprising $X^1$, $X^2$, $X^3$ and $X^4$, and the asterisk indicates the point of attachment to E; and E is hetAr²C1-C6 alkyl- wherein the alkyl portion is optionally substituted with 1-3 fluoros and hetAr² is as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

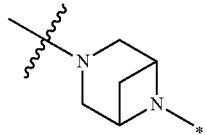

wherein the wavy line indicates the point of attachment of Ring D to the ring comprising $X^1$, $X^2$, $X^3$ and $X^4$, and the asterisk indicates the point of attachment to E; and E is hetAr²C(=O)— and hetAr² is as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

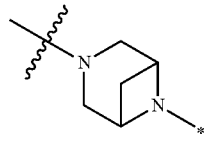

wherein the wavy line indicates the point of attachment of Ring D to the ring comprising $X^1$, $X^2$, $X^3$ and $X^4$, and the asterisk indicates the point of attachment to E; and E is hetAr²C1-C6 alkyl- wherein the alkyl portion is optionally substituted with 1-3 fluoros and hetAr² is as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hydroxyC2-C6 alkyl- wherein the alkyl portion is optionally substituted with a C3-C6 cycloalkylidene ring; Ring D is

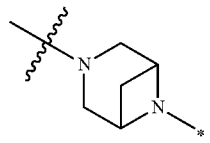 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E; and E is hetAr²C1-C6 alkyl- wherein the alkyl portion is optionally substituted with 1-3 fluoros and hetAr² is as defined for Formula I-B. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hetAr¹C1-C3 alkyl-, wherein hetAr¹ is as defined for Formula I-B; Ring D is

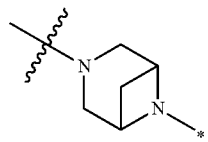 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr²C1-C6 alkyl, wherein the alkyl portion is optionally substituted with 1-3 fluoros and hetAr² is as defined for Formula I-B. In one embodiment, Ring D is unsubstituted.

In one embodiment, hetAr² is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hetAr¹C1-C3 alkyl-, wherein hetAr¹ is as defined for Formula I-B; Ring D is

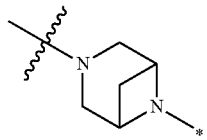 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr²C(=O)—, wherein hetAr² is as defined for Formula I-B. In one embodiment, Ring D is unsubstituted. In one embodiment, hetAr² is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hetAr¹C1-C3 alkyl-, wherein hetAr¹ is as defined for Formula I-B; Ring D is

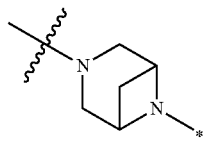 [SMILES: *N1CC2CC(C1)N2C]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is Ar¹R³NC(=O)— wherein Ar¹ and R³ are as defined for Formula I-B. In one embodiment, Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is hetAr¹C1-C3 alkyl-, wherein hetAr¹ is as defined for Formula I-B; Ring D is

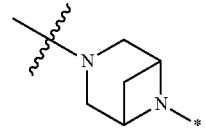

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is (C1-C6 alkyl)SO₂—. In one embodiment, Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (hetCyc$^a$)C1-C3 alkyl-, wherein hetCyc$^a$ is as defined for Formula I-B; Ring D is

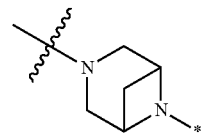 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr²C1-C6 alkyl, wherein the alkyl portion is optionally substituted with 1-3 fluoros and hetAr² is as defined for Formula I-B. In one embodiment, Ring D is unsubstituted. In one embodiment, hetAr² is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (hetCyc$^a$)C1-C3 alkyl-, wherein hetCyc$^a$ is as defined for Formula I-B; Ring D is

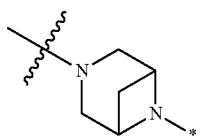 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is hetAr$^2$C(=O)—, wherein hetAr$^2$ is as defined for Formula I-B. In one embodiment, Ring D is unsubstituted. In one embodiment, hetAr$^2$ is a 5-6 membered heteroaryl ring having 1-2 ring heteroatoms independently selected from N and O and is optionally substituted with one or more substituents independently selected from the group consisting of halogen, C1-C6 alkyl (optionally substituted with 1-3 fluoros), and C1-C6 alkoxy (optionally substituted with 1-3 fluoros). In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (hetCyc$^a$)C1-C3 alkyl-, wherein hetCyc$^a$ is as defined for Formula I-B; Ring D is

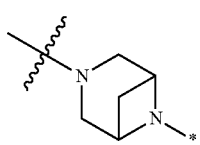 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is Ar$^1$R$^3$NC(=O)— wherein Ar$^1$ and R$^3$ are as defined for Formula I-B. In one embodiment, Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment of Formula I-B, $X^1$ is N, and $X^2$, $X^3$ and $X^4$ are CH; or $X^1$ and $X^3$ are N, and $X^2$ and $X^4$ are CH; A is CN; B is (hetCyc$^a$)C1-C3 alkyl-, wherein hetCyc$^a$ is as defined for Formula I-B; Ring D is

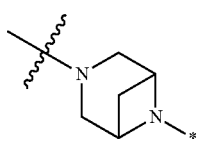 [SMILES: *N1CC2CC(C1)N2*]

wherein the wavy line indicates the point of attachment of Ring D to the ring comprising $X^1$, $X^2$, $X^3$ and $X^4$, and the asterisk indicates the point of attachment to E, wherein Ring D is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group; and E is (C1-C6 alkyl)SO$_2$—. In one embodiment, Ring D is unsubstituted. In one embodiment, $X^1$ is N; and $X^2$, $X^3$ and $X^4$ are CH. In one embodiment, $X^1$ and $X^3$ are N; and $X^2$ and $X^4$ are CH.

In one embodiment, Formula I includes compounds of Formula I-C wherein:

$X^1$, $X^2$, $X^3$ and $X^4$ are independently CH, CF or N, wherein zero, one or two of $X^1$, $X^2$, $X^3$ and $X^4$ is N;

A is H, CN, Cl, CH$_3$—, CH$_3$CH$_2$—, cyclopropyl, —CH$_2$CN or —CH(CN)CH$_3$;

B is
(a) hydrogen,
(b) C1-C6 alkyl optionally substituted with 1-3 fluoros,
(c) hydroxyC2-C6 alkyl- wherein the alkyl portion is optionally substituted with a C3-C6 cycloalkylidene ring,
(d) dihydroxyC3-C6 alkyl-, wherein the alkyl portion is optionally substituted with a C3-C6 cycloalkylidene ring,
(e) (C1-C6 alkoxy)C1-C6 alkyl- optionally substituted with 1-3 fluoros,
(f) (R$^1$R$^2$N)C1-C6 alkyl- wherein R$^1$ and R$^2$ are independently H or C1-C6 alkyl (optionally substituted with 1-3 fluoros);
(g) hetAr$^1$C1-C3 alkyl-, wherein hetAr$^1$ is a 5-6 membered heteroaryl ring having 1-3 ring heteroatoms independently selected from N, O and S and is optionally substituted with one or more independently selected C1-C6 alkyl substituents;
(h) (C3-C6 cycloalkyl)C1-C3 alkyl-,
(i) (hetCyc$^a$)C1-C3 alkyl-, or
(j) hetCyc$^a$;

hetCyc$^a$ is a 4-6 membered heterocyclic ring having 1-2 ring heteroatoms independently selected from N and O and is optionally substituted with OH, C1-C6 alkyl (optionally substituted with 1-3 fluoros) or hydroxyC1-C6 alkyl-;

Ring D is

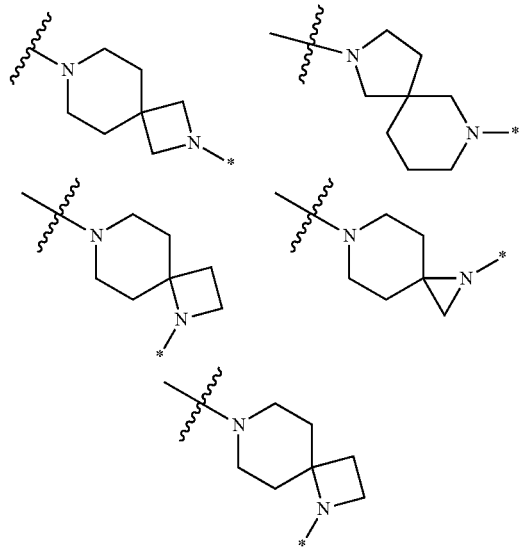

E is
(a) hydrogen,
(b) C1-C6 alkyl optionally substituted with 1-3 fluoros,
(d) (C1-C6 alkyl)C(=O)— wherein said alkyl portion is optionally substituted with 1-3 fluoros or with a $R^g R^h N$— substituent wherein $R^g$ and $R^h$ are independently H or C1-C6 alkyl,
(f) (C1-C6 alkoxy)C(=O),
(l) hetAr$^2$C(=O)—,
(o) R$^3$R$^4$NC(=O)—,
(s) Ar$^1$SO$_2$—,
(t) hetAr$^2$SO$_2$—,
(v) Ar$^1$C(=O)—,
(cc) hetAr$^2$, or
(dd) C3-C6 cycloalkyl;
R$^3$ is H or C1-C6 alkyl; and
R$^4$ is C1-C6 alkyl.

In one embodiment of Formula I-C, X$^1$ is N; X$^2$, X$^3$ and X$^4$ are CH.

In one embodiment of Formula I-C, A is CN.

In one embodiment of Formula I-C, X$^1$ is N; X$^2$, X$^3$ and X$^4$ are CH; and A is CN.

In one embodiment of Formula I-C, B is (C1-C6 alkoxy) C1-C6 alkyl- optionally substituted with 1-3 fluoros, or hydroxyC2-C6 alkyl- wherein the alkyl portion is optionally substituted with a C3-C6 cycloalkylidene ring.

In one embodiment of Formula I-C, B is (C1-C6 alkoxy) C1-C6 alkyl- optionally substituted with 1-3 fluoros. In one embodiment of Formula I-C, B is (C1-C6 alkoxy)C2-C6 alkyl-optionally substituted with 1-3 fluoros.

In one embodiment of Formula I-C, B is hydroxyC2-C6 alkyl- wherein the alkyl portion is optionally substituted with a C3-C6 cycloalkylidene ring. In one embodiment, the alkyl portion of the B group is unsubstituted.

In one embodiment of Formula I-C, X$^1$ is N; X$^2$, X$^3$ and X$^4$ are CH; A is CN; and B is (C1-C6 alkoxy)C1-C6 alkyl optionally substituted with 1-3 fluoros.

In one embodiment of Formula I-C, X$^2$ is N; X$^1$, X$^3$ and X$^4$ are CH; A is CN; B is hydroxyC2-C6 alkyl-, wherein the alkyl portion is optionally substituted with a C3-C6 cycloalkylidene ring; and E is (C1-C6 alkoxy)C(=O)—.

In one embodiment of Formula I-C, X$^1$ is N; X$^2$, X$^3$ and X$^4$ are CH; A is CN; and B is hydroxyC2-C6 alkyl- wherein the alkyl portion is optionally substituted with a C3-C6 cycloalkylidene ring. In one embodiment, the alkyl portion of the B group is unsubstituted.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include monohydrochloride, dihydrochloride, trifluoroacetic acid, and di-trifluoroacetic acid salts. In one embodiment, compounds of Formula I include trifluoroacetic acid and dihydrochloride salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

In one embodiment, the compounds of Formula I include the compounds of Examples 1-561 and stereoisomers and pharmaceutically acceptable salts and solvates thereof. In one embodiment, the compounds of Examples 1-561 are in the free base form. In one embodiment, the compounds of Examples 1-561 are dihydrochloride, and trifluoroacetic acid salts.

The term "pharmaceutically acceptable" indicates that the compound, or salt or composition thereof is compatible chemically and/or toxicologically with the other ingredients comprising a formulation and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C, $^{14}$C or mixtures thereof; when nitrogen is mentioned, it is understood to refer to $^{13}$N, $^{14}$N, $^{15}$N or mixtures thereof; when oxygen is mentioned, it is understood to refer to $^{14}$O, $^{15}$O, $^{16}$O, $^{17}$O, $^{18}$O or mixtures thereof; and when fluoro is mentioned, it is understood to refer to $^{18}$F, $^{19}$F or mixtures thereof. The compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

For illustrative purposes, Schemes 1-6 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

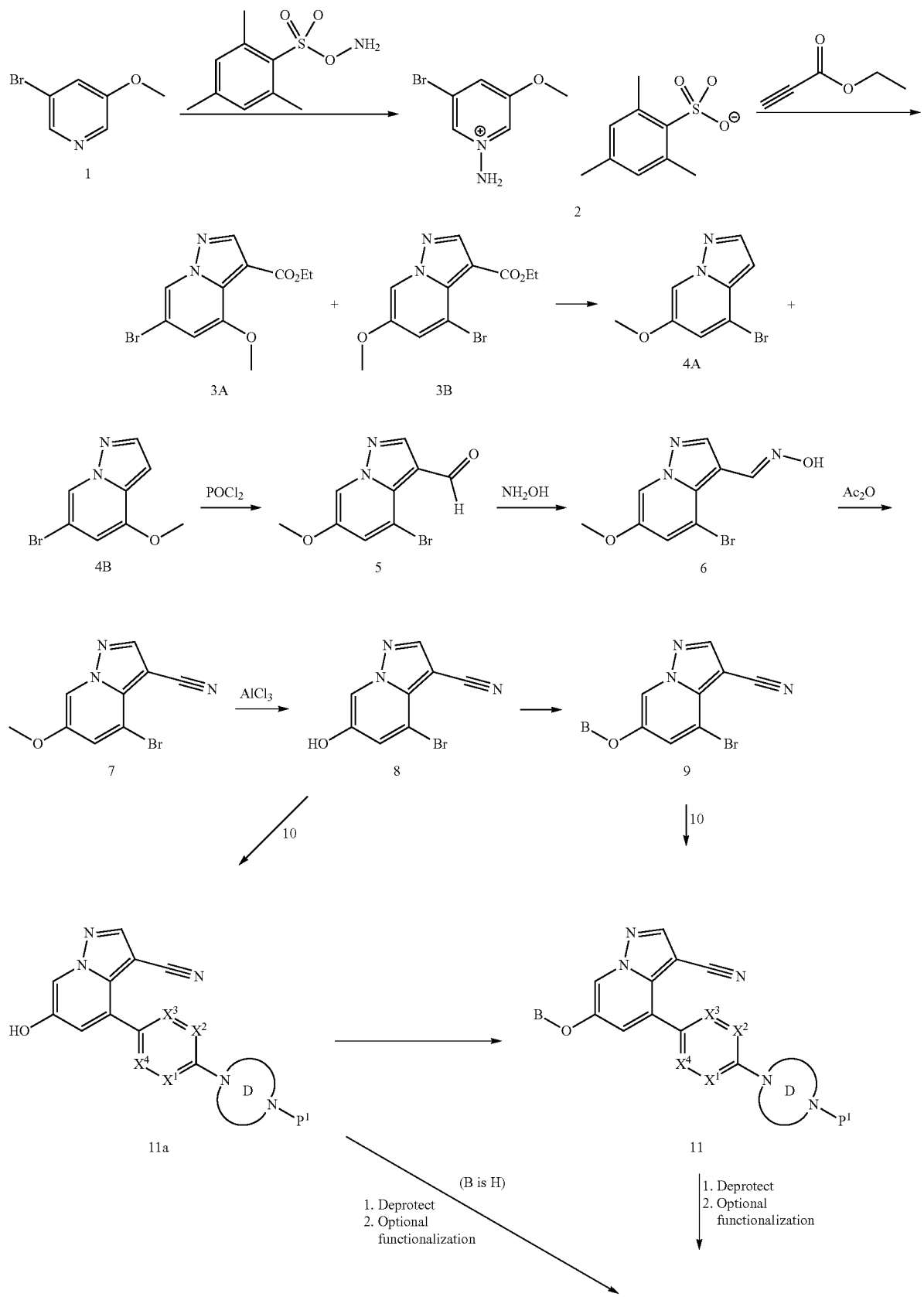
SCHEME 1

Scheme 1 shows a general scheme for the synthesis of compound 12 wherein A is CN, and B, $X^1$, $X^2$, $X^3$, $X^4$, Ring D and E are as defined for Formula I.

Compound 2 is obtained by treating 3-bromo-5-methoxypyridine (compound 1), which is commercially available, with O-(mesitylsulfonyl)hydroxylamine. The O-mesitylsulfonylhydroxylamine may be prepared as described in Mendiola, J., et al., Org. Process Res. Dev. 2009, 13(2), 263-267. Compound 2 may be reacted with ethyl propiolate to provide a mixture of compounds 3A and 3B, which typically are obtained in a ratio of approximately 2:1 to 9:1, respectively. The mixture of compounds 3A and 3B may be treated with 48% HBr at elevated temperatures, followed by recrystallization or chromatography purifications, to isolate compound 4A as the minor isomer and compound 4B as the major isomer. After isolation, compound 4A may be treated with $POCl_3$ to provide compound 5. The formyl group may be converted to an oxime group using $NH_2OH$ to provide compound 6. The oxime group may be converted to a nitrile group using acetic anhydride to provide compound 7. The methoxy group of compound 7 may be converted to a hydroxy group by treating compound 7 with aluminum trichloride to provide compound 8.

To prepare compound 12 wherein B is hydrogen, compound 12 may be prepared by coupling compound 8 with the corresponding boronic ester compound 10 (wherein Ring D, $X^1$, $X^2$, $X^3$ and $X^4$ are as defined for Formula I; $P^1$ is an amino protecting group; Z is —$B(OR^x)(OR^y)$ and $R^z$ and $R^y$ are H or (1-6C)alkyl, or $R^x$ and $R^y$ together with the atoms to which they are connected form a 5-6 membered ring optionally substituted with 1-4 substituents selected from (C1-C3 alkyl)) to provide compound 11a using appropriate palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures). The protecting group $P^1$ on Ring D of compound 11a may be removed under standard conditions (for example, a Boc group may be removed by treating compound 11a to acidic conditions, e.g., HCl) to provide compound 12 wherein B is hydrogen and E is hydrogen. Alternatively, the deprotected Ring D may be functionalized (i.e., reacted or treated with an appropriate reagent) to introduce the E group under standard conditions such as described below to provide compound 12 wherein B is hydrogen and E is as defined for Formula I except that E is not hydrogen.

Alternatively, to prepare compound 12 wherein B is as defined for Formula I other than hydrogen, compound 11a may be reacted with a reagent such as C1-C6 alkyl-OH optionally substituted with 1-3 fluoros, hydroxyC2-C6 alkyl-OH, dihydroxyC3-C6 alkyl-OH, (C1-C6 alkoxy)C1-C6 alkyl-X optionally substituted with 1-3 fluoros, $(R^1R^2N)$ C1-C6 alkyl-OH wherein $R^1$ and $R^2$ are as defined for Formula I, hetAr$^1$C1-C3 alkyl-OH, (C3-C6 cycloalkyl)C1-C3 alkyl-OH, (hetCyc$^a$)C1-C3alkyl-OH, or hetCyc$^a$-OH, wherein hetAr$^1$ and hetCyc$^a$ are defined for Formula I, and wherein each of said reagents ins optionally substituted with a protecting group, under Mitsunobu reaction conditions (e.g., $PPh_3$ and diisopropyl azodicarboxylate) to provide compound 11. Compound 12 may then be prepared from compound 11 as described above, followed by removal of the protecting group on B if present.

As an alternative process for preparing compound 12 wherein B is as defined for Formula I other than hydrogen, compound 9 may be prepared by reacting compound 8 with reagent such as C1-C6 alkyl-X optionally substituted with 1-3 fluoros, hydroxyC2-C6 alkyl-X, dihydroxyC3-C6 alkyl-X, (C1-C6 alkoxy)C1-C6 alkyl-X optionally substituted with 1-3 fluoros, $(R^1R^2N)$C1-C6 alkyl-X wherein $R^1$ and $R^2$ are as defined for Formula I, hetAr$^1$C1-C3 alkyl-X, (C3-C6 cycloalkyl)C1-C3 alkyl-X, (hetCyc$^a$)C1-C3 alkyl-X, or hetCyc$^a$-X, wherein hetAr$^1$ and hetCyc$^a$ are defined for Formula I and X is a leaving atom or group (such as a halide or triflate), in the presence of a suitable base (e.g., a metal alkali carbonate, such as potassium carbonate), wherein each of said reagents is optionally substituted with a protecting group (e.g., a t-butyldimethylsilyl group if the B group has one or two additional hydroxy groups). For example, when B is C1-C6 alkyl optionally substituted with 1-3 fluoros, compound 9 may be prepared by reacting compound 8 with C1-C6 alkyl-X wherein said alkyl is optionally substituted with 1-3 fluoros and X is a halogen such as Br or Cl, or a leaving group such as triflate. Compound 11 may then be prepared by coupling compound 9 with the corresponding boronic ester compound 10 using appropriate palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures). Compound 12 may then be prepared from compound 11 as described above, followed by removal of the protecting group on B if present.

SCHEME 2

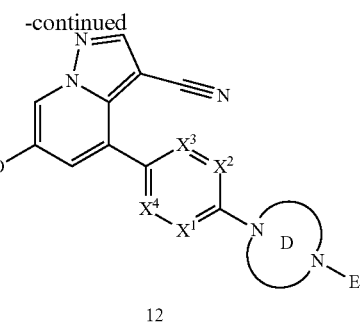
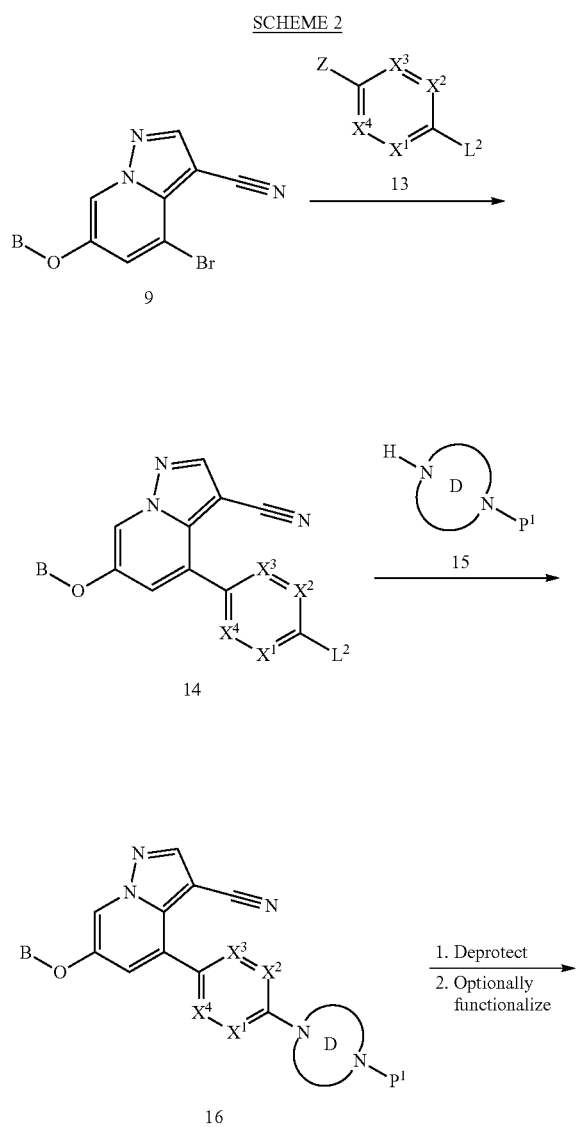

Scheme 2 shows another general scheme for the synthesis of compound 12 wherein A is CN, and B, $X^1$, $X^2$, $X^3$, $X^4$, Ring D and E are as defined for Formula I.

Compound 9 (prepared, e.g., as described in Scheme 1) in which B is as defined for Formula I, may be coupled with the corresponding boronic ester 13 (wherein $X^1$, $X^2$, $X^3$ and $X^4$ are as defined for Formula I; $L^2$ is a leaving group such as a triflate or halide); Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)), using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures) to provide compound 14. Compound 16 may be prepared by coupling compound 14 with compound 15 wherein Ring D is as defined for Formula I and $P^1$ is an amino protecting group, under appropriate S$_N$Ar conditions (for example, optionally in the presence of a base such as K$_2$CO$_3$ and at elevated temperature).

The protecting group $P^1$ on Ring D ring of compound 16 may be removed under standard conditions (for example, a Boc group may be removed by treating compound 1 to acidic conditions, e.g., HCl) to provide compound 12 wherein E is H. Alternatively, the deprotected Ring D may be functionalized (i.e., reacted or treated with an appropriate reagent) to introduce the E group under standard conditions such as described below to provide compound 12 wherein E is as defined for Formula I except that E is not H.

SCHEME 3

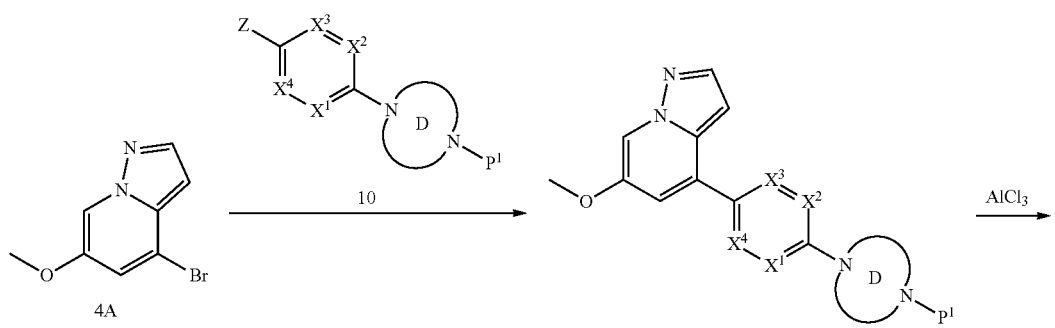

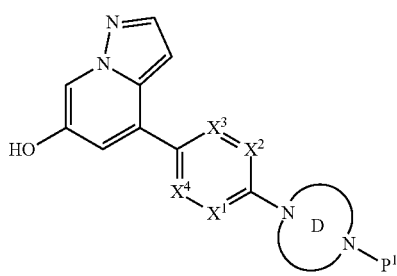

19

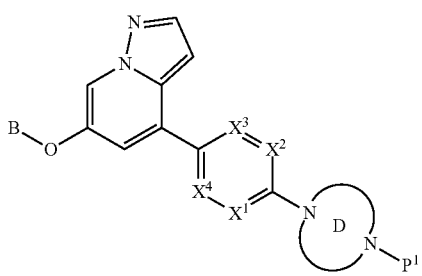

20

1. Deprotect (B = H)
2. Optional functionalization

1. Deprotect
2. Optional functionalization

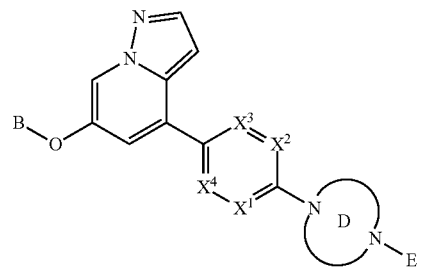

21

Scheme 3 shows a general scheme for the synthesis of Compound 21 wherein A is H, and B, $X^1$, $X^2$, $X^3$, $X^4$, Ring D and E are as defined for Formula I.

Compound 18 may be prepared by coupling compound 4A (prepared e.g., as described in Scheme 1) with the corresponding boronic ester compound 10 (wherein Ring D, $X^1$, $X^2$, $X^3$ and $X^4$ are as defined for Formula I; $P^1$ is an amino protecting group; Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures. Compound 19 may be prepared by treating compound 18 with aluminum trichloride.

To prepare compound 21 wherein B is as defined for Formula I other than hydrogen, compound 20 may be prepared by reacting compound 19 with reagent such as C1-C6 alkyl-X optionally substituted with 1-3 fluoros, hydroxyC2-C6 alkyl-X, dihydroxyC3-C6 alkyl-X, (C1-C6 alkoxy)C1-C6 alkyl-X optionally substituted with 1-3 fluoros, (R$^1$R$^2$N)C1-C6 alkyl-X wherein R$^1$ and R$^2$ are as defined for Formula I, hetAr$^1$C1-C3 alkyl-X, (C3-C6 cycloalkyl)C1-C3 alkyl-X, (hetCyc$^a$)C1-C3alkyl-X or hetCyc$^a$-X, wherein hetAr$^1$ and hetCyc$^a$ are as defined for Formula I and X is a leaving atom or group (such as a halide or triflate), wherein each of said reagents is optionally substituted with a protecting group (e.g., a t-butyldimethylsilyl group if the B group has one or two additional hydroxy groups). For example, when B is C1-C6 alkyl optionally substituted with 1-3 fluoros, compound may be prepared by reacting compound 19 with a C1-C6 alkyl-X wherein said alkyl is optionally substituted with 1-3 fluoros and X is a halogen such as Br or Cl, or a leaving group such as triflate. The protecting group $P^1$ on Ring D ring of compound 20 may be removed under standard conditions (for example, a Boc group may be removed by treating compound 20 to acidic conditions, e.g., HCl) to provide compound 21 wherein E is H. Alternatively, the deprotected Ring D of compound 21 may be functionalized (i.e., reacted or treated with an appropriate reagent) to introduce the E group under standard conditions such as described below to provide compound 21 wherein E is as defined for Formula I except that E is not H.

Alternatively, to prepare compound 21 wherein B is as defined for Formula I other than hydrogen, compound 19 may be reacted with a reagent such as C1-C6 alkyl-OH optionally substituted with 1-3 fluoros, hydroxyC2-C6 alkyl-OH, dihydroxyC3-C6 alkyl-OH, (C1-C6 alkoxy)C1-C6 alkyl-X optionally substituted with 1-3 fluoros, (R$^1$R$^2$N) C1-C6 alkyl-OH wherein R$^1$ and R$^2$ are as defined for Formula I, hetAr$^1$C1-C3 alkyl-OH, (C3-C6 cycloalkyl)C1-C3 alkyl-OH, (hetCyc$^a$)C1-C3alkyl-OH, or hetCyc$^a$-OH, wherein hetAr$^1$ and hetCyc$^a$ are defined for Formula I, wherein each of said reagents is optionally substituted with a protecting group, under Mitsunobu reaction conditions (e.g., PPh$_3$ and diisopropyl azodicarboxylate) to provide compound 20. Compound 21 may then be prepared from compound 20 as described above, followed by removal of the protecting group on B if present.

When group B is hydrogen, compound 21 may be prepared from compound 19 according to the deprotection and optional functionalization steps described herein.

SCHEME 4

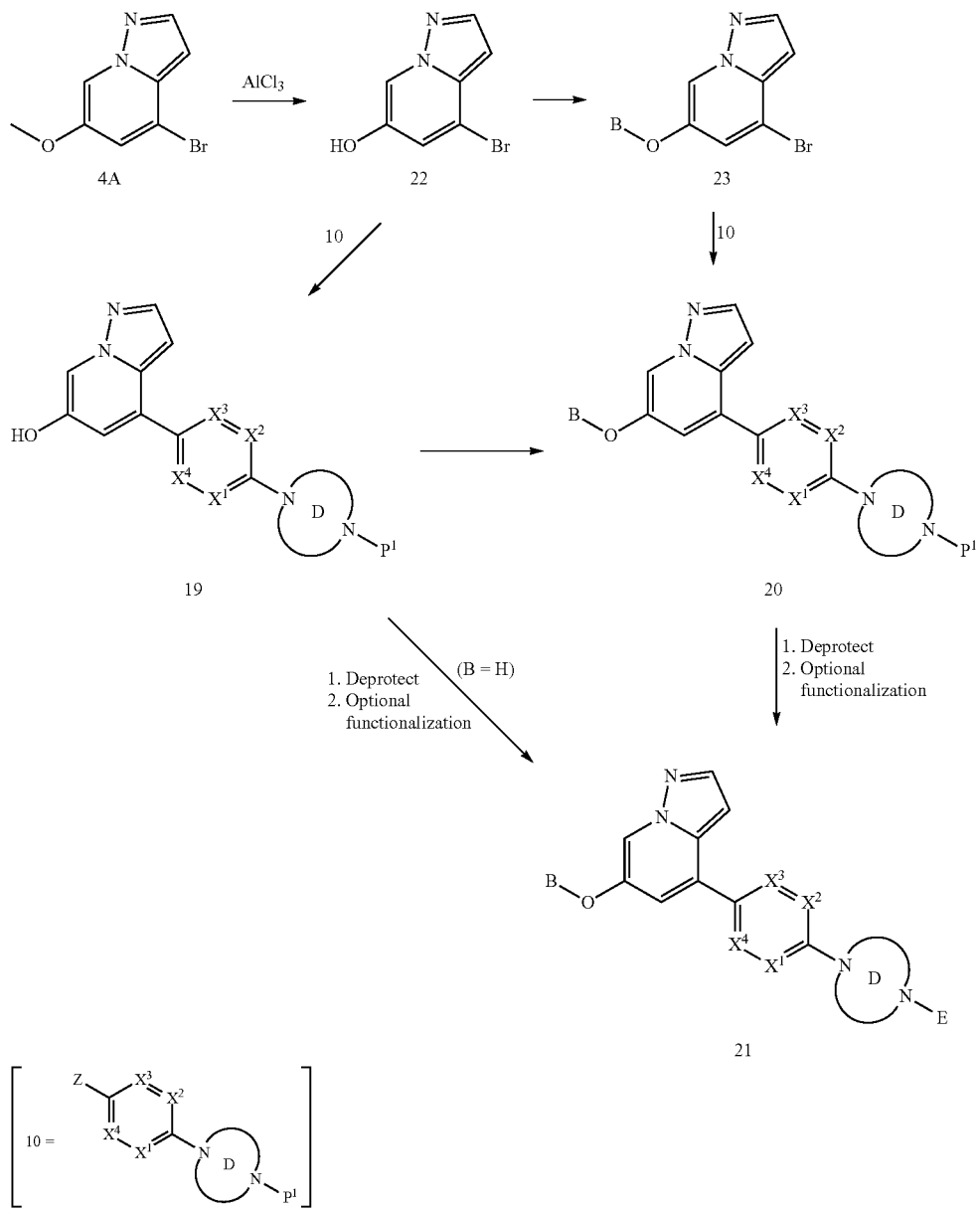

Scheme 4 shows an alternative general scheme for the synthesis of Compound 21 wherein A is H, and B, $X^1$, $X^2$, $X^3$, $X^4$, Ring D and E are as defined for Formula I.

Compound 22 may be prepared by treating compound 4A (prepared e.g., as described in Scheme 1) with aluminum trichloride.

To prepare compound 21 wherein B is hydrogen, compound 19 may be prepared by coupling compound 22 with the corresponding boronic ester compound 10 (wherein Ring D, $X^1$, $X^2$, $X^3$ and $X^4$ are as defined for Formula I; $P^1$ is an amino protecting group; Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures). Compound 21 may be prepared from compound 19 according to the process described for Scheme 3.

Alternatively, to prepare compound 21 wherein B is as defined for Formula I other than hydrogen, compound 23 may be prepared by reacting compound 22 with reagent such as C1-C6 alkyl-X optionally substituted with 1-3 fluoros, hydroxyC2-C6 alkyl-X, dihydroxyC3-C6 alkyl-X, (C1-C6 alkoxy)C1-C6 alkyl-X optionally substituted with 1-3 fluoros, (R$^1$R$^2$N)C1-C6 alkyl-X wherein R$^1$ and R$^2$ are as defined for Formula I, hetAr$^1$C1-C3 alkyl-X, (C3-C6 cycloalkyl)C1-C3 alkyl-X, (hetCyc$^a$)C1-C3 alkyl-X or hetCyc$^a$-X, wherein hetAr$^1$ and hetCyc$^a$ are defined for Formula I and X is a leaving atom or group (such as a halide or triflate), wherein each of said reagents is optionally substituted with a protecting group (e.g., a t-butyldimethylsilyl group if the B group has one or two additional hydroxy groups). For example, when B is C1-C6 alkyl optionally substituted with 1-3 fluoros, compound 23 may be prepared by reacting compound 22 with a C1-C6 alkyl-X wherein said alkyl is optionally substituted with 1-3 fluoros and X is a halogen such as Br or Cl, or a leaving group such as triflate. Compound 20 may be prepared by coupling compound 23 with compound 10 as described in Scheme 3. Compound 21 may be prepared from compound 20 according to the process described for Scheme 3.

Alternatively, to prepare compound 21 wherein B is as defined for Formula I other than hydrogen, compound 19 may be reacted with a reagent such as C1-C6 alkyl-OH optionally substituted with 1-3 fluoros, hydroxyC2-C6 alkyl-OH, dihydroxyC3-C6 alkyl-OH, (C1-C6 alkoxy)C1-C6 alkyl-X optionally substituted with 1-3 fluoros, ($R^1R^2N$)C1-C6 alkyl-OH wherein $R^1$ and $R^2$ are as defined for Formula I, hetAr$^1$C1-C3 alkyl-OH, (C3-C6 cycloalkyl)C1-C3 alkyl-OH, (hetCyc$^a$)C1-C3alkyl-OH, or hetCyc$^a$-OH, wherein hetAr$^1$ and hetCyc$^a$ are defined for Formula I, wherein each of said reagents is optionally substituted with a protecting group, under Mitsunobu reaction conditions (e.g., PPh$_3$ and diisopropyl azodicarboxylate) to provide compound 20. Compound 21 may then be prepared from compound 20 as described for Scheme 3, followed by removal of the protecting group on B if present.

prepared by reacting compound 22 with reagent such as C1-C6 alkyl-X optionally substituted with 1-3 fluoros, hydroxyC2-C6 alkyl-X, dihydroxyC3-C6 alkyl-X, (C1-C6 alkoxy)C1-C6 alkyl-X optionally substituted with 1-3 fluoros, ($R^1R^2N$)C1-C6 alkyl-X wherein $R^1$ and $R^2$ are as defined for Formula I, hetAr$^1$C1-C3 alkyl-X, (C3-C6 cycloalkyl)C1-C3 alkyl-X, (hetCyc$^a$)C1-C3 alkyl-X or hetCyc$^a$-X, wherein hetAr$^1$ and hetCyc$^a$ are defined for Formula I and X is a leaving atom or group (such as a halide or triflate), wherein each of said reagents is optionally substituted with a protecting group (e.g., a t-butyldimethylsilyl group if the B group has one or two additional hydroxy groups). For example, when B is C1-C6 alkyl optionally substituted with 1-3 fluoros, compound may be prepared by reacting compound 22 with a C1-C6 alkyl-X wherein said alkyl is optionally substituted with 1-3 fluoros and X is a halogen such as Br or Cl, or a leaving group such as triflate.

Compound 24 may be prepared by reacting compound 23 with the boronic ester 13 (wherein $X^1$, $X^2$, $X^3$ and $X^4$ are as defined for Formula I; $L^2$ is a leaving group such as a triflate or halide); Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally

SCHEME 5

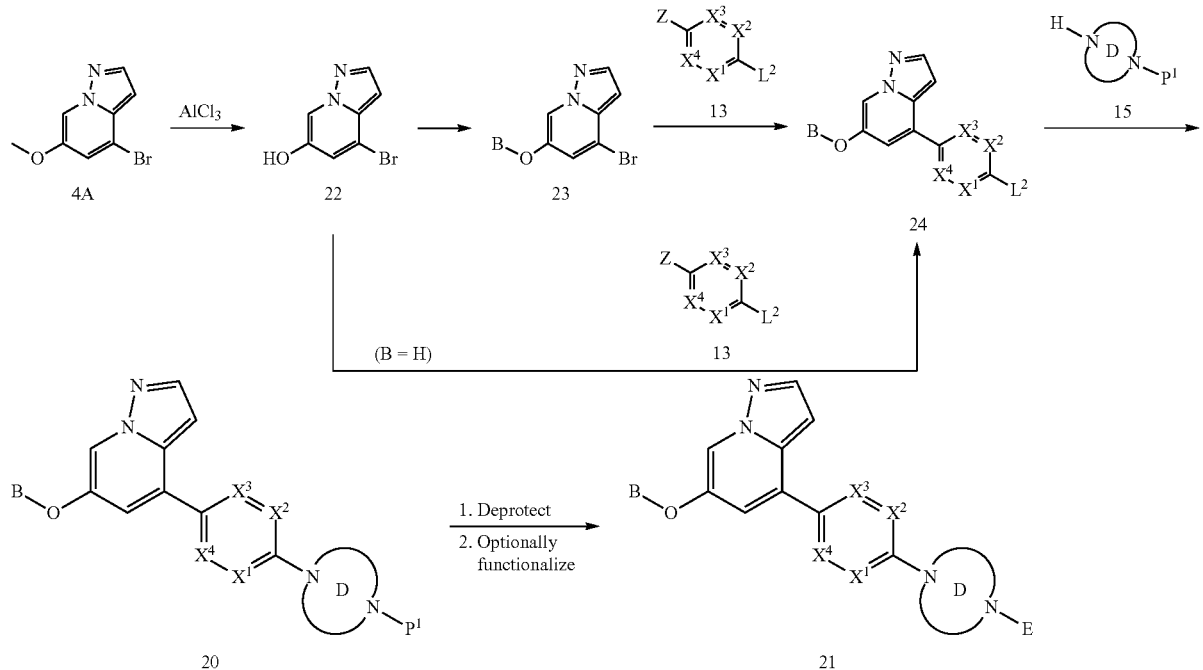

Scheme 5 shows an alternative general scheme for the synthesis of Compound 21 wherein A is H, and B, $X^1$, $X^2$, $X^3$, $X^4$, Ring D and E are as defined for Formula I.

Compound 22 may be prepared by treating compound 4A (prepared e.g., as described in Scheme 1) with aluminum trichloride.

To prepare compound 21 wherein B is as defined for Formula I other than hydrogen, compound 23 may be a ligand in the presence of an inorganic base, for example, Pd(PPh$_3$)$_4$ and Na$_2$CO$_3$ in dioxane at elevated temperatures).

To prepare compound 21 wherein B is hydrogen, compound 24 may be prepared by reacting compound 22 directly with compound 13 as described above.

Compound 20 may be prepared by coupling compound 24 with compound 15 wherein P$^1$ is an amino protecting group under appropriate S$_N$Ar conditions (for example, optionally in the presence of a base such as K$_2$CO$_3$ and at elevated temperature).

Compound 21 may be prepared from compound 20 according to the process described for Scheme 3.

alkoxy)C1-C6 alkyl-X optionally substituted with 1-3 fluoros, (R$^1$R$^2$N)C1-C6 alkyl-X wherein R$^1$ and R$^2$ are as defined for Formula I, hetAr$^1$C1-C3 alkyl-X, (C3-C6 cycloalkyl)C1-C3 alkyl-X, (hetCyc$^a$)C1-C3 alkyl-X or hetCyc$^a$-X, wherein hetAr$^1$ and hetCyc$^a$ are defined for For-

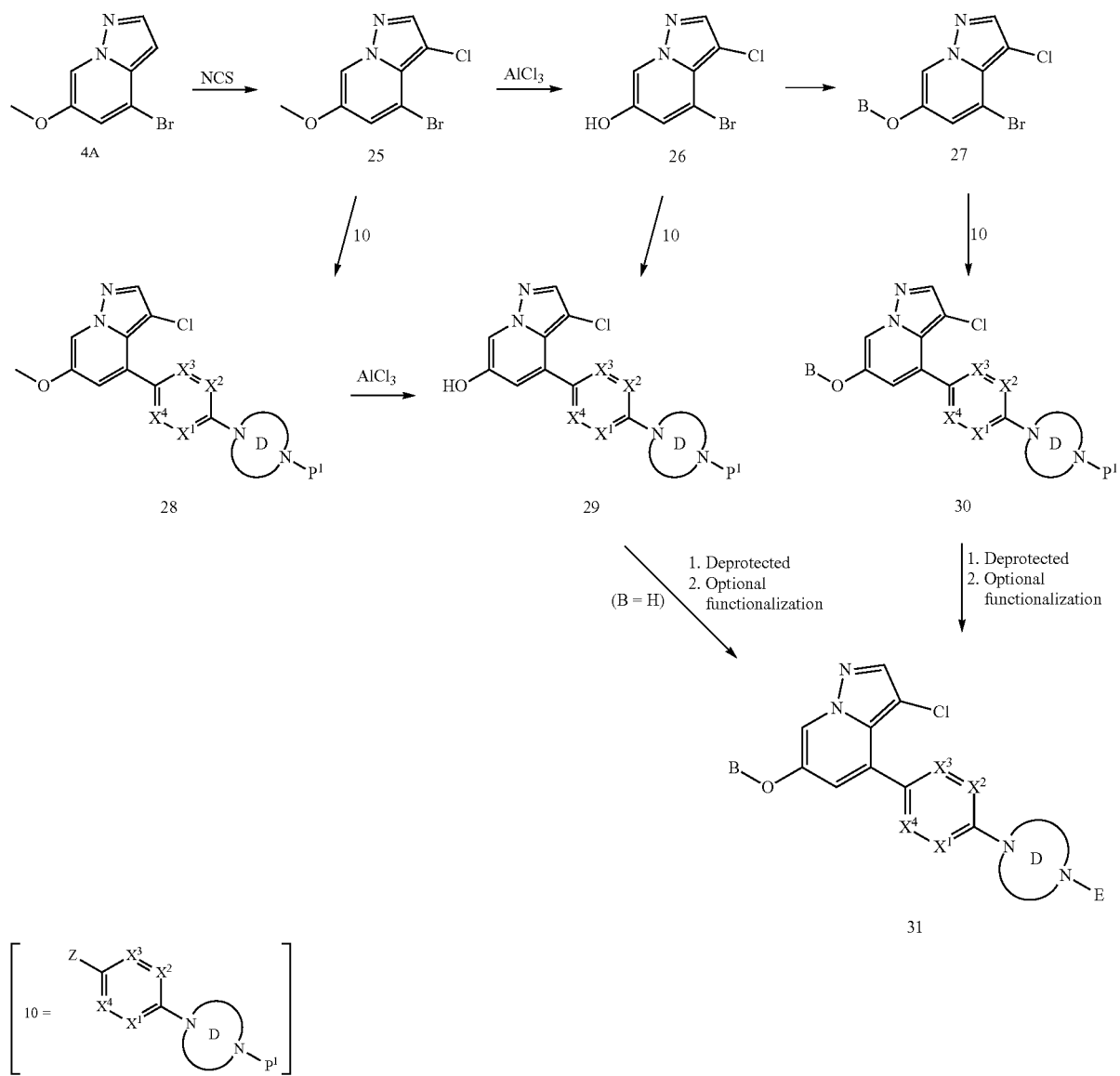

SCHEME 6

Scheme 6 shows a general scheme for the synthesis of Compound 31 wherein A is Cl, and B, X$^1$, X$^2$, X$^3$, X$^4$, Ring D and E are as defined for Formula I.

Compound 25 may be prepared by treating compound 4A (prepared e.g., as described in Scheme 1) with aluminum trichloride.

Compound 26 may be prepared by treating compound 25 with aluminum trichloride.

To prepare compound 31 wherein B is as defined for Formula I other than hydrogen, compound 27 may be prepared by reacting compound 26 with reagent such as C1-C6 alkyl-X optionally substituted with 1-3 fluoros, hydroxyC2-C6 alkyl-X, dihydroxyC3-C6 alkyl-X, (C1-C6 mula I and X is a leaving atom or group (such as a halide or triflate), wherein each of said reagents is optionally substituted with a protecting group (e.g., a t-butyldimethylsilyl group if the B group has one or two additional hydroxy groups). For example, when B is C1-C6 alkyl optionally substituted with 1-3 fluoros, compound may be prepared by reacting compound 26 with a C1-C6 alkyl-X wherein said alkyl is optionally substituted with 1-3 fluoros and X is a halogen such as Br or Cl, or a leaving group such as triflate.

Compounds 28 (wherein group B is methyl), 29 (wherein group B is hydrogen) and 30 (wherein group B is other than hydrogen) may be prepared by coupling compounds 25, 26 and 27, respectively, with the corresponding boronic ester compound 10 (wherein Ring D, $X^1$, $X^2$, $X^3$ and $X^4$ are as defined for Formula I; $P^1$ is an amino protecting group; Z is —B(OR$^x$)(OR$^y$) and $R^z$ and $R^y$ are H or (1-6C)alkyl, or $R^x$ and $R^y$ together with the atoms to which they are connected form a 5-6 membered ring optionally substituted with 1-4 substituents selected from (C1-C3 alkyl)) using appropriate palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures).

The protecting group $P^1$ on Ring D of compound 29 or 30 may be removed under standard conditions (for example, a Boc group may be removed by treating compound 29 or 30 to acidic conditions, e.g., HCl) to provide compound 31 wherein E is H. Alternatively, the deprotected Ring D may be functionalized (i.e., reacted or treated with an appropriate reagent) to include the E group under standard conditions such as described below to provide compound 31 wherein E is as defined for Formula I except that E is not H.

Ring D of compounds 12, 21 and 31 described in Schemes 1-6 may be functionalized (i.e., reacted or treated with an appropriate reagent) to include an E group, wherein E is any of the E groups defined for Formula I with the exception of hydrogen, using standard chemistry well known to persons skilled in the art. As used herein, the term "functionalized" refers to a process step in which a compound of Formula 12, 21 or 31 wherein E is hydrogen is reacted or treated with an appropriate reagent to provide a compound of Formula 12, 21 or 31 wherein E is as defined for Formula I other than hydrogen.

For example, a compound of Formula I wherein E is (C1-C6 alkyl)C(=O)— optionally substituted with one to three fluoros; (hydroxy C2-C6 alkyl)C(=O)— optionally substituted with one to three fluoros; (C1-C6 alkoxy)C(=O)—; (C3-C6 cycloalkyl)C(=O)— (wherein said cycloalkyl is optionally substituted with (C1-C6 alkoxy)C1-C6 alkyl or a 5-6 membered heteroaryl ring having 1-3 ring heteroatoms independently selected from N and O); Ar$^1$(C1-C6 alkyl)C(=O)— (wherein the alkyl portion is optionally substituted with OH, hydroxyC1-C6 alkyl-, or C1-C6 alkoxy); hetAr$^2$(C1-C6 alkyl)C(=O)— (wherein the alkyl portion is optionally substituted with OH, hydroxyC1-C6 alkyl, or C1-C6 alkoxy); or hetCyc$^1$(C1-C6 alkyl)C(=O)—, may be obtained by treating compound 12 having a deprotected Ring D (i.e., compound 12 wherein E is hydrogen) with a corresponding carboxylic acid using conventional amide bond formation conditions, for example by treating the corresponding carboxylic acid with an activating agent (e.g., HATU), followed by addition of the compound 12 having a deprotected Ring D (i.e., wherein E is H) in the presence of a base (e.g., an amine base such as DIEA) in an appropriate solvent (such as DMA) to provide a functionalized compound 12 (i.e., in this instance compound 12 wherein E is (C1-C6 alkyl)C(=O)— optionally substituted with one to three fluoros; (hydroxy C2-C6 alkyl)C(=O)— optionally substituted with one to three fluoros; (C1-C6 alkoxy)C(=O)—; (C3-C6 cycloalkyl)C(=O)— (wherein said cycloalkyl is optionally substituted with (C1-C6 alkoxy)C1-C6 alkyl- or a 5-6 membered heteroaryl ring having 1-3 ring heteroatoms independently selected from N and O); Ar$^1$(C1-C6 alkyl)C(=O)— (wherein the alkyl portion is optionally substituted with OH, hydroxyC1-C6 alkyl-, or C1-C6 alkoxy); hetAr$^2$(C1-C6 alkyl)C(=O)— (wherein the alkyl portion is optionally substituted with OH, hydroxyC1-C6 alkyl-, or C1-C6 alkoxy); or hetCyc$^1$(C1-C6 alkyl)C(=O)—). The same chemistry may be utilized with compounds 21 and 31 to prepare functionalized compounds 21 and 31 (i.e., in this instance compounds 21 and 31, respectively, wherein E is (C1-C6 alkyl)C(=O)— optionally substituted with one to three fluoros; (hydroxy C2-C6 alkyl)C(=O)— optionally substituted with one to three fluoros; (C1-C6 alkoxy)C(=O)—; (C3-C6 cycloalkyl)C(=O)— (wherein said cycloalkyl is optionally substituted with (C1-C6 alkoxy)C1-C6 alkyl- or a 5-6 membered heteroaryl ring having 1-3 ring heteroatoms independently selected from N and O); Ar$^1$(C1-C6 alkyl)C(=O)— (wherein the alkyl portion is optionally substituted with OH, hydroxyC1-C6 alkyl-, or C1-C6 alkoxy); hetAr$^2$(C1-C6 alkyl)C(=O)— (wherein the alkyl portion is optionally substituted with OH, hydroxyC1-C6 alkyl-, or (C1-C6) alkoxy); or hetCyc$^1$(C1-C6 alkyl)C(=O)—).

As another example, a compound of Formula I wherein E is hetCyc$^1$C(=O)— or R$^3$R$^4$NC(=O)— may be prepared by first activating the deprotected ring nitrogen in Ring D of compound 12 (i.e., wherein E is H) with triphosgene in the presence of DIEA and in a solvent such as DCM, followed by addition of an amine reagent having the formula hetCyc$^1$-H or R$^3$R$^4$NH (wherein hetCyc$^1$-H is a saturated 4-6 membered heterocycle having 1-2 ring heteroatoms independently selected from N, O and S wherein the ring has at least one ring N atom and the "—H" indicates that the hydrogen is on the ring nitrogen atom, wherein said heterocycle is optionally substituted with one or more independently selected C1-C6 alkoxy substituents) to provide a functionalized compound 12 (i.e., in this instance compound 12 wherein E is hetCyc$^1$C(=O)— or R$^3$R$^4$NC(=O)—). The same chemistry may be utilized with compounds 21 and 31 to prepare functionalized compounds 21 and 31 (i.e., in this instance compound 21 and 31, respectively, wherein E is hetCyc$^1$C(=O)— or R$^3$R$^4$NC(=O)—).

As another example, a compound of Formula I wherein E is C1-C6 alkyl optionally substituted with one to three fluoros, (C1-C6 alkoxy)C1-C6 alkyl- optionally substituted with 1-3 fluoros, Ar$^1$C1-C6 alkyl-, hetAr$^2$C1-C6 alkyl- wherein the alkyl portion is optionally substituted with 1-3 fluoros, or hetCyc$^1$C1-C6 alkyl-, may be prepared by treating deprotected compound 12 (i.e., wherein E is H) with a corresponding reagent having the formula C1-C6 alkyl-X optionally substituted with one to three fluoros, (C1-C6 alkoxy)C1-C6 alkyl-X optionally substituted with 1-3 fluoros, Ar$^1$C1-C6 alkyl-X, hetAr$^2$C1-C6 alkyl-X, or hetCyc$^1$C1-C6 alkyl-X wherein X is Br or Cl, in the presence of a base such as DIEA in a solvent at ambient or elevated temperatures) to provide a functionalized compound 12 (i.e., in this instance compound 12 wherein E is C1-C6 alkyl optionally substituted with one to three fluoros, (C1-C6 alkoxy)C1-C6 alkyl optionally substituted with 1-3 fluoros, Ar$^1$C1-C6 alkyl-, hetAr$^2$C1-C6 alkyl- wherein the alkyl portion is optionally substituted with 1-3 fluoros, or hetCyc$^1$C1-C6 alkyl-). The same chemistry may be utilized with compounds 21 and 31 to prepare functionalized compounds 21 and 31 (i.e., in this instance in this instance compound 21 and 31, respectively, wherein E is C1-C6 alkyl optionally substituted with one to three fluoros, (C1-C6 alkoxy)C1-C6 alkyl- optionally substituted with 1-3 fluoros, Ar$^1$C1-C6 alkyl-, hetAr$^2$C1-C6 alkyl- wherein the alkyl portion is optionally substituted with 1-3 fluoros, or hetCyc$^1$C1-C6 alkyl-).

As another example, a compound of Formula I wherein E is C1-C6 alkyl optionally substituted with one to three fluoros; (C1-C6 alkoxy)C1-C6 alkyl- optionally substituted with 1-3 fluoros; Ar$^1$C1-C6 alkyl-, hetAr$^2$C1-C6 alkyl- wherein the alkyl portion is optionally substituted with 1-3 fluoros, or hetCyc¹C1-C6 alkyl-), may be prepared by treating deprotected compound 12 (i.e., wherein E is H), with corresponding aldehyde, e.g., (C1-C5 alkyl(C=O)H optionally substituted with one to three fluoros; (C1-C6 alkoxy)(C1-C5 alkyl)C(=O)H optionally substituted with one to three fluoros; Ar¹(C1-C5 alkyl)C(=O)H; hetAr²(C1-C5 alkyl)C(=O)H; or hetCyc¹(C1-C5 alkyl)-C(=O)H, in the presence of a reducing agent, e.g., NaBH(AcO)₃ to provide a functionalized compound 12 (i.e., in this instance compound 12 wherein E is C1-C6 alkyl optionally substituted with one to three fluoros; (C1-C6 alkoxy)C1-C6 alkyl- optionally substituted with 1-3 fluoros; Ar¹C1-C6 alkyl-, hetAr²C1-C6 alkyl- wherein the alkyl portion is optionally substituted with 1-3 fluoros, or hetCyc¹C1-C6 alkyl-). The same chemistry may be utilized with compounds 21 and 31 to prepare functionalized compounds 21 and 31 (i.e., in this instance in this instance compounds 21 and 31, respectively, wherein E is C1-C6 alkyl optionally substituted with one to three fluoros; (C1-C6 alkoxy)C1-C6 alkyl- optionally substituted with 1-3 fluoros; Ar¹C1-C6 alkyl-, hetAr²C1-C6 alkyl- wherein the alkyl portion is optionally substituted with 1-3 fluoros, or hetCyc¹C1-C6 alkyl-).

Accordingly, also provided herein is a process for preparing of a compound of Formula I or a pharmaceutically acceptable salt thereof as defined herein which comprises:

(a) for a compound of Formula I wherein E is H, A is CN, —CH₂CN or —CH(CN)CH₃ and B, X¹, X², X³, X⁴, and Ring D are as defined for Formula I, coupling a corresponding compound 9 having the formula

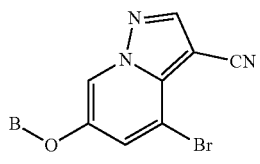

9 wherein B is as defined for Formula I, with a corresponding boronic ester of the formula 10

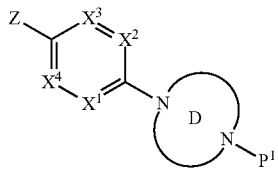

10 wherein P¹ is an amino protecting group, Z is —B(OR^x)(OR^y) wherein R^x and R^y are H or C1-C6 alkyl, or R^x and R^y together with the atoms to which they are connected form a 5-6 membered ring optionally substituted with 1-4 substituents selected from C1-C3 alkyl, and X¹, X², X³ and X⁴ are as defined for Formula I, in the presence of a palladium catalyst and optionally a ligand and in the presence of a base, followed by removal of the protecting group; or (b) for a compound of Formula I wherein A, B, X¹, X², X³, X⁴, Ring D and E are as defined for Formula I with the exception that E is not hydrogen, functionalizing a corresponding compound of the formula

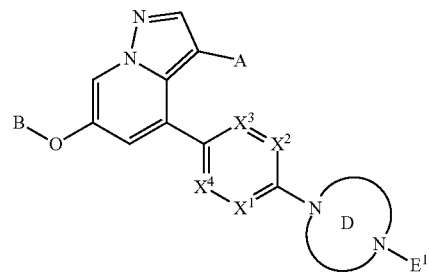

wherein A, Ring D, B, X¹, X², X³ and X⁴ are as defined for Formula I and E¹ is hydrogen; or (c) for a compound of Formula I wherein A is CN, and Ring D, B, X¹, X², X³, X⁴ and E are as defined for Formula I, reacting a corresponding compound of the formula 14

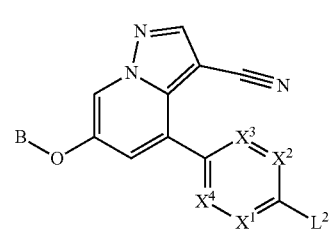

14 wherein B, X¹, X², X³ and X⁴ are as defined for Formula I and L² is a leaving group or atom, with a compound of the formula 15

15 wherein P¹ is an amino protecting group, followed by removing the protecting group P¹ and optionally functionalizing Ring D; or (d) for a compound of Formula I wherein E is H, A is CN, and B, X¹, X², X³, X⁴, and Ring D are as defined for Formula I, coupling a compound of formula 14

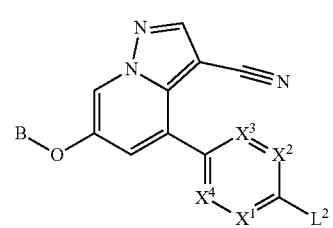

14 wherein L² is a leaving group or atom and B, X¹, X², X³, and X⁴ are as defined for Formula I, with a compound of formula 15

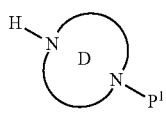

wherein $P^1$ is an amino protecting group, followed by removing the protecting group $P^1$; or (e) for a compound of Formula I wherein A is H, B is H, and $X^1$, $X^2$, $X^3$, $X^4$, Ring D and E are as defined for Formula I, treating a compound of formula 18

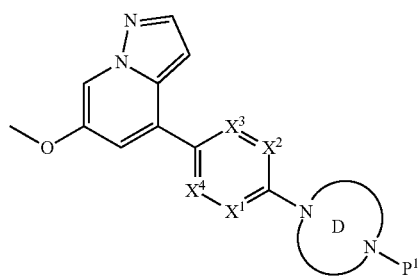

wherein $P^1$ is an amino protecting group and $X^1$, $X^2$, $X^3$, $X^4$, Ring D are as defined for Formula I, with aluminum trichloride to provide compound 19

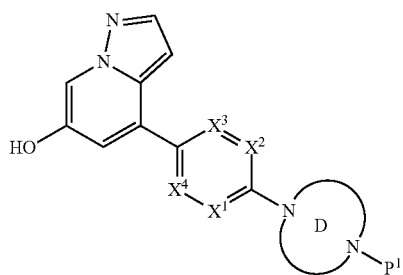

wherein Ring D, $X^1$, $X^2$, $X^3$, and $X^4$ are as defined for Formula I and $P^1$ is an amino protecting group;

followed by removal of the protecting group $P^1$ and optionally functionalizing Ring D; or (f) for a compound of Formula I wherein A is H, B is C1-C6 alkyl optionally substituted with 1-3 fluoros, hydroxyC2-C6 alkyl, dihydroxyC3-C6 alkyl, (C1-C6 alkoxy)C1-C6 alkyl optionally substituted with 1-3 fluoros, $(R^1R^2N)$C1-C6 alkyl, (hetAr$^1$)C1-C3 alkyl, (C3-C6 cycloalkyl)C1-C3 alkyl, (hetCyc$^a$)C1-C3 alkyl, or hetCyc$^a$, wherein $R^1$, $R^2$, hetAr$^1$, hetCyc$^a$, $X^1$, $X^2$, $X^3$, $X^4$, Ring D and E are as defined for Formula I, (i) treating a compound of formula 18

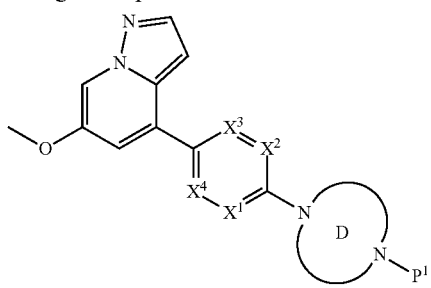

wherein $P^1$ is an amino protecting group and $X^1$, $X^2$, $X^3$, $X^4$ and Ring D are as defined for Formula I, with aluminum trichloride to provide compound 19

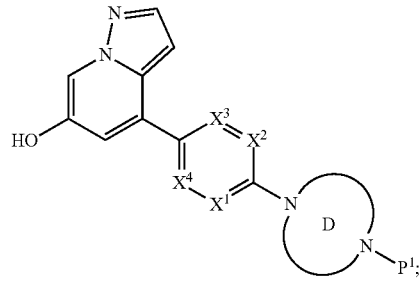

wherein Ring D is as defined for Formula I, $P^1$ is an amino protecting group, and $X^1$, $X^2$, $X^3$, and $X^4$ are as defined for Formula I;

(ii) reacting compound 19 with C1-C6 alkyl-X optionally substituted with 1-3 fluoros, hydroxyC2-C6 alkyl-X wherein the alkyl portion is optionally substituted with a C3-C6 cycloalkylidene ring, dihydroxyC3-C6 alkyl-X, (C1-C6 alkoxy)C1-C6 alkyl-X optionally substituted with 1-3 fluoros, $(R^1R^2N)$C1-C6 alkyl-X, (hetAr$^1$)C1-C3 alkyl-X, (C3-C6 cycloalkyl)C1-C3 alkyl-X, (hetCyc$^a$)C1-C3 alkyl-X, or hetCyc$^a$-X, wherein $R^1$, $R^2$, hetAr$^1$ and hetCyc$^a$ are as defined for Formula I and X is a leaving atom or group such as a halide or a triflate, in the presence of a base, to provide compound 20

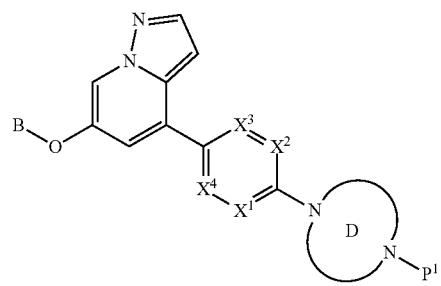

wherein Ring D is as defined for D of Formula I, $P^1$ is an amino protecting group, $X^1$, $X^2$, $X^3$, and $X^4$ are as defined for Formula I and B is C1-C6 alkyl optionally substituted with 1-3 fluoros, hydroxyC2-C6 alkyl, dihydroxyC3-C6 alkyl, (C1-C6 alkoxy)C1-C6 alkyl optionally substituted with 1-3 fluoros, $(R^1R^2N)$C1-C6 alkyl, (hetAr$^1$)C1-C3 alkyl, (C3-C6 cycloalkyl)C1-C3 alkyl, (hetCyc$^a$)C1-C3 alkyl, or hetCyc$^a$, wherein $R^1$, $R^2$, hetAr$^1$, hetCyc$^a$ are as defined for Formula I, followed by removal of the protecting group $P^1$ and optionally functionalizing Ring D; or (g) for a compound of Formula I wherein A is H or Cl, B is H, and $X^1$, $X^2$, $X^3$, $X^4$, Ring D and E are as defined for Formula I, treating a compound of formula

123

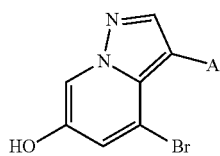

wherein A is H or Cl with a corresponding boronic ester of formula 10

10

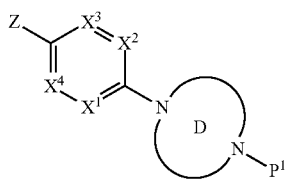

wherein Ring D, X$^1$, X$^2$, X$^3$ and X$^4$ are as defined for Formula I; P$^1$ is an amino protecting group; Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from C1-C3 alkyl, to provide a compound of formula 19

19

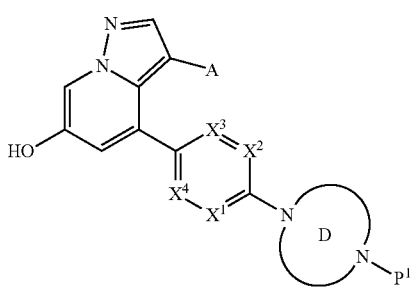

wherein Ring D, X$^1$, X$^2$, X$^3$, and X$^4$ are as defined for Formula I, P$^1$ is an amino protecting group and A is H or Cl, followed by removal of the protecting group P$^1$ and optionally functionalizing Ring D; or (h) for a compound of Formula I wherein A is H or Cl, and B, X$^1$, X$^2$, X$^3$, X$^4$, Ring D and E are as defined for Formula I, coupling a compound of the formula

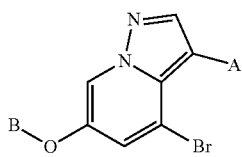

wherein A is H or Cl, and B is as defined for Formula I, with a corresponding boronic ester of formula 10

124

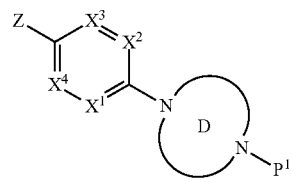

wherein Ring D, X$^1$, X$^2$, X$^3$ and X$^4$ are as defined for Formula I; P$^1$ is an amino protecting group, and Z is —B(OR$^x$)(OR$^y$) and R$^z$ and R$^y$ are H or (1-6C)alkyl, or R$^x$ and R$^y$ together with the atoms to which they are connected form a 5-6 membered ring optionally substituted with 1-4 substituents selected from C1-C3 alkyl, in the presence of a palladium catalyst and optionally a ligand and in the presence of a base, to provide a compound of the formula

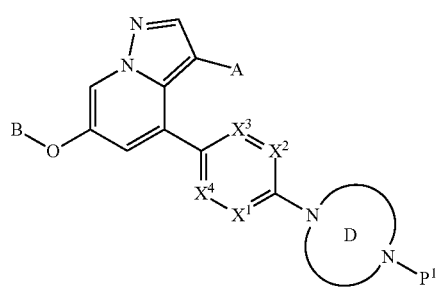

wherein Ring D, X$^1$, X$^2$, X$^3$, X$^4$ and B are as defined for Formula I; A is H or Cl; and P$^1$ is an amino protecting group, followed by removal of the protecting group P$^1$ and optionally functionalizing Ring D;

(i) for a compound of Formula I wherein A is H, and B, X$^1$, X$^2$, X$^3$, X$^4$, Ring D and E are as defined for Formula I, coupling a compound of formula 24

24

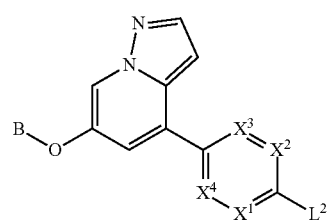

wherein L$^2$ is a leaving group and B, X$^1$, X$^2$, X$^3$, and X$^4$ are as defined for Formula I, with a compound of formula 15

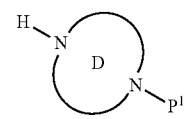

wherein P$^1$ is an amino protecting group and Ring D is as defined for Formula I, to provide a compound of formula 20

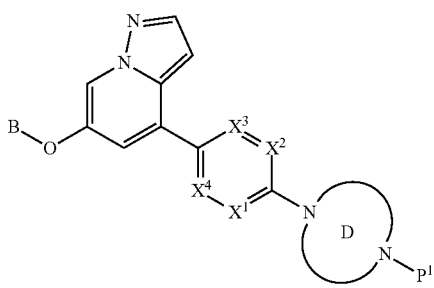

wherein $P^1$ is an amino protecting group, and Ring D, $X^1$, $X^2$, $X^3$, $X^4$, and B are as defined for Formula I, followed by removal of the protecting group $P^1$ and optionally functionalizing Ring D; and removing any additional protecting groups if present and optionally forming a pharmaceutically acceptable salt thereof.

The term "amino protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amino protecting groups are acetyl, trifluoroacetyl, t-butyloxycarbonyl ("Boc"), benzyloxycarbonyl ("CBz") and 9-fluorenylmethyleneoxycarbonyl ("Fmoc"). Further examples of these groups, and other protecting groups, are found in T. W. Greene, et al., Greene's Protective Groups in Organic Synthesis. New York: Wiley Interscience, 2006.

Hydroxy groups may be protected with any convenient hydroxy protecting group, for example as described in T. W. Greene, et al., Greene's Protective Groups in Organic Synthesis. New York: Wiley Interscience, 2006. Examples include benzyl, trityl, silyl ethers, and the like.

Nitrogen atoms in compounds described in any of the above methods may be protected with any convenient nitrogen protecting group, for example as described in Greene & Wuts, eds., "Protecting Groups in Organic Synthesis", $2^{nd}$ ed. New York; John Wiley & Sons, Inc., 1991. Examples of nitrogen protecting groups include acyl and alkoxycarbonyl groups, such as t-butoxycarbonyl (BOC), phenoxycarbonyl, and [2-(trimethylsilyl)ethoxy]methyl (SEM).

The ability of test compounds to act as RET inhibitors may be demonstrated by the assay described in Example A. $IC_{50}$ values are shown in Table 5.

In some embodiments, the compounds provided herein exhibit potent and selective RET inhibition. For example, the compounds provided herein exhibit nanomolar potency against wild type RET and select RET mutants, including the KIF5B-RET fusion and V804M gatekeeper mutation, with minimal activity against related kinases.

In some embodiments, the compounds of Formula I or a pharmaceutically acceptable salt or solvate thereof, selectively target a RET kinase. For example, a compound of Formula I or a pharmaceutically acceptable salt or solvate thereof, can selectively target a RET kinase over another kinase or non-kinase target.

In some embodiments, a compound of Formula I or a pharmaceutically acceptable salt or solvate thereof, exhibits at least a 30-fold selectivity for a RET kinase over another kinase. For example, a compound of Formula I or a pharmaceutically acceptable salt or solvate thereof, exhibits at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 200-fold selectivity; at least 300-fold selectivity; at least 400-fold selectivity; at least 500-fold selectivity; at least 600-fold selectivity; at least 700-fold selectivity; at least 800-fold selectivity; at least 900-fold selectivity; or at least 1000-fold selectivity for a RET kinase over another kinase. In some embodiments, selectivity for a RET kinase over another kinase is measured in a cellular assay (e.g., a cellular assay as provided herein).

In some embodiments, the compounds provided herein can exhibit selectivity for a RET kinase over a KDR kinase (e.g., VEGFR2). In some embodiments, the selectivity for a RET kinase over a KDR kinase is observed without loss of gatekeeper mutant potency. In some embodiments, the selectivity over a KDR kinase is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 150-fold selectivity; at least 200-fold selectivity; at least 250-fold selectivity; at least 300-fold selectivity; at least 350-fold selectivity; or at least 400-fold selectivity) as compared to the inhibition of KIF5B-RET (i.e. the compounds were more potent against KIF5B-RET than KDR). In some embodiments, the selectivity for a RET kinase over a KDR kinase is about 30-fold. In some embodiments, the selectivity for a RET kinase over a KDR kinase is at least 100-fold. In some embodiments, the selectivity for a RET kinase over a KDR kinase is at least 150-fold. In some embodiments, the selectivity for a RET kinase over a KDR kinase is at least 400-fold. Without being bound by any theory, potent KDR kinase inhibition is believed to be a common feature among multikinase inhibitors (MKIs) that target RET and may be the source of the dose-limiting toxicities observed with such compounds.

In some embodiments, inhibition of V804M was similar to that observed for wild-type RET. For example, inhibition of V804M was within about 2-fold (e.g., about 5-fold, about 7-fold, about 10-fold) of inhibition of wild-type RET (i.e. the compounds were similarly potent against wild-type RET and V804M). In some embodiments, selectivity for a wild-type or V804M RET kinase over another kinase is measured in an enzyme assay (e.g., an enzyme assay as provided herein). In some embodiments, the compounds provided herein exhibit selective cytotoxicity to RET-mutant cells.

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor.

In some embodiments, the compounds of Formula I or a pharmaceutically acceptable salt or solvate thereof, exhibit one or more of high GI absorption, low clearance, and low potential for drug-drug interactions.

Compounds of Formula I are useful for treating diseases and disorders which can be treated with a RET kinase inhibitor, such as RET-associated diseases and disorders, e.g., proliferative disorders such as cancers, including hematological cancers and solid tumors, and gastrointestinal disorders such as IBS.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with a dysregulation of a RET gene, a RET protein, or expression or activity, or level of any of the same (a RET-associated cancer) (e.g., as determined using a regulatory agency-approved, e.g., FDA-approved, assay or kit). In some embodiments, the subject has a tumor that is positive for a dysregulation of a RET gene, a RET protein, or expression or activity, or level of any of the same (e.g., as determined using a regulatory agency-approved assay or kit). The subject can be a subject with a tumor(s) that is positive for a dysregulation of a RET gene, a RET protein, or expression or activity, or level of any of the same (e.g., identified as positive using a regulatory agency-approved, e.g., FDA-approved, assay or kit). The subject can be a subject whose tumors have a dysregulation of a RET gene, a RET protein, or expression or activity, or a level of the same (e.g., where the tumor is identified as such using a regulatory agency-approved, e.g., FDA-approved, kit or assay). In some embodiments, the subject is suspected of having a RET-associated cancer. In some embodiments, the subject has a clinical record indicating that the subject has a tumor that has a dysregulation of a RET gene, a RET protein, or expression or activity, or level of any of the same (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula I are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "RET-associated disease or disorder" as used herein refers to diseases or disorders associated with or having a dysregulation of a RET gene, a RET kinase (also called herein RET kinase protein), or the expression or activity or level of any (e.g., one or more) of the same (e.g., any of the types of dysregulation of a RET gene, a RET kinase, a RET kinase domain, or the expression or activity or level of any of the same described herein). Non-limiting examples of a RET-associated disease or disorder include, for example, cancer and gastrointestinal disorders such as irritable bowel syndrome (IBS).

The term "RET-associated cancer" as used herein refers to cancers associated with or having a dysregulation of a RET gene, a RET kinase (also called herein RET kinase protein), or expression or activity, or level of any of the same. Non-limiting examples of a RET-associated cancer are described herein.

The phrase "dysregulation of a RET gene, a RET kinase, or the expression or activity or level of any of the same" refers to a genetic mutation (e.g., a RET gene translocation that results in the expression of a fusion protein, a deletion in a RET gene that results in the expression of a RET protein that includes a deletion of at least one amino acid as compared to the wild-type RET protein, a mutation in a RET gene that results in the expression of a RET protein with one or more point mutations, or an alternative spliced version of a RET mRNA that results in a RET protein having a deletion of at least one amino acid in the RET protein as compared to the wild-type RET protein) or a RET gene amplification that results in overexpression of a RET protein or an autocrine activity resulting from the overexpression of a RET gene in a cell that results in a pathogenic increase in the activity of a kinase domain of a RET protein (e.g., a constitutively active kinase domain of a RET protein) in a cell. As another example, a dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of RET that includes a functional kinase domain, and a second portion of a partner protein (i.e., that is not RET). In some examples, dysregulation of a RET gene, a RET protein, or expression or activity or level of any of the same can be a result of a gene translocation of one RET gene with another non-RET gene. Non-limiting examples of fusion proteins are described in Table 1. Non-limiting examples of RET kinase protein point mutations/insertions/deletions are described in Table 2. Additional examples of RET kinase protein mutations (e.g., point mutations) are RET inhibitor resistance mutations. Non-limiting examples of RET inhibitor resistance mutations are described in Tables 3 and 4.

The term "wildtype" or "wild-type" describes a nucleic acid (e.g., a RET gene or a RET mRNA) or protein (e.g., a RET protein) that is found in a subject that does not have a RET-associated disease, e.g., a RET-associated cancer (and optionally also does not have an increased risk of developing a RET-associated disease and/or is not suspected of having a RET-associated disease), or is found in a cell or tissue from a subject that does not have a RET-associated disease, e.g., a RET-associated cancer (and optionally also does not have an increased risk of developing a RET-associated disease and/or is not suspected of having a RET-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating cancer (e.g., a RET-associated cancer) in a patient in need of such treatment, the method comprising administering to the patient a therapeutically effective amount of a compound of Formula I or a pharmaceutically acceptable salt or solvate thereof or a pharmaceutical composition thereof. For example, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of a compound of Formula I or a pharmaceutically acceptable salt or solvate thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions. Non-limiting examples of RET kinase protein point mutations/insertions/deletions are described in Table 2. In some embodiments, the RET kinase protein point mutations/insertions/deletions are selected from the group consisting of M918T, M918V, C634W, V804L, and V804M. In some embodiments, a compound of Formula I is selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt or solvate thereof.

In some embodiments of any of the methods or uses described herein, the cancer (e.g., RET-associated cancer) is a hematological cancer. In some embodiments of any of the methods or uses described herein, the cancer (e.g., RET-associated cancer) is a solid tumor. In some embodiments of any of the methods or uses described herein, the cancer (e.g., RET-associated cancer) is lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), thyroid ademona, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., RET-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are RET-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CMML.

In some embodiments, the cancer (e.g., the RET-associated cancer) is a solid tumor. Examples of solid tumors (e.g., solid tumors that are RET-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the patient is a human.

Compounds of Formula I and pharmaceutically acceptable salts and solvates thereof are also useful for treating a RET-associated cancer.

Accordingly, also provided herein is a method for treating a patient diagnosed with or identified as having a RET-associated cancer, e.g., any of the exemplary RET-associated cancers disclosed herein, comprising administering to the patient a therapeutically effective amount of a compound of Formula I or a pharmaceutically acceptable salt or solvate thereof, or a pharmaceutical composition thereof as defined herein.

Dysregulation of a RET kinase, a RET gene, or the expression or activity or level of any (e.g., one or more) of the same can contribute to tumorigenesis. For example, a dysregulation of a RET kinase, a RET gene, or expression or activity or level of any of the same can be a translocation, overexpression, activation, amplification, or mutation of a RET kinase, a RET gene, or a RET kinase domain. Translocation can include translocations involving the RET kinase domain, mutations can include mutations involving the RET ligand-binding site, and amplification can be of a RET gene. Other dysregulations can include RET mRNA splice variants and RET autocrine/paracrine signaling, which can also contribute to tumorigenesis.

In some embodiments, the dysregulation of a RET gene, a RET kinase, or expression or activity or level of any of the same, includes overexpression of wild-type RET kinase (e.g., leading to autocrine activation). In some embodiments, the dysregulation of a RET gene, a RET kinase protein, or expression or activity or level of any of the same, includes overexpression, activation, amplification, or mutation in a chromosomal segment comprising the RET gene or a portion thereof, including, for example, the kinase domain portion, or a portion capable of exhibiting kinase activity.

In some embodiments, the dysregulation of a RET gene, a RET kinase protein, or expression or activity or level of any of the same, includes one or more chromosome translocations or inversions resulting in a RET gene fusion. In some embodiments, the dysregulation of a RET gene, a RET kinase protein, or expression or activity or level of any of the same, is a result of genetic translocations in which the expressed protein is a fusion protein containing residues from a non-RET partner protein, and includes a minimum of a functional RET kinase domain.

Non-limiting examples of RET fusion proteins are shown in Table 1.

TABLE 1

Exemplary RET Fusion Partners and Cancers

| Fusion Partner | Non-limiting Exemplary RET-Associated Cancer(s) |
|---|---|
| BCR | Chronic Myelomonocytic Leukemia (CMML) |
| CLIP1 | Adenocarcinoma |
| KIF5B | NSCLC, Ovarian Cancer, Spitzoid Neoplasms; Lung Adenocarcinoma[3, 4, 14, 28]; Adenosquamous Carcinomas[15] |
| CCDC6 (also called PTC1, D10S170, or H4) | NSCLC, Colon Cancer, Papillary Thyroid Cancer; Adenocarcinomas; Lung Adenocarcinoma; Metastatic Colorectal Cancer[5]; Adenosquamous Carcinomas[15], Breast Cancer[30] |
| PTC1ex9 (a novel CCDC6 rearrangement) | Metastatic papillary thyroid cancer[2] |
| NCOA4 (also called PTC3, ELE1, and RFG) | Papillary Thyroid Cancer[21], NSCLC, Colon Cancer, Salivary Gland Cancer, Metastatic Colorectal Cancer[5]; Lung Adenocarcinoma[15]; |

TABLE 1-continued

Exemplary RET Fusion Partners and Cancers

| Fusion Partner | Non-limiting Exemplary RET-Associated Cancer(s) |
|---|---|
| | Adenosquamous Carcinomas[15] Diffuse Sclerosing Variant of Papillary Thyroid Cancer[16], Breast Cancer[30], Acinic Cell Carcinoma[32], Mammary Analog Secretory Carcinoma[33] |
| TRIM33 (also called PTC7 and RFG7) | NSCLC, Papillary Thyroid Cancer |
| ERC1 (also called ELKS) | Papillary Thyroid Cancer, Breast Cancer |
| FGFR1OP | CMML, Primary Myelofibrosis with secondary Acute Myeloid Leukemia |
| MBD1 (also known as PCM1) | Papillary Thyroid Cancer |
| RAB61P2 | Papillary Thyroid Cancer |
| PRKAR1A (also called PTC2) | Papillary Thyroid Cancer |
| TRIM24 (also called PTC6) | Papillary Thyroid Cancer |
| KTN1 (also called PTC8) | Papillary Thyroid Cancer |
| GOLGA5 (also called PTC5) | Papillary Thyroid Cancer, Spitzoid Neoplasms |
| HOOK3 | Papillary Thyroid Cancer |
| KIAA1468 (also called PTC9 and RFG9) | Papillary Thyroid Cancer, Lung Adenocarcinoma[8, 12] |
| TRIM27 (also called RFP) | Papillary Thyroid Cancer |
| AKAP13 | Papillary Thyroid Cancer |
| FKBP15 | Papillary Thyroid Cancer |
| SPECC1L | Papillary Thyroid Cancer; Thyroid Gland Carcinoma |
| TBL1XR1 | Papillary Thyroid Cancer; Thyroid Gland Carcinoma |
| CEP55 | Diffuse Gastric Cancer[7] |
| CUX1 | Lung Adenocarcinoma |
| ACBD5 | Papillary Thyroid Carcinoma |
| MYH13 | Medullary Thyroid Carcinoma[1] |
| Uncharacterized | Inflammatory Myofibroblastic Tumor[6] |
| PIBF1 | Bronchiolus Lung Cell Carcinoma[9] |
| KIAA1217 (also called SKT) | Papillary Thyroid Cancer[10, 13] Lung Adenocarcinoma[14] NSCLC[14] |
| MPRIP | NSCLC[11] |
| HRH4-RET | Thyroid cancer and/or paillary thyroid carcinoma[17] |
| Ria-RET | Thyroid cancer and/or papillary thyroid carcinoma[17] |
| RFG8 | Papillary thyroid carcinoma[18] |
| FOXP4 | Lung adenocarcinoma[19] |
| MYH10 | Infantile myofibromatosis[20] |
| HTIF1 | Various[22] |
| TIF1G | Various[22] |
| H4L | Various[22] |
| PTC4 (a novel NCO4/ELE1 rearrangement) | Papillary thyroid cancer[23] |
| FRMD4A | NSCLC[24] |
| SQSTM1 | Papillary thyroid carcinoma[25] |
| AFAP1L2 | Papillary thyroid carcinoma[25] |
| AFAP1 | NSCLC[31] |
| PPFIBP2 | Papillary thyroid carcinoma[25] |
| EML4 | Papillary thyroid cancer[26] |
| PARD3 | NSCLC[27] |
| UVELD | Papillary thyroid cancer[29] |
| RASGEF1A | Breast cancer[30] |
| TEL | In vitro[34] |
| RUFY1 | Colorectal Cancer[35] |
| OLFM4 | Small-Bowel Cancer[36] |
| UEVLD | Papillary Thyroid Carcinoma[37] |
| DLG5 | Non-Anaplastic Thyroid (NAT) Cancer[38] |
| RRBP1 | Colon Cancer[39] |

[1]Grubbs et al., J. Clin. Endocrinol. Metab. 100: 788-793, 2015.
[2]Halkova et al., Human Pathology 46: 1962-1969, 2015.
[3]U.S. Pat. No. 9,297,011
[4]U.S. Pat. No. 9,216,172
[5]Le Rolle et al., Oncotarget. 6(30): 28929-37, 2015.
[6]Antonescu et al., Am J Surg Pathol. 39(7): 957-67, 2015.
[7]U.S. Patent Application Publication No. 2015/0177246.
[8]U.S. Patent Application Publication No. 2015/0057335.
[9]Japanese Patent Application Publication No. 2015/109806A.
[10]Chinese Patent Application Publication No. 105255927A.
[11]Fang, et al. Journal of Thoracic Oncology 11.2 (2016): S21-S22.
[12]European Patent Application Publication No. EP3037547A1.
[13]Lee et al., Oncotarget. DOI: 10.18632/oncotarget.9137, e-published ahead of printing, 2016.
[14]Saito et al., Cancer Science 107: 713-720, 2016.
[15]Pirker et al., Transl. Lung Cancer Res. 4(6): 797-800, 2015.
[16]Joung et al., Histopathology 69(1): 45-53, 2016.
[17]PCT Patent Application Publication No. WO 2016/141169.
[18]Klugbauer et al., Cancer Res., 60(24): 7028-32, 2000.
[19]Bastien et al., Journal of Molecular Diagnostics, 18(6): 1027, Abstract Number: S120, 2016 Annual Meeting of the Association for Molecular Pathology, Charlotte, NC, 2016.
[20]Rosenzweig et al., Pediatr Blood Cancer, doi: 10.1002/pbc.26377, 2016.
[21]Su et al., PLoS One, 11(111): e0165596, 2016.
[22]U.S. Pat. No. 9,487,491.
[23]Fugazzola et al., Oncogene, 13(5): 1093-7, 1996.
[24]Velcheti et al., J Thorac Oncol., 12(2): e15-e16. doi: 10.1016/j.jtho.2016.11.274, 2017.
[25]Iyama et al., Thyroid, doi: 10.1089/thy.2016.0673, 2017.
[26]Demeure et al., World J Surg.. 38(6): 1296-305. doi: 10.1007/s00268-014-2485-3, 2014.
[27]Sabari et al., Oncoscience, Advance Publications, www.impactjournals.com/oncoscience/files/papers/1/345/345.pdf, 2017.
[28]U.S. Patent Application Publication No. 2017/0014413.
[29]Lu et al., Oncotarget, doi: 10.18632/oncotarget.17412, [Epub ahead of print], 2017.
[30]Hirshfield et al., Cancer Research, (February 2017) Vol. 77, No. 4, Supp. 1. Abstract Number: P3-07-02. Meeting Info: 39th Annual CTRC-AACR San Antonio Breast Cancer Symposium. San Antonio, TX, United States. 6 Dec. 2016-10 Dec. 2016.
[31]Morgensztern et al., Journal of Thoracic Oncology, (January 2017) Vol. 12, No. 1, Supp. 1, pp. S717-S718, Abstract Number: P1.07-035, Meeting Info: 17th World Conference of the International Association for the Study of Lung Cancer, IASLC 2016. Vienna, Austria. 4 Dec. 2016.
[32]Dogan et al., Laboratory Investigation, (February 2017) Vol. 97, Supp. 1, pp. 323A. Abstract Number: 1298, Meeting Info: 106th Annual Meeting of the United States and Canadian Academy of Pathology, USCAP 2017. San Antonio, TX, United States.
[33]Dogan et al., MODERN PATHOLOGY, Vol. 30, Supp. [2], pp. 323A-323A. MA 1298, 2017.
[34]PCT Patent Application Publication No. WO 2017/146116.
[35]PCT Patent Application Publication No. WO 2017/122815.
[36]Reeser et al., J. Mol. Diagn., 19(5): 682-696, doi: 10.1016/j.jmoldx.2017.05.006, 2017.
[37]Lu et al., Oncotarget, 8(28): 45784-45792, doi: 10.18632/oncotarget.17412, 2017.
[38]Ibrahimpasic et al., Clin. Cancer Res., doi: 10.1158/1078-0432.CCR-17-1183, 2017.
[39]Kloosterman et al., Cancer Res., 77(14): 3814-3822. doi: 10.1158/0008-5472.CAN-16-3563, 2017.

In some embodiments, the dysregulation of a RET gene, a RET kinase, or expression or activity or level of any of the same, includes one or more deletions (e.g., deletion of an amino acid at position 4), insertions, or point mutation(s) in a RET kinase. In some embodiments, the dysregulation of a RET gene, a RET kinase, or expression or activity or level of any of the same, includes a deletion of one or more residues from the RET kinase, resulting in constitutive activity of the RET kinase domain.

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2).

TABLE 2

Activating RET Kinase Protein Point Mutations/Insertions/Deletions
Exemplary RET Point Mutations Amino acid position 2
Amino acid position 3
Amino acid position 4
Amino acid position 5
Amino acid position 6
Amino acid position 7
Amino acid position 8
Amino acid position 11
Amino acid position 12
Amino acid position 13
Amino acid position 20
Amino acid position 32 (e.g., S32L)
Amino acid position 34 (e.g., D34S)
Amino acid position 40 (e.g., L40P)
Amino acid position 56 (e.g., L56M)[30]
Amino acid position 64 (e.g., P64L)
Amino acid position 67 (e.g., R67H)
Amino acid position 114 (e.g., R114H)
Amino acid position 136 (e.g., glutamic acid to stop codon)
Amino acid position 145 (e.g., V145G)
Amino acid position 180 (e.g., arginine to stop codon)
Amino acid position 200
Amino acid position 292 (e.g., V292M)
Amino acid position 294
Amino acid position 321 (e.g., G321R)
Amino acid position 330 (e.g., R330Q)
Amino acid position 338 (e.g., T338I)
Amino acid position 360 (e.g., R360W)
Amino acid position 373 (e.g., alanine to frameshift)
Amino acid position 393 (e.g., F393L)
Amino acid position 423 (e.g., G423R)[27]
Amino acid position 432
Amino acid position 446 (e.g., G446R)[28]
Δ Amino acid residues 505-506 (6-Base Pair In-Frame Germline Deletion in Exon 7)[3]
Amino acid position 510 (e.g., A510V)
Amino acid position 511 (e.g., E511K)
Amino acid position 513 (e.g., G513D)[7*]
Amino acid position 515 (e.g., C515S, C515W[4])
Amino acid position 525 (e.g., R525W)[7*]
Amino acid position 531 (e.g., C531R, or 9 base pair duplication[2])
Amino acid position 532 (e.g., duplication)[2]
Amino acid position 533 (e.g., G533C, G533S)
Amino acid position 550 (e.g., G550E)
Amino acid position 591 (e.g., V591I)
Amino acid position 593 (e.g., G593E)
Amino acid position 595 (e.g., E595D and E595A)[18]
Amino acid position 600 (e.g., R600Q)
Amino acid position 602 (e.g., I602V)[6]
Amino acid position 603 (e.g., K603Q, K603E[2])
Amino acid position 606 (e.g., Y606C)
Amino acid position 609 (e.g., C609Y, C609S, C609G, C609R, C609F, C609W, C609C[32])
Amino acid position 611 (e.g., C611R, C611S, C611G, C611Y, C611F, C611W)
Amino acid position 616 (e.g., E616Q)[23]
Amino acid position 618 (e.g., C618S, C618Y, C618R, C618Y, C618G, C618F, C618W)
Amino acid position 619 (e.g., F619F)
Amino acid position 620 (e.g., C620S, C620W, C620R, C620G, C620L, C620Y, C620F)
Amino acid position 623 (e.g., E623K)
Amino acid position 624 (e.g., D624N)
Amino acid position 630 (e.g., C630A, C630R, C630S, C630Y, C630F, C630W)

TABLE 2-continued

Activating RET Kinase Protein Point Mutations/Insertions/Deletions
Exemplary RET Point Mutations Amino acid position 631 (e.g., D631N, D631Y, D631A, D631G, D631V, D631E,)
Amino acid position 632 (e.g., E632K, E632G[5, 11])
Δ Amino acid residues 632-633 (6-Base Pair In-Frame Germline Deletion in Exon 11)[9]
Amino acid position 633 (e.g., 9 base pair duplication[2])
Amino acid position 634 (e.g., C634W, C634Y, C634S, C634R, C634F, C634G, C634L, C634A, or C634T, or an insertion ELCR[2], or a 12 base pair duplication[2]) (e.g., causing MTC)
Amino acid position 635 (e.g., R635G)
Amino acid position 636 (e.g., T636P[2], T636M[4])
Amino acid position 640 (e.g., A640G)
Amino acid position 641 (e.g., A641S, A641T[8])
Amino acid position 648 (e.g., V648I)
Amino acid position 649 (e.g., S649L)[28]
Amino acid position 664 (e.g., A664D)
Amino acid position 665 (e.g., H665Q)
Amino acid position 666 (e.g., K666E, K666M, K666N, K666R)
Amino acid position 675 (T675T, silent nucleotide change)[18]
Amino acid position 686 (e.g., S686N)
Amino acid position 689 (e.g., S689T)[18]
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K)[6]
Amino acid position 732 (e.g., E732K)[20]
Amino acid position 736 (e.g., G736R)[6]
Amino acid position 748 (e.g., G748C)
Amino acid position 750 (e.g., A750P)
Amino acid position 765 (e.g., S765P)
Amino acid position 766 (e.g., P766S, P766M[6])
Amino acid position 768 (e.g., E768Q, E768D)
Amino acid position 769 (e.g., L769L)
Amino acid position 770 (e.g., R770Q)
Amino acid position 771 (e.g., D771N)
Amino acid position 777 (e.g., N777S)
Amino acid position 778 (e.g., V778I)
Amino acid position 781 (e.g., Q781R)
Amino acid position 788 (e.g., I788I[32])
Amino acid position 790 (e.g., L790F)
Amino acid position 791 (e.g., Y791F, Y791N[24])
Amino acid position 802
Amino acid position 804 (e.g., V804L[15, 16], V804M[15, 16], V804E[12]) (e.g., causing MTC)
Amino acid position 805 (e.g., E805K)
Amino acid position 804/805 (e.g., V804M/E805K)[17]
Amino acid position 806 (e.g., Y806F, Y806S[12], Y806G, Y806C[2, 12, 14], Y806E[14], Y806H[12], Y806N[12], Y806Y[32])
Amino acid position 810 (e.g., G810R[12], G810S[12], G810A[13])
Amino acid position 818 (e.g., E818K)
Amino acid position 819 (e.g., S819I)
Amino acid position 823 (e.g., G823E)
Amino acid position 826 (e.g., Y826M, Y826S)[10]
Amino acid position 833 (e.g., R833C)
Amino acid position 836 (e.g., S836S)[19]
Amino acid position 841 (e.g., P841L, P841P)
Amino acid position 843 (e.g., E843D)
Amino acid position 844 (e.g., R844W, R844Q, R844L)
Amino acid position 848 (e.g., M848T)
Amino acid position 852 (e.g., I852M)
Amino acid position 865 (e.g., L865V)[12]
Amino acid position 870 (e.g., L870F)[12]
Amino acid position 873 (e.g., R873W)
Amino acid position 876 (e.g., A876V)
Amino acid position 881 (e.g., L881V)
Amino acid position 882
Amino acid position 883 (e.g., A883F, A883S, A883T)
Amino acid position 884 (e.g., E884K)
Amino acid position 886 (e.g., R886W)
Amino acid position 891 (e.g., S891A, S891S[32])

TABLE 2-continued

Activating RET Kinase Protein Point Mutations/Insertions/Deletions
Exemplary RET Point Mutations Amino acid position 897 (e.g., R897Q)
Amino acid position 898 (e.g., D898V)
Amino acid position 900 (e.g., Y900F)[22]
Amino acid position 901 (e.g., E901K)
Amino acid position 904 (e.g., S904F, S904S, S904C[2])
Amino acid position 905 (e.g., Y905F)[22]
Amino acid position 907 (e.g., K907E, K907M)
Amino acid position 908 (e.g., R908K)
Amino acid position 911 (e.g., G911D)
Amino acid position 912 (e.g., R912P, R912Q)
Amino acid position 918 (e.g., M918T[2], M918V, M918L[6]) (e.g., causing MTC)
Amino acid position 919 (e.g., A919V)
Amino acid position 921 (e.g., E921K)
Amino acid position 922 (e.g., S922P, S922Y)
Amino acid position 930 (e.g., T930M)
Amino acid position 961 (e.g., F961L)
Amino acid position 972 (e.g., R972G)
Amino acid position 981 (e.g., Y981F)[22]
Amino acid position 982 (e.g., R982C)
Amino acid position 1009 (e.g., M1009V)
Amino acid position 1015 (e.g., Y1015F)[22]
Amino acid position 1017 (e.g., D1017N)
Amino acid position 1041 (e.g., V1041G)
Amino acid position 1064 (e.g., M1064T)
Amino acid position 1096 (e.g., Y1096F)[21]
RET + 3[1]
(In-Frame Deletion in Exons 6 and 11)[25]
(3bp In-Frame Deletion in Exon 15)[26]
Nucleotide position 2136 + 2 (e.g., 2136 + 2T > G)[29]
(del632-636 ins6)[31]
Amino acid positions 791 and 852 (e.g., Y791F + I852M)[31]
Amino acid positions 634 and 852 (e.g., C634R + I852M)[31]

[1]U.S. Patent Application Publication No. 2014/0272951.
[2]Krampitz et al., Cancer 120: 1920-1931, 2014.
[3]Latteyer, et al., J. Clin. Endocrinol. Metab. 101(3): 1016-22, 2016.
[4]Silva, et al. Endocrine 49.2: 366-372, 2015.
[5]Scollo, et al., Endocr. J. 63(1): 87-91, 2016.
[6]Jovanovic, et al., Prilozi 36(1): 93-107, 2015.
[7]Qi, et al., Oncotarget. 6(32): 33993-4003, 2015. *R525W and G513D appear to act in combination with S891A to enchance oncogenic activity.
[8]Kim, et al. ACTA ENDOCRINOLOGICA-BUCHAREST 11.2, 189-194, 2015.
[9]Cecchirini, et al. Oncogene, 14, 2609-2612, 1997.
[10]Karrasch, et al. Eur. Thyroid J., 5(1): 73-7, 2016.
[11]Scollo et al., Endocr. J. 63: 87-91, 2016.
[12]PCT Patent Application Publication No. WO 2016/127074.
[13]Huang et al., Mol. Cancer Ther., 2016 Aug 5. pii: molcanther.0258.2016. [Epub ahead of print].
[14]Carlomagno, et al., Endocr. Rel. Cancer 16(1): 233-41, 2009.
[15]Yoon et al., J. Med. Chem. 59(1): 358-73, 2016.
[16]U.S. Pat. No. 8,629,135.
[17]Cranston, et al., Cancer Res. 66(20): 10179-87, 2006.
[18]Kheiroddin et al., Clin. Lab. 62(5): 871-6, 2016.
[19]Ceolin et al., PLoS One. 11(2): e0147840, doi: 10.1371/journal.pone.0147840, 2016.
[20]Nadezda et al., Summer Undergraduate Research Programs (SURP) Student Abstracts, University of Oklahoma Health Sciences Center, 2016.
[21]Liu et al., J. Biol. Chem., 271(10): 5309-12, 1995.
[22]Kato et al., Cancer Res., 62: 2414-22, 2002.
[23]Grey et al., Endocrine Pathology, doi: 10.1007/s12022-016-9451-6, 2016.
[24]De Almeida et al., Endocrine Reviews, 2016, Vol. 37, No. 2, Supp. Supplement 1. Abstract Number: SUN-068; 98th Annual Meeting and Expo of the Endocrine Society, ENDO 2016. Boston, MA, US. 1 Apr. 2016-4 Apr. 2016.
[25]Vanden et al., Annals of Oncology, 2016, Vol. 27, Supp. Supplement 6. Abstract Number: 427PD; 41st European Society for Medical Oncology Congress, ESMP 2016. Copenhagen, Denmark. 7 Oct. 2016-11 Oct. 2016.
[26]Romei et al., European Thyroid Journal (August 2016) Vol. 5, Supp. Supplement 1, pp. 75; 39th Annual Meeting of the European Thyroid Association, ETA 2016. Copenhagen, Denmark. 3 Sep. 2016-6 Sep. 2016.
[27]Lee et al., Oncotarget, 8(4): 6579-6588, doi: 10.18632/oncotarget.14172, 2017.
[28]Zhang et al., Laboratory Investigation, (February 2017) Vol. 97, Supp. 1, pp. 209A. Abstract Number: 840, Meeting Info: 106th Annual Meeting of the United States and Canadian Academy of Pathology, USCAP 2017. San Antonio, TX, United States.
[29]Borecka et al., European Journal of Cancer, (July 2016) Vol. 61, No. 1, pp. S26, Abstract Number: 162, Meeting Info: 24th Biennial Congress of the European Association for Cancer Research, EACR 2016. Manchester, United Kingdom.
[30]Corsello et al., Endocrine Reviews, (JUN 2014) Vol. 35, No. 3, Suppl. S, pp. SUN-0322, Meeting Info.: 96th Annual Meeting and Expo of the Endocrine-Society, Chicago, IL, USA, Jun. 21-24, 2014.
[31]Gazizova et al., Endocrine Reviews, (JUN 2014) Vol. 35, No. 3, Suppl. S, pp. SAT-0304, Meeting Info.: 96th Annual Meeting and Expo of the Endocrine-Society, Chicago, IL, USA, Jun. 21-24, 2014.
[32]Sromek et al., Endocr Pathol., doi: 10.1007/s12022-017-9487-2, 2017.

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2a).

TABLE 2a

Exemplary activating RET Kinase Protein Point
Mutations/Insertions/Deletions
Exemplary RET Point Mutations Amino acid position 20
Amino acid position 32 (e.g., S32L)
Amino acid position 34 (e.g., D34S)
Amino acid position 40 (e.g., L40P)
Amino acid position 64 (e.g., P64L)
Amino acid position 67 (e.g., R67H)
Amino acid position 114 (e.g., R114H)
Amino acid position 145 (e.g., V145G)
Amino acid position 200
Amino acid position 292 (e.g., V292M)
Amino acid position 294
Amino acid position 321 (e.g., G321R)
Amino acid position 330 (e.g., R330Q)
Amino acid position 338 (e.g., T338I)
Amino acid position 360 (e.g., R360W)
Amino acid position 393 (e.g., F393L)
Amino acid position 432
Δ Amino acid residues 505-506 (6-Base Pair In-Frame Germline Deletion in Exon 7)
Amino acid position 510 (e.g., A510V)
Amino acid position 511 (e.g., E511K)
Amino acid position 513 (e.g., G513D)
Amino acid position 515 (e.g., C515S, C515W[4])
Amino acid position 525 (e.g., R525W)
Amino acid position 531 (e.g., C531R, or 9 base pair duplication)
Amino acid position 532 (e.g., duplication)
Amino acid position 533 (e.g., G533C, G533S)
Amino acid position 550 (e.g., G550E)
Amino acid position 591 (e.g., V591I)
Amino acid position 593 (e.g., G593E)
Amino acid position 595 (e.g., E595D and E595A)
Amino acid position 600 (e.g., R600Q)
Amino acid position 602 (e.g., I602V)
Amino acid position 603 (e.g., K603Q, K603E)
Amino acid position 606 (e.g., Y606C)
Amino acid position 609 (e.g., C609Y, C609S, C609G, C609R, C609F, C609W)
Amino acid position 611 (e.g., C611R, C611S, C611G, C611Y, C611F, C611W)
Amino acid position 616 (e.g., E616Q)
Amino acid position 618 (e.g., C618S, C618Y, C618R, C618G, C618F, C618W)
Amino acid position 620 (e.g., C620S, C620W, C620R, C620G, C620L, C620Y, C620F)
Amino acid position 623 (e.g., E623K)
Amino acid position 624 (e.g., D624N)
Amino acid position 630 (e.g., C630A, C630R, C630S, C630Y, C630F, C630W)
Amino acid position 631 (e.g., D631N, D631Y, D631A, D631G, D631V, D631E,)
Amino acid position 632 (e.g., E632K, E632G)
Δ Amino acid residues 632-633 (6-Base Pair In-Frame Germline Deletion in Exon 11)
Amino acid position 633 (e.g., 9 base pair duplication)
Amino acid position 634 (e.g., C634W, C634Y, C634S, C634R, C634F, C634G, C634L, C634A, or

TABLE 2a-continued

Exemplary activating RET Kinase Protein Point
Mutations/Insertions/Deletions
Exemplary RET Point Mutations C634T, or an insertion ELCR, or a 12 base pair
duplication) (e.g., causing MTC)
Amino acid position 635 (e.g., R635G)
Amino acid position 636 (e.g., T636P, T636M)
Amino acid position 640 (e.g., A640G)
Amino acid position 641 (e.g., A641S, A641T)
Amino acid position 648 (e.g., V648I)
Amino acid position 649 (e.g., S649L)
Amino acid position 664 (e.g., A664D)
Amino acid position 665 (e.g., H665Q)
Amino acid position 666 (e.g., K666E, K666M, K666N, K666R)
Amino acid position 686 (e.g., S686N)
Amino acid position 689 (e.g., S689T)
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K)
Amino acid position 732 (e.g., E732K)
Amino acid position 736 (e.g., G736R)
Amino acid position 748 (e.g., G748C)
Amino acid position 750 (e.g., A750P)
Amino acid position 765 (e.g., S765P)
Amino acid position 766 (e.g., P766S, P766M)
Amino acid position 768 (e.g., E768Q, E768D)
Amino acid position 769 (e.g., L769L)
Amino acid position 770 (e.g., R770Q)
Amino acid position 771 (e.g., D771N)
Amino acid position 777 (e.g., N777S)
Amino acid position 778 (e.g., V778I)
Amino acid position 781 (e.g., Q781R)
Amino acid position 790 (e.g., L790F)
Amino acid position 791 (e.g., Y791F, Y791N)
Amino acid position 802
Amino acid position 804 (e.g., V804L, V804M, V804E) (e.g., causing MTC)
Amino acid position 805 (e.g., E805K)
Amino acid position 804/805 (e.g., V804M/E805K)
Amino acid position 806 (e.g., Y806F, Y806S, Y806G, Y806C, Y806E, Y806H, Y806N)
Amino acid position 810 (e.g., G810R, G810S, G810A)
Amino acid position 818 (e.g., E818K)
Amino acid position 819 (e.g., S819I)
Amino acid position 823 (e.g., G823E)
Amino acid position 826 (e.g., Y826M, Y826S)
Amino acid position 833 (e.g., R833C)
Amino acid position 836 (e.g., S836S)
Amino acid position 841 (e.g., P841L, P841P)
Amino acid position 843 (e.g., E843D)
Amino acid position 844 (e.g., R844W, R844Q, R844L)
Amino acid position 848 (e.g., M848T)
Amino acid position 852 (e.g., I852M)
Amino acid position 865 (e.g., L865V)
Amino acid position 870 (e.g., L870F)
Amino acid position 873 (e.g., R873W)
Amino acid position 876 (e.g., A876V)
Amino acid position 881 (e.g., L881V)
Amino acid position 882
Amino acid position 883 (e.g., A883F, A883S, A883T)
Amino acid position 884 (e.g., E884K)
Amino acid position 886 (e.g., R886W)
Amino acid position 891 (e.g., S891A)
Amino acid position 897 (e.g., R897Q)
Amino acid position 898 (e.g., D898V)
Amino acid position 900 (e.g., Y900F)
Amino acid position 901 (e.g., E901K)
Amino acid position 904 (e.g., S904F, S904S, S904C)
Amino acid position 907 (e.g., K907E, K907M)
Amino acid position 908 (e.g., R908K)
Amino acid position 911 (e.g., G911D)
Amino acid position 912 (e.g., R912P, R912Q)
Amino acid position 918 (e.g., M918T, M918V, M918L) (e.g., causing MTC)

TABLE 2a-continued

Exemplary activating RET Kinase Protein Point
Mutations/Insertions/Deletions
Exemplary RET Point Mutations Amino acid position 919 (e.g., A919V)
Amino acid position 921 (e.g., E921K)
Amino acid position 922 (e.g., S922P, S922Y)
Amino acid position 930 (e.g., T930M)
Amino acid position 961 (e.g., F961L)
Amino acid position 972 (e.g., R972G)
Amino acid position 982 (e.g., R982C)
Amino acid position 1009 (e.g., M1009V)
Amino acid position 1015 (e.g., Y1015F)
Amino acid position 1017 (e.g., D1017N)
Amino acid position 1041 (e.g., V1041G)
Amino acid position 1064 (e.g., M1064T)
Amino acid position 1096 (e.g., Y1096F)
RET + 3
(In-Frame Deletion in Exons 6 and 11)
(3bp In-Frame Deletion in Exon 15)

In some embodiments, the dysregulation of a RET gene, a RET kinase, or expression or activity or level of any of the same, includes a splice variation in a RET mRNA which results in an expressed protein that is an alternatively spliced variant of RET having at least one residue deleted (as compared to the wild-type RET kinase) resulting in a constitutive activity of a RET kinase domain.

A "RET kinase inhibitor" as defined herein includes any compound exhibiting RET inhibition activity. In some embodiments, a RET kinase inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitors can exhibit inhibition activity ($IC_{50}$) against a RET kinase of less than about 25 nM, less than about 10 nM, less than about 5 nM, or less than about 1 nM as measured in an assay as provided herein.

As used herein, a "first RET kinase inhibitor" or "first RET inhibitor" is a RET kinase inhibitor as defined herein, but which does not include a compound of Formula I or a pharmaceutically acceptable salt or solvate thereof as defined herein. As used herein, a "second RET kinase inhibitor" or a "second RET inhibitor" is a RET kinase inhibitor as defined herein, but which does not include a compound of Formula I or a pharmaceutically acceptable salt or solvate thereof as defined herein. When both a first and a second RET inhibitor are present in a method provided herein, the first and second RET kinase inhibitor are different.

In some embodiments, the dysregulation of a RET gene, a RET kinase, or expression or activity or level of any of the same, includes at least one point mutation in a RET gene that results in the production of a RET kinase that has one or more amino acid substitutions or insertions or deletions in a RET gene that results in the production of a RET kinase that has one or more amino acids inserted or removed, as compared to the wild-type RET kinase. In some cases, the resulting RET kinase is more resistant to inhibition of its phosphotransferase activity by one or more first RET kinase inhibitor(s), as compared to a wildtype RET kinase or a RET kinase not including the same mutation. Such mutations, optionally, do not decrease the sensitivity of the cancer cell or tumor having the RET kinase to treatment with a compound of Formula I or a pharmaceutically acceptable salt or solvate thereof (e.g., as compared to a cancer cell or a tumor that does not include the particular RET inhibitor resistance mutation). In such embodiments, a RET inhibitor resistance mutation can result in a RET kinase that has one or more of an increased $V_{max}$, a decreased $K_m$ for ATP, and an increased $K_D$ for a first RET kinase inhibitor, when in the presence of a first RET kinase inhibitor, as compared to a wildtype RET kinase or a RET kinase not having the same mutation in the presence of the same first RET kinase inhibitor.

In other embodiments, the dysregulation of a RET gene, a RET kinase, or expression or activity or level of any of the same, includes at least one point mutation in a RET gene that results in the production of a RET kinase that has one or more amino acid substitutions as compared to the wild-type RET kinase, and which has increased resistance to a compound of Formula I or a pharmaceutically acceptable salt or solvate thereof, as compared to a wildtype RET kinase or a RET kinase not including the same mutation. In such embodiments, a RET inhibitor resistance mutation can result in a RET kinase that has one or more of an increased $V_{max}$, a decreased $K_m$, and a decreased $K_D$ in the presence of a compound of Formula I or a pharmaceutically acceptable salt or solvate thereof, as compared to a wildtype RET kinase or a RET kinase not having the same mutation in the presence of the same compound of Formula I or a pharmaceutically acceptable salt or solvate thereof.

Examples of RET inhibitor resistance mutations can, e.g., include point mutations, insertions, or deletions in and near the ATP binding site in the tertiary structure of RET kinase, including but not limited to the gatekeeper residue, P-loop residues, residues in or near the DFG motif, and ATP cleft solvent front amino acid residues. Additional examples of these types of mutations include changes in residues that may affect enzyme activity and/or drug binding including but are not limited to residues in the activation loop, residues near or interacting with the activation loop, residues contributing to active or inactive enzyme conformations, changes including mutations, deletions, and insertions in the loop proceeding the C-helix and in the C-helix. Specific residues or residue regions that may be changed (and are RET inhibitor resistance mutations) include but are not limited to those listed in Table 3 based on the human wildtype RET protein sequence (e.g., SEQ ID NO: 1). Additional examples of RET inhibitor resistance mutation positions are shown in Table 4. Changes to these residues may include single or multiple amino acid changes, insertions within or flanking the sequences, and deletions within or flanking the sequences.

```
Exemplary Sequence of Mature Human RET
Protein
                                          (SEQ ID NO: 1)
MAKATSGAAG LRLLLLLLLP LLGKVALGLY FSRDAYWEKL

YVDQAAGTPL LYVHALRDAP EEVPSFRLGQ HLYGTYRTRL

HENNWICIQE DTGLLYLNRS LDHSSWEKLS VRNRGFPLLT

VYLKVFLSPT SLREGECQWP GCARVYFSFF NTSFPACSSL

KPRELCFPET RPSFRIRENR PPGTFHQFRL LPVQFLCPNI

SVAYRLLEGE GLPFRCAPDS LEVSTRWALD REQREKYELV

AVCTVHAGAR EEVVMVPFPV TVYDEDDSAP TFPAGVDTAS

AVVEFKRKED TVVATLRVFD ADVVPASGEL VRRYTSTLLP

GDTWAQQTFR VEHWPNETSV QANGSFVRAT VHDYRLVLNR
```

```
                    -continued
NLSISENRTM QLAVLVNDSD FQGPGAGVLL LHFNVSVLPV

SLHLPSTYSL SVSRRARRFA QIGKVCVENC QAFSGINVQY

KLHSSGANCS TLGVVTSAED TSGILFVNDT KALRRPKCAE

LHYMVVATDQ QTSRQAQAQL LVTVEGSYVA EEAGCPLSCA

VSKRRLECEE CGGLGSPTGR CEWRQGDGKG ITRNFSTCSP

STKTCPDGHC DVVETQDINI CPQDCLRGSI VGGHEPGEPR

GIKAGYGTCN CFPEEEKCFC EPEDIQDPLC DELCRTVIAA

AVLFSFIVSV LLSAFCIHCY HKFAHKPPIS SAEMTFRRPA

QAFPVSYSSS GARRPSLDSM ENQVSVDAFK ILEDPKWEFP

RKNLVLGKTL GEGEFGKVVK ATAFHLKGRA GYTTVAVKML

KENASPSELR DLLSEFNVLK QVNHPHVIKL YGACSQDGPL

LLIVEYAKYG SLRGFLRESR KVGPGYLGSG GSRNSSSLDH

PDERALTMGD LISFAWQISQ GMQYLAEMKL VHRDLAARNI

LVAEGRKMKI SDFGLSRDVY EEDSYVKRSQ GRIPVKWMAI

ESLFDHIYTT QSDVWSFGVL LWEIVTLGGN PYPGIPPERL

FNLLKTGHRM ERPDNCSEEM YRLMLQCWKQ EPDKRPVFAD

ISKDLEKMMV KRRDYLDLAA STPSDSLIYD DGLSEEETPL

VDCNNAPLPR ALPSTWIENK LYGMSDPNWP GESPVPLTRA

DGTNTGFPRY PNDSVYANWM LSPSAAKLMD TFDS
```

In some embodiments, compounds of Formula I and pharmaceutically acceptable salts and solvates are useful in treating patients that develop cancers with RET inhibitor resistance mutations (e.g., that result in an increased resistance to a first RET inhibitor, e.g., a substitution at amino acid position 804, e.g., V804M, V804L, or V804E, and/or one or more RET inhibitor resistance mutations listed in Tables 3 and 4) by either dosing in combination or as a follow-up therapy to existing drug treatments (e.g., other RET kinase inhibitors; e.g., first and/or second RET kinase inhibitors). Exemplary first and second RET kinase inhibitors are described herein. In some embodiments, a first or second RET kinase inhibitor can be selected from the group consisting of cabozantinib, vandetanib, alectinib, sorafenib, lenvatinib, ponatinib, dovitinib, sunitinib, foretinib, BLU667, and BLU6864.

In some embodiments, compounds of Formula I or pharmaceutically acceptable salts and solvates thereof are useful for treating a cancer that has been identified as having one or more RET inhibitor resistance mutations (that result in an increased resistance to a first or second RET inhibitor, e.g., a substitution at amino acid position 804, e.g., V804M, V804L, or V804E). Non-limiting examples of RET inhibitor resistance mutations are listed in Tables 3 and 4.

TABLE 3

RET Inhibitor Resistance Mutations
Exemplary RET Resistance Mutations

Amino acid position 732 (e.g., E732K)[7]
Amino acid position 788 (e.g., I788N)[8]
Amino acid position 804 (e.g., V804M[1, 2], V804L[1, 2], V804E[6])
Amino acid position 804/805 (e.g., V804M/E805K)[3]

TABLE 3-continued

RET Inhibitor Resistance Mutations
Exemplary RET Resistance Mutations

Amino acid position 806 (e.g., Y806C[4, 6], Y806E[4], Y806S[6], Y806H[6], Y806N[6])
Amino acid position 810 (e.g., G810A[5], G810R[6], G810S[6])
Amino acid position 865 (e.g., L865V[6])
Amino acid position 870 (e.g., L870F[6])

[1]Yoon et al., J. Med. Chem. 59(1): 358-73, 2016.
[2]U.S. Pat. No. 8,629,135.
[3]Cranston, et al., Cancer Res. 66(20): 10179-87, 2006.
[4]Carlomagno, et al., Endocr. Rel. Cancer 16(1): 233-41, 2009.
[5]Huang et al., Mol. Cancer Ther., 2016 Aug 5. pii: molcanther.0258.2016. [Epub ahead of print].
[6]PCT Patent Application Publication No. WO 2016/127074.
[7]Nadezda et al., Summer Undergraduate Research Programs (SURP) Student Abstracts, University of Oklahoma Health Sciences Center, 2016.
[8]Plenker et al., Sci. Transl. Med., 9(394), doi: 10.1126/scitranslmed.aah6144, 2017.

TABLE 4

Additional Exemplary Amino Acid Positions of RET Inhibitor Resistance Mutations

| RET Amino Acid and Position | Exemplary Mutation | Mechanistic Resistance Rationale |
|---|---|---|
| L730 | P | Steric hindrance and/or active conformational effect |
| G731 | V | Steric hindrance and/or active conformational effect |
| E732 | K | Steric hindrance and/or active conformational effect |
| G733 | V | Steric hindrance and/or active conformational effect |
| E734 | K | Steric hindrance and/or active conformational effect |
| L760 | M | Active conformational effect |
| K761 | E | Active conformational effect |
| E762 | K | Active conformational effect |
| N763 | D | Active conformational effect |
| A764 | V | Active conformational effect |
| S765 | N | Active conformational effect |
| P766 | A | Active conformational effect |
| S767 | C | Active conformational effect |
| E768 | K | Active conformational effect |
| L779 | M | Steric hindrance and/or active conformational effect |
| I788 | M | Steric hindrance and/or active conformational effect |
| M868 | R | Steric hindrance and/or active conformational effect |
| K869 | E | Steric hindrance and/or active conformational effect |
| L870 | Q | Steric hindrance and/or active conformational effect |
| V871 | M | Steric hindrance and/or active conformational effect |
| H872 | R | Steric hindrance and/or active conformational effect |
| R873 | P | Steric hindrance and/or active conformational effect |
| D874 | Y | Steric hindrance and/or active conformational effect |
| L881 | R | Steric hindrance and/or active conformational effect |
| L895 | M | Active conformational effect |
| S896 | N | Active conformational effect |
| R897 | C | Active conformational effect |
| D898 | Y | Active conformational effect |
| V899 | G | Active conformational effect |
| Y900 | D | Active conformational effect |
| E901 | K | Active conformational effect |
| E902 | K | Active conformational effect |
| D903 | Y | Active conformational effect |
| S904 | C | Active conformational effect |
| Y905 | D | Active conformational effect |
| V906 | M | Active conformational effect |
| K907 | E | Active conformational effect |
| R908 | P | Active conformational effect |
| S909 | C | Active conformational effect |
| Q910 | R | Active conformational effect |
| G911 | C | Active conformational effect |
| R912 | P | Active conformational effect |

The oncogenic role of RET was firstly described in papillary thyroid carcinoma (PTC) (Grieco et al., Cell, 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (Greco et al., Q. J. Nucl. Med. Mol. Imaging, 2009, 53, 440-54), therefore driving its ectopic expression in thyroid cells. Fusion proteins generated by such rearrangements are termed "RET/PTC" proteins. For example, RET/PTC 1 is a fusion between CCDD6 and RET that is commonly found in papillary thyroid carcinomas. Similarly, both RET/PTC3 and RET/PTC4 are fusions of ELE1 and RET that are commonly found in papillary thyroid carcinomas, although the fusion events resulting RET/PTC3 and RET/PTC4 lead to different proteins with different molecular weights (see e.g., Fugazzola et al., Oncogene, 13(5):1093-7, 1996). Some RET fusions associated with PTC are not referred to as "RET/PTC", but instead are referred to as the the fusion protein inself. For example, fusion between RET and both ELKS and PCM1 are found in PTCs, but the fusion proteins are referred to as ELKS-RET and PCM1-RET (see e.g., Romei and Elisei, Front. Endocrinol. (Lausanne), 3:54, doi: 10.3389/fendo.2012.00054, 2012). The role of RET-PTC rearrangements in the pathogenesis of PTC has been confirmed in transgenic mice (Santoro et al., Oncogene, 1996, 12, 1821-6). To date, a variety of fusion partners have been identified, from PTC and other cancer types, all providing a protein/protein interaction domain that induces ligand-independent RET dimerization and constitutive kinase activity (see, e.g., Table 1). Recently, a 10.6 Mb pericentric inversion in chromosome 10, where RET gene maps, has been identified in about 2% of lung adenocarcinoma patients, generating different variants of the chimeric gene KIF5B-RET (Ju et al., Genome Res., 2012, 22, 436-45; Kohno et al., 2012, Nature Med., 18, 375-7; Takeuchi et al., Nature Med., 2012, 18, 378-81; Lipson et al., 2012, Nature Med., 18, 382-4). The fusion transcripts are highly expressed and all the resulting chimeric proteins contain the N-terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what has been observed with RET-PTC fusion proteins, KIF5B-RET is constitutively phosphorylated and induces NIH-3T3 transformation and IL-3 independent growth of BA-F3 cells. However, other RET fusion proteins have been identified in lung adenocarcinoma patients, such as the CCDC6-RET fusion protein, which has been found to play a key role in the proliferation of the human lung adenocarcinoma cell line LC-2/ad (Journal of Thoracic Oncology, 2012, 7(12):1872-1876). RET inhibitors have been shown to be useful in treating lung cancers involving RET rearrangements (Drilon, A. E. et al. J Clin Oncol 33, 2015 (suppl; abstr 8007)). RET fusion proteins have also been identified in patients having colorectal cancer (Song Eun-Kee, et al. International Journal of Cancer, 2015, 136: 1967-1975).

Besides rearrangements of the RET sequence, gain of function point mutations of RET proto-oncogene are also driving oncogenic events, as shown in medullary thyroid carcinoma (MTC), which arises from parafollicular calcitonin-producing cells (de Groot, et al., Endocrine Rev., 2006, 27, 535-60; Wells and Santoro, Clin. Cancer Res., 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., *Science*, 2007, 318, 1108-13) and small cell lung carcinoma (*Jpn. J. Cancer Res.*, 1995, 86, 1127-30).

RET signaling components have been found to be expressed in primary breast tumors and to functionally interact with estrogen receptor-cc pathway in breast tumor cell lines (Boulay et al., *Cancer Res.* 2008, 68, 3743-51; Plaza-Menacho et al., *Oncogene*, 2010, 29, 4648-57), while RET expression and activation by GDNF family ligands could play an important role in perineural invasion by different types of cancer cells (Ito et al., *Surgery*, 2005, 138, 788-94; Gil et al., J. Natl. Cancer Inst., 2010, 102, 107-18; Iwahashi et al., Cancer, 2002, 94, 167-74).

RET is also expressed in 30-70% of invasive breast cancers, with expression being relatively more frequent in estrogen receptor-positive tumors (Plaza-Menacho, I., et al., *Oncogene*, 2010, 29, 4648-4657; Esseghir, S., et al., *Cancer Res.*, 2007, 67, 11732-11741; Morandi, A., et al., *Cancer Res.*, 2013, 73, 3783-3795; Gattelli, A., *EMBO Mol. Med.*, 2013, 5, 1335-1350).

The identification of RET rearrangements has been reported in a subset of (patient-derived xenograft) PDX established from colorectal cancer. Although the frequency of such events in colorectal cancer patients remains to be defined, these data suggest a role of RET as a target in this indication (Gozgit et al., AACR Annual Meeting 2014). Studies have shown that the RET promoter is frequently methylated in colorectal cancers, and heterozygous missense mutations, which are predicted to reduce RET expression, are identified in 5-10% of cases, which suggests that RET might have some features of a tumor suppressor in sporadic colon cancers (Luo, Y., et al., *Oncogene*, 2013, 32, 2037-2047; Sjoblom, T., et al., *Science*, 2006, 268-274; Cancer Genome Atlas Network, *Nature*, 2012, 487, 330-337).

An increasing number of tumor types are now being shown to express substantial levels of wild-type RET kinase that could have implications for tumor progression and spread. RET is expressed in 50-65% of pancreatic ductal carcinomas, and expression is more frequent in metastatic and higher grade tumors (Ito, Y, et al., *Surgery*, 2005, 138, 788-794; Zeng, Q., et al., *J. Int. Med. Res.* 2008, 36, 656-664).

In neoplasms of hematopoietic lineages, RET is expressed in acute myeloid leukemia (AML) with monocytic differentiation, as well as in CMML (Gattei, V. et al., *Blood*, 1997, 89, 2925-2937; Gattei, V., et al., *Ann. Hematol*, 1998, 77, 207-210; Camos, M., *Cancer Res.* 2006, 66, 6947-6954). Recent studies have identified rare chromosomal rearrangements that involve RET in patients with chronic myelomonocytic leukemia (CMML). CMML is frequently associated with rearrangements of several tyrosine kinases, which result in the expression of chimeric cytosolic oncoproteins that lead to activation of RAS pathways (Kohlmann, A., et al., *J. Clin. Oncol.* 2010, 28, 2858-2865). In the case of RET, gene fusions that link RET with BCR (BCR-RET) or with fibroblast growth factor receptor 1 oncogene partner (FGFR1OP-RET) were transforming in early hematopoietic progenitor cells and could shift maturation of these cells towards monocytic paths, probably through the initiation of RET-mediated RAS signaling (Ballerini, P., et al., *Leukemia*, 2012, 26, 2384-2389).

RET expression has also been shown to occur in several other tumor types, including prostate cancer, small-cell lung carcinoma, melanoma, renal cell carcinoma, and head and neck tumors (Narita, N., et al., *Oncogene*, 2009, 28, 3058-3068; Mulligan, L. M., et al., *Genes Chromosomes Cancer*, 1998, 21, 326-332; Flavin, R., et al., *Urol. Oncol.*, 2012, 30, 900-905; Dawson, D. M., *J Natl Cancer Inst*, 1998, 90, 519-523).

In neuroblastoma, RET expression and activation by GFLs has roles in tumor cell differentiation, potentially collaborating with other neurotrophic factor receptors to down regulate N-Myc, the expression of which is a marker of poor prognosis (Hofstra, R. M., W., et al., *Hum. Genet.* 1996, 97, 362-364; Petersen, S. and Bogenmann, E., *Oncogene*, 2004, 23, 213-225; Brodeur, G. M., *Nature Ref Cancer*, 2003, 3, 203-216).

Multitargeted inhibitors which cross react with RET are known (Borrello, M. G., et al., *Expert Opin. Ther. Targets*, 2013, 17(4), 403-419; International Patent Application Nos. WO 2014/141187, WO 2014/184069, and WO 2015/079251).

Accordingly, provided herein are methods for treating a patient diagnosed with (or identified as having) a cancer that include administering to the patient a therapeutically effective amount of a compound of Formula I or a pharmaceutically acceptable salt or solvate thereof. Also provided herein are methods for treating a patient identified or diagnosed as having a RET-associated cancer that include administering to the patient a therapeutically effective amount of a compound of Formula I or a pharmaceutically acceptable salt or solvate thereof or a pharmaceutical composition thereof. In some embodiments, the patient that has been identified or diagnosed as having a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods for treating cancer in a patient in need thereof, the method comprising: (a) determining if the cancer in the patient is a RET-associated cancer; and (b) if the cancer is determined to be a RET-associated cancer, administering to the patient a therapeutically effective amount of a compound of Formula I or a pharmaceutically acceptable salt or solvate thereof or a pharmaceutical composition thereof. Some embodiments of these methods further include administering to the subject another anticancer agent (e.g., a second RET inhibitor, a second compound of Formula I or a pharmaceutically acceptable salt or solvate thereof, or immunotherapy). In some embodiments, the subject was previously treated with a first RET inhibitor or previously treated with another anticancer treatment, e.g., resection of the tumor or radiation therapy. In some embodiments, the patient is determined to have a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods of treating a patient that include performing an assay on a sample obtained from the patient to determine whether the patient has a dysregulation of a RET gene, a RET kinase, or expression or activity or level of any of the same, and administering (e.g., specifically or selectively administering) a therapeutically effective amount of a compound of Formula I or a pharmaceutically acceptable salt or solvate thereof or a pharmaceutical composition thereof to the patient determined to have a dysregulation of a RET gene, a RET kinase, or expression or activity or level of any of the same. Some embodiments of these methods further include administering to the subject another anticancer agent (e.g., a second RET inhibitor, a second compound of Formula I or a pharmaceutically acceptable salt or solvate thereof, or immunotherapy). In some embodiments of these methods, the subject was previously treated with a first RET inhibitor or previously treated with another anticancer treatment, e.g., resection of a tumor or radiation therapy. In some embodiments, the patient is a patient suspected of having a RET-associated cancer, a patient presenting with one or more symptoms of a RET-associated cancer, or a patient having an elevated risk of developing a RET-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. Additional, non-limiting assays that may be used in these methods are described herein. Additional assays are also known in the art. In some embodiments, the dysregulation of a RET gene, a RET kinase, or expression or activity or level of any of the same includes one or more RET inhibitor resistance mutations.

Also provided is a compound of Formula I or a pharmaceutically acceptable salt or solvate thereof or a pharmaceutical composition thereof for use in treating a RET-associated cancer in a patient identified or diagnosed as having a RET-associated cancer through a step of performing an assay (e.g., an in vitro assay) on a sample obtained from the patient to determine whether the patient has a dysregulation of a RET gene, a RET kinase, or expression or activity or level of any of the same, where the presence of a dysregulation of a RET gene, a RET kinase, or expression or activity or level of any of the same, identifies that the patient has a RET-associated cancer. Also provided is the use of a compound of Formula I or a pharmaceutically acceptable salt or solvate thereof for the manufacture of a medicament for treating a RET-associated cancer in a patient identified or diagnosed as having a RET-associated cancer through a step of performing an assay on a sample obtained from the patient to determine whether the patient has a dysregulation of a RET gene, a RET kinase, or expression or activity or level of any of the same where the presence of dysregulation of a RET gene, a RET kinase, or expression or activity or level of any of the same, identifies that the patient has a RET-associated cancer. Some embodiments of any of the methods or uses described herein further include recording in the patient's clinical record (e.g., a computer readable medium) that the patient is determined to have a dysregulation of a RET gene, a RET kinase, or expression or activity or level of any of the same, through the performance of the assay, should be administered a compound of Formula I or a pharmaceutically acceptable salt or solvate thereof or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the dysregulation of a RET gene, a RET kinase, or expression or activity or level of any of the same includes one or more RET inhibitor resistance mutations.

Also provided is a compound of Formula I or a pharmaceutically acceptable salt or solvate thereof, for use in the treatment of a cancer in a patient in need thereof or a patient identified or diagnosed as having a RET-associated cancer. Also provided is the use of a compound of Formula I or a pharmaceutically acceptable salt or solvate thereof for the manufacture of a medicament for treating a cancer in a patient identified or diagnosed as having a RET-associated cancer. In some embodiments, the cancer is a RET-associated cancer, for example, a RET-associated cancer having one or more RET inhibitor resistance mutations. In some embodiments, a patient is identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the sample. As provided herein, a RET-associated cancer includes those described herein and known in the art.

In some embodiments of any of the methods or uses described herein, the patient has been identified or diagnosed as having a cancer with a dysregulation of a RET gene, a RET kinase, or expression or activity or level of any of the same. In some embodiments of any of the methods or uses described herein, the patient has a tumor that is positive for a dysregulation of a RET gene, a RET kinase, or expression or activity or level of any of the same. In some embodiments of any of the methods or uses described herein, the patient can be a patient with a tumor(s) that is positive for a dysregulation of a RET gene, a RET kinase, or expression or activity or level of any of the same. In some embodiments of any of the methods or uses described herein, the patient can be a patient whose tumors have a dysregulation of a RET gene, a RET kinase, or expression or activity or level of any of the same. In some embodiments of any of the methods or uses described herein, the patient is suspected of having a RET-associated cancer (e.g., a cancer having one or more RET inhibitor resistance mutations). In some embodiments, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of a compound of Formula I or a pharmaceutically acceptable salt or solvate thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions/deletions. Non-limiting examples of RET kinase protein point mutations/insertions/deletions are described in Table 2. In some embodiments, the RET kinase protein point mutations/insertions/deletions are selected from the group consisting of M918T, M918V, C634W, V804L, and V804M. In some embodiments, the dysregulation of a RET gene, a RET kinase, or the expression or activity or level of any of the same includes one or more RET inhibitor resistance mutations. Non-limiting examples of RET inhibitor resistance mutations are described in Tables 3 and 4. In some embodiments, the RET inhibitor resistance mutation is V804M. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

In some embodiments of any of the methods or uses described herein, the patient has a clinical record indicating that the patient has a tumor that has a dysregulation of a RET gene, a RET kinase, or expression or activity or level of any of the same (e.g., a tumor having one or more RET inhibitor resistance mutations). In some embodiments, the clinical record indicates that the patient should be treated with one or more of the compounds of Formula I or a pharmaceutically acceptable salts or solvates thereof or compositions provided herein. In some embodiments, the cancer with a dysregulation of a RET gene, a RET kinase, or expression or activity or level of any of the same is a cancer having one or more RET inhibitor resistance mutations. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

Also provided are methods of treating a patient that include administering a therapeutically effective amount of a compound of Formula I or a pharmaceutically acceptable salt or solvate thereof to a patient having a clinical record that indicates that the patient has a dysregulation of a RET gene, a RET kinase, or expression or activity or level of any of the same. Also provided is the use of a compound of Formula I or a pharmaceutically acceptable salt or solvate thereof for the manufacture of a medicament for treating a RET-associated cancer in a patient having a clinical record that indicates that the patient has a dysregulation of a RET gene, a RET kinase, or expression or activity or level of any of the same. Some embodiments of these methods and uses can further include: a step of performing an on a sample obtained from the patient to determine whether the patient has a dysregulation of a RET gene, a RET kinase, or expression or activity or level of any of the same, and recording the information in a patient's clinical file (e.g., a computer readable medium) that the patient has been identified to have a dysregulation of a RET gene, a RET kinase, or expression or activity or level of any of the same. In some embodiments, the assay is an in vitro assay. For example, an assay that utilizes next generation sequencing, immunohistochemistry, or break apart FISH analysis. In some embodiments, the assay is a regulatory agency-approved, e.g., FDA-approved, kit. In some embodiments, the dysregulation of a RET gene, RET kinase, or expression or activity or level of any of the same includes one or more RET inhibitor resistance mutations.

Also provided herein is a method of treating a subject. The method includes performing an assay on a sample obtained from the subject to determine whether the subject has a dysregulation of a RET gene, a RET protein, or expression or level of any of the same. The method also includes administering to a subject determined to have a dysregulation of a RET gene, a RET protein, or expression or activity, or level of any of the same a therapeutically effective amount of a compound of Formula I or a pharmaceutically acceptable salt or solvate thereof. In some embodiments, the dysregulation in a RET gene, a RET kinase protein, or expression or activity of the same is a gene or chromosome translocation that results in the expression of a RET fusion protein (e.g., any of the RET fusion proteins described herein). In some embodiments, the RET fusion can be selected from a KIF5B-RET fusion and a CCDC6-RET fusion. In some embodiments, the dysregulation in a RET gene, a RET kinase protein, or expression or activity or level of any of the same is one or more point mutation in the RET gene (e.g., any of the one or more of the RET point mutations described herein). The one or more point mutations in a RET gene can result, e.g., in the translation of a RET protein having one or more of the following amino acid substitutions: M918T, M918V, C634W, V804L, and V804M. In some embodiments, the dysregulation in a RET gene, a RET kinase protein, or expression or activity or level of any of the same is one or more RET inhibitor resistance mutations (e.g., any combination of the one or more RET inhibitor resistance mutations described herein). Some embodiments of these methods further include administering to the subject another anticancer agent (e.g., a second RET inhibitor a second compound of Formula I or a pharmaceutically acceptable salt or solvate thereof, or immunotherapy).

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the patient has previously been treated with another anticancer agent, e.g., another RET inhibitor (e.g., a compound that is not a compound of General Formula I) or a multi-kinase inhibitor. In some embodiments, the brain tumor is a metastatic brain tumor. In some embodiments, the patient has previously been treated with another anticancer agent, e.g., another RET inhibitor (e.g., a compound that is not a compound of General Formula I) or a multi-kinase inhibitor.

Also provided are methods (e.g., in vitro methods) of selecting a treatment for a patient identified or diagnosed as having a RET-associated cancer. Some embodiments can further include administering the selected treatment to the patient identified or diagnosed as having a RET-associated cancer. For example, the selected treatment can include administration of a therapeutically effective amount of a compound of Formula I or a pharmaceutically acceptable salt or solvate thereof. Some embodiments can further include a step of performing an assay on a sample obtained from the patient to determine whether the patient has a dysregulation of a RET gene, a RET kinase, or expression or activity or level of any of the same, and identifying and diagnosing a patient determined to have a dysregulation of a RET gene, a RET kinase, or expression or activity or level of any of the same, as having a RET-associated cancer. In some embodiments, the cancer is a RET-associated cancer having one or more RET inhibitor resistance mutations. In some embodiments, the patient has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient. In some embodiments, the RET-associated cancers is a cancer described herein or known in the art. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit.

Also provided herein are methods of selecting a treatment for a patient, wherein the methods include a step of performing an assay on a sample obtained from the patient to determine whether the patient has a dysregulation of a RET gene, a RET kinase, or expression or activity or level of any of the same (e.g., one or more RET inhibitor resistance mutations), and identifying or diagnosing a patient determined to have a dysregulation of a RET gene, a RET kinase, or expression or activity or level of any of the same, as having a RET-associated cancer. Some embodiments further include administering the selected treatment to the patient identified or diagnosed as having a RET-associated cancer. For example, the selected treatment can include administration of a therapeutically effective amount of a compound of Formula I or a pharmaceutically acceptable salt or solvate thereof to the patient identified or diagnosed as having a RET-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit.

Also provided are methods of selecting a patient for treatment, wherein the methods include selecting, identifying, or diagnosing a patient having a RET-associated cancer, and selecting the patient for treatment including administration of a therapeutically-effective amount of a compound of Formula I or a pharmaceutically acceptable salt or solvate thereof. In some embodiments, identifying or diagnosing a patient as having a RET-associated cancer can include a step of performing an assay on a sample obtained from the patient to determine whether the patient has a dysregulation of a RET gene, a RET kinase, or expression or activity or level of any of the same, and identifying or diagnosing a patient determined to have a dysregulation of a RET gene, a RET kinase, or expression or activity or level of any of the same, as having a RET-associated cancer. In some embodiments, the method of selecting a treatment can be used as a part of a clinical study that includes administration of various treatments of a RET-associated cancer. In some embodiments, a RET-associated cancer is a cancer having one or more RET inhibitor resistance mutations. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the dysregulation of the RET gene, the RET kinase, or expression or activity or level of any of the same includes one or more RET inhibitor resistance mutations.

In some embodiments of any of the methods or uses described herein, an assay used to determine whether the patient has a dysregulation of a RET gene, or a RET kinase, or expression or activity or level of any of the same, using a sample from a patient can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a RET gene, a RET kinase, or expression or activity or levels of any of the same (see, e.g., the references cited herein). In some embodiments, the dysregulation of the RET gene, the RET kinase, or expression or activity or level of any of the same includes one or more RET inhibitor resistance mutations. In some embodiments, the sample is a biological sample or a biopsy sample (e.g., a paraffin-embedded biopsy sample) from the patient. In some embodiments, the patient is a patient suspected of having a RET-associated cancer, a patient having one or more symptoms of a RET-associated cancer, and/or a patient that has an increased risk of developing a RET-associated cancer)

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as kinase inhibitors, signal transduction inhibitors and/or monoclonal antibodies. Compounds of Formula I therefore may also be useful as adjuvants to cancer treatment, that is, they can be used in combination with one or more additional therapies or therapeutic agents, for example a chemotherapeutic agent that works by the same or by a different mechanism of action.

In some embodiments of any the methods described herein, the compound of Formula I (or a pharmaceutically acceptable salt or solvate thereof) is administered in combination with a therapeutically effective amount of at least one additional therapeutic agent selected from one or more additional therapies or therapeutic (e.g., chemotherapeutic) agents.

Non-limiting examples of additional therapeutic agents include: other RET-targeted therapeutic agents (i.e. a first or second RET kinase inhibitor), receptor tyrosine kinase-targeted therapeutic agents, signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

In some embodiments, the other RET-targeted therapeutic is a multikinase inhibitor exhibiting RET inhibition activity. In some embodiments, the other RET-targeted therapeutic inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitors can exhibit inhibition activity ($IC_{50}$) against a RET kinase of less than about 25 nM, less than about 10 nM, less than about 5 nM, or less than about 1 nM as measured in an assay as provided herein.

Non-limiting examples of RET-targeted therapeutic agents include alectinib, apatinib, cabozantinib (XL-184), dovitinib, lenvatinib, motesanib, nintedanib, ponatinib, regorafenib, sitravatinib (MGCD516), sunitinib, sorafenib, vatalanib, vandetanib, AUY-922 (5-(2,4-Dihydroxy-5-isopropyl-phenyl)-N-ethyl-4-[4-(morpholinomethyl)phenyl] isoxazole-3-carboxamide), BLU6864, BLU-667, DCC-2157, GSK3179106, NVP-AST487 (1-[4-[(4-ethylpiperazin-1-yl)methyl]-3-(trifluoromethyl)phenyl]-3-[4-[6-(methylamino)pyrimidin-4-yl]oxyphenyl]urea), PZ-1, RPI-1 (1,3-dihydro-5,6-dimethoxy-3-[(4-hydroxyphenyl) methylene]-H-indol-2-one), RXDX-105 (1-(3-((6,7-dimethoxyquinazolin-4-yl)oxy)phenyl)-3-(5-(1,1,1-trifluoro-2-methylpropan-2-yl)isoxazol-3-yl)urea), SPP86 (1-Isopropyl-3-(phenylethynyl)-1H-pyrazolo[3,4-d]pyrimidin-4-amine), and TG101209 (N-(1,1-dimethylethyl)-3-[[5-methyl-2-[[4-(4-methyl-1-piperazinyl)phenyl]amino]-4-pyrimidinyl]amino]-benzenesulfonamide).

Additional examples of other RET kinase inhibitors include those described in U.S. Pat. Nos. 9,150,517 and 9,149,464, and International Publication No. WO 2014075035, all of which are hereby incorporated by reference. For example, in some embodiments the other RET inhibitor is a compound of formula I:

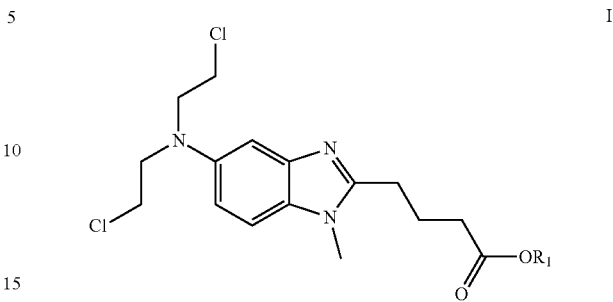

wherein $R_1$ is $C_6$-$C_{24}$alkyl or polyethylene glycol; or a pharmaceutically acceptable salt form thereof. In some embodiments, the other RET inhibitor is 4-{5-[bis-(chloroethyl)-amino]-1-methyl-1H-benzimidazol-2-yl}butyric acid dodecyl ester.

Additional examples of other RET kinase inhibitors include those described in International Publication No. WO 2016127074, which is hereby incorporated by reference. For example, in some embodiments, the other RET inhibitor is a compound of Formula (I) or a pharmaceutically acceptable salt thereof, wherein:

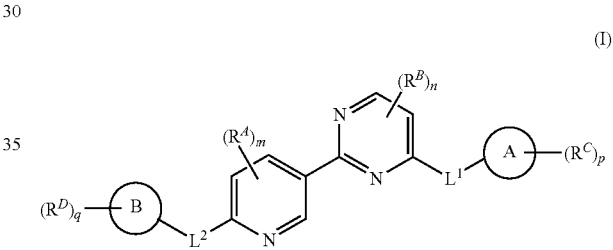

wherein Rings A and B are each independently selected from aryl, heteroaryl, cycloalkyl and heterocyclyl;

each $L^1$ and $L^2$ is independently selected from a bond, —(C1-C6 alkylene)-, —(C2-C6alkenylene)-, —(C2-C6 alkynylene)-, —(C1-C6 haloalkylene)-, —(C1-C6 heteroalkylene)-, —C(O)—, —O—, —S—, —S(O), —S(O)$_2$—, —N($R^1$)—, —O—(C1-C6 alkylene)-, —(C1-C6 alkylene)-O—, —N($R^1$)—C(O)—, —C(O)N($R^1$)—, —(C1-C6 alkylene)-N($R^1$)—, —N($R^1$)—(C1-C6 alkylene)-, —N($R^1$)—C(O)—(C1-C6 alkylene)-, —(C1-C6 alkylene)-N($R^1$)—C(O)—, —C(O)—N($R^1$)—(C1-C6 alkylene)-, —(C1-C6 alkylene)-C(O)—N($R^1$)—, —N($R^1$)—S(O)$_2$—, —S(O)$_2$—N($R^1$)—, —N($R^1$)—S(O)$_2$—(C1-C6 alkylene)-, and —S(O)$_2$—N($R^1$)—(C1-C6 alkylene)-; wherein each alkylene, alkenylene, alkynylene, haloalkylene, and heteroalkylene is independently substituted with 0-5 occurrences of R';

each $R^A$ and $R^B$ is independently selected from C1-C6 alkyl, C1-C6 alkoxy, halo, C1-C6 haloalkyl, C1-C6 hydroxyalkyl, C1-C6 heteroalkyl, and —N($R^1$)($R^1$); wherein each alkyl, alkoxy, haloalkyl, hydroxyalkyl, and hydroxyalkyl is independently substituted with 0-5 occurrences of Ra;

each $R^C$ and $R^D$ is independently selected from C1-C6 alkyl, C2-C6 alkenyl, C2-C6 alkynyl, C1-C6 alkoxy, halo, C1-C6 heteroalkyl, C1-C6 haloalkyl, C1-C6 haloalkoxy, C1-C6 hydroxyalkyl, cycloalkyl, aryl, heteroaryl, aryloxy, aralkyl, heterocyclyl, heterocyclylalkyl, nitro, cyano, —C(O)R¹, —OC(O)R¹, —C(O)OR¹, —(C1-C6 alkylene)-C(O)R¹, —SR¹, —S(O)₂R¹, —S(O)₂—N(R¹)(R¹), —(C1-C6 alkylene)-S(O)₂R¹, —(C1-C6 alkylene)-S(O)₂—N(R¹)(R¹), —N(R¹)(R¹)—C(O)—N(R¹)(R¹)—N(R¹)—C(O)R¹, —N(R¹)—C(O)OR¹, —(C1-C6 alkylene)-N(R¹)—C(O)R¹, —N(R¹)S(O)₂R¹, and —P(O)(R¹)(R¹); wherein each of alkyl, alkenyl, alkynyl, alkoxy, heteroalkyl, haloalkyl, haloalkoxy, hydroxyalkyl, cycloalkyl, aryl, heteroaryl, aryloxy, aralkyl, heterocyclyl, and heterocyclylalkyl is independently substituted with 0-5 occurrences of R$^a$; or 2 R$^C$ or 2 R$^D$ together with the carbon atom(s) to which they are attached form a cycloalkyl or heterocyclyl ring independently substituted with 0-5 occurrences of R$^a$;

each R¹ is independently selected from hydrogen, hydroxyl, halo, thiol, C1-C6 alkyl, C1-C6 thioalkyl, C1-C6 alkoxy, C1-C6 haloalkyl, C1-C6 hydroxyalkyl, C1-C6 heteroalkyl, cycloalkyl, cycloalkylalkyl, heteroarylalkyl, heterocyclyl, and heterocyclylalkyl, wherein each of alkyl, thioalkyl, alkoxy, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of R$^b$, or 2 R¹ together with the atom(s) to which they are attached form a cycloalkyl or heterocyclyl ring independently substituted with 0-5 occurrences of R$^b$;

each R$^a$ and R$^b$ is independently C1-C6 alkyl, halo, hydroxyl, C1-C6 haloalkyl, C1-C6 heteroalkyl, C1-C6 hydroxyalkyl, C1-C6 alkoxy, cycloalkyl, heterocyclyl, or cyano, wherein each of alkyl, haloalkyl, heteroalkyl, hydroxyalkyl, alkoxy, cycloalkyl and heterocyclyl is independently substituted with 0-5 occurrences of R';

each R' is C1-C6 alkyl, C1-C6 heteroalkyl, halo, hydroxyl, C1-C6 haloalkyl, C1-C6 hydroxyalkyl, cycloalkyl or cyano; or 2 R', together with the atom(s) to which they are attached form a cycloalkyl or heterocyclyl ring;

m is 0, 1, 2, or 3;

n is 0, 1, or 2; and p and q are each independently 0, 1, 2, 3, or 4. For example, a RET inhibitor can be selected from the group consisting of:

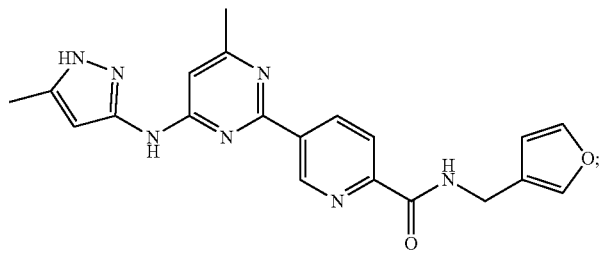

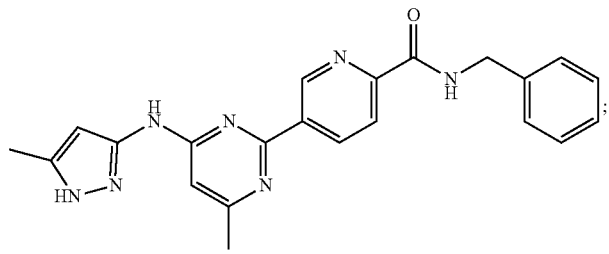

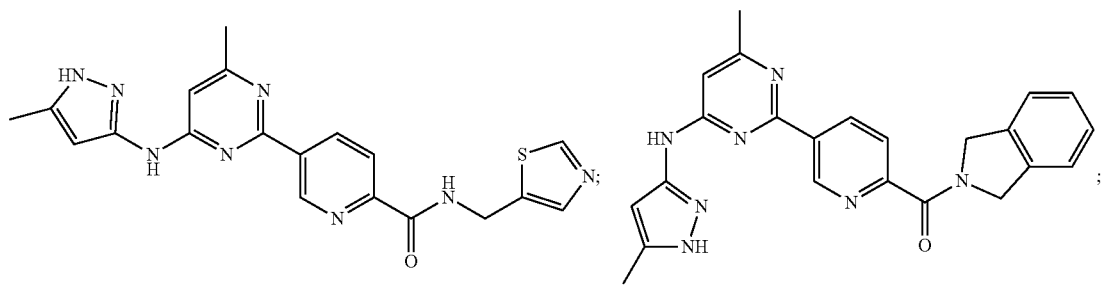

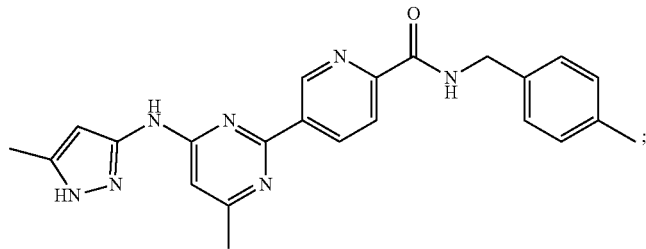

-continued
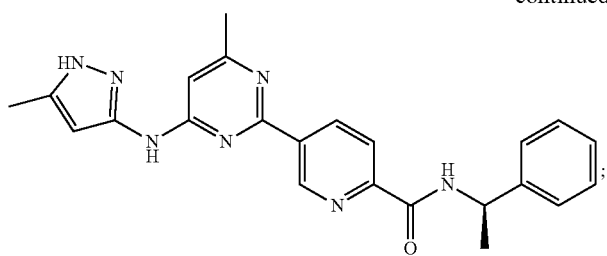
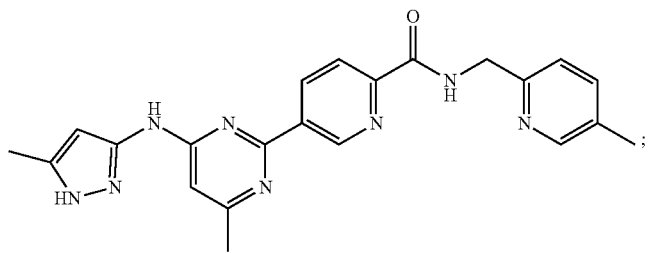
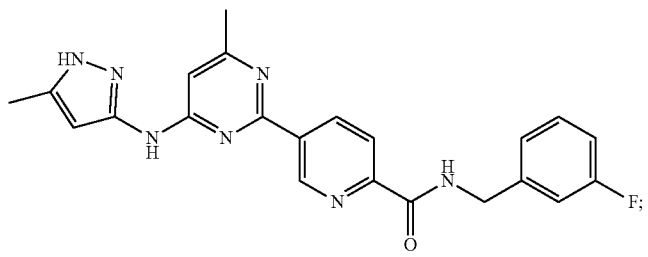
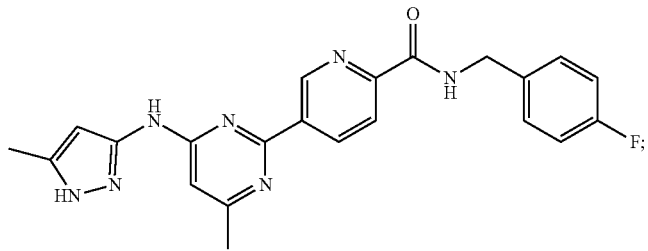
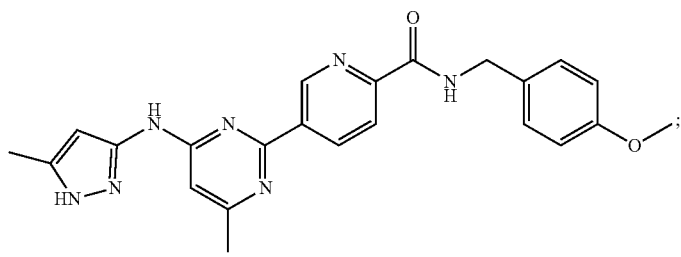
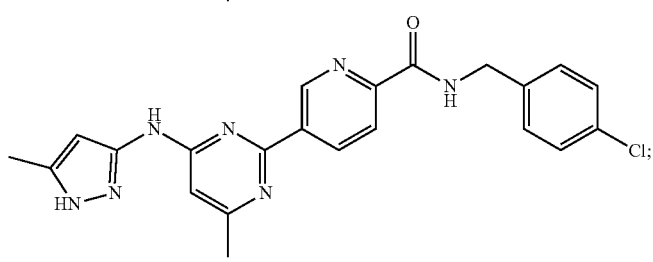

-continued
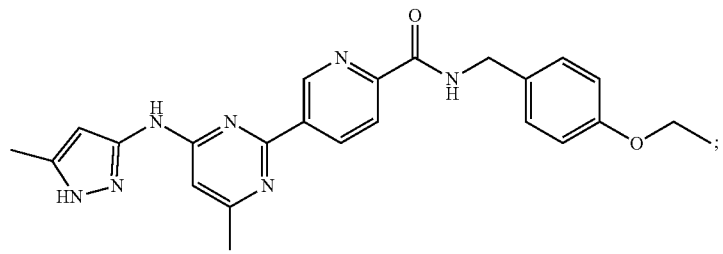
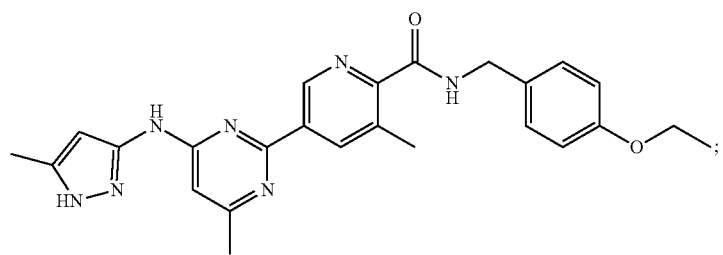
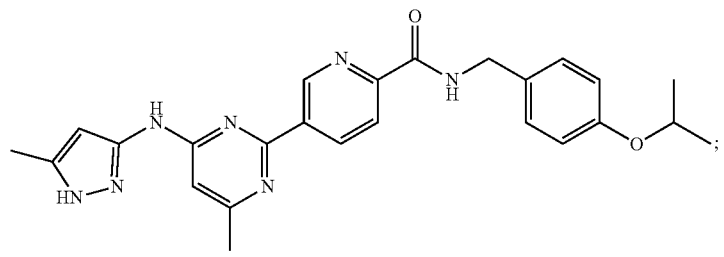
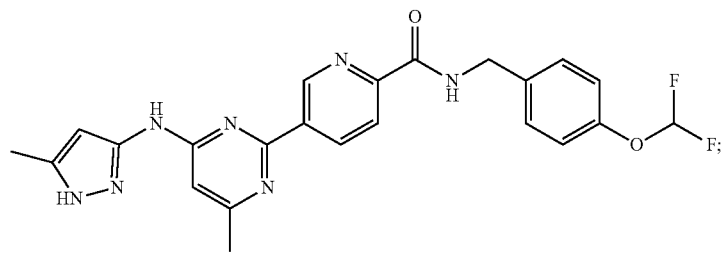
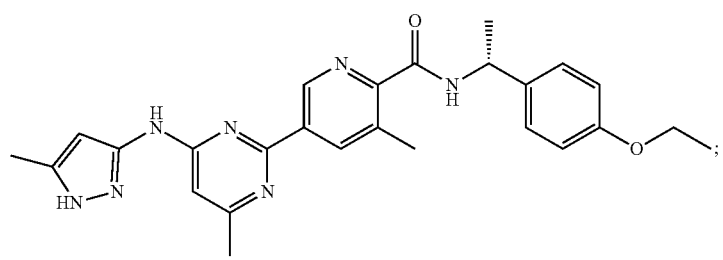
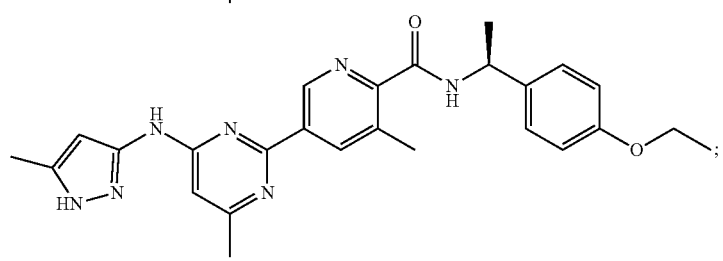

-continued
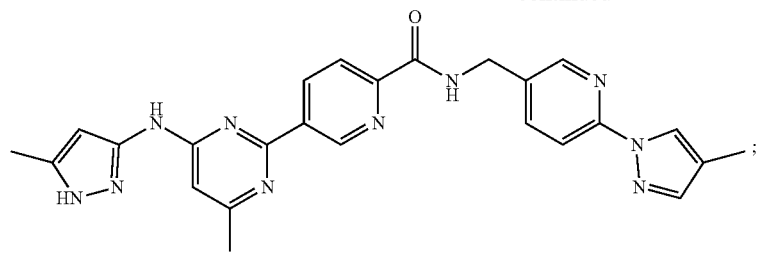
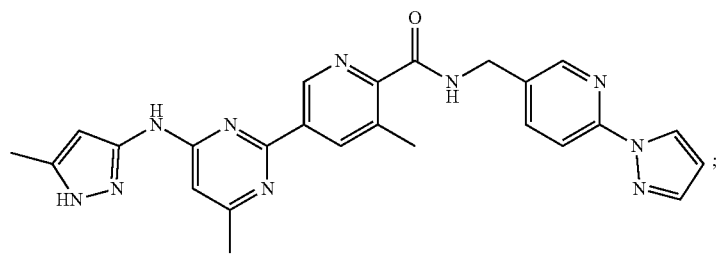
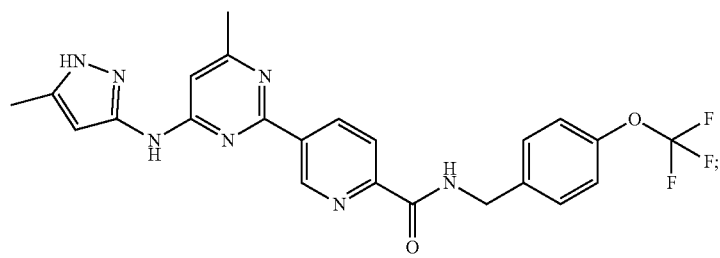
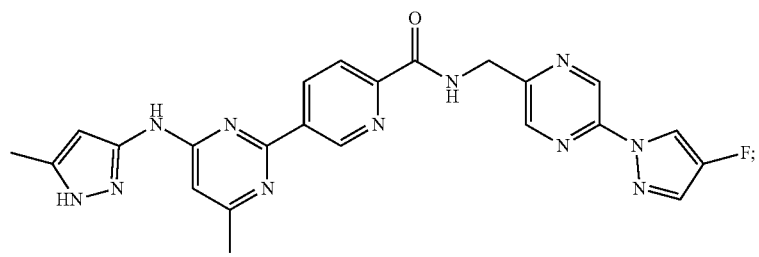
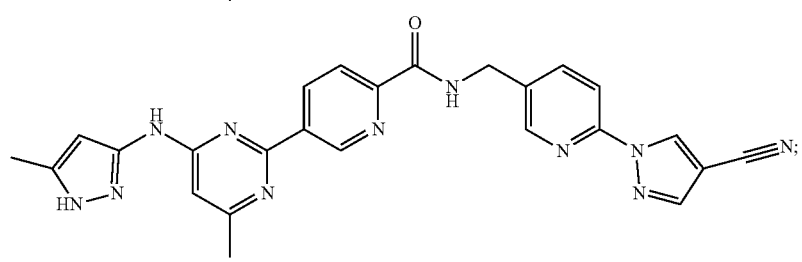
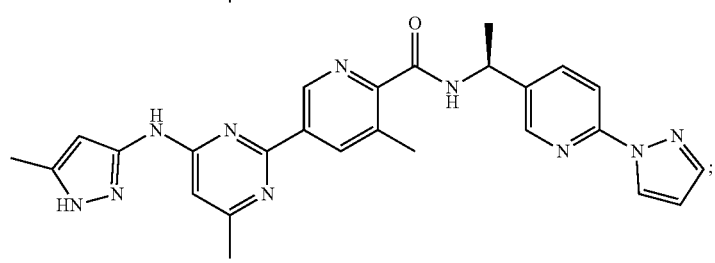

-continued
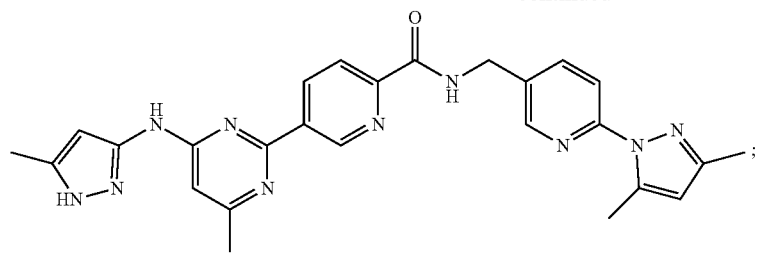
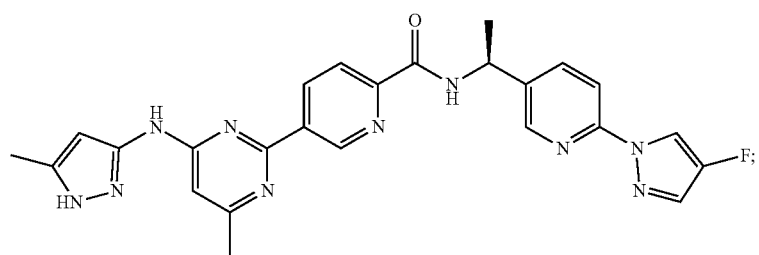
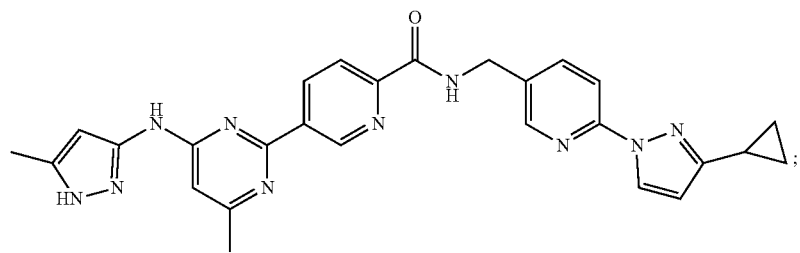
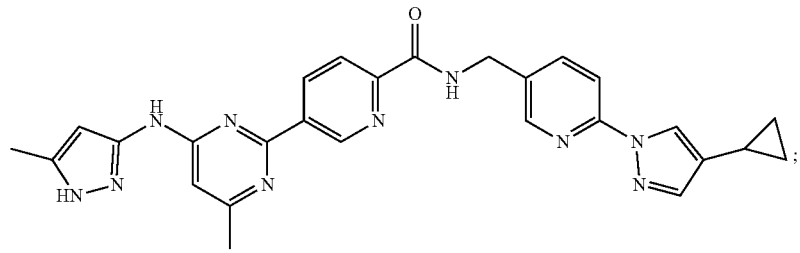
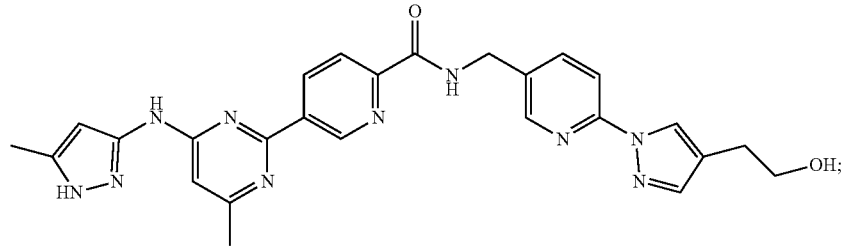
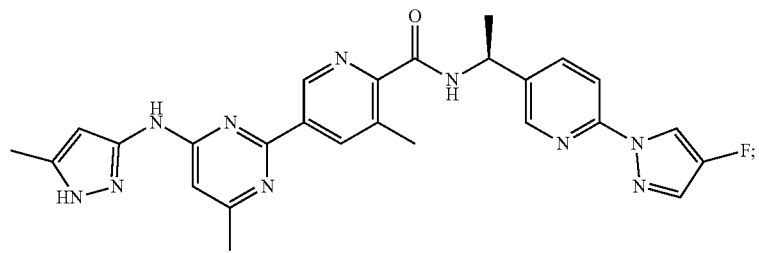

-continued
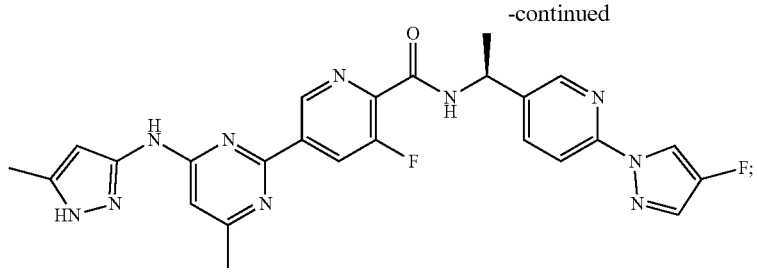
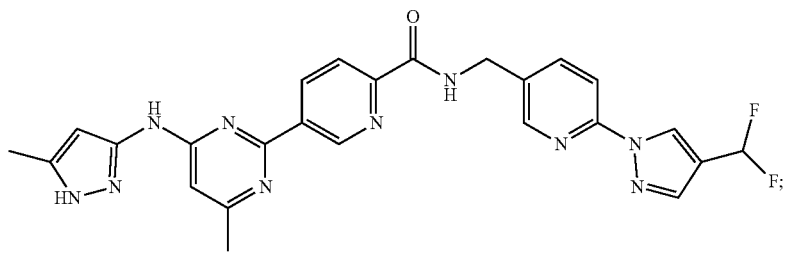
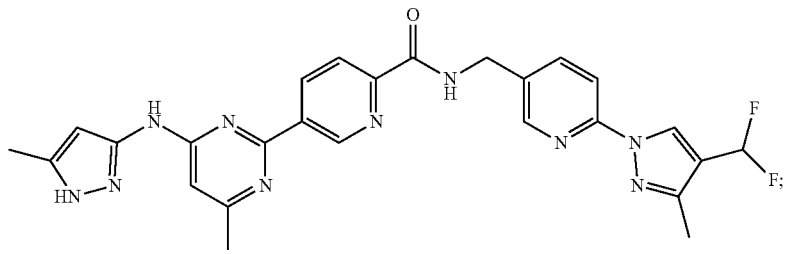
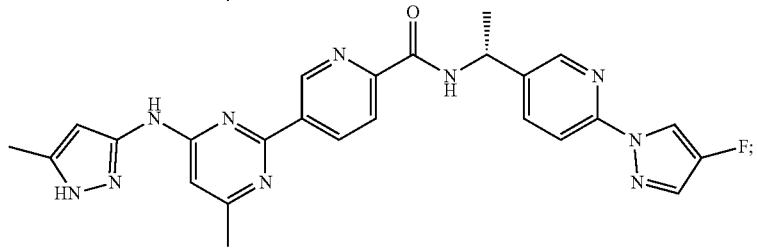
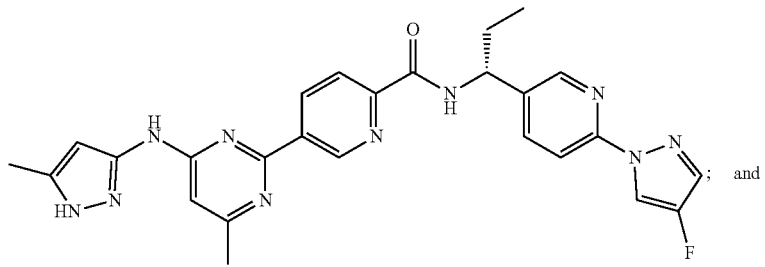
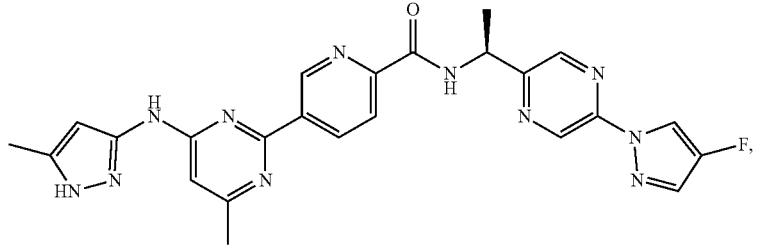
or a pharmaceutically acceptable salt thereof.
In some embodiments, a RET inhibitor is selected from the group consisting of: ABT-348 (N-[4-[4-Amino-7-[1-(2-hydroxyethyl)-1H-pyrazol-4-yl]thieno[3,2-c]pyridin-3-yl]phenyl]-N'-(3-fluorophenyl)urea); AD-57, which has the structure:

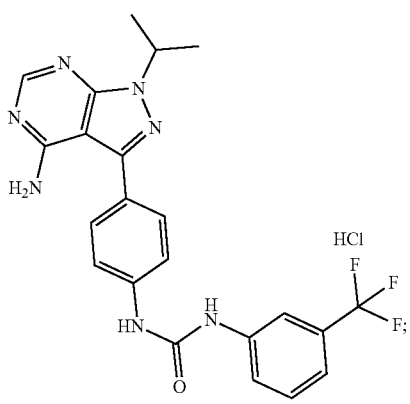 [SMILES: CC(C)n1nc(-c2ccc(NC(=O)Nc3cccc(C(F)(F)F)c3)cc2)c2c(N)ncnc21 ; Cl]

AD-80 (1-(4-(4-amino-1-isopropyl-1H-pyrazolo[3,4-d]pyrimidin-3-yl)phenyl)-3-(2-fluoro-5-(trifluoromethyl)phenyl)urea); ALW-II-41-27 (N-(5-((4-((4-ethylpiperazin-1-yl)methyl)-3-(trifluoromethyl)phenyl)carbamoyl)-2-methylphenyl)-5-(thiophen-2-yl)nicotinamide); Amuvatinib (MP470) (N-(benzo[d][1,3]dioxol-5-ylmethyl)-4-(benzofuro[3,2-d]pyrimidin-4-yl)piperazine-1-carbothioamide); BPR1J373 (a derivative of 5-phenylthhiazol-2-ylamine-pyriminide); CLM3; doramapimod (BIRB-796) (1-(3-(tert-butyl)-1-(p-tolyl)-1H-pyrazol-5-yl)-3-(4-(2-morpholinoethoxy)naphthalen-1-yl)urea); DS-5010; famitinib (5-[2-(diethyl amino)ethyl]-2-[(Z)-(5-fluoro-2-oxo-1H-indol-3-ylidene)methyl]-3-methyl-6,7-dihydro-1H-pyrrolo[3,2-c]pyridin-4-one); fedratinib (SAR 302503, TG101348) (N-(tert-butyl)-3-((5-methyl-2-((4-(2-(pyrrolidin-1-yl)ethoxy)phenyl)amino)pyrimidin-4-yl)amino)benzenesulfonamide); GSK3179106; GSK3352589; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); NVP-BBT594 (5-((6-acetamidopyrimidin-4-yl)oxy)-N-(4-((4-methylpiperazin-1-yl)methyl)-3-(trifluoromethyl)phenyl)indoline-1-carboxamide); PP2 (4-amino-5-(4-chlorophenyl)-7-(dimethylethyl)pyrazolo[3,4-d]pyrimidine); PP242 (2-(4-amino-1-isopropyl-1H-pyrazolo[3,4-d]pyrimidin-3-yl)-1H-indol-5-ol); quizartinib (AC220) (1-(5-(tert-butyl)isoxazol-3-yl)-3-(4-(7-(2-morpholinoethoxy)benzo[d]imidazo[2,1-b]thiazol-2-yl)phenyl)urea); semaxanib (SU5416, VEGFR2 Kinase Inhibitor III) ((Z)-3-((3,5-dimethyl-1H-pyrrol-2-yl)methylene)indolin-2-one); SU4984 (3-[4-(1-formylpiperazin-4-yl)benzylidenyl]-2-indolinone); Withaferin A ((4β,5β,6β,22R)-4,27-Dihydroxy-5,6:22,26-diepoxyergosta-2,24-diene-1,26-dione); XL-999 ((Z)-5-((1-ethylpiperidin-4-yl)amino)-3-((3-fluorophenyl)(5-methyl-1H-imidazol-2-yl)methylene)indolin-2-one); XMD 15-44 (N-(4-((4-ethylpiperazin-1-yl)methyl)-3-(trifluoromethyl)phenyl)-4-methyl-3-(pyridin-3-ylethynyl)benzamide); Y078-DM1 (antibody drug conjugate composed of a RET antibody (Y078) linked to a derivative of the cytotoxic agent maytansine); and Y078-DM1 (antibody drug conjugate composed of a RET antibody (Y078) linked to a derivative of the cytotoxic agent maytansine).

Further examples of RET inhibitors include: N-(2-fluoro-5-trifluoromethylphenyl)-N'-{4'-[(2"-benzamido)pyridin-4"-ylamino]phenyl}urea; 1-isopropyl-3-(phenylethynyl)-1H-pyrazolo[3,4-d]pyrimidin-4-amine; 3-((6,7-dimethoxyquinazolin-4-yl)amino)-4-fluoro-2-methylphenol; N-(5-(tert-butyl)isoxazol-3-yl)-2-(4-(imidazo[1,2-a]pyridin-6-yl)phenyl)acetamide; N-(5-(tert-butyl)isoxazol-3-yl)-2-(3-(imidazo[1,2-b]pyridazin-6-yloxy)phenyl)acetamide; 2-amino-6-{[2-(4-chlorophenyl)-2-oxoethyl]sulfanyl}-4-(3-thienyl)pyridine-3,5-dicarbonitrile; and 3-arylureidobenzylidene-indolin-2-ones.

Yet other therapeutic agents include RET inhibitors such as those described, for example, in U.S. Pat. Nos. 7,504,509; 8,299,057; 8,399,442; 8,067,434; 8,937,071; 9,006,256; and 9,035,063; U.S. Publication Nos. 2014/0121239; 20160176865; 2011/0053934; 2011/0301157; 2010/0324065; 2009/0227556; 2009/0130229; 2009/0099167; 2005/0209195; International Publication Nos. WO 2016/037578; WO 2016/038519; WO 2016/038552; WO 2014/184069; WO 2014/072220; WO 2012/053606; WO 2009/017838; WO 2008/031551; WO 2007/136103; WO 2007/087245; WO 2007/057399; WO 2005/051366; WO 2005/062795; and WO 2005/044835; and J. Med. Chem. 2012, 55 (10), 4872-4876, all of which are hereby incorporated by reference in their entireties.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Go 6976, GNF-5837, GTx-186, GW 441756, LOXO-101, MGCD516, PLX7486, RXDX101, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in Cancer Chemother. Pharmacol. 75(1):131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea), described in ACS Med. Chem. Lett. 3(2): 140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in Cancer 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl) ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in *Int. J. Cancer* 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl) imidazo[1,2-b]pyridazin-3-yl)-[2,4'-bipyridin]-2'-yl)piperidin-4-ol as described in *ACS Med. Chem. Lett.* 6(5):562-567, 2015; GTx-186 and others, as described in *PLoS One* 8(12):e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J. Med. Chem.* 51(15): 4672-4684, 2008; PHA-739358 (danusertib), as described in *Mol. Cancer Ther.* 6:3158, 2007; Go 6976 (5,6,7,13-tetrahydro-13-methyl-5-oxo-12H-indolo[2,3-a]pyrrolo[3,4-c] carbazole-12-propanenitrile), as described in *J. Neurochem.* 72:919-924, 1999; GW441756 ((3Z)-3-[(1-methylindol-3-yl)methylidene]-1H-pyrrolo[3,2-b]pyridin-2-one), as described in IJAE 115:117, 2010; milciclib (PHA-848125AC), described in *J. Carcinog.* 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2 (1H)-one mono 2-hydroxypropanoate hydrate); sitravatinib (N-(3-fluoro-4-((2-(5-(((2-methoxyethyl)amino)methyl) pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl) phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3] benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG- 1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is bacillus Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS 11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB 1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S(E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224 all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Accordingly, also provided herein is a method of treating cancer, comprising administering to a patient in need thereof a pharmaceutical combination for treating cancer which comprises (a) a compound of Formula I or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or a pharmaceutically acceptable salt or solvate thereof and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a RET gene, a RET protein, or expression or activity, or level of any of the same.

These additional therapeutic agents may be administered with one or more doses of the compound of Formula I, or a pharmaceutically acceptable salt or solvate thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer in a patient in need thereof, which comprises (a) a compound of Formula I or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula I or pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a patient in need thereof. In one embodiment the patient is a human. In some embodiments, the cancer is a RET-associated cancer. For example, a RET-associated cancer having one or more RET inhibitor resistance mutations.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., a chemotherapeutic agent), are both administered to a patient simultaneously in the form of a single composition or dosage. The term "non-fixed combination" means that a compound of Formula I or a pharmaceutically acceptable salt or solvate thereof and at least one additional therapeutic agent (e.g., chemotherapeutic agent) are formulated as separate compositions or dosages such that they may be administered to a patient in need thereof simultaneously, concurrently or sequentially with variable intervening time limits, wherein such administration provides effective levels of the two or more compounds in the body of the patient. These also apply to cocktail therapies, e.g. the administration of three or more active ingredients Accordingly, also provided herein is a method of treating a cancer, comprising administering to a patient in need thereof a pharmaceutical combination for treating cancer which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or pharmaceutically acceptable salt or solvate thereof and the additional therapeutic agent are together effective in treating the cancer. In one embodiment, the compound of Formula I or pharmaceutically acceptable salt or solvate thereof, and the additional therapeutic agent are administered simultaneously as separate dosages. In one embodiment, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, the compound of Formula I or pharmaceutically acceptable salt or solvate thereof, and the additional therapeutic agent are administered simultaneously as a combined dosage. In some embodiments, the cancer is a RET-associated cancer. For example, a RET-associated cancer having one or more RET inhibitor resistance mutations.

Also provided herein is a method of treating a disease or disorder mediated by RET in a patient in need of such treatment, the method comprising administering to the patient a therapeutically effective amount of a compound of Formula I or a pharmaceutically acceptable salt or solvate thereof or a pharmaceutical composition thereof. In some embodiments, the disease or disorder mediated by RET is a dysregulation of RET gene, a RET kinase, or expression or activity or level of any of the same. For example the dysregulation of a RET gene, a RET kinase, or expression or activity or level of any of the same includes one or more RET inhibitor resistance mutations. A disease or disorder mediated by RET can include any disease, disorder or condition that is directly or indirectly linked to expression or activity of RET, including overexpression and/or abnormal activity levels. In one embodiment, the disease is cancer (e.g., a RET-associated cancer). In one embodiment, the cancer is any of the cancers or RET-associated cancers described herein.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. For example, overexpression of glial cell-derived neurotrophic factor (GDNF) and its RET receptor tyrosine kinase have been correlated with cancer proliferation and metastasis. See, e.g., Zeng, Q. et al. *J. Int. Med. Res.* (2008) 36(4): 656-64.

Accordingly, also provided herein are methods for inhibiting, preventing, aiding in the prevention, or decreasing the symptoms of metastasis of a cancer in a patient in need thereof, the method comprising administering to the patient a therapeutically effective amount of a compound of Formula I or a pharmaceutically acceptable salt or solvate thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. In some embodiments, the cancer is a RET-associated cancer. In some embodiments, the compound of Formula I or a pharmaceutically acceptable salt or solvate thereof is used in combination with an additional therapy or another therapeutic agent, including a chemotherapeutic agent, such as a kinase inhibitor. For example, a first or second RET kinase inhibitor.

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a RET-associated cancer that include: selecting, identifying, or diagnosing a patient as having a RET-associated cancer, and administering a therapeutically effective amount of a compound of Formula I or a pharmaceutically acceptable salt or solvate thereof to the patient selected, identified, or diagnosed as having a RET-associated cancer. Also provided are methods of decreasing the risk of developing a metastasis or an additional metastasis in a patient having a RET-associated cancer that includes administering a therapeutically effective amount of a compound of Formula I or a pharmaceutically acceptable salt or solvent thereof to a patient having a RET-associated cancer. The decrease in the risk of developing a metastasis or an additional metastasis in a patient having a RET-associated cancer can be compared to the risk of developing a metastasis or an additional metastasis in the patient prior to treatment, or as compared to a patient or a population of patients having a similar or the same RET-associated cancer that has received no treatment or a different treatment. In some embodiments, the RET-associated cancer is a RET-associated cancer having one or more RET inhibitor resistance mutations.

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

As used herein, a "first RET kinase inhibitor" or "first RET inhibitor" is a RET kinase inhibitor as defined herein, but which does not include a compound of Formula I or a pharmaceutically acceptable salt or solvate thereof as defined herein. As used herein, a "second RET kinase inhibitor" or a "second RET inhibitor" is a RET kinase inhibitor as defined herein, but which does not include a compound of Formula I or a pharmaceutically acceptable salt or solvate thereof as defined herein. When both a first and a second RET inhibitor are present in a method provided herein, the first and second RET kinase inhibitor are different.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the first RET inhibitor. Also provided are methods of treating a subject identified as having a cancer cell that has one or more RET inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of cabozantinib, vandetanib, alectinib, sorafenib, lenvatinib, ponatinib, dovitinib, sunitinib, foretinib, BLU667, and BLU6864. In some embodiments, the methods further comprise (after (b)) (c) determining whether a cancer cell in a sample obtained from the subject has at least one RET inhibitor resistance mutation; and (d) administering a compound of Formula I, or a pharmaceutically acceptable salt of solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of cabozantinib, vandetanib, alectinib, sorafenib, lenvatinib, ponatinib, dovitinib, sunitinib, foretinib, BLU667, and BLU6864. In some embodiments, the methods further comprise (after (b)) (c) determining whether a cancer cell in a sample obtained from the subject has at least one RET inhibitor resistance mutation; and (d) administering a compound of Formula I selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt of solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Table 2 in a sample from the subject; and (b) administering to the subject a therapeutically effective amount of a first RET inhibitor, wherein the first RET inhibitor is selected from the group consisting of cabozantinib, vandetanib, alectinib, sorafenib, lenvatinib, ponatinib, dovitinib, sunitinib, foretinib, BLU667, and BLU6864. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt of solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of cabozantinib, vandetanib, alectinib, sorafenib, lenvatinib, ponatinib, dovitinib, sunitinib, foretinib, BLU667, and BLU6864. In some embodiments, the methods further comprise (after (b)) (c) determining whether a cancer cell in a sample obtained from the subject has the RET inhibitor resistance mutation V804M; and (d) administering a compound of Formula I or a pharmaceutically acceptable salt or solvate thereof selected from the group consisting of a compound of Formula I selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt of solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I, or a pharmaceutically acceptable salt of solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of cabozantinib, vandetanib, alectinib, sorafenib, lenvatinib, ponatinib, dovitinib, sunitinib, foretinib, BLU667, and BLU6864, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiv) Example No. 461-480; xxv) Example No. 481-500; xxv) Example No. 501-520; xxvi) Example No. 521-540; or xxvii) Example No. 541-561, or a pharmaceutically acceptable salt of solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of cabozantinib, vandetanib, alectinib, sorafenib, lenvatinib, ponatinib, dovitinib, sunitinib, foretinib, BLU667, and BLU6864, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Table 2 in a sample from the subject; and (b) administering to the subject a therapeutically effective amount of a compound of Formula I selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt of solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of cabozantinib, vandetanib, alectinib, sorafenib, lenvatinib, ponatinib, dovitinib, sunitinib, foretinib, BLU667, and BLU6864, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt of solvate thereof. In some embodiments, the methods further comprise (after (b)) (c) determining whether a cancer cell in a sample obtained from the subject has the RET inhibitor resistance mutation V804M; and (d) administering a second RET inhibitor, wherein the second RET inhibitor is selected from the group consisting of cabozantinib, vandetanib, alectinib, sorafenib, lenvatinib, ponatinib, dovitinib, sunitinib, foretinib, BLU667, and BLU6864, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation.

Also, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt of solvate thereof. In some embodiments, the methods further comprise (after (b)) (c) determining whether a cancer cell in a sample obtained from the subject has at least one RET inhibitor resistance mutation; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Table 2 in a sample from the subject; and (b) administering to the subject a therapeutically effective amount of a compound of Formula I or a pharmaceutically acceptable salt or solvate thereof selected from the group consisting of a compound of Formula I selected from i) Example No. 1-20; ii) Example No. 21-40; iii) Example No. 41-60; iv) Example No. 61-80; v) Example No. 81-100; vi) Example No. 101-120; vii)

Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt of solvate thereof. In some embodiments, the methods further comprise (after (b)) (c) determining whether a cancer cell in a sample obtained from the subject has at least one RET inhibitor resistance mutation of Tables 3 or 4; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, a second RET inhibitor selected from the group consisting ofcabozantinib, vandetanib, alectinib, sorafenib, lenvatinib, ponatinib, dovitinib, sunitinib, foretinib, BLU667, and BLU6864 is administered in step (d). In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-480; xxiv) Example No. 481-500; xxv) Example No. 501-520; xxvi) Example No. 521-540; or xxvii) Example No. 541-561, or a pharmaceutically acceptable salt of solvate thereof. In some embodiments, the methods further comprise (after (b)) (c) determining whether a cancer cell in a sample obtained from the subject has the RET inhibitor resistance mutation V804M; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, a second RET inhibitor selected from the group consisting of cabozantinib, vandetanib, alectinib, sorafenib, lenvatinib, ponatinib, dovitinib, sunitinib, foretinib, BLU667, and BLU6864 is administered in step (d).

Also provided are methods of selecting a treatment for a subject having a cancer that include: identifying a subject having a cancer cell that has one or more RET inhibitor resistance mutations; and selecting a treatment that includes administration of a compound of Formula I or a pharmaceutically acceptable salt or solvate thereof. In some embodiments, the one or more RET inhibitor resistance mutations confer increased resistance to a cancer cell or tumor to treatment with a first RET inhibitor. In some embodiments, the compound of Formula I or a pharmaceutically acceptable salt or solvate thereof is administered in combination with the first RET inhibitor. Also provided are methods of selecting a treatment for a subject having a cancer that include: selecting a treatment that includes administration of a compound of Formula I or a pharmaceutically acceptable salt or solvate thereof for a subject identified as having a cancer cell that has one or more RET inhibitor resistance mutations. Also provided are methods of selecting a subject having a cancer for a treatment that does not include a first RET inhibitor as a monotherapy that include: identifying a subject having a cancer cell that has one or more RET inhibitor resistance mutations; and selecting the identified subject for a treatment that includes a compound of Formula I or a pharmaceutically acceptable salt or solvate thereof. Also provided are methods of selecting a subject having a cancer for a treatment that does not include a first RET inhibitor as a monotherapy that include: selecting a subject identified as having a cancer cell that has one or more RET inhibitor resistance mutations for a treatment that includes administration of a compound of Formula I or a pharmaceutically acceptable salt or solvate thereof. In some embodiments, the one or more RET inhibitor resistance mutations include one or more RET inhibitor resistance mutations listed in Tables 3 and 4. In some embodiments, the one or more RET inhibitor resistance mutations can include a substitution at amino acid position 804, e.g., V804M, V804L, or V804E.

Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject having a cancer cell that has one or more RET inhibitor resistance mutations has a decreased likelihood of having a positive response (i.e. an increased likelihood of having a negative response) to treatment with a first RET inhibitor as a monotherapy. Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject not having a cancer cell that has one or more RET inhibitor resistance mutations has an increased likelihood of having a positive response to treatment with a first RET inhibitor as a monotherapy as compared to a subject having a cancer cell that has one or more RET inhibitor resistance mutations. Also provided are methods of predicting the efficacy of treatment with a first RET inhibitor as a monotherapy in a subject having cancer that include: determining whether a cancer cell in a sample obtained from the subject has one or more RET inhibitor resistance mutations; and determining that treatment with a first RET inhibitor as a monotherapy is less likely to be effective in a subject having a cancer cell in a sample obtained from the subject that has one or more RET inhibitor resistance mutations. Also provided are methods of predicting the efficacy of treatment with a first RET inhibitor as a monotherapy in a subject having cancer that include: determining that treatment with a first RET inhibitor as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a compound of Formula I or a pharmaceutically acceptable salt or solvate thereof as a monotherapy or in conjunction with another anticancer agent to the subject if the subject has a cancer cell that has at least one RET inhibitor resistance mutation; or (d) administering additional doses of the first RET inhibitor of step (a) to the subject if the subject has a cancer cell that does not have a RET inhibitor resistance mutation. In some embodiments, where the subject is administered additional doses of the first RET inhibitor of step (a), the subject can also be administered another anticancer agent (e.g., a second RET inhibitor or a compound of Formula I or a pharmaceutically acceptable salt or solvate thereof, or immunotherapy). In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a second RET inhibitor as a monotherapy or in conjunction with another anticancer agent to the subject if the subject has a cancer cell that has at least one RET inhibitor resistance mutation; or (d) administering additional doses of the first RET inhibitor step (a) to the subject if the subject has a cancer cell that does not have a RET inhibitor resistance mutation. In some embodiments, where the subject is administered additional doses of the first RET inhibitor of step (a), the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy.

Also provided are methods of treating a subject having a cancer (e.g., a RET-associated cancer) that include: (a) determining whether a cancer cell in a sample obtained from a subject having a cancer and previously administered one or more doses of a first RET inhibitor, has one or more RET inhibitor resistance mutations; and (b) administering a compound of Formula I or a pharmaceutically acceptable salt or solvate thereof as a monotherapy or in conjunction with another anticancer agent to the subject if the subject has a cancer cell that has at least one RET inhibitor resistance mutation; or (c) administering additional doses of the first RET inhibitor previously administered to the subject if the subject has cancer cell that does not have a RET inhibitor resistance mutation. In some embodiments, where the subject is administered additional doses of the first RET inhibitor previously administered to the subject, the subject can also be administered another anticancer agent (e.g., a compound of Formula I or a pharmaceutically acceptable salt or solvate thereof, or immunotherapy). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (b), another anticancer agent can be the first RET inhibitor administered in step (a).

Also provided are methods of treating a subject having a cancer that include: (a) determining whether a cancer cell in a sample obtained from a subject having a cancer and previously administered one or more doses of a first RET inhibitor has one or more RET inhibitor resistance mutations; and (b) administering a second RET inhibitor as a monotherapy or in conjunction with another anticancer agent to the subject if the subject has a cancer cell that has at least one RET inhibitor resistance mutation; or (c) administering additional doses of the first RET inhibitor previously administered to the subject if the subject has a cancer cell that does not have a RET inhibitor resistance mutation. In some embodiments, where the subject is administered additional doses of the first RET inhibitor previously administered to the subject, the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments of (b), another anticancer agent can be the first RET inhibitor administered in step (a).

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a compound of Formula I or a pharmaceutically acceptable salt or solvate thereof as a monotherapy or in conjunction with another anticancer agent for the subject if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a second RET inhibitor as a monotherapy or in conjunction with another anticancer agent if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments, another RET can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a compound of Formula I or a pharmaceutically acceptable salt or solvate thereof as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula I or a pharmaceutically acceptable salt or solvate thereof) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a second RET inhibitor as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula I or a pharmaceutically acceptable salt or solvate thereof, or an immunotherapy) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments, another RET can be the first RET inhibitor administered in step (a).

Also provided are methods of determining a subject's risk for developing a cancer that has some resistance to a first RET inhibitor that include: determining whether a cell in a sample obtained from the subject has one or more RET inhibitor resistance mutations; and identifying a subject having a cell that has one or more RET inhibitor resistance mutations, as having an increased likelihood of developing a cancer that has some resistance to the first RET inhibitor. Also provided are methods of determining a subject's risk for developing a cancer that has some resistance to a first RET inhibitor that include: identifying a subject having a cell that has one or more RET inhibitor resistance mutations, as having an increased likelihood of developing a cancer that has some resistance to the first RET inhibitor. Also provided are methods of determining the presence of a cancer that has some resistance to a first RET inhibitor that include: determining whether a cancer cell in a sample obtained from the subject has one or more RET inhibitor resistance mutations; and determining that the subject having a cancer cell that has one or more RET inhibitor resistance mutations has a cancer that has some resistance to the first RET inhibitor. Also provided are methods of determining the presence of a cancer that has some resistance to a first RET inhibitor in a subject that include: determining that a subject having a cancer cell that has one or more RET inhibitor resistance mutations, has a cancer that has some resistance to the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

In some embodiments of any of the methods described herein, a RET inhibitor resistance mutation that confers increased resistance to a cancer cell or tumor to treatment with a first RET inhibitor can be any of the RET inhibitor resistance mutations listed in Table 3 or 4 (e.g., a substitution at amino acid position 804, e.g., V804M, V804L, or V804E).

In some embodiments, the presence of one or more RET inhibitor resistance mutations in a tumor causes the tumor to be more resistant to treatment with a compound of Formula I or a pharmaceutically acceptable salt or solvate thereof. Methods useful when a RET inhibitor resistance mutation causes the tumor to be more resistant to treatment with a compound of Formula I or a pharmaceutically acceptable salt or solvate thereof are described below. For example, provided herein are methods of treating a subject having a cancer that include: identifying a subject having a cancer cell that has one or more RET inhibitor resistance mutations; and administering to the identified subject a treatment that does not include a compound of Formula I or a pharmaceutically acceptable salt or solvate thereof as a monotherapy (e.g., a second RET kinase inhibitor). Also provided are methods of treating a subject identified as having a cancer cell that has one or more RET inhibitor resistance mutations that include administering to the subject a treatment that does not include a compound of Formula I or a pharmaceutically acceptable salt or solvate thereof as a monotherapy (e.g., a second RET kinase inhibitor). In some embodiments, the one or more RET inhibitor resistance mutations confer increased resistance to a cancer cell or tumor to treatment with a compound of Formula I or a pharmaceutically acceptable salt or solvate thereof.

Also provided are methods of selecting a treatment for a subject having a cancer that include: identifying a subject having a cancer cell that has one or more RET inhibitor resistance mutations; and selecting a treatment that does not include a compound of Formula I or a pharmaceutically acceptable salt or solvate thereof as a monotherapy for the identified subject (e.g., a second RET kinase inhibitor). Also provided are methods of selecting a treatment for a subject having a cancer that include: selecting a treatment that does not include a compound of Formula I or a pharmaceutically acceptable salt or solvate thereof as a monotherapy (e.g., a second RET kinase inhibitor) for a subject identified as having a cancer cell that has one or more RET inhibitor resistance mutations. Also provided are methods of selecting a subject having a cancer for a treatment that does not include a compound of Formula I or a pharmaceutically acceptable salt or solvate thereof as a monotherapy (e.g., a second RET kinase inhibitor) that include: identifying a subject having a cancer cell that has one or more RET inhibitor resistance mutations; and selecting the identified subject for a treatment that does not include a compound of Formula I or a pharmaceutically acceptable salt or solvate thereof as a monotherapy (e.g., a second RET kinase inhibitor). Also provided are methods of selecting a subject having a cancer for a treatment that does not include a compound of Formula I or a pharmaceutically acceptable salt or solvate thereof as a monotherapy (e.g., a second RET kinase inhibitor) that include: selecting a subject identified as having a cancer cell that has one or more RET inhibitor resistance mutations for a treatment that does not include a compound of Formula I or a pharmaceutically acceptable salt or solvate thereof as a monotherapy. In some embodiments, the one or more RET inhibitor resistance mutations confer increased resistance to a cancer cell or tumor to treatment with a compound of Formula I or a pharmaceutically acceptable salt or solvate thereof.

Also provided are methods of determining the likelihood that a subject having a cancer will have a positive response to treatment with a compound of Formula I or a pharmaceutically acceptable salt or solvate thereof as a monotherapy that include: determining whether a cancer cell in a sample obtained from the subject has one or more RET inhibitor resistance mutations; and determining that the subject having the cancer cell that has one or more RET inhibitor resistance mutations has a decreased likelihood of having a positive response to treatment with a compound of Formula I or a pharmaceutically acceptable salt or solvate thereof as a monotherapy. Also provided are methods of determining the likelihood that a subject having cancer will have a positive response to treatment with a compound of Formula I or a pharmaceutically acceptable salt or solvate thereof as a monotherapy that include: determining that a subject having a cancer cell that has one or more RET inhibitor resistance mutations has a decreased likelihood of having a positive response to treatment with a compound of Formula I or a pharmaceutically acceptable salt or solvate thereof as a monotherapy. Also provided are methods of predicting the efficacy of treatment with a compound of Formula I or a pharmaceutically acceptable salt or solvate thereof as a monotherapy in a subject having cancer that include: determining whether a cancer cell in a sample obtained from the subject has one or more RET inhibitor resistance mutations; and determining that treatment with a compound of Formula I or a pharmaceutically acceptable salt or solvate thereof as a monotherapy is less likely to be effective in a subject having a cancer cell in a sample obtained from the subject that has one or more RET inhibitor resistance mutations. Also provided are methods of predicting the efficacy of treatment with a compound of Formula I or a pharmaceutically acceptable salt or solvate thereof as a monotherapy in a subject having cancer that include: determining that treatment with a compound of Formula I or a pharmaceutically acceptable salt or solvate thereof as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with a compound of Formula I or a pharmaceutically acceptable salt or solvate thereof.

Also provided are methods of treating a subject having a cancer that include: (a) administering one or more doses of a compound of Formula I or a pharmaceutically acceptable salt or solvate thereof for a period of time; (b) after (a), determining whether a cancer cell in a sample obtained from the subject has one or more RET inhibitor resistance mutations; and (c) administering a second RET inhibitor or a second compound of Formula I or a pharmaceutically acceptable salt or solvate thereof as a monotherapy or in conjunction with another anticancer agent to a subject having a cancer cell that has one or more RET inhibitor resistance mutations; or (d) administering additional doses of the compound of Formula I or a pharmaceutically acceptable salt or solvate thereof of step (a) to a subject having a cancer cell that does not have a RET inhibitor resistance mutation. In some embodiments, where the subject is administered additional doses of the compound of Formula I or a pharmaceutically acceptable salt or solvate thereof of step (a), the subject can also be administered another anticancer agent or a second compound of Formula I or a pharmaceutically acceptable salt or solvate thereof. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of treating a subject having a cancer that include: (a) determining whether a cancer cell in a sample obtained from a subject having a cancer and previously administered one or more doses of a compound of Formula I or a pharmaceutically acceptable salt or solvate thereof, has one or more RET inhibitor resistance mutations; (b) administering a second RET inhibitor or a second compound of Formula I or a pharmaceutically acceptable salt or solvate thereof as a monotherapy or in conjunction with another anticancer agent to a subject having a cancer cell that has one or more RET inhibitor resistance mutations; or (c) administering additional doses of the compound of Formula I or a pharmaceutically acceptable salt or solvate thereof previously administered to a subject having a cancer cell that does not have a RET inhibitor resistance mutation. In some embodiments, where the subject is administered additional doses of the compound of Formula I or a pharmaceutically acceptable salt or solvate thereof of step (a), the subject can also be administered another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of selecting a treatment for a subject having a cancer that include: (a) administering one or more doses of a compound of Formula I or a pharmaceutically acceptable salt or solvate thereof to the subject for a period of time; (b) after (a), determining whether a cancer cell in a sample obtained from the subject has one or more RET inhibitor resistance mutations; and (c) selecting a second RET inhibitor or a second compound of Formula I or a pharmaceutically acceptable salt or solvate thereof as a monotherapy or in conjunction with another anticancer agent for the subject if the subject has a cancer cell that has a RET inhibitor resistance mutation; or (d) selecting additional doses of the compound of Formula I or a pharmaceutically acceptable salt or solvate thereof of step (a) for the subject if the subject has a cancer cell that does not have a RET inhibitor resistance mutation. In some embodiments, where additional doses of a compound of Formula I or a pharmaceutically acceptable salt or solvate thereof of step (a) are selected for the subject, the method can also include further selecting another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of selecting a treatment for a subject having a cancer that include: (a) determining whether a cancer cell in a sample obtained from a subject having a cancer and previously administered one or more doses of a compound of Formula I or a pharmaceutically acceptable salt or solvate thereof, has one or more RET inhibitor resistance mutations; (b) selecting a second RET inhibitor or a second compound of Formula I or a pharmaceutically acceptable salt or solvate thereof as a monotherapy or in conjunction with another anticancer agent for the subject if the subject has a cancer cell that has a RET inhibitor resistance mutation; or (c) selecting additional doses of the compound of Formula I or a pharmaceutically acceptable salt or solvate thereof previously administered to the subject if the subject has a cancer cell that does not have a RET inhibitor resistance mutation. In some embodiments, where additional doses of the compound of Formula I or a pharmaceutically acceptable salt or solvate thereof of step (a) are selected for the subject, the method can also include further selecting another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of determining a subject's risk for developing a cancer that has some resistance to a compound of Formula I or a pharmaceutically acceptable salt or solvate thereof that include: determining whether a cell in a sample obtained from the subject has one or more RET inhibitor resistance mutations; and identifying the subject if the subject has a cell that has one or more RET inhibitor resistance mutations as having an increased likelihood of developing a cancer that has some resistance to a compound of Formula I or a pharmaceutically acceptable salt or solvate thereof. Also provided are methods of determining a subject's risk for developing a cancer that has some resistance to a compound of Formula I or a pharmaceutically acceptable salt or solvate thereof that include: identifying a subject having a cell that has one or more RET inhibitor resistance mutations as having an increased likelihood of developing a cancer that has some resistance to a compound of Formula I or a pharmaceutically acceptable salt or solvate thereof. Also provided are methods of determining the presence of a cancer that has some resistance to a compound of Formula I or a pharmaceutically acceptable salt or solvate thereof that includes: determining whether a cancer cell in a sample obtained from the subject has one or more RET inhibitor resistance mutations; and determining that the subject having the cancer cell that has one or more RET inhibitor resistance mutations has a cancer that has some resistance to a compound of Formula I or a pharmaceutically acceptable salt or solvate thereof. Also provided are methods of determining the presence of a cancer that has some resistance to a compound of Formula I or a pharmaceutically acceptable salt or solvate thereof in a subject that include: determining that a subject having a cancer cell that has one or more RET inhibitor resistance mutations has a cancer that has some resistance to a compound of Formula I or a pharmaceutically acceptable salt or solvate thereof. In some embodiments, the one or more RET inhibitor resistance mutations confer increased resistance to a cancer cell or tumor to treatment with a compound of Formula I or a pharmaceutically acceptable salt or solvate thereof.

In some embodiments of any of the methods described herein, a RET inhibitor resistance mutation that confers increased resistance to a cancer cell or tumor to treatment with a compound of Formula I or a pharmaceutically acceptable salt or solvate thereof, can be any of the RET inhibitor resistance mutations listed in Table 3 or 4.

Methods of determining the level of resistance of a cancer cell or a tumor to a RET inhibitor (e.g., any of the RET inhibitors described herein or known in the art) can be determined using methods known in the art. For example, the level of resistance of a cancer cell to a RET inhibitor can be assessed by determining the $IC_{50}$ of a RET inhibitor (e.g., any of the RET inhibitors described herein or known in the art) on the viability of a cancer cell. In other examples, the level of resistance of a cancer cell to a RET inhibitor can be assessed by determining the growth rate of the cancer cell in the presence of a RET inhibitor (e.g., any of the RET inhibitors described herein). In other examples, the level of resistance of a tumor to a RET inhibitor can be assessed by determining the mass or size of one or more tumors in a subject over time during treatment with a RET inhibitor (e.g., any of the RET inhibitors described herein). In other examples, the level of resistance of a cancer cell or a tumor to a RET inhibitor can be indirectly assessed by determining the activity of a RET kinase including one or more of the RET inhibitor resistance mutations (i.e., the same RET kinase expressed in a cancer cell or a tumor in a subject). The level of resistance of a cancer cell or tumor having one or more RET inhibitor resistance mutations to a RET inhibitor is relative to the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein). For example, the determined level of resistance of a cancer cell or a tumor having one or more RET inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein).

RET is thought to play an important role in the development and survival of afferent nociceptors in the skin and gut. RET kinase knock-out mice lack enteric neurons and have other nervous system anomalies suggesting that a functional RET kinase protein product is necessary during development (Taraviras, S. et al., *Development*, 1999, 126:2785-2797). Moreover population studies of patients with Hirschsprung's disease characterized by colonic obstruction due to lack of normal colonic enervation have a higher proportion of both familial and sporadic loss of function RET mutations (Butler Tjaden N., et al., *Transl. Res.*, 2013, 162: 1-15). Irritable bowel syndrome (IBS) is a common illness affecting 10-20% of individuals in developed countries and is characterized by abnormal bowel habits, bloating and visceral hypersensitivity (Camilleri, M., *N. Engl. J. Med.*, 2012, 367: 1626-1635). While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in many IBS patients the sensitization of the peripheral nervous system results in visceral hypersensitivity or allodynia (Keszthelyi, D., *Eur. J. Pain*, 2012, 16: 1444-1454). See, e.g., U.S. Publication No. 2015/0099762.

Accordingly, provided herein are methods for treating a patient diagnosed with (or identified as having) an irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, and inflammatory bowel disease that include administering to the patient a therapeutically effective amount of a compound of Formula I or a pharmaceutically acceptable salt or solvate thereof.

Also provided herein are methods for treating a patient identified or diagnosed as having a RET-associated irritable bowel syndrome (IBS) (e.g., a patient that has been identified or diagnosed as having a RET-associated irritable bowel syndrome (IBS) through the use of a regulatory agency-approved, e.g., FDA-approved, kit for identifying dysregulation of a RET gene, a RET kinase, or expression or activity or level of any of the same, in a patient or a biopsy sample from the patient) that include administering to the patient a therapeutically effective amount of a compound of Formula I or a pharmaceutically acceptable salt or solvate thereof.

Also provided herein are methods for treating pain associated with IBS that include administering to the patient a therapeutically effective amount of a compound of Formula I or a pharmaceutically acceptable salt or solvate thereof. In some embodiments, a compound of Formula I or a pharmaceutically acceptable salt or solvate thereof is administered in combination with another therapeutic agent useful for treating one or more symptoms of IBS.

Also provided are methods for treating an irritable bowel syndrome (IBS) in a patient in need thereof, the method comprising: (a) determining if the irritable bowel syndrome (IBS) in the patient is a RET-associated IBS (e.g., using a regulatory-agency approved, e.g., FDA-approved, kit for identifying dysregulation of a RET gene, a RET kinase, or expression or activity or level of any of the same, in a patient or a biopsy sample from the patient, or by performing any of the non-limiting examples of assays described herein); and (b) if the IBS is determined to be a RET-associated IBS, administering to the patient a therapeutically effective amount of a compound of Formula I or a pharmaceutically acceptable salt or solvate thereof.

In some embodiments, the compounds of the present invention are useful for treating irritable bowel syndrome (IBS) in combination with one or more additional therapeutic agents or therapies effective in treating the irritable bowel syndrome that work by the same or a different mechanism of action. The at least one additional therapeutic agent may be administered with a compound of Formula I or a pharmaceutically acceptable salt or solvate thereof as part of the same or separate dosage forms, via the same or different routes of administration, and on the same or different administration schedules according to standard pharmaceutical practice known to one skilled in the art.

Non-limiting examples of additional therapeutics for the treatment of irritable bowel syndrome (IBS) include probiotics, fiber supplements (e.g., psyllium, methylcellulose), anti-diarrheal medications (e.g., loperamide), bile acid binders (e.g., cholestyramine, colestipol, colesevelam), anticholinergic and antispasmodic medications (e.g., hyoscyamine, dicyclomine), antidepressant medications (e.g., tricyclic antidepressant such as imipramine or notriptyline or a selective serotonin reuptake inhibitor (SSRI) such as fluoxetine or paroxetine), antibiotics (e.g., rifaximin), alosetron, and lubiprostone.

Accordingly, also provided herein are methods of treating irritable bowel syndrome (IBS), comprising administering to a patient in need thereof a pharmaceutical combination for treating IBS which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of IBS, wherein the amounts of the compound of Formula I or pharmaceutically acceptable salt or solvate thereof and the additional therapeutic agent are together effective in treating the IBS. In one embodiment, the compound of Formula I or pharmaceutically acceptable salt or solvate thereof, and the additional therapeutic agent are administered simultaneously as separate dosages. In one embodiment, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, compound of Formula I or pharmaceutically acceptable salt or solvate thereof, and the additional therapeutic agent are administered simultaneously as a combined dosage.

Also provided herein is (i) a pharmaceutical combination for treating irritable bowel syndrome in a patient in need thereof, which comprises (a) a compound of Formula I or a pharmaceutically acceptable salt or solvate thereof, (b) at least one additional therapeutic agent (e.g., any of the exemplary additional therapeutic agents described herein for treating irritable bowel syndrome or known in the art), and (c) optionally at least one pharmaceutically acceptable carrier for simultaneous, separate or sequential use for the treatment of irritable bowel syndrome, wherein the amounts of the compound of Formula I or pharmaceutically acceptable salt or solvate thereof and of the additional therapeutic agent are together effective in treating the irritable bowel syndrome; (ii) a pharmaceutical composition comprising such a combination; (iii) the use of such a combination for the preparation of a medicament for the treatment of irritable bowel syndrome; and (iv) a commercial package or product comprising such a combination as a combined preparation for simultaneous, separate or sequential use; and to a method of treatment of irritable bowel syndrome in a patient in need thereof. In one embodiment the patient is a human.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., an agent effective in treating irritable bowel syndrome), are both administered to a patient simultaneously in the form of a single composition or dosage. The term "non-fixed combination" means that a compound of Formula I or a pharmaceutically acceptable salt or solvate thereof and at least one additional therapeutic agent (e.g., an agent effective in treating irritable bowel syndrome) are formulated as separate compositions or dosages, such that they may be administered to a patient in need thereof simultaneously, concurrently or sequentially with variable intervening time limits, wherein such administration provides effective levels of the two or more compounds in the body of the patient. In one embodiment, the compound of Formula I and the additional therapeutic agent are formulated as separate unit dosage forms, wherein the separate dosages forms are suitable for either sequential or simultaneous administration. These also apply to cocktail therapies, e.g. the administration of three or more active ingredients.

In some embodiments, a compound provided herein can be used as an agent for supportive care for a patient undergoing cancer treatment. For example, a compound of Formula I or a pharmaceutically acceptable salt or solvate thereof, can be useful to reduce one or more symptoms associated with treatment with one or more cancer therapies such as diarrheal or constipations complications and/or abdominal pain. See, for example, U.S. Publication No. 2015/0099762 and Hoffman, J. M. et al. *Gastroenterology* (2012) 142:844-854. Accordingly, a compound, or a pharmaceutically acceptable salt thereof, or composition provided herein can be administered to a patient to address one or more complications associated with cancer treatment (e.g., gastrointestinal complications such as diarrhea, constipation, or abdominal pain).

In some embodiments, a therapeutically effective amount of a compound of Formula I or a pharmaceutically acceptable salt or solvate thereof, can be administered to a patient undergoing cancer treatment (e.g., a patient experiencing an adverse event associated with cancer treatment such as an immune-related adverse event or a gastrointestinal complication including diarrhea, constipation, and abdominal pain). For example, a compound provided herein, or a pharmaceutically acceptable salt thereof, can be used in the treatment of colitis or IBS associated with administration of a checkpoint inhibitor; see, e.g., Postow, M. A. et al. *Journal of Clinical Oncology* (2015) 33: 1974-1982. In some such embodiments, a compound provided herein, or a pharmaceutically acceptable salt thereof, can be formulated to exhibit low bioavailability and/or be targeted for delivery in the gastrointestinal tract. See, for example, U.S. Pat. No. 6,531,152.

Also provided is a method for inhibiting RET kinase activity in a cell, comprising contacting the cell with a compound of Formula I. In one embodiment, the contacting is in vitro. In one embodiment, the contacting is in vivo. In one embodiment, the contacting is in vivo, wherein the method comprises administering an effective amount of a compound of Formula I or a pharmaceutically acceptable salt or solvate thereof to a subject having a cell having RET kinase activity. In some embodiments, the cell is a cancer cell. In one embodiment, the cancer cell is any cancer as described herein. In some embodiments, the cancer cell is a RET-associated cancer cell. In some embodiments, the cell is a gastrointestinal cell.

Also provided is a method for inhibiting RET kinase activity in a mammalian cell, comprising contacting the cell with a compound of Formula I. In one embodiment, the contacting is in vitro. In one embodiment, the contacting is in vivo. In one embodiment, the contacting is in vivo, wherein the method comprises administering an effective amount of a compound of Formula I or a pharmaceutically acceptable salt or solvate thereof to a mammal having a cell having RET kinase activity. In some embodiments, the mammalian cell is a mammalian cancer cell. In one embodiment, the mammalian cancer cell is any cancer as described herein. In some embodiments, the mammalian cancer cell is a RET-associated cancer cell. In some embodiments, the mammalian cell is a gastrointestinal cell.

As used herein, the term "contacting" refers to the bringing together of indicated moieties in an in vitro system or an in vivo system. For example, "contacting" a RET kinase with a compound provided herein includes the administration of a compound provided herein to an individual or patient, such as a human, having a RET kinase, as well as, for example, introducing a compound provided herein into a sample containing a cellular or purified preparation containing the RET kinase.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein The phrase "effective amount" means an amount of compound that, when administered to a patient in need of such treatment, is sufficient to (i) treat a RET kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the patient in need of treatment, but can nevertheless be routinely determined by one skilled in the art.

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable Also provided herein are pharmaceutical compositions which contain, as the active ingredient, a compound of Formula I or a pharmaceutically acceptable salt or solvate thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In one embodiment, the composition is formulated for oral administration. In one embodiment, the composition is formulated as a tablet or capsule.

The compositions comprising a compound of Formula I or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound for Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

Provided herein are pharmaceutical kits useful, for example, in the treatment of RET-associated diseases or disorders, such as cancer or irritable bowel syndrome (IBS), which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following examples illustrate the invention.

Biological Examples

Example A

RET Enzyme Assay

Compounds of Formula I were screened for their ability to inhibit wildtype and V804M mutant RET kinase using CisBio's HTRF® KinEASE™-TK assay technology. Briefly, N-terminal GST tagged recombinant human RET cytoplasmic domain (aa 658-end) from Eurofins (0.25 nM RET; Catalog No. 14-570M) or N-terminal GST tagged recombinant human V804M mutant RET cytoplasmic domain (aa 658-end) from Millipore (0.25 nM enzyme; Catalog No. 14-760) was incubated with 250 nM TK-substrate biotin (CisBio, part of Catalog No. 62TKOPEC) and 1 mM ATP along with test compound in a buffer consisting of 25 mM HEPES pH 7.4, 10 mM $MgCl_2$, 0.01% Triton X-100, and 2% DMSO in a volume of 8 µL. Compounds were typically prepared in a threefold serial dilution in DMSO and added to the assay to give the appropriate final concentration. After a 30-minute incubation at 22° C., the reaction was quenched by adding 8 µL of quench solution containing 31.25 nM Sa-XL665 and 1×TK-ab-Cryptate in HTRF detection buffer (all from CisBio, part of Cat. No. 62TKOPEC). After a 1 hour incubation at 22° C., the extent of reaction was determined using a PerkinElmer EnVision multimode plate reader via HTRF dual wavelength detection, and the percent of control (POC) was calculated using a ratiometric emission factor. 100 POC was determined using no test compounds and 0 POC was determined using pre-quenched control reactions. The POC values were fit to a 4 parameter logistic curve, and the $IC_{50}$ is defined as the concentration of inhibitor at which the POC equals 50 for the fitted curve. The IC$_{50}$ values for the compounds tested in this assay are provided in Table 5.

Example B

RET Cell Assay

The cellular potency of a compound inhibiting RET kinase was determined in HEK-293 cells expressing a Kif5b-RET fusion protein. Briefly, HEK-293 cells expressing a Kif5b-RET fusion protein were plated at 50K cells/well in 96 well poly-D-Lysine coated plates the day prior to the assay. The cells were incubated for 1 hour with test compound in DMEM (Dulbecco's Modified Eagle Medium) at a final DMSO concentration of 0.5%. Compounds were typically prepared in a three fold serial dilution in DMSO and added to the assay to give the appropriate final concentration. After 1 hour the media was removed, the cells were fixed with 3.8% formaldehyde for 20 min, washed with PBS, and permeabilized for 10 min with 100% methanol. The plates were then washed with PBS-0.05% Tween20, and blocked with LI-COR Blocking solution (LI-COR catalog #927-40000) for 1 hour. Plates were washed with PBS-0.05% Tween20, then incubated with anti-phospho-RET (Tyr1062) (Santa Cruz catalog #sc-20252-R) antibody and anti-GAPDH (Millipore catalog # MAB374) antibody for 2 hours. The plates were washed with PBS-0.05% Tween20, and incubated with anti-rabbit 680 (Molecular Probes catalog No. A21109) and anti-mouse 800 (LI-COR catalog No. 926-32210) secondary antibodies for 1 hour. All antibodies were diluted in LI-COR Block containing 0.05% Tween. The plates were washed with PBS-0.05% Tween20, 100 µL PBS was added to each well, and the plates were read on a LI-COR Aerius fluorescent plate reader. The phospho-RET signal was normalized to the GAPDH signal. 100 POC (percent of control) was determined using no test compounds and 0 POC was determined using 1 µM of a control inhibitor. The POC values were fit to a 4 parameter logistic curve. The IC$_{50}$ value is the point where the curve crosses 50 POC. The IC$_{50}$ values for the compounds tested in this assay are provided in Table 5.

Example C

RET G810R Mutant Assay

The potency of a compound inhibiting G81 OR mutant RET kinase was determined using CisBio's HTRF Kinase-TK assay technology. The assays contained G810R mutant RET produced at Array Biopharma, Inc. (1 nM enzyme—p1982 Lot. No. 160713. The kinase was incubated with 250 nM TK-substrate biotin (CisBio, part of Catalog #62TKO-PEC) and 1 mM ATP along with test compound in a buffer consisting of 25 mM HEPES, pH 7.4, 10 mM MgCl$_2$, 0.01% Triton X-100, and 2% DMSO in a volume of 8 µL. Compounds were typically prepared as a three-fold serial dilution in DMSO and added to the assay to give the appropriate final concentration. After a 60-min incubation at 22° C., the reaction was quenched by adding 8 µL of quench solution containing 31.25 nM Sa-XL665 and 1× TK-Ab-Cryptate in HTRF detection buffer (all from CisBio, part of cat #62TKOPEC). After a 1-h incubation at 22° C., the extent of reaction was determined using a PerkinElmer EnVision multimode plate reader via HTRF dual wavelength detection, and the percent of control (POC) was calculated using a ratiometric emission factor. One hundred POC was determined using no test compounds, and 0 POC was determined using pre-quenched control reactions. A 4-parameter logistic curve was fit to the POC values as a function of the concentration of compound, and the IC$_{50}$ value was the point where the best-fit curve crossed 50 POC.

TABLE 5

IC$_{50}$'s of compounds tested in the assay of Examples A, B and C

| Ex# | RET Enzyme (wild type) IC$_{50}$ (nM) | RET enzyme (V804M) IC$_{50}$ (nM) | KIF5B-RET pTYR1062 Cell IC$_{50}$ (nM) | RET enzyme (G810R) IC$_{50}$ (nM) |
|---|---|---|---|---|
| 1 | 24.0 | 145.2 | 1074.2 | N/A |
| 2 | 32.1 | 176.2 | 70.3 | 202.3 |
| 3 | 16.1 | 90.2 | 37.8 | N/A |
| 4 | 92.1 | 10000.0 | 437.2 | N/A |
| 5 | 15.4 | 66.9 | 30.8 | N/A |
| 6 | 16.8 | 61.8 | 22.4 | N/A |
| 7 | 25.2 | 141.4 | 23.3 | N/A |
| 8 | 66.2 | 315.7 | 95.2 | N/A |
| 9 | 14.9 | 95.8 | 32.6 | N/A |
| 10 | 110.1 | 492.8 | N/A | N/A |
| 11 | 42.5 | 143.1 | 89.7 | N/A |
| 12 | 9.5 | 46.6 | 24.0 | N/A |
| 13 | 19.2 | 95.6 | 38.6 | N/A |
| 14 | 165.4 | 1135.1 | N/A | N/A |
| 15 | 264.0 | 1839.1 | N/A | N/A |
| 16 | 14.1 | 45.0 | 133.9 | N/A |
| 17 | 18.1 | 62.8 | 11.8 | N/A |
| 18 | 11.7 | 116.4 | 37.4 | N/A |
| 19 | 11.4 | 40.0 | 40.6 | N/A |
| 20 | 30.9 | 127.7 | 39.4 | N/A |
| 21 | 20.2 | 94.2 | 14.5 | 255.1 |
| 22 | 50.3 | 239.1 | 100.2 | N/A |
| 23 | 39.9 | 463.1 | 111.5 | N/A |
| 24 | 31.0 | 241.5 | 99.7 | 611.3 |
| 25 | 258.8 | 1693.0 | N/A | N/A |
| 26 | 4048.1 | 5174.2 | N/A | N/A |
| 27 | 3545.8 | 10000.0 | N/A | N/A |
| 28 | 1314.8 | 10000.0 | N/A | N/A |
| 29 | 345.1 | 2124.0 | N/A | N/A |
| 30 | 433.8 | 4733.4 | N/A | N/A |
| 31 | 13.5 | 88.2 | 26.5 | N/A |
| 32 | 69.6 | 409.7 | 85.6 | N/A |
| 33 | 9.9 | 88.1 | 21.1 | N/A |
| 34 | 19.7 | 138.2 | 19.9 | N/A |
| 35 | 209.8 | 1263.8 | N/A | N/A |
| 36 | 62.4 | 534.0 | 120.0 | N/A |
| 37 | 80.4 | 963.4 | 160.5 | N/A |
| 38 | 353.4 | 3915.7 | N/A | N/A |
| 39 | 15.1 | 97.2 | 23.5 | N/A |
| 40 | 63.2 | 802.4 | 193.7 | N/A |
| 41 | 25.2 | 208.7 | 54.1 | N/A |
| 42 | 33.0 | 188.5 | 107.8 | N/A |
| 43 | 25.9 | 59.1 | 1991.1 | N/A |
| 44 | 54.5 | 396.5 | 175.0 | N/A |
| 45 | 138.2 | 901.3 | N/A | N/A |
| 46 | 60.8 | 735.8 | 88.6 | N/A |
| 47 | 29.5 | 239.7 | 50.5 | N/A |
| 48 | 22.1 | 44.3 | 5.4 | 182.4 |
| 49 | 12.5 | 101.3 | 24.1 | N/A |
| 50 | 12.6 | 60.7 | 18.9 | N/A |
| 51 | 14.0 | 62.0 | 46.6 | N/A |
| 52 | 15.4 | 80.6 | 59.8 | N/A |
| 53 | 15.6 | 181.0 | 54.8 | N/A |
| 54 | 16.6 | 84.4 | 40.8 | N/A |
| 55 | 17.2 | 89.1 | 202.1 | N/A |
| 56 | 20.3 | 222.0 | 99.6 | N/A |
| 57 | 22.3 | 131.0 | 92.1 | N/A |
| 58 | 23.2 | 225.2 | 68.0 | N/A |
| 59 | 24.3 | 147.6 | 95.0 | N/A |
| 60 | 32.4 | 220.9 | 125.1 | N/A |
| 61 | 34.6 | 254.8 | 129.3 | N/A |
| 62 | 38.1 | 253.9 | 133.7 | N/A |
| 63 | 18.5 | 67.1 | 12.9 | 550.1 |
| 64 | 73.1 | 644.9 | 241.3 | N/A |
| 65 | 208.7 | 1451.6 | N/A | N/A |
| 66 | 54.6 | 250.1 | 157.2 | N/A |
| 67 | 6588.9 | 10000.0 | N/A | N/A |

TABLE 5-continued

IC$_{50}$'s of compounds tested in the assay of Examples A, B and C

| Ex# | RET Enzyme (wild type) IC$_{50}$ (nM) | RET enzyme (V804M) IC$_{50}$ (nM) | KIF5B-RET pTYR1062 Cell IC$_{50}$ (nM) | RET enzyme (G810R) IC$_{50}$ (nM) |
|---|---|---|---|---|
| 68 | 166.2 | 1329.1 | N/A | N/A |
| 69 | 222.7 | 678.9 | N/A | N/A |
| 70 | 469.9 | 3978.2 | N/A | N/A |
| 71 | 56.4 | 341.5 | 165.7 | N/A |
| 72 | 36.3 | 271.3 | 89.0 | N/A |
| 73 | 107.8 | 601.8 | N/A | N/A |
| 74 | 76.3 | 492.4 | 287.0 | N/A |
| 75 | 128.2 | 768.6 | N/A | N/A |
| 76 | 133.0 | 656.6 | N/A | N/A |
| 77 | 277.0 | 1133.2 | N/A | N/A |
| 78 | 180.1 | 920.8 | N/A | N/A |
| 79 | 241.6 | 968.2 | N/A | N/A |
| 80 | 1212.3 | 5647.2 | N/A | N/A |
| 81 | 728.9 | 4512.1 | N/A | N/A |
| 82 | 2656.5 | 8939.1 | N/A | N/A |
| 83 | 72.7 | 410.3 | 382.8 | N/A |
| 84 | 124.1 | 748.4 | N/A | N/A |
| 85 | 209.6 | 1003.6 | N/A | N/A |
| 86 | 120.8 | 696.6 | N/A | N/A |
| 87 | 215.6 | 1075.1 | N/A | N/A |
| 88 | 34.3 | 151.2 | 30.0 | N/A |
| 89 | 261.7 | 1190.6 | N/A | N/A |
| 90 | 454.6 | 1712.2 | N/A | N/A |
| 91 | 163.3 | 764.6 | N/A | N/A |
| 92 | 32.2 | 152.5 | 35.9 | N/A |
| 93 | 157.5 | 771.8 | N/A | N/A |
| 94 | 88.1 | 702.5 | 370.6 | N/A |
| 95 | 136.6 | 952.6 | N/A | N/A |
| 96 | 62.8 | 593.9 | 271.5 | N/A |
| 97 | 39.1 | 255.9 | 90.1 | 487.0 |
| 98 | 21.4 | 152.1 | 269.8 | N/A |
| 99 | 20.0 | 125.2 | 20.7 | N/A |
| 100 | 14.1 | 91.3 | 43.4 | N/A |
| 101 | 60.4 | 465.3 | 346.3 | N/A |
| 102 | 69.0 | 535.9 | 149.7 | N/A |
| 103 | 95.2 | 786.8 | 224.0 | N/A |
| 104 | 476.6 | 3574.3 | N/A | N/A |
| 105 | 45.4 | 237.2 | 138.3 | N/A |
| 106 | 33.3 | 360.8 | 58.5 | N/A |
| 107 | 47.2 | 457.7 | 67.4 | N/A |
| 108 | 54.6 | 543.1 | 102.95 | N/A |
| 108 | 25.2 | N/A | 91.7 | N/A |
| 110 | 8.1 | 18.5 | 4.5 | 90.0 |
| 111 | 16.4 | 74.9 | 10.5 | N/A |
| 112 | 25.7 | 162.9 | 40.4 | N/A |
| 113 | 614.9 | 4754.7 | N/A | N/A |
| 114 | 109.9 | 843.6 | N/A | N/A |
| 115 | 15.0 | 70.5 | 16.6 | 54.3 |
| 116 | 103.8 | 1255.1 | 221.8 | N/A |
| 117 | 51.6 | 322.0 | 135.9 | N/A |
| 118 | 19.2 | 103.8 | 32.8 | N/A |
| 119 | 32.1 | 147.9 | 48.3 | N/A |
| 120 | 37.3 | 275.1 | 72.3 | N/A |
| 121 | 34.3 | 181.8 | 20.3 | N/A |
| 122 | 80.4 | 790.4 | 213.8 | N/A |
| 123 | 36.8 | 276.9 | 50.0 | N/A |
| 124 | 152.6 | 1075.5 | 294.6 | N/A |
| 125 | 27.5 | 310.4 | 69.2 | N/A |
| 126 | 91.5 | 708.9 | 181.3 | N/A |
| 127 | 41.9 | 228.5 | 201.5 | N/A |
| 128 | 10.2 | 24.0 | 2.5 | 575.7 |
| 129 | 21.6 | 179.2 | 24.1 | N/A |
| 130 | 30.9 | 183.7 | 20.1 | N/A |
| 131 | 41.5 | 422.5 | 113.5 | N/A |
| 132 | 256.3 | 1332.2 | 593.3 | N/A |
| 133 | 124.4 | 914.8 | N/A | N/A |
| 134 | 33.1 | 398.3 | 109.7 | N/A |
| 135 | 77.0 | 756.1 | 173.9 | N/A |
| 136 | 13.1 | 26.1 | 3.9 | 386.6 |
| 137 | 43.7 | 252.0 | 27.1 | N/A |
| 138 | 41.9 | 360.9 | 87.7 | N/A |
| 139 | 237.5 | 1733.1 | N/A | N/A |
| 140 | 23.5 | 219.7 | 96.2 | N/A |
| 141 | 85.5 | 651.3 | 159.0 | N/A |
| 142 | 51.0 | 319.0 | 59.1 | N/A |
| 143 | 36.3 | 276.0 | 46.5 | N/A |
| 144 | 39.3 | 220.6 | 37.4 | N/A |
| 145 | 55.1 | 560.5 | 115.5 | N/A |
| 146 | 113.7 | 712.2 | N/A | N/A |
| 147 | 84.2 | 867.7 | 256.2 | N/A |
| 148 | 144.5 | 1206.0 | N/A | N/A |
| 149 | 49.4 | 328.1 | 100.8 | N/A |
| 150 | 432.5 | 5390.5 | N/A | N/A |
| 151 | 490.4 | 5556.6 | N/A | N/A |
| 152 | 122.8 | 1986.9 | N/A | N/A |
| 153 | 36.7 | 283.5 | 69.7 | N/A |
| 154 | 26.2 | 180.3 | 26.8 | N/A |
| 155 | 28.0 | 146.1 | 45.0 | N/A |
| 156 | 31.9 | 157.6 | 20.5 | N/A |
| 157 | 35.0 | 346.0 | 72.3 | N/A |
| 158 | 100.6 | 703.4 | 130.9 | N/A |
| 159 | 270.8 | 1356.1 | N/A | N/A |
| 160 | 34.8 | 397.3 | 86.6 | N/A |
| 161 | 86.3 | 634.0 | 119.6 | N/A |
| 162 | 67.0 | 562.6 | 246.7 | N/A |
| 163 | 14.0 | 24.1 | 4.2 | 530.7 |
| 164 | 18.6 | 154.0 | 22.1 | N/A |
| 165 | 25.3 | 123.1 | 21.6 | N/A |
| 166 | 29.3 | 84.2 | 22.6 | N/A |
| 167 | 35.3 | 320.9 | 89.5 | N/A |
| 168 | 50.4 | 212.9 | 50.8 | N/A |
| 169 | 63.0 | 299.4 | 109.3 | N/A |
| 170 | 68.6 | 426.2 | 146.2 | N/A |
| 171 | 144.4 | 912.1 | N/A | N/A |
| 172 | 268.6 | 1788.4 | N/A | N/A |
| 173 | 46.9 | 244.2 | 44.8 | N/A |
| 174 | 13.3 | 52.2 | 6.8 | 847.2 |
| 175 | 19.9 | 37.9 | 2.9 | N/A |
| 176 | 24.5 | 74.5 | 10.1 | N/A |
| 177 | 134.4 | 839.7 | N/A | N/A |
| 178 | 28.4 | 79.8 | 12.2 | N/A |
| 179 | 32.1 | 110.8 | 25.4 | N/A |
| 180 | 23.2 | 63.2 | 15.7 | N/A |
| 181 | 91.0 | 674.8 | 165.4 | N/A |
| 182 | 634.3 | 3688.8 | N/A | N/A |
| 183 | 15.1 | 34.1 | 6.4 | 472.6 |
| 184 | 21.6 | 82.5 | 17.0 | 3097.4 |
| 185 | 27.0 | 185.2 | 36.6 | N/A |
| 186 | 20.2 | 149.0 | 36.9 | N/A |
| 187 | 56.2 | 499.6 | 254.5 | N/A |
| 188 | 69.2 | 692.5 | 160.5 | N/A |
| 189 | 82.7 | 789.6 | 211.3 | N/A |
| 190 | 443.6 | 5301.9 | N/A | N/A |
| 191 | 37.3 | 207.3 | 111.6 | N/A |
| 192 | 12.3 | 282.3 | 44.7 | N/A |
| 193 | 38.3 | 372.5 | 38.6 | N/A |
| 194 | 57.8 | 610.2 | 106.8 | N/A |
| 195 | 30.5 | 178.1 | 73.6 | N/A |
| 196 | 78.1 | 567.2 | 238.3 | N/A |
| 197 | 149.4 | 1533.8 | N/A | N/A |
| 198 | 59.1 | 356.1 | 193.0 | N/A |
| 199 | 50.3 | 449.9 | 91.5 | N/A |
| 200 | 461.7 | 5324.1 | N/A | N/A |
| 201 | 59.0 | 273.6 | 90.0 | N/A |
| 202 | 278.2 | 2284.8 | N/A | N/A |
| 203 | 253.6 | 3034.5 | N/A | N/A |
| 204 | 103.7 | 581.8 | 131.7 | N/A |
| 205 | 18.2 | 89.0 | 11.7 | N/A |
| 206 | 61.3 | 519.1 | 78.0 | N/A |
| 207 | 27.4 | 123.0 | 18.8 | N/A |
| 208 | 33.3 | 234.5 | 40.4 | N/A |
| 209 | 41.3 | 288.1 | 39.7 | N/A |

TABLE 5-continued

IC$_{50}$'s of compounds tested in the assay of Examples A, B and C

| Ex# | RET Enzyme (wild type) IC$_{50}$ (nM) | RET enzyme (V804M) IC$_{50}$ (nM) | KIF5B-RET pTYR1062 Cell IC$_{50}$ (nM) | RET enzyme (G810R) IC$_{50}$ (nM) |
|---|---|---|---|---|
| 210 | 34.5 | 196.7 | 57.2 | 786.7 |
| 211 | 113.5 | 901.6 | N/A | N/A |
| 212 | 222.7 | 2022.5 | N/A | N/A |
| 213 | 25.2 | 253.7 | 78.3 | N/A |
| 214 | 54.4 | 338.0 | 148.8 | N/A |
| 215 | 108.5 | 753.1 | N/A | N/A |
| 216 | 29.1 | 211.8 | 73.3 | N/A |
| 217 | 27.0 | 189.9 | 68.4 | N/A |
| 218 | 85.6 | 499.9 | 194.1 | N/A |
| 219 | 77.8 | 423.7 | 92.3 | N/A |
| 220 | 101.8 | 661.0 | 181.7 | N/A |
| 221 | 54.9 | 293.0 | 55.0 | N/A |
| 222 | 40.8 | 273.9 | 40.9 | N/A |
| 223 | 57.1 | 438.6 | 62.1 | N/A |
| 224 | 125.7 | 1033.3 | N/A | N/A |
| 225 | 56.7 | 447.9 | 101.7 | N/A |
| 226 | 36.3 | 382.8 | 95.6 | N/A |
| 227 | 49.8 | 379.7 | 76.3 | N/A |
| 228 | 45.3 | 388.9 | 76.4 | N/A |
| 229 | 100.0 | 946.3 | 124.3 | N/A |
| 230 | 908.8 | 9120.4 | N/A | N/A |
| 231 | 398.9 | 2999.9 | N/A | N/A |
| 232 | 41.9 | 223.7 | 60.0 | N/A |
| 233 | 194.3 | 1040.2 | N/A | N/A |
| 234 | 533.5 | 4156.4 | N/A | N/A |
| 235 | 306.4 | 3651.1 | N/A | N/A |
| 236 | 348.3 | 3801.2 | N/A | N/A |
| 237 | 37.7 | 213.2 | 28.7 | N/A |
| 238 | 42.4 | 347.8 | 87.5 | N/A |
| 239 | 48.9 | 498.9 | 125.6 | N/A |
| 240 | 62.4 | 566.0 | 137.0 | N/A |
| 241 | 69.6 | 560.0 | 142.1 | N/A |
| 242 | 30.5 | 161.4 | 21.3 | N/A |
| 243 | 46.3 | 150.4 | 70.2 | N/A |
| 244 | 107.4 | 476.9 | N/A | N/A |
| 245 | 543.5 | 10000.0 | N/A | N/A |
| 246 | 413.8 | 7839.8 | N/A | N/A |
| 247 | 49.6 | 324.3 | 33.8 | N/A |
| 248 | 21.8 | 42.0 | 7.3 | N/A |
| 249 | 10.6 | 37.3 | 8.1 | N/A |
| 250 | 19.8 | 62.6 | 10.5 | N/A |
| 251 | 35.0 | 222.7 | 22.1 | 1828.5 |
| 252 | 29.9 | 59.0 | 10.9 | 3738.7 |
| 253 | 51.3 | 1141.8 | 85.5 | N/A |
| 254 | 14.8 | 85.7 | 36.8 | 104.5 |
| 255 | 14.4 | 128.3 | 22.2 | 80.1 |
| 256 | 39.3 | 512.3 | 445.1 | N/A |
| 257 | 483.3 | 6165.2 | N/A | N/A |
| 258 | 660.5 | 1914.6 | N/A | N/A |
| 259 | 74.9 | 930.5 | 251.5 | N/A |
| 260 | 240.5 | 3455.9 | N/A | N/A |
| 261 | 30.7 | 61.4 | 10.7 | 58.7 |
| 262 | 92.8 | 549.5 | 58.9 | 872.3 |
| 263 | 93.2 | 1133.3 | 173.0 | N/A |
| 264 | 117.2 | 1326.1 | N/A | 938.2 |
| 265 | 156.5 | 1451.0 | N/A | N/A |
| 266 | 643.9 | 3333.3 | N/A | N/A |
| 267 | 121.7 | 1293.1 | N/A | N/A |
| 268 | 2835.2 | 8899.5 | N/A | N/A |
| 269 | 3789.0 | 10000.0 | N/A | N/A |
| 270 | 271.5 | 2977.8 | 1667.0 | N/A |
| 271 | 514.0 | 4965.8 | N/A | N/A |
| 272 | 69.8 | 982.3 | 673.4 | N/A |
| 273 | 109.4 | 1109.1 | N/A | N/A |
| 274 | 223.4 | 1756.1 | N/A | N/A |
| 275 | 965.2 | 9236.5 | N/A | N/A |
| 276 | 63.2 | 274.7 | 64.3 | N/A |
| 277 | 9.7 | 80.8 | 76.6 | N/A |
| 278 | 35.6 | 237.8 | 47.3 | N/A |
| 279 | 64.9 | 704.7 | 136.8 | N/A |
| 280 | 10.2 | 90.4 | 9.0 | N/A |
| 281 | 9.4 | 19.3 | 5.4 | N/A |
| 282 | 20.0 | 49.1 | 8.1 | N/A |
| 283 | 31.9 | 107.5 | 8.1 | N/A |
| 284 | 13.8 | 55.5 | 13.3 | N/A |
| 285 | 13.1 | 84.9 | 24.1 | N/A |
| 286 | 28.9 | 150.9 | 27.7 | N/A |
| 287 | 17.9 | 121.9 | 30.1 | N/A |
| 288 | 26.5 | 215.5 | 47.3 | N/A |
| 289 | 36.8 | 209.1 | 54.8 | N/A |
| 290 | 52.2 | 393.1 | 84.6 | N/A |
| 291 | 43.4 | 547.9 | 86.2 | N/A |
| 292 | 43.8 | 177.8 | 99.8 | N/A |
| 293 | 47.7 | 487.0 | 129.3 | N/A |
| 294 | 59.3 | 430.5 | 134.2 | N/A |
| 295 | 53.4 | 181.3 | 195.8 | N/A |
| 296 | 83.7 | 448.4 | 300.8 | N/A |
| 297 | 102.3 | 1091.2 | 787.6 | N/A |
| 298 | 33.9 | 234.8 | 31.4 | N/A |
| 299 | 33.5 | 302.0 | 29.5 | N/A |
| 300 | 31.0 | 257.6 | 50.2 | N/A |
| 301 | 24.0 | 181.0 | 113.1 | N/A |
| 302 | 65.1 | 504.4 | 158.5 | N/A |
| 303 | 75.0 | 605.4 | 264.1 | N/A |
| 304 | 100.2 | 652.5 | 383.3 | N/A |
| 305 | 108.1 | 680.5 | N/A | N/A |
| 306 | 125.4 | 881.5 | N/A | N/A |
| 307 | 229.0 | 1552.5 | N/A | N/A |
| 308 | 255.8 | 2199.0 | N/A | N/A |
| 309 | 140.5 | 1056.1 | N/A | N/A |
| 310 | 319.2 | 3631.3 | N/A | N/A |
| 311 | 117.4 | 215.0 | N/A | N/A |
| 312 | 20.8 | 287.9 | 26.1 | N/A |
| 313 | 13.7 | 132.1 | 9.2 | N/A |
| 314 | 28.9 | 308.4 | 36.1 | N/A |
| 315 | 9.6 | 23.2 | 4.9 | N/A |
| 316 | 31.9 | 221.4 | 38.2 | N/A |
| 317 | 20.7 | 196.6 | 44.3 | N/A |
| 318 | 69.5 | 345.6 | 142.7 | N/A |
| 319 | 53.5 | 674.9 | 166.2 | N/A |
| 320 | 88.8 | 701.8 | 1667.0 | N/A |
| 321 | 94.7 | 757.0 | 1667.0 | N/A |
| 322 | 223.4 | 1490.6 | N/A | N/A |
| 323 | 9.9 | 21.6 | 4.0 | N/A |
| 324 | 11.4 | 15.5 | 10.9 | N/A |
| 325 | 24.2 | 103.6 | 27.8 | N/A |
| 326 | 41.1 | 368.2 | 78.8 | N/A |
| 327 | 94.7 | 517.6 | 314.1 | N/A |
| 328 | 82.4 | 586.8 | 444.5 | N/A |
| 329 | 106.7 | 337.0 | N/A | N/A |
| 330 | 45.4 | 372.1 | 93.2 | N/A |
| 331 | 9.4 | 30.8 | 10.3 | N/A |
| 332 | 14.6 | 75.5 | 24.4 | N/A |
| 333 | 29.4 | 218.1 | 33.2 | N/A |
| 334 | 38.5 | 251.0 | 46.0 | N/A |
| 335 | 39.4 | 218.5 | 47.1 | N/A |
| 336 | 45.3 | 334.8 | 164.0 | N/A |
| 337 | 12.6 | 30.0 | 4.6 | N/A |
| 338 | 33.6 | 568.2 | 70.4 | N/A |
| 339 | 51.7 | 756.7 | 236.9 | N/A |
| 340 | 65.1 | 582.7 | 769.3 | N/A |
| 341 | 79.2 | 397.2 | 1667.0 | N/A |
| 342 | 63.8 | 309.7 | 1667.0 | N/A |
| 343 | 55.3 | 329.9 | 970.1 | N/A |
| 344 | 65.6 | 552.2 | 175.1 | N/A |
| 345 | 26.8 | 140.5 | 37.5 | N/A |
| 346 | 35.2 | 172.7 | 45.9 | N/A |
| 347 | 77.9 | 832.3 | 161.1 | N/A |
| 348 | 183.9 | 1196.6 | N/A | N/A |
| 349 | 55.7 | 348.7 | 260.8 | N/A |
| 350 | 77.2 | 225.7 | 96.1 | N/A |
| 351 | 313.9 | 2730.6 | N/A | N/A |

TABLE 5-continued

IC$_{50}$'s of compounds tested in the assay of Examples A, B and C

| Ex# | RET Enzyme (wild type) IC$_{50}$ (nM) | RET enzyme (V804M) IC$_{50}$ (nM) | KIF5B-RET pTYR1062 Cell IC$_{50}$ (nM) | RET enzyme (G810R) IC$_{50}$ (nM) |
|---|---|---|---|---|
| 352 | 2379.9 | 10000.0 | N/A | N/A |
| 353 | 89.3 | 570.5 | 128.6 | N/A |
| 354 | 3347.1 | 10000.0 | N/A | N/A |
| 355 | 405.4 | 5472.6 | N/A | N/A |
| 356 | 242.1 | 2291.9 | N/A | N/A |
| 357 | 154.1 | 2082.0 | N/A | N/A |
| 358 | 50.3 | 710.0 | 150.6 | N/A |
| 359 | 60.7 | 1477.2 | 100.2 | N/A |
| 360 | 190.6 | 2393.4 | N/A | N/A |
| 361 | 62.5 | 288.0 | 102.7 | N/A |
| 362 | 170.0 | 732.6 | N/A | N/A |
| 363 | 31.7 | 88.9 | 24.8 | N/A |
| 364 | 257.3 | 1895.7 | N/A | N/A |
| 365 | 47.8 | 187.1 | 61.0 | N/A |
| 366 | 22.3 | 47.5 | 19.3 | N/A |
| 367 | 109.1 | 1098.7 | N/A | N/A |
| 368 | 19.8 | 47.2 | 30.3 | N/A |
| 369 | 16.2 | 36.9 | 12.1 | N/A |
| 370 | 19.4 | 56.5 | 13.5 | N/A |
| 371 | 28.9 | 147.3 | 35.7 | N/A |
| 372 | 33.9 | 78.7 | 35.7 | N/A |
| 373 | 277.5 | 2974.6 | N/A | N/A |
| 374 | 581.6 | 6256.9 | N/A | N/A |
| 375 | 113.1 | 1561.6 | N/A | N/A |
| 376 | 164.8 | 2788.1 | N/A | N/A |
| 377 | 69.9 | 977.2 | 149.0 | N/A |
| 378 | 110.3 | 1374.6 | N/A | N/A |
| 379 | 474.9 | 4809.7 | N/A | N/A |
| 380 | 127.5 | 1994.2 | N/A | N/A |
| 381 | 147.5 | 1714.8 | N/A | N/A |
| 382 | 31.2 | 134.0 | 28.9 | N/A |
| 383 | 32.8 | 257.8 | 55.3 | N/A |
| 384 | 77.4 | 598.8 | 381.7 | N/A |
| 385 | 59.5 | 401.8 | 112.0 | N/A |
| 386 | 193.8 | 2911.9 | N/A | N/A |
| 387 | 355.0 | 4202.6 | N/A | N/A |
| 388 | 72.6 | 551.6 | 223.5 | N/A |
| 389 | 44.3 | 236.7 | 50.2 | N/A |
| 390 | 69.2 | 621.2 | 231.1 | N/A |
| 391 | 459.9 | 5367.8 | N/A | N/A |
| 392 | 170.9 | 3419.2 | N/A | N/A |
| 393 | 706.7 | 7376.4 | N/A | N/A |
| 394 | 111.6 | 887.1 | N/A | N/A |
| 395 | 365.2 | 2494.9 | N/A | N/A |
| 396 | 110.9 | 1859.9 | N/A | N/A |
| 397 | 75.6 | 668.0 | 51.9 | N/A |
| 398 | 197.0 | 3411.4 | N/A | N/A |
| 399 | 86.8 | 1309.2 | 129.2 | N/A |
| 400 | 110.0 | 1427.0 | N/A | N/A |
| 401 | 94.9 | 1249.8 | 261.5 | N/A |
| 402 | 114.1 | 1349.6 | N/A | N/A |
| 403 | 50.3 | 738.7 | 105.0 | N/A |
| 404 | 293.8 | 6841.7 | N/A | N/A |
| 405 | 48.2 | 331.7 | 70.0 | N/A |
| 406 | 46.5 | 299.7 | 46.2 | N/A |
| 408 | 159.2 | 3136.0 | N/A | N/A |
| 409 | 502.1 | 5012.6 | N/A | N/A |
| 410 | 69.6 | 1038.4 | 1667.0 | N/A |
| 411 | 264.3 | 2912.5 | 1667.0 | N/A |
| 412 | 184.1 | 2524.7 | N/A | N/A |
| 413 | 388.6 | 3712.7 | N/A | N/A |
| 414 | 298.0 | 3136.0 | 990.0 | N/A |
| 415 | 61.6 | 767.8 | 146.5 | N/A |
| 416 | 14.1 | 48.3 | 9.3 | N/A |
| 417 | 109.3 | 974.6 | N/A | N/A |
| 418 | 340.4 | 3890.4 | N/A | N/A |
| 419 | 402.4 | 5308.7 | N/A | N/A |
| 420 | 280.2 | 4516.5 | N/A | N/A |
| 421 | 135.3 | 685.8 | N/A | N/A |
| 422 | 27.4 | 101.6 | 256.9 | N/A |
| 423 | 15.0 | 82.9 | 13.7 | N/A |
| 424 | 102.3 | 736.4 | N/A | N/A |
| 425 | 21.2 | 162.0 | 49.7 | 3238.7 |
| 426 | 24.5 | 157.0 | 23.5 | 1489.0 |
| 427 | 38.7 | 448.8 | 51.1 | 3764.4 |
| 428 | 24.1 | 135.4 | 33.4 | 1742.5 |
| 429 | 38.5 | 452.6 | 34.2 | 5466.1 |
| 430 | 45.1 | 333.2 | 25.1 | 4137.1 |
| 431 | 4.5 | 12.3 | 2.4 | N/A |
| 432 | 29.5 | 155.5 | 20.8 | N/A |
| 433 | 14.2 | 28.4 | 3.3 | 246.8 |
| 434 | 9.3 | 18.1 | 2.8 | N/A |
| 435 | 9.5 | 25.0 | 6.5 | N/A |
| 436 | 34.3 | 117.9 | 11.5 | 351.1 |
| 437 | 19.0 | 138.8 | 11.1 | 278.0 |
| 438 | 10.4 | 53.4 | 5.2 | 104.8 |
| 439 | 22.6 | 47.0 | 5.7 | 128.1 |
| 440 | 13.2 | 32.6 | 36.4 | N/A |
| 441 | 45.3 | 433.6 | 63.2 | N/A |
| 442 | 13.8 | 21.5 | 2.0 | 100.6 |
| 443 | 6.5 | 11.9 | 0.8 | N/A |
| 444 | 7.8 | 16.1 | 3.6 | 68.5 |
| 445 | 8.2 | 24.0 | 2.5 | N/A |
| 446 | 9.5 | 44.7 | 10.0 | 119.7 |
| 447 | 18.2 | 32.1 | 2.7 | 213.4 |
| 448 | 9.6 | 20.4 | 94.5 | N/A |
| 449 | 11.9 | 28.7 | 2.9 | 400.8 |
| 450 | 11.4 | 31.3 | 12.6 | 112.7 |
| 451 | 8.3 | 14.7 | 7.6 | 52.4 |
| 452 | 12.4 | 28.4 | 2.9 | 281.7 |
| 453 | 9.2 | 29.3 | 227.2 | N/A |
| 454 | 16.3 | 47.9 | 8.2 | 1938.2 |
| 455 | 23.2 | 53.3 | 5.5 | 904.7 |
| 456 | 14.7 | 30.0 | 6.7 | N/A |
| 457 | 22.4 | 35.4 | 2.8 | 521.9 |
| 458 | 59.0 | 210.4 | 29.7 | 4116.7 |
| 459 | 10.6 | 56.1 | 15.5 | 123.0 |
| 460 | 12.9 | 27.4 | 2.3 | 207.5 |
| 461 | 5.6 | 16.4 | 90.8 | N/A |
| 462 | 9.0 | 11.9 | 17.5 | 84.8 |
| 463 | 22.8 | 158.5 | 256.1 | N/A |
| 464 | 38.8 | 252.8 | 61.3 | N/A |
| 465 | 48.5 | 289.1 | 103.2 | N/A |
| 466 | 9.7 | 46.4 | 19.3 | N/A |
| 467 | 13.5 | 31.8 | 10.2 | N/A |
| 468 | 4.8 | 10.2 | 6.0 | N/A |
| 469 | 12.0 | 27.3 | 17.6 | N/A |
| 470 | 5.5 | 10.4 | 4.0 | 41.0 |
| 471 | 18.3 | 29.5 | 10.6 | 175.3 |
| 472 | 14.5 | 77.0 | 30.1 | N/A |
| 473 | 17.4 | 58.4 | 8.2 | 642.2 |
| 474 | 33.7 | 88.3 | 22.1 | N/A |
| 475 | 20.0 | 50.0 | 3.4 | 252. |
| 476 | 20.0 | 55.1 | 21.3 | N/A |
| 477 | 35.4 | 95.0 | 28.9 | N/A |
| 478 | 18.3 | 39.9 | 3.2 | 208.3 |
| 479 | 12.6 | 51.4 | 10.4 | 242.0 |
| 480 | 7.4 | 29.3 | 8.3 | N/A |
| 481 | 28.4 | 65.4 | 18.8 | N/A |
| 482 | 9.1 | 22.9 | 25.9 | N/A |
| 483 | 19.4 | 28.3 | 6.8 | 159.2 |
| 484 | 38.2 | 75.2 | 14.4 | 814.4 |
| 485 | 289.6 | 4217.1 | N/A | N/A |
| 486 | 21.7 | 162.4 | 101.8 | N/A |
| 487 | 64.7 | 632.9 | 134.6 | N/A |
| 488 | 80.7 | 321.9 | 144.4 | N/A |
| 489 | 12.5 | 35.9 | 2.7 | 614.5 |
| 490 | 28.2 | 67.5 | 13.2 | N/A |
| 491 | 19.7 | 75.5 | 38.0 | N/A |
| 492 | 86.1 | 518.8 | 122.8 | N/A |
| 493 | 15.3 | 74.6 | 35.2 | N/A |
| 494 | 76.8 | 269.4 | 195.4 | N/A |

TABLE 5-continued

IC$_{50}$'s of compounds tested in the assay of Examples A, B and C

| Ex# | RET Enzyme (wild type) IC$_{50}$ (nM) | RET enzyme (V804M) IC$_{50}$ (nM) | KIF5B-RET pTYR1062 Cell IC$_{50}$ (nM) | RET enzyme (G810R) IC$_{50}$ (nM) |
|---|---|---|---|---|
| 495 | 20.6 | 139.9 | 37.5 | N/A |
| 496 | 30.1 | 114.1 | 34.8 | N/A |
| 497 | 23.5 | 115.9 | 29.3 | N/A |
| 498 | 41.4 | 48.9 | 57.3 | N/A |
| 499 | 42.5 | 70.2 | 49.5 | N/A |
| 500 | 170.3 | 325.4 | N/A | N/A |
| 501 | 102.4 | 298.9 | 100.7 | N/A |
| 502 | 487.6 | 931.3 | N/A | N/A |
| 503 | 692.5 | 6084.2 | N/A | N/A |
| 504 | 25 | 140 | 88 | >10000 |
| 505 | 256 | 4286 | NA | 2662 |
| 506 | 213 | 638 | NA | 3427 |
| 507 | 10 | 77 | 15 | 79 |
| 508 | 28 | 117 | 64 | 143 |
| 509 | 14 | 91 | NA | 147 |
| 510 | 18 | 111 | NA | 192 |
| 511 | 61 | 514 | NA | 841 |
| 512 | 38 | 224 | NA | 380 |
| 513 | 276 | 2250 | NA | 3009 |
| 514 | 572 | 2430 | NA | 2231 |
| 515 | 108 | 1122 | NA | 1990 |
| 516 | 93 | 885 | NA | 1117 |
| 517 | 295 | 1766 | NA | 2474 |
| 518 | 28 | 579 | 192 | 476 |
| 519 | 235 | 2386 | NA | 1487 |
| 520 | 730 | 5111 | NA | 6810 |
| 521 | 78 | 695 | 170 | 1329 |
| 522 | 81 | 695 | NA | 1290 |
| 523 | 51 | 483 | 96 | 473 |
| 524 | 314 | 2114 | NA | 2780 |
| 525 | 1415 | 3518 | NA | 3633 |
| 526 | 90 | 817 | NA | 997 |
| 527 | 292 | 4765 | NA | 2041 |
| 528 | 148 | 1541 | NA | 1392 |
| 529 | 66 | 584 | 73 | 839 |
| 530 | 70 | 698 | 94 | 941 |
| 531 | 58 | 1322 | 176 | 2327 |
| 532 | 301 | 5330 | NA | 8885 |
| 533 | 124 | 767 | NA | 876 |
| 534 | 104 | 625 | NA | 1051 |
| 535 | 18 | 54 | 16 | 1534 |
| 536 | 43 | 256 | 18 | 1761 |
| 537 | 371 | 5945 | NA | NA |
| 538 | 172 | 1489 | NA | NA |
| 539 | 35 | 250 | 127 | NA |
| 540 | 72 | 559 | 210 | NA |
| 541 | 170 | 1253 | NA | NA |
| 542 | 12 | 150 | 18 | 229 |
| 543 | 7 | 31 | 9 | 102 |
| 544 | 4 | 28 | 8 | 65 |
| 545 | 12 | 74 | 51 | 1136 |
| 546 | 23 | 77 | 28 | 284 |
| 547 | 5 | 16 | 5 | 39 |
| 548 | 17 | 153 | 35 | 374 |
| 549 | 10 | 144 | 13 | 535 |
| 550 | 12 | 62 | 17 | 433 |
| 551 | 3 | 11 | 7 | 323 |
| 552 | 1 | 7 | 15 | 101 |
| 553 | 2 | 11 | 39 | 153 |
| 554 | 19 | 207 | 28 | 727 |
| 555 | 19 | 114 | 33 | 868 |
| 556 | 4 | 91 | 162 | 153 |
| 557 | 2529 | 1372 | NA | 3679 |
| 558 | 230 | 585 | NA | 3621 |
| 559 | 10 | 88 | 23.8 | 301.8 |
| 560 | 43.5 | 334.7 | 105.35 | 1462.9 |
| 561 | 165.3 | 972.7 | 292.65 | 2461.5 |

N/A = not available

Synthetic Examples

Synthesis of Synthetic Intermediates

Intermediate P1

4-Bromo-6-hydroxypyrazolo[1,5-a]pyridine-3-carbonitrile

Part A: Preparation of O-(mesitylsulfonyl)hydroxylamine

Step 1: Preparation of tert-butyl (mesitylsulfonyl)oxycarbamate

To a 0° C. solution of 2,4,6-trimethylbenzene-1-sulfonyl chloride (10.0 g, 45.72 mmol) and tert-butyl hydroxycarbamate (6.088 g, 45.72 mmol) in MTBE (100 mL) was added TEA (14.46 mL, 48.01 mmol) dropwise while stirring. The resulting suspension was stirred at 0° C. for an additional 30 min and then warmed to ambient temperature. The reaction was then diluted with water (100 mL), adjusted to pH 4 with 1 N HCl$_{(aq)}$. The organic layer was dried (Na$_2$SO$_4$), filtered and concentrated to yield the title compound initially as a yellowish oil, which upon drying overnight under high vacuum became a white solid (12.89 g, 89% yield). $^1$H NMR (CDCl$_3$) δ 7.66 (br s, 1H), 6.98 (s, 2H), 2.67 (s, 6H), 2.32 (s, 3H), 1.31 (s, 9H).

Step 2: Preparation of O-(mesitylsulfonyl)hydroxylamine

To TFA (117 mL, 1521 mmol) at 0° C. was slowly added tert-butyl (mesitylsulfonyl)oxycarbamate (39.0 g, 124 mmol) over 25 min. The reaction mixture was stirred at 0° C. for 1.5 h and then quenched with the sequential addition of crushed ice and water. The resulting thick suspension was vigorously stirred at ambient temperature for 5 min. Without allowing the filter cake to run dry, the solids were collected by careful vacuum filtration followed by subsequent rinsing with water (4 L) until the filtrate reached pH 6 (Caution: explosion risk exists with dry compound at ambient temperature). The wet filter cake was taken up in DCM (150 mL) and the resulting biphasic solution was separated. The DCM layer was dried over MgSO$_4$ for 30 min and then filtered and rinsed with DCM (420 mL) to provide the title compound as a 0.22 M solution in DCM Part B: Preparation of 4-Bromo-6-hydroxypyrazolo [1,5-a]pyridine-3-carbonitrile Step 1: Preparation of 1-amino-3-bromo-5-methoxypyridin-1-ium 2,4,6-trimethylbenzenesulfonate To a solution of O-(mesitylsulfonyl)hydroxylamine (Part A, 26.6 g, 117 mmol) in DCM (570 mL) cooled to 0° C. was added 3-bromo-5-methoxypyridine (22.1 g, 117 mmol) in portions. The reaction mixture was stirred for 1 h at 0° C. then treated with additional 3-bromo-5-methoxypyridine (250 mg, 1.39 mmol) and stirred for an additional 2 h at 0° C. The reaction mixture was diluted with $Et_2O$ (600 mL), stirred at 0° C. for 10 min and then vacuum filtered, rinsed with $Et_2O$ (3×250 mL). Upon reduction in volume by about ⅓, the filtrate yielded additional precipitate which was collected by filtration. Both filter cakes were dried in vacuo to provide the title compound (39.3 g, 83% yield). $^1H$ NMR $(CDCl_3)$ δ 9.25 (br s, 1H), 8.99 (m, 1H), 8.74 (m, 1H), 7.46 (m, 1H), 6.83 (s, 2H), 3.92 (s, 3H), 2.65 (s, 6H), 2.22 (s, 3H).

Step 2: Preparation of Ethyl 6-bromo-4-methoxypyrazolo[1,5-a]pyridine-3-carboxylate and Ethyl 4-bromo-6-methoxypyrazolo[1,5-a]pyridine-3-carboxylate To a magnetically stirred white suspension of 1-amino-3-bromo-5-methoxypyridin-1-ium 2,4,6-trimethylbenzenesulfonate (33.24 g, 82.42 mmol) in DMF (82 mL) at ambient temperature was added TEA (22.98 mL, 164.8 mmol), followed by dropwise addition of ethyl propiolate (16.71 mL, 164.8 mmol). After vigorous stirring for 2 d, the reaction was slowly quenched via portion-wise addition to rapidly stirring ice water (820 mL). The mixture was stirred at ambient temperature for 10 min and then vacuum filtered. Solids collected were rinsed with water and air-dried, yielding the title compounds as an orange solid in an isomeric ratio of about 4:1 (by $^1H$ NMR) with the 6-Br isomer as the major isomer (21 g). The wet solid isomeric mixture (about 75% w/w) was directly used in Step 3 without further purification. MS (apci) m/z=298.9, 300.9 (M+H). Regioisomeric ratio was determined by MeO chemical shift in $^1H$ NMR $(CDCl_3)$ δ 3.98 (6-Br isomer) vs. 3.83 (4-Br isomer).

Step 3: Preparation of 6-bromo-4-methoxypyrazolo[1,5-a]pyridine (P1) and 4-bromo-6-methoxypyrazolo[1,5-a]pyridine The isomeric mixture of ethyl 6-bromo-4-methoxypyrazolo[1,5-a]pyridine-3-carboxylate and ethyl 4-bromo-4-methoxypyrazolo[1,5-a]pyridine-3-carboxylate from Step 2 (15 g, 50.1 mmol) was added to 48% HBr (114 mL) while stirring, then heated at 80° C. for 90 min followed by stirring at ambient temperature overnight. The resulting suspension was vacuum filtered and rinsed with water. The aqueous filtrate and the filter cake were treated independently. The filter cake was taken up in MTBE and vacuum filtered to remove insoluble impurities. The MTBE filtrate was dried over anhydrous $Na_2SO_4$, filtered and concentrated in vacuo to yield 6-bromo-4-methoxypyrazolo[1,5-a]pyridine as a beige solid (about 98:2 6-/4-Br; 5.08 g). MS (apci) m/z=226.9, 228.9 (M+H). $^1H$ NMR $(CDCl_3)$ δ 8.26 (m, 1H), 7.82 (d, 1H), 6.61 (m, 1H), 6.43 (m, 1H), 3.94 (s, 3H). Independently the original aqueous reaction mixture filtrate was extracted with EtOAc (2×500 mL). The combined organic extracts were dried $(Na_2SO_4)$, filtered and concentrated in vacuo. The crude residue was taken up in DCM (50 mL) and then filtered to remove insoluble solids. Concentration of the DCM filtrate under vacuum followed by silica chromatography (0 to 50% EtOAc/hexanes) yielded a second batch of 6-bromo-4-methoxypyrazolo[1,5-a]pyridine (Intermediate P1) as white solid (upper $R_f$ spot, 2.06 g), as well as the minor isomer title compound 4-bromo-6-methoxypyrazolo[1,5-a]pyridine (Intermediate P2) also as white solid (lower $R_f$ spot, 1.32 g). MS (apci) m/z=226.9, 228.9 (M+H). $^1H$ NMR $(CDCl_3)$ δ 8.02 (m, 1H), 7.85 (d, 1H), 7.17 (d, 1H), 6.55 (m, 1H), 3.80 (s, 3H).

Step 4: Preparation of 4-bromo-6-methoxypyrazolo[1,5-a]pyridine-3-carbaldehyde

A solution of 4-bromo-6-methoxypyrazolo[1,5-a]pyridine (5.0 g, 22 mmol) in DMF (220 mL) was cooled to 0° C. and then slowly treated with $POCl_3$ (6.2 mL, 66 mmol). The reaction was warmed to ambient temperature and stirred overnight. The reaction mixture was cooled to 0° C., quenched with water (220 mL), and basified with 6 M $NaOH_{(aq)}$ to pH 9-10. The reaction mixture was stirred for 1 h and then vacuum filtered. The solids were rinsed sequentially with water (3×50 mL) and MTBE (3×50 mL). The collected solid was suspended in DCM (500 mL) and stirred in a sonicating bath for 30 min and then vacuum filtered. The filtrate was retained, while the filter cake was taken up in water (300 mL) and extracted with DCM. The organic extracts, along with the retained DCM filtrate, were combined and dried over anhydrous $Na_2SO_4$, then filtered and concentrated in vacuo to provide the title compound (4.84 g, 86% yield). MS (apci), m/z=256.9 (M+H).

Step 5: Preparation of 4-bromo-6-methoxypyrazolo[1,5-a]pyridine-3-carbaldehyde oxime To a suspension of 4-bromo-6-methoxypyrazolo[1,5-a]pyridine-3-carbaldehyde (4.84 g, 19.0 mmol) in EtOH (253 mL) at ambient temperature was added water (127 mL) and hydroxylamine hydrochloride (1.98 g, 28.5 mmol). After stirring at 50° C. overnight, the reaction mixture was cooled to ambient temperature and concentrated in vacuo. The residue was suspended in water (150 mL) and then quenched slowly with saturated $NaHCO_{3(aq)}$ (30 mL). After stirring for 1 hour at ambient temperature the suspension was vacuum filtered and the filter cake rinsed sequentially with $H_2O$ (500 mL) and MTBE (100 mL) to yield the title compound as a 2:1 E/Z mixture (5.13 g, quantitative yield), which was used in the next step without further purification. MS (apci) m/z=271.9 (M+H).

Step 6

Preparation of 4-bromo-6-methoxypyrazolo[1,5-a]pyridine-3-carbonitrile. The E/Z mixture of 4-bromo-6-methoxypyrazolo[1,5-a]pyridine-3-carbaldehyde oxime (4.95 g, 18.33 mmol) in acetic anhydride (172.9 mL, 1833 mmol) was stirred at 140° C. for 25 h, and then cooled to ambient temperature. The resulting suspension was further cooled in an ice bath for 15 min and then vacuum filtered and rinsed sequentially with water (200 mL) and MTBE (300 mL) to provide the title compound (3.74 g, 81% yield). $^1H$ NMR ($d^6$-DMSO) δ 8.70 (s, 1H), 8.60 (s, 1H), 7.78 (s, 1H), 3.83 (s, 3H).

Step 7: Preparation of 4-Bromo-6-hydroxypyrazolo[1,5-a]pyridine-3-carbonitrile

A slurry of 4-bromo-6-methoxypyrazolo[1,5-a]pyridine-3-carbonitrile (50.0 g, 198.4 mmol) in DCE (500 mL) was treated with $AlCl_3$ (79.34 g, 595.1 mmol). Under a $N_{2(g)}$ atmosphere, the resulting mixture was stirred 19 h at 76° C., before cooling to room temperature. Using THF (1750 mL) as a rinse solvent, the reaction mixture was poured into a mechanically stirred suspension of sodium sulfate decahydrate (10 eq, 639 g) in THF (1000 mL). After stirring overnight at ambient temperature, the resulting suspension was filtered, and the solids were rinsed with additional THF (2×250 mL). The filtrate was concentrated in vacuo, and the resulting solid was dried under high vacuum for 3 days to afford the title compound (46.18 g, 98% yield) in sufficient purity for subsequent use. $^1$H NMR (d$^6$-DMSO) δ 10.48 (s, 1H), 8.58 (s, 1H), 8.38 (d, 1H), 7.64 (3, 1H).

Intermediate P2

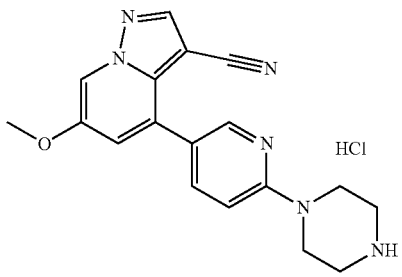 [SMILES: COc1cc(-c2ccc(N3CCNCC3)nc2)c2c(C#N)cnn2c1 ; Cl]

6-Methoxy-4-(6-(piperazin-1-yl)pyridin-3-yl)pyrazolo[1,5-a]pyridine-3-carbonitrile hydrochloride Step 1: Preparation of tert-butyl 4-(5-(3-cyano-6-methoxypyrazolo[1,5-a]pyridin-4-yl)pyridin-2-yl)piperazine-1-carboxylate A stirred solution of 4-bromo-6-methoxypyrazolo[1,5-a]pyridine-3-carbonitrile (Intermediate P1, step 6 of Part B; 425 mg, 1.69 mmol) in dioxane (33.7 mL) was treated with tert-butyl 4-(5-(4,4,5,5-tetramethyl-1,3,2-dioxaborolan-2-yl)pyridin-2-yl)piperazine-1-carboxylate (985 mg, 2.53 mmol) and 2 M K$_2$CO$_{3(aq)}$ (1.69 mL, 3.37 mmol). After purging with N$_{2(g)}$ for 5 min, the mixture was treated with X-phos (161 mg, 0.337 mmol) and Pd$_2$(dba)$_3$ (77.2 mg, 0.0843 mmol), and purged again with N$_{2(g)}$ for an additional 5 min. The resulting reaction mixture was stirred overnight at 80° C., then cooled to ambient temperature and diluted with water. The biphasic mixture was extracted with EtOAc, and the combined organic extracts were dried over anhydrous Na$_2$SO$_{4(s)}$, filtered, and concentrated in vacuo. The crude residue was purified by silica chromatography (0-50% 20% MeOH/DCM in EtOAc as the gradient eluent) to cleanly provide the title compound (842 mg, quantitative yield).

Step 2: Preparation of 6-methoxy-4-(6-(piperazin-1-yl)pyridin-3-yl)pyrazolo[1,5-a]pyridine-3-carbonitrile hydrochloride A solution of tert-butyl 4-(5-(3-cyano-6-methoxypyrazolo[1,5-a]pyridin-4-yl)pyridin-2-yl)piperazine-1-carboxylate (842 mg, 1.94 mmol) in 20% MeOH/DCM (20 mL) was treated with 5 to 6 N HCl in iPrOH (5 mL, 1.94 mmol). After stirring for 6 h at ambient temperature, the suspension was vacuum filtered. The filter cake was washed with water to cleanly provide the title compound as the hydrochloride salt (459 mg, 71% yield).

Intermediate P3

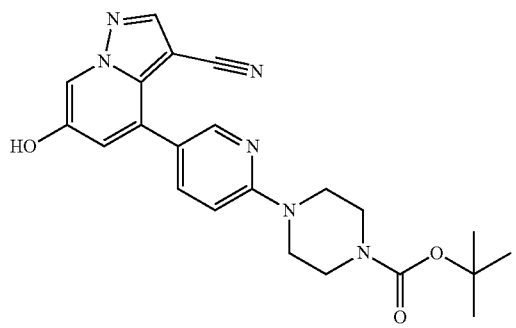 [SMILES: CC(C)(C)OC(=O)N1CCN(c2ccc(-c3cc(O)cn4ncc(C#N)c34)cn2)CC1]

tert-butyl 4-(5-(3-cyano-6-hydroxypyrazolo[1,5-a]pyridin-4-yl)pyridin-2-yl)piperazine-1-carboxylate A mixture of 4-bromo-6-hydroxypyrazolo[1,5-a]pyridine-3-carbonitrile (Intermediate P1; 1.20 g, 5.04 mmol) and tert-butyl 4-(5-(4,4,5,5-tetramethyl-1,3,2-dioxaborolan-2-yl)pyridin-2-yl)piperazine-1-carboxylate (2.36 g, 6.05 mmol) in 2 M Na$_2$CO$_{3(aq)}$ (2.63 mL, 5.25 mmol) and dioxane (2 mL) was sparged with N$_{2(g)}$ for 5 min. The mixture was treated with Pd(PPh$_3$)$_4$ (121 mg, 0.105 mmol), and sparged with N$_{2(g)}$ for an additional 5 min. The resulting mixture was stirred for 16 h at 80° C. under an atmosphere of N$_{2(g)}$. The mixture was cooled to ambient temperature and treated with water (100 mL). The resulting biphasic mixture was extracted with DCM. The combined organic extracts were dried over anhydrous MgSO$_{4(s)}$, filtered, and concentrated in vacuo. The residue was purified by C18 reverse phase chromatography (5-90% ACN/water as the gradient eluent). The purified, but yellow colored, residue was dissolved in DCM and then treated with activated charcoal. The charcoal mixture was filtered through Celite®, rinsing with additional DCM before concentrating the filtrate in vacuo to cleanly provide the title compound (1.55 g, 73% yield). MS (apci) m/z=421.1 (M+H).

Intermediate P4

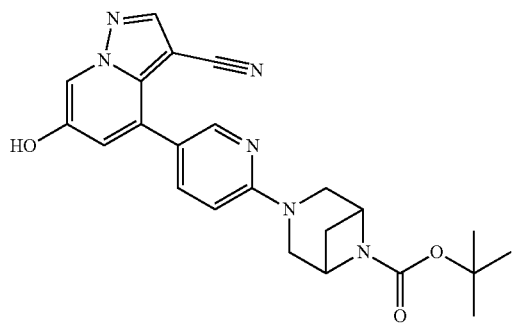 [SMILES: CC(C)(C)OC(=O)N1C2CC1CN(c1ccc(-c3cc(O)cn4ncc(C#N)c34)cn1)C2]

tert-butyl 3-(5-(3-cyano-6-hydroxypyrazolo[1,5-a]pyridin-4-yl)pyridin-2-yl)-3,6-diazabicyclo[3.1.1]heptane-6-carboxylate In a pressure vessel, a solution of 4-bromo-6-hydroxypyrazolo[1,5-a]pyridine-3-carbonitrile (Intermediate P1;

181 mg, 0.761 mmol) in dioxane (7.61 mL) was treated with (6-(6-(tert-butoxycarbonyl)-3,6-diazabicyclo[3.1.1]heptan-3-yl)pyridin-3-yl)boronic acid (Intermediate R4; 243 mg, 0.761 mmol), Pd(PPh$_3$)$_4$ (44.0 mg, 0.0381 mmol) and 2 M Na$_2$CO$_{3(aq)}$ (381 µL, 0.761 mmol). The resulting mixture was sparged with Ar$_{(g)}$, then the vessel was sealed and the mixture was stirred overnight at 80° C. Subsequently the reaction mixture was diluted with water and extracted with EtOAc. The combined organic extracts were washed with water and brine, then dried over anhydrous Na$_2$SO$_{4(s)}$, filtered, and concentrated in vacuo. The crude residue was purified by silica chromatography (25-100% EtOAc in Hexanes as the gradient eluent) to cleanly provide the title compound (72 mg, 22% yield). MS (apci) m/z=433.2 (M+H).

Intermediate P5

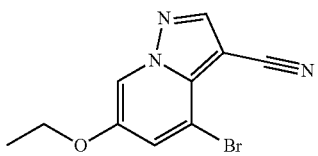

4-Bromo-6-ethoxypyrazolo[1,5-a]pyridine-3-carbonitrile

A solution of 4-bromo-6-hydroxypyrazolo[1,5-a]pyridine-3-carbonitrile (Intermediate P1; 4.0 g, 16.80 mmol) in DMA (100 mL) was treated with K$_2$CO$_{3(s)}$ (7.0 g, 51 mmol) and iodoethane (2.0 mL, 25 mmol) and then stirred for 3 hrs at 60° C. The reaction mixture was cooled to ambient temperature and then quenched with 1:1 NH$_4$OH/Water. The resulting suspension was filtered, and the solids were isolated to provide the title compound (4.35 g, 97% yield) in sufficient purity for subsequent use.

Intermediate P6

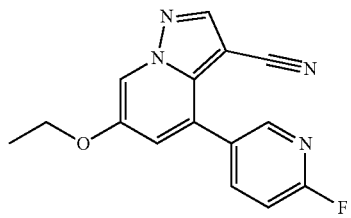 [SMILES: CCOc1cc(-c2ccc(F)nc2)c2c(C#N)cnn2c1]

6-Ethoxy-4-(6-fluoropyridin-3-yl)pyrazolo[1,5-a]pyridine-3-carbonitrile

In a pressure vessel, a solution of 4-bromo-6-ethoxypyrazolo[1,5-a]pyridine-3-carbonitrile (Intermediate P5; 500 mg, 1.88 mmol) in dioxane (9.40 mL) was treated sequentially with 2-fluoro-5-(4,4,5,5-tetramethyl-1,3,2-dioxaborolan-2-yl)pyridine (629 mg, 2.82 mmol), Pd(PPh$_3$)$_4$ (217 mg, 0.188 mmol) and 2 M Na$_2$CO$_{3(aq)}$ (4.70 mL, 9.40). The resulting mixture was sparged with Ar$_{(g)}$ and then the vessel was sealed. The mixture was stirred 8 h at 90° C., and then overnight at ambient temperature. The reaction mixture was diluted with water and extracted with EtOAc. The combined organic extracts were washed with water and brine, dried over anhydrous Na$_2$SO$_{4(s)}$, filtered and concentrated in vacuo. The crude residue was purified by silica chromatography (25-100% EtOAc in hexanes as the gradient eluent) to cleanly provide the title compound (500 mg, 94% yield). MS (apci) m/z=283.1 (M+H).

Intermediate P7

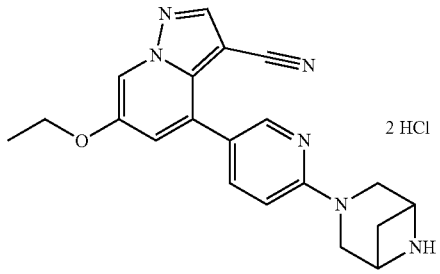 [SMILES: CCOc1cc(-c2ccc(N3CC4CC(C3)N4)nc2)c2c(C#N)cnn2c1]

4-(6-(3,6-diazabicyclo[3.1.1]heptan-3-yl)pyridin-3-yl)-6-ethoxypyrazolo[1,5-a]pyridine-3-carbonitrile dihydrochloride Two methods (Method A and Method B, as shown below) were used to prepare this intermediate.

Method A

Step 1: Preparation of tert-butyl 3-(5-(3-cyano-6-ethoxypyrazolo[1,5-a]pyridin-4-yl)pyridin-2-yl)-3,6-diazabicyclo[3.1.1]heptane-6-carboxylate A mixture of 6-ethoxy-4-(6-fluoropyridin-3-yl)pyrazolo[1,5-a]pyridine-3-carbonitrile (Intermediate P6; 347 mg, 1.23 mmol), tert-butyl 3,6-diazabicyclo[3.1.1]heptane-6-carboxylate (365.6 mg, 1.844 mmol) and K$_2$CO$_{3(s)}$ (1.699 g, 12.29 mmol) in DMSO (6.15 mL) was stirred for 3 days at 80° C. The reaction mixture was cooled to ambient temperature, then diluted with water and extracted with DCM. The combined organic extracts were washed with brine, then dried over anhydrous Na$_2$SO$_{4(s)}$, filtered and concentrated in vacuo. The crude residue was purified by silica chromatography (50-100% EtOAc in Hexanes as the gradient eluent) to cleanly provide the title compound (434.5 mg, 77% yield). MS (apci) m/z=461.2 (M+H).

Step 2: Preparation of 4-(6-(3,6-diazabicyclo[3.1.1]heptan-3-yl)pyridin-3-yl)-6-ethoxypyrazolo[1,5-a]pyridine-3-carbonitrile dihydrochloride A solution of tert-butyl 3-(5-(3-cyano-6-ethoxypyrazolo[1,5-a]pyridin-4-yl)pyridin-2-yl)-3,6-diazabicyclo[3.1.1]heptane-6-carboxylate (44 mg, 0.096 mmol) in DCM (2 mL) was treated with 4N HCl in dioxanes (2 mL). The resulting mixture was stirred for 2 h at ambient temperature before introducing additional 4N HCl in dioxanes (2 mL). After stirring for an additional 1 hour at ambient temperature, the reaction mixture was concentrated in vacuo to cleanly provide the title compound (34 mg, quantitative yield). MS (apci) m/z=361.1 (M+H).

Method B

Step 1: Preparation of tert-butyl 3-(5-(3-cyano-6-ethoxypyrazolo[1,5-a]pyridin-4-yl)pyridin-2-yl)-3,6-diazabicyclo[3.1.1]heptane-6-carboxylate In a pressure vessel, a solution of 4-bromo-6-ethoxypyrazolo[1,5-a]pyridine-3-carbonitrile (Intermediate P5; 38 mg, 0.14 mmol) in dioxane (1.4 mL) was treated sequentially with (6-(6-(tert-butoxycarbonyl)-3,6-diazabicyclo[3.1.1]heptan-3-yl)pyridin-3-yl)boronic acid (Intermediate R4; 50 mg, 0.16 mmol), Pd(PPh$_3$)$_4$ (8.2 mg, 0.007 mmol) and 2 M Na$_2$CO$_{3(aq)}$ (0.7 mL, 0.14 mmol). The resulting mixture was sparged with Ar$_{(g)}$, then the vessel was sealed. The mixture was stirred 8 h at 90° C., and then overnight at ambient temperature. The reaction mixture was diluted with water and extracted with EtOAc. The combined organic extracts were washed with water and brine, then dried over anhydrous Na$_2$SO$_{4(s)}$, filtered and concentrated in vacuo. The crude residue was purified by silica chromatography (25-100% EtOAc in hexanes as the gradient eluent) to cleanly provide the title compound (44 mg, 67% yield). MS (apci) m/z=461.2 (M+H).

Step 2: Preparation of 4-(6-(3,6-diazabicyclo[3.1.1]heptan-3-yl)pyridin-3-yl)-6-ethoxypyrazolo[1,5-a]pyridine-3-carbonitrile dihydrochloride Same as in Step 2 of Method A above.

Intermediate P8

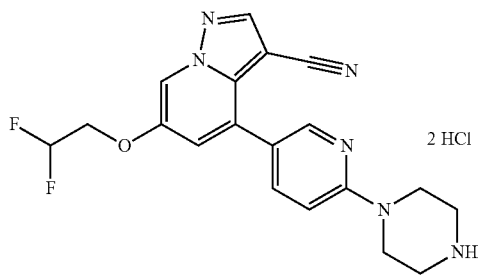 [SMILES: N#Cc1cnn2cc(OCC(F)F)cc(-c3ccc(N4CCNCC4)nc3)c12]

6-(2,2-difluoroethoxy)-4-(6-(piperazin-1-yl)pyridin-3-yl)pyrazolo[1,5-a]pyridine-3-carbonitrile dihydrochloride

Step 1: Preparation of tert-butyl 4-(5-(3-cyano-6-(2,2-difluoroethoxy)pyrazolo[1,5-a]pyridin-4-yl)pyridin-2-yl)piperazine-1-carboxylate 2,2,2-trifluoroacetate A mixture of tert-butyl 4-(5-(3-cyano-6-hydroxypyrazolo[1,5-a]pyridin-4-yl)pyridin-2-yl)piperazine-1-carboxylate (Intermediate P3; 88 mg, 0.21 mmol), 2-bromo-1,1-difluoroethane (36.4 mg, 0.251 mmol) and K$_2$CO$_{3(s)}$ (86.78 mg, 0.6279 mmol) in DMF (2.09 mL) was stirred 24 h at 50° C. Subsequently, additional 2-bromo-1,1-difluoroethane (36.40 mg, 0.2512 mmol) was introduced, and the resulting mixture was stirred an additional 6 h at 50° C. After cooling to ambient temperature, the reaction mixture was diluted with water and extracted with EtOAc. The combined organic extracts were washed with brine, then dried over anhydrous Na$_2$SO$_{4(s)}$, filtered, and concentrated in vacuo. The crude residue was purified by C18 reverse phase chromatography (5-95% ACN in water with 0.1% TFA as the gradient eluent) to cleanly provide the title compound as the 2,2,2-trifluoroacetate salt (30 mg, 26% yield). MS (apci) m/z=485.2 (M+H).

Step 2: Preparation of 6-(2,2-difluoroethoxy)-4-(6-(piperazin-1-yl)pyridin-3-yl)pyrazolo[1,5-a]pyridine-3-carbonitrile dihydrochloride A solution of tert-butyl 4-(5-(3-cyano-6-(2,2-difluoroethoxy)pyrazolo[1,5-a]pyridin-4-yl)pyridin-2-yl)piperazine-1-carboxylate 2,2,2-trifluoroacetate (30 mg, 0.0619 mmol) in DCM (1 mL) was treated dropwise with 4 M HCl in dioxanes (1 mL, 4.00 mmol). The resulting mixture was stirred overnight at ambient temperature, and then additional 4 M HCl in dioxanes (1 mL, 4.00 mmol) was introduced. The reaction was monitored for completion by LCMS and upon completion was concentrated in vacuo, azeotroping with Et$_2$O (3×10 mL), to afford the title compound as the dihydrochloride salt (23.8 mg, quantitative yield). MS (apci) m/z=385.1 (M+H).

Intermediate P9

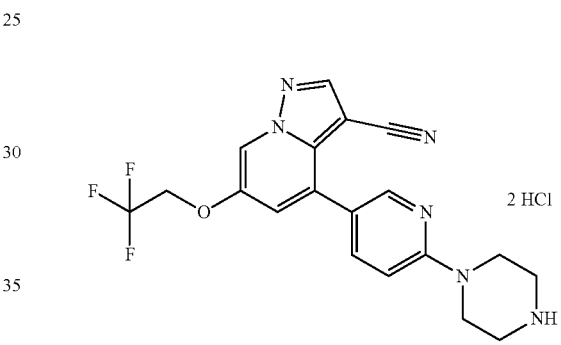

4-(6-(piperazin-1-yl)pyridin-3-yl)-6-(2,2,2-trifluoroethoxy)pyrazolo[1,5-a]pyridine-3-carbonitrile dihydrochloride

Step 1: Preparation of tert-butyl 4-(5-(3-cyano-6-(2,2,2-trifluoroethoxy)pyrazolo[1,5-a]pyridin-4-yl)pyridin-2-yl)piperazine-1-carboxylate A solution of tert-butyl 4-(5-(3-cyano-6-hydroxypyrazolo[1,5-a]pyridin-4-yl)pyridin-2-yl)piperazine-1-carboxylate (Intermediate P3; 100 mg, 0.238 mmol) in DMF (1.19 mL) was treated with DIEA (124.6 µL, 0.7135 mmol) and 2,2,2-trifluoroethyl trifluoromethanesulfonate (51.40 µL, 0.3567 mmol). The resulting mixture was stirred 4 h at ambient temperature before quenching with water. The reaction mixture was partitioned between EtOAc, water and brine. The resulting organic extracts were washed with brine, then dried over anhydrous MgSO$_{4(s)}$, filtered, and concentrated in vacuo. The crude residue was purified by silica chromatography (0-20% MeOH in DCM as the gradient eluent) to cleanly provide the title compound (30 mg, 25% yield). MS (apci) m/z=503.2 (M+H).

Step 2: Preparation of 4-(6-(piperazin-1-yl)pyridin-3-yl)-6-(2,2,2-trifluoroethoxy)pyrazolo[1,5-a]pyridine-3-carbonitrile dihydrochloride A solution of tert-butyl 4-(5-(3-cyano-6-(2,2,2-trifluoroethoxy)pyrazolo[1,5-a]pyridin-4-yl)pyridin-2-yl)piperazine-1-carboxylate (30 mg, 0.060 mmol) in DCM (1 mL) was treated dropwise with 4 M HCl in dioxanes (1 mL, 4.00 mmol). The resulting mixture was stirred overnight at ambient temperature, and then additional 4 M HCl in dioxanes (1 mL, 4.00 mmol) was introduced. The reaction was monitored for completion by LCMS, and upon completion was concentrated in vacuo, azeotroping with Et$_2$O (3×10 mL), to afford the title compound as the dihydrochloride salt (24 mg, quantitative yield). MS (apci) m/z=403.1 (M+H).

Intermediate P10

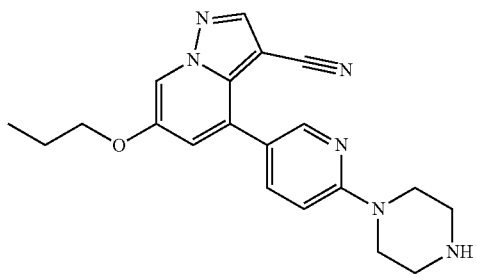 [SMILES: CCCOc1cc(-c2ccc(N3CCNCC3)nc2)c2c(C#N)cnn2c1]

4-(6-(piperazin-1-yl)pyridin-3-yl)-6-propoxypyrazolo[1,5-a]pyridine-3-carbonitrile Step 1: Preparation of tert-butyl 4-(5-(3-cyano-6-propoxypyrazolo[1,5-a]pyridin-4-yl)pyridin-2-yl)piperazine-1-carboxylate A stirred mixture of tert-butyl 4-(5-(3-cyano-6-hydroxypyrazolo[1,5-a]pyridin-4-yl)pyridin-2-yl)piperazine-1-carboxylate (Intermediate P3; 101.3 mg, 0.2409 mmol) and K$_2$CO$_{3(s)}$ (66.59 mg, 0.4818 mmol) in DMF (1.21 mL) was treated slowly with 1-bromopropane (24.1 μL, 0.265 mmol). The resulting mixture was stirred for 3 h at 80° C. After cooling to ambient temperature, the reaction mixture was diluted with EtOAc, then washed with water and brine. The combined organic extracts were dried over anhydrous Na$_2$SO$_{4(s)}$, filtered, and concentrated in vacuo. The crude residue was purified by silica chromatography (0-6% MeOH in DCM as the gradient eluent) to cleanly provide the title compound (100 mg, 90% yield). MS (apci) m/z=463.2 (M+H).

Step 2: Preparation of 4-(6-(piperazin-1-yl)pyridin-3-yl)-6-propoxypyrazolo[1,5-a]pyridine-3-carbonitrile A solution of tert-butyl 4-(5-(3-cyano-6-propoxypyrazolo[1,5-a]pyridin-4-yl)pyridin-2-yl)piperazine-1-carboxylate (100 mg, 0.216 mmol) in DCM (1.08 mL) was treated with TFA (1.08 mL, 0.2162 mmol), and stirred for 3 h at ambient temperature. The reaction mixture was diluted with EtOAc and washed with saturated Na$_2$CO$_{3(aq)}$ and brine. The combined organic extracts were dried over anhydrous Na$_2$SO$_{4(s)}$, filtered, and concentrated in vacuo to cleanly provide the title compound (78 mg, 100% yield). MS (apci) m/z=363.2 (M+H).

All intermediate compounds in Table AA and their Boc protected piperazine precursors were prepared and purified using a similar method to that described for the synthesis of Intermediate P10. In each case, 1-bromopropane was replaced with the appropriate alkyl halide, and an appropriate gradient eluent was used for the chromatographic purification of each t-butyl carbamate precursor. Reactions were monitored for completion by LCMS, and reaction durations were adjusted accordingly.

TABLE AA

| Int. # | Structure | Chemical Name | MS (apci) m/z |
|---|---|---|---|
| P11 | 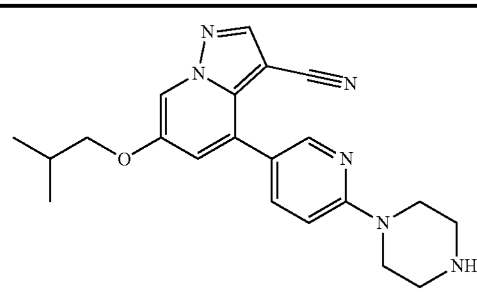 | 6-isobutoxy-4-(6-(piperazin-1-yl)pyridin-3-yl)pyrazolo[1,5-a]pyridine-3-carbonitrile | 377.2 (M + H) |
| P12 | 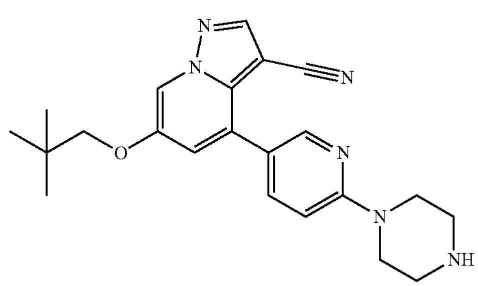 [SMILES: CC(C)(C)COc1cc(-c2ccc(N3CCNCC3)nc2)c2c(C#N)cnn2c1] | 6-(neopentyloxy)-4-(6-(piperazin-1-yl)pyridin-3-yl)pyrazolo[1,5-a]pyridine-3-carbonitrile | 391.2 (M + H) |

TABLE AA-continued

| Int. # | Structure | Chemical Name | MS (apci) m/z |
|---|---|---|---|
| P13 | 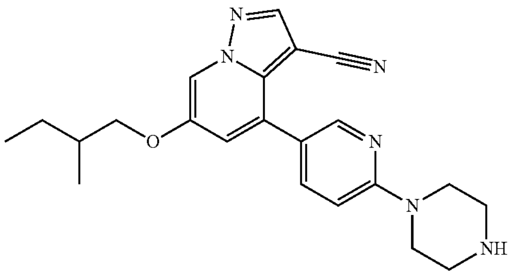 [SMILES: CCC(C)COc1cc(-c2ccc(N3CCNCC3)nc2)c2c(C#N)cnn2c1] | 6-(2-methylbutoxy)-4-(6-(piperazin-1-yl)pyridin-3-yl)pyrazolo[1,5-a]pyridine-3-carbonitrile | 391.2 (M + H) |
| P14 | 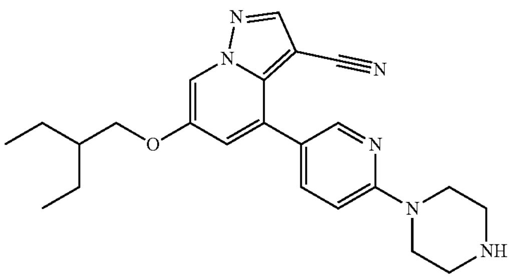 [SMILES: CCC(CC)COc1cc(-c2ccc(N3CCNCC3)nc2)c2c(C#N)cnn2c1] | 6-(2-ethylbutoxy)-4-(6-(piperazin-1-yl)pyridin-3-yl)pyrazolo[1,5-a]pyridine-3-carbonitrile | 405.2 (M + H) |
| P15 | 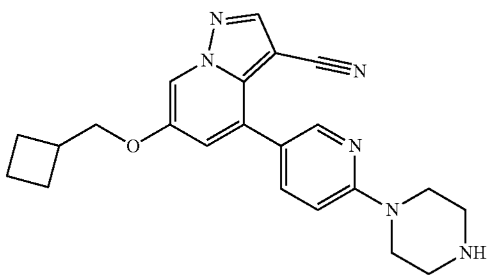 [SMILES: N#Cc1cnn2cc(OCC3CCC3)cc(-c3ccc(N4CCNCC4)nc3)c12] | 6-(cyclobutylmethoxy)-4-(6-(piperazin-1-yl)pyridin-3-yl)pyrazolo[1,5-a]pyridine-3-carbonitrile | 389.2 (M + H) |

Intermediate P16

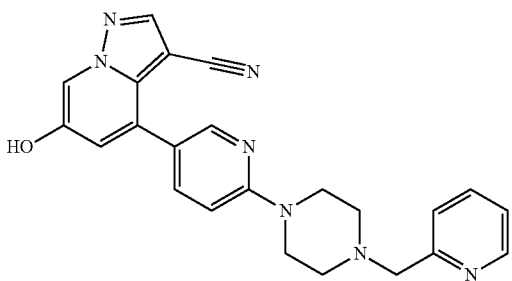 [SMILES: N#Cc1cnn2cc(O)cc(-c3ccc(N4CCN(Cc5ccccn5)CC4)nc3)c12]

6-hydroxy-4-(6-(4-(pyridin-2-ylmethyl)piperazin-1-yl)pyridin-3-yl)pyrazolo[1,5-a]pyridine-3-carbonitrile In a pressure vessel, a mixture of 4-bromo-6-hydroxypyrazolo[1,5-a]pyridine-3-carbonitrile (Intermediate P1; 100 mg, 0.420 mmol) and 1-(pyridin-2-ylmethyl)-4-(5-(4,4,5,5-tetramethyl-1,3,2-dioxaborolan-2-yl)pyridin-2-yl)piperazine (Intermediate R9; 192 mg, 0.504 mmol) in dioxane (4 mL) and 2 M Na$_2$CO$_{3(aq)}$ (1.05 mL, 2.10 mmol) was sparged with N$_{2(g)}$ for 5 min. The mixture was treated with Pd(PPh$_3$)$_4$ (48.5 mg, 0.0420 mmol) and sparged with N$_{2(g)}$ for an additional 5 min. The vessel was sealed, and the mixture was stirred for 15 h at 80° C. The mixture was cooled to ambient temperature, then diluted with water (5 mL) and treated with 2 M HCl$_{(aq)}$ (0.9 mL). The resulting biphasic mixture was extracted with DCM. The combined organic extracts were dried over anhydrous MgSO$_{4(s)}$, filtered, and concentrated in vacuo. The residue was purified by C18 reverse phase chromatography (5-90% ACN/water as the gradient eluent) to afford the title compound (34 mg, 20% yield). MS (apci) m/z=412.1 (M+H).

Intermediate P17

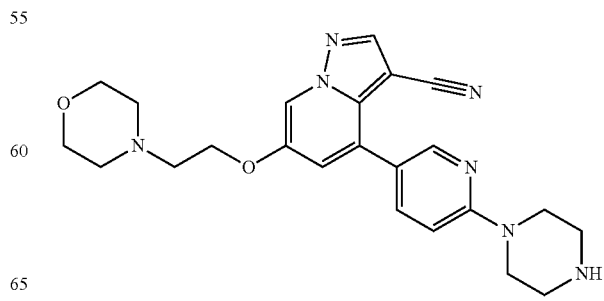

6-(2-morpholinoethoxy)-4-(6-(piperazin-1-yl)pyridin-3-yl)pyrazolo[1,5-a]pyridine-3-carbonitrile Step 1: Preparation of tert-butyl 4-(5-(3-cyano-6-(2-morpholinoethoxy)pyrazolo[1,5-a]pyridin-4-yl)pyridin-2-yl)piperazine-1-carboxylate A cold (0° C.) solution of PPh₃ (444 mg, 1.69 mmol) in 1:1 DCM:THF (10.0 mL) was treated with DIAD (333 μL, 1.69 mmol), and stirred for 15 min at 0° C. The resulting 0° C. mixture was treated with a solution of tert-butyl 4-(5-(3-cyano-6-hydroxypyrazolo[1,5-a]pyridin-4-yl)pyridin-2-yl)piperazine-1-carboxylate (Intermediate P3; 356 mg, 0.847 mmol) and 2-morpholinoethan-1-ol (207 μL, 1.69 mmol) in 1:1 DCM:THF (20.0 mL). After stirring overnight at room temperature, the reaction mixture was concentrated in vacuo, and purified by silica gel chromatography (5-30% MeOH in EtOAc as the gradient eluent) to afford the title compound (303 mg, 67% yield). MS (apci) m/z=534.2 (M+H).

Step 2: Preparation of 6-(2-morpholinoethoxy)-4-(6-(piperazin-1-yl)pyridin-3-yl)pyrazolo[1,5-a]pyridine-3-carbonitrile A solution of tert-butyl 4-(5-(3-cyano-6-(2-morpholinoethoxy)pyrazolo[1,5-a]pyridin-4-yl)pyridin-2-yl)piperazine-1-carboxylate (303 mg, 0.568 mmol) in DCM (4.0 mL) was treated with TFA (2.0 mL). The resulting mixture was stirred for 30 min at ambient temperature, then purified by C18 reverse phase chromatography (5-95% ACN/water with 0.1% TFA as the gradient eluent) to afford the title compound as the TFA salt. The salt was partitioned between 4:1 DCM:iPrOH and saturated NaHCO₃(aq). The combined organic extracts were separated, dried over anhydrous Na₂SO₄(s), filtered and concentrated in vacuo to cleanly provide the title compound (100 mg, 41% yield). MS (apci) m/z=434.1 (M+H).

Intermediate P18

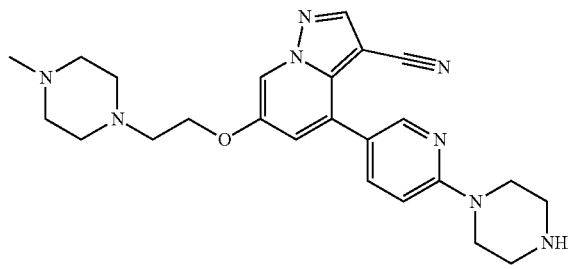 [SMILES: CN1CCN(CCOc2cc(-c3ccc(N4CCNCC4)nc3)c3c(C#N)cnn3c2)CC1]

6-(2-(4-methylpiperazin-1-yl)ethoxy)-4-(6-(piperazin-1-yl)pyridin-3-yl)pyrazolo[1,5-a]pyridine-3-carbonitrile Step 1: Preparation of tert-butyl 4-(5-(3-cyano-6-(2-(4-methylpiperazin-1-yl)ethoxy)pyrazolo[1,5-a]pyridin-4-yl)pyridin-2-yl)piperazine-1-carboxylate A cold (0° C.) solution of PPh₃ (233.9 mg, 0.8919 mmol) in 1:1 DCM:THF (6.0 mL) was treated with DIAD (175.6 μL, 0.8919 mmol) and stirred for 15 min at 0° C. The resulting 0° C. mixture was treated with a solution of tert-butyl 4-(5-(3-cyano-6-hydroxypyrazolo[1,5-a]pyridin-4-yl)pyridin-2-yl)piperazine-1-carboxylate (Intermediate P3; 250.0 mg, 0.5946 mmol) and 1-(N-hydroxyethyl)-4-methyl piperazine (102.9 mg, 0.7135 mmol) in 1:1 DCM:THF (12.0 mL). After stirring overnight at room temperature, the reaction mixture was concentrated in vacuo and purified by silica gel chromatography (1-30% DCM-MeOH with 2% NH₄OH as the gradient eluent) to afford the title compound which was immediately carried on to step 2. MS (apci) m/z=547.2 (M+H).

Step 2: Preparation of 6-(2-(4-methylpiperazin-1-yl)ethoxy)-4-(6-(piperazin-1-yl)pyridin-3-yl)pyrazolo[1,5-a]pyridine-3-carbonitrile A solution of tert-butyl 4-(5-(3-cyano-6-(2-(4-methylpiperazin-1-yl)ethoxy)pyrazolo[1,5-a]pyridin-4-yl)pyridin-2-yl)piperazine-1-carboxylate in 1:1 DCM:TFA (6.0 mL) was stirred for 15 min at ambient temperature then concentrated in vacuo. The residue was purified by C18 reverse phase chromatography (5-95% water-ACN with 0.1% TFA as the gradient eluent) to afford the title compound as the TFA salt. The TFA salt was partitioned between 4:1 DCM:iPrOH and saturated NaHCO₃(aq). The combined organic extracts were dried over anhydrous Na₂SO₄(s), filtered and concentrated in vacuo to afford the title compound (146.4 mg, 55% yield). MS (apci) m/z=447.2 (M+H).

Intermediate P19

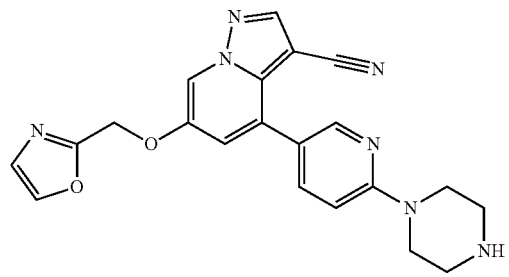 [SMILES: N#Cc1cnn2cc(OCc3ncco3)cc(-c3ccc(N4CCNCC4)nc3)c12]

6-(oxazol-2-ylmethoxy)-4-(6-(piperazin-1-yl)pyridin-3-yl)pyrazolo[1,5-a]pyridine-3-carbonitrile Step 1: Preparation of tert-butyl 4-(5-(3-cyano-6-(oxazol-2-ylmethoxy)pyrazolo[1,5-a]pyridin-4-yl)pyridin-2-yl)piperazine-1-carboxylate A room temperature mixture of tert-butyl 4-(5-(3-cyano-6-hydroxypyrazolo[1,5-a]pyridin-4-yl)pyridin-2-yl)piperazine-1-carboxylate (Intermediate P3; 77.5 mg, 0.184 mmol) and K₂CO₃(s) (50.9 mg, 0.369 mmol) in DMF (1.84 mL) was treated with 2-(chloromethyl)oxazole (43.3 μL, 0.369 mmol). The resulting mixture was stirred for 1 hour at 80° C., and then additional 2-(chloromethyl)oxazole (10 μL, 0.0852 mmol) was added. After stirring 3 days at 80° C., the reaction mixture was cooled to ambient temperature. The mixture was diluted with EtOAc and washed with water and brine. The combined organic extracts were dried over anhydrous Na₂SO₄(s), filtered, and concentrated in vacuo. The crude residue was purified by silica chromatography (10-

90% EtOAc in Hexanes as the gradient eluent) to cleanly provide the title compound (44 mg, 48% yield). MS (apci) m/z=501.8 (M+H).

Step 2: Preparation of 6-(oxazol-2-ylmethoxy)-4-(6-(piperazin-1-yl)pyridin-3-yl)pyrazolo[1,5-a]pyridine-3-carbonitrile A solution of tert-butyl 4-(5-(3-cyano-6-(oxazol-2-ylmethoxy)pyrazolo[1,5-a]pyridin-4-yl)pyridin-2-yl)piperazine-1-carboxylate (44 mg, 0.088 mmol) in DCM (880 μL) was treated with TFA (880 μL, 0.088 mmol), then stirred for 1 hour at ambient temperature. The resulting mixture was diluted with DCM and neutralized with saturated Na$_2$CO$_{3(aq)}$. The biphasic mixture was extracted with DCM. The combined organic extracts were washed with saturated NaHCO$_{3(aq)}$ and brine, then dried over anhydrous Na$_2$SO$_{4(s)}$, filtered and concentrated in vacuo to cleanly provide the title compound (30 mg, 85% yield). MS (apci) m/z=401.8 (M+H).

Intermediate P20

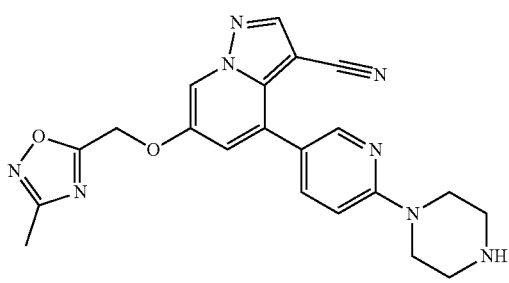 [SMILES: Cc1noc(COc2cc(-c3ccc(N4CCNCC4)nc3)c3c(C#N)cnn3c2)n1]

6-((3-methyl-1,2,4-oxadiazol-5-yl)methoxy)-4-(6-(piperazin-1-yl)pyridin-3-yl)pyrazolo[1,5-a]pyridine-3-carbonitrile Step 1: Preparation of tert-butyl 4-(5-(3-cyano-6-((3-methyl-1,2,4-oxadiazol-5-yl)methoxy)pyrazolo[1,5-a]pyridin-4-yl)pyridin-2-yl)piperazine-1-carboxylate A room temperature mixture of tert-butyl 4-(5-(3-cyano-6-hydroxypyrazolo[1,5-a]pyridin-4-yl)pyridin-2-yl)piperazine-1-carboxylate (Intermediate P3; 83 mg, 0.120 mmol) and K$_2$CO$_{3(s)}$ (54.6 mg, 0.395 mmol) in DMF (1.97 mL) was treated with 5-(chloromethyl)-3-methyl-1,2,4-oxadiazole (40.5 μL, 0.395 mmol) and stirred 3.5 h at 80° C. The resulting mixture was cooled to ambient temperature, diluted with EtOAc, and washed with water and brine. The combined organic extracts were dried over anhydrous Na$_2$SO$_{4(s)}$, filtered, and concentrated in vacuo. The crude residue was purified by silica chromatography (10-90% EtOAc in Hexanes as the gradient eluent) to cleanly provide the title compound (70.9 mg, 70% yield). MS (apci) m/z=516.8 (M+H).

Step 2: Preparation of 6-((3-methyl-1,2,4-oxadiazol-5-yl)methoxy)-4-(6-(piperazin-1-yl)pyridin-3-yl)pyrazolo[1,5-a]pyridine-3-carbonitrile A solution of tert-butyl 4-(5-(3-cyano-6-((3-methyl-1,2,4-oxadiazol-5-yl)methoxy)pyrazolo[1,5-a]pyridin-4-yl)pyridin-2-yl)piperazine-1-carboxylate (70.9 mg, 0.137 mmol) in DCM (1.37 mL) was treated with TFA (1.37 mL, 0.137 mmol), then stirred for 1 hour at ambient temperature. The resulting mixture was diluted with DCM, and neutralized with saturated Na$_2$CO$_{3(aq)}$. The biphasic mixture was extracted with DCM. The combined organic extracts were washed with saturated NaHCO$_{3(aq)}$ and brine, then dried over anhydrous Na$_2$SO$_{4(s)}$, filtered and concentrated in vacuo to cleanly provide the title compound (21 mg, 37% yield). MS (apci) m/z=416.8 (M+H).

Intermediate P21

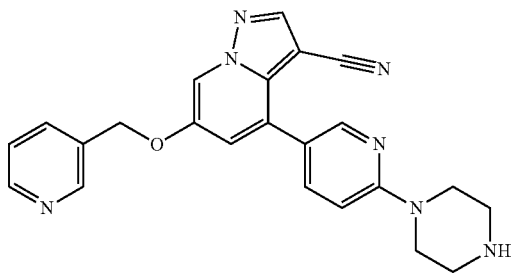 [SMILES: N#Cc1cnn2cc(OCc3cccnc3)cc(-c3ccc(N4CCNCC4)nc3)c12]

4-(6-(piperazin-1-yl)pyridin-3-yl)-6-(pyridin-3-ylmethoxy)pyrazolo[1,5-a]pyridine-3-carbonitrile Step 1: Preparation of tert-butyl 4-(5-(3-cyano-6-(pyridin-3-ylmethoxy)pyrazolo[1,5-a]pyridin-4-yl)pyridin-2-yl)piperazine-1-carboxylate A mixture of tert-butyl 4-(5-(3-cyano-6-hydroxypyrazolo[1,5-a]pyridin-4-yl)pyridin-2-yl)piperazine-1-carboxylate (Intermediate P3; 0.1002 g, 0.2383 mmol) and pyridin-3-ylmethanol (25.45 μL, 0.2621 mmol) in THF (1.19 mL) was treated with PPh$_3$ (125.0 mg, 0.4766 mmol). The resulting mixture was sparged with Ar$_{(g)}$ for 3 min before introducing DIAD (92.67 μL, 0.4766 mmol). After sparging with Ar$_{(g)}$ for an additional 1 min, the reaction mixture was stirred 1 hour at ambient temperature. The mixture was diluted with water and extracted with DCM. The combined organic extracts were extracted sequentially with water and brine, then dried over anhydrous Na$_2$SO$_{4(s)}$, filtered and concentrated in vacuo. The residue was purified by silica chromatography (1-6% MeOH in DCM as the gradient eluent) to cleanly provide the title compound (107 mg, 88% yield). MS (apci) m/z=412.2 [(M-Boc)+H].

Step 2: Preparation of 4-(6-(piperazin-1-yl)pyridin-3-yl)-6-(pyridin-3-ylmethoxy)pyrazolo[1,5-a]pyridine-3-carbonitrile A solution of tert-butyl 4-(5-(3-cyano-6-(pyridin-3-ylmethoxy)pyrazolo[1,5-a]pyridin-4-yl)pyridin-2-yl)piperazine-1-carboxylate (107 mg, 0.209 mmol) in DCM (1.05 mL) was treated with TFA (48.3 μL, 0.627 mmol), then stirred for 30 min at ambient temperature. The resulting mixture was diluted with DCM and neutralized with saturated Na$_2$CO$_{3(aq)}$. The biphasic mixture was diluted with saturated NaHCO$_{3(aq)}$, and extracted with DCM. The combined organic extracts were washed with water and brine, then dried over anhydrous Na$_2$SO$_{4(s)}$, filtered and concen- Intermediate P22

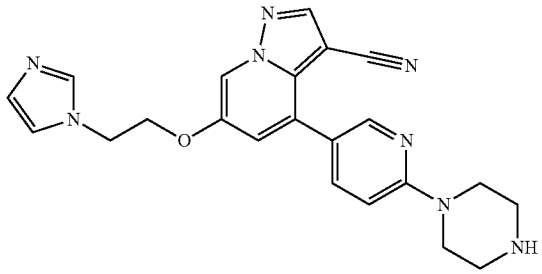 [SMILES: N#Cc1cnn2cc(OCCn3ccnc3)cc(-c3ccc(N4CCNCC4)nc3)c12]

6-(2-(1H-imidazol-1-yl)ethoxy)-4-(6-(piperazin-1-yl)pyridin-3-yl)pyrazolo[1,5-a]pyridine-3-carbonitrile Step 1: Preparation of tert-butyl 4-(5-(6-(2-(1H-imidazol-1-yl)ethoxy)-3-cyanopyrazolo[1,5-a]pyridin-4-yl)pyridin-2-yl)piperazine-1-carboxylate A mixture of tert-butyl 4-(5-(3-cyano-6-hydroxypyrazolo[1,5-a]pyridin-4-yl)pyridin-2-yl)piperazine-1-carboxylate (Intermediate P3; 0.1002 g, 0.2383 mmol) and 2-(1H-imidazol-1-yl)ethan-1-ol (23.04 µL, 0.2383 mmol) in THF (1.19 mL) was treated with PPh$_3$ (78.13 mg, 0.2979 mmol). The resulting mixture was sparged with Ar$_{(g)}$ for 3 min before introducing DIAD (57.92 µL, 0.2979 mmol). After sparging with Ar$_{(g)}$ for an additional 2 min, the reaction mixture was stirred 15 h at ambient temperature. The reaction mixture was treated with additional 2-(1H-imidazol-1-yl)ethan-1-ol (23.04 µL, 0.2383 mmol), PPh$_3$ (62.50 mg, 0.2383 mmol) and DIAD (46.34 µL, 0.2383 mmol), and allowed to stir 4 h at ambient temperature. The mixture was diluted with water and extracted with DCM. The combined organic extracts were washed with water and brine, then dried over anhydrous Na$_2$SO$_{4(s)}$, filtered and concentrated in vacuo. The residue was purified by silica chromatography (1-9% MeOH in DCM as the gradient eluent) to cleanly provide the title compound (24 mg, 20% yield). MS (apci) m/z=515.2 (M+H).

Step 2: Preparation of 6-(2-(1H-imidazol-1-yl)ethoxy)-4-(6-(piperazin-1-yl)pyridin-3-yl)pyrazolo[1,5-a]pyridine-3-carbonitrile A solution of tert-butyl 4-(5-(6-(2-(1H-imidazol-1-yl)ethoxy)-3-cyanopyrazolo[1,5-a]pyridin-4-yl)pyridin-2-yl)piperazine-1-carboxylate (24 mg, 0.0466 mmol) in DCM (933 µL) was treated with TFA (933 µL, 0.0466 mmol), then stirred for 1 hour at ambient temperature. The resulting mixture was diluted with DCM, and treated dropwise with Na$_2$CO$_{3(aq)}$ until gas evolution from the solution ceased. The biphasic mixture was diluted with saturated NaHCO$_{3(aq)}$, and extracted with DCM. The combined organic extracts were washed with brine, then dried over anhydrous Na$_2$SO$_{4(s)}$, filtered and concentrated in vacuo to cleanly provide the title compound (19.4 mg, quantitative yield). MS (apci) m/z=415.2 (M+H).

Intermediate P23

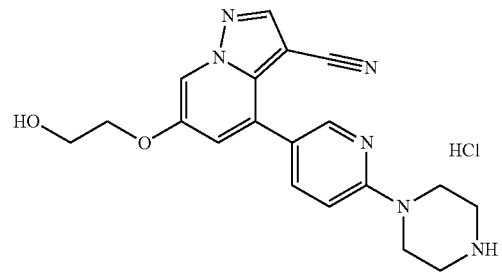 [SMILES: N#Cc1cnn2cc(OCCO)cc(-c3ccc(N4CCNCC4)nc3)c12 ; Cl]

6-(2-hydroxyethoxy)-4-(6-(piperazin-1-yl)pyridin-3-yl)pyrazolo[1,5-a]pyridine-3-carbonitrile hydrochloride Step 1: Preparation of tert-butyl 4-(5-(6-(2-((tert-butyldimethylsilyl)oxy)ethoxy)-3-cyanopyrazolo[1,5-a]pyridin-4-yl)pyridin-2-yl)piperazine-1-carboxylate A mixture of tert-butyl 4-(5-(3-cyano-6-hydroxypyrazolo[1,5-a]pyridin-4-yl)pyridin-2-yl)piperazine-1-carboxylate (Intermediate P3; 250 mg, 0.595 mmol), (2-bromoethoxy)(tert-butyl)dimethylsilane (128 µL, 0.743 mmol), and K$_2$CO$_{3(s)}$ (247 mg, 1.78 mmol) in DMF (2.97 mL) was stirred for 1 day at 50° C. After cooling to ambient temperature, the reaction mixture was purified directly by silica chromatography (0-100% EtOAc/hexanes gradient eluent) to cleanly provide the title compound (30 mg, 26% yield). MS (apci) m/z=579.8 (M+H).

Step 2: Preparation of 6-(2-hydroxyethoxy)-4-(6-(piperazin-1-yl)pyridin-3-yl)pyrazolo[1,5-a]pyridine-3-carbonitrile hydrochloride A solution tert-butyl 4-(5-(6-(2-((tert-butyldimethylsilyl)oxy)ethoxy)-3-cyanopyrazolo[1,5-a]pyridin-4-yl)pyridin-2-yl)piperazine-1-carboxylate (325 mg, 0.562 mmol) in DCM (2.81 mL) was treated dropwise with 4 M HCl in dioxanes (2.81 mL, 11.2 mmol). The resulting mixture was stirred for 1 hour at ambient temperature. The resulting white precipitate was concentrated in vacuo to afford the title compound as the hydrochloride salt (225 mg, quantitative yield). MS (apci) m/z=364.9 (M+H)

Intermediate P24

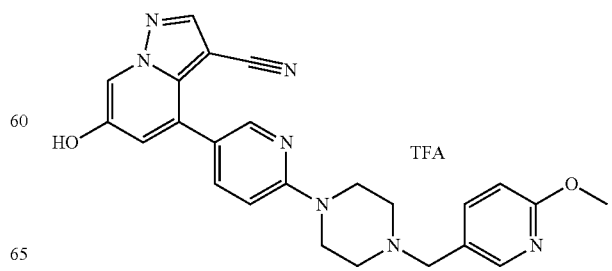

6-hydroxy-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate A mixture of 4-bromo-6-hydroxypyrazolo[1,5-a]pyridine-3-carbonitrile (Intermediate P1; 100 mg, 0.420 mmol), 1-((6-methoxypyridin-3-yl)methyl)-4-(5-(4,4,5,5-tetramethyl-1,3,2-dioxaborolan-2-yl)pyridin-2-yl)piperazine (Intermediate R10; 207 mg, 0.504 mmol), Pd(PPh$_3$)$_4$ (19.4 mg, 0.0168 mmol), 2 M Na$_2$CO$_{3(aq)}$ (630 µL, 1.26 mmol) and 1,4-dioxane (2.80 mL) was sparged with N$_{2(g)}$, then stirred overnight at 85° C. under an atmosphere of N$_{2(g)}$. The mixture was cooled to ambient temperature, filtered through a syringe filter and purified directly by C18 reverse phase chromatography (5-95% ACN/water with 0.1% TFA as the gradient eluent) to afford the title compound as the 2,2,2-trifluoroacetate salt (145 mg, 62% yield). MS (apci) m/z=442.2 (M+H).

Intermediate P25

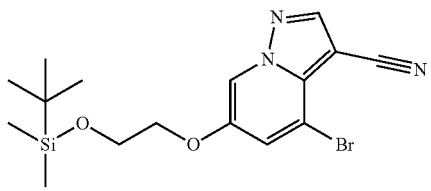 [SMILES: CC(C)(C)[Si](C)(C)OCCOc1cc(Br)c2c(C#N)cnn2c1]

4-Bromo-6-(2-((tert-butyldimethylsilyl)oxy)ethoxy)pyrazolo[1,5-a]pyridine-3-carbonitrile A mixture of (2-bromoethoxy)(tert-butyl)dimethylsilane (451 µL, 2.10 mmol), 4-bromo-6-hydroxypyrazolo[1,5-a]pyridine-3-carbonitrile (Intermediate P1; 500 mg, 2.10 mmol) and K$_2$CO$_{3(s)}$ (871 mg, 6.30 mmol) in DMF (10.5 mL) was stirred for 1 day at 50° C. After cooling to ambient temperature, the reaction mixture was diluted with EtOAc and washed with water and brine. The resulting organic extracts were directly purified by silica chromatography (0-100% EtOAc/hexanes as the gradient eluent) to cleanly provide the title compound (420 mg, 49% yield).

Intermediate P26

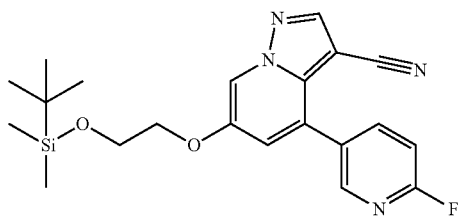 [SMILES: CC(C)(C)[Si](C)(C)OCCOc1cc(-c2ccc(F)nc2)c2c(C#N)cnn2c1]

6-(2-((tert-butyldimethylsilyl)oxy)ethoxy)-4-(6-fluoropyridin-3-yl)pyrazolo[1,5-a]pyridine-3-carbonitrile In a pressure vessel, a solution of 4-bromo-6-(2-((tert-butyldimethylsilyl)oxy)ethoxy)pyrazolo[1,5-a]pyridine-3-carbonitrile (Intermediate P25; 420 mg, 1.06 mmol) in dioxane (10.6 mL) was treated sequentially with 2-fluoro-5-(4,4,5,5-tetramethyl-1,3,2-dioxaborolan-2-yl)pyridine (355 mg, 1.59 mmol), Pd(PPh$_3$)$_4$ (61.2 mg, 0.530 mmol) and 2 M Na$_2$CO$_{3(aq)}$ (2.65 mL, 5.30). The resulting mixture was sparged with Ar$_{(g)}$ and the vessel was sealed. The mixture was stirred 8 h at 90° C., and then overnight at ambient temperature. The reaction mixture was diluted with water and extracted with EtOAc. The combined organic extracts were washed with water (10 mL) and brine (10 mL), then were dried over anhydrous Na$_2$SO$_{4(s)}$, filtered and concentrated in vacuo. The crude residue was purified by silica chromatography (using 0-15% MeOH in DCM as the gradient eluent) to afford impure title compound. The impure material was re-subjected to silica chromatography (0-50% EtOAc in Hexanes as the gradient eluent) to cleanly provide the title compound (351 mg, 80% yield). $^1$H NMR (400 MHz, DMSO-d$_6$-) δ: 8.81 (d, 1H, J=2.0 Hz), 8.61 (s, 1H), 8.48 (d, 1H, J=2.7 Hz), 8.25 (td, 1H, J=7.8, 2.7 Hz), 7.47 (d, 1H, J=1.9 Hz), 7.38 (dd, 1H, J=7.8, 2.3 Hz), 4.21 (t, 2H, J=4.3 Hz), 3.97 (t, 2H, J=4.7 Hz), 0.86 (s, 9H), 0.08 (s, 6H).

Intermediate P27

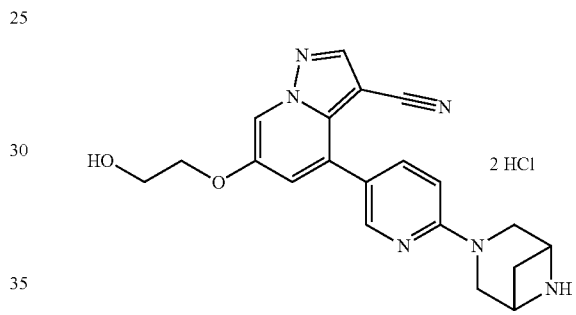

4-(6-(3,6-diazabicyclo[3.1.1]heptan-3-yl)pyridin-3-yl)-6-(2-hydroxyethoxy)pyrazolo[1,5-a]pyridine-3-carbonitrile dihydrochloride Step 1: Preparation of tert-butyl 3-(5-(3-cyano-6-(2-hydroxyethoxy)pyrazolo[1,5-a]pyridin-4-yl)pyridin-2-yl)-3,6-diazabicyclo[3.1.1]heptane-6-carboxylate A mixture of 6-(2-((tert-butyldimethylsilyl)oxy)ethoxy)-4-(6-fluoropyridin-3-yl)pyrazolo[1,5-a]pyridine-3-carbonitrile (Intermediate P26; 110 mg, 0.267 mmol), 3,6-diazabicyclo[3.1.1]heptane-6-carboxylic acid tert-butyl ester (159 mg, 0.800 mmol) in DMSO (2.5 mL) was stirred 1 hour at 110° C. After cooling to ambient temperature, the mixture was diluted with water, and the resulting suspension was filtered. The solids were isolated and purified by silica chromatography (0-20% MeOH in DCM as the gradient eluent) to cleanly provide the title compound (22 mg, 17% yield) which was carried on to step 2. MS (apci) m/z=591.2 (M+H).

Step 2: Preparation of 4-(6-(3,6-diazabicyclo[3.1.1]heptan-3-yl)pyridin-3-yl)-6-(2-hydroxyethoxy)pyrazolo[1,5-a]pyridine-3-carbonitrile hydrochloride A solution of tert-butyl 3-(5-(3-cyano-6-(2-hydroxyethoxy)pyrazolo[1,5-a]pyridin-4-yl)pyridin-2-yl)-3,6-diazabicyclo[3.1.1]heptane-6-carboxylate (22 mg, 0.046 mmol) in DCM (2 mL) was treated with 4 N HCl in dioxanes (3 mL, 0.046 mmol). The resulting mixture was stirred overnight at ambient temperature, then concentrated in vacuo to afford the title compound as the dihydrochloride salt (17 mg, quantitative yield). MS (apci) m/z=377.2 (M+H).

Intermediate P28

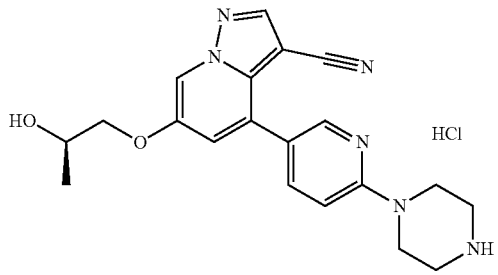

(R)-6-(2-hydroxypropoxy)-4-(6-(piperazin-1-yl)pyridin-3-yl)pyrazolo[1,5-a]pyridine-3-carbonitrile hydrochloride A solution of tert-butyl (R)-4-(5-(3-cyano-6-(2-hydroxypropoxy)pyrazolo[1,5-a]pyridin-4-yl)pyridin-2-yl)piperazine-1-carboxylate (Example 116; 68.3 mg, 0.143 mmol) in DCM (714 µL) was treated with TFA (110 µL, 1.43 mmol). The resulting mixture was stirred for 1 day at ambient temperature, before concentrating the mixture in vacuo to afford the TFA salt of the title compound. The TFA salt was converted to the HCl salt by dissolving the salt in 6 N HCl in iPrOH then concentrating mixture in vacuo, cleanly affording the title compound as the hydrochloride salt (59.2 mg, quantitative yield). MS (apci) m/z=379.2 (M+H).

Intermediate P29

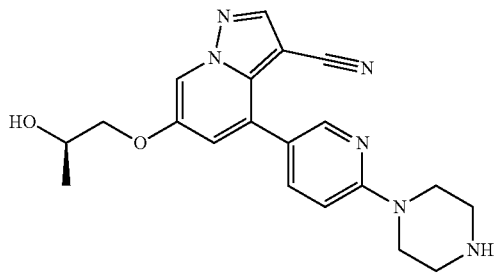

(R)-6-(2-hydroxypropoxy)-4-(6-(piperazin-1-yl)pyridin-3-yl)pyrazolo[1,5-a]pyridine-3-carbonitrile A solution of tert-butyl (R)-4-(5-(3-cyano-6-(2-hydroxypropoxy)pyrazolo[1,5-a]pyridin-4-yl)pyridin-2-yl)piperazine-1-carboxylate (Example 116; 40 mg, 0.084 mmol) in DCM (418 µL) was treated with TFA (64 µL, 0.84 mmol), then stirred for 1 day at ambient temperature. The resulting mixture was partitioned between DCM\ and 2 M $K_2CO_{3(aq)}$. The aqueous phase was back-extracted with DCM. The combined organic extracts were concentrated in vacuo to cleanly provide the title compound (7.2 mg, 23% yield). MS (apci) m/z=379.2 (M+H).

Intermediate P30

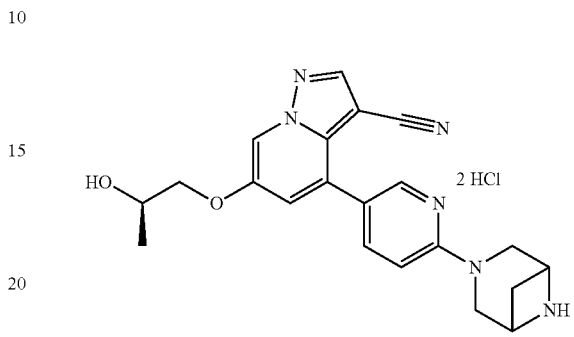

4-(6-(3,6-diazabicyclo[3.1.1]heptan-3-yl)pyridin-3-yl)-6-((R)-2-hydroxypropoxy)pyrazolo[1,5-a]pyridine-3-carbonitrile dihydrochloride Step 1: Preparation of tert-butyl 3-(5-(3-cyano-6-((R)-2-hydroxypropoxy)pyrazolo[1,5-a]pyridin-4-yl)pyridin-2-yl)-3,6-diazabicyclo[3.1.1]heptane-6-carboxylate A suspension of tert-butyl 3-(5-(3-cyano-6-hydroxypyrazolo[1,5-a]pyridin-4-yl)pyridin-2-yl)-3,6-diazabicyclo[3.1.1]heptane-6-carboxylate (Intermediate P4; 40 mg, 0.0925 mmol) in DMF (462 µL) was treated with $K_2CO_{3(s)}$ (328.7 mg, 2.378 mmol), and stirred 15 min at ambient temperature. The resulting mixture was treated with a solution of (R)-2-methyloxirane (32.4 µL, 0.462 mmol) in DMF (462 µL) The reaction mixture was stirred for 4 h at ambient temperature, then overnight at 50° C., before introducing additional (R)-2-methyloxirane (130 µL, 1.85 mmol). The resulting mixture was stirred overnight at 50° C., and was cooled to ambient temperature. The reaction mixture was purified directly by silica chromatography (0-100% ethyl acetate in hexanes as the gradient eluent) to cleanly provide the title compound (16 mg, 28% yield). MS (apci) m/z=491.2 (M+H).

Step 2: Preparation of 4-(6-(3,6-diazabicyclo[3.1.1]heptan-3-yl)pyridin-3-yl)-6-((R)-2-hydroxypropoxy)pyrazolo[1,5-a]pyridine-3-carbonitrile dihydrochloride A solution of tert-butyl 3-(5-(3-cyano-6-((R)-2-hydroxypropoxy)pyrazolo[1,5-a]pyridin-4-yl)pyridin-2-yl)-3,6-diazabicyclo[3.1.1]heptane-6-carboxylate (step 1; 16 mg, 0.0254 mmol) in DCM (2 mL) was treated with 4 N HCl in dioxanes (2 mL). The resulting mixture was stirred for 1 hour at ambient temperature and then concentrated in vacuo to afford the title compound as the dihydrochloride salt (11.8 mg, quantitative yield). MS (apci) m/z=391.2 (M+H).

Intermediate P31

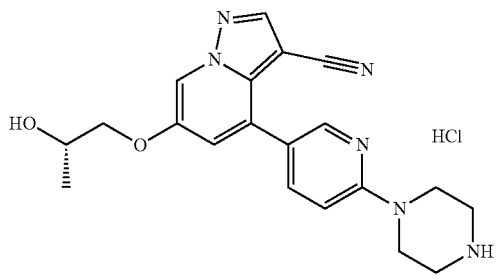 [SMILES: C[C@H](O)COc1cc(-c2ccc(N3CCNCC3)nc2)c2c(C#N)cnn2c1 ; Cl]

(S)-6-(2-hydroxypropoxy)-4-(6-(piperazin-1-yl)pyridin-3-yl)pyrazolo[1,5-a]pyridine-3-carbonitrile hydrochloride Step 1: Preparation of tert-butyl (S)-4-(5-(3-cyano-6-(2-hydroxypropoxy)pyrazolo[1,5-a]pyridin-4-yl)pyridin-2-yl)piperazine-1-carboxylate A suspension of tert-butyl 4-(5-(3-cyano-6-hydroxypyrazolo[1,5-a]pyridin-4-yl)pyridin-2-yl)piperazine-1-carboxylate (Intermediate P3; 200 mg, 0.476 mmol) in DMF (2.38 mL) was treated with K₂CO₃₍s₎ (329 mg, 2.38 mmol) and stirred 15 min at ambient temperature. The resulting mixture was treated with a solution of (S)-2-methyloxirane (138 mg, 2.38 mmol) in DMF (1 mL). The reaction mixture was stirred for 1 day at 50° C., then purified directly by silica chromatography (0-100% DCM in hexanes followed by 20% DCM/MeOH as eluents) to cleanly provide the title compound (176 mg, 77%). MS (apci) m/z=478.9 (M+H).

Step 2: Preparation of (S)-6-(2-hydroxypropoxy)-4-(6-(piperazin-1-yl)pyridin-3-yl)pyrazolo[1,5-a]pyridine-3-carbonitrile hydrochloride A solution of tert-butyl (S)-4-(5-(3-cyano-6-(2-hydroxypropoxy)pyrazolo[1,5-a]pyridin-4-yl)pyridin-2-yl)piperazine-1-carboxylate (step 1) in 1:1 DCM:TFA (2 mL) was stirred 30 min at ambient temperature. The reaction mixture was concentrated in vacuo, and the residue was treated with 6 N HCl in iPrOH (2 mL). The resulting mixture was stirred for 1 hour at ambient temperature and then concentrated in vacuo to afford the title compound (153 mg, 100% yield). MS (apci) m/z=378.9 (M+H).

Intermediate P32

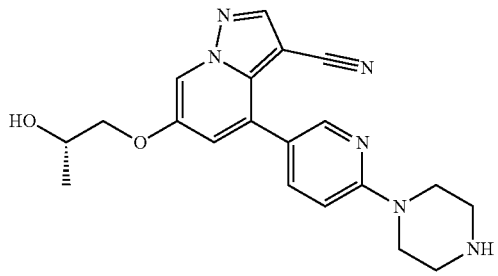 [SMILES: C[C@H](O)COc1cc(-c2ccc(N3CCNCC3)nc2)c2c(C#N)cnn2c1]

(S)-6-(2-hydroxypropoxy)-4-(6-(piperazin-1-yl)pyridin-3-yl)pyrazolo[1,5-a]pyridine-3-carbonitrile A solution of tert-butyl (S)-4-(5-(3-cyano-6-(2-hydroxypropoxy)pyrazolo[1,5-a]pyridin-4-yl)pyridin-2-yl)piperazine-1-carboxylate (Intermediate 31, Step 1; 17 mg, 0.036 mmol) and TFA (27 μL, 0.36 mmol) in DCM (178 μL) was stirred overnight at ambient temperature. The reaction mixture was partitioned between DCM and 2 M K₂CO₃₍aq₎. The aqueous phase was back extracted with DCM. The combined organic extracts were concentrated in vacuo to afford the title compound (13 mg, 97% yield). MS (apci) m/z=379.1 (M+H).

Intermediate P33

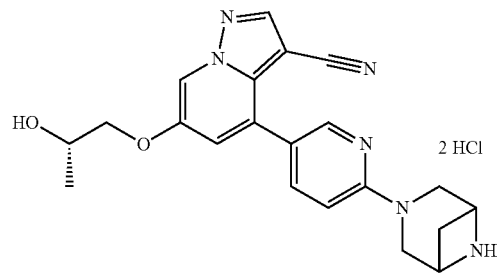 [SMILES: C[C@H](O)COc1cc(-c2ccc(N3CC4CC(C3)N4)nc2)c2c(C#N)cnn2c1 ; "2 HCl"]

4-(6-(3,6-diazabicyclo[3.1.1]heptan-3-yl)pyridin-3-yl)-6-((S)-2-hydroxypropoxy)pyrazolo[1,5-a]pyridine-3-carbonitrile dihydrochloride Step 1: Preparation of tert-butyl 3-(5-(3-cyano-6-((S)-2-hydroxypropoxy)pyrazolo[1,5-a]pyridin-4-yl)pyridin-2-yl)-3,6-diazabicyclo[3.1.1]heptane-6-carboxylate A suspension tert-butyl 3-(5-(3-cyano-6-hydroxypyrazolo[1,5-a]pyridin-4-yl)pyridin-2-yl)-3,6-diazabicyclo[3.1.1]heptane-6-carboxylate (Intermediate P4; 40 mg, 0.093 mmol) in DMF (462 μL) was treated with K₂CO₃₍s₎ (63.9 mg, 0.462 mmol) and stirred 15 min at ambient temperature. The resulting mixture was treated with a solution of (S)-2-methyloxirane (32.4 μL, 0.462 mmol) in DMF (462 μL). The reaction mixture was stirred for 4 h at ambient temperature, then overnight at 50° C., before introducing additional (S)-2-methyloxirane (97.2 μL, 1.39 mmol). The reaction mixture was stirred overnight at 50° C., and then cooled to ambient temperature. The resultant mixture was partitioned between EtOAc and water and extracted with EtOAc. The combined organic extracts were washed with brine, then dried over anhydrous Na₂SO₄₍s₎, filtered, and concentrated in vacuo. The residue was purified directly by silica chromatography (0-100% EtOAc in Hexanes as the gradient eluent) to cleanly provide the title compound (15 mg, 28% yield). MS (apci) m/z=491.2 (M+H).

Step 2: Preparation of 4-(6-(3,6-diazabicyclo[3.1.1]heptan-3-yl)pyridin-3-yl)-6-((S)-2-hydroxypropoxy)pyrazolo[1,5-a]pyridine-3-carbonitrile dihydrochloride A solution of tert-butyl 3-(5-(3-cyano-6-((S)-2-hydroxypropoxy)pyrazolo[1,5-a]pyridin-4-yl)pyridin-2-yl)-3,6-diazabicyclo[3.1.1]heptane-6-carboxylate (step 1; 15 mg, 0.026 mmol) in DCM (3 mL) was treated with 4 N HCl in dioxanes (3 mL) and stirred overnight at ambient temperature. The reaction mixture was concentrated in vacuo to afford the title compound (12 mg, quantitative yield). MS (apci) m/z=391.2 (M+H).

Intermediate P34

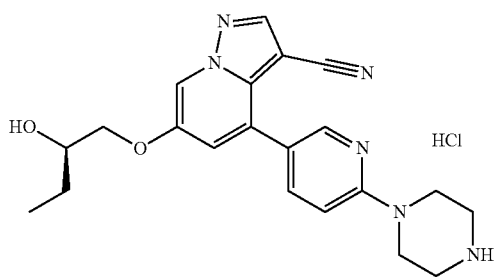

(R)-6-(2-hydroxybutoxy)-4-(6-(piperazin-1-yl)pyridin-3-yl)pyrazolo[1,5-a]pyridine-3-carbonitrile hydrochloride Step 1: Preparation of tert-butyl (R)-4-(5-(3-cyano-6-(2-hydroxybutoxy)pyrazolo[1,5-a]pyridin-4-yl)pyridin-2-yl)piperazine-1-carboxylate A solution of tert-butyl 4-(5-(3-cyano-6-hydroxypyrazolo[1,5-a]pyridin-4-yl)pyridin-2-yl)piperazine-1-carboxylate (Intermediate P3; 200 mg, 0.476 mmol) in DMF (2.38 mL) was treated with $K_2CO_{3(s)}$ (329.0 mg, 2.38 mmol), and stirred 15 min at ambient temperature. The resulting mixture was treated slowly with a solution of (R)-2-ethyloxirane (171 mg, 2.38 mmol) in DMF (1 mL). The reaction mixture was stirred for 1 day at 50° C., then purified directly by silica chromatography (using a stepwise gradient of 0-100% DCM in Hexanes followed by 20% DCM/MeOH as eluents) to cleanly provide the title compound (190 mg, 81.4%). MS (apci) m/z=492.9 (M+H).

Step 2: Preparation of (R)-6-(2-hydroxybutoxy)-4-(6-(piperazin-1-yl)pyridin-3-yl)pyrazolo[1,5-a]pyridine-3-carbonitrile hydrochloride A solution of (R)-tert-butyl 4-(5-(3-cyano-6-(2-hydroxybutoxy)pyrazolo[1,5-a]pyridin-4-yl)pyridin-2-yl)piperazine-1-carboxylate in 1:1 DCM:TFA (3 mL) was allowed to stir 30 min at ambient temperature. The mixture was concentrated in vacuo. The residue was taken up in 6 N HCl in iPrOH (3 mL) then immediately concentrated in vacuo to afford the title compound as the hydrochloride salt (166 mg, 100% yield). MS (apci) m/z=392.9 (M+H).

Intermediate P35

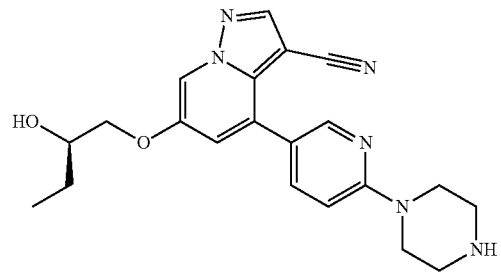

(R)-6-(2-hydroxybutoxy)-4-(6-(piperazin-1-yl)pyridin-3-yl)pyrazolo[1,5-a]pyridine-3-carbonitrile A solution of (R)-tert-butyl 4-(5-(3-cyano-6-(2-hydroxybutoxy)pyrazolo[1,5-a]pyridin-4-yl)pyridin-2-yl)piperazine-1-carboxylate (Intermediate P34, Step 1; 52.5 mg, 0.107 mmol) in DCM (1.07 mL) was treated with TFA (1.07 mL, 0.107 mmol), then stirred 5 days at ambient temperature. The reaction mixture was diluted with EtOAc and washed with saturated $Na_2CO_{3(aq)}$ and brine. The combined organic extracts were dried over anhydrous $Na_2SO_{4(s)}$, filtered, and concentrated in vacuo to afford the title compound (41.9 mg, quantitative yield). MS (apci) m/z=392.9 (M+H).

Intermediate P36

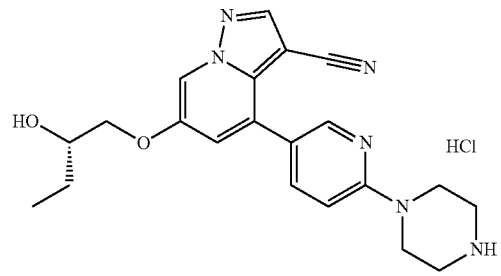 [SMILES: CC[C@H](O)COc1cc(-c2ccc(N3CCNCC3)nc2)c2c(C#N)cnn2c1 ; Cl]

(S)-6-(2-hydroxybutoxy)-4-(6-(piperazin-1-yl)pyridin-3-yl)pyrazolo[1,5-a]pyridine-3-carbonitrile hydrochloride Step 1: Preparation of tert-butyl (S)-4-(5-(3-cyano-6-(2-hydroxybutoxy)pyrazolo[1,5-a]pyridin-4-yl)pyridin-2-yl)piperazine-1-carboxylate A solution of tert-butyl 4-(5-(3-cyano-6-hydroxypyrazolo[1,5-a]pyridin-4-yl)pyridin-2-yl)piperazine-1-carboxylate (Intermediate P3; 200 mg, 0.476 mmol) in DMF (2.38 mL) was treated with $K_2CO_{3(s)}$ (329.0 mg, 2.38 mmol) and stirred 15 min at ambient temperature. The resulting mixture was treated slowly with a solution of (S)-2-ethyloxirane (171 mg, 2.38 mmol) in DMF (1 mL). After stirring for 1 day at 50° C., the reaction mixture was purified directly by silica chromatography (0-100% DCM in hexanes followed by 20% DCM/MeOH as eluents) to cleanly provide the title compound (175 mg, 75% yield). MS (apci) m/z=492.8 (M+H).

Step 2: Preparation of (S)-6-(2-hydroxybutoxy)-4-(6-(piperazin-1-yl)pyridin-3-yl)pyrazolo[1,5-a]pyridine-3-carbonitrile hydrochloride A solution of tert-Butyl (S)-4-(5-(3-cyano-6-(2-hydroxybutoxy)pyrazolo[1,5-a]pyridin-4-yl)pyridin-2-yl)piperazine-1-carboxylate in 1:1 DCM:TFA (3 mL) was allowed to stir 30 min at ambient temperature. The mixture was concentrated in vacuo. The residue was taken up in 6 N HCl in iPrOH (3 mL) and then immediately concentrated in vacuo to afford the title compound as the hydrochloride salt (153 mg, 100% yield). MS (apci) m/z=392.8 (M+H).

Intermediate P37

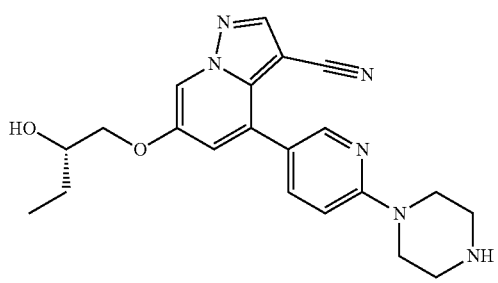 [SMILES: CC[C@H](O)COc1cc(-c2ccc(N3CCNCC3)nc2)c2c(C#N)cnn2c1]

(S)-6-(2-hydroxybutoxy)-4-(6-(piperazin-1-yl)pyridin-3-yl)pyrazolo[1,5-a]pyridine-3-carbonitrile A solution of tert-butyl (S)-4-(5-(3-cyano-6-(2-hydroxybutoxy)pyrazolo[1,5-a]pyridin-4-yl)pyridin-2-yl)piperazine-1-carboxylate (Intermediate P36, Step 1; 86 mg, 0.17 mmol) in DCM (1.2 mL) was treated with TFA (1.2 mL, 0.17 mmol), then stirred 5 days at ambient temperature. The reaction mixture was diluted with EtOAc and washed with saturated Na$_2$CO$_{3(aq)}$ and brine. The combined organic extracts were dried over anhydrous Na$_2$SO$_{4(s)}$, filtered, and concentrated in vacuo to afford the title compound (30 mg, 44% yield). MS (apci) m/z=392.9 (M+H).

Intermediate P38

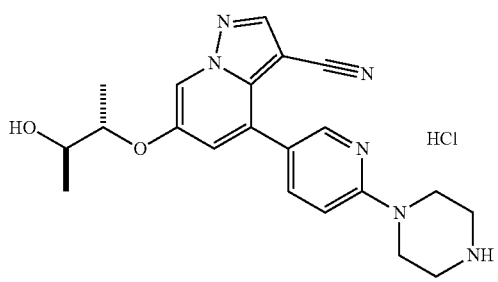 [SMILES: C[C@H](Oc1cc(-c2ccc(N3CCNCC3)nc2)c2c(C#N)cnn2c1)[C@@H](C)O ; Cl]

6-(((2S*,3R*)-3-hydroxybutan-2-yl)oxy)-4-(6-(piperazin-1-yl)pyridin-3-yl)pyrazolo[1,5-a]pyridine-3-carbonitrile hydrochloride Step 1: Preparation of tert-butyl 4-(5-(3-cyano-6-(((2S*,3R*)-3-hydroxybutan-2-yl)oxy)pyrazolo[1,5-a]pyridin-4-yl)pyridin-2-yl)piperazine-1-carboxylate A suspension of tert-butyl 4-(5-(3-cyano-6-hydroxypyrazolo[1,5-a]pyridin-4-yl)pyridin-2-yl)piperazine-1-carboxylate (Intermediate P3; 200 mg, 0.476 mmol) in DMF (1 mL) was treated with K$_2$CO$_{3(s)}$ (329 mg, 2.38 mmol), and stirred 15 min at ambient temperature. The resulting mixture was treated with a solution of (2R*,3R*)-2,3-dimethyloxirane (171 mg, 2.38 mmol) in DMF (1 mL). The reaction mixture was stirred for 2 days at ambient temperature, and then purified directly by silica chromatography (using a stepwise gradient of 0-100% DCM in Hexanes followed by 20% DCM/MeOH as eluents) to cleanly provide the title compound (223 mg, 95.6%). MS (apci) m/z=492.8 (M+H).

Step 2: Preparation of 6-(((2S*,3R*)-3-hydroxybutan-2-yl)oxy)-4-(6-(piperazin-1-yl)pyridin-3-yl)pyrazolo[1,5-a]pyridine-3-carbonitrile hydrochloride A solution of tert-butyl 4-(5-(3-cyano-6-(((2S,3R)-3-hydroxybutan-2-yl)oxy)pyrazolo[1,5-a]pyridin-4-yl)pyridin-2-yl)piperazine-1-carboxylate in 1:1 DCM:TFA (3 mL) was stirred for 30 min at ambient temperature. The reaction mixture was concentrated in vacuo. The residue was treated with 6 N HCl in iPrOH (3 mL), then immediately concentrated in vacuo to afford the title compound as the hydrochloride salt (195 mg, 100% yield). MS (apci) m/z=392.9 (M+H).

Intermediate P39

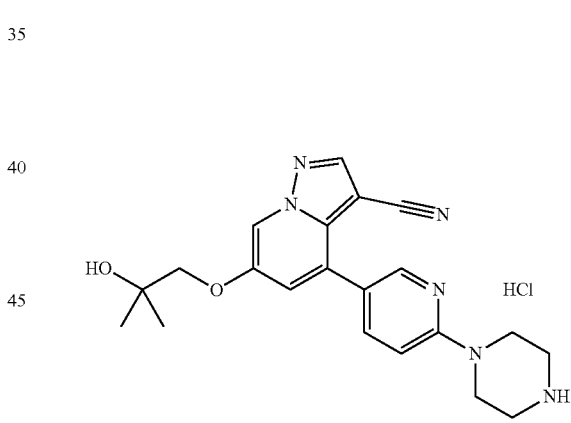

6-(2-hydroxy-2-methylpropoxy)-4-(6-(piperazin-1-yl)pyridin-3-yl)pyrazolo[1,5-a]pyridine-3-carbonitrile hydrochloride A solution of tert-butyl 4-(5-(3-cyano-6-(2-hydroxy-2-methylpropoxy)pyrazolo[1,5-a]pyridin-4-yl)pyridin-2-yl)piperazine-1-carboxylate (Example 152; 234 mg, 0.476 mmol) in 1:1 DCM:TFA (3 mL) was stirred for 30 min at ambient temperature. The reaction mixture was concentrated in vacuo. The residue was treated with 6 N HCl in iPrOH (3 mL) and then immediately concentrated in vacuo to afford the title compound as the hydrochloride salt (187 mg, 92% yield). MS (apci) m/z=393.2 (M+H).

Intermediate P40

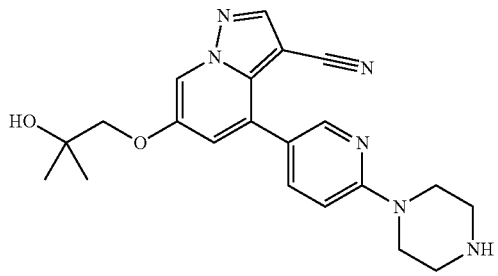 [SMILES: CC(C)(O)COc1cc(-c2ccc(N3CCNCC3)nc2)c2c(C#N)cnn2c1]

6-(2-hydroxy-2-methylpropoxy)-4-(6-(piperazin-1-yl)pyridin-3-yl)pyrazolo[1,5-a]pyridine-3-carbonitrile A solution of tert-butyl 4-(5-(3-cyano-6-(2-hydroxy-2-methylpropoxy)pyrazolo[1,5-a]pyridin-4-yl)pyridin-2-yl)piperazine-1-carboxylate (Example 152; 17 mg, 0.035 mmol) in DCM (173 μL) was treated with TFA (27 μL, 0.35 mmol), then stirred 1 day at ambient temperature. The reaction mixture was partitioned between DCM (10 mL) and 2 M $K_2CO_{3(aq)}$ (5 mL). The aqueous phase was extracted with DCM. The organic extracts were combined and concentrated in vacuo to afford the title compound (14 mg, quantitative yield). MS (apci) m/z=393.2 (M+H).

Intermediate P41

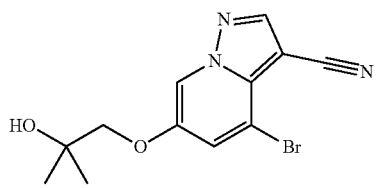 [SMILES: CC(C)(O)COc1cc(Br)c2c(C#N)cnn2c1]

4-Bromo-6-(2-hydroxy-2-methylpropoxy)pyrazolo[1,5-a]pyridine-3-carbonitrile

In a pressure vessel, a mixture of 4-bromo-6-hydroxy-pyrazolo[1,5-a]pyridine-3-carbonitrile (Intermediate P1; 10.0 g, 42.0 mmol) and $K_2CO_{3(s)}$ (17.4 g, 126 mmol) in DMF (50 mL) was treated with 2,2-dimethyloxirane (36.9 mL, 420 mmol). After sealing the vessel, the reaction mixture was stirred for 12 h at 60° C., then for 12 h at 85° C. The mixture was allowed to cool to ambient temperature. The room temperature mixture was poured into water (400 mL), then stirred for 1 hour at ambient temperature. The resultant suspension was vacuum filtered and the filter cake was rinsed with water. The solids were collected and dried in vacuo to cleanly provide the title compound (11 g, 84% yield).

Intermediate P42

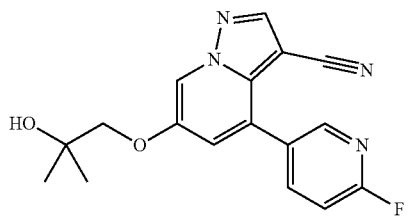 [SMILES: CC(C)(O)COc1cc(-c2ccc(F)nc2)c2c(C#N)cnn2c1]

4-(6-fluoropyridin-3-yl)-6-(2-hydroxy-2-methylpropoxy)pyrazolo[1,5-a]pyridine-3-carbonitrile A mixture of 4-bromo-6-(2-hydroxy-2-methylpropoxy)pyrazolo[1,5-a]pyridine-3-carbonitrile (Intermediate P41; 10.0 g, 32.2 mmol), 2-fluoro-5-(4,4,5,5-tetramethyl-1,3,2-dioxaborolan-2-yl)pyridine (10.8 g, 48.4 mmol) and Pd(PPh$_3$)$_4$ (1.12 g, 0.967 mmol) in dioxane (200 mL) was treated with 2 M $Na_2CO_{3(aq)}$ (64.5 mL, 129 mmol). The resulting mixture was sparged with $Ar_{(g)}$, then stirred for 12 h at 85° C. under an atmosphere of $N_{2(g)}$. After cooling to ambient temperature, the resultant mixture was poured into cold water (1.5 L). The pH of the mixture was adjusted to about pH 6 with the addition of 10% citric acid. After stirring for 1 hour at ambient temperature, the resultant suspension was vacuum filtered. The solids were collected and dried in vacuo to cleanly provide the title compound (10 g, 95% yield).

Intermediate P43

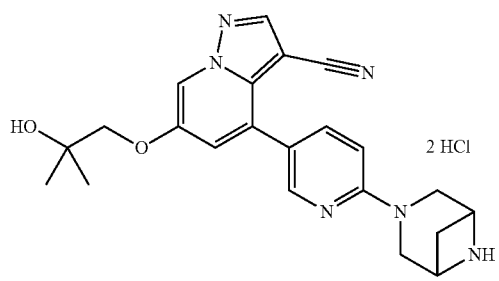 [SMILES: CC(C)(O)COc1cc(-c2ccc(N3CC4CC(C3)N4)nc2)c2c(C#N)cnn2c1]

4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride Step 1: Preparation of tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate A mixture of 4-(6-fluoropyridin-3-yl)-6-(2-hydroxy-2-methylpropoxy)pyrazolo[1,5-a]pyridine-3-carbonitrile (Intermediate P42; 1.70 g, 8.55 mmol), 3,6-diaza-bicyclo[3.1.1]heptane-6-carboxylic acid tert-butyl ester (1.70 g, 8.55 mmol) and $K_2CO_{3(s)}$ (7.88 g, 57.0 mmol) in DMSO (7 mL) was stirred 12 h at 90° C. The resultant thick slurry was diluted with additional DMSO (2 mL) and stirred for 12 h at 90° C. The mixture was cooled to ambient temperature and diluted with water (100 mL). The aqueous mixture was washed with DCM. The combined organic extracts were dried over anhydrous MgSO$_{4(s)}$, filtered and concentrated in vacuo. The crude residue was purified by silica chromatography (30-80% EtOAc/Hexanes as the gradient eluent system) to cleanly provide the title compound (2.87 g, 100% yield). MS (apci) m/z=505.2 (M+H).

Step 2: Preparation of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride A solution of tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (see step 1; 3.05 g, 6.04 mmol) in DCM (20 mL) was treated with 4 N HCl in dioxanes (15.1 mL, 60.4 mmol). The resulting mixture was stirred for 12 h at ambient temperature, and then concentrated in vacuo. The crude residue was diluted with DCM and toluene, and then sonicated before concentrating in vacuo to afford the title compound as the dihydrochloride salt (2.44 g, quantitative yield). MS (apci) m/z=405.2 (M+H).

Intermediate P44

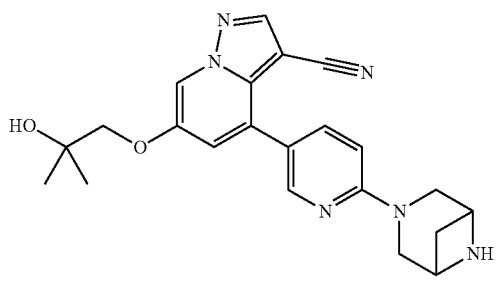 [SMILES: CC(C)(O)COc1cc(-c2ccc(N3CC4CC(C3)N4)nc2)c2c(C#N)cnn2c1]

4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile A solution of tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (Intermediate P43, step 2; 2.0 g, 4.2 mmol) in DCM (42 mL) was washed with 1 N NaOH$_{(aq)}$. The combined aqueous extracts were back extracted with DCM. All organic extracts then were combined, washed with brine, then passed through a PS frit and concentrated in vacuo to afford the title compound (244 mg). As a significant amount of desired product remained in the aqueous extracts, the combined aqueous extracts were subjected to a series of extractions, first with 20% iPrOH in DCM (3×50 mL). The aqueous extracts were then treated with NaCl, and stirred 3 h with 20% iPrOH in DCM (200 mL). The aqueous extracts were separated and diluted with MeOH (500 mL). The resultant suspension was filtered and all organic extracts from the extraction sequence were combined and concentrated in vacuo to provide a total recovery of 1.75 g of the title compound contaminated with inorganic salts. The contaminated material was triturated with DCM and filtered, and the filtrate was concentrated in vacuo to cleanly provide the title compound (1.26 g, 74% yield). MS (apci) m/z=405.2 (M+H).

Intermediate P45

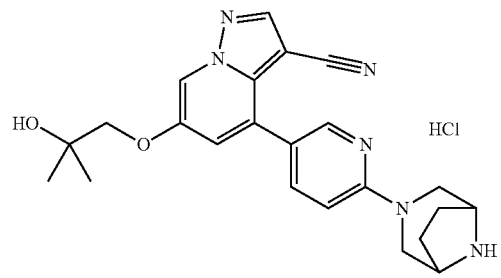 [SMILES: CC(C)(O)COc1cc(-c2ccc(N3CC4CCC(C3)N4)nc2)c2c(C#N)cnn2c1 ; Cl]

4-(6-(3,8-diazabicyclo[3.2.1]octan-3-yl)pyridin-3-yl)-6-(2-hydroxy-2-methylpropoxy)pyrazolo[1,5-a]pyridine-3-carbonitrile hydrochloride Step 1: Preparation of tert-butyl 3-(5-(3-cyano-6-(2-hydroxy-2-methylpropoxy)pyrazolo[1,5-a]pyridin-4-yl)pyridin-2-yl)-3,8-diazabicyclo[3.2.1]octane-8-carboxylate A mixture of 4-bromo-6-(2-hydroxy-2-methylpropoxy)pyrazolo[1,5-a]pyridine-3-carbonitrile (Intermediate P41; 45 mg, 0.145 mmol), (6-(8-(tert-butoxycarbonyl)-3,8-diazabicyclo[3.2.1]octan-3-yl)pyridin-3-yl)boronic acid (Intermediate R11; 53.2 mg, 0.160 mmol), and Pd(PPh$_3$)$_4$ (16.8 mg, 0.0145 mmol) in 2 M Na$_2$CO$_{3(aq)}$ (363 μL, 0.725 mmol) and dioxane (725 μL) was sparged with N$_{2(g)}$, then stirred for 3 h at 100° C. under an atmosphere of N$_{2(g)}$. The mixture was cooled to ambient temperature and was concentrated in vacuo, yielding crude title compound (64 mg) that was directly used in the next step. MS (apci) m/z=519.2 (M+H).

Step 2: Preparation of 4-(6-(3,8-diazabicyclo[3.2.1]octan-3-yl)pyridin-3-yl)-6-(2-hydroxy-2-methylpropoxy)pyrazolo[1,5-a]pyridine-3-carbonitrile hydrochloride A solution of tert-butyl 3-(5-(3-cyano-6-(2-hydroxy-2-methylpropoxy)pyrazolo[1,5-a]pyridin-4-yl)pyridin-2-yl)-3,8-diazabicyclo[3.2.1]octane-8-carboxylate (64 mg, 0.12 mmol) in 1:1 DCM:TFA (1 mL) was stirred for 15 min at ambient temperature, and then concentrated in vacuo. The residue was purified by C18 reverse phase chromatography (5-95% ACN in water with 0.1% TFA as the gradient eluent) to cleanly provide the title compound as the TFA salt. The TFA salt was treated with 6 N HCl in iPrOH (2 mL), then immediately concentrated in vacuo to afford the title compound as the hydrochloride salt (24 mg, 43% overall yield). MS (apci) m/z=419.2 (M+H).

Intermediate P48

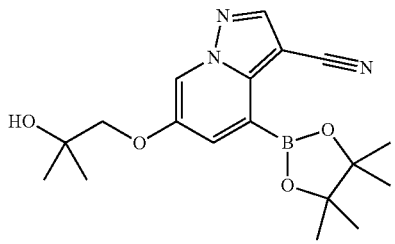 [SMILES: CC(C)(O)COc1cc(B2OC(C)(C)C(C)(C)O2)c2c(C#N)cnn2c1]

6-(2-hydroxy-2-methylpropoxy)-4-(4,4,5,5-tetramethyl-1,3,2-dioxaborolan-2-yl)pyrazolo[1,5-a]pyridine-3-carbonitrile In a pressure vessel, a mixture of 4-bromo-6-(2-hydroxy-2-methylpropoxy)pyrazolo[1,5-a]pyridine-3-carbonitrile (Intermediate P41; 2.0 g, 6.4 mmol), bis(pinacolato)diboron (2.5 g, 9.7 mmol), PdCl$_2$(dppf).CH$_2$Cl$_2$ (0.53 g, 0.64 mmol), and KOAc (1.9 g, 19 mmol) in dioxane (15 mL) was sparged with Ar$_{(g)}$ for 10 min. The vessel was sealed and the mixture was stirred overnight at 90° C. After cooling to room temperature, the reaction mixture was diluted with EtOAc (100 mL). The resulting suspension was filtered, and the filter cake was washed with EtOAc. The filtrate was concentrated in vacuo, and the residue was purified by silica chromatography (25% EtOAc in Hexanes as the eluent) to afford the title compound (2.2 g, 91% yield). $^1$H-NMR (400 MHz, CDCl$_3$) δ: 8.19 (s, 1H), 8.17 (d, J=2.3 Hz, 1H), 7.66 (d, J=2.3 Hz, 1H), 3.80 (s, 2H), 1.41 (s, 12H), 1.35 (s, 6H).

Intermediate P49

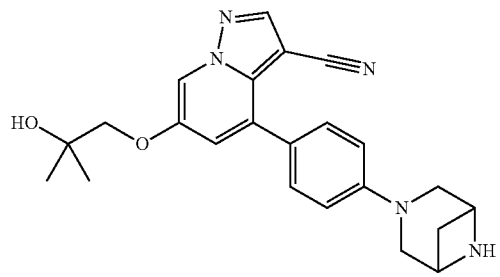 [SMILES: CC(C)(O)COc1cc(-c2ccc(N3CC4CC(C3)N4)cc2)c2c(C#N)cnn2c1]

4-(4-(3,6-diazabicyclo[3.1.1]heptan-3-yl)phenyl)-6-(2-hydroxy-2-methylpropoxy)pyrazolo[1,5-a]pyridine-3-carbonitrile Step 1: Preparation of tert-butyl 3-(4-(3-cyano-6-(2-hydroxy-2-methylpropoxy)pyrazolo[1,5-a]pyridin-4-yl)phenyl)-3,6-diazabicyclo[3.1.1]heptane-6-carboxylate In a pressure vessel, a mixture of 6-(2-hydroxy-2-methylpropoxy)-4-(4,4,5,5-tetramethyl-1,3,2-dioxaborolan-2-yl)pyrazolo[1,5-a]pyridine-3-carbonitrile (Intermediate P48; 0.100 g, 0.280 mmol), tert-butyl 3-(4-bromophenyl)-3,6-diazabicyclo[3.1.1]heptane-6-carboxylate (Intermediate R14; 98.9 mg, 0.280 mmol), X-Phos (26.7 mg, 0.0560 mmol) and Pd$_2$(dba)$_3$ (12.8 mg, 0.0140 mmol) in dioxane (1.0 mL) was sparged with Ar$_{(g)}$ for 1 min. The mixture was treated with 2 M K$_3$PO$_{4(aq)}$ (420 μL, 0.840 mmol), and then sparged with Ar$_{(g)}$ for an additional 3 min before sealing the vessel. The resulting reaction mixture was stirred overnight at 85° C. After cooling to ambient temperature, the reaction mixture was purified directly by silica chromatography (10% acetone in DCM as the eluent) to afford the title compound (86 mg, 43% yield). MS (apci) m/z=404.2 (des-Boc M+H).

Step 2: Preparation of 4-(4-(3,6-diazabicyclo[3.1.1]heptan-3-yl)phenyl)-6-(2-hydroxy-2-methylpropoxy)pyrazolo[1,5-a]pyridine-3-carbonitrile A solution of tert-butyl 3-(4-(3-cyano-6-(2-hydroxy-2-methylpropoxy)pyrazolo[1,5-a]pyridin-4-yl)phenyl)-3,6-diazabicyclo[3.1.1]heptane-6-carboxylate (86 mg, 0.17 mmol) in DCM (0.5 mL) was treated with TFA (26 μL, 3.4 mmol). The resulting mixture was stirred for 2 h at ambient temperature, then concentrated in vacuo. The residue was suspended in 1 M NaOH$_{(aq)}$ (pH 14). The resulting aqueous mixture was salted out with NaCl$_{(s)}$ and extracted with CHCl$_3$. The combined organic extracts were dried over anhydrous MgSO$_{4(s)}$, filtered and concentrated in vacuo to afford the title compound (62 mg, 90% yield). MS (apci) m/z=404.2 (M+H).

Intermediate P50

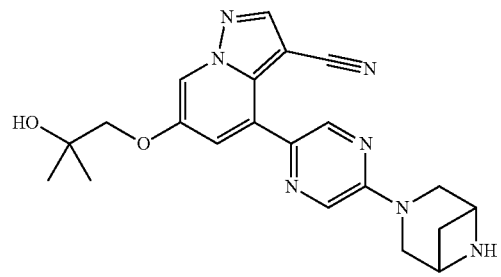 [SMILES: CC(C)(O)COc1cc(-c2cnc(N3CC4CC(C3)N4)cn2)c2c(C#N)cnn2c1]

4-(5-(3,6-diazabicyclo[3.1.1]heptan-3-yl)pyrazin-2-yl)-6-(2-hydroxy-2-methylpropoxy)pyrazolo[1,5-a]pyridine-3-carbonitrile Step 1: Preparation of tert-butyl 3-(5-(3-cyano-6-(2-hydroxy-2-methylpropoxy)pyrazolo[1,5-a]pyridin-4-yl)pyrazin-2-yl)-3,6-diazabicyclo[3.1.1]heptane-6-carboxylate In a pressure vessel, a mixture of 6-(2-hydroxy-2-methylpropoxy)-4-(4,4,5,5-tetramethyl-1,3,2-dioxaborolan-2-yl)pyrazolo[1,5-a]pyridine-3-carbonitrile (Intermediate P48; 0.100 g, 0.280 mmol), tert-butyl 3-(5-chloropyrazin-2-yl)-3,6-diazabicyclo[3.1.1]heptane-6-carboxylate (Intermediate R15; 91.4 mg, 0.294 mmol), X-Phos (26.7 mg, 0.0560 mmol) and Pd$_2$(dba)$_3$ (12.8 mg, 0.0140 mmol) in dioxane (1.0 mL) was sparged with Ar$_{(g)}$ for 1 min. The mixture was treated with 2 M K$_3$PO$_{4(aq)}$ (420 μL, 0.840 mmol), and then sparged with Ar$_{(g)}$ for an additional 3 min before sealing the vessel. The resulting reaction mixture was stirred overnight at 85° C. After cooling to ambient temperature, the reaction mixture was purified directly by silica chromatography (20% acetone in DCM as the eluent) to afford the title compound (62 mg, 37% yield).

Step 2: Preparation of 4-(5-(3,6-diazabicyclo[3.1.1]heptan-3-yl)pyrazin-2-yl)-6-(2-hydroxy-2-methylpropoxy)pyrazolo[1,5-a]pyridine-3-carbonitrile A solution of tert-butyl 3-(5-(3-cyano-6-(2-hydroxy-2-methylpropoxy)pyrazolo[1,5-a]pyridin-4-yl)pyrazin-2-yl)-3,6-diazabicyclo[3.1.1]heptane-6-carboxylate (68 mg, 0.13 mmol) in DCM (0.5 mL) was treated with TFA (21 μL, 2.7 mmol). The resulting mixture was stirred for 2 h at ambient temperature, then concentrated the mixture in vacuo. The residue was suspended in 1 M NaOH$_{(aq)}$ (pH 14). The resulting aqueous mixture was salted out with NaCl$_{(s)}$ and extracted with DCM. The combined organic extracts were dried over anhydrous MgSO$_{4(s)}$, filtered and concentrated in vacuo to afford the title compound (39 mg, 64% yield). MS (apci) m/z=406.2 (M+H).

Intermediate P51

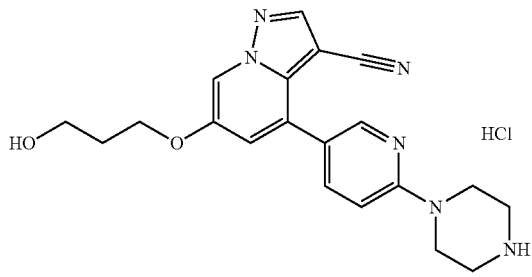 [SMILES: N#Cc1cnn2cc(OCCCO)cc(-c3ccc(N4CCNCC4)nc3)c12 ; Cl]

6-(3-hydroxypropoxy)-4-(6-(piperazin-1-yl)pyridin-3-yl)pyrazolo[1,5-a]pyridine-3-carbonitrile hydrochloride Step 1: Preparation of tert-butyl 4-(5-(6-(3-((tert-butyldimethylsilyl)oxy)propoxy)-3-cyanopyrazolo[1,5-a]pyridin-4-yl)pyridin-2-yl)piperazine-1-carboxylate A solution of tert-butyl 4-(5-(3-cyano-6-hydroxypyrazolo[1,5-a]pyridin-4-yl)pyridin-2-yl)piperazine-1-carboxylate (Intermediate P3; 250 mg, 0.595 mmol), (3-bromopropoxy)(tert-butyl)dimethylsilane (136 μL, 0.743 mmol) and K$_2$CO$_3$ $_{(s)}$ (247 mg, 1.78 mmol) in DMF (2.97 mL) was stirred for 1 day at 50° C. After cooling to ambient temperature, the mixture was purified directly by silica chromatography (0-100% EtOAc in hexanes) to cleanly provide the title compound (334 mg, 95% yield). MS (apci) m/z=593.8 (M+H).

Step 2: Preparation of 6-(3-hydroxypropoxy)-4-(6-(piperazin-1-yl)pyridin-3-yl)pyrazolo[1,5-a]pyridine-3-carbonitrile hydrochloride A solution of tert-butyl 4-(5-(6-(3-((tert-butyldimethylsilyl)oxy)propoxy)-3-cyanopyrazolo[1,5-a]pyridin-4-yl)pyridin-2-yl)piperazine-1-carboxylate (334 mg, 0.563 mmol) in DCM (2.82 mL) was treated with 4 N HCl in dioxanes (2.82 mL, 11.3 mmol), and then stirred 1 hour at ambient temperature. The resulting suspension was concentrated to afford the title compound as the hydrochloride salt (234 mg, quantitative yield). MS (apci) m/z=378.9 (M+H).

Intermediate P52

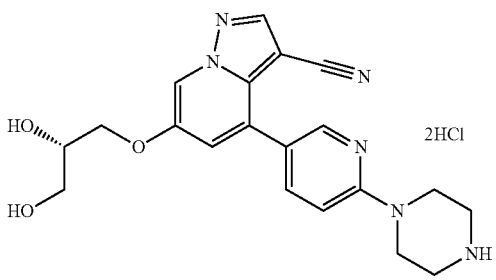 [SMILES: N#Cc1cnn2cc(OC[C@@H](O)CO)cc(-c3ccc(N4CCNCC4)nc3)c12]

(S)-6-(2,3-dihydroxypropoxy)-4-(6-(piperazin-1-yl)pyridin-3-yl)pyrazolo[1,5-a]pyridine-3-carbonitrile dihydrochloride Step 1: Preparation tert-butyl (R)-4-(5-(3-cyano-6-((2,2-dimethyl-1,3-dioxolan-4-yl)methoxy)pyrazolo[1,5-a]pyridin-4-yl)pyridin-2-yl)piperazine-1-carboxylate A mixture of tert-butyl 4-(5-(3-cyano-6-hydroxypyrazolo[1,5-a]pyridin-4-yl)pyridin-2-yl)piperazine-1-carboxylate (Intermediate P3; 150 mg, 0.357 mmol), (S)-4-(chloromethyl)-2,2-dimethyl-1,3-dioxolane (53.4 μL, 0.392 mmol) and Cs$_2$CO$_{3(s)}$ (389 mg, 1.20 mmol) in DMF (3.57 mL) was stirred overnight at 100° C. After cooling to ambient temperature, the mixture was diluted with water and extracted with EtOAc. The combined organic extracts were washed with brine, then dried over anhydrous Na$_2$SO$_{4(s)}$, filtered and concentrated in vacuo. The crude residue was purified by silica chromatography (30-100% EtOAc in Hexanes as the gradient eluent) to afford the title compound (71 mg, 37% yield). MS (apci) m/z=535.3 (M+H).

Step 2: Preparation of (S)-6-(2,3-dihydroxypropoxy)-4-(6-(piperazin-1-yl)pyridin-3-yl)pyrazolo[1,5-a]pyridine-3-carbonitrile dihydrochloride A solution of tert-butyl (R)-4-(5-(3-cyano-6-((2,2-dimethyl-1,3-dioxolan-4-yl)methoxy)pyrazolo[1,5-a]pyridin-4-yl)pyridin-2-yl)piperazine-1-carboxylate (71 mg, 0.106 mmol) in DCM (2 mL) was treated with 4 N HCl in dioxanes (3 mL), and then stirred for 2 h at ambient temperature. The resulting mixture was concentrated in vacuo to afford the title compound as the hydrochloride salt (41.9 mg, quantitative yield). MS (apci) m/z=395.2 (M+H).

Intermediate P53

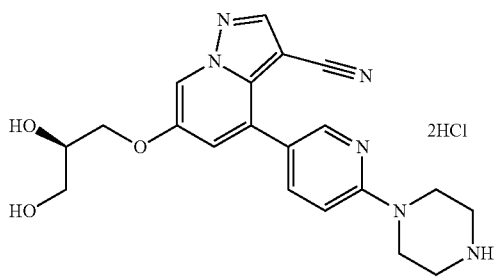 [SMILES: N#Cc1cnn2cc(OC[C@H](O)CO)cc(-c3ccc(N4CCNCC4)nc3)c12]

(R)-6-(2,3-dihydroxypropoxy)-4-(6-(piperazin-1-yl)pyridin-3-yl)pyrazolo[1,5-a]pyridine-3-carbonitrile dihydrochloride Step 1: Preparation of tert-butyl (S)-4-(5-(3-cyano-6-((2,2-dimethyl-1,3-dioxolan-4-yl)methoxy)pyrazolo[1,5-a]pyridin-4-yl)pyridin-2-yl)piperazine-1-carboxylate A mixture of tert-butyl 4-(5-(3-cyano-6-hydroxypyrazolo[1,5-a]pyridin-4-yl)pyridin-2-yl)piperazine-1-carboxylate (130 mg, 0.309 mmol), (R)-4-(chloromethyl)-2,2-dimethyl-1,3-dioxolane (46.6 µL, 0.340 mmol) and $Cs_2CO_{3(s)}$ (337 mg, 1.04 mmol) in DMF (3.09 mL) was stirred overnight at 100° C. After cooling to ambient temperature, the mixture was diluted with water and extracted with EtOAc. The combined organic extracts were washed with brine, then dried over anhydrous $Na_2SO_{4(s)}$, filtered and concentrated in vacuo. The crude residue was purified by silica chromatography (30-100% EtOAc in Hexanes as the gradient eluent) to afford the title compound (40 mg, 24% yield). MS (apci) m/z=535.3 (M+H).

Step 2: Preparation of (R)-6-(2,3-dihydroxypropoxy)-4-(6-(piperazin-1-yl)pyridin-3-yl)pyrazolo[1,5-a]pyridine-3-carbonitrile dihydrochloride A solution of tert-butyl (S)-4-(5-(3-cyano-6-((2,2-dimethyl-1,3-dioxolan-4-yl)methoxy)pyrazolo[1,5-a]pyridin-4-yl)pyridin-2-yl)piperazine-1-carboxylate (step 1; 40 mg, 0.075 mmol) in DCM (1 mL) was treated with 4 N HCl in dioxanes (2 mL), and then stirred for 6 h at ambient temperature. The resulting mixture was concentrated in vacuo to afford the title compound as the hydrochloride salt (30 mg, quantitative yield). MS (apci) m/z=395.2 (M+H).

Intermediate P54

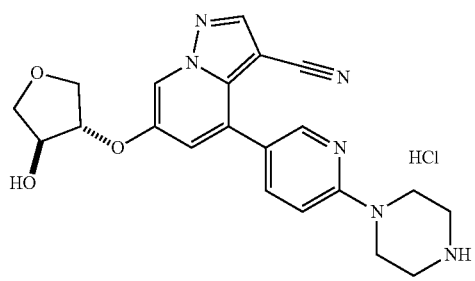

6-(((3S,4S)-4-hydroxytetrahydrofuran-3-yl)oxy)-4-(6-(piperazin-1-yl)pyridin-3-yl)pyrazolo[1,5-a]pyridine-3-carbonitrile hydrochloride Step 1: Preparation of tert-butyl 4-(5-(3-cyano-6-(((3S,4S)-4-hydroxytetrahydrofuran-3-yl)oxy)pyrazolo[1,5-a]pyridin-4-yl)pyridin-2-yl)piperazine-1-carboxylate A suspension of tert-butyl 4-(5-(3-cyano-6-hydroxypyrazolo[1,5-a]pyridin-4-yl)pyridin-2-yl)piperazine-1-carboxylate (Intermediate P3; 115 mg, 0.274 mmol) in DMF (1.37 mL) was treated with $K_2CO_{3(s)}$ (189 mg, 1.37 mmol), then stirred for 15 min at ambient temperature before adding (1R,5S)-3,6-dioxabicyclo[3.1.0]hexane (118 mg, 1.37 mmol) as a solution in DMF (1 mL). The resulting mixture was stirred for 1 day at 50° C., then purified directly by silica chromatography (0-100% DCM in hexanes followed by 20% DCM/MeOH as eluents) to afford the title compound. MS (apci) m/z=508.8 (M+H).

Step 2: Preparation of 6-(((3S,4S)-4-hydroxytetrahydrofuran-3-yl)oxy)-4-(6-(piperazin-1-yl)pyridin-3-yl)pyrazolo[1,5-a]pyridine-3-carbonitrile hydrochloride A solution of tert-butyl 4-(5-(3-cyano-6-(((3S,4S)-4-hydroxytetrahydrofuran-3-yl)oxy)pyrazolo[1,5-a]pyridin-4-yl)pyridin-2-yl)piperazine-1-carboxylate (in 1:1 DCM:TFA (2 mL) was stirred 30 min at ambient temperature, then concentrated in vacuo. The residue was taken up in 6 N HCl in iPrOH (2 mL) and subsequently concentrated in vacuo to afford the title compound as the hydrochloride salt (83 mg, 69% overall yield). MS (apci) m/z=406.8 (M+H).

Intermediate P55

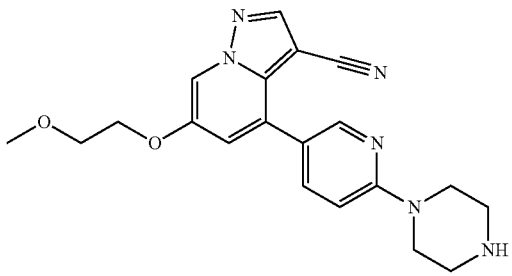 [SMILES: COCCOc1cc(-c2ccc(N3CCNCC3)nc2)c2c(C#N)cnn2c1]

6-(2-methoxyethoxy)-4-(6-(piperazin-1-yl)pyridin-3-yl)pyrazolo[1,5-a]pyridine-3-carbonitrile Step 1: Preparation of tert-butyl 4-(5-(3-cyano-6-(2-methoxyethoxy)pyrazolo[1,5-a]pyridin-4-yl)pyridin-2-yl)piperazine-1-carboxylate A cold (0° C.) solution of $PPh_3$ (377.9 mg, 1.441 mmol) in 1:1 DCM:THF (10 mL) was treated with DIAD (283.7 µL, 1.441 mmol) and stirred for 15 min at 0° C. The resulting 0° C. mixture was treated with a 1:1 DCM:THF (20.0 mL) solution of tert-butyl 4-(5-(3-cyano-6-hydroxypyrazolo[1,5-a]pyridin-4-yl)pyridin-2-yl)piperazine-1-carboxylate (Intermediate P3; 403.9 mg, 0.9606 mmol) and 2-methoxyethanol (90.90 µL, 1.153 mmol). The reaction mixture was stirred for 30 min at room temperature, then concentrated in vacuo and purified by silica (50-100% Hexanes-EtOAc as the gradient eluent) to afford the title compound which was immediately carried on to step 2. MS (apci) m/z=547.2 (M+H).

Step 2: Preparation of 6-(2-methoxyethoxy)-4-(6-(piperazin-1-yl)pyridin-3-yl)pyrazolo[1,5-a]pyridine-3-carbonitrile A solution of the tert-butyl 4-(5-(3-cyano-6-(2-methoxyethoxy)pyrazolo[1,5-a]pyridin-4-yl)pyridin-2-yl)piperazine-1-carboxylate in 1:1 DCM:TFA (10 mL) was stirred for 15 min at ambient temperature then concentrated in vacuo. The residue was purified by C18 reverse phase chromatography (5-95% water-ACN with 0.1% TFA as the gradient eluent) to afford the title compound as the TFA salt. The TFA salt was partitioned between 4:1 DCM:iPrOH and saturated NaHCO$_{3(aq)}$. The resulting organic extracts were dried over anhydrous Na$_2$SO$_{4(s)}$, filtered and concentrated in vacuo to afford the title compound (196.1 mg, 54% yield). MS (apci) m/z=479.2 (M+H).

Intermediate P56

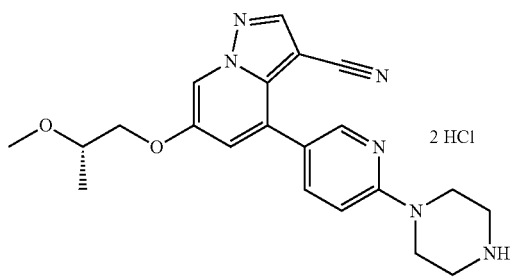 [SMILES: CO[C@@H](C)COc1cc(-c2ccc(N3CCNCC3)nc2)c2c(C#N)cnn2c1]

(S)-6-(2-methoxypropoxy)-4-(6-(piperazin-1-yl)pyridin-3-yl)pyrazolo[1,5-a]pyridine-3-carbonitrile dihydrochloride Step 1: Preparation of tert-butyl (S)-4-(5-(3-cyano-6-(2-methoxypropoxy)pyrazolo[1,5-a]pyridin-4-yl)pyridin-2-yl)piperazine-1-carboxylate A cold (0° C.) solution of PPh$_3$ (210 mg, 0.799 mmol) in 1:1 DCM:THF (4 mL) was treated with DIAD (155 µL, 0.799 mmol) and stirred for 15 min at 0° C. The resulting 0° C. mixture was treated with a 1:1 DCM:THF (4.0 mL) suspension of (S)-2-methoxypropan-1-ol (72.0 mg, 0.799 mmol) and tert-butyl 4-(5-(3-cyano-6-hydroxypyrazolo[1,5-a]pyridin-4-yl)pyridin-2-yl)piperazine-1-carboxylate (Intermediate P3; 168 mg, 0.400 mmol). The resulting mixture was stirred for 17 h at room temperature and then concentrated in vacuo. The residue was purified by silica (0-100% acetone-hexanes as the gradient eluent) to afford the title compound (242 mg, quantitative yield). MS (apci) m/z=493.2 (M+H).

Step 2: Preparation of (S)-6-(2-methoxypropoxy)-4-(6-(piperazin-1-yl)pyridin-3-yl)pyrazolo[1,5-a]pyridine-3-carbonitrile dihydrochloride A solution of the tert-butyl (S)-4-(5-(3-cyano-6-(2-methoxypropoxy)pyrazolo[1,5-a]pyridin-4-yl)pyridin-2-yl)piperazine-1-carboxylate (197 mg, 0.400 mmol) in DCM (2 mL) was treated with 5-6 M HCl in iPrOH (4 mL, 20.0 mmol) and stirred for 1 hour at ambient temperature. The mixture was concentrated in vacuo, azeotroping with Et$_2$O (5 mL), to cleanly provide the title compound as the dihydrochloride salt (233 mg, quantitative yield). MS (apci) m/z=393.2 (M+H).

Intermediate P57

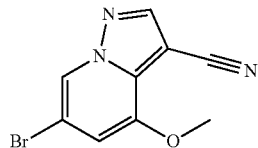

6-bromo-4-methoxypyrazolo[1,5-a]pyridine-3-carbonitrile

To a solution of 1-amino-3-bromo-5-methoxypyridin-1-ium 2,4,6-trimethylbenzenesulfonate (Intermediate P1, Part B, Step 1, 400 g, 0.99 mol) in acetonitrile (3.2 L) was added 2-chloroacrylonitrile (130 g, 1.49 mol). The reaction was cooled in an ice-water bath to near 0° C. before DBU (559 g, 3.67 mol) was added dropwise. After warming to room temperature and stirred for 16 h, the reaction mixture was poured into water (9.6 L) and filtered. The isolated wet solid was taken up in DCM and the aqueous phase was removed. The organic layer was filtered through a pad of silica (800 g) and washed with DCM. The organic filtrate was concentrated under reduced pressure to yield the crude product, which was triturated with MTBE (450 mL), filtered and dried under vacuum to give the title compound as off-white powder (75 g, 30% yield). $^1$H NMR (CDCl$_3$) δ 8.32 (m, 1H), 8.12 (s, 1H), 6.74 (m, 1H), 4.03 (s, 3H).

Intermediate P58

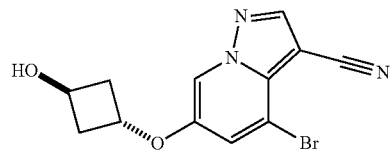

4-bromo-6-(((1r,3r)-3-hydroxycyclobutoxy)pyrazolo[1,5-a]pyridine-3-carbonitrile

Under an inert atmosphere (N$_{2(g)}$), a mixture of 4-bromo-6-hydroxypyrazolo[1,5-a]pyridine-3-carbonitrile (Intermediate P1; 0.250 g, 1.05 mmol) and K$_2$CO$_{3(s)}$ (0.435 g, 3.15 mmol) in DMF (1 mL) was stirred for 10 min at ambient temperature. The mixture was treated with (1s,3s)-3-hydroxycyclobutyl 4-methylbenzenesulfonate (Intermediate R18; 0.254 g, 1.05 mmol). The reaction vessel was sealed, and the mixture was stirred for 2 d at 50° C., then for 2 d at 65° C. After cooling to ambient temperature, the reaction mixture was poured into 1:1 brine/water (50 mL), diluted with MTBE (20 mL) and stirred vigorously for 20 min. The biphasic suspension was vacuum filtered, the solids were collected, and the filtrate was extracted with EtOAc (2×50 mL). The combined organic extracts were dried over anhydrous MgSO$_{4(s)}$, filtered and concentrated in vacuo. The residue from the filtrate was combined with the solids from the filtration and purified by silica chromatography (using 1:1 EtOAc:Hexanes as the eluent) to cleanly provide the title compound (100 mg, 26% yield). $^1$H NMR (400 MHz, CDCl$_3$) δ 8.18 (s, 1H), 7.90 (d, 1H), 7.39 (d, 1H), 4.82 (m, 1H), 4.65 (m, 1H), 4.97 (m, 4H).

Intermediate P59

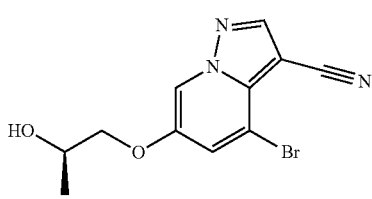 [SMILES: C[C@@H](O)COc1cc(Br)c2c(C#N)cnn2c1]

(R)-4-bromo-6-(2-hydroxypropoxy)pyrazolo[1,5-a]pyridine-3-carbonitrile

A mixture of 4-bromo-6-hydroxypyrazolo[1,5-a]pyridine-3-carbonitrile (Intermediate P1; 500 mg, 2.10 mmol) in DMF (4 mL) was treated sequentially with K$_2$CO$_{3(s)}$ (1.451 g, 10.5 mmol) and (R)-2-methyloxirane (2.21 mL, 31.5 mmol). The reaction mixture was stirred for 3 d at 50° C. in a sealed vessel. After cooling to ambient temperature, the reaction mixture was purified directly by C18 reverse phase chromatography (using 5-90% ACN:water as the gradient eluent) to cleanly provide the title compound (365 mg, 59% yield). $^1$H NMR (400 MHz, CDCl$_3$) δ 8.21 (s, 1H), 8.14 (d, 1H), 7.49 (d, 1H), 4.25 (m, 1H), 3.96 (dd, 1H), 3.86 (dd, 1H), 1.33 (d, 3H).

Intermediate P60

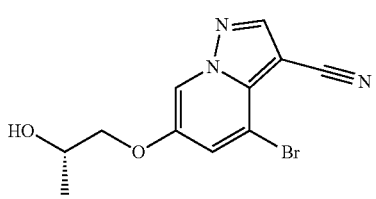 [SMILES: C[C@H](O)COc1cc(Br)c2c(C#N)cnn2c1]

(S)-4-bromo-6-(2-hydroxypropoxy)pyrazolo[1,5-a]pyridine-3-carbonitrile

A mixture of 4-bromo-6-hydroxypyrazolo[1,5-a]pyridine-3-carbonitrile (Intermediate P1; 500 mg, 2.10 mmol) in DMF (4 mL) was treated sequentially with K$_2$CO$_{3(s)}$ (1451 mg, 10.5 mmol) and (S)-2-methyloxirane (1830 mg, 31.5 mmol). The reaction mixture was stirred for 3 d at 50° C. in a sealed vessel. After cooling to ambient temperature, the reaction mixture was diluted with water (50 mL) and extracted with DCM (2×50 mL). The combined organic extracts were washed with brine (50 mL). The resultant emulsion was filtered through a coarse glass frit, and the biphasic filtrate was separated. The organic extracts were washed again with brine (50 mL), then dried over anhydrous MgSO$_{4(s)}$, filtered and concentrated in vacuo. The crude residue was purified by silica chromatography (using 0-90% EtOAc/Hexanes as the gradient eluent) to cleanly provide the title compound (357 mg, 57% yield). $^1$H NMR (400 MHz, CDCl$_3$) δ 8.21 (s, 1H), 8.14 (d, 1H), 7.49 (d, 1H), 4.25 (m, 1H), 3.96 (dd, 1H), 3.86 (dd, 1H), 1.33 (d, 3H).

Intermediate P61

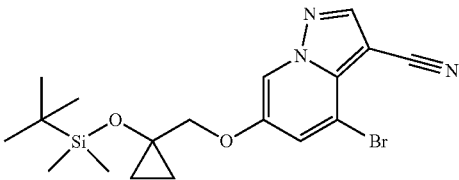 [SMILES: CC(C)(C)[Si](C)(C)OC1(COc2cc(Br)c3c(C#N)cnn3c2)CC1]

4-bromo-6-((1-((tert-butyldimethylsilyl)oxy)cyclopropyl)methoxy)pyrazolo[1,5-a]pyridine-3-carbonitrile A cold (0° C.) solution of triphenylphosphine (885.9 mg, 3.378 mmol) in 1:1 THF:DCM (10 mL) was treated with DIAD (665.0 µL, 3.378 mmol), then stirred for 15 min at 0° C. The resulting mixture was treated with a solution of 4-bromo-6-hydroxypyrazolo[1,5-a]pyridine-3-carbonitrile (Intermediate P1; 536.0 mg, 2.252 mmol) and (1-((tert-butyldimethylsilyl)oxy)cyclopropyl)methanol (Intermediate R19; 546.8 mg, 2.702 mmol) in 1:1 THF:DCM (10 mL). After stirring for 1 h at ambient temperature, the reaction mixture was concentrated in vacuo. The crude residue was purified by silica chromatography (using 5-75% Hexanes-EtOAc as the gradient eluent) to cleanly provide the title compound (404.2 mg, 42% yield). $^1$H NMR (400 MHz, CDCl$_3$) δ 8.19 (s, 1H), 8.08-8.07 (d, 1H), 7.49-7.48 (d, 1H), 3.95 (s, 2H), 0.94-0.89 (m, 2H), 0.85 (s, 9H), 0.76-0.73 (m, 2H), 0.14 (s, 6H).

Intermediate P62

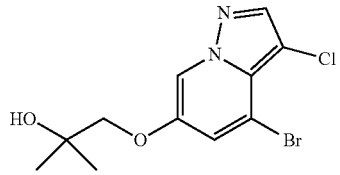 [SMILES: CC(C)(O)COc1cc(Br)c2c(Cl)cnn2c1]

1-((4-bromo-3-chloropyrazolo[1,5-a]pyridin-6-yl)oxy)-2-methylpropan-2-ol

Step 1: Preparation of 4-bromo-3-chloro-6-methoxypyrazolo[1,5-a]pyridine

A suspension of 4-bromo-6-methoxypyrazolo[1,5-a]pyridine (Intermediate P1, Part B, step 3; 15 g, 66 mmol) in DCM (100 mL) was treated with NCS (8.821 g, 66.06 mmol), and the mixture was sonicated for 5 min. After stirring the resulting mixture overnight at ambient temperature, additional NCS (1.25 g) was introduced. The reaction mixture was stirred for an additional 6 h, then diluted with Et₂O (100 mL), stirred for 10 min and sonicated for 2 min at ambient temperature. The resultant suspension was vacuum filtered, rinsing the solids with Et₂O (2×100 mL). The filtrate was diluted with additional Et₂O (100 mL), then sonicated and vacuum filtered. The solids from both filtrations were combined to afford the title compound (18.69 g, quantitative yield). MS (apci) m/z=260.9, 263.0 (M+H).

Step 2: Preparation of 4-bromo-3-chloropyrazolo[1, 5-a]pyridin-6-ol

Under an atmosphere of N$_{2(g)}$, (4-bromo-3-chloro-6-methoxypyrazolo[1,5-a]pyridine (7.59 g, 29.0 mmol) was suspended in DCE (290 mL), then slowly (5 min) treated with AlCl₃ (11.6 g, 87.1 mmol). The resulting mixture was stirred overnight at 76° C. After cooling to ambient temperature, the reaction mixture was diluted with DMA (75 mL) causing a slight exotherm. The DCE was removed in vacuo, and the residual material was diluted with water (125 mL). The aqueous suspension was stirred at 0° C. for 30 min, then cold filtered under vacuum. The solids were rinsed with cold (0° C.) water (50 mL), and dried in vacuo to afford the title compound (7.00 g, 98% yield). The crude material was dissolved in anhydrous DMA (150 mL) and filtered through a silica plug, rinsing the plug with additional anhydrous DMA (7×50 mL). A portion of the filtrate (300 mL) was carried on to Step 3. MS (apci) m/z=246.9, 248.9 (M+H).

Step 3: Preparation of 1-((4-bromo-3-chloropyrazolo[1,5-a]pyridin-6-yl)oxy)-2-methylpropan-2-ol A 0.06 M solution of 4-bromo-3-chloropyrazolo[1,5-a]pyridin-6-ol in DMA (300 mL, 17.0 mmol was treated with K₂CO$_{3(s)}$ (23.5 g, 170 mmol) and 2,2-dimethyloxirane (7.45 mL, 84.9 mmol). After stirring the reaction mixture for 3 h at 55° C., additional 2,2-dimethyloxirane (7.45 mL, 84.9 mmol) was introduced. The sluggish reaction was stirred overnight at 55° C., before a second aliquot of K₂CO$_{3(s)}$ (10 g, 72.3 mmol) and additional 2,2-dimethyloxirane (7.45 mL, 84.9 mmol) were introduced. The reaction was stirred for 2 h at 85° C. in an effort to drive the reaction to completion. After cooling to ambient temperature, the reaction mixture was quenched with the addition of 1:1 saturated NH₄Cl$_{(aq)}$:water (200 mL). The quenched reaction mixture was washed with EtOAc (5×), and the combined organic extracts were dried over anhydrous Na₂SO$_{4(s)}$, filtered and concentrated in vacuo. The residue was triturated with water (100 mL), and the solids were collected by vacuum filtration to cleanly provide the title compound (2.62 g, 34% yield). MS (apci) m/z=319.0, 321.0 (M+H).

Intermediate P63

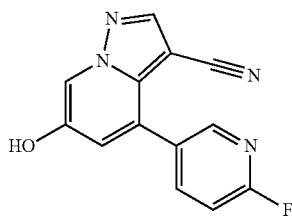 [SMILES: N#Cc1cnn2cc(O)cc(-c3ccc(F)nc3)c12]

4-(6-fluoropyridin-3-yl)-6-hydroxypyrazolo[1,5-a]pyridine-3-carbonitrile

Step 1: Preparation of 6-bromo-4-hydroxypyrazolo[1,5-a]pyridine-3-carbonitrile

Under an inert atmosphere (N$_{2(g)}$), a solution of 6-bromo-4-methoxypyrazolo[1,5-a]pyridine-3-carbonitrile (Intermediate P57; 200 g, 873 mmol) in DMA (2494 mL) was stirred at 40° C., and treated dropwise (3 drops/second) with 2 M NaOH$_{(aq)}$ (105 mL, 1746 mmol) then with water (5 mL; to rinse the addition funnel). Dodecyl mercaptan (418 mL, 1746 mmol) was added dropwise (3 drops/second). The resulting reaction mixture was stirred for 2 h at 40° C. After cooled to ambient temperature, the reaction mixture was poured into cold (~10° C.) water (8 L), and the pH was adjusted to ~5 with the addition of a 10% aqueous solution of citric acid. The quenched reaction mixture was stirred for 4 h at ambient temperature then left resting 12 h at ambient temperature to allow more precipitate to form. The mixture was then stirred 1 h at ambient temperature before it was vacuum filtered, rinsing with water (1.5 L). The filter cake was dried in vacuo for 2 h, then triturated with heptane (2 L), filtered and dried in vacuo to afford the title compound (181 g, 87% yield). ¹H NMR (400 MHz, d⁶-DMSO) δ 11.81 (br s, 1H), 8.82 (d, 1H), 8.55 (s, 1H), 6.87 (d, 1H).

Step 2: Preparation of 6-bromo-3-cyanopyrazolo[1,5-a]pyridin-4-yl trifluoromethanesulfonate Under an inert atmosphere (N$_{2(g)}$), a cold (4° C.) suspension of 6-bromo-4-hydroxypyrazolo[1,5-a]pyridine-3-carbonitrile (Step 1; 100 g, 420.1 mmol) in DMA (2100 mL) was treated slowly (10 min) with DIEA (146.7 mL, 840.2 mmol). The cold solution (2° C.) was treated dropwise (3 drops/second) with a solution of 1,1,1-trifluoro-N-phenyl-N-((trifluoromethyl)sulfonyl)methanesulfonamide (157.6 g, 441.1 mmol) in DMA (80 mL). The reaction mixture was stirred at low temperature (0-13° C.) for 4 h. The reaction mixture was poured slowly (15 min) into ice water (8 L). The quenched reaction mixture was stirred for 1 h at ambient temperature. The resulting suspension was vacuum filtered through a cloth filter paper, compacting the filter cake with a spatula and rinsing with cool water (3 L). The resultant filter cake was dried in vacuo for 3 d to afford the title compound (148.5 g, 96% yield). ¹H NMR (400 MHz, d⁶-DMSO) δ 9.60 (d, 1H), 8.85 (s, 1H), 8.22 (d, 1H).

Step 3: Preparation of 6-bromo-4-(6-fluoropyridin-3-yl)pyrazolo[1,5-a]pyridine-3-carbonitrile A cold (0° C.) mixture of 6-bromo-3-cyanopyrazolo[1,5-a]pyridin-4-yl trifluoromethanesulfonate (Step 2; 98.5 g, 253 mmol) and 2-fluoro-5-(4,4,5,5-tetramethyl-1,3,2-dioxaborolan-2-yl)pyridine (56.4 g, 253 mmol) in dioxane (2 L) was sparged with Ar$_{(g)}$ for 5 min. The cold mixture was treated with PdCl₂(dppf)CH₂Cl₂ (8.26 g, 10.1 mmol), and sparged again with Ar$_{(g)}$ for 5 min. While stirring the resulting mixture at 0° C., a solution of KOAc (49.6 g, 506 mmol) in water (500 mL) was added to the mixture under an inert atmosphere (N$_{2(g)}$). The mixture was mechanically stirred overnight at ambient temperature under positive pressure of N$_{2(g)}$. The reaction mixture was poured into water (7 L), and stirred for 5 h at ambient temperature. The resulting suspension was filtered, and rinsed with MTBE (1 L). The resultant filter cake was dried in vacuo to afford the title compound (75 g, 94% yield). ¹H NMR (400 MHz, d⁶-DMSO) δ 9.49 (d, 1H), 8.73 (s, 1H), 8.50 (m, 1H), 8.27 (m, 1H), 7.86 (d, 1H), 7.40 (m, 1H).

Step 4: Preparation of 4-(6-fluoropyridin-3-yl)-6-(4,4,5,5-tetramethyl-1,3,2-dioxaborolan-2-yl)pyrazolo[1,5-a]pyridine-3-carbonitrile A suspension of 6-bromo-4-(6-fluoropyridin-3-yl)pyrazolo[1,5-a]pyridine-3-carbonitrile (Step 3; 55.1 g, 174 mmol), bis(pinacolato)diboron (46.3 g, 182 mmol), and KOAc (51.2 g, 521 mmol) in DMSO (430 mL) was sparged with Ar$_{(g)}$ for 10 min. The reaction mixture was treated with PdCl$_2$(dppf)CH$_2$Cl$_2$ (1.42 g, 1.74 mmol), and sparged with Ar$_{(g)}$ for an additional 10 min. The resulting mixture was mechanically stirred for 16 h at 70° C. under positive pressure of N$_{2(g)}$. After cooling to ambient temperature, the reaction mixture was diluted with 1:1 EtOAc:water (4.0 L), and stirred for 1 h. The resulting suspension was filtered. The solids were rinsed sequentially with water (500 mL) and EtOAc (500 mL), and the biphasic filtrate was separated. The organic layer was temporarily set aside while the aqueous layer was extracted with EtOAc (2×1 L). The organic extracts were combined, washed with water (2×1 L) and brine (500 mL), then dried over anhydrous Na$_2$SO$_{4(s)}$, and filtered. The filtrate was treated with Si-Thiol resin (2 g; to scavenge residual Pd), and stirred for 16 h at ambient temperature. The suspension was filtered, the resin was rinsed with EtOAc, and the filtrate was concentrated in vacuo. The crude material was subjected to silica chromatography (using 5-60% Hexanes-Acetone as the gradient eluent). Fractions containing the desired compound were combined and concentrated in vacuo affording semi-pure material. The semi-pure material was recrystallized in batches by dissolving a portion of the material (12.3 g) in acetone (120 mL) at 60° C. The hot solution was treated with Hexanes (120 mL), then allowed to cool to ambient temperature before placing in a −18° C. freezer for 2 h. The cold suspension was vacuum filtered, rinsing the pure solids with ambient temperature hexanes. Repeating this recrystallization process on the remaining crude material allowed for clean isolation of the title compound (46.2 g, 73%). $^1$H NMR (400 MHz, CDCl$_3$) δ 8.99-8.98 (d, 1H), 8.77 (s, 1H), 8.49-8.48 (m, 1H), 8.27-8.22 (m, 1H), 7.57-7.56 (d, 1H), 7.38-7.35 (m, 1H), 1.34 (s, 12H).

Step 5: Preparation of 4-(6-fluoropyridin-3-yl)-6-hydroxypyrazolo[1,5-a]pyridine-3-carbonitrile A cold (0° C.) solution of 4-(6-fluoropyridin-3-yl)-6-(4,4,5,5-tetramethyl-1,3,2-dioxaborolan-2-yl)pyrazolo[1,5-a]pyridine-3-carbonitrile (Step 4; 22.96 g, 57.06 mmol) in THF (315 mL, 0.2 M) was treated with 2 M NaOH$_{(aq)}$ (142.6 mL, 285.3 mmol) followed by dropwise addition of 35 wt % H$_2$O$_{2(aq)}$ (29.97 mL, 342.3 mmol). The resulting mixture was stirred for 3 h at 0° C., before quenching with 3 M Na$_2$S$_2$O$_{3(aq)}$ (114.1 mL, 342.3 mmol) at 0° C. The quenched mixture was stirred for 16 h at ambient temperature, before partitioning the mixture between MTBE (1 L) and water (200 mL). The biphasic mixture was stirred for 15 min and then filtered, rinsing with additional water. The resulting biphasic filtrate was separated, and the organic extracts from the filtrate were washed with 0.1 M NaOH$_{(aq)}$ (200 mL). The aqueous extracts were combined, washed with MTBE (500 mL) then acidified to pH ~5 using solid citric acid. The resulting aqueous suspension was diluted with additional water (250 mL), stirred for 30 min, and then filtered. The solids were rinsed with water, and dried in vacuo to afford the title compound (11.3 g, 66% yield). MS (APCI Neg), m/z=253.0 (M−H).

Intermediate P64

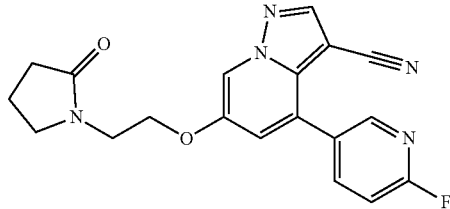 [SMILES: N#Cc1cnn2cc(OCCN3CCCC3=O)cc(-c3ccc(F)nc3)c12]

4-(6-fluoropyridin-3-yl)-6-(2-(2-oxopyrrolidin-1-yl)ethoxy)pyrazolo[1,5-a]pyridine-3-carbonitrile A solution of 4-(6-fluoropyridin-3-yl)-6-hydroxypyrazolo[1,5-a]pyridine-3-carbonitrile (Intermediate P63; 200 mg, 0.787 mmol) in DMA (6 mL) was treated sequentially with Cs$_2$CO$_{3(s)}$ (769 mg, 2.36 mmol) and 1-(2-chloroethyl)pyrrolidin-2-one (139 mg, 0.944 mmol). The reaction mixture was stirred overnight at 100° C. in a sealed vessel. After cooling to ambient temperature, the resulting mixture was partitioned between water and DCM then extracted with DCM (3×). The combined organic extracts were washed with brine (1×) then dried over anhydrous Na$_2$SO$_{4(s)}$, filtered and concentrated in vacuo. The crude residue was purified by silica chromatography (using 0-10% MeOH in DCM with 0.1% NH$_4$OH as the gradient eluent) to afford the title compound (115 mg, 34% yield). MS (apci), m/z=366.1 (M+H).

Intermediate P65

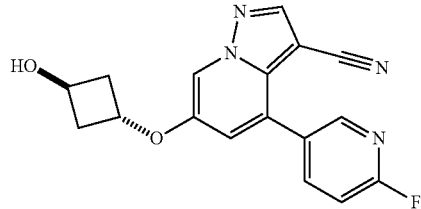

4-(6-fluoropyridin-3-yl)-6-((1r,3r)-3-hydroxycyclobutoxy)pyrazolo[1,5-a]pyridine-3-carbonitrile A mixture of 4-bromo-6-((1r,3r)-3-hydroxycyclobutoxy)pyrazolo[1,5-a]pyridine-3-carbonitrile (Intermediate P58; 0.100 g, 0.325 mmol), 2-fluoro-5-(4,4,5,5-tetramethyl-1,3,2-dioxaborolan-2-yl)pyridine (629 mg, 2.82 mmol), and Pd(PPh$_3$)$_4$ (217 mg, 0.188 mmol) in dioxane (1 mL) was sparged with Ar$_{(g)}$ for 1 min then treated with 2 M K$_2$CO$_{3(aq)}$ (0.470 mL, 0.974 mmol). The resulting mixture was sparged with Ar$_{(g)}$ for 3 min, before sealing the reaction vessel. The mixture was stirred 3 d at 90° C. After cooling to ambient temperature, the reaction mixture was purified directly by silica chromatography (using 40% EtOAc in hexanes as the eluent) to cleanly provide the title compound (96 mg, 91% yield). MS (apci) m/z=325.1 (M+H).

Intermediate P66

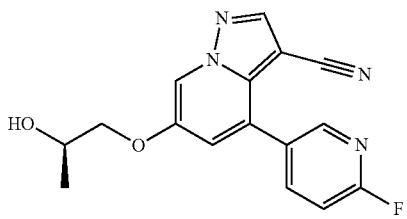

(R)-4-(6-fluoropyridin-3-yl)-6-(2-hydroxypropoxy)pyrazolo[1,5-a]pyridine-3-carbonitrile In a pressure tube, a solution of (R)-4-bromo-6-(2-hydroxypropoxy)pyrazolo[1,5-a]pyridine-3-carbonitrile (Intermediate P59; 365 mg, 1.23 mmol) in dioxane (6 mL) was treated with 2-fluoro-5-(4,4,5,5-tetramethyl-1,3,2-dioxaborolan-2-yl)pyridine (330 mg, 1.48 mmol) and 2 M Na$_2$CO$_{3(aq)}$ (1849 µL, 3.70 mmol), then sparged with N$_{2(g)}$ for 5 min. The resulting mixture was treated with Pd(PPh$_3$)$_4$ (35.6 mg, 0.0308 mmol), then sparged again with N$_{2(g)}$ for 5 min, before sealing the vessel. The reaction mixture was stirred for 22 h at 80° C. After cooling to ambient temperature, the mixture was diluted with water (25 mL), and stirred for 1 h. The resulting suspension was vacuum filtered, and the solids were collected to cleanly provide the title compound (229 mg, 60% yield). MS (apci) m/z=313.1 (M+H).

Intermediate P67

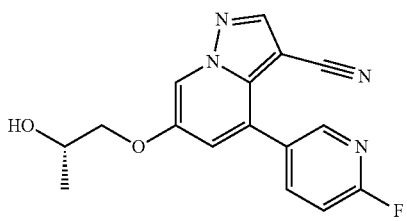 [SMILES: C[C@H](O)COc1cc(-c2ccc(F)nc2)c2c(C#N)cnn2c1]

(S)-4-(6-fluoropyridin-3-yl)-6-(2-hydroxypropoxy)pyrazolo[1,5-a]pyridine-3-carbonitrile In a pressure tube, a solution of (S)-4-bromo-6-(2-hydroxypropoxy)pyrazolo[1,5-a]pyridine-3-carbonitrile (Intermediate P60; 357 mg, 1.21 mmol) in dioxane (6 mL) was treated with 2-fluoro-5-(4,4,5,5-tetramethyl-1,3,2-dioxaborolan-2-yl)pyridine (323 mg, 1.45 mmol), and 2 M Na$_2$CO$_{3(aq)}$ (1808 µL, 3.62 mmol) was sparged with N$_{2(g)}$ for 5 min. The resulting mixture was treated with Pd(PPh$_3$)$_4$ (34.8 mg, 0.0301 mmol) then sparged again with N$_{2(g)}$ for 5 min, before sealing the vessel. The reaction mixture was stirred for 22 h at 80° C. After cooling to ambient temperature, the reaction mixture was diluted with water (25 mL) and stirred for 1 h. The resulting suspension was vacuum filtered and the solids were collected to cleanly provide the title compound (191 mg, 51% yield). MS (apci) m/z=313.1 (M+H).

Intermediate P68

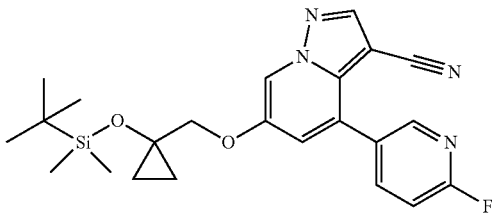 [SMILES: CC(C)(C)[Si](C)(C)OC1(COc2cc(-c3ccc(F)nc3)c3c(C#N)cnn3c2)CC1]

6-((1-((tert-butyldimethylsilyl)oxy)cyclopropyl)methoxy)-4-(6-fluoropyridin-3-yl)pyrazolo[1,5-a]pyridine-3-carbonitrile A solution of 4-bromo-6-((1-((tert-butyldimethylsilyl)oxy)cyclopropyl)methoxy)pyrazolo[5-a]pyridine-3-carbonitrile (Intermediate P61; 404.2 mg, 0.9569 mmol), in 4:1 dioxane:water (10 mL) was treated 2-fluoro-5-(4,4,5,5-tetramethyl-1,3,2-dioxaborolan-2-yl)pyridine (234.8 mg, 1.053 mmol), Pd(PPh$_3$)$_4$ (110.6 mg, 0.09569 mmol) and K$_2$CO$_{3(s)}$ (396.8 mg, 2.871 mmol). The resulting mixture was sparged with Ar$_{(g)}$, before sealing the reaction vessel. The mixture was stirred for 16 h at 90° C. After cooling to ambient temperature, the reaction mixture was diluted with 4:1 DCM:iPrOH, washed with water (1×), then dried over anhydrous Na$_2$SO$_{4(s)}$, filtered, and concentrated in vacuo. The crude residue was purified by silica chromatography (using 5-75% Hexanes-EtOAc as the gradient eluent) to cleanly provide the title compound (292.6 mg, 70% yield). $^1$H NMR (400 MHz, CDCl$_3$) δ 8.40-8.39 (m, 1H), 8.21 (s, 1H), 8.18-8.17 (d, 1H), 8.04-8.00 (m, 1H), 7.20-7.19 (d, 1H), 7.14-7.11 (m, 1H), 4.01 (s, 2H), 0.95-0.92 (m, 2H), 0.85 (s, 9H), 0.80-0.75 (m, 2H), 0.14 (s, 6H).

Intermediate P69

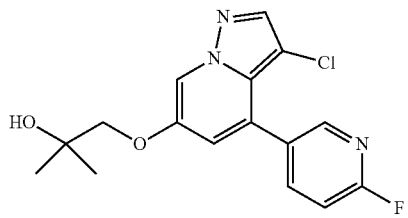 [SMILES: CC(C)(O)COc1cc(-c2ccc(F)nc2)c2c(Cl)cnn2c1]

1-((3-chloro-4-(6-fluoropyridin-3-yl)pyrazolo[1,5-a]pyridin-6-yl)oxy)-2-methylpropan-2-ol In a pressure vessel, a mixture of 1-((4-bromo-3-chloropyrazolo[1,5-a]pyridin-6-yl)oxy)-2-methylpropan-2-ol (Intermediate P61; 1.44 g, 4.51 mmol), 2-fluoro-5-(4,4,5,5-tetramethyl-1,3,2-dioxaborolan-2-yl)pyridine (1.51 g, 6.76 mmol) and Pd(PPh$_3$)$_4$ (260 mg, 0.225 mmol) in dioxane (50 mL) was treated with 2 M Na$_2$CO$_{3(aq)}$ (15 mL, 27 mmol). The resulting mixture was sparged with N$_{2(g)}$ for 10 min, before sealing the vessel. The reaction mixture was stirred overnight at 90° C. After cooling to ambient temperature, the resultant mixture was diluted with water (75 mL), and extracted with MTBE (3×75 mL). The combined organic extracts were dried over anhydrous $Na_2SO_{4(s)}$, filtered and concentrated in vacuo. The crude residue was purified by silica chromatography (using 0-100% EtOAc/Hexanes as the gradient eluent) to afford the title compound (370 mg, 25% yield). MS (apci) m/z=336.1 (M+H).

Intermediate P70A: 4-(6-(3,6-diazabicyclo[3.1.1] heptan-3-yl)pyridin-3-yl)-6-hydroxypyrazolo[1,5-a] pyridine-3-carbonitrile and Intermediate P70B: 4-(6-(3,6-diazabicyclo[3.1.1]heptan-3-yl)pyridin-3-yl)-6-hydroxypyrazolo[1,5-a]pyridine-3-carbonitrile dihydrochloride

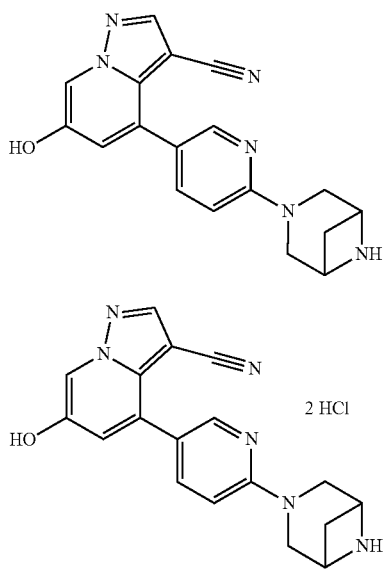

Step 1. Preparation of tert-butyl 3-(5-(3-cyano-6-hydroxypyrazolo[1,5-a]pyridin-4-yl)pyridin-2-yl)-3,6-diazabicyclo[3.1.1]heptane-6-carboxylate A solution of 4-(6-fluoropyridin-3-yl)-6-hydroxypyrazolo[1,5-a]pyridine-3-carbonitrile (Intermediate P63; 1.256 g, 4.941 mmol) and tert-butyl 3,6-diazabicyclo[3.1.1]heptane-6-carboxylate (1.371 g, 6.917 mmol) in DMSO (6 mL) was treated with DIEA (1.721 mL, 9.881 mmol). The reaction vessel was sealed, and the mixture was stirred 24 h at 60° C. Additional tert-butyl 3,6-diazabicyclo[3.1.1]heptane-6-carboxylate (0.586 g) was introduced, and the reaction mixture was stirred 72 h at 60° C. After cooling to ambient temperature, the reaction mixture was poured into water (60 mL), and the resulting suspension was vacuum filtered. The solids were collected, then dissolved in EtOAc, dried over anhydrous $Na_2SO_{4(s)}$, filtered and concentrated in vacuo. Separately, the aqueous filtrate was back extracted with 4:1 DCM:iPrOH (4×), and the combined organic extracts were concentrated in vacuo. The crude residue and solids from the filtration were both purified by silica chromatography (using 0-95% DCM:Acetone as the gradient eluent) to afford the title compound (1.0 g, 49% yield). MS (apci), m/z=433.2 (M+H).

Step 2: Preparation of 4-(6-(3,6-diazabicyclo[3.1.1] heptan-3-yl)pyridin-3-yl)-6-hydroxypyrazolo[1,5-a] pyridine-3-carbonitrile and 4-(6-(3,6-diazabicyclo [3.1.1]heptan-3-yl)pyridin-3-yl)-6-hydroxypyrazolo [1,5-a]pyridine-3-carbonitrile dihydrochloride A solution of tert-butyl 3-(5-(3-cyano-6-hydroxypyrazolo [1,5-a]pyridin-4-yl)pyridin-2-yl)-3,6-diazabicyclo[3.1.1] heptane-6-carboxylate (1.0 g, 2.40 mmol) was dissolved in 1:1 TFA:DCM (5 mL), diluted with DCM (5 mL) and stirred for 45 min at ambient temperature. The resulting mixture was concentrated in vacuo, and the residue was partitioned between 4:1 DCM:iPrOH and saturated $NaHCO_{3(aq)}$. The biphasic mixture was extracted with 4:1 DCM:iPrOH (3×), and the combined organic extracts were dried over anhydrous $Na_2SO_{4(s)}$, filtered, and concentrated in vacuo to afford Intermediate P70A: 4-(6-(3,6-diazabicyclo[3.1.1]heptan-3-yl)pyridin-3-yl)-6-hydroxypyrazolo[1,5-a]pyridine-3-carbonitrile (322.9 mg, 40% yield). MS (apci), m/z=333.1 (M+H). Separately, the $NaHCO_{3(aq)}$ extracts were concentrated in vacuo, and the residue was dissolved in 4:1 DCM:iPrOH. The suspension was vacuum filtered and the filtrate was dried over anhydrous $Na_2SO_{4(s)}$, filtered, and concentrated in vacuo. This residue was dissolved in MeOH and treated with concentrated HCl (10 mL). The suspension was filtered, and concentrated in vacuo to remove the MeOH, before diluting with MeOH (10 mL) and MTBE (40 mL). The resulting suspension was sonicated for a few minutes, then filtered. The solids were rinsed with MTBE and dried in vacuo to afford Intermediate P70B: 4-(6-(3,6-diazabicyclo[3.1.1]heptan-3-yl)pyridin-3-yl)-6-hydroxypyrazolo[1,5-a]pyridine-3-carbonitrile dihydrochloride (450.7 mg, 46% yield). MS (apci), m/z=333.2 (M+H).

Intermediate P71

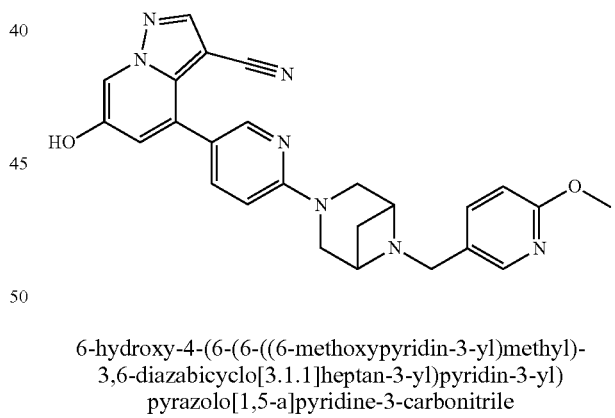

6-hydroxy-4-(6-(6-(((6-methoxypyridin-3-yl)methyl)-3,6-diazabicyclo[3.1.1]heptan-3-yl)pyridin-3-yl) pyrazolo[1,5-a]pyridine-3-carbonitrile A solution of 4-(6-(3,6-diazabicyclo[3.1.1]heptan-3-yl) pyridin-3-yl)-6-hydroxypyrazolo[1,5-a]pyridine-3-carbonitrile (Intermediate P70B; 322.9 mg, 0.9715 mmol) in DCM (10 mL) was treated sequentially with 6-methoxynicotinaldehyde (137.1 mg, 1.943 mmol) and 2 drops of glacial acetic acid. The mixture was stirred for 15 min at ambient temperature then treated with $NaBH(AcO)_3$ (514.8 mg, 2.429 mmol). The resulting mixture was stirred overnight at ambient temperature, before introducing additional 6-methoxynicotinaldehyde (34 mg) and $NaBH(AcO)_3$ (103 mg). The resulting mixture was stirred until LCMS indicated consumption of the starting material, before concentrating the

Intermediate P72

6-hydroxy-4-(6-(6-(6-methoxynicotinoyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-hydroxypyrazolo[1,5-a]pyridine-3-carbonitrile (Intermediate P70B; 187.7 mg, 0.5647 mmol) in DCM (11.3 mL) was treated with 2-methoxy-5-pyridinecarboxylic acid (86.48 mg, 0.5647 mmol), HATU (257.7 mg, 0.6776 mmol), and DIEA (393.5 µL, 2.259 mmol) and the resulting mixture was for 16 h at ambient temperature, before sequentially introducing additional 2-methoxy-5-pyridinecarboxylic acid (43.23 mg, 0.2824 mmol) and DIEA (199 µL, 1.13 mmol). The reaction mixture was stirred overnight at ambient temperature. The reaction mixture was concentrated in vacuo. The residue was dissolved in EtOAc, and washed with saturated NH$_4$Cl$_{(aq)}$. The organic extracts were purified directly by silica chromatography (using 0-10% MeOH/DCM as the gradient eluent) to afford the title compound (68.6 mg, 26% yield). MS (apci) m/z=468.2 (M+H).

mixture. The residue was diluted with 4:1 DCM:iPrOH and extracted with water (2×). The combined aqueous extracts were back extracted with 4:1 DCM:iPrOH (3×). The organic extracts were combined, then dried over anhydrous Na$_2$SO$_4$ $_{(s)}$, filtered and concentrated in vacuo. The residue was purified by C18 reverse phase chromatography (using 5-95% water-ACN with 0.1% TFA as the gradient eluent) to afford the title compound as the TFA salt. The TFA salt was diluted with 4:1 DCM:iPrOH and extracted with saturated NaHCO$_{3(aq)}$. The aqueous extracts were washed with 4:1 DCM:iPrOH (3×), then the combined organic extracts were dried over anhydrous Na$_2$SO$_{4(s)}$, filtered and concentrated in vacuo to cleanly provide the title compound (27.4 mg, 6% yield). MS (apci) m/z=454.2 (M+H).

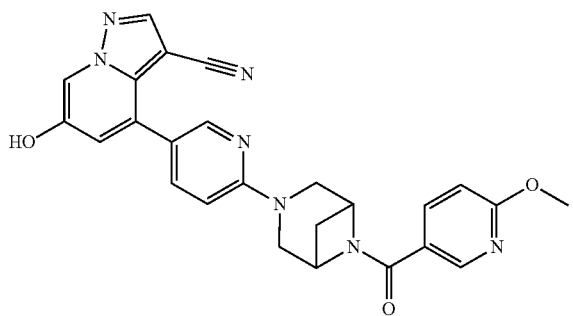 [SMILES: COc1ccc(C(=O)N2C3CC2CN(c2ccc(-c4cc(O)cn5ncc(C#N)c45)cn2)C3)cn1]

Intermediate P73

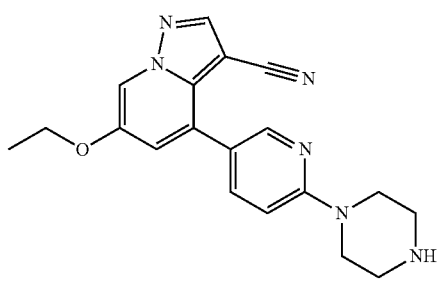 [SMILES: CCOc1cc(-c2ccc(N3CCNCC3)nc2)c2c(C#N)cnn2c1]

6-ethoxy-4-(6-(piperazin-1-yl)pyridin-3-yl)pyrazolo[1,5-a]pyridine-3-carbonitrile A solution of 6-ethoxy-4-(6-fluoropyridin-3-yl)pyrazolo[1,5-a]pyridine-3-carbonitrile (Intermediate P6; 255.7 mg, 0.9058 mmol) in DMSO (3.6 mL) was treated with tert-butyl 1-piperazinecarboxylate (337.4 mg, 1.812 mmol) and DIEA (315.6 µL, 1.812 mmol), and then stirred for 16 h at 90° C. After cooling to ambient temperature, the reaction mixture was diluted with EtOAc, and extracted sequentially with water (3×) and brine (1×). The combined organic extracts were washed with brine, then dried over anhydrous Na$_2$SO$_4$ $_{(s)}$, filtered and concentrated in vacuo. The crude residue was dissolved in 1:1 DCM:TFA (5.0 mL). After stirring for 30 min at ambient temperature, the mixture was concentrated in vacuo. The residue was purified by C18 reverse phase chromatography (using 5-95% water-ACN with 0.1% TFA as the gradient eluent). Fractions containing the desired compound were combined, dissolved in 4:1 DCM:iPrOH, and then extracted with saturated NaHCO$_{3(aq)}$. The organic extracts were dried over anhydrous Na$_2$SO$_{4(s)}$, filtered and concentrated in vacuo to cleanly provide the title compound (261.9 mg, 83% yield). MS (apci) m/z=349.2 (M+H).

Intermediate P74

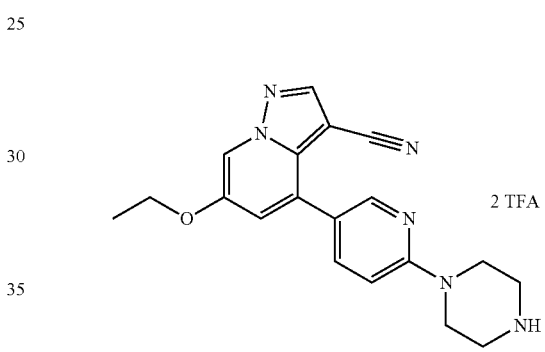

6-ethoxy-4-(6-(piperazin-1-yl)pyridin-3-yl)pyrazolo[1,5-a]pyridine-3-carbonitrile bis(2,2,2-trifluoroacetate)

A solution of tert-butyl 4-(5-(3-cyano-6-ethoxypyrazolo[1,5-a]pyridin-4-yl)pyridin-2-yl)piperazine-1-carboxylate (Example 29; 413 mg, 0.921 mmol) in DCM (8 mL) was treated with TFA (2 mL). After stirring for 1 h at ambient temperature, the mixture was concentrated in vacuo to cleanly provide the title compound (quantitative yield). MS (apci) m/z=349.2 (M+H).

Intermediate P75

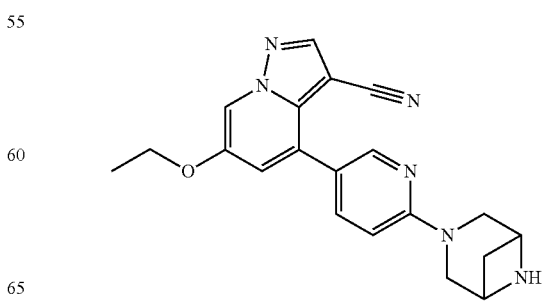

4-(6-(3,6-diazabicyclo[3.1.1]heptan-3-yl)pyridin-3-yl)-6-ethoxypyrazolo[1,5-a]pyridine-3-carbonitrile A mixture of 6-ethoxy-4-(6-fluoropyridin-3-yl)pyrazolo[1,5-a]pyridine-3-carbonitrile (Intermediate P6; 347 mg, 1.23 mmol) and tert-butyl 3,6-diazabicyclo[3.1.1]heptane-6-carboxylate (176.6 mg, 0.8908 mmol) in DMSO (0.8 mL) was treated with DIEA (221.7 µL, 1.273 mmol). The mixture was stirred for 3 days at 60° C. in a sealed vessel. After cooling to ambient temperature, the reaction mixture was diluted with EtOAc, and extracted with water (3×) and brine (1×). The organic extracts were then dried over anhydrous $Na_2SO_{4(s)}$, filtered and concentrated in vacuo. The crude residue was purified by silica chromatography (using 0-100% EtOAc in hexanes as the gradient eluent) to cleanly afford tert-butyl 3-(5-(3-cyano-6-ethoxypyrazolo[1,5-a]pyridin-4-yl)pyridin-2-yl)-3,6-diazabicyclo[3.1.1]heptane-6-carboxylate. This material was suspended in DCM (1.0 mL), and treated with 1:1 TFA:DCM (0.25 mL). After stirring for 7 h at ambient temperature, the reaction mixture was concentrated in vacuo. The residue was dissolved in 4:1 DCM:iPrOH, and extracted with saturated $NaHCO_{3(aq)}$. The combined organic extracts were dried over anhydrous $Na_2SO_{4(s)}$, filtered and concentrated in vacuo to cleanly provide the title compound (67.1 mg, 29% yield). MS (apci) m/z=361.2 (M+H).

Intermediate P76

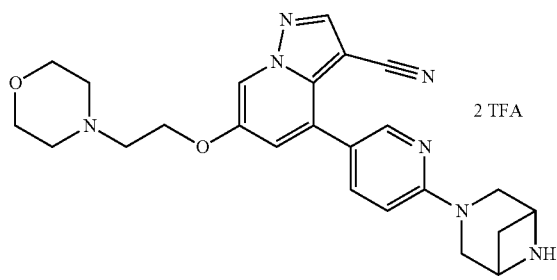 [SMILES: N#Cc1cnn2cc(OCCN3CCOCC3)cc(-c3ccc(N4CC5CC(C4)N5)nc3)c12]

4-(6-(3,6-diazabicyclo[3.1.1]heptan-3-yl)pyridin-3-yl)-6-(2-morpholinoethoxy)pyrazolo[1,5-a]pyridine-3-carbonitrile bis(2,2,2-trifluoroacetate)

Step 1: Preparation of tert-butyl 3-(5-(3-cyano-6-(2-morpholinoethoxy)pyrazolo[1,5-a]pyridin-4-yl)pyridin-2-yl)-3,6-diazabicyclo[3.1.1]heptane-6-carboxylate A solution of tert-butyl 3-(5-(3-cyano-6-hydroxypyrazolo[1,5-a]pyridin-4-yl)pyridin-2-yl)-3,6-diazabicyclo[3.1.1]heptane-6-carboxylate (Intermediate P4; 350 mg, 0.809 mmol) in DMA (4046 µL) was treated sequentially with $K_2CO_{3(s)}$ (336 mg, 2.43 mmol) and 4-(2-Chloroethyl)morpholine (218 µL, 1.62 mmol). The reaction mixture was stirred overnight at 50° C. in a sealed vessel. The reaction mixture was cooled to ambient temperature, then diluted with water (10 mL). The resulting suspension was vacuum filtered, rinsing the solids with water (2×10 mL), then with $Et_2O$ (2×10 mL). The solids were dried in vacuo to afford the title compound (380 mg, 86% yield). MS (apci) m/z=546.3 (M+H).

Step 2: Preparation of 4-(6-(3,6-diazabicyclo[3.1.1]heptan-3-yl)pyridin-3-yl)-6-(2-morpholinoethoxy)pyrazolo[1,5-a]pyridine-3-carbonitrile bis(2,2,2-trifluoroacetate)

A solution of tert-butyl 3-(5-(3-cyano-6-(2-morpholinoethoxy)pyrazolo[1,5-a]pyridin-4-yl)pyridin-2-yl)-3,6-diazabicyclo[3.1.1]heptane-6-carboxylate (Step 1; 380 mg, 0.696 mmol) in DCM (2 mL) was treated with TFA (2 mL). The resulting mixture was stirred for 10 min at ambient temperature, and then concentrated in vacuo to cleanly provide the title compound (400 mg, quantitative yield). MS (apci) m/z=446.2 (M+H).

Intermediate P77

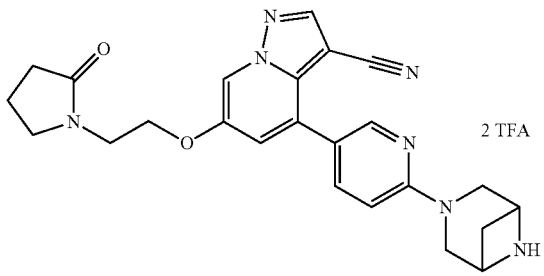 [SMILES: N#Cc1cnn2cc(OCCN3CCCC3=O)cc(-c3ccc(N4CC5CC(C4)N5)nc3)c12]

4-(6-(3,6-diazabicyclo[3.1.1]heptan-3-yl)pyridin-3-yl)-6-(2-(2-oxopyrrolidin-1-yl)ethoxy)pyrazolo[1,5-a]pyridine-3-carbonitrile bis(2,2,2-trifluoroacetate)

Step 1: Preparation of tert-butyl 3-(5-(3-cyano-6-(2-(2-oxopyrrolidin-1-yl)ethoxy)pyrazolo[1,5-a]pyridin-4-yl)pyridin-2-yl)-3,6-diazabicyclo[3.1.1]heptane-6-carboxylate A mixture of 4-(6-fluoropyridin-3-yl)-6-(2-(2-oxopyrrolidin-1-yl)ethoxy)pyrazolo[1,5-a]pyridine-3-carbonitrile (Intermediate P64; 115 mg, 0.315 mmol), tert-butyl 3,6-diazabicyclo[3.1.1]heptane-6-carboxylate (93.6 mg, 0.472 mmol) and $K_2CO_{3(s)}$ (218 mg, 1.57 mmol) in DMSO (630 µL) was stirred overnight at 60° C. After cooling to ambient temperature, the reaction mixture was partitioned between water and DCM then extracted with DCM (5×). The combined organic extracts were washed with brine (1×), then dried over anhydrous $Na_2SO_{4(s)}$, filtered and concentrated in vacuo. The crude residue was purified by silica chromatography (using 0-100% EtOAc in Hexanes then 0-10% MeOH in EtOAc as the gradient eluent) to afford the title compound (85 mg, 30% yield). MS (apci) m/z=544.3 (M+H).

Step 2: Preparation of 4-(6-(3,6-diazabicyclo[3.1.1]heptan-3-yl)pyridin-3-yl)-6-(2-(2-oxopyrrolidin-1-yl)ethoxy)pyrazolo[1,5-a]pyridine-3-carbonitrile bis(2,2,2-trifluoroacetate)

A solution of tert-butyl 3-(5-(3-cyano-6-(2-(2-oxopyrrolidin-1-yl)ethoxy)pyrazolo[1,5-a]pyridin-4-yl)pyridin-2-yl)-3,6-diazabicyclo[3.1.1]heptane-6-carboxylate (Step 1; 85 mg, 0.094 mmol) in DCM (1 mL) was treated with TFA (1 mL). The resulting mixture was stirred overnight at ambient temperature, and then concentrated in vacuo to Intermediate P78

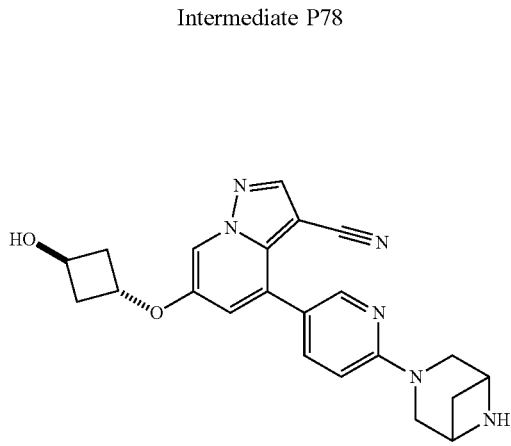

4-(6-(3,6-diazabicyclo[3.1.1]heptan-3-yl)pyridin-3-yl)-6-((1r,3r)-3-hydroxycyclobutoxy)pyrazolo[1,5-a]pyridine-3-carbonitrile Step 1: Preparation of tert-butyl 3-(5-(3-cyano-6-((1r,3 r)-3-hydroxycyclobutoxy)pyrazolo[1,5-a]pyridin-4-yl)pyridin-2-yl)-3,6-diazabicyclo[3.1.1]heptane-6-carboxylate A mixture of 4-(6-fluoropyridin-3-yl)-6-((1r,3r)-3-hydroxycyclobutoxy)pyrazolo[1,5-a]pyridine-3-carbonitrile (Intermediate P65; 50 mg, 0.15 mmol), tert-butyl 3,6-diazabicyclo[3.1.1]heptane-6-carboxylate (0.046 g, 0.23 mmol) and $K_2CO_{3(s)}$ (0.11 g, 0.77 mmol) in DMSO (0.25 mL) was stirred overnight at 85° C. The reaction mixture was cooled to ambient temperature, diluted with water (1 mL), and extracted with DCM (3 mL). The organic extracts were purified by silica chromatography (using 10% acetone in DCM with 0.05% NH4OH as the gradient eluent) to cleanly provide the title compound (56 mg, 61% yield). MS (apci) m/z=503.2 (M+H).

Step 2: Preparation of 4-(6-(3,6-diazabicyclo[3.1.1] heptan-3-yl)pyridin-3-yl)-6-((1r,3r)-3-hydroxycyclobutoxy)pyrazolo[1,5-a]pyridine-3-carbonitrile A solution of tert-butyl 3-(5-(3-cyano-6-((1r,3r)-3-hydroxycyclobutoxy)pyrazolo[1,5-a]pyridin-4-yl)pyridin-2-yl)-3,6-diazabicyclo[3.1.1]heptane-6-carboxylate (Step 1; 56 mg, 0.095 mmol) in DCM (0.5 mL) was treated with TFA (0.11 mL). The resulting mixture was stirred for 4 h at ambient temperature, and then concentrated in vacuo. The pH of residue was adjusted to pH 14 with the addition of 1 M NaOH. The aqueous mixture was salted out with solid NaCl, then extracted with CHCl3 (2×20 mL). The combined organic extracts were dried over anhydrous $MgSO_{4(s)}$, filtered and concentrated in vacuo to cleanly provide the title compound (55 mg, quantitative yield). MS (apci) m/z=403.2 (M+H).

Intermediate P79

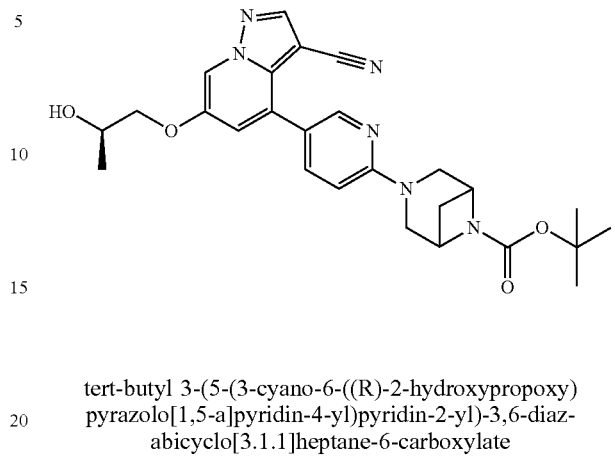

tert-butyl 3-(5-(3-cyano-6-((R)-2-hydroxypropoxy) pyrazolo[1,5-a]pyridin-4-yl)pyridin-2-yl)-3,6-diazabicyclo[3.1.1]heptane-6-carboxylate A mixture of (R)-4-(6-fluoropyridin-3-yl)-6-(2-hydroxypropoxy)pyrazolo[1,5-a]pyridine-3-carbonitrile (Intermediate P66; 100 mg, 0.320 mmol) 3,6-diaza-bicyclo[3.1.1] heptane-6-carboxylic acid tert-butyl ester (95.2 mg, 0.480 mmol) and $K_2CO_{3(s)}$ (443 mg, 3.20 mmol) in DMSO (1601 µL) was stirred for 3 d at 80° C. The reaction mixture was cooled to ambient temperature, then diluted with water (10 mL), and extracted with DCM (4×10 mL). The combined organic extracts were washed with brine (10 mL), then dried over anhydrous $Na_2SO_{4(s)}$, filtered, and concentrated in vacuo. The crude residue was purified by silica chromatography (using 50-100% EtOAc in Hexanes as the gradient eluent) to cleanly provide the title compound (97 mg, 62% yield). MS (apci) m/z=491.2 (M+H).

Intermediate P80

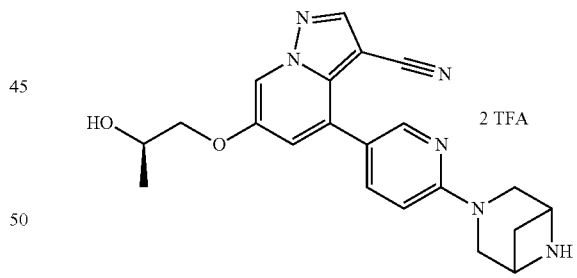

4-(6-(3,6-diazabicyclo[31.1]heptan-3-yl)pyridin-3-yl)-6-((R)-2-hydroxypropoxy)pyrazolo[1,5-a]pyridine-3-carbonitrile bis(2,2,2-trifluoroacetate)

A solution of tert-butyl 3-(5-(3-cyano-6-((R)-2-hydroxypropoxy)pyrazolo[1,5-a]pyridin-4-yl)pyridin-2-yl)-3,6-diazabicyclo[3.1.1]heptane-6-carboxylate (Intermediate P79; 97 mg, 0.20 mmol) in DCM (2 mL) was treated with TFA (2 mL). The resulting mixture was stirred overnight at ambient temperature, and then concentrated in vacuo to afford the title compound (122 mg, quantitative yield). MS (apci) m/z=391.15 (M+H).

Intermediate P81

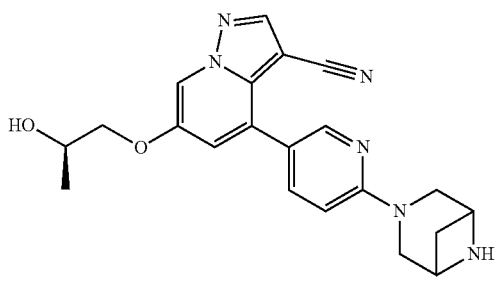 [SMILES: C[C@@H](O)COc1cc(-c2ccc(N3CC4CC(C3)N4)nc2)c2c(C#N)cnn2c1]

4-(6-(3,6-diazabicyclo[3.1.1]heptan-3-yl)pyridin-3-yl)-6-((R)-2-hydroxypropoxy)pyrazolo[1,5-a]pyridine-3-carbonitrile A solution of tert-butyl 3-(5-(3-cyano-6-((R)-2-hydroxypropoxy)pyrazolo[1,5-a]pyridin-4-yl)pyridin-2-yl)-3,6-diazabicyclo[3.1.1]heptane-6-carboxylate (Intermediate P79; 131 mg, 0.267 mmol) in DCM (2 mL) was treated with TFA (2 mL). The resulting mixture was stirred overnight at ambient temperature, and then concentrated in vacuo. The residue was purified by silica chromatography (using 0-100% (2% NH$_4$OH/20% MeOH/78% DCM) in DCM as the gradient eluent) to afford the title compound (75 mg, 72% yield). MS (apci) m/z=391.20 (M+H).

Intermediate P82

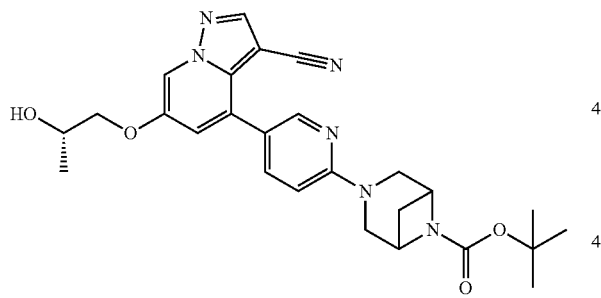

tert-butyl 3-(5-(3-cyano-6-((S)-2-hydroxypropoxy)pyrazolo[1,5-a]pyridin-4-yl)pyridin-2-yl)-3,6-diazabicyclo[3.1.1]heptane-6-carboxylate A mixture of (S)-4-(6-fluoropyridin-3-yl)-6-(2-hydroxypropoxy)pyrazolo[1,5-a]pyridine-3-carbonitrile (Intermediate P67; 100 mg, 0.320 mmol), tert-butyl 3,6-diazabicyclo[3.1.1]heptane-6-carboxylate (95.2 mg, 0.480 mmol) and K$_2$CO$_{3(s)}$ (443 mg, 3.20 mmol) in DMSO (1601 μL) was stirred for 3 d at 80° C. The reaction mixture was cooled to ambient temperature, then diluted with water (10 mL) and extracted with DCM (4×10 mL). The combined organic extracts were washed with brine (10 mL), then dried over anhydrous Na$_2$SO$_{4(s)}$, filtered, and concentrated in vacuo. The crude residue was purified by silica chromatography (using 50-100% EtOAc in Hexanes as the gradient eluent) to cleanly provide the title compound (92 mg, 59% yield). MS (apci) m/z=491.2 (M+H).

Intermediate P83

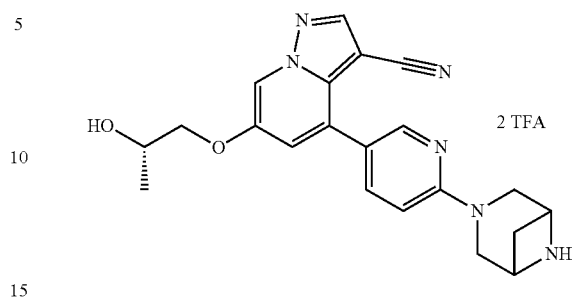

4-(6-(3,6-diazabicyclo[3.1.1]heptan-3-yl)pyridin-3-yl)-6-((S)-2-hydroxypropoxy)pyrazolo[1,5-a]pyridine-3-carbonitrile bis(2,2,2-trifluoroacetate)

A solution of tert-butyl 3-(5-(3-cyano-6-((S)-2-hydroxypropoxy)pyrazolo[1,5-a]pyridin-4-yl)pyridin-2-yl)-3,6-diazabicyclo[3.1.1]heptane-6-carboxylate (Intermediate P82; 92 mg, 0.188 mmol) in DCM (1 mL) was treated with TFA (1 mL). The resulting mixture was stirred overnight at ambient temperature, and then concentrated in vacuo to afford the title compound (116 mg, quantitative yield). MS (apci) m/z=391.20 (M+H).

Intermediate P84

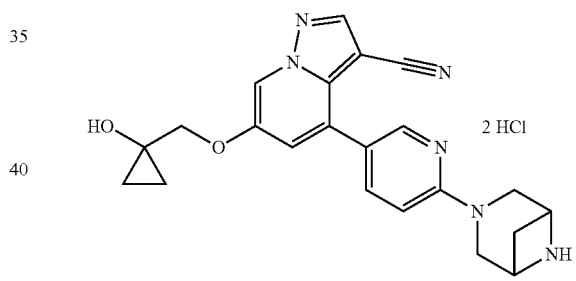

4-(6-(3,6-diazabicyclo[3.1.1]heptan-3-yl)pyridin-3-yl)-6-((1-hydroxycyclopropyl)methoxy)pyrazolo[1,5-a]pyridine-3-carbonitrile dihydrochloride Step 1: Preparation of tert-butyl 3-(5-(3-cyano-6-((1-hydroxycyclopropyl)methoxy)pyrazolo[1,5-a]pyridin-4-yl)pyridin-2-yl)-3,6-diazabicyclo[31.1]heptane-6-carboxylate A solution of 6-((1-((tert-butyldimethylsilyl)oxy)cyclopropyl)methoxy)-4-(6-fluoropyridin-3-yl)pyrazolo[1,5-a]pyridine-3-carbonitrile (Intermediate P68; 292.6 mg, 0.6672 mmol) in DMSO (1.3 mL) was treated with 3,6-diazabicyclo[3.1.1]heptane-6-carboxylic acid tert-butyl ester (158.7 mg, 0.8006 mmol) and K$_2$CO$_{3(s)}$ (922.0 mg, 6.672 mmol) was stirred for 14 d at 90° C. The reaction mixture was cooled to ambient temperature, then diluted with water and extracted with EtOAc (2×). The combined organic extracts were washed with water (3×) and brine (1×), then dried over anhydrous Na$_2$SO$_{4(s)}$, filtered, and concentrated in vacuo. The crude residue was purified by silica chromatography (using 5-95% DCM-Acetone as the gradient eluent) to cleanly provide the title compound which was immediately carried on to Step 2. MS (apci) m/z=503.2 (M+H).

Step 2: Preparation of 4-(6-(3,6-diazabicyclo[3.1.1] heptan-3-yl)pyridin-3-yl)-6-((1-hydroxycyclopropyl) methoxy)pyrazolo[1,5-a]pyridine-3-carbonitrile dihydrochloride A solution of tert-butyl 3-(5-(3-cyano-6-((1-hydroxycyclopropyl)methoxy)pyrazolo[1,5-a]pyridin-4-yl)pyridin-2-yl)-3,6-diazabicyclo[3.1.1]heptane-6-carboxylate (Step 1; assume 0.6672 mmol) in 1:1 DCM:TFA (2 mL) was stirred for 15 min at ambient temperature, and then concentrated in vacuo. The residue was dissolved in 6 M HCl in iPrOH (4448 µL, 26.69 mmol), sonicated for several minutes, then concentrated in vacuo to cleanly provide the title compound (121 mg, 38% yield). MS (apci) m/z=403.2 (M+H).

Intermediate P85

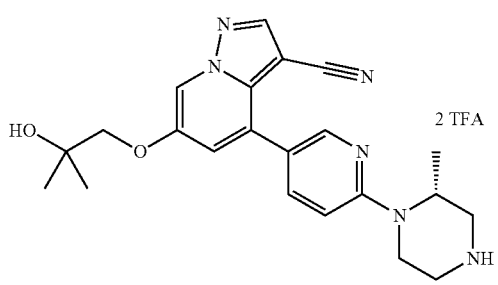 [SMILES: C[C@@H]1CNCCN1c1ccc(-c2cc(OCC(C)(C)O)cn3ncc(C#N)c23)cn1]

(R)-6-(2-hydroxy-2-methylpropoxy)-4-(6-(2-methylpiperazin-1-yl)pyridin-3-yl)pyrazolo[1,5-a]pyridine-3-carbonitrile bis(2,2,2-trifluoroacetate)

Step 1: Preparation of tert-butyl (R)-4-(5-(3-cyano-6-(2-hydroxy-2-methylpropoxy)pyrazolo[1,5-a]pyridin-4-yl)pyridin-2-yl)-3-methylpiperazine-1-carboxylate A mixture of 4-(6-fluoropyridin-3-yl)-6-(2-hydroxy-2-methylpropoxy)pyrazolo[1,5-a]pyridine-3-carbonitrile (Intermediate P42; 1.70 g, 8.55 mmol), tert-butyl (R)-3-methylpiperazine-1-carboxylate (123 mg, 0.613 mmol) and K$_2$CO$_{3(s)}$ (212 mg, 1.53 mmol) in DMSO (409 µL) was stirred 5 d at 80° C. After cooling to ambient temperature, resulting mixture was diluted with water (5 mL) and extracted with DCM (4×5 mL). The combined organic extracts were dried over anhydrous Na$_2$SO$_{4(s)}$, filtered and concentrated in vacuo. The crude residue was purified by silica chromatography (using 0-100% EtOAc in Hexanes as the gradient eluent) to afford the title compound (10 mg, 6% yield). MS (apci) m/z=507.3 (M+H).

Step 2: Preparation of (R)-6-(2-hydroxy-2-methylpropoxy)-4-(6-(2-methylpiperazin-1-yl)pyridin-3-yl) pyrazolo[1,5-a]pyridine-3-carbonitrile bis(2,2,2-trifluoroacetate)

A solution of tert-butyl (R)-4-(5-(3-cyano-6-(2-hydroxy-2-methylpropoxy)pyrazolo[1,5-a]pyridin-4-yl)pyridin-2-yl)-3-methylpiperazine-1-carboxylate (Step 1; 10 mg, 0.020 mmol) in DCM (1 mL) was treated with TFA (0.5 mL). The resulting mixture was stirred for 2 h at ambient temperature, and then concentrated in vacuo to afford the title compound (13 mg, quantitative yield). MS (apci) m/z=407.2 (M+H).

Intermediate P86

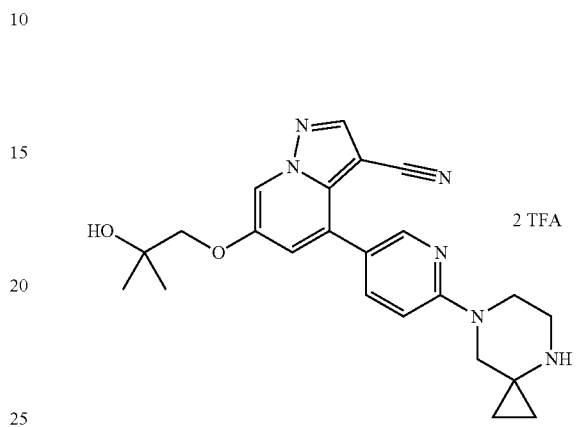

4-(6-(4,7-diazaspiro[2.5]octan-7-yl)pyridin-3-yl)-6-(2-hydroxy-2-methylpropoxy)pyrazolo[1,5-a]pyridine-3-carbonitrile bis(2,2,2-trifluoroacetate)

Step 1: Preparation of tert-butyl 7-(5-(3-cyano-6-(2-hydroxy-2-methylpropoxy)pyrazolo[1,5-a]pyridin-4-yl)pyridin-2-yl)-4,7-diazaspiro[2.5]octane-4-carboxylate A mixture of 4-(6-fluoropyridin-3-yl)-6-(2-hydroxy-2-methylpropoxy)pyrazolo[1,5-a]pyridine-3-carbonitrile (Intermediate P42; 50 mg, 0.15 mmol), tert-butyl 4,7-diazaspiro[2.5]octane-4-carboxylate (65 mg, 0.31 mmol) and K$_2$CO$_{3(s)}$ (212 mg, 1.5 mmol) in DMSO (766 µL) was stirred 23 h at 80° C. After cooling to ambient temperature, resulting mixture was diluted with water (10 mL) and extracted with DCM (4×10 mL). The combined organic extracts were washed with brine (10 mL), then dried over anhydrous Na$_2$SO$_{4(s)}$, filtered and concentrated in vacuo. The crude residue was purified by silica chromatography (using 0-100% EtOAc in Hexanes as the gradient eluent) to afford the title compound (69 mg, 87% yield). MS (apci) m/z=519.2 (M+H).

Step 2: Preparation of 4-(6-(4,7-diazaspiro[2.5]octan-7-yl)pyridin-3-yl)-6-(2-hydroxy-2-methylpropoxy)pyrazolo[1,5-a]pyridine-3-carbonitrile bis (2,2,2-trifluoroacetate)

A solution of tert-butyl 7-(5-(3-cyano-6-(2-hydroxy-2-methylpropoxy)pyrazolo[1,5-a]pyridin-4-yl)pyridin-2-yl)-4,7-diazaspiro[2.5]octane-4-carboxylate (Step 1; 69 mg, 0.13 mmol) in DCM (2 mL) was treated with TFA (1 mL). The resulting mixture was stirred overnight at ambient temperature, and then concentrated in vacuo to afford the title compound (86 mg, quantitative yield). MS (apci) m/z=419.2 (M+H).

Intermediate P87

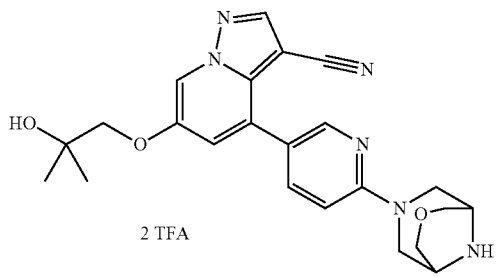 [SMILES: CC(C)(O)COc1cc(-c2ccc(N3CC4COCC(C3)N4)nc2)c2c(C#N)cnn2c1]

4-(6-(3-oxa-7,9-diazabicyclo[3.3.1]nonan-7-yl)pyridin-3-yl)-6-(2-hydroxy-2-methylpropoxy)pyrazolo[1,5-a]pyridine-3-carbonitrile bis(2,2,2-trifluoroacetate)

Step 1: Preparation of tert-butyl 7-(5-(3-cyano-6-(2-hydroxy-2-methylpropoxy)pyrazolo[1,5-a]pyridin-4-yl)pyridin-2-yl)-3-oxa-7,9-diazabicyclo[3.3.1]nonane-9-carboxylate A mixture of 4-(6-fluoropyridin-3-yl)-6-(2-hydroxy-2-methylpropoxy)pyrazolo[1,5-a]pyridine-3-carbonitrile (Intermediate P42; 100 mg, 0.306 mmol), tert-butyl 3-oxa-7,9-diazabicyclo[3.3.1]nonane-9-carboxylate (105 mg, 0.460 mmol) and $K_2CO_{3(s)}$ (127 mg, 0.919 mmol) in DMSO (409 μL) was stirred 48 h at 90° C. After cooling to ambient temperature, resulting mixture was diluted with water (10 mL). The resulting suspension was filtered, and the solids were collected to afford the title compound (160 mg, 98% yield). MS (apci) m/z=535.3 (M+H).

Step 2: Preparation of 4-(6-(3-oxa-7,9-diazabicyclo[3.3.1]nonan-7-yl)pyridin-3-yl)-6-(2-hydroxy-2-methylprop oxy)pyrazolo[1,5-a]pyridine-3-carbonitrile bis(2,2,2-trifluoroacetate)

A solution of tert-butyl 7-(5-(3-cyano-6-(2-hydroxy-2-methylpropoxy)pyrazolo[1,5-a]pyridin-4-yl)pyridin-2-yl)-3-oxa-7,9-diazabicyclo[3.3.1]nonane-9-carboxylate (Step 1; 160 mg, 0.299 mmol) in DCM (1 mL) was treated with TFA (1 mL). The resulting mixture was stirred for 2 h at ambient temperature, and then concentrated in vacuo to afford the title compound (198 mg, quantitative yield). MS (apci) m/z=435.3 (M+H).

Intermediate P88

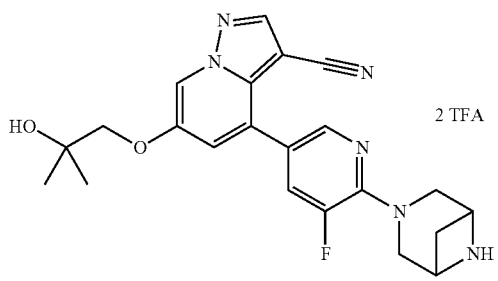 [SMILES: CC(C)(O)COc1cc(-c2cnc(N3CC4CC(C3)N4)c(F)c2)c2c(C#N)cnn2c1]

4-(6-(3,6-diazabicyclo[3.1.1]heptan-3-yl)-5-fluoropyridin-3-yl)-6-(2-hydroxy-2-methylpropoxy)pyrazolo[1,5-a]pyridine-3-carbonitrile bis(2,2,2-trifluoroacetate)

Step 1: Preparation of tert-butyl 3-(5-(3-cyano-6-(2-hydroxy-2-methylpropoxy)pyrazolo[1,5-a]pyridin-4-yl)-3-fluoropyridin-2-yl)-3,6-diazabicyclo[3.1.1]heptane-6-carboxylate A mixture of 4-Bromo-6-(2-hydroxy-2-methylpropoxy)pyrazolo[1,5-a]pyridine-3-carbonitrile (Intermediate P41; 15 mg, 0.049 mmol), (6-(6-(tert-butoxycarbonyl)-3,6-diazabicyclo[3.1.1]heptan-3-yl)-5-fluoropyridin-3-yl)boronic acid (Intermediate R; 20 mg, 0.059 mmol), $K_2CO_{3(s)}$ (68 mg, 0.49 mmol) and $Pd(PPh_3)_4$ (5.7 mg, 0.005 mmol) in dioxane (250 μL) and water (200 μL) was purged with $Ar_{(g)}$. The resulting mixture was stirred overnight at 85° C., then purified directly by silica chromatography (using 0-100% EtOAc in Hexanes as the gradient eluent) to cleanly provide the title compound (14 mg, 54% yield). MS (apci) m/z=467.15 (M+H).

Step 2: Preparation of 4-(6-(3,6-diazabicyclo[3.1.1]heptan-3-yl)-5-fluoropyridin-3-yl)-6-(2-hydroxy-2-methylpropoxy)pyrazolo[1,5-a]pyridine-3-carbonitrile bis(2,2,2-trifluoroacetate)

A solution of tert-butyl 3-(5-(3-cyano-6-(2-hydroxy-2-methylpropoxy)pyrazolo[1,5-a]pyridin-4-yl)-3-fluoropyridin-2-yl)-3,6-diazabicyclo[3.1.1]heptane-6-carboxylate (Step 1; 14 mg, 0.027 mmol) in DCM (1 mL) was treated with TFA (1 mL). The resulting mixture was stirred for 1 h at ambient temperature, and then concentrated in vacuo to afford the title compound (17 mg, quantitative yield). MS (apci) m/z=423.10 (M+H).

Intermediate P89

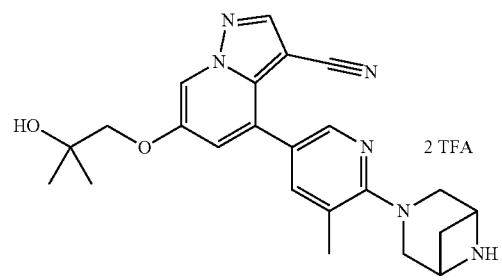 [SMILES: Cc1cc(-c2cc(OCC(C)(C)O)cn3ncc(C#N)c23)cnc1N1CC2CC(C1)N2]

4-(6-(3,6-diazabicyclo[3.1.1]heptan-3-yl)-5-methylpyridin-3-yl)-6-(2-hydroxy-2-methylpropoxy)pyrazolo[1,5-a]pyridine-3-carbonitrile bis(2,2,2-trifluoroacetate)

Step 1: Preparation of 4-(6-fluoro-5-methylpyridin-3-yl)-6-(2-hydroxy-2-methylpropoxy)pyrazolo[1,5-a]pyridine-3-carbonitrile In a pressure vessel, a solution of 4-bromo-6-(2-hydroxy-2-methylpropoxy)pyrazolo[1,5-a]pyridine-3-carbonitrile (Intermediate P41; 150 mg, 0.484 mmol) in dioxane (200 mL) was treated sequentially with 2-fluoro-3-methylpyridine-5-boronic acid (112 mg, 0.725 mmol) and Pd(PPh$_3$)$_4$ (55.9 mg, 0.0484 mmol) and 2 M Na$_2$CO$_{3(aq)}$ (1209 μL, 2.42 mmol). The resulting mixture was sparged with Ar$_{(g)}$, the vessel was sealed, and the mixture was stirred overnight at 90° C. After cooling to ambient temperature, the resultant suspension was partitioned between DCM (10 mL) and water (10 mL), and extracted with DCM (3×10 mL). The combined organic extracts were washed with water and brine, then dried over anhydrous Na$_2$SO$_{4(s)}$, filtered, and concentrated in vacuo. The crude residue was purified by silica chromatography (0-100% EtOAc in Hexanes as the gradient eluent) to cleanly provide the title compound (60 mg, 36% yield). MS (apci) m/z=341.1 (M+H).

Step 2: Preparation of tert-butyl 3-(5-(3-cyano-6-(2-hydroxy-2-methylpropoxy)pyrazolo[1,5-a]pyridin-4-yl)-3-methylpyridin-2-yl)-3,6-diazabicyclo[3.1.1]heptane-6-carboxylate A mixture of 4-(6-fluoro-5-methylpyridin-3-yl)-6-(2-hydroxy-2-methylpropoxy)pyrazolo[1,5-a]pyridine-3-carbonitrile (Step 1; 60 mg, 0.18 mmol), tert-butyl 3,6-diazabicyclo[3.1.1]heptane-6-carboxylate (70 mg, 0.35 mmol) and K$_2$CO$_{3(s)}$ (244 mg, 1.8 mmol) in DMSO (881 μL) was stirred for 23 h at 80° C. The resultant suspension was partitioned between DCM (10 mL) and water (10 mL), and extracted with DCM (3×10 mL). The combined organic extracts were washed with water and brine, then dried over anhydrous Na$_2$SO$_{4(s)}$, filtered, and concentrated in vacuo. The crude residue was purified by silica chromatography (0-100% EtOAc in Hexanes as the gradient eluent) to cleanly provide the title compound (8.4 mg, 9% yield). MS (apci) m/z=519.2 (M+H).

Step 3: Preparation of 4-(6-(3,6-diazabicyclo[3.1.1]heptan-3-yl)-5-methylpyridin-3-yl)-6-(2-hydroxy-2-methylpropoxy)pyrazolo[1,5-a]pyridine-3-carbonitrile bis(2,2,2-trifluoroacetate)

A solution of tert-butyl 3-(5-(3-cyano-6-(2-hydroxy-2-methylpropoxy)pyrazolo[1,5-a]pyridin-4-yl)-3-methylpyridin-2-yl)-3,6-diazabicyclo[3.1.1]heptane-6-carboxylate (Step 2; 8.4 mg, 0.016 mmol) in DCM (1 mL) was treated with TFA (1 mL). The resulting mixture was stirred for 1 h at ambient temperature, and then concentrated in vacuo to afford the title compound (10 mg, quantitative yield). MS (apci) m/z=419.2 (M+H).

Intermediate P90

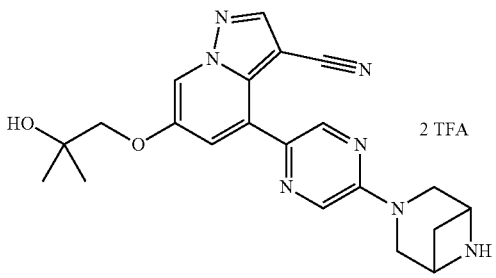 [SMILES: CC(C)(O)COc1cc(-c2cnc(N3CC4CC(C3)N4)cn2)c2c(C#N)cnn2c1]

4-(5-(3,6-diazabicyclo[3.1.1]heptan-3-yl)pyrazin-2-yl)-6-(2-hydroxy-2-methylpropoxy)pyrazolo[1,5-a]pyridine-3-carbonitrile bis(2,2,2-trifluoroacetate)

A solution of tert-butyl 3-(5-(3-cyano-6-(2-hydroxy-2-methylpropoxy)pyrazolo[1,5-a]pyridin-4-yl)pyrazin-2-yl)-3,6-diazabicyclo[3.1.1]heptane-6-carboxylate (Intermediate P50, Step 1; 20 mg, 0.040 mmol) in DCM (1 mL) was treated with TFA (1 mL). The resulting mixture was stirred overnight at ambient temperature, and then concentrated in vacuo to afford the title compound (25 mg, quantitative yield). MS (apci) m/z=406.15 (M+H).

Intermediate P91

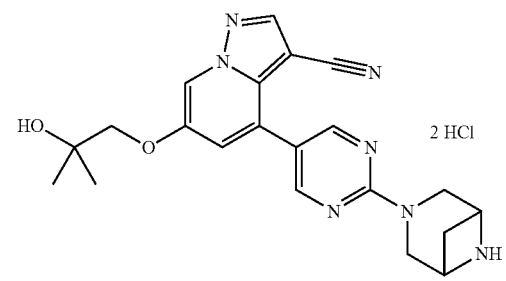 [SMILES: CC(C)(O)COc1cc(-c2cnc(N3CC4CC(C3)N4)nc2)c2c(C#N)cnn2c1]

4-(2-(3,6-diazabicyclo[3.1.1]heptan-3-yl)pyrimidin-5-yl)-6-(2-hydroxy-2-methylpropoxy)pyrazolo[1,5-a]pyridine-3-carbonitrile dihydrochloride Step 1: Preparation of tert-butyl 3-(5-(3-cyano-6-(2-hydroxy-2-methylpropoxy)pyrazolo[1,5-a]pyridin-4-yl)pyrimidin-2-yl)-3,6-diazabicyclo[3.1.1]heptane-6-carboxylate In a pressure vessel, a mixture of 4-bromo-6-(2-hydroxy-2-methylpropoxy)pyrazolo[1,5-a]pyridine-3-carbonitrile (Intermediate P41; 68 mg, 0.22 mmol), tert-butyl 3-(5-(4,4,5,5-tetramethyl-1,3,2-dioxaborolan-2-yl)pyrimidin-2-yl)-3,6-diazabicyclo[3.1.1]heptane-6-carboxylate (Intermediate R21; 88 mg, 0.22 mmol) and Pd(PPh$_3$)$_4$ (25 mg, 0.022 mmol) in dioxane (730 μL) was sparged with Ar$_{(g)}$ for 30 seconds before introducing 2 M K$_2$CO$_{3(aq)}$ (420 μL, 0.840 mmol). The resulting mixture was sparged with Ar$_{(g)}$ for an additional 2 min, before sealing the vessel. The reaction mixture was stirred overnight at 80° C. After cooling to ambient temperature, the reaction mixture was purified directly by silica chromatography (using 15% acetone in DCM as the eluent) to afford the title compound (53 mg, 44% yield). MS (apci) m/z=450.2 (M+H); 406.2 (des-Boc M).

Step 2: Preparation of 4-(2-(3,6-diazabicyclo[3.1.1]heptan-3-yl)pyrimidin-5-yl)-6-(2-hydroxy-2-methylpropoxy)pyrazolo[1,5-a]pyridine-3-carbonitrile dihydrochloride A solution of tert-butyl 3-(5-(3-cyano-6-(2-hydroxy-2-methylpropoxy)pyrazolo[1,5-a]pyridin-4-yl)pyrimidin-2-yl)-3,6-diazabicyclo[3.1.1]heptane-6-carboxylate (Step 1; 53 mg, 0.105 mmol) in DCM (0.5 mL) was treated with 4 M HCl in dioxane (524 μL, 2.10 mmol). The resulting suspension was diluted with MeOH (250 μL), and the solution was stirred overnight at ambient temperature. The reaction mixture was concentrated in vacuo to afford the title compound (54 mg, quantitative yield). MS (apci) m/z=406.2 (M+H).

Intermediate P92

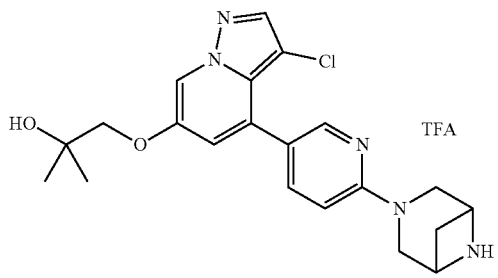 [SMILES: CC(C)(O)COc1cc(-c2ccc(N3CC4CC(C3)N4)nc2)c2c(Cl)cnn2c1]

1-((4-(6-(3,6-diazabicyclo[3.1.1]heptan-3-yl)pyridin-3-yl)-3-chloropyrazolo[1,5-a]pyridin-6-yl)oxy)-2-methylpropan-2-ol 2,2,2-trifluoroacetate Step 1: Preparation of tert-butyl 3-(5-(3-chloro-6-(2-hydroxy-2-methylpropoxy)pyrazolo[1,5-a]pyridin-4-yl)pyridin-2-yl)-3,6-diazabicyclo[3.1.1]heptane-6-carboxylate A mixture of 1-((3-chloro-4-(6-fluoropyridin-3-yl)pyrazolo[1,5-a]pyridin-6-yl)oxy)-2-methylpropan-2-ol (Intermediate P69; 258 mg, 0.768 mmol), tert-butyl 3,6-diazabicyclo[3.1.1]heptane-6-carboxylate (229 mg, 1.15 mmol) and $K_2CO_{3(s)}$ (425 mg, 3.07 mmol) in DMSO (1.5 mL) was stirred overnight at 90° C. in a sealed vessel. The reaction mixture was treated with additional tert-butyl 3,6-diazabicyclo[3.1.1]heptane-6-carboxylate (40 mg) and $K_2CO_{3(s)}$ (100 mg), and stirred overnight at 105° C. The reaction mixture was cooled to ambient temperature, then diluted with DCM/water. The biphasic mixture was washed with DCM (3×). The combined organic extracts were dried over anhydrous $Na_2SO_{4(s)}$, filtered and concentrated in vacuo. The crude residue was purified by silica chromatography (using 0-100% EtOAc/Hexanes as the gradient eluent) to cleanly provide the title compound (330 mg, 84% yield). MS (apci) m/z=514.2 (M+H).

Step 2: Preparation of 1-((4-(6-(3,6-diazabicyclo[3.1.1]heptan-3-yl)-pyridin-3-yl)-3-chloropyrazolo[1,5-a]pyridin-6-yl)oxy)-2-methylpropan-2-ol 2,2,2-trifluoroacetate A solution of tert-butyl 3-(5-(3-chloro-6-(2-hydroxy-2-methylpropoxy)pyrazolo[1,5-a]pyridin-4-yl)pyridin-2-yl)-3,6-diazabicyclo[3.1.1]heptane-6-carboxylate (Step 1; 330 mg, 0.642 mmol) in DCM (5 mL) was treated with TFA (1.5 mL). The resulting mixture was concentrated in vacuo to afford the title compound (392 mg, quantitative yield). MS (apci) m/z=414.1 (M+H).

Intermediate P93

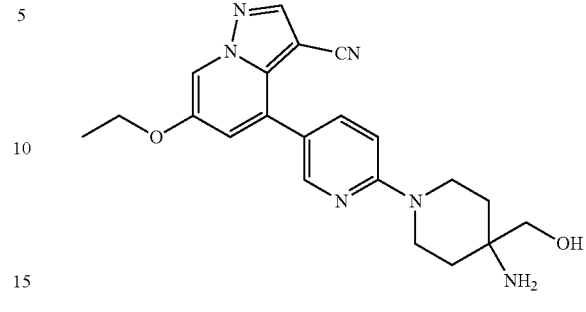

4-(6-(4-amino-4-(hydroxymethyl)piperidin-1-yl)pyridin-3-yl)-6-ethoxypyrazolo[1,5-a]pyridine-3-carbonitrile Step 1: Preparation of methyl 4-((tert-butoxycarbonyl)amino)-1-(5-(3-cyano-6-ethoxypyrazolo[1,5-a]pyridin-4-yl)pyridin-2-yl)piperidine-4-carboxylate To a solution of 6-ethoxy-4-(6-fluoropyridin-3-yl)pyrazolo[1,5-a]pyridine-3-carbonitrile (Intermediate P6, 303.4 mg, 1.075 mmol) in DMSO (21.50 mL) was added 4-N-Boc-amino-piperidine-4-carboxylic acid methyl ester (416.5 mg, 1.612 mmol) and potassium carbonate (297.1 mg, 2.150 mmol). The reaction mixture was stirred at 110° C. for 72 h. The reaction mixture was diluted with water and extracted with EtOAc. The combined organic extracts were dried over anhydrous $MgSO_{4(s)}$ and concentrated in vacuo. The crude residue was purified by silica chromatography (0-100% EtOAc in hexanes as the gradient eluent) to afford the title compound (76.7 mg, 13.7% yield) in sufficient purity for step 2. MS (apci) m/z=521.2 (M+H).

Step 2: Preparation of tert-butyl (1-(5-(3-cyano-6-ethoxypyrazolo[1,5-a]pyridin-4-yl)pyridin-2-yl)-4-(hydroxymethyl)piperidin-4-yl)carbamate To a solution of lithium borohydride (0.0120 mL, 0.365 mmol) in THF (0.912 mL) was added methyl 4-((tert-butoxycarbonyl)amino)-1-(5-(3-cyano-6-ethoxypyrazolo[1,5-a]pyridin-4-yl)pyridin-2-yl)piperidine-4-carboxylate (47.5 mg, 0.0912 mmol). The reaction mixture was stirred at rt for 2 h. The reaction mixture was concentrated in vacuo, and the residue was diluted with EtOAc and washed with brine. The organic extract was dried over anhydrous $MgSO_{4(s)}$ and concentrated in vacuo to afford the title compound (65.9 mg), which was used in the next step without further purifications. MS (apci) m/z=493.2 (M+H).

Step 3: Preparation of 4-(6-(4-amino-4-(hydroxymethyl)piperidin-1-yl)pyridin-3-yl)-6-ethoxypyrazolo[1,5-a]pyridine-3-carbonitrile A solution of tert-butyl (1-(5-(3-cyano-6-ethoxypyrazolo[1,5-a]pyridin-4-yl)pyridin-2-yl)-4-(hydroxymethyl)piperidin-4-yl)carbamate (65.9 mg, 0.134 mmol) in DCM (1 mL) was treated with TFA (0.2 mL, 2.68 mmol). The reaction mixture was stirred at rt 30 min and then concentrated in vacuo. The residue was taken up in DCM and washed with saturated $Na_2CO_3$. The aqueous fraction was extracted with DCM, and the combined organic extracts were dried over anhydrous MgSO$_{4(s)}$ and concentrated in vacuo to afford the title compound (35.6 mg, 68% yield). MS (apci) m/z=393.2 (M+H).

Intermediate P94

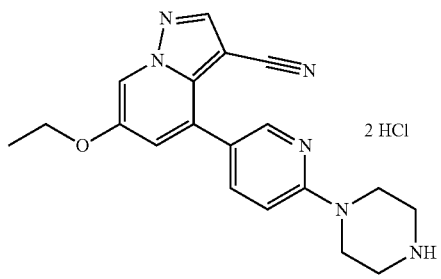 [SMILES: CCOc1cc(-c2ccc(N3CCNCC3)nc2)c2c(C#N)cnn2c1]

6-ethoxy-4-(6-(piperazin-1-yl)pyridin-3-yl)pyrazolo[1,5-a]pyridine-3-carbonitrile dihydrochloride Step 1: Preparation of tert-butyl 4-(5-(3-cyano-6-ethoxypyrazolo[1,5-a]pyridin-4-yl)pyridin-2-yl)piperazine-1-carboxylate A solution of tert-butyl 4-(5-(3-cyano-6-hydroxypyrazolo[1,5-a]pyridin-4-yl)pyridin-2-yl)piperazine-1-carboxylate (Intermediate P3; 500 mg, 1.19 mmol) in DMF (3.96 mL) was treated sequentially with K$_2$CO$_{3(s)}$ (329 mg, 2.38 mmol) and iodoethane (143 µL, 1.78 mmol), then stirred for 18 h at ambient temperature. The reaction mixture was poured slowly into water (32 mL). The resulting suspension was stirred for 15 min. The slurry was filtered, rinsing the solids with water (3×10 mL). After air drying, the solids were collected to afford the title compound (530 mg, 99% yield). MS (apci) m/z=449.2 (M+H).

Step 2: Preparation of 6-ethoxy-4-(6-(piperazin-1-yl)pyridin-3-yl)pyrazolo[1,5-a]pyridine-3-carbonitrile dihydrochloride A slurry of tert-butyl 4-(5-(3-cyano-6-ethoxypyrazolo[1,5-a]pyridin-4-yl)pyridin-2-yl)piperazine-1-carboxylate (Step 1; 530 mg, 1.18 mmol) in MeOH (5.91 mL) was treated dropwise with 5-6 N HCl in iPrOH (4.73 mL, 23.6 mmol). The resulting mixture was stirred for 3 h at ambient temperature, and then additional 5-6 N HCl in iPrOH (4.73 mL, 23.6 mmol) was introduced. After stirring for an additional 24 h at ambient temperature, the reaction mixture was vacuum filtered, rinsing the solids sequentially with MeOH (3×1 mL) and MTBE (3×10 mL). The solids were dried in vacuo, and collected to afford the title compound (445 mg, 89% yield). MS (apci) m/z=349.2 (M+H).

Intermediate P95

4-(6-fluoropyridin-3-yl)-6-(2-morpholinoethoxy)pyrazolo[1,5-a]pyridine-3-carbonitrile Method A Step 1: Preparation of 4-bromo-6-(2-morpholinoethoxy)pyrazolo[1,5-a]pyridine-3-carbonitrile A solution of 4-bromo-6-hydroxypyrazolo[1,5-a]pyridine-3-carbonitrile (Intermediate P1, 1000 mg, 4.201 mmol) in DMA (21.005 L) was treated with potassium carbonate (1742 mg, 12.60 mmol) and 4-(2-chloroethyl)morpholine (1.132 mL, 8.402 mmol). The reaction mixture was stirred at 50° C. for 72 h. After cooling to ambient temperature, the reaction mixture was quenched with saturated NaCl$_{(aq)}$. The resultant precipitate was isolated by filtration to afford the title compound (1475 mg, 4.200 mmol, 99% yield) in sufficient purity for step 2. MS (apci) m/z=351 (M+).

Step 2: Preparation of 4-(6-fluoropyridin-3-yl)-6-(2-morpholinoethoxy)pyrazolo[1,5-a]pyridine-3-carbonitrile A solution of 4-bromo-6-(2-morpholinoethoxy)pyrazolo[1,5-a]pyridine-3-carbonitrile (0.83 g, 1.394 mmol) in 1,4-dioxane (1000 mL) was treated with 2-Fluoro-5-(4,4,5,5-tetramethyl-1,3,2-dioxaborolan-2-yl)pyridine (373.2181 mg, 1.673 mmol), tetrakis(triphenylphosphine)palladium (0) (32.22577 mg, 0.0279 mmol), and aqueous potassium carbonate (2.092 mL, 4.183 mmol). The reaction mixture was sparged with argon and stirred at 90° C. for 16 h. After cooling to ambient temperature, the reaction mixture was diluted with MTBE and washed with 1N NaOH. The aqueous fractions were extracted with MTBE then adjusted to pH 4 with 4N HCl. Saturated NaCl$_{(aq)}$ was added and the aqueous mixture was extracted with 4:1 DCM/IPA. The combined organic extracts were dried over anhydrous Na$_2$SO$_{4(s)}$, filtered and concentrated in vacuo to afford the title compound (0.341 g, 0.928 mmol, 66.6% yield). MS (apci) m/z=368.1 (M+H).

Method B

A suspension of 4-(6-fluoropyridin-3-yl)-6-hydroxypyrazolo[1,5-a]pyridine-3-carbonitrile (Intermediate P63; 1.00 g, 3.93 mmol) in DMA (8 mL) was treated sequentially with K$_2$CO$_3$ (1.63 g, 11.8 mmol) and 4-(2-chloroethyl)morpholine (883 mg, 5.90 mmol). The resulting mixture stirred for 19 h at 55° C. After cooling to ambient temperature, the resultant mixture was diluted with water (50 mL), and extracted with DCM (3×30 mL). The combined organic extracts were washed with brine (3×50 mL), dried over anhydrous MgSO$_{4(s)}$, filtered and concentrated in vacuo. The crude residue was purified by silica chromatography (using 5-100% Acetone/Hexanes as the gradient eluent) to cleanly provide the title compound (870 mg, 60% yield). MS (apci) m/z=368.1 (M+H).

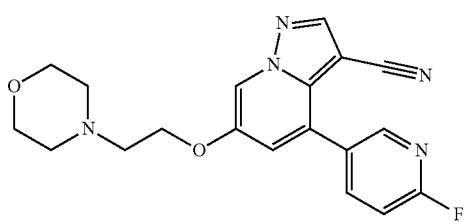 [SMILES: N#Cc1cnn2cc(OCCN3CCOCC3)cc(-c3ccc(F)nc3)c12]

Intermediate P96

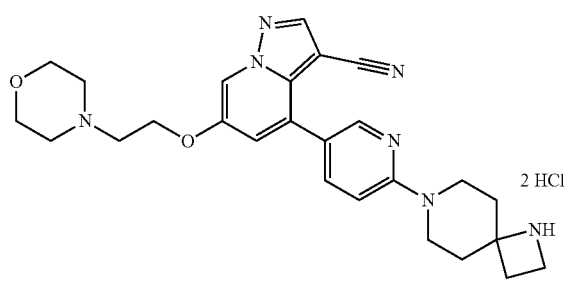 [SMILES: N#Cc1cnn2cc(OCCN3CCOCC3)cc(-c3ccc(N4CCC5(CCN5)CC4)nc3)c12]

4-(6-(1,7-diazaspiro[3.5]nonan-7-yl)pyridin-3-yl)-6-(2-morpholinoethoxy)pyrazolo[1,5-a]pyridine-3-carbonitrile dihydrochloride A solution of tert-butyl 7-(5-(3-cyano-6-(2-morpholinoethoxy)pyrazolo[1,5-a]pyridin-4-yl)pyridin-2-yl)-1,7-diazaspiro[3.5]nonane-1-carboxylate (Example 535; 625 mg, 1.09 mmol) in DCM (3 mL) was treated with 5-6 M HCl in iPrOH (3.05 mL, 15.3 mmol), and stirred for 3 h at ambient temperature. The resulting mixture was diluted with MeOH (3 mL), and stirred for 1 h at ambient temperature. The resulting suspension was filtered, rinsing the isolated solids with Et$_2$O (5×1 mL). The filtrate was re-filtered, and the isolated solids were combined and dried under high vacuum to afford the title compound (532.3 mg, 89% yield). MS (apci) m/z=474.2 (M+H).

Intermediate P97

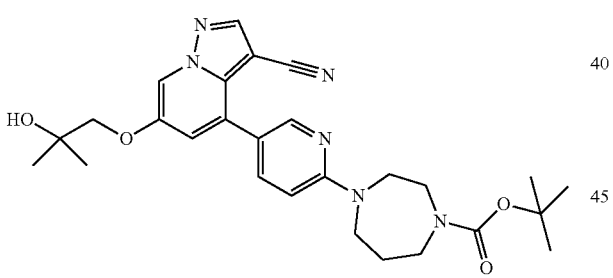

tert-butyl 4-(5-(3-cyano-6-(2-hydroxy-2-methylpropoxy)pyrazolo[1,5-a]pyridin-4-yl)pyridin-2-yl)-1,4-diazepane-1-carboxylate In a sealed pressure tube, a mixture of 4-(6-fluoropyridin-3-yl)-6-(2-hydroxy-2-methylpropoxy)pyrazolo[1,5-a]pyridine-3-carbonitrile (Intermediate P42; 300 mg, 0.919 mmol), tert-butyl 1,4-diazepane-1-carboxylate (552 mg, 2.76 mmol) and TEA (1.03 mL, 7.35 mmol) in DMSO (1.8 mL) was stirred overnight at 95° C. After cooling to ambient temperature, the reaction mixture was diluted with DCM, and quenched with saturated NH$_4$Cl$_{(aq)}$. After phase separation, the aqueous extracts were washed with additional DCM (3×). The combined organic extracts then were dried over anhydrous Na$_2$SO$_{4(s)}$, filtered and concentrated in vacuo. The crude residue was purified by silica chromatography (using 0-100% EtOAc/Hexanes as the gradient eluent) to cleanly afford the title compound (400 mg, 86% yield). MS (apci) m/z=507.3 (M+H).

Intermediate P98

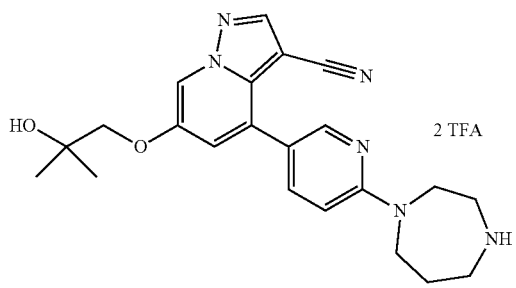 [SMILES: CC(C)(O)COc1cc(-c2ccc(N3CCCNCC3)nc2)c2c(C#N)cnn2c1]

4-(6-(1,4-diazepan-1-yl)pyridin-3-yl)-6-(2-hydroxy-2-methylpropoxy)pyrazolo[1,5-a]pyridine-3-carbonitrile bis(2,2,2-trifluoroacetate)

A suspension of tert-butyl 4-(5-(3-cyano-6-(2-hydroxy-2-methylpropoxy)pyrazolo[1,5-a]pyridin-4-yl)pyridin-2-yl)-1,4-diazepane-1-carboxylate (Intermediate P97; 400 mg, 0.790 mmol) in DCM (2.0 mL) was treated with TFA (1.29 mL, 15.8 mmol), and stirred for 4 h at ambient temperature. The resulting mixture was concentrated in vacuo to afford the title compound (501 mg, 100% yield). MS (apci) m/z=407.2 (M+H).

Intermediate P99

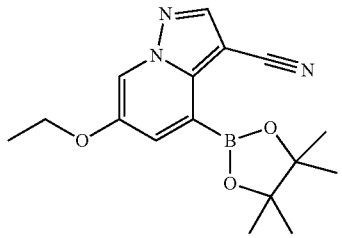 [SMILES: CCOc1cc(B2OC(C)(C)C(C)(C)O2)c2c(C#N)cnn2c1]

6-ethoxy-4-(4,4,5,5-tetramethyl-1,3,2-dioxaborolan-2-yl)pyrazolo[1,5-a]pyridine-3-carbonitrile In a pressure vessel, a mixture of 4-bromo-6-ethoxypyrazolo[1,5-a]pyridine-3-carbonitrile (Intermediate P5; 570 mg, 2.14 mmol), bis(pinacolato)diboron (5.44 g, 21.4 mmol), PdCl$_2$(dppf).CH$_2$Cl$_2$ (174 mg, 0.214 mmol), and KOAc (1.05 g, 10.7 mmol) in dioxane (21.4 mL) was sparged with Ar$_{(g)}$, for 10 min. The vessel was sealed, and the mixture was stirred overnight at 90° C. After cooling to ambient temperature, the reaction mixture was diluted with DCM, and filtered through GF/F paper. The filtrate was concentrated in vacuo. The crude residue was purified twice by silica chromatography (using 0-10% MeOH in EtOAc, then with 0-100% Hexanes in EtOAc as the gradient eluent) to afford the title compound in sufficient purity for further use (772 mg, ca 63% yield based on 55% purity). MS (apci) m/z=314.1 (M+H).

Intermediate P100

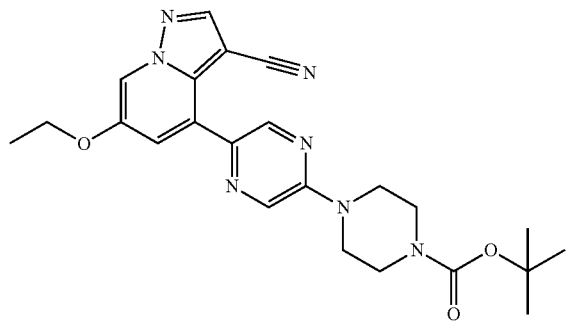 [SMILES: CCOc1cc(-c2cnc(N3CCN(C(=O)OC(C)(C)C)CC3)cn2)c2c(C#N)cnn2c1]

tert-butyl 4-(5-(3-cyano-6-ethoxypyrazolo[1,5-a]pyridin-4-yl)pyrazin-2-yl)piperazine-1-carboxylate A mixture of 6-ethoxy-4-(4,4,5,5-tetramethyl-1,3,2-dioxaborolan-2-yl)pyrazolo[1,5-a]pyridine-3-carbonitrile (Intermediate P99; 40 mg, 0.13), tert-butyl 4-(5-chloropyrazin-2-yl)piperazine-1-carboxylate (Intermediate R23; 38 mg, 0.13 mmol), 2 M $K_3PO_{4(aq)}$ (192 µL, 0.38 mmol), X-phos (12 mg, 0.026 mmol) and $Pd_2(dba)_3$ (5.8 mg, 0.0064 mmol) in dioxane (639 µL) was sparged with $Ar_{(g)}$ for 3 min, and then the vessel was sealed. The reaction mixture was stirred overnight at 80° C. After cooling to ambient temperature, the reaction mixture was diluted with water and extracted with DCM. The combined organic extracts were washed sequentially with water (2×) and brine (1×), and then dried over anhydrous $Na_2SO_{4(s)}$, filtered and concentrated in vacuo. The crude residue was purified by silica chromatography (using 10-100% EtOAc in Hexanes as the gradient eluent) to cleanly afford the title compound (49 mg, 85% yield). MS (apci) m/z=450.2 (M+H).

Intermediate P101

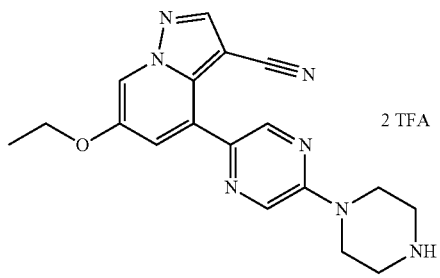 [SMILES: CCOc1cc(-c2cnc(N3CCNCC3)cn2)c2c(C#N)cnn2c1]

6-ethoxy-4-(5-(piperazin-1-yl)pyrazin-2-yl)pyrazolo[1,5-a]pyridine-3-carbonitrile bis(2,2,2-trifluoroacetate)

A suspension of tert-butyl 4-(5-(3-cyano-6-ethoxypyrazolo[1,5-a]pyridin-4-yl)pyrazin-2-yl)piperazine-1-carboxylate (Intermediate P100; 27 mg, 0.060 mmol) in DCM (2.0 mL) was treated with TFA (2 mL, 26.1 mmol), and stirred overnight at ambient temperature. The resulting mixture was concentrated in vacuo to afford the title compound (35 mg, quantitative yield). MS (apci) m/z=350.2 (M+H).

Intermediate P102

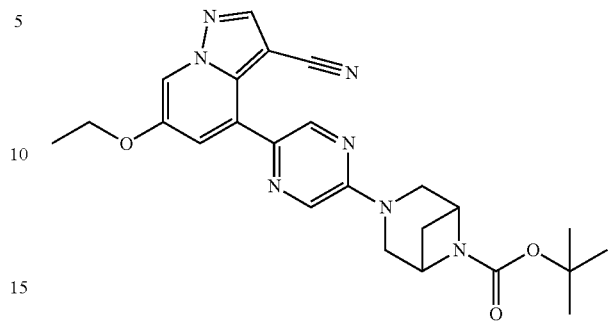

tert-butyl 3-(5-(3-cyano-6-ethoxypyrazolo[1,5-a]pyridin-4-yl)pyrazin-2-yl)-3,6-diazabicyclo[3.1.1]heptane-6-carboxylate A mixture of 6-ethoxy-4-(4,4,5,5-tetramethyl-1,3,2-dioxaborolan-2-yl)pyrazolo[1,5-a]pyridine-3-carbonitrile (Intermediate P99; 150 mg, 0.479 mmol), tert-butyl 3-(5-chloropyrazin-2-yl)-3,6-diazabicyclo[3.1.1]heptane-6-carboxylate (Intermediate R15; 149 mg, 0.479 mmol), 2 M $K_3PO_{4(aq)}$ (718 µL, 1.44 mmol), X-phos (45.7 mg, 0.0958 mmol) and $Pd_2(dba)_3$ (21.9 mg, 0.0239 mmol) in dioxane (2.40 mL) was sparged with $Ar_{(g)}$ for 3 min, and then the vessel was sealed. The reaction mixture was stirred overnight at 80° C. After cooling to ambient temperature, the reaction mixture was purified directly by silica chromatography (using 0-100% EtOAc in Hexanes as the gradient eluent) to cleanly afford the title compound (95 mg, 43% yield). MS (apci) m/z=478.2 (M+H).

Intermediate P103

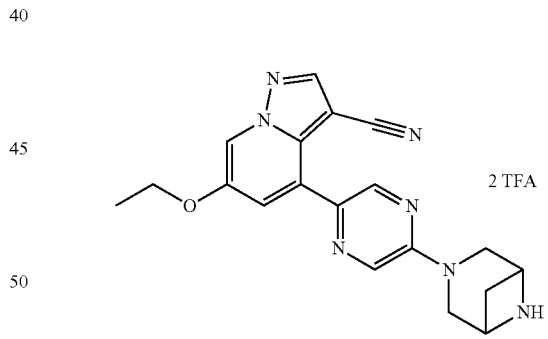

4-(5-(3,6-diazabicyclo[3.1.1]heptan-3-yl)pyrazin-2-yl)-6-ethoxypyrazolo[1,5-a]pyridine-3-carbonitrile bis(2,2,2-trifluoroacetate)

A suspension of tert-butyl 3-(5-(3-cyano-6-ethoxypyrazolo[1,5-a]pyridin-4-yl)pyrazin-2-yl)-3,6-diazabicyclo[3.1.1]heptane-6-carboxylate (Intermediate P102; 95 mg, 0.206 mmol) in DCM (1.0 mL) was treated with TFA (1 mL, 13.1 mmol), and stirred for 1 h at ambient temperature. The reaction mixture was diluted with $Et_2O$ (20 mL). The resulting precipitate was collected, and dried in vacuo to afford the title compound (100 mg, 82.4% yield). MS (apci) m/z=362.1 (M+H).

Intermediate P104

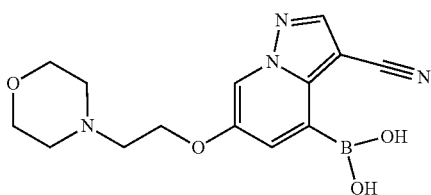 [SMILES: N#Cc1cnn2cc(OCCN3CCOCC3)cc(B(O)O)c12]

(3-cyano-6-(2-morpholinoethoxy)pyrazolo[1,5-a]pyridin-4-yl)boronic acid

In a pressure vessel, a mixture of 4-bromo-6-(2-morpholinoethoxy)pyrazolo[1,5-a]pyridine-3-carbonitrile (Intermediate P95; Method A, Step 1; 200 mg, 0.336 mmol), bis(pinacolato)diboron (1.446 g, 5.694 mmol), PdCl$_2$(dppf).CH$_2$Cl$_2$ (46.4 mg, 0.0570 mmol) and KOAc (167.7 mg, 1.709 mmol) in dioxane (3.36 mL) was sparged with Ar$_{(g)}$ for 10 min. The vessel was sealed, and the mixture was stirred overnight at 90° C. After cooling to ambient temperature, the reaction mixture was diluted with DCM, and filtered through GF/F paper. The filtrate was concentrated in vacuo, and the residue was purified by silica chromatography (using a stepped gradient 0-20% MeOH in DCM with 2% NH$_4$OH, followed by 98% MeOH with 2% NH$_4$OH as the gradient eluent system). The purified residue was dissolved in DCM (2 mL) and triturated with Et$_2$O (5 mL). The resulting suspension was filtered, and the solids were isolated to cleanly afford the title compound (60 mg, 56% yield). MS (apci) m/z=317.1 (M+H).

Intermediate P105

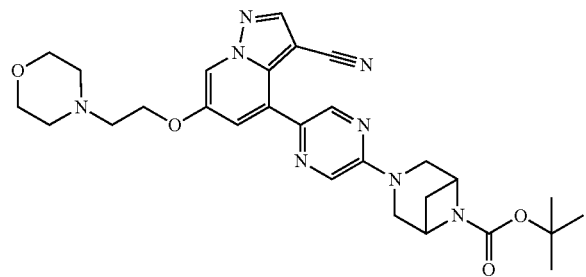 [SMILES: CC(C)(C)OC(=O)N1C2CC1CN(c1cnc(-c3cc(OCCN4CCOCC4)cn4ncc(C#N)c34)cn1)C2]

tert-butyl 3-(5-(3-cyano-6-(2-morpholinoethoxy)pyrazolo[1,5-a]pyridin-4-yl)pyrazin-2-yl)-3,6-diazabicyclo[3.1.1]heptane-6-carboxylate A mixture of (3-cyano-6-(2-morpholinoethoxy)pyrazolo[1,5-a]pyridin-4-yl)boronic acid (Intermediate P104; 60 mg, 0.190 mmol), tert-butyl 3-(5-chloropyrazin-2-yl)-3,6-diazabicyclo[3.1.1]heptane-6-carboxylate (Intermediate R15; 61.9 mg, 0.199 mmol), X-phos (18.1 mg, 0.0380 mmol) and Pd$_2$(dba)$_3$ (8.69 mg, 0.00949 mmol) in dioxane (949 μL) was treated with 2 M K$_3$PO$_{4(aq)}$ (285 μL, 0.569 mmol). The resulting mixture was sparged with Ar$_{(g)}$, and then the vessel was sealed. The reaction mixture was stirred overnight at 80° C. After cooling to ambient temperature, the reaction mixture was diluted with EtOAc, and filtered through GF/F paper. The filtrate was concentrate in vacuo, and the residue was purified by silica chromatography (using 10% MeOH in DCM with 0.1% NH$_4$OH as the gradient eluent) to cleanly afford the title compound (18 mg, 17% yield). MS (apci) m/z=547.3 (M+H).

Intermediate P106

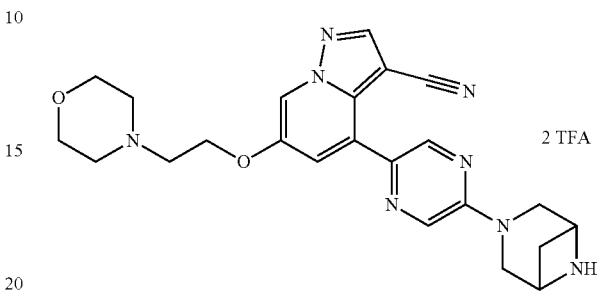

4-(5-(3,6-diazabicyclo[3.1.1]heptan-3-yl)pyrazin-2-yl)-6-(2-morpholinoethoxy)pyrazolo[1,5-a]pyridine-3-carbonitrile bis(2,2,2-trifluoroacetate)

A suspension of tert-butyl 3-(5-(3-cyano-6-(2-morpholinoethoxy)pyrazolo[1,5-a]pyridin-4-yl)pyrazin-2-yl)-3,6-diazabicyclo[3.1.1]heptane-6-carboxylate (Intermediate P105; 18 mg, 0.0329 mmol) in DCM (1.0 mL) was treated with TFA (1 mL, 13.1 mmol), and stirred for 30 min at ambient temperature. The resulting mixture was concentrated in vacuo. The resulting residue was azeotroped with Et$_2$O (3×5 mL) to afford the title compound (22.2 mg, quantitative yield). MS (apci) m/z=447.2 (M+H).

Intermediate P107

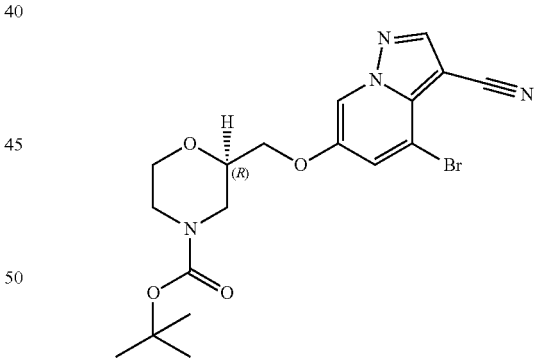

tert-butyl (R)-2-(((4-bromo-3-cyanopyrazolo[1,5-a]pyridin-6-yl)oxy)methyl)morpholine-4-carboxylate A mixture of (R)-tert-Butyl 2-(bromomethyl)morpholine-4-carboxylate (300 mg, 1.07 mmol) and 4-bromo-6-hydroxypyrazolo[1,5-a]pyridine-3-carbonitrile (Intermediate P1; 255 mg, 1.07 mmol) in DMA (2.14 mL) was treated with Cs$_2$CO$_{3(s)}$ (1.05 g, 3.21 mmol), then stirred overnight at 60° C. After cooling to ambient temperature, the mixture was diluted with DCM, and washed sequentially with water (3×) and brine (1×). The organic extracts were concentrated in vacuo to afford the title compound (468 mg, quantitative yield). ¹H NMR (CDCl₃) δ 8.12 (s, 1H), 7.43 (d, 1H), 7.24 (s, 1H), 7.24, 3.90-4.05 (m, 4H), 3.70-3.89 (m, 2H), 3.42-3.55 (m, 2H), 1.39 (s, 12H).

Intermediate P108

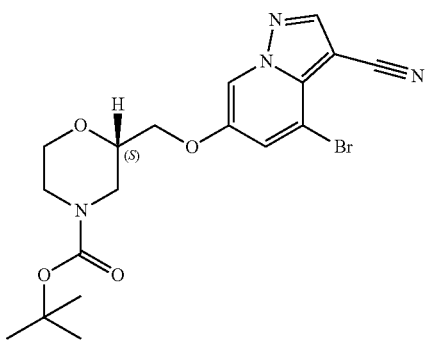

tert-butyl (S)-2-(((4-bromo-3-cyanopyrazolo[1,5-a]pyridin-6-yl)oxy)methyl)morpholine-4-carboxylate The title compound (468 mg, quantitative yield) was prepared using a similar procedure to that described for the synthesis of tert-butyl (R)-2-(((4-bromo-3-cyanopyrazolo[1,5-a]pyridin-6-yl)oxy)methyl)morpholine-4-carboxylate (Intermediate P107), replacing (R)-tert-Butyl 2-(bromomethyl)morpholine-4-carboxylate with tert-butyl (S)-2-(bromomethyl)morpholine-4-carboxylate. ¹H NMR (CDCl₃) δ 8.12 (s, 1H), 7.43 (d, 1H), 7.24 (s, 1H) 3.90-4.05 (m, 4H), 3.70-3.89 (m, 2H), 3.42-3.55 (m, 2H), 1.39 (s, 12H).

Intermediate P109

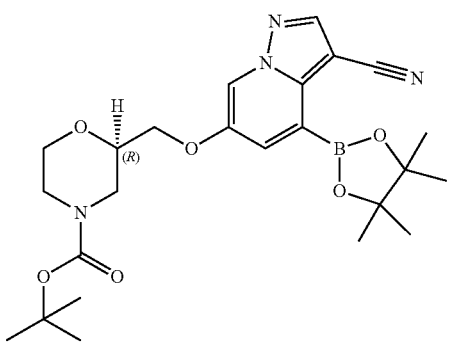

tert-butyl (R)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate In a pressure vessel, a mixture of tert-butyl (R)-2-(((4-bromo-3-cyanopyrazolo[1,5-a]pyridin-6-yl)oxy)methyl)morpholine-4-carboxylate (Intermediate P107; 468 mg, 0.749 mmol), bis(pinacolato)diboron (1.90 g, 7.49 mmol), PdCl₂(dppf)·CH₂Cl₂ (61.0 mg, 0.0749 mmol) and KOAc (368 mg, 3.75 mmol) in dioxane (7.49 mL) was sparged with Ar₍g₎ for 10 min. The vessel was sealed, and the mixture was stirred overnight at 80° C. After cooling to ambient temperature, the reaction mixture was diluted with DCM, and filtered through GF/F paper. The filtrate was concentrated in vacuo, and the residue was triturated with pentane. The pentane suspension was filtered, and the solids were isolated to afford the title compound (200 mg, 80% yield). ¹HNMR (CDCl₃) δ 8.21 (s, 1H), 7.69 (d, 1H), 7.30 (s, 1H), 3.99-4.10 (m, 2H), 3.78-3.98 (m, 2H), 3.56-3.65 (m, 2H), 1.49 (s, 9H), 1.43 (s, 12H).

Intermediate P110

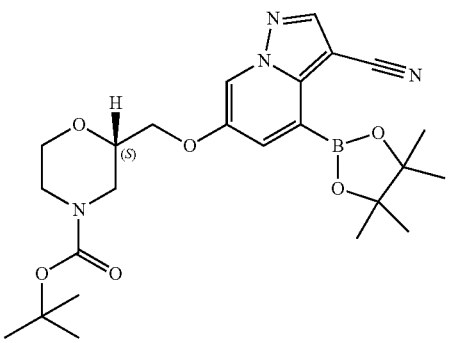

tert-butyl (S)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate The title compound (191 mg, 40% yield) was prepared using a similar procedure to that described for the synthesis of tert-butyl (R)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate (Intermediate P109), replacing tert-butyl (R)-2-(((4-bromo-3-cyanopyrazolo[1,5-a]pyridin-6-yl)oxy)methyl)morpholine-4-carboxylate (Intermediate P107) with tert-butyl (S)-2-(((4-bromo-3-cyanopyrazolo[1,5-a]pyridin-6-yl)oxy)methyl)morpholine-4-carboxylate (Intermediate P108). ¹HNMR (CDCl₃) δ 8.21 (s, 1H), 7.69 (d, 1H), 7.30 (s, 1H), 3.99-4.10 (m, 2H), 3.78-3.98 (m, 2H), 3.56-3.65 (m, 2H), 1.49 (s, 9H), 1.43 (s, 12H).

Intermediate P111

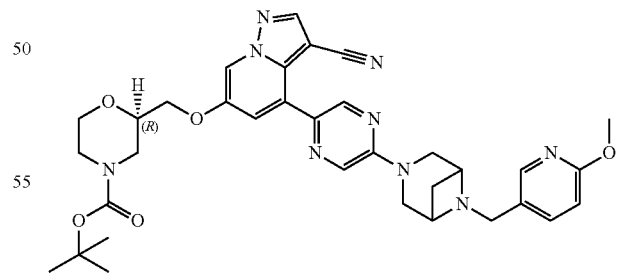

tert-butyl (2R)-2-(((3-cyano-4-(5-(6-((6-methoxypyridin-3-yl)methyl)-3,6-diazabicyclo[3.1.1]heptan-3-yl)pyrazin-2-yl)pyrazolo[1,5-a]pyridin-6-yl)oxy)methyl)morpholine-4-carboxylate A mixture of tert-butyl (R)-2-(((3-cyano-4-(4,4,5,5-tetramethyl-1,3,2-dioxaborolan-2-yl)pyrazolo[1,5-a]pyridin- 6-yl)oxy)methyl)morpholine-4-carboxylate (Intermediate P109; 117 mg, 0.169 mmol), 3-(5-chloropyrazin-2-yl)-6-((6-methoxypyridin-3-yl)methyl)-3,6-diazabicyclo[3.1.1]heptane (Intermediate R25; 56 mg, 0.17 mmol) in dioxane (844 μL) was treated with 2 M K$_3$PO$_{4(aq)}$ (253 μL, 0.506 mmol), X-phos (16 mg, 0.34 mmol) and Pd$_2$(dba)$_3$ (20 mg, 0.084 mmol). The resulting mixture was sparged with Ar$_{(g)}$ for 10 min, and then the vessel was sealed. The reaction mixture was stirred overnight at 80° C. After cooling to ambient temperature, the reaction mixture was diluted with DCM, and washed sequentially with water (3×) and brine (1×). The organic extracts were concentrated in vacuo, and the residue was purified by silica chromatography (using 0-100% mix solvent of 9:1 DCM:MeOH spiked with 1% NH$_4$OH in DCM as the gradient eluent) to cleanly afford the title compound (59.8 mg, 54% yield). MS (apci) m/z=654.3 (M+H)

Intermediate P112

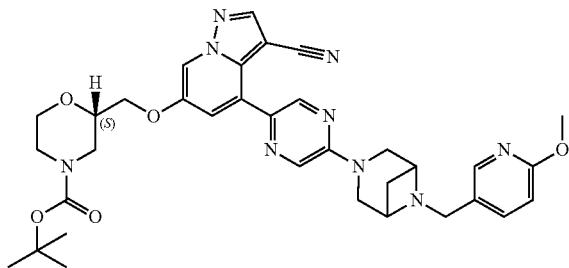

tert-butyl (2S)-2-(((3-cyano-4-(5-(6-((6-methoxy-pyridin-3-yl)methyl)-3,6-diazabicyclo[3.1.1]heptan-3-yl)pyrazin-2-yl)pyrazolo[1,5-a]pyridin-6-yl)oxy)methyl)morpholine-4-carboxylate The title compound (55.9 mg, 51% yield) was prepared using a similar procedure to that described for the synthesis of tert-butyl (2R)-2-(((3-cyano-4-(5-(6-((6-methoxypyridin-3-yl)methyl)-3,6-diazabicyclo[3.1.1]heptan-3-yl)pyrazin-2-yl)pyrazolo[1,5-a]pyridin-6-yl)oxy)methyl)morpholine-4-carboxylate (Intermediate P111), replacing tert-butyl (R)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate (Intermediate P109) with tert-butyl (S)-2-(((3-cyano-4-(4,4,5,5-tetramethyl-1,3,2-dioxaborolan-2-yl)pyrazolo[1,5-a]pyridin-6-yl)oxy)methyl)morpholine-4-carboxylate (Intermediate P110). $^1$HNMR (CDCl$_3$) δ 8.21 (s, 1H), 7.69 (d, 1H), 7.30 (s, 1H), 3.99-4.10 (m, 2H), 3.78-3.98 (m, 2H), 3.56-3.65 (m, 2H), 1.49 (s, 9H), 1.43 (s, 12H).

Intermediate P113

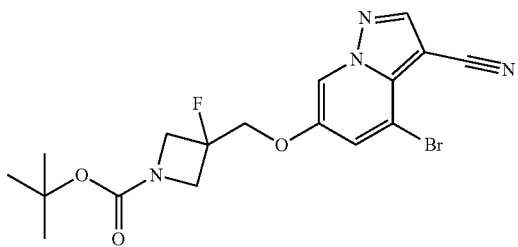 [SMILES: CC(C)(C)OC(=O)N1CC(F)(COc2cc(Br)c3c(C#N)cnn3c2)C1]

tert-butyl 3-(((4-bromo-3-cyanopyrazolo[1,5-a]pyridin-6-yl)oxy)methyl)-3-fluoroazetidine-1-carboxylate A mixture of 4-bromo-6-hydroxypyrazolo[1,5-a]pyridine-3-carbonitrile (Intermediate P1; 591.9 mg, 2.486 mmol) in DMA (12.43 mL) was treated with K$_2$CO$_{3(s)}$ (1.031 g, 7.459 mmol) and tert-butyl 3-(bromomethyl)-3-fluoroazetidine-1-carboxylate (1.0 g, 3.7 mmol), then stirred for 3 h at 60° C. After cooling to ambient temperature, the mixture was diluted with brine, and the resultant suspension was filtered. The isolated solids were washed with water (5×). The filtrate was set aside, and the isolated solids were dissolved in DCM. The DCM solution was concentrated in vacuo to afford the title compound (553 mg). The filtrate was extracted with 4:1 DCM:iPrOH (4×). The combined organic extracts were washed with brine (2×), then dried over anhydrous Na$_2$SO$_{4(s)}$, filtered, and concentrated in vacuo to afford additional title compound (500 mg). The solids from the filtration and from the work up of the filtrate were combined, and dried in vacuo to cleanly provide the title compound (1.033 g, 98% yield). MS (apci) m/z=423 (M+H).

Intermediate P114

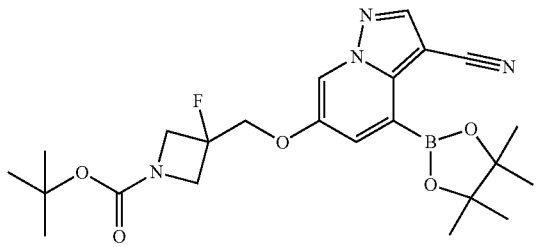 [SMILES: CC(C)(C)OC(=O)N1CC(F)(COc2cc(B3OC(C)(C)C(C)(C)O3)c3c(C#N)cnn3c2)C1]

tert-butyl 3-(((3-cyano-4-(4,4,5,5-tetramethyl-1,3,2-dioxaborolan-2-yl)pyrazolo[1,5-a]pyridin-6-yl)oxy)methyl)-3-fluoroazetidine-1-carboxylate In a pressure tube, a solution of tert-butyl 3-(((4-bromo-3-cyanopyrazolo[1,5-a]pyridin-6-yl)oxy)methyl)-3-fluoroazetidine-1-carboxylate (Intermediate P113; 200 mg, 0.470 mmol) in dioxane (3.14 mL) was treated with bis(pinacolato)diboron (239 mg, 0.941 mmol) and KOAc (138 mg, 1.41 mmol). The resulting mixture was sparged with Ar$_{(g)}$, for 5 min, then PdCl$_2$ (dpp).CH$_2$Cl$_2$ (38.3 mg, 0.0470 mmol) was introduced. The resulting mixture was sparged for an additional 5 min with Ar$_{(g)}$, then the vessel was sealed. The reaction mixture was stirred overnight at 80° C., then cooled to ambient temperature, and diluted with pentane. The pentane mixture was filtered through GF/F paper, then concentrated in vacuo to afford the title compound in a 1:1 ratio with bis(pinacolato)diboron (400 mg, ca. 90% yield based on 50% purity). $^1$H NMR (CDCl$_3$) δ 8.20 (m, 3H), 7.66 (d, 1H), 4.15 (m, 6H), 1.44 (s, 9H), 1.40 (s, 12H).

Intermediate P115

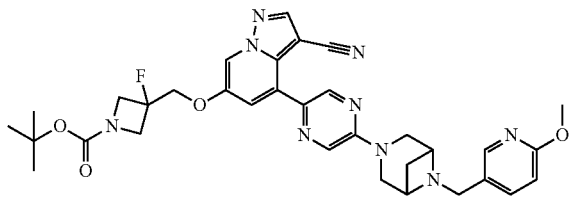 [SMILES: COc1ccc(CN2C3CC2CN(c2cnc(-c4cc(OCC5(F)CN(C(=O)OC(C)(C)C)C5)cn5ncc(C#N)c45)cn2)C3)cn1]

tert-butyl 3-(((3-cyano-4-(5-(6-((6-methoxypyridin-3-yl)methyl)-3,6-diazabicyclo[3.1.1]heptan-3-yl)pyrazin-2-yl)pyrazolo[1,5-a]pyridin-6-yl)oxy)methyl)-3-fluoroazetidine-1-carboxylate A mixture of tert-butyl 3-(((3-cyano-4-(4,4,5,5-tetramethyl-1,3,2-dioxaborolan-2-yl)pyrazolo[1,5-a]pyridin-6-yl)oxy)methyl)-3-fluoroazetidine-1-carboxylate (Intermediate P114; 75 mg, 0.16 mmol), 3-(5-chloropyrazin-2-yl)-6-((6-methoxypyridin-3-yl)methyl)-3,6-diazabicyclo[3.1.1]heptane (Intermediate R25; 70 mg, 0.11 mmol), X-phos (10 mg, 0.021 mmol) and Pd$_2$(dba)$_3$ (4.8 mg, 0.0053 mmol) in dioxane (529 µL) was treated with 2 M K$_3$PO$_{4(aq)}$ (159 µL, 0.320 mmol). The resulting mixture was sparged with Ar$_{(g)}$ for 10 min, and then the reaction vessel was sealed. The mixture was stirred overnight at 80° C. After cooling to ambient temperature, the reaction mixture was diluted with DCM, and washed sequentially with water and brine. The organic extracts were dried over anhydrous Na$_2$SO$_{4(s)}$, filtered, and concentrated in vacuo. The crude residue was purified by silica chromatography (using 0-100% EtOAc in Hexanes then 0-10% MeOH with 0.1% NH$_4$OH in EtOAc as the gradient eluents) to cleanly afford the title compound (48 mg, 71% yield). MS (apci) m/z=642.3 (M+H).

Intermediate P116

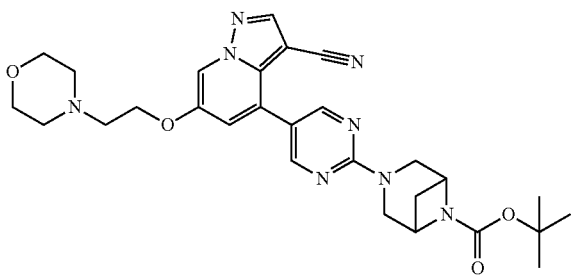 [SMILES: CC(C)(C)OC(=O)N1C2CC1CN(c1ncc(-c3cc(OCCN4CCOCC4)cn4ncc(C#N)c34)cn1)C2]

tert-butyl 3-(5-(3-cyano-6-(2-morpholinoethoxy)pyrazolo[1,5-a]pyridin-4-yl)pyrimidin-2-yl)-3,6-diazabicyclo[3.1.1]heptane-6-carboxylate A mixture of tert-butyl 3-(5-(4,4,5,5-tetramethyl-1,3,2-dioxaborolan-2-yl)pyrimidin-2-yl)-3,6-diazabicyclo[3.1.1]heptane-6-carboxylate (Intermediate R21; 360 mg, 0.895 mmol) and K$_2$CO$_{3(s)}$ (618 mg, 4.47 mmol) in dioxane (8.95 mL) and water (895 µL) was treated with 4-bromo-6-(2-morpholinoethoxy)pyrazolo[1,5-a]pyridine-3-carbonitrile (Intermediate P79, Step 1; 314 mg, 0.895 mmol) and Pd(PPh$_3$)$_4$ (103 mg, 0.0895 mmol). The resulting mixture was sparged with Ar$_{(g)}$ before sealing the reaction vessel. The mixture was stirred for 16 h at 80° C. After cooling to ambient temperature, the reaction mixture was partitioned between 4:1 DCM:iPrOH and brine. After phase separation, the organic extracts were washed with additional brine (2×), and then dried over anhydrous Na$_2$SO$_{4(s)}$, filtered, and concentrated in vacuo. The crude residue was purified by silica chromatography (using 0-100% EtOAc in Hexanes then 0-20% MeOH in EtOAc as the gradient eluents) to cleanly afford the title compound (336 mg, 69% yield). MS (apci) m/z=491.2 (M-tBu).

Intermediate P117

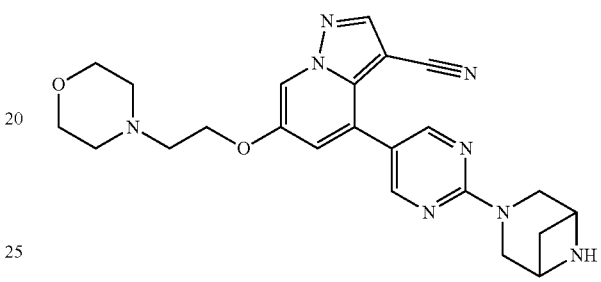

4-(2-(3,6-diazabicyclo[3.1.1]heptan-3-yl)pyrimidin-5-yl)-6-(2-morpholinoethoxy)pyrazolo[1,5-a]pyridine-3-carbonitrile A suspension of tert-butyl 3-(5-(3-cyano-6-(2-morpholinoethoxy)pyrazolo[1,5-a]pyridin-4-yl)pyrimidin-2-yl)-3,6-diazabicyclo[3.1.1]heptane-6-carboxylate (Intermediate P116; 336 mg, 0.615 mmol) in DCM (2.05 mL) was treated with TFA (474 µL, 6.15 mmol), and stirred for 5 h at ambient temperature. Additional TFA (2 mL, 26.1 mmol) was introduced, and the reaction mixture was stirred for an additional 30 min at ambient temperature. The resulting mixture was neutralized with saturated NaHCO$_{3(aq)}$ (30 mL), and the biphasic mixture was extracted with 4:1 DCM:iPrOH. The combined organic extracts were washed with brine, then dried over anhydrous Na$_2$SO$_{4(s)}$, filtered, and concentrated in vacuo to afford the title compound (236 mg, 86% yield). MS (apci) m/z=447.3 (M+H).

Intermediate P118

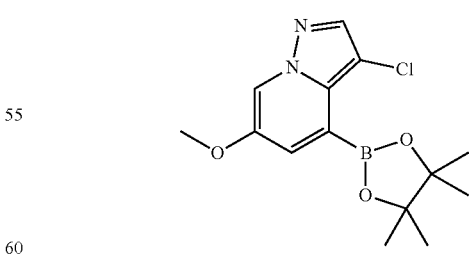

3-chloro-6-methoxy-4-(4,4,5,5-tetramethyl-1,3,2-dioxaborolan-2-yl)pyrazolo[1,5-a]pyridine A mixture of 4-bromo-3-chloro-6-methoxypyrazolo[1,5-a]pyridine (Intermediate P62, Step 1; 152 mg, 0.581 mmol), PdCl$_2$(dppf).CH$_2$Cl$_2$ (23.7 mg, 0.029 mmol), KOAc (285 mg, 2.91 mmol) and bis(pinacolato)diboron (443 mg, 1.74 mmol) in dioxane (5.8 mL) was sparged with Ar$_{(g)}$. The reaction vessel was sealed, and the mixture was stirred for 2 h 15 min at 90° C. After cooling to ambient temperature, the reaction mixture was filtered through Celite®. The filtrate was concentrated in vacuo to afford the title compound (102 mg, 57%). MS (apci) m/z=309.1 (M+H).

Intermediate P119

1-(4-bromo-6-methoxypyrazolo[1,5-a]pyridin-3-yl)ethan-1-ol

A cold (0° C.) suspension of 4-bromo-6-methoxypyrazolo[1,5-a]pyridine-3-carbaldehyde (Intermediate P1, Part B, Step 4; 128 mg, 0.502 mmol) in THF (5.02 mL) was treated in dropwise fashion with a 3 M solution of CH$_3$MgBr in Et$_2$O (201 µL, 0.602 mmol). Following the addition of the CH$_3$MgBr, the mixture was allowed to warm to ambient temperature. The resulting mixture was stirred for 1 h at ambient temperature before quenching with saturated NH$_4$Cl$_{(aq)}$. The biphasic mixture was concentrated in vacuo to remove the organic solvents. The residual aqueous suspension was filtered, rinsing with water. The solids were collected and dried in vacuo to afford the title compound (130 mg, 96% yield). MS (apci) m/z=272.9 (M+H).

Intermediate P120

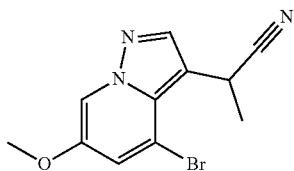 [SMILES: COc1cc(Br)c2c(C(C)C#N)cnn2c1]

2-(4-bromo-6-methoxypyrazolo[1,5-a]pyridin-3-yl)propanenitrile

A cold (0° C.) solution of TMSCN (243 µL, 1.81 mmol) in DCM (2 mL) was treated sequentially with BF$_3$.Et$_2$O (172 µL, 1.36 mmol), and 1-(4-bromo-6-methoxypyrazolo[1,5-a]pyridin-3-yl)ethan-1-ol (Intermediate P119; 123 mg, 0.454 mmol) in DCM (2 mL). The resulting mixture was allowed to slowly warm to ambient temperature. The mixture was stirred for an additional 2 h at ambient temperature before quenching with saturated NaHCO$_{3(aq)}$. The resulting biphasic mixture was extracted with DCM, and the organic extracts were concentrated in vacuo. The crude residue was purified by silica chromatography (using 0-25% EtOAc in Hexanes as the gradient eluent) to afford the title compound (70 mg, 55% yield). MS (apci) m/z=282.0 (M+H).

Intermediate P121

(4-bromo-6-methoxypyrazolo[1,5-a]pyridin-3-yl)methanol

A suspension of 4-bromo-6-methoxypyrazolo[1,5-a]pyridine-3-carbaldehyde (Intermediate P1, Part B, Step 4; 1.10 g, 4.31 mmol) in MeOH (21.6 mL) and THF (21.6 mL) was treated with NaBH$_4$ (163 mg, 4.31 mmol), then stirred for 20 h at ambient temperature. Additional NaBH$_4$ (163 mg, 4.31 mmol) was introduced, and the mixture was stirred for an additional 2 h at ambient temperature. The resulting mixture was concentrated in vacuo, and the residue was suspended in water (50 mL). The resulting aqueous suspension was filtered, rinsing with water. The solids were collected and dried in vacuo to afford the title compound (1.05 g, 95% yield). MS (apci) m/z=259.1 (M+H).

Intermediate P122

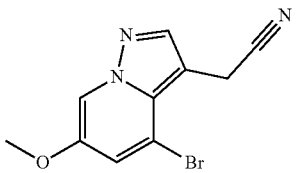

2-(4-bromo-6-methoxypyrazolo[1,5-a]pyridin-3-yl)acetonitrile

A cold (0° C.) solution of TMSCN (323 µL, 2.41 mmol) in DCM (3 mL) was treated sequentially with BF$_3$.Et$_2$O (229 µL, 1.81 mmol), and (4-bromo-6-methoxypyrazolo[1,5-a]pyridin-3-yl)methanol (Intermediate P121; 155 mg, 0.603 mmol). The resulting mixture was allowed to slowly warm to ambient temperature. The mixture was stirred for an additional 2 h at ambient temperature before quenching with saturated NaHCO$_{3(aq)}$. The resulting biphasic mixture was extracted with DCM, and the organic extracts were concentrated in vacuo. The crude residue was purified by silica chromatography (using 0-30% EtOAc in Hexanes as the gradient eluent) to afford the title compound (43 mg, 27% yield). MS (apci) m/z=268.0 (M+H).

Intermediate R1

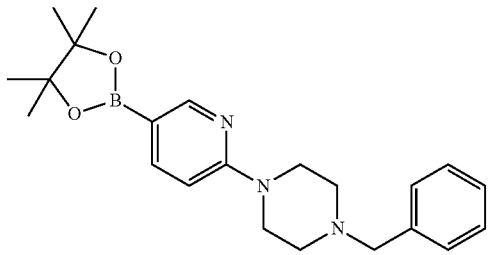 [SMILES: CC1(C)OB(c2ccc(N3CCN(Cc4ccccc4)CC3)nc2)OC1(C)C]

1-Benzyl-4-(5-(4,4,5,5-tetramethyl-1,3,2-dioxaborolan-2-yl)pyridin-2-yl)piperazine A solution of 1-(5-(4,4,5,5-tetramethyl-1,3,2-dioxaborolan-2-yl)pyridin-2-yl)piperazine hydrochloride (1.00 g, 3.07 mmol) in DMF (5 mL) was treated with (bromomethyl)benzene (0.438 mL, 3.69 mmol) and TEA (1.28 mL, 9.21 mmol). After stirring overnight at ambient temperature, the mixture was treated with water and sonicated for 10 min. The resulting white suspension was filtered, and the solids were washed with water and hexanes to afford the title compound (0.84 g, 72% yield). MS (apci) m/z=298.1 $(B(OH)_2$ M+H).

Intermediate R2

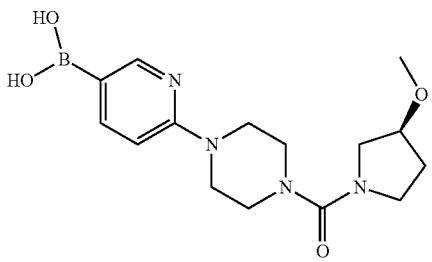 [SMILES: CO[C@H]1CCN(C(=O)N2CCN(c3ccc(B(O)O)cn3)CC2)C1]

(S)-(6-(4-(3-methoxypyrrolidine-1-carbonyl)piperazin-1-yl)pyridin-3-yl)boronic acid A solution of (6-(piperazin-1-yl)pyridin-3-yl)boronic acid (1.5 g, 7.25 mmol) in DMA (36.2 mL, 7.25 mmol) was treated with DIEA (5.05 mL, 29.0 mmol), and allowed to stir for 20 min at ambient temperature. The mixture was treated with 4-nitrophenyl carbonochloridate (2.92 g, 14.5 mmol), and allowed to stir overnight at ambient temperature. The mixture was then treated with DIEA (5 mL, 29.0 mmol) and (S)-3-methoxypyrrolidine (3.66 g, 36.2 mmol) and allowed to stir for 3 days at ambient temperature. The reaction mixture was diluted with water and extracted with 20% MeOH/DCM. The combined organic extracts were dried over anhydrous $Na_2SO_{4(s)}$, filtered, and concentrated in vacuo. The crude residue was purified by C18 reverse phase chromatography (0-40% ACN/$H_2O$). The isolated product was then taken up in MeOH and loaded onto an Isolute® SCX column. The column was flushed with MeOH (2 column volumes) and then with 4 N $NH_4OH$ in MeOH to cleanly provide the title compound (1.0 g, 41% yield). MS (apci) m/z=335.1 (M+H).

Intermediate R4

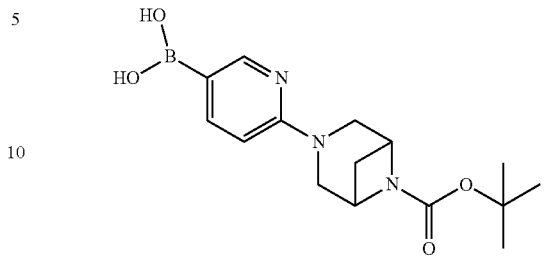

(6-(6-(tert-butoxycarbonyl)-3,6-diazabicyclo[3.1.1]heptan-3-yl)pyridin-3-yl)boronic acid

Method 1

Step 1: Preparation of tert-butyl 3-(5-bromopyridin-2-yl)-3,6-diazabicyclo[3.1.1]heptane-6-carboxylate A suspension of 3,6-diaza-bicyclo[3.1.1]heptane-6-carboxylic acid tert-butyl ester (1.046 g, 5.27 mmol), 5-bromo-2-fluoropyridine (919 mg, 5.22 mmol) and $K_2CO_{3(s)}$ (3.61 g, 26.1 mmol) in DMSO (5.22 mL) was stirred for 1 day at 90° C. After cooling to ambient temperature, the reaction mixture was partitioned between EtOAc and water. The organic extracts were washed with additional water, then dried over anhydrous $Na_2SO_{4(s)}$, filtered, and concentrated in vacuo. Purification of the crude residue by silica chromatography (0-50% Hexanes/EtOAc as gradient eluent) provided the title compound (1.80 g, 97% yield). MS (apci) m/z=354.0 (M+1), 356.1 (M+2).

Step 2: Preparation of (6-(6-(tert-butoxycarbonyl)-3,6-diazabicyclo[3.1.1]heptan-3-yl)pyridin-3-yl)boronic acid A mixture of tert-butyl 3-(5-bromopyridin-2-yl)-3,6-diazabicyclo[3.1.1]heptane-6-carboxylate (1.80 g, 5.08 mmol), bis(pinacolato)diboron (3.87 g, 15.2 mmol), $PdCl_2(dppf)$·$CH_2Cl_2$ (414 mg, 0.508 mmol), and KOAc (1.50 g, 15.2 mmol) in dioxane (5.75 mL) was sparged with $N_{2(g)}$, then stirred for 3 h at 80° C. After cooling to room temperature, the reaction mixture was diluted with DCM and washed with water. The aqueous extracts were washed with DCM. All of the DCM extracts were combined and dried over anhydrous $Na_2SO_{4(s)}$, filtered, and concentrated in vacuo. The crude residue was sonicated with hexanes (200 mL) and ether (50 mL) for 5 min, and the resulting gray suspension was filtered. The collected solids were triturated with MeOH, and the resulting suspension was filtered to afford the title compound as a white solid (840 mg, 52% yield). MS (apci) m/z=320.2 (M+H).

Method 2

Preparation of (6-(6-(tert-butoxycarbonyl)-3,6-diazabicyclo[3.1.1]heptan-3-yl)pyridin-3-yl)boronic acid A suspension of 3,6-diaza-bicyclo[3.1.1]heptane-6-carboxylic acid tert-butyl ester (182 mg, 0.918 mmol), 2-fluoro-5-(4,4,5,5-tetramethyl-1,3,2-dioxaborolan-2-yl)pyridine (819 mg, 3.67 mmol) and $K_2CO_{3(s)}$ (634 mg, 4.59 mmol) in DMSO (918 μL) was heated to 90° C., then treated with water (5 mL). The resulting mixture was stirred for 1 hour at 90° C., then cooled to ambient temperature and filtered to cleanly provide the title compound (1.0 g, 41% yield). MS (apci) m/z=320.1 (M+H).

Intermediate R5

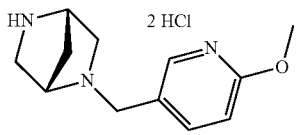 [SMILES: COc1ccc(CN2C[C@@H]3C[C@H]2CN3)cn1]

(1S,4S)-2-((6-methoxypyridin-3-yl)methyl)-2,5-diazabicyclo[2.2.1]heptane dihydrochloride Step 1: Preparation of tert-butyl (1S,4S)-5-(6-methoxypyridin-3-yl)-2,5-diazabicyclo[2.2.1]heptane-2-carboxylate A solution of tert-butyl (1S,4S)-(−)-2,5-diazabicyclo(2.2.1)heptane-2-carboxylate (500 mg, 2.52 mmol) in DCE (12.6 mL) was treated sequentially with 6-methoxynicotinaldehyde (691.7 mg, 5.044 mmol) and NaBH(AcO)₃ (1.60 g, 7.57 mmol). After stirring overnight at ambient temperature, the reaction mixture was concentrated in vacuo. The residue was purified by silica chromatography (0-20% MeOH in DCM as the gradient eluent) to cleanly provide the title compound (725.4 mg, 90% yield). MS (apci) m/z=320.2 (M+H).

Step 2: Preparation of (1S,4S)-2-(6-methoxypyridin-3-yl)-2,5-diazabicyclo[2.2.1]heptane dihydrochloride A solution of tert-butyl (1S,4S)-5-(6-methoxypyridin-3-yl)-2,5-diazabicyclo[2.2.1]heptane-2-carboxylate (725.4 mg, 2.271 mmol) in DCM (5 mL) was treated with 4 N HCl in dioxanes (5 mL). The resulting mixture was stirred for 1 hour at ambient temperature then concentrated in vacuo, azeotroping with toluene (3×3 mL), to afford the title compound as the dihydrochloride salt (663.6 mg, 90% yield). MS (apci) m/z=220.2 (M+H).

Intermediate R6

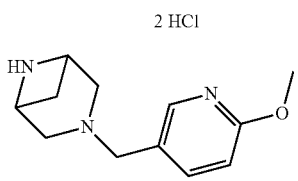 [SMILES: COc1ccc(CN2CC3CC(C2)N3)cn1]

3-((6-methoxypyridin-3-yl)methyl)-3,6-diazabicyclo[3.1.1]heptane dihydrochloride Step 1: Preparation of tert-butyl 3-((6-methoxypyridin-3-yl)methyl)-3,6-diazabicyclo[3.1.1]heptane-6-carboxylate A solution of 3,6-diaza-bicyclo[3.1.1]heptane-6-carboxylic acid tert-butyl ester (250 mg, 1.26 mmol) in DCE (6.31 mL) was treated sequentially with 6-methoxynicotinaldehyde (346 mg, 2.52 mmol) and NaBH(AcO)₃ (802 mg, 3.78 mmol). The mixture was stirred 5 h at ambient temperature. The reaction mixture was concentrated in vacuo, and the residue was purified by silica chromatography (0-100% [4:1 DCM:MeOH with 2% NH₄OH] in DCM as the gradient eluent) to afford the title compound in sufficient purity for subsequent use (420 mg, quantitative yield). MS (apci) m/z=320.2 (M+H).

Step 2: Preparation of 3-((6-methoxypyridin-3-yl)methyl)-3,6-diazabicyclo[3.1.1]heptane dihydrochloride A solution of tert-butyl 3-((6-methoxypyridin-3-yl)methyl)-3,6-diazabicyclo[3.1.1]heptane-6-carboxylate (step 1; 420 mg, 1.31 mmol) in DCM (2 mL) was treated with 4 N HCl in dioxanes (4 mL). The reaction mixture was stirred overnight at ambient temperature. The resulting precipitate was filtered to cleanly provide the title as the dihydrochloride salt (341 mg, 93% yield). MS (apci) m/z=220.2 (M+H).

Intermediate R7

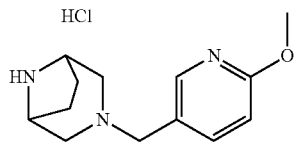 [SMILES: COc1ccc(CN2CC3CCC(C2)N3)cn1 ; Cl]

3-((6-methoxypyridin-3-yl)methyl)-3,8-diazabicyclo[3.2.1]octane hydrochloride

Step 1: Preparation of tert-butyl 3-((6-methoxypyridin-3-yl)methyl)-3,8-diazabicyclo[3.2.1]octane-8-carboxylate A solution of tert-butyl 3,8-diazabicyclo[3.2.1]octane-8-carboxylate (1.0 g, 4.71 mmol) in DCE (23.6 mL) was treated sequentially with 6-methoxynicotinaldehyde (711 mg, 5.18 mmol) and NaBH(AcO)₃ (1.50 g, 7.07 mmol). The mixture was stirred for 1 day at ambient temperature, then additional 6-methoxynicotinaldehyde (711 mg, 5.18 mmol) and NaBH(AcO)₃ (1.50 g, 7.07 mmol) were added. After stirring for 1 day at ambient temperature, the resulting mixture was concentrated in vacuo. The residue was purified by silica chromatography (0-100% EtOAc/Hexanes as the gradient eluent to afford the title compound in sufficient purity for subsequent use (1.50 g, 96% yield). MS (apci) m/z=334.2 (M+H).

Step 2: Preparation of 3-(6-methoxypyridin-3-yl)methyl)-3,8-diazabicyclo[3.2.1]octane hydrochloride A solution of tert-butyl 3-((6-methoxypyridin-3-yl)methyl)-3,8-diazabicyclo[3.2.1]octane-8-carboxylate (1.5 g, 4.50 mmol) in 6 N HCl in iPrOH (15 mL) was stirred overnight at ambient temperature. The reaction mixture was concentrated in vacuo to cleanly provide the title as the hydrochloride salt (1.15 g, 95% yield). MS (apci) m/z=234.1 (M+H).

Intermediate R9

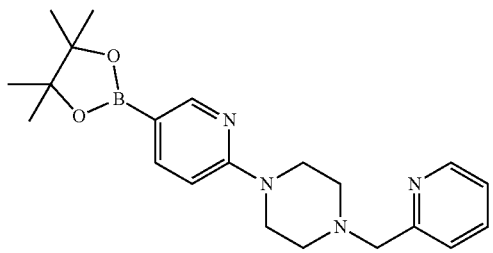 [SMILES: CC1(C)OB(c2ccc(N3CCN(Cc4ccccn4)CC3)nc2)OC1(C)C]

1-(pyridin-2-ylmethyl)-4-(5-(4,4,5,5-tetramethyl-1,3,2-dioxaborolan-2-yl)pyridin-2-yl)piperazine A suspension of 1-(5-(4,4,5,5-tetramethyl-1,3,2-dioxaborolan-2-yl)pyridin-2-yl)piperazine (1.00 g, 3.46 mmol) in DMF (5 mL) was treated with picolinaldehyde (0.556 g, 5.19 mmol), Me$_4$N(AcO)$_3$BH (1.82 g, 6.92 mmol) and TEA (1.45 mL, 10.4 mmol). The resulting mixture was stirred overnight at ambient temperature before quenching with water. The quenched suspension was filtered, and the collected solids were washed with water and hexanes to afford the title compound (500 mg, 38% yield). MS (apci) m/z=299.1 (B(OH)$_2$M+H).

Intermediate R10

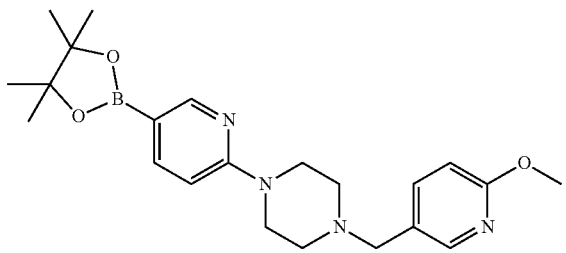

1-((6-methoxypyridin-3-yl)methyl)-4-(5-(4,4,5,5-tetramethyl-1,3,2-dioxaborolan-2-yl)pyridin-2-yl)piperazine

Step 1: Purification of 97% pure commercial 6-methoxynicotinaldehyde

A suspension of 97% commercial 6-methoxynicotinaldehyde (200 g, 1458.4 mmol) in hexanes (750 mL) was heated with a heat gun to dissolve most of the solids. The resulting hot solution containing orange solids was filtered through a preheated filter funnel into a preheated flask. The hot filtrate was stirred and allowed to slowly cool to ambient temperature. The room temperature solution was allowed to rest for 2 days at room temperature. The resultant suspension was filtered and the collected solids were washed with hexanes to cleanly provide the title compound (163.93 g, 82% recovery).

Step 2: Preparation of 1-((6-methoxypyridin-3-yl)methyl)-4-(5-(4,4,5,5-tetramethyl-1,3,2-dioxaborolan-2-yl)pyridin-2-yl)piperazine A mixture of 1-(5-(4,4,5,5-tetramethyl-1,3,2-dioxaborolan-2-yl)pyridin-2-yl)piperazine (5 g, 17.3 mmol) and 6-methoxynicotinaldehyde (2.85 g, 20.7 mmol) in DCE (85 mL) was treated with NaBH(AcO)$_3$ (7.3 g, 35 mmol). The resulting mixture was stirred for 2.5 hr at ambient temperature, then concentrated in vacuo to half the original volume (about 40 mL). The resulting mixture was diluted with EtOAc, then washed with saturated NaHCO$_{3(aq)}$ and brine. The combined organic extracts were dried over anhydrous Na$_2$SO$_{4(s)}$, filtered, and concentrated in vacuo to afford the title compound (4.86 mg, 69% yield). MS (apci) m/z=411.2 (M+H).

Intermediate R11

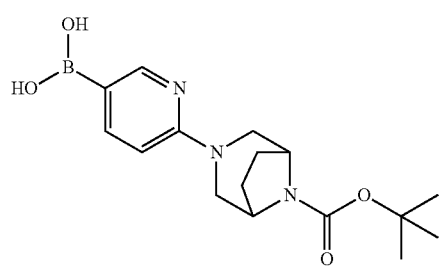 [SMILES: CC(C)(C)OC(=O)N1C2CCC1CN(c1ccc(B(O)O)cn1)C2]

(6-(8-(tert-butoxycarbonyl)-3,8-diazabicyclo[3.2.1]octan-3-yl)pyridin-3-yl)boronic acid A suspension of tert-butyl 3,8-diazabicyclo[3.2.1]octane-8-carboxylate hydrochloride (153 mg, 0.616 mmol), 2-fluoro-5-(4,4,5,5-tetramethyl-1,3,2-dioxaborolan-2-yl)pyridine (125 mg, 0.560 mmol) and K$_2$CO$_{3(s)}$ (387 mg, 2.80 mmol) in DMSO (5 mL) was stirred for 1 day at 90° C., then cooled to ambient temperature. The resulting suspension was filtered, and the solids were collected to cleanly provide the title compound (55 mg, 30% yield). MS (apci) m/z=334.2 (M+H).

Intermediate R12

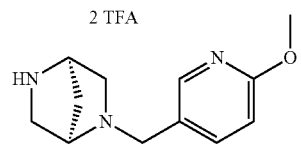 [SMILES: COc1ccc(CN2C[C@H]3C[C@@H]2CN3)cn1 ; "2 TFA"]

(1R,4R)-2-((6-methoxypyridin-3-yl)methyl)-2,5-diazabicyclo[2.2.1]heptane bis(2,2,2-trifluoroacetate)

Step 1: Preparation of tert-butyl (1R,4R)-5-((6-methoxypyridin-3-yl)methyl)-2,5-diazabicyclo[2.2.1]heptane-2-carboxylate A solution of (1R,4R)-2,5-Diaza-bicyclo[2.2.1]heptane-2-carboxylic acid tert-butyl ester (250 mg, 1.26 mmol) in DCE (6.31 mL) was treated sequentially with 6-methoxynicotinaldehyde (346 mg, 2.52 mmol) and NaBH(AcO)$_3$ (802 mg, 3.78 mmol), then stirred overnight at ambient temperature. The resulting mixture was concentrated in vacuo, and the residue was purified by silica chromatography (0-20%

MeOH in DCM as the gradient eluent) to cleanly provide the title compound (20 mg, 5% yield). MS (apci) m/z=320.2 (M+H).

Step 2: Preparation of (1R,4R)-2-((6-methoxypyridin-3-yl)methyl)-2,5-diazabicyclo[2.2.1]heptane bis(2,2,2-trifluoroacetate)

A solution of tert-butyl (1R,4R)-5-((6-methoxypyridin-3-yl)methyl)-2,5-diazabicyclo[2.2.1]heptane-2-carboxylate (20 mg, 0.063 mmol) in DCM (1 mL) was treated with TFA (0.5 mL). The resulting mixture was stirred for 2 h at ambient temperature, then concentrated in vacuo to afford the title compound as the bis-trifluoroacetate salt (28 mg, quantitative yield). MS (apci) m/z=220.2 (M+H).

Intermediate R14

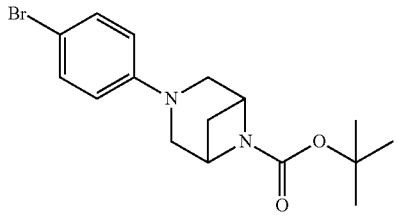

tert-butyl 3-(4-bromophenyl)-3,6-diazabicyclo[3.1.1]heptane-6-carboxylate

A mixture of 1-bromo-4-iodobenzene (0.500 g, 1.77 mmol), tert-butyl 3,6-diazabicyclo[3.1.1]heptane-6-carboxylate (0.491 g, 2.47 mmol), $Cs_2CO_{3(s)}$ (1.15 g, 3.53 mmol), CuI (16.8 mg, 0.0884 mmol) and 2-isobutyrylcyclohexan-1-one (59.5 mg, 0.353 mmol) in DMF (1.5 mL) was sparged with $Ar_{(g)}$ for 5 min, then stirred for 4 days at ambient temperature. The reaction mixture was treated with additional CuI (16.8 mg, 0.0884 mmol), then sparged with $Ar_{(g)}$ for 5 min and stirred at 35° C. for 1 h. The mixture was partitioned between brine and MTBE. The organic layer was separated and washed with additional brine and saturated $NH_4Cl_{(aq)}$. The aqueous extracts were combined and back extracted with MTBE. The MTBE extracts were combined, then dried over anhydrous $MgSO_{4(s)}$, filtered, and concentrated in vacuo. The crude residue was purified by silica chromatography (DCM as the eluent) to cleanly provide the title compound (190 mg, 30% yield). MS (apci) m/z=353.0 (M+1); 355.1 (M+2) with Br pattern.

Intermediate R15

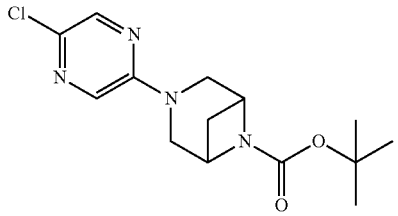 [SMILES: CC(C)(C)OC(=O)N1C2CC1CN(c1cnc(Cl)cn1)C2]

tert-butyl 3-(5-chloropyrazin-2-yl)-3,6-diazabicyclo[3.1.1]heptane-6-carboxylate A mixture of tert-butyl 3,6-diazabicyclo[3.1.1]heptane-6-carboxylate (266 mg, 1.34 mmol), 2,5-dichloropyrazine (260 mg, 1.74 mmol) and $K_2CO_{3(s)}$ (927 mg, 6.71 mmol) in DMSO (1.5 mL) was stirred for 2 h at 80° C., then overnight at 85° C. After cooling to ambient temperature, the mixture was diluted with water and stirred vigorously until the ensuing exotherm dissipated. The aqueous mixture was extracted with $Et_2O$, and the biphasic mixture was filtered and separated. The aqueous phase was extracted with DCM, and the $Et_2O$ and DCM extracts were combined. The combined organic extracts were dried over anhydrous $MgSO_{4(s)}$, filtered, and concentrated in vacuo. The residue was purified by silica chromatography (10% EtOAc in DCM with 0.05% $NH_4OH$ as the eluent) to cleanly provide the title compound (286 mg, 69% yield). MS (apci) m/z=311.0 (M+1); 313.2 (M+2) with C1 pattern.

Intermediate R16

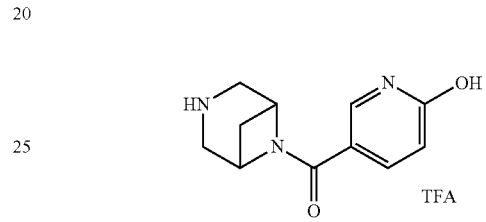

(3,6-diazabicyclo[3.1.1]heptan-6-yl)(6-hydroxypyridin-3-yl)methanone 2,2,2-trifluoroacetate Step 1: Preparation of tert-butyl 6-(6-hydroxynicotinoyl)-3,6-diazabicyclo[3.1.1]heptane-3-carboxylate A suspension of tert-butyl 3,6-diazabicyclo[3.1.1]heptane-3-carboxylate (0.363 g, 1.83 mmol), 6-hydroxynicotinic acid (0.382 g, 2.75 mmol), N-ethyl-N-isopropylpropan-2-amine (1.59 ml, 9.15 mmol), and HATU (0.766 g, 2.01 mmol) in DMF (2 mL) was stirred overnight at ambient temperature. The reaction mixture was diluted with DCM and water. The resulting suspension was filtered to yield the title compound as solid (250 mg, 43% yield).

Step 2: Preparation of (3,6-diazabicyclo[3.1.1]heptan-6-yl)(6-hydroxypyridin-3-yl)methanone 2,2,2-trifluoroacetate A solution of tert-butyl 6-(6-hydroxynicotinoyl)-3,6-diazabicyclo[3.1.1]heptane-3-carboxylate (Step 1; 250 mg, 0.783 mmol) in DCM (7.83 mL) was treated with TFA (1.20 mL). The resulting mixture was stirred for 2 h at ambient temperature, then concentrated in vacuo to afford the title compound assuming quantitative yield.

Intermediate R17

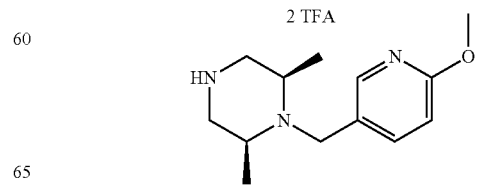

(2R,6S)-1-((6-methoxypyridin-3-yl)methyl)-2,6-dimethylpiperazine bis(2,2,2-trifluoroacetate)

Step 1: Preparation of tert-butyl (3S,5R)-3,5-dimethylpiperazine-1-carboxylate

A solution of tert-butyl (3S,5R)-3,5-dimethylpiperazine-1-carboxylate (50 mg, 0.23 mmol) in DCE (1.17 mL) was treated sequentially with 6-methoxynicotinaldehyde (64 mg, 0.47 mmol) and NaBH(AcO)$_3$ (148 mg, 0.70 mmol), then stirred for 1 h at ambient temperature. The resulting mixture was concentrated in vacuo, and the residue was purified by silica chromatography (using a gradient of 0-100% DCM in Hexanes then 0-60% (2% NH$_4$OH/20% MeOH/78% DCM) in DCM as the gradient eluent) to cleanly provide the title compound (26 mg, 33% yield). MS (apci) m/z=336.2 (M+H).

Step 2: Preparation of (2S,6R)-1-((6-methoxypyridin-3-yl)methyl)-2,6-dimethylpiperazine bis(2,2,2-trifluoroacetate)

A solution of tert-butyl (3S,5R)-4-((6-methoxypyridin-3-yl)methyl)-3,5-dimethylpiperazine-1-carboxylate (26 mg, 0.078 mmol) was dissolved in 1 mL DCM and treated with TFA (1 mL), then stirred for 2 h at ambient temperature. The resulting mixture was concentrated in vacuo to cleanly provide the title compound (36 mg, 33% yield). MS (apci) m/z=336.2 (M+H).

Intermediate R18

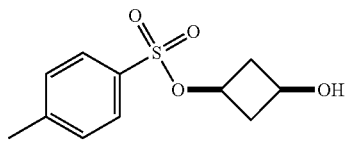

(1s,3s)-3-hydroxycyclobutyl 4-methylbenzenesulfonate

A solution of (1s,3s)-3-(tosyloxy)cyclobutyl pivalate (3.5 g, 10.7 mmol) in DCM (20 mL) was cooled to −78° C., then treated slowly with DIBAL-H (25 wt % in toluene, 12.6 mL, 18.8 mmol). The resulting mixture was stirred for 1 h at −78° C. The mixture was quenched by slowly adding Na$_2$SO$_4$.10H$_2$O at −78° C., and then allowed to warm to ambient temperature. The resulting suspension was vacuum filtered and the solids were washed with minimal MTBE. The resultant filtrate was concentrated in vacuo, and the residue was purified by silica chromatography (30% EtOAc in hexanes) to provide the title compound (1.54 g, 59% yield). $^1$H-NMR (400 MHz, CDCl$_3$) δ 7.78 (d, 2H), 7.34 (d, 2H), 4.37-4.44 (m, 1H), 3.86-3.94 (m, 1H), 2.66-2.73 (m, 2H), 2.45 (s, 3H), 2.08-2.15 (m, 2H), 1.78 (d, 1H).

Intermediate R19

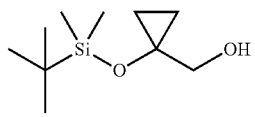

(1-((tert-butyldimethylsilyl)oxy)cyclopropyl)methanol

Step 1: Preparation of methyl 1-((tert-butyldimethylsilyl)oxy)cyclopropane-1-carboxylate A solution of methyl 1-hydroxy-1-cyclopropane carboxylate (2.03 g, 17.5 mmol) in DMF (35 mL) was treated sequentially with imidazole (1.19 g, 17.5 mmol) and tert-butyldimethylsilyl chloride (2.77 g, 18.4 mmol). The resulting mixture was stirred for 60 h at ambient temperature. The reaction mixture was diluted with water, and extracted with Et$_2$O (2×). The organic extracts were washed with water (3×) and brine (1×), then dried over anhydrous Na$_2$SO$_{4(s)}$, filtered and concentrated in vacuo to afford the title compound (3.45 g, 86% yield). $^1$H NMR (400 MHz, CDCl$_3$) δ 3.71 (s, 3H), 1.33-1.30 (m, 2H), 1.08-1.05 (m, 2H), 0.87 (s, 9H), 0.14 (s, 6H).

Step 2: Preparation of ((1-((tert-butyldimethylsilyl)oxy)cyclopropyl)methanol

A solution of methyl 1-((tert-butyldimethylsilyl)oxy)cyclopropane-1-carboxylate (Step 1; 3.45 g, 15.0 mmol) in THF (150 mL) was cooled to 0° C., then treated slowly with 25 wt % DIBAL-H in toluene (25.2 mL, 37.4 mmol). The resulting mixture was stirred for 1 h at ambient temperature. The mixture was cooled to 0° C., and quenched by slowly adding aqueous 0.5 M Sodium potassium L(+)-tartrate tetrahydrate (Rochelle Salt; 50 mL). The quenched mixture was diluted with Et$_2$O, and stirred for 15 min at ambient temperature. The resulting suspension was vacuum filtered, and the solids were washed with minimal Et$_2$O. The filtrate was washed with water (1×) and brine (1×), then dried over anhydrous Na$_2$SO$_{4(s)}$, filtered and concentrated in vacuo to afford the title compound (1.71 mg, 56% yield). $^1$H NMR (400 MHz, CDCl$_3$) δ 3.55-3.54 (d, 2H), 0.87 (s, 9H), 0.79-0.76 (m, 2H), 0.60-0.57 (m, 2H), 0.12 (s, 6H).

Intermediate R20

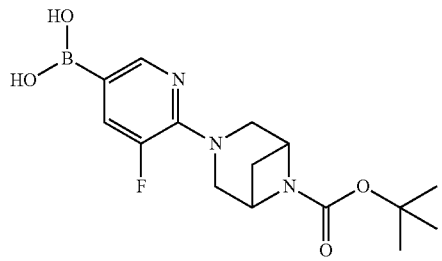 [SMILES: CC(C)(C)OC(=O)N1C2CC1CN(c1ncc(B(O)O)cc1F)C2]

(6-(6-(tert-butoxycarbonyl)-3,6-diazabicyclo[3.1.1]heptan-3-yl)-5-fluoropyridin-3-yl)boronic acid A solution of (5,6-difluoropyridin-3-yl)boronic acid (20 mg, 0.13 mmol), tert-butyl 3,6-diazabicyclo[3.1.1]heptane-6-carboxylate (50 mg, 0.25 mmol) and K$_2$CO$_{3(s)}$ (174 mg, 1.3 mmol) in dioxane (629 μL) was stirred for 3 days at 80° C. The reaction mixture was concentrated in vacuo to provide the title compound (20 mg, quantitative yield) of sufficient purity for use without further purification. MS (apci) m/z=338.1 (M+H).

301

Intermediate R21

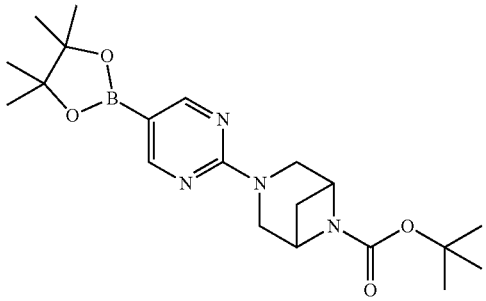 [SMILES: CC(C)(C)OC(=O)N1C2CC1CN(c1ncc(B3OC(C)(C)C(C)(C)O3)cn1)C2]

tert-butyl 3-(5-(4,4,5,5-tetramethyl-1,3,2-dioxaborolan-2-yl)pyrimidin-2-yl)-3,6-diazabicyclo[3.1.1]heptane-6-carboxylate A mixture of 2-fluoro-5-(4,4,5,5-tetramethyl-1,3,2-dioxaborolan-2-yl)pyrimidine (0.311 g, 1.39 mmol), tert-butyl 3,6-diazabicyclo[3.1.1]heptane-6-carboxylate (0.303 g, 1.53 mmol) and DIEA (0.484 mL, 2.78 mmol) in DMF (9.25 mL) was stirred overnight at ambient temperature. The reaction mixture was worked up with EtOAc and water. The organic layer was washed with water and brine, then dried (Na$_2$SO$_4$), filtered and concentrated. The residue was purified by silica chromatography (10-90% EtOAc in hexanes) to afford the title compound (68 mg, 12% yield).

Intermediate R22

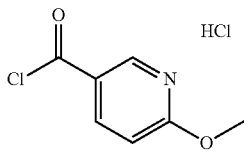

6-methoxynicotinoyl chloride hydrochloride

A suspension of 6-methoxynicotinic acid (18 mg, 0.12 mmol) in SOCl$_2$ (1 mL, 0.12 mmol) was stirred for 30 min at 80° C. After cooling to ambient temperature, the solution was concentrated in vacuo to afford the crude title compound, which was directly used in the next step without further purifications.

Intermediate R23

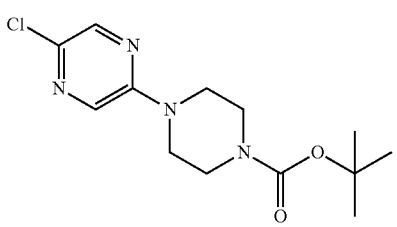 [SMILES: CC(C)(C)OC(=O)N1CCN(c2cnc(Cl)cn2)CC1]

302 tert-butyl 4-(5-chloropyrazin-2-yl)piperazine-1-carboxylate

A solution of 2,5-dichloropyrazine (1.03 g, 6.91 mmol) in DMSO (10 mL) was treated sequentially with K$_2$CO$_{3(s)}$ (2.867 g, 20.74 mmol) and tert-butyl piperazine-1-carboxylate (1.288 g, 6.914 mmol), then stirred overnight at 75° C. After cooling to ambient temperature, the mixture was partitioned between EtOAc (10 mL) and water (20 mL). After phase separation, the organic extracts were concentrated in vacuo to provide the title compound (1.928 g, 93% yield). MS (apci) m/z=199.1 (M-Boc). $^1$H NMR (CDCl$_3$) δ 8.07 (m, 1H), 7.86 (m, 1H), 3.56 (s, 8H), 1.48 (s, 9H).

Intermediate R24

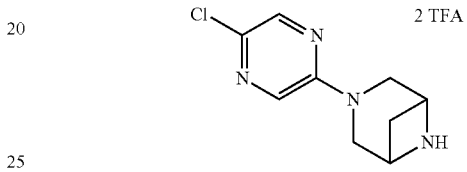

3-(5-chloropyrazin-2-yl)-3,6-diazabicyclo[3.1.1]heptane bis(2,2,2-trifluoroacetate)

A mixture of tert-butyl 3-(5-chloropyrazin-2-yl)-3,6-diazabicyclo[3.1.1]heptane-6-carboxylate (Intermediate R15; 300 mg, 0.965 mmol) in DCM (3.0 mL) was treated with TFA (3.0 mL, 39 mmol), and stirred for 1 h at ambient temperature. The resulting mixture was diluted with Et$_2$O (20 mL). The resulting suspension was filtered, and the isolated solids were dried under high vacuum to afford the title compound (284 mg, 67% yield). MS (apci) m/z=211.1 (M+H).

Intermediate R25

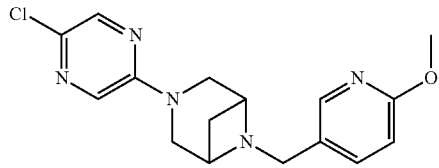 [SMILES: COc1ccc(CN2C3CC2CN(c2cnc(Cl)cn2)C3)cn1]

3-(5-chloropyrazin-2-yl)-6-((6-methoxypyridin-3-yl)methyl)-3,6-diazabicyclo[3.1.1]heptane A solution of 3-(5-chloropyrazin-2-yl)-3,6-diazabicyclo[3.1.1]heptane bis(2,2,2-trifluoroacetate) (Intermediate R24; 284 mg, 0.647 mmol) in DCM (6.47 mL) was treated with 6-methoxynicotinaldehyde (266 mg, 1.94 mmol) and NaBH(AcO)$_3$ (686 mg, 3.24 mmol), then stirred for 1 h at ambient temperature. The reaction mixture was diluted with DCM, and quenched with saturated NH$_4$Cl$_{(aq)}$. After phase separation in a PS Frit with DCM the organic extracts were concentrated in vacuo to afford the crude title compound, which was used in the next step without further purifications assuming quantitative yield. MS (apci) m/z=298.1 (M-Cl).

303

Intermediate R26

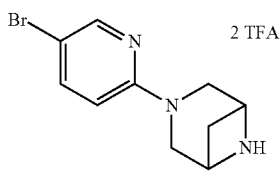 [SMILES: Brc1ccc(N2CC3CC(C2)N3)nc1 ; "2 TFA"]

3-(5-bromopyridin-2-yl)-3,6-diazabicyclo[3.1.1]
heptane bis(2,2,2-trifluoroacetate)

A mixture of tert-butyl 3-(5-bromopyridin-2-yl)-3,6-diazabicyclo[3.1.1]heptane-6-carboxylate (Intermediate R4, Step 1, Method 1; 470 mg, 1.3 mmol), in DCM (2.0 mL) was treated with TFA (2.0 mL, 26.1 mmol), and stirred for 1 h at ambient temperature. The resulting mixture was concentrated in vacuo to afford the title compound (478 mg, 75% yield). MS (apci) m/z=256.0 (M+H).

Intermediate R27

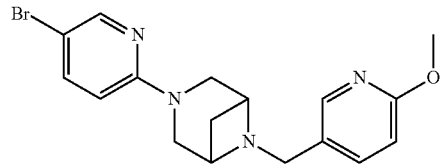

3-(5-bromopyridin-2-yl)-6-((6-methoxypyridin-3-yl)
methyl)-3,6-diazabicyclo[3.1.1]heptane A mixture of 3-(5-bromopyridin-2-yl)-3,6-diazabicyclo[3.1.1]heptane bis(2,2,2-trifluoroacetate) (Intermediate R26; 478 mg, 1.3 mmol) and 6-methoxynicotinaldehyde (267 mg, 1.95 mmol) in DCM (10 mL) was treated with NaBH(AcO)$_3$ (551 mg, 2.60 mmol). The resulting mixture was stirred for 30 min at ambient temperature before TEA (544 µL, 3.90 mmol) was introduced. The reaction mixture was stirred for 16 h at ambient temperature. The resulting mixture was quenched with saturated NaHCO$_{3(aq)}$, and then the biphasic mixture was extracted with DCM. The organic extracts were concentrated in vacuo, and the residue was purified by silica chromatography (using 0-5% MeOH in DCM as the gradient eluent) to cleanly afford the title compound (163 mg, 33% yield). MS (apci) m/z=377.1 (M+H).

Intermediate R28

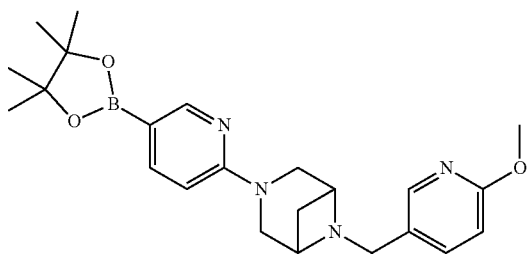

304

6-(((6-methoxypyridin-3-yl)methyl)-3-(5-(4,4,5,5-tetramethyl-1,3,2-dioxaborolan-2-yl)pyridin-2-yl)-3,
6-diazabicyclo[3.1.1]heptane A mixture of 3-(5-bromopyridin-2-yl)-6-((6-methoxypyridin-3-yl)methyl)-3,6-diazabicyclo[3.1.1]heptane (Intermediate R27; 150 mg, 0.400), bis(pinacolato)diboron (305 mg, 1.20 mmol), PdCl$_2$(dppf).CH$_2$Cl$_2$ (32.6 mg, 0.0400 mmol) and KOAc (118 mg, 1.20 mmol) in dioxane (4.00 mL) was sparged with Ar$_{(g)}$, then stirred overnight at 80° C. After cooling to ambient temperature, the reaction mixture was diluted with EtOAc, then filtered. The filtrate was concentrated in vacuo, and the residue was purified by silica chromatography (using 50-100% Hexanes:EtOAc as the gradient eluent) to afford the title compound (118 mg, 70% yield). MS (apci) m/z=341.2 (corresponding boronic acid M+H).

Preparation of Synthetic Examples

Example 1

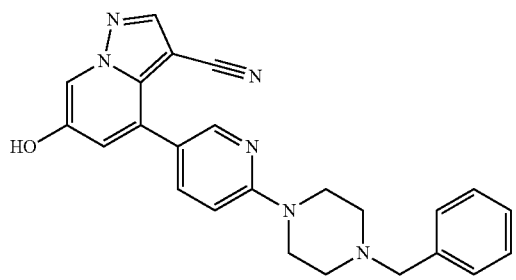 [SMILES: N#Cc1cnn2cc(O)cc(-c3ccc(N4CCN(Cc5ccccc5)CC4)nc3)c12]

4-(6-(benzylpiperazin-1-yl)pyridin-3-yl)-6-hydroxy-pyrazolo[1,5-a]pyridine-3-carbonitrile In a pressure vessel, 4-bromo-6-methoxypyrazolo[1,5-a]pyridine-3-carbonitrile (Intermediate P1; 0.25 g, 1.05 mmol), 1-benzyl-4-(5-(4,4,5,5-tetramethyl-1,3,2-dioxaborolan-2-yl)pyridin-2-yl)piperazine (Intermediate R1; 0.478 g, 1.26 mmol) and Pd(PPh$_3$)$_4$ (0.121 g, 0.105 mmol) were suspended in 2 M Na$_2$CO$_{3(aq)}$ (2.63 mL, 5.25 mmol) and 1,4-dioxane (2 mL). The resulting mixture was sparged with N$_{2(g)}$. The vessel was sealed, and the mixture was stirred for 5 h at 100° C. The reaction mixture was cooled to room temperature, and then treated with water (10 mL). The resulting biphasic mixture was extracted with several portions of DCM in a PS frit. The combined organic extracts were concentrated in vacuo, and then purified by C18 reverse phase chromatography (5-95% water-ACN with 0.1% TFA as the gradient eluent) to afford the title compound as the TFA salt. The salt was partitioned between 4:1 DCM:iPrOH and saturated NaHCO$_{3(aq)}$. The resulting organic extracts were dried over anhydrous Na$_2$SO$_{4(s)}$, filtered and concentrated in vacuo to cleanly provide the title compound (262.5 mg, 61% yield). MS (apci) m/z=411.2 (M+H).

Example 2

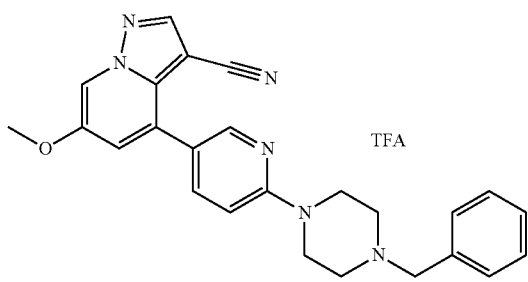 [SMILES: COc1cc(-c2ccc(N3CCN(Cc4ccccc4)CC3)nc2)c2c(C#N)cnn2c1]

TFA 4-(6-(4-benzylpiperazin-1-yl)pyridin-3-yl)-6-methoxypyrazolo[1,5-a]pyridine-3-carbonitrile 2,2,2-trifluoroacetate A solution of 6-methoxy-4-(6-(piperazin-1-yl)pyridin-3-yl)pyrazolo[1,5-a]pyridine-3-carbonitrile hydrochloride (Intermediate P2; 25 mg, 0.075 mmol) in DMA (750 µL) was treated with TEA (78 µL, 0.45 mmol) and (bromomethyl)benzene (18 µL, 0.15 mmol), and allowed to stir overnight at ambient temperature. The mixture was diluted with water and extracted with EtOAc. The combined organic extracts were dried over anhydrous $Na_2SO_{4(s)}$, filtered, and concentrated in vacuo. The crude residue was purified by C18 reverse phase chromatography (5-95% ACN/water with 0.1% TFA as the gradient eluent) to afford the title compound (11.9 mg, 37% yield). MS (apci) m/z=425.2 (M+H).

Example 3

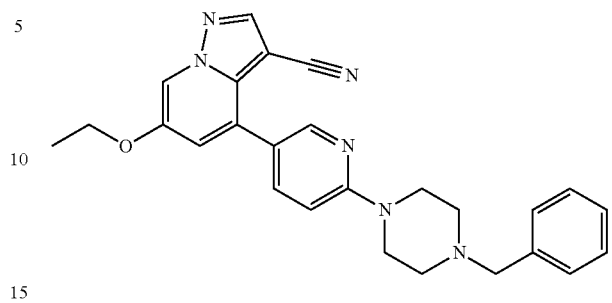

4-(6-(4-benzylpiperazin-1-yl)pyridin-3-yl)-6-ethoxypyrazolo[1,5-a]pyridine-3-carbonitrile A solution of 4-(6-(4-benzylpiperazin-1-yl)pyridin-3-yl)-6-hydroxypyrazolo[1,5-a]pyridine-3-carbonitrile (Example 1; 30 mg, 0.0731 mmol) in DMF (500 µL) was treated sequentially with $K_2CO_{3(s)}$ (20.2 mg, 0.146 mmol) and bromoethane (10.9 µL, 0.146 mmol), and then stirred 16 h at 50° C. After cooling to ambient temperature, the reaction mixture was directly purified by C18 reverse phase chromatography (10-100% ACN/$H_2O$ as the gradient eluent) to afford the title compound (11.0 mg, 34% yield). MS (apci) m/z=439.2 (M+H).

The compounds in Table A were prepared using a similar method to that described for the synthesis of Example 3, replacing bromoethane with the appropriate alkyl halide. Reactions were monitored for completion by LCMS, and reaction durations were adjusted accordingly. Each of the title compounds were cleanly isolated following C18 reverse phase chromatography using an appropriate gradient. Where noted (*) persistent colored impurities were removed by sequential dissolution in DCM, treatment with activated charcoal, filtration through Celite® and concentration in vacuo.

TABLE A

| Ex # | Structure | Chemical Name | MS (apci) m/z |
|---|---|---|---|
| 4 | 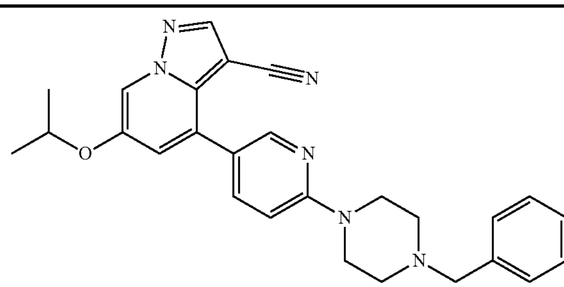 | 4-(6-(4-benzylpiperazin-1-yl)pyridin-3-yl)-6-isopropoxypyrazolo[1,5-a]pyridine-3-carbonitrile | 453.2 (M + H) |
| 5 | 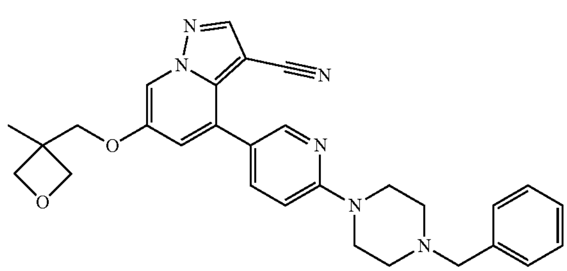 [SMILES: CC1(COc2cc(-c3ccc(N4CCN(Cc5ccccc5)CC4)nc3)c3c(C#N)cnn3c2)COC1] | 4-(6-(4-benzylpiperazin-1-yl)pyridin-3-yl)-6-((3-methyloxetan-3-yl)methoxy)pyrazolo[1,5-a]pyridine-3-carbonitrile | 495.2 (M + H) |

TABLE A-continued

| Ex # | Structure | Chemical Name | MS (apci) m/z |
|---|---|---|---|
| 6 | 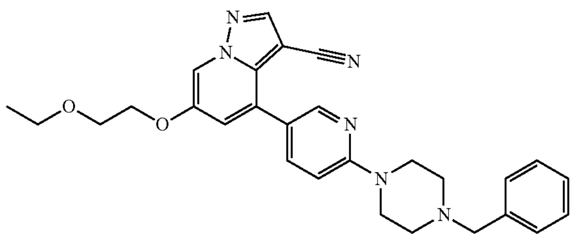 [SMILES: CCOCCOc1cc(-c2ccc(N3CCN(Cc4ccccc4)CC3)nc2)c2c(C#N)cnn2c1] | 4-(6-(4-benzylpiperazin-1-yl)pyridin-3-yl)-6-(2-ethoxyethoxy)pyrazolo[1,5-a]pyridine-3-carbonitrile | 483.2 (M + H) |
| 7 | 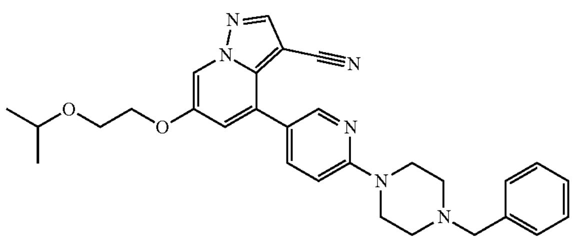 [SMILES: CC(C)OCCOc1cc(-c2ccc(N3CCN(Cc4ccccc4)CC3)nc2)c2c(C#N)cnn2c1] | 4-(6-(4-benzylpiperazin-1-yl)pyridin-3-yl)-6-(2-isopropoxyethoxy)pyrazolo[1,5-a]pyridine-3-carbonitrile | 497.2 (M + H) |
| 8 | 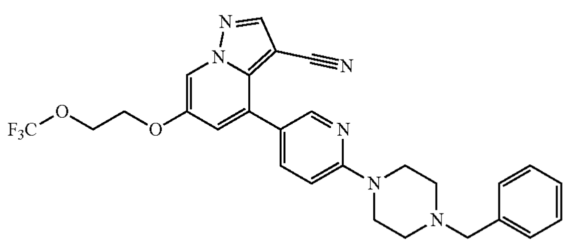 [SMILES: N#Cc1cnn2cc(OCCOC(F)(F)F)cc(-c3ccc(N4CCN(Cc5ccccc5)CC4)nc3)c12] | 4-(6-(4-benzylpiperazin-1-yl)pyridin-3-yl)-6-(2-(trifluoromethoxy)ethoxy)pyrazolo[1,5-a]pyridine-3-carbonitrile | 523.2 (M + H) |
| 9 | 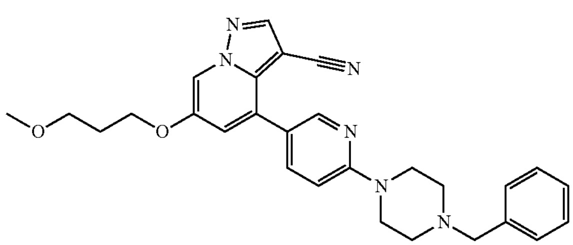 [SMILES: COCCCOc1cc(-c2ccc(N3CCN(Cc4ccccc4)CC3)nc2)c2c(C#N)cnn2c1] | 4-(6-(4-benzylpiperazin-1-yl)pyridin-3-yl)-6-(3-methoxypropoxy)pyrazolo[1,5-a]pyridine-3-carbonitrile | 483.2 (M + H) |
| 10 | 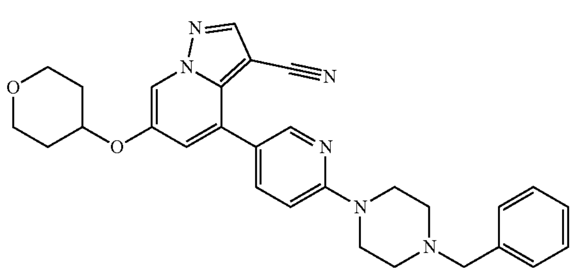 [SMILES: N#Cc1cnn2cc(OC3CCOCC3)cc(-c3ccc(N4CCN(Cc5ccccc5)CC4)nc3)c12] | 4-(6-(4-benzylpiperazin-1-yl)pyridin-3-yl)-6-((tetrahydro-2H-pyran-4-yl)oxy)pyrazolo[1,5-a]pyridine-3-carbonitrile | 495.2 (M + H) |
| 11 | 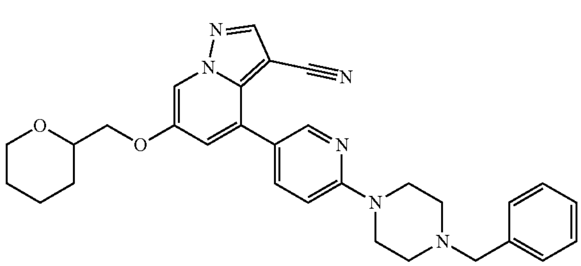 [SMILES: N#Cc1cnn2cc(OCC3CCCCO3)cc(-c3ccc(N4CCN(Cc5ccccc5)CC4)nc3)c12] | 4-(6-(4-benzylpiperazin-1-yl)pyridin-3-yl)-6-((tetrahydro-2H-pyran-2-yl)methoxy)pyrazolo[1,5-a]pyridine-3-carbonitrile | 509.2 (M + H) |

Example 12

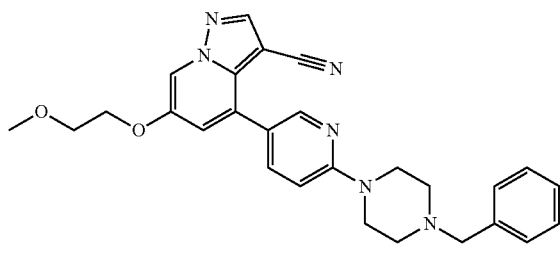 [SMILES: COCCOc1cc(-c2ccc(N3CCN(Cc4ccccc4)CC3)nc2)c2c(C#N)cnn2c1]

4-(6-(4-benzylpiperazin-1-yl)pyridin-3-yl)-6-(2-methoxyethoxy)pyrazolo[1,5-a]pyridine-3-carbonitrile A solution of 4-(6-(4-benzylpiperazin-1-yl)pyridin-3-yl)-6-hydroxypyrazolo[1,5-a]pyridine-3-carbonitrile (Example 1; 32.3 mg, 0.0787 mmol) in DMF (800 μL) was treated sequentially with $K_2CO_{3(s)}$ (21.8 mg, 0.157 mmol) and 2-bromoethyl methyl ether (14.8 μL, 0.157 mmol), and then stirred 16 h at 50° C. After cooling to ambient temperature, the reaction mixture was diluted with EtOAc, and washed with water and brine. The combined organic extracts were dried over anhydrous $Na_2SO_{4(s)}$, filtered, and concentrated in vacuo. The residue was purified by C18 reverse phase chromatography (5-95% water-ACN with 0.1% TFA as the gradient eluent) to cleanly provide the title compound as the TFA salt. The salt was partitioned between 4:1 DCM:iPrOH and saturated $NaHCO_{3(aq)}$. The resulting organic extracts were dried over anhydrous $Na_2SO_{4(s)}$, filtered and concentrated in vacuo to afford the title compound (19.3 mg, 52% yield). MS (apci) m/z=469.2 (M+H).

Example 13

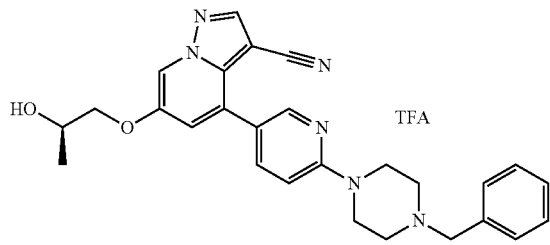 [SMILES: C[C@@H](O)COc1cc(-c2ccc(N3CCN(Cc4ccccc4)CC3)nc2)c2c(C#N)cnn2c1]

(R)-4-(6-(4-benzylpiperazin-1-yl)pyridin-3-yl)-6-(2-hydroxypropoxy)pyrazolo[1,5-a]pyridine-3-carbonitrile 2,2,2-trifluoroacetate A solution of (R)-6-(2-hydroxypropoxy)-4-(6-(piperazin-1-yl)pyridin-3-yl)pyrazolo[1,5-a]pyridine-3-carbonitrile hydrochloride (Intermediate P28; 6 mg, 0.0145 mmol) in DCE (145 μL)/MeOH (5 drops) was treated sequentially with benzaldehyde (3.07 mg, 0.0289 mmol) and NaBH(AcO)$_3$ (12.3 mg, 0.0578 mmol). The resulting mixture was stirred for 1 hour at ambient temperature and then purified directly by C18 reverse phase chromatography (5-95% water-ACN with 0.1% TFA as the gradient eluent) to cleanly provide the title compound as the TFA salt (7.5 mg, 89% yield). MS (apci) m/z=468.9 (M+H).

Example 14

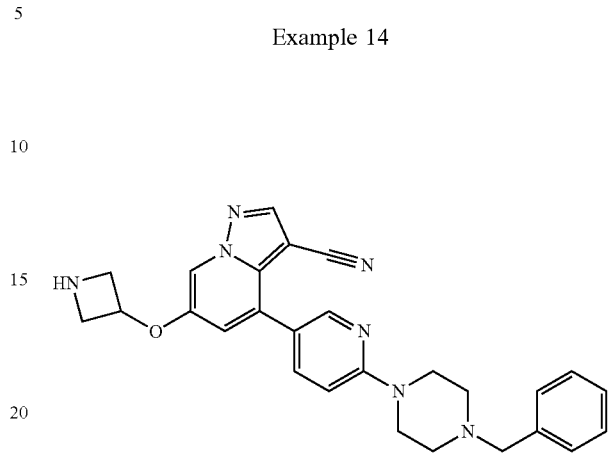

6-(azetidin-3-yloxy)-4-(6-(4-benzylpiperazin-1-yl)pyridin-3-yl)pyrazolo[1,5-a]pyridine-3-carbonitrile

Step 1: Preparation of tert-butyl 3-((4-(6-(4-benzylpiperazin-1-yl)pyridin-3-yl)-3-cyanopyrazolo[1,5-a]pyridin-6-yl)oxy)azetidine-1-carboxylate A solution of 4-(6-(4-benzylpiperazin-1-yl)pyridin-3-yl)-6-hydroxypyrazolo[1,5-a]pyridine-3-carbonitrile (Example 1; 27.8 mg, 0.0678 mmol) in DMF (1.4 mL) was treated with $K_2CO_{3(s)}$ (468 mg, 0.339 mmol) and 1-Boc-3-iodoazetidine (38.3 mg, 0.135 mmol) and then stirred for 16 h at 80° C. After cooling to ambient temperature, the reaction mixture was diluted with EtOAc and washed with water and brine. The combined organic extracts were dried over anhydrous $Na_2SO_{4(s)}$, filtered, and concentrated in vacuo. Purification by silica chromatography (0-30% DCM-MeOH with 2% $NH_4OH$ as the gradient eluent) provided the title compound, which was carried directly into step 2. MS (apci) m/z=566.2 (M+H).

Step 2: Preparation of 6-(azetidin-3-yloxy)-4-(6-(4-benzylpiperazin-1-yl)pyridin-3-yl)pyrazolo[1,5-a]pyridine-3-carbonitrile A solution of tert-butyl 3-((4-(6-(4-benzylpiperazin-1-yl)pyridin-3-yl)-3-cyanopyrazolo[1,5-a]pyridin-6-yl)oxy)azetidine-1-carboxylate in 1:1 DCM:TFA (2 mL) was stirred for 30 min at ambient temperature. The mixture was concentrated in vacuo, and purified by C18 reverse phase chromatography (5-95% water-ACN with 0.1% TFA as the gradient eluent) to cleanly provide the title compound as the TFA salt. The salt was partitioned between 4:1 DCM:iPrOH and saturated $NaHCO_{3(aq)}$. The resulting organic extracts were dried over anhydrous $Na_2SO_{4(s)}$, filtered and concentrated in vacuo to afford the title compound (16.9 mg, 54% yield). MS (apci) m/z=466.2 (M+H).

Example 15

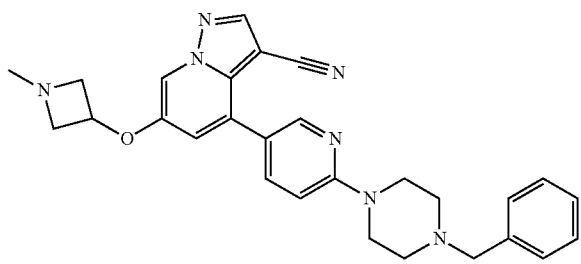 [SMILES: CN1CC(Oc2cc(-c3ccc(N4CCN(Cc5ccccc5)CC4)nc3)c3c(C#N)cnn3c2)C1]

4-(6-(4-Benzylpiperazin-1-yl)pyridin-3-yl)-6-((1-methylazetidin-3-yl)oxy)pyrazolo[1,5-a]pyridine-3-carbonitrile A solution of 6-(azetidin-3-yloxy)-4-(6-(4-benzylpiperazin-1-yl)pyridin-3-yl)pyrazolo[1,5-a]pyridine-3-carbonitrile (Example 14; 12.4 mg, 0.0266 mmol) in formic acid (401.9 µL) was treated with formaldehyde (200.1 µL, 2.664 mmol). The resulting mixture was stirred for 16 h at 80° C. before introducing additional formaldehyde (200.1 µL, 2.664 mmol) and formic acid (200 µL). The mixture was stirred for 60 h at 80° C. After cooling to room temperature, the mixture was concentrated in vacuo, and purified by C18 reverse phase chromatography (5-95% ACN/water with 0.1% TFA as the gradient eluent) to afford the title compound as the TFA salt. The salt was partitioned between 4:1 DCM:iPrOH and saturated NaHCO$_{3(aq)}$. The resulting organic extracts were separated, dried over anhydrous Na$_2$SO$_{4(s)}$, filtered and concentrated in vacuo to afford the title compound (6.7 mg, 47% yield). MS (apci) m/z=480.2 (M+H).

Example 16

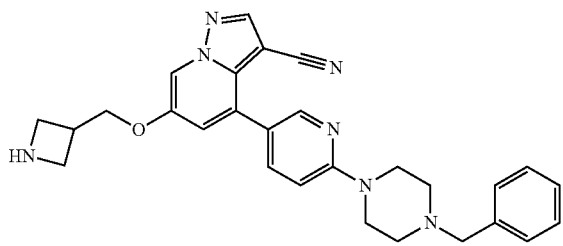 [SMILES: N#Cc1cnn2cc(OCC3CNC3)cc(-c3ccc(N4CCN(Cc5ccccc5)CC4)nc3)c12]

6-(Azetidin-3-ylmethoxy)-4-(6-(4-benzylpiperazin-1-yl)pyridin-3-yl)pyrazolo[1,5-a]pyridine-3-carbonitrile

Step 1: Preparation of tert-butyl 3-(((4-(6-(4-benzylpiperazin-1-yl)pyridin-3-yl)-3-cyanopyrazolo[1,5-a]pyridin-6-yl)oxy)methyl)azetidine-1-carboxylate A cold (0° C.) solution of PPh$_3$ (77 mg, 0.29 mmol) in 1:1 DCM:THF (2.0 mL) was treated with DIAD (58 µL, 0.29 mmol), and stirred for 15 min at 0° C. The resulting 0° C. mixture was treated with a solution of (4-(6-(4-benzylpiperazin-1-yl)pyridin-3-yl)-6-hydroxypyrazolo[1,5-a]pyridine-3-carbonitrile (Example 1; 60 mg, 0.15 mmol) and 1-Boc-azetidine-3-yl methanol (55 mg, 0.29 mmol) in 1:1 DCM:THF (4.0 mL). After stirring overnight at room temperature, the reaction mixture was concentrated in vacuo, and purified by C18 reverse phase chromatography (5-95% ACN/water with 0.1% TFA as the gradient eluent) to afford the title compound as the TFA salt. The salt was partitioned between 4:1 DCM:iPrOH and saturated NaHCO$_{3(aq)}$. The resulting organic extracts were separated, dried over anhydrous Na$_2$SO$_{4(s)}$, filtered and concentrated in vacuo to afford the title compound (28 mg, 33% yield). MS (apci) m/z=580.2 (M+H).

Step 2: Preparation of 6-(azetidin-3-ylmethoxy)-4-(6-(4-benzylpiperazin-1-yl)pyridin-3-yl)pyrazolo[1,5-a]pyridine-3-carbonitrile A solution of tert-butyl 3-(((4-(6-(4-benzylpiperazin-1-yl)pyridin-3-yl)-3-cyanopyrazolo[1,5-a]pyridin-6-yl)oxy)methyl)azetidine-1-carboxylate in DCM (4 mL) was treated with TFA (2.0 mL). The resulting mixture was stirred for 30 min at ambient temperature, and then purified directly by C18 reverse phase chromatography (5-95% ACN/water with 0.1% TFA as the gradient eluent) to afford the title compound as the TFA salt. The salt was partitioned between 4:1 DCM:iPrOH and saturated NaHCO$_{3(aq)}$. The resulting organic extracts were separated, dried over anhydrous Na$_2$SO$_{4(s)}$, filtered and concentrated in vacuo to cleanly provide the title compound (43 mg, 62% yield). MS (apci) m/z=480.2 (M+H).

Example 17

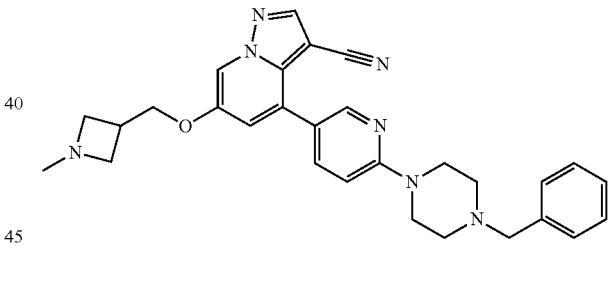

4-(6-(4-benzylpiperazin-1-yl)pyridin-3-yl)-6-((1-methylazetidin-3-yl)methoxy)pyrazolo[1,5-a]pyridine-3-carbonitrile A solution of 6-(azetidin-3-ylmethoxy)-4-(6-(4-benzylpiperazin-1-yl)pyridin-3-yl)pyrazolo[1,5-a]pyridine-3-carbonitrile (Example 16; 22 mg, 0.046 mmol) in formic acid (3.46 µL) was treated with formaldehyde (1.28 µL, 45.9 mmol). The resulting mixture was stirred for 5 days at 80° C. After cooling to room temperature, the mixture was concentrated in vacuo. The residue was partitioned between 4:1 DCM:iPrOH and saturated NaHCO$_{3(aq)}$. The resulting organic extracts were combined, dried over anhydrous Na$_2$SO$_{4(s)}$, filtered and concentrated in vacuo. The crude residue was purified by C18 reverse phase chromatography (5-95% ACN/water with 0.1% TFA as the gradient eluent), followed by silica gel chromatography (10-40% MeOH in EtOAc as the gradient eluent) to cleanly provide the title compound (3 mg, 13% yield). MS (apci) m/z=494.2 (M+H).

Example 18

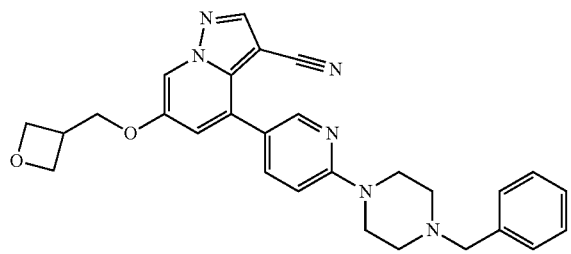 [SMILES: N#Cc1cnn2cc(OCC3COC3)cc(-c3ccc(N4CCN(Cc5ccccc5)CC4)nc3)c12]

4-(6-(4-benzylpiperazin-1-yl)pyridin-3-yl)-6-(oxetan-3-ylmethoxy)pyrazolo[1,5-a]pyridine-3-carbonitrile A cold (0° C.) solution of PPh$_3$ (51 mg, 0.19 mmol) in 1:1 DCM:THF (2.0 mL) was treated with DIAD (38 µL, 0.19 mmol) and stirred for 15 min at 0° C. The resulting 0° C. mixture was treated with a solution of (4-(6-(4-benzylpiperazin-1-yl)pyridin-3-yl)-6-hydroxypyrazolo[1,5-a]pyridine-3-carbonitrile (Example 1; 40 mg, 0.097 mmol) and oxetan-3-ylmethanol (17 mg, 0.19 mmol) in 1:1 DCM:THF (3.0 mL). The reaction mixture was stirred for 1 hour at 0° C., then for 1 hour at room temperature. The mixture was directly purified by C18 reverse phase chromatography (5-95% ACN/water with 0.1% TFA as the gradient eluent) to afford the title compound as the TFA salt. The salt was partitioned between 4:1 DCM:iPrOH and saturated NaHCO$_{3(aq)}$. The resulting organic extracts were combined, dried over anhydrous Na$_2$SO$_{4(s)}$, filtered and concentrated in vacuo to afford the title compound (28 mg, 60% yield). MS (apci) m/z=481.2 (M+H).

Example 19

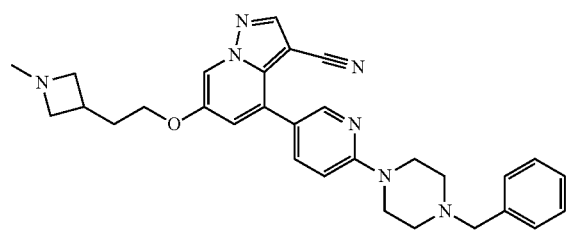 [SMILES: CN1CC(CCOc2cc(-c3ccc(N4CCN(Cc5ccccc5)CC4)nc3)c3c(C#N)cnn3c2)C1]

4-(6-(4-Benzylpiperazin-1-yl)pyridin-3-yl)-6-(2-(1-methylazetidin-3-yl)ethoxy)pyrazolo[1,5-a]pyridine-3-carbonitrile The title compound was prepared using a similar procedure to that described for Example 18, replacing oxetan-3-ylmethanol with 2-(1-methylazetidin-3-yl)ethanol. Following chromatographic purification (10-30% MeOH in DCM as the gradient eluent), the title compound was isolated cleanly (16 mg, 32% yield). MS (apci) m/z=508.3 (M+H).

Example 20

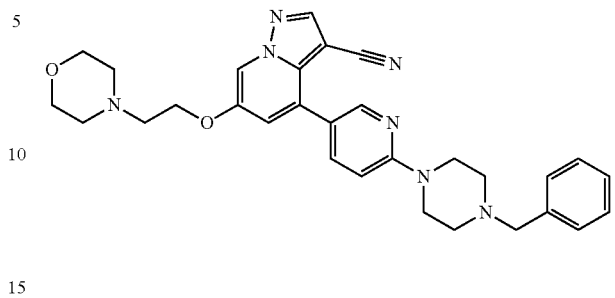

4-(6-(4-Benzylpiperazin-1-yl)pyridin-3-yl)-6-(2-morpholinoethoxy)pyrazolo[1,5-a]pyridine-3-carbonitrile A solution of 4-(6-(4-benzylpiperazin-1-yl)pyridin-3-yl)-6-hydroxypyrazolo[1,5-a]pyridine-3-carbonitrile (Example 1; 28.2 mg, 0.0687 mmol) in DMF (0.8 mL) was treated with 4-(2-chloroethyl)morpholine hydrochloride (25.6 mg, 0.137 mmol) and K$_2$CO$_{3(s)}$ (47.5 mg, 0.344 mmol), then stirred 16 h at 50° C. After cooling to ambient temperature, the reaction mixture was diluted with water and extracted with EtOAc. The combined organic extracts were washed with water and brine, then dried over anhydrous Na$_2$SO$_{4(s)}$, filtered, and concentrated in vacuo. Purification of the resulting crude product by C18 reverse phase chromatography (5-95% water-ACN with 0.1% TFA as the gradient eluent) cleanly provided the title compound as the TFA salt. The salt was partitioned between 4:1 DCM:iPrOH and saturated NaHCO$_{3(aq)}$. The resulting organic extracts were combined, dried over anhydrous Na$_2$SO$_{4(s)}$, filtered and concentrated in vacuo to afford the title compound (19.9 mg, 55% yield). MS (apci) m/z=524.2 (M+H). $^1$H NMR (400 MHz, DMSO-d$^6$) δ: 8.70-8.69 (d, 1H), 8.57 (s, 1H), 8.32-8.31 (d, 1H), 7.78-7.75 (dd, 1H), 7.35-7.25 (m, 6H), 6.93-6.91 (d, 1H), 4.23-4.20 (t, 2H), 3.60-3.56 (m, 8H), 3.53 (s, 2H), 2.74-2.71 (t, 2H), 2.50-2.47 (m, 8H).

Example 21

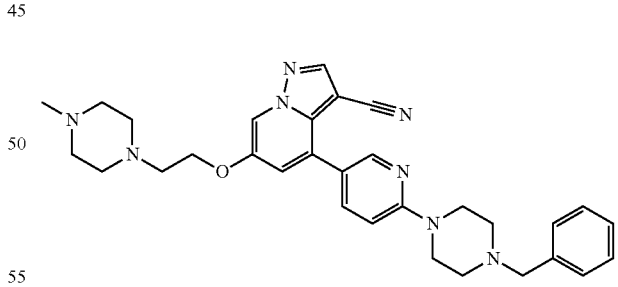

4-(6-(4-Benzylpiperazin-1-yl)pyridin-3-yl)-6-(2-(4-methylpiperazin-1-yl)ethoxy)pyrazolo[1,5-a]pyridine-3-carbonitrile A cold (0° C.) solution of PPh$_3$ (32.6 mg, 0.124 mmol) in 1:1 DCM:THF (1.0 mL) was treated with DIAD (24.5 µL, 0.124 mmol), and stirred for 15 min at 0° C. The resulting 0° C. mixture was treated with a solution of (4-(6-(4-benzylpiperazin-1-yl)pyridin-3-yl)-6-hydroxypyrazolo[1,5-a]pyridine-3-carbonitrile (Example 1; 34.0 mg, 0.0828 mmol) and 1-(N-hydroxyethyl)-4-methyl piperazine (14.3 mg, 0.0994 mmol) in 1:1 DCM:THF (2.0 mL). The reaction mixture was stirred for 16 h at room temperature and then concentrated in vacuo. Purification of the crude residue by C18 reverse phase chromatography (5-95% water-ACN with 0.1% TFA as the gradient eluent) cleanly provided the title compound as the TFA salt. The salt was converted to the free base by partitioning between 4:1 DCM:iPrOH and saturated NaHCO$_{3(aq)}$. The resulting organic extracts were combined, dried over anhydrous Na$_2$SO$_{4(s)}$, filtered and concentrated in vacuo to afford the title compound (20.1 mg, 45% yield). MS (apci) m/z=537.2 (M+H). $^1$H NMR (400 MHz, DMSO-d$^6$) δ: 8.70-8.69 (d, 1H), 8.57 (s, 1H), 8.32-8.31 (d, 1H), 7.78-7.75 (dd, 1H), 7.52 (s, 1H), 7.35-7.25 (m, 5H), 6.93-6.91 (d, 1H), 4.21-4.18 (t, 2H), 3.60-3.57 (m, 4H), 3.53 (s, 2H), 3.18-3.13 (q, 2H), 2.73-2.70 (t, 2H), 2.50-2.47 (m, 8H), 2.13 (s, 3H), 1.32-1.28 (t, 2H).

Example 22

4-(6-(4-benzylpiperazin-1-yl)pyridin-3-yl)-6-(2-(dimethylamino)ethoxy)pyrazolo[1,5-a]pyridine-3-carbonitrile The title compound was prepared using a similar procedure to that described for Example 21, replacing 1-(N-hydroxyethyl)-4-methyl piperazine with N,N-dimethylethanolamine. After the salt was converted to the free base, an additional purification by silica chromatography (1-30% DCM-MeOH with 2% NH$_4$OH as the gradient eluent) was performed to cleanly isolate the title compound (12.2 mg, 37% yield). MS (apci) m/z=482.2 (M+H).

Example 23

4-(6-(4-(3-hydroxy-2-phenylpropanoyl)piperazin-1-yl)pyridin-3-yl)-6-methoxypyrazolo[1,5-a]pyridine-3-carbonitrile A solution of 6-methoxy-4-(6-(piperazin-1-yl)pyridin-3-yl)pyrazolo[1,5-a]pyridine-3-carbonitrile hydrochloride (Intermediate P2; 25 mg, 0.0748 mmol) in DCM (1 mL) was treated with DIEA (78.1 μL, 0.449 mmol), 3-hydroxy-2-phenylpropanoic acid (24.8 mg, 0.150 mmol) and HATU (33 mg, 0.086 mmol), then stirred overnight at ambient temperature. The resulting mixture was extracted with EtOAc, and the combined organic extracts were dried over anhydrous Na$_2$SO$_{4(s)}$, filtered, and concentrated in vacuo. Purification of the crude residue by C18 reverse phase chromatography (0-75% ACN/water as the gradient eluent) cleanly provided the title compound (15.7 mg, 41% yield). MS (apci) m/z=483.2 (M+H).

Example 24

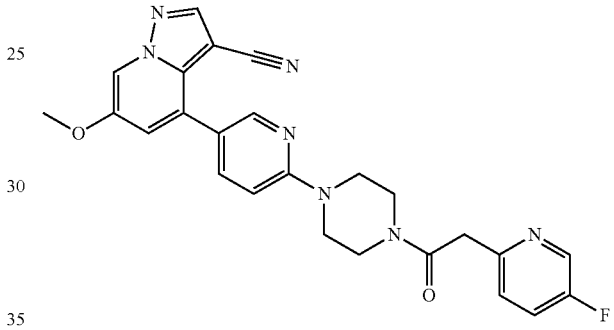

4-(6-(4-(2-(5-Fluoropyridin-2-yl)acetyl)piperazin-1-yl)pyridin-3-yl)-6-methoxypyrazolo[1,5-a]pyridine-3-carbonitrile The title compound (17 mg, 45% yield) was prepared and purified using a similar procedure to that described for Example 23, replacing 3-hydroxy-2-phenylpropanoic acid with 2-(5-fluoropyridin-2-yl)acetic acid, and using 6 equivalents of DIEA instead of 5 equivalents. MS (apci) m/z=472.2 (M+H).

Example 25

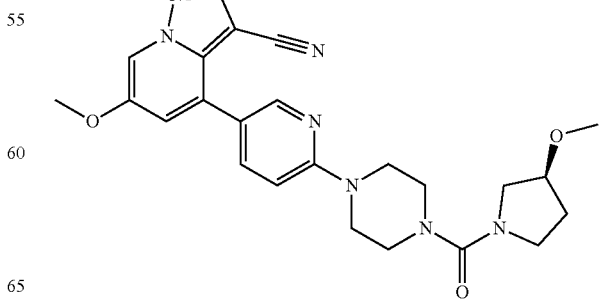

(S)-6-methoxy-4-(6-(4-(3-methoxypyrrolidine-1-carbonyl)piperazin-1-yl)pyridin-3-yl)pyrazolo[1,5-a]pyridine-3-carbonitrile A stirred solution of 4-bromo-6-methoxypyrazolo[1,5-a]pyridine-3-carbonitrile (Intermediate P1, Step 6 of Part B; 20 mg, 0.079 mmol) in dioxane (2.0 mL) was treated with (S)-(6-(4-(3-methoxypyrrolidine-1-carbonyl)piperazin-1-yl)pyridin-3-yl)boronic acid (Intermediate R2; 40 mg, 0.12 mmol) and 2 M $K_2CO_{3(aq)}$ (79 μL, 0.16 mmol), and then purged with $N_{2(g)}$ for 5 min. The mixture was treated with X-Phos (7.6 mg, 0.016 mmol) and $Pd_2(dba)_3$ (3.6 mg, 0.0040 mmol), then purged again with $N_{2(g)}$ for 5 min. The resulting degassed mixture was stirred overnight at 80° C. After cooling to ambient temperature, the reaction mixture was diluted with water and extracted with EtOAc. The combined organic extracts were dried over anhydrous $Na_2SO_{4(s)}$, filtered, and concentrated in vacuo. Purification of the crude residue by silica chromatography (0-50%, 20% MeOH/DCM in EtOAc as the gradient eluent) cleanly provided the title compound (22 mg, 58% yield). MS (apci) m/z=462.2 (M+H).

Example 26

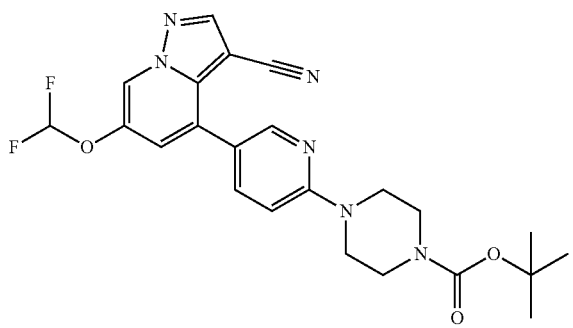 [SMILES: CC(C)(C)OC(=O)N1CCN(c2ccc(-c3cc(OC(F)F)cn4ncc(C#N)c34)cn2)CC1]

tert-butyl 4-(5-(3-cyano-6-(difluoromethoxy)pyrazolo[1,5-a]pyridin-4-yl)pyridin-2-yl)piperazine-1-carboxylate In a pressure vessel, a solution of tert-butyl 4-(5-(3-cyano-6-hydroxypyrazolo[1,5-a]pyridin-4-yl)pyridin-2-yl)piperazine-1-carboxylate (Intermediate P3; 150 mg, 0.357 mmol) in ACN (2 mL) and 30 wt % $KOH_{(aq)}$ (1.78 mL, 0.357 mmol) was cooled to −78° C., then treated with 2-chloro-2,2-difluoro-1-phenylethanone (262.9 μL, 1.784 mmol) before sealing the vessel. The reaction mixture was allowed to warm to ambient temperature over a period of 1 hour, and subsequently stirred for 4 h at 80° C. Upon cooling to room temperature, the resulting mixture was diluted with water and extracted with DCM. The combined organic extracts were washed with brine, and the ensuing emulsion was filtered through a glass frit. After separation from the emulsion, the organic extracts were dried over anhydrous $MgSO_{4(s)}$, filtered, and concentrated in vacuo. The crude material was purified by silica chromatography (0-75% acetone/hexanes as the gradient eluent) to cleanly provide the title compound (58 mg, 35% yield). MS (apci) m/z=471.1 (M+H).

Example 27

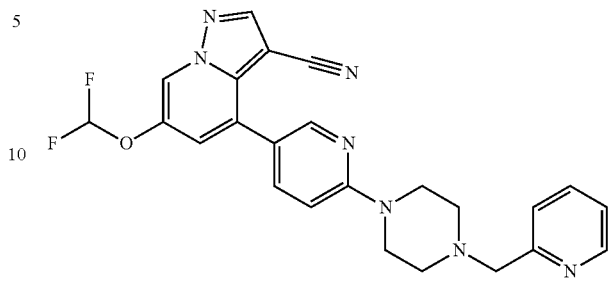

6-(Difluoromethoxy)-4-(6-(4-(pyridin-2-ylmethyl)piperazin-1-yl)pyridin-3-yl)pyrazolo[1,5-a]pyridine-3-carbonitrile

Step 1: Preparation of 6-(Difluoromethoxy)-4-(6-(piperazin-1-yl)pyridin-3-yl)pyrazolo[1,5-a]pyridine-3-carbonitrile dihydrochloride A solution of tert-butyl 4-(5-(3-cyano-6-(difluoromethoxy)pyrazolo[1,5-a]pyridin-4-yl)pyridin-2-yl)piperazine-1-carboxylate (Example 27, 57 mg, 0.121 mmol) in DCM (2 mL) was treated with 5-6 M HCl in iPrOH (4 mL, 20.0 mmol) then stirred at ambient temperature for 2 h. The reaction mixture was concentrated in vacuo to cleanly provide the title compound (51.2 mg, 95% yield). MS (apci) m/z=371.1 (M+H).

Step 2: Preparation of 6-(Difluoromethoxy)-4-(6-(4-(pyridin-2-ylmethyl)piperazin-1-yl)pyridin-3-yl)pyrazolo[1,5-a]pyridine-3-carbonitrile A solution of 6-(difluoromethoxy)-4-(6-(piperazin-1-yl)pyridin-3-yl)pyrazolo[1,5-a]pyridine-3-carbonitrile dihydrochloride from the previous step (15 mg, 0.034 mmol) in DCE (1.3 mL) was treated sequentially with picolinaldehyde (6.5 μL, 0.068 mmol) and $NaBH(AcO)_3$ (22 mg, 0.10 mmol). The resulting mixture was stirred for 17 h at ambient temperature and then quenched with MeOH (0.5 mL). The quenched mixture was purified directly by silica chromatography (using 0-100% acetone/hexanes as the gradient eluent) to cleanly provide the title compound (14.0 mg, 90% yield). MS (apci) m/z=462.1 (M+H). $^{19}F$ NMR ($CDCl_3$) δ−81.9 (1F), −82.1 (1F).

Example 28

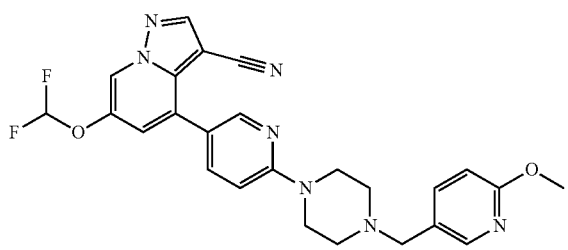 [SMILES: COc1ccc(CN2CCN(c3ccc(-c4cc(OC(F)F)cn5ncc(C#N)c45)cn3)CC2)cn1]

6-(difluoromethoxy)-4-(6-(4-((6-methoxypyridin-3-yl)methyl)piperazin-1-yl)pyridin-3-yl)pyrazolo[1,5-a]pyridine-3-carbonitrile The title compound (12.5 mg, 75% yield) was prepared and purified using a similar procedure to that described for Example 27, replacing picolinaldehyde with 6-methoxynicotinaldehyde. MS (apci) m/z=492.2 (M+H). $^{19}$F NMR (CDCl$_3$) δ−81.9 (1F), −82.1 (1F).

Example 29

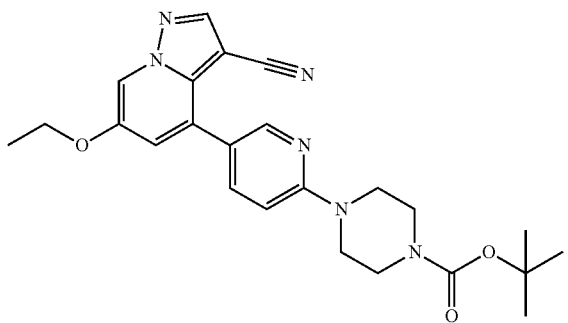

tert-butyl 4-(5-(3-cyano-6-ethoxypyrazolo[1,5-a]pyridin-4-yl)pyridin-2-yl)piperazine-1-carboxylate A mixture of tert-butyl 4-(5-(3-cyano-6-hydroxypyrazolo[1,5-a]pyridin-4-yl)pyridin-2-yl)piperazine-1-carboxylate (Intermediate P3; 400 mg, 0.951 mmol) in DMF (10 mL) was treated sequentially with K$_2$CO$_{3(s)}$ (263 mg, 1.90 mmol) and bromoethane (142 µL, 1.90 mmol), then stirred for 19 h at 50° C. After cooling to ambient temperature, the reaction mixture was purified directly by C18 reverse phase chromatography (5-90% ACN/water as the gradient eluent) to cleanly provide the title compound (289 mg, 68% yield). MS (apci) m/z=449.2 (M+H).

Example 30

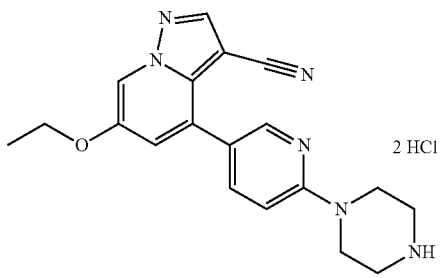 [SMILES: CCOc1cc(-c2ccc(N3CCNCC3)nc2)c2c(C#N)cnn2c1]

6-Ethoxy-4-(6-(piperazin-1-yl)pyridin-3-yl)pyrazolo[1,5-a]pyridine-3-carbonitrile dihydrochloride A solution of tert-butyl 4-(5-(3-cyano-6-ethoxypyrazolo[1,5-a]pyridin-4-yl)pyridin-2-yl)piperazine-1-carboxylate (Example 29; 148 mg, 0.330 mmol) in DCM (2 mL) was treated dropwise with 5-6 M HCl in iPrOH (4 mL, 20.0 mmol) and then stirred at ambient temperature for 5 h. The reaction mixture was concentrated in vacuo, azeotroping with Et$_2$O (3×10 mL) to cleanly provide the title compound as the dihydrochloride salt (116 mg, quantitative yield). MS (apci) m/z=349.1 (M+H).

Example 31

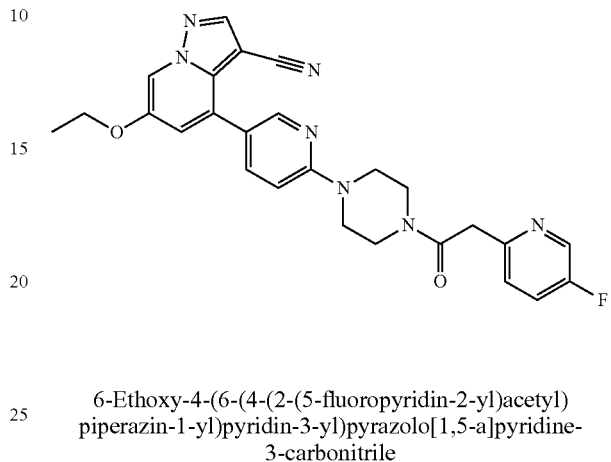

6-Ethoxy-4-(6-(4-(2-(5-fluoropyridin-2-yl)acetyl)piperazin-1-yl)pyridin-3-yl)pyrazolo[1,5-a]pyridine-3-carbonitrile A solution of 6-ethoxy-4-(6-(piperazin-1-yl)pyridin-3-yl)pyrazolo[1,5-a]pyridine-3-carbonitrile dihydrochloride (Example 30; 30 mg, 0.086 mmol) in DCM (1 mL) was treated with DIEA (0.030 mL, 0.17 mmol), 2-(5-fluoropyridin-2-yl)acetic acid (16 mg, 0.10 mmol) and HATU (33 mg, 0.086 mmol). The resulting mixture was stirred overnight at ambient temperature and then concentrated in vacuo. The residue was purified by silica chromatography (0-100% of 20% MeOH/DCM with 2% NH$_4$OH in DCM as the gradient eluent). Fractions containing the title compound were combined, concentrated in vacuo, and then triturated with EtOH (1.5 mL) and water (1.5 mL). The resulting white precipitate was collected by filtration to cleanly provide the title compound (3.2 mg, 8% yield). MS (apci) m/z=486.2 (M+H). $^1$H NMR (400 MHz, DMSO-d$^6$) δ: 8.38 (t, 1H, J=1.6 Hz), 8.31 (d, 1H, J=2.0), 8.17 (s, 1H), 8.09 (d, 1H, J=2.3 Hz), 7.71 (dd, 1H, J=6.3, 2.7 Hz), 7.37 (dd, 2H, J=4.3, 1.6 Hz), 7.06 (d, 1H, J=2.0), 6.73 (d, 1H, J=8.6 Hz), 4.07 (q, 2H, J=7.0 Hz), 3.95 (s, 2H), 3.78-3.74 (m, 4H), 3.63-3.57 (m, 4H), 1.48 (t, 3H, J=6.7 Hz).

Example 32

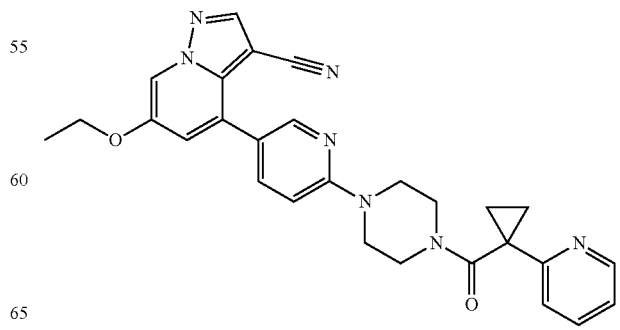

6-ethoxy-4-(6-(4-(1-(pyridin-2-yl)cyclopropane-1-carbonyl)piperazin-1-yl)pyridin-3-yl)pyrazolo[1,5-a]pyridine-3-carbonitrile The title compound (14.9 mg, 35% yield) was prepared and purified using a similar procedure to that described for Example 31, replacing 2-(5-fluoropyridin-2-yl)acetic acid with 1-(pyridin-2-yl)cyclopropanecarboxylic acid. MS (apci) m/z=494.2 (M+H).

Example 33

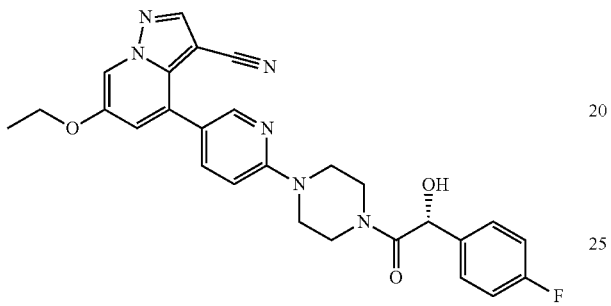

(R)-6-ethoxy-4-(6-(4-(2-(4-fluorophenyl)-2-hydroxyacetyl)piperazin-1-yl)pyridin-3-yl)pyrazolo[1,5-a]pyridine-3-carbonitrile The title compound was prepared using a similar procedure to that described for Example 31, replacing 2-(5-fluoropyridin-2-yl)acetic acid with (R)-2-(4-fluorophenyl)-2-hydroxyacetic acid. Additional changes to the procedure included increasing the amount of DIEA used (5 equivalents) and reducing the reaction duration to 1 hour. Following silica chromatography (using stepwise gradient of 0-100% EtOAc in hexanes then EtOAc with 10% MeOH as eluents), the title compound was isolated cleanly (17 mg, 62% yield). MS (apci) m/z=501.2 (M+H).

Example 34

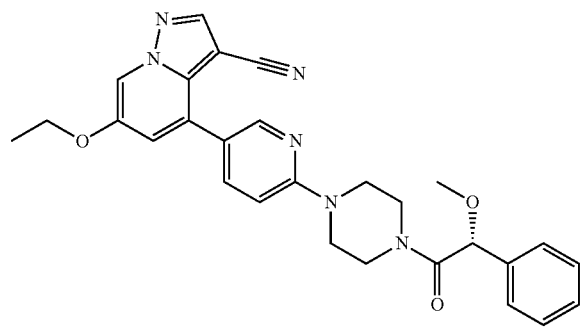 [SMILES: CCOc1cc(-c2ccc(N3CCN(C(=O)[C@H](OC)c4ccccc4)CC3)nc2)c2c(C#N)cnn2c1]

(R)-6-ethoxy-4-(6-(4-(2-methoxy-2-phenylacetyl)piperazin-1-yl)pyridin-3-yl)pyrazolo[1,5-a]pyridine-3-carbonitrile A solution of 6-ethoxy-4-(6-(piperazin-1-yl)pyridin-3-yl)pyrazolo[1,5-a]pyridine-3-carbonitrile dihydrochloride (Example 30; 30 mg, 0.086 mmol) in DCM (1.72 mL) was treated with DIEA (60 μL, 0.344 mmol), (R)-2-methoxy-2-phenylacetic acid (17.2 mg, 0.103 mmol) and HATU (39.3 mg, 0.103 mmol). The resulting mixture was stirred for 16 h at ambient temperature and then concentrated in vacuo. The residue was purified by silica chromatography (0-20% MeOH in DCM as the gradient eluent) to cleanly provide the title compound (19.9 mg, 47% yield). MS (apci) m/z=497.2 (M+H). $^1$H NMR (400 MHz, CDCl$_3$) δ: 8.27 (d, 1H, J=2.0 Hz), 8.23 (s, 1H), 8.21 (d, 1H, J=2.0 Hz), 7.74 (dd, 1H, J=9.0, 2.7 Hz), 7.46-7.34 (m, 5H), 7.14 (d, 1H, J=2.3 Hz), 6.80 (d, 1H, J=9.0), 5.12 (s, 1H), 4.10 (q, 2H, J=7.0 Hz), 3.88-3.52 (m, 6H), 3.50 (s, 3H), 3.48-3.38 (m, 1H), 3.32-3.20 (m, 1H), 1.50 (t, 3H, J=6.65 Hz).

Example 35

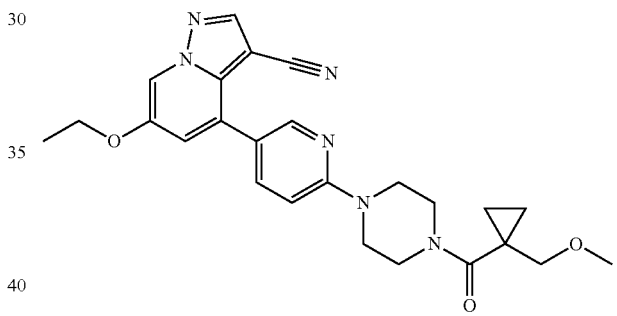

6-ethoxy-4-(6-(4-(1-(methoxymethyl)cyclopropane-1-carbonyl)piperazin-1-yl)pyridin-3-yl)pyrazolo[1,5-a]pyridine-3-carbonitrile A mixture of 6-ethoxy-4-(6-(piperazin-1-yl)pyridin-3-yl)pyrazolo[1,5-a]pyridine-3-carbonitrile dihydrochloride (Example 30; 10.8 mg, 0.0827 mmol), 1-(methoxymethyl)cyclopropanecarboxylic acid (10.8 mg, 0.0827 mmol), DIEA (24.0 μL, 0.138 mmol) and HATU (26.2 mg, 0.0689 mmol) in DCM (1 mL) was stirred overnight at ambient temperature and then concentrated in vacuo. The residue was purified by C18 reverse phase chromatography (5-95% ACN in water with 0.1% TFA as the gradient eluent) to cleanly provide the title compound as the TFA salt. The salt was partitioned between saturated NaHCO$_{3(aq)}$ (2 mL) and EtOAc (3 mL). The aqueous extracts were washed with additional EtOAc. The EtOAc extracts were combined and concentrated in vacuo. Purification of the resulting crude product by silica chromatography (0-100% acetone in DCM as the gradient eluent) to afforded the title compound (6.1 mg, 19% yield). MS (apci) m/z=461.2 (M+H).

Example 36

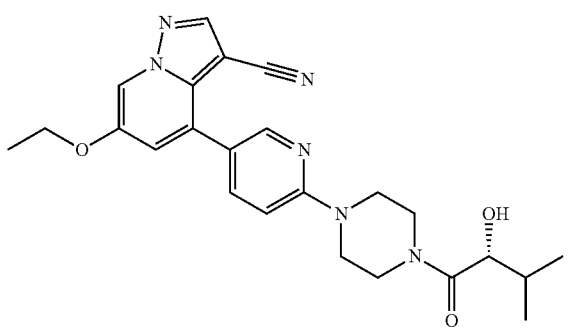 [SMILES: CCOc1cc(-c2ccc(N3CCN(C(=O)[C@H](O)C(C)C)CC3)nc2)c2c(C#N)cnn2c1]

(R)-6-ethoxy-4-(6-(4-(2-hydroxy-3-methylbutanoyl)piperazin-1-yl)pyridin-3-yl)pyrazolo[1,5-a]pyridine-3-carbonitrile Using a similar procedure to that described for Example 35, replacing 1-(methoxymethyl)cyclopropanecarboxylic acid with (R)-2-hydroxy-3-methylbutanoic acid and using 4 equivalents of DIEA, the title compound was isolated (10.8 mg, 28% yield). MS (apci) m/z=448.9 (M+H).

Example 37

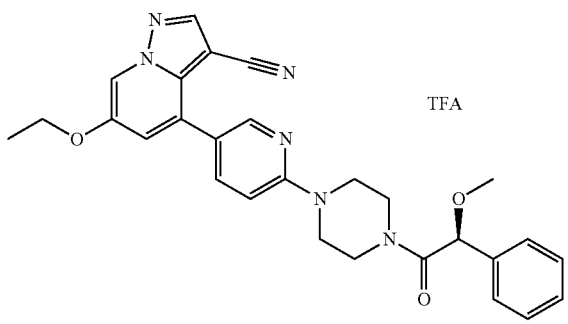 [SMILES: CCOc1cc(-c2ccc(N3CCN(C(=O)[C@@H](OC)c4ccccc4)CC3)nc2)c2c(C#N)cnn2c1]

(S)-6-ethoxy-4-(6-(4-(2-methoxy-2-phenylacetyl)piperazin-1-yl)pyridin-3-yl)pyrazolo[1,5-a]pyridine-3-carbonitrile 2,2,2-trifluoroacetate A solution of 6-ethoxy-4-(6-(piperazin-1-yl)pyridin-3-yl)pyrazolo[1,5-a]pyridine-3-carbonitrile dihydrochloride (Example 30; 30 mg, 0.0861 mmol) in DCM (1.72 mL) was treated with (S)-2-methoxy-2-phenylacetic acid (17.2 mg, 0.103 mmol), HATU (39.3 mg, 0.103 mmol) and DIEA (60.0 µL, 0.344 mmol). The resulting mixture was stirred 16 h at ambient temperature and then concentrated in vacuo. The residue was purified by C18 reverse phase chromatography (5-95% ACN in water with 0.1% TFA as the gradient eluent) to cleanly provide the title compound (13.9 mg, 32.5% yield). MS (apci) m/z=497.2 (M+H).

Example 38

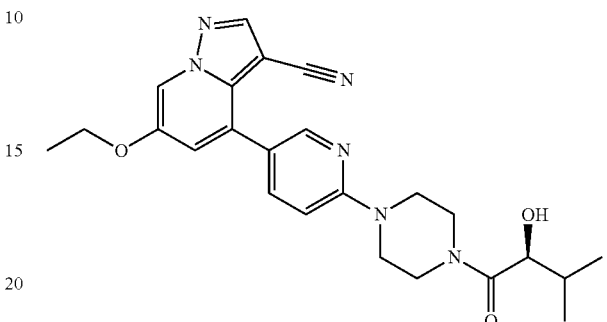

(S)-6-ethoxy-4-(6-(4-(2-hydroxy-3-methylbutanoyl)piperazin-1-yl)pyridin-3-yl)pyrazolo[1,5-a]pyridine-3-carbonitrile A solution of 6-ethoxy-4-(6-(piperazin-1-yl)pyridin-3-yl)pyrazolo[1,5-a]pyridine-3-carbonitrile dihydrochloride (Example 30; 10.8 mg, 0.0827 mmol) in DCM (1.72 mL) was treated with (S)-2-hydroxy-3-methylbutanoic acid (12.2 mg, 0.103 mmol), HATU (39.3 mg, 0.103 mmol) and DIEA (60.0 µL, 0.344 mmol) was stirred for 16 h at ambient temperature and then concentrated in vacuo. The residue was purified by C18 reverse phase chromatography (5-95% ACN in water with 0.1% TFA as the gradient eluent) to cleanly provide the title compound as the TFA salt. The salt was neutralized with saturated $NaHCO_{3(aq)}$, and extracted with EtOAc (3 mL). The combined organic extracts were dried over anhydrous $Na_2SO_{4(s)}$, filtered, and concentrated in vacuo to afford the title compound (13.6 mg, 35% yield). MS (apci) m/z=448.9 (M+H).

The compounds in Table B were prepared and purified and salts were converted to the free base (except where noted *) using a similar method to that described for the synthesis of Example 38, replacing (S)-2-hydroxy-3-methylbutanoic acid with the appropriate carboxylic acid. Reactions were monitored for completion by LCMS, and reaction durations were adjusted accordingly.

TABLE B

| Ex # | Structure | Chemical Name | MS (apci) m/z |
|---|---|---|---|
| 39 | 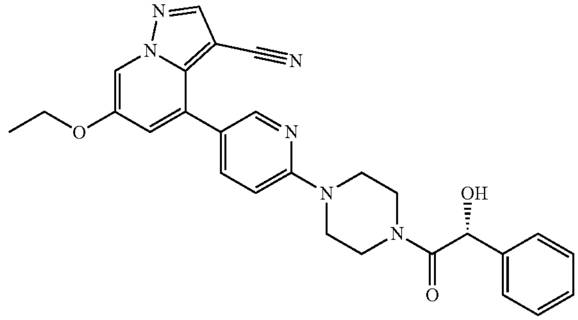 [SMILES: CCOc1cc(-c2ccc(N3CCN(C(=O)[C@H](O)c4ccccc4)CC3)nc2)c2c(C#N)cnn2c1] | (R)-6-ethoxy-4-(6-(4-(2-hydroxy-2-phenylacetyl)piperazin-1-yl)pyridin-3-yl)pyrazolo[1,5-a]pyridine-3-carbonitrile | 482.8 (M + H) |

TABLE B-continued

| Ex # | Structure | Chemical Name | MS (apci) m/z |
|---|---|---|---|
| 40 | 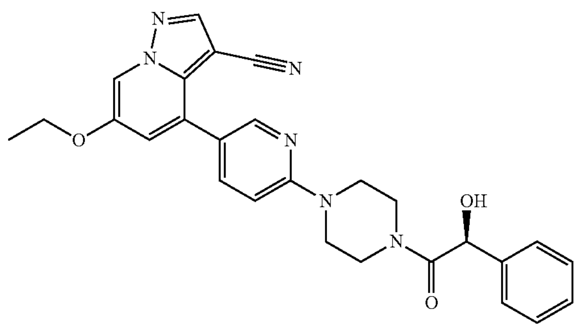 [SMILES: CCOc1cc(-c2ccc(N3CCN(C(=O)[C@@H](O)c4ccccc4)CC3)nc2)c2c(C#N)cnn2c1] | (S)-6-ethoxy-4-(6-(4-(2-hydroxy-2-phenylacetyl)piperazin-1-yl)pyridin-3-yl)pyrazolo[1,5-a]pyridine-3-carbonitrile | 482.8 (M + H) |

*the free base was obtained by dissolving the TFA salt in MeOH and filtering through an Agilent PL-HCO₃ PM SPE filter

Example 41

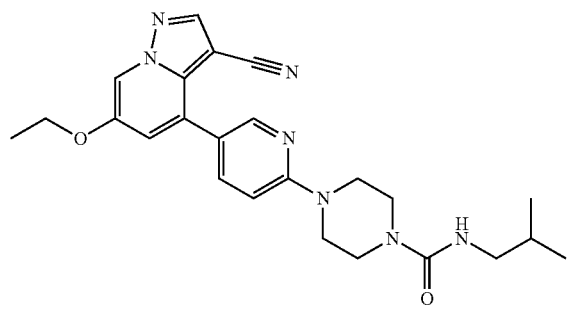 [SMILES: CCOc1cc(-c2ccc(N3CCN(C(=O)NCC(C)C)CC3)nc2)c2c(C#N)cnn2c1]

4-(5-(3-Cyano-6-ethoxypyrazolo[1,5-a]pyrazin-4-yl)pyridin-2-yl)-N-isobutylpiperazine-1-carboxamide A solution of 6-ethoxy-4-(6-(piperazin-1-yl)pyridin-3-yl)pyrazolo[1,5-a]pyridine-3-carbonitrile dihydrochloride (Example 30; 10.8 mg, 0.0827 mmol) in anhydrous DMA (1 mL) was treated with DIEA (45.1 µL, 0.258 mmol), and allowed to stir for 0.5 h at ambient temperature. The mixture was treated dropwise with 1-isocyanato-2-methylpropane (8.54 mg, 0.0861 mmol) and allowed to stir for 1 hour at room temperature before quenching with water. The resulting white precipitate was collected by filtration, then purified by silica chromatography (0-100% acetone in DCM as the gradient eluent) to cleanly provide the title compound (14.8 mg, 38% yield). MS (apci) m/z=447.9 (M+H).

Example 42

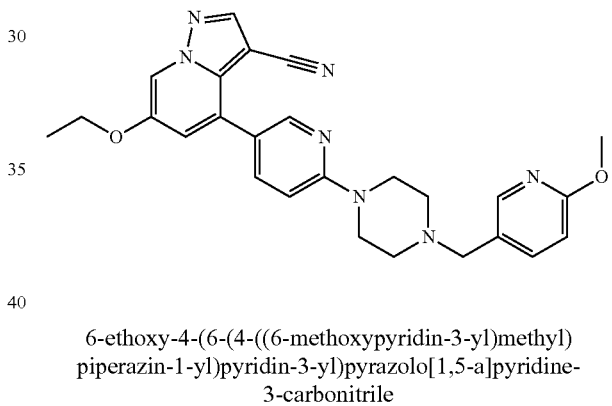

6-ethoxy-4-(6-(4-((6-methoxypyridin-3-yl)methyl)piperazin-1-yl)pyridin-3-yl)pyrazolo[1,5-a]pyridine-3-carbonitrile A solution of 6-ethoxy-4-(6-(piperazin-1-yl)pyridin-3-yl)pyrazolo[1,5-a]pyridine-3-carbonitrile (Example 30; 30 mg, 0.086 mmol) in DCE (861 µL) was treated sequentially 6-methoxynicotinaldehyde (24 mg, 0.17 mmol) and NaBH(AcO)₃ (55 mg, 0.26 mmol). The resulting mixture was stirred for 2 h at ambient temperature and then concentrated in vacuo. The residue was purified by silica chromatography (0-100% acetone in DCM as the gradient eluent) to cleanly provide the title (23 mg, 57% yield). MS (apci) m/z=469.8 (M+H).

The compounds in Table C were prepared using a similar method to that described for the synthesis of Example 42, replacing 6-methoxynicotinaldehyde with the appropriate aldehyde. Reactions were monitored for completion by LCMS, and reaction durations were adjusted accordingly. Each compound was cleanly isolated following chromatographic purification using an appropriate gradient eluent. Some chromatographic conditions resulted in the isolation of the TFA salt of the title compound. Where noted (*), an additional neutralization using an Agilent PL-HCO₃ MP SPE filter was necessary to isolate the salt free title compound.

TABLE C

| Ex # | Structure | Chemical Name | MS (apci) m/z |
|---|---|---|---|
| 43 | 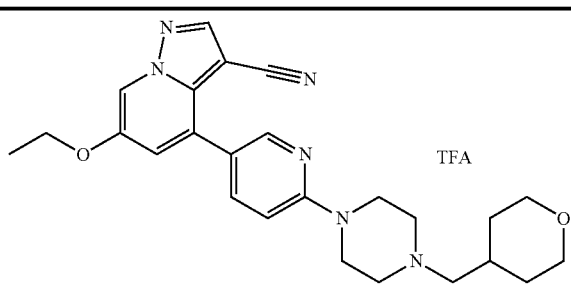 | 6-ethoxy-4-(6-(4-((tetrahydro-2H-pyran-4-yl)methyl)piperazin-1-yl)pyridin-3-yl)pyrazolo[1,5-a]pyridine-3-carbonitrile 2,2,2-trifluoroacetate | 447.2 (M + H) |
| 44 | 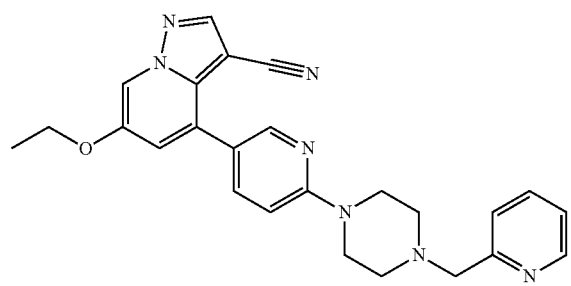 [SMILES: CCOc1cc(-c2ccc(N3CCN(Cc4ccccn4)CC3)nc2)c2c(C#N)cnn2c1] | 6-ethoxy-4-(6-(4-(pyridin-2-ylmethyl)piperazin-1-yl)pyridin-3-yl)pyrazolo[1,5-a]pyridine-3-carbonitrile | 440.2 (M + H) |
| 45 | 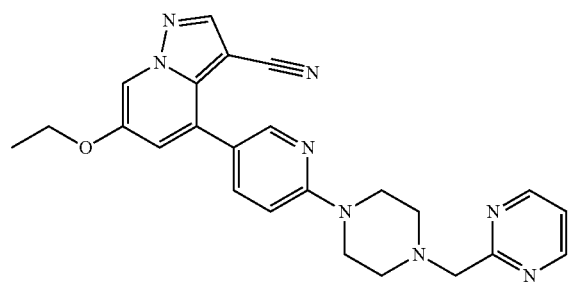 [SMILES: CCOc1cc(-c2ccc(N3CCN(Cc4ncccn4)CC3)nc2)c2c(C#N)cnn2c1] | 6-ethoxy-4-(6-(4-(pyrimidin-2-ylmethyl)piperazin-1-yl)pyridin-3-yl)pyrazolo[1,5-a]pyridine-3-carbonitrile | 441.2 (M + H) |

Example 46

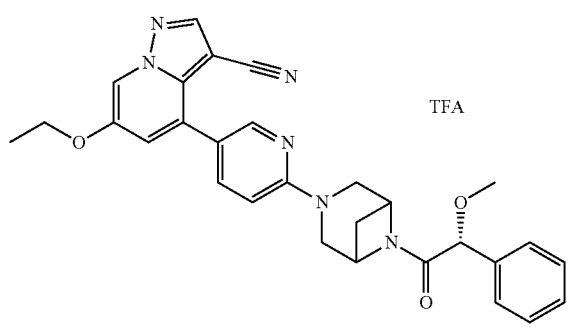 [SMILES: CCOc1cc(-c2ccc(N3CC4CC(C3)N4C(=O)[C@H](OC)c3ccccc3)nc2)c2c(C#N)cnn2c1]

6-ethoxy-4-(6-(6-((R)-2-methoxy-2-phenylacetyl)-3,6-diazabicyclo[3.1.1]heptan-3-yl)pyridin-3-yl)pyrazolo[1,5-a]pyridine-3-carbonitrile 2,2,2-trifluoroacetate A solution of 4-(6-(3,6-diazabicyclo[3.1.1]heptan-3-yl)pyridin-3-yl)-6-ethoxypyrazolo[1,5-a]pyridine-3-carbonitrile dihydrochloride (Intermediate P7; 17.2 mg, 0.0477 mmol) in DCM (954 μL) was treated with (R)-2-methoxy-2-phenylacetic acid (9.52 mg, 0.0573 mmol), HATU (21.8 mg, 0.0573 mmol) and DIEA (33.3 μL, 0.191 mmol). After stirring overnight at ambient temperature, the reaction mixture was concentrated in vacuo. The residue was purified by silica chromatography (0-20% MeOH in DCM as the gradient eluent) and then by C18 reverse phase chromatography (5-95% ACN in water with 0.1% TFA as the gradient eluent) to afford the title compound as the TFA salt. The salt was lyophilized overnight to afford the title compound (16.1 mg, 66% yield). MS (apci) m/z=509.2 (M+H).

Example 47

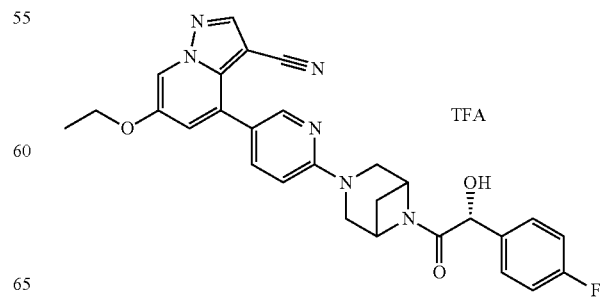

6-ethoxy-4-(6-(6-((R)-2-(4-fluorophenyl)-2-hydroxyacetyl)-3,6-diazabicyclo[3.1.1]heptan-3-yl)pyridin-3-yl)pyrazolo[1,5-a]pyridine-3-carbonitrile 2,2,2-trifluoroacetate A solution of 4-(6-(3,6-diazabicyclo[3.1.1]heptan-3-yl)pyridin-3-yl)-6-ethoxypyrazolo[1,5-a]pyridine-3-carbonitrile dihydrochloride (Intermediate P7; 17.2 mg, 0.0477 mmol) in DCM (954 µL) was treated with (R)-2-(4-fluorophenyl)-2-hydroxyacetic acid (9.74 mg, 0.0573 mmol), HATU (21.8 mg, 0.0573 mmol) and DIEA (33.3 µL, 0.191 mmol). The reaction mixture was stirred overnight at ambient temperature and then concentrated in vacuo. The residue was purified by silica chromatography (0-20% MeOH in DCM as the gradient eluent) and then by C18 reverse phase chromatography (5-95% ACN in water with 0.1% TFA as the gradient eluent) to afford the title compound as the TFA salt. The salt was lyophilized overnight to afford the title compound (8.8 mg, 36% yield). MS (apci) m/z=513.2 (M+H).

Example 48

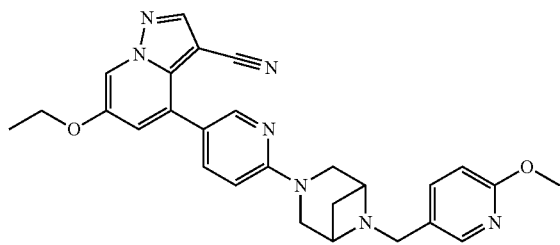 [SMILES: CCOc1cc(-c2ccc(N3CC4CC(C3)N4Cc3ccc(OC)nc3)nc2)c2c(C#N)cnn2c1]

6-ethoxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-ethoxypyrazolo[1,5-a]pyridine-3-carbonitrile dihydrochloride (Intermediate P7; 34 mg, 0.094 mmol) in DCE (472 µL) was treated sequentially with 6-methoxynicotinaldehyde (26 mg, 0.19 mmol) and NaBH(AcO)$_3$ (60 mg, 0.28 mmol). After stirring overnight at ambient temperature, the mixture was purified directly by silica chromatography (0-10% MeOH in DCM as the gradient eluent) to cleanly provide the title compound (10 mg, 22% yield). MS (apci) m/z=482.2 (M+H).

The compounds in Table D were prepared using a similar method to that described for the synthesis of Example 48, replacing 6-methoxynicotinaldehyde with the appropriate aldehyde. Reactions were monitored for completion by LCMS, and reaction durations were adjusted accordingly. Each compound was cleanly isolated following chromatographic purification using an appropriate gradient eluent. Some chromatographic conditions resulted in the isolation of the TFA salt of the title compound. Where noted (*), an additional neutralization using an Agilent PL-HCO$_3$ MP SPE filter was necessary to isolate the salt free title compound.

TABLE D

| Ex # | Structure | Chemical Name | MS (apci) m/z |
|---|---|---|---|
| 49 | 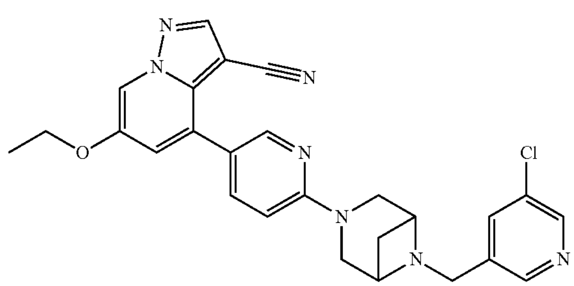 [SMILES: CCOc1cc(-c2ccc(N3CC4CC(C3)N4Cc3cncc(Cl)c3)nc2)c2c(C#N)cnn2c1] | 4-(6-(6-((5-chloropyridin-3-yl)methyl)-3,6-diazabicyclo[3.1.1]heptan-3-yl)pyridin-3-yl)-6-ethoxypyrazolo[1,5-a]pyridine-3-carbonitrile | 486.2 (M + H) |
| 50 | 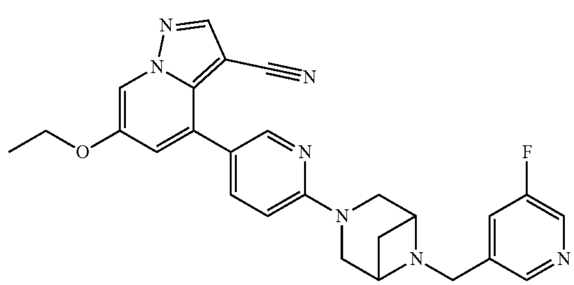 [SMILES: CCOc1cc(-c2ccc(N3CC4CC(C3)N4Cc3cncc(F)c3)nc2)c2c(C#N)cnn2c1] | 6-ethoxy-4-(6-(6-((5-fluoropyridin-3-yl)methyl)-3,6-diazabicyclo[3.1.1]heptan-3-yl)pyridin-3-yl)pyrazolo[1,5-a]pyridine-3-carbonitrile | 470.2 (M + H) |

TABLE D-continued

| Ex # | Structure | Chemical Name | MS (apci) m/z |
|---|---|---|---|
| 51 | 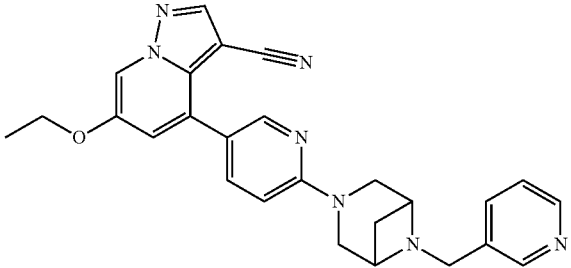 [SMILES: CCOc1cc(-c2ccc(N3CC4CC(C3)N4Cc3cccnc3)nc2)c2c(C#N)cnn2c1] | 6-ethoxy-4-(6-(6-(pyridin-3-ylmethyl)-3,6-diazabicyclo[3.1.1]heptan-3-yl)pyridin-3-yl)pyrazolo[1,5-a]pyridine-3-carbonitrile | 452.2 (M + H) |
| 52 | 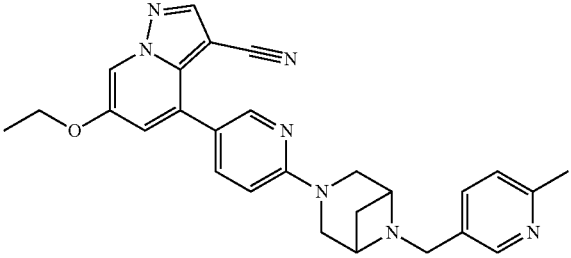 [SMILES: CCOc1cc(-c2ccc(N3CC4CC(C3)N4Cc3ccc(C)nc3)nc2)c2c(C#N)cnn2c1] | 6-ethoxy-4-(6-(6-((6-methylpyridin-3-yl)methyl)-3,6-diazabicyclo[3.1.1]heptan-3-yl)pyridin-3-yl)pyrazolo[1,5-a]pyridine-3-carbonitrile | 466.2 (M + H) |
| 53 | 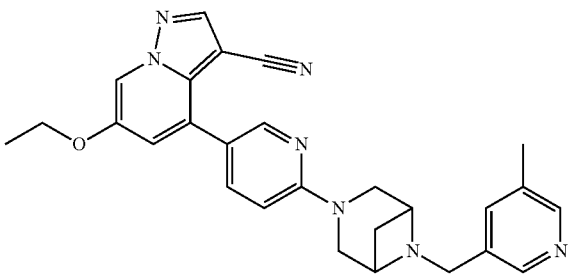 [SMILES: CCOc1cc(-c2ccc(N3CC4CC(C3)N4Cc3cncc(C)c3)nc2)c2c(C#N)cnn2c1] | 6-ethoxy-4-(6-(6-((5-methylpyridin-3-yl)methyl)-3,6-diazabicyclo[3.1.1]heptan-3-yl)pyridin-3-yl)pyrazolo[1,5-a]pyridine-3-carbonitrile | 466.2 (M + H) |
| 54 | 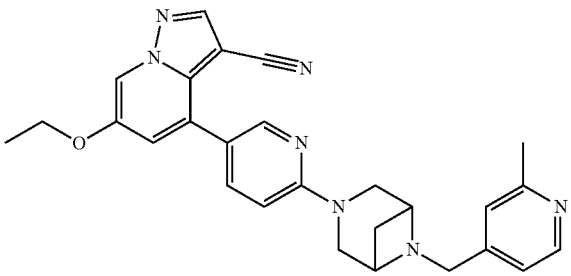 [SMILES: CCOc1cc(-c2ccc(N3CC4CC(C3)N4Cc3ccnc(C)c3)nc2)c2c(C#N)cnn2c1] | 6-ethoxy-4-(6-(6-((2-methylpyridin-4-yl)methyl)-3,6-diazabicyclo[3.1.1]heptan-3-yl)pyridin-3-yl)pyrazolo[1,5-a]pyridine-3-carbonitrile | 466.2 (M + H) |
| 55 | 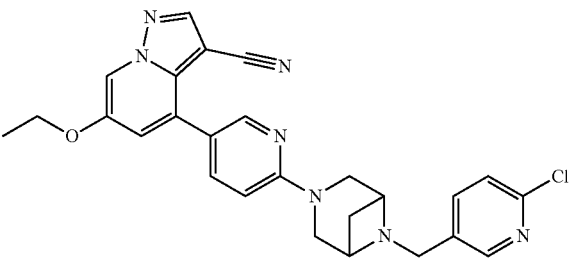 [SMILES: CCOc1cc(-c2ccc(N3CC4CC(C3)N4Cc3ccc(Cl)nc3)nc2)c2c(C#N)cnn2c1] | 4-(6-(6-((6-chloropyridin-3-yl)methyl)-3,6-diazabicyclo[3.1.1]heptan-3-yl)pyridin-3-yl)-6-ethoxypyrazolo[1,5-a]pyridine-3-carbonitrile | 486.2 (M + H) |

TABLE D-continued

| Ex # | Structure | Chemical Name | MS (apci) m/z |
|---|---|---|---|
| 56 | 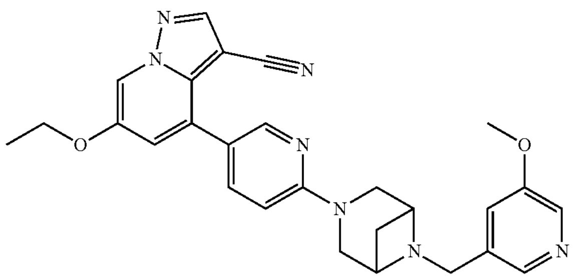 [SMILES: CCOc1cc(-c2ccc(N3CC4CC(C3)N4Cc3cncc(OC)c3)nc2)c2c(C#N)cnn2c1] | 6-ethoxy-4-(6-(6-((5-methoxypyridin-3-yl)methyl)-3,6-diazabicyclo[3.1.1]heptan-3-yl)pyridin-3-yl)pyrazolo[1,5-a]pyridine-3-carbonitrile | 482.2 (M + H) |
| 57 | 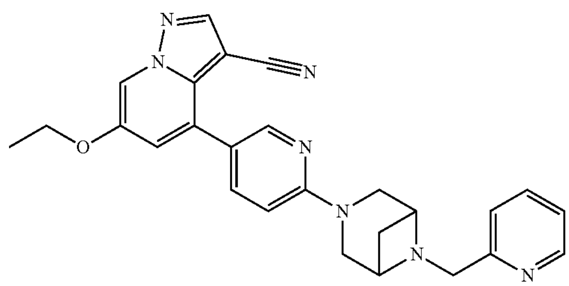 [SMILES: CCOc1cc(-c2ccc(N3CC4CC(C3)N4Cc3ccccn3)nc2)c2c(C#N)cnn2c1] | 6-ethoxy-4-(6-(6-(pyridin-2-ylmethyl)-3,6-diazabicyclo[3.1.1]heptan-3-yl)pyridin-3-yl)pyrazolo[1,5-a]pyridine-3-carbonitrile | 452.2 (M + H) |
| 58 | 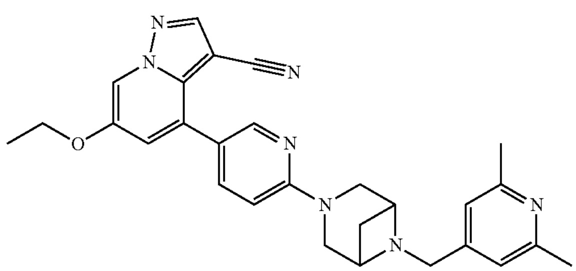 [SMILES: CCOc1cc(-c2ccc(N3CC4CC(C3)N4Cc3cc(C)nc(C)c3)nc2)c2c(C#N)cnn2c1] | 4-(6-(6-((2,6-dimethylpyridin-4-yl)methyl)-3,6-diazabicyclo[3.1.1]heptan-3-yl)pyridin-3-yl)-6-ethoxypyrazolo[1,5-a]pyridine-3-carbonitrile | 480.2 (M + H) |
| 59 | 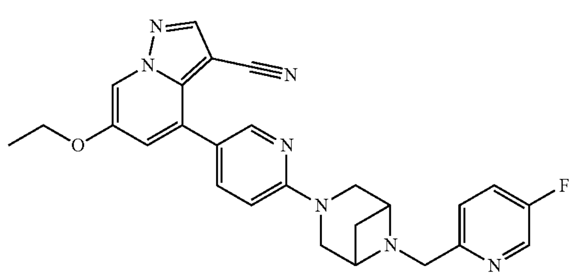 [SMILES: CCOc1cc(-c2ccc(N3CC4CC(C3)N4Cc3ccc(F)cn3)nc2)c2c(C#N)cnn2c1] | 6-ethoxy-4-(6-(6-((5-fluoropyridin-2-yl)methyl)-3,6-diazabicyclo[3.1.1]heptan-3-yl)pyridin-3-yl)pyrazolo[1,5-a]pyridine-3-carbonitrile | 470.2 (M + H) |
| 60 | 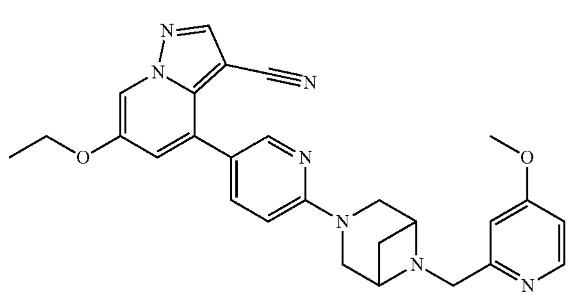 [SMILES: CCOc1cc(-c2ccc(N3CC4CC(C3)N4Cc3cc(OC)ccn3)nc2)c2c(C#N)cnn2c1] | 6-ethoxy-4-(6-(6-((4-methoxypyridin-2-yl)methyl)-3,6-diazabicyclo[3.1.1]heptan-3-yl)pyridin-3-yl)pyrazolo[1,5-a]pyridine-3-carbonitrile | 482.2 (M + H) |

TABLE D-continued

| Ex # | Structure | Chemical Name | MS (apci) m/z |
|---|---|---|---|
| 61 | 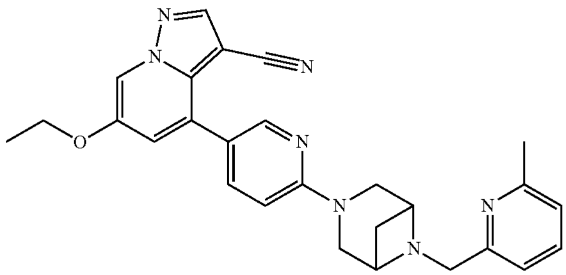 [SMILES: CCOc1cc(-c2ccc(N3CC4CC(C3)N4Cc3cccc(C)n3)nc2)c2c(C#N)cnn2c1] | 6-ethoxy-4-(6-(6-((6-methylpyridin-2-yl)methyl)-3,6-diazabicyclo[3.1.1]heptan-3-yl)pyridin-3-yl)pyrazolo[1,5-a]pyridine-3-carbonitrile | 466.2 (M + H) |
| 62 | 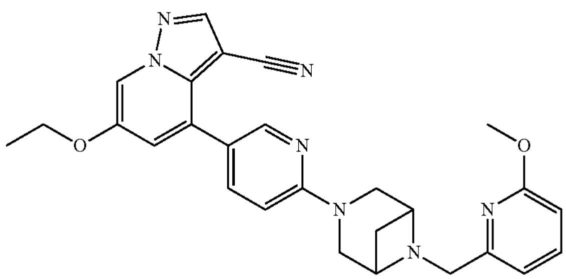 [SMILES: CCOc1cc(-c2ccc(N3CC4CC(C3)N4Cc3cccc(OC)n3)nc2)c2c(C#N)cnn2c1] | 6-ethoxy-4-(6-(6-((6-methoxypyridin-2-yl)methyl)-3,6-diazabicyclo[3.1.1]heptan-3-yl)pyridin-3-yl)pyrazolo[1,5-a]pyridine-3-carbonitrile | 482.2 (M + H) |

Example 63

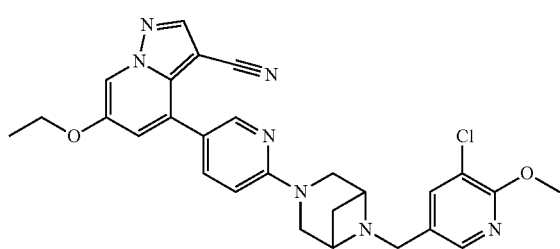 [SMILES: CCOc1cc(-c2ccc(N3CC4CC(C3)N4Cc3cnc(OC)c(Cl)c3)nc2)c2c(C#N)cnn2c1]

4-(6-(6-((5-Chloro-6-methoxypyridin-3-yl)methyl)-3,6-diazabicyclo[3.1.1]heptan-3-yl)pyridin-3-yl)-6-ethoxypyrazolo[1,5-a]pyridine-3-carbonitrile A solution of 4-(6-(3,6-diazabicyclo[3.1.1]heptan-3-yl)pyridin-3-yl)-6-ethoxypyrazolo[1,5-a]pyridine-3-carbonitrile dihydrochloride (Intermediate P7; 30 mg, 0.0692 mmol) in DCM (692 µL) was treated with DIEA (30.1 µL, 0.173 mmol). After stirring for 5 min at room temperature, the reaction mixture was treated sequentially with 5-chloro-6-methoxynicotinaldehyde (13.1 mg, 0.0762 mmol) and NaBH(AcO)$_3$ (29.3 mg, 0.138 mmol). The mixture was stirred overnight at ambient temperature. The resulting suspension was diluted with DCM, and then treated dropwise with MeOH until a homogeneous solution had formed. After concentrating the quenched mixture in vacuo, the residue was purified by silica chromatography (hexanes first followed by 0-10% MeOH in DCM with 2% NH$_4$OH as the gradient eluent) to cleanly provide the title compound (19.8 mg, 55% yield). MS (apci) m/z=516.2 (M+H).

Example 64

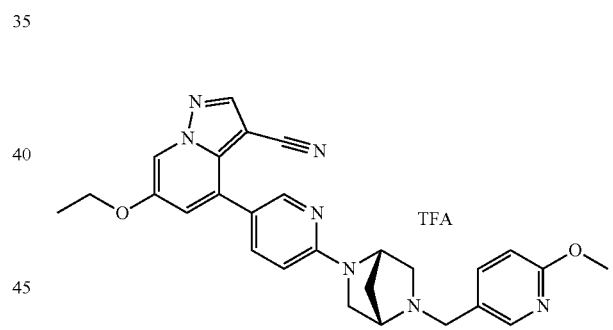

6-ethoxy-4-(6-((1S,4S)-5-((6-methoxypyridin-3-yl)methyl)-2,5-diazabicyclo[2.2.1]heptan-2-yl)pyridin-3-yl)pyrazolo[1,5-a]pyridine-3-carbonitrile 2,2,2-trifluoroacetate A mixture of 6-ethoxy-4-(6-fluoropyridin-3-yl)pyrazolo[1,5-a]pyridine-3-carbonitrile (Intermediate P6; 20 mg, 0.071 mmol), (1S,4S)-2-((6-methoxypyridin-3-yl)methyl)-2,5-diazabicyclo[2.2.1]heptane dihydrochloride (Intermediate R5; 62 mg, 0.21 mmol) and K$_2$CO$_{3(s)}$ (49 mg, 0.35 mmol) in DMSO (709 µL) was stirred 3 days at 80° C. After cooling to ambient temperature, the reaction mixture was diluted with MeOH, filtered and purified by C18 reverse phase chromatography (5-95% ACN in water with 0.1% TFA as the gradient eluent) to afford the title compound as the TFA salt (32 mg, 76% yield). MS (apci) m/z=482.2 (M+H).

Example 65

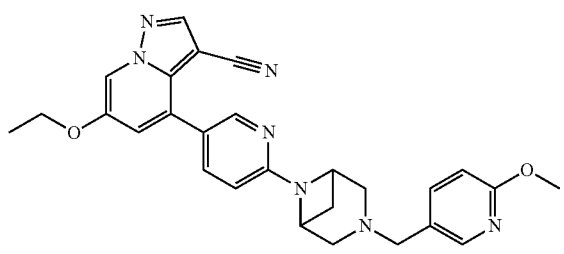 [SMILES: CCOc1cc(-c2ccc(N3C4CC3CN(Cc3ccc(OC)nc3)C4)nc2)c2c(C#N)cnn2c1]

6-ethoxy-4-(6-(3-((6-methoxypyridin-3-yl)methyl)-3,6-diazabicyclo[3.1.1]heptan-6-yl)pyridin-3-yl)pyrazolo[1,5-a]pyridine-3-carbonitrile A mixture of 6-ethoxy-4-(6-fluoropyridin-3-yl)pyrazolo[1,5-a]pyridine-3-carbonitrile (Intermediate P6; 20 mg, 0.071 mmol), 3-((6-methoxypyridin-3-yl)methyl)-3,6-diazabicyclo[3.1.1]heptane dihydrochloride (Intermediate R6; 23 mg, 0.078 mmol) and $K_2CO_{3(s)}$ (49 mg, 0.35 mmol) in DMSO (709 μL) was stirred 3 h at 110° C. Additional 3-((6-methoxypyridin-3-yl)methyl)-3,6-diazabicyclo[3.1.1]heptane dihydrochloride (37 mg, 0.127 mmol) was introduced, and the reaction mixture was allowed to stir overnight at 110° C. After cooling to ambient temperature, the reaction mixture was filtered and purified by C18 reverse phase chromatography (5-95% ACN in water with 0.1% TFA as the gradient eluent) to afford the title compound as the TFA salt. The TFA salt was dissolved in MeOH and filtered through an Agilent PL-HCO_3 MP SPE tube to neutralize, and the filtrate was concentrated in vacuo to afford the title compound (10 mg, 29% yield). MS (apci) m/z=482.2 (M+H).

Example 66

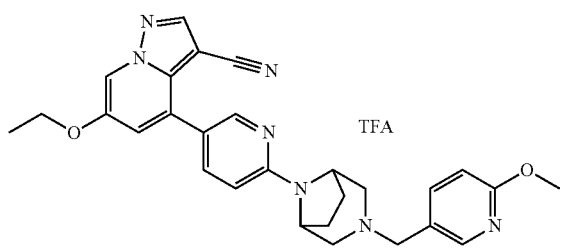 [SMILES: CCOc1cc(-c2ccc(N3C4CCC3CN(Cc3ccc(OC)nc3)C4)nc2)c2c(C#N)cnn2c1]

6-ethoxy-4-(6-(3-((6-methoxypyridin-3-yl)methyl)-3,8-diazabicyclo[3.2.1]octan-8-yl)pyridin-3-yl)pyrazolo[1,5-a]pyridine-3-carbonitrile 2,2,2-trifluoroacetate A mixture of 6-ethoxy-4-(6-fluoropyridin-3-yl)pyrazolo[1,5-a]pyridine-3-carbonitrile (Intermediate P6; 20 mg, 0.071 mmol), 3-((6-methoxypyridin-3-yl)methyl)-3,8-diazabicyclo[3.2.1]octane hydrochloride (Intermediate R7; 57 mg, 0.21 mmol) and $K_2CO_{3(s)}$ (49 mg, 0.35 mmol) in DMSO (709 μL) was stirred at 80° C., and monitored for completion by LCMS. The reaction mixture was cooled to ambient temperature, then filtered and purified by C18 reverse phase chromatography (5-95% ACN in water with 0.1% TFA as the gradient eluent) to afford the title compound (1.0 mg, 3% yield). MS (apci) m/z=496.3 (M+H).

Example 67

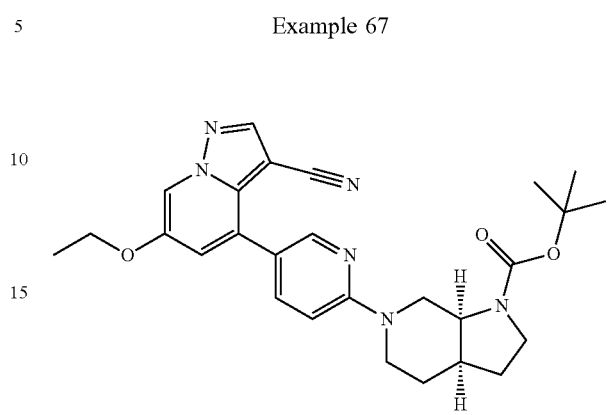

tert-butyl (3aR,7aS)-6-(5-(3-cyano-6-ethoxypyrazolo[1,5-a]pyridin-4-yl)pyridin-2-yl)octahydro-1H-pyrrolo[2,3-c]pyridine-1-carboxylate A suspension of 6-ethoxy-4-(6-fluoropyridin-3-yl)pyrazolo[1,5-a]pyridine-3-carbonitrile (Intermediate P6; 60 mg, 0.213 mmol) in DMSO (500 μL) was treated with tert-butyl (3aR,7aS)-octahydro-1H-pyrrolo[2,3-c]pyridine-1-carboxylate (96.2 mg, 0.425 mmol) and $K_2CO_{3(s)}$ (120 mg, 0.85 mmol) and stirred for 10 h at 90° C. The resulting mixture was cooled to ambient temperature and quenched with 1:1 NH_4OH/Water. The quenched mixture was extracted with DCM. The combined organic extracts were dried over anhydrous $Na_2SO_{4(s)}$, filtered, and concentrated in vacuo. The residue was purified by C18 reverse phase chromatography (20-90% ACN/water as the gradient eluent) to afford the title compound (77.1 mg, 74% yield). MS (apci) m/z=489.2 (M+H).

Example 68

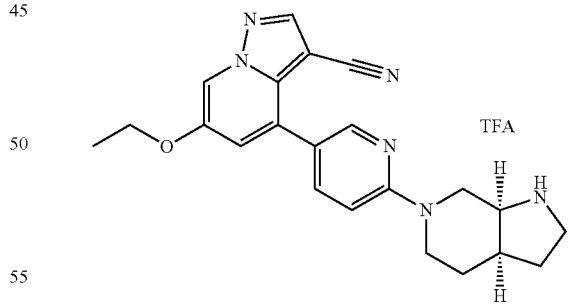

6-ethoxy-4-(6-((3aS,7aS)-octahydro-6H-pyrrolo[2,3-c]pyridin-6-yl)pyridin-3-yl)pyrazolo[1,5-a]pyridine-3-carbonitrile (TFA salt)

A solution of tert-butyl (3aR,7aS)-6-(5-(3-cyano-6-ethoxypyrazolo[1,5-a]pyridin-4-yl)pyridin-2-yl)octahydro-1H-pyrrolo[2,3-c]pyridine-1-carboxylate (Example 67; 77.1 mg, 0.158 mmol) in DCM (500 μL) was treated with TFA (120.8 μL, 1.58 mmol) was stirred for 5 h at ambient temperature. The reaction mixture was diluted with MeOH (1 mL) and purified by C18 reverse phase chromatography (5-95% ACN in water with 0.01% TFA as the gradient eluent) to afford the title compound (51.4 mg, 84% yield). MS (apci) m/z=389.2 (M+H).

Example 69

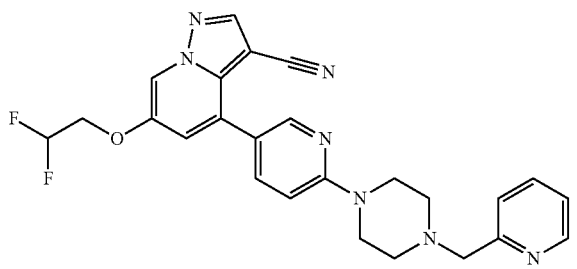 [SMILES: N#Cc1cnn2cc(OCC(F)F)cc(-c3ccc(N4CCN(Cc5ccccn5)CC4)nc3)c12]

6-(2,2-difluoroethoxy)-4-(6-(4-(pyridin-2-ylmethyl)piperazin-1-yl)pyridin-3-yl)pyrazolo[1,5-a]pyridine-3-carbonitrile A solution of 6-(2,2-difluoroethoxy)-4-(6-(piperazin-1-yl)pyridin-3-yl)pyrazolo[1,5-a]pyridine-3-carbonitrile dihydrochloride (Intermediate P8; 23.8 mg, 0.0619 mmol) in DCE (619 μL) was treated sequentially with picolinaldehyde (11.7 μL, 0.124 mmol) and NaBH(AcO)$_3$ (39.4 mg, 0.186 mmol). The resulting mixture was stirred for 1 hour at ambient temperature, and then concentrated in vacuo. The crude residue was purified by silica chromatography (0-100% acetone in DCM as the gradient eluent) to cleanly provide the title compound (15.0 mg, 51% yield). MS (apci) m/z=476.2 (M+H).

Example 70

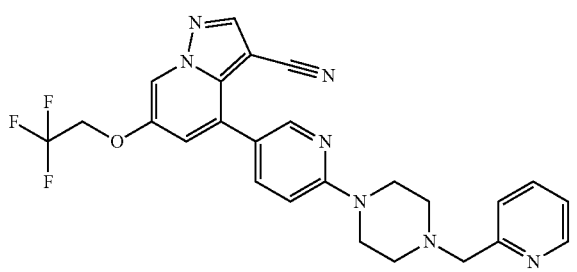 [SMILES: N#Cc1cnn2cc(OCC(F)(F)F)cc(-c3ccc(N4CCN(Cc5ccccn5)CC4)nc3)c12]

4-(6-(4-(pyridin-2-ylmethyl)piperazin-1-yl)pyridin-3-yl)-6-(2,2,2-trifluoroethoxy)pyrazolo[1,5-a]pyridine-3-carbonitrile A solution of 4-(6-(piperazin-1-yl)pyridin-3-yl)-6-(2,2,2-trifluoroethoxy)pyrazolo[1,5-a]pyridine-3-carbonitrile dihydrochloride (Intermediate P9; 24 mg, 0.060 mmol) in DCE (619 μL) was treated sequentially with picolinaldehyde (11.4 μL, 0.119 mmol) and NaBH(AcO)$_3$ (37.494 mg, 0.1789 mmol). After stirring for 1 hour at ambient temperature, the reaction mixture was concentrated in vacuo. The crude residue was purified by silica chromatography (0-100% acetone in DCM as the gradient eluent) to cleanly provide the title compound (14.6 mg, 50% yield). MS (apci) m/z=494.2 (M+H).

Example 71

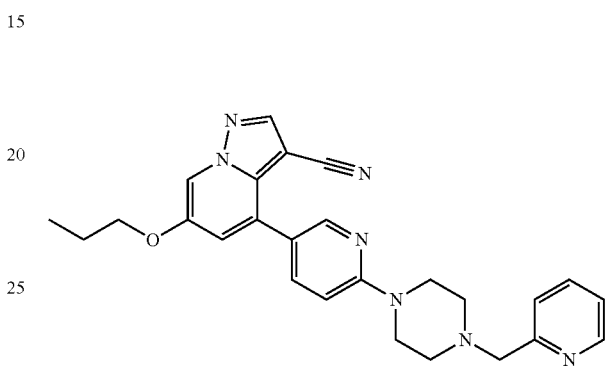

6-propoxy-4-(6-(4-(pyridin-2-ylmethyl)piperazin-1-yl)pyridin-3-yl)pyrazolo[1,5-a]pyridine-3-carbonitrile A solution of 4-(6-(piperazin-1-yl)pyridin-3-yl)-6-propoxypyrazolo[1,5-a]pyridine-3-carbonitrile (Intermediate P10; 26 mg, 0.072 mmol) in DCE (717 μL) was treated sequentially with picolinaldehyde (6.9 μL, 0.072 mmol) and NaBH(AcO)$_3$ (45.6 mg, 0.215 mmol). After stirring overnight at ambient temperature, the reaction mixture was purified directly by silica chromatography (0-5% MeOH in DCM as the gradient eluent) to cleanly provide the title compound (23.5 mg, 72% yield). MS (apci) m/z=454.2 (M+H).

The compounds in Table E were prepared using a similar method to that described for the synthesis of Example 71, replacing picolinaldehyde with the appropriate aldehyde and/or treating Intermediate P10 with the appropriate Intermediate from Table AA. Reactions were monitored for completion by LCMS, and reaction durations were adjusted accordingly. Each compound was cleanly isolated following chromatographic purification using an appropriate gradient eluent. Some chromatographic conditions resulted in the isolation of the TFA salt of the title compound. Where noted (*), an additional neutralization of the TFA salt was accomplished by dissolving the salt in DCM followed by sequential extraction of the solution with saturated NaHCO$_{3(aq)}$, and brine, drying the combined organic extracts over anhydrous Na$_2$SO$_{4(s)}$, filtering, and concentrating in vacuo to isolate the free base of the title compound.

TABLE E

| Ex # | Structure | Chemical Name | MS (apci) m/z |
|---|---|---|---|
| 72 | 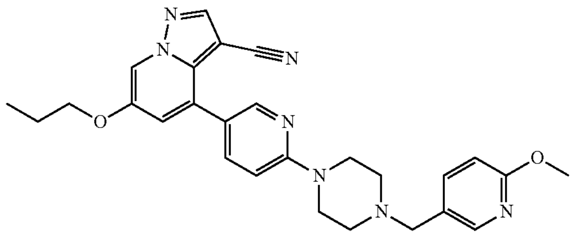 [SMILES: CCCOc1cc(-c2ccc(N3CCN(Cc4ccc(OC)nc4)CC3)nc2)c2c(C#N)cnn2c1] | 4-(6-(4-((6-methoxypyridin-3-yl)methyl)piperazin-1-yl)pyridin-3-yl)-6-propoxypyrazolo[1,5-a]pyridine-3-carbonitrile | 484.2 (M + H) |
| 73 | 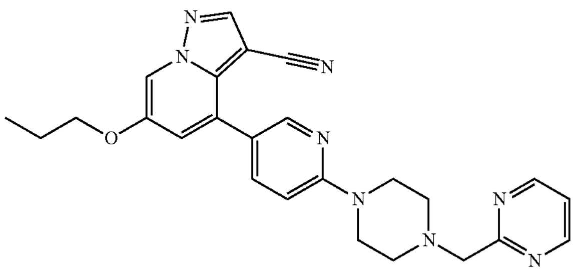 [SMILES: CCCOc1cc(-c2ccc(N3CCN(Cc4ncccn4)CC3)nc2)c2c(C#N)cnn2c1] | 6-propoxy-4-(6-(4-(pyrimidin-2-ylmethyl)piperazin-1-yl)pyridin-3-yl)pyrazolo[1,5-a]pyridine-3-carbonitrile | 455.2 (M + H) |
| 74 | 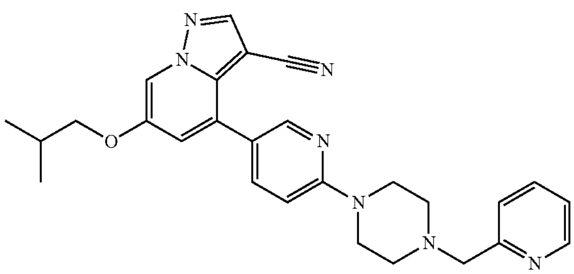 [SMILES: CC(C)COc1cc(-c2ccc(N3CCN(Cc4ccccn4)CC3)nc2)c2c(C#N)cnn2c1] | 6-isobutoxy-4-(6-(4-(pyridin-2-ylmethyl)piperazin-1-yl)pyridin-3-yl)pyrazolo[1,5-a]pyridine-3-carbonitrile | 468.2 (M + H) |
| 75 | 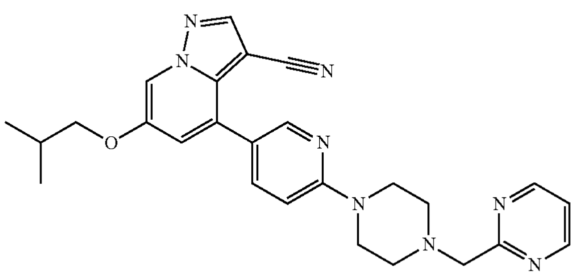 [SMILES: CC(C)COc1cc(-c2ccc(N3CCN(Cc4ncccn4)CC3)nc2)c2c(C#N)cnn2c1] | 6-isobutoxy-4-(6-(4-(pyrimidin-2-ylmethyl)piperazin-1-yl)pyridin-3-yl)pyrazolo[1,5-a]pyridine-3-carbonitrile | 469.2 (M + H) |
| 76 | 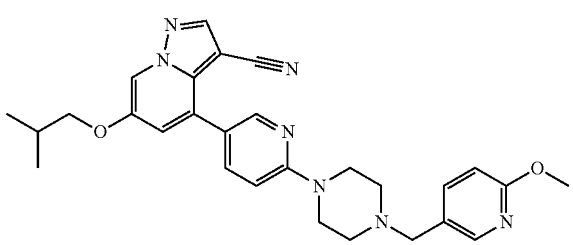 [SMILES: COc1ccc(CN2CCN(c3ccc(-c4cc(OCC(C)C)cn5ncc(C#N)c45)cn3)CC2)cn1] | 6-isobutoxy-4-(6-(4-((6-methoxypyridin-3-yl)methyl)piperazin-1-yl)pyridin-3-yl)pyrazolo[1,5-a]pyridine-3-carbonitrile | 498.2 (M + H) |
| 77 | 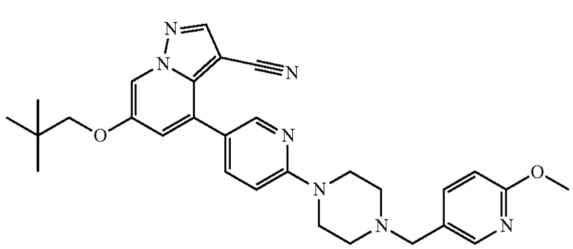 [SMILES: COc1ccc(CN2CCN(c3ccc(-c4cc(OCC(C)(C)C)cn5ncc(C#N)c45)cn3)CC2)cn1] | 4-(6-(4-((6-methoxypyridin-3-yl)methyl)piperazin-1-yl)pyridin-3-yl)-6-(neopentyloxy)pyrazolo[1,5-a]pyridine-3-carbonitrile | 512.3 (M + H) |

TABLE E-continued

| Ex # | Structure | Chemical Name | MS (apci) m/z |
|---|---|---|---|
| 78 | 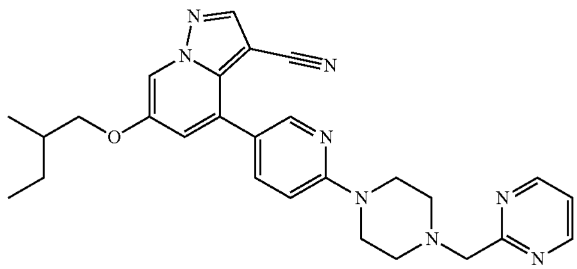 [SMILES: CCC(C)COc1cc(-c2ccc(N3CCN(Cc4ncccn4)CC3)nc2)c2c(C#N)cnn2c1] | 6-(2-methylbutoxy)-4-(6-(4-(pyrimidin-2-ylmethyl)piperazin-1-yl)pyridin-3-yl)pyrazolo[1,5-a]pyridine-3-carbonitrile | 483.3 (M + H) |
| 79 | 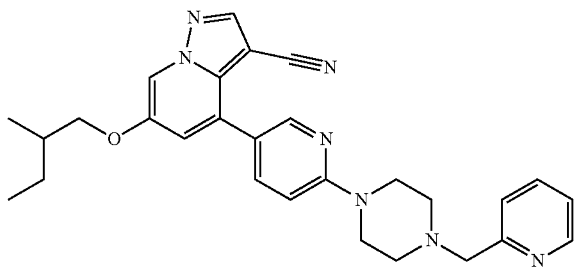 [SMILES: CCC(C)COc1cc(-c2ccc(N3CCN(Cc4ccccn4)CC3)nc2)c2c(C#N)cnn2c1] | 6-(2-methylbutoxy)-4-(6-(4-(pyridin-2-ylmethyl)piperazin-1-yl)pyridin-3-yl)pyrazolo[1,5-a]pyridine-3-carbonitrile | 482.3 (M + H) |
| 80 | 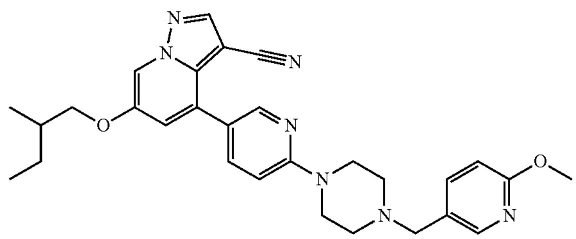 [SMILES: CCC(C)COc1cc(-c2ccc(N3CCN(Cc4ccc(OC)nc4)CC3)nc2)c2c(C#N)cnn2c1] | 4-(6-(4-((6-methoxypyridin-3-yl)methyl)piperazin-1-yl)pyridin-3-yl)-6-(2-methylbutoxy)pyrazolo[1,5-a]pyridine-3-carbonitrile | 512.3 (M + H) |
| 81 | 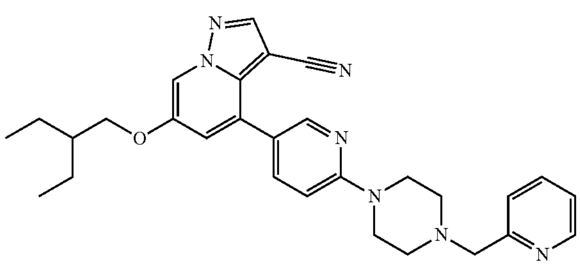 [SMILES: CCC(CC)COc1cc(-c2ccc(N3CCN(Cc4ccccn4)CC3)nc2)c2c(C#N)cnn2c1] | 6-(2-ethylbutoxy)-4-(6-(4-(pyridin-2-ylmethyl)piperazin-1-yl)pyridin-3-yl)pyrazolo[1,5-a]pyridine-3-carbonitrile | 496.3 (M + H) |
| 82 | 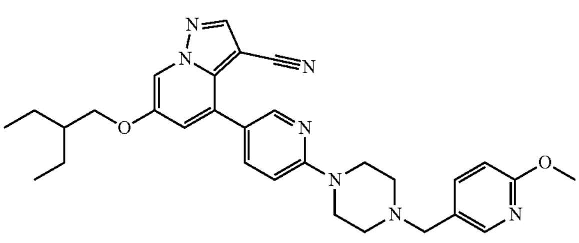 [SMILES: CCC(CC)COc1cc(-c2ccc(N3CCN(Cc4ccc(OC)nc4)CC3)nc2)c2c(C#N)cnn2c1] | 6-(2-ethylbutoxy)-4-(6-(4-((6-methoxypyridin-3-yl)methyl)piperazin-1-yl)pyridin-3-yl)pyrazolo[1,5-a]pyridine-3-carbonitrile | 526.3 (M + H) |
| 83 | 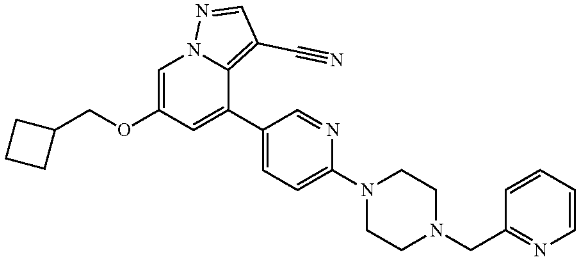 [SMILES: N#Cc1cnn2cc(OCC3CCC3)cc(-c3ccc(N4CCN(Cc5ccccn5)CC4)nc3)c12] | 6-(cyclobutylmethoxy)-4-(6-(4-(pyridin-2-ylmethyl)piperazin-1-yl)pyridin-3-yl)pyrazolo[1,5-a]pyridine-3-carbonitrile | 480.2 (M + H) |

TABLE E-continued

| Ex # | Structure | Chemical Name | MS (apci) m/z |
|---|---|---|---|
| 84 | 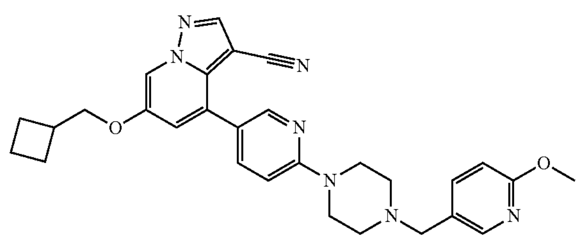 [SMILES: COc1ccc(CN2CCN(c3ccc(-c4cc(OCC5CCC5)cn5ncc(C#N)c45)cn3)CC2)cn1] | 6-(cyclobutylmethoxy)-4-(6-(4-((6-methoxypyridin-3-yl)methyl)piperazin-1-yl)pyridin-3-yl)pyrazolo[1,5-a]pyridine-3-carbonitrile | 510.2 (M + H) |
| 85 | 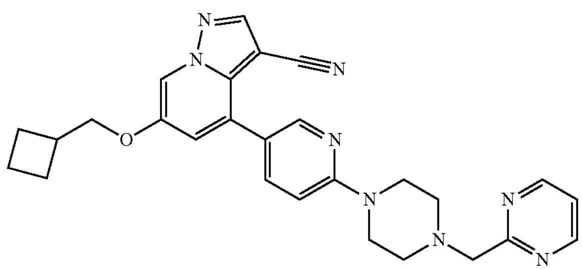 | 6-(cyclobutylmethoxy)-4-(6-(4-(pyrimidin-2-ylmethyl)piperazin-1-yl)pyridin-3-yl)pyrazolo[1,5-a]pyridine-3-carbonitrile | 481.2 (M + H) |

Example 86

6-((3-methyl oxetan-3-yl)methoxy)-4-(6-(4-(pyridin-2-ylmethyl)piperazin-1-yl)pyridin-3-yl)pyrazolo[1,5-a]pyridine-3-carbonitrile A suspension of 6-hydroxy-4-(6-(4-(pyridin-2-ylmethyl)piperazin-1-yl)pyridin-3-yl)pyrazolo[1,5-a]pyridine-3-carbonitrile (Intermediate P16; 17.3 mg, 0.0420 mmol) in DMF (500 μL) was treated sequentially with $K_2CO_{3(s)}$ (11.6 mg, 0.0841 mmol) and 3-(bromomethyl)-3-methyloxetane (12 μL, 0.0841 mmol). The resulting mixture was stirred for 16 h at 50° C. The mixture was cooled to ambient temperature, then diluted with ACN (0.3 mL), filtered, and rinsed with ACN. The filtrate was directly purified by C18 reverse phase chromatography (5-95% ACN/water as the gradient eluent) to afford the title compound (2.1 mg, 10% yield). MS (apci) m/z=496.2 (M+H).

Example 87

4-(6-(4-(3-methylbutanoyl)piperazin-1-yl)pyridin-3-yl)-6-(2-morpholinoethoxy)pyrazolo[1,5-a]pyridine-3-carbonitrile A solution of 6-(2-morpholinoethoxy)-4-(6-(piperazin-1-yl)pyridin-3-yl)pyrazolo[1,5-a]pyridine-3-carbonitrile (Intermediate P17; 21.7 mg, 0.0501 mmol) in DCM (1.1 mL) was treated sequentially with DIEA (34.9 μL, 0.200 mmol) and isovaleryl chloride (7.32 μL, 0.0601 mmol). The resulting mixture was stirred for 16 hours at ambient temperature. The mixture was concentrated in vacuo, and the residue was purified by silica chromatography (20:1 DCM/MeOH as the eluent) to afford the title compound (18 mg, 70% yield). MS (apci) m/z=518.2 (M+H).

Example 88

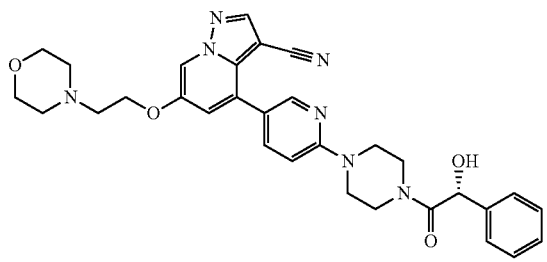 [SMILES: N#Cc1cnn2cc(OCCN3CCOCC3)cc(-c3ccc(N4CCN(C(=O)[C@H](O)c5ccccc5)CC4)nc3)c12]

(R)-4-(6-(4-(2-hydroxy-2-phenylacetyl)piperazin-1-yl)pyridin-3-yl)-6-(2-morpholinoethoxy)pyrazolo[1,5-a]pyridine-3-carbonitrile A solution of 6-(2-morpholinoethoxy)-4-(6-(piperazin-1-yl)pyridin-3-yl)pyrazolo[1,5-a]pyridine-3-carbonitrile (Intermediate P17; 22 mg, 0.051 mmol) in DMF (4 mL) was treated with D-(−)-mandelic acid (11.6 mg, 0.0761 mmol), HATU (33 mg, 0.086 mmol) and DIEA (88.4 µL, 0.507 mmol). After stirring for 16 h at ambient temperature, the mixture was diluted with EtOAc and extracted with water. The combined organic extracts were dried over anhydrous Na$_2$SO$_{4(s)}$, filtered, and concentrated in vacuo. The residue was purified by C18 reverse phase chromatography (5-95% ACN/water with 0.1% TFA as the gradient eluent) to afford the title compound as the TFA salt. The salt was partitioned between 4:1 DCM:iPrOH and saturated NaHCO$_{3(aq)}$. The resulting organic extracts were combined, dried over anhydrous Na$_2$SO$_{4(s)}$, filtered and concentrated in vacuo as the gradient eluent) to afford the title compound (25 mg, 87% yield). MS (apci) m/z=568.2 (M+H).

Example 89

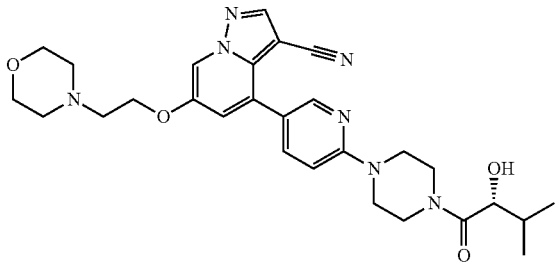 [SMILES: CC(C)[C@@H](O)C(=O)N1CCN(c2ccc(-c3cc(OCCN4CCOCC4)cn4ncc(C#N)c34)cn2)CC1]

(R)-4-(6-(4-(2-hydroxy-3-methylbutanoyl)piperazin-1-yl)pyridin-3-yl)-6-(2-morpholinoethoxy)pyrazolo[1,5-a]pyridine-3-carbonitrile The title compound (21 mg, 83% yield) was prepared and purified using a similar procedure to that described for Example 88, replacing D-(−)-mandelic acid with (R)-2-hydroxy-3-methylbutanoic acid (1.2 equivalents), and increasing the amounts of HATU (1.2 equivalents) and DIEA (10 equivalents). MS (apci) m/z=534.2 (M+H).

Example 90

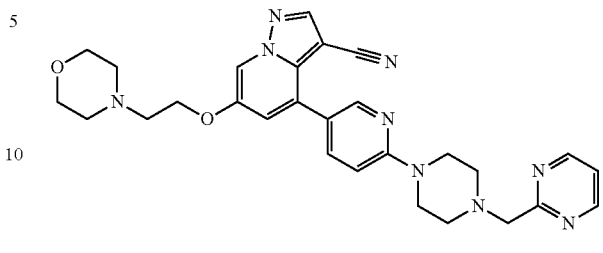

6-(2-morpholinoethoxy)-4-(6-(4-(pyrimidin-2-ylmethyl)piperazin-1-yl)pyridin-3-yl)pyrazolo[1,5-a]pyridine-3-carbonitrile A solution of 6-(2-morpholinoethoxy)-4-(6-(piperazin-1-yl)pyridin-3-yl)pyrazolo[1,5-a]pyridine-3-carbonitrile (Intermediate P17; 16 mg, 0.037 mmol) in DMF (2 mL) was treated sequentially with pyrimidine-2-carbaldehyde (14.0 mg, 0.129 mmol), NaBH(AcO)$_3$ (15.6 mg, 0.0738 mmol) and acetic acid (22.2 mg, 0.369 mmol). The resulting mixture was stirred for 3 days at ambient temperature. The reaction mixture was extracted with EtOAc and water. The combined organic extracts then were dried over anhydrous Na$_2$SO$_{4(s)}$, filtered, and concentrated in vacuo. The residue was purified by C18 reverse phase chromatography (5-95% ACN/water with 0.1% TFA as the gradient eluent) and then by silica chromatography (using a stepwise gradient of 20:1 DCM/MeOH followed by 10:1 DCM/MeOH as eluents) to afford the title compound (9 mg, 46% yield). MS (apci) m/z=526.2 (M+H).

Example 91

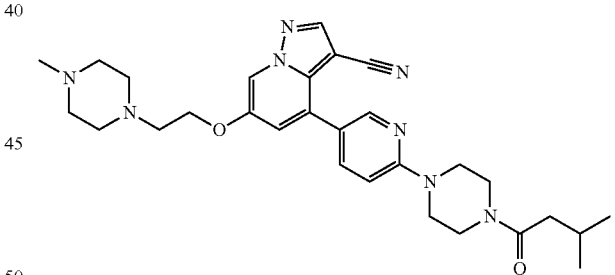

4-(6-(4-(3-methylbutanoyl)piperazin-1-yl)pyridin-3-yl)-6-(2-(4-methylpiperazin-1-yl)ethoxy)pyrazolo[1,5-a]pyridine-3-carbonitrile A solution of 6-(2-(4-methylpiperazin-1-yl)ethoxy)-4-(6-(piperazin-1-yl)pyridin-3-yl)pyrazolo[1,5-a]pyridine-3-carbonitrile (Intermediate P18; 24.5 mg, 0.0549 mmol) in DCM (1.1 mL) was treated sequentially with DIEA (38.2 µL, 0.219 mmol) and isovaleryl chloride (8.03 µL, 0.0658 mmol). The resulting mixture was stirred for 16 h at ambient temperature. The residue was concentrated in vacuo, then purified by C18 reverse phase chromatography (5-95% ACN in water with 0.1% TFA as the gradient eluent) to afford the title compound as the TFA salt. The TFA salt was partitioned between 4:1 DCM:iPrOH and saturated NaHCO$_{3(aq)}$. The Example 92

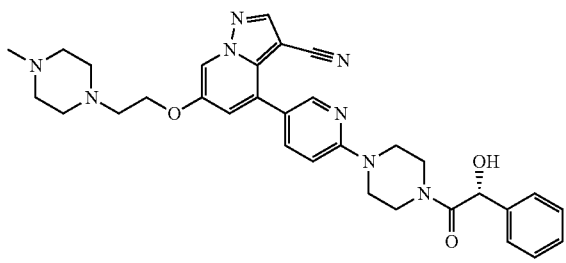 [SMILES: CN1CCN(CCOc2cc(-c3ccc(N4CCN(C(=O)[C@H](O)c5ccccc5)CC4)nc3)c3c(C#N)cnn3c2)CC1]

(R)-4-(6-(4-(2-hydroxy-2-phenylacetyl)piperazin-1-yl)pyridin-3-yl)-6-(2-(4-methylpiperazin-1-yl)ethoxy)pyrazolo[1,5-a]pyridine-3-carbonitrile A solution of 6-(2-(4-methylpiperazin-1-yl)ethoxy)-4-(6-(piperazin-1-yl)pyridin-3-yl)pyrazolo[1,5-a]pyridine-3-carbonitrile (Intermediate P18; 20.2 mg, 0.0452 mmol) in DCM (1 mL) was treated with D-(−)-mandelic acid (8.26 mg, 0.0543 mmol), HATU (20.6 mg, 0.0543 mmol) and DIEA (23.6 μL, 0.136 mmol), and stirred for 16 h at ambient temperature. The mixture was concentrated in vacuo, and then purified by C18 reverse phase chromatography (5-95% ACN in water with 0.1% TFA as the gradient eluent) to afford the title compound as the TFA salt. The TFA salt was partitioned between 4:1 DCM:iPrOH and saturated NaHCO$_{3(aq)}$. The combined organic extracts were dried over anhydrous Na$_2$SO$_{4(s)}$, filtered and concentrated in vacuo to afford the title compound (19.1 mg, 73% yield). MS (apci) m/z=581.2 (M+H).

Example 93

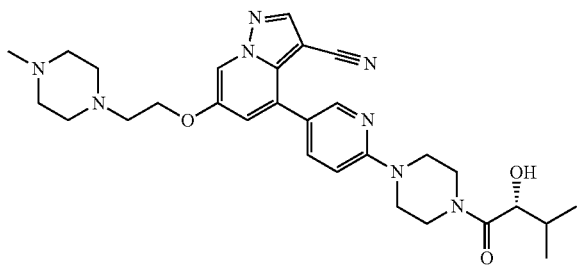 [SMILES: CC(C)[C@@H](O)C(=O)N1CCN(c2ccc(-c3cc(OCCN4CCN(C)CC4)cn4ncc(C#N)c34)cn2)CC1]

(R)-4-(6-(4-(2-hydroxy-3-methylbutanoyl)piperazin-1-yl)pyridin-3-yl)-6-(2-(4-methylpiperazin-1-yl)ethoxy)pyrazolo[1,5-a]pyridine-3-carbonitrile The title compound (17.9 mg, 74% yield) was prepared using a similar procedure to that described for Example 92, replacing D-(−)-mandelic acid with (R)-2-hydroxy-3-methylbutanoic acid. MS (apci) m/z=547.2 (M+H).

Example 94

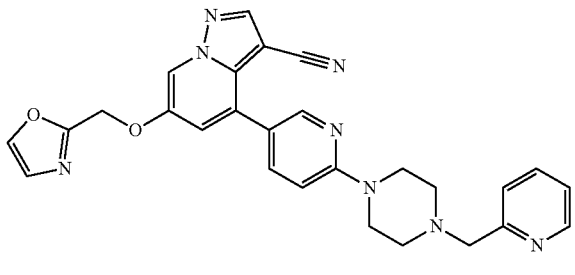 [SMILES: N#Cc1cnn2cc(OCc3ncco3)cc(-c3ccc(N4CCN(Cc5ccccn5)CC4)nc3)c12]

6-(oxazol-2-ylmethoxy)-4-(6-(4-(pyridin-2-ylmethyl)piperazin-1-yl)pyridin-3-yl)pyrazolo[1,5-a]pyridine-3-carbonitrile A solution of 6-(oxazol-2-ylmethoxy)-4-(6-(piperazin-1-yl)pyridin-3-yl)pyrazolo[1,5-a]pyridine-3-carbonitrile (Intermediate P19; 15 mg, 0.037 mmol) in DCE (74.7 μL) was treated sequentially with picolinaldehyde (4.29 μL, 0.0448 mmol) and NaBH(AcO)$_3$ (23.8 mg, 0.112 mmol). The mixture was stirred overnight at ambient temperature, then purified directly by silica chromatography (0-5% MeOH in DCM as the gradient eluent) to afford the title compound (10 mg, 54% yield). MS (apci) m/z=492.8 (M+H).

Example 95

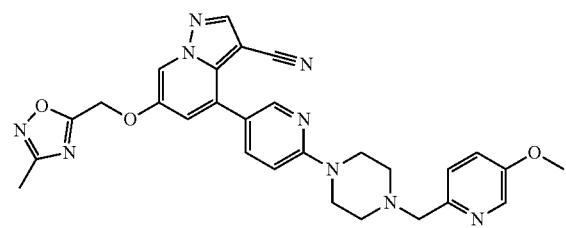 [SMILES: COc1ccc(CN2CCN(c3ccc(-c4cc(OCc5nc(C)no5)cn5ncc(C#N)c45)cn3)CC2)nc1]

4-(6-(4-((6-methoxypyridin-3-yl)methyl)piperazin-1-yl)pyridin-3-yl)-6-((3-methyl-1,2,4-oxadiazol-5-yl)methoxy)pyrazolo[1,5-a]pyridine-3-carbonitrile A solution of 6-((3-methyl-1,2,4-oxadiazol-5-yl)methoxy)-4-(6-(piperazin-1-yl)pyridin-3-yl)pyrazolo[1,5-a]pyridine-3-carbonitrile (Intermediate P20; 20 mg, 0.048 mmol) in DCE (961 μL) was treated sequentially with 6-methoxynicotinaldehyde (7.9 mg, 0.058 mmol) and NaBH(AcO)$_3$ (30.5 mg, 0.144 mmol). The resulting mixture was stirred overnight at ambient temperature, then purified directly by silica chromatography (0-5% MeOH in DCM as the gradient eluent) to afford the title compound (16.8 mg, 65% yield). MS (apci) m/z=537.8 (M+H).

Example 96

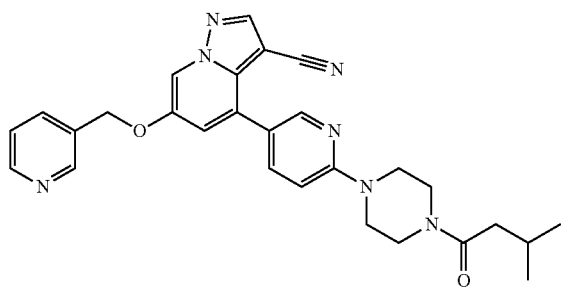 [SMILES: CC(C)CC(=O)N1CCN(c2ccc(-c3cc(OCc4cccnc4)cn4ncc(C#N)c34)cn2)CC1]

4-(6-(4-(3-methylbutanoyl)piperazin-1-yl)pyridin-3-yl)-6-(pyridin-3-ylmethoxy)pyrazolo[1,5-a]pyridine-3-carbonitrile A solution of 4-(6-(piperazin-1-yl)pyridin-3-yl)-6-(pyridin-3-ylmethoxy)pyrazolo[1,5-a]pyridine-3-carbonitrile (Intermediate P21; 43 mg, 0.105 mmol) and 3-methylbutanoyl chloride (15.4 µL, 0.125 mmol) in DCM (1.05 mL) was treated with TEA (14.6 µL, 0.105 mmol). The resulting mixture was stirred for 2 h at ambient temperature. The resulting mixture was purified directly by silica chromatography (1-5% MeOH in DCM as the gradient eluent) and again by C18 reverse phase chromatography (60:40 ACN: water with 2% TFA as the gradient eluent) to afford the title compound as the TFA salt. The TFA salt was partitioned between DCM and saturated NaHCO$_{3(aq)}$. The combined organic extracts were washed with water and brine, then dried over anhydrous Na$_2$SO$_{4(s)}$, filtered and concentrated in vacuo to afford the title compound (5 mg, 10% yield). MS (apci) m/z=496.2 (M+H).

Example 97

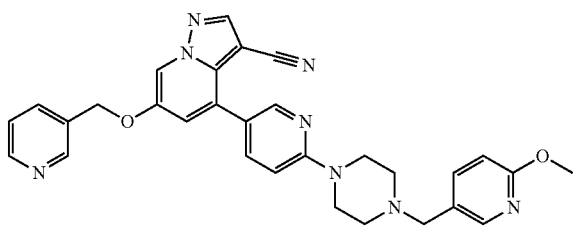 [SMILES: COc1ccc(CN2CCN(c3ccc(-c4cc(OCc5cccnc5)cn5ncc(C#N)c45)cn3)CC2)cn1]

4-(6-(4-((6-methoxypyridin-3-yl)methyl)piperazin-1-yl)pyridin-3-yl)-6-(pyridin-3-ylmethoxy)pyrazolo[1,5-a]pyridine-3-carbonitrile A solution of 4-(6-(piperazin-1-yl)pyridin-3-yl)-6-(pyridin-3-ylmethoxy)pyrazolo[1,5-a]pyridine-3-carbonitrile (Intermediate P21; 43 mg, 0.105 mmol) in DCE (1.05 mL) was treated sequentially with 6-methoxynicotinaldehyde (17.2 mg, 0.125 mmol) and NaBH(AcO)$_3$ (66.5 mg, 0.314 mmol). The resulting mixture was stirred for 1 hour at ambient temperature. The resulting mixture was purified directly by silica chromatography (1-5% MeOH in DCM as the gradient eluent) and then by C18 reverse phase chromatography (60:40 ACN:water with 2% TFA as the gradient eluent) to afford the title compound as the TFA salt. The TFA salt was partitioned between DCM and saturated NaHCO$_3$ $_{(aq)}$. The resulting organic extracts were washed with water and brine, then dried over anhydrous Na$_2$SO$_{4(s)}$, filtered and concentrated in vacuo to afford the title compound (10.4 mg, 19% yield). MS (apci) m/z=533.2 (M+H).

Example 98

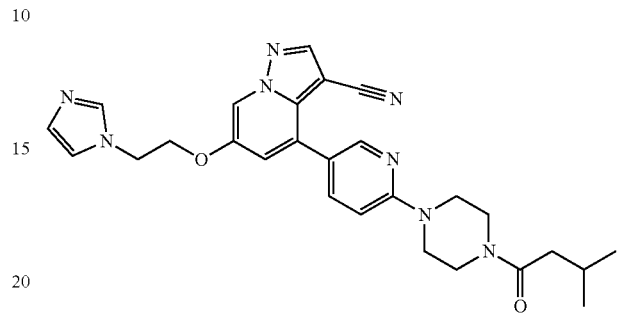

6-(2-(1H-imidazol-1-yl)ethoxy)-4-(6-(4-(3-methylbutanoyl)piperazin-1-yl)pyridin-3-yl)pyrazolo[1,5-a]pyridine-3-carbonitrile A solution of 6-(2-(1H-imidazol-1-yl)ethoxy)-4-(6-(piperazin-1-yl)pyridin-3-yl)pyrazolo[1,5-a]pyridine-3-carbonitrile (Intermediate P22; 20 mg, 0.048 mmol) and 3-methylbutanoyl chloride (5.9 µL, 0.048 mmol) in DCM (483 µL) was treated with TEA (6.7 µL, 0.048 mmol). The resulting mixture was stirred for 1.5 h at ambient temperature. The mixture was concentrated in vacuo, and the residue was purified by C18 reverse phase chromatography (60:40 ACN: water with 2% TFA as the gradient eluent) to afford the title compound as the TFA salt. The TFA salt was partitioned between DCM and saturated NaHCO$_{3(aq)}$ and the biphasic mixture was extracted with DCM. The combined organic extracts were washed with brine, then dried over anhydrous Na$_2$SO$_{4(s)}$, filtered and concentrated in vacuo to cleanly provide the title compound (10.4 mg, 43% yield). MS (apci) m/z=499.3 (M+H).

Example 99

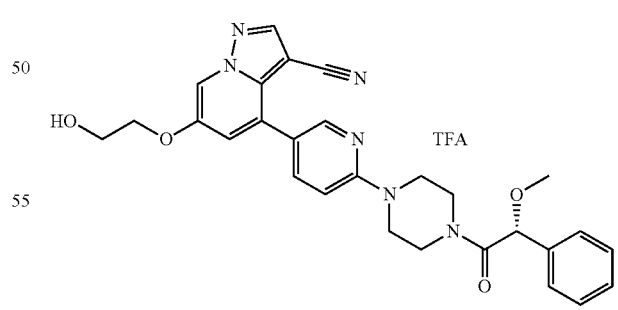

(R)-6-(2-hydroxyethoxy)-4-(6-(4-(2-methoxy-2-phenylacetyl)piperazin-1-yl)pyridin-3-yl)pyrazolo[1,5-a]pyridine-3-carbonitrile 2,2,2-trifluoroacetate A solution of 6-(2-hydroxyethoxy)-4-(6-(piperazin-1-yl)pyridin-3-yl)pyrazolo[1,5-a]pyridine-3-carbonitrile hydrochloride (Intermediate P23; 20 mg, 0.050 mmol), (R)-2-methoxy-2-phenylacetic acid (9.12 mg, 0.0549 mmol), HATU (20.9 mg, 0.0549 mmol) and DIEA (34.9 µL, 0.200 mmol) in DCM (249 µL) was stirred for 1 hour at ambient temperature. The mixture was concentrated in vacuo, and then purified by C18 reverse phase chromatography (5-95% ACN in water with 0.1% TFA as the gradient eluent) to afford the title compound as the TFA salt (18 mg, 58% yield). MS (apci) m/z=513.2 (M+H). $^1$H NMR (400 MHz, DMSO-d$^6$) δ: 8.38 (d, 1H, J=2.0 Hz), 8.26 (s, 1H), 8.22 (d, 1H, J=2.3 Hz), 7.68 (dd, 1H, J=8.6, 2.3 Hz), 7.44-7.32 (m, 5H), 7.20 (d, 1H, J=2.3 Hz), 6.82 (d, 1H, J=9.0 Hz), 5.20 (s, 1H), 4.12 (t, 2H, J=4.3 Hz), 3.89 (t, 2H, J=4.3 Hz), 3.75-3.46 (m, 7H), 3.41 (s, 5H), 3.21-3.16 (m, 1H).

The compounds in Table F were prepared using a similar method to that described for the synthesis of Example 99, replacing (R)-2-methoxy-2-phenylacetic acid with the appropriate carboxylic. Reactions were monitored for completion by LCMS, and reaction durations were adjusted accordingly. Each compound was cleanly isolated following chromatographic purification using an appropriate gradient eluent. Most chromatographic conditions resulted in the isolation of the 2,2,2-trifluoroacetate salt of the title compound.

TABLE F

| Ex # | Structure | Chemical Name | MS (apci) m/z |
|---|---|---|---|
| 100 | 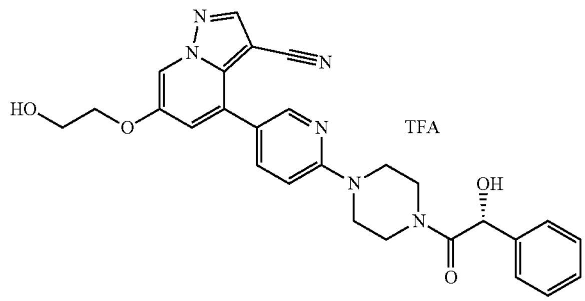 [SMILES: N#Cc1cnn2cc(OCCO)cc(-c3ccc(N4CCN(C(=O)[C@H](O)c5ccccc5)CC4)nc3)c12] | (R)-4-(6-(4-(2-hydroxy-2-phenylacetyl)piperazin-1-yl)pyridin-3-yl)-6-(2-hydroxyethoxy)pyrazolo[1,5-a]pyridine-3-carbonitrile 2,2,2-trifluoroacetate | 498.8 (M + H) |
| 101 | 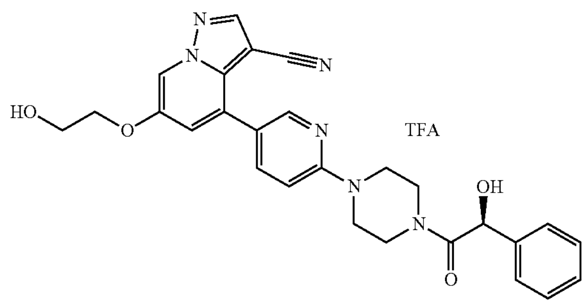 [SMILES: N#Cc1cnn2cc(OCCO)cc(-c3ccc(N4CCN(C(=O)[C@@H](O)c5ccccc5)CC4)nc3)c12] | (S)-4-(6-(4-(2-hydroxy-2-phenylacetyl)piperazin-1-yl)pyridin-3-yl)-6-(2-hydroxyethoxy)pyrazolo[1,5-a]pyridine-3-carbonitrile 2,2,2-trifluoroacetate | 498.8 (M + H) |
| 102 | 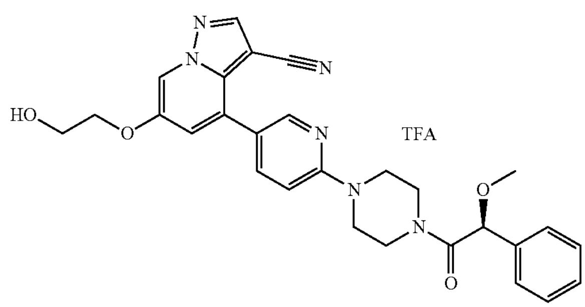 [SMILES: CO[C@H](C(=O)N1CCN(c2ccc(-c3cc(OCCO)cn4ncc(C#N)c34)cn2)CC1)c1ccccc1] | (S)-6-(2-hydroxyethoxy)-4-(6-(4-(2-methoxy-2-phenylacetyl)piperazin-1-yl)pyridin-3-yl)pyrazolo[1,5-a]pyridine-3-carbonitrile 2,2,2-trifluoroacetate | 512.8 (M + H) |
| 103 | 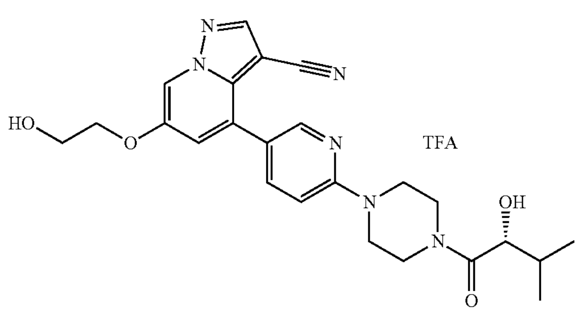 [SMILES: CC(C)[C@@H](O)C(=O)N1CCN(c2ccc(-c3cc(OCCO)cn4ncc(C#N)c34)cn2)CC1] | (R)-4-(6-(4-(2-hydroxy-3-methylbutanoyl)piperazin-1-yl)pyridin-3-yl)-6-(2-hydroxyethoxy)pyrazolo[1,5-a]pyridine-3-carbonitrile 2,2,2-trifluoroacetate | 464.8 (M + H) |

TABLE F-continued

| Ex # | Structure | Chemical Name | MS (apci) m/z |
|---|---|---|---|
| 104 | 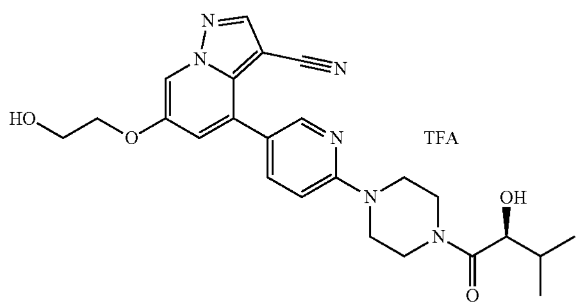 [SMILES: CC(C)[C@H](O)C(=O)N1CCN(c2ccc(-c3cc(OCCO)cn4ncc(C#N)c34)cn2)CC1] | (S)-4-(6-(4-(2-hydroxy-3-methylbutanoyl)piperazin-1-yl)pyridin-3-yl)-6-(2-hydroxyethoxy)pyrazolo[1,5-a]pyridine-3-carbonitrile 2,2,2-trifluoroacetate | 464.9 (M + H) |

Example 105

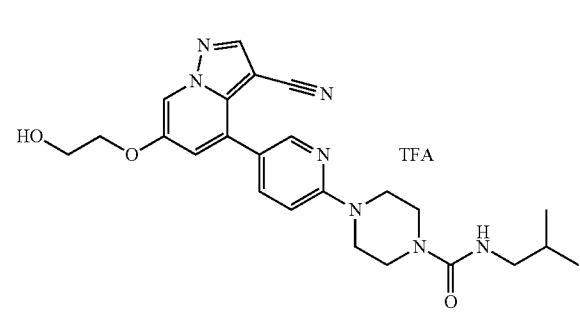 [SMILES: CC(C)CNC(=O)N1CCN(c2ccc(-c3cc(OCCO)cn4ncc(C#N)c34)cn2)CC1 ; "TFA"]

4-(5-(3-cyano-6-(2-hydroxyethoxy)pyrazolo[1,5-a]pyridin-4-yl)pyridin-2-yl)-N-isobutylpiperazine-1-carboxamide 2,2,2-trifluoroacetate A cold (0° C.) solution of 6-(2-hydroxyethoxy)-4-(6-(piperazin-1-yl)pyridin-3-yl)pyrazolo[1,5-a]pyridine-3-carbonitrile hydrochloride (Intermediate P23; 11 mg, 0.027 mmol) and DIEA (24.0 µL, 0.137 mmol) in DMA (549 µL) was treated with 4-nitrophenyl chloroformate (5.81 mg, 0.0288 mmol). After stirring the mixture for 1 hour at 0° C., isobutylamine (10.0 mg, 0.137 mmol) was added. The mixture was stirred for 1 day at 80° C., before introducing additional isobutyl amine (10 mg, 0.137 mmol). The mixture was stirred for an additional 4 h at 80° C., cooled to ambient temperature, diluted with MeOH and directly purified by C18 reverse phase chromatography (5-95% ACN in water with 0.1% TFA as the gradient eluent) to afford the title compound as the TFA salt (10 mg, 63% yield). MS (apci) m/z=463.9 (M+H).

Example 106

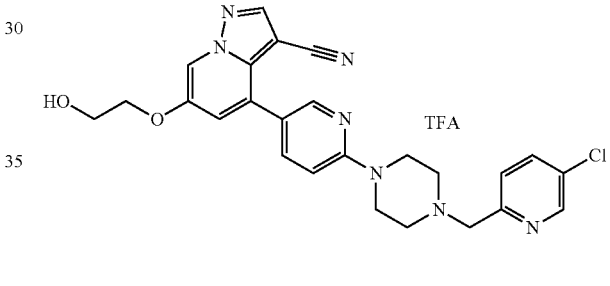

4-(6-(4-((5-chloropyridin-2-yl)methyl)piperazin-1-yl)pyridin-3-yl)-6-(2-hydroxyethoxy)pyrazolo[1,5-a]pyridine-3-carbonitrile 2,2,2-trifluoroacetate A solution of 6-(2-hydroxyethoxy)-4-(6-(piperazin-1-yl)pyridin-3-yl)pyrazolo[1,5-a]pyridine-3-carbonitrile hydrochloride (Intermediate P23; 11.6 mg, 0.0289 mmol), 5-chloropicolinaldehyde (8.19 mg, 0.0579 mmol) and NaBH(AcO)₃ (18.4 mg, 0.0868 mmol) in DCE (579 µL) was stirred for 1 day at ambient temperature. The resulting reaction mixture was diluted with MeOH, filtered through a micron filter and purified by C18 reverse phase chromatography (5-95% ACN in water with 0.1% TFA as the gradient eluent) to afford the title compound as the 2,2,2-trifluoroacetate salt (16.9 mg, 97% yield). MS (apci) m/z=490.1 (M+H).

The compounds in Table G were prepared using a similar method to that described for the synthesis of Example 106, replacing 5-chloropicolinaldehyde with the appropriate aldehyde. Reactions were monitored for completion by LCMS, and reaction durations were adjusted accordingly. Each compound was cleanly isolated following chromatographic purification using an appropriate gradient eluent. Most chromatographic conditions resulted in the isolation of the 2,2,2-trifluoroacetate salt of the title compound.

TABLE G

| Ex # | Structure | Chemical Name | MS (apci) m/z |
|---|---|---|---|
| 107 | 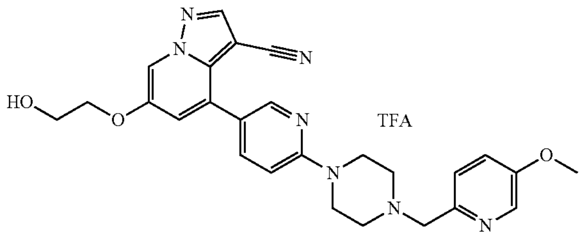 [SMILES: COc1ccc(CN2CCN(c3ccc(-c4cc(OCCO)cn5ncc(C#N)c45)cn3)CC2)nc1] | 6-(2-hydroxyethoxy)-4-(6-(4-((5-methoxypyridin-2-yl)methyl)piperazin-1-yl)pyridin-3-yl)pyrazolo[1,5-a]pyridine-3-carbonitrile 2,2,2-trifluoroacetate | 486.2 (M + H) |
| 108 | 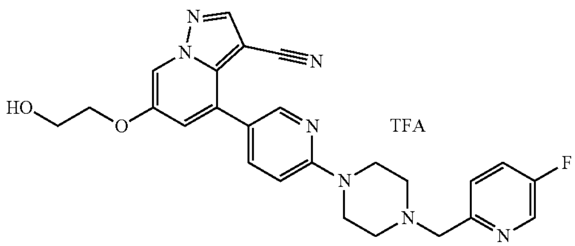 [SMILES: N#Cc1cnn2cc(OCCO)cc(-c3ccc(N4CCN(Cc5ccc(F)cn5)CC4)nc3)c12] | 4-(6-(4-((5-fluoropyridin-2-yl)methyl)piperazin-1-yl)pyridin-3-yl)-6-(2-hydroxyethoxy)pyrazolo[1,5-a]pyridine-3-carbonitrile 2,2,2-trifluoroacetate | 474.2 (M + H) |

Example 109

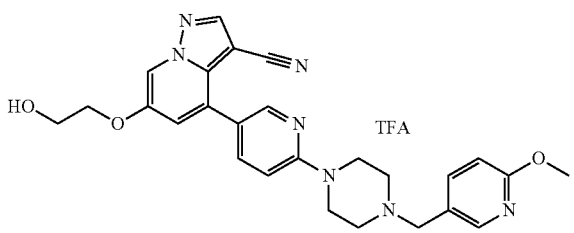 [SMILES: COc1ccc(CN2CCN(c3ccc(-c4cc(OCCO)cn5ncc(C#N)c45)cn3)CC2)cn1 ; "TFA"]

6-(2-hydroxyethoxy)-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate Step 1: Preparation of 6-(2-((tert-butyldimethyl silyl)oxy)ethoxy)-4-(6-(4-((6-methoxypyridin-3-yl)methyl)piperazin-1-yl)pyridin-3-yl)pyrazolo[1,5-a]pyridine-3-carbonitrile A mixture of 6-hydroxy-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate (Intermediate P24; 9.5 mg, 0.017 mmol), (2-bromoethoxy)(tert-butyl)dimethylsilane (5.1 mg, 0.022 mmol) and $K_2CO_{3(s)}$ (8.9 mg, 0.065 mmol) in DMF (108 μL) was stirred for 1 day at 50° C. After cooling to ambient temperature the reaction mixture was directly purified by silica chromatography (0-100% EtOAc/hexanes as the gradient eluent) to afford the title compound (12 mg, 93% yield). MS (apci) m/z=600.8 (M+H).

Step 2: Preparation of 6-(2-hydroxyethoxy)-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate A solution of 6-(2-((tert-butyldimethylsilyl)oxy)ethoxy)-4-(6-(4-((6-methoxypyridin-3-yl)methyl)piperazin-1-yl)pyridin-3-yl)pyrazolo[1,5-a]pyridine-3-carbonitrile (12 mg, 0.020 mmol) in THF (2 mL) was treated with TBAF (100 μL, 0.10 mmol), was stirred for 3 d at ambient temperature. The resulting suspension was filtered and the solids were washed with MeOH. The filtrate was concentrated and purified by C18 reverse phase chromatography (5-95% ACN in water with 0.1% TFA as the gradient eluent) to afford the title compound as the 2,2,2-trifluoroacetate salt (6.8 mg, 57% yield). MS (apci) m/z=485.8 (M+H).

Example 110

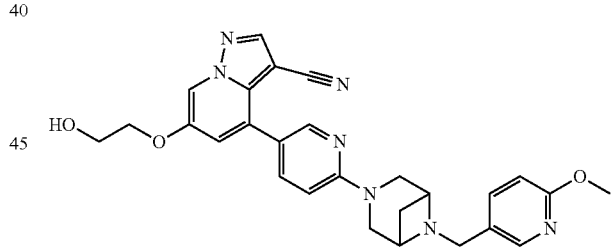

6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-(2-hydroxyethoxy)pyrazolo[1,5-a]pyridine-3-carbonitrile hydrochloride (Intermediate P27; 17 mg, 0.045 mmol) in DCE (226 μL) was treated sequentially with 6-methoxynicotinaldehyde (12 mg, 0.090 mmol) and NaBH(AcO)$_3$ (29 mg, 0.14 mmol). After stirring for 3 h at ambient temperature, the reaction mixture was concentrated in vacuo and purified by silica chromatography (0-20% MeOH in DCM as the gradient eluent) to cleanly provide the title compound (2.7 mg, 12% yield). MS (apci) m/z=498.2 (M+H). $^1$H NMR (400 MHz, CD$_3$OD) δ: 8.66 (d, 1H, J=2.0 Hz), 8.56 (s, 1H), 8.37 (d, 1H, J=2.7 Hz), 8.04 (d, 1H, J=2.0

Hz), 7.81 (dd, 1H, J=9.0, 2.7 Hz), 7.65 (dd, 1H, J=8.6, 2.3 Hz), 7.26 (d, 1H, J=2.3 Hz), 6.76 (d, 1H, J=9.0 Hz), 6.73 (d, 1H, J=8.6 Hz), 4.93 (t, 1H, J=5.5 Hz), 4.11 (t, 2H, J=4.7 Hz), 3.79 (s, 3H), 3.73 (m, 3H), 3.69 (br s, 1H), 3.64 (d, 2H, J=5.9 Hz), 3.51 (br d, 2H), 3.47 (s, 2H), 2.47 (m, 1H), 1.55 (d, 1H, J=8.6 Hz).

The compounds in Table H were prepared using a similar method to that described for the synthesis of Example 110, replacing 6-methoxynicotinaldehyde with the appropriate aldehyde. Reactions were monitored for completion by LCMS, and reaction durations were adjusted accordingly. Each compound was cleanly isolated following chromatographic purification using an appropriate gradient eluent.

2-carboxylate (247 mg, 1.09 mmol) in DMSO (2.5 mL) was subjected to microwave irradiation at 125° C. for 1 hour. The reaction mixture was partitioned between water and DCM and extracted with DCM. The combined organic extracts were dried over anhydrous $Na_2SO_{4(s)}$, filtered and concentrated in vacuo. The residue was dissolved in DCM (2 mL) and treated with 4 N HCl in dioxanes (2 mL). After stirring overnight at ambient temperature, the mixture was concentrated in vacuo. The residue was purified by silica chromatography (0-100% [20% MeOH with 2% $NH_4OH$] in DCM as the gradient eluent) to cleanly provide the title compound (115 mg, 78% yield). MS (apci) m/z=405.2 (M+H).

TABLE H

| Ex # | Structure | Chemical Name | MS (apci) m/z |
|---|---|---|---|
| 111 | 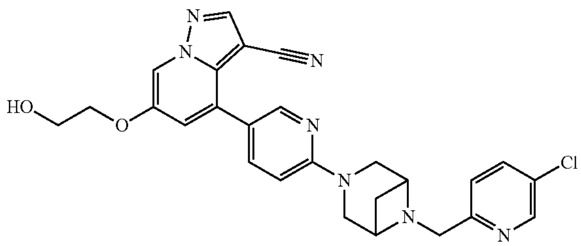 [SMILES: N#Cc1cnn2cc(OCCO)cc(-c3ccc(N4CC5CC(C4)N5Cc4ccc(Cl)cn4)nc3)c12] | 4-(6-(6-((5-chloropyridin-2-yl)methyl)-3,6-diazabicyclo[3.1.1]heptan-3-yl)pyridin-3-yl)-6-(2-hydroxyethoxy)pyrazolo[1,5-a]pyridine-3-carbonitrile | 502.2 (M + H) |
| 112 | 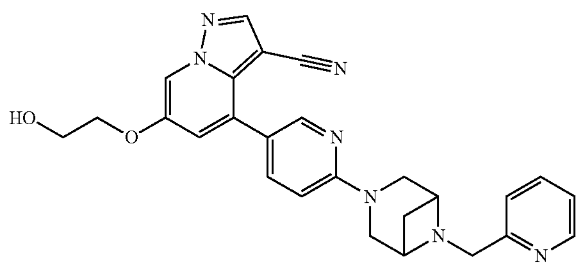 [SMILES: N#Cc1cnn2cc(OCCO)cc(-c3ccc(N4CC5CC(C4)N5Cc4ccccn4)nc3)c12] | 6-(2-hydroxyethoxy)-4-(6-(6-(pyridin-2-ylmethyl)-3,6-diazabicyclo[3.1.1]heptan-3-yl)pyridin-3-yl)pyrazolo[1,5-a]pyridine-3-carbonitrile | 468.2 (M + H) |

Example 113

Example 114

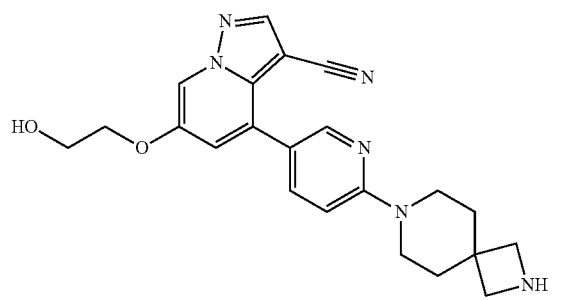 [SMILES: N#Cc1cnn2cc(OCCO)cc(-c3ccc(N4CCC5(CC4)CNC5)nc3)c12]

4-(6-(2,7-diazaspiro[3.5]nonan-7-yl)pyridin-3-yl)-6-(2-hydroxyethoxy)pyrazolo[1,5-a]pyridine-3-carbonitrile In a microwave vessel, a suspension of 6-(2-((tert-butyldimethylsilyl)oxy)ethoxy)-4-(6-fluoropyridin-3-yl)pyrazolo[1,5-a]pyridine-3-carbonitrile (Intermediate P26; 150 mg, 0.364 mmol) and tert-butyl 2,7-diazaspiro[3.5]nonane-

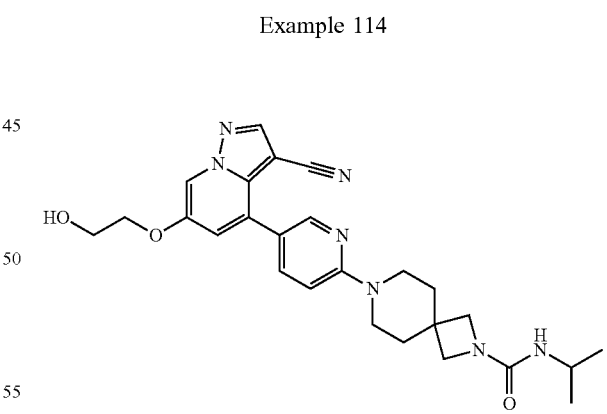

7-(5-(3-cyano-6-(2-hydroxyethoxy)pyrazolo[1,5-a]pyridin-4-yl)pyridin-2-yl)-N-isopropyl-2,7-diazaspiro[3.5]nonane-2-carboxamide A solution of 4-(6-(2,7-diazaspiro[3.5]nonan-7-yl)pyridin-3-yl)-6-(2-hydroxyethoxy)pyrazolo[1,5-a]pyridine-3-carbonitrile (Example 113; 20 mg, 0.049 mmol) in anhydrous DMSO (246 μL) was treated sequentially with DIEA (26 μL, 0.15 mmol) and 2-isocyanatopropane (4.2 mg, 0.049 mmol) and stirred overnight at ambient temperature. The reaction mixture was purified directly by silica chromatography (0-20% MeOH in DCM as the gradient eluent) and then by C18 reverse phase chromatography (5-95% ACN in water with 0.1% TFA as the gradient eluent) to cleanly provide the TFA salt of the title compound. The salt was dissolved in MeOH, filtered through an Agilent PL-HCO₃ MP SPE tube to neutralize, and the filtrate was concentrated in vacuo to cleanly provide the title compound (9.1 mg, 38% yield). MS (apci) m/z=490.2 (M+H).

Example 115

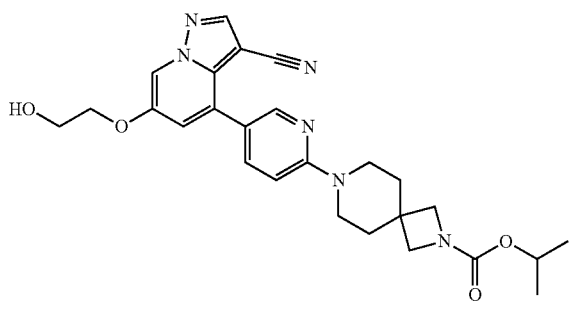 [SMILES: CC(C)OC(=O)N1CC2(CCN(c3ccc(-c4cc(OCCO)cn5ncc(C#N)c45)cn3)CC2)C1]

Isopropyl 7-(5-(3-cyano-6-(2-hydroxyethoxy)pyrazolo[1,5-a]pyridin-4-yl)pyridin-2-yl)-2,7-diazaspiro[3.5]nonane-2-carboxylate A solution of 4-(6-(2,7-diazaspiro[3.5]nonan-7-yl)pyridin-3-yl)-6-(2-hydroxyethoxy)pyrazolo[1,5-a]pyridine-3-carbonitrile (Example 113; 20 mg, 0.049 mmol) in DCM (247 µL) was treated sequentially with DIEA (43.2 µL, 0.247 mmol) and isopropyl carbonochloridate (7.70 µL, 0.0544 mmol) and stirred overnight at ambient temperature. The reaction mixture was concentrated in vacuo, and the residue was purified by silica chromatography (0-15% MeOH in DCM as the gradient eluent) to cleanly provide the title compound (6.7 mg, 28% yield). MS (apci) m/z=491.2 (M+H).

Example 116

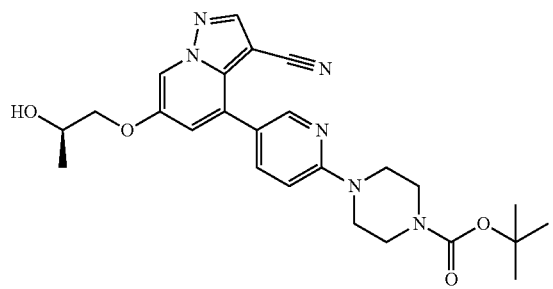 [SMILES: C[C@@H](O)COc1cc(-c2ccc(N3CCN(C(=O)OC(C)(C)C)CC3)nc2)c2c(C#N)cnn2c1]

tert-butyl (R)-4-(5-(3-cyano-6-(2-hydroxypropoxy)pyrazolo[1,5-a]pyridin-4-yl)pyridin-2-yl)piperazine-1-carboxylate A solution of tert-butyl 4-(5-(3-cyano-6-hydroxypyrazolo[1,5-a]pyridin-4-yl)pyridin-2-yl)piperazine-1-carboxylate (Intermediate P3; 200 mg, 0.476 mmol) in DMF (5 mL) was treated sequentially with $K_2CO_{3(s)}$ (328.7 mg, 2.378 mmol) and (R)-2-methyloxirane (166.6 µL, 2.378 mmol). After stirring for 22 h at 40° C., the reaction mixture was treated with additional (R)-2-methyloxirane (166.6 µL, 2.378 mmol) and the reaction temperature was increased to 50° C. An additional aliquot of (R)-2-methyloxirane (166.6 µL, 2.378 mmol) was added, and the mixture was stirred for 3 days at 50° C. The resulting mixture was cooled to ambient temperature, then purified directly by C18 reverse phase chromatography (5-90% ACN/water as the gradient eluent) to cleanly provide the title compound (121.5 mg, 53% yield). MS (apci) m/z=479.2 (M+H).

Example 117

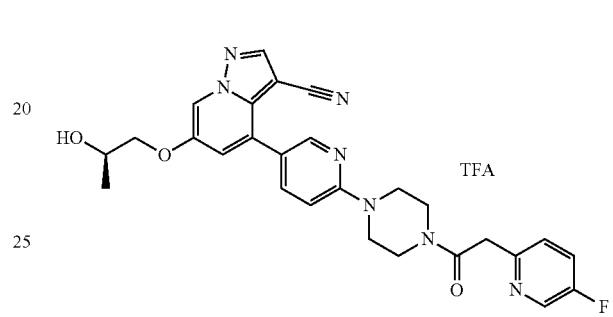

(R)-4-(6-(4-(2-(5-fluoropyridin-2-yl)acetyl)piperazin-1-yl)pyridin-3-yl)-6-(2-hydroxypropoxy)pyrazolo[1,5-a]pyridine-3-carbonitrile 2,2,2-trifluoroacetate A solution of (R)-6-(2-hydroxypropoxy)-4-(6-(piperazin-1-yl)pyridin-3-yl)pyrazolo[1,5-a]pyridine-3-carbonitrile hydrochloride (Intermediate P28; 7.2 mg, 0.017 mmol), 2-(5-fluoropyridin-2-yl)acetic acid (4.04 mg, 0.0260 mmol) and DIEA (15.2 µL, 0.0868 mmol) in DCM (347 µL) was treated with HATU (7.26 mg, 0.0191 mmol), then stirred overnight at ambient temperature. The formation of a diacylated product (MS (apci) m/z=652) required treating the mixture with $K_2CO_{3(s)}$ (328.7 mg, 2.378 mmol) in MeOH. The resulting mixture was stirred overnight at ambient temperature, then filtered and purifying by C18 reverse phase chromatography (5-95% ACN in water with 0.1% TFA as the gradient eluent) to cleanly provide the title compound as the 2,2,2-trifluoroacetate salt (10 mg, 92% yield). MS (apci) m/z=516.8 (M+2).

Example 118

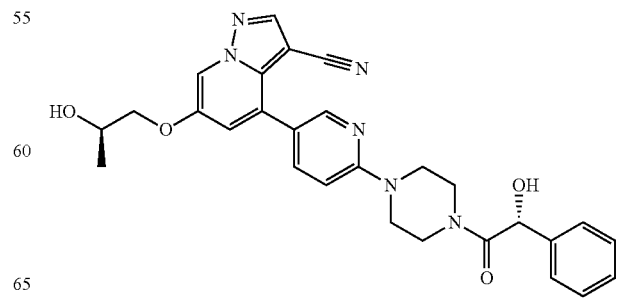

4-(6-(4-((R)-2-hydroxy-2-phenylacetyl)piperazin-1-yl)pyridin-3-yl)-6-((R)-2-hydroxypropoxy)pyrazolo[1,5-a]pyridine-3-carbonitrile A solution of (R)-6-(2-hydroxypropoxy)-4-(6-(piperazin-1-yl)pyridin-3-yl)pyrazolo[1,5-a]pyridine-3-carbonitrile hydrochloride (Intermediate P28; 100 mg, 0.241 mmol), D-(−)-mandelic acid (45.8 mg, 0.301 mmol) and DIEA (210 µL, 1.21 mmol) in DCM (1.21 mL) was treated with HATU (110 mg, 0.289 mmol), then stirred overnight at ambient temperature. The reaction mixture was filtered, and the filtrate was purified by C18 reverse phase chromatography (5-95% ACN in water with 0.1% TFA as the gradient eluent) to afford the title compound as a TFA salt. The salt was dissolved in DCM and MeOH and purified by silica chromatography (0-20% MeOH in DCM as the eluent) to cleanly provide the title compound (68 mg, 45% yield). MS (apci) m/z=512.8 (M+H). $^1$H NMR (400 MHz, CDCl$_3$—) δ: 8.31 (s, 1H), 8.17 (s, 1H), 8.14 (s, 1H), 7.73 (dd, 1H, J=9.0, 2.0 Hz), 7.39-7.32 (m, 5H), 7.10 (s, 1H), 6.71 (d, 1H, J=9.0 Hz), 5.25 (s, 1H), 4.38 (br m, 2H), 4.23 (m, 1H), 4.00-3.95 (m, 2H), 3.88-3.78 (m, 2H), 3.65-3.60 (m, 2H), 3.44-3.39 (m, 2H), 1.31 (d, 3H, J=6.2 Hz).

The compounds in Table I were prepared using a similar method to that described for the synthesis of Example 118, replacing D-(−)-mandelic acid with the appropriate aldehyde, and using varied amounts of HATU (1.1-1.25 equivalents) and DIEA (3.5-5 equivalents). Reactions were monitored for completion by LCMS, and reaction durations were adjusted accordingly. Each compound was cleanly isolated following a single chromatographic purification using an appropriate gradient eluent. Some chromatographic conditions resulted in the isolation of the 2,2,2-trifluoroacetate salt of the title compound.

TABLE I

| Ex # | Structure | Chemical Name | MS (apci) m/z |
|---|---|---|---|
| 119 | 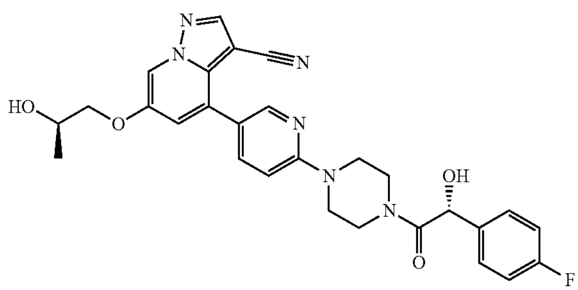 [SMILES: C[C@@H](O)COc1cc(-c2ccc(N3CCN(C(=O)[C@H](O)c4ccc(F)cc4)CC3)nc2)c2c(C#N)cnn2c1] | 4-(6-(4-((R)-2-(4-fluorophenyl)-2-hydroxyacetyl)piperazin-1-yl)pyridin-3-yl)-6-((R)-2-hydroxypropoxy)pyrazolo[1,5-a]pyridine-3-carbonitrile | 531.2 (M + H) |
| 120 | 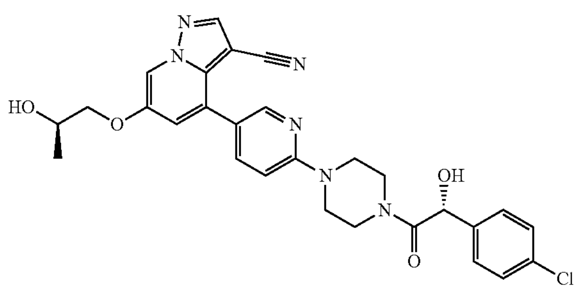 [SMILES: C[C@@H](O)COc1cc(-c2ccc(N3CCN(C(=O)[C@H](O)c4ccc(Cl)cc4)CC3)nc2)c2c(C#N)cnn2c1] | 4-(6-(4-((R)-2-(4-chlorophenyl)-2-hydroxyacetyl)piperazin-1-yl)pyridin-3-yl)-6-((R)-2-hydroxypropoxy)pyrazolo[1,5-a]pyridine-3-carbonitrile | 547.2 (M + H) |
| 121 | 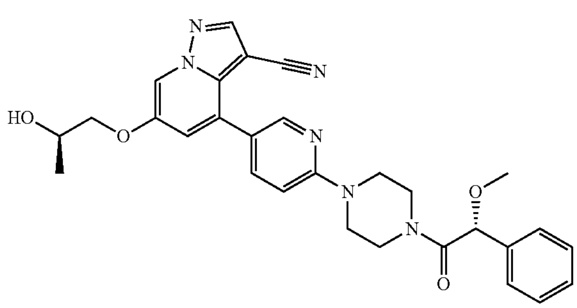 [SMILES: CO[C@@H](C(=O)N1CCN(c2ccc(-c3cc(OC[C@@H](C)O)cn4ncc(C#N)c34)cn2)CC1)c1ccccc1] | 6-((R)-2-hydroxypropoxy)-4-(6-(4-((R)-2-methoxy-2-phenylacetyl)piperazin-1-yl)pyridin-3-yl)pyrazolo[1,5-a]pyridine-3-carbonitrile | 527.2 (M + H) |

TABLE I-continued

| Ex # | Structure | Chemical Name | MS (apci) m/z |
|---|---|---|---|
| 122 | 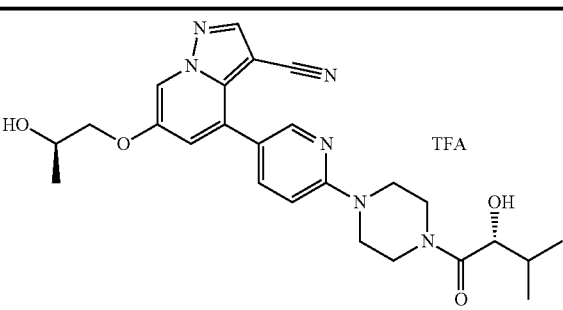 | 4-(6-(4-((R)-2-hydroxy-3-methylbutanoyl)piperazin-1-yl)pyridin-3-yl)-6-((R)-2-hydroxypropoxy)pyrazolo[1,5-a]pyridine-3-carbonitrile 2,2,2-trifluoroacetate | 478.9 (M + H) |

Example 123

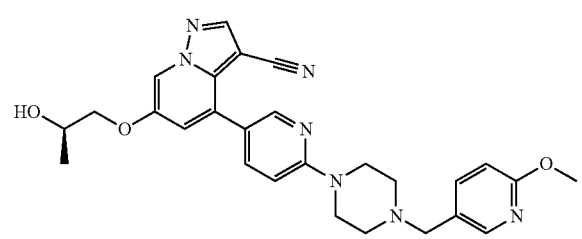 [SMILES: COc1ccc(CN2CCN(c3ccc(-c4cc(OC[C@@H](C)O)cn5ncc(C#N)c45)cn3)CC2)cn1]

(R)-6-(2-hydroxypropoxy)-4 (6-(4-((6-methoxypyridin-3-yl)methyl)piperazin-1-yl)pyridin-3-yl)pyrazolo[1,5-a]pyridine-3-carbonitrile A solution of (R)-6-(2-hydroxypropoxy)-4-(6-(piperazin-1-yl)pyridin-3-yl)pyrazolo[1,5-a]pyridine-3-carbonitrile (Intermediate P29; 15 mg, 0.040 mmol) and 6-methoxynicotinaldehyde (10.9 mg, 0.0793 mmol) in DCE (396 μL) was treated with NaBH(AcO)₃ (33.6 mg, 0.159 mmol), and stirred for 1 day at 50° C. The resulting mixture was cooled to ambient temperature and purified directly by silica chromatography (0-20% DCM/MeOH as the gradient eluent). The isolated product was further purified by C18 reverse phase chromatography (5-95% water-ACN with 0.1% TFA as the gradient eluent) to cleanly providing the title compound as the TFA salt. The TFA salt was dissolved in MeOH and sonicated with K₂CO₃₍s₎. The resulting suspension was filtered, and concentrated in vacuo to cleanly provide the title compound (6.5 mg, 33% yield). MS (apci) m/z=500.2 (M+H). ¹H NMR (400 MHz, DMSO-d⁶) δ: 8.42 (s, 1H), 8.30 (br s, 1H), 8.27 (d, 1H, J=2.0 Hz), 8.07 (d, 1H, J=2.3 Hz), 7.74 (dd, 1H, J=8.3, 2.3 Hz), 7.71 (dd, 1H, J=8.2, 2.0 Hz), 7.25 (d, 1H, J=2.0 Hz), 6.91 (d, 1H, J=9.0 Hz), 6.79 (d, 1H, J=8.6 Hz), 4.15-4.11 (m, 1H), 4.00 (dd, 1H, J=9.0, 5.4 Hz), 3.92 (dd, 1H, J=9.4, 7.4 Hz), 3.89 (s, 3H), 3.64-3.62 (m, 4H), 3.53 (s, 2H), 2.58-2.56 (m, 4H), 1.28 (d, 2H, J=6.3 Hz).

Example 124

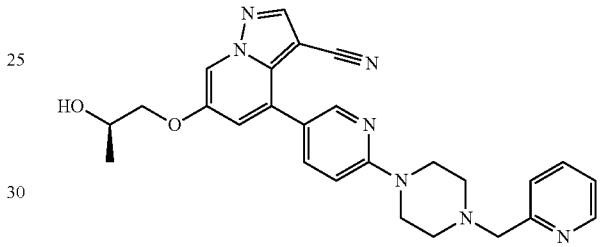

(R)-6-(2-hydroxypropoxy)-4-(6-(4-(pyridin-2-ylmethyl)piperazin-1-yl)pyridin-3-yl)pyrazolo[1,5-a]pyridine-3-carbonitrile A solution of (R)-6-(2-hydroxypropoxy)-4-(6-(piperazin-1-yl)pyridin-3-yl)pyrazolo[1,5-a]pyridine-3-carbonitrile (Intermediate P29; 15 mg, 0.040 mmol) in DCE (396 μL) and MeOH (5 drops) was treated with picolinaldehyde (7.6 μL, 0.079 mmol) and NaBH(AcO)₃ (33.6 mg, 0.159 mmol). The resulting mixture was stirred overnight at 50° C., before introducing additional NaBH(AcO)₃ (33.6 mg, 0.159 mmol). The resulting mixture was stirred an additional 2 h at 50° C., then cooled to ambient temperature. The reaction mixture was purified directly by silica chromatography (0-20% DCM/MeOH as the gradient eluent) to cleanly provide the title compound (12 mg, 64% yield). MS (apci) m/z=470.2 (M+H).

Example 125

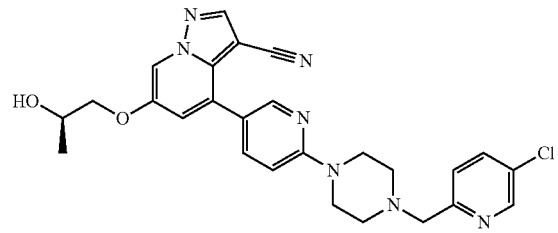

(R)-4-(6-(4-((5-chloropyridin-2-yl)methyl)piperazin-1-yl)pyridin-3-yl)-6-(2-hydroxypropoxy)pyrazolo[1,5-a]pyridine-3-carbonitrile A solution of (R)-6-(2-hydroxypropoxy)-4-(6-(piperazin-1-yl)pyridin-3-yl)pyrazolo[1,5-a]pyridine-3-carbonitrile hydrochloride (Intermediate P28; 11 mg, 0.027 mmol), 5-chloropicolinaldehyde (7.5 mg, 0.053 mmol) and NaBH(AcO)$_3$ (17 mg, 0.080 mmol) in DCE (530 µL) was stirred for 1 day at ambient temperature. The resulting mixture was purified directly by silica chromatography (using a stepwise gradient of 0-100% EtOAc in hexanes followed by 10% MeOH in EtOAc as the eluents) to cleanly provide the title compound (7 mg, 52% yield). MS (apci) m/z=504.2 (M+H).

Example 126

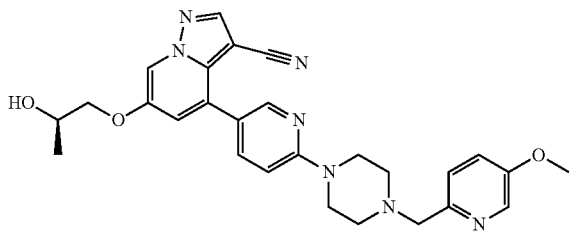 [SMILES: COc1ccc(CN2CCN(c3ccc(-c4cc(OC[C@@H](C)O)cn5ncc(C#N)c45)cn3)CC2)nc1]

(R)-6-(2-hydroxypropoxy)-4-(6-(4-((5-methoxypyridin-2-yl)methyl)piperazin-1-yl)pyridin-3-yl)pyrazolo[1,5-a]pyridine-3-carbonitrile The title compound (13 mg, 98% yield) was prepared and purified using a similar procedure to that described for Example 125, replacing 5-chloropicolinaldehyde with 5-methoxypicolinaldehyde. MS (apci) m/z=500.2 (M+H).

Example 127

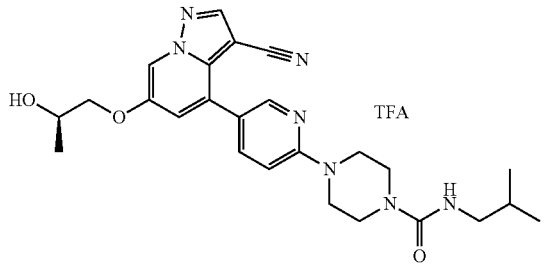 [SMILES: CC(C)CNC(=O)N1CCN(c2ccc(-c3cc(OC[C@@H](C)O)cn4ncc(C#N)c34)cn2)CC1]

(R)-4-(5-(3-cyano-6-(2-hydroxypropoxy)pyrazolo[1,5-a]pyridin-4-yl)pyridin-2-yl)-N-isobutylpiperazine-1-carboxamide 2,2,2-trifluoroacetate A cold (0° C.) solution of (R)-6-(2-hydroxypropoxy)-4-(6-(piperazin-1-yl)pyridin-3-yl)pyrazolo[1,5-a]pyridine-3-carbonitrile hydrochloride (Intermediate P28; 15 mg, 0.0362 mmol) and DIEA (31.6 µL, 0.181 mmol) in DMA (723 µL) was treated with 4-nitrophenyl chloroformate (8.74 mg, 0.0434 mmol). After stirring the mixture for 1 hour at 0° C., isobutylamine (13.2 mg, 0.181 mmol) was added. The resulting mixture was stirred for 1 day at 80° C., before adding additional isobutyl amine (13 mg, 0.181 mmol). The mixture was stirred for 4 h at 80° C. The resulting mixture was diluted with MeOH and directly purified by C18 reverse phase chromatography (5-95% ACN in water with 0.1% TFA as the gradient eluent) to afford the title compound as the 2,2,2-trifluoroacetate salt (15.6 mg, 73% yield). MS (apci) m/z=477.9 (M+H).

Example 128

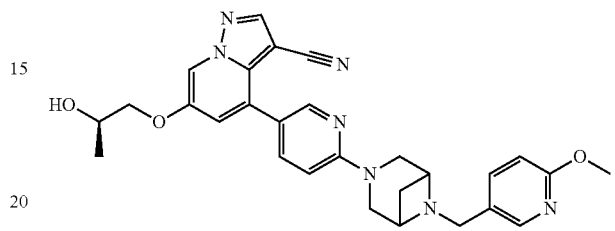

6-((R)-2-hydroxypropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-((R)-2-hydroxypropoxy)pyrazolo[1,5-a]pyridine-3-carbonitrile dihydrochloride (Intermediate P30; 11.8 mg, 0.0276 mmol) in DCE (396 µL) was treated sequentially with 6-methoxynicotinaldehyde (7.58 mg, 0.0553 mmol) and NaBH(AcO)$_3$ (17.6 mg, 0.0829 mmol). The resulting mixture was stirred overnight at ambient temperature and then concentrated in vacuo. The residue was purified by silica chromatography (0-20% MeOH in DCM as the gradient eluent) to cleanly provide the title compound (7 mg, 50% yield). MS (apci) m/z=512.2 (M+H).

Example 129

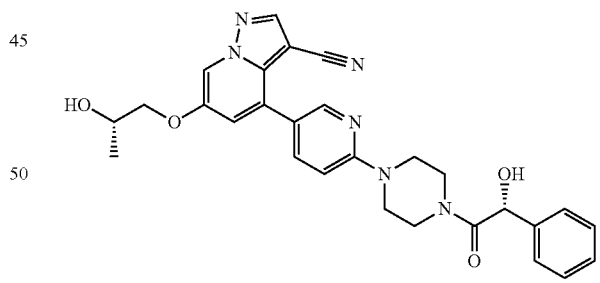

4-(6-(4-((R)-2-hydroxy-2-phenylacetyl)piperazin-1-yl)pyridin-3-yl)-6-((S)-2-hydroxypropoxy)pyrazolo[1,5-a]pyridine-3-carbonitrile A solution of (S)-6-(2-hydroxypropoxy)-4-(6-(piperazin-1-yl)pyridin-3-yl)pyrazolo[1,5-a]pyridine-3-carbonitrile hydrochloride (Intermediate P31; 13.8 mg, 0.0333 mmol), (R)-2-hydroxy-2-phenylacetic acid (5.31 mg, 0.0349 mmol), DIEA (20.3 µL, 0.116 mmol) in DCM (333 µL) was treated with HATU (13.9 mg, 0.0366 mmol), then stirred for 1 hour at ambient temperature. The reaction mixture was loaded directly onto a flash column equilibrated with hexanes and eluted with 0-100% DCM/hexanes to 0-20% MeOH in DCM gradient to cleanly provide the title compound (8 mg, 47% yield). MS (apci) m/z=513.2 (M+H).

Example 130

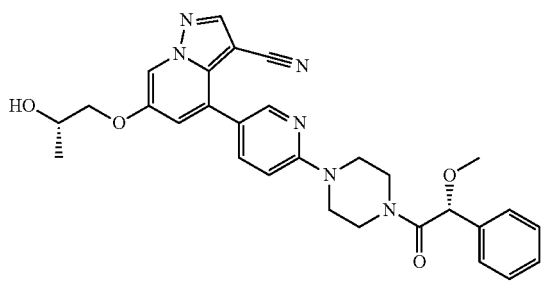 [SMILES: CO[C@@H](C(=O)N1CCN(c2ccc(-c3cc(OC[C@H](C)O)cn4ncc(C#N)c34)cn2)CC1)c1ccccc1]

6-((S)-2-hydroxypropoxy)-4-(6-(4-((R)-2-methoxy-2-phenylacetyl)piperazin-1-yl)pyridin-3-yl)pyrazolo[1,5-a]pyridine-3-carbonitrile The title compound (8 mg, 49% yield) was prepared and purified using a similar procedure to that described for Example 129, replacing (R)-2-hydroxy-2-phenylacetic acid with (R)-2-methoxy-2-phenylacetic acid. MS (apci) m/z=527.2 (M+H).

Example 131

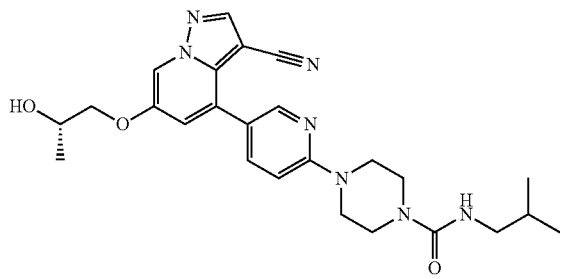 [SMILES: CC(C)CNC(=O)N1CCN(c2ccc(-c3cc(OC[C@H](C)O)cn4ncc(C#N)c34)cn2)CC1]

(S)-4-(5-(3-cyano-6-(2-hydroxypropoxy)pyrazolo[1,5-a]pyridin-4-yl)pyridin-2-yl)-N-isobutylpiperazine-1-carboxamide A cold (0° C.) solution of (S)-6-(2-hydroxypropoxy)-4-(6-(piperazin-1l-yl)pyridin-3-yl)pyrazolo[1,5-a]pyridine-3-carbonitrile hydrochloride (Intermediate P31; 15.6 mg, 0.0376 mmol) and DIEA (32.8 µL, 0.188 mmol) in DMA (752 µL) was treated with 4-nitrophenyl chloroformate (7.96 mg, 0.0395 mmol). After stirring the mixture for 1 hour at 0° C., isobutylamine (13.7 mg, 0.188 mmol) was added. The resulting mixture was stirred for 1 day at 80° C., and then additional isobutyl amine (13.7 mg, 0.188 mmol) was added. The mixture was stirred for 4 h at 80° C. The resulting mixture was diluted with MeOH and directly purified by C18 reverse phase chromatography (5-95% ACN/water with 0.1% TFA as the gradient eluent). The isolated product was further purified by silica chromatography (0-20% MeOH in DCM with 1% NH$_4$OH as the gradient eluent) to afford the title compound (4 mg, 22% yield). MS (apci) m/z=478.2 (M+H).

Example 132

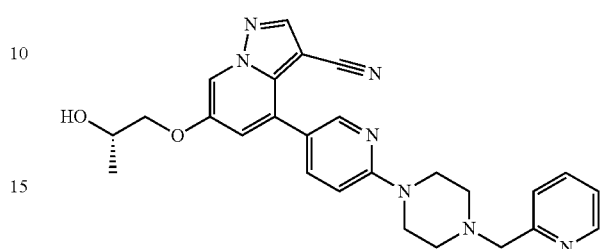

(S)-6-(2-hydroxypropoxy)-4-(6-(4-(pyridin-2-ylmethyl)piperazin-1-yl)pyridin-3-yl)pyrazolo[1,5-a]pyridine-3-carbonitrile A solution of (S)-6-(2-hydroxypropoxy)-4-(6-(piperazin-1-yl)pyridin-3-yl)pyrazolo[1,5-a]pyridine-3-carbonitrile (Intermediate P32; 20 mg, 0.053 mmol) and picolinaldehyde (6.3 µL, 0.066 mmol) in DMF (528.5 µL) was treated with NaBH(AcO)$_3$ (22.4 mg, 0.106 mmol). After stirring 1 day at ambient temperature, the mixture was filtered through a syringe filter and then concentrated in vacuo. The residue was purified by C18 reverse phase chromatography (5-95% water-ACN with 0.1% TFA as the gradient eluent) to cleanly provide the title compound as the TFA salt. The TFA salt was dissolved in 4:1 DCM/MeOH (20 mL) and treated with K$_2$CO$_{3(s)}$ (10 mL) to cleanly provide the title compound (17 mg, 69% yield). MS (apci) m/z=470.2 (M+H).

Example 133

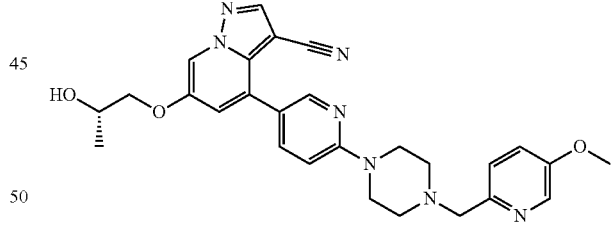

(S)-6-(2-hydroxypropoxy)-4-(6-(4-((5-methoxypyridin-2-yl)methyl)piperazin-1-yl)pyridin-3-yl)pyrazolo[1,5-a]pyridine-3-carbonitrile A solution of (S)-6-(2-hydroxypropoxy)-4-(6-(piperazin-1-yl)pyridin-3-yl)pyrazolo[1,5-a]pyridine-3-carbonitrile hydrochloride (Intermediate P31; 11 mg, 0.027 mmol), 5-methoxypicolinaldehyde (7.3 mg, 0.053 mmol) and NaBH(AcO)$_3$ (17 mg, 0.080 mmol) in DMF (530 µL) was stirred for 1 day at ambient temperature. The reaction mixture was purified directly by silica chromatography (using a stepwise gradient of 0-100% EtOAc in Hexanes followed by 10% MeOH/EtOAc as eluents) to cleanly provide the title compound (13 mg, 98% yield). MS (apci) m/z=500.2 (M+H).

Example 134

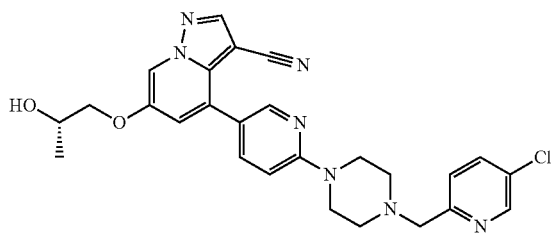 [SMILES: C[C@H](O)COc1cc(-c2ccc(N3CCN(Cc4ccc(Cl)cn4)CC3)nc2)c2c(C#N)cnn2c1]

(S)-4-(6-(4-((5-chloropyridin-2-yl)methyl)piperazin-1-yl)pyridin-3-yl)-6-(2-hydroxypropoxy)pyrazolo[1,5-a]pyridine-3-carbonitrile The title compound (8 mg, 60% yield) was prepared and purified using a similar procedure to that described for Example 133, replacing 5-methoxypicolinaldehyde with 5-chloropicolinaldehyde. MS (apci) m/z=504.2 (M+H).

Example 135

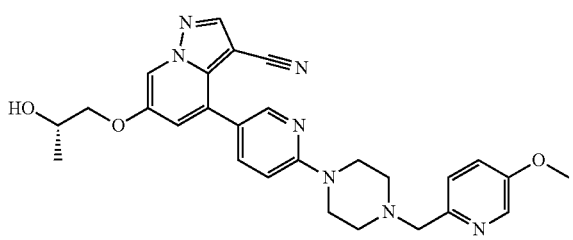 [SMILES: COc1ccc(CN2CCN(c3ccc(-c4cc(OC[C@H](C)O)cn5ncc(C#N)c45)cn3)CC2)nc1]

(S)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile A solution of 6-hydroxy-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate (Intermediate P24; 10 mg, 0.018 mmol) and K$_2$CO$_{3(s)}$ (16 mg, 0.11 mmol) in DMF (227 µL) was treated with and (S)-2-methyloxirane (13 mg, 0.23 mmol). The resulting mixture was stirred 1 day at 50° C. The reaction mixture was loaded directly onto a flash column equilibrated with hexanes and eluted with 0-100% DCM/hexanes then 0-20% MeOH in DCM to cleanly provide the title compound (5.5 mg, 49% yield). MS (apci) m/z=499.8 (M+H).

Example 136

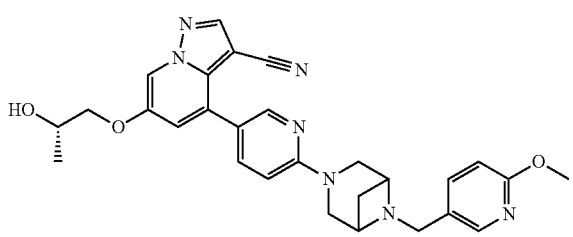 [SMILES: COc1ccc(CN2C3CC2CN(c2ccc(-c4cc(OC[C@H](C)O)cn5ncc(C#N)c45)cn2)C3)cn1]

6-((S)-2-hydroxypropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-((S)-2-hydroxypropoxy)pyrazolo[1,5-a]pyridine-3-carbonitrile dihydrochloride (Intermediate P33; 13.1 mg, 0.0261 mmol) in DCE (130 µL) was treated sequentially with 6-methoxynicotinaldehyde (7.15 mg, 0.0522 mmol) and NaBH(AcO)$_3$ (16.6 mg, 0.0782 mmol). The resulting mixture was stirred for 1 hour at ambient temperature and then concentrated in vacuo. The residue was purified by silica chromatography (0-20% MeOH in DCM as the gradient eluent) to cleanly provide the title compound (7 mg, 53% yield). MS (apci) m/z=512.2 (M+H).

Example 137

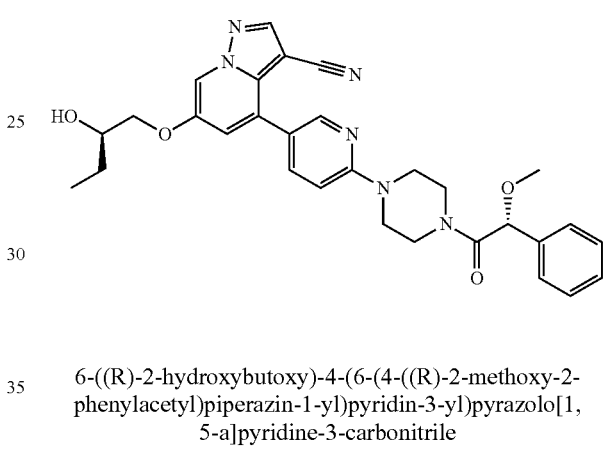

6-((R)-2-hydroxybutoxy)-4-(6-(4-((R)-2-methoxy-2-phenylacetyl)piperazin-1-yl)pyridin-3-yl)pyrazolo[1,5-a]pyridine-3-carbonitrile A solution of (R)-6-(2-hydroxybutoxy)-4-(6-(piperazin-1-yl)pyridin-3-yl)pyrazolo[1,5-a]pyridine-3-carbonitrile hydrochloride (Intermediate P34; 11.4 mg, 0.0266 mmol), (R)-2-methoxy-2-phenylacetic acid (4.64 mg, 0.0279 mmol) and DIEA (16.2 µL, 0.0930 mmol) in DCM (266 µL, 0.0266 mmol) was treated with HATU (11.1 mg, 0.0292 mmol) and stirred for 1 hour at ambient temperature. The reaction mixture was loaded directly onto a flash column equilibrated with hexanes and eluted with 0-100% DCM/hexanes and then 0-20% MeOH in DCM to cleanly provide the title compound (5.6 mg, 39% yield). MS (apci) m/z=541.2 (M+H).

Example 138

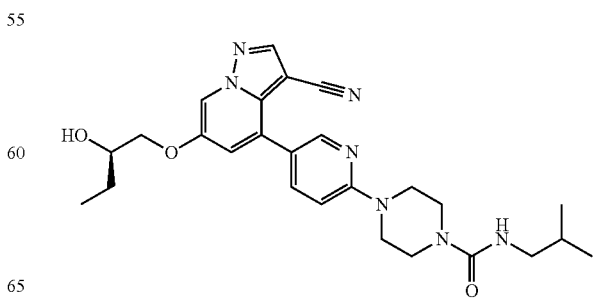

(R)-4-(5-(3-cyano-6-(2-hydroxybutoxy)pyrazolo[1,5-a]pyridin-4-yl)pyridin-2-yl)-N-isobutylpiperazine-1-carboxamide A cold (0° C.) solution of (R)-6-(2-hydroxybutoxy)-4-(6-(piperazin-1-yl)pyridin-3-yl)pyrazolo[1,5-a]pyridine-3-carbonitrile hydrochloride (Intermediate P34; 15.3 mg, 0.0357 mmol) and DIEA (31.2 μL, 0.178 mmol) in DMA (713 μL) was treated with 4-nitrophenyl chloroformate (7.55 mg, 0.0375 mmol). After stirring the mixture for 1 hour at 0° C., isobutylamine (13.0 mg, 0.178 mmol) was added. The resulting mixture was stirred 1 day at 80° C., and then additional isobutyl amine (13 mg, 0.178 mmol) was added. The mixture was stirred for 4 h at 80° C., then diluted with MeOH and directly purified by C18 reverse phase chromatography (5-95% ACN/water with 0.1% TFA as the gradient eluent). The isolated product was further purified by silica chromatography (0-20% DCM/MeOH/1% NH$_4$OH as the gradient eluent) to afford the title compound (2.02 mg, 11% yield). MS (apci) m/z=492.2 (M+H).

Example 139

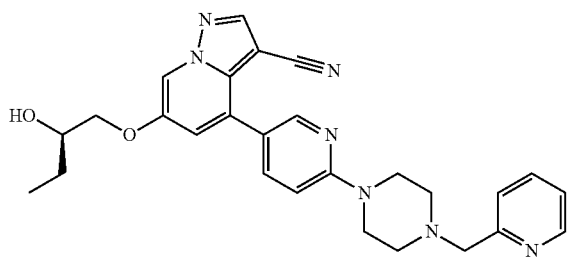 [SMILES: CC[C@@H](O)COc1cc(-c2ccc(N3CCN(Cc4ccccn4)CC3)nc2)c2c(C#N)cnn2c1]

(R)-6-(2-hydroxybutoxy)-4-(6-(4-(pyridin-2-ylmethyl)piperazin-1-yl)pyridin-3-yl)pyrazolo[1,5-a]pyridine-3-carbonitrile A solution of (R)-6-(2-hydroxybutoxy)-4-(6-(piperazin-1-yl)pyridin-3-yl)pyrazolo[1,5-a]pyridine-3-carbonitrile (Intermediate P35; 15.3 mg, 0.0357 mmol) and picolinaldehyde (3.38 μL, 0.0382 mmol) in DCE (764 μL) was treated with NaBH(AcO)$_3$ (8.1 mg, 0.0382 mmol). The resulting mixture was stirred overnight at ambient temperature, and then purified directly by silica chromatography (0-5% MeOH in DCM as the gradient eluent) to cleanly provide the title compound (4 mg, 22% yield). MS (apci) m/z=483.9 (M+H).

Example 140

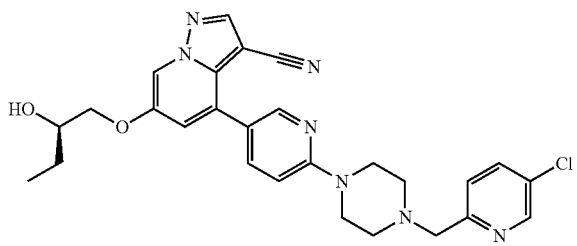 [SMILES: CC[C@@H](O)COc1cc(-c2ccc(N3CCN(Cc4ccc(Cl)cn4)CC3)nc2)c2c(C#N)cnn2c1]

(R)-4-(6-(4-((5-chloropyridin-2-yl)methyl)piperazin-1-yl)pyridin-3-yl)-6-(2-hydroxybutoxy)pyrazolo[1,5-a]pyridine-3-carbonitrile A solution of (R)-6-(2-hydroxybutoxy)-4-(6-(piperazin-1-yl)pyridin-3-yl)pyrazolo[1,5-a]pyridine-3-carbonitrile hydrochloride (Intermediate P34; 11 mg, 0.026 mmol), 5-chloropicolinaldehyde (7.3 mg, 0.051 mmol) and NaBH(AcO)$_3$ (16 mg, 0.077 mmol) in DCE (513 μL) was stirred 1 day at ambient temperature. The reaction mixture was purified directly by silica chromatography (using a stepwise gradient of 0-100% EtOAc in Hexanes followed by 10% MeOH/EtOAc as the eluents) to cleanly provide the title compound (7 mg, 53% yield). MS (apci) m/z=518.2 (M+H).

Example 141

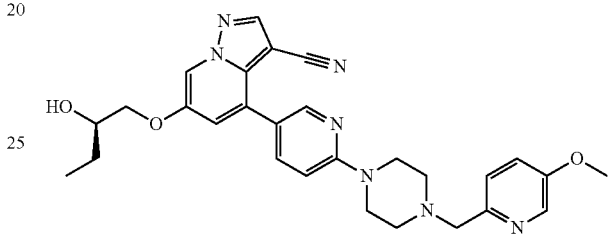

(R)-6-(2-hydroxybutoxy)-4-(6-(4-((5-methoxypyridin-2-yl)methyl)piperazin-1-yl)pyridin-3-yl)pyrazolo[1,5-a]pyridine-3-carbonitrile The title compound (8 mg, 61% yield) was prepared and purified using a similar procedure to that described for Example 140, replacing 5-chloropicolinaldehyde with 5-methoxypicolinaldehyde. MS (apci) m/z=514.2 (M+H).

Example 142

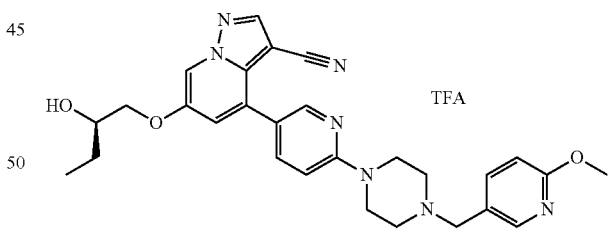

(R)-6-(2-hydroxybutoxy)-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate A mixture of 6-hydroxy-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate (Intermediate P24; 10 mg, 0.018 mmol), (R)-(+)-1,2-Epoxybutane (1.63 mg, 0.0227 mmol) and K$_2$CO$_{3(s)}$ (9.39 mg, 0.0680 mmol) in DMF (113 μL) was stirred 1 day at 50° C. The reaction mixture was filtered and purified directly by C18 reverse phase chromatography (5-95% ACN/water with 0.1% TFA as the gradient eluent) to cleanly provide the title compound as the 2,2,2-trifluoroacetate salt (14 mg, 99% yield). MS (apci) m/z=513.8 (M+H).

Example 143

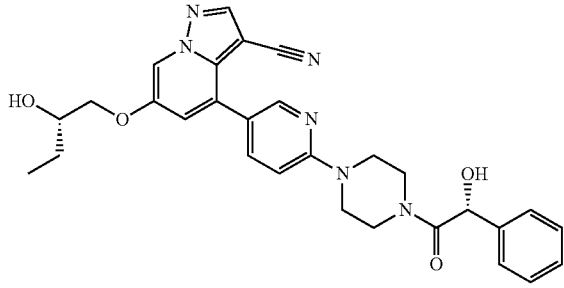 [SMILES: CC[C@H](O)COc1cc(-c2ccc(N3CCN(C(=O)[C@H](O)c4ccccc4)CC3)nc2)c2c(C#N)cnn2c1]

4-(6-(4-((R)-2-hydroxy-2-phenylacetyl)piperazin-1-yl)pyridin-3-yl)-6-((S)-2-hydroxybutoxy)pyrazolo[1,5-a]pyridine-3-carbonitrile A solution of (S)-6-(2-hydroxybutoxy)-4-(6-(piperazin-1-yl)pyridin-3-yl)pyrazolo[1,5-a]pyridine-3-carbonitrile hydrochloride (Intermediate P36; 17.2 mg, 0.0401 mmol), (R)-2-hydroxy-2-phenylacetic acid (6.41 mg, 0.0421 mmol), DIEA (24.5 μL, 0.140 mmol) in DCM (401 μL) was treated with HATU (16.8 mg, 0.0441 mmol), and then stirred 1 hour at ambient temperature. The reaction mixture was loaded directly onto a flash column equilibrated with hexanes and eluted with a gradient of 0-100% DCM/hexanes and then 0-20% MeOH in DCM to cleanly provide the title compound (7.5 mg, 3369% yield). MS (apci) m/z=527.2 (M+H).

Example 144

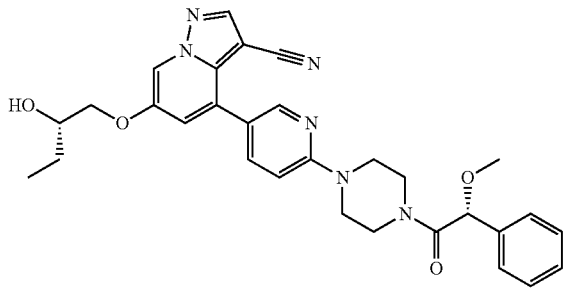 [SMILES: CC[C@H](O)COc1cc(-c2ccc(N3CCN(C(=O)[C@H](OC)c4ccccc4)CC3)nc2)c2c(C#N)cnn2c1]

6-((S)-2-hydroxybutoxy)-4-(6-(4-((R)-2-methoxy-2-phenylacetyl)piperazin-1-yl)pyridin-3-yl)pyrazolo[1,5-a]pyridine-3-carbonitrile The title compound (8 mg, 30% yield) was prepared and purified using a similar procedure to that described for Example 143, replacing (R)-2-hydroxy-2-phenylacetic acid with (R)-2-methoxy-2-phenylacetic acid. MS (apci) m/z=541.2 (M+H).

Example 145

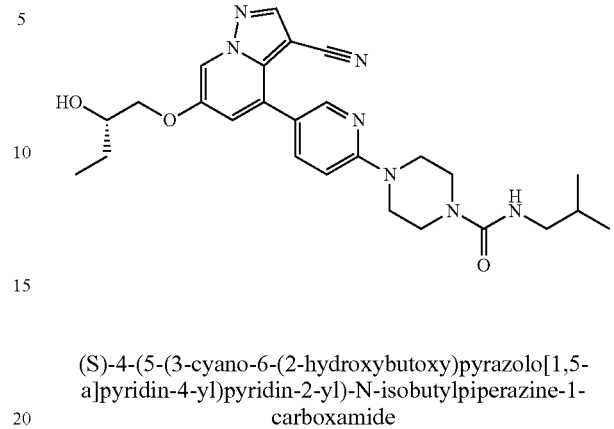

(S)-4-(5-(3-cyano-6-(2-hydroxybutoxy)pyrazolo[1,5-a]pyridin-4-yl)pyridin-2-yl)-N-isobutylpiperazine-1-carboxamide A cold (0° C.) solution of (S)-6-(2-hydroxybutoxy)-4-(6-(piperazin-1-yl)pyridin-3-yl)pyrazolo[1,5-a]pyridine-3-carbonitrile hydrochloride (Intermediate P36; 23 mg, 0.0536 mmol) and DIEA (46.8 μL, 0.127 mmol) in DMA (1.072 mL) was treated with 4-nitrophenyl chloroformate (11.3 mg, 0.0563 mmol). After stirring the mixture for 1 hour at 0° C., isobutylamine (19.6 mg, 0.268 mmol) was added. The resulting mixture was stirred 1 day at 80° C., and then additional isobutyl amine (11 mg, 0.06 mmol) was added. The mixture was stirred for an additional 4 h at 80° C., then cooled to ambient temperature, diluted with MeOH and directly purified by C18 reverse phase (5-95% ACN water with 0.1% TFA as the gradient eluent). The isolated product was further purified by silica chromatography (0-20% MeOH in DCM with 0.1% NH₄OH as the gradient eluent) to afford the title compound (3 mg, 11% yield). MS (apci) m/z=492.3 (M+H).

Example 146

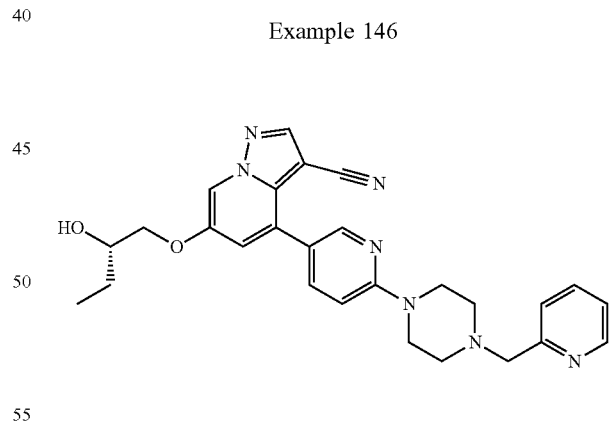

(S)-6-(2-hydroxybutoxy)-4-(6-(4-(pyridin-2-ylmethyl)piperazin-1-yl)pyridin-3-yl)pyrazolo[1,5-a]pyridine-3-carbonitrile A stirred solution of (S)-6-(2-hydroxybutoxy)-4-(6-(piperazin-1-yl)pyridin-3-yl)pyrazolo[1,5-a]pyridine-3-carbonitrile (Intermediate P37; 14 mg, 0.0357 mmol) and picolinaldehyde (3.79 μL, 0.0428 mmol) in DCE (713.5 μL) was treated with NaBH(AcO)₃ (22.7 mg, 0.107 mmol). The resulting mixture was stirred overnight at ambient temperature and then purified directly by silica chromatography (0-5% MeOH in DCM as the gradient eluent) to cleanly provide the title compound (5.4 mg, 31% yield). MS (apci) m/z=483.8 (M+H).

Example 147

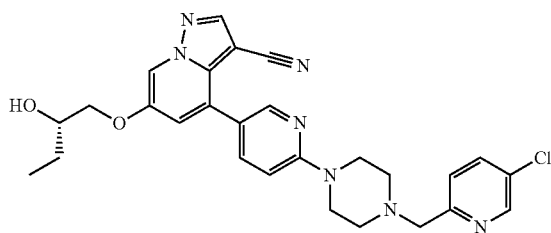 [SMILES: CC[C@H](O)COc1cc(-c2ccc(N3CCN(Cc4ccc(Cl)cn4)CC3)nc2)c2c(C#N)cnn2c1]

(S)-4-(6-(4-((5-chloropyridin-2-yl)methyl)piperazin-1-yl)pyridin-3-yl)-6-(2-hydroxybutoxy)pyrazolo[1,5-a]pyridine-3-carbonitrile A solution of (S)-6-(2-hydroxybutoxy)-4-(6-(piperazin-1-yl)pyridin-3-yl)pyrazolo[1,5-a]pyridine-3-carbonitrile hydrochloride (Intermediate P36; 11 mg, 0.026 mmol), 5-chloropicolinaldehyde (7.3 mg, 0.051 mmol) and NaBH(AcO)₃ (16 mg, 0.077 mmol) in DCE (513 μL) was stirred 1 day at ambient temperature. The reaction mixture was purified directly by silica chromatography (using a stepwise gradient of 0-100% EtOAc in Hexanes followed by 10% MeOH/EtOAc as eluents) to cleanly provide the title compound (9 mg, 68% yield). MS (apci) m/z=518.2 (M+H).

Example 148

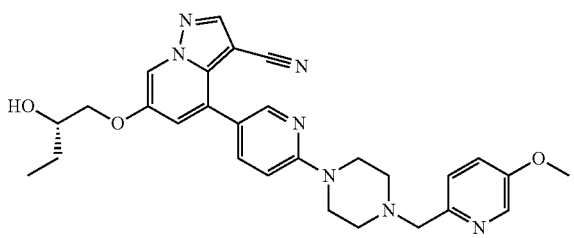 [SMILES: CC[C@H](O)COc1cc(-c2ccc(N3CCN(Cc4ccc(OC)cn4)CC3)nc2)c2c(C#N)cnn2c1]

(S)-6-(2-hydroxybutoxy)-4-(6-(4-((5-methoxypyridin-2-yl)methyl)piperazin-1-yl)pyridin-3-yl)pyrazolo[1,5-a]pyridine-3-carbonitrile The title compound (6.5 mg, 49% yield) was prepared and purified using a similar procedure to that described for Example 147, replacing 5-chloropicolinaldehyde with 5-methoxypicolinaldehyde. MS (apci) m/z=514.2 (M+H).

Example 149

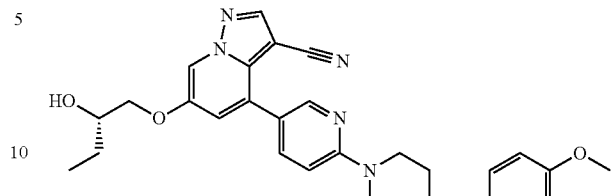

(S)-6-(2-hydroxybutoxy)-4-(6-(4-((6-methoxypyridin-3-yl)methyl)piperazin-1-yl)pyridin-3-yl)pyrazolo[1,5-a]pyridine-3-carbonitrile A solution of (S)-6-(2-hydroxybutoxy)-4-(6-(piperazin-1-yl)pyridin-3-yl)pyrazolo[1,5-a]pyridine-3-carbonitrile (Intermediate P37; 11 mg, 0.026 mmol) in DCE (513 μL) was treated sequentially with 6-methoxynicotinaldehyde (5.87 mg, 0.0428 mmol) and NaBH(AcO)₃ (22.7 mg, 0.107 mmol). The resulting mixture was stirred overnight at ambient temperature and then purified directly by silica chromatography (0-5% MeOH in DCM as the gradient eluent) to cleanly provide the title compound (8.3 mg, 45% yield). MS (apci) m/z=513.8 (M+H).

Example 150

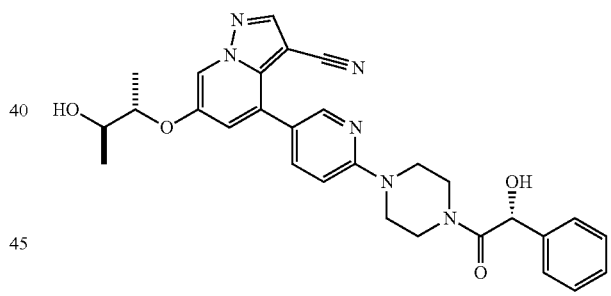

4-(6-(4-((R)-2-hydroxy-2-phenylacetyl)piperazin-1-yl)pyridin-3-yl)-6-(((2S*,3R*)-3-hydroxybutan-2-yl)oxy)pyrazolo[1,5-a]pyridine-3-carbonitrile A solution of 6-(((2S*,3R*)-3-hydroxybutan-2-yl)oxy)-4-(6-(piperazin-1-yl)pyridin-3-yl)pyrazolo[1,5-a]pyridine-3-carbonitrile hydrochloride (Intermediate P38; 25 mg, 0.0583 mmol), (R)-2-hydroxy-2-phenylacetic acid (9.31 mg, 0.0612 mmol) and DIEA (35.6 μL, 0.204 mmol) in DCM (583 μL) was treated with HATU (24.4 mg, 0.0641 mmol), and then stirred for 1 hour at ambient temperature. The reaction mixture was purified directly by C18 reverse phase chromatography (5-95% ACN/water with 0.1% TFA as the gradient eluent). The isolated product was further purified by silica chromatography (0-20% MeOH in DCM with 0.1% NH₄OH as the gradient eluent) to cleanly provide the title compound (2 mg, 7% yield). MS (apci) m/z=527.2 (M+H).

Example 151

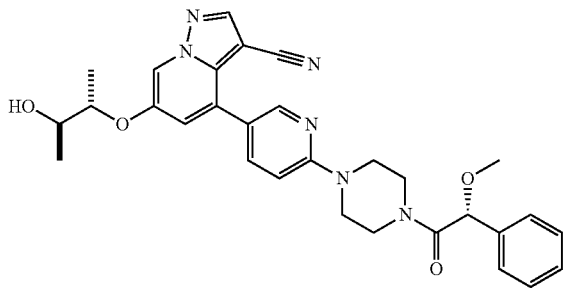 [SMILES: CO[C@@H](C(=O)N1CCN(c2ccc(-c3cc(O[C@@H](C)[C@@H](C)O)cn4ncc(C#N)c34)cn2)CC1)c1ccccc1]

6-(((2S,3R)-3-hydroxybutan-2-yl)oxy)-4-(6-(4-((R)-2-methoxy-2-phenylacetyl)piperazin-1-yl)pyridin-3-yl)pyrazolo[1,5-a]pyridine-3-carbonitrile The title compound (3 mg, 10% yield) was prepared and purified using a similar procedure to that described for Example 150, replacing (R)-2-hydroxy-2-phenylacetic acid with (R)-2-methoxy-2-phenylacetic acid. MS (apci) m/z=541.2 (M+H).

Example 152

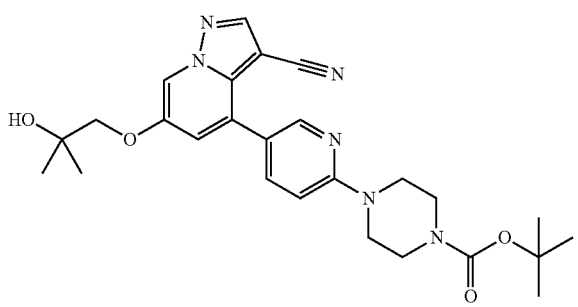 [SMILES: CC(C)(O)COc1cc(-c2ccc(N3CCN(C(=O)OC(C)(C)C)CC3)nc2)c2c(C#N)cnn2c1]

tert-butyl 4-(5-(3-cyano-6-(2-hydroxy-2-methylpropoxy)pyrazolo[1,5-a]pyridin-4-yl)pyridin-2-yl)piperazine-1-carboxylate A suspension of tert-butyl 4-(5-(3-cyano-6-hydroxypyrazolo[1,5-a]pyridin-4-yl)pyridin-2-yl)piperazine-1-carboxylate (Intermediate P3; 200 mg, 0.476 mmol) in DMF (5 mL) was treated sequentially with $K_2CO_{3(s)}$ (329 mg, 2.38 mmol) and 2,2-dimethyloxirane (171 mg, 2.38 mmol). After stirring overnight at 40° C., the reaction mixture was treated with additional 2,2-dimethyloxirane (171 mg, 2.38 mmol), and the reaction temperature was increased temperature to 50° C. The mixture was stirred for 24 h at 50° C., and then another aliquot of 2,2-dimethyloxirane (171 mg, 2.38 mmol) was added. The resulting mixture was stirred for 3 days at 50° C. The reaction mixture was cooled to ambient temperature and purified directly by C18 reverse phase chromatography (5-90% ACN/water as the gradient eluent) to cleanly provide the title compound (89.6 mg, 38% yield). MS (apci) m/z=493.3 (M+H).

Example 153

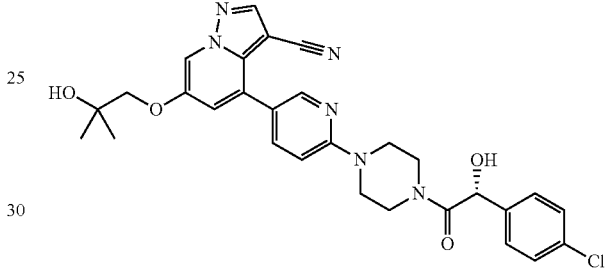

(R)-4-(6-(4-(2-(4-chlorophenyl)-2-hydroxyacetyl)piperazin-1-yl)pyridin-3-yl)-6-(2-hydroxy-2-methylpropoxy)pyrazolo[1,5-a]pyridine-3-carbonitrile 6-(2-hydroxy-2-methylpropoxy)-4-(6-(piperazin-1-yl)pyridin-3-yl)pyrazolo[1,5-a]pyridine-3-carbonitrile hydrochloride (Intermediate P39; 30 mg, 0.0699 mmol), (R)-2-(4-chlorophenyl)-2-hydroxyacetic acid (13.1 mg, 0.0699 mmol), DIEA (61.1 µL, 0.350 mmol) and HATU (33.2 mg, 0.0874 mmol) were added sequentially to DCM (0.7 mL). The resultant suspension was stirred for 1 hour at ambient temperature. The reaction mixture was purified directly by silica chromatography (using a stepwise gradient of 0-100% EtOAc in hexanes followed by 10% MeOH/EtOAc as eluents) to cleanly provide the title compound (28 mg, 71% yield). MS (apci) m/z=561.2 (M+H).

The compounds in Table J were prepared using a similar method to that described for the synthesis of Example 153, replacing (R)-2-(4-chlorophenyl)-2-hydroxyacetic acid with the appropriate carboxylic acid, and using varied amounts of HATU (1.1-1.25 equivalents) and DIEA (1-3.5 equivalents). Reactions were monitored for completion by LCMS, and reaction durations were adjusted accordingly. Title compounds were cleanly isolated following chromatographic purification using an appropriate gradient eluent.

TABLE J

| Ex # | Structure | Chemical Name | MS (apci) m/z |
|---|---|---|---|
| 154 | 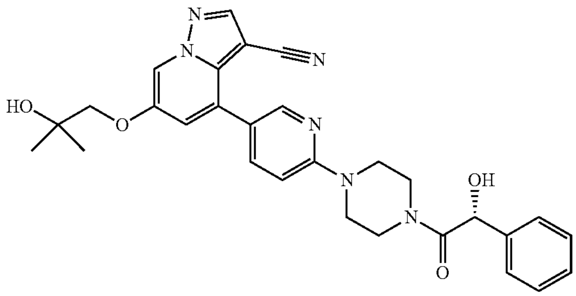 [SMILES: CC(C)(O)COc1cc(-c2ccc(N3CCN(C(=O)[C@H](O)c4ccccc4)CC3)nc2)c2c(C#N)cnn2c1] | (R)-6-(2-hydroxy-2-methylpropoxy)-4-(6-(4-(2-hydroxy-2-phenylacetyl)piperazin-1-yl)pyridin-3-yl)pyrazolo[1,5-a]pyridine-3-carbonitrile | 527.2 (M + H) |
| 155 | 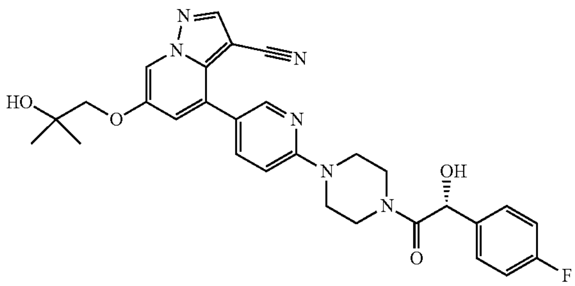 [SMILES: CC(C)(O)COc1cc(-c2ccc(N3CCN(C(=O)[C@H](O)c4ccc(F)cc4)CC3)nc2)c2c(C#N)cnn2c1] | (R)-4-(6-(4-(2-(4-fluorophenyl)-2-hydroxyacetyl)piperazin-1-yl)pyridin-3-yl)-6-(2-hydroxy-2-methylpropoxy)pyrazolo[1,5-a]pyridine-3-carbonitrile | 545.3 (M + H) |
| 156 | 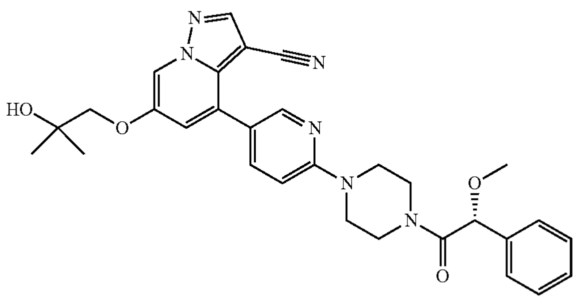 [SMILES: CO[C@@H](C(=O)N1CCN(c2ccc(-c3cc(OCC(C)(C)O)cn4ncc(C#N)c34)cn2)CC1)c1ccccc1] | (R)-6-(2-hydroxy-2-methylpropoxy)-4-(6-(4-(2-methoxy-2-phenylacetyl)piperazin-1-yl)pyridin-3-yl)pyrazolo[1,5-a]pyridine-3-carbonitrile | 541.2 (M + H) |

Example 157

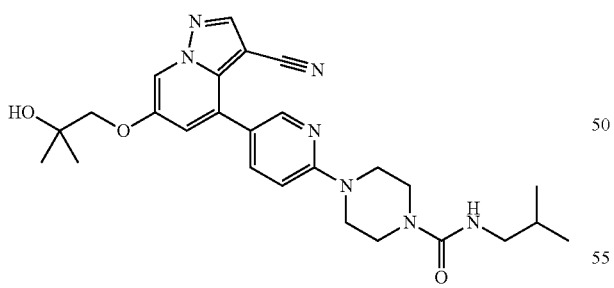

4-(5-(3-cyano-6-(2-hydroxy-2-methylpropoxy)pyrazolo[1,5-a]pyridin-4-yl)pyridin-2-yl)-N-isobutylpiperazine-1-carboxamide A cold (0° C.) solution of 6-(2-hydroxy-2-methylpropoxy)-4-(6-(piperazin-1-yl)pyridin-3-yl)pyrazolo[1,5-a]pyridine-3-carbonitrile hydrochloride (Intermediate P39; 15 mg, 0.035 mmol) and DIEA (30.5 μL, 0.175 mmol) in DMA (699 μL) was treated with 4-nitrophenyl chloroformate (7.40 mg, 0.0367 mmol). After stirring the mixture for 1 hour at 0° C., isobutylamine (7.40 mg, 0.0367 mmol) was added. The resulting mixture was stirred 1 day at 80° C., and then additional isobutyl amine (8 mg, 0.04 mmol) was added. The mixture was stirred for 4 h at 80° C. The mixture was diluted with MeOH and directly purified by C18 reverse phase (5-95% ACN water with 0.1% TFA as the gradient eluent) and then by silica chromatography (0-20% MeOH in DCM with 1% NH₄OH as the gradient eluent) to afford the title compound (5.6 mg, 33% yield). MS (apci) m/z=492.3 (M+H).

Example 158

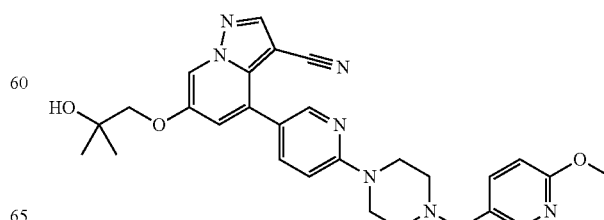

6-(2-hydroxy-2-methylpropoxy)-4-(6-(4-((6-methoxypyridin-3-yl)methyl)piperazin-1-yl)pyridin-3-yl)pyrazolo[1,5-a]pyridine-3-carbonitrile A solution of 6-(2-hydroxy-2-methylpropoxy)-4-(6-(piperazin-1-yl)pyridin-3-yl)pyrazolo[1,5-a]pyridine-3-carbonitrile (Intermediate P40; 15 mg, 0.038 mmol) and 6-methoxynicotinaldehyde (10.5 mg, 0.0764 mmol) in DCE (382 µL) was treated with NaBH(AcO)$_3$ (32.4 mg, 0.153 mmol) and stirred 1 day at 50° C. The mixture was cooled to ambient temperature and then purified directly by silica chromatography (0-20% DCM/MeOH as the gradient eluent). The isolated was further purified by C18 reverse phase chromatography (5-95% ACN/water with 0.1% TFA as the gradient eluent) to cleanly provide the title compound as the TFA salt. The TFA salt was dissolved in MeOH and sonicated with K$_2$CO$_{3(s)}$. The resulting suspension was filtered, and the filtrate was concentrated in vacuo to cleanly provide the title compound (6.9 mg, 35% yield). MS (apci) m/z=514.3 (M+H).

Example 159

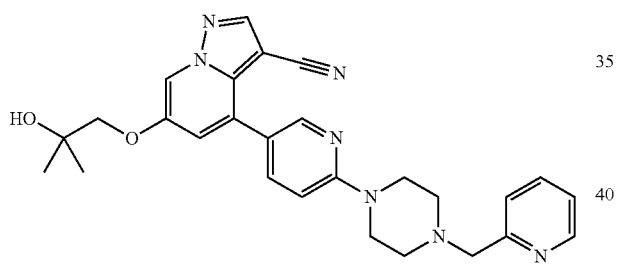

6-(2-hydroxy-2-methylpropoxy)-4-(6-(4-(pyridin-2-ylmethyl)piperazin-1-yl)pyridin-3-yl)pyrazolo[1,5-a]pyridine-3-carbonitrile A solution of 6-(2-hydroxy-2-methylpropoxy)-4-(6-(piperazin-1-yl)pyridin-3-yl)pyrazolo[1,5-a]pyridine-3-carbonitrile (Intermediate P40; 20 mg, 0.051 mmol) and picolinaldehyde (6.1 µL, 0.064 mmol) in DMF (510 µL) was treated with NaBH(AcO)$_3$ (21.6 mg, 0.102 mmol) and stirred 1 day at ambient temperature. The mixture was filtered through a syringe filter and then concentrated in vacuo. The crude residue was purified directly by C18 reverse phase chromatography (5-95% ACN/water with 0.1% TFA as the gradient eluent) to provide the title compound as the TFA salt. The TFA salt was dissolved in 4:1 DCM/MeOH (10 mL treated with K$_2$CO$_{3(s)}$ in an ultrasound bath. The resulting suspension was filtered, and the filtrate was concentrated in vacuo to cleanly provide the title compound (11 mg, 45% yield). MS (apci) m/z=484.2 (M+H).

Example 160

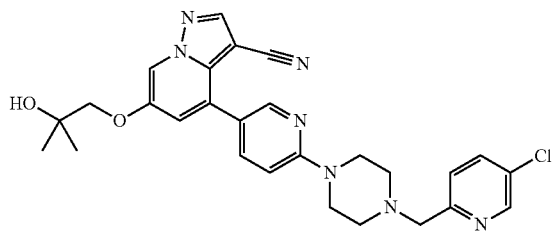 [SMILES: CC(C)(O)COc1cc(-c2ccc(N3CCN(Cc4ccc(Cl)cn4)CC3)nc2)c2c(C#N)cnn2c1]

4-(6-(4-((5-chloropyridin-2-yl)methyl)piperazin-1-yl)pyridin-3-yl)-6-(2-hydroxy-2-methylpropoxy)pyrazolo[1,5-a]pyridine-3-carbonitrile A solution of 6-(2-hydroxy-2-methylpropoxy)-4-(6-(piperazin-1-yl)pyridin-3-yl)pyrazolo[1,5-a]pyridine-3-carbonitrile hydrochloride (Intermediate P39; 11 mg, 0.026 mmol), 5-chloropicolinaldehyde (7.3 mg, 0.051 mmol), NaBH(AcO)$_3$ (16 mg, 0.077 mmol), in DCE (513 µL) was stirred 1 day at ambient temperature. The mixture was purified directly by silica chromatography (eluting with a stepwise gradient of 0-100% EtOAc in Hexanes followed by 10% MeOH/EtOAc) to cleanly provide the title compound (7 mg, 53% yield). MS (apci) m/z=518.2 (M+H).

Example 161

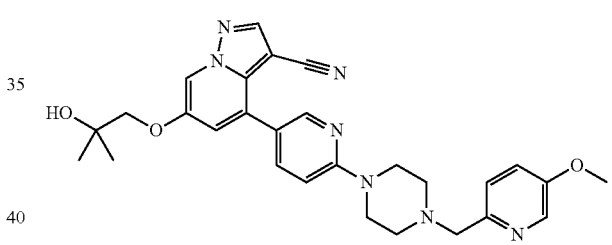

6-(2-hydroxy-2-methylpropoxy)-4-(6-(4-((5-methoxypyridin-2-yl)methyl)piperazin-1-yl)pyridin-3-yl)pyrazolo[1,5-a]pyridine-3-carbonitrile The title compound (8.89 mg, 68% yield) was prepared and purified using a similar procedure to that described for Example 160, replacing 5-chloropicolinaldehyde with 5-methoxypicolinaldehyde. MS (apci) m/z=514.2 (M+H).

Example 162

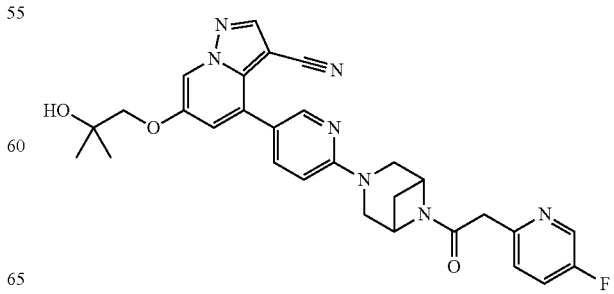

385

4-(6-(6-(2-(5-fluoropyridin-2-yl)acetyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile (Intermediate P44; 25 mg, 0.0618 mmol) in DCM (1.24 mL) was treated sequentially with 2-(5-fluoropyridin-2-yl)acetic acid (11.5 mg, 0.0742 mmol), HATU (28.2 mg, 0.0742 mmol) and DIEA (43.1 µL, 0.247 mmol), then stirred overnight at ambient temperature. The reaction mixture was purified directly by silica chromatography (using a stepwise gradient of 0-100% DCM in Hexanes followed by 0-60% [78% DCM/20% MeOH/2% NH$_4$OH] in DCM as eluents) to cleanly provide the title compound (2.94 mg, 9% yield). MS (apci) m/z=542.2 (M+H).

Example 163

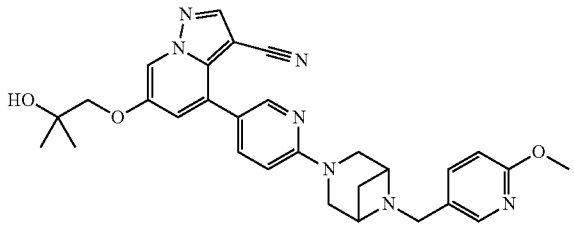

386

6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 12.2 mg, 0.0277 mmol) in DCE (513 µL) was treated sequentially with 6-methoxynicotinaldehyde (7.59 mg, 0.0553 mmol) and NaBH(AcO)$_3$ (17.6 mg, 0.0830 mmol), then stirred overnight at ambient temperature. The mixture was concentrated in vacuo, and the residue was purified by silica chromatography (0-20% MeOH in DCM as the gradient eluent) to cleanly provide the title compound (13.59 mg, 93% yield). MS (apci) m/z=526.2 (M+H). $^1$H NMR (400 MHz, DMSO-d$^6$) δ: 8.64 (d, 1H, J=2.3 Hz), 8.55 (s, 1H), 8.38 (d, 1H, J=2.3 Hz), 8.04 (d, 1H, J=2.3 Hz), 7.80 (dd, 1H, J=8.6, 2.3 Hz), 7.64 (dd, 1H, J=8.6, 2.3 Hz), 7.27 (d, 1H, J=2.0 Hz), 6.76 (d, 1H, J=8.6 Hz), 6.73 (d, 1H, J=8.2 Hz), 4.67 (s, 1H), 3.85 (s, 2H), 3.79 (s, 3H), 3.72 (d, 2H, J=12.5 Hz), 3.64 (d, 2H, J=5.9 Hz), 3.51 (br d, 2H), 3.47 (s, 2H), 2.47 (m, 1H), 1.55 (d, 1H), 1.20 (s, 6H).

The compounds in Table K were prepared using a similar method to that described for the synthesis of Example 163, replacing 6-methoxynicotinaldehyde with the appropriate aldehyde (1 or 2 equivalents). Reactions were monitored for completion by LCMS, and reaction durations were adjusted accordingly. Title compounds were cleanly isolated following chromatographic purification using an appropriate gradient eluent.

TABLE K

| Ex # | Structure | Chemical Name | MS (apci) m/z |
|---|---|---|---|
| 164 | 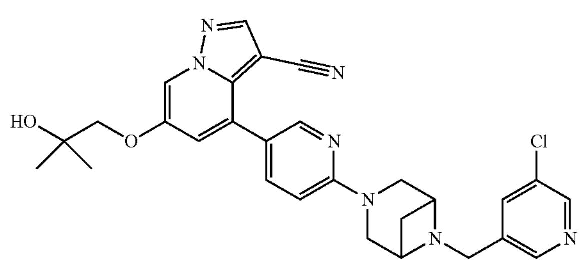 [SMILES: CC(C)(O)COc1cc(-c2ccc(N3CC4CC(C3)N4Cc3cncc(Cl)c3)nc2)c2c(C#N)cnn2c1] | 4-(6-(6-((5-chloropyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 530.2 (M + H) |
| 165 | 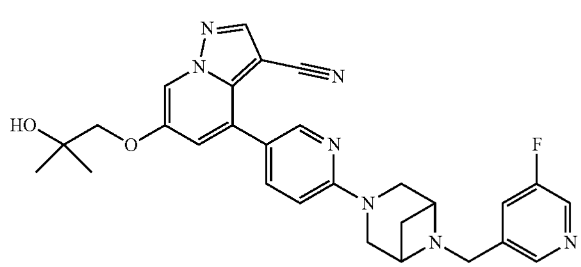 [SMILES: CC(C)(O)COc1cc(-c2ccc(N3CC4CC(C3)N4Cc3cncc(F)c3)nc2)c2c(C#N)cnn2c1] | 4-(6-(6-((5-fluoropyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 514.2 (M + H) |

TABLE K-continued

| Ex # | Structure | Chemical Name | MS (apci) m/z |
|---|---|---|---|
| 166 | 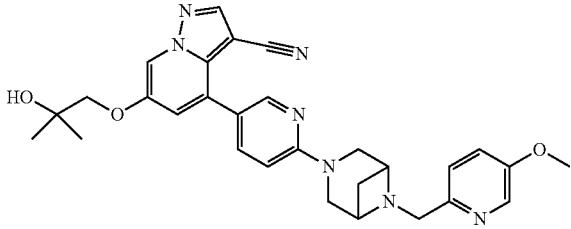 [SMILES: COc1ccc(CN2C3CC2CN(c2ccc(-c4cc(OCC(C)(C)O)cn5ncc(C#N)c45)cn2)C3)nc1] | 6-(2-hydroxy-2-methylpropoxy)-4-(6-(6-((5-methoxypyridin-2-yl)methyl)-3,6-diazabicyclo[3.1.1]heptan-3-yl)pyridin-3-yl)pyrazolo[1,5-a]pyridine-3-carbonitrile | 526.2 (M + H) |
| 167 | 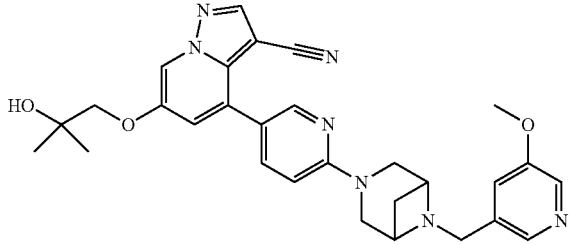 [SMILES: COc1cncc(CN2C3CC2CN(c2ccc(-c4cc(OCC(C)(C)O)cn5ncc(C#N)c45)cn2)C3)c1] | 6-(2-hydroxy-2-methylpropoxy)-4-(6-(6-((5-methoxypyridin-3-yl)methyl)-3,6-diazabicyclo[3.1.1]heptan-3-yl)pyridin-3-yl)pyrazolo[1,5-a]pyridine-3-carbonitrile | 526.2 (M + H) |
| 168 | 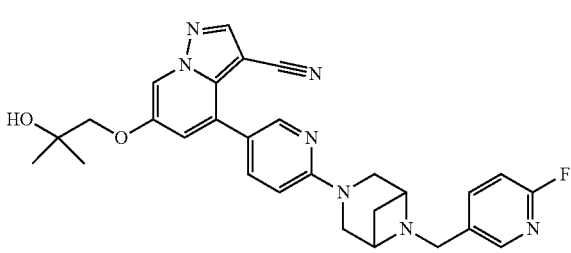 [SMILES: CC(C)(O)COc1cc(-c2ccc(N3CC4CC(C3)N4Cc3ccc(F)nc3)nc2)c2c(C#N)cnn2c1] | 4-(6-(6-((6-fluoropyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 514.25 (M + H) |
| 169 | 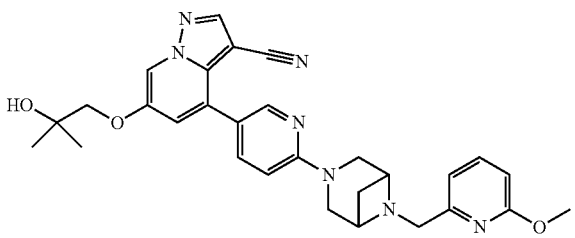 [SMILES: COc1cccc(CN2C3CC2CN(c2ccc(-c4cc(OCC(C)(C)O)cn5ncc(C#N)c45)cn2)C3)n1] | 6-(2-hydroxy-2-methylpropoxy)-4-(6-(6-((6-methoxypyridin-2-yl)methyl)-3,6-diazabicyclo[3.1.1]heptan-3-yl)pyridin-3-yl)pyrazolo[1,5-a]pyridine-3-carbonitrile | 526.2 (M + H) |
| 170 | 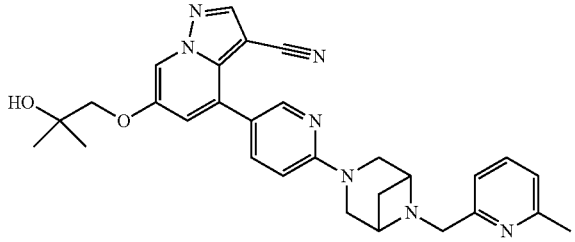 [SMILES: Cc1cccc(CN2C3CC2CN(c2ccc(-c4cc(OCC(C)(C)O)cn5ncc(C#N)c45)cn2)C3)n1] | 6-(2-hydroxy-2-methylpropoxy)-4-(6-(6-((6-methylpyridin-2-yl)methyl)-3,6-diazabicyclo[3.1.1]heptan-3-yl)pyridin-3-yl)pyrazolo[1,5-a]pyridine-3-carbonitrile | 510.2 (M + H) |
| 171 | 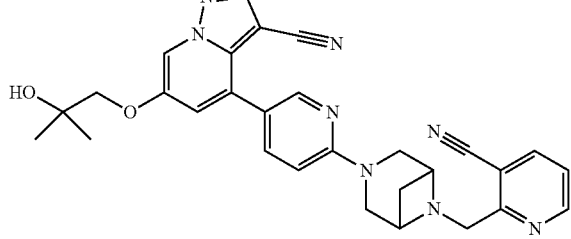 | 4-(6-(6-((3-cyanopyridin-2-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 521.2 (M + H) |

TABLE K-continued

| Ex # | Structure | Chemical Name | MS (apci) m/z |
|---|---|---|---|
| 172 | 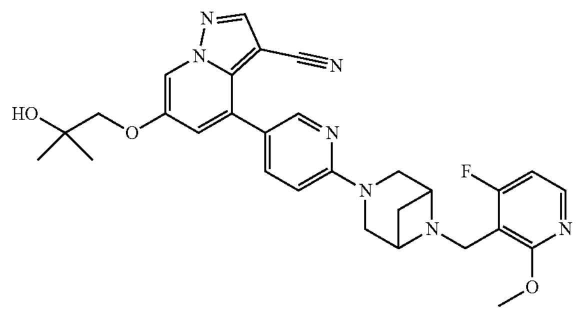 [SMILES: COc1nccc(F)c1CN1C2CC1CN(c1ccc(-c3cc(OCC(C)(C)O)cn4ncc(C#N)c34)cn1)C2] | 4-(6-(6-((4-fluoro-2-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 544.2 (M + H) |

Example 173

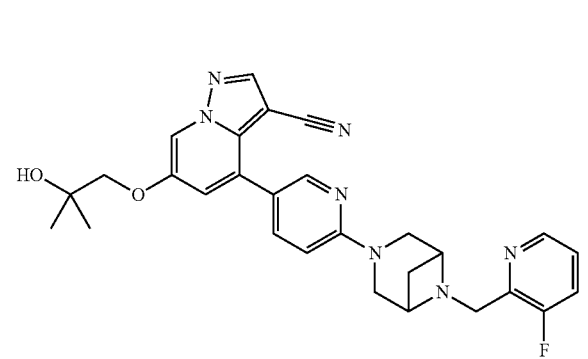 [SMILES: CC(C)(O)COc1cc(-c2ccc(N3CC4CC(C3)N4Cc3ncccc3F)nc2)c2c(C#N)cnn2c1]

4-(6-(6-((3-fluoropyridin-2-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 25.3 mg, 0.0530 mmol), in DCM (1 mL) was treated sequentially with 3-fluoro-2-formylpyridine (19.9 mg, 0.159 mmol), NaBH(AcO)$_3$ (33.7 mg, 0.159 mmol) and AcOH (2 drops). After stirring for 60 h at ambient temperature, the resulting mixture was concentrated in vacuo. The crude residue was purified by C18 reverse phase chromatography (5-95% water-ACN with 0.1% TFA as the gradient eluent) to cleanly provide the title compound as the TFA salt. The TFA salt was partitioned between 4:1 DCM iPrOH and saturated NaHCO$_{3(aq)}$. The combined organic extracts were dried over anhydrous Na$_2$SO$_{4(s)}$, filtered, and concentrated in vacuo to afford the title compound (18.2 mg, 67% yield). MS (apci) m/z=514.2 (M+H).

Example 174

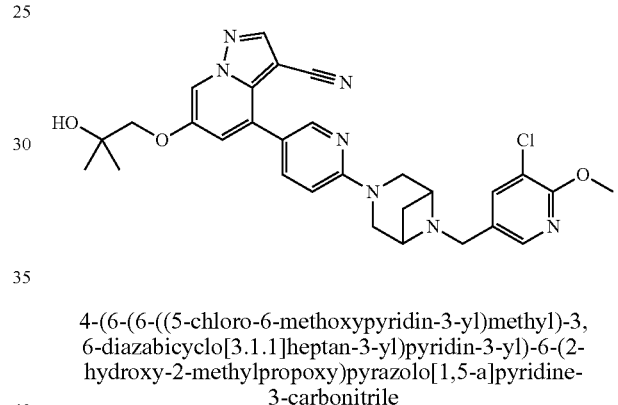

4-(6-(6-((5-chloro-6-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 30 mg, 0.063 mmol), in DCM (1 mL) was treated with DIEA (27 µL, 0.16 mmol) and stirred for 5 min at ambient temperature. The resulting mixture was treated sequentially with 5-chloro-6-methoxynicotinaldehyde (11 mg, 0.063 mmol) and NaBH(AcO)$_3$ (27 mg, 0.13 mmol). After stirring 12 h at ambient temperature, the reaction mixture was diluted with DCM and washed with 10% Na$_2$CO$_{3(aq)}$. The combined organic extracts were dried over anhydrous MgSO$_{4(s)}$, filtered, and concentrated in vacuo. The residue was purified by silica chromatography (10% MeOH/DCM with 1% NH$_4$OH as the eluent) to cleanly provide the title compound (22 mg, 63% yield). MS (apci) m/z=560.3 (M+H).

The compounds in Table L were prepared using a similar method to that described for the synthesis of Example 174, replacing 5-chloro-6-methoxynicotinaldehyde with the appropriate aldehyde. Reactions were monitored for completion by LCMS, and reaction durations were adjusted accordingly. Title compounds were cleanly isolated following chromatographic purification using an appropriate gradient eluent. Where noted (*), the aqueous work up was omitted, and direct chromatographic purification of the solubilized reaction mixture was used to isolate the title compound.

TABLE L

| Ex # | Structure | Chemical Name | MS (apci) m/z |
|---|---|---|---|
| 175 | 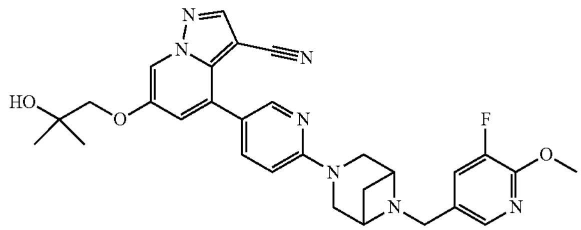 [SMILES: COc1ncc(CN2C3CC2CN(c2ccc(-c4cc(OCC(C)(C)O)cn5ncc(C#N)c45)cn2)C3)cc1F] | 4-(6-(6-((5-fluoro-6-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 544.2 (M + H) |
| 176 | 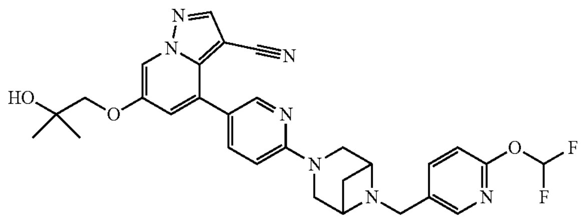 [SMILES: CC(C)(O)COc1cc(-c2ccc(N3CC4CC(C3)N4Cc3ccc(OC(F)F)nc3)nc2)c2c(C#N)cnn2c1] | 4-(6-(6-((6-(difluoromethoxy)pyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 562.2 (M + H) |
| 177 | 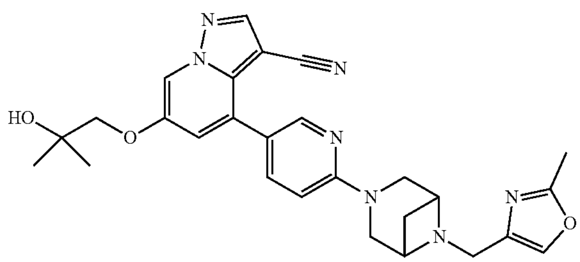 [SMILES: Cc1nc(CN2C3CC2CN(c2ccc(-c4cc(OCC(C)(C)O)cn5ncc(C#N)c45)cn2)C3)co1] | 6-(2-hydroxy-2-methylpropoxy)-4-(6-(6-((2-methyloxazol-4-yl)methyl)-3,6-diazabicyclo[3.1.1]heptan-3-yl)pyridin-3-yl)pyrazolo[1,5-a]pyridine-3-carbonitrile | 500.2 (M + H) |

Example 178

Example 179

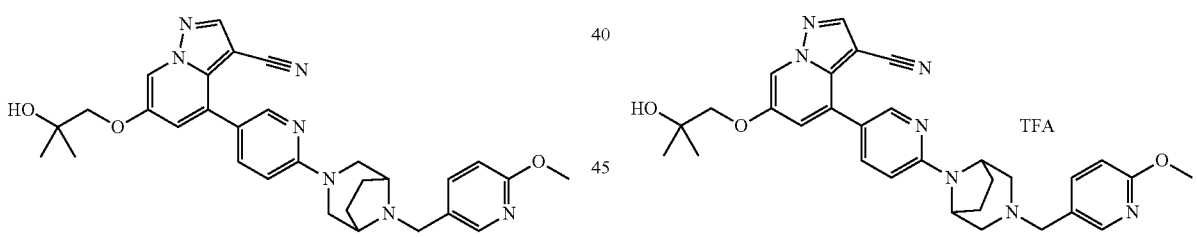

6-(2-hydroxy-2-methylpropoxy)-4-(6-(8-((6-methoxypyridin-3-yl)methyl)-3,8-diazabicyclo[3.2.1]octan-3-yl)pyridin-3-yl)pyrazolo[1,5-a]pyridine-3-carbonitrile 6-(2-hydroxy-2-methylpropoxy)-4-(6-(3-((6-methoxypyridin-3-yl)methyl)-3,8-diazabicyclo[3.2.1]octan-8-yl)pyridin-3-yl)pyrazolo[1,5-a]pyridine-3-carbonitrile 2,2,2-trifluoroacetate A mixture of 4-(6-(3,8-diazabicyclo[3.2.1]octan-3-yl)pyridin-3-yl)-6-(2-hydroxy-2-methylpropoxy)pyrazolo[1,5-a]pyridine-3-carbonitrile hydrochloride (Intermediate P45; 24 mg, 0.053 mmol), 6-methoxynicotinaldehyde (36.17 mg, 0.2638 mmol) and NaBH(AcO)$_3$ (55.9 mg, 0.264 mmol) in DCE (264 µL) was stirred overnight at ambient temperature. The mixture was partitioned between DCM saturated NaHCO$_{3(aq)}$, and extracted with DCM. The combined organic extracts were dried over anhydrous Na$_2$SO$_{4(s)}$, filtered and concentrated in vacuo. The residue was purified by silica chromatography (0-20% DCM/MeOH as the gradient eluent) to cleanly provide the title compound (19.76 mg, 69% yield). MS (apci) m/z=540.3 (M+H).

A mixture of 4-(6-fluoropyridin-3-yl)-6-(2-hydroxy-2-methylpropoxy)pyrazolo[1,5-a]pyridine-3-carbonitrile (Intermediate P42; 20 mg, 0.0613 mmol), 3-((6-methoxypyridin-3-yl)methyl)-3,8-diazabicyclo[3.2.1]octane hydrochloride (Intermediate R7; 49.6 mg, 0.184 mmol) and K$_2$CO$_{3(s)}$ (42.4 mg, 0.306 mmol) in DMSO (613 µL) was stirred at 80° C. until complete (as determined by LCMS). The reaction mixture was cooled to ambient temperature and then filtered. The residue was directly purified by C18 reverse phase chromatography (5-95% ACN in water with 0.1% TFA as the gradient eluent) to afford the title compound as the 2,2,2-trifluoroacetate salt (28.14 mg, 85% yield). MS (apci) m/z=540.3 (M+H).

The compounds in Table M were prepared using a similar method to that described for the synthesis of Example 179, replacing 3-((6-methoxypyridin-3-yl)methyl)-3,8-diazabicyclo[3.2.1]octane hydrochloride (Intermediate R7) with the appropriate bicyclic-piperazine intermediate (Intermediate R5, R6, or R12), and where noted (*), 15 equivalents of $K_2CO_{3(s)}$ were used. Reactions were monitored for completion by LCMS, and reaction durations were adjusted accordingly. Title compounds were cleanly isolated following chromatographic purification using an appropriate gradient eluent. Some chromatographic conditions resulted in the isolation of the 2,2,2-trifluoroacetate salt of the title compound.

6-(2-hydroxy-2-methylpropoxy)-4-(4-(6-((6-methoxypyridin-3-yl)methyl)-3,6-diazabicyclo[3.1.1]heptan-3-yl)phenyl)pyrazolo[1,5-a]pyridine-3-carbonitrile A mixture of 4-(5-(3,6-diazabicyclo[3.1.1]heptan-3-yl)pyrazin-2-yl)-6-(2-hydroxy-2-methylpropoxy)pyrazolo[1,5-a]pyridine-3-carbonitrile (Intermediate P49; 63 mg, 0.16 mmol), 6-methoxynicotinaldehyde (27.8 mg, 0.20 mmol) and AcOH (1.8 μL, 0.031 mmol) in DCM (1 mL) was stirred 10 min at ambient temperature before adding $NaBH(AcO)_3$ (49.6 mg, 0.23 mmol). The resulting mixture was stirred overnight at ambient temperature. The reaction mixture was purified directly by silica chromatography (20% acetone in DCM with 0.05% $NH_4OH$ as the eluent) to cleanly provide the title compound (27 mg, 31% yield). MS (apci) m/z=525.3 (M+H).

TABLE M

| Ex # | Structure | Chemical Name | MS (apci) m/z |
|---|---|---|---|
| 180 | 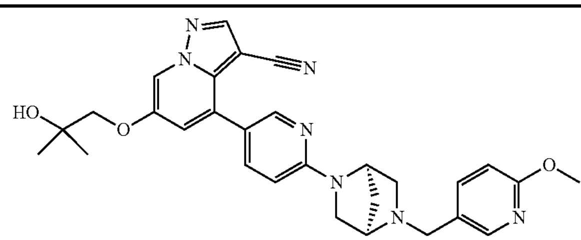 | 6-(2-hydroxy-2-methylpropoxy)-4-(6-((1R,4R)-5-((6-methoxypyridin-3-yl)methyl)-2,5-diazabicyclo[2.2.1]heptan-2-yl)pyridin-3-yl)pyrazolo[1,5-a]pyridine-3-carbonitrile | 526.3 (M + H) |
| 181 | 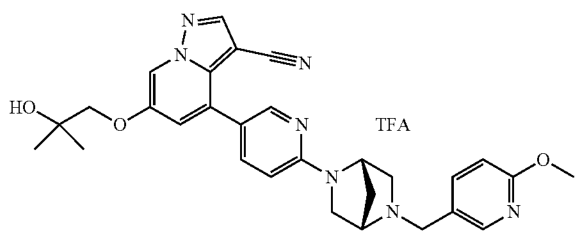 [SMILES: COc1ccc(CN2C[C@@H]3C[C@H]2CN3c2ccc(-c3cc(OCC(C)(C)O)cn4ncc(C#N)c34)cn2)cn1] | 6-(2-hydroxy-2-methylpropoxy)-4-(6-((1S,4S)-5-((6-methoxypyridin-3-yl)methyl)-2,5-diazabicyclo[2.2.1]heptan-2-yl)pyridin-3-yl)pyrazolo[1,5-a]pyridine-3-carbonitrile 2,2,2-trifluoroacetate | 526.2 (M + H) |
| 182 | 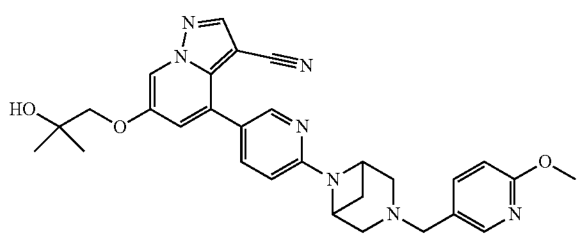 [SMILES: COc1ccc(CN2CC3CC(C2)N3c2ccc(-c3cc(OCC(C)(C)O)cn4ncc(C#N)c34)cn2)cn1] | 6-(2-hydroxy-2-methylpropoxy)-4-(6-(3-((6-methoxypyridin-3-yl)methyl)-3,6-diazabicyclo[3.1.1]heptan-6-yl)pyridin-3-yl)pyrazolo[1,5-a]pyridine-3-carbonitrile | 526.2 (M + H) |

Example 183

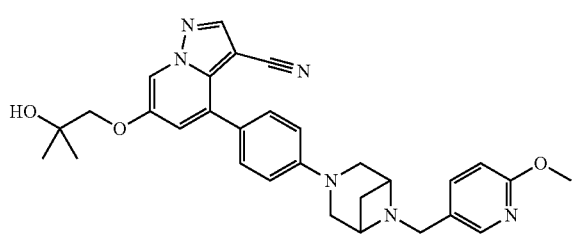

Example 184

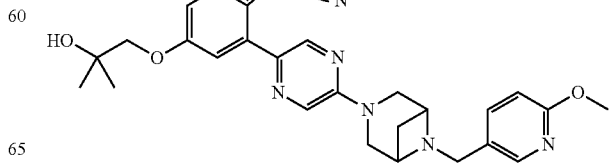

6-(2-hydroxy-2-methylpropoxy)-4-(5-(6-((6-methoxypyridin-3-yl)methyl)-3,6-diazabicyclo[3.1.1]heptan-3-yl)pyrazin-2-yl)pyrazolo[1,5-a]pyridine-3-carbonitrile The title compound (24 mg, 47% yield) was prepared and purified using a similar procedure to that described for Example 183, replacing 4-(5-(3,6-diazabicyclo[3.1.1]heptan-3-yl)pyrazin-2-yl)-6-(2-hydroxy-2-methylpropoxy)pyrazolo[1,5-a]pyridine-3-carbonitrile (Intermediate P49) with 4-(5-(3,6-diazabicyclo[3.1.1]heptan-3-yl)pyrazin-2-yl)-6-(2-hydroxy-2-methylpropoxy)pyrazolo[1,5-a]pyridine-3-carbonitrile (Intermediate P50). MS (apci) m/z=527.2 (M+H).

Example 185

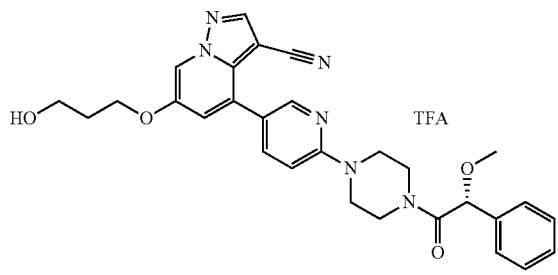 [SMILES: CO[C@@H](C(=O)N1CCN(c2ccc(-c3cc(OCCCO)cn4ncc(C#N)c34)cn2)CC1)c1ccccc1 ; "TFA"]

(R)-6-(3-hydroxypropoxy)-4-(6-(4-(2-methoxy-2-phenylacetyl)piperazin-1-yl)pyridin-3-yl)pyrazolo[1,5-a]pyridine-3-carbonitrile 2,2,2-trifluoroacetate A solution of 6-(3-hydroxypropoxy)-4-(6-(piperazin-1-yl)pyridin-3-yl)pyrazolo[1,5-a]pyridine-3-carbonitrile hydrochloride (Intermediate P51; 21 mg, 0.051 mmol), (R)-2-methoxy-2-phenylacetic acid (10.1 mg, 0.061 mmol), HATU (23.1 mg, 0.061 mmol) and DIEA (26.2 μL, 0.20 mmol) were suspended in DCM (253 μL). The resultant suspension was stirred for 1 hour at ambient temperature. The reaction mixture was purified directly by C18 reverse phase chromatography (5-95% ACN/water with 0.1% TFA as the gradient eluent) to cleanly provide the title compound (22.2 mg, 69% yield). MS (apci) m/z=526.8 (M+H).

The compounds in Table Q were prepared using a similar method to that described for the synthesis of Example 185, replacing (R)-2-methoxy-2-phenylacetic acid with the appropriate carboxylic acid. Reactions were monitored for completion by LCMS, and reaction durations were adjusted accordingly. Title compounds were cleanly isolated following chromatographic purification using an appropriate gradient eluent.

TABLE Q

| Ex # | Structure | Chemical Name | MS (apci) m/z |
|---|---|---|---|
| 186 | 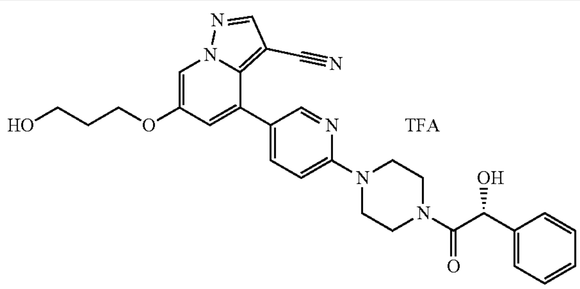 [SMILES: N#Cc1cnn2cc(OCCCO)cc(-c3ccc(N4CCN(C(=O)[C@H](O)c5ccccc5)CC4)nc3)c12] | (R)-4-(6-(4-(2-hydroxy-2-phenylacetyl)piperazin-1-yl)pyridin-3-yl)-6-(3-hydroxypropoxy)pyrazolo[1,5-a]pyridine-3-carbonitrile 2,2,2-trifluoroacetate | 512.8 (M + H) |
| 187 | 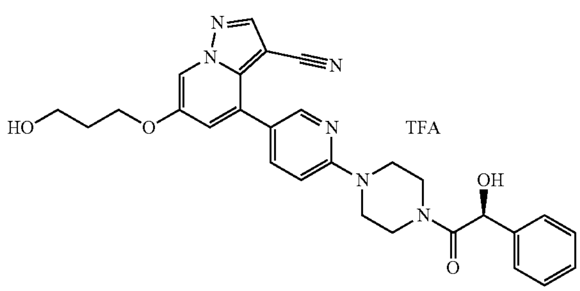 [SMILES: N#Cc1cnn2cc(OCCCO)cc(-c3ccc(N4CCN(C(=O)[C@@H](O)c5ccccc5)CC4)nc3)c12] | (S)-4-(6-(4-(2-hydroxy-2-phenylacetyl)piperazin-1-yl)pyridin-3-yl)-6-(3-hydroxypropoxy)pyrazolo[1,5-a]pyridine-3-carbonitrile 2,2,2-trifluoroacetate | 512.8 (M + H) |
| 188 | 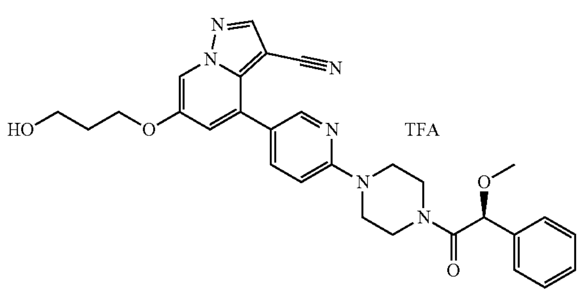 [SMILES: CO[C@H](C(=O)N1CCN(c2ccc(-c3cc(OCCCO)cn4ncc(C#N)c34)cn2)CC1)c1ccccc1] | (S)-6-(3-hydroxypropoxy)-4-(6-(4-(2-methoxy-2-phenylacetyl)piperazin-1-yl)pyridin-3-yl)pyrazolo[1,5-a]pyridine-3-carbonitrile 2,2,2-trifluoroacetate | 526.8 (M + H) |

TABLE Q-continued

| Ex # | Structure | Chemical Name | MS (apci) m/z |
|---|---|---|---|
| 189 | 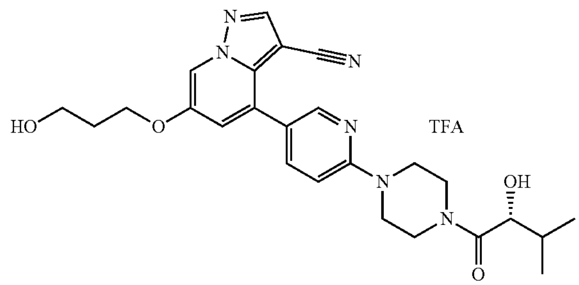 [SMILES: CC(C)[C@@H](O)C(=O)N1CCN(c2ccc(-c3cc(OCCCO)cn4ncc(C#N)c34)cn2)CC1] | (R)-4-(6-(4-(2-hydroxy-3-methylbutanoyl)piperazin-1-yl)pyridin-3-yl)-6-(3-hydroxypropoxy)pyrazolo[1,5-a]pyridine-3-carbonitrile 2,2,2-trifluoroacetate | 478.9 (M + H) |
| 190 | 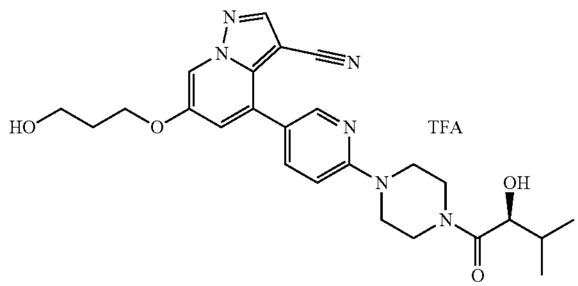 [SMILES: CC(C)[C@H](O)C(=O)N1CCN(c2ccc(-c3cc(OCCCO)cn4ncc(C#N)c34)cn2)CC1] | (S)-4-(6-(4-(2-hydroxy-3-methylbutanoyl)piperazin-1-yl)pyridin-3-yl)-6-(3-hydroxypropoxy)pyrazolo[1,5-a]pyridine-3-carbonitrile 2,2,2-trifluoroacetate | 478.9 (M + H) |

*1.1 equivalents HATU and 1.1 equivilants D-(-)-Mandelic acid were used in this example Example 191

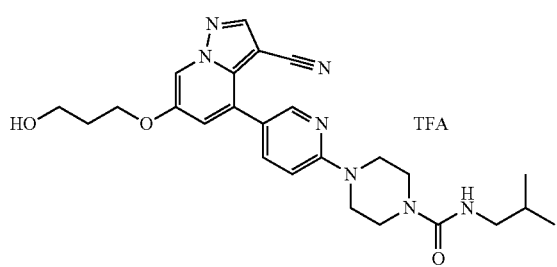 [SMILES: CC(C)CNC(=O)N1CCN(c2ccc(-c3cc(OCCCO)cn4ncc(C#N)c34)cn2)CC1 ; "TFA"]

4-(5-(3-cyano-6-(3-hydroxypropoxy)pyrazolo[1,5-a]pyridin-4-yl)pyridin-2-yl)-N-isobutylpiperazine-1-carboxamide 2,2,2-trifluoroacetate A cold (0° C.) solution of 6-(3-hydroxypropoxy)-4-(6-(piperazin-1-yl)pyridin-3-yl)pyrazolo[1,5-a]pyridine-3-carbonitrile hydrochloride (Intermediate P51; 14 mg, 0.0337 mmol) and DIEA (29.5 µL, 0.169 mmol) in DMA (675 µL) was treated with 4-nitrophenyl chloroformate (7.14 mg, 0.0354 mmol). After stirring the mixture for 1 hour at 0° C., isobutylamine (12.3 mg, 0.169 mmol) was added. The resulting mixture was stirred for 1 day at 80° C. before adding additional isobutyl amine (12 mg, 0.17 mmol). The mixture was stirred for 4 h at 80° C. The resulting mixture was diluted with MeOH and directly purified by C18 reverse phase (5-95% ACN/water with 0.1% TFA as the gradient eluent) to afford the title compound (12.8 mg, 64% yield). MS (apci) m/z=477.9 (M+H).

Example 192

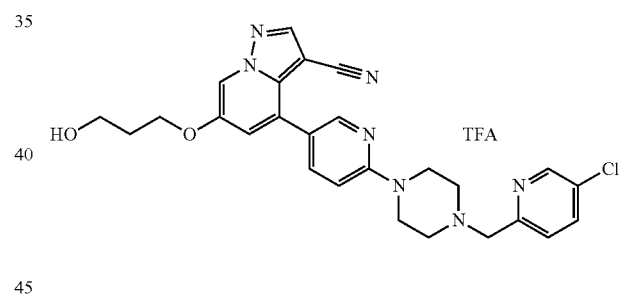

4-(6-(4-((5-chloropyridin-2-yl)methyl)piperazin-1-yl)pyridin-3-yl)-6-(3-hydroxypropoxy)pyrazolo[1,5-a]pyridine-3-carbonitrile 2,2,2-trifluoroacetate A mixture of 6-(3-hydroxypropoxy)-4-(6-(piperazin-1-yl)pyridin-3-yl)pyrazolo[1,5-a]pyridine-3-carbonitrile hydrochloride (Intermediate P51; 12.1 mg, 0.0292 mmol), 5-chloropicolinaldehyde (8.26 mg, 0.0583 mmol) and NaBH(AcO)$_3$ (18.5 mg, 0.0875 mmol) in DCE (583 µL) was stirred for 1 day at ambient temperature. The mixture was purified directly by C18 reverse phase (5-95% ACN/water with 0.1% TFA as the gradient eluent) to afford the title compound (17.1 mg, 95% yield). MS (apci) m/z=504.2 (M+H).

The compounds in Table R were prepared using a similar method to that described for the synthesis of Example 192, replacing (5-chloropicolinaldehyde with the appropriate aldehyde. Reactions were monitored for completion by LCMS, and reaction durations were adjusted accordingly. Title compounds were cleanly isolated following chromatographic purification using an appropriate gradient eluent.

TABLE R

| Ex # | Structure | Chemical Name | MS (apci) m/z |
|---|---|---|---|
| 193 | 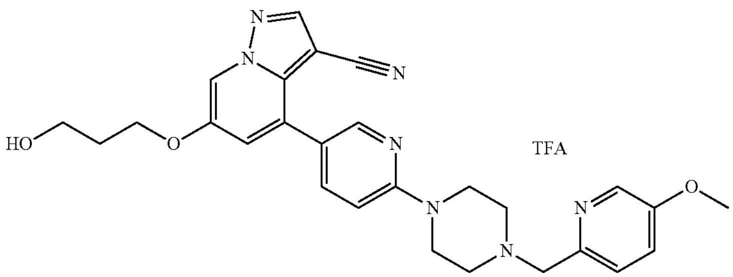 [SMILES: COc1ccc(CN2CCN(c3ccc(-c4cc(OCCCO)cn5ncc(C#N)c45)cn3)CC2)nc1] | 6-(3-hydroxypropoxy)-4-(6-(4-((5-methoxypyridin-2-yl)methyl)piperazin-1-yl)pyridin-3-yl)pyrazolo[1,5-a]pyridine-3-carbonitrile 2,2,2-trifluoroacetate | 500.2 (M + H) |
| 194 | 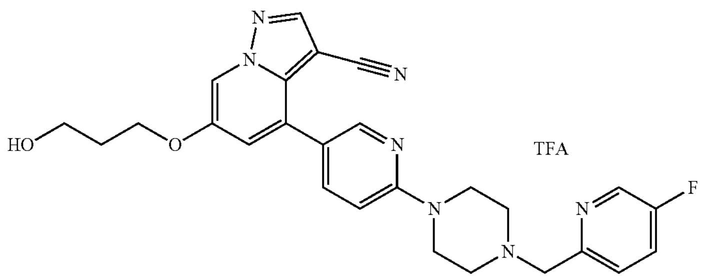 [SMILES: N#Cc1cnn2cc(OCCCO)cc(-c3ccc(N4CCN(Cc5ccc(F)cn5)CC4)nc3)c12] | 4-(6-(4-((5-fluoropyridin-2-yl)methyl)piperazin-1-yl)pyridin-3-yl)-6-(3-hydroxypropoxy)pyrazolo[1,5-a]pyridine-3-carbonitrile 2,2,2-trifluoroacetate | 488.2 (M + H) |

Example 195

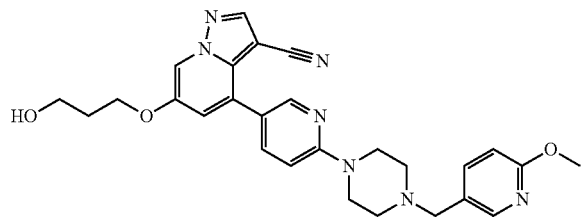 [SMILES: COc1ccc(CN2CCN(c3ccc(-c4cc(OCCCO)cn5ncc(C#N)c45)cn3)CC2)cn1]

6-(3-hydroxypropoxy)-4-(6-(4-((6-methoxypyridin-3-yl)methyl)piperazin-1-yl)pyridin-3-yl)pyrazolo[1,5-a]pyridine-3-carbonitrile Step 1: Preparation of 6-(3-((tert-butyldimethylsilyl)oxy)propoxy)-4-(6-(4-((6-methoxypyridin-3-yl)methyl)piperazin-1-yl)pyridin-3-yl)pyrazolo[1,5-a]pyridine-3-carbonitrile A mixture of 6-hydroxy-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate (Intermediate P24: 28 mg, 0.0634 mmol), (3-bromopropoxy)(tert-butyl)dimethylsilane (14.5 µL, 0.0793 mmol) and $K_2CO_{3(s)}$ (26.3 mg, 0.190 mmol) in DMF (317 µL) was stirred 1 day at 50° C. After cooling to ambient temperature, the reaction mixture was purified directly by silica chromatography (0-100% EtOAc/hexanes as the gradient eluent) to cleanly provide the title compound (420 mg, 49% yield). MS (apci) m/z=614.9 (M+H).

Step 2: Preparation of 6-(3-hydroxypropoxy)-4-(6-(4-((6-methoxypyridin-3-yl)methyl)piperazin-1-yl)pyridin-3-yl)pyrazolo[1,5-a]pyridine-3-carbonitrile A solution of 6-(3-((tert-butyldimethylsilyl)oxy)propoxy)-4-(6-(4-((6-methoxypyridin-3-yl)methyl)piper-azin-1-yl)pyridin-3-yl)pyrazolo[1,5-a]pyridine-3-carbonitrile (35 mg, 0.0570 mmol) in THF (1.14 mL) was treated with TBAF (114 µL, 0.114 mmol), was stirred for 1d at 60° C. The resulting mixture was directly purified first by C18 reverse phase chromatography (5-95% ACN/water with 0.1% TFA as the gradient eluent) then by silica chromatography (0-20% DCM/MeOH as the gradient eluent) to afford the title compound (8.8 mg, 31% yield). MS (apci) m/z=499.8 (M+H).

Example 196

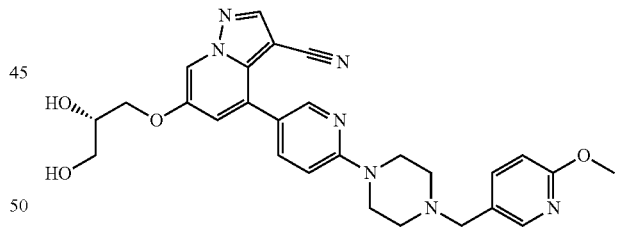

(S)-6-(2,3-dihydroxypropoxy)-4-(6-(4-((6-methoxypyridin-3-yl)methyl)piperazin-1-yl)pyridin-3-yl)pyrazolo[1,5-a]pyridine-3-carbonitrile A mixture of (S)-6-(2,3-dihydroxypropoxy)-4-(6-(piperazin-1-yl)pyridin-3-yl)pyrazolo[1,5-a]pyridine-3-carbonitrile dihydrochloride (Intermediate P52; 20 mg, 0.0507 mmol) in DCE (507 µL) was treated sequentially with 6-methoxy-3-pyridinecarboxaldehyde (6.95 mg, 0.0507 mmol) and $NaBH(AcO)_3$ (32.2 mg, 0.152 mmol) and then stirred overnight at ambient temperature. The mixture was purified directly by silica chromatography (0-20% MeOH in DCM as the gradient eluent) to afford the title compound (11.4 mg, 44% yield). MS (apci) m/z=516.2 (M+H).

Example 197

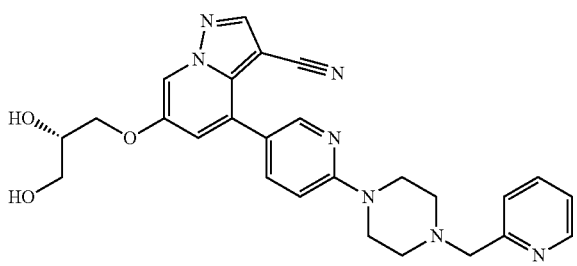 [SMILES: N#Cc1cnn2cc(OC[C@@H](O)CO)cc(-c3ccc(N4CCN(Cc5ccccn5)CC4)nc3)c12]

(S)-6-(2,3-dihydroxypropoxy)-4-(6-(4-(pyridin-2-ylmethyl)piperazin-1-yl)pyridin-3-yl)pyrazolo[1,5-a]pyridine-3-carbonitrile The title compound (1.2 mg, 5% yield) was prepared and purified using a similar procedure to that described for Example 196, replacing 6-methoxy-3-pyridinecarboxaldehyde with picolinaldehyde (2 equivalents). MS (apci) m/z=486.2 (M+H).

Example 198

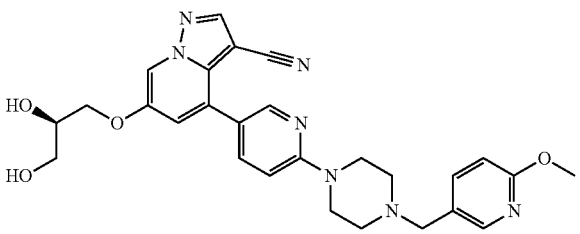 [SMILES: COc1ccc(CN2CCN(c3ccc(-c4cc(OC[C@H](O)CO)cn5ncc(C#N)c45)cn3)CC2)cn1]

(R)-6-(2,3-dihydroxypropoxy)-4-(6-(4-((6-methoxy-pyridin-3-yl)methyl)piperazin-1-yl)pyridin-3-yl)pyrazolo[1,5-a]pyridine-3-carbonitrile The title compound (5.1 mg, 30% yield) was prepared and purified using a similar procedure to that described for Example 196, replacing (S)-6-(2,3-dihydroxypropoxy)-4-(6-(piperazin-1-yl)pyridin-3-yl)pyrazolo[1,5-a]pyridine-3-carbonitrile dihydrochloride (Intermediate P52) with (R)-6-(2,3-dihydroxypropoxy)-4-(6-(piperazin-1-yl)pyridin-3-yl)pyrazolo[1,5-a]pyridine-3-carbonitrile dihydrochloride (Intermediate P53), and using 2 equivalents of 6-methoxy-3-pyridinecarboxaldehyde. MS (apci) m/z=516.2 (M+H).

Example 199

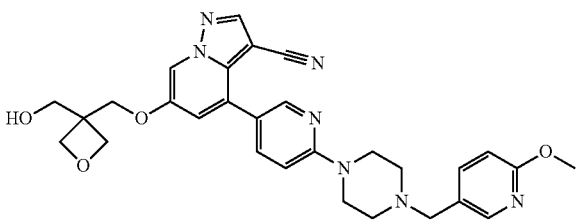 [SMILES: COc1ccc(CN2CCN(c3ccc(-c4cc(OCC5(CO)COC5)cn5ncc(C#N)c45)cn3)CC2)cn1]

6-((3-(hydroxymethyl)oxetan-3-yl)methoxy)-4-(6-(4-((6-methoxypyridin-3-yl)methyl)piperazin-1-yl)pyridin-3-yl)pyrazolo[1,5-a]pyridine-3-carbonitrile A mixture of 6-hydroxy-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate (Intermediate P24: 39 mg, 0.088 mmol), [3-(bromomethyl)oxetan-3-yl]methanol (48.0 mg, 0.265 mmol) and $K_2CO_{3(s)}$ (61.0 mg, 0.442 mmol) in DMF (883 µL) was stirred 1 hour at 90° C. After cooling to ambient temperature, the reaction mixture was purified directly by silica chromatography (using a stepwise gradient of 0-100% EtOAc in hexanes followed by EtOAc with 10% MeOH as eluents) to cleanly provide the title compound (21 mg, 44% yield). MS (apci) m/z=542.3 (M+H).

Example 200

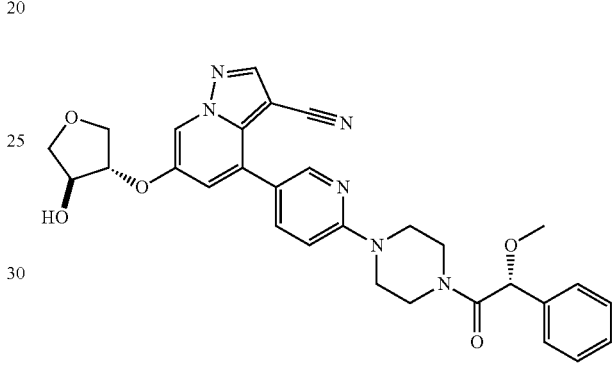

6-(((3S,4S)-4-hydroxytetrahydrofuran-3-yl)oxy)-4-(6-(4-((R)-2-methoxy-2-phenylacetyl)piperazin-1-yl)pyridin-3-yl)pyrazolo[1,5-a]pyridine-3-carbonitrile A solution of 6-(((3S,4S)-4-hydroxytetrahydrofuran-3-yl)oxy)-4-(6-(piperazin-1-yl)pyridin-3-yl)pyrazolo[1,5-a]pyridine-3-carbonitrile hydrochloride (Intermediate P54; 19 mg, 0.043 mmol), (R)-2-methoxy-2-phenylacetic acid (7.49 mg, 0.0450 mmol) and DIEA (26.2 µL, 0.150 mmol) in DCM (429 µL) was treated with HATU (17.9 mg, 0.0472 mmol). After stirring for 1 hour at ambient temperature, the reaction mixture was directly purified by C18 reverse phase chromatography (5-95% ACN/water with 0.1% TFA as the gradient eluent) and then by silica chromatography (0-20% DCM/MeOH/$NH_4OH$ as the gradient eluent) to cleanly provide the title compound (3 mg, 13% yield). MS (apci) m/z=555.2 (M+H).

Example 201

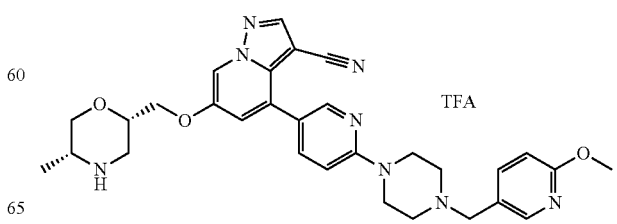

4-(6-(4-((6-methoxypyridin-3-yl)methyl)piperazin-1-yl)pyridin-3-yl)-6-(((2S,5R)-5-methylmorpholin-2-yl)methoxy)pyrazolo[1,5-a]pyridine-3-carbonitrile 2,2,2-trifluoroacetate Step 1: Preparation of tert-butyl (2S,5R)-2-(((3-cyano-4-(6-(4-((6-methoxypyridin-3-yl)methyl)piperazin-1-yl)pyridin-3-yl)pyrazolo[1,5-a]pyridin-6-yl)oxy)methyl)-5-methylmorpholine-4-carboxylate A mixture of 6-hydroxy-4-(6-(4-((6-methoxypyridin-3-yl)methyl)piperazin-1-yl)pyridin-3-yl)pyrazolo[1,5-a]pyridine-3-carbonitrile 2,2,2-trifluoroacetate (Intermediate P24; 15 mg, 0.0340 mmol), tert-Butyl (2S,5R)-2-(hydroxymethyl)-5-methylmorpholine-4-carboxylate (12.6 mg, 0.0408 mmol) and K$_2$CO$_{3(s)}$ (4.70 mg, 0.0340 mmol) in DMF (1 mL) was stirred 1 day at 50° C. After cooling to ambient temperature, the reaction mixture was loaded directly onto a flash column equilibrated with hexanes and eluted with 0-100% DCM/hexanes then 0-20% MeOH in DCM to afford the title compound (8 mg, 36% yield). MS (apci) m/z=656.2 (M+H).

Step 2: Preparation of 4-(6-(4-((6-methoxypyridin-3-yl)methyl)piperazin-1-yl)pyridin-3-yl)-6-(((2S,5R)-5-methylmorpholin-2-yl)methoxy)pyrazolo[1,5-a]pyridine-3-carbonitrile 2,2,2-trifluoroacetate A solution of tert-butyl (2S,5R)-2-(((3-cyano-4-(6-(4-((6-methoxypyridin-3-yl)methyl)piperazin-1-yl)pyridin-3-yl)pyrazolo[15-a]pyridin-6-yl)oxy)methyl)-5-methylmorpholine-4-carboxylate (0.012 mmol) in DCM (611 µL) was treated with TFA (47 µL, 0.61 mmol). The reaction mixture was stirred for 10 min at ambient temperature and then concentrated in vacuo. The crude residue was purified by C18 reverse phase chromatography (5-95% ACN/water with 0.1% TFA as the gradient eluent) to cleanly provide the title compound as the 2,2,2-trifluoroacetate salt (3.3 mg, 40% yield). MS (apci) m/z=554.8 (M+H).

Example 202

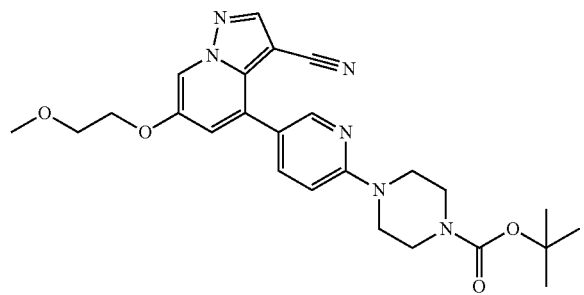 [SMILES: COCCOc1cc(-c2ccc(N3CCN(C(=O)OC(C)(C)C)CC3)nc2)c2c(C#N)cnn2c1]

tert-butyl 4-(5-(3-cyano-6-(2-methoxyethoxy)pyrazolo[1,5-a]pyridin-4-yl)pyridin-2-yl)piperazine-1-carboxylate A solution of tert-butyl 4-(5-(3-cyano-6-hydroxypyrazolo[1,5-a]pyridin-4-yl)pyridin-2-yl)piperazine-1-carboxylate (Intermediate P3; 400 mg, 0.951 mmol) in DMF (8 mL) was treated sequentially with K$_2$CO$_{3(s)}$ (4.70 mg, 0.0340 mmol) and a solution of 1-bromo-2-methoxyethane (264 mg, 1.90 mmol) in DMF (2 mL). The resulting mixture was stirred for 19 h at 50° C. After cooling to ambient temperature, the reaction mixture was purified directly by C18 reverse phase chromatography (5-90% ACN/water as the gradient eluent) to afford the title compound (345 mg, 76% yield). MS (apci) m/z=479.2 (M+H).

Example 203

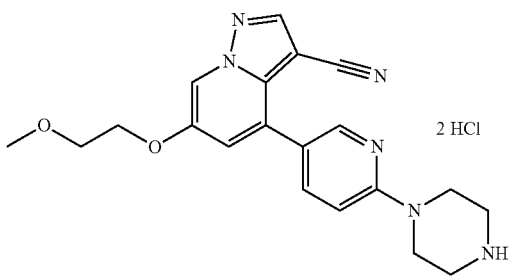 [SMILES: COCCOc1cc(-c2ccc(N3CCNCC3)nc2)c2c(C#N)cnn2c1]

6-(2-methoxyethoxy)-4-(6-(piperazin-1-yl)pyridin-3-yl)pyrazolo[1,5-a]pyridine-3-carbonitrile dihydrochloride A solution of tert-butyl 4-(5-(3-cyano-6-(2-methoxyethoxy)pyrazolo[1,5-a]pyridin-4-yl)pyridin-2-yl)piperazine-1-carboxylate (Example 202; 343 mg, 0.717 mmol) in DCM (2 mL) was treated with 5-6 M HCl in iPrOH (4 mL, 20.0 mmol) and stirred for 1 hour at ambient temperature. The mixture was diluted with DCM and MeOH and concentrated in vacuo to afford the title compound as the dihydrochloride salt (322 mg, quantitative yield). MS (apci) m/z=379.2 (M+H).

Example 204

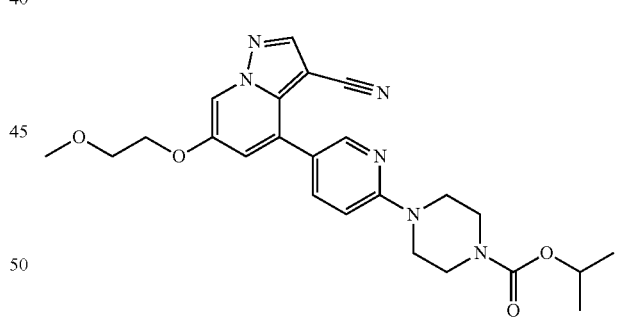

6-(2-methoxyethoxy)-4-(6-(4-(3-methylbutanoyl)piperazin-1-yl)pyridin-3-yl)pyrazolo[1,5-a]pyridine-3-carbonitrile A solution of 6-(2-methoxyethoxy)-4-(6-(piperazin-1-yl)pyridin-3-yl)pyrazolo[1,5-a]pyridine-3-carbonitrile (Intermediate P55; 20.1 mg, 0.0531 mmol) in DCM (1.0 mL) was treated sequentially with DIEA (37.0 µL, 0.212 mmol) and isovaleryl chloride (7.77 µL, 0.0637 mmol). The resulting mixture was stirred for 16 h at ambient temperature. The mixture was concentrated in vacuo, and the residue was purified by C18 reverse phase chromatography (5-95% water-ACN with 0.1% TFA as the gradient eluent) to afford the title compound as the TFA salt. The TFA salt was partitioned between 4:1 DCM:iPrOH and saturated NaHCO$_{3(aq)}$. The combined organic extracts were dried over anhydrous Na$_2$SO$_{4(s)}$, filtered and concentrated in vacuo to afford the title compound (22.0 mg, 90% yield). MS (apci) m/z=463.2 (M+H).

Example 205

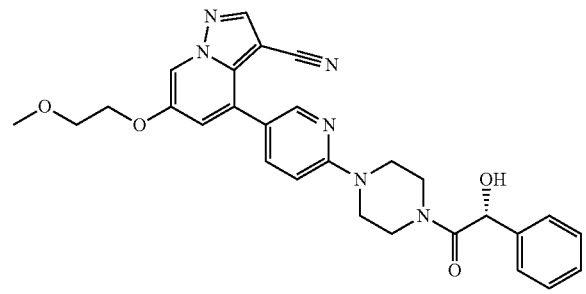 [SMILES: COCCOc1cc(-c2ccc(N3CCN(C(=O)[C@H](O)c4ccccc4)CC3)nc2)c2c(C#N)cnn2c1]

(R)-4-(6-(4-(2-hydroxy-2-phenylacetyl)piperazin-1-yl)pyridin-3-yl)-6-(2-methoxyethoxy)pyrazolo[1,5-a]pyridine-3-carbonitrile A solution of 6-(2-methoxyethoxy)-4-(6-(piperazin-1-yl)pyridin-3-yl)pyrazolo[1,5-a]pyridine-3-carbonitrile (Intermediate P54; 20.8 mg, 0.0550 mmol) in DCM (429 μL) was treated sequentially with D-(−)-Mandelic acid (10 mg, 0.0660 mmol), HATU (25.1 mg, 0.0660 mmol) and DIEA (38.3 μL, 0.220 mmol). After stirring for 16 h at ambient temperature, the reaction mixture was concentrated in vacuo. The residue was purified by C18 reverse phase chromatography (5-95% water-ACN with 0.1% TFA as the gradient eluent) to afford the title compound as the TFA salt. The TFA salt was partitioned between 4:1 DCM:iPrOH and saturated NaHCO$_{3(aq)}$. The combined organic extracts were dried over anhydrous Na$_2$SO$_{4(s)}$, filtered and concentrated in vacuo to afford the title compound (18.6 mg, 66% yield). MS (apci) m/z=513.2 (M+H). $^1$H NMR (400 MHz, DMSO-d$^6$) δ: 8.69-8.68 (d, 1H), 8.56 (s, 1H), 8.32-8.31 (d, 1H), 7.78-7.76 (dd, 1H), 7.41-7.27 (m, 6H), 6.92-6.90 (d, 1H), 5.74-5.72 (d, 1H), 5.48-5.46 (d, 1H), 4.42-4.22 (m, 2H), 3.70-3.68 (m, 2H), 3.65-3.20 (m, 11H).

Example 206

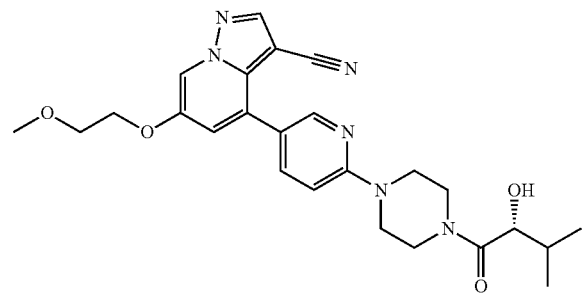 [SMILES: COCCOc1cc(-c2ccc(N3CCN(C(=O)[C@H](O)C(C)C)CC3)nc2)c2c(C#N)cnn2c1]

(R)-4-(6-(4-(2-hydroxy-3-methylbutanoyl)piperazin-1-yl)pyridin-3-yl)-6-(2-methoxyethoxy)pyrazolo[1,5-a]pyridine-3-carbonitrile The title compound (21.1 mg, 81% yield) was prepared and purified using a similar procedure to that described for Example 205, replacing D-(−)-Mandelic acid with (R)-2-hydroxy-3-methylbutanoic acid. MS (apci) m/z=479.2 (M+H).

Example 207

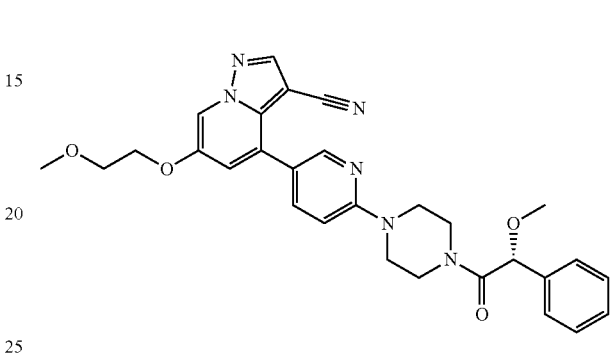

(R)-4-(6-(4-(2-methoxy-2-phenylacetyl)piperazin-1-yl)pyridin-3-yl)-6-(2-methoxyethoxy)pyrazolo[1,5-a]pyridine-3-carbonitrile A solution of 6-(2-methoxyethoxy)-4-(6-(piperazin-1-yl)pyridin-3-yl)pyrazolo[1,5-a]pyridine-3-carbonitrile dihydrochloride (Example 203; 9.7 mg, 0.021 mmol) in DCM (300 μL) was treated sequentially with (R)-2-methoxy-2-phenylacetic acid (5.4 mg, 0.032 mmol), DIEA (15 μL, 0.086 mmol) and HATU (12 mg, 0.032 mmol). After stirring for 17 h at ambient temperature, the reaction mixture was purified directly by silica chromatography (10-100% acetone/hexanes as the gradient eluent) to afford impure title compound (15 mg). This material was purified by C18 reverse phase chromatography (5-95% water-ACN as the gradient eluent) to cleanly provide the title compound (7.0 mg, 62% yield). MS (apci) m/z=527.2 (M+H).

Example 208

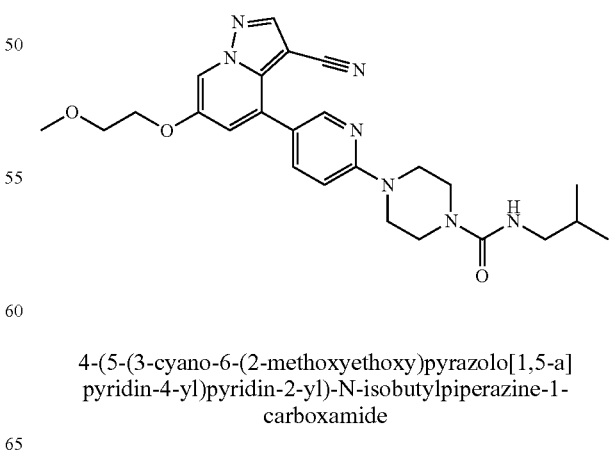

4-(5-(3-cyano-6-(2-methoxyethoxy)pyrazolo[1,5-a]pyridin-4-yl)pyridin-2-yl)-N-isobutylpiperazine-1-carboxamide A solution of 6-(2-methoxyethoxy)-4-(6-(piperazin-1-yl)pyridin-3-yl)pyrazolo[1,5-a]pyridine-3-carbonitrile (Intermediate P54; 24.7 mg, 0.0653 mmol) in DMA (1.3 mL) was treated sequentially with DIEA (114 μL, 0.653 mmol) and 4-nitrophenyl chloroformate (15.8 mg, 0.0783 mmol). After stirring the mixture for 1 hour at ambient temperature, isobutylamine (32.4 μL, 0.326 mmol) was added. The resulting mixture was stirred for 16 h at 80° C. After cooling to ambient temperature, the resulting mixture was diluted with EtOAc, and washed successively with water and brine. The combined organic extracts were dried over anhydrous $Na_2SO_{4(s)}$, filtered and concentrated in vacuo. The residue was purified by C18 reverse phase chromatography (5-95% water-ACN with 0.1% TFA as the gradient eluent) to afford the title compound as the TFA salt. The TFA salt was partitioned between 4:1 DCM:iPrOH and saturated $NaHCO_{3(aq)}$. The resulting organic extracts were dried over anhydrous $Na_2SO_{4(s)}$, filtered and concentrated in vacuo to afford the title compound (10.2 mg, 33% yield). MS (apci) m/z=478.3 (M+H).

Example 209

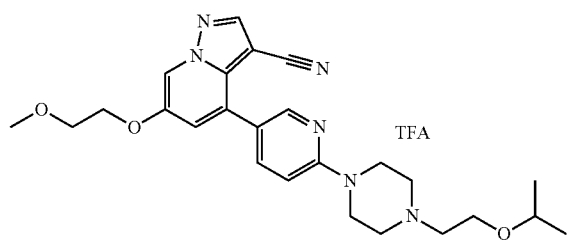 [SMILES: COCCOc1cc(-c2ccc(N3CCN(CCOC(C)C)CC3)nc2)c2c(C#N)cnn2c1]

4-(6-(4-(2-isopropoxyethyl)piperazin-1-yl)pyridin-3-yl)-6-(2-methoxyethoxy)pyrazolo[1,5-a]pyridine-3-carbonitrile 2,2,2-trifluoroacetate A solution of 6-(2-methoxyethoxy)-4-(6-(piperazin-1-yl)pyridin-3-yl)pyrazolo[1,5-a]pyridine-3-carbonitrile (Intermediate P54; 15 mg, 0.0396 mmol) in DMF (400 μL) was treated sequentially with DIEA (27.7 μL, 0.159 mmol) and 2-(2-bromoethoxy)propane (20 μL, 0.119 mmol) and stirred for 3 days at 50° C. After cooling to ambient temperature, the reaction mixture was filtered, rinsed with ACN (0.6 mL) prior to purification by C18 reverse phase chromatography (5-95% ACN in water with 0.1% TFA as the gradient eluent) to afford the title compound as the TFA salt (16.4 mg, 89% yield). MS (apci) m/z=465.2 (M+H).

Example 210

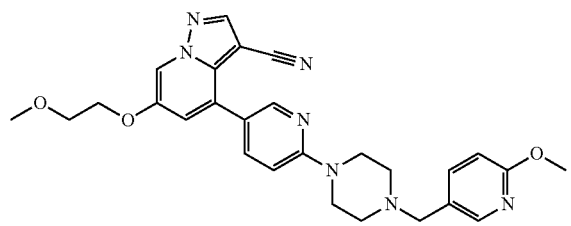

6-(2-methoxyethoxy)-4-(6-(4-((6-methoxypyridin-3-yl)methyl)piperazin-1-yl)pyridin-3-yl)pyrazolo[1,5-a]pyridine-3-carbonitrile A solution of (6-(2-methoxyethoxy)-4-(6-(piperazin-1-yl)pyridin-3-yl)pyrazolo[1,5-a]pyridine-3-carbonitrile (Intermediate P54; 14.3 mg, 0.0378 mmol) in DCE (400 μL) was treated sequentially with 6-methoxynicotinaldehyde (10.4 mg, 0.0756 mmol) and $NaBH(AcO)_3$ (24 mg, 0.113 mmol), and then stirred overnight at ambient temperature. The mixture was diluted with water (5 mL) and extracted with DCM. The combined organic extracts were dried over anhydrous $MgSO_{4(s)}$, filtered and concentrated in vacuo. The crude product was purified directly by silica chromatography (0-100% acetone/hexanes as the gradient eluent) to cleanly provide the title compound (15.6 mg, 83% yield). MS (apci) m/z=500.2 (M+H). $^1$H NMR (400 MHz, $CDCl_3$) δ: 8.31 (d, 1H), 8.19 (s, 1H), 8.15 (d, 1H), 8.08 (d, 1H), 7.70 (dd, 1H), 7.62 (br d, 1H), 7.15 (d, 1H), 6.75 (m, 2H), 4.18 (m, 2H), 3.95 (s, 3H), 3.80 (m, 2H), 3.65 (m, 4H), 3.50 (br s, 2H), 3.47 (s, 3H), 2.56 (m, 4H).

Example 211

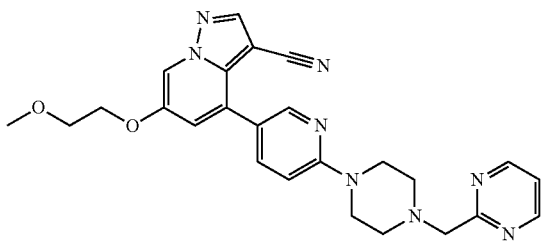 [SMILES: COCCOc1cc(-c2ccc(N3CCN(Cc4ncccn4)CC3)nc2)c2c(C#N)cnn2c1]

6-(2-methoxyethoxy)-4-(6-(4-(pyrimidin-2-ylmethyl)piperazin-1-yl)pyridin-3-yl)pyrazolo[1,5-a]pyridine-3-carbonitrile The title compound was prepared and purified using a similar procedure to that described for Example 210, replacing 6-methoxynicotinaldehyde with pyrimidine-2-carbaldehyde, using saturated $NaHCO_{3(aq)}$ in place of water in the work up, and 25-100% acetone/hexanes as the gradient eluent in the purification to cleanly provide the title compound (16.6 mg, 89% yield). MS (apci) m/z=471.2 (M+H).

Example 212

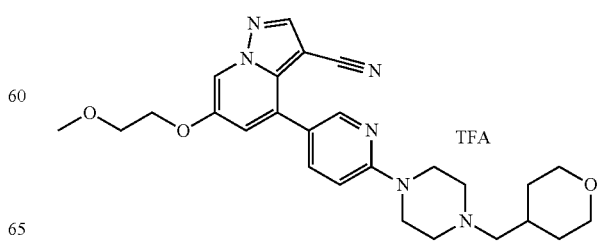

6-(2-methoxyethoxy)-4-(6-(4-((tetrahydro-2H-pyran-4-yl)methyl)piperazin-1-yl)pyridin-3-yl)pyrazolo[1,5-a]pyridine-3-carbonitrile 2,2,2-trifluoroacetate The title compound was prepared and purified using a similar procedure to that described for Example 210, replacing 6-methoxynicotinaldehyde with tetrahydro-2H-pyran-4-carbaldehyde, using 1 M Na$_2$CO$_{3(aq)}$ in place of water in the work up, and purifying by C18 reverse phase chromatography with 5-95% ACN/water with 0.1% TFA as the gradient eluent to cleanly provide the title compound as the 2,2,2-trifluoroacetate salt (17.9 mg, 89% yield). MS (apci) m/z=477.2 (M+H).

Example 213

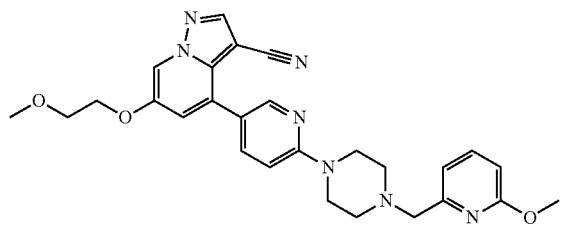

6-(2-methoxyethoxy)-4-(6-(4-((6-methoxypyridin-2-yl)methyl)piperazin-1-yl)pyridin-3-yl)pyrazolo[1,5-a]pyridine-3-carbonitrile A solution of (6-(2-methoxyethoxy)-4-(6-(piperazin-1-yl)pyridin-3-yl)pyrazolo[1,5-a]pyridine-3-carbonitrile dihydrochloride (Example 203; 9.8 mg, 0.0217 mmol) in DCE (300 µL) was treated sequentially with 6-methoxypicolinaldehyde (5.22 µL, 0.434 mmol) and NaBH(AcO)$_3$ (13.8 mg, 0.0651 mmol), and then stirred for 16 h at ambient temperature. The mixture was quenched with MeOH (0.5 mL) and purified directly by silica chromatography (10-100% acetone/hexanes as the gradient eluent) to cleanly provide the title compound (10.2 mg, 94% yield). MS (apci) m/z=500.3 (M+H).

The compounds in Table S were prepared using a similar method to that described for the synthesis of Example 213, replacing 6-methoxypicolinaldehyde with the appropriate aldehyde. Reactions were monitored for completion by LCMS, and reaction durations were adjusted accordingly. Title compounds were cleanly isolated following chromatographic purification using an appropriate gradient eluent.

TABLE S

| Ex # | Structure | Chemical Name | MS (apci) m/z |
|---|---|---|---|
| 214 | 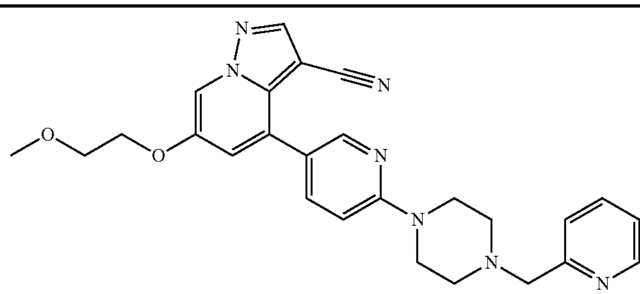 | 6-(2-methoxyethoxy)-4-(6-(4-(pyridin-2-ylmethyl)piperazin-1-yl)pyridin-3-yl)pyrazolo[1,5-a]pyridine-3-carbonitrile | 470.2 (M + H) |
| 215 | 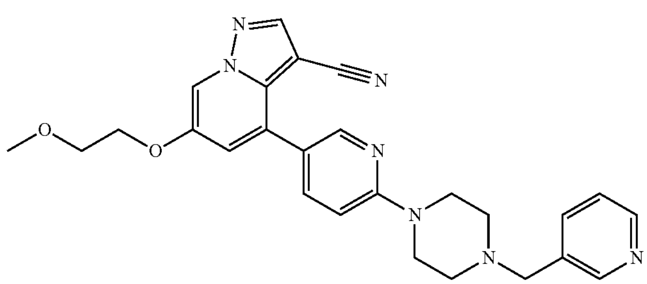 [SMILES: COCCOc1cc(-c2ccc(N3CCN(Cc4cccnc4)CC3)nc2)c2c(C#N)cnn2c1] | 6-(2-methoxyethoxy)-4-(6-(4-(pyridin-3-ylmethyl)piperazin-1-yl)pyridin-3-yl)pyrazolo[1,5-a]pyridine-3-carbonitrile | 470.2 (M + H) |
| 216 | 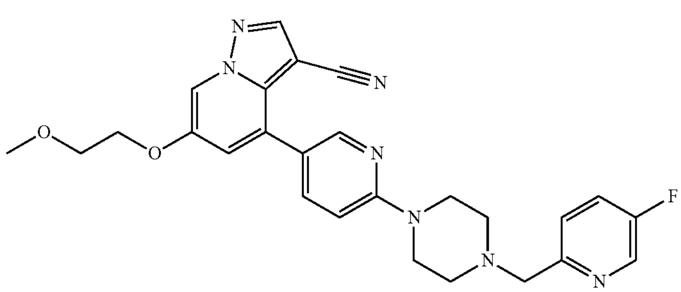 [SMILES: COCCOc1cc(-c2ccc(N3CCN(Cc4ccc(F)cn4)CC3)nc2)c2c(C#N)cnn2c1] | 4-(6-(4-((5-fluoropyridin-2-yl)methyl)piperazin-1-yl)pyridin-3-yl)-6-(2-methoxyethoxy)pyrazolo[1,5-a]pyridine-3-carbonitrile | 488.2 (M + H) |

TABLE S-continued

| Ex # | Structure | Chemical Name | MS (apci) m/z |
|---|---|---|---|
| 217 | 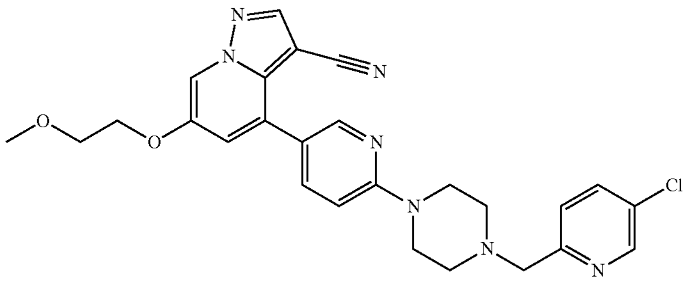 [SMILES: COCCOc1cc(-c2ccc(N3CCN(Cc4ccc(Cl)cn4)CC3)nc2)c2c(C#N)cnn2c1] | 4-(6-(4-((5-chloropyridin-2-yl)methyl)piperazin-1-yl)pyridin-3-yl)-6-(2-methoxyethoxy)pyrazolo[1,5-a]pyridine-3-carbonitrile | 504.2 (M + H) |
| 218 | 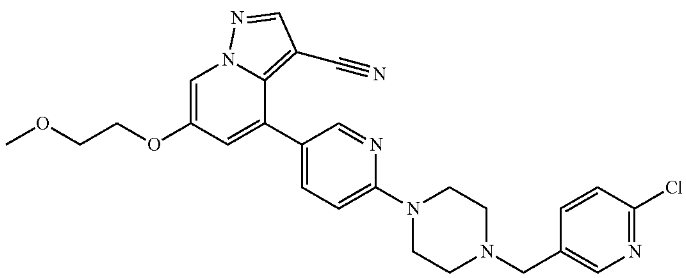 [SMILES: COCCOc1cc(-c2ccc(N3CCN(Cc4ccc(Cl)nc4)CC3)nc2)c2c(C#N)cnn2c1] | 4-(6-(4-((6-chloropyridin-3-yl)methyl)piperazin-1-yl)pyridin-3-yl)-6-(2-methoxyethoxy)pyrazolo[1,5-a]pyridine-3-carbonitrile | 504.2 (M + H) |
| 219 | 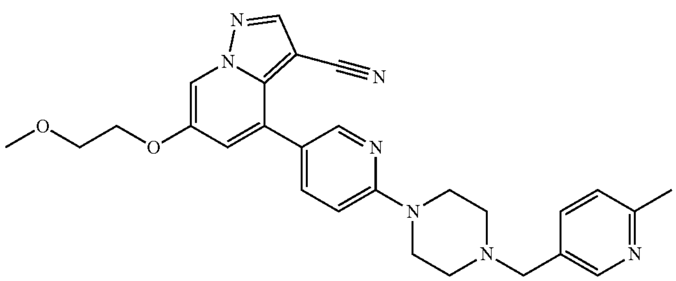 | 6-(2-methoxyethoxy)-4-(6-(4-((6-methylpyridin-3-yl)methyl)piperazin-1-yl)pyridin-3-yl)pyrazolo[1,5-a]pyridine-3-carbonitrile | 484.2 (M + H) |
| 220 | 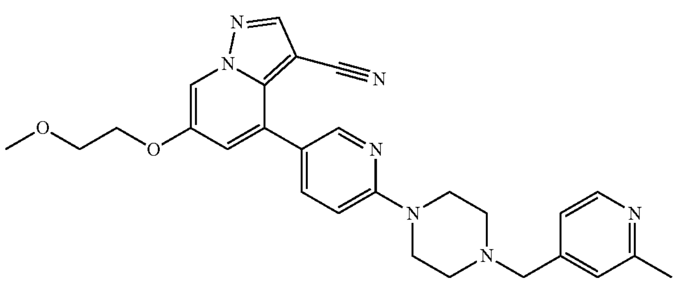 | 6-(2-methoxyethoxy)-4-(6-(4-((2-methylpyridin-4-yl)methyl)piperazin-1-yl)pyridin-3-yl)pyrazolo[1,5-a]pyridine-3-carbonitrile | 484.3 (M + H) |
| 221 | 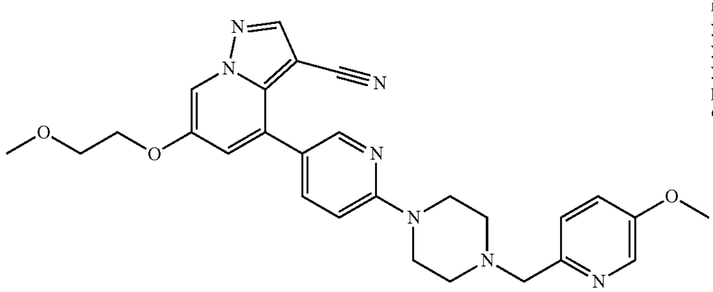 | 6-(2-methoxyethoxy)-4-(6-(4-((5-methoxypyridin-2-yl)methyl)piperazin-1-yl)pyridin-3-yl)pyrazolo[1,5-a]pyridine-3-carbonitrile | 500.2 (M + H) |

TABLE S-continued

| Ex # | Structure | Chemical Name | MS (apci) m/z |
|---|---|---|---|
| 222 | 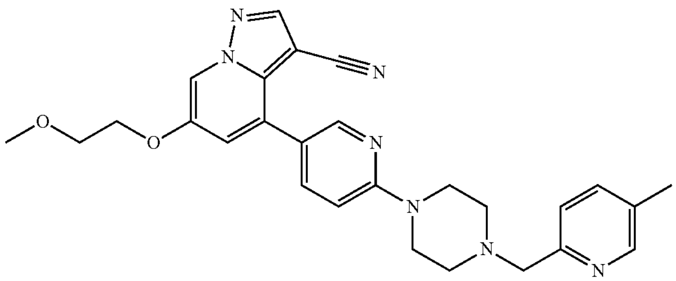 | 6-(2-methoxyethoxy)-4-(6-(4-((5-methylpyridin-2-yl)methyl)piperazin-1-yl)pyridin-3-yl)pyrazolo[1,5-a]pyridine-3-carbonitrile | 484.3 (M + H) |
| 223 | 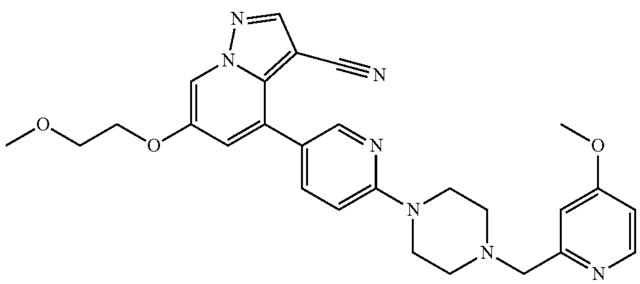 [SMILES: COCCOc1cc(-c2ccc(N3CCN(Cc4cc(OC)ccn4)CC3)nc2)c2c(C#N)cnn2c1] | 6-(2-methoxyethoxy)-4-(6-(4-((4-methoxypyridin-2-yl)methyl)piperazin-1-yl)pyridin-3-yl)pyrazolo[1,5-a]pyridine-3-carbonitrile | 500.2 (M + H) |
| 224 | 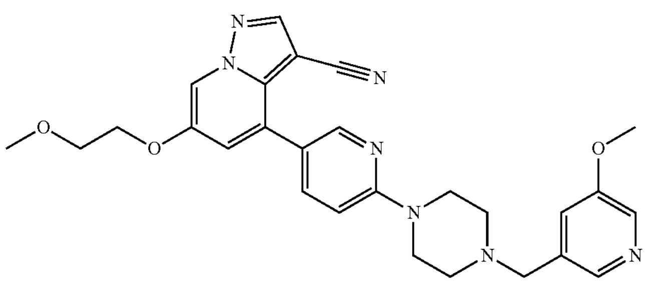 | 6-(2-methoxyethoxy)-4-(6-(4-((5-methoxypyridin-3-yl)methyl)piperazin-1-yl)pyridin-3-yl)pyrazolo[1,5-a]pyridine-3-carbonitrile | 500.2 (M + H) |
| 225 | 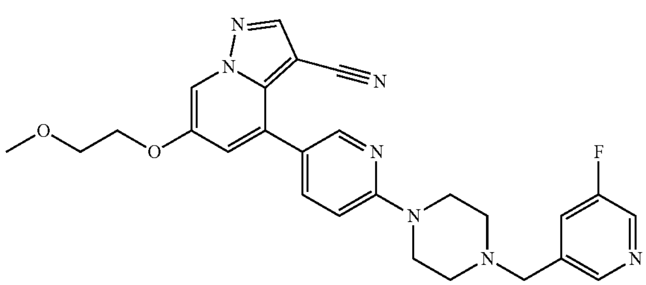 | 4-(6-(4-((5-fluoropyridin-3-yl)methyl)piperazin-1-yl)pyridin-3-yl)-6-(2-methoxyethoxy)pyrazolo[1,5-a]pyridine-3-carbonitrile | 488.2 (M + H) |
| 226 | 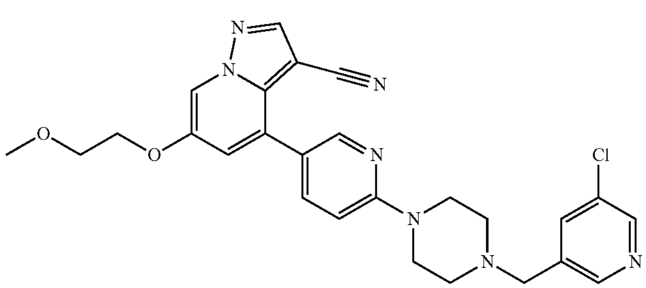 [SMILES: COCCOc1cc(-c2ccc(N3CCN(Cc4cncc(Cl)c4)CC3)nc2)c2c(C#N)cnn2c1] | 4-(6-(4-((5-chloropyridin-3-yl)methyl)piperazin-1-yl)pyridin-3-yl)-6-(2-methoxyethoxy)pyrazolo[1,5-a]pyridine-3-carbonitrile | 504.2 (M + H) |

TABLE S-continued

| Ex # | Structure | Chemical Name | MS (apci) m/z |
|---|---|---|---|
| 227 | 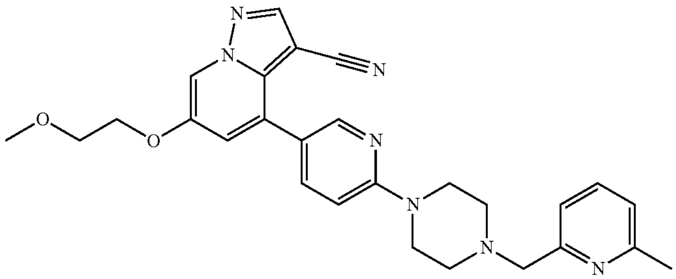 | 6-(2-methoxyethoxy)-4-(6-(4-((6-methylpyridin-2-yl)methyl)piperazin-1-yl)pyridin-3-yl)pyrazolo[1,5-a]pyridine-3-carbonitrile | 484.3 (M + H) |
| 228 | 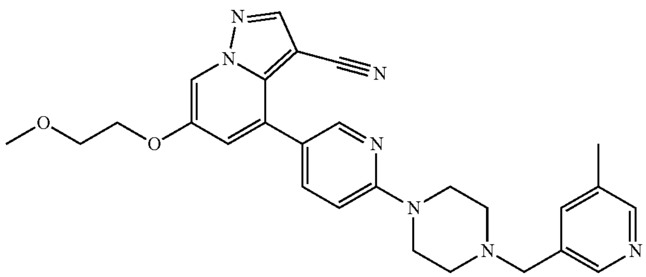 [SMILES: COCCOc1cc(-c2ccc(N3CCN(Cc4cncc(C)c4)CC3)nc2)c2c(C#N)cnn2c1] | 6-(2-methoxyethoxy)-4-(6-(4-((5-methylpyridin-3-yl)methyl)piperazin-1-yl)pyridin-3-yl)pyrazolo[1,5-a]pyridine-3-carbonitrile | 484.2 (M + H) |
| 229 | 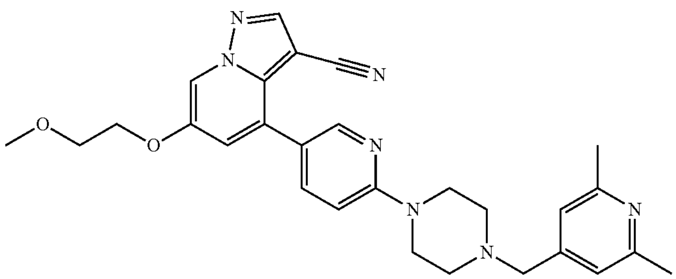 | 4-(6-(4-((2,6-dimethylpyridin-4-yl)methyl)piperazin-1-yl)pyridin-3-yl)-6-(2-methoxyethoxy)pyrazolo[1,5-a]pyridine-3-carbonitrile | 498.3 (M + H) |

Example 230

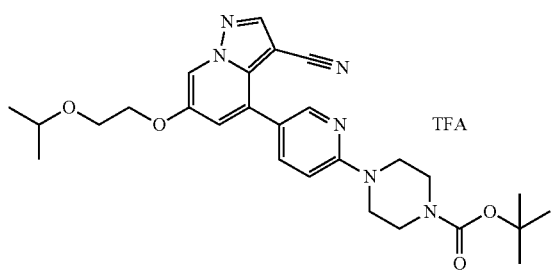 [SMILES: CC(C)OCCOc1cc(-c2ccc(N3CCN(C(=O)OC(C)(C)C)CC3)nc2)c2c(C#N)cnn2c1]

tert-butyl 4-(5-(3-cyano-6-(2-isopropoxyethoxy)pyrazolo[1,5-a]pyridin-4-yl)pyridin-2-yl)piperazine-1-carboxylate 2,2,2-trifluoroacetate A solution of tert-butyl 4-(5-(3-cyano-6-hydroxypyrazolo[1,5-a]pyridin-4-yl)pyridin-2-yl)piperazine-1-carboxylate (Intermediate P3; 200 mg, 0.476 mmol) in DMF (5 mL) was treated sequentially with $K_2CO_{3(s)}$ (131 mg, 0.951 mmol) and 2-(2-bromoethoxy)propane (16 μL, 0.951 mmol). The resulting mixture was stirred for 17 h at 50° C. After cooling to ambient temperature, the reaction mixture was filtered through an Acrodisc® syringe filter, rinsing with ACN. The filtrate was purified directly by C18 reverse phase chromatography (5-95 ACN/water with 0.1% TFA as the gradient eluent) to afford the title compound as the 2,2,2-trifluoroacetate salt (75.5 mg, 26% yield). MS (apci) m/z=507.2 (M+H).

Example 231

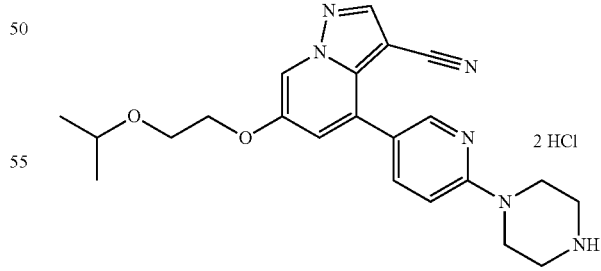

6-(2-isopropoxyethoxy)-4-(6-(piperazin-1-yl)pyridin-3-yl)pyrazolo[1,5-a]pyridine-3-carbonitrile dihydrochloride A solution of tert-butyl 4-(5-(3-cyano-6-(2-isopropoxyethoxy)pyrazolo[1,5-a]pyridin-4-yl)pyridin-2-yl)piperazine-1-carboxylate 2,2,2-trifluoroacetate (Example 230; 74 mg, 0.119 mmol) in DCM (2 mL) was treated with 5-6 M HCl in iPrOH (4 mL, 20.0 mmol), and stirred for 1 hour at ambient temperature. The mixture was concentrated in vacuo, azeotroping with Et$_2$O (3×5 mL), to cleanly provide the title compound as the dihydrochloride salt (54.7 mg, 96% yield). MS (apci) m/z=407.2 (M+H).

Example 232

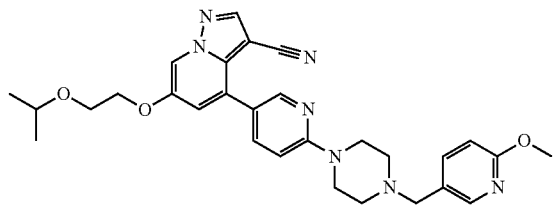 [SMILES: COc1ccc(CN2CCN(c3ccc(-c4cc(OCCOC(C)C)cn5ncc(C#N)c45)cn3)CC2)cn1]

6-(2-isopropoxyethoxy)-4-(6-(4-((6-methoxypyridin-3-yl)methyl)piperazin-1-yl)pyridin-3-yl)pyrazolo[1,5-a]pyridine-3-carbonitrile A solution of 6-(2-isopropoxyethoxy)-4-(6-(piperazin-1-yl)pyridin-3-yl)pyrazolo[1,5-a]pyridine-3-carbonitrile dihydrochloride (Example 231; 11.5 mg, 0.0240 mmol) in DCE (400 μL) was treated sequentially with 6-methoxynicotinaldehyde (6.58 mg, 0.0480 mmol) and NaBH(AcO)$_3$ (15.3 mg, 0.0720 mmol). After stirring for 24 h at ambient temperature, additional 6-methoxynicotinaldehyde (5 mg) and NaBH(AcO)$_3$ (10 mg) were introduced. The mixture was stirred for 39 h at ambient temperature and then diluted with water and extracted with DCM. The combined organic extracts were dried over anhydrous MgSO$_{4(s)}$, filtered and concentrated in vacuo. The crude product was purified directly by silica chromatography (25-100% acetone/hexanes as the gradient eluent) to cleanly provide the title compound (9.6 mg, 76% yield). MS (apci) m/z=528.2 (M+H).

Example 233

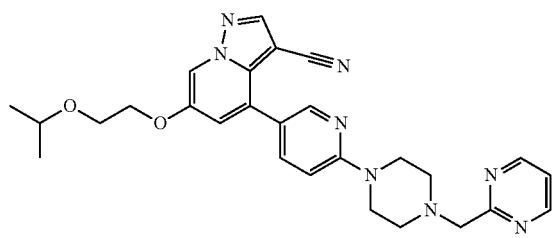 [SMILES: CC(C)OCCOc1cc(-c2ccc(N3CCN(Cc4ncccn4)CC3)nc2)c2c(C#N)cnn2c1]

6-(2-isopropoxyethoxy)-4-(6-(4-(pyrimidin-2-ylmethyl)piperazin-1-yl)pyridin-3-yl)pyrazolo[1,5-a]pyridine-3-carbonitrile The title compound was prepared and purified using a similar procedure to that described for Example 232, replacing 6-methoxynicotinaldehyde with pyrimidine-2-carbaldehyde, using saturated NaHCO$_{3(aq)}$ in place of water in the work up, and 25-100% acetone/hexanes as the gradient eluent in the purification to cleanly provide the title compound (11.8 mg, 76% yield). MS (apci) m/z=499.2 (M+H).

Example 234

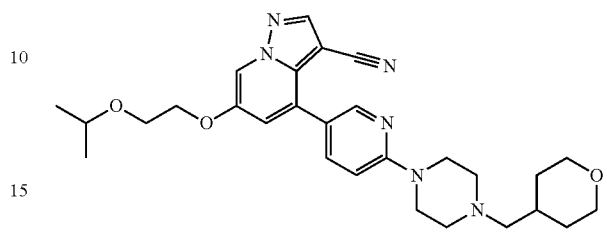

6-(2-isopropoxyethoxy)-4-(6-(4-((tetrahydro-2H-pyran-4-yl)methyl)piperazin-1-yl)pyridin-3-yl)pyrazolo[1,5-a]pyridine-3-carbonitrile The title compound was prepared and purified using a similar procedure to that described for Example 232, replacing 6-methoxynicotinaldehyde with tetrahydro-2H-pyran-4-carbaldehyde, using saturated NaHCO$_{3(aq)}$ in place of water in the work up, and 25-100% acetone/hexanes as the gradient eluent in the purification to afford the title compound cleanly (11.8 mg, 75% yield). MS (apci) m/z=505.2 (M+H).

Example 235

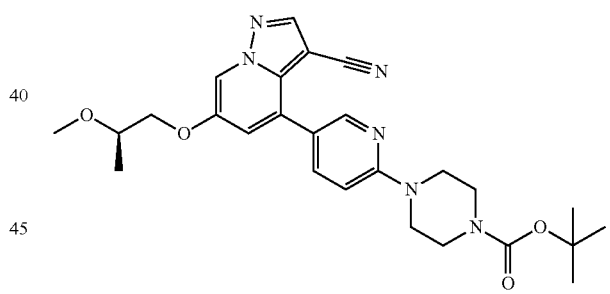

tert-butyl (R)-4-(5-(3-cyano-6-(2-methoxypropoxy)pyrazolo[1,5-a]pyridin-4-yl)pyridin-2-yl)piperazine-1-carboxylate A cold (0° C.) solution of tert-butyl (R)-4-(5-(3-cyano-6-(2-hydroxypropoxy)pyrazolo[1,5-a]pyridin-4-yl)pyridin-2-yl)piperazine-1-carboxylate (Example 116; 120 mg, 0.251 mmol) in DMF (2.5 mL) was treated with NaH(s) (18.1 mg, 0.752 mmol) and stirred for 25 min at 0° C., before adding iodomethane (47.04 μL, 0.752 mmol). The reaction mixture was stirred for 90 min at ambient temperature. The resulting mixture was quenched with the addition of MeOH (0.5 mL), and then purified directly by C18 reverse phase chromatography (5-90% ACN/water as the gradient eluent) to cleanly provide the title compound (102.2 mg, 83% yield). MS (apci) m/z=493.3 (M+H).

Example 236

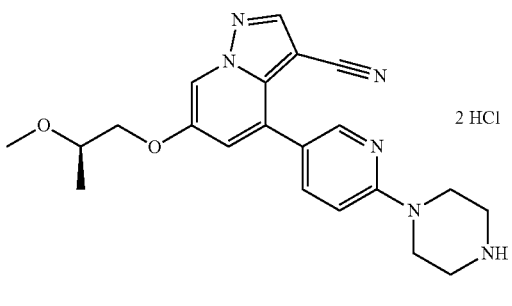 [SMILES: CO[C@H](C)COc1cc(-c2ccc(N3CCNCC3)nc2)c2c(C#N)cnn2c1]

(R)-6-(2-methoxypropoxy)-4-(6-(piperazin-1-yl)pyridin-3-yl)pyrazolo[1,5-a]pyridine-3-carbonitrile dihydrochloride A solution of tert-butyl (R)-4-(5-(3-cyano-6-(2-methoxypropoxy)pyrazolo[1,5-a]pyridin-4-yl)pyridin-2-yl)piperazine-1-carboxylate (Example 235; 74 mg, 0.119 mmol) in DCM (2 mL) was treated with 5-6 M HCl in iPrOH (4 mL, 20.0 mmol), and stirred for 2 h at ambient temperature. The suspension was concentrated in vacuo to cleanly provide the title compound as the dihydrochloride salt (86.7 mg, 91% yield). MS (apci) m/z=393.2 (M+H).

Example 237

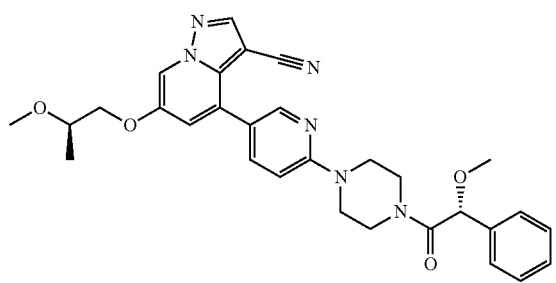 [SMILES: CO[C@H](C)COc1cc(-c2ccc(N3CCN(C(=O)[C@H](OC)c4ccccc4)CC3)nc2)c2c(C#N)cnn2c1]

4-(6-(4-((R)-2-methoxy-2-phenylacetyl)piperazin-1-yl)pyridin-3-yl)-6-((R)-2-methoxypropoxy)pyrazolo[1,5-a]pyridine-3-carbonitrile A solution of (R)-6-(2-methoxypropoxy)-4-(6-(piperazin-1-yl)pyridin-3-yl)pyrazolo[1,5-a]pyridine-3-carbonitrile dihydrochloride (Example 236; 10.0 mg, 0.0215 mmol) in DCM (300 µL) was treated sequentially with (R)-2-methoxy-2-phenylacetic acid (5.36 mg, 0.0322 mmol), DIEA (15 µL, 0.086 mmol) and HATU (12.3 mg, 0.0322 mmol). After stirring for 17 h at ambient temperature, the reaction mixture was purified directly by silica chromatography (10-100% acetone/hexanes as the gradient eluent) to cleanly provide the title compound (10.4 mg, 90% yield). MS (apci) m/z=541.2 (M+H).

Example 238

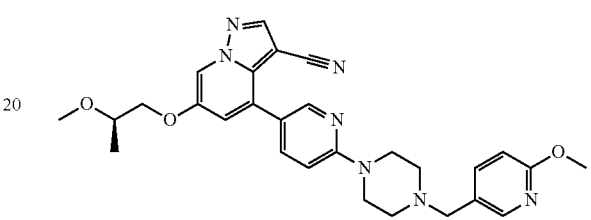

(R)-6-(2-methoxypropoxy)-4-(6-(4-((6-methoxypyridin-3-yl)methyl)piperazin-1-yl)pyridin-3-yl)pyrazolo[1,5-a]pyridine-3-carbonitrile A solution of (R)-6-(2-methoxypropoxy)-4-(6-(piperazin-1-yl)pyridin-3-yl)pyrazolo[1,5-a]pyridine-3-carbonitrile dihydrochloride (Example 236; 9.4 mg, 0.020 mmol) in DCE (300 µL) was treated sequentially with 6-methoxynicotinaldehyde (5.5 mg, 0.040 mmol) and NaBH(AcO)$_3$ (13 mg, 0.061 mmol), and then stirred for 16 h at ambient temperature. The mixture was quenched with MeOH (500 µL) and purified directly by silica chromatography (10-100% acetone/hexanes as the gradient eluent) to cleanly provide the title compound (9.3 mg, 90% yield). MS (apci) m/z=514.3 (M+H).

The compounds in Table T were prepared using a similar method to that described for the synthesis of Example 238, replacing 6-methoxynicotinaldehyde with the appropriate aldehyde. Reactions were monitored for completion by LCMS, and reaction durations were adjusted accordingly. Title compounds were cleanly isolated following chromatographic purification using an appropriate gradient eluent.

TABLE T

| Ex # | Structure | Chemical Name | MS (apci) m/z |
|---|---|---|---|
| 239 | 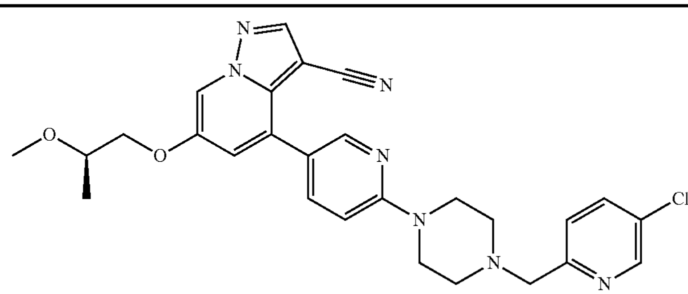 | (R)-4-(6-(4-((5-chloropyridin-2-yl)methyl)piperazin-1-yl)pyridin-3-yl)-6-(2-methoxypropoxy)pyrazolo[1,5-a]pyridine-3-carbonitrile | 518.2 (M + H) |

TABLE T-continued

| Ex # | Structure | Chemical Name | MS (apci) m/z |
|---|---|---|---|
| 240 | 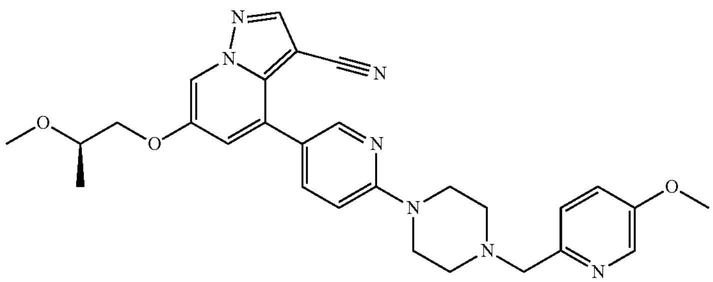 | (R)-6-(2-methoxypropoxy)-4-(6-(4-((5-methoxypyridin-2-yl)methyl)piperazin-1-yl)pyridin-3-yl)pyrazolo[1,5-a]pyridine-3-carbonitrile | 514.2 (M + H) |
| 241 | 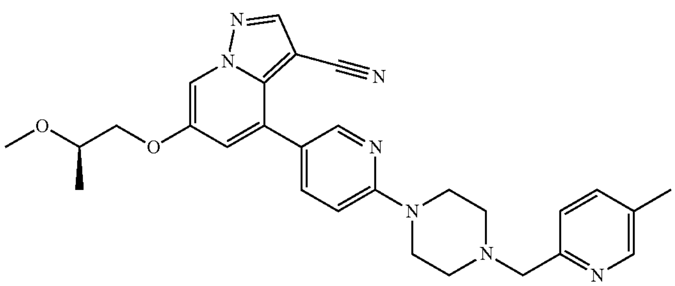 | (R)-6-(2-methoxypropoxy)-4-(6-(4-((5-methylpyridin-2-yl)methyl)piperazin-1-yl)pyridin-3-yl)pyrazolo[1,5-a]pyridine-3-carbonitrile | 498.2 (M + H) |

Example 242

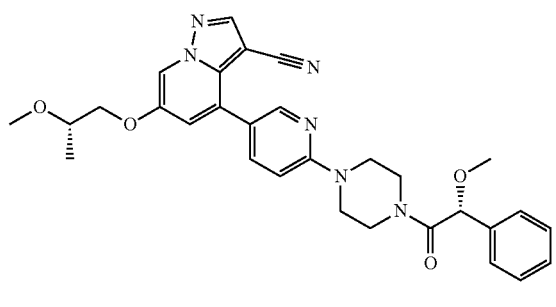 [SMILES: CO[C@@H](C)COc1cc(-c2ccc(N3CCN(C(=O)[C@H](OC)c4ccccc4)CC3)nc2)c2c(C#N)cnn2c1]

4-(6-(4-((R)-2-methoxy-2-phenylacetyl)piperazin-1-yl)pyridin-3-yl)-6-((S)-2-methoxypropoxy)pyrazolo[1,5-a]pyridine-3-carbonitrile A solution of (S)-6-(2-methoxypropoxy)-4-(6-(piperazin-1-yl)pyridin-3-yl)pyrazolo[1,5-a]pyridine-3-carbonitrile dihydrochloride (Intermediate P56; 10.4 mg, 0.0223 mmol) in DCM (300 μL) was treated sequentially with (R)-2-methoxy-2-phenylacetic acid (5.57 mg, 0.0335 mmol), DIEA (15.6 μL, 0.0894 mmol) and HATU (12.7 mg, 0.0335 mmol). After stirring for 17 h at ambient temperature, the reaction mixture was purified directly by silica chromatography (10-100% acetone/hexanes as the gradient eluent) to afford impure title compound. The impure material was subjected to a second chromatography, C18 reverse phase (5-95% ACN/water as the gradient eluent) to cleanly provide the title compound (1.6 mg, 13% yield). MS (apci) m/z=541.3 (M+H).

Example 243

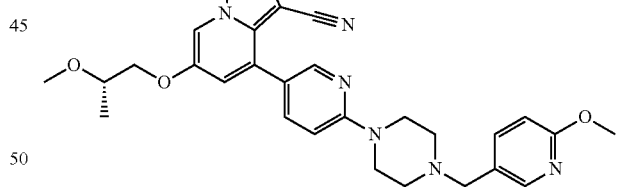

(S)-6-(2-methoxypropoxy)-4-(6-(4-((6-methoxypyridin-3-yl)methyl)piperazin-1-yl)pyridin-3-yl)pyrazolo[1,5-a]pyridine-3-carbonitrile A solution of (S)-6-(2-methoxypropoxy)-4-(6-(piperazin-1-yl)pyridin-3-yl)pyrazolo[1,5-a]pyridine-3-carbonitrile dihydrochloride (Intermediate P56; 21 mg, 0.036 mmol) in DCE (400 μL) was treated sequentially with 6-methoxynicotinaldehyde (9.9 mg, 0.072 mmol) and NaBH(AcO)$_3$ (23 mg, 0.11 mmol), and then stirred for 18 h at ambient temperature. The mixture was purified directly by silica chromatography (0-100% acetone/hexanes as the gradient eluent) to cleanly provide the title compound (8.5 mg, 46% yield). MS (apci) m/z=514.2 (M+H).

Example 244

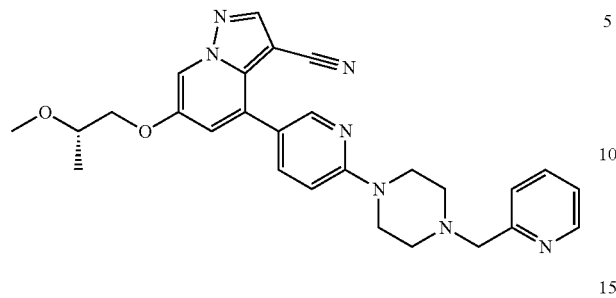

(S)-6-(2-methoxypropoxy)-4-(6-(4-(pyridin-2-ylmethyl)piperazin-1-yl)pyridin-3-yl)pyrazolo[1,5-a]pyridine-3-carbonitrile The title compound was prepared and purified using a similar procedure to that described for Example 243, replacing 6-methoxynicotinaldehyde with picolinaldehyde to afford the title compound cleanly (8.2 mg, 47% yield). MS (apci) m/z=484.2 (M+H).

Example 245

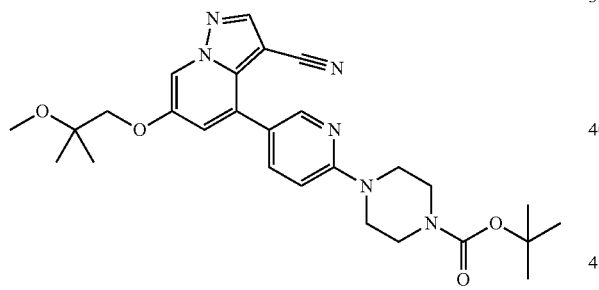

tert-butyl 4-(5-(3-cyano-6-(2-methoxy-2-methylpropoxy)pyrazolo[1,5-a]pyridin-4-yl)pyridin-2-yl)piperazine-1-carboxylate A cold (0° C.) solution of tert-butyl 4-(5-(3-cyano-6-(2-hydroxy-2-methylpropoxy)pyrazolo[1,5-a]pyridin-4-yl)pyridin-2-yl)piperazine-1-carboxylate (Example 152; 68 mg, 0.138 mmol) in DMF (1.4 mL) was treated with NaH(s) (9.94 mg, 0.414 mmol) and stirred for 25 min at 0° C., before introducing iodomethane (25.9 μL, 0.414 mmol). The reaction mixture was stirred 90 min at ambient temperature. The resulting mixture was quenched with the addition of MeOH (500 μL), and then purified directly by C18 reverse phase chromatography (5-90% ACN/water as the gradient eluent) to cleanly provide the title compound (52.5 mg, 75% yield). MS (apci) m/z=507.3 (M+H).

Example 246

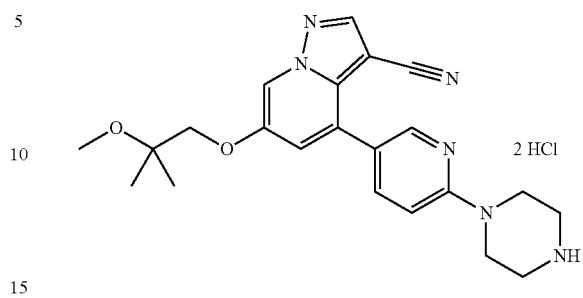

6-(2-methoxy-2-methylpropoxy)-4-(6-(piperazin-1-yl)pyridin-3-yl)pyrazolo[1,5-a]pyridine-3-carbonitrile dihydrochloride A solution of tert-butyl 4-(5-(3-cyano-6-(2-methoxy-2-methylpropoxy)pyrazolo[1,5-a]pyridin-4-yl)pyridin-2-yl)piperazine-1-carboxylate (Example 245; 67 mg, 0.132 mmol) in DCM (2 mL) was treated with 5-6 M HCl in iPrOH (4 mL, 20.0 mmol), and stirred for 2 h at ambient temperature. The solution was concentrated in vacuo to cleanly provide the title compound as the dihydrochloride salt (63.5 mg, quantitative yield). MS (apci) m/z=407.2 (M+H).

Example 247

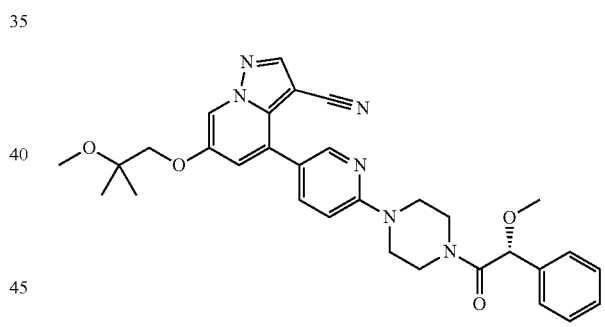

(R)-6-(2-methoxy-2-methylpropoxy)-4-(6-(4-(2-methoxy-2-phenylacetyl)piperazin-1-yl)pyridin-3-yl)pyrazolo[1,5-a]pyridine-3-carbonitrile A suspension of 6-(2-methoxy-2-methylpropoxy)-4-(6-(piperazin-1-yl)pyridin-3-yl)pyrazolo[1,5-a]pyridine-3-carbonitrile dihydrochloride (Example 246; 10.4 mg, 0.0217 mmol) in DCM (300 μL) was treated sequentially with (R)-2-methoxy-2-phenylacetic acid ((5.41 mg, 0.0325 mmol), DIEA (15.1 μL, 0.0868 mmol) and HATU (12.4 mg, 0.0325 mmol). After stirring for 17 h at ambient temperature, the reaction mixture was purified directly by silica chromatography (0-100% acetone/hexanes as the gradient eluent) to cleanly provide the title compound (11.9 mg, 99% yield). MS (apci) m/z=555.3 (M+H).

Example 248

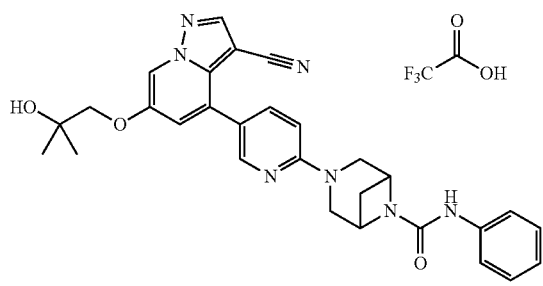 [SMILES: CC(C)(O)COc1cc(-c2ccc(N3CC4CC(C3)N4C(=O)Nc3ccccc3)nc2)c2c(C#N)cnn2c1 ; O=C(O)C(F)(F)F]

3-(5-(3-cyano-6-(2-hydroxy-2-methylpropoxy)pyrazolo[1,5-a]pyridin-4-yl)pyridin-2-yl)-N-phenyl-3,6-diazabicyclo[3.1.1]heptane-6-carboxamide 2,2,2-trifluoroacetate To a suspension of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43, 0.030 g, 0.063 mmol) in DMA (0.75 mL) was added triethylamine (0.044 mL, 0.31 mmol) followed by isocyanatobenzene (9 mg, 0.075 mmol) at ambient temperature. After overnight stirring, the reaction mixture was partitioned between DCM and water. After phase-separation, the aqueous layer was extracted with DCM. The organic extracts were combined, dried over sodium sulfate, filtered and concentrated. The crude material was purified using Gilson Prep HPLC (5-95% ACN/water with 0.1% TFA) to yield the title compound as white solid (0.019 g, 48.0% yield). $^1$H NMR (CDCl$_3$) δ 8.41 (m, 1H), 8.20-8.22 (m, 2H), 8.00-8.03 (m, 1H), 7.39-7.43 (m, 2H), 7.18-7.22 (m, 3H), 6.99-7.03 (m, 2H), 4.56 (m, 2H), 4.39-4.42 (m, 2H), 3.86 (s, 2H), 3.69-3.75 (m, 2H), 2.80-2.84 (m, 1H), 1.60-1.62 (m, 1H), 1.38 (s, 6H). MS (apci) m/z=524.2 (M+H).

Example 249

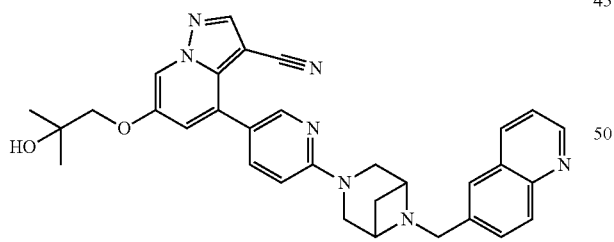

6-(2-hydroxy-2-methylpropoxy)-4-(6-(6-(quinolin-6-ylmethyl)-3,6-diazabicyclo[3.1.1]heptan-3-yl)pyridin-3-yl)pyrazolo[1,5-a]pyridine-3-carbonitrile To a suspension of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43, 25 mg, 0.0524 mmol) in 1,2-dichloroethane (0.3 mL) was added quinoline-6-carbaldehyde (8.23 mg, 0.0524 mmol) followed by sodium triacetoxyhydroborate (33.3 mg, 0.157 mmol) at ambient temperature. After 4 hours of stirring, the reaction mixture was purified by silica gel chromatography (using 0-100% DCM in hexanes and then 0-100% [20% MeOH with 2% NH$_4$OH] in DCM as the gradient eluent) to yield the title compound (14.8 mg, 51.8% yield). $^1$H NMR (CD$_3$OD) δ 8.76 (m, 1H), 8.33 (m, 1H), 8.27 (d, 1H), 8.22-8.25 (m, 2H), 7.96-7.99 (d, 1H), 7.82 (m, 1H), 7.75-7.80 (m, 2H), 7.43-7.47 (m, 4H), 7.24 (d, 1H), 6.77-6.80 (d, 1H), 3.83-3.92 (m, 8H), 3.59-3.64 (d, 2H), 2.71-2.78 (m, 1H), 1.69-1.72 (d, 1H), 1.33 (s, 6H). MS (apci) m/z=546.3 (M+H).

Example 250

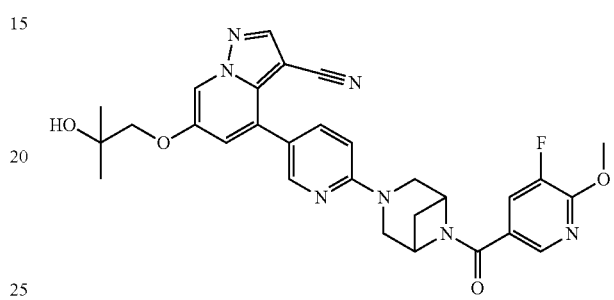

4-(6-(6-(5-fluoro-6-methoxynicotinoyl)-3,6-diazabicyclo[3.1.1]heptan-3-yl)pyridin-3-yl)-6-(2-hydroxy-2-methylpropoxy)pyrazolo[1,5-a]pyridine-3-carbonitrile To a suspension of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43, 25 mg, 0.05237 mmol) in DCM (1 mL) was added 5-Fluoro-6-methoxynicotinic acid (11.7 mg, 0.069 mmol), HATU (23.9 mg, 0.063 mmol), and DIEA (36 μL, 0.21 mmol) at ambient temperature. After stirring for two hours, the reaction mixture was concentrated in vacuo and purified using silica gel chromatography (0-20% EtOAc/MeOH as the gradient eluent) to yield the title compound (15.4 mg, 52.8% yield). $^1$H NMR (CD$_3$OD) δ 8.39-8.41 (d, 1H), 8.28-8.30 (m, 2H), 8.25-8.27 (d, 1H), 7.71-7.77 (m, 2H), 7.25-7.27 (d, 1H), 6.73-6.76 (d, 1H), 4.86-4.95 (br.m, 1H), 4.66-4.75 (br.m, 1H), 4.18-4.29 (br.m, 1H), 3.60-3.77 (m, 3H), 2.91-2.99 (m, 1H), 1.73-1.79 (d, 1H), 1.32 (s, 6H). MS (apci) m/z=558.2 (M+H).

Example 251

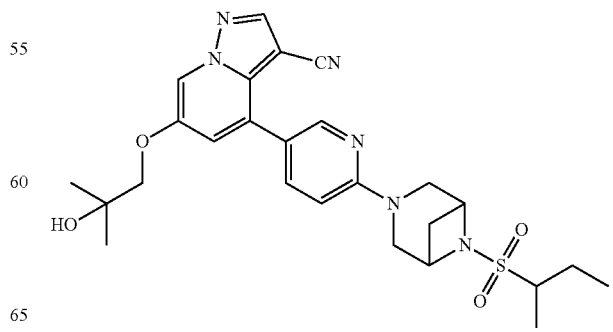

4-(6-(6-(sec-butylsulfonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile To a suspension of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43, 0.0278 g, 0.0582 mmol) in DCM (1.0 mL) was added triethylamine (0.032 mL, 0.233 mmol) followed by sec-butylsulfonyl chloride (10.0 mg, 0.064 mmol) at ambient temperature. After stirring for one hour the reaction mixture was treated with additional triethylamine (15.8 µL, 0.116 mmol) and sec-butylsulfonyl chloride (20.0 mg, 0.128 mmol) and stirred at ambient temperature for an additional 17 h. After stirring overnight, the reaction mixture was concentrated in vacuo and purified using Gilson Preparative HPLC (5-95% water/ACN with 0.1% TFA as the gradient eluent). The desired fractions were then combined and partitioned between 4:1 DCM:IPA and saturated aqueous NaHCO₃. The organic extracts were combined and dried over sodium sulfate, filtered, and concentrated to yield the title compound as a white solid (7.5 mg, 23.3% yield). MS (apci) m/z=525.2 (M+H).

Example 252

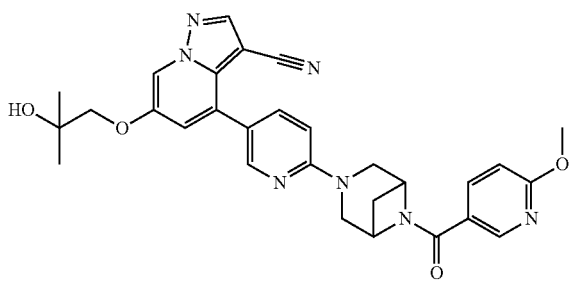 [SMILES: COc1ccc(C(=O)N2C3CC2CN(c2ccc(-c4cc(OCC(C)(C)O)cn5ncc(C#N)c45)cn2)C3)cn1]

6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile To a suspension of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43, 0.6 g, 1.26 mmol) in DCM (25 mL) was added 2-methoxy-5-pyridinecarboxylic acid (0.231 g, 1.51 mmol), HATU (0.573 g, 1.51 mmol), and DIEA (0.876 mL, 5.03 mmol). The reaction mixture was stirred at ambient temperature overnight, and then additional DIEA (0.220 mL, 1.26 mmol) was added. The reaction mixture was stirred at ambient temperature overnight. The reaction mixture was partitioned between DCM (40 mL) and saturated aqueous ammonium chloride (40 mL). After phase separation, the aqueous layer was extracted with DCM (3×25 mL). The organic extracts were combined, dried over sodium sulfate, filtered and concentrated. The crude material was purified using silica gel chromatography (using 0-10% EtOAc/MeOH as the gradient eluent). The isolated product was dissolved in DCM (10 mL), treated with activated charcoal, filtered through Celite® and rinsed with DCM. The filtrate was concentrated in vacuo to yield the title product. (470 mg, 69.3% yield) ¹H NMR (DMSO-d⁶) δ 8.60-8.65 (d, 1H), 8.53 (s, 1H), 8.49-8.51 (m, 1H), 8.28-8.31 (d, 1H), 7.91-7.95 (m, 1H), 7.73-7.78 (m, 1H), 7.23-7.25 (m, 1H), 6.81-6.85 (m, 1H), 6.65-6.69 (d, 1H), 4.84-4.94 (br.m, 1H), 4.66 (s, 1H), 4.51-4.63 (br.m, 1H), 4.04-4.20 (br.m, 1H), 3.88 (s, 3H), 3.83 (s, 2H), 3.60-3.63 (m, 2H), 3.42-3.53 (br.m, 1H), 2.75-2.85 (m, 1H), 1.63-1.69 (m, 1H), 1.18 (s, 6H). MS (apci) m/z=540.2 (M+H).

Example 253

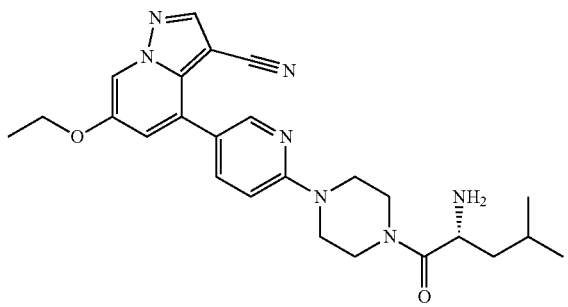 [SMILES: CCOc1cc(-c2ccc(N3CCN(C(=O)[C@H](N)CC(C)C)CC3)nc2)c2c(C#N)cnn2c1]

4-(6-(4-(D-leucyl)piperazin-1-yl)pyridin-3-yl)-6-ethoxypyrazolo[1,5-a]pyridine-3-carbonitrile Step 1: Preparation of tert-butyl (R)-(1-(4-(5-(3-cyano-6-ethoxypyrazolo[1,5-a]pyridin-4-yl)pyridin-2-yl)piperazin-1-yl)-4-methyl-1-oxopentan-2-yl)carbamate A solution of 6-ethoxy-4-(6-(piperazin-1-yl)pyridin-3-yl)pyrazolo[1,5-a]pyridine-3-carbonitrile bis(2,2,2-trifluoroacetate) (Intermediate P74; 64 mg, 0.184 mmol) in DMF (4 mL) was treated sequentially with HATU (138 mg, 0.36 mmol), (tert-butoxycarbonyl)-D-leucine (42.5 mg, 0.184 mmol) and DIEA (192 µL, 1.10 mmol). The reaction mixture was stirred overnight at ambient temperature, and then directly purified by C18 reverse phase chromatography (using 5-95% ACN in water with 0.1% TFA as the gradient eluent). Fractions containing the desired product were collected, treated with saturated NaHCO₃ and extracted with 20% IPA in DCM. The organics were dried over MgSO₄, filtered and concentrated to cleanly afford the title compound (39 mg, 38% yield). MS (apci) m/z=562.3 (M+H).

Step 2: Preparation of 4-(6-(4-(D-leucyl)piperazin-1-yl)pyridin-3-yl)-6-ethoxypyrazolo[1,5-a]pyridine-3-carbonitrile A solution of tert-butyl (R)-(1-(4-(5-(3-cyano-6-ethoxypyrazolo[1,5-a]pyridin-4-yl)pyridin-2-yl)piperazin-1-yl)-4-methyl-1-oxopentan-2-yl)carbamate (Step 1; 39 mg, 0.069 mmol) in DCM (4 mL) was treated with TFA (2 mL), and stirred for 30 min at ambient temperature then concentrated in vacuo. The residue was purified C18 reverse phase chromatography (using 5-95% ACN in water with 0.1% TFA as the gradient eluent). Fractions containing the desired product were collected, treated with saturated NaHCO₃ and extracted with 20% IPA in DCM. The organic layer was dried over MgSO₄, filtered and concentrated to cleanly afford the title compound. (25 mg, 78% yield). MS (apci) m/z=462.3 (M+H).

Example 254

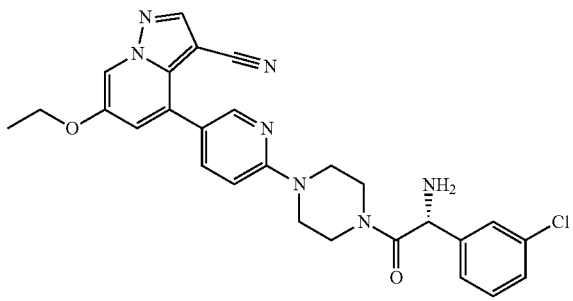 [SMILES: CCOc1cc(-c2ccc(N3CCN(C(=O)[C@H](N)c4cccc(Cl)c4)CC3)nc2)c2c(C#N)cnn2c1]

(R)-4-(6-(4-(2-amino-2-(3-chlorophenyl)acetyl)piperazin-1-yl)pyridin-3-yl)-6-ethoxypyrazolo[1,5-a]pyridine-3-carbonitrile

Step 1: Preparation of tert-butyl (R)-(1-(3-chlorophenyl)-2-(4-(5-(3-cyano-6-ethoxypyrazolo[1,5-a]pyridin-4-yl)pyridin-2-yl)piperazin-1-yl)-2-oxoethyl)carbamate A solution of 6-ethoxy-4-(6-(piperazin-1-yl)pyridin-3-yl)pyrazolo[1,5-a]pyridine-3-carbonitrile (Intermediate P73; 261.9 mg, 0.7517 mmol) in DMF (7.5 mL) was treated with 2 (R)-2-((tert-butoxycarbonyl)amino)-2-(3-chlorophenyl)acetic acid (429.6 mg, 1.503 mmol) and HATU (571.6 mg, 1.503 mmol), then stirred for 2 h at ambient temperature. The resulting mixture was diluted with EtOAc, then extracted with water (3×) and brine (1×). The organic extracts were dried over anhydrous $Na_2SO_{4(s)}$, filtered and concentrated in vacuo to afford the title compound which was used directly in step 2 without further purification (assumed quantitative yield). MS (apci) m/z=616.3 (M+H).

Step 2: Preparation of (R)-4-(6-(4-(2-amino-2-(3-chlorophenyl)acetyl)piperazin-1-yl)pyridin-3-yl)-6-ethoxypyrazolo[1,5-a]pyridine-3-carbonitrile Crude tert-butyl (R)-(1-(3-chlorophenyl)-2-(4-(5-(3-cyano-6-ethoxypyrazolo[1,3,5-a]pyridin-4-yl)pyridin-2-yl)piperazin-1-yl)-2-oxoethyl)carbamate (Step 1; 0.7517 mmol) was dissolved in 1:1 DCM:TFA (7.5 mL), stirred for 30 min at ambient temperature, and then concentrated in vacuo. The residue was purified by C18 reverse phase chromatography (using 5-90% water-ACN with 0.1% TFA as the gradient eluent). Fractions containing the desired compound were diluted with 4:1 DCM:iPrOH and extracted with saturated $NaHCO_{3(aq)}$. The organic extracts were dried over anhydrous $Na_2SO_{4(s)}$, filtered and concentrated in vacuo. The residue required further purification by silica chromatography (using 1-30% DCM-MeOH with 2% $NH_4OH$ as the gradient eluent) to cleanly afford the title compound (110.4 mg, 28% yield). MS (apci) m/z=516.2 (M+H).

Example 255

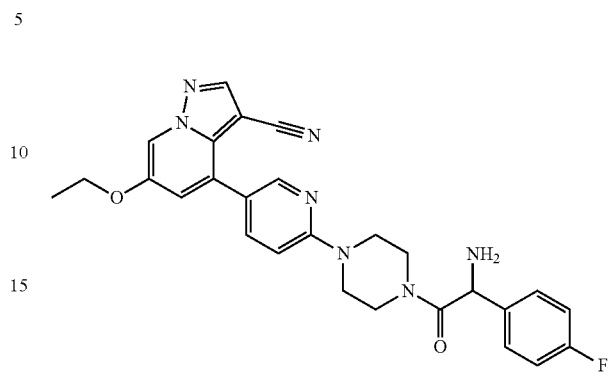

4-(6-(4-(2-amino-2-(4-fluorophenyl)acetyl)piperazin-1-yl)pyridin-3-yl)-6-ethoxypyrazolo[1,5-a]pyridine-3-carbonitrile

Step 1: Preparation of tert-butyl (2-(4-(5-(3-cyano-6-ethoxypyrazolo[1,5-a]pyridin-4-yl)pyridin-2-yl)piperazin-1-yl)-1-(4-fluorophenyl)-2-oxoethyl)carbamate A mixture of 6-ethoxy-4-(6-(piperazin-1-yl)pyridin-3-yl)pyrazolo[1,5-a]pyridine-3-carbonitrile (Intermediate P73; 53 mg, 0.15 mmol), (R)—N—(R)-2-((tert-butoxycarbonyl)amino)-2-(4-fluorophenyl)acetic acid (41 mg, 0.15 mmol) and HATU (174 mg, 0.46 mmol) in DCM (761 µL) was treated with DIEA (106 µL, 0.61 mmol). The reaction mixture was stirred overnight at ambient temperature, and then filtered. The filtrate was concentrated in vacuo and purified by silica chromatography (using 0-10% DCM/MeOH as the gradient eluent) to afford the title compound (racemization occurred under these conditions) (87 mg, 95% yield). MS (apci) m/z=500.2 (M+H).

Step 2: Preparation of 4-(6-(4-(2-amino-2-(4-fluorophenyl)acetyl)piperazin-1-yl)pyridin-3-yl)-6-ethoxypyrazolo[1,5-a]pyridine-3-carbonitrile A solution of tert-butyl (2-(4-(5-(3-cyano-6-ethoxypyrazolo[1,5-a]pyridin-4-yl)pyridin-2-yl)piperazin-1-yl)-1-(4-fluorophenyl)-2-oxoethyl)carbamate (Step 1; 87 mg, 0.15 mmol) in DCM (1.45 mL) was treated with TFA (112 µL). The resulting mixture was stirred overnight at ambient temperature, and then concentrated in vacuo. The crude residue was purified by silica chromatography (using 0-10% $CHCl_3$/MeOH as the gradient eluent). Fractions containing the desired compound were combined and concentrated in vacuo. The residue was triturated with DCM/Hexanes, then concentrated in vacuo to cleanly afford the title compound assuming quantitative yield. MS (apci) m/z=500.2 (M+H).

Example 256

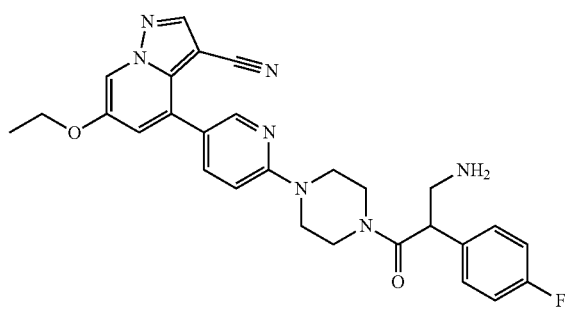 [SMILES: CCOc1cc(-c2ccc(N3CCN(C(=O)C(CN)c4ccc(F)cc4)CC3)nc2)c2c(C#N)cnn2c1]

4-(6-(4-(3-amino-2-(4-fluorophenyl)propanoyl)piperazin-1-yl)pyridin-3-yl)-6-ethoxypyrazolo[1,5-a]pyridine-3-carbonitrile Step 1: Preparation of tert-butyl (3-(4-(5-(3-cyano-6-ethoxypyrazolo[1,5-a]pyridin-4-yl)pyridin-2-yl)piperazin-1-yl)-2-(4-fluorophenyl)-3-oxopropyl)carbamate A mixture of 6-ethoxy-4-(6-(piperazin-1-yl)pyridin-3-yl)pyrazolo[1,5-a]pyridine-3-carbonitrile (Intermediate P73; 42 mg, 0.12 mmol), 3-{[(tert-butoxy)carbonyl]amino}-2-(4-fluorophenyl)propanoic acid (34 mg, 0.12 mmol) and HATU (138 mg, 0.36 mmol) in DCM (603 µL) was treated with DIEA (42 µL, 0.24 mmol). The reaction mixture was stirred for 1 h at ambient temperature, and then directly purified by silica chromatography (using 0-10% CHCl$_3$/MeOH with 0-1% NH$_4$OH as the gradient eluent). Fractions containing the desired compound were combined, concentrated in vacuo and then triturated with Hexanes to cleanly afford the title compound (42 mg, 57% yield). MS (apci) m/z=514.3 (M-Boc).

Step 2: Preparation of 4-(6-(4-(3-amino-2-(4-fluorophenyl)propanoyl)piperazin-1-yl)pyridin-3-yl)-6-ethoxypyrazolo[1,5-a]pyridine-3-carbonitrile A solution of tert-butyl (3-(4-(5-(3-cyano-6-ethoxypyrazolo[1,5-a]pyridin-4-yl)pyridin-2-yl)piperazin-1-yl)-2-(4-fluorophenyl)-3-oxopropyl)carbamate (Step 1; 42 mg, 0.068 mmol) in DCM (684 µL) was treated with TFA (53 µL), and stirred overnight at ambient temperature. The resulting mixture was purified directly by silica chromatography (using 0-10% CHCl$_3$/MeOH with 0-1% NH$_4$OH as the gradient eluent). Fractions containing the desired compound were combined, concentrated in vacuo, then triturated with Hexanes to cleanly afford the title compound (35, quantitative yield). MS (apci) m/z=514.2 (M+H).

Example 257

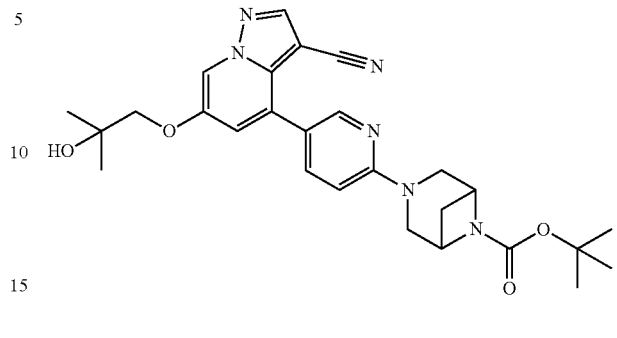

tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate A mixture of 4-(6-fluoropyridin-3-yl)-6-(2-hydroxy-2-methylpropoxy)pyrazolo[1,5-a]pyridine-3-carbonitrile (Intermediate P42; 1.70 g, 8.55 mmol), 3,6-diaza-bicyclo[3.1.1]heptane-6-carboxylic acid tert-butyl ester (1.70 g, 8.55 mmol) and K$_2$CO$_{3(s)}$ (7.88 g, 57.0 mmol) in DMSO (7 mL) was stirred 12 h at 90° C. The resultant thick slurry was diluted with additional DMSO (2 mL) and stirred for 12 h at 90° C. The mixture was cooled to ambient temperature and diluted with water (100 mL). The aqueous mixture was washed with DCM. The combined organic extracts were dried over anhydrous MgSO$_{4(s)}$, filtered and concentrated in vacuo. The crude residue was purified by silica chromatography (30-80% EtOAc/Hexanes as the gradient eluent system) to cleanly provide the title compound (2.87 g, 100% yield). MS (apci) m/z=505.2 (M+H).

Example 258

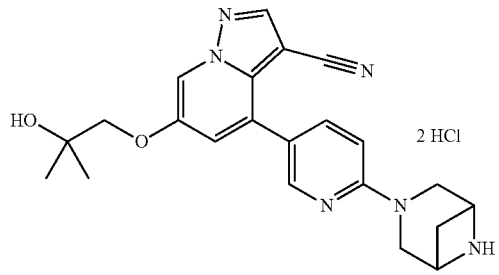 [SMILES: CC(C)(O)COc1cc(-c2ccc(N3CC4CC(C3)N4)nc2)c2c(C#N)cnn2c1]

4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride A solution of tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (Example 257; 3.05 g, 6.04 mmol) in DCM (20 mL) was treated with 4 N HCl in dioxanes (15.1 mL, 60.4 mmol). The resulting mixture was stirred for 12 h at ambient temperature, and then concentrated in vacuo. It was diluted with DCM and toluene, and then sonicated before concentrating in vacuo to Example 259

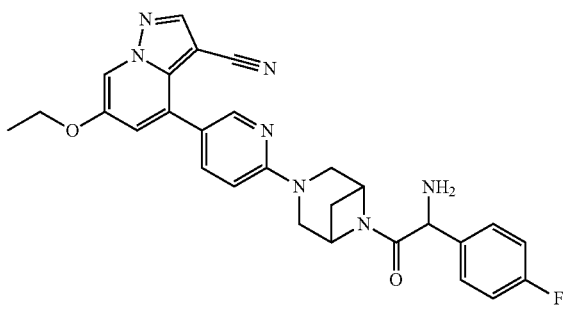 [SMILES: CCOc1cc(-c2ccc(N3CC4CC(C3)N4C(=O)C(N)c3ccc(F)cc3)nc2)c2c(C#N)cnn2c1]

4-(6-(6-(2-amino-2-(4-fluorophenyl)acetyl)-3,6-diazabicyclo[3.1.1]heptan-3-yl)pyridin-3-yl)-6-ethoxypyrazolo[1,5-a]pyridine-3-carbonitrile Step 1: Preparation of tert-butyl (2-(3-(5-(3-cyano-6-ethoxypyrazolo[1,5-a]pyridin-4-yl)pyridin-2-yl)-3,6-diazabicyclo[3.1.1]heptan-6-yl)-1-(4-fluorophenyl)-2-oxoethyl)carbamate A mixture of 4-(6-(3,6-diazabicyclo[3.1.1]heptan-3-yl)pyridin-3-yl)-6-ethoxypyrazolo[1,5-a]pyridine-3-carbonitrile (Intermediate P75; 30 mg, 0.083 mmol), (R)-2-((tert-butoxycarbonyl)amino)-2-(4-fluorophenyl)acetic acid (22 mg, 0.083 mmol) and HATU (95 mg, 0.25 mmol) in DCM (416 µL) was treated with DIEA (58 µL, 0.33 mmol), and stirred for 1 h at ambient temperature. The reaction mixture was concentrated in vacuo, diluted with water and vacuum filtered. The solids collected were dissolved in DCM, dried over anhydrous $Na_2SO_{4(s)}$, filtered and concentrated in vacuo to cleanly provide the title compound (racemization occurred under these conditions) (15 mg, 29% yield). MS (apci) m/z=512.2 (M+H).

Step 2: Preparation of 4-(6-(6-(2-amino-2-(4-fluorophenyl)acetyl)-3,6-diazabicyclo[3.1.1]heptan-3-yl)pyridin-3-yl)-6-ethoxypyrazolo[1,5-a]pyridine-3-carbonitrile A solution of tert-butyl (2-(3-(5-(3-cyano-6-ethoxypyrazolo[1,5-a]pyridin-4-yl)pyridin-2-yl)-3,6-diazabicyclo[3.1.1]heptan-6-yl)-1-(4-fluorophenyl)-2-oxoethyl)carbamate (Step 1; 15 mg, 0.025 mmol) in DCM (245 µL) was treated with TFA (19 µL), and stirred overnight at ambient temperature. The resulting mixture was purified directly by silica chromatography (using 0-10% $CHCl_3$/MeOH with 0-1% $NH_4OH$ as the gradient eluent). Fractions containing the desired compound were combined and concentrated in vacuo. The residue was triturated with DCM/Hexanes then concentrated in vacuo to cleanly afford the title compound (2 mg, 16% yield). MS (apci) m/z=512.2 (M+H).

Example 260

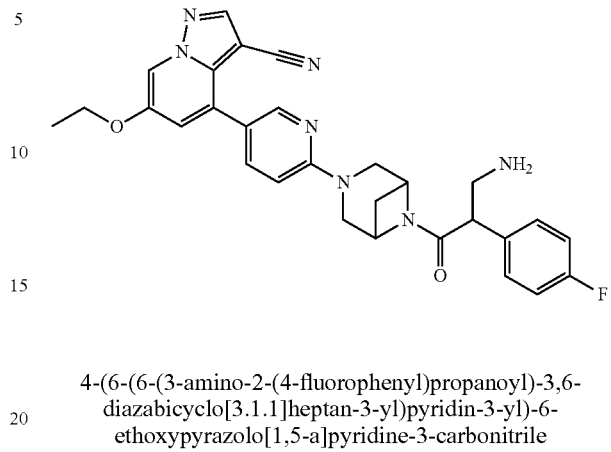

4-(6-(6-(3-amino-2-(4-fluorophenyl)propanoyl)-3,6-diazabicyclo[3.1.1]heptan-3-yl)pyridin-3-yl)-6-ethoxypyrazolo[1,5-a]pyridine-3-carbonitrile The title compound was prepared and purified using a similar two step procedure described in Example 259, replacing (R)-2-((tert-butoxycarbonyl)amino)-2-(4-fluorophenyl)acetic acid with 3-((tert-butoxycarbonyl)amino)-2-(4-fluorophenyl)propanoic acid, and using less DIEA (2 equiv) in step 1. Trituration with hexanes in the final step afforded the title compound (34 mg, 69% overall yield). MS (apci) m/z=526.2 (M+H).

Example 261

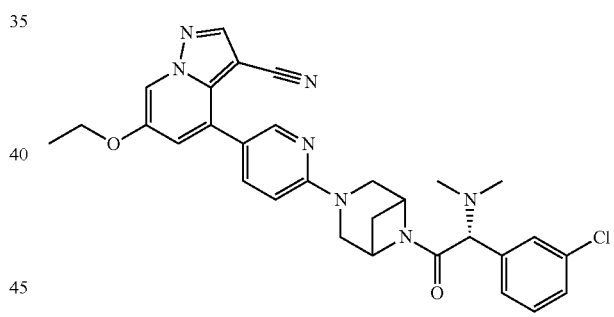

(R)-4-(6-(4-(2-(3-chlorophenyl)-2-(dimethylamino)acetyl)piperazin-1-yl)pyridin-3-yl)-6-ethoxypyrazolo[1,5-a]pyridine-3-carbonitrile A mixture of (R)-4-(6-(4-(2-amino-2-(3-chlorophenyl)acetyl)piperazin-1-yl)pyridin-3-yl)-6-ethoxypyrazolo[1,5-a]pyridine-3-carbonitrile (Example 254; 56.8 mg, 0.110 mmol) in 1:1 DCM:MeOH (1.1 mL) was treated sequentially with formaldehyde (82.7 µL, 1.10 mmol) and $NaBH(AcO)_3$ (117 mg, 0.550 mmol). After stirring overnight at ambient temperature, the reaction mixture was concentrated in vacuo. The residue was purified by C18 reverse phase chromatography (using 5-95% ACN in water with 0.1% TFA as the gradient eluent). The fractions containing the desired compound were combined and extracted with 4:1DCM:iPrOH and saturated $NaHCO_{3(aq)}$. The organic extracts were dried over anhydrous $Na_2SO_{4(s)}$, filtered and concentrated in vacuo to cleanly provide the title compound (47.8 mg, 80% yield). MS (apci) m/z=544.3 (M+H).

The compounds in Table U were prepared using a similar method to that described for the synthesis of Example 261, replacing (R)-4-(6-(4-(2-amino-2-(3-chlorophenyl)acetyl)piperazin-1-yl)pyridin-3-yl)-6-ethoxypyrazolo[1,5-a]pyridine-3-carbonitrile with the appropriate amine Example listed in the table. Reactions were monitored for completion by LCMS, as such reaction durations (and the need for supplemental reagent amounts) were adjusted accordingly. The title compounds were isolated following a chromatographic purification utilizing an appropriate gradient eluent. Where noted (*)-, and when chromatographic conditions did not result in the isolation of the TFA salt of the title compound, the secondary basic work up following the chromatographic purification, utilized in Example 261, was omitted.

TABLE U

| Ex # | Amine used | Structure | Chemical Name | MS (apci) m/z |
|---|---|---|---|---|
| 262 | Ex. 255 | 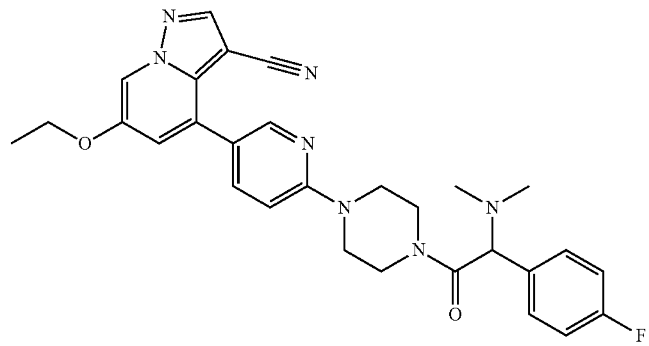 [SMILES: CCOc1cc(-c2ccc(N3CCN(C(=O)C(c4ccc(F)cc4)N(C)C)CC3)nc2)c2c(C#N)cnn2c1] | 4-(6-(4-(2-(dimethylamino)-2-(4-fluorophenyl)acetyl)piperazin-1-yl)pyridin-3-yl)-6-ethoxypyrazolo[1,5-a]pyridine-3-carbonitrile | 528.30 (M + H) |
| 263 | Ex. 256 | 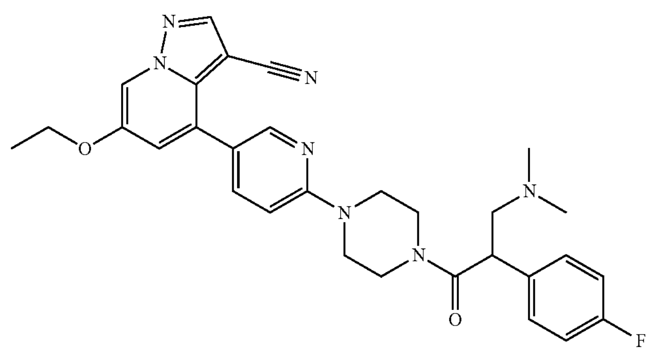 [SMILES: CCOc1cc(-c2ccc(N3CCN(C(=O)C(CN(C)C)c4ccc(F)cc4)CC3)nc2)c2c(C#N)cnn2c1] | 4-(6-(4-(3-(dimethylamino)-2-(4-fluorophenyl)propanoyl)piperazin-1-yl)pyridin-3-yl)-6-ethoxypyrazolo[1,5-a]pyridine-3-carbonitrile | 542.30 (M + H) |
| 264 | Ex. 264 | 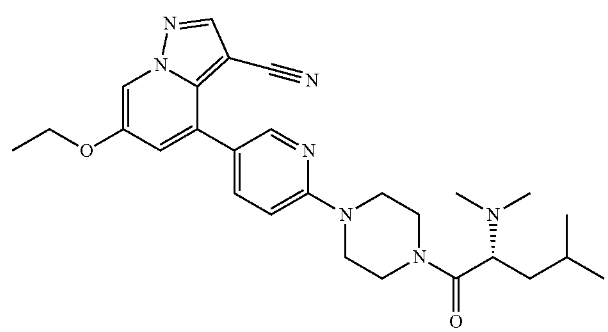 [SMILES: CCOc1cc(-c2ccc(N3CCN(C(=O)[C@@H](CC(C)C)N(C)C)CC3)nc2)c2c(C#N)cnn2c1] | 4-(6-(4-(dimethyl-D-leucyl)piperazin-1-yl)pyridin-3-yl)-6-ethoxypyrazolo[1,5-a]pyridine-3-carbonitrile | 490.30 (M + H) |
| 265 | Ex. 259 | 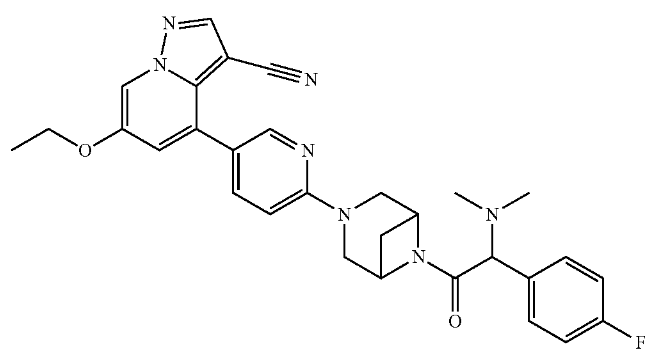 [SMILES: CCOc1cc(-c2ccc(N3CC4CC(C3)N4C(=O)C(c3ccc(F)cc3)N(C)C)nc2)c2c(C#N)cnn2c1] | 4-(6-(6-(2-(dimethylamino)-2-(4-fluorophenyl)acetyl)-3,6-diazabicyclo[3.1.1]heptan-3-yl)pyridin-3-yl)-6-ethoxypyrazolo[1,5-a]pyridine-3-carbonitrile | 540.2 (M + H) |

TABLE U-continued

| Ex # | Amine used | Structure | Chemical Name | MS (apci) m/z |
|------|-----------|-----------|---------------|---------------|
| 266 | Ex. 260 | 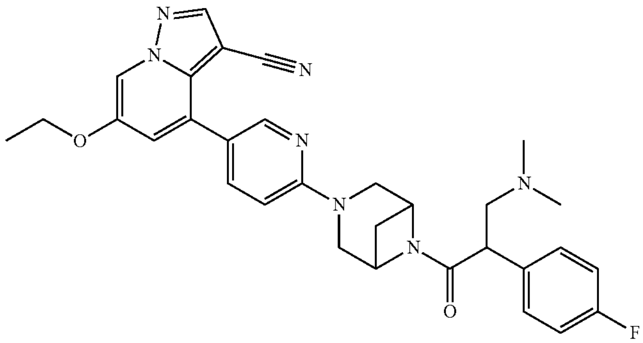 [SMILES: CCOc1cc(-c2ccc(N3CC4CC(C3)N4C(=O)C(CN(C)C)c3ccc(F)cc3)nc2)c2c(C#N)cnn2c1] | 4-(6-(6-(3-(dimethylamino)-2-(4-fluorophenyl)propanoyl)-3,6-diazabicyclo[3.1.1]heptan-3-yl)pyridin-3-yl)-6-ethoxypyrazolo[1,5-a]pyridine-3-carbonitrile | 554.2 (M + H) |

* Purification was accomplished using C18 reverse phase chromatography (5-95% ACN in water with 0.1% TFA) followed by a second silica chromatography (2-5% MeOH in DCM).

Example 267

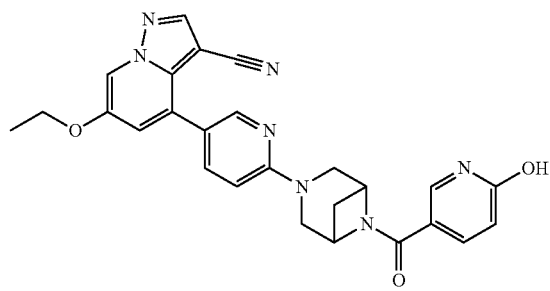 [SMILES: CCOc1cc(-c2ccc(N3CC4CC(C3)N4C(=O)c3ccc(O)nc3)nc2)c2c(C#N)cnn2c1]

6-ethoxy-4-(6-(6-(6-hydroxynicotinoyl)-3,6-diazabicyclo[3.1.1]heptan-3-yl)pyridin-3-yl)pyrazolo[1,5-a]pyridine-3-carbonitrile In a pressure vessel, a mixture of 6-ethoxy-4-(6-fluoropyridin-3-yl)pyrazolo[1,5-a]pyridine-3-carbonitrile (Intermediate P6; 0.266 g, 0.941 mmol), (6-diazabicyclo[3.1.1]heptan-6-yl)(6-hydroxypyridin-3-yl)methanone bis(2,2,2-trifluoroacetate) (Intermediate R; 0.172 g, 0.385 mmol) and TEA (2.19 mL, 15.7 mmol) was suspended in DMSO (5 mL). The vessel was sealed, and then the reaction mixture was stirred for 2 h at 90° C. Additional TEA (2 mL) was introduced, and the reaction was stirred at 100° C. for 5 d in the sealed vessel. After cooling to ambient temperature, the resulting mixture was diluted with DCM, and quenched with saturated NH$_4$Cl$_{(aq)}$. The quenched mixture was extracted with DCM (3×). The combined organic extracts were dried over anhydrous Na$_2$SO$_{4(s)}$, filtered and concentrated in vacuo. The crude residue was purified by C18 reverse phase chromatography (using 5-95% ACN in water with 0.1% TFA as the gradient eluent), and again by silica chromatography (using 0-25% ((9:1 MeOH/NH$_4$OH) in DCM) as the gradient eluent) to cleanly provide the title compound (117 mg, 63% yield). MS (apci) m/z=482.2 (M+H).

Example 268: 6-ethoxy-4-(6-(6-(6-propoxynicotinoyl)-3,6-diazabicyclo[3.1.1]heptan-3-yl)pyridin-3-yl)pyrazolo[1,5-a]pyridine-3-carbonitrile 2,2,2-trifluoroacetate and Example 269: 6-ethoxy-4-(6-(6-(6-oxo-1-propyl-1,6-dihydropyridine-3-carbonyl)-3,6-diazabicyclo[3.1.1]heptan-3-yl)pyridin-3-yl)pyrazolo[1,5-a]pyridine-3-carbonitrile 2,2,2-trifluoroacetate

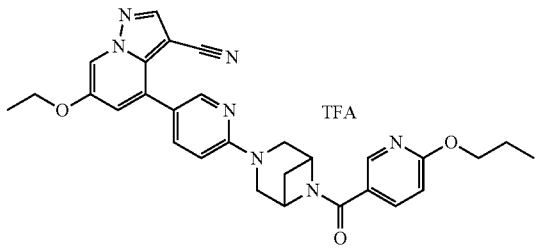

Ex. 268

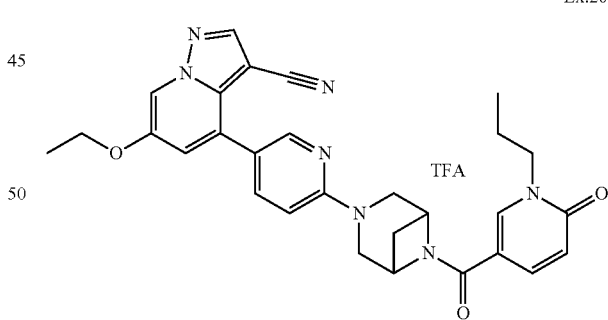

Ex.269

A solution of 6-ethoxy-4-(6-(6-(6-hydroxynicotinoyl)-3,6-diazabicyclo[3.1.1]heptan-3-yl)pyridin-3-yl)pyrazolo[1,5-a]pyridine-3-carbonitrile (Example 267; 8 mg, 0.017 mmol) in DMSO (0.4 mL) was treated with NaH (0.6 mg, 0.025 mmol), and stirred for 20 min at ambient temperature. The resulting suspension was treated with 1-iodopropane (17 µL, 0.17 mmol), and stirred overnight at 85° C. After cooling to ambient temperature, the reaction mixture was diluted with DCM, and quenched with saturated NH$_4$Cl$_{(aq)}$. The biphasic mixture was extracted with DCM (3×). The combined organic extracts were dried over anhydrous Na$_2$SO$_{4(s)}$, filtered, and concentrated in vacuo. The crude residue was purified by C18 reverse phase chromatography (using 5-95% ACN in water with 0.1% TFA as the gradient eluent) to independently afford the title compounds representing coupling products of the tautomeric starting material. Example 268: 6-ethoxy-4-(6-(6-(6-propoxynicotinoyl)-3,6-diazabicyclo[3.1.1]heptan-3-yl)pyridin-3-yl)pyrazolo[1,5-a]pyridine-3-carbonitrile 2,2,2-trifluoroacetate (1.2 mg, 14% yield). LCMS (apci): Tr=2.01 min, m/z=524.2 (M+H). Example 269: 6-ethoxy-4-(6-(6-(6-oxo-1-propyl-1,6-dihydropyridine-3-carbonyl)-3,6-diazabicyclo[3.1.1]heptan-3-yl)pyridin-3-yl)pyrazolo[1,5-a]pyridine-3-carbonitrile 2,2,2-trifluoroacetate (4.8 mg, 55% yield). LCMS (apci): Tr=1.73 min, m/z=524.2 (M+H).

Example 270

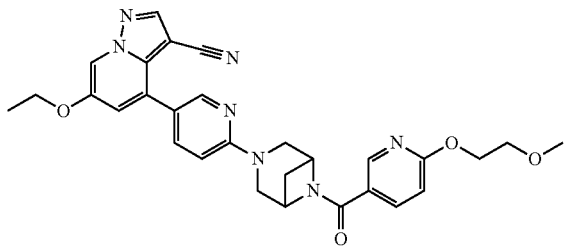 [SMILES: CCOc1cc(-c2ccc(N3CC4CC(C3)N4C(=O)c3ccc(OCCOC)nc3)nc2)c2c(C#N)cnn2c1]

6-ethoxy-4-(6-(6-(6-(2-methoxyethoxy)nicotinoyl)-3,6-diazabicyclo[3.1.1]heptan-3-yl)pyridin-3-yl)pyrazolo[1,5-a]pyridine-3-carbonitrile A solution of 6-ethoxy-4-(6-(6-(6-hydroxynicotinoyl)-3,6-diazabicyclo[3.1.1]heptan-3-yl)pyridin-3-yl)pyrazolo[1,5-a]pyridine-3-carbonitrile (Example 267; 18 mg, 0.037 mmol) in DMSO (0.4 mL) was treated with NaH (1.8 mg, 0.075 mmol), and stirred for 20 min at ambient temperature. The resulting suspension was treated with 1-bromo-2-methoxyethane (40 µL, 0.037 mmol), and stirred overnight at 85° C. After cooling to ambient temperature, the reaction mixture was diluted with DCM, and quenched with saturated NH$_4$Cl$_{(aq)}$. The biphasic mixture was extracted with DCM (3×). The combined organic extracts were dried over anhydrous Na$_2$SO$_{4(s)}$, filtered, and concentrated in vacuo. The crude residue was purified by silica phase chromatography (using 0-30% MeOH/EtOAc as the gradient eluent) to cleanly afford the title compound (2.5 mg, 12% yield). MS (apci) m/z=540.2 (M+H).

Example 271

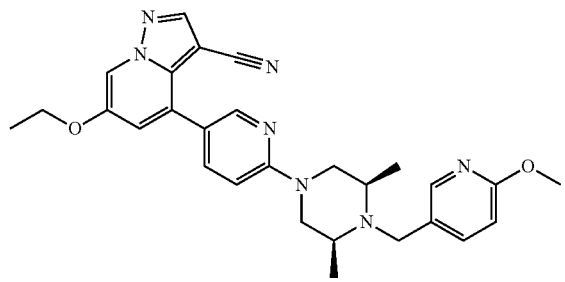 [SMILES: CCOc1cc(-c2ccc(N3C[C@@H](C)N(Cc4ccc(OC)nc4)[C@@H](C)C3)nc2)c2c(C#N)cnn2c1]

6-ethoxy-4-(6-((3S,5R)-4-((6-methoxypyridin-3-yl)methyl)-3,5-dimethylpiperazin-1-yl)pyridin-3-yl)pyrazolo[1,5-a]pyridine-3-carbonitrile A mixture of 6-ethoxy-4-(6-fluoropyridin-3-yl)pyrazolo[1,5-a]pyridine-3-carbonitrile (Intermediate P6; 14.6 mg, 0.0518) and (2S,6R)-1-((6-methoxypyridin-3-yl)methyl)-2,6-dimethylpiperazine bis(2,2,2-trifluoroacetate) (Intermediate R17; 36 mg, 0.078 mmol) and K$_2$CO$_{3(s)}$ (71.6 mg, 0.518 mmol) in DMSO (104 µL) was stirred overnight at 80° C. The reaction mixture was cooled to ambient temperature, then purified directly by C18 reverse phase chromatography (using 5-95% ACN in water with 0.1% TFA as the gradient eluent), and again by silica chromatography (using 0-20% MeOH in DCM with 2% NH$_4$OH as the gradient eluent) to cleanly provide the title compound (5.45 mg, 21% yield). MS (apci) m/z=498.3 (M+H).

Example 272

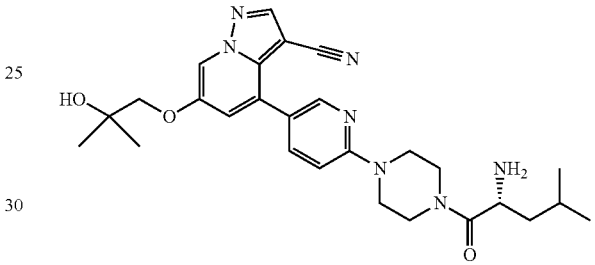

4-(6-(4-(D-leucyl)piperazin-1-yl)pyridin-3-yl)-6-(2-hydroxy-2-methylpropoxy)pyrazolo[1,5-a]pyridine-3-carbonitrile Step 1: Preparation of tert-butyl (R)-(1-(4-(5-(3-cyano-6-(2-hydroxy-2-methylpropoxy)pyrazolo[1,5-a]pyridin-4-yl)pyridin-2-yl)piperazin-1-yl)-4-methyl-1-oxopentan-2-yl)carbamate A solution of 6-(2-hydroxy-2-methylpropoxy)-4-(6-(piperazin-1-yl)pyridin-3-yl)pyrazolo[1,5-a]pyridine-3-carbonitrile bis TFA salt (81 mg, 0.206 mmol) in DCM (6 mL) was treated sequentially with (tert-butoxycarbonyl)-D-leucine (47.7 mg, 0.206 mmol), HATU (94.2 mg, 0.248 mmol) and DIEA (216 µL, 1.24 mmol) then stirred for 3 h at ambient temperature. The resulting mixture was purified directly by C18 reverse phase chromatography (using 5-95% water:ACN with 0.1% TFA as the gradient eluent). Fractions containing the desired product were collected, treated with saturated NaHCO$_3$ and extracted with 20% IPA in DCM. The organics were dried over MgSO$_4$, filtered and concentrated to afford the title compound, which was directly used in the next step assuming quantitative yield. MS (apci) m/z=606.4 (M+H).

Step 2: Preparation of 4-(6-(4-(D-leucyl)piperazin-1-yl)pyridin-3-yl)-6-(2-hydroxy-2-methylpropoxy) pyrazolo[1,5-a]pyridine-3-carbonitrile A solution of tert-butyl (R)-(1-(4-(5-(3-cyano-6-(2-hydroxy-2-methylpropoxy)pyrazolo[1,5-a]pyridin-4-yl)pyridin-2-yl)piperazin-1-yl)-4-methyl-1-oxopentan-2-yl)carbamate (Step 1, assumed 125 mg, 0.21 mmol) in DCM (4 mL) was treated with TFA (2 mL), and stirred for 30 min at ambient temperature. After concentrating in vacuo, the reaction mixture was purified by C18 reverse phase chromatography (5-95% ACN in water with 0.1% TFA as the gradient eluent). Fractions containing the desired product were collected, treated with saturated NaHCO₃ and extracted with 20% IPA in DCM. The organics were dried over MgSO₄, filtered and concentrated to cleanly afford the title compound (34 mg, 33% yield over 2 steps). MS (apci) m/z=506.3 (M+H).

Example 273

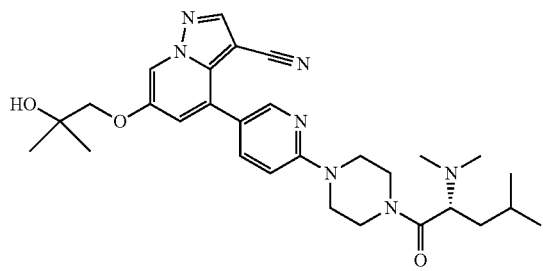 [SMILES: CC(C)C[C@H](C(=O)N1CCN(c2ccc(-c3cc(OCC(C)(C)O)cn4ncc(C#N)c34)cn2)CC1)N(C)C]

4-(6-(4-(dimethyl-D-leucyl)piperazin-1-yl)pyridin-3-yl)-6-(2-hydroxy-2-methylpropoxy)pyrazolo[1,5-a]pyridine-3-carbonitrile A mixture of 4-(6-(4-(D-leucyl)piperazin-1-yl)pyridin-3-yl)-6-(2-hydroxy-2-methylpropoxy)pyrazolo[1,5-a]pyridine-3-carbonitrile (34 mg, 0.067 mmol) and formaldehyde (50.1 µL, 0.672 mmol) in DCM (672 µL) was treated with NaBH(AcO)₃ (71.3 mg, 0.336 mmol). After stirring overnight at ambient temperature, the reaction mixture was concentrated in vacuo. The residue was purified by C18 reverse phase chromatography (5-95% ACN in water with 0.1% TFA as the gradient eluent). Fractions containing the desired product were collected, treated with saturated NaHCO₃ and extracted with 20% IPA in DCM. The organics were dried over MgSO₄, filtered and concentrated to cleanly afford the title compound (31 mg, 86% yield). MS (apci) m/z=534.3 (M+H).

Example 274

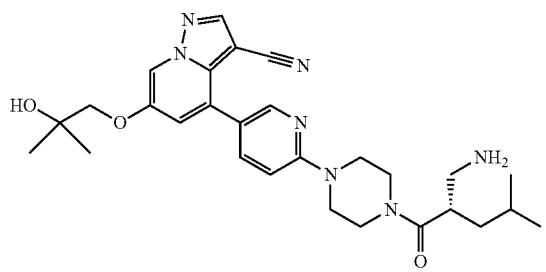 [SMILES: CC(C)C[C@@H](CN)C(=O)N1CCN(c2ccc(-c3cc(OCC(C)(C)O)cn4ncc(C#N)c34)cn2)CC1]

(S)-4-(6-(4-(2-(aminomethyl)-4-methylpentanoyl)piperazin-1-yl)pyridin-3-yl)-6-(2-hydroxy-2-methylpropoxy)pyrazolo[1,5-a]pyridine-3-carbonitrile Step 1: Preparation of tert-butyl (S)-(2-(4-(5-(3-cyano-6-(2-hydroxy-2-methylpropoxy)pyrazolo[1,3,5-a]pyridin-4-yl)pyridin-2-yl)piperazine-1-carbonyl)-4-methylpentyl)carbamate A solution of 6-(2-hydroxy-2-methylpropoxy)-4-(6-(piperazin-1-yl)pyridin-3-yl)pyrazolo[1,5-a]pyridine-3-carbonitrile hydrochloride (Intermediate P39; 52 mg, 0.112 mmol) in DMF (4 mL) was treated sequentially with HATU (51.0 mg, 0.151 mmol), (S)-2-(((tert-butoxycarbonyl)amino)methyl)-4-methylpentanoic acid (30.2 mg, 0.123 mmol) and DIEA (77.9 µL, 0.447), then stirred overnight at ambient temperature. The resulting mixture was purified directly by C18 reverse phase chromatography (using 5-95% water: ACN with 0.1% TFA as the gradient eluent). Fractions containing the desired product were collected, treated with saturated NaHCO₃ and extracted with 20% IPA in DCM. The organics were dried over MgSO₄, filtered and concentrated to afford the title compound (51 mg, 74% yield). MS (apci) m/z=620.4 (M+H).

Step 2: Preparation of (S)-4-(6-(4-(2-(aminomethyl)-4-methylpentanoyl)piperazin-1-yl)pyridin-3-yl)-6-(2-hydroxy-2-methylpropoxy)pyrazolo[1,5-a]pyridine-3-carbonitrile A solution of tert-butyl (S)-(2-(4-(5-(3-cyano-6-(2-hydroxy-2-methylpropoxy)pyrazolo[1,5-a]pyridin-4-yl)pyridin-2-yl)piperazine-1-carbonyl)-4-methylpentyl)carbamate (Step 1; 51 mg, 0.082 mmol) in DCM (4 mL) was treated with TFA (2 mL), and stirred for 30 min at ambient temperature. After concentrating in vacuo, the reaction mixture was purified by C18 reverse phase chromatography (using 5-95% ACN in water with 0.1% TFA as the gradient eluent). Fractions containing the desired product were collected, treated with saturated NaHCO₃ and extracted with 20% IPA in DCM. The organics were dried over MgSO₄, filtered and concentrated to cleanly afford the title compound (35 mg, 82% yield). MS (apci) m/z=520.3 (M+H).

Example 275

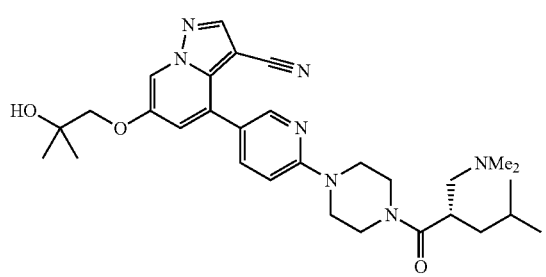 [SMILES: CC(C)C[C@@H](CN(C)C)C(=O)N1CCN(c2ccc(-c3cc(OCC(C)(C)O)cn4ncc(C#N)c34)cn2)CC1]

(S)-4-(6-(4-(2-((dimethylamino)methyl)-4-methylpentanoyl)piperazin-1-yl)pyridin-3-yl)-6-(2-hydroxy-2-methylpropoxy)pyrazolo[1,5-a]pyridine-3-carbonitrile A mixture of (S)-4-(6-(4-(2-(aminomethyl)-4-methylpentanoyl)piperazin-1-yl)pyridin-3-yl)-6-(2-hydroxy-2-methylpropoxy)pyrazolo[1,5-a]pyridine-3-carbonitrile (33 mg, 0.0635 mmol) and formaldehyde (47.3 µL, 0.635 mmol) in DCM (635 µL) was treated with NaBH(AcO)$_3$ (67.3 mg, 0.318 mmol). After stirring for 3 h at ambient temperature, the reaction mixture was concentrated in vacuo. The residue was purified by C18 reverse phase chromatography (using 5-95% ACN in water with 0.1% TFA as the gradient eluent). Fractions containing the desired product were collected, treated with saturated NaHCO$_3$ and extracted with 20% IPA in DCM. The organics were dried over MgSO$_4$, filtered and concentrated to cleanly afford the title compound (13 mg, 37% yield). MS (apci) m/z=548.3 (M+H).

Example 276

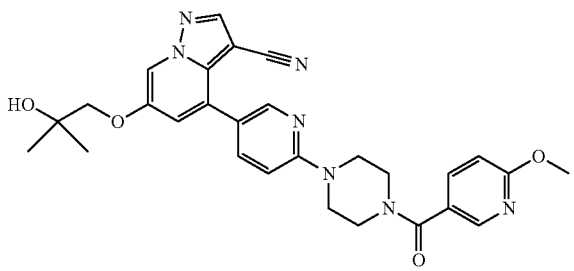 [SMILES: COc1ccc(C(=O)N2CCN(c3ccc(-c4cc(OCC(C)(C)O)cn5ncc(C#N)c45)cn3)CC2)cn1]

6-(2-hydroxy-2-methylpropoxy)-4-(6-(4-(6-methoxynicotinoyl)piperazin-1-yl)pyridin-3-yl)pyrazolo[1,5-a]pyridine-3-carbonitrile A mixture of 6-(2-hydroxy-2-methylpropoxy)-4-(6-(piperazin-1-yl)pyridin-3-yl)pyrazolo[1,5-a]pyridine-3-carbonitrile (Intermediate P40; 25 mg, 0.064 mmol) in DCM (1.3 mL) was treated sequentially with 2-methoxy-5-pyridinecarboxylic acid (11.71 mg, 0.07644 mmol), HATU (29.07 mg, 0.07644 mmol) and DIEA (44.38 µL, 0.2548 mmol), then stirred for 5 h at ambient temperature. The resulting mixture was purified directly by silica chromatography (using 40-100% EtOAc in Hexanes as the gradient eluent) to afford semi-pure material. The semi-pure material was subjected to a second silica chromatography (using 0-100% DCM in Hexanes then 0-60% (2% NH$_4$OH/20% MeOH/78% DCM) in DCM as the gradient eluent) to cleanly provide the title compound (14.91 mg, 44% yield). MS (apci) m/z=528.2 (M+H).

Example 277

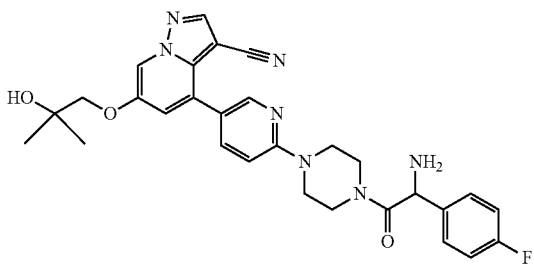 [SMILES: CC(C)(O)COc1cc(-c2ccc(N3CCN(C(=O)C(N)c4ccc(F)cc4)CC3)nc2)c2c(C#N)cnn2c1]

4-(6-(4-(2-amino-2-(4-fluorophenyl)acetyl)piperazin-1-yl)pyridin-3-yl)-6-(2-hydroxy-2-methylpropoxy)pyrazolo[1,5-a]pyridine-3-carbonitrile Step 1: Preparation of tert-butyl (2-(4-(5-(3-cyano-6-(2-hydroxy-2-methylpropoxy)pyrazolo[1,5-a]pyridin-4-yl)pyridin-2-yl)piperazin-1-yl)-1-(4-fluorophenyl)-2-oxoethyl)carbamate A mixture of 6-(2-hydroxy-2-methylpropoxy)-4-(6-(piperazin-1-yl)pyridin-3-yl)pyrazolo[1,5-a]pyridine-3-carbonitrile hydrochloride (Intermediate P39; 50 mg, 0.12 mmol), (R)-2-((tert-butoxycarbonyl)amino)-2-(4-fluorophenyl)acetic acid (31 mg, 0.12 mmol) and HATU (133 mg, 0.35 mmol) in DCM (583 µL) was treated with DIEA (122 µL, 0.70 mmol). The reaction mixture was stirred for 1 h at ambient temperature. The resulting suspension was vacuum filtered. The filtrate was purified directly by C18 reverse phase chromatography (5-95% ACN in water with 0.1% TFA). The fractions containing desired product were combined, diluted with 4:1 DCM:iPrOH washed with saturated NaHCO$_{3(aq)}$ and brine. The organic layer was then dried over anhydrous Na$_2$SO$_{4(s)}$, filtered and concentrated in vacuo to afford the title compound (61 mg, 81% yield). MS (apci) m/z=644.4 (M+H).

Step 2: Preparation of 4-(6-(4-(2-amino-2-(4-fluorophenyl)acetyl)piperazin-1-yl)pyridin-3-yl)-6-(2-hydroxy-2-methylpropoxy)pyrazolo[1,5-a]pyridine-3-carbonitrile A solution of tert-butyl (2-(4-(5-(3-cyano-6-(2-hydroxy-2-methylpropoxy)pyrazolo[1,5-a]pyridin-4-yl)pyridin-2-yl)piperazin-1-yl)-1-(4-fluorophenyl)-2-oxoethyl)carbamate (Step 1; 61 mg, 0.095 mmol) in DCM (948 µL) was treated with TFA (73 µL), and stirred overnight at ambient temperature. The reaction mixture was purified directly by C18 reverse phase chromatography (using 5-95% ACN in water with 0.1% TFA as the gradient eluent). The fractions containing the desired product were combined, then partitioned between 4:1DCM:iPrOH and saturated NaHCO$_{3(aq)}$. The organic extracts were washed with brine, then dried over anhydrous Na$_2$SO$_{4(s)}$, filtered, and concentrated in vacuo. The residue was triturated with DCM/Hexanes and then concentrated in vacuo to cleanly afford the title compound (3.4 mg, 7% yield). MS (apci) m/z=544.2 (M+H).

Example 278

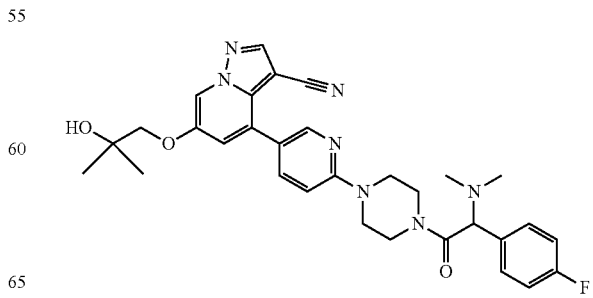

4-(6-(4-(2-(dimethylamino)-2-(4-fluorophenyl)
acetyl)piperazin-1-yl)pyridin-3-yl)-6-(2-hydroxy-2-
methylpropoxy)pyrazolo[1,5-a]pyridine-3-carbonitrile A mixture of 4-(6-(4-(2-amino-2-(4-fluorophenyl)acetyl) piperazin-1-yl)pyridin-3-yl)-6-(2-hydroxy-2-methylpropoxy)pyrazolo[1,5-a]pyridine-3-carbonitrile (Example 277; 30 mg, 0.055 mmol) in DCM (552 µL) was treated sequentially with formaldehyde (16.4 µL, 0.221 mmol) and NaBH(AcO)$_3$ (58.5 mg, 0.276 mmol). After stirring for 1 h at ambient temperature, the reaction mixture was filtered. The resulting filtrate was concentrated in vacuo, and the residue was purified directly by C18 reverse phase chromatography (using 5-95% ACN in water with 0.1% TFA as the gradient eluent). The fractions containing the desired compound were combined then partitioned between 4:1DCM: iPrOH and saturated NaHCO$_{3(aq)}$. The organic extracts were washed with brine, then dried over anhydrous Na$_2$SO$_{4(s)}$, filtered, and concentrated in vacuo. The residue was triturated with DCM/Hexanes and then concentrated in vacuo to cleanly afford the title compound (13.7 mg, 43% yield). MS (apci) m/z=572.3 (M+H).

Example 279

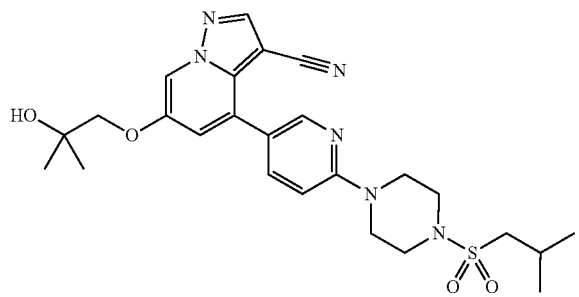 [SMILES: CC(C)CS(=O)(=O)N1CCN(c2ccc(-c3cc(OCC(C)(C)O)cn4ncc(C#N)c34)cn2)CC1]

6-(2-hydroxy-2-methylpropoxy)-4-(6-(4-(isobutyl-
sulfonyl)piperazin-1-yl)pyridin-3-yl)pyrazolo[1,5-a]
pyridine-3-carbonitrile A solution of 6-(2-hydroxy-2-methylpropoxy)-4-(6-(piperazin-1-yl)pyridin-3-yl)pyrazolo[1,5-a]pyridine-3-carbonitrile hydrochloride (Intermediate P39; 24.1 mg, 0.0562 mmol) in DCM (500 µL) was treated sequentially with TEA (38.1 µL, 0.281 mmol) and isobutanesulfonyl chloride (8.07 µL, 0.0618 mmol). The resulting mixture was stirred overnight at ambient temperature, and then concentrated in vacuo. The crude residue was purified by C18 reverse phase chromatography (using 5-95% water:ACN with 0.1% TFA as the gradient eluent). Fractions containing the desired compound were combined and partitioned between 4:1 DCM:iPrOH and saturated NaHCO$_{3(aq)}$. The aqueous extracts were back extracted with 4:1 DCM:iPrOH (2×). The combined organic extracts were dried over anhydrous Na$_2$SO$_{4(s)}$, filtered, and concentrated in vacuo to cleanly provide the title compound (14.3 mg, 50% yield). MS (apci) m/z=513.2 (M+H).

Example 280

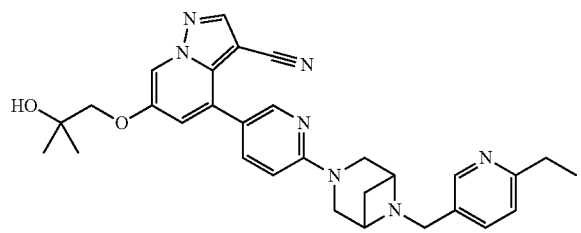 [SMILES: CCc1ccc(CN2C3CC2CN(c2ccc(-c4cc(OCC(C)(C)O)cn5ncc(C#N)c45)cn2)C3)cn1]

4-(6-(6-(((6-ethylpyridin-3-yl)methyl)-3,6-diazabicy-
clo[3.1.1]heptan-3-yl)pyridin-3-yl)-6-(2-hydroxy-2-
methylpropoxy)pyrazolo[1,5-a]pyridine-3-carbonitrile A mixture of 4-(6-(3,6-diazabicyclo[3.1.1]heptan-3-yl) pyridin-3-yl)-6-(2-hydroxy-2-methylpropoxy)pyrazolo[1,5-a]pyridine-3-carbonitrile dihydrochloride (Intermediate P43; 20 mg, 0.042 mmol) in DCM (0.5 mL) was treated sequentially with 6-ethylnicotinaldehyde (11.33 mg, 0.08379 mmol) and NaBH(AcO)$_3$ (26.64 mg, 0.1257 mmol). After stirring 3 h at ambient temperature, the reaction mixture was purified directly by silica chromatography (using 0-20% DCM/MeOH with 2% NH$_4$OH as the gradient eluent) to cleanly provide the title compound (18.03 mg, 82% yield). MS (apci) m/z=524.2 (M+H).

The compounds in Table V were prepared using a similar method to that described for the preparation of Example 280, replacing 6-ethylnicotinaldehyde with the appropriate aldehyde and DCM with DCE as the reaction solvent. Reactions were monitored for completion by LCMS. As such reaction durations, and the need for supplemental reagent amounts were adjusted accordingly. Where noted (*) a few drops of glacial acetic acid were included after the addition of the NaBH(AcO)$_3$. The title compounds were isolated following a chromatographic purification utilizing an appropriate gradient eluent. When chromatographic conditions resulted in the isolation of the TFA salt of the title compound, the chromatographic purification was followed by a basic work up of the salt. Basic work up conditions involved partitioning the TFA salt between DCM or 1:1 DCM:MeOH and saturated NaHCO$_{3(aq)}$ (and where necessary additional extraction with water and/or brine), then separation of organic extracts, drying over anhydrous Na$_2$SO$_{4(s)}$, filtration and concentration in vacuo to afford the title compound in free base form.

TABLE V

| Ex # | Structure | Chemical Name | MS (apci) m/z |
|---|---|---|---|
| 281 | 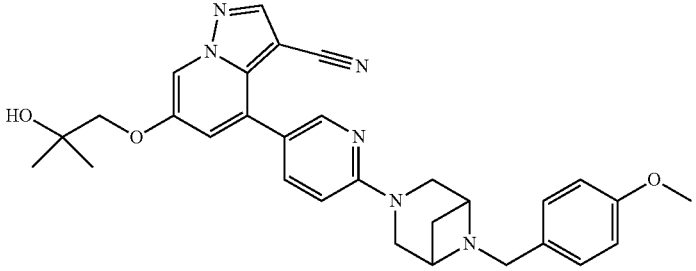 [SMILES: COc1ccc(CN2C3CC2CN(c2ccc(-c4cc(OCC(C)(C)O)cn5ncc(C#N)c45)cn2)C3)cc1] | 6-(2-hydroxy-2-methylpropoxy)-4-(6-(6-(4-methoxybenzyl)-3,6-diazabicyclo[3.1.1]heptan-3-yl)pyridin-3-yl)pyrazolo[1,5-a]pyridine-3-carbonitrile | 525.2 (M + H) |
| 282 | 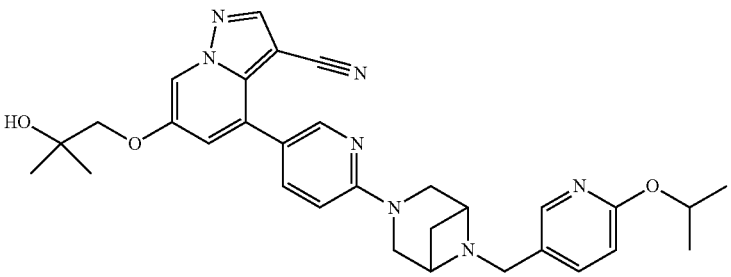 [SMILES: CC(C)Oc1ccc(CN2C3CC2CN(c2ccc(-c4cc(OCC(C)(C)O)cn5ncc(C#N)c45)cn2)C3)cn1] | 6-(2-hydroxy-2-methylpropoxy)-4-(6-(6-((6-isopropoxypyridin-3-yl)methyl)-3,6-diazabicyclo[3.1.1]heptan-3-yl)pyridin-3-yl)pyrazolo[1,5-a]pyridine-3-carbonitrile | 554.2 (M + H) |
| 283 | 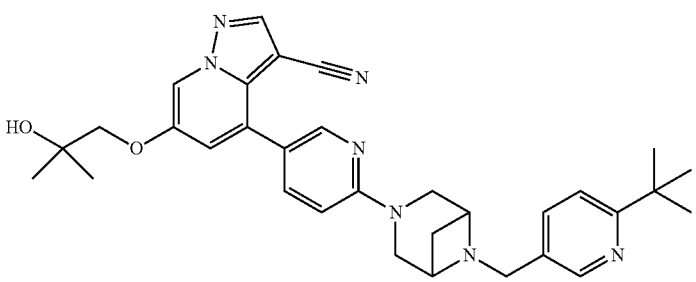 [SMILES: CC(C)(O)COc1cc(-c2ccc(N3CC4CC(C3)N4Cc3ccc(C(C)(C)C)nc3)nc2)c2c(C#N)cnn2c1] | 4-(6-(6-((6-(tert-butyl)pyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 552.4 (M + H) |
| 284 | 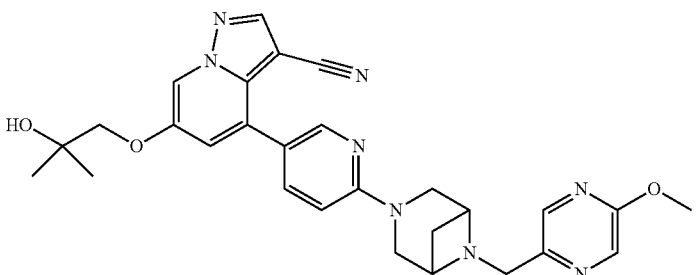 | 6-(2-hydroxy-2-methylpropoxy)-4-(6-(6-((5-methoxypyrazin-2-yl)methyl)-3,6-diazabicyclo[3.1.1]heptan-3-yl)pyridin-3-yl)pyrazolo[1,5-a]pyridine-3-carbonitrile | 527.2 (M + H) |
| 285 | 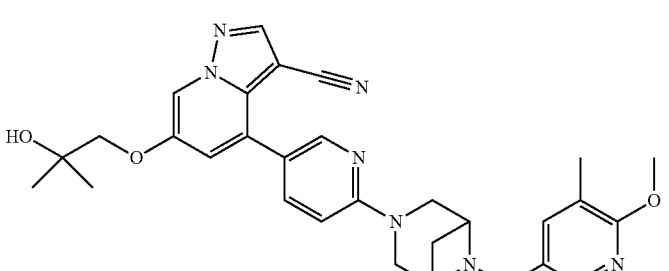 | 6-(2-hydroxy-2-methylpropoxy)-4-(6-(6-((6-methoxy-5-methylpyridin-3-yl)methyl)-3,6-diazabicyclo[3.1.1]heptan-3-yl)pyridin-3-yl)pyrazolo[1,5-a]pyridine-3-carbonitrile | 540.3 (M + H) |

TABLE V-continued

| Ex # | Structure | Chemical Name | MS (apci) m/z |
|---|---|---|---|
| 286 | 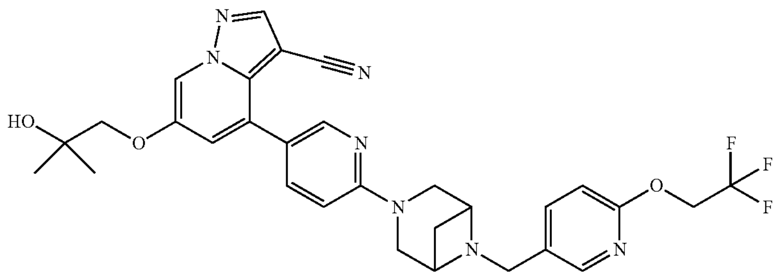 [SMILES: CC(C)(O)COc1cc(-c2ccc(N3CC4CC(C3)N4Cc3ccc(OCC(F)(F)F)nc3)nc2)c2c(C#N)cnn2c1] | 6-(2-hydroxy-2-methylpropoxy)-4-(6-(6-((6-(2,2,2-trifluoroethoxy)pyridin-3-yl)methyl)-3,6-diazabicyclo[3.1.1]heptan-3-yl)pyridin-3-yl)pyrazolo[1,5-a]pyridine-3-carbonitrile | 594.2 (M + H) |
| 287 | 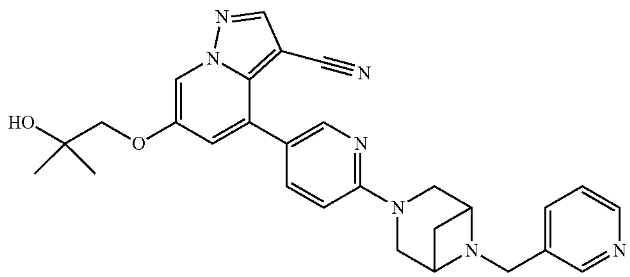 [SMILES: CC(C)(O)COc1cc(-c2ccc(N3CC4CC(C3)N4Cc3cccnc3)nc2)c2c(C#N)cnn2c1] | 6-(2-hydroxy-2-methylpropoxy)-4-(6-(6-(pyridin-3-ylmethyl)-3,6-diazabicyclo[3.1.1]heptan-3-yl)pyridin-3-yl)pyrazolo[1,5-a]pyridine-3-carbonitrile | 496.2 (M + H) |
| 288 | 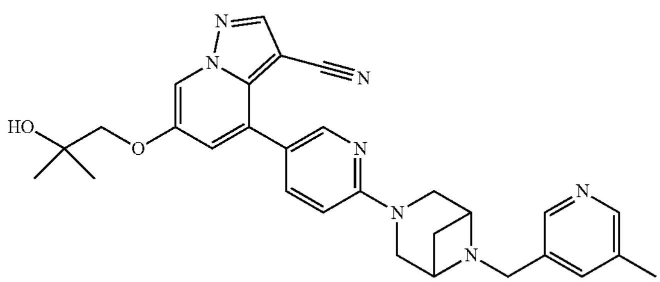 [SMILES: Cc1cncc(CN2C3CC2CN(c2ccc(-c4cc(OCC(C)(C)O)cn5ncc(C#N)c45)cn2)C3)c1] | 6-(2-hydroxy-2-methylpropoxy)-4-(6-(6-((5-methylpyridin-3-yl)methyl)-3,6-diazabicyclo[3.1.1]heptan-3-yl)pyridin-3-yl)pyrazolo[1,5-a]pyridine-3-carbonitrile | 510.2 (M + H) |
| 289 | 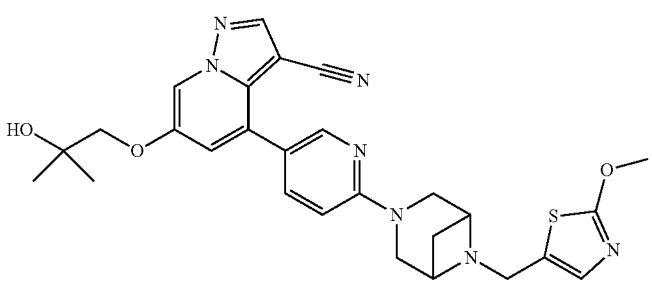 [SMILES: COc1ncc(CN2C3CC2CN(c2ccc(-c4cc(OCC(C)(C)O)cn5ncc(C#N)c45)cn2)C3)s1] | 6-(2-hydroxy-2-methylpropoxy)-4-(6-(6-((2-methoxythiazol-5-yl)methyl)-3,6-diazabicyclo[3.1.1]heptan-3-yl)pyridin-3-yl)pyrazolo[1,5-a]pyridine-3-carbonitrile | 532.2 (M + H) |
| 290 | 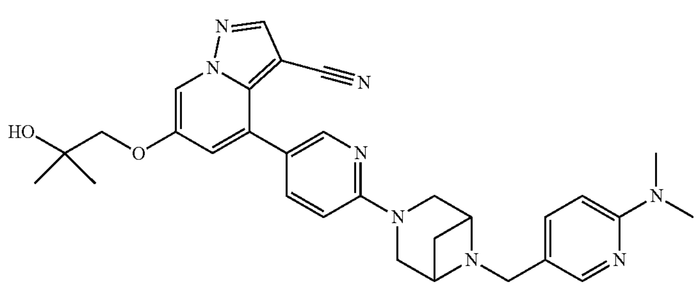 [SMILES: CN(C)c1ccc(CN2C3CC2CN(c2ccc(-c4cc(OCC(C)(C)O)cn5ncc(C#N)c45)cn2)C3)cn1] | 4-(6-(6-((6-(dimethylamino)pyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 539.25 (M + H) |

TABLE V-continued

| Ex # | Structure | Chemical Name | MS (apci) m/z |
|---|---|---|---|
| 291 | 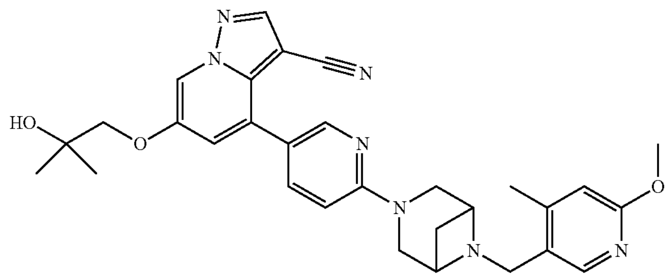 [SMILES: COc1cc(C)c(CN2C3CC2CN(c2ccc(-c4cc(OCC(C)(C)O)cn5ncc(C#N)c45)cn2)C3)cn1] | 6-(2-hydroxy-2-methylpropoxy)-4-(6-(6-((6-methoxy-4-methylpyridin-3-yl)methyl)-3,6-diazabicyclo[3.1.1]heptan-3-yl)pyridin-3-yl)pyrazolo[1,5-a]pyridine-3-carbonitrile | 540.3 (M + H) |
| 292 | 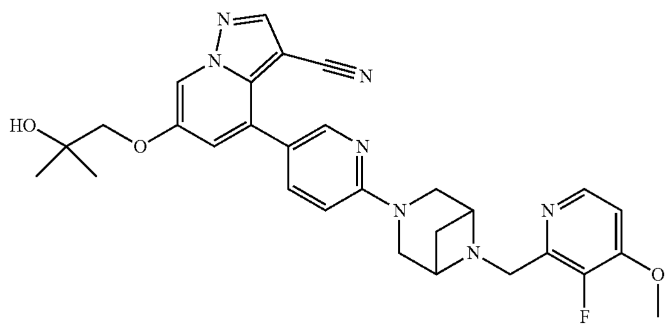 [SMILES: COc1ccnc(CN2C3CC2CN(c2ccc(-c4cc(OCC(C)(C)O)cn5ncc(C#N)c45)cn2)C3)c1F] | 4-(6-(6-((3-fluoro-4-methoxypyridin-2-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 544.3 (M + H) |
| 293 | 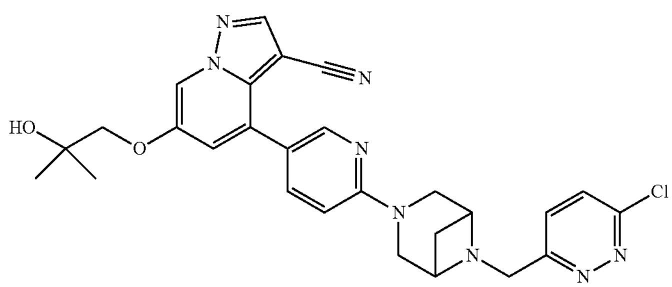 [SMILES: CC(C)(O)COc1cc(-c2ccc(N3CC4CC(C3)N4Cc3ccc(Cl)nn3)nc2)c2c(C#N)cnn2c1] | 4-(6-(6-((6-chloropyridazin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 531.2 (M + H) |
| 294 | 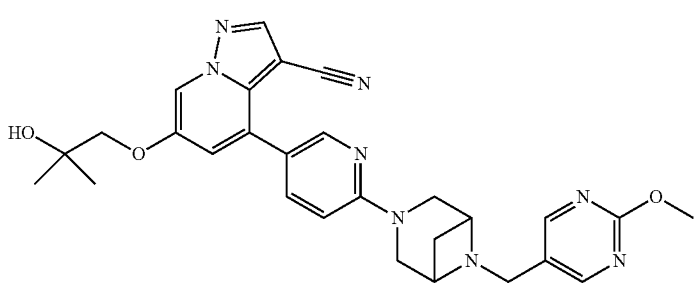 [SMILES: COc1ncc(CN2C3CC2CN(c2ccc(-c4cc(OCC(C)(C)O)cn5ncc(C#N)c45)cn2)C3)cn1] | 6-(2-hydroxy-2-methylpropoxy)-4-(6-(6-((2-methoxypyrimidin-5-yl)methyl)-3,6-diazabicyclo[3.1.1]heptan-3-yl)pyridin-3-yl)pyrazolo[1,5-a]pyridine-3-carbonitrile | 527.25 (M + H) |
| 295 | 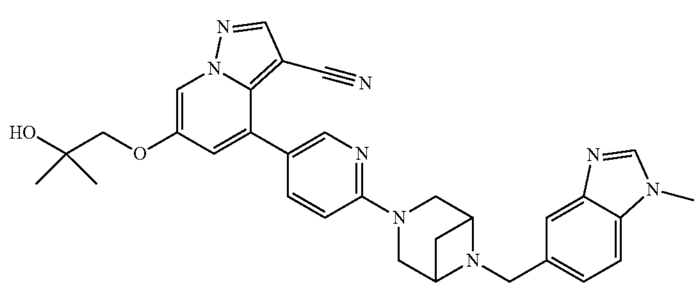 [SMILES: Cn1cnc2cc(CN3C4CC3CN(c3ccc(-c5cc(OCC(C)(C)O)cn6ncc(C#N)c56)cn3)C4)ccc21] | 6-(2-hydroxy-2-methylpropoxy)-4-(6-(6-((1-methyl-1H-benzo[d]imidazol-5-yl)methyl)-3,6-diazabicyclo[3.1.1]heptan-3-yl)pyridin-3-yl)pyrazolo[1,5-a]pyridine-3-carbonitrile | 549.3 (M + H) |

TABLE V-continued

| Ex # | Structure | Chemical Name | MS (apci) m/z |
|---|---|---|---|
| 296 | 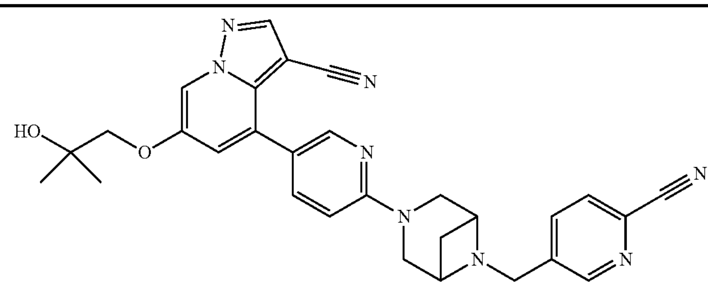 | 4-(6-(6-((6-cyanopyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 521.15 (M + H) |
| 297 | 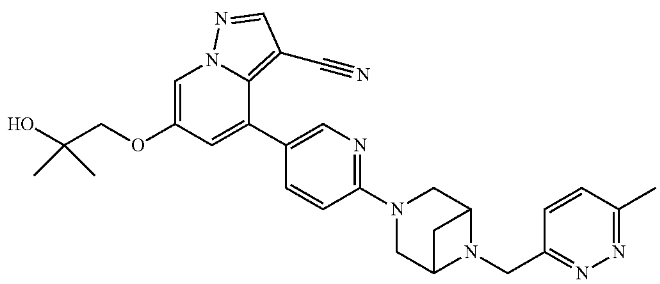 [SMILES: Cc1ccc(CN2C3CC2CN(c2ccc(-c4cc(OCC(C)(C)O)cn5ncc(C#N)c45)cn2)C3)nn1] | 6-(2-hydroxy-2-methylpropoxy)-4-(6-(6-((6-methylpyridazin-3-yl)methyl)-3,6-diazabicyclo[3.1.1]heptan-3-yl)pyridin-3-yl)pyrazolo[1,5-a]pyridine-3-carbonitrile | 511.3 (M + H) |

Example 298

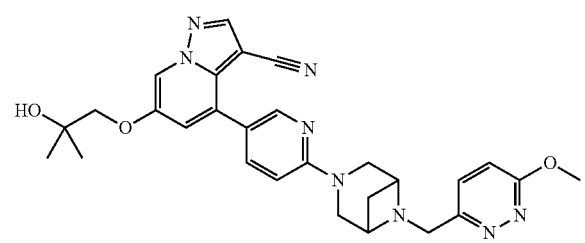 [SMILES: COc1ccc(CN2C3CC2CN(c2ccc(-c4cc(OCC(C)(C)O)cn5ncc(C#N)c45)cn2)C3)nn1]

6-(2-hydroxy-2-methylpropoxy)-4-(6-(6-((6-methoxypyridazin-3-yl)methyl)-3,6-diazabicyclo[3.1.1]heptan-3-yl)pyridin-3-yl)pyrazolo[1,5-a]pyridine-3-carbonitrile A mixture of 4-(6-(6-((6-chloropyridazin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile (Example 293; 56.2 mg, 0.106 mmol) in MeOH (0.5 mL) was treated with 30 wt % NaOMe (98.3 μL, 0.529 mmol). The resulting mixture was stirred for 5 h at 60° C. After cooling to ambient temperature, the reaction mixture was concentrated in vacuo. The residue was purified directly by silica chromatography (using 50-100% EtOAc in Hexanes then 0-20% MeOH in EtOAc as the gradient eluent) to cleanly provide the title compound (49.38 mg, 89% yield). MS (apci) m/z=527.2 (M+H).

Example 299

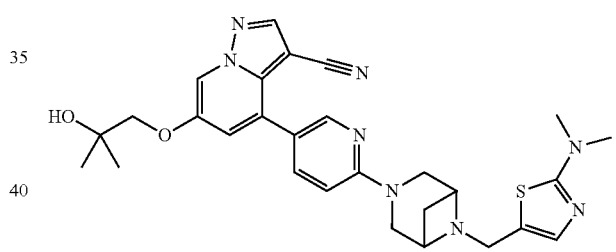

4-(6-(6-((2-(dimethylamino)thiazol-5-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 52.8 mg, 0.111 mmol) and 2-(dimethylamino)thiazole-5-carbaldehyde (86.38 mg, 0.5530 mmol) in DCE (0.5 mL) was treated with NaBH(AcO)$_3$ (140.6 mg, 0.6636 mmol). After stirring 7 h at ambient temperature, the reaction mixture was diluted with DCM, extracted with water, then dried over anhydrous Na$_2$SO$_{4(s)}$, filtered, and concentrated in vacuo. The residue was purified by silica chromatography (using 0-50% DCM/MeOH as the gradient eluent) to cleanly provide the title compound (54.2 mg, 90% yield). MS (apci) m/z=545.2 (M+H).

The compounds in Table W were prepared using a similar method to that described for the preparation of Example 299, replacing the 2-(dimethylamino)thiazole-5-carbaldehyde with the appropriate aldehyde. Reactions were monitored for completion by LCMS. As such reaction durations, and the need for supplemental reagent amounts were adjusted accordingly. Where noted (*) the aqueous work up prior to chromatography was omitted. The title compounds were isolated following a chromatographic purification utilizing an appropriate gradient eluent. When chromatographic conditions resulted in the isolation of the TFA salt of the title compound, the chromatographic purification was followed by a basic work up. Basic work up conditions involved dissolution of the TFA salt in DCM containing TEA (1 mL), extraction with water, then separation of organic extracts and concentration in vacuo to afford the title compound in free base form.

TABLE W

| Ex # | Structure | Chemical Name | MS (apci) m/z |
|---|---|---|---|
| 300 | 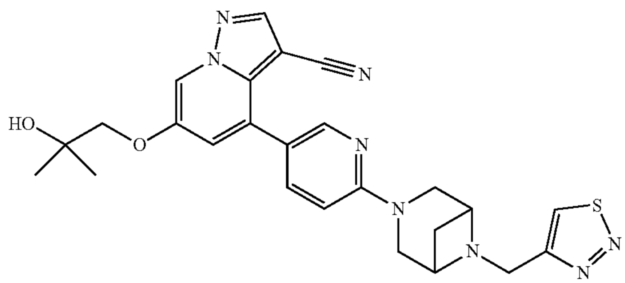 [SMILES: CC(C)(O)COc1cc(-c2ccc(N3CC4CC(C3)N4Cc3csnn3)nc2)c2c(C#N)cnn2c1] | 4-(6-(6-((1,2,3-thiadiazol-4-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 503.1 (M + H) |
| 301 | 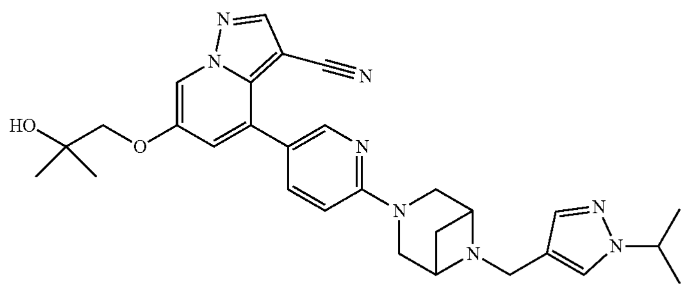 [SMILES: CC(C)n1cc(CN2C3CC2CN(c2ccc(-c4cc(OCC(C)(C)O)cn5ncc(C#N)c45)cn2)C3)cn1] | 6-(2-hydroxy-2-methylpropoxy)-4-(6-(6-((1-isopropyl-1H-pyrazol-4-yl)methyl)-3,6-diazabicyclo[3.1.1]heptan-3-yl)pyridin-3-yl)pyrazolo[1,5-a]pyridine-3-carbonitrile | 527.25 (M + H) |
| 302 | 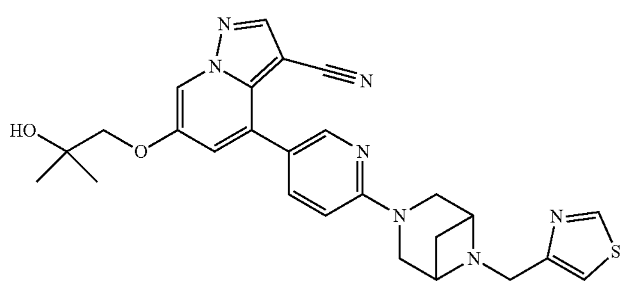 [SMILES: CC(C)(O)COc1cc(-c2ccc(N3CC4CC(C3)N4Cc3cscn3)nc2)c2c(C#N)cnn2c1] | 6-(2-hydroxy-2-methylpropoxy)-4-(6-(6-(thiazol-4-ylmethyl)-3,6-diazabicyclo[3.1.1]heptan-3-yl)pyridin-3-yl)pyrazolo[1,5-a]pyridine-3-carbonitrile | 502.1 (M + H) |
| 303 | 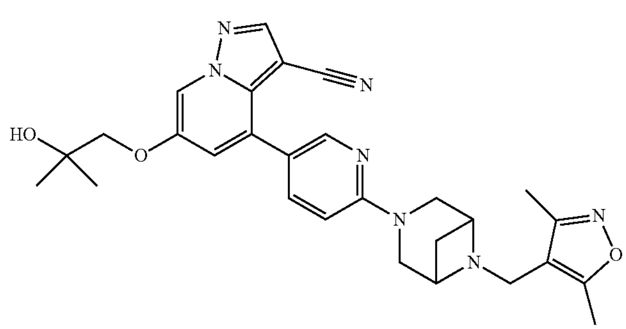 [SMILES: Cc1noc(C)c1CN1C2CC1CN(c1ccc(-c3cc(OCC(C)(C)O)cn4ncc(C#N)c34)cn1)C2] | 4-(6-(6-((3,5-dimethylisoxazol-4-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 513.2 (M + H) |

TABLE W-continued

| Ex # | Structure | Chemical Name | MS (apci) m/z |
|---|---|---|---|
| 304 | 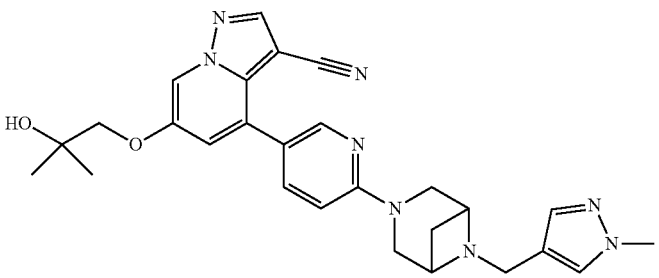 [SMILES: Cn1cc(CN2C3CC2CN(c2ccc(-c4cc(OCC(C)(C)O)cn5ncc(C#N)c45)cn2)C3)cn1] | 6-(2-hydroxy-2-methylpropoxy)-4-(6-(6-((1-methyl-1H-pyrazol-4-yl)methyl)-3,6-diazabicyclo[3.1.1]heptan-3-yl)pyridin-3-yl)pyrazolo[1,5-a]pyridine-3-carbonitrile | 499.2 (M + H) |
| 305 | 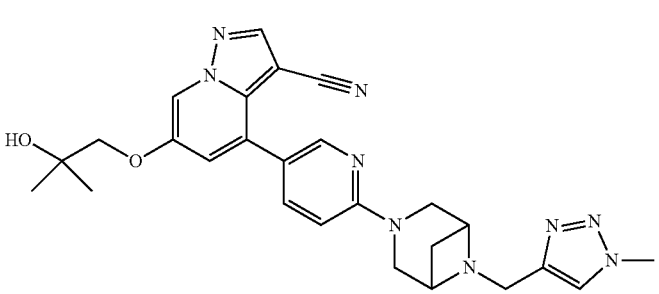 | 6-(2-hydroxy-2-methylpropoxy)-4-(6-(6-((1-methyl-1H-1,2,3-triazol-4-yl)methyl)-3,6-diazabicyclo[3.1.1]heptan-3-yl)pyridin-3-yl)pyrazolo[1,5-a]pyridine-3-carbonitrile | 500.2 (M + H) |
| 306 | 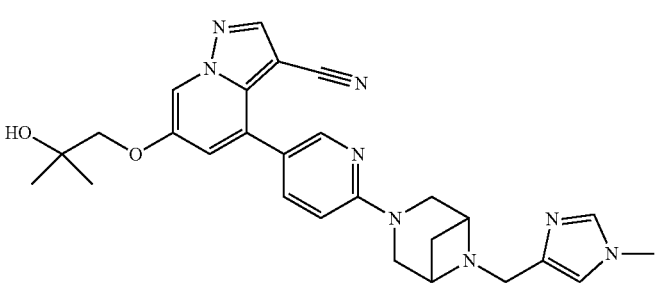 [SMILES: Cn1cnc(CN2C3CC2CN(c2ccc(-c4cc(OCC(C)(C)O)cn5ncc(C#N)c45)cn2)C3)c1] | 6-(2-hydroxy-2-methylpropoxy)-4-(6-(6-((1-methyl-1H-imidazol-4-yl)methyl)-3,6-diazabicyclo[3.1.1]heptan-3-yl)pyridin-3-yl)pyrazolo[1,5-a]pyridine-3-carbonitrile | 499.2 (M + H) |
| 307 | 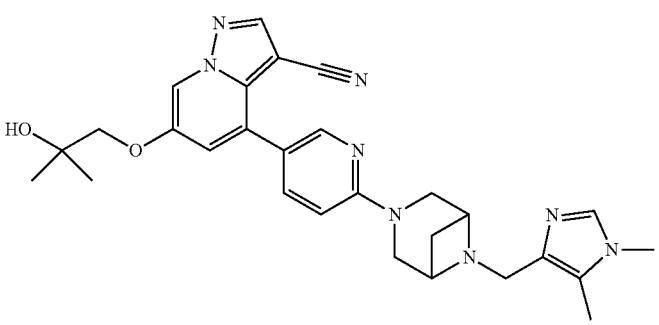 [SMILES: Cc1c(CN2C3CC2CN(c2ccc(-c4cc(OCC(C)(C)O)cn5ncc(C#N)c45)cn2)C3)ncn1C] | 4-(6-(6-((1,5-dimethyl-1H-imidazol-4-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 513.2 (M + H) |
| 308 | 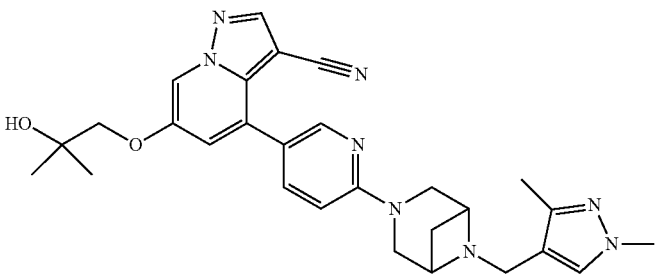 [SMILES: Cc1nn(C)cc1CN1C2CC1CN(c1ccc(-c3cc(OCC(C)(C)O)cn4ncc(C#N)c34)cn1)C2] | 4-(6-(6-((1,3-dimethyl-1H-pyrazol-4-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 513.2 (M + H) |

TABLE W-continued

| Ex # | Structure | Chemical Name | MS (apci) m/z |
|---|---|---|---|
| 309 | 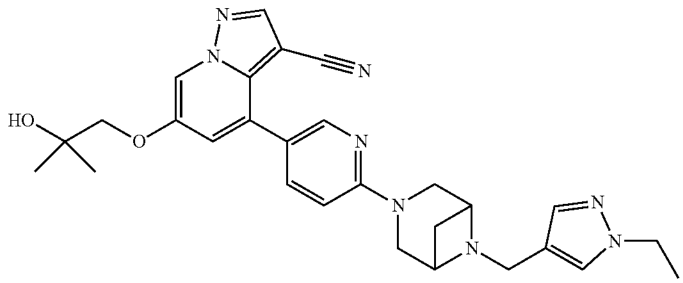 [SMILES: CCn1cc(CN2C3CC2CN(c2ccc(-c4cc(OCC(C)(C)O)cn5ncc(C#N)c45)cn2)C3)cn1] | 4-(6-(6-((1-ethyl-1H-pyrazol-4-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 513.2 (M + H) |
| 310 | 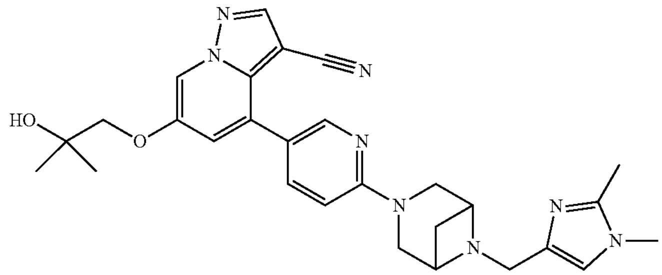 [SMILES: Cc1nc(CN2C3CC2CN(c2ccc(-c4cc(OCC(C)(C)O)cn5ncc(C#N)c45)cn2)C3)cn1C] | 4-(6-(6-((1,2-dimethyl-1H-imidazol-4-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 513.25 (M + H) |
| 311 | 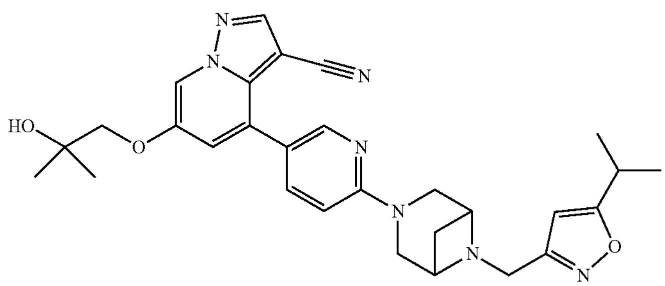 [SMILES: CC(C)c1cc(CN2C3CC2CN(c2ccc(-c4cc(OCC(C)(C)O)cn5ncc(C#N)c45)cn2)C3)no1] | 6-(2-hydroxy-2-methylpropoxy)-4-(6-(6-((5-isopropylisoxazol-3-yl)methyl)-3,6-diazabicyclo[3.1.1]heptan-3-yl)pyridin-3-yl)pyrazolo[1,5-a]pyridine-3-carbonitrile | 528.2 (M + H) |

Example 312

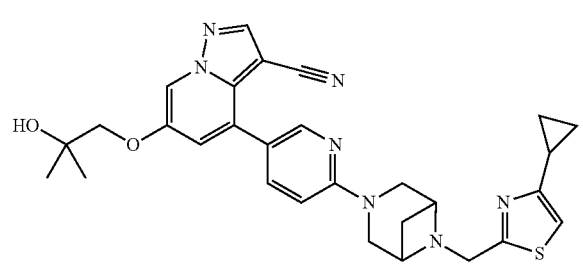 [SMILES: CC(C)(O)COc1cc(-c2ccc(N3CC4CC(C3)N4Cc3nc(C4CC4)cs3)nc2)c2c(C#N)cnn2c1]

4-(6-(6-((4-cyclopropylthiazol-2-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 52 mg, 0.109 mmol) and 4-cyclopropyl-thiazole-2-carbaldehyde (17.5 μL, 0.114 mmol) in DCE (1.09 mL) was treated with NaBH(AcO)$_3$ (69.3 mg, 0.327 mmol). After stirring overnight at ambient temperature, the reaction mixture was diluted with DCE (1 mL), and treated with additional 4-cyclopropyl-thiazole-2-carbaldehyde (67 μL, 0.43 mmol) and NaBH(AcO)$_3$ (69.3 mg, 0.327 mmol). The mixture was stirred for an additional 1.5 h at ambient temperature, diluted with water (20 mL), and then extracted with DCM (2×10 mL). The combined organic extracts were washed with brine (10 mL), then dried over anhydrous Na$_2$SO$_{4(s)}$, filtered, and concentrated in vacuo. The residue was purified by C18 reverse phase chromatography (using 5-95% ACN in water with 0.1% TFA as the gradient eluent) affording the title compound as the TFA salt. The TFA salt was diluted with saturated NaHCO$_{3(aq)}$, then extracted with DCM (2×10 mL). The combined organic extracts were washed with brine (10 mL), then dried over anhydrous Na$_2$SO$_{4(s)}$, filtered, and concentrated in vacuo to afford the title compound (28.7 mg, 46% yield). MS (apci) m/z=542.3 (M+H).

Example 313

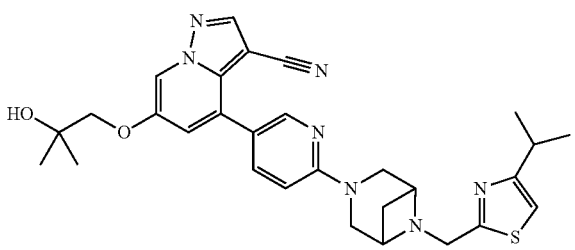 [SMILES: CC(C)c1csc(CN2C3CC2CN(c2ccc(-c4cc(OCC(C)(C)O)cn5ncc(C#N)c45)cn2)C3)n1]

6-(2-hydroxy-2-methylpropoxy)-4-(6-(6-((4-isopropylthiazol-2-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 52 mg, 0.109 mmol) and 4-isopropyl-1,3-thiazole-2-carbaldehyde (16.9 μL, 0.109 mmol) in DCE (1.09 mL) was treated with NaBH(AcO)$_3$ (69.3 mg, 0.327 mmol). After stirring overnight at ambient temperature, the reaction mixture was diluted with DCE (1 mL), and treated with additional 4-cyclopropyl-thiazole-2-carbaldehyde (67 μL, 0.43 mmol) and NaBH(AcO)$_3$ (69.3 mg, 0.327 mmol). The reaction mixture was stirred for an additional 1.5 h at ambient temperature, diluted with water (20 mL), and then extracted with DCM (2×10 mL). The combined organic extracts were washed with brine (10 mL), then dried over anhydrous Na$_2$SO$_{4(s)}$, filtered, and concentrated in vacuo. The residue was purified by C18 reverse phase chromatography (using 5-95% ACN in water with 0.1% TFA as the gradient eluent) affording the title compound as the TFA salt. The TFA salt was diluted with saturated NaHCO$_{3(aq)}$, then extracted with DCM (2×10 mL). The combined organic extracts were washed with brine (10 mL), then dried over anhydrous Na$_2$SO$_{4(s)}$, filtered, and concentrated in vacuo to afford the title compound (27.8 mg, 45% yield). MS (apci) m/z=544.3 (M+H).

Example 314

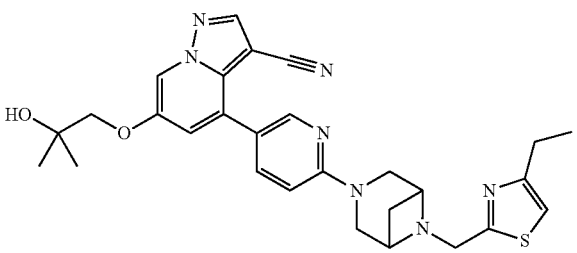 [SMILES: CCc1csc(CN2C3CC2CN(c2ccc(-c4cc(OCC(C)(C)O)cn5ncc(C#N)c45)cn2)C3)n1]

4-(6-(6-((4-ethylthiazol-2-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 52 mg, 0.109 mmol) and 4-ethyl-2-thiazolecarboxaldehyde (46.1 μL, 0.327 mmol) in DCE (1.09 mL) was treated with NaBH(AcO)$_3$ (139 mg, 0.654 mmol). After stirring for 4 h at ambient temperature, the reaction mixture was concentrated in vacuo. The residue was purified by C18 reverse phase chromatography (using 5-95% ACN in water with 0.1% TFA as the gradient eluent) affording the title compound as the TFA salt. The TFA salt was diluted with saturated NaHCO$_{3(aq)}$, then extracted with DCM (2×10 mL). The combined organic extracts were washed with brine (10 mL), then dried over anhydrous Na$_2$SO$_{4(s)}$, filtered, and concentrated in vacuo to afford the title compound (15.8 mg, 27% yield). MS (apci) m/z=530.3 (M+H).

Example 315

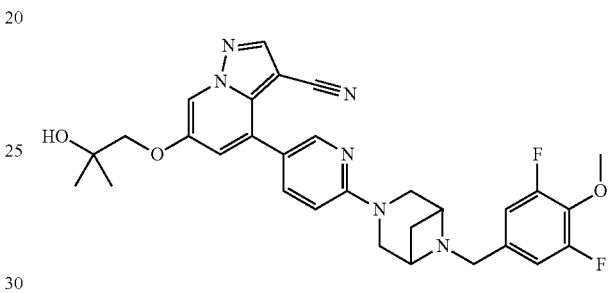

4-(6-(6-(3,5-difluoro-4-methoxybenzyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 22 mg, 0.046 mmol) in DCE (230 μL) was treated sequentially with 3,5-difluoro-4-methoxybenzaldehyde (7.932 mg, 0.04608 mmol) and NaBH(AcO)$_3$ (29.3 mg, 0.138 mmol). After stirring 1 h at ambient temperature, the reaction mixture was purified directly by silica chromatography (using 0-100% DCM in Hexanes, then 0-60% (2% NH$_4$OH/20% MeOH/78% DCM) in DCM as the gradient eluent) to afford the title compound (13.9 mg, 54% yield). MS (apci) m/z=561.2 (M+H).

The compounds in Table X were prepared using a similar method to that described for the preparation of Example 315, replacing the 3,5-difluoro-4-methoxybenzaldehyde with the appropriate aldehyde. Reactions were monitored for completion by LCMS. As such reaction durations and the need for supplemental reagent amounts were adjusted accordingly. The title compounds were isolated following a chromatographic purification utilizing an appropriate gradient eluent. When chromatographic conditions resulted in the isolation of the TFA salt of the title compound, chromatography was followed by a basic work up. Basic work up conditions involved dissolution of the TFA salt in in MeOH (1 mL), filtration through basic resin (Stratospheres MP-HCO$_3$, 100 mg), rinsing with MeOH until no product by UV, concentration of the filtrate in vacuo, and subsequent azeotroping of residual water with Et$_2$O to cleanly afford the title compound in free base form.

TABLE X

| Ex # | Structure | Chemical Name | MS (apci) m/z |
|---|---|---|---|
| 316 | 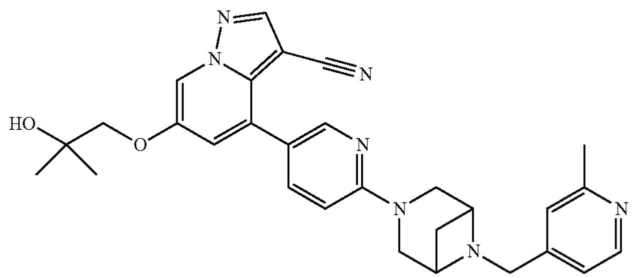 [SMILES: Cc1cc(CN2C3CC2CN(c2ccc(-c4cc(OCC(C)(C)O)cn5ncc(C#N)c45)cn2)C3)ccn1] | 6-(2-hydroxy-2-methylpropoxy)-4-(6-(6-((2-methylpyridin-4-yl)methyl)-3,6-diazabicyclo[3.1.1]heptan-3-yl)pyridin-3-yl)pyrazolo[1,5-a]pyridine-3-carbonitrile | 510.2 (M + H) |
| 317 | 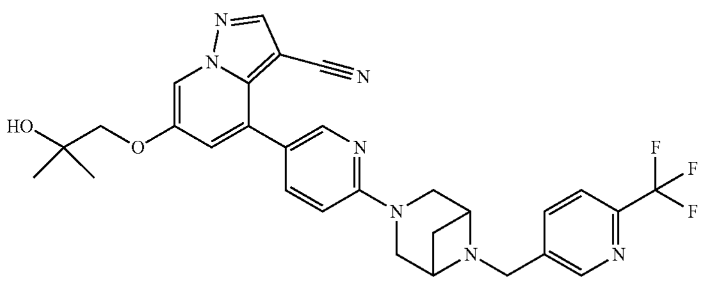 [SMILES: CC(C)(O)COc1cc(-c2ccc(N3CC4CC(C3)N4Cc3ccc(C(F)(F)F)nc3)nc2)c2c(C#N)cnn2c1] | 6-(2-hydroxy-2-methylpropoxy)-4-(6-(6-((6-(trifluoromethyl)pyridin-3-yl)methyl)-3,6-diazabicyclo[3.1.1]heptan-3-yl)pyridin-3-yl)pyrazolo[1,5-a]pyridine-3-carbonitrile | 564.2 (M + H) |
| 318 | 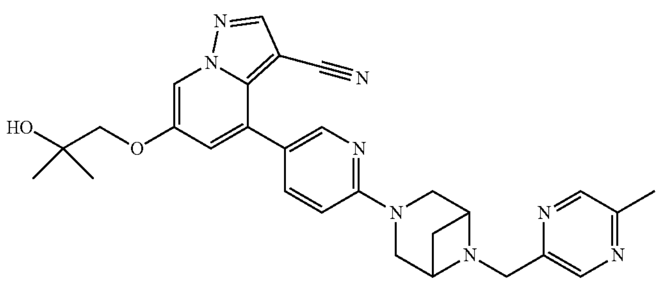 [SMILES: Cc1cnc(CN2C3CC2CN(c2ccc(-c4cc(OCC(C)(C)O)cn5ncc(C#N)c45)cn2)C3)cn1] | 6-(2-hydroxy-2-methylpropoxy)-4-(6-(6-((5-methylpyrazin-2-yl)methyl)-3,6-diazabicyclo[3.1.1]heptan-3-yl)pyridin-3-yl)pyrazolo[1,5-a]pyridine-3-carbonitrile | 511.25 (M + H) |
| 319 | 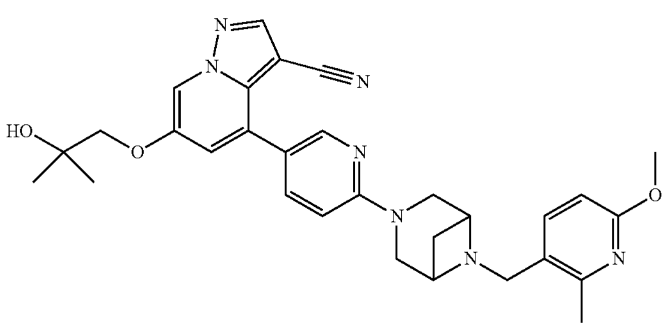 [SMILES: COc1ccc(CN2C3CC2CN(c2ccc(-c4cc(OCC(C)(C)O)cn5ncc(C#N)c45)cn2)C3)c(C)n1] | 6-(2-hydroxy-2-methylpropoxy)-4-(6-(6-((6-methoxy-2-methylpyridin-3-yl)methyl)-3,6-diazabicyclo[3.1.1]heptan-3-yl)pyridin-3-yl)pyrazolo[1,5-a]pyridine-3-carbonitrile | 540.3 (M + H) |
| 320 | 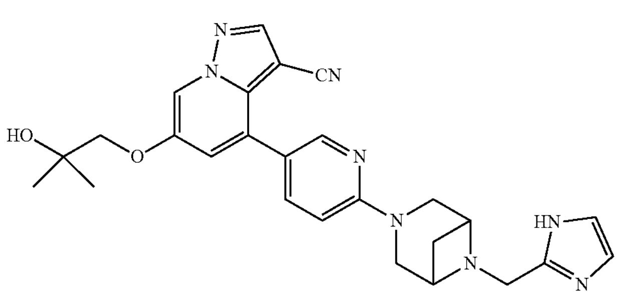 [SMILES: CC(C)(O)COc1cc(-c2ccc(N3CC4CC(C3)N4Cc3ncc[nH]3)nc2)c2c(C#N)cnn2c1] | 4-(6-(6-((1H-imidazol-2-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 485.2 (M + H) |

TABLE X-continued

| Ex # | Structure | Chemical Name | MS (apci) m/z |
|---|---|---|---|
| 321 | 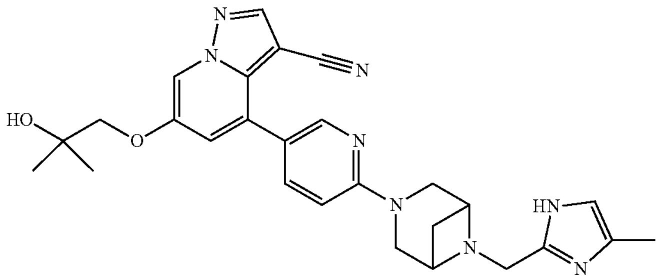 [SMILES: Cc1c[nH]c(CN2C3CC2CN(c2ccc(-c4cc(OCC(C)(C)O)cn5ncc(C#N)c45)cn2)C3)n1] | 6-(2-hydroxy-2-methylpropoxy)-4-(6-(6-((4-methyl-1H-imidazol-2-yl)methyl)-3,6-diazabicyclo[3.1.1]heptan-3-yl)pyridin-3-yl)pyrazolo[1,5-a]pyridine-3-carbonitrile | 499.2 (M + H) |
| 322 | 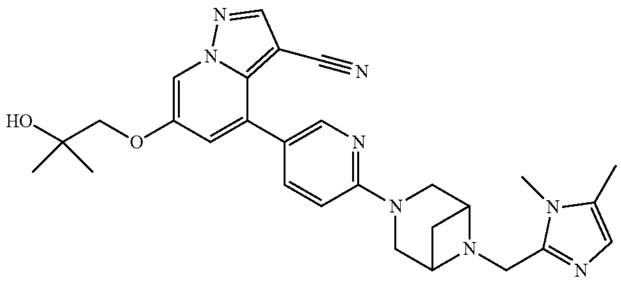 [SMILES: Cc1cnc(CN2C3CC2CN(c2ccc(-c4cc(OCC(C)(C)O)cn5ncc(C#N)c45)cn2)C3)n1C] | 4-(6-(6-((1,5-dimethyl-1H-imidazol-2-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 513.2 (M + H) |

Example 323

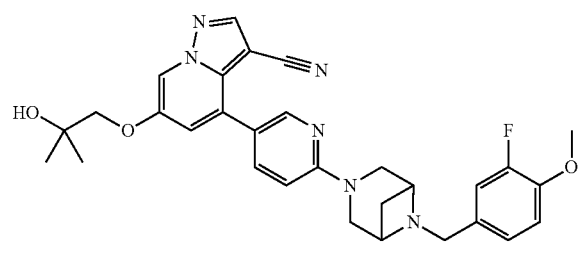 [SMILES: COc1ccc(CN2C3CC2CN(c2ccc(-c4cc(OCC(C)(C)O)cn5ncc(C#N)c45)cn2)C3)cc1F]

4-(6-(6-(3-fluoro-4-methoxybenzyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A suspension of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 32.2 mg, 0.0675 mmol) in DCM (675 µL) and DIEA (29.4 µL, 0.169 mmol) was stirred for 5 min at ambient temperature, then treated sequentially with 3-fluoro-4-methoxybenzaldehyde (20.8 mg, 0.135 mmol) and NaBH(AcO)$_3$ (42.9 mg, 0.202 mmol). After stirring overnight at ambient temperature, the reaction mixture was passed through a syringe filter (0.45 µm), rinsing with DCM until no additional UV active material was detected in the DCM rinse. The combined DCM rinses were purified by silica chromatography (using 0-100% DCM in Hexane then 0-100% (2% NH$_4$OH/20% MeOH/78% DCM) in DCM as the gradient eluent as the gradient eluent) to afford the title compound (22.3 mg, 61% yield). MS (apci) m/z=543.2 (M+H).

The compounds in Table Y were prepared using a similar method to that described for the preparation of Example 323, replacing the 3-fluoro-4-methoxybenzaldehyde with the appropriate aldehyde. Reactions were monitored for completion by LCMS, and as such reaction durations were adjusted accordingly. The title compounds were isolated following a filtration via syringe filter and chromatographic purification utilizing an appropriate gradient eluent.

TABLE Y

| Ex # | Structure | Chemical Name | MS (apci) m/z |
|---|---|---|---|
| 324 | 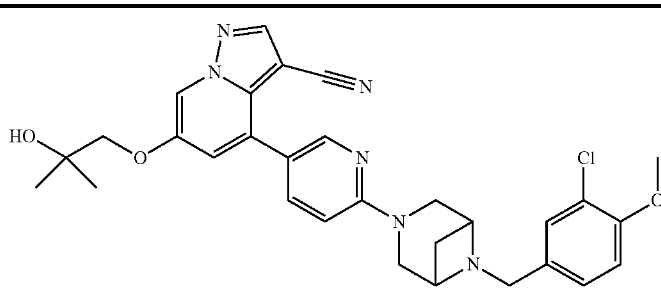 | 4-(6-(6-(3-chloro-4-methoxybenzyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 559.2 (M + H) |

TABLE Y-continued

| Ex # | Structure | Chemical Name | MS (apci) m/z |
|---|---|---|---|
| 325 | 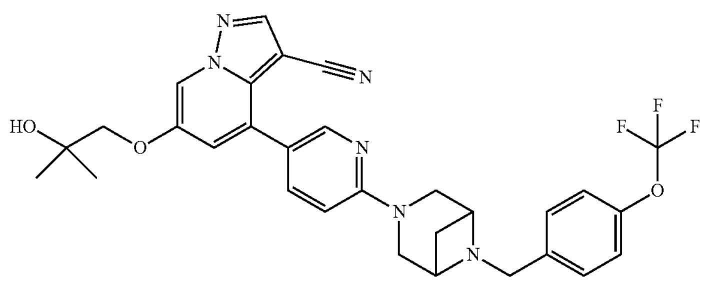 [SMILES: CC(C)(O)COc1cc(-c2ccc(N3CC4CC(C3)N4Cc3ccc(OC(F)(F)F)cc3)nc2)c2c(C#N)cnn2c1] | 6-(2-hydroxy-2-methylpropoxy)-4-(6-(6-(4-(trifluoromethoxy)benzyl)-3,6-diazabicyclo[3.1.1]heptan-3-yl)pyridin-3-yl)pyrazolo[1,5-a]pyridine-3-carbonitrile | 579.2 (M + H) |
| 326 | 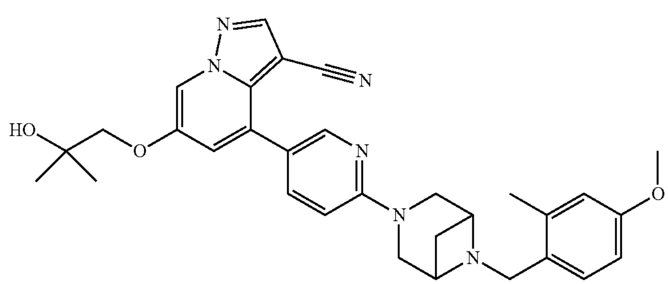 [SMILES: COc1ccc(CN2C3CC2CN(c2ccc(-c4cc(OCC(C)(C)O)cn5ncc(C#N)c45)cn2)C3)c(C)c1] | 6-(2-hydroxy-2-methylpropoxy)-4-(6-(6-(4-methoxy-2-methylbenzyl)-3,6-diazabicyclo[3.1.1]heptan-3-yl)pyridin-3-yl)pyrazolo[1,5-a]pyridine-3-carbonitrile | 539.2 (M + H) |
| 327 | 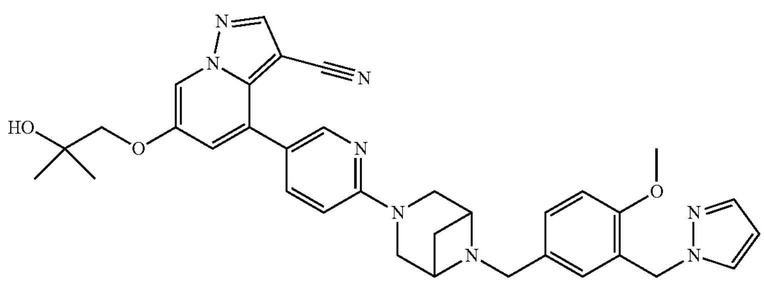 [SMILES: COc1ccc(CN2C3CC2CN(c2ccc(-c4cc(OCC(C)(C)O)cn5ncc(C#N)c45)cn2)C3)cc1Cn1cccn1] | 4-(6-(6-(3-((1H-pyrazol-1-yl)methyl)-4-methoxybenzyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 605.3 (M + H) |
| 328 | 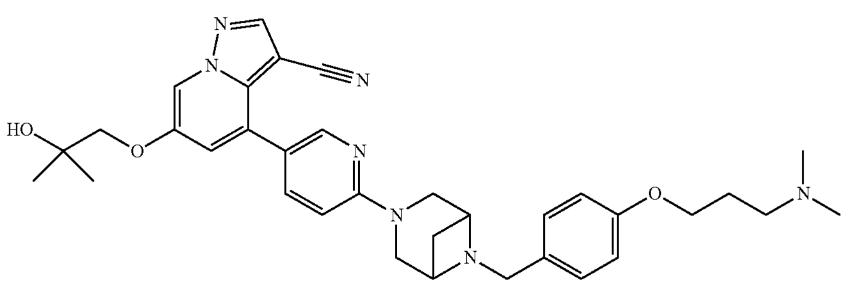 [SMILES: CN(C)CCCOc1ccc(CN2C3CC2CN(c2ccc(-c4cc(OCC(C)(C)O)cn5ncc(C#N)c45)cn2)C3)cc1] | 4-(6-(6-(4-(3-(dimethylamino)propoxy)benzyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 596.3 (M + H) |
| 329 | 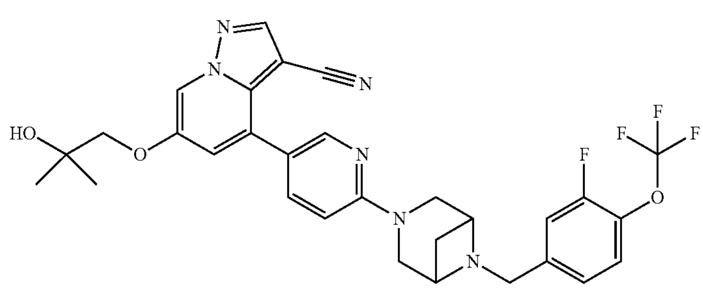 [SMILES: CC(C)(O)COc1cc(-c2ccc(N3CC4CC(C3)N4Cc3ccc(OC(F)(F)F)c(F)c3)nc2)c2c(C#N)cnn2c1] | 4-(6-(6-(3-fluoro-4-(trifluoromethoxy)benzyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 597.2 (M + H) |

Example 330

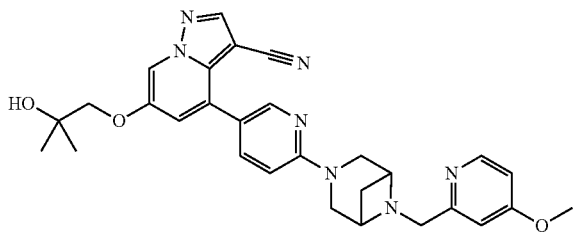 [SMILES: COc1ccnc(CN2C3CC2CN(c2ccc(-c4cc(OCC(C)(C)O)cn5ncc(C#N)c45)cn2)C3)c1]

6-(2-hydroxy-2-methylpropoxy)-4-(6-(6-((4-methoxypyridin-2-yl)methyl)-3,6-diazabicyclo[3.1.1]heptan-3-yl)pyridin-3-yl)pyrazolo[1,5-a]pyridine-3-carbonitrile A suspension of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 30.1 mg, 0.0631 mmol) and DIEA (27.5 μL, 0.158 mmol) in DCM (631 μL) was stirred for 5 min at ambient temperature. The reaction mixture was treated sequentially with 4-methoxypicolinaldehyde (8.65 mg, 0.0631 mmol) and NaBH(AcO)$_3$ (26.7 mg, 0.126 mmol). The reaction mixture was stirred for 3 d at ambient temperature. The resulting suspension was diluted with a minimal amount of DCM, then MeOH was added dropwise until the mixture became homogeneous. The DCM/MeOH solution was purified directly by silica chromatography (using 0-100% DCM in Hexane then 0-100% (2% NH$_4$OH/20% MeOH/78% DCM) in DCM as the gradient eluent as the gradient eluent) to afford the title compound (27.2 mg, 82% yield). MS (apci) m/z=526.2 (M+H).

The compounds in Table Z were prepared and worked up using a similar method to that described for the preparation of Example 330, replacing the 4-methoxypicolinaldehyde with the appropriate aldehyde. Reactions were monitored for completion by LCMS, and as such reaction durations were adjusted accordingly. The title compounds were isolated either by direct chromatographic purification utilizing an appropriate gradient eluent or where noted (*), chromatographic purification with an appropriate eluent was preceded by an aqueous work up of the reaction, consisting of dilution with DCM, extraction with saturated NaHCO$_{3(aq)}$, drying of organic extracts over anhydrous MgSO$_{4(s)}$, filtration, and concentration in vacuo.

TABLE Z

| Ex # | Structure | Chemical Name | MS (apci) m/z |
|---|---|---|---|
| 331 | 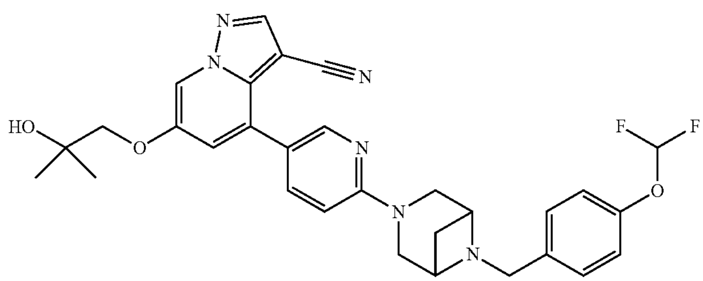 [SMILES: CC(C)(O)COc1cc(-c2ccc(N3CC4CC(C3)N4Cc3ccc(OC(F)F)cc3)nc2)c2c(C#N)cnn2c1] | 4-(6-(6-(4-(difluoromethoxy)benzyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 561.2 (M + H) |
| 332 | 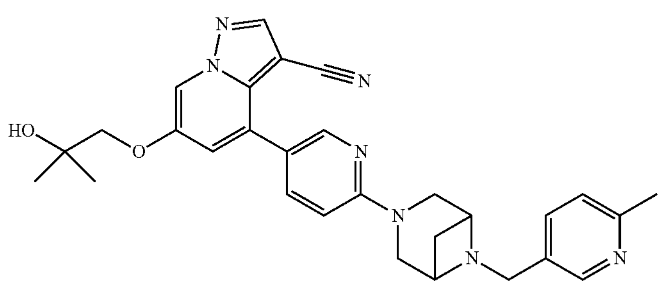 [SMILES: Cc1ccc(CN2C3CC2CN(c2ccc(-c4cc(OCC(C)(C)O)cn5ncc(C#N)c45)cn2)C3)cn1] | 6-(2-hydroxy-2-methylpropoxy)-4-(6-(6-((6-methylpyridin-3-yl)methyl)-3,6-diazabicyclo[3.1.1]heptan-3-yl)pyridin-3-yl)pyrazolo[1,5-a]pyridine-3-carbonitrile | 510.2 (M + H) |
| 333 | 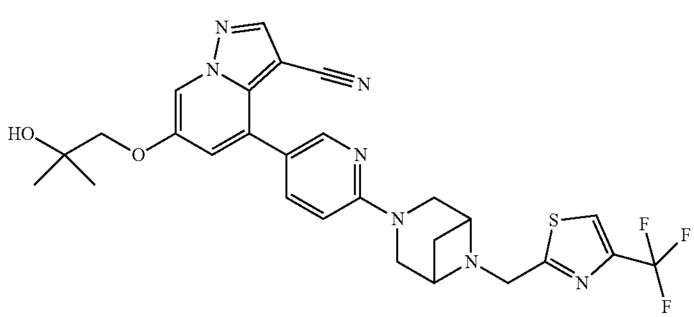 [SMILES: CC(C)(O)COc1cc(-c2ccc(N3CC4CC(C3)N4Cc3nc(C(F)(F)F)cs3)nc2)c2c(C#N)cnn2c1] | 6-(2-hydroxy-2-methylpropoxy)-4-(6-(6-((4-(trifluoromethyl)thiazol-2-yl)methyl)-3,6-diazabicyclo[3.1.1]heptan-3-yl)pyridin-3-yl)pyrazolo[1,5-a]pyridine-3-carbonitrile | 570.2 (M + H) |

TABLE Z-continued

| Ex # | Structure | Chemical Name | MS (apci) m/z |
|---|---|---|---|
| 334 | 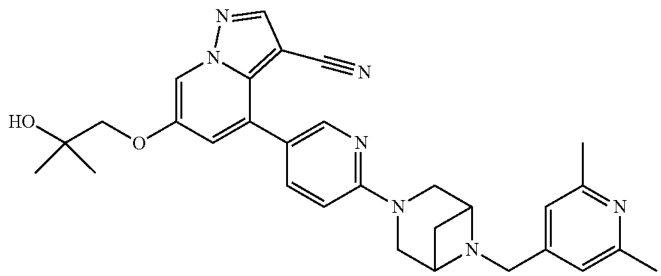 [SMILES: Cc1cc(CN2C3CC2CN(c2ccc(-c4cc(OCC(C)(C)O)cn5ncc(C#N)c45)cn2)C3)cc(C)n1] | 4-(6-(6-((2,6-dimethylpyridin-4-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 524.2 (M + H) |
| 335 | 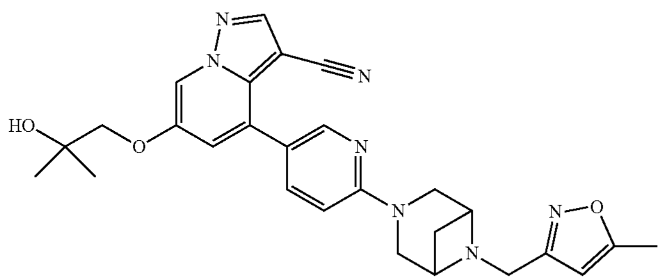 [SMILES: Cc1cc(CN2C3CC2CN(c2ccc(-c4cc(OCC(C)(C)O)cn5ncc(C#N)c45)cn2)C3)no1] | 6-(2-hydroxy-2-methylpropoxy)-4-(6-(6-((5-methylisoxazol-3-yl)methyl)-3,6-diazabicyclo[3.1.1]heptan-3-yl)pyridin-3-yl)pyrazolo[1,5-a]pyridine-3-carbonitrile | 500.2 (M + H) |
| 336 | 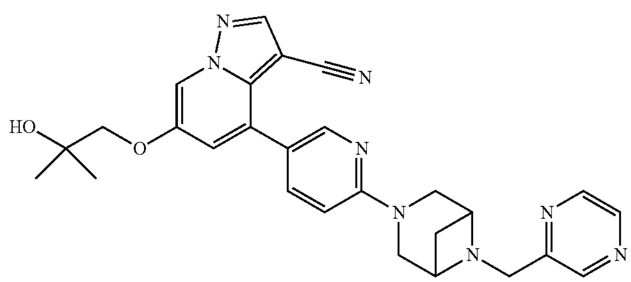 [SMILES: CC(C)(O)COc1cc(-c2ccc(N3CC4CC(C3)N4Cc3cnccn3)nc2)c2c(C#N)cnn2c1] | 6-(2-hydroxy-2-methylpropoxy)-4-(6-(6-(pyrazin-2-ylmethyl)-3,6-diazabicyclo[3.1.1]heptan-3-yl)pyridin-3-yl)pyrazolo[1,5-a]pyridine-3-carbonitrile | 497.2 (M + H) |
| 337 | 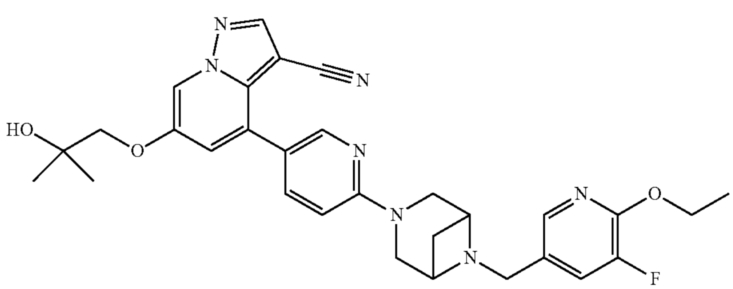 [SMILES: CCOc1ncc(CN2C3CC2CN(c2ccc(-c4cc(OCC(C)(C)O)cn5ncc(C#N)c45)cn2)C3)cc1F] | 4-(6-(6-((6-ethoxy-5-fluoropyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 558.3 (M + H) |
| 338 | 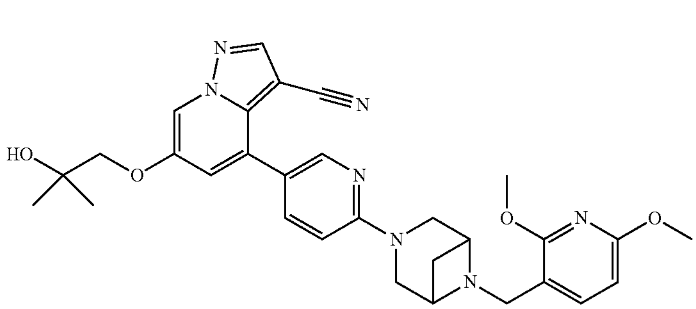 [SMILES: COc1ccc(CN2C3CC2CN(c2ccc(-c4cc(OCC(C)(C)O)cn5ncc(C#N)c45)cn2)C3)c(OC)n1] | 4-(6-(6-((2,6-dimethoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 556.3 (M + H) |

TABLE Z-continued

| Ex # | Structure | Chemical Name | MS (apci) m/z |
|---|---|---|---|
| 339 | 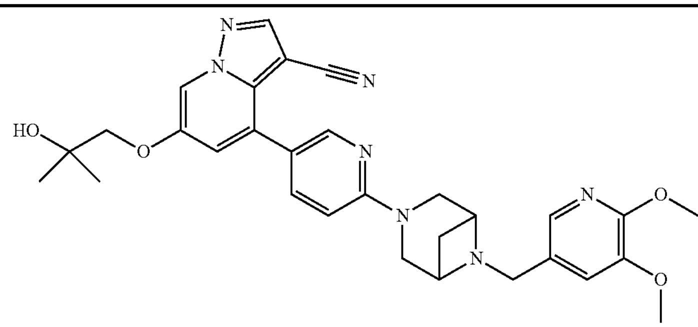 | 4-(6-(6-((5,6-dimethoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 556.3 (M + H) |

Example 340

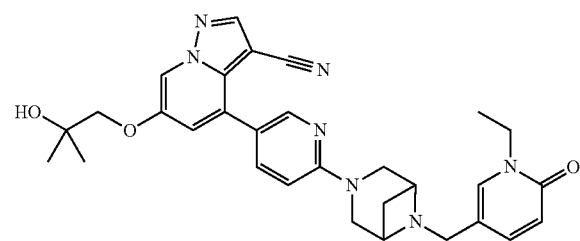 [SMILES: CCn1cc(CN2C3CC2CN(c2ccc(-c4cc(OCC(C)(C)O)cn5ncc(C#N)c45)cn2)C3)ccc1=O]

4-(6-(6-((1-ethyl-6-oxo-1,6-dihydropyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 50 mg, 0.105 mmol) in DCM (524 μL) and TEA (43.8 μL, 0.314 mmol) was stirred for 5 min at ambient temperature. The reaction mixture was treated sequentially with 1-ethyl-6-oxo-1,6-dihydropyridine-3-carbaldehyde (23.7 mg, 0.157 mmol) and NaBH(AcO)₃ (44.4 mg, 0.209 mmol). After stirring overnight at ambient temperature, additional 1-ethyl-6-oxo-1,6-dihydropyridine-3-carbaldehyde and NaBH(AcO)₃ were introduced. The reaction mixture was stirred overnight at ambient temperature. The resulting suspension was diluted with DCM (1 mL) and washed with water (3×1 mL). The combined aqueous extracts were extracted with DCM (1 mL). The combined organic extracts were washed with brine, passed through a PS frit, and concentrated in vacuo to remove most solvent (ca. 1 mL remaining). The solution was diluted with Heptane (1 mL), to form a suspension. The suspension was vacuum filtered, rinsing with additional Heptane (3×1 mL). The solids were collected and air dried to afford the title compound (9.2 mg, 16% yield). MS (apci) m/z=540.3 (M+H).

The compounds in Table AA were prepared, worked up and purified using a similar method to that described for the preparation of Example 340, replacing the 1-ethyl-6-oxo-1,6-dihydropyridine-3-carbaldehyde with the appropriate aldehyde. Reactions were monitored for completion by LCMS, and as such reaction durations were adjusted accordingly. The title compounds were cleanly isolated following filtration using Heptane or MTBE as the rinse solvent.

TABLE AA

| Ex # | Structure | Chemical Name | MS (apci) m/z |
|---|---|---|---|
| 341 | 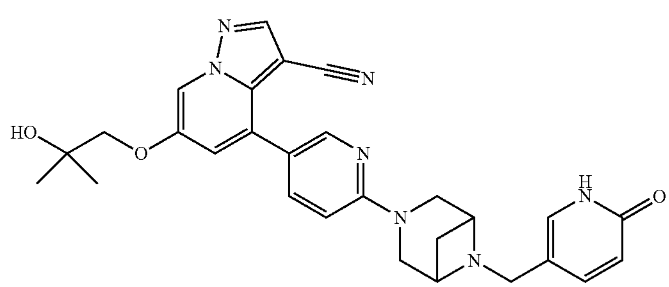 [SMILES: CC(C)(O)COc1cc(-c2ccc(N3CC4CC(C3)N4Cc3ccc(=O)[nH]c3)nc2)c2c(C#N)cnn2c1] | 6-(2-hydroxy-2-methylpropoxy)-4-(6-(6-((6-oxo-1,6-dihydropyridin-3-yl)methyl)-3,6-diazabicyclo[3.1.1]heptan-3-yl)pyridin-3-yl)pyrazolo[1,5-a]pyridine-3-carbonitrile | 512.3 (M + H) |

TABLE AA-continued

| Ex # | Structure | Chemical Name | MS (apci) m/z |
|---|---|---|---|
| 342 | 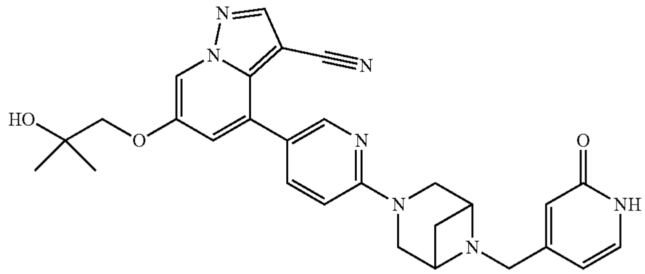 [SMILES: CC(C)(O)COc1cc(-c2ccc(N3CC4CC(C3)N4Cc3cc[nH]c(=O)c3)nc2)c2c(C#N)cnn2c1] | 6-(2-hydroxy-2-methylpropoxy)-4-(6-(6-((2-oxo-1,2-dihydropyridin-4-yl)methyl)-3,6-diazabicyclo[3.1.1]heptan-3-yl)pyridin-3-yl)pyrazolo[1,5-a]pyridine-3-carbonitrile | 512.3 (M + H) |
| 343 | 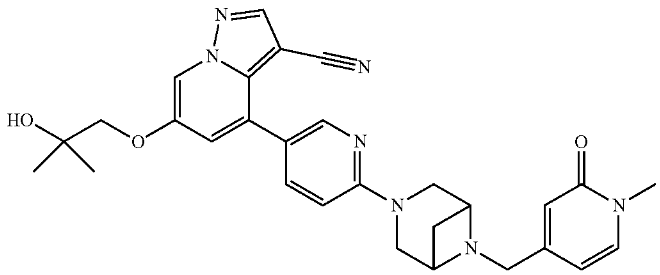 [SMILES: Cn1ccc(CN2C3CC2CN(c2ccc(-c4cc(OCC(C)(C)O)cn5ncc(C#N)c45)cn2)C3)cc1=O] | 6-(2-hydroxy-2-methylpropoxy)-4-(6-(6-((1-methyl-2-oxo-1,2-dihydropyridin-4-yl)methyl)-3,6-diazabicyclo[3.1.1]heptan-3-yl)pyridin-3-yl)pyrazolo[1,5-a]pyridine-3-carbonitrile | 526.2 (M + H) |

Example 344

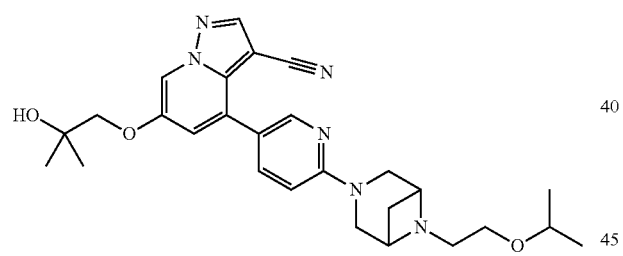

6-(2-hydroxy-2-methylpropoxy)-4-(6-(6-(2-isopropoxyethyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 20 mg, 0.0419 mmol) in DMSO (419 μL) was treated with 2-(2-bromoethoxy)propane (21.0 mg, 0.126 mmol) and TEA (28.4 μL, 0.209 mmol). The resulting mixture was stirred 16 h at 50° C. then for an additional 16 h at 70° C. After cooling to ambient temperature, the reaction mixture was purified directly by silica chromatography (using 0-100% DCM in Hexane then 0-60% (2% NH$_4$OH/20% MeOH/78% DCM) in DCM as the gradient eluent) to afford the title compound (6.1 mg, 28% yield). MS (apci) m/z=491.3 (M+H).

Example 345

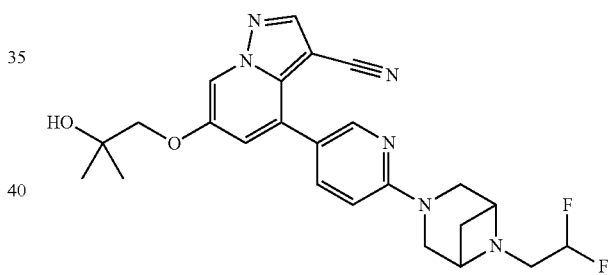

4-(6-(6-(2,2-difluoroethyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 31.3 mg, 0.0656 mmol) in DMF (656 μL) was treated with DIEA (57.1 μL, 0.328 mmol) and stirred for 15 min at ambient temperature. 2,2-Difluoroethyl trifluoromethanesulfonate (70.2 mg, 0.328 mmol) was added, and the mixture was stirred for 1 h at ambient temperature. The resulting mixture was diluted with Et$_2$O (40 mL) and washed with water (3×10 mL). The organic extracts were dried over anhydrous MgSO$_{4(s)}$, vacuum filtered through a pad of Celite® 545 and concentrated in vacuo. The residue was dissolved in the minimum amount of DCM, and then MeOH was added dropwise to create a homogeneous solution that was purified by silica chromatography (using 0-100% DCM in Hexane then 0-100% (2% NH$_4$OH/20% MeOH/78%

DCM) in DCM as the gradient eluent as the gradient eluent) to afford the title compound (9.1 mg, 30% yield). MS (apci) m/z=469.2 (M+H).

Example 346

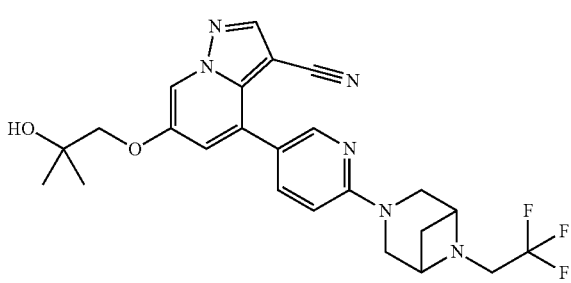 [SMILES: CC(C)(O)COc1cc(-c2ccc(N3CC4CC(C3)N4CC(F)(F)F)nc2)c2c(C#N)cnn2c1]

6-(2-hydroxy-2-methylpropoxy)-4-(6-(6-(2,2,2-trifluoroethyl)-3,6-diazabicyclo[3.1.1]heptan-3-yl)pyridin-3-yl)pyrazolo[1,5-a]pyridine-3-carbonitrile The title compound (17.6 mg, 51% yield) was prepared using a similar procedure, work up and purification to that described for Example 345, replacing 2,2-difluoroethyl trifluoromethanesulfonate with 2,2,2-trifluoroethyl triflate. MS (apci) m/z=487.2 (M+H).

Example 347

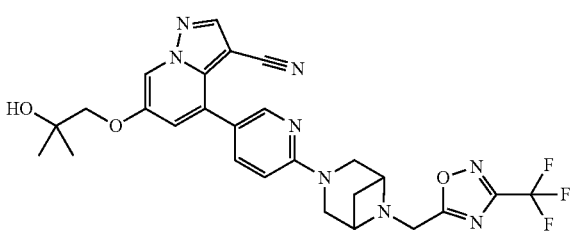 [SMILES: CC(C)(O)COc1cc(-c2ccc(N3CC4CC(C3)N4Cc3nc(C(F)(F)F)no3)nc2)c2c(C#N)cnn2c1]

6-(2-hydroxy-2-methylpropoxy)-4-(6-(6-((3-(trifluoromethyl)-1,2,4-oxadiazol-5-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 33.2 mg, 0.0695 mmol) in DMF (695 µL) was treated with DIEA (60.6 µL, 0.348 mmol), then stirred for 15 min at ambient temperature before adding 5-(chloromethyl)-3-(trifluoromethyl)-1,2,4-oxadiazole (64.9 mg, 0.348 mmol). After stirring the resulting mixture for 1 h at ambient temperature, the reaction mixture was diluted with Et₂O (40 mL) then extracted with water (3×10 mL). The organic extracts were dried over anhydrous MgSO₄(s), vacuum filtered through a pad of Celite® 545 and concentrated in vacuo. The residue was purified by silica chromatography (using 0-100% DCM in Hexane then 0-100% (2% NH₄OH/20% MeOH/78% DCM) in DCM as the gradient eluent as the gradient eluent) to afford the title compound (22.2 mg, 58% yield). MS (apci) m/z=555.2 (M+H).

Example 348

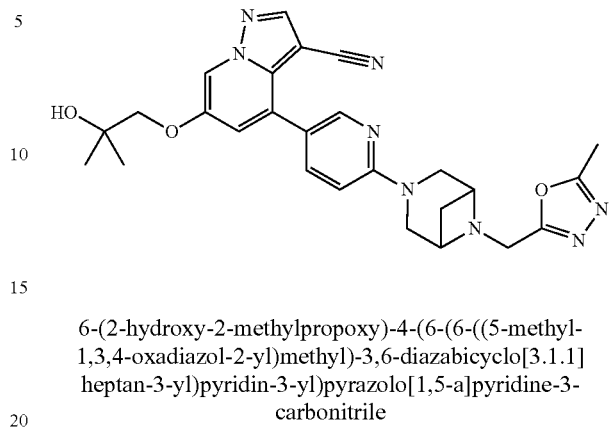

6-(2-hydroxy-2-methylpropoxy)-4-(6-(6-((5-methyl-1,3,4-oxadiazol-2-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 20 mg, 0.0419 mmol) in DMSO (837.9 µL) was treated with Cs₂CO₃(s) (54.60 mg, 0.1676 mmol) and 2-(chloromethyl)-5-methyl-1,3,4-oxadiazole (5.553 mg, 0.04189 mmol). The resulting mixture was stirred 16 h at 50° C. After cooling to ambient temperature, the reaction mixture was partitioned between DCM (1 mL) and water (5 mL), and then extracted with DCM (3×5 mL). The combined organic extracts were washed with brine (5 mL), then dried over anhydrous Na₂SO₄(s), filtered and concentrated in vacuo. The crude residue was purified by silica chromatography (using 0-100% DCM in Hexane then 0-60% (2% NH₄OH/20% MeOH/78% DCM) in DCM as the gradient eluent) to afford the title compound (10.06 mg, 46% yield). MS (apci) m/z=501.2 (M+H).

Example 349

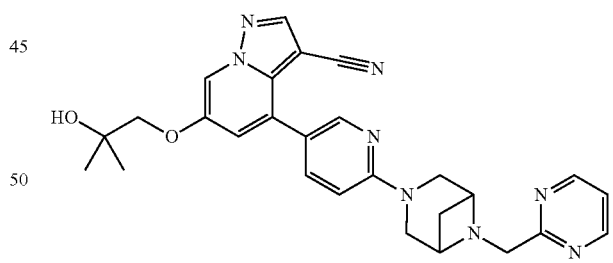

6-(2-hydroxy-2-methylpropoxy)-4-(6-(6-(pyrimidin-2-ylmethyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 40 mg, 0.084 mmol) in DMF (170 µL) was treated with 2-(chloromethyl)pyrimidine hydrochloride (0.015 g, 0.092 mmol) and TEA (58 µL, 0.42 mmol). The resulting mixture was stirred overnight at 50° C. then for an additional 16 h at 70° C. After cooling to ambient temperature, the reaction mixture was poured into water (2 mL), and stirred vigorously. The resulting suspension was vacuum filtered through a nylon membrane, rinsing the solids with water (2 mL) and Et$_2$O (2 mL). After the water rinse had passed through the filter, and the Et$_2$O had been decanted from the top of the solids (ca. 5 min), the solids were dissolved in EtOAc/MeOH, and concentrated in vacuo to afford the title compound (30 mg, 66% yield). MS (apci) m/z=497.2 (M+H).

Example 350

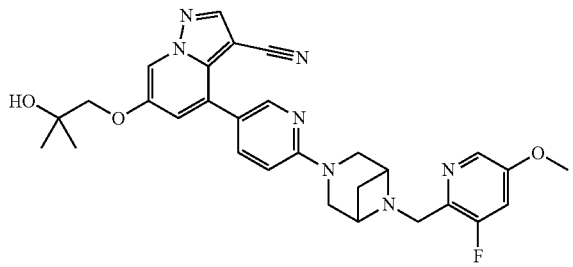 [SMILES: COc1cnc(CN2C3CC2CN(c2ccc(-c4cc(OCC(C)(C)O)cn5ncc(C#N)c45)cn2)C3)c(F)c1]

4-(6-(6-((3-fluoro-5-methoxypyridin-2-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 25.2 mg, 0.0528 mmol) and (3-fluoro-5-methoxypyridin-2-yl)methyl methanesulfonate (43.5 mg, 0.185 mmol) in DMSO (500 µL) was treated with DIEA (46.0 µL, 0.264 mmol). The resulting mixture was stirred for 16 h at 70° C. temperature. After cooling to ambient temperature, the reaction mixture was purified directly by C18 reverse phase chromatography (using 5-95% water-ACN with 0.1% TFA as the gradient eluent). Fractions containing the desired compound were combined, diluted with 4:1 DCM:iPrOH, and then extracted with saturated NaHCO$_{3(aq)}$. The organic extracts were dried over anhydrous Na$_2$SO$_{4(s)}$, filtered, and concentrated in vacuo to cleanly provide the title compound (9.5 mg, 33% yield). MS (apci) m/z=544.3 (M+H).

Example 351

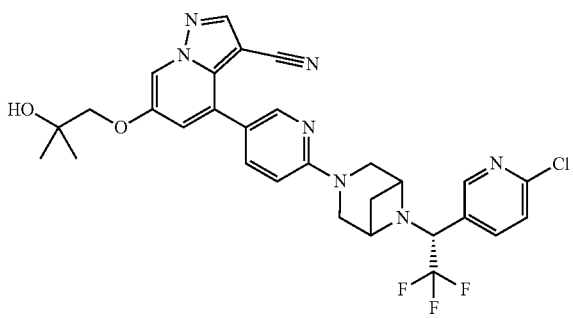 [SMILES: CC(C)(O)COc1cc(-c2ccc(N3CC4CC(C3)N4[C@H](c3ccc(Cl)nc3)C(F)(F)F)nc2)c2c(C#N)cnn2c1]

4-(6-(6-((R)-1-(6-chloropyridin-3-yl)-2,2,2-trifluoroethyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A mixture of (S)-1-(6-chloropyridin-3-yl)-2,2,2-trifluoroethan-1-ol (43.2 mg, 0.204 mmol) and Lutidine (25.1 µL, 0.216 mmol) in ACN (500 µL) was stirred for 10 min at −42° C. (dry ice/ACN cooling bath). The cold mixture was treated slowly with Tf-O-Tf (35.3 µL, 0.210 mmol). The resulting mixture was stirred for 1 h at −42° C. before introducing a solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile (Intermediate P44; 50 mg, 0.124 mmol) and DIEA (43.2 µL, 0.358 mmol) in DMA (500 µL). After stirred for 18 h at ambient temperature, the reaction mixture was directly purified by reverse phase chromatography (5-95% ACN in water with 0.1% TFA as the gradient eluent) followed by a second silica chromatography (0-100% DCM in hexane then 0-60% (2% NH$_4$OH/20% MeOH/78% DCM) in DCM as the gradient eluent) to afford the title compound (22 mg, 30% yield). MS (apci) m/z=598.2 (M+H).

Example 352

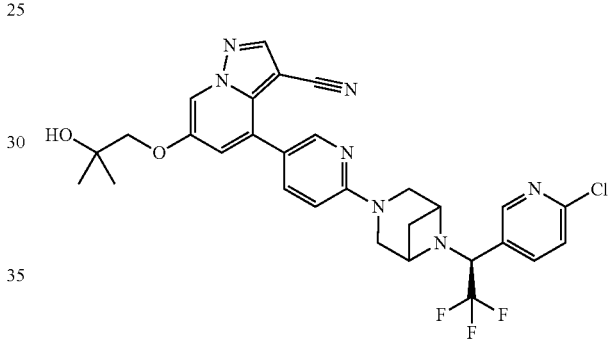

4-(6-(6-((S)-1-(6-chloropyridin-3-yl)-2,2,2-trifluoroethyl)-3,6-diazabicyclo[3.1.1]heptan-3-yl)pyridin-3-yl)-6-(2-hydroxy-2-methylpropoxy)pyrazolo[1,5-a]pyridine-3-carbonitrile The title compound (41 mg, 56% yield) was prepared, worked up and purified using a similar procedure to that described for Example 351, replacing (S)-1-(6-chloropyridin-3-yl)-2,2,2-trifluoroethan-1-ol with (R)-1-(6-chloropyridin-3-yl)-2,2,2-trifluoroethan-1-ol. MS (apci) m/z=598.2 (M+H).

Example 353

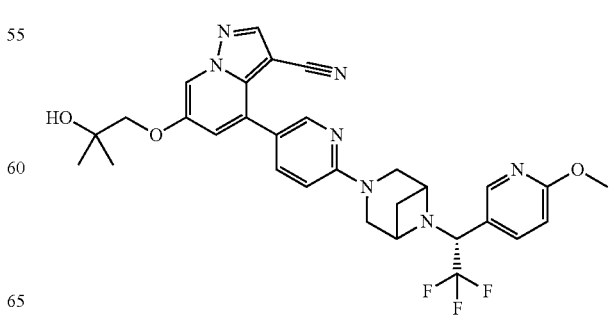

6-(2-hydroxy-2-methylpropoxy)-4-(6-(6-((R)-2,2,2-trifluoro-1-(6-methoxypyridin-3-yl)ethyl)-3,6-diazabicyclo[3.1.1]heptan-3-yl)pyridin-3-yl)pyrazolo[1,5-a]pyridine-3-carbonitrile A solution of 4-(6-(6-((R)-1-(6-chloropyridin-3-yl)-2,2,2-trifluoroethyl)-3,6-diazabicyclo[3.1.1]heptan-3-yl)pyridin-3-yl)-6-(2-hydroxy-2-methylpropoxy)pyrazolo[1,5-a]pyridine-3-carbonitrile (Example 351; 50 mg, 0.124 mmol) in MeOH (500 μL) was treated with 30 wt % NaOMe in MeOH (31.1 μL, 0.167 mmol), then stirred overnight at 70° C. After cooling to ambient temperature, the reaction mixture was purified directly by silica chromatography (using 0-100% DCM in Hexane then 0-60% (2% $NH_4OH$/20% MeOH/78% DCM) in DCM as the gradient eluent) to afford the title compound (18 mg, 91% yield). MS (apci) m/z=594.2 (M+H).

Example 354

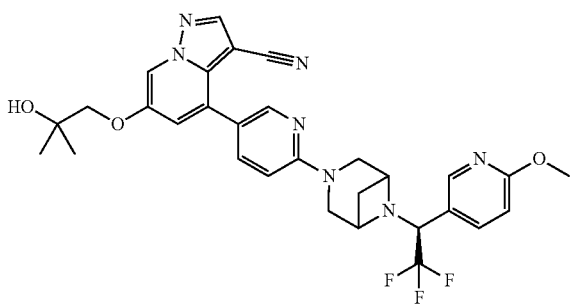 [SMILES: COc1ccc([C@H](N2C3CC2CN(c2ccc(-c4cc(OCC(C)(C)O)cn5ncc(C#N)c45)cn2)C3)C(F)(F)F)cn1]

6-(2-hydroxy-2-methylpropoxy)-4-(6-(6-((S)-2,2,2-trifluoro-1-(6-methoxypyridin-3-yl)ethyl)-3,6-diazabicyclo[3.1.1]heptan-3-yl)pyridin-3-yl)pyrazolo[1,5-a]pyridine-3-carbonitrile The title compound (7.42 mg, 75% yield) was prepared, worked up and purified using a similar procedure to that described for Example 353, replacing 4-(6-(6-((R)-1-(6-chloropyridin-3-yl)-2,2,2-trifluoroethyl)-3,6-diazabicyclo[3.1.1]heptan-3-yl)pyridin-3-yl)-6-(2-hydroxy-2-methylpropoxy)pyrazolo[1,5-a]pyridine-3-carbonitrile with 4-(6-(6-((S)-1-(6-chloropyridin-3-yl)-2,2,2-trifluoroethyl)-3,6-diazabicyclo[3.1.1]heptan-3-yl)pyridin-3-yl)-6-(2-hydroxy-2-methylpropoxy)pyrazolo[1,5-a]pyridine-3-carbonitrile (Example 352). MS (apci) m/z=594.25 (M+H).

Example 355

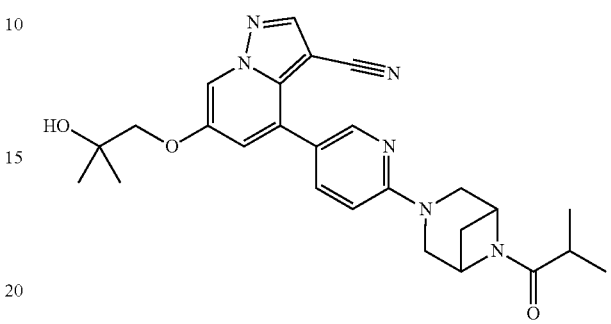

6-(2-hydroxy-2-methylpropoxy)-4-(6-(6-isobutyryl-3,6-diazabicyclo[3.1.1]heptan-3-yl)pyridin-3-yl)pyrazolo[1,5-a]pyridine-3-carbonitrile A mixture of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 20 mg, 0.0419 mmol) and DIEA (36.5 μL, 0.209 mmol) in DCM (209 μL) was treated with isobutyryl chloride (4.91 mg, 0.0461 mmol), and the mixture was stirred for 2 h at ambient temperature. The resulting mixture was concentrated in vacuo, then purified by silica chromatography (using 50-100% EtOAc in Hexanes, then 0-20% MeOH in EtOAc as the gradient eluent) to afford the title compound (9.31 mg, 47% yield). MS (apci) m/z=475.2 (M+H).

The compounds in Table BB were prepared and purified using a similar method to that described for the preparation of Example 355, replacing the isobutyryl chloride with the appropriate acid chloride. Reactions were monitored for completion by LCMS, and as such, reaction durations were adjusted accordingly. The title compounds were isolated by chromatographic purification utilizing an appropriate gradient eluent.

TABLE BB

| Ex # | Structure | Chemical Name | MS (apci) m/z |
|---|---|---|---|
| 356 | ![structure] | 4-(6-(6-(cyclopropanecarbonyl)-3,6-diazabicyclo[3.1.1]heptan-3-yl)pyridin-3-yl)6-(2-hydroxy-2-methylpropoxy)pyrazolo[1,5-a]pyridine-3-carbonitrile | 473.2 (M + H) |

TABLE BB-continued

| Ex # | Structure | Chemical Name | MS (apci) m/z |
|---|---|---|---|
| 357 | 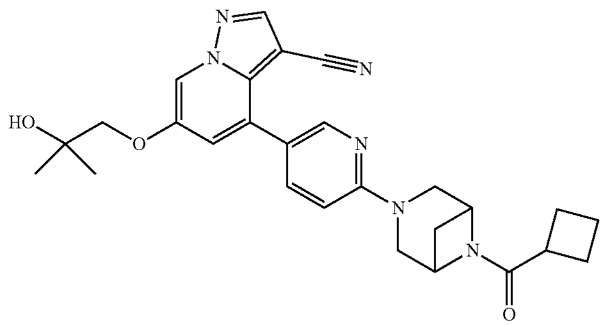 [SMILES: CC(C)(O)COc1cc(-c2ccc(N3CC4CC(C3)N4C(=O)C3CCC3)nc2)c2c(C#N)cnn2c1] | 4-(6-(6-(cyclobutanecarbonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 487.2 (M + H) |
| 358 | 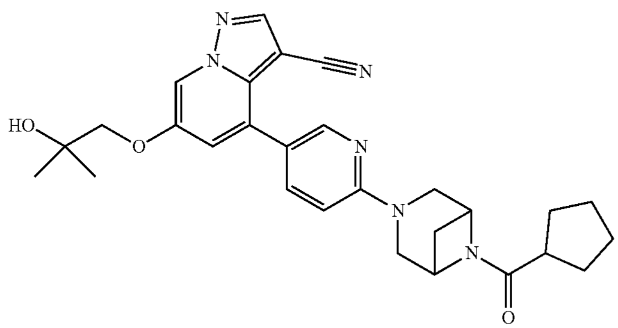 [SMILES: CC(C)(O)COc1cc(-c2ccc(N3CC4CC(C3)N4C(=O)C3CCCC3)nc2)c2c(C#N)cnn2c1] | 4-(6-(6-(cyclopentanecarbonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 501.3 (M + H) |
| 359 | 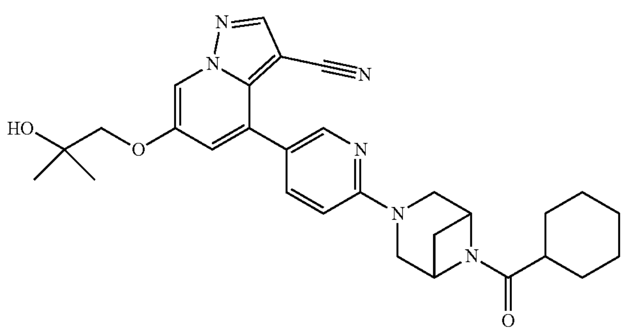 [SMILES: CC(C)(O)COc1cc(-c2ccc(N3CC4CC(C3)N4C(=O)C3CCCCC3)nc2)c2c(C#N)cnn2c1] | 4-(6-(6-(cyclohexanecarbonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 515.3 (M + H) |
| 360 | 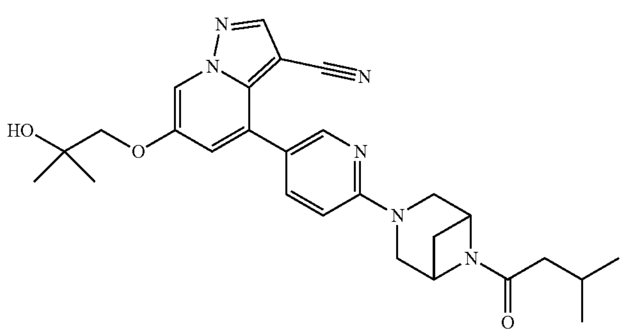 [SMILES: CC(C)CC(=O)N1C2CC1CN(c1ccc(-c3cc(OCC(C)(C)O)cn4ncc(C#N)c34)cn1)C2] | 6-(2-hydroxy-2-methylpropoxy)-4-(6-(6-(3-methylbutanoyl)-3,6-diazabicyclo[3.1.1]heptan-3-yl)pyridin-3-yl)pyrazolo[1,5-a]pyridine-3-carbonitrile | 489.3 (M + H) |

Example 361: 6-(2-hydroxy-2-methylpropoxy)-4-(6-(6-(2,2,2-trifluoroacetyl)-3,6-diazabicyclo[3.1.1]heptan-3-yl)pyridin-3-yl)pyrazolo[1,5-a]pyridine-3-carbonitrile and Example 362: 1-((3-cyano-4-(6-(6-(2,2,2-trifluoroacetyl)-3,6-diazabicyclo[3.1.1]heptan-3-yl)pyridin-3-yl)pyrazolo[1,5-a]pyridin-6-yl)oxy)-2-methylpropan-2-yl 2,2,2-trifluoroacetate

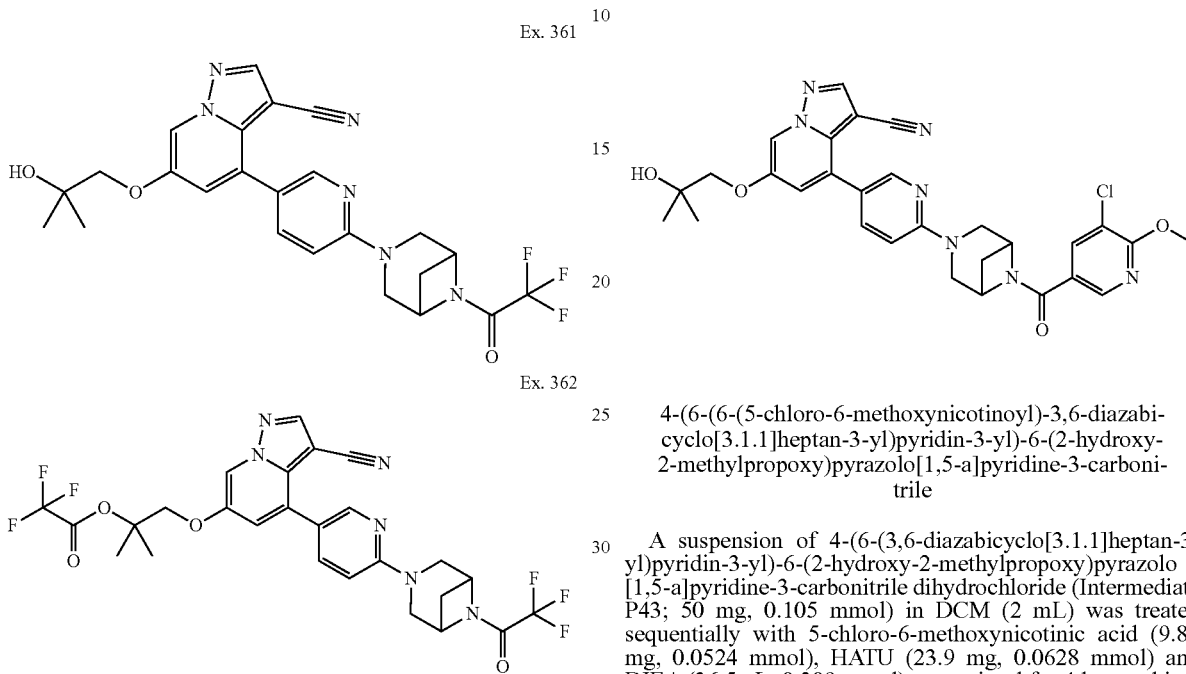

A mixture of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 50 mg, 0.105 mmol) in DCM (524 µL) was treated with TEA (43.8 µL, 0.314 mmol). The resulting suspension was cooled in an ice bath, then treated 2,2,2-trifluoroacetic anhydride (26.4 mg, 0.126 mmol). The cooling bath was removed, and the reaction mixture was stirred for 1.5 h at ambient temperature. The resulting mixture was purified directly by C18 reverse phase chromatography (5-90% ACN/water as the gradient eluent) to independently afford the title compounds representing mono- and di-coupling products of the starting material: Example 361: 6-(2-hydroxy-2-methylpropoxy)-4-(6-(6-(2,2,2-trifluoroacetyl)-3,6-diazabicyclo[3.1.1]heptan-3-yl)pyridin-3-yl)pyrazolo[1,5-a]pyridine-3-carbonitrile (18.3 mg, 35% yield). MS (apci) m/z=501.2 (M+H). Example 362: 1-((3-cyano-4-(6-(6-(2,2,2-trifluoroacetyl)-3,6-diazabicyclo[3.1.1]heptan-3-yl)pyridin-3-yl)pyrazolo[1,5-a]pyridin-6-yl)oxy)-2-methylpropan-2-yl 2,2,2-trifluoroacetate (26.8 mg, 42% yield). MS (apci) m/z=597.2 (M+H).

Example 363

4-(6-(6-(5-chloro-6-methoxynicotinoyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A suspension of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 50 mg, 0.105 mmol) in DCM (2 mL) was treated sequentially with 5-chloro-6-methoxynicotinic acid (9.82 mg, 0.0524 mmol), HATU (23.9 mg, 0.0628 mmol) and DIEA (36.5 µL, 0.209 mmol). was stirred for 4 h at ambient temperature. The reaction mixture was purified directly by silica chromatography (using 50-100% EtOAc in Hexanes then 0-20% MeOH in EtOAc as the gradient eluent) to cleanly provide the title compound (18.3 mg, 61% yield). MS (apci) m/z=574.2 (M+H).

Except where noted (*), the compounds in Table CC were prepared using a similar method to that described for the preparation of Example 363, replacing the 5-chloro-6-methoxynicotinic acid with the appropriate carboxylic acid (1.0-1.2 equivalents). Reactions were monitored for completion by LCMS. As such, reaction durations and the addition of supplemental reagents were adjusted accordingly. The title compounds were isolated by chromatographic purification utilizing an appropriate gradient eluent.

TABLE CC

| Ex # | Structure | Chemical Name | MS (apci) m/z |
|---|---|---|---|
| 364 | 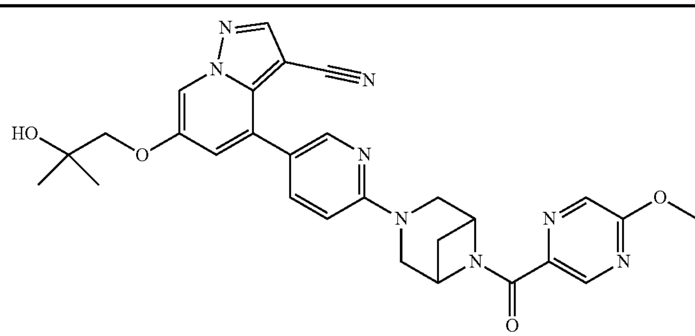 | 6-(2-hydroxy-2-methylpropoxy)-4-(6-(6-(5-methoxypyrazine-2-carbonyl)-3,6-diazabicyclo[3.1.1]heptan-3-yl)pyridin-3-yl)pyrazolo[1,5-a]pyridine-3-carbonitrile | 541.2 (M + H) |

TABLE CC-continued

| Ex # | Structure | Chemical Name | MS (apci) m/z |
|---|---|---|---|
| 365 | 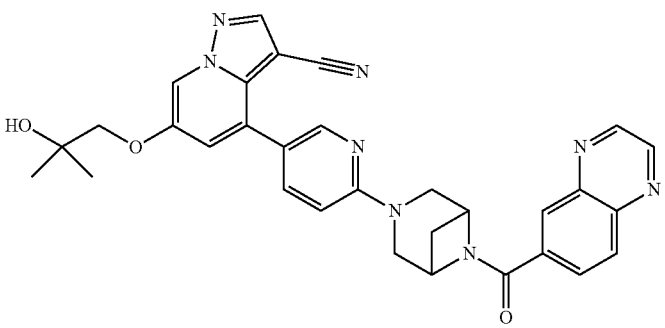 [SMILES: CC(C)(O)COc1cc(-c2ccc(N3CC4CC(C3)N4C(=O)c3ccc4nccnc4c3)nc2)c2c(C#N)cnn2c1] | 6-(2-hydroxy-2-methylpropoxy)-4-(6-(6-(quinoxaline-6-carbonyl)-3,6-diazabicyclo[3.1.1]heptan-3-yl)pyridin-3-yl)pyrazolo[1,5-a]pyridine-3-carbonitrile | 561.2 (M + H) |
| 366 | 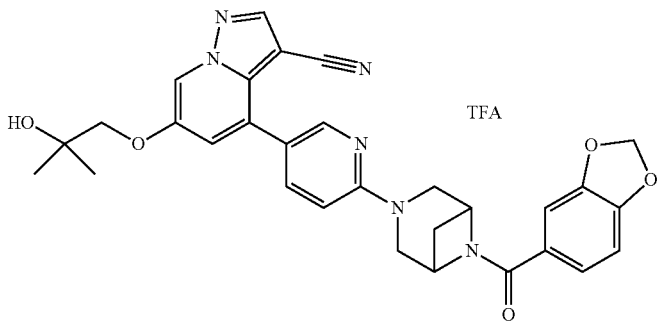 [SMILES: CC(C)(O)COc1cc(-c2ccc(N3CC4CC(C3)N4C(=O)c3ccc4c(c3)OCO4)nc2)c2c(C#N)cnn2c1] | 4-(6-(6-(benzo[d][1,3]dioxole-5-carbonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile 2,2,2-trifluoroacetate | 553.2 (M + H) |
| 367 | 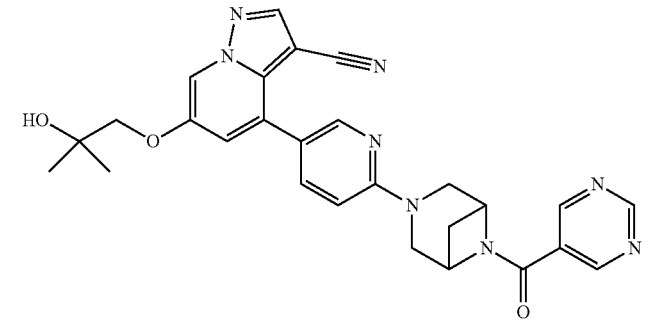 [SMILES: CC(C)(O)COc1cc(-c2ccc(N3CC4CC(C3)N4C(=O)c3cncnc3)nc2)c2c(C#N)cnn2c1] | 6-(2-hydroxy-2-methylpropoxy)-4-(6-(6-(pyrimidine-5-carbonyl)-3,6-diazabicyclo[3.1.1]heptan-3-yl)pyridin-3-yl)pyrazolo[1,5-a]pyridine-3-carbonitrile | 511.2 (M + H) |
| 368 | 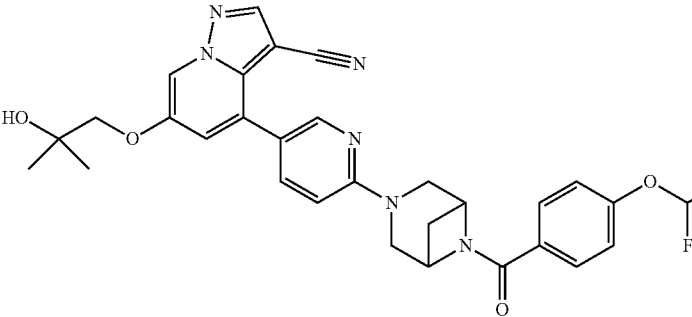 | 4-(6-(6-(4-(difluoromethoxy)benzoyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 575.2 (M + H) |

TABLE CC-continued

| Ex # | Structure | Chemical Name | MS (apci) m/z |
|---|---|---|---|
| 369 | 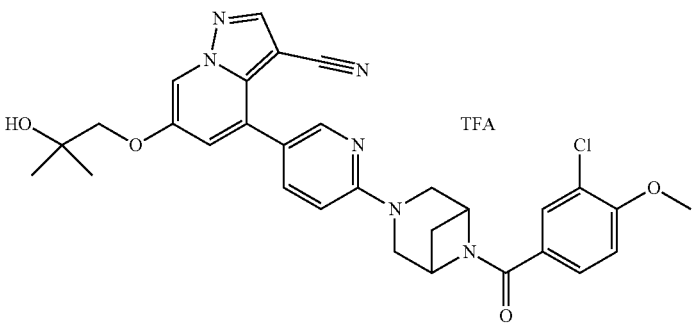 [SMILES: COc1ccc(C(=O)N2C3CC2CN(c2ccc(-c4cc(OCC(C)(C)O)cn5ncc(C#N)c45)cn2)C3)cc1Cl] | 4-(6-(6-(3-chloro-4-methoxybenzoyl)-3,6-diazabicyclo[3.1.1]heptan-3-yl)pyridin-3-yl)-6-(2-hydroxy-2-methylpropoxy)pyrazolo[1,5-a]pyridine-3-carbonitrile 2,2,2-trifluoroacetate | 573.2 (M + H) |
| 370 | 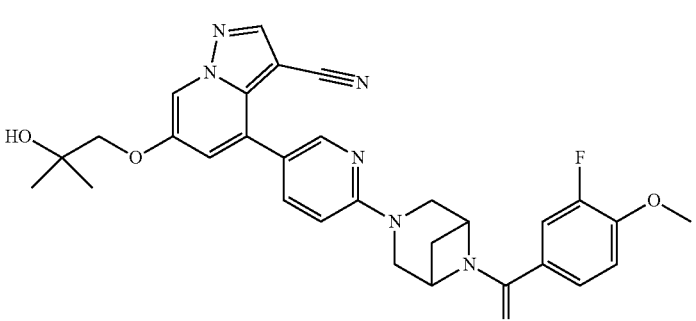 | 4-(6-(6-(3-fluoro-4-methoxybenzoyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 557.2 (M + H) |
| 371 | 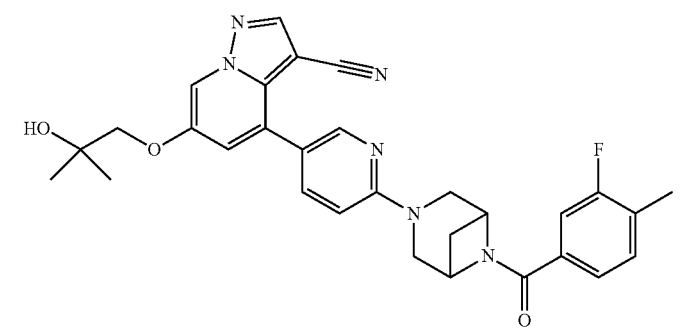 [SMILES: Cc1ccc(C(=O)N2C3CC2CN(c2ccc(-c4cc(OCC(C)(C)O)cn5ncc(C#N)c45)cn2)C3)cc1F] | 4-(6-(6-(3-fluoro-4-methylbenzoyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 541.2 (M + H) |
| 372 | 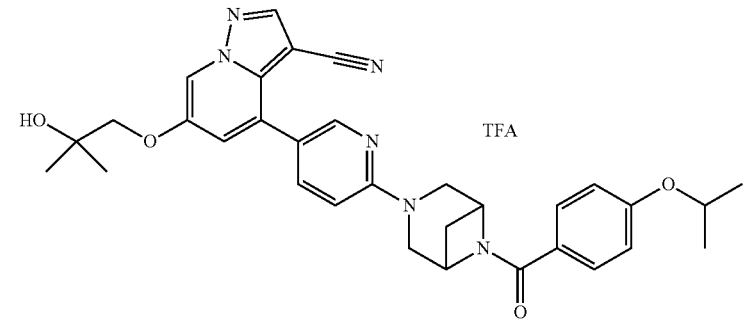 [SMILES: CC(C)Oc1ccc(C(=O)N2C3CC2CN(c2ccc(-c4cc(OCC(C)(C)O)cn5ncc(C#N)c45)cn2)C3)cc1] | 6-(2-hydroxy-2-methylpropoxy)-4-(6-(6-(4-isopropoxybenzoyl)-3,6-diazabicyclo[3.1.1]heptan-3-yl)pyridin-3-yl)pyrazolo[1,5-a]pyridine-3-carbonitrile 2,2,2-trifluoroacetate | 567.25 (M + H) |

TABLE CC-continued

| Ex # | Structure | Chemical Name | MS (apci) m/z |
|---|---|---|---|
| 373 | 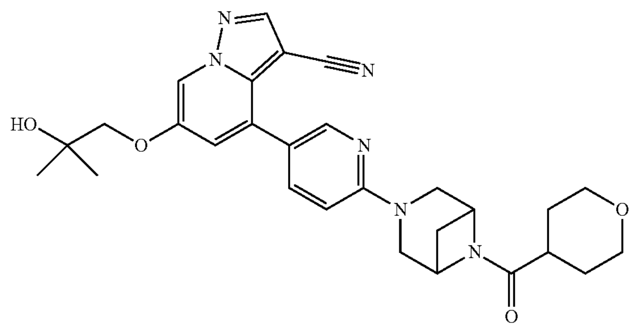 [SMILES: CC(C)(O)COc1cc(-c2ccc(N3CC4CC(C3)N4C(=O)C3CCOCC3)nc2)c2c(C#N)cnn2c1] | 6-(2-hydroxy-2-methylpropoxy)-4-(6-(6-(tetrahydro-2H-pyran-4-carbonyl)-3,6-diazabicyclo[3.1.1]heptan-3-yl)pyridin-3-yl)pyrazolo[1,5-a]pyridine-3-carbonitrile | 517.4 (M + H) |
| 374 | 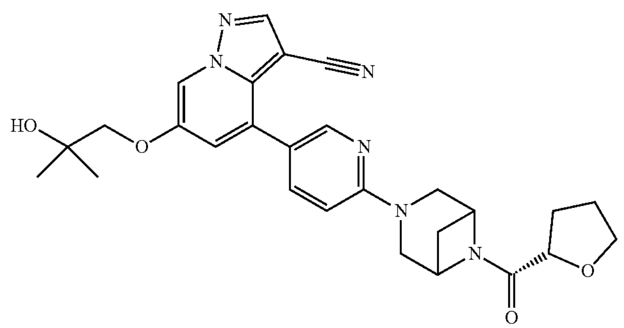 | 6-(2-hydroxy-2-methylpropoxy)-4-(6-(6-((S)-tetrahydrofuran-2-carbonyl)-3,6-diazabicyclo[3.1.1]heptan-3-yl)pyridin-3-yl)pyrazolo[1,5-a]pyridine-3-carbonitrile | 503.3 (M + H) |
| 375 | 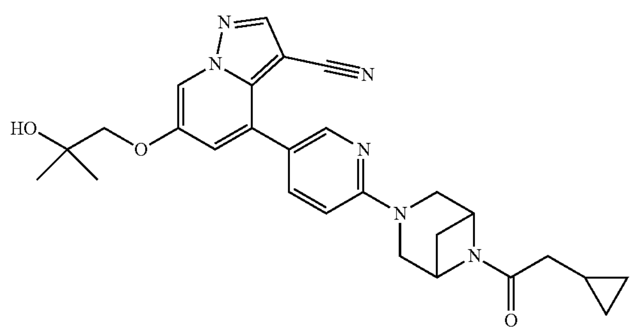 [SMILES: CC(C)(O)COc1cc(-c2ccc(N3CC4CC(C3)N4C(=O)CC3CC3)nc2)c2c(C#N)cnn2c1] | 4-(6-(6-(2-cyclopropylacetyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 487.3 (M + H) |
| 376 | 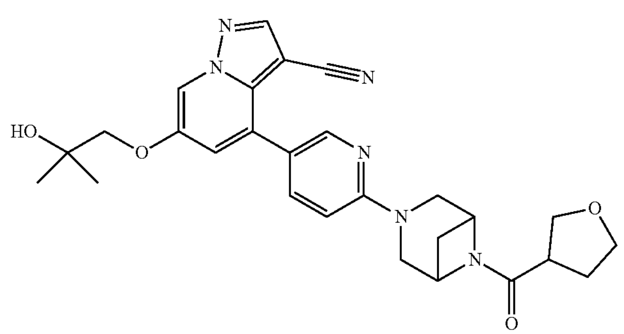 [SMILES: CC(C)(O)COc1cc(-c2ccc(N3CC4CC(C3)N4C(=O)C3CCOC3)nc2)c2c(C#N)cnn2c1] | 6-(2-hydroxy-2-methylpropoxy)-4-(6-(6-(tetrahydrofuran-3-carbonyl)-3,6-diazabicyclo[3.1.1]heptan-3-yl)pyridin-3-yl)pyrazolo[1,5-a]pyridine-3-carbonitrile | 503.25 (M + H) |

TABLE CC-continued

| Ex # | Chemical Name | MS (apci) m/z |
|---|---|---|
| 377 | 6-(2-hydroxy-2-methylpropoxy)-4-(6-(6-((1r,4r)-4-methylcyclohexane-1-carbonyl)-3,6-diazabicyclo[3.1.1]heptan-3-yl)pyridin-3-yl)pyrazolo[1,5-a]pyridine-3-carbonitrile | 529.3 (M + H) |
| 378 | 6-(2-hydroxy-2-methylpropoxy)-4-(6-(6-((R)-tetrahydrofuran-2-carbonyl)-3,6-diazabicyclo[3.1.1]heptan-3-yl)pyridin-3-yl)pyrazolo[1,5-a]pyridine-3-carbonitrile | 503.25 (M + H) |
| 379 | 6-(2-hydroxy-2-methylpropoxy)-4-(6-(6-(3-hydroxy-3-methylbutanoyl)-3,6-diazabicyclo[3.1.1]heptan-3-yl)pyridin-3-yl)pyrazolo[1,5-a]pyridine-3-carbonitrile | 505.25 (M + H) |
| 380 | 4-(6-(6-(3,3-dimethylcyclobutane-1-carbonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 515.3 (M + H) |

TABLE CC-continued

| Ex # | Structure | Chemical Name | MS (apci) m/z |
|---|---|---|---|
| 381 | 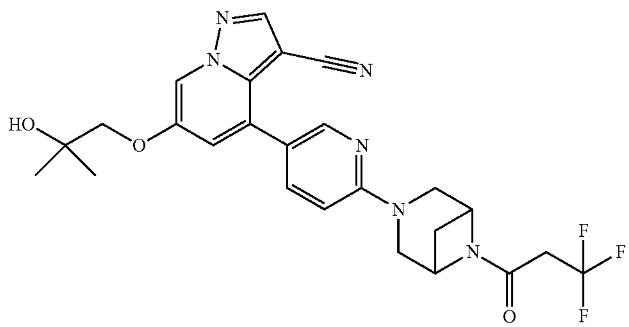 [SMILES: CC(C)(O)COc1cc(-c2ccc(N3CC4CC(C3)N4C(=O)CC(F)(F)F)nc2)c2c(C#N)cnn2c1] | 6-(2-hydroxy-2-methylpropoxy)-4-(6-(6-(3,3,3-trifluoropropanoyl)-3,6-diazabicyclo[3.1.1]heptan-3-yl)pyridin-3-yl)pyrazolo[1,5-a]pyridine-3-carbonitrile | 515.2 (M + H) |
| 382 | 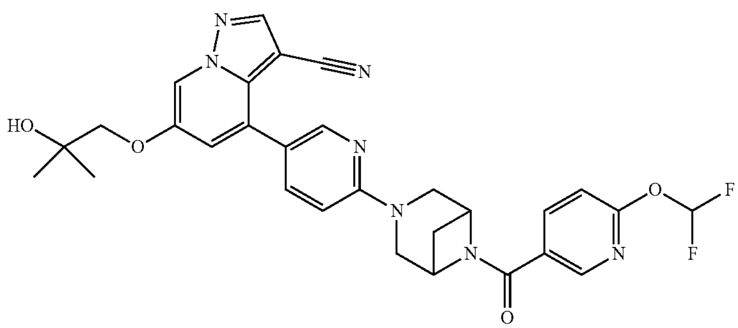 [SMILES: CC(C)(O)COc1cc(-c2ccc(N3CC4CC(C3)N4C(=O)c3ccc(OC(F)F)nc3)nc2)c2c(C#N)cnn2c1] | 4-(6-(6-(6-(difluoromethoxy)nicotinoyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 576.2 (M + H) |
| 383 | 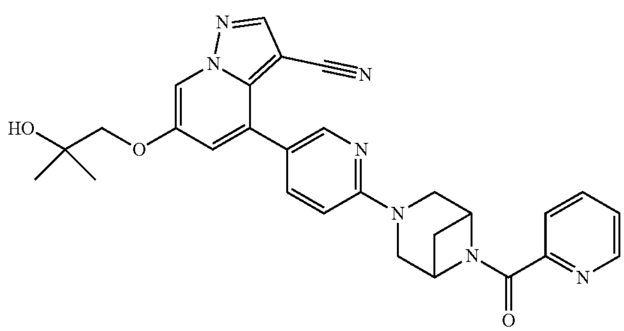 [SMILES: CC(C)(O)COc1cc(-c2ccc(N3CC4CC(C3)N4C(=O)c3ccccn3)nc2)c2c(C#N)cnn2c1] | 6-(2-hydroxy-2-methylpropoxy)-4-(6-(6-picolinoyl-3,6-diazabicyclo[3.1.1]heptan-3-yl)pyridin-3-yl)pyrazolo[1,5-a]pyridine-3-carbonitrile | 510.2 (M + H) |
| 384 | 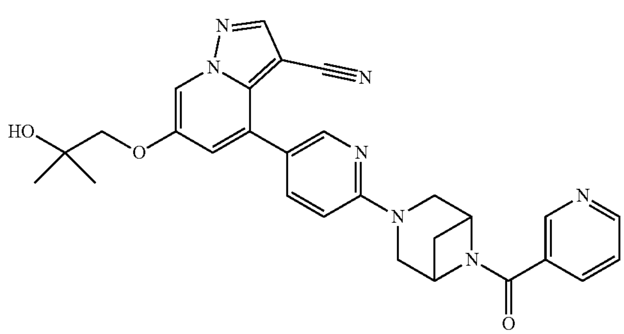 [SMILES: CC(C)(O)COc1cc(-c2ccc(N3CC4CC(C3)N4C(=O)c3cccnc3)nc2)c2c(C#N)cnn2c1] | 6-(2-hydroxy-2-methylpropoxy)-4-(6-(6-nicotinoyl-3,6-diazabicyclo[3.1.1]heptan-3-yl)pyridin-3-yl)pyrazolo[1,5-a]pyridine-3-carbonitrile | 510.25 (M + H) |

TABLE CC-continued

| Ex # | Structure | Chemical Name | MS (apci) m/z |
|---|---|---|---|
| 385 | 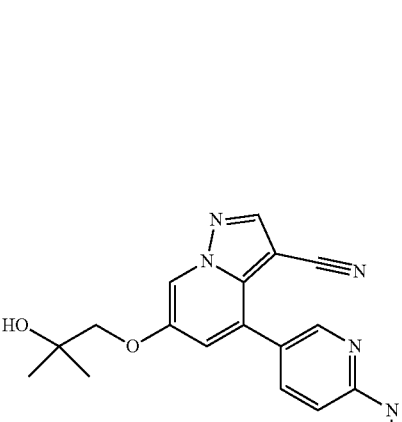 | 6-(2-hydroxy-2-methylpropoxy)-4-(6-(6-(5-methylpicolinoyl)-3,6-diazabicyclo[3.1.1]heptan-3-yl)pyridin-3-yl)pyrazolo[1,5-a]pyridine-3-carbonitrile | 524.2 (M + H) |
| 386 | 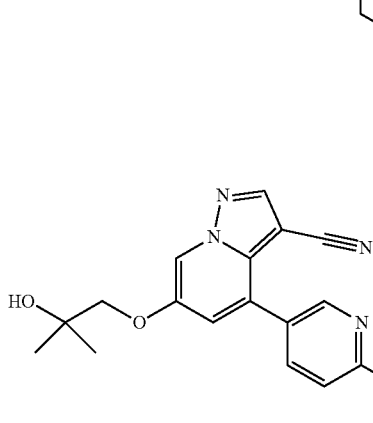 | 6-(2-hydroxy-2-methylpropoxy)-4-(6-(6-(4-methoxycyclohexane-1-carbonyl)-3,6-diazabicyclo[3.1.1]heptan-3-yl)pyridin-3-yl)pyrazolo[1,5-a]pyridine-3-carbonitrile | 545.3 (M + H) |
| 387 | 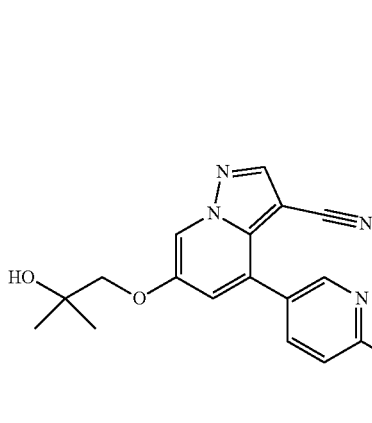 | 6-(2-hydroxy-2-methylpropoxy)-4-(6-(6-(3-methylpicolinoyl)-3,6-diazabicyclo[3.1.1]heptan-3-yl)pyridin-3-yl)pyrazolo[1,5-a]pyridine-3-carbonitrile | 524.2 (M + H) |
| 388 | 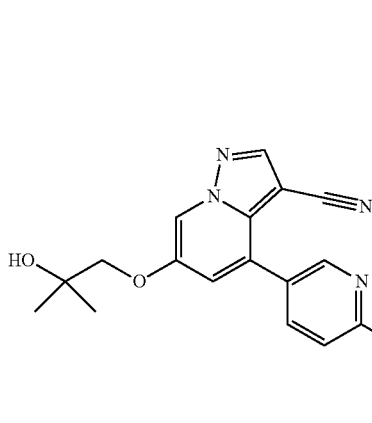 | 6-(2-hydroxy-2-methylpropoxy)-4-(6-(6-(6-methylpicolinoyl)-3,6-diazabicyclo[3.1.1]heptan-3-yl)pyridin-3-yl)pyrazolo[1,5-a]pyridine-3-carbonitrile | 524.2 (M + H) |

TABLE CC-continued

| Ex # | Structure | Chemical Name | MS (apci) m/z |
|---|---|---|---|
| 389 | 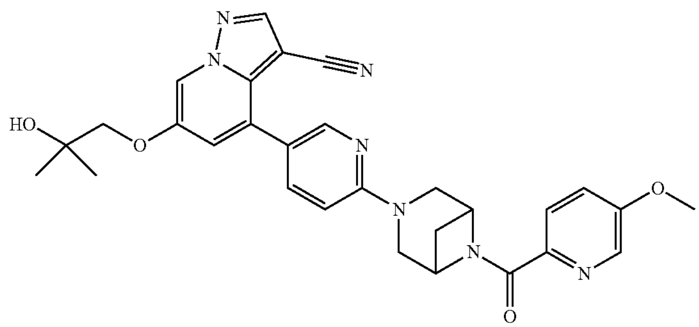 [SMILES: COc1ccc(C(=O)N2C3CC2CN(c2ccc(-c4cc(OCC(C)(C)O)cn5ncc(C#N)c45)cn2)C3)nc1] | 6-(2-hydroxy-2-methylpropoxy)-4-(6-(6-(5-methoxypicolinoyl)-3,6-diazabicyclo[3.1.1]heptan-3-yl)pyridin-3-yl)pyrazolo[1,5-a]pyridine-3-carbonitrile | 540.2 (M + H) |
| 390 | 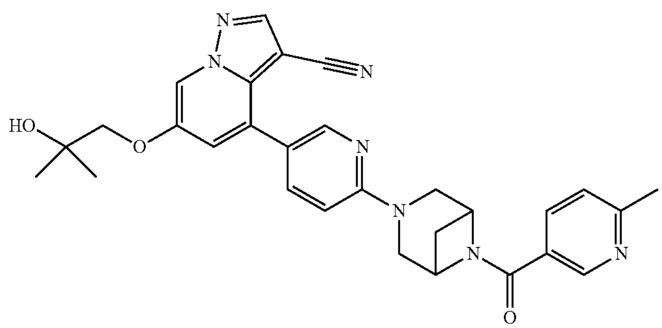 [SMILES: Cc1ccc(C(=O)N2C3CC2CN(c2ccc(-c4cc(OCC(C)(C)O)cn5ncc(C#N)c45)cn2)C3)cn1] | 6-(2-hydroxy-2-methylpropoxy)-4-(6-(6-(6-methylnicotinoyl)-3,6-diazabicyclo[3.1.1]heptan-3-yl)pyridin-3-yl)pyrazolo[1,5-a]pyridine-3-carbonitrile | 524.25 (M + H) |
| 391 | 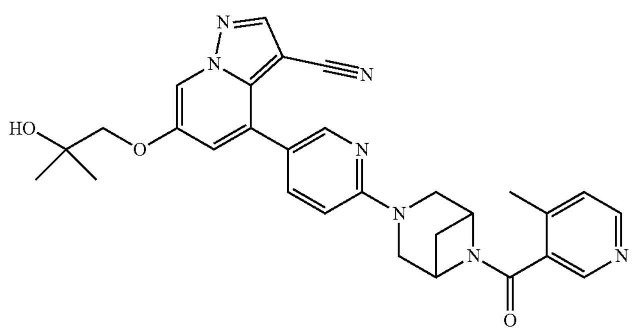 [SMILES: Cc1ccncc1C(=O)N1C2CC1CN(c1ccc(-c3cc(OCC(C)(C)O)cn4ncc(C#N)c34)cn1)C2] | 6-(2-hydroxy-2-methylpropoxy)-4-(6-(6-(4-methylnicotinoyl)-3,6-diazabicyclo[3.1.1]heptan-3-yl)pyridin-3-yl)pyrazolo[1,5-a]pyridine-3-carbonitrile | 524.2 (M + H) |
| 392 | 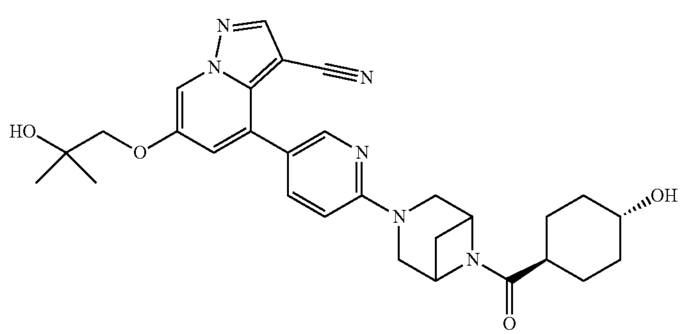 [SMILES: CC(C)(O)COc1cc(-c2ccc(N3CC4CC(C3)N4C(=O)[C@H]3CC[C@H](O)CC3)nc2)c2c(C#N)cnn2c1] | 6-(2-hydroxy-2-methylpropoxy)-4-(6-(6-((1r,4r)-4-hydroxycyclohexane-1-carbonyl)-3,6-diazabicyclo[3.1.1]heptan-3-yl)pyridin-3-yl)pyrazolo[1,5-a]pyridine-3-carbonitrile | 531.3 (M + H) |

TABLE CC-continued

| Ex # | Chemical Name | MS (apci) m/z |
|---|---|---|
| 393 | 6-(2-hydroxy-2-methylpropoxy)-4-(6-(6-(2-methylnicotinoyl)-3,6-diazabicyclo[3.1.1]heptan-3-yl)pyridin-3-yl)pyrazolo[1,5-a]pyridine-3-carbonitrile | 524.2 (M + H) |
| 394 | 6-(2-hydroxy-2-methylpropoxy)-4-(6-(6-(4-methylpicolinoyl)-3,6-diazabicyclo[3.1.1]heptan-3-yl)pyridin-3-yl)pyrazolo[1,5-a]pyridine-3-carbonitrile | 524.2 (M + H) |
| 395 | 6-(2-hydroxy-2-methylpropoxy)-4-(6-(6-((1r,3r)-3-methoxycyclobutane-1-carbonyl)-3,6-diazabicyclo[3.1.1]heptan-3-yl)pyridin-3-yl)pyrazolo[1,5-a]pyridine-3-carbonitrile | 517.2 (M + H) |
| 396 | 6-(2-hydroxy-2-methylpropoxy)-4-(6-(6-(5-methoxynicotinoyl)-3,6-diazabicyclo[3.1.1]heptan-3-yl)pyridin-3-yl)pyrazolo[1,5-a]pyridine-3-carbonitrile | 540.2 (M + H) |

TABLE CC-continued

| Ex # | Structure | Chemical Name | MS (apci) m/z |
|---|---|---|---|
| 397 | 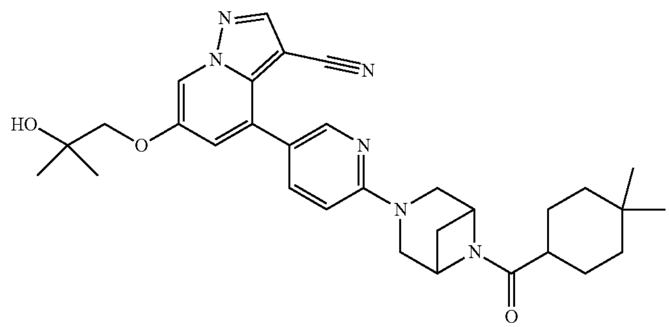 [SMILES: CC(C)(O)COc1cc(-c2ccc(N3CC4CC(C3)N4C(=O)C3CCC(C)(C)CC3)nc2)c2c(C#N)cnn2c1] | 4-(6-(6-(4,4-dimethylcyclohexane-1-carbonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 543.3 (M + H) |
| 398 | 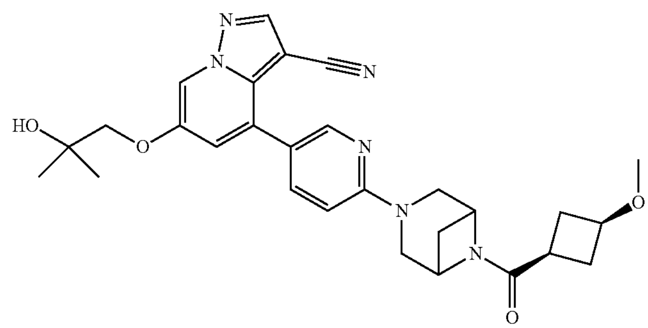 [SMILES: CO[C@H]1C[C@@H](C(=O)N2C3CC2CN(c2ccc(-c4cc(OCC(C)(C)O)cn5ncc(C#N)c45)cn2)C3)C1] | 6-(2-hydroxy-2-methylpropoxy)-4-(6-(6-((1s,3s)-3-methoxycyclobutane-1-carbonyl)-3,6-diazabicyclo[3.1.1]heptan-3-yl)pyridin-3-yl)pyrazolo[1,5-a]pyridine-3-carbonitrile | 517.3 (M + H) |
| 399 | 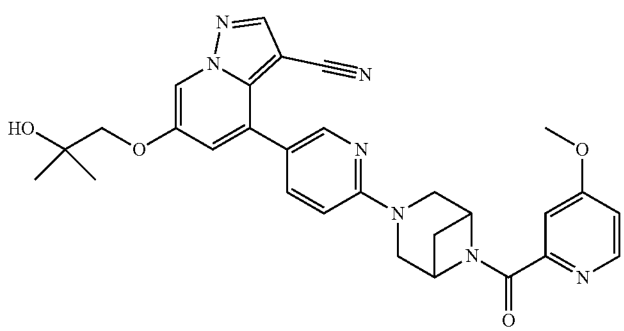 [SMILES: COc1ccnc(C(=O)N2C3CC2CN(c2ccc(-c4cc(OCC(C)(C)O)cn5ncc(C#N)c45)cn2)C3)c1] | 6-(2-hydroxy-2-methylpropoxy)-4-(6-(6-(4-methoxypicolinoyl)-3,6-diazabicyclo[3.1.1]heptan-3-yl)pyridin-3-yl)pyrazolo[1,5-a]pyridine-3-carbonitrile | 540.2 (M + H) |
| 400 | 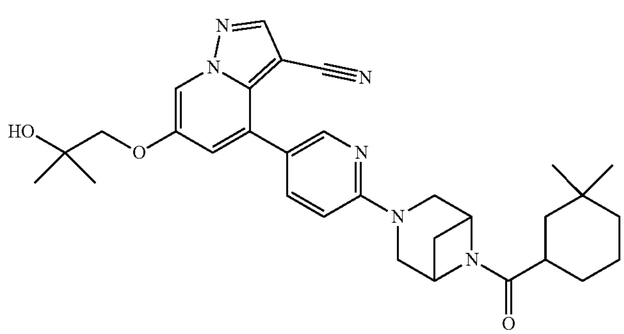 [SMILES: CC(C)(O)COc1cc(-c2ccc(N3CC4CC(C3)N4C(=O)C3CCCC(C)(C)C3)nc2)c2c(C#N)cnn2c1] | 4-(6-(6-(3,3-dimethylcyclohexane-1-carbonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 543.3 (M + H) |

TABLE CC-continued

| Ex # | Structure | Chemical Name | MS (apci) m/z |
|---|---|---|---|
| 401 | 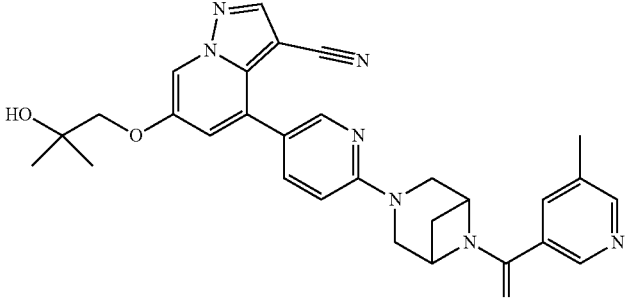 | 6-(2-hydroxy-2-methylpropoxy)-4-(6-(6-(5-methylnicotinoyl)-3,6-diazabicyclo[3.1.1]heptan-3-yl)pyridin-3-yl)pyrazolo[1,5-a]pyridine-3-carbonitrile | 524.2 (M + H) |
| 402 | 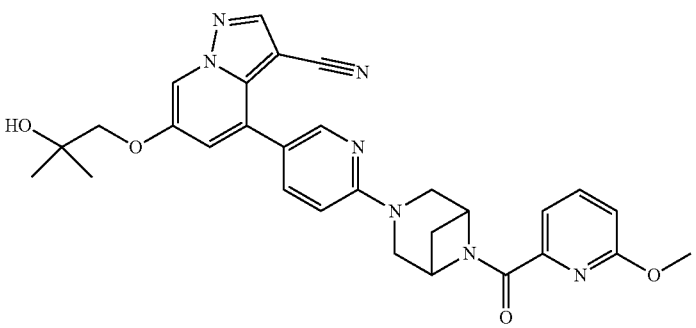 [SMILES: COc1cccc(C(=O)N2C3CC2CN(c2ccc(-c4cc(OCC(C)(C)O)cn5ncc(C#N)c45)cn2)C3)n1] | 6-(2-hydroxy-2-methylpropoxy)-4-(6-(6-(6-methoxypicolinoyl)-3,6-diazabicyclo[3.1.1]heptan-3-yl)pyridin-3-yl)pyrazolo[1,5-a]pyridine-3-carbonitrile | 540.2 (M + H) |
| 403 | 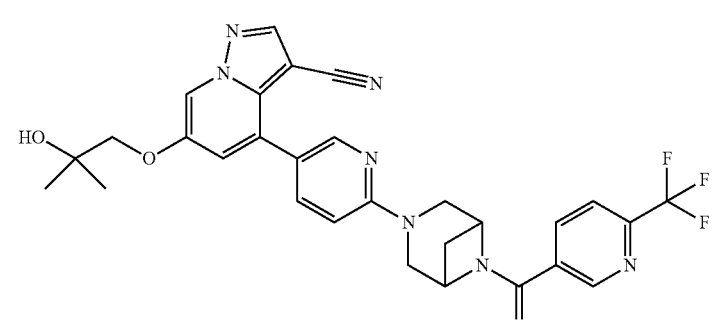 | 6-(2-hydroxy-2-methylpropoxy)-4-(6-(6-(6-(trifluoromethyl)nicotinoyl)-3,6-diazabicyclo[3.1.1]heptan-3-yl)pyridin-3-yl)pyrazolo[1,5-a]pyridine-3-carbonitrile | 578.2 (M + H) |
| 404 | 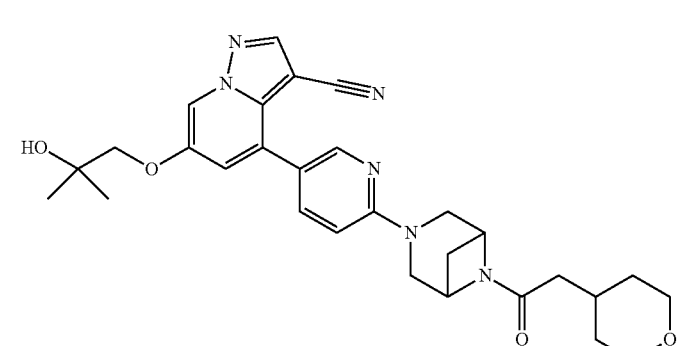 | 6-(2-hydroxy-2-methylpropoxy)-4-(6-(6-(2-(tetrahydro-2H-pyran-4-yl)acetyl)-3,6-diazabicyclo[3.1.1]heptan-3-yl)pyridin-3-yl)pyrazolo[1,5-a]pyridine-3-carbonitrile | 531.3 (M + H) |

TABLE CC-continued

| Ex # | Structure | Chemical Name | MS (apci) m/z |
|---|---|---|---|
| 405 | 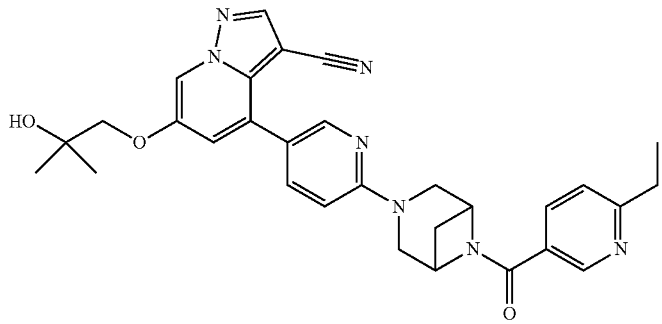 [SMILES: CCc1ccc(C(=O)N2C3CC2CN(c2ccc(-c4cc(OCC(C)(C)O)cn5ncc(C#N)c45)cn2)C3)cn1] | 4-(6-(6-(6-ethylnicotinoyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 538.3 (M + H) |
| 406 | 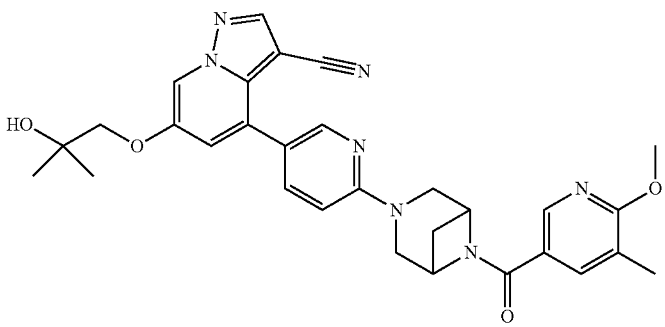 [SMILES: COc1ncc(C(=O)N2C3CC2CN(c2ccc(-c4cc(OCC(C)(C)O)cn5ncc(C#N)c45)cn2)C3)cc1C] | 6-(2-hydroxy-2-methylpropoxy)-4-(6-(6-(6-methoxy-5-methylnicotinoyl)-3,6-diazabicyclo[3.1.1]heptan-3-yl)pyridin-3-yl)pyrazolo[1,5-a]pyridine-3-carbonitrile | 554.2 (M + H) |

\* Example 406 employed 3 equivalents of HATU and employed an aqueous work up involving extraction of the reaction mixture with saturated NH$_4$Cl$_{(aq)}$ prior to chromatographic purification.

Example 407

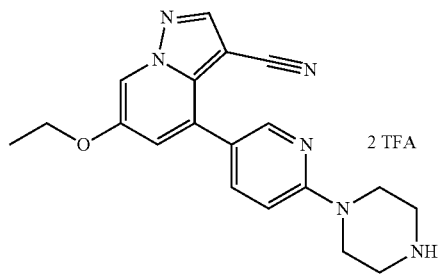 [SMILES: CCOc1cc(-c2ccc(N3CCNCC3)nc2)c2c(C#N)cnn2c1]

6-ethoxy-4-(6-(piperazin-1-yl)pyridin-3-yl)pyrazolo[1,5-a]pyridine-3-carbonitrile bis(2,2,2-trifluoroacetate)

A solution of tert-butyl 4-(5-(3-cyano-6-ethoxypyrazolo[1,5-a]pyridin-4-yl)pyridin-2-yl)piperazine-1-carboxylate (Example 29; 413 mg, 0.921 mmol) in DCM (8 mL) was treated with TFA (2 mL). After stirring for 1 h at ambient temperature, the mixture was concentrated in vacuo to cleanly provide the title compound (quantitative yield). MS (apci) m/z=349.2 (M+H).

Example 408

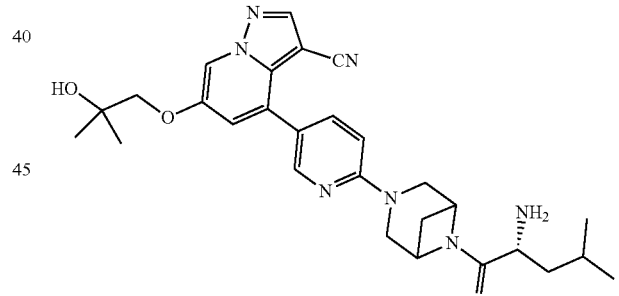

4-(6-(6-(D-leucyl)-3,6-diazabicyclo[3.1.1]heptan-3-yl)pyridin-3-yl)-6-(2-hydroxy-2-methylpropoxy)pyrazolo[1,5-a]pyridine-3-carbonitrile Step 1: Preparation of tert-butyl ((2R)-1-(3-(5-(3-cyano-6-(2-hydroxy-2-methylpropoxy)pyrazolo[1,5-a]pyridin-4-yl)pyridin-2-yl)-3,6-diazabicyclo[3.1.1]heptan-6-yl)-4-methyl-1-oxopentan-2-yl)carbamate A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 60 mg, 0.126 mmol) in DMF (4 mL) was treated sequentially with (tert-butoxycarbonyl)-D-leucine (32.0 mg, 0.138 mmol), HATU (57.3 mg, 0.151 mmol) and DIEA (57.3 μL, 0.503 mmol), then stirred overnight at ambient temperature. The resulting mixture was purified directly by silica chromatography (using 50-100% EtOAc in Hexanes as the gradient eluent) to afford the title compound (75 mg, 97% yield). MS (apci) m/z=618.4 (M+H).

Step 2: Preparation of 4-(6-(6-(D-leucyl)-3,6-diazabicyclo[3.1.1]heptan-3-yl)pyridin-3-yl)-6-(2-hydroxy-2-methyl prop oxy)pyrazolo[1,5-a]pyridine-3-carbonitrile A solution of tert-butyl ((2R)-1-(3-(5-(3-cyano-6-(2-hydroxy-2-methylpropoxy)pyrazolo[1,5-a]pyridin-4-yl)pyridin-2-yl)-3,6-diazabicyclo[3.1.1]heptan-6-yl)-4-methyl-1-oxopentan-2-yl)carbamate (Step 1; 75 mg, 0.12 mmol) in DCM (4 mL) was treated with TFA (2 mL), and stirred for 30 min at ambient temperature. After concentrating in vacuo, the reaction mixture was purified by C18 reverse phase chromatography (5-95% ACN in water with 0.1% TFA as the gradient eluent). Fractions containing the desired product were collected, treated with saturated NaHCO₃ and extracted with 20% IPA in DCM. The organic layer was dried over MgSO₄, filtered and concentrated. The material was further purified by silica chromatography (using 5-10% MeOH in DCM as the gradient eluent) to cleanly afford the title compound (44, 70% yield). MS (apci) m/z=518.3 (M+H).

Example 409

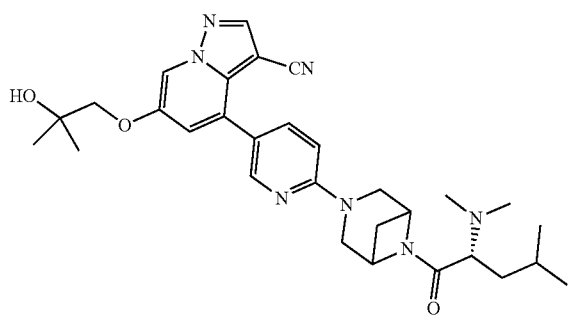 [SMILES: CC(C)C[C@H](C(=O)N1C2CC1CN(c1ccc(-c3cc(OCC(C)(C)O)cn4ncc(C#N)c34)cn1)C2)N(C)C]

4-(6-(6-(dimethyl-D-leucyl)-3,6-diazabicyclo[3.1.1]heptan-3-yl)pyridin-3-yl)-6-(2-hydroxy-2-methyl-propoxy)pyrazolo[1,5-a]pyridine-3-carbonitrile A mixture of 4-(6-(6-(D-leucyl)-3,6-diazabicyclo[3.1.1]heptan-3-yl)pyridin-3-yl)-6-(2-hydroxy-2-methylpropoxy)pyrazolo[1,5-a]pyridine-3-carbonitrile (Example 408; 40 mg, 0.0773 mmol) and formaldehyde (57.5 µL, 0.773 mmol) in DCM (773 µL) was treated with NaBH(AcO)₃ (81.9 mg, 0.386 mmol). After stirring for 3 h at ambient temperature, the reaction mixture was concentrated in vacuo. The residue was purified by C18 reverse phase chromatography (5-95% ACN in water with 0.1% TFA as the gradient eluent). Fractions containing the desired product were collected, treated with saturated NaHCO₃ and extracted with 20% IPA in DCM. The organics were dried over MgSO₄, filtered and concentrated. The material was further purified by silica chromatography (using 2-5% MeOH in DCM as the gradient eluent) to cleanly afford the title compound (23 mg, 55% yield). MS (apci) m/z=546.3 (M+H).

Example 410

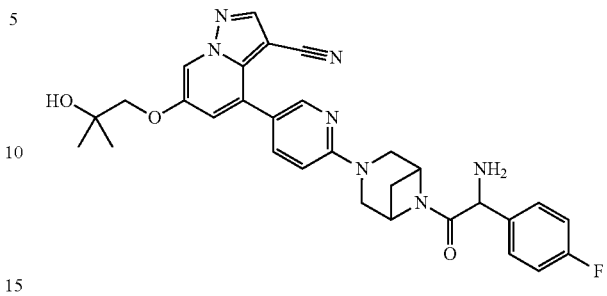

4-(6-(6-(2-amino-2-(4-fluorophenyl)acetyl)-3,6-diazabicyclo[3.1.1]heptan-3-yl)pyridin-3-yl)-6-(2-hydroxy-2-methylpropoxy)pyrazolo[1,5-a]pyridine-3-carbonitrile Step 1: Preparation of tert-butyl ((1R)-2-(3-(5-(3-cyano-6-(2-hydroxy-2-methylpropoxy)pyrazolo[1,5-a]pyridin-4-yl)pyridin-2-yl)-3,6-diazabicyclo[3.1.1]heptan-6-yl)-1-(4-fluorophenyl)-2-oxoethyl)carbamate A mixture of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 100 mg, 0.209 mmol), (R)-2-((tert-butoxycarbonyl)amino)-2-(4-fluorophenyl)acetic acid (56.4 mg, 0.209 mmol) and HATU (240 mg, 0.628 mmol) in DMF (1.05 mL) was treated with DIEA (146 µL, 0.838 mmol). The reaction mixture was stirred for 30 min at ambient temperature, and then filtered. The resulting filtrate was concentrated in vacuo, and the residue was purified by silica chromatography (using 0-10% CHCl₃/MeOH with 0-1% NH₄OH as the gradient eluent) to afford the title compound (137.36 mg, quantitative yield). MS (apci) m/z=656.2 (M+H).

Step 2: Preparation of 4-(6-(6-(((R)-2-amino-2-(4-fluorophenyl)acetyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of tert-butyl ((1R)-2-(3-(5-(3-cyano-6-(2-hydroxy-2-methylpropoxy)pyrazolo[1,5-a]pyridin-4-yl)pyridin-2-yl)-3,6-diazabicyclo[3.1.1]heptan-6-yl)-1-(4-fluorophenyl)-2-oxoethyl)carbamate (Step 1; 137.36 mg, 0.209 mmol) in DCM (418 µL) was treated with TFA (161 µL), and stirred for 70 min at ambient temperature. After concentrating in vacuo, the reaction mixture was purified first by silica chromatography (using CHCl₃/MeOH with 0-1% NH₄OH as the gradient eluent), then by C18 reverse phase chromatography (5-95% ACN in water with 0.1% TFA as the gradient eluent) then again by silica chromatography (5-10% MeOH in DCM with 1% NH₄OH as the gradient eluent) to cleanly afford the title compound (112.6 mg, 97% yield). MS (apci) m/z=556.2 (M+H).

Example 411

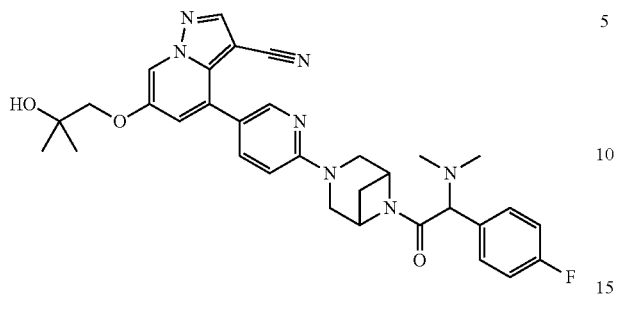

4-(6-(6-(2-(dimethylamino)-2-(4-fluorophenyl)
acetyl)-3,6-diazabicyclo[3.1.1]heptan-3-yl)pyridin-
3-yl)-6-(2-hydroxy-2-methylpropoxy)pyrazolo[1,5-
a]pyridine-3-carbonitrile A mixture of 4-(6-(6-(2-amino-2-(4-fluorophenyl)acetyl)-3,6-diazabicyclo[3.1.1]heptan-3-yl)pyridin-3-yl)-6-(2-hydroxy-2-methylpropoxy)pyrazolo[1,5-a]pyridine-3-carbonitrile (Example 410; 102 mg, 0.184 mmol) in DCM (1.8 mL) was treated sequentially with formaldehyde (82.7 μL, 1.10 mmol) and NaBH(AcO)$_3$ (195 mg, 0.918 mmol). After stirring for 2 h at ambient temperature, the reaction mixture was purified directly by silica chromatography (using 0-10% CHCl$_3$/MeOH with 0-1% NH$_4$OH as the gradient eluent) to afford semi-pure title compound. The semi-pure material was suspended in DCM, triturated with Hexanes, then concentrated in vacuo to cleanly afford the title compound (24.6 mg, 40% yield). MS (apci) m/z=584.3 (M+H).

Example 412

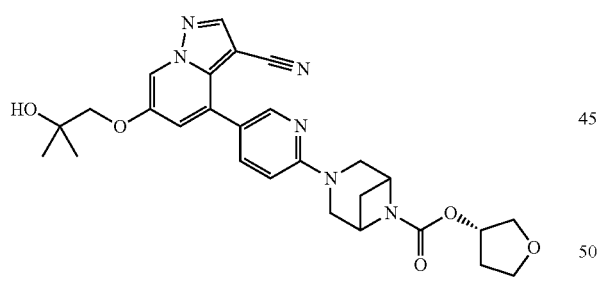

(S)-tetrahydrofuran-3-yl 3-(5-(3-cyano-6-(2-hy-
droxy-2-methylpropoxy)pyrazolo[1,5-a]pyridin-4-yl)
pyridin-2-yl)-3,6-diazabicyclo[3.1.1]heptane-6-car-
boxylate A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile (Intermediate P44; 50 mg, 0.12 mmol) in DCM (618 μL) was treated sequentially with (S)-tetrahydrofuran-3-yl carbonochloridate (20 mg, 0.14 mmol) and TEA (17 μL, 0.12 mmol). After stirring for 1 h at ambient temperature, the reaction mixture was purified by C18 reverse phase chromatography (using 5-50% ACN/water as the gradient eluent). Fractions containing the desired compound were combined and partitioned between 4:1 DCM:iPrOH and saturated NaHCO$_{3(aq)}$. The aqueous extracts were back extracted with 4:1 DCM:iPrOH (2×). The combined organic extracts were dried over anhydrous Na$_2$SO$_{4(s)}$, filtered, and concentrated in vacuo to cleanly provide the title compound (64 mg, 99% yield). MS (apci) m/z=519.3 (M+H).

Example 413

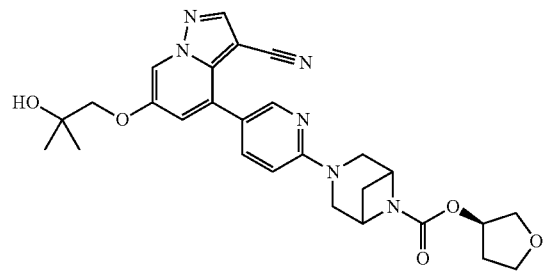 [SMILES: CC(C)(O)COc1cc(-c2ccc(N3CC4CC(C3)N4C(=O)O[C@@H]3CCOC3)nc2)c2c(C#N)cnn2c1]

(R)-tetrahydrofuran-3-yl 3-(5-(3-cyano-6-(2-hy-
droxy-2-methylpropoxy)pyrazolo[1,5-a]pyridin-4-yl)
pyridin-2-yl)-3,6-diazabicyclo[3.1.1]heptane-6-car-
boxylate The title compound (64 mg, 99% yield) was prepared, worked up and purified using a similar procedure to that described for Example 412, replacing (S)-tetrahydrofuran-3-yl carbonochloridate with (R)-tetrahydrofuran-3-yl carbonochloridate. MS (apci) m/z=519.2 (M+H).

Example 414

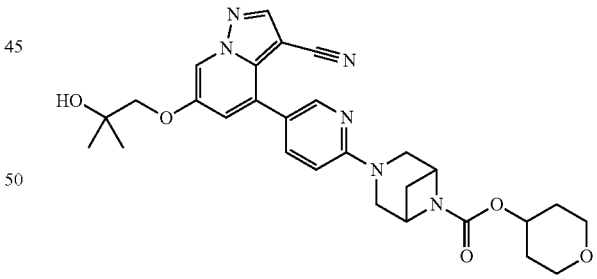

tetrahydro-2H-pyran-4-yl 3-(5-(3-cyano-6-(2-hy-
droxy-2-methylpropoxy)pyrazolo[1,5-a]pyridin-4-yl)
pyridin-2-yl)-3,6-diazabicyclo[3.1.1]heptane-6-car-
boxylate The title compound (60 mg, 90% yield) was prepared, worked up and purified using a similar procedure to that described for Example 412, replacing (S)-tetrahydrofuran-3-yl carbonochloridate with tetrahydro-2H-pyran-4-yl carbonochloridate. MS (apci) m/z=533.3 (M+H).

Example 415

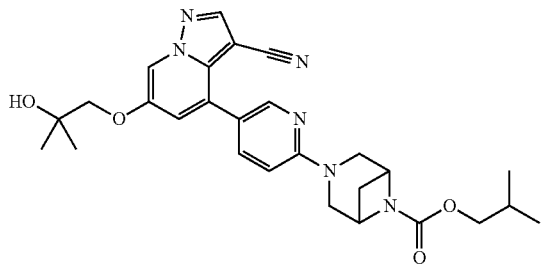 [SMILES: CC(C)COC(=O)N1C2CC1CN(c1ccc(-c3cc(OCC(C)(C)O)cn4ncc(C#N)c34)cn1)C2]

isobutyl 3-(5-(3-cyano-6-(2-hydroxy-2-methyl-propoxy)pyrazolo[1,5-a]pyridin-4-yl)pyridin-2-yl)-3,6-diazabicyclo[3.1.1]heptane-6-carboxylate A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 20 mg, 0.0419 mmol) in DCM (400 μL) was treated with TEA (29.2 μL, 0.12 mmol) and isobutyl carbonochloridate (17.2 mg, 0.126 mmol). After stirring for 2 h at ambient temperature, the reaction mixture was partitioned between DCM and saturated $NH_4Cl_{(aq)}$. The aqueous extracts were back extracted with DCM (3×). The combined organic extracts were dried over anhydrous $Na_2SO_{4(s)}$, filtered, and concentrated in vacuo. The residue was purified by silica chromatography (using 0-25% MeOH/EtOAc as the gradient eluent) to cleanly provide the title compound (15.4 mg, 73% yield). MS (apci) m/z=505.3 (M+H).

Example 416

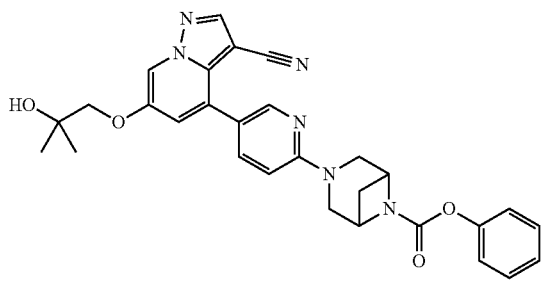 [SMILES: CC(C)(O)COc1cc(-c2ccc(N3CC4CC(C3)N4C(=O)Oc3ccccc3)nc2)c2c(C#N)cnn2c1]

phenyl 3-(5-(3-cyano-6-(2-hydroxy-2-methyl-propoxy)pyrazolo[1,5-a]pyridin-4-yl)pyridin-2-yl)-3,6-diazabicyclo[3.1.1]heptane-6-carboxylate The title compound was prepared using a similar procedure, work up, and purification to that described for Example 415, replacing isobutyl carbonochloridate (3 equivalents) with phenyl carbonochloridate (1 equivalent) and replacing TEA (5 equivalents) with DIEA (10 equivalents). Additionally, the reaction duration was extended to 4 h. Following a similar work up and silica chromatography (0-25% MeOH/EtOAc as the gradient eluent) the title compound was cleanly isolated (20 mg, 30% yield). MS (apci) m/z=525.2 (M+H).

Example 417

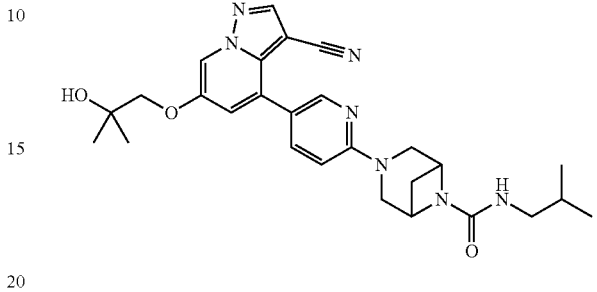

3-(5-(3-cyano-6-(2-hydroxy-2-methylpropoxy)pyrazolo[1,5-a]pyridin-4-yl)pyridin-2-yl)-N-isobutyl-3,6-diazabicyclo[3.1.1]heptane-6-carboxamide A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 32.6 mg, 0.0806 mmol) in DMA (403 μL) was treated with DIEA (140 μL, 0.12 mmol) and 4-nitrophenyl chloroformate (19.5 mg, 0.0967 mmol). The resulting mixture was stirred for 1 h at ambient temperature, allowing the formation of 4-nitrophenyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate. The reaction mixture was treated with 2-methylpropan-1-amine (40 μL, 0.40 mmol), and stirred for 21 h at 80° C. After cooling to ambient temperature, the reaction mixture was quenched with water (10 mL), and extracted with DCM (3×5 mL). The combined organic extracts were washed with water (3×10 mL), and brine (10 mL). The organic extracts were dried over anhydrous $Na_2SO_{4(s)}$, filtered and concentrated in vacuo. The crude residue was purified by C18 reverse phase chromatography (using 5-95% water-ACN with 0.1% TFA as the gradient eluent). Fractions containing the desired compound were combined and extracted with saturated $NaHCO_{3(aq)}$. The aqueous extracts were back extracted with DCM (3×5 mL). The combined organic extracts were washed with brine (10 mL), dried over anhydrous $Na_2SO_{4(s)}$, filtered and concentrated in vacuo to cleanly provide the title compound (18.2 mg, 45% yield). MS (apci) m/z=504.3 (M+H).

The compounds in Table DD were prepared using a similar method to that described for the preparation of Example 417, replacing the 2-methylpropan-1-amine in the urea coupling was replaced with the appropriate amine, and DMF was used instead of DMA. All reactions were monitored for completion by LCMS, and as such reaction times were adjusted accordingly. Reactions were quenched with saturated $NH_4Cl_{(aq)}$, followed by a similar aqueous work up to that described in Example 417. Title compounds were isolated using silica chromatography (using 0-25% MeOH/EtOAc as the gradient eluent), omitting the post chromatographic aqueous work up.

TABLE DD

| Ex # | Structure | Chemical Name | MS (apci) m/z |
|---|---|---|---|
| 418 | 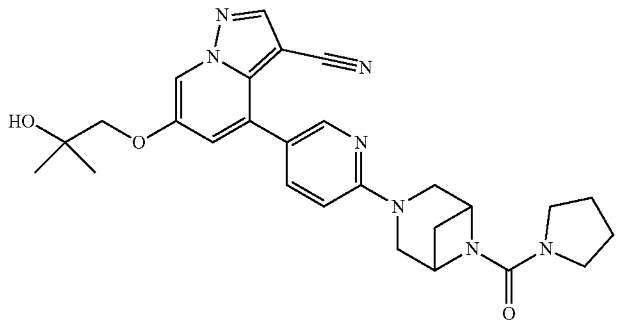 [SMILES: CC(C)(O)COc1cc(-c2ccc(N3CC4CC(C3)N4C(=O)N3CCCC3)nc2)c2c(C#N)cnn2c1] | 6-(2-hydroxy-2-methylpropoxy)-4-(6-(6-(pyrrolidine-1-carbonyl)-3,6-diazabicyclo[3.1.1]heptan-3-yl)pyridin-3-yl)pyrazolo[1,5-a]pyridine-3-carbonitrile | 502.3 (M + H) |
| 419 | 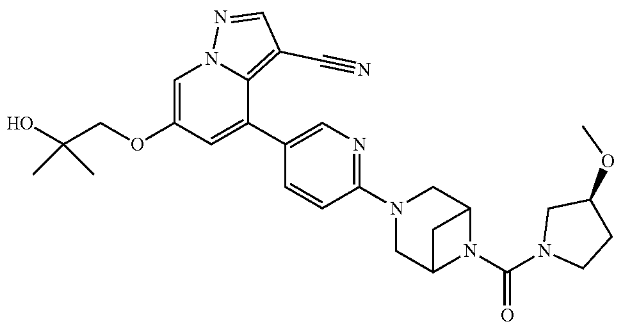 [SMILES: CO[C@H]1CCN(C(=O)N2C3CC2CN(c2ccc(-c4cc(OCC(C)(C)O)cn5ncc(C#N)c45)cn2)C3)C1] | 6-(2-hydroxy-2-methylpropoxy)-4-(6-(6-((S)-3-methoxypyrrolidine-1-carbonyl)-3,6-diazabicyclo[3.1.1]heptan-3-yl)pyridin-3-yl)pyrazolo[1,5-a]pyridine-3-carbonitrile | 532.3 (M + H) |
| 420 | 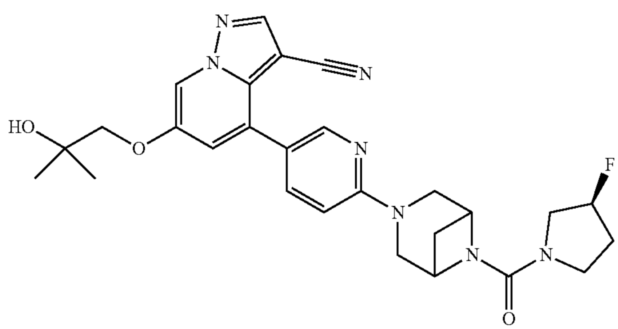 [SMILES: CC(C)(O)COc1cc(-c2ccc(N3CC4CC(C3)N4C(=O)N3CC[C@H](F)C3)nc2)c2c(C#N)cnn2c1] | 4-(6-(6-((S)-3-fluoropyrrolidine-1-carbonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 520.3 (M + H) |

Example 421

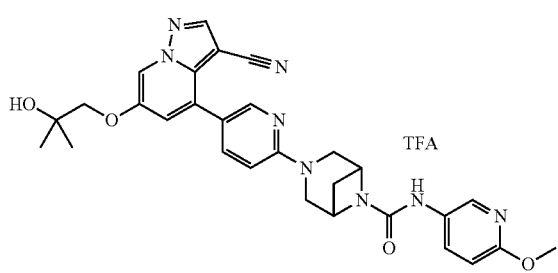 [SMILES: COc1ccc(NC(=O)N2C3CC2CN(c2ccc(-c4cc(OCC(C)(C)O)cn5ncc(C#N)c45)cn2)C3)cn1]

3-(5-(3-cyano-6-(2-hydroxy-2-methylpropoxy)pyrazolo[1,5-a]pyridin-4-yl)pyridin-2-yl)-N-(6-methoxypyridin-3-yl)-3,6-diazabicyclo[3.1.1]heptane-6-carboxamide 2,2,2-trifluoroacetate A 0° C. solution of triphosgene (18.6 mg, 0.0628 mmol) in DCM (250 µL) was treated with DIEA (72.4 µL, 0.419 mmol) and 6-methoxypyridin-3-amine (9.75 mg, 0.0786 mmol). The resulting mixture was stirred for 1 h at 0° C. 4-(6-(3,6-Diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 25 mg, 0.0524 mmol) was added to the cold (0° C.) solution. The resulting mixture was stirred overnight at ambient temperature, before quenching with water. The biphasic mixture was extracted with DCM (3×) in a Biotage Phase separator column. The combined organic extracts were concentrated in vacuo, and the crude residue was purified by C18 reverse phase chromatography (using 5-95% water-ACN with 0.1% TFA as the gradient eluent) to cleanly provide the title compound (13.4 mg, 46% yield). MS (apci) m/z=555.2 (M+H).

Example 422

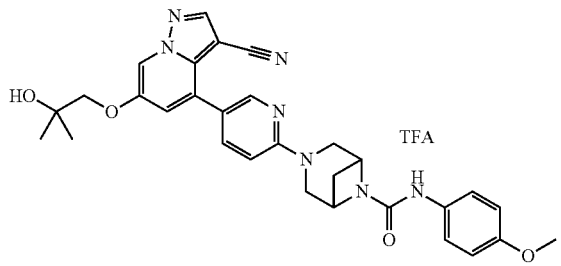 [SMILES: COc1ccc(NC(=O)N2C3CC2CN(c2ccc(-c4cc(OCC(C)(C)O)cn5ncc(C#N)c45)cn2)C3)cc1]

3-(5-(3-cyano-6-(2-hydroxy-2-methylpropoxy)pyrazolo[1,5-a]pyridin-4-yl)pyridin-2-yl)-N-(4-methoxyphenyl)-3,6-diazabicyclo[3.1.1]heptane-6-carboxamide 2,2,2-trifluoroacetate A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 30 mg, 0.0628 mmol) in DMA (750 μL) was treated with TEA (43.8 μL, 0.314 mmol) and 1-isocyanato-4-methoxybenzene (14.1 g, 0.0943 mmol). After stirring for 2 h at 50° C., the reaction mixture was cooled to ambient temperature, diluted with DCM, and quenched with water. The aqueous extracts were back extracted with DCM (3×), and the organic extracts were combined, dried over anhydrous $Na_2SO_{4(s)}$, filtered and concentrated in vacuo. The residue was purified by C18 reverse phase chromatography (using 5-95% water-ACN with 0.1% TFA as the gradient eluent) to cleanly provide the title compound (27 mg, 78% yield). MS (apci) m/z=554.2 (M+H).

Example 423

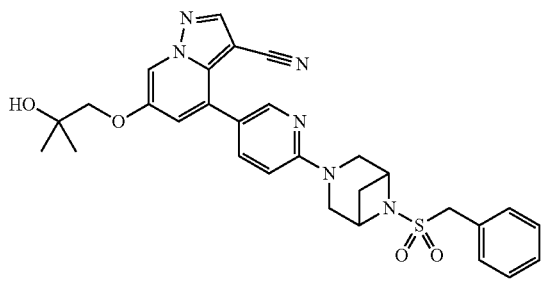 [SMILES: CC(C)(O)COc1cc(-c2ccc(N3CC4CC(C3)N4S(=O)(=O)Cc3ccccc3)nc2)c2c(C#N)cnn2c1]

4-(6-(6-(benzylsulfonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A mixture of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 26.0 mg, 0.0545 mmol) in DCM (1.0 mL) was treated sequentially with TEA (29.6 μL, 0.218 mmol) and phenylmethanesulfonyl chloride (11.4 mg, 0.0599 mmol). After stirring the reaction mixture for 1 h at ambient temperature, additional with TEA (29.6 μL, 0.218 mmol) and phenylmethanesulfonyl chloride (11.4 mg, 0.0599 mmol) were introduced sequentially. The resulting mixture was stirred for 16 h at ambient temperature, and then concentrated in vacuo. The crude residue was purified by C18 reverse phase chromatography (using 5-95% water-ACN with 0.1% TFA as the gradient eluent). Fractions containing the desired compound were combined and partitioned between 4:1 DCM:iPrOH and saturated $NaHCO_{3(aq)}$. The aqueous extracts were back extracted with 4:1 DCM:iPrOH (2×). The combined organic extracts were dried over anhydrous $Na_2SO_{4(s)}$, filtered, and concentrated in vacuo to cleanly provide the title compound (25.2 mg, 83% yield). MS (apci) m/z=559.2 (M+H).

The compounds in Table EE were prepared using a similar method to that described for the preparation of Example 423, replacing phenylmethanesulfonyl chloride with the appropriate sulfonyl chloride, and where noted (*) replacing TEA with DIEA. All reactions were monitored for completion by LCMS. As such reaction durations and the need for supplemental reagent amounts were adjusted accordingly. Title compounds were isolated following chromatographic purification using an appropriate gradient eluent. Chromatography was followed by the basic work up described in Example 423 in preparations in which an acid modifier (e.g. 0.1% TFA) was employed in the gradient eluent conditions.

TABLE EE

| Ex # | Structure | Chemical Name | MS (apci) m/z |
|---|---|---|---|
| 424 | 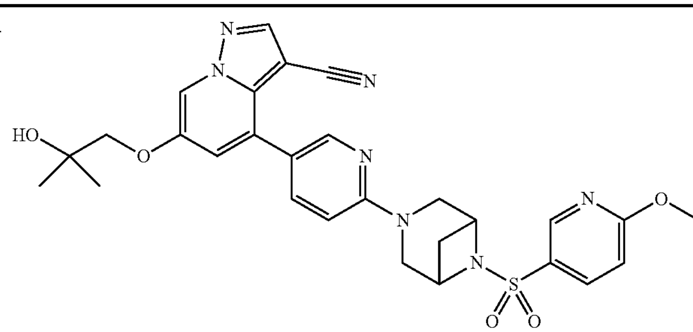 | 6-(2-hydroxy-2-methylpropoxy)-4-(6-(6-((6-methoxypyridin-3-yl)sulfonyl)-3,6-diazabicyclo[3.1.1]heptan-3-yl)pyridin-3-yl)pyrazolo[1,5-a]pyridine-3-carbonitrile | 576.2 (M + H) |

TABLE EE-continued

| Ex # | Structure | Chemical Name | MS (apci) m/z |
|---|---|---|---|
| 425 | 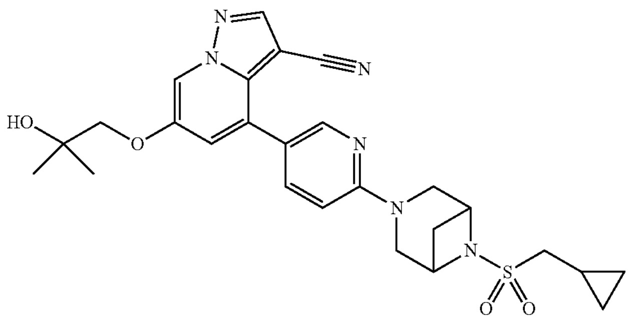 [SMILES: CC(C)(O)COc1cc(-c2ccc(N3CC4CC(C3)N4S(=O)(=O)CC3CC3)nc2)c2c(C#N)cnn2c1] | 4-(6-(6-((cyclopropylmethyl)sulfonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile | 523.5 (M + H) |
| 426 | 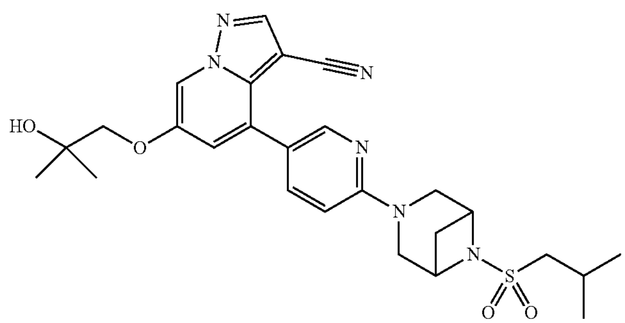 [SMILES: CC(C)CS(=O)(=O)N1C2CC1CN(c1ccc(-c3cc(OCC(C)(C)O)cn4ncc(C#N)c34)cn1)C2] | 6-(2-hydroxy-2-methylpropoxy)-4-(6-(6-(isobutylsulfonyl)-3,6-diazabicyclo[3.1.1]heptan-3-yl)pyridin-3-yl)pyrazolo[1,5-a]pyridine-3-carbonitrile | 525.3 (M + H) |
| 427 | 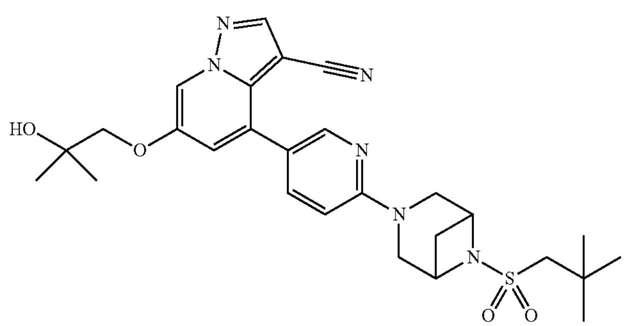 [SMILES: CC(C)(C)CS(=O)(=O)N1C2CC1CN(c1ccc(-c3cc(OCC(C)(C)O)cn4ncc(C#N)c34)cn1)C2] | 6-(2-hydroxy-2-methylpropoxy)-4-(6-(6-(neopentylsulfonyl)-3,6-diazabicyclo[3.1.1]heptan-3-yl)pyridin-3-yl)pyrazolo[1,5-a]pyridine-3-carbonitrile | 539.3 (M + H) |
| 428 | 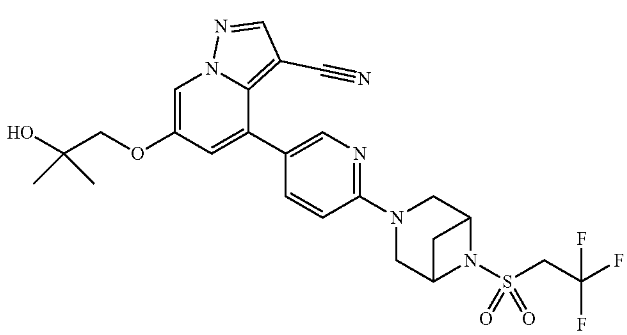 [SMILES: CC(C)(O)COc1cc(-c2ccc(N3CC4CC(C3)N4S(=O)(=O)CC(F)(F)F)nc2)c2c(C#N)cnn2c1] | 6-(2-hydroxy-2-methylpropoxy)-4-(6-(6-((2,2,2-trifluoroethyl)sulfonyl)-3,6-diazabicyclo[3.1.1]heptan-3-yl)pyridin-3-yl)pyrazolo[1,5-a]pyridine-3-carbonitrile | 551.2 (M + H) |

Example 429

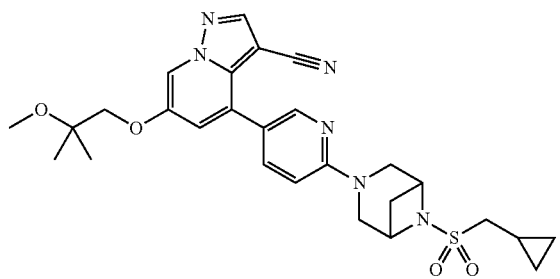 [SMILES: COC(C)(C)COc1cc(-c2ccc(N3CC4CC(C3)N4S(=O)(=O)CC3CC3)nc2)c2c(C#N)cnn2c1]

4-(6-(6-(((cyclopropylmethyl)sulfonyl)-3,6-diazabicyclo[3.1.1]heptan-3-yl)pyridin-3-yl)-6-(2-methoxy-2-methylpropoxy)pyrazolo[1,5-a]pyridine-3-carbonitrile At ambient temperature, 4-(6-(6-(((Cyclopropylmethyl)sulfonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile (Example 425; 8.9 mg, 0.0170 mmol) was added to a stirring suspension of 60 wt % NaH dispersion in mineral oil (1.36 mg, 0.218 mmol) in DMF (500 μL). The resulting mixture was treated with iodomethane (1.17 μL, 0.0187 mmol), and stirred for 16 h at ambient temperature. The resulting mixture was diluted with EtOAc, washed with water (3×) and brine (1×). The organic extracts were dried over $Na_2SO_{4(s)}$, then filtered, and concentrated in vacuo. The crude residue was purified by C18 reverse phase chromatography (using 5-95% water-ACN with 0.1% TFA as the gradient eluent). Fractions containing the desired compound were combined and partitioned between 4:1 DCM:iPrOH and saturated $NaHCO_{3(aq)}$. The aqueous extracts were back extracted with 4:1 DCM:iPrOH (2×). The combined organic extracts were dried over anhydrous $Na_2SO_{4(s)}$, filtered, and concentrated in vacuo to afford the title compound (6.2 mg, 68% yield). MS (apci) m/z=537.2 (M+H).

Example 430

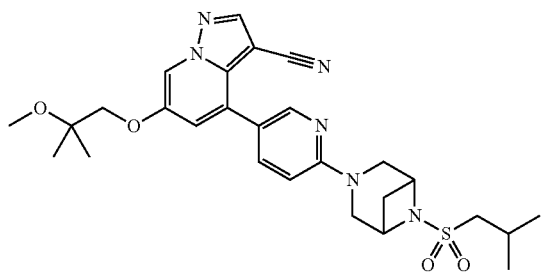 [SMILES: COC(C)(C)COc1cc(-c2ccc(N3CC4CC(C3)N4S(=O)(=O)CC(C)C)nc2)c2c(C#N)cnn2c1]

4-(6-(6-(isobutylsulfonyl)-3,6-diazabicyclo[3.1.1]heptan-3-yl)pyridin-3-yl)-6-(2-methoxy-2-methylpropoxy)pyrazolo[1,5-a]pyridine-3-carbonitrile The title compound (6.6 mg, 35% yield) was prepared, worked up and purified using a similar procedure to that described for Example 429, replacing 4-(6-(6-(((cyclopropylmethyl)sulfonyl)-3,6-diazabicyclo[3.1.1]heptan-3-yl)pyridin-3-yl)-6-(2-hydroxy-2-methylpropoxy)pyrazolo[1,5-a]pyridine-3-carbonitrile with 6-(2-hydroxy-2-methylpropoxy)-4-(6-(6-(isobutylsulfonyl)-3,6-diazabicyclo[3.1.1]heptan-3-yl)pyridin-3-yl)pyrazolo[1,5-a]pyridine-3-carbonitrile (Example 426). MS (apci) m/z=539.2 (M+H).

Example 431

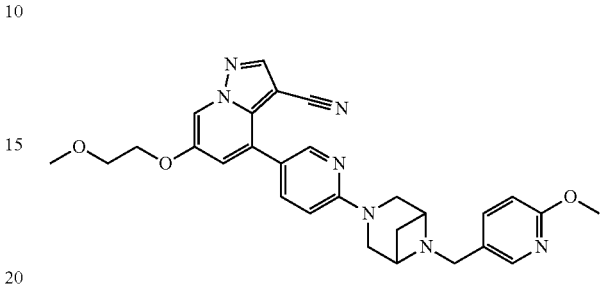

6-(2-methoxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A mixture of 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 30 mg, 0.066 mmol) $K_2CO_{3(s)}$ (11 mg, 0.079 mmol) and 1-bromo-2-methoxyethane (11 mg, 0.079 mmol) in DMF (400 μL) was stirred overnight at 90° C. After cooling to ambient temperature, the reaction mixture was diluted with DCM, washed with water (3×) and brine (1×). The organic extracts were dried over anhydrous $Na_2SO_{4(s)}$, filtered and concentrated in vacuo. The crude residue was purified by C18 reverse phase chromatography (using 5-95% water:ACN with 0.1% TFA as the gradient eluent) to afford the TFA salt of the title compound. The TFA salt was partitioned between DCM and saturated $NaHCO_{3(aq)}$. The organic extracts were washed with brine, then dried over anhydrous $Na_2SO_{4(s)}$, filtered, and concentrated in vacuo. The residue was triturated with DCM/Hexanes to cleanly afford the title compound (9.3 mg, 46% yield). MS (apci) m/z=512.2 (M+H).

Example 432

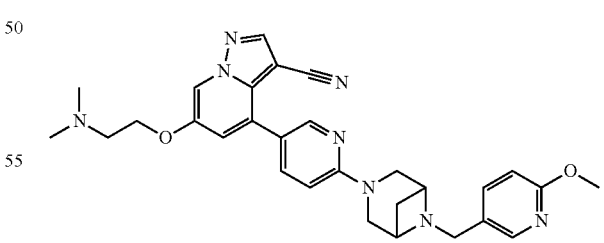

6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 6-hydroxy-4-(6-(6-((6-methoxypyridin-3-yl)methyl)-3,6-diazabicyclo[3.1.1]heptan-3-yl)pyridin-3-yl)

pyrazolo[1,5-a]pyridine-3-carbonitrile (Intermediate P71; 26.9 mg, 0.0593 mmol) in DMA (119 µL) was treated sequentially with Cs$_2$CO$_{3(s)}$ (77.3 mg, 0.237 mmol) and (2-bromoethyl)dimethylamine (8.9 mg, 0.083 mmol) then stirred overnight at 60° C. After cooling to ambient temperature, the reaction mixture was diluted with EtOAc, washed with water (3×) and brine (1×). The combine organic extracts were dried over anhydrous Na$_2$SO$_{4(s)}$, filtered and concentrated in vacuo. The crude residue was diluted with 60:40 ACN/water with 2% TFA and the solution was purified by C18 reverse phase chromatography (using 5-95% water:ACN with 0.1% TFA as the gradient eluent) to afford the TFA salt of the title compound. The TFA salt was dissolved in MeOH (5 mL), passed through a P1-HCO3 resin, and concentrated in vacuo to cleanly afford the title compound (1.2 mg, 4% yield). MS (apci) m/z=525.3 (M+H). $^1$H NMR (400 MHz, CD$_3$OD) δ 8.37 (d, 1H), 8.18 (s, 1H), 8.12 (d, 1H), 8.08 (d, 1H), 7.75 (dd, 1H), 7.60 (dd, 1H), 7.15 (d, 1H), 6.89 (d, 1H), 6.64 (d, 1H), 4.09 (t, 2H), 3.89 (s, 3H), 3.77 (m, 4H), 3.55 (m, 4H), 2.99 (s, 1H), 2.91 (s, 1H), 2.78 (t, 3H), 2.65 (m, 1H), 2.35 (s, 6H), 1.63 (d, 1H).

Example 433

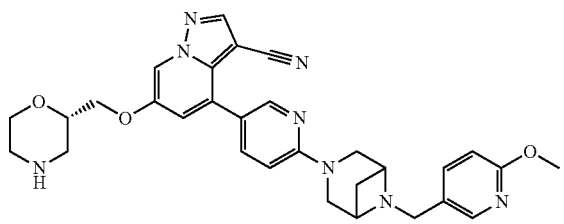 [SMILES: COc1ccc(CN2C3CC2CN(c2ccc(-c4cc(OC[C@@H]5CNCCO5)cn5ncc(C#N)c45)cn2)C3)cn1]

4-(6-(6-(((6-methoxypyridin-3-yl)methyl)-3,6-diazabicyclo[3.1.1]heptan-3-yl)pyridin-3-yl)-6-(((S)-morpholin-2-yl)methoxy)pyrazolo[1,5-a]pyridine-3-carbonitrile Step 1: Preparation of tert-butyl (2S)-2-(((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)methyl)morpholine-4-carboxylate A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 15.5 mg, 0.0342 mmol) in DMA (684 µL) was treated sequentially with Cs$_2$CO$_{3(s)}$ (12.2 mg, 0.0376 mmol) and (S)-tert-Butyl 2-(bromomethyl)morpholine-4-carboxylate (14.4 mg, 0.0513 mmol), sparging with Ar$_{(g)}$ for 10 min between reagents, and then again for 1 min after the amine addition. The reaction mixture was stirred overnight at 60° C. After cooling to ambient temperature, the reaction mixture was diluted with EtOAc (10 mL), and washed with water (10 mL). The aqueous wash was back extracted with EtOAc (2×5 mL). The combined organic extracts were washed with water (2×10 mL) and brine (10 mL), then dried over anhydrous Na$_2$SO$_{4(s)}$, filtered, and concentrated in vacuo to afford the title compound (22.3 mg, quantitative yield). MS (apci) m/z=653.4 (M+H).

Step 2: Preparation of 4-(6-(6-(((6-methoxypyridin-3-yl)methyl)-3,6-diazabicyclo[3.1.1]heptan-3-yl)pyridin-3-yl)-6-(((S)-morpholin-2-yl)methoxy)pyrazolo[1,5-a]pyridine-3-carbonitrile A solution of tert-butyl (2S)-2-(((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)methyl)morpholine-4-carboxylate (Step 1; 22.3 mg, 0.0342 mmol) in DCM (2.2 mL) was treated with TFA (2.63 mL), and stirred for 20 min at ambient temperature. The reaction mixture was concentrated in vacuo, and the residue was purified by C18 reverse phase chromatography (using 60-40% ACN/water with 2% TFA as the gradient eluent). Fractions containing the desired compound were combined and extracted with saturated NaHCO$_{3(aq)}$ (10 mL) and DCM (2×10 mL). The combined organic extracts were dried over anhydrous Na$_2$SO$_{4(s)}$, filtered, and concentrated in vacuo to afford the title compound (4.9 mg, 26% yield). MS (apci) m/z=553.3 (M+H).

Example 434

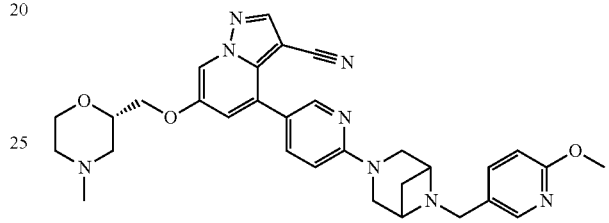

4-(6-(6-(((6-methoxypyridin-3-yl)methyl)-3,6-diazabicyclo[3.1.1]heptan-3-yl)pyridin-3-yl)-6-(((S)-4-methylmorpholin-2-yl)methoxy)pyrazolo[1,5-a]pyridine-3-carbonitrile A solution of 4-(6-(6-(((6-methoxypyridin-3-yl)methyl)-3,6-diazabicyclo[3.1.1]heptan-3-yl)pyridin-3-yl)-6-(((S)-morpholin-2-yl)methoxy)pyrazolo[1,5-a]pyridine-3-carbonitrile (Example 433; 10 mg, 0.0181 mmol) in DCM (0.362 mL) ( ) was treated sequentially with formaldehyde (6.80 µL, 0.0905 mmol) and NaBH(AcO)$_3$ (38.4 mg, 0.181 mmol). After stirring for 24 h at ambient temperature, the reaction mixture was concentrated in vacuo. The crude residue was diluted with 60-40% ACN/water with 2% TFA and the solution was purified by C18 reverse phase chromatography (using 5-95% water:ACN with 0.1% TFA as the gradient eluent) to afford the TFA salt of the title compound. The TFA salt was dissolved in MeOH and passed through a P1-HCO3 resin to afford the title compound (4.1 mg, 40% yield). MS (apci) m/z=567.3 (M+H).

Example 435

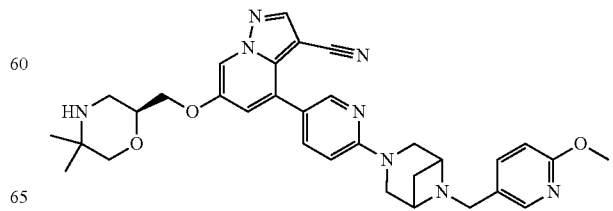

6-(((S)-5,5-dimethylmorpholin-2-yl)methoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile Step 1: Preparation of tert-butyl (2S)-24-(3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)methyl)-5,5-dimethylmorpholine-4-carboxylate A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 42 mg, 0.093 mmol) in DMF (464 μL) was treated sequentially with tert-butyl (S)-5,5-dimethyl-2-(((methylsulfonyl)oxy)methyl)morpholine-4-carboxylate (30 mg, 0.093 mmol) and $Cs_2CO_{3(s)}$ (76 mg, 0.23 mmol). The reaction mixture was stirred for 36 h at ambient temperature, then at 60° C. until the reaction had reached 60% completion by LCMS. After cooling to ambient temperature, the reaction mixture was diluted with EtOAc and extracted with water. The combined organic extracts were dried over anhydrous $Na_2SO_{4(s)}$, filtered and concentrated in vacuo. The crude residue was purified by silica chromatography (using 0-50% EtOAc in Hexanes as the eluent) to afford the title compound (6.5 mg, 10% yield). MS m/z 681.3 (M+H)

Step 2: Preparation of 64-(S)-5,5-dimethylmorpholin-2-yl)methoxy)-4-(6-(6-(6-methoxypyridin-3-yl)methyl)-3,6-diazabicyclo[3.1.1]heptan-3-yl)pyridin-3-yl)pyrazolo[1,5-a]pyridine-3-carbonitrile A solution of tert-butyl (2S)-2-(((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)methyl)-5,5-dimethylmorpholine-4-carboxylate (Step 1; 6.5 mg, 0.0095 mmol) in 1:1 TFA:DCM (2 mL) and stirred for 1 h at ambient temperature. The reaction mixture was: The crude residue was diluted with 60-40% ACN/water with 2% TFA and the solution was purified by C18 reverse phase chromatography (using 5-95% water:ACN with 0.1% TFA as the gradient eluent) to afford the TFA salt of the title compound. The TFA salt was dissolved in MeOH and passed through a P1-HCO3 resin to afford the title compound. (4.1 mg, 74% yield). MS (apci) m/z=581.3 (M+H).

Example 436

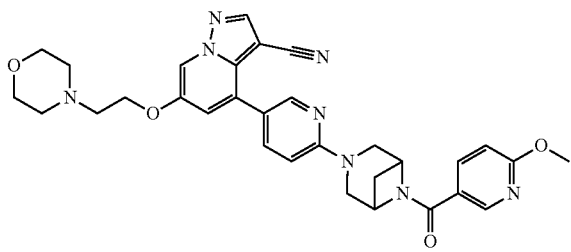 [SMILES: COc1ccc(C(=O)N2C3CC2CN(c2ccc(-c4cc(OCCN5CCOCC5)cn5ncc(C#N)c45)cn2)C3)cn1]

4-(6-(6-(6-methoxynicotinoyl)-3,6-diazabicyclo[3.1.1]heptan-3-yl)pyridin-3-yl)-6-(2-morpholinoethoxy)pyrazolo[1,5-a]pyridine-3-carbonitrile A solution of 4-(6-(3,6-diazabicyclo[3.1.1]heptan-3-yl)pyridin-3-yl)-6-(2-morpholinoethoxy)pyrazolo[1,5-a]pyridine-3-carbonitrile bis(2,2,2-trifluoroacetate) (Intermediate P76; 40 mg, 0.090 mmol) in DCM (2.5 mL) was treated sequentially with 6-methoxynicotinic acid (16.5 mg, 0.108 mmol), HATU (41.0 mg, 0.108 mmol) and DIEA (62.6 μL, 0.359 mmol). After stirring overnight at ambient temperature, additional DIEA (220 μL, 1.26 mmol) was introduced, and the reaction was stirred overnight at ambient temperature. The reaction mixture was partitioned between DCM (40 mL) and saturated $NH_4Cl_{(aq)}$ (40 mL). The aqueous extracts were back extracted with DCM (3×25 mL). The combined organic extracts were dried over anhydrous $Na_2SO_{4(s)}$, filtered, and concentrated in vacuo. The crude residue was purified by silica chromatography (using 0-10% MeOH in EtOAc as the gradient eluent) to cleanly afford the title compound (19 mg, 36% yield). MS (apci) m/z=581.3 (M+H).

Example 437

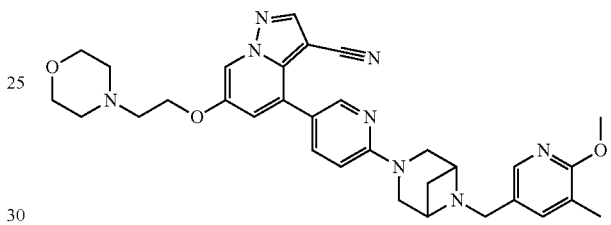

4-(6-(6-((6-methoxy-5-methylpyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile A solution of 4-(6-(3,6-diazabicyclo[3.1.1]heptan-3-yl)pyridin-3-yl)-6-(2-morpholinoethoxy)pyrazolo[1,5-a]pyridine-3-carbonitrile bis(2,2,2-trifluoroacetate) (Intermediate P76; 41 mg, 0.061 mmol) and 6-methoxy-5-methylnicotinaldehyde (21 mg, 0.14 mmol) in DCM (2 mL)( ) was treated with $NaBH(AcO)_3$ (39 mg, 0.18 mmol). After stirring for 5 h at ambient temperature, the reaction mixture was partitioned between water and DCM, then extracted with DCM (3×). The combined organic extracts were dried over anhydrous $Na_2SO_{4(s)}$, filtered and concentrated in vacuo. The crude residue was purified by silica chromatography (using 0-20% MeOH in DCM with 0.2% $NH_4OH$ as the gradient eluent) to afford the title compound (22 mg, 62% yield). MS (apci) m/z=581.3 (M+H).

Example 438

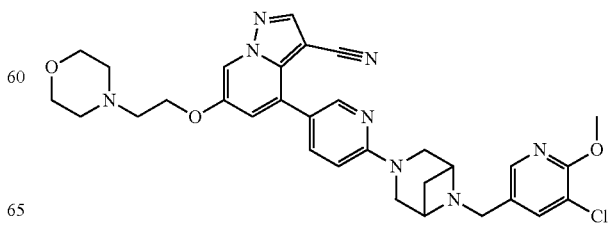

4-(6-(6-((5-chloro-6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile A solution of 4-(6-(3,6-diazabicyclo[3.1.1]heptan-3-yl)pyridin-3-yl)-6-(2-morpholinoethoxy)pyrazolo[1,5-a]pyridine-3-carbonitrile bis(2,2,2-trifluoroacetate) (Intermediate P76; 50 mg, 0.074 mmol) and 5-chloro-6-methoxynicotinaldehyde (31 mg, 0.18 mmol) in DCM (3 mL) ( ) was treated with NaBH(AcO)$_3$ (57 mg, 0.27 mmol). After stirring the reaction mixture overnight at ambient temperature, additional NaBH(AcO)$_3$ (38 mg, 0.18 mmol) was introduced, and the reaction was stirred for an additional 5 h at ambient temperature. The reaction mixture was partitioned between water and DCM, then extracted with DCM (3×). The combined organic extracts were dried over anhydrous Na$_2$SO$_{4(s)}$, filtered, and concentrated in vacuo. The crude residue was purified by silica chromatography (0-20% MeOH in DCM with 0.2% NH$_4$OH as the gradient eluent) to afford the title compound (7 mg, 16% yield). MS (apci) m/z=601.3 (M+H).

Example 439

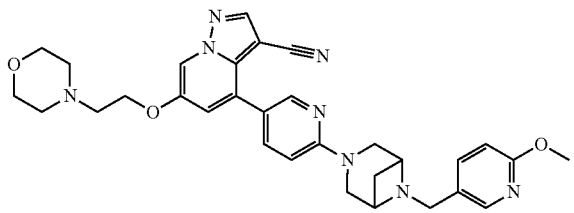 [SMILES: COc1ccc(CN2C3CC2CN(c2ccc(-c4cc(OCCN5CCOCC5)cn5ncc(C#N)c45)cn2)C3)cn1]

4-(6-(6-(((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 25.8 mg, 0.0569 mmol) in DMA (113.8 μL) was treated sequentially with Cs$_2$CO$_{3(s)}$ (74.14 mg, 0.2276 mmol) and 4-(2-chloroethyl)morpholine (15.65 μL, 0.1138 mmol), then stirred overnight at 60° C. After cooling to ambient temperature, the reaction mixture was diluted with EtOAc, and extracted sequentially with water (3×) and brine (1×). The combined organic extracts were washed with brine, then dried over anhydrous Na$_2$SO$_{4(s)}$, filtered, and concentrated in vacuo. The crude residue was diluted with 60-40% ACN/water with 2% TFA and the solution was purified by C18 reverse phase chromatography (using 5-95% water:ACN with 0.1% TFA as the gradient eluent) to afford the TFA salt of the title compound. The TFA salt was dissolved in MeOH and passed through a P1-HCO3 resin to afford the title compound. (8.8 mg, 27% yield). MS (apci) m/z=567.3 (M+H). $^1$H NMR (400 MHz, CD$_3$OD) δ 8.48 (d, 1H), 8.34 (m, 2H), 8.09 (d, 1H), 7.83 (dd, 1H), 7.71 (dd, 1H), 7.28 (d, 1H), 6.88 (d, 1H), 6.78 (d, 1H), 4.26 (t, 2H), 3.89 (m, 5H), 3.79 (d, 2H), 3.72 (t, 4H), 3.64 (m, 4H), 2.87 (t, 2H), 2.70 (m, 1H), 2.62 (t, 4H), 1.69 (d, 1H).

Example 440

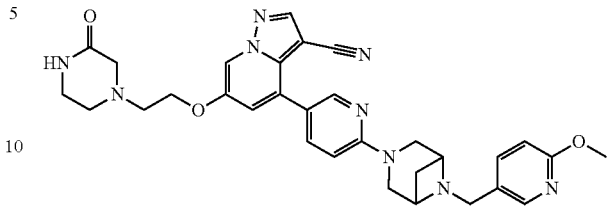

4-(6-(6-(((6-methoxypyridin-3-yl)methyl)-3,6-diazabicyclo[3.1.1]heptan-3-yl)pyridin-3-yl)-6-(2-(3-oxopiperazin-1-yl)ethoxy)pyrazolo[1,5-a]pyridine-3-carbonitrile Step 1: Preparation of 6-(2-chloroethoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile 2,2,2-trifluoroacetate A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 75 mg, 0.165 mmol) in DMF (1654 μL) was treated sequentially with K$_2$CO$_{3(s)}$ anhydrous (112 mg, 0.827) and 1-chloro-2-iodoethane (45.4 μL, 0.496 mmol). The reaction mixture was stirred overnight at ambient temperature. The resulting mixture was diluted with EtOAc and extracted with water, then the organic extracts were dried over anhydrous Na$_2$SO$_{4(s)}$, filtered and concentrated in vacuo. The crude residue was purified by C18 reverse phase chromatography (using 5-95% water:ACN with 0.1% TFA as the gradient eluent) to afford the title compound. (60 mg, 66% yield). MS (apci) m/z=516.2 (M+H).

Step 2: Preparation of 4-(6-(6-(((6-methoxypyridin-3-yl)methyl)-3,6-diazabicyclo[3.1.1]heptan-3-yl)pyridin-3-yl)-6-(2-(3-oxopiperazin-1-yl)ethoxy)pyrazolo[1,5-a]pyridine-3-carbonitrile A solution of 6-(2-chloroethoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile 2,2,2-trifluoroacetate (Step 1; 6.5 mg, 0.0095 mmol) in DMA (635 μL) was treated with 2-oxopiperzaine (9.53 mg, 0.0952 mmol), and stirred overnight at 80° C. Additional 2-oxopiperzaine (3.18 mg) was introduced, and the mixture was stirred overnight at 80° C. The reaction mixture was purified directly by C18 reverse phase chromatography (using 5-95% ACN in water with 0.1% TFA as the gradient eluent) to afford the title compound as the TFA salt. The TFA salt was subjected to purification by silica chromatography (using 0-10% MeOH in DCM with 0.1% NH$_4$OH as the gradient eluent) to afford the title compound (1.17 mg, 6% yield). MS (apci) m/z=580.4 (M+H).

Example 441

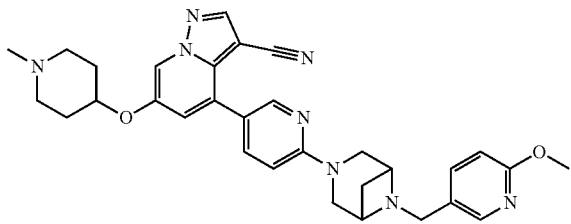

4-(6-(6-(((6-methoxypyridin-3-yl)methyl)-3,6-diazabicyclo[3.1.1]heptan-3-yl)pyridin-3-yl)-6-((1-methylpiperidin-4-yl)oxy)pyrazolo[1,5-a]pyridine-3-carbonitrile Step 1: Preparation of tert-butyl 4-((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)piperidine-1-carboxylate A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 50 mg, 0.11 mmol) in DMA (1103 μL) was treated sequentially with $Cs_2CO_{3(s)}$ (108 mg, 0.33 mmol) and tert-butyl 4-bromopiperidine-1-carboxylate (35 mg, 0.13 mmol) then stirred for 48 h at 60° C. Additional tert-butyl 4-bromopiperidine-1-carboxylate (29 mg) was introduced, and the reaction was stirred for 3 d at 60° C. After cooling to ambient temperature, the reaction mixture was partitioned between DCM (10 mL) and water (10 mL), and then extracted with DCM (5×10 mL). The combined organic extracts were dried over anhydrous $Na_2SO_{4(s)}$, filtered and concentrated in vacuo. The crude residue was purified by silica chromatography (using 0-10% MeOH in EtOAc as the gradient eluent) to cleanly afford the title compound (21 mg, 27% yield). MS (apci) m/z=637.3 (M+H).

Step 2: Preparation of 4-(6-(6-(((6-methoxypyridin-3-yl)methyl)-3,6-diazabicyclo[3.1.1]heptan-3-yl)pyridin-3-yl)-6-(piperidin-4-yloxy)pyrazolo[1,5-a]pyridine-3-carbonitrile A solution of tert-butyl 4-((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)piperidine-1-carboxylate (Step 1; 21 mg, 0.033 mmol) in DCM (1 mL) was treated with TFA (1 mL), and stirred overnight at ambient temperature. The reaction mixture was concentrated in vacuo and the residue was purified by silica chromatography (using 0-10% MeOH in DCM with 0.1% $NH_4OH$ as the gradient eluent) to afford the title compound (20 mg, quantitative yield) in acceptable purity for the next step. MS (apci) m/z=537.2 (M+H).

Step 3: Preparation of 4-(6-(6-(((6-methoxypyridin-3-yl)methyl)-3,6-diazabicyclo[3.1.1]heptan-3-yl)pyridin-3-yl)-6-((1-methylpiperidin-4-yl)oxy)pyrazolo[1,5-a]pyridine-3-carbonitrile A mixture of 4-(6-(6-(((6-methoxypyridin-3-yl)methyl)-3,6-diazabicyclo[3.1.1]heptan-3-yl)pyridin-3-yl)-6-(piperidin-4-yloxy)pyrazolo[1,5-a]pyridine-3-carbonitrile (Step 2; 20 mg, 0.033 mmol) in DCM (523 μL) was treated sequentially with formaldehyde (9.83 μL, 0.131 mmol) and NaBH(AcO)$_3$ (55.4 mg, 0.262 mmol). After stirring for 4 h at ambient temperature, the reaction mixture was diluted with MeOH, then filtered. The filtrate was purified directly by silica chromatography (using 0-100% DCM in Hexanes and then 0-10% MeOH in DCM with 0.1% $NH_4OH$ as the gradient eluent) to cleanly afford the title compound (2.5 mg, 17% yield). MS (apci) m/z=551.3 (M+H).

Example 442

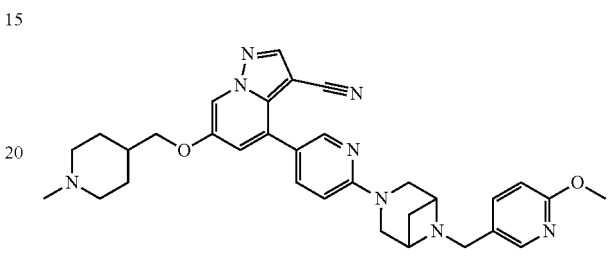

4-(6-(6-(((6-methoxypyridin-3-yl)methyl)-3,6-diazabicyclo[3.1.1]heptan-3-yl)pyridin-3-yl)-6-((1-methylpiperidin-4-yl)methoxy)pyrazolo[1,5-a]pyridine-3-carbonitrile Step 1: Preparation of tert-butyl 4-(((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)methyl)piperidine-1-carboxylate 2,2,2-trifluoroacetate A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 50 mg, 0.11 mmol) in DMA (1103 μL) was treated sequentially with $Cs_2CO_{3(s)}$ (108 mg, 0.33 mmol) and tert-butyl 4-(bromomethyl)piperidine-1-carboxylate (46 mg, 0.17 mmol), then stirred overnight at 80° C. After cooling to ambient temperature, the reaction mixture was purified directly by C18 reverse phase chromatography (using 5-95% ACN in Water with 0.1% TFA as the gradient eluent) to cleanly afford the title compound (49 mg, 58% yield). MS (apci) m/z=651.4 (M+H).

Step 2: Preparation of 4-(6-(6-(((6-methoxypyridin-3-yl)methyl)-3,6-diazabicyclo[3.1.1]heptan-3-yl)pyridin-3-yl)-6-(piperidin-4-ylmethoxy)pyrazolo[1,5-a]pyridine-3-carbonitrile bis(2,2,2-trifluoroacetate)

A solution of tert-butyl 4-(((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)methyl)piperidine-1-carboxylate 2,2,2-trifluoroacetate (Step 1; 49 mg, 0.064 mmol) in DCM (1 mL) was treated with TFA (1 mL), and stirred overnight at ambient temperature. The reaction mixture was treated with additional TFA (1 mL), and allowed to stir until LCMS indicated complete consumption of starting material. The reaction mixture was concentrated in vacuo, and the residue was purified by C18 reverse phase chromatography (using 5-95% ACN in Water with 0.1% TFA as the gradient eluent) to afford the title compound (30 mg, 70% yield). MS (apci) m/z=551.3 (M+H).

Step 3: Preparation of 4-(6-(6-(((6-methoxypyridin-3-yl)methyl)-3,6-diazabicyclo[3.1.1]heptan-3-yl)pyridin-3-yl)-6-((1-methylpiperidin-4-yl)methoxy)pyrazolo[1,5-a]pyridine-3-carbonitrile A solution of 4-(6-(6-(((6-methoxypyridin-3-yl)methyl)-3,6-diazabicyclo[3.1.1]heptan-3-yl)pyridin-3-yl)-6-(piperidin-4-ylmethoxy)pyrazolo[1,5-a]pyridine-3-carbonitrile bis (2,2,2-trifluoroacetate) (Step 2; 15 mg, 0.0226 mmol) in DCM (500 μL) was treated sequentially with formaldehyde (16.8 μL, 0.226 mmol) and NaBH(AcO)₃ (23.9 mg, 0.113 mmol). After stirring overnight at ambient temperature, additional NaBH(AcO)₃ (23.9 mg, 0.113 mmol) was introduced, and the reaction mixture was stirred at ambient temperature until LCMS indicated complete consumption of starting material. The reaction mixture was purified directly by silica chromatography (using 0-10% MeOH in DCM with 0.1% NH₄OH as the gradient eluent) to cleanly afford the title compound (1 mg, 8% yield). MS (apci) m/z=565.4 (M+H).

Example 443

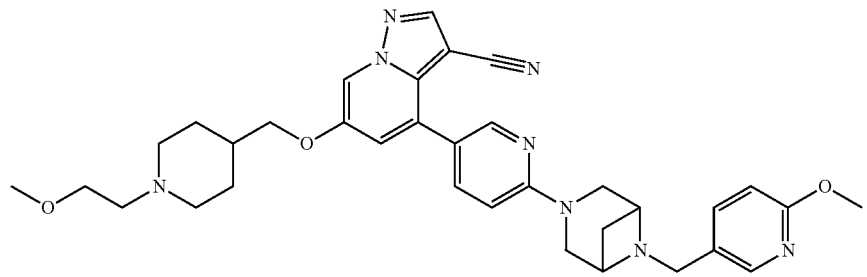

6-((1-(2-methoxyethyl)piperidin-4-yl)methoxy)-4-(6-(6-(6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(6-(((6-methoxypyridin-3-yl)methyl)-3,6-diazabicyclo[3.1.1]heptan-3-yl)pyridin-3-yl)-6-(piperidin-4-ylmethoxy)pyrazolo[1,5-a]pyridine-3-carbonitrile bis (2,2,2-trifluoroacetate) (Example 442, Step 2; 15 mg, 0.023 mmol) in DMA (112.8 μL) was treated sequentially with potassium carbonate (16 mg, 0.11 mmol) and 1-bromo-2-methoxyethane (4.6 μL, 0.045 mmol). After stirring overnight at 60° C., the reaction mixture was cooled to ambient temperature, and then purified directly by C18 reverse phase chromatography (using 5-95% ACN in Water with 0.1% TFA as the gradient eluent) to afford the TFA salt of the title compound. The TFA salt was dissolved in MeOH and passed through a P1-HCO3 resin, and concentrated in vacuo to cleanly afford the title compound (6 mg, 43% yield). MS (apci) m/z=609.3 (M+H).

Example 444

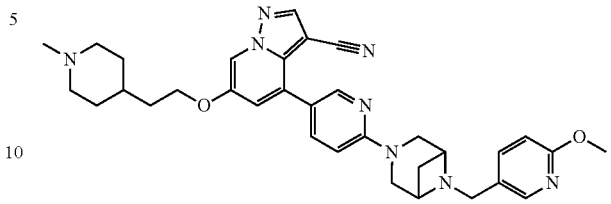

4-(6-(6-(((6-methoxypyridin-3-yl)methyl)-3,6-diazabicyclo[3.1.1]heptan-3-yl)pyridin-3-yl)-6-(2-(1-methylpiperidin-4-yl)ethoxy)pyrazolo[1,5-a]pyridine-3-carbonitrile Step 1: Preparation of tert-butyl 4-(2-((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)ethyl)piperidine-1-carboxylate A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 47.5 mg, 0.105 mmol) in DMA (1047 μL) was treated sequentially with Cs₂CO₃(s) (102 mg, 0.314 mmol) and tert-Butyl 4-(2-bromoethyl)piperidine-1-carboxylate (61.2 mg, 0.209 mmol) then stirred overnight at 80° C. After cooling to ambient temperature, the reaction mixture was diluted with water (2 mL). The resulting suspension was filtered, and the solids were rinsed with water (10 mL) and Et₂O (5 mL) then dried in vacuo to cleanly afford the title compound (51.5 mg, 74% yield). MS (apci) m/z=665.4 (M+H).

Step 2: Preparation of 4-(6-(6-(((6-methoxypyridin-3-yl)methyl)-3,6-diazabicyclo[3.1.1]heptan-3-yl)pyridin-3-yl)-6-(2-(piperidin-4-yl)ethoxy)pyrazolo[1,5-a]pyridine-3-carbonitrile bis(2,2,2-trifluoroacetate A solution of tert-butyl 4-(2-((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)ethyl)piperidine-1-carboxylate (Step 1; 51.5 mg, 0.0775 mmol) in DCM (1 mL) was treated with TFA (1.5 mL), and stirred for 1 h at ambient temperature. The reaction mixture was concentrated in vacuo to afford the title compound (61.4 mg, quantitative yield). MS (apci) m/z=565.3 (M+H).

Step 3: Preparation of 4-(6-(6-(((6-methoxypyridin-3-yl)methyl)-3,6-diazabicyclo[3.1.1]heptan-3-yl) pyridin-3-yl)-6-(2-(1-methylpiperidin-4-yl)ethoxy) pyrazolo[1,5-a]pyridine-3-carbonitrile A solution of 4-(6-(6-(((6-methoxypyridin-3-yl)methyl)-3, 6-diazabicyclo[3.1.1]heptan-3-yl)pyridin-3-yl)-6-(2-(piperidin-4-yl)ethoxy)pyrazolo[1,5-a]pyridine-3-carbonitrile bis (2,2,2-trifluoroacetate) (Step 2; 30.7 mg, 0.0387 mmol) in DCM (1000 μL) was treated sequentially with formaldehyde (5.82 μL, 0.0775 mmol) and NaBH(AcO)$_3$ (24.6 mg, 0.116 mmol). After stirring for 30 min at ambient temperature, the reaction mixture was purified directly by silica chromatography (using 0-100% DCM in Hexanes then 0-10% MeOH in DCM with 0.1% NH$_4$OH as the gradient eluent) to cleanly afford the title compound (1.61 mg, 7% yield). MS (apci) m/z=579.3 (M+H).

Example 445

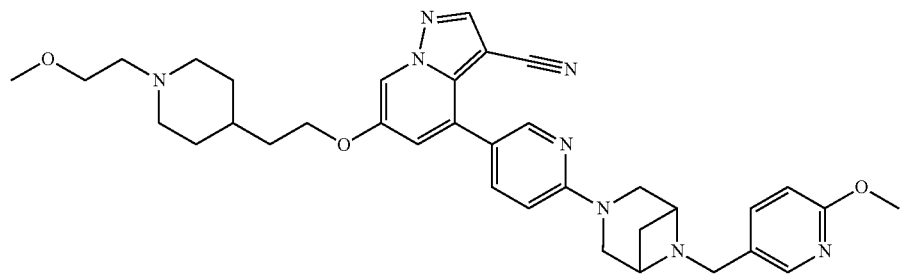

6-(2-(1-(2-methoxyethyl)piperidin-4-yl)ethoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile A mixture of 4-(6-(6-(((6-methoxypyridin-3-yl)methyl)-3, 6-diazabicyclo[3.1.1]heptan-3-yl)pyridin-3-yl)-6-(2-(piperidin-4-yl)ethoxy)pyrazolo[1,5-a]pyridine-3-carbonitrile bis (2,2,2-trifluoroacetate) (Example 444, Step 2; 31 mg, 0.039 mmol) in DMA (196 μL) was treated sequentially with potassium carbonate (27 mg, 0.20 mmol) and 1-bromo-2-methoxyethane (7.4 μL, 0.078 mmol). The resulting mixture was stirred at 60° C. until LCMS indicated complete consumption of starting material. The reaction mixture was cooled to ambient temperature, and purified directly by C18 reverse phase chromatography (using 5-95% ACN in water with 0.1% TFA as the gradient eluent) to afford the TFA salt of the title compound. The TFA salt was dissolved in MeOH, passed through a P1-HCO3 resin and concentrated in vacuo to cleanly afford the title compound (17.1 mg, 70% yield). MS (apci) m/z=623.4 (M+H).

Example 446

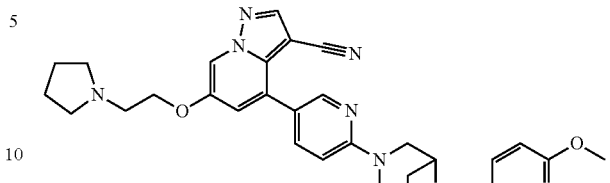

4-(6-(6-(((6-methoxypyridin-3-yl)methyl)-3,6-diazabicyclo[3.1.1]heptan-3-yl)pyridin-3-yl)-6-(2-(pyrrolidin-1-yl)ethoxy)pyrazolo[1,5-a]pyridine-3-carbonitrile A solution of 6-hydroxy-4-(6-(6-(((6-methoxypyridin-3-yl)methyl)-3,6-diazabicyclo[3.1.1]heptan-3-yl)pyridin-3-yl) pyrazolo[1,5-a]pyridine-3-carbonitrile (Intermediate P71; 28 mg, 0.062 mmol) in DMF (309 μL) was treated sequentially with K$_2$CO$_{3(s)}$ (26 mg, 0.19 mmol) and 1-(2-chloroethyl)pyrrolidine (9.9 mg, 0.074 mmol), then stirred overnight at 60° C. After cooling to ambient temperature, the reaction mixture was concentrated in vacuo. The crude residue was dissolved in 1 mL of 60:40 ACN/water with 2% TFA and purified by C18 reverse phase chromatography (using 5-95% ACN in H$_2$O with 0.1% TFA as the gradient eluent) to afford the TFA salt of the title compound. The TFA salt was dissolved in MeOH (5 mL), passed through a P1-HCO3 resin, and concentrated in vacuo to cleanly afford the title compound (22 mg, 65% yield). MS (apci) m/z=551.3 (M+H).

Example 447

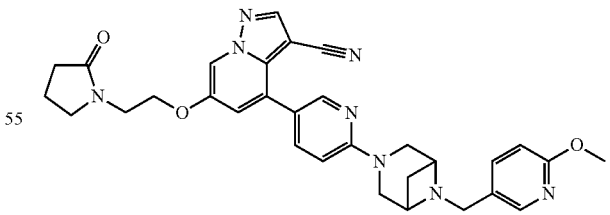

4-(6-(6-(((6-methoxypyridin-3-yl)methyl)-3,6-diazabicyclo[3.1.1]heptan-3-yl)pyridin-3-yl)-6-(2-(2-oxopyrrolidin-1-yl)ethoxy)pyrazolo[1,5-a]pyridine-3-carbonitrile A solution of 4-(6-(3,6-diazabicyclo[3.1.1]heptan-3-yl) pyridin-3-yl)-6-(2-(2-oxopyrrolidin-1-yl)ethoxy)pyrazolo

[1,5-a]pyridine-3-carbonitrile bis(2,2,2-trifluoroacetate) (Intermediate P77; 42 mg, 0.063 mmol) in DCM (500 µL) was treated with 6-methoxy-3-pyridinecarboxaldehyde (42.9 mg, 0.313 mmol) and NaBH(AcO)$_3$ (133 mg, 0.625 mmol). After stirring the reaction mixture 3 h at ambient temperature, the reaction mixture was concentrated in vacuo. The crude residue was purified by C18 reverse phase chromatography (using 5-95% ACN in water with 0.1% TFA as the gradient eluent) to afford the title compound as the TFA salt of the title compound. The TFA salt was dissolved in MeOH, passed through a P1-HCO3 resin and concentrated in vacuo to cleanly afford the title compound (6.80 mg, 19% yield). MS (apci) m/z=565.3 (M+H).

Example 448

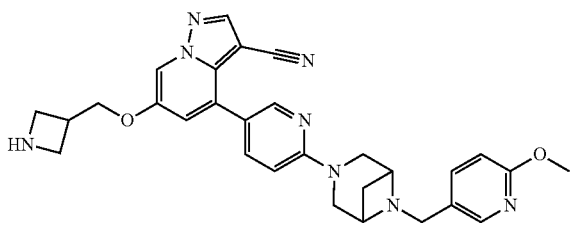 [SMILES: COc1ccc(CN2C3CC2CN(c2ccc(-c4cc(OCC5CNC5)cn5ncc(C#N)c45)cn2)C3)cn1]

6-(azetidin-3-ylmethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile Step 1: Preparation of tert-butyl 3-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)azetidine-1-carboxylate A solution of 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 75.8 mg, 0.167 mmol) in DMA (334 µL) was treated sequentially with Cs$_2$CO$_{3(s)}$ (218 mg, 0.669 mmol) and 3-bromomethyl-azetidine-1-carboxylic acid tert-butyl ester (62.7 mg, 0.251 mmol), then stirred overnight at 60° C. After cooling to ambient temperature, the reaction mixture was concentrated in vacuo then purified by silica chromatography (using 0-10% MeOH in DCM with 0.1% NH$_4$OH as the gradient eluent —) to cleanly afford the title compound (52.4 mg, 50% yield). MS m/z=623.4 (M+H)

Step 2: Preparation of 6-(azetidin-3-ylmethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of tert-butyl 3-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)azetidine-1-carboxylate (Step 1; 52.4 mg, 0.0841 mmol) in DCM (1 mL) was treated with TFA (1 mL), and stirred for 1 h at ambient temperature. The reaction mixture was concentrated in vacuo, and the residue was dissolved in 1 mL of 60:40 ACN/water with 2% TFA and purified by C18 reverse phase chromatography (using 5-95% ACN in H$_2$O with 0.1% TFA as the gradient eluent) to afford the TFA salt of the title compound. The TFA salt was dissolved in MeOH, passed through a P1-HCO3 resin and concentrated in vacuo to cleanly afford the title compound (43.2 mg, 98% yield). MS (apci) m/z=523.2 (M+H).

Example 449

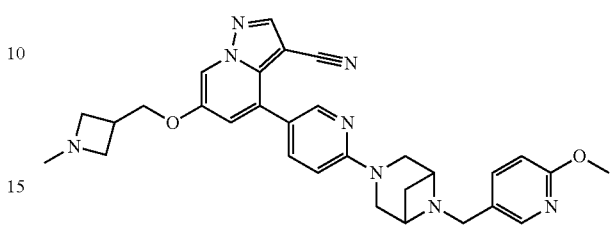

4-(6-(6-(((6-methoxypyridin-3-yl)methyl)-3,6-diazabicyclo[3.1.1]heptan-3-yl)pyridin-3-yl)-6-((1-methylazetidin-3-yl)methoxy)pyrazolo[1,5-a]pyridine-3-carbonitrile A solution of 6-(azetidin-3-ylmethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Example 448, Step 2; 20 mg, 0.038 mmol) in DCM (0.38 mL) was treated sequentially with formaldehyde (14.4 µL, 0.191 mmol) and NaBH(AcO)$_3$ (81.1 mg, 0.383 mmol). The reaction mixture was stirred at ambient temperature until LCMS indicated complete consumption of starting material. The resulting mixture was purified directly by C18 reverse phase chromatography (using 5-95% ACN in H$_2$O with 0.1% TFA as the gradient eluent)) to afford the TFA salt of the title compound. The TFA salt was dissolved in MeOH, passed through a P1-HCO3 resin, then dried over anhydrous Na$_2$SO$_{4(s)}$, filtered, and concentrated in vacuo to cleanly afford the title compound (4.1 mg, 20% yield). MS (apci) m/z=537.3 (M+H).

Example 450

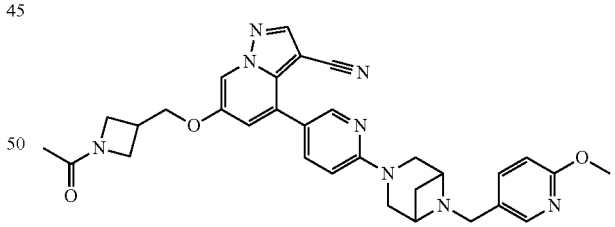

6-((1-acetylazetidin-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile Step 1: Preparation of tert-butyl 3-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)azetidine-1-carboxylate A solution of 6-hydroxy-4-(6-(6-((6-methoxypyridin-3-yl)methyl)-3,6-diazabicyclo[3.1.1]heptan-3-yl)pyridin-3-yl)

pyrazolo[1,5-a]pyridine-3-carbonitrile (Intermediate P71; 50 mg, 0.11 mmol) in DMF (551 μL) was treated sequentially with K$_2$CO$_{3(s)}$ (46 mg, 0.33 mmol) and 3-bromomethyl-azetidine-1-carboxylic acid tert-butyl ester (33 mg, 0.13 mmol), then stirred overnight at 60° C. After cooling to ambient temperature, the reaction mixture was concentrated in vacuo. The residue was dissolved in 1 mL of 60:40 ACN/water with 2% TFA and purified by C18 reverse phase chromatography (using 5-95% ACN in H$_2$O with 0.1% TFA as the gradient eluent) to afford the TFA salt of the title compound. The TFA salt was dissolved in MeOH, passed through a P1-HCO3 resin and concentrated in vacuo to cleanly afford the title compound (41 mg, 59% yield). MS (apci) m/z=623.3 (M+H). Tert-butyl 3-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)azetidine-1-carboxylate (41 mg, 0.066 mmol) was dissolved in 1:1 TFA:DCM (2 mL) and stirred for 1 h at ambient temperature. The solution was concentrated in vacuo. The residue was dissolved in DCM (0.3 mL) and treated with TEA (18.57 μL, 0.1332 mmol) followed by acetic anhydride (9.38 μL, 0.1 mmol). Reaction stirred 48 h at ambient temperature until LCMS indicated complete consumption of starting material. The reaction solution was diluted with DCM (20 mL) and washed with brine (3×10 mL) and dried over anhydrous MgSO$_{4(s)}$, filtered, and concentrated in vacuo. The crude residue was purified by silica chromatography (using 10% MeOH in DCM with 0.1% NH$_4$OH as the gradient eluent) to afford the title compound (13.4 mg, 36% yield). MS (apci) m/z=565.3 (M+H).

directly then purified by silica chromatography (10% MeOH in DCM with 0.1% NH$_4$OH as the gradient eluent) to cleanly afford the title compound (81 mg, quantitative yield). MS m/z=641.3 (M+H)

Step 2: Preparation of 6-((3-fluoroazetidin-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of tert-butyl 3-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)-3-fluoroazetidine-1-carboxylate (Step 1; 81 mg, 0.13 mmol) in DCM (2 mL) was treated with TFA (2 mL), and stirred for 1 h at ambient temperature. The reaction mixture was concentrated in vacuo, and the residue was purified by C18 reverse phase chromatography (using 5-95% ACN in water with 0.1% TFA as the gradient eluent) to afford the TFA salt of the title compound. The TFA salt was dissolved in MeOH, passed through a P1-HCO3 resin and concentrated in vacuo to cleanly afford the title compound (15 mg, 22% yield). MS (apci) m/z=541.3 (M+H).

Example 451

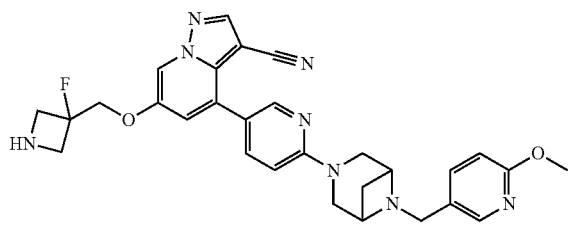 [SMILES: COc1ccc(CN2C3CC2CN(c2ccc(-c4cc(OCC5(F)CNC5)cn5ncc(C#N)c45)cn2)C3)cn1]

6-((3-fluoroazetidine-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile Step 1: Preparation of tert-butyl 3-(((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)methyl)-3-fluoroazetidine-1-carboxylate A solution of 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 51.5 mg, 0.114 mmol) in DMF (0.5 mL)) was treated sequentially with Cs$_2$CO$_{3(s)}$ (148 mg, 0.454 mmol) and tert-butyl 3-(bromomethyl)azetidine-1-carboxylate (45.7 mg, 0.170 mmol) then stirred at 60° C. until LCMS indicated complete consumption of starting material. After cooling to ambient temperature, the reaction mixture was purified Example 452

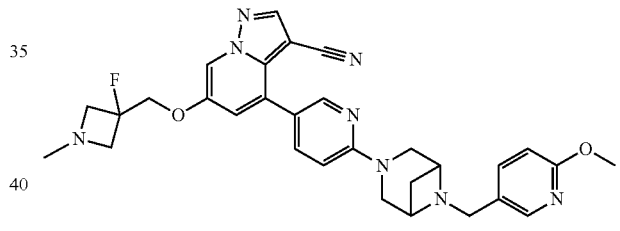

6-((3-fluoro-1-methylazetidin-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 6-((3-fluoroazetidine-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Example 451, Step 2; 13 mg, 0.0240 mmol) in ( ) DMA (0.2 mL) was treated sequentially with formaldehyde (9.03 μL, 0.120 mmol) and NaBH(AcO)$_3$ (51 mg, 0.240 mmol). The reaction mixture was stirred at 60° C. until LCMS indicated complete consumption of starting material. The reaction mixture was concentrated in vacuo, and the crude residue was dissolved in 1 mL of 60:40 ACN/water with 2% TFA and purified by C18 reverse phase chromatography (using 5-95% ACN in H$_2$O with 0.1% TFA as the gradient eluent) to afford the TFA salt of the title compound. The TFA salt was dissolved in MeOH (5 mL), passed through a P1-HCO3 resin, then concentrated in vacuo to cleanly afford the title compound (6.4 mg, 48% yield). MS (apci) m/z=555.3 (M+H).

Example 453

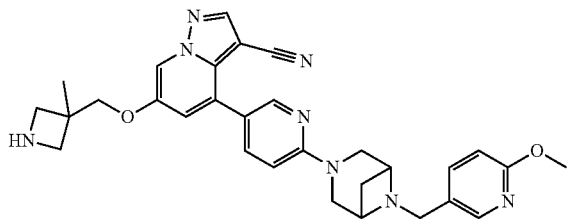 [SMILES: COc1ccc(CN2C3CC2CN(c2ccc(-c4cc(OCC5(C)CNC5)cn5ncc(C#N)c45)cn2)C3)cn1]

4-(6-(6-(((6-methoxypyridin-3-yl)methyl)-3,6-diazabicyclo[3.1.1]heptan-3-yl)pyridin-3-yl)-6-((3-methylazetidin-3-yl)methoxy)pyrazolo[1,5-a]pyridine-3-carbonitrile

Step 1: Preparation of tert-butyl 34-(3-cyano-4-(6-(6-(6-methoxypyridin-3-yl)methyl)-3,6-diazabicyclo[3.1.1]heptan-3-yl)pyridin-3-yl)pyrazolo[1,5-a]pyridin-6-yl)oxy)methyl)-3-methylazetidine-1-carboxylate A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 50 mg, 0.110 mmol) in DMA (0.3 mL) was treated sequentially with Cs$_2$CO$_{3(s)}$ (144 mg, 0.441 mmol) and tert-butyl 3-(bromomethyl)-3-methylazetidine-1-carboxylate (30.8 µL, 0.110 mmol), then stirred overnight at 60° C. After cooling to ambient temperature, the reaction mixture was diluted with EtOAc, washed with water (3×) and brine (1×). The combine organic extracts were dried over anhydrous Na$_2$SO$_{4(s)}$, filtered, and concentrated in vacuo. The crude residue was dissolved in 1 mL of 60:40 ACN/water with 2% TFA and purified by C18 reverse phase chromatography (using 5-95% ACN in H$_2$O with 0.1% TFA as the gradient eluent) to afford the TFA salt of the title compound. The TFA salt was dissolved in MeOH (5 mL), passed through a P1-HCO3 resin, then concentrated in vacuo to cleanly afford the title compound (38.9 mg, 55% yield). MS m/z=637.3 (M+H).

Step 2: Preparation of 4-(6-(6-(((6-methoxypyridin-3-yl)methyl)-3,6-diazabicyclo[3.1.1]heptan-3-yl)pyridin-3-yl)-6-((3-methylazetidin-3-yl)methoxy)pyrazolo[1,5-a]pyridine-3-carbonitrile A solution of tert-butyl 3-(((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)methyl)-3-methylazetidine-1-carboxylate (Step 1; 38.9 mg, 0.0611 mmol) in 1:1 DCM:TFA (mL) (was stirred for 1 h at ambient temperature. The crude residue was dissolved in 1 mL of 60:40 ACN/water with 2% TFA and purified by C18 reverse phase chromatography (using 5-95% ACN in H$_2$O with 0.1% TFA as the gradient eluent) to afford the TFA salt of the title compound. The TFA salt was dissolved in MeOH (5 mL), passed through a P1-HCO3 resin, and then concentrated in vacuo to cleanly afford the title compound (9 mg, 41% yield). MS (apci) m/z=537.2 (M+H).

Example 454

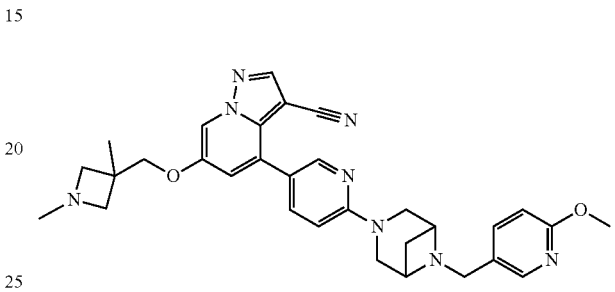

6-((1,3-dimethylazetidin-3-yl)methoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(6-(((6-methoxypyridin-3-yl)methyl)-3,6-diazabicyclo[3.1.1]heptan-3-yl)pyridin-3-yl)-6-((3-methylazetidin-3-yl)methoxy)pyrazolo[1,5-a]pyridine-3-carbonitrile (Example 453, Step 2; 16 mg, 0.0298 mmol) in DMA 0.1 mL ( ) was treated sequentially with formaldehyde (11.2 µL, 0.149 mmol) and NaBH(AcO)$_3$ (63.2 mg, 0.298 mmol). The reaction mixture was stirred overnight at 60° C. The reaction mixture was cooled to ambient temperature, and concentrated in vacuo. The crude residue was purified by C18 reverse phase chromatography (using 5-95% ACN:water with 0.1% TFA as the gradient eluent) to afford the TFA salt of the title compound. The TFA salt was dissolved in MeOH, passed through a P1-HCO3 resin, dried over anhydrous Na$_2$SO$_{4(s)}$, filtered and concentrated in vacuo to cleanly afford the title compound (5.6 mg, 34% yield). MS (apci) m/z=551.3 (M+H).

Example 455

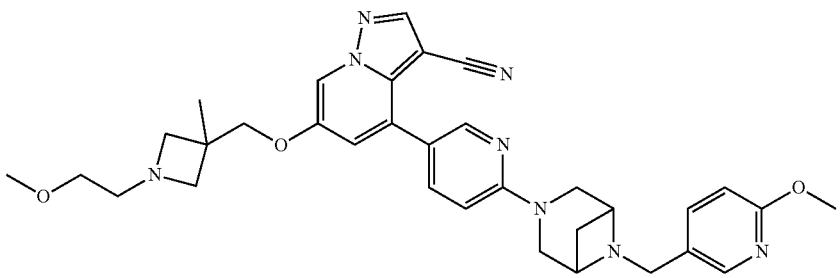

6-((1-(2-methoxyethyl)-3-methylazetidin-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A mixture of 4-(6-(6-((6-methoxypyridin-3-yl)methyl)-3,6-diazabicyclo[3.1.1]heptan-3-yl)pyridin-3-yl)-6-((3-methylazetidin-3-yl)methoxy)pyrazolo[1,5-a]pyridine-3-carbonitrile (Example 453, Step 2; 17.3 mg, 0.03224 mmol) in DMA 0.15 mL ( ) was treated sequentially with potassium carbonate (22.28 mg, 0.1612 mmol) and 1-bromo-2-methoxyethane (6.06 µL, 0.0645 mmol). The resulting mixture was stirred overnight at 70° C. The reaction mixture was cooled to ambient temperature, and purified directly by C18 reverse phase chromatography (using 5-95% ACN:water with 0.1% TFA as the gradient eluent) to afford the TFA salt of the title compound. The TFA salt was dissolved in MeOH, passed through a P1-HCO3 resin and concentrated in vacuo to cleanly afford the title compound (10.26 mg, 54% yield). MS (apci) m/z=595.3 (M+H).

Example 456

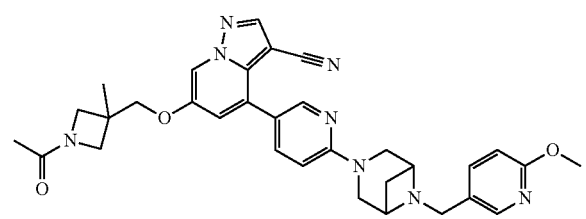 [SMILES: COc1ccc(CN2C3CC2CN(c2ccc(-c4cc(OCC5(C)CN(C(C)=O)C5)cn5ncc(C#N)c45)cn2)C3)cn1]

6-((1-acetyl-3-methylazetidin-3-yl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(6-((6-methoxypyridin-3-yl)methyl)-3,6-diazabicyclo[3.1.1]heptan-3-yl)pyridin-3-yl)-6-((3-methylazetidin-3-yl)methoxy)pyrazolo[1,5-a]pyridine-3-carbonitrile (Example 453, Step 2; 31.7 mg, 0.0591 mmol) in DCM ( ) was treated sequentially with TEA (16.47 µL, 0.1181 mmol) and acetic anhydride (6.32 µL, 0.0886 mmol). The resulting mixture was stirred at ambient temperature until LCMS indicated complete consumption of starting material. The reaction mixture was diluted with DCM (40 mL), washed with brine (3×20 mL) then dried over anhydrous $MgSO_{4(s)}$, filtered and concentrated in vacuo. The crude residue was dissolved into DCM (2 mL) then purified using silica chromatography (using 0-10% MeOH in DCM with 0.1% $NH_4OH$ as the gradient eluent) to afford the title compound (19 mg, 56% yield). MS (apci) m/z=579.3 (M+H).

Example 457

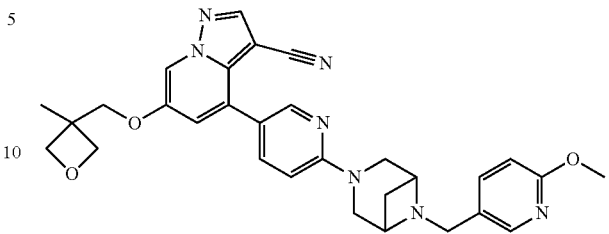

4-(6-(6-((6-methoxypyridin-3-yl)methyl)-3,6-diazabicyclo[3.1.1]heptan-3-yl)pyridin-3-yl)-6-((3-methyloxetan-3-yl)methoxy)pyrazolo[1,5-a]pyridine-3-carbonitrile The title compound (6.2 mg, 20% yield) was prepared, worked up and purified using a similar procedure to that described for Example 432, replacing (2-bromoethyl)dimethylamine with 3-(bromomethyl)-3-methyloxetane. MS (apci) m/z=538.3 (M+H).

Example 458

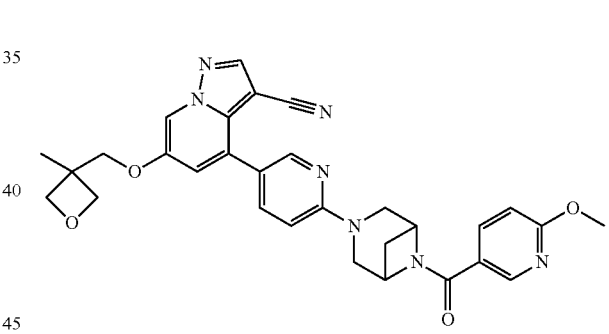

4-(6-(6-(6-methoxynicotinoyl)-3,6-diazabicyclo[3.1.1]heptan-3-yl)pyridin-3-yl)-6-((3-methyloxetan-3-yl)methoxy)pyrazolo[1,5-a]pyridine-3-carbonitrile A solution of 6-hydroxy-4-(6-(6-(6-methoxynicotinoyl)-3,6-diazabicyclo[3.1.1]heptan-3-yl)pyridin-3-yl)pyrazolo[1,5-a]pyridine-3-carbonitrile (Intermediate P72; 36 mg, 0.077 mmol) in DCM (0.2 mL) was treated sequentially with HATU (35.13 mg, 0.09240 mmol), 3-(Bromomethyl)-3-methyloxetane (10.60 µL, 0.0924 mmol) and DIEA (53.29 µL, 0.3080 mmol). After stirring the reaction mixture for 3 d at ambient temperature, $K_2CO_{3(s)}$ (4 eq) was added. The resulting mixture was stirred overnight at 50° C. After cooling to ambient temperature, the reaction mixture was purified directly by silica phase chromatography (using 0-20% DCM/MeOH as the gradient eluent), then triturated with MTBE to afford the title compound (1.13 mg, 3% yield). MS (apci) m/z=552.2 (M+H).

Example 459

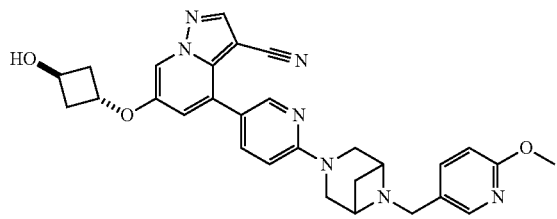

6-((1r,3r)-3-hydroxycyclobutoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-((1r,3r)-3-hydroxycyclobutoxy)pyrazolo[1,5-a]pyridine-3-carbonitrile (Intermediate P78; 55 mg, 0.14 mmol) in DCM (1.0 mL) was treated sequentially with 6-methoxynicotinaldehyde (22 mg, 0.16 mmol) and glacial acetic acid (1.6 µL, 0.027 mmol), then stirred for 10 min at ambient temperature before treating with NaBH(AcO)₃ (43 mg, 0.2 mmol). The reaction mixture was stirred for 2 h at ambient temperature, in a sealed vessel. The resulting mixture was concentrated, and the residue was purified by C18 reverse phase chromatography (5-95% water-ACN with 0.1% TFA as the gradient eluent) to afford the title compound as the TFA ester. The TFA ester was diluted with MeOH (1 mL) and treated with $K_2CO_{3(s)}$ (0.19 g, 1.4 mmol). The resulting mixture was stirred overnight at ambient temperature, then concentrated in vacuo. The residue was diluted with DCM (20 mL), and the resulting suspension was filtered. The filtrate was concentrated in vacuo and the residue was purified by silica chromatography (using 25% acetone in DCM with 0.05% NH₄OH as the eluent) to afford the title compound (11 mg, 15% yield). MS (apci) m/z=524.2 (M+H).

Example 460

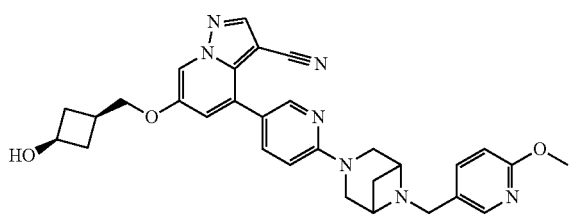 [SMILES: COc1ccc(CN2C3CC2CN(c2ccc(-c4cc(OC[C@H]5C[C@@H](O)C5)cn5ncc(C#N)c45)cn2)C3)cn1]

6-(((1s,3s)-3-hydroxycyclobutyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 25 mg, 0.0551 mmol) in DMA (551 µL) was treated sequentially with $Cs_2CO_{3(s)}$ (53.9 mg, 0.165 mmol) and (1s,3s)-3-(bromomethyl)cyclobutan-1-ol, cis (10.9 mg, 0.0662 mmol) then stirred overnight at 100° C. After cooling to ambient temperature, the reaction mixture was purified directly by C18 reverse phase chromatography (using 5-95% ACN in water with 0.1% TFA as the gradient eluent) to afford the TFA salt of the title compound. The TFA salt was dissolved in MeOH (1 mL), passed through a P1-HCO3 resin, and concentrated in vacuo to cleanly afford the title compound (6.2 mg, 21% yield). MS (apci) m/z=538.3 (M+H).

Example 461

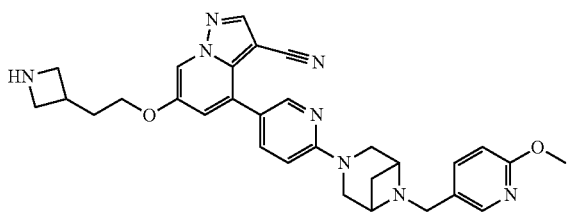 [SMILES: COc1ccc(CN2C3CC2CN(c2ccc(-c4cc(OCCC5CNC5)cn5ncc(C#N)c45)cn2)C3)cn1]

6-(2-(azetidin-3-yl)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile)

Step 1: Preparation of tert-butyl 3-(2-(3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)ethyl)azetidine-1-carboxylate A solution of 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 50 mg, 0.110 mmol) in DMA (0.55 mL) ( ) was treated sequentially with $K_2CO_{3(s)}$ (61 mg, 0.44 mmol) and tert-butyl 3-(2-iodoethyl)azetidine-1-carboxylate (41 mg, 0.13 mmol), then stirred overnight at 60° C. Additional tert-butyl 3-(2-iodoethyl)azetidine-1-carboxylate (41 mg, 0.13 mmol) was added, and the reaction was stirred at 60° C. until LCMS indicated complete consumption of starting material. After cooling to ambient temperature, the reaction mixture was diluted with EtOAc, and washed with water (3×) and brine (1×). The combine organic extracts were dried over anhydrous $Na_2SO_{4(s)}$, filtered, and concentrated in vacuo. The crude residue was purified by C18 reverse phase chromatography (using 5-95% ACN in water with 0.1% TFA as the gradient eluent) to cleanly afford the title compound (70 mg, quantitative yield). MS m/z=637.4 (M+H).

Step 2: Preparation of 4 6-(2-(azetidin-3-yl)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of tert-butyl 3-(2-((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)ethyl)azetidine-1-carboxylate (Step 1; 40.1 mg, 0.0630 mmol) in DCM (2 mL) was treated with TFA (2 mL), and stirred at ambient temperature until LCMS indicated complete consumption of starting material. The reaction mixture was concentrated in vacuo to afford the TFA salt of the title compound. The TFA salt was purified by silica chromatography (using 5-95% DCM/MeOH with 1% NH₄OH as the gradient eluent) to cleanly afford the title compound (mg, 9 mg, 36.2% yield). MS (apci) m/z=537.2 (M+H).

Example 462

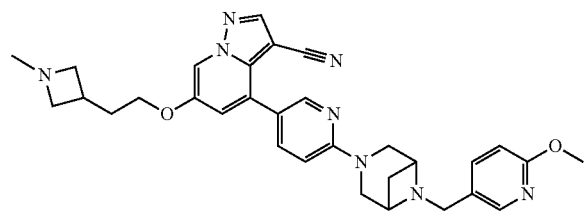

4-(6-(6-(((6-methoxypyridin-3-yl)methyl)-3,6-diazabicyclo[3.1.1]heptan-3-yl)pyridin-3-yl)-6-(2-(1-methylazetidin-3-yl)ethoxy)pyrazolo[1,5-a]pyridine-3-carbonitrile A solution of 4 6-(2-(azetidin-3-yl)ethoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile bis(2,2,2-trifluoroacetate) (Example 461, Step 2; 34 mg, 0.0523 mmol) in DMA (0.26 mL) was treated sequentially with formaldehyde (7.26 µL, 0.261 mmol) and NaBH(AcO)$_3$ (111 mg, 0.523 mmol). The reaction mixture was stirred overnight at 60° C. The reaction mixture was cooled to ambient temperature and concentrated in vacuo. The crude residue was purified by C18 reverse phase chromatography (using 5-95% ACN:water with 0.1% TFA as the gradient eluent) to afford the TFA salt of the title compound. The TFA salt was dissolved in MeOH (5 mL), passed through a P1-HCO3 resin, and concentrated in vacuo to cleanly afford the title compound (5 mg, 17% yield). MS (apci) m/z=551.4 (M+H).

Example 463

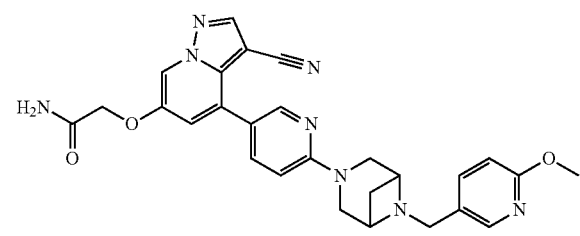 [SMILES: COc1ccc(CN2C3CC2CN(c2ccc(-c4cc(OCC(N)=O)cn5ncc(C#N)c45)cn2)C3)cn1]

2-((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)acetamide The title compound was prepared using a similar procedure to that described for Example 460, except that the reaction was conducted at 60° C., ACN replaced DMA as the reaction solvent, 4 equivalents of Cs$_2$CO$_{3(s)}$ were used, 2-bromoacetamide (1.5 equivalents) replaced (1s,3s)-3-(bromomethyl)cyclobutan-1-ol, cis as the alkyl halide and the purification step was omitted. Upon completion, the reaction mixture was cooled to ambient temperature. The reaction mixture was filtered and concentrated in vacuo to cleanly afford the title compound (28 mg, 96% yield). MS (apci) m/z=511.2 (M+H).

Example 464

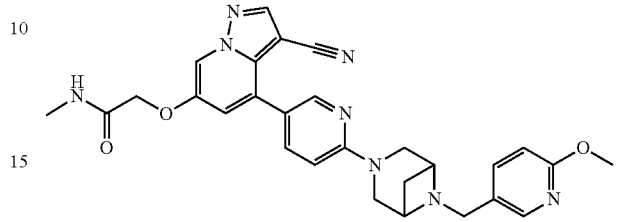

2-((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)-N-methylacetamide A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 25 mg, 0.055 mmol) in DMA (551 µL) was treated sequentially with Cs$_2$CO$_{3(s)}$ (72 mg, 0.22 mmol), KI (9.2 mg, 0.055 mmol) and 2-chloro-N-methylacetamide (8.9 mg, 0.083 mmol), then stirred overnight at 60° C. After cooling to ambient temperature, the reaction mixture was concentrated in vacuo, and the residue was purified by C18 reverse phase chromatography (using 5-95% ACN:water with 0.1% TFA as the gradient eluent) to afford the TFA salt of the title compound. The TFA salt was dissolved in MeOH (5 mL), passed through a P1-HCO3 resin, and concentrated in vacuo to cleanly afford the title compound (8.5 mg, 29% yield). MS (apci) m/z=525.2 (M+H).

Example 465

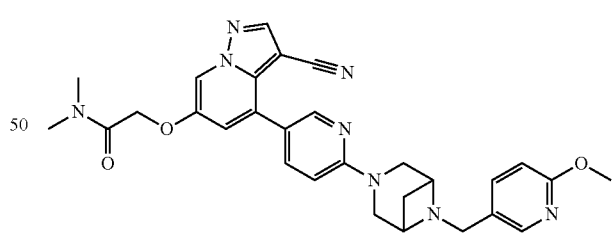

2-((3-cyano-4-(6-(6-(((6-methoxypyridin-3-yl)methyl)-3,6-diazabicyclo[3.1.1]heptan-3-yl)pyridin-3-yl)pyrazolo[1,5-a]pyridin-6-yl)oxy)-N,N-dimethylacetamide The title compound (5.74 mg, 16% yield) was prepared, worked up and purified using a similar procedure to that described for Example 432, replacing (2-bromoethyl)dimethylamine with chloroacetyldimethylamine. MS (apci) m/z=539.2 (M+H).

Example 466

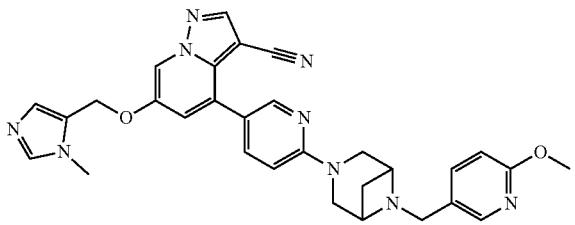 [SMILES: COc1ccc(CN2C3CC2CN(c2ccc(-c4cc(OCc5cncn5C)cn5ncc(C#N)c45)cn2)C3)cn1]

4-(6-(6-(((6-methoxypyridin-3-yl)methyl)-3,6-diaz-abicyclo[3.1.1]heptan-3-yl)pyridin-3-yl)-6-((1-methyl-1H-imidazol-5-yl)methoxy)pyrazolo[1,5-a]pyridine-3-carbonitrile The title compound (11 mg, 30% yield) was prepared and purified using a similar procedure to that described for Example 470, except that 4 equivalents of $Cs_2CO_{3(s)}$ were used, and 5-(chloromethyl)-1-methyl-1H-imidazole (1.5 equivalents) replaced N-(2-chloroethyl)-imidazole hydrochloride as the alkyl halide. MS (apci) m/z=548.2 (M+H).

Example 467

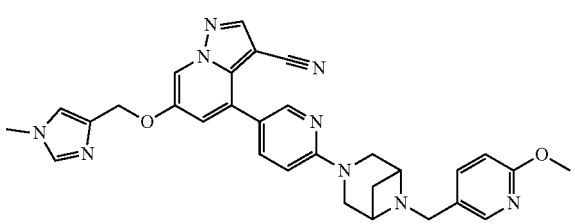

4-(6-(6-(((6-methoxypyridin-3-yl)methyl)-3,6-diaz-abicyclo[3.1.1]heptan-3-yl)pyridin-3-yl)-6-((1-methyl-1H-imidazol-4-yl)methoxy)pyrazolo[1,5-a]pyridine-3-carbonitrile A solution of 6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 25 mg, 0.055 mmol) in DMA (551 µL) was treated sequentially with $Cs_2CO_{3(s)}$ (54 mg, 0.17 mmol), and 4-(chloromethyl)-1-methyl-1H-imidazole (11 mg, 0.083 mmol) then stirred overnight at 100° C. After cooling to ambient temperature, the reaction mixture was partitioned between DCM and water. The resulting organic extracts were purified by silica chromatography (using column 0-10% MeOH with 1% $NH_4OH$ as gradient eluent) then by a second silica chromatography (using 0-100% EtOAc in Hexanes then 0-10% MeOH in EtOAc as the gradient eluent) to cleanly afford the title compound (4 mg, 13% yield). MS (apci) m/z=548.2 (M+H). $^1H$ NMR (400 MHz, $CDCl_3$) δ 8.38 (d, 1H), 8.35 (d, 1H), 8.20 (s, 1H), 8.10 (d, 1H), 7.77 (dd, 1H), 7.62 (dd, 1H), 7.48 (d, 1H), 7.18 (d, 1H), 7.03 (d, 1H), 6.71 (d, 1H), 6.67 (d, 1H), 5.08 (s, 2H), 3.92 (s, 3H), 3.82, (m, 4H), 3.69 (s, 3H), 3.59 (m, 4H), 2.69 (m, 1H), 1.66 (d, 1H).

Example 468

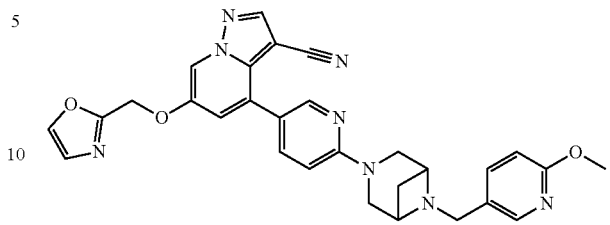

4-(6-(6-(((6-methoxypyridin-3-yl)methyl)-3,6-diaz-abicyclo[3.1.1]heptan-3-yl)pyridin-3-yl)-6-(oxazol-2-ylmethoxy)pyrazolo[1,5-a]pyridine-3-carbonitrile The title compound (11 mg, 30% yield) was prepared and purified using a similar procedure to that described for Example 460, except that the reaction was conducted at ambient temperature, DMF replaced DMA as the reaction solvent, 4 equivalents of $Cs_2CO_{3(s)}$ were used, 2-chloromethyl-oxazole (2.9 equivalents) replaced (1s,3s)-3-(bromomethyl)cyclobutan-1-ol, cis as the alkyl halide, and the gradient eluent used in purification was 0-50% water/ACN with 0.1% TFA. The TFA salt was dissolved in MeOH (5 mL), passed through a P1-HCO3 resin, and concentrated in vacuo to cleanly afford the title compound. MS (apci) m/z=535.2 (M+H)

Example 469

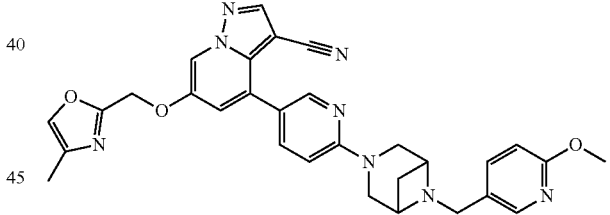

4-(6-(6-(((6-methoxypyridin-3-yl)methyl)-3,6-diaz-abicyclo[3.1.1]heptan-3-yl)pyridin-3-yl)-6-((4-methyloxazol-2-yl)methoxy)pyrazolo[1,5-a]pyridine-3-carbonitrile The title compound (11 mg, 30% yield) was prepared and purified using a similar procedure to that described for Example 460, except that the reaction was conducted at ambient temperature, DMF replaced DMA as the reaction solvent, 4 equivalents of $Cs_2CO_{3(s)}$ were used, 2-(chloromethyl)-4-methyloxazole replaced (1s,3s)-3-(bromomethyl)cyclobutan-1-ol, cis as the alkyl halide, and the gradient eluent used in purification was 0-50% water/ACN with 0.1% TFA. The TFA salt was dissolved in MeOH (5 mL), passed through a P1-HCO3 resin, and concentrated in vacuo to cleanly afford the title compound. MS (apci) m/z=549.3 (M+H)

Example 470

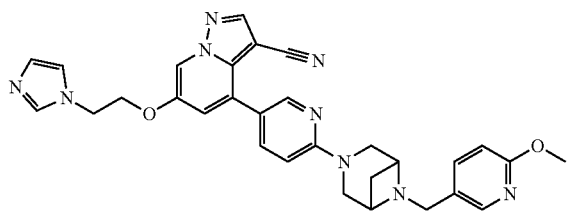 [SMILES: COc1ccc(CN2C3CC2CN(c2ccc(-c4cc(OCCn5ccnc5)cn5ncc(C#N)c45)cn2)C3)cn1]

6-(2-(1H-imidazol-1-yl)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 30 mg, 0.066 mmol) in DMA (132 μL) was treated sequentially with $K_2CO_{3(s)}$ (9.1 mg, 0.066 mmol) and N-(2-chloroethyl)-imidazole hydrochloride (13 mg, 0.079 mmol), then stirred overnight at 60° C. After cooling to ambient temperature, the reaction mixture was diluted with EtOAc, washed with water (3×) and brine (1×). The organic extracts were dried over anhydrous $Na_2SO_{4(s)}$, filtered and concentrated in vacuo. The crude residue was purified by C18 reverse phase chromatography (using 60:40 MeCN/water with 2% TFA as the gradient eluent) to afford the TFA salt of the title compound. The TFA salt was dissolved in MeOH (5 mL), passed through a P1-HCO3 resin, and concentrated in vacuo to cleanly afford the title compound (19 mg, 52% yield). MS (apci) m/z=548.3 (M+H).

Example 471

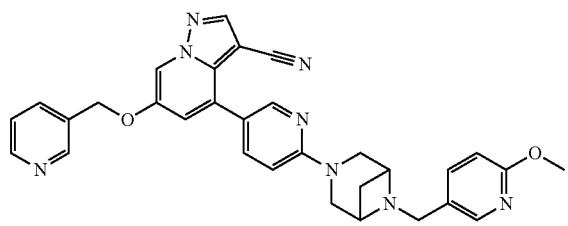 [SMILES: COc1ccc(CN2C3CC2CN(c2ccc(-c4cc(OCc5cccnc5)cn5ncc(C#N)c45)cn2)C3)cn1]

4-(6-(6-((6-methoxypyridin-3-yl)methyl)-3,6-diazabicyclo[3.1.1]heptan-3-yl)pyridin-3-yl)-6-(pyridin-3-ylmethoxy)pyrazolo[1,5-a]pyridine-3-carbonitrile The title compound (2.8 mg, 9% yield) was prepared and purified using a similar procedure to that described for Example 446, except that DMA was used in place of DMF, 4 equivalents of $Cs_2CO_{3(s)}$ were used, and 3-(iodomethyl)pyridine hydroiodide (1.5 equivalents) replaced 1-(2-chloroethyl)pyrrolidine as the alkyl halide. MS (apci) m/z=545.2 (M+H).

Example 472

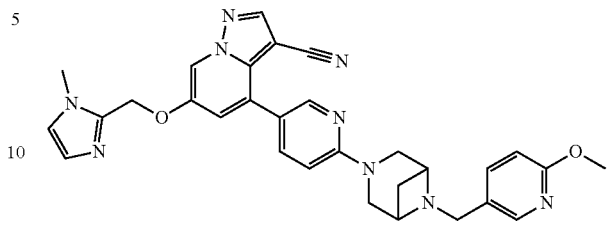

4-(6-(6-((6-methoxypyridin-3-yl)methyl)-3,6-diazabicyclo[3.1.1]heptan-3-yl)pyridin-3-yl)-6-((1-methyl-1H-imidazol-2-yl)methoxy)pyrazolo[1,5-a]pyridine-3-carbonitrile The title compound (2.8 mg, 9% yield) was prepared and purified using a similar procedure to that described for Example 446, except that DMA was used in place of DMF, 4 equivalents of $Cs_2CO_{3(s)}$ were used, and 2-(chloromethyl)-1-methyl-1H-imidazole replaced 1-(2-chloroethyl)pyrrolidine as the alkyl halide. MS (apci) m/z=548.3 (M+H).

Example 473

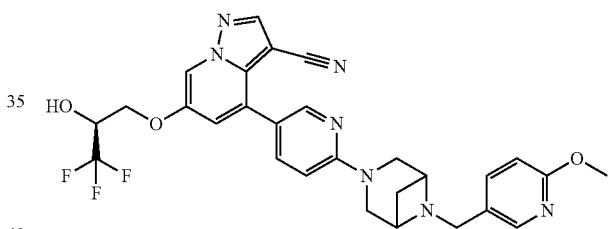

4-(6-(6-((6-methoxypyridin-3-yl)methyl)-3,6-diazabicyclo[3.1.1]heptan-3-yl)pyridin-3-yl)-6-((S)-3,3,3-trifluoro-2-hydroxypropoxy)pyrazolo[1,5-a]pyridine-3-carbonitrile A solution of 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 25 mg, 0.055 mmol) in DMA (551.3 μL) was treated sequentially with $Cs_2CO_{3(s)}$ (53.88 mg, 0.1654 mmol) and (S)-(−)-3,3,3-trifluoro-1,2-epoxypropane (7.160 μL, 0.08269 mmol) then stirred overnight at 80° C. Additional (S)-(−)-3,3,3-trifluoro-1,2-epoxypropane (2.38 μL) was introduced, and the reaction was stirred overnight at 80° C. After cooling to ambient temperature, the reaction mixture was purified directly by silica chromatography (using 0-100% EtOAc in Hexanes then 0-10% MeOH in EtOAc as the gradient eluent) then again by C18 reverse phase chromatography (using 5-95% water-ACN with 0.1% TFA as the gradient eluent) to afford the TFA salt of the title compound. The TFA salt was dissolved in MeOH (5 mL), passed through a P1-HCO3 resin, and concentrated in vacuo to cleanly afford the title compound (1 mg, 3% yield). MS (apci) m/z=566.2 (M+H).

Example 474

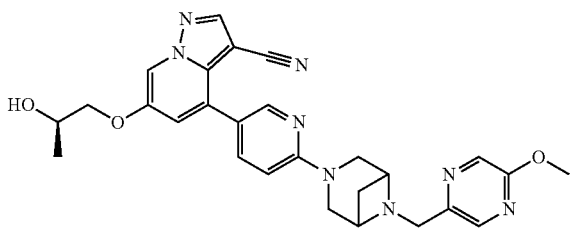 [SMILES: COc1cnc(CN2C3CC2CN(c2ccc(-c4cc(OC[C@@H](C)O)cn5ncc(C#N)c45)cn2)C3)cn1]

6-((R)-2-hydroxypropoxy)-4-(6-(6-((5-methoxy-pyrazin-2-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-((R)-2-hydroxypropoxy)pyrazolo[1,5-a]pyridine-3-carbonitrile bis(2,2,2-trifluoroacetate) (Intermediate P80; 25 mg, 0.0404 mmol) in DCE (202 μL) was treated sequentially with 5-methoxypyrazine-2-carbaldehyde (11 mg, 0.081 mmol), then with NaBH(AcO)₃ (26 mg, 0.12 mmol). After stirring for 1 h at ambient temperature, the reaction mixture was purified directly by silica chromatography (using 0-100% DCM in Hexanes then 0-60% (2% NH₄OH/20% MeOH/78% DCM) in DCM as the gradient eluent) to afford the title compound (10 mg, 48% yield). MS (apci) m/z=513.2 (M+H).

Example 475

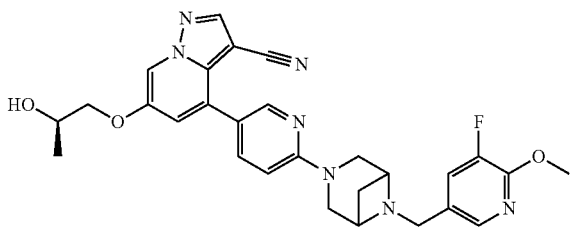 [SMILES: COc1ncc(CN2C3CC2CN(c2ccc(-c4cc(OC[C@@H](C)O)cn5ncc(C#N)c45)cn2)C3)cc1F]

4-(6-(6-((5-fluoro-6-methoxypyridin-3-yl)methyl)-3,6-diazabicyclo[3.1.1]heptan-3-yl)pyridin-3-yl)-6-((R)-2-hydroxypropoxy)pyrazolo[1,5-a]pyridine-3-carbonitrile The title compound (1.36 mg, 6% yield) was prepared and purified using a similar procedure to that described for Example 474, following by LCMS for reaction completion and replacing 5-methoxypyrazine-2-carbaldehyde with 5-fluoro-6-methoxynicotinaldehyde. MS (apci) m/z=530.2 (M+H).

Example 476

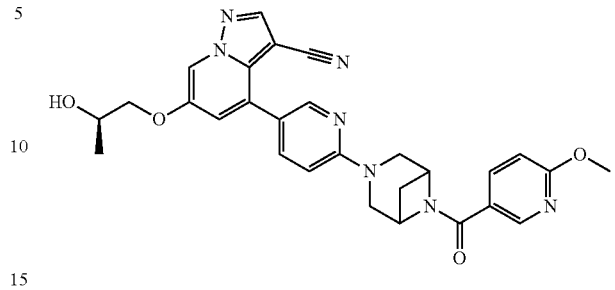

6-((R)-2-hydroxypropoxy)-4-(6-(6-(6-methoxynico-tinoyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-((R)-2-hydroxypropoxy)pyrazolo[1,5-a]pyridine-3-carbonitrile (Intermediate P81; 75 mg, 0.19 mmol) in DCM (3842 μL) was treated sequentially with 2-methoxy-5-pyridinecarboxylic acid (35.30 mg, 0.2305 mmol), HATU (87.65 mg, 0.2305 mmol), and DIEA (133.8 μL, 0.7684 mmol) was stirred for 2 h at ambient temperature. The reaction mixture was purified directly by silica chromatography (using a gradient of 50-100% EtOAc in Hexanes then 0-20% MeOH in EtOAc as the gradient eluent) to afford the title compound (47.92 mg, 47% yield). MS (apci) m/z=526.2 (M+H).

Example 477

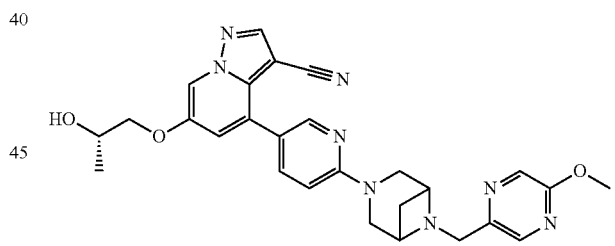

6-((S)-2-hydroxypropoxy)-4-(6-(6-((5-methoxy-pyrazin-2-yl)methyl)-3,6-diazabicyclo[3.1.1]heptan-3-yl)pyridin-3-yl)pyrazolo[1,5-a]pyridine-3-carbonitrile The title compound (7.91 mg, 38% yield) was prepared and purified using a similar procedure to that described for Example 474, following by LCMS for reaction completion, replacing 4-(6-(3,6-diazabicyclo[3.1.1]heptan-3-yl)pyridin-3-yl)-6-((R)-2-hydroxypropoxy)pyrazolo[1,5-a]pyridine-3-carbonitrile bis(2,2,2-trifluoroacetate) with 4-(6-(3,6-diazabicyclo[3.1.1]heptan-3-yl)pyridin-3-yl)-6-((S)-2-hydroxypropoxy)pyrazolo[1,5-a]pyridine-3-carbonitrile bis(2,2,2-trifluoroacetate) (Intermediate P83). MS (apci) m/z=513.2 (M+H).

Example 478

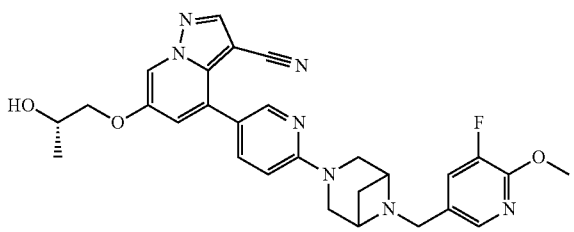 [SMILES: COc1ncc(CN2C3CC2CN(c2ccc(-c4cc(OC[C@H](C)O)cn5ncc(C#N)c45)cn2)C3)cc1F]

4-(6-(6-((5-fluoro-6-methoxypyridin-3-yl)methyl)-3,
6-diazabicyclo[3.1.1]heptan-3-yl)pyridin-3-yl)-6-
((S)-2-hydroxypropoxy)pyrazolo[1,5-a]pyridine-3-
carbonitrile The title compound (5.37 mg, 25% yield) was prepared and purified using a similar procedure to that described for Example 474, following by LCMS for reaction completion, replacing 5-methoxypyrazine-2-carbaldehyde with 5-fluoro-6-methoxynicotinaldehyde and replacing 4-(6-(3,6-diazabicyclo[3.1.1]heptan-3-yl)pyridin-3-yl)-6-((R)-2-hydroxypropoxy)pyrazolo[1,5-a]pyridine-3-carbonitrile bis(2,2,2-trifluoroacetate) with 4-(6-(3,6-diazabicyclo[3.1.1]heptan-3-yl)pyridin-3-yl)-6-((S)-2-hydroxypropoxy)pyrazolo[1,5-a]pyridine-3-carbonitrile bis(2,2,2-trifluoroacetate) (Intermediate P 83). MS (apci) m/z=530.2 (M+H).

Example 479

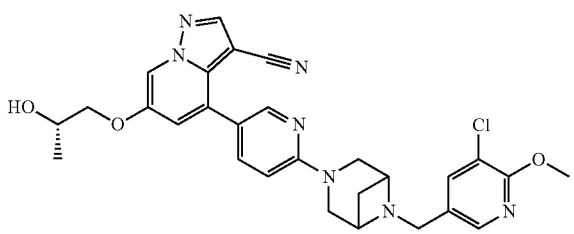 [SMILES: COc1ncc(CN2C3CC2CN(c2ccc(-c4cc(OC[C@H](C)O)cn5ncc(C#N)c45)cn2)C3)cc1Cl]

4-(6-(6-((5-chloro-6-methoxypyridin-3-yl)methyl)-3,
6-diazabicyclo[3.1.1]heptan-3-yl)pyridin-3-yl)-6-
((S)-2-hydroxypropoxy)pyrazolo[1,5-a]pyridine-3-
carbonitrile The title compound (4.66 mg, 26% yield) was prepared and purified using a similar procedure to that described for Example 474, following by LCMS for reaction completion, replacing 5-methoxypyrazine-2-carbaldehyde with 5-chloro-6-methoxynicotinaldehyde and replacing 4-(6-(3,6-diazabicyclo[3.1.1]heptan-3-yl)pyridin-3-yl)-6-((R)-2-hydroxypropoxy)pyrazolo[1,5-a]pyridine-3-carbonitrile bis(2,2,2-trifluoroacetate) with 4-(6-(3,6-diazabicyclo[3.1.1]heptan-3-yl)pyridin-3-yl)-6-((S)-2-hydroxypropoxy)pyrazolo[1,5-a]pyridine-3-carbonitrile bis(2,2,2-trifluoroacetate) (Intermediate P83). MS (apci) m/z=546.2 (M+H).

Example 480

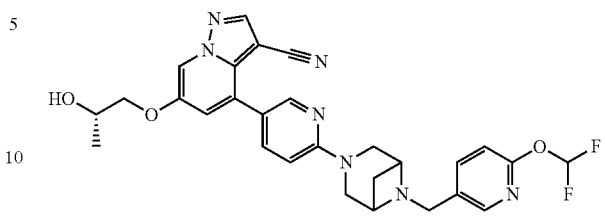

4-(6-(6-((6-(difluoromethoxy)pyridin-3-yl)methyl)-
3,6-diazabicyclo[3.1.1]heptan-3-yl)pyridin-3-yl)-6-
((S)-2-hydroxypropoxy)pyrazolo[1,5-a]pyridine-3-
carbonitrile The title compound (9.19 mg, 52% yield) was prepared and purified using a similar procedure to that described for Example 474, following by LCMS for reaction completion, replacing 5-methoxypyrazine-2-carbaldehyde with 6-(difluoromethoxy)nicotinaldehyde and replacing 4-(6-(3,6-diazabicyclo[3.1.1]heptan-3-yl)pyridin-3-yl)-6-((R)-2-hydroxypropoxy)pyrazolo[1,5-a]pyridine-3-carbonitrile bis(2,2,2-trifluoroacetate) with 4-(6-(3,6-diazabicyclo[3.1.1]heptan-3-yl)pyridin-3-yl)-6-((S)-2-hydroxypropoxy)pyrazolo[1,5-a]pyridine-3-carbonitrile bis(2,2,2-trifluoroacetate) (Intermediate P83). MS (apci) m/z=548.2 (M+H).

Example 481

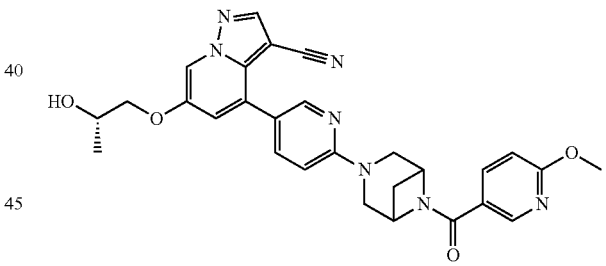

6-((S)-2-hydroxypropoxy)-4-(6-(6-(6-methoxynicoti-
noyl)-3,6-diazabicyclo[3.1.1]heptan-3-yl)pyridin-3-
yl)pyrazolo[1,5-a]pyridine-3-carbonitrile A solution of 4-(6-(3,6-diazabicyclo[3.1.1]heptan-3-yl)pyridin-3-yl)-6-((S)-2-hydroxypropoxy)pyrazolo[1,5-a]pyridine-3-carbonitrile bis(2,2,2-trifluoroacetate) (Intermediate P83; 20 mg, 0.032 mmol) in DCM (646.4 µL) was treated sequentially with 2-methoxy-5-pyridinecarboxylic acid (5.942 mg, 0.03880 mmol), HATU (14.75 mg, 0.03880 mmol), and DIEA (22.53 µL, 0.1293 mmol) was stirred for 2 h at ambient temperature. The reaction mixture was purified directly by silica chromatography (using a gradient of 0-100% DCM in Hexanes then 0-60% (2% NH$_4$OH/20% MeOH/78% DCM) in DCM as the gradient eluent) to afford the title compound (13.85 mg, 81% yield). MS (apci) m/z=526.2 (M+H).

Example 482

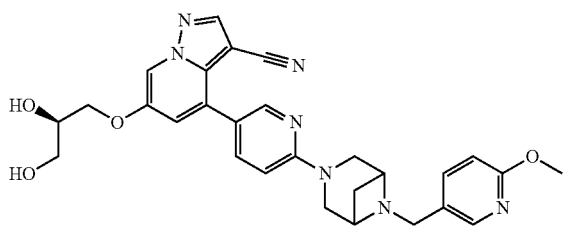

6-((R)-2,3-dihydroxypropoxy)-4-(6-(6-((6-methoxy-pyridin-3-yl)methyl)-3,6-diazabicyclo[3.1.1]heptan-3-yl)pyridin-3-yl)pyrazolo[1,5-a]pyridine-3-carbonitrile The title compound (5.74 mg, 16% yield) was prepared and purified using a similar procedure to that described for Example 460, replacing (1s,3s)-3-(bromomethyl)cyclobutan-1-ol, cis with (R)-4-chloromethyl-2,2-dimethyl-1,3-dioxolane (1.2 equivalents). MS (apci) m/z=528.3 (M+H).

Example 483

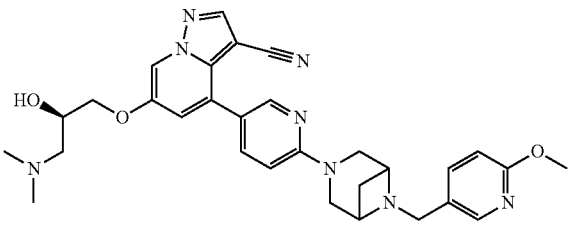

6-((R)-3-(dimethylamino)-2-hydroxypropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile

Step 1: Preparation of tert-butyl ((2R)-3-((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)-2-hydroxypropyl)carbamate bis(2,2,2-trifluoroacetate)

A solution of 6-hydroxy-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (Intermediate P71; 50 mg, 0.110 mmol) in DMA (221 μL) was treated sequentially with $K_2CO_{3(s)}$ (60.9 mg, 0.441 mmol) and (R)-1-(t-butoxycarbonyl)-2,3-oxiranylamine (22.9 μL, 0.132 mmol), then stirred for 16 h at 60° C. Additional (R)-1-(t-butoxycarbonyl)-2,3-oxiranylamine (9.54 μL) was introduced, and the reaction was stirred for 16 h again at 60° C. After cooling to ambient temperature, the reaction mixture was diluted with EtOAc, washed with water (3×) and then with brine (1×). The organic extracts were dried over anhydrous $Na_2SO_{4(s)}$, filtered, and concentrated in vacuo. The crude residue was purified by C18 reverse phase chromatography (using 5-95% water-ACN with 0.1% TFA as the gradient eluent) to cleanly afford the title compound (19.5 mg, 28% yield). MS m/z=627.3 (M+H)

Step 2: Preparation of 6-((R)-3-amino-2-hydroxy-propoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile bis(2,2,2-trifluoroacetate)

A solution of tert-butyl ((2R)-3-((3-cyano-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)-2-hydroxypropyl)carbamate (Step 1; 16.2 mg, 0.0258 mmol) in DCM (1 mLmL) was treated with TFA (1 mL) and stirred for 1 h at ambient temperature. The reaction mixture was concentrated in vacuo to afford the title compound assuming quantitative yield. MS m/z=527.3 (M+H).

Step 3: Preparation of 6-((R)-3-(dimethylamino)-2-hydroxypropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A mixture of 6-((R)-3-amino-2-hydroxypropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile bis(2,2,2-trifluoroacetate (19.5 mg, 0.0258 mmol) in DCM (258 μL) was treated sequentially with formaldehyde (19.2 μL, 0.258 mmol) and $NaBH(AcO)_3$ (27.4 mg, 0.129 mmol). After stirring overnight at ambient temperature, the reaction mixture was diluted with EtOAc, washed with water (3×) and then with brine (1×). The organic extracts were dried over anhydrous $Na_2SO_{4(s)}$, filtered and concentrated in vacuo. The crude residue was purified by C18 reverse phase chromatography (using 5-95% water-ACN with 0.1% TFA as the gradient eluent) to cleanly afford the title compound (6.2 mg, 43% yield). MS (apci) m/z=555.3 (M+H).

Example 484

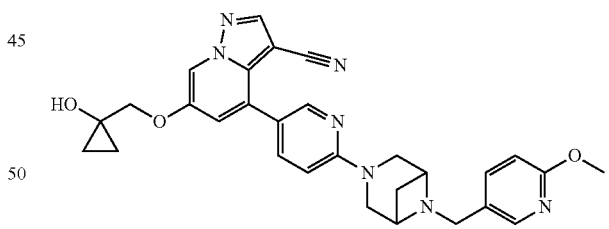

6-((1-hydroxycyclopropyl)methoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile A solution of 4-(6-(3,6-diazabicyclo[3.1.1]heptan-3-yl)pyridin-3-yl)-6-((1-hydroxycyclopropyl)methoxy)pyrazolo[1,5-a]pyridine-3-carbonitrile dihydrochloride (Intermediate P84; 50.7 mg, 0.107 mmol) and 6-methoxynicotinaldehyde (137.1 mg, 1.943 mmol) in DCM (1.0 mL) was treated sequentially with $NaBH(AcO)_3$ (514.8 mg, 2.429 mmol) and 3 drops of glacial acetic acid. The resulting mixture was stirred for 16 h at ambient temperature before sequentially introducing additional 6-methoxynicotinaldehyde (29.3 mg, 0.213 mmol) and NaBH(AcO)$_3$ (45.2 mg, 0.213 mmol). The resulting mixture was stirred for 20 h at ambient temperature. The reaction mixture was purified directly by C18 reverse phase chromatography (using 5-95% water-ACN with 0.1% TFA as the gradient eluent) to afford the title compound as the TFA salt. The TFA salt was diluted with 4:1 DCM:iPrOH, and extracted with saturated NaHCO$_{3(aq)}$. The organic extracts were dried over anhydrous Na$_2$SO$_{4(s)}$, filtered, and concentrated in vacuo. The residue was re-purified by silica chromatography (using 1-30% DCM-MeOH with 2% NH$_4$OH as the gradient eluent) to cleanly afford the title compound (13.2 mg, 24% yield). MS (apci) m/z=524.2 (M+H).

Example 485

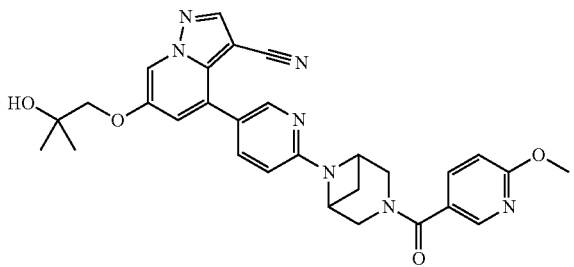 [SMILES: COc1ccc(C(=O)N2CC3CC(C2)N3c2ccc(-c3cc(OCC(C)(C)O)cn4ncc(C#N)c34)cn2)cn1]

6-(2-hydroxy-2-methylpropoxy)-4-(6-(3-(6-methoxynicotinoyl)-3,6-diazabicyclo[3.1.1]heptan-6-yl)pyridin-3-yl)pyrazolo[1,5-a]pyridine-3-carbonitrile Step 1: Preparation of tert-butyl 6-(5-(3-cyano-6-(2-hydroxy-2-methylpropoxy)pyrazolo[1,5-a]pyridin-4-yl)pyridin-2-yl)-3,6-diazabicyclo[3.1.1]heptane-3-carboxylate Under inert atmosphere (N$_{2(g)}$), a mechanically stirred suspension of 3,6-diaza-bicyclo[3.1.1]heptane-6-carboxylic acid tert-butyl ester (49.3 g, 249 mmol) in DMSO (200 mL) was treated with 4-(6-fluoropyridin-3-yl)-6-(2-hydroxy-2-methylpropoxy)pyrazolo[1,5-a]pyridine-3-carbonitrile (Intermediate P42; 58 g, 178 mmol), and DIEA (93.1 mL, 533 mmol) was stirred 42 h at 90° C. After cooling to ambient temperature, the reaction mixture was poured into ice water (2 L). The aqueous mixture was stirred for 15 min before Heptane (1 L) was added. The biphasic mixture was stirred vigorously for 2 h. The resulting biphasic suspension was vacuum filtered and the solids were rinsed sequentially with water (3×200 mL) and heptane (3×200 mL) to afford a product mixture containing 5-20% of the title compound, tert-butyl 6-(5-(3-cyano-6-(2-hydroxy-2-methylpropoxy)pyrazolo[1,5-a]pyridin-4-yl)pyridin-2-yl)-3,6-diazabicyclo[3.1.1]heptane-3-carboxylate, along with the regioisomer, tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (Intermediate P43, step 1) (92 g, quantitative yield). The regioisomeric mixture was carried into Step 2 without separating (note: 3,6-diaza-bicyclo[3.1.1]heptane-6-carboxylic acid tert-butyl ester can partially isomerize to the regioisomer, 3,6-diaza-bicyclo[3.1.1]heptane-3-carboxylic acid tert-butyl ester, under these reaction conditions.) MS (apci) m/z=505.3 (M+H).

Step 2: Preparation of 4-(6-(3,6-diazabicyclo[3.1.1]heptan-6-yl)pyridin-3-yl)-6-(2-hydroxy-2-methylpropoxy)pyrazolo[1,5-a]pyridine-3-carbonitrile dihydrochloride Under inert atmosphere (N$_{2(g)}$), a 0° C. solution of the regioisomeric mixture of tert-butyl 6-(5-(3-cyano-6-(2-hydroxy-2-methylpropoxy)pyrazolo[1,5-a]pyridin-4-yl)pyridin-2-yl)-3,6-diazabicyclo[3.1.1]heptane-3-carboxylate and tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (Step 1; 92 g, 182 mmol) in DCM (456 mL) was treated dropwise, over a period of 15 min, with TFA (281 mL). The resulting mixture was allowed to warm to ambient temperature. After stirring for 3 h at ambient temperature, the reaction mixture was concentrated in vacuo. Under inert atmosphere (N$_{2(g)}$), the resultant oil was diluted with MeOH (600 mL) and cooled to 0° C. The cold (0° C.) solution was treated dropwise over a 15 min period with 5 M HCl in propanol (365 mL, 1823 mmol). After stirring for 30 min at ambient temperature, the resulting mixture was vacuum filtered, rinsing the solids with MeOH (150 mL). Under inert atmosphere (N$_{2(g)}$), the crude solids were suspended in 4:1MTBE:MeOH (500 mL), cooled to 0° C., then treated again with 5 M HCl in propanol (73 mL, 364.6 mmol). After stirring for 15 min at ambient temperature, the resulting suspension was filtered, rinsing the solids with 4:1 MTBE:MeOH (200 mL). The solids were collected and dried in vacuo to afford a product mixture containing 5-20% of the title compound, 4-(6-(3,6-diazabicyclo[3.1.1]heptan-6-yl)pyridin-3-yl)-6-(2-hydroxy-2-methylpropoxy)pyrazolo[1,5-a]pyridine-3-carbonitrile dihydrochloride along with it's regioisomer, 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43, step 2) (80.2 g, quantitative yield). The regioisomeric mixture was carried into Step 3 without separating. MS (apci) m/z=405.2 (M+H).

Step 3: Preparation of 6-(2-hydroxy-2-methylpropoxy)-4-(6-(3-(6-methoxynicotinoyl)-3,6-diazabicyclo[3.1.1]heptan-6-yl)pyridin-3-yl)pyrazolo[1,5-a]pyridine-3-carbonitrile A solution of the regioisomeric mixture of 4-(6-(3,6-diazabicyclo[3.1.1]heptan-6-yl)pyridin-3-yl)-6-(2-hydroxy-2-methylpropoxy)pyrazolo[1,5-a]pyridine-3-carbonitrile dihydrochloride along with it's regioisomer, 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Step 2; 2.16 g, 4.52 mmol) in DMSO (22.6 mL) was treated sequentially with 6-methoxynicotinic acid (0.831 g, 5.43 mmol), DIEA (2.52 mL, 14.5 mmol) and HATU (2.06 g, 5.43 mmol). The reaction mixture was stirred for 1 h at ambient temperature. The resulting suspension was vacuum filtered, and the solids were collected. The solids were recrystallized from hot EtOAc, cooling to ambient temperature overnight. The crystalline material was collected by filtration, and the filtrate was concentrated in vacuo. The residue from the filtrate was purified by silica chromatography. The residue from the chromatographic purification and the solids collected by filtration were combined and dissolved in ACN (12 mL). The mixture was stirred at 82° C., then cooled to ambient temperature, diluted with water (18 mL), and stirred for 2 d at ambient temperature. The resulting suspension was vacuum filtered to afford a product mixture (1.63 g, 67% yield) containing 5-20% of the title compound, 6-(2-hydroxy-2-methylpropoxy)-4-(6-(3-(6-methoxynicotinoyl)-3,6-diazabicyclo[3.1.1]heptan-6-yl)pyridin-3-yl)pyrazolo[1,5-a]pyridine-3-carbonitrile, along with the regioisomer, 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile. The regioisomeric mixture was separated in Step 4.

Step 4: Isolation of 6-(2-hydroxy-2-methylpropoxy)-4-(6-(3-(6-methoxynicotinoyl)-3,6-diazabicyclo[3.1.1]heptan-6-yl)pyridin-3-yl)pyrazolo[1,5-a]pyridine-3-carbonitrile A solution of the regioisomeric mixture of 6-(2-hydroxy-2-methylpropoxy)-4-(6-(3-(6-methoxynicotinoyl)-3,6-diazabicyclo[3.1.1]heptan-6-yl)pyridin-3-yl)pyrazolo[1,5-a]pyridine-3-carbonitrile and 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile (50 mg, 0.0927 mmol) in 60:40 ACN:water with 2% TFA (1.2 mL) was purified by C18 reverse phase chromatography (using 25-75% ACN:water with 0.1% TFA as the gradient eluent) to independently afford the TFA salt of 6-(2-hydroxy-2-methylpropoxy)-4-(6-(3-(6-methoxynicotinoyl)-3,6-diazabicyclo[3.1.1]heptan-6-yl)pyridin-3-yl)pyrazolo[1,5-a]pyridine-3-carbonitrile. The TFA salt was diluted with saturated NaHCO$_{3(aq)}$ (10 mL) and extracted with DCM (2×10 mL). The combined organic extracts were dried over anhydrous Na$_2$SO$_{4(s)}$, filtered and concentrated in vacuo to afford the title compound (26.4 mg, 53% recovery) free from the regioisomer. MS (apci) m/z=540.3 (M+H).

Example 486

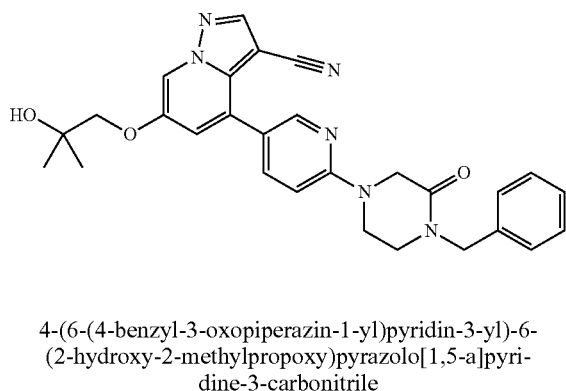

4-(6-(4-benzyl-3-oxopiperazin-1-yl)pyridin-3-yl)-6-(2-hydroxy-2-methylpropoxy)pyrazolo[1,5-a]pyridine-3-carbonitrile In a microwave vessel, a solution of 4-(6-fluoropyridin-3-yl)-6-(2-hydroxy-2-methylpropoxy)pyrazolo[1,5-a]pyridine-3-carbonitrile (Intermediate P42; 25.0 mg, 0.0766 mmol) and 1-benzyl-piperazin-2-one (58.2 mg, 0.306 mmol) in DMA (2 mL) was treated with TEA (52.0 µl, 0.383 mmol). The reaction vessel was sealed, and the reaction mixture was subjected to microwave irradiation at 150° C. for 14 h. The reaction mixture was cooled to ambient temperature, then diluted with EtOAc, washed with water (3×) and brine (1×), then concentrated in vacuo. The crude residue was purified by C18 reverse phase chromatography (using 5-95% ACN in water with 0.1% TFA as the gradient eluent) to afford the TFA salt of the title compound. The TFA salt was dissolved in 4:1 DCM/iPrOH, and extracted with saturated NaHCO$_{3(aq)}$. The organic extracts were dried over anhydrous Na$_2$SO$_{4(s)}$, filtered, and concentrated in vacuo to cleanly afford the title compound (14.3 mg, 38% yield). MS (apci) m/z=497.2 (M+H).

Example 487

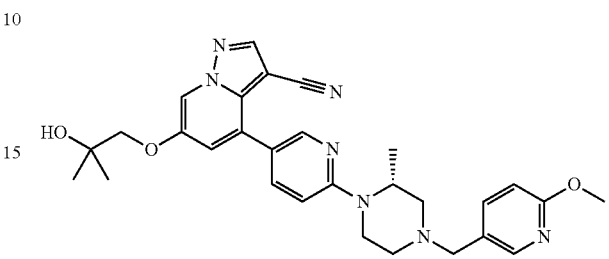

(R)-6-(2-hydroxy-2-methylpropoxy)-4-(6-(4-((6-methoxypyridin-3-yl)methyl)-2-methylpiperazin-1-yl)pyridin-3-yl)pyrazolo[1,5-a]pyridine-3-carbonitrile A solution of (R)-6-(2-hydroxy-2-methylpropoxy)-4-(6-(2-methylpiperazin-1-yl)pyridin-3-yl)pyrazolo[1,5-a]pyridine-3-carbonitrile bis(2,2,2-trifluoroacetate) (Intermediate P85; 13 mg, 0.0205 mmol) in DCE (512 µL) was treated sequentially with 6-methoxynicotinaldehyde (5.62 mg, 0.0410 mmol) and NaBH(AcO)$_3$ (13.0 mg, 0.0615 mmol). After stirring the reaction mixture 1 h at ambient temperature, the reaction mixture was purified directly by silica chromatography (using 0-100% DCM in Hexanes then 0-60% (2% NH$_4$OH/20% MeOH/78% DCM) in DCM as the gradient eluent) to afford the title compound (1.80 mg, 17% yield). MS (apci) m/z=528.3 (M+H).

Example 488

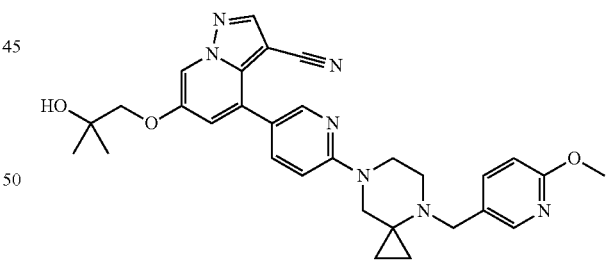

6-(2-hydroxy-2-methylpropoxy)-4-(6-(4-((6-methoxypyridin-3-yl)methyl)-4,7-diazaspiro[2.5]octan-7-yl)pyridin-3-yl)pyrazolo[1,5-a]pyridine-3-carbonitrile A solution of 4-(6-(4,7-diazaspiro[2.5]octan-7-yl)pyridin-3-yl)-6-(2-hydroxy-2-methylpropoxy)pyrazolo[1,5-a]pyridine-3-carbonitrile bis(2,2,2-trifluoroacetate) (Intermediate P86; 20 mg, 0.031 mmol) in DCE (155 µL) was treated sequentially with 6-methoxynicotinaldehyde (8.5 mg, 0.062 mmol) and NaBH(AcO)$_3$ (20 mg, 0.093 mmol). After stirring the reaction mixture 1 h at ambient temperature, the reaction mixture was purified directly by silica chromatography (using 0-100% DCM in Hexanes then 0-60% (2% NH4OH/20% MeOH/78% DCM) in DCM as the gradient eluent) to afford the title compound (1.0 mg, 6% yield). MS (apci) m/z=540.3 (M+H).

Example 489

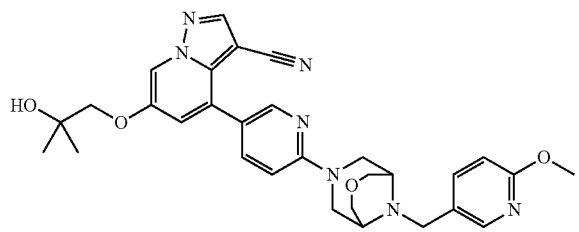 [SMILES: COc1ccc(CN2C3COCC2CN(c2ccc(-c4cc(OCC(C)(C)O)cn5ncc(C#N)c45)cn2)C3)cn1]

6-(2-hydroxy-2-methylpropoxy)-4-(6-(9-((6-methoxypyridin-3-yl)methyl)-3-oxa-7,9-diazabicyclo[3.3.1]nonan-7-yl)pyridin-3-yl)pyrazolo[1,5-a]pyridine-3-carbonitrile A solution of 4-(6-(3-oxa-7,9-diazabicyclo[3.3.1]nonan-7-yl)pyridin-3-yl)-6-(2-hydroxy-2-methylpropoxy)pyrazolo[1,5-a]pyridine-3-carbonitrile bis(2,2,2-trifluoroacetate (Intermediate P 87; 28 mg, 0.042 mmol) in DCM (1 mL) was treated sequentially with TEA (27 µL, 0.19 mmol), 6-methoxynicotinaldehyde (8.5 mg, 0.062 mmol) and NaBH(AcO)3 (27 mg, 0.13 mmol). After stirring the reaction mixture 12 h at ambient temperature, the reaction mixture was diluted with water and extracted with DCM. The organic extracts were dried over anhydrous $Na_2SO_{4(s)}$, filtered and concentrated in vacuo. The crude residue was purified by silica chromatography (using 10% MeOH/DCM with 1% NH4OH as the eluent) to afford the title compound (7.5 mg, 31% yield). MS (apci) m/z=556.3 (M+H).

Example 490

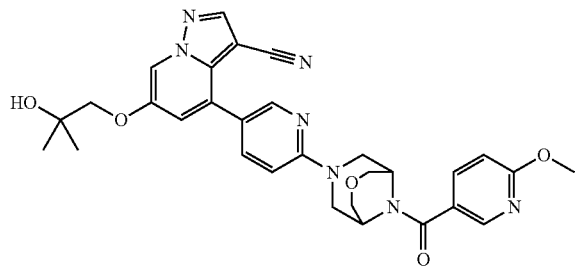 [SMILES: COc1ccc(C(=O)N2C3COCC2CN(c2ccc(-c4cc(OCC(C)(C)O)cn5ncc(C#N)c45)cn2)C3)cn1]

6-(2-hydroxy-2-methylpropoxy)-4-(6-(9-(6-methoxynicotinoyl)-3-oxa-7,9-diazabicyclo[3.3.1]nonan-7-yl)pyridin-3-yl)pyrazolo[1,5-a]pyridine-3-carbonitrile A mixture of 4-(6-(3-oxa-7,9-diazabicyclo[3.3.1]nonan-7-yl)pyridin-3-yl)-6-(2-hydroxy-2-methylpropoxy)pyrazolo[1,5-a]pyridine-3-carbonitrile bis(2,2,2-trifluoroacetate (Intermediate P87; 28 mg, 0.042 mmol), 6-methoxynicotinic acid (15 mg, 0.097 mmol) and HATU (27 mg, 0.071 mmol) in DMSO (600 µL) was treated with and TEA (27 µL, 0.19 mmol). After stirring for 12 h at ambient temperature, the reaction mixture was poured into water (5 mL) and stirred for 1 h at ambient temperature. The resulting suspension was filtered, rinsing with water. The solids were collected and purified by silica chromatography (using 10% MeOH/DCM with 1% NH4OH as the eluent) to cleanly afford the title compound (5 mg, 21% yield). MS (apci) m/z=570.2 (M+H).

Example 491

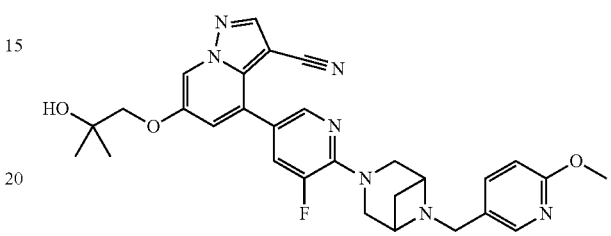

4-(5-fluoro-6-(6-(((6-methoxypyridin-3-yl)methyl)-3,6-diazabicyclo[3.1.1]heptan-3-yl)pyridin-3-yl)-6-(2-hydroxy-2-methylpropoxy)pyrazolo[1,5-a]pyridine-3-carbonitrile A solution of 4-(6-(3,6-diazabicyclo[3.1.1]heptan-3-yl)-5-fluoropyridin-3-yl)-6-(2-hydroxy-2-methylpropoxy)pyrazolo[1,5-a]pyridine-3-carbonitrile bis(2,2,2-trifluoroacetate) (14 mg, 0.0215 mmol) (Intermediate P88; 28 mg, 0.064 mmol) in DCE (108 µL) was treated sequentially 6-methoxynicotinaldehyde (5.90 mg, 0.0430 mmol) and NaBH(AcO)3 (13.7 mg, 0.0646 mmol). After stirring the reaction mixture 1 h at ambient temperature, the reaction mixture was purified directly by silica chromatography (using 0-100% DCM in Hexanes then 0-60% (2% NH4OH/20% MeOH/78% DCM) in DCM as the gradient eluent) to afford the title compound (6.17 mg, 53% yield). MS (apci) m/z=544.2 (M+H).

Example 492

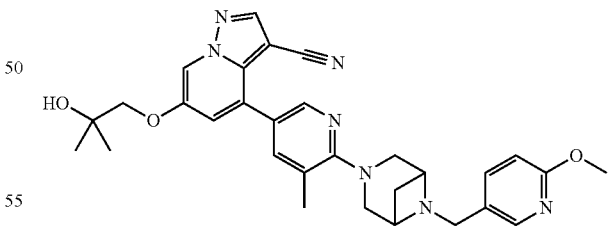

6-(2-hydroxy-2-methylpropoxy)-4-(6-(6-((6-methoxypyridin-3-yl)methyl)-3,6-diazabicyclo[3.1.1]heptan-3-yl)-5-methylpyridin-3-yl)pyrazolo[1,5-a]pyridine-3-carbonitrile A solution of 4-(6-(3,6-diazabicyclo[3.1.1]heptan-3-yl)-5-methylpyridin-3-yl)-6-(2-hydroxy-2-methylpropoxy)pyrazolo[1,5-a]pyridine-3-carbonitrile bis(2,2,2-trifluoroacetate) (Intermediate P89; 10 mg, 0.0155 mmol) in DCE (77.3 µL) was treated sequentially 6-methoxynicotinaldehyde (4.24 mg, 0.0309 mmol) and NaBH(AcO)₃ (9.83 mg, 0.0464 mmol). After stirring for 1 h at ambient temperature, the reaction mixture was purified directly by silica chromatography (using 0-100% DCM in Hexanes then 0-60% (2% NH₄OH/20% MeOH/78% DCM) in DCM as the gradient eluent) to afford the title compound (3.41 mg, 41% yield). MS (apci) m/z=540.2 (M+H).

Example 493

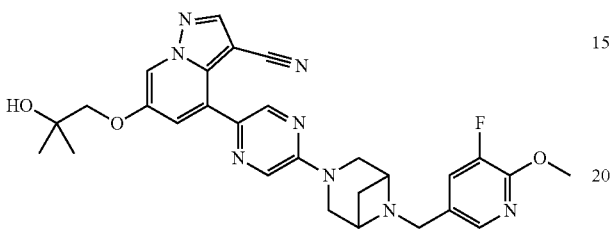

4-(5-(6-((5-fluoro-6-methoxypyridin-3-yl)methyl)-3,6-diazabicyclo[3.1.1]heptan-3-yl)pyrazin-2-yl)-6-(2-hydroxy-2-methylpropoxy)pyrazolo[1,5-a]pyridine-3-carbonitrile A solution of 4-(5-(3,6-diazabicyclo[3.1.1]heptan-3-yl)pyrazin-2-yl)-6-(2-hydroxy-2-methylpropoxy)pyrazolo[1,5-a]pyridine-3-carbonitrile bis(2,2,2-trifluoroacetate) (Intermediate P90; 25 mg, 0.0395 mmol) in DCE (197 µL) was treated sequentially with 5-fluoro-6-methoxynicotinaldehyde (12.2 mg, 0.0789 mmol) and NaBH(AcO)₃ (25.1 mg, 0.118 mmol). After stirring for 1 h at ambient temperature, the reaction mixture was purified directly by silica chromatography (using 0-100% DCM in Hexanes then 0-60% (2% NH₄OH/20% MeOH/78% DCM) in DCM as the gradient eluent) to afford the title compound (8.17 mg, 38% yield). MS (apci) m/z=545.2 (M+H).

Example 494

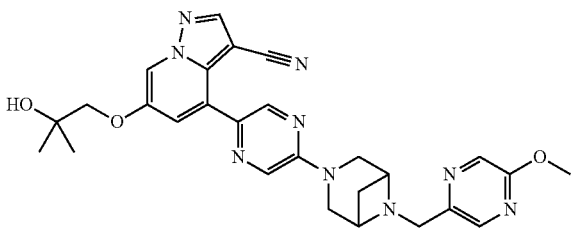 [SMILES: COc1cnc(CN2C3CC2CN(c2cnc(-c4cc(OCC(C)(C)O)cn5ncc(C#N)c45)cn2)C3)cn1]

6-(2-hydroxy-2-methylpropoxy)-4-(5-(6-((5-methoxypyrazin-2-yl)methyl)-3,6-diazabicyclo[3.1.1]heptan-3-yl)pyrazin-2-yl)pyrazolo[1,5-a]pyridine-3-carbonitrile The title compound (2.1 mg, 10% yield) was prepared and purified using a similar procedure to that described for Example 493, replacing 5-fluoro-6-methoxynicotinaldehyde with 5-methoxypyrazine-2-carboxaldehyde. MS (apci) m/z=528.2 (M+H).

Example 495

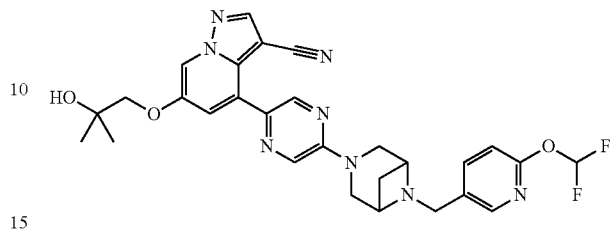

4-(5-(6-((6-(difluoromethoxy)pyridin-3-yl)methyl)-3,6-diazabicyclo[3.1.1]heptan-3-yl)pyrazin-2-yl)-6-(2-hydroxy-2-methylpropoxy)pyrazolo[1,5-a]pyridine-3-carbonitrile The title compound (3.81 mg, 17% yield) was prepared and purified using a similar procedure to that described for Example 493, replacing 5-fluoro-6-methoxynicotinaldehyde with 6-(difluoromethoxy)nicotinaldehyde MS (apci) m/z=563.2 (M+H).

Example 496

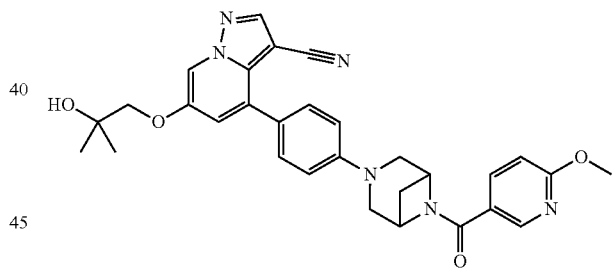

6-(2-hydroxy-2-methylpropoxy)-4-(4-(6-(6-methoxynicotinoyl)-3,6-diazabicyclo[3.1.1]heptan-3-yl)phenyl)pyrazolo[1,5-a]pyridine-3-carbonitrile A solution of 4-(4-(3,6-diazabicyclo[3.1.1]heptan-3-yl)phenyl)-6-(2-hydroxy-2-methylpropoxy)pyrazolo[1,5-a]pyridine-3-carbonitrile (Intermediate P49; 20 mg, 0.05 mmol) in DCM (600 µL) was treated sequentially with 6-methoxynicotinic acid (8.350 mg, 0.05452 mmol), HATU (22.62 mg, 0.05948 mmol) and DIEA (34.54 µL, 0.1983 mmol). After stirring for 4 h at ambient temperature, the reaction mixture was purified directly by silica chromatography (using 50-100% EtOAc in Hexanes then 0-20% MeOH in EtOAc as the gradient eluent) to cleanly afford the title compound (20.48 mg, 77% yield). MS (apci) m/z=539.2 (M+H).

Example 497

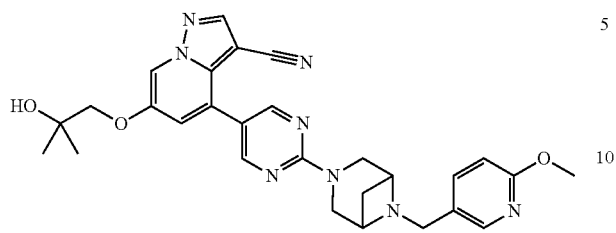

6-(2-hydroxy-2-methylpropoxy)-4-(2-(6-((6-methoxypyridin-3-yl)methyl)-3,6-diazabicyclo[3.1.1]heptan-3-yl)pyrimidin-5-yl)pyrazolo[1,5-a]pyridine-3-carbonitrile A solution of 4-(2-(3,6-diazabicyclo[3.1.1]heptan-3-yl)pyrimidin-5-yl)-6-(2-hydroxy-2-methylpropoxy)pyrazolo[1,5-a]pyridine-3-carbonitrile dihydrochloride (Intermediate P91; 54 mg, 0.11 mmol) in DCM (1 mL) was treated sequentially with 6-methoxynicotinaldehyde (23 mg, 0.17 mmol), NaBH(AcO)$_3$ (120 mg, 0.56 mmol) and DMA (500 µL). After stirring overnight at ambient temperature, the reaction mixture was purified directly by silica chromatography (using 5% MeOH in DCM as the eluent) to afford the title compound (29 mg, 48% yield). MS (apci) m/z=527.2 (M+H).

Example 498

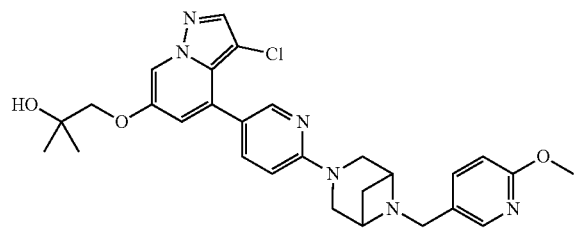 [SMILES: COc1ccc(CN2C3CC2CN(c2ccc(-c4cc(OCC(C)(C)O)cn5ncc(Cl)c45)cn2)C3)cn1]

1-((3-chloro-4-(6-(6-((6-methoxypyridin-3-yl)methyl)-3,6-diazabicyclo[3.1.1]heptan-3-yl)pyridin-3-yl)pyrazolo[1,5-a]pyridin-6-yl)oxy)-2-methylpropan-2-ol A solution of 1-((4-(6-(3,6-diazabicyclo[3.1.1]heptan-3-yl)pyridin-3-yl)-3-chloropyrazolo[1,5-a]pyridin-6-yl)oxy)-2-methylpropan-2-ol 2,2,2-trifluoroacetate (Intermediate P92; 50 mg, 0.098 mmol) in DMA (750 µL) was treated with TEA (150 µL, 0.098 mmol), 6-methoxynicotinaldehyde (40 mg, 0.29 mmol) and NaBH(AcO)$_3$ (62.1 mg, 0.293 mmol). After stirring for 3 h at ambient temperature, the reaction mixture was quenched with water and extracted with DCM (3×). The combined organic extracts were dried over anhydrous Na$_2$SO$_{4(s)}$, filtered and concentrated in vacuo. The crude residue was purified by silica chromatography (using 0-20% MeOH (2% NH$_4$OH)/DCM with as the gradient eluent) to afford the title compound (49.5 mg, 95% yield). MS (apci) m/z=535.2 (M+H).

Example 499

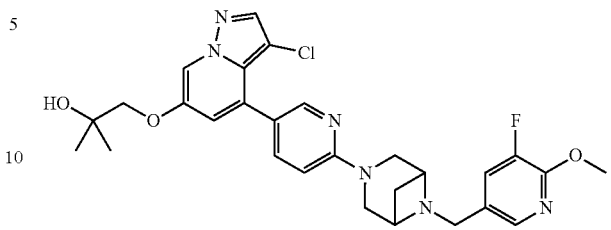

1-((3-chloro-4-(6-(6-((5-fluoro-6-methoxypyridin-3-yl)methyl)-3,6-diazabicyclo[3.1.1]heptan-3-yl)pyridin-3-yl)pyrazolo[1,5-a]pyridin-6-yl)oxy)-2-methylpropan-2-ol The title compound (45 mg, 83% yield) was prepared and purified using a similar procedure to that described for Example 498, replacing 6-methoxynicotinaldehyde with 5-fluoro-6-methoxynicotinaldehyde. MS (apci) m/z=553.2 (M+H).

Example 500

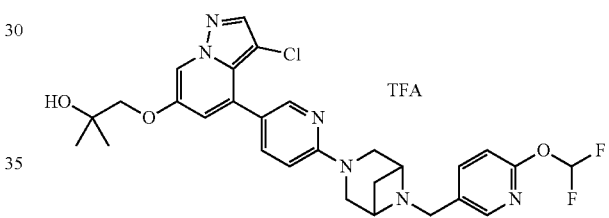

1-((3-chloro-4-(6-(6-((6-(difluoromethoxy)pyridin-3-yl)methyl)-3,6-diazabicyclo[3.1.1]heptan-3-yl)pyridin-3-yl)pyrazolo[1,5-a]pyridin-6-yl)oxy)-2-methylpropan-2-ol 2,2,2-trifluoroacetate The title compound was prepared using a similar procedure to that described for Example 498, replacing 6-methoxynicotinaldehyde with 6-(difluoromethoxy)nicotinaldehyde, using excess TEA (6 equivalents), and extending the reaction duration from 3 h to overnight. Following C18 reverse phase chromatography (using 5-95% ACN/water with 0.1% TFA as the gradient eluent), the title compound was isolated (17.2 mg, 44% yield). MS (apci) m/z=571.2 (M+H).

Example 501

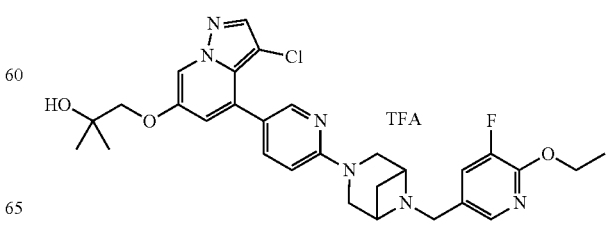

1-((3-chloro-4-(6-(6-((6-ethoxy-5-fluoropyridin-3-yl)methyl)-3,6-diazabicyclo[3.1.1]heptan-3-yl)pyridin-3-yl)pyrazolo[1,5-a]pyridin-6-yl)oxy)-2-methyl-propan-2-ol 2,2,2-trifluoroacetate The title compound was prepared using a similar procedure to that described for Example 498, replacing 6-methoxynicotinaldehyde with 6-ethoxy-5-fluoronicotinaldehyde, using excess TEA (6 equivalents), and extending the reaction duration from 3 h to overnight. Following C18 reverse phase chromatography (using 5-95% ACN/water with 0.1% TFA as the gradient eluent), the title compound was isolated (13.5 mg, 33% yield) MS (apci) m/z=567.2 (M+H).

Example 502

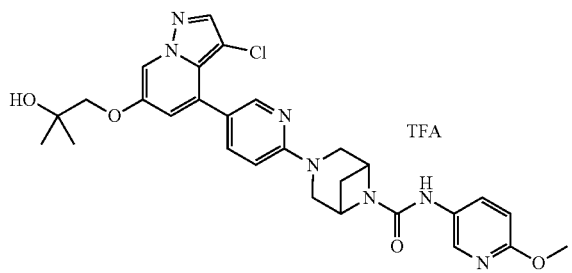 [SMILES: COc1ccc(NC(=O)N2C3CC2CN(c2ccc(-c4cc(OCC(C)(C)O)cn5ncc(Cl)c45)cn2)C3)cn1]

3-(5-(3-chloro-6-(2-hydroxy-2-methylpropoxy)pyrazolo[1,5-a]pyridin-4-yl)pyridin-2-yl)-N-(6-methoxypyridin-3-yl)-3,6-diazabicyclo[3.1.1]heptane-6-carboxamide 2,2,2-trifluoroacetate A cold (0° C.) solution of triphosgene (16.6 mg, 0.0561 mmol) in DCM (250 µL) was treated with DIEA (64.6 µL, 0.374 mmol) and 6-methoxypyridin-3-amine (8.70 mg, 0.0701 mmol). The resulting mixture was stirred for 1 h at 0° C. 1-((4-(6-(3,6-Diazabicyclo[3.1.1]heptan-3-yl)pyridin-3-yl)-3-chloropyrazolo[1,5-a]pyridin-6-yl)oxy)-2-methyl-propan-2-ol 2,2,2-trifluoroacetate (Intermediate P92; 30 mg, 0.0467 mmol) was added to the cold (0° C.) triphosgene solution. The resulting mixture was stirred overnight at ambient temperature before quenching with water. The biphasic mixture was extracted with DCM (3×) in a PS Frit. The combined organic extracts were concentrated in vacuo, and the crude residue was purified by C18 reverse phase chromatography (using 5-95% water-ACN with 0.1% TFA as the gradient eluent) to cleanly provide the title compound (11.5 mg, 44% yield). MS (apci) m/z=564.2 (M+H).

Example 503

6-(2-hydroxy-2-methylpropoxy)-4-(6-(2-((6-methoxypyridin-3-yl)methyl)-2,7-diazaspiro[3.5]nonan-7-yl)pyridin-3-yl)pyrazolo[1,5-a]pyridine-3-carbonitrile Step 1: Preparation of tert-butyl 2-((6-methoxypyridin-3-yl)methyl)-2,7-diazaspiro[3.5]nonane-7-carboxylate To a suspension of tert-butyl 2,7-diazaspiro[3.5]nonane-7-carboxylate hydrochloride (100 mg, 0.381 mmol) in 1,2-dichloroethane (761 µL) was added 6-methoxynicotinaldehyde (104 mg, 0.761 mmol) followed by sodium triacetoxyhydroborate (242 mg, 1.14 mmol). After stirring overnight at ambient temperature, the reaction was directly purified by silica chromatography (30-100% EtOAc in hexanes) to yield the title compound (100 mg, 76% yield). LCMS m/z 348.2 (M+H).

Step 2: Preparation of 2-((6-methoxypyridin-3-yl)methyl)-2,7-diazaspiro[3.5]nonane bis(2,2,2-trifluoroacetate)

To a solution of tert-butyl 2-((6-methoxypyridin-3-yl)methyl)-2,7-diazaspiro[3.5]nonane-7-carboxylate (100 mg, 0.288 mmol) in DCM (3 mL) was added TFA (3 mL). After stirred at rt for 1 h, the reaction was concentrated in vacuo to yield the title compound, which was directly used in the next step assuming quantitative yield. LCMS m/z 248.1 (M+H).

Step 3. Preparation of 6-(2-hydroxy-2-methylpropoxy)-4-(6-(2-((6-methoxypyridin-3-yl)methyl)-2,7-diazaspiro[3.5]nonan-7-yl)pyridin-3-yl)pyrazolo[1,5-a]pyridine-3-carbonitrile A mixture of 2-((6-methoxypyridin-3-yl)methyl)-2,7-diazaspiro[3.5]nonane bis(2,2,2-trifluoroacetate) (131.1 mg, 0.27 mmol), 4-(6-fluoropyridin-3-yl)-6-(2-hydroxy-2-methylpropoxy)pyrazolo[1,5-a]pyridine-3-carbonitrile (Intermediate P42; 40 mg, 0.12 mmol) and K$_2$CO$_3$ (169 mg, 1.2 mmol) in DMSO (613 µL) was stirred overnight at 80° C. The reaction mixture was partitioned between DCM and water (10 mL each). After phase-separation, the aqueous layer was extracted with DCM (3×10 mL). The organic extracts were combined and washed with brine (10 mL), then dried (Na$_2$SO$_4$), filtered and concentrated. The residue was purified with silica chromatography (0-100% EtOAc in hexanes followed by 0-20% MeOH in EtOAc) to yield the title product as solid (16 mg, 24% yield). LCMS m/z: 554.2 (M+H).

Example 504

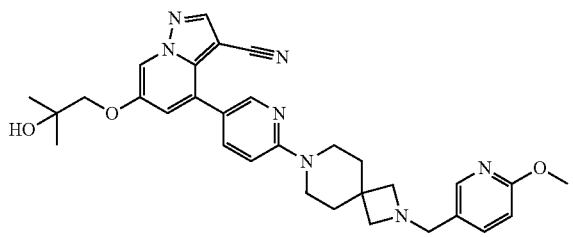 [SMILES: COc1ccc(CN2CC3(CCN(c4ccc(-c5cc(OCC(C)(C)O)cn6ncc(C#N)c56)cn4)CC3)C2)cn1]

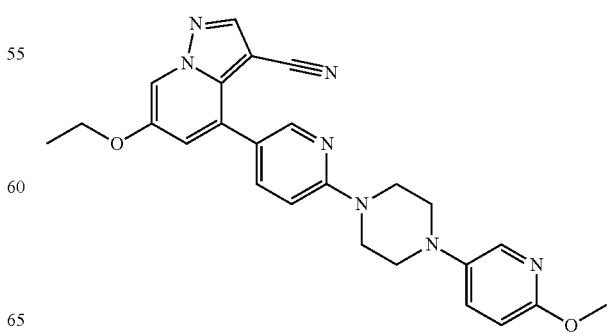

6-ethoxy-4-(6-(4-(6-methoxypyridin-3-yl)piperazin-1-yl)pyridin-3-yl)pyrazolo[1,5-a]pyridine-3-carbonitrile A mixture of 6-ethoxy-4-(6-(piperazin-1-yl)pyridin-3-yl) pyrazolo[1,5-a]pyridine-3-carbonitrile dihydrochloride (Intermediate P94; 50 mg, 0.12 mmol), 5-bromo-2-methoxypyridine (23.04 μL, 0.1780 mmol), KOtBu (66.58 mg, 0.5934 mmol), Pd$_2$(dba)$_3$·CHCl$_3$ (6.142 mg, 0.005934 mmol) and X-phos (11.31 mg, 0.02373 mmol) in toluene (1187 μL) was sparged with N$_{2(g)}$ for 30 seconds. After sealing the reaction vessel, the reaction mixture was stirred for 17 h at 100° C. The reaction mixture was cooled to ambient temperature and partitioned between water (10 mL) and DCM (10 mL). After phase separation, the aqueous extracts were washed with additional DCM (3×5 mL). The combined DCM extracts were dried over anhydrous Na$_2$SO$_4$ (s), filtered and concentrated in vacuo. The crude residue was purified by C18 reverse phase chromatography (using 5-55% ACN in water as the gradient eluent) to cleanly afford the title compound (2.8 mg, 5% yield). A significant amount of additional title compound remained in the aqueous extracts. The aqueous extracts were concentrated in vacuo, and the residue was purified by C18 reverse phase chromatography (using 5-45% ACN in water as the gradient eluent) to cleanly afford additional title compound (6 mg, 11% yield). The title compound isolated from both chromatographic purifications was combined (9 mg, 16% yield). MS (apci) m/z=456.2 (M+H).

Example 505

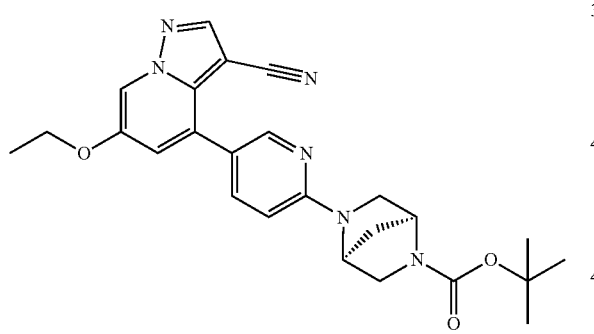

tert-butyl (1S,4S)-5-(5-(3-cyano-6-ethoxypyrazolo[1,5-a]pyridin-4-yl)pyridin-2-yl)-2,5-diazabicyclo[2.2.1]heptane-2-carboxylate A slurry of 6-ethoxy-4-(6-fluoropyridin-3-yl)pyrazolo[1,5-a]pyridine-3-carbonitrile (Intermediate P6; 100 mg, 0.354 mmol), tert-butyl (1S,4S)-2,5-diazabicyclo[2.2.1]heptane-2-carboxylate (84.3 mg, 0.425 mmol), and DIEA (185 μL, 1.06 mmol) in DMSO (886 μL) was stirred for 23 h at 90° C. Additional tert-butyl (1S,4S)-2,5-diazabicyclo[2.2.1]heptane-2-carboxylate (ca. 20 mg, 0.10 mmol) was introduced, and the mixture was stirred for an additional 3 d at 90° C. After cooling to ambient temperature, the resultant slurry was stirred for 2 h. The slurry was vacuum filtered, rinsing the solids sequentially with several drops of DMSO and MTBE (3×1 mL). The filtrate was poured slowly into water (7 mL), and the suspension was stirred for 1 h at ambient temperature. The aqueous suspension was vacuum filtered, and the solids were rinsed with water (3×5 mL) and heptane (3×5 mL). The isolated solids from both filtrations were combined to cleanly afford the title compound (149.2 mg, 90% yield). MS (apci) m/z=461.2 (M+H).

Example 506

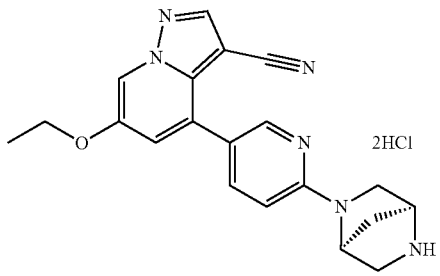 [SMILES: CCOc1cc(-c2ccc(N3C[C@@H]4C[C@H]3CN4)nc2)c2c(C#N)cnn2c1]

4-(6-((1S,4S)-2,5-diazabicyclo[2.2.1]heptan-2-yl)pyridin-3-yl)-6-ethoxypyrazolo[1,5-a]pyridine-3-carbonitrile dihydrochloride At ambient temperature, a suspension of tert-butyl (1S,4S)-5-(5-(3-cyano-6-ethoxypyrazolo[1,5-a]pyridin-4-yl)pyridin-2-yl)-2,5-diazabicyclo[2.2.1]heptane-2-carboxylate (Example 505; 88.8 mg, 0.193 mmol) in MeOH (386 μL) was treated with concentrated (12 M) HCl (321 μL, 3.86 mmol). The resulting solution was stirred for 17 h at ambient temperature before diluting with additional MeOH (1 mL). The mixture was concentrated in vacuo, and the residue was suspended in MTBE (2 mL) and MeOH (0.5 mL). The resultant slurry was vortexed and sonicated briefly and then vacuum filtered. The solids were rinsed with MTBE and EtOAc and dried in vacuo to cleanly afford the title compound (64.2 mg, 77% yield). MS (apci) m/z=361.2 (M+H).

Example 507

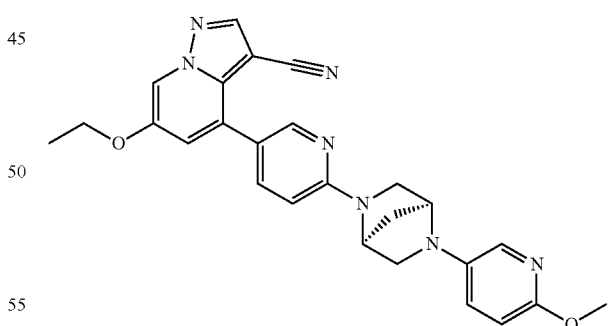

6-ethoxy-4-(6-((1S,4S)-5-(6-methoxypyridin-3-yl)-2,5-diazabicyclo[2.2.1]heptan-2-yl)pyridin-3-yl)pyrazolo[1,5-a]pyridine-3-carbonitrile A mixture of 4-(6-((1S,4S)-2,5-diazabicyclo[2.2.1]heptan-2-yl)pyridin-3-yl)-6-ethoxypyrazolo[1,5-a]pyridine-3-carbonitrile dihydrochloride (Example 506; 25 mg, 0.058 mmol), 5-bromo-2-methoxypyridine (11.20 μL, 0.08654 mmol), KOtBu (22.66 mg, 0.2019 mmol), Pd$_2$(dba)$_3$·CHCl$_3$ (2.986 mg, 0.002885 mmol) and X-phos (5.501 mg, 0.01154 mmol) in toluene (576.9 μL) was sparged with $N_{2(g)}$ for 30 seconds. After sealing the reaction vessel, the reaction mixture was stirred for 2 d at 100° C. The reaction mixture was cooled to ambient temperature, then directly purified by C18 reverse phase chromatography (using 5-65% ACN in water as the gradient eluent) to cleanly afford the title compound (12.5 mg, 44% yield). MS (apci) m/z=468.2 (M+H).

Example 508

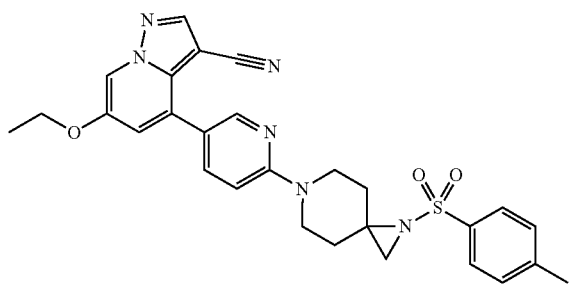 [SMILES: CCOc1cc(-c2ccc(N3CCC4(CC3)CN4S(=O)(=O)c3ccc(C)cc3)nc2)c2c(C#N)cnn2c1]

6-ethoxy-4-(6-(1-tosyl-1,6-diazaspiro[2.5]octan-6-yl)pyridin-3-yl)pyrazolo[1,5-a]pyridine-3-carbonitrile A mixture of 4-(6-(4-amino-4-(hydroxymethyl)piperidin-1-yl)pyridin-3-yl)-6-ethoxypyrazolo[1,5-a]pyridine-3-carbonitrile dihydrochloride (Intermediate P93; 78.5 mg, 0.200 mmol), TsCl (114 mg, 0.600 mmol), DMAP (4.89 mg, 0.0400 mmol) and TEA (139 μL, 1.00 mmol) in DCM (3 mL) was stirred for 1.5 h at ambient temperature. Additional TsCl (38 mg, 0.20 mmol) was added. After stirring for an additional 15 h at ambient temperature, the mixture was purified directly by silica chromatography (using 0-50% EtOAc in Hexanes as the gradient eluent) to afford the title compound (55 mg, 52% yield). MS (apci) m/z=529.2 (M+H).

Example 509

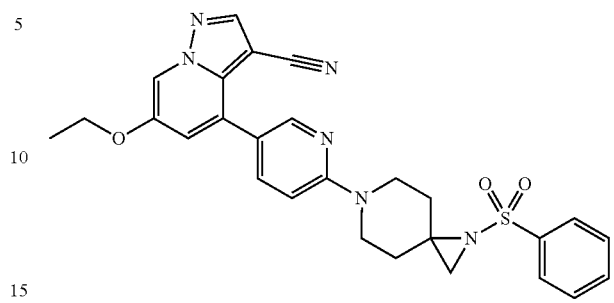

6-ethoxy-4-(6-(1-(phenylsulfonyl)-1,6-diazaspiro[2.5]octan-6-yl)pyridin-3-yl)pyrazolo[1,5-a]pyridine-3-carbonitrile A suspension of 4-(6-(4-amino-4-(hydroxymethyl)piperidin-1-yl)pyridin-3-yl)-6-ethoxypyrazolo[1,5-a]pyridine-3-carbonitrile (Intermediate P93; 40 mg, 0.10 mmol) and TEA (57 μL, 0.41 mmol) in DCM (2 mL) was treated sequentially with benzenesulfonyl chloride (32.52 μL, 0.2548 mmol) and DMAP (1.245 mg, 0.01019 mmol). The resulting mixture was stirred for 22 h at ambient temperature. The reaction mixture was purified directly by silica chromatography (using 0-70% EtOAc in Hexanes as the gradient eluent) to afford the title compound (26 mg, 50% yield). MS (apci) m/z=515.2 (M+H).

The compounds in Table FF were prepared using a similar method to that described in the synthesis of 6-ethoxy-4-(6-(1-(phenylsulfonyl)-1,6-diazaspiro[2.5]octan-6-yl)pyridin-3-yl)pyrazolo[1,5-a]pyridine-3-carbonitrile (Example 509), replacing benzenesulfonyl chloride with the appropriate sulfonyl chloride. DMAP was omitted in the preparation of Example 510. Reactions were monitored for completion by LCMS. Title compounds were isolated following chromatographic purification using an appropriate gradient eluent.

TABLE FF

| Ex # | Structure | Chemical Name | MS apci (m/z) |
|---|---|---|---|
| 510 | 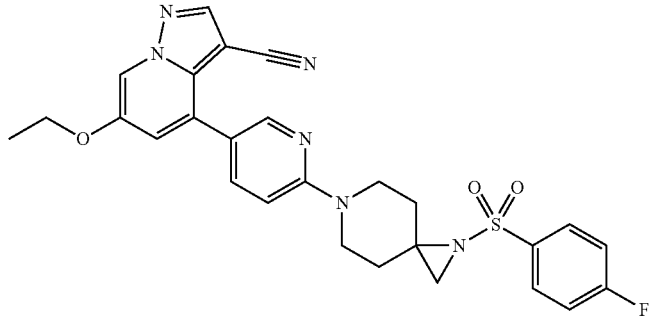 [SMILES: CCOc1cc(-c2ccc(N3CCC4(CC3)CN4S(=O)(=O)c3ccc(F)cc3)nc2)c2c(C#N)cnn2c1] | 6-ethoxy-4-(6-(1-((4-fluorophenyl)sulfonyl)-1,6-diazaspiro[2.5]octan-6-yl)pyridin-3-yl)pyrazolo[1,5-a]pyridine-3-carbonitrile | 533.1 (M + H) |

TABLE FF-continued

| Ex # | Structure | Chemical Name | MS apci (m/z) |
|---|---|---|---|
| 511 | 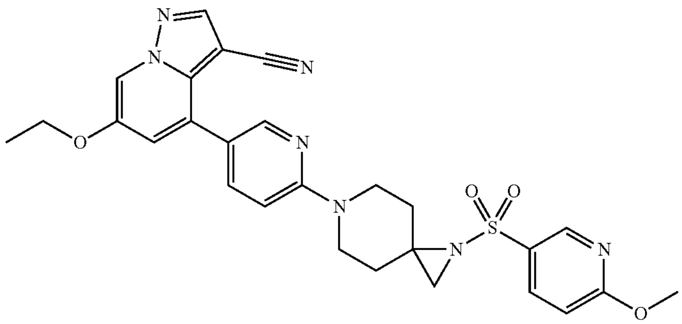 [SMILES: CCOc1cc(-c2ccc(N3CCC4(CC3)CN4S(=O)(=O)c3ccc(OC)nc3)nc2)c2c(C#N)cnn2c1] | 6-ethoxy-4-(6-(1-((6-methoxypyridin-3-yl)sulfonyl)-1,6-diazaspiro[2.5]octan-6-yl)pyridin-3-yl)pyrazolo[1,5-a]pyridine-3-carbonitrile | 546.1 (M + H) |
| 512 | 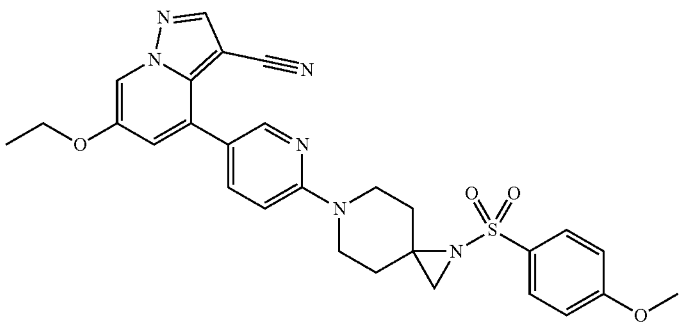 [SMILES: CCOc1cc(-c2ccc(N3CCC4(CC3)CN4S(=O)(=O)c3ccc(OC)cc3)nc2)c2c(C#N)cnn2c1] | 6-ethoxy-4-(6-(1-((4-methoxyphenyl)sulfonyl)-1,6-diazaspiro[2.5]octan-6-yl)pyridin-3-yl)pyrazolo[1,5-a]pyridine-3-carbonitrile | 545.2 (M + H) |

6-ethoxy-4-(6-(1-(4-fluorobenzoyl)-1,6-diazaspiro[2.5]octan-6-yl)pyridin-3-yl)pyrazolo[1,5-a]pyridine-3-carbonitrile A suspension of 4-(6-(4-amino-4-(hydroxymethyl)piperidin-1-yl)pyridin-3-yl)-6-ethoxypyrazolo[1,5-a]pyridine-3-carbonitrile (Intermediate P93; 40 mg, 0.10 mmol) and TEA (56.82 µL, 0.4077 mmol) in DCM (2 mL) was treated with 4-fluorobenzoyl chloride (14.67 µL, 0.1223 mmol), and stirred for 45 min at ambient temperature. The mixture was treated with MsCl (9.466 µL, 0.1223 mmol), stirred for 1 h at ambient temperature, and then treated with DBU (2 drops). The resulting mixture was stirred for an additional 15 h at ambient temperature and then for 1.5 h at 40° C. After cooling to ambient temperature, the reaction mixture was concentrated in vacuo. The residue was purified by silica chromatography (using 0-50% EtOAc in Hexanes as the gradient eluent) to afford the title compound (11 mg, 22% yield). MS (apci) m/z=497.1 (M+H).

Example 514

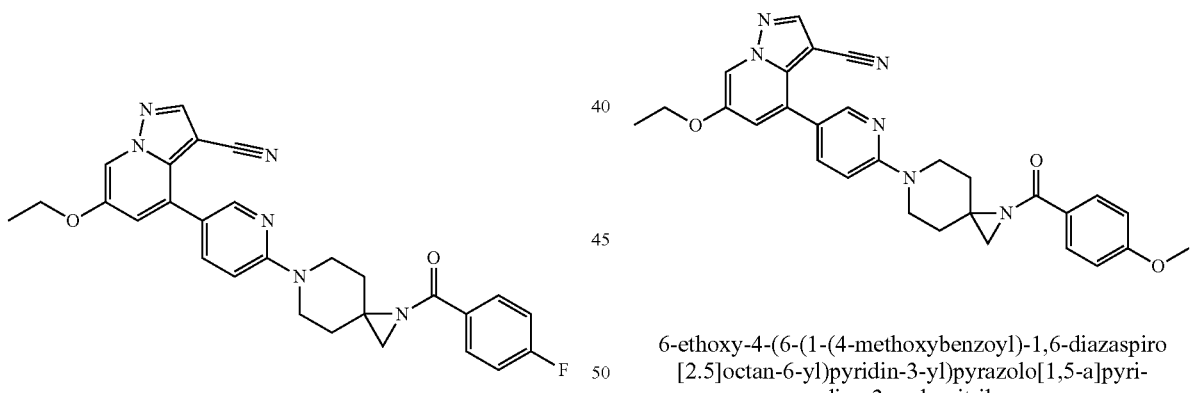

6-ethoxy-4-(6-(1-(4-methoxybenzoyl)-1,6-diazaspiro[2.5]octan-6-yl)pyridin-3-yl)pyrazolo[1,5-a]pyridine-3-carbonitrile A suspension of 4-(6-(4-amino-4-(hydroxymethyl)piperidin-1-yl)pyridin-3-yl)-6-ethoxypyrazolo[1,5-a]pyridine-3-carbonitrile (Intermediate P93; 40 mg, 0.10 mmol) and TEA (56.8 µL, 0.408 mmol) in DCM (2 mL) was treated with 4-methoxybenzoyl chloride (16.6 µL, 0.122 mmol), and stirred for 45 min at ambient temperature. The mixture was treated with MsCl (9.47 µL, 0.122 mmol), stirred for 2 h at ambient temperature, and then treated with DBU (2 drops). The resulting mixture was stirred for an additional 15 h at ambient temperature and then for 1.5 h at 40° C. After cooling to ambient temperature, the reaction mixture was concentrated in vacuo. The residue was purified by silica chromatography (using 0-50% EtOAc in Hexanes as the gradient eluent) to afford the title compound (3 mg, 6% yield). MS (apci) m/z=509.2 (M+H).

Example 515

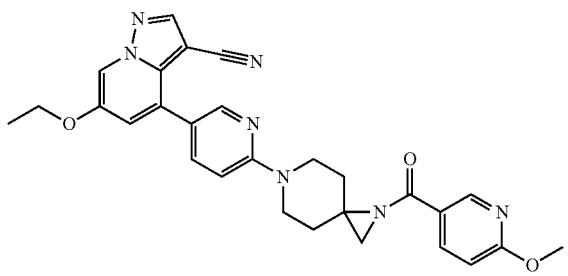 [SMILES: CCOc1cc(-c2ccc(N3CCC4(CC3)CN4C(=O)c3ccc(OC)nc3)nc2)c2c(C#N)cnn2c1]

6-ethoxy-4-(6-(1-(6-methoxynicotinoyl)-1,6-diaz-aspiro[2.5]octan-6-yl)pyridin-3-yl)pyrazolo[1,5-a]pyridine-3-carbonitrile A suspension of 4-(6-(4-amino-4-(hydroxymethyl)piperidin-1-yl)pyridin-3-yl)-6-ethoxypyrazolo[1,5-a]pyridine-3-carbonitrile (Intermediate P93; 40 mg, 0.10 mmol) and TEA (56.8 μL, 0.408 mmol) in DCM (1 mL) was treated with a solution of 6-methoxynicotinoyl chloride hydrochloride (Intermediate R22; 21.0 mg, 0.122 mmol) in DCM (0.5 mL) and stirred for 45 min at ambient temperature. The mixture was treated with MsCl (9.46 μL, 0.122 mmol), stirred for 30 min at ambient temperature, and then treated with DBU (61.6 μL, 0.408 mmol). The resulting mixture was stirred for 2 h at 40° C. After cooling to ambient temperature, the reaction mixture was purified directly by silica chromatography (using 0-50% EtOAc in Hexanes with 2% TEA as the gradient eluent) to afford the title compound (12 mg, 23% yield). MS (apci) m/z=510.2 (M+H).

Example 516

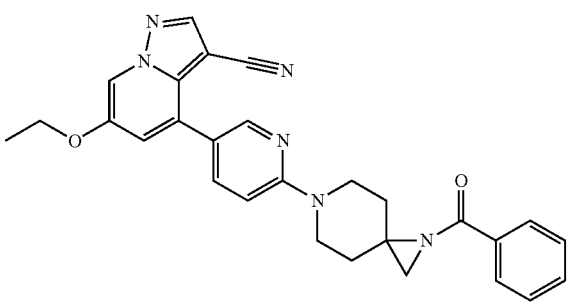 [SMILES: CCOc1cc(-c2ccc(N3CCC4(CC3)CN4C(=O)c3ccccc3)nc2)c2c(C#N)cnn2c1]

4-(6-(1-benzoyl-1,6-diazaspiro[2.5]octan-6-yl)pyridin-3-yl)-6-ethoxypyrazolo[1,5-a]pyridine-3-carbonitrile Step 1: Preparation of (4-benzamido-1-(5-(3-cyano-6-ethoxypyrazolo[1,5-a]pyridin-4-yl)pyridin-2-yl)piperidin-4-yl)methyl methanesulfonate A suspension of 4-(6-(4-amino-4-(hydroxymethyl)piperidin-1-yl)pyridin-3-yl)-6-ethoxypyrazolo[1,5-a]pyridine-3-carbonitrile (Intermediate P93; 40 mg, 0.10 mmol) and TEA (56.8 μL, 0.408 mmol) in DCM (2 mL) was treated with benzoyl chloride (14.2 μL, 0.122 mmol), and stirred for 30 min at ambient temperature. The mixture was treated with MsCl (9.47 μL, 0.122 mmol) and stirred for 1.5 h at ambient temperature. The mixture was concentrated in vacuo. The residue was purified by silica chromatography (using 0-100% EtOAc in Hexanes as the gradient eluent) to afford the title compound (28 mg, 48% yield). MS (apci) m/z=479.1 (M+H).

Step 2: Preparation of 4-(6-(1-benzoyl-1,6-diazaspiro[2.5]octan-6-yl)pyridin-3-yl)-6-ethoxypyrazolo[1,5-a]pyridine-3-carbonitrile A solution of (4-benzamido-1-(5-(3-cyano-6-ethoxypyrazolo[1,5-a]pyridin-4-yl)pyridin-2-yl)piperidin-4-yl)methyl methanesulfonate (Step 1; 28 mg, 0.049 mmol) in THF (1 mL) was treated with DBU (15 μL, 0.097 mmol). The resulting mixture was stirred 15 h at ambient temperature, then for 1 h at 50° C. After cooling to ambient temperature, the reaction mixture was concentrated in vacuo. The residue was purified by silica chromatography (using 0-50% EtOAc in Hexanes as the gradient eluent) to afford the title compound (22 mg, 94% yield). MS (apci) m/z=479.1 (M+H).

Example 517

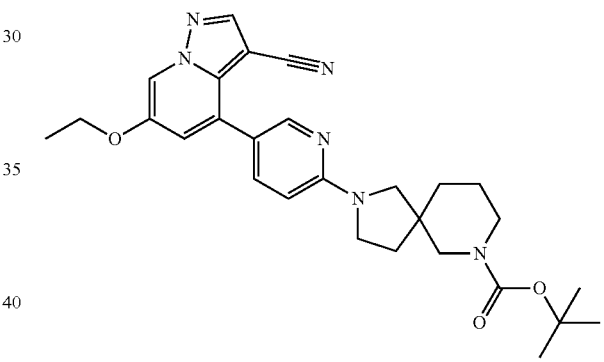

tert-butyl 2-(5-(3-cyano-6-ethoxypyrazolo[1,5-a]pyridin-4-yl)pyridin-2-yl)-2,7-diazaspiro[4.5]decane-7-carboxylate A slurry of 6-ethoxy-4-(6-fluoropyridin-3-yl)pyrazolo[1,5-a]pyridine-3-carbonitrile (Intermediate P6; 108 mg, 0.383 mmol), tert-butyl 2,7-diazaspiro[4.5]decane-7-carboxylate (110 mg, 0.459 mmol) and DIEA (200 μL, 1.15 mmol) in DMSO (957 μL) was stirred for 23 h at 90° C. Additional tert-butyl 2,7-diazaspiro[4.5]decane-7-carboxylate (ca. 20 mg, 0.083 mmol) was introduced. The resulting mixture was stirred for an additional 3 d at 90° C. After cooling to ambient temperature, the reaction mixture was poured slowly into water (8 mL). The resulting suspension was stirred for 2 h at ambient temperature before vacuum filtering. The isolated solids were rinsed with water (3×5 mL), then dissolved in MTBE (25 mL). The MTBE solution was dried over anhydrous $Na_2SO_{4(s)}$, filtered, and concentrated in vacuo. The crude residue was purified by C18 reverse phase chromatography (using 5-55% ACN in water as the gradient eluent) to cleanly afford the title compound (56 mg, 29% yield). MS (apci) m/z=503.25 (M+H).

Example 518

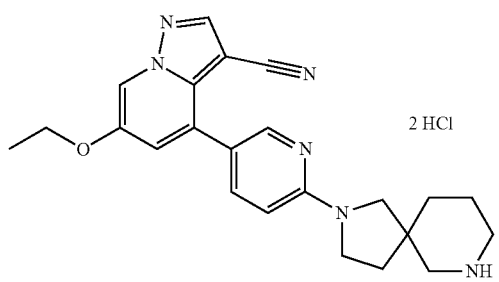 [SMILES: CCOc1cc(-c2ccc(N3CCC4(CCCNC4)C3)nc2)c2c(C#N)cnn2c1]

4-(6-(2,7-diazaspiro[4.5]decan-2-yl)pyridin-3-yl)-6-ethoxypyrazolo[1,5-a]pyridine-3-carbonitrile dihydrochloride A solution of tert-butyl 2-(5-(3-cyano-6-ethoxypyrazolo[1,5-a]pyridin-4-yl)pyridin-2-yl)-2,7-diazaspiro[4.5]decane-7-carboxylate (Example 517; 54 mg, 0.11 mmol) in DCM (1.1 mL) was treated with 5-6 N HCl in iPrOH (430 µL, 2.1 mmol). The reaction mixture was stirred at for 1 h at ambient temperature before diluting with MTBE (2 mL). The resulting suspension was vacuum filtered, and the solids were collected to afford the title compound (45 mg, 87% yield). MS (apci) m/z=403.2 (M+H).

Example 519

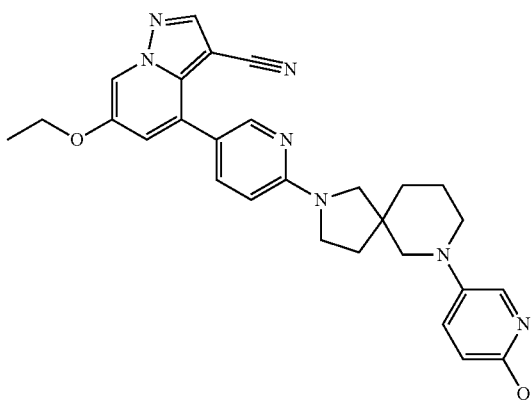

6-ethoxy-4-(6-(7-(6-methoxypyridin-3-yl)-2,7-diazaspiro[4.5]decan-2-yl)pyridin-3-yl)pyrazolo[1,5-a]pyridine-3-carbonitrile A mixture of 4-(6-(2,7-diazaspiro[4.5]decan-2-yl)pyridin-3-yl)-6-ethoxypyrazolo[1,5-a]pyridine-3-carbonitrile dihydrochloride (Example 518; 25 mg, 0.053 mmol), 5-bromo-2-methoxypyridine (10.21 µL, 0.07888 mmol), KOtBu (29.50 mg, 0.2629 mmol), Pd$_2$(dba)$_3$·CHCl$_3$ (2.722 mg, 0.002629 mmol) and X-phos (5.014 mg, 0.01052 mmol) in toluene (525.9 µL) was sparged with N$_{2(g)}$ for 30 seconds. After sealing the reaction vessel under N$_{2(g)}$, the reaction mixture was stirred for 26 h at 100° C. After cooling to ambient temperature, the reaction mixture was concentrated in vacuo. The crude residue was purified by C18 reverse phase chromatography (using 5-50% ACN in water as the gradient eluent) to cleanly afford the title compound (14 mg, 50% yield). MS (apci) m/z=510.2 (M+H).

Example 520

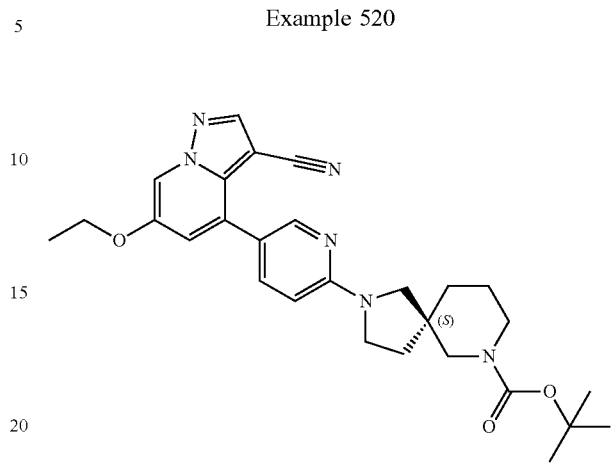

tert-butyl (S)-2-(5-(3-cyano-6-ethoxypyrazolo[1,5-a]pyridin-4-yl)pyridin-2-yl)-2,7-diazaspiro[4.5]decane-7-carboxylate A slurry of 6-ethoxy-4-(6-fluoropyridin-3-yl)pyrazolo[1,5-a]pyridine-3-carbonitrile (Intermediate P6; 108 mg, 0.383 mmol), tert-butyl (S)-2,7-diazaspiro[4.5]decane-7-carboxylate (purchased from WuXi AppTec, 110 mg, 0.459 mmol) and DIEA (200 µL, 1.15 mmol) in DMSO (957 µL) was stirred for 3 h at 90° C. Additional tert-butyl (S)-2,7-diazaspiro[4.5]decane-7-carboxylate (18 mg, 0.075 mmol) was introduced. The resulting mixture was stirred for an additional 24 h at 90° C. After cooling to ambient temperature, the reaction mixture was poured slowly into water (8 mL). The resulting suspension was stirred for 15 min at ambient temperature and then vacuum filtered. The isolated solids were rinsed with water (3×5 mL) and dried under high vacuum overnight to cleanly afford the title compound (166 mg, 84% yield). MS (apci) m/z=503.2 (M+H).

Example 521

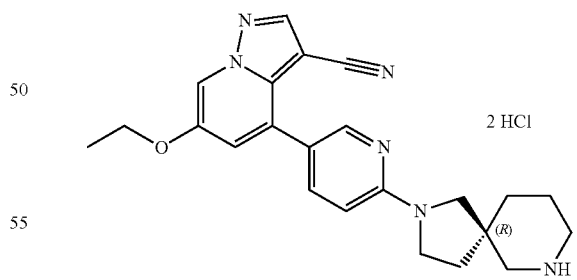

(R)-4-(6-(2,7-diazaspiro[4.5]decan-2-yl)pyridin-3-yl)-6-ethoxypyrazolo[1,5-a]pyridine-3-carbonitrile dihydrochloride Method A A solution of tert-butyl (S)-2-(5-(3-cyano-6-ethoxypyrazolo[1,5-a]pyridin-4-yl)pyridin-2-yl)-2,7-diazaspiro[4.5]decane-7-carboxylate (Example 520; 150 mg, 0.298 mmol) in 5-6 N HCl in iPrOH (1.19 mL, 5.97 mmol) was stirred at for 2 h at ambient temperature before diluting with EtOH (1 mL). The resulting suspension was stirred for 15 min and then vacuum filtered. The isolated solids were rinsed sequentially with EtOH (3×200 μL) and Et₂O (3×1 mL) and set aside. The filtrate was diluted with MeOH, and concentrated in vacuo. The solid residue was combined with the solids from the filtration and dried under high vacuum over night to cleanly afford the title compound (141 mg, 99% yield). MS (apci) m/z=403.2 (M+H).

Method B

Racemic 4-(6-(2,7-diazaspiro[4.5]decan-2-yl)pyridin-3-yl)-6-ethoxypyrazolo[1,5-a]pyridine-3-carbonitrile dihydrochloride (Example 518; 10 mg, 0.021 mmol) was partitioned between saturated Na₂CO₃₍aq₎ and CHCl₃. Following phase separation, the organic extracts were dissolved in a mix solvent of MeOH:IPA:DIEA (80:20:0.1) then subjected to SFC chiral HPLC (ChiralTech IA; 5 to 70% Solvent A in Solvent B; Solvent A=MeOH:IPA:DIEA/80:20:0.1; Solvent B=CO₂). Fractions containing Peak 1 of this chiral separation were isolated, combined, and concentrated in vacuo to afford (R)-4-(6-(2,7-diazaspiro[4.5]decan-2-yl)pyridin-3-yl)-6-ethoxypyrazolo[1,5-a]pyridine-3-carbonitrile (3.5 mg, 83% yield). MS (apci) m/z=403.2 (M+H). The chirality was assigned by chiral HPLC comparison of the material collected from Peak 1 with (R)-4-(6-(2,7-diazaspiro[4.5]decan-2-yl)pyridin-3-yl)-6-ethoxypyrazolo[1,5-a]pyridine-3-carbonitrile dihydrochloride prepared according to Method A for the preparation of (R)-4-(6-(2,7-diazaspiro[4.5]decan-2-yl)pyridin-3-yl)-6-ethoxypyrazolo[1,5-a]pyridine-3-carbonitrile (3.5 mg, 83% yield).

Example 522

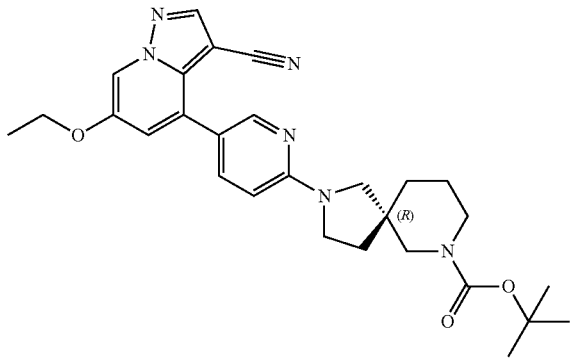

tert-butyl (R)-2-(5-(3-cyano-6-ethoxypyrazolo[1,5-a]pyridin-4-yl)pyridin-2-yl)-2,7-diazaspiro[4.5]decane-7-carboxylate A slurry of 6-ethoxy-4-(6-fluoropyridin-3-yl)pyrazolo[1,5-a]pyridine-3-carbonitrile (Intermediate P6; 108 mg, 0.383 mmol), tert-butyl (R)-2,7-diazaspiro[4.5]decane-7-carboxylate (purchased from WuXi AppTec, 110 mg, 0.459 mmol) and DIEA (200 μL, 1.15 mmol) in DMSO (957 μL) was stirred for 3 h at 90° C. Additional tert-butyl (R)-2,7-diazaspiro[4.5]decane-7-carboxylate (18 mg, 0.075 mmol) was introduced. The resulting mixture was stirred for an additional 24 h at 90° C. After cooling to ambient temperature, the reaction mixture was poured slowly into water (8 mL). The resulting suspension was stirred for 2 h at ambient temperature before vacuum filtering. The isolated solids were rinsed with water (3×5 mL), and then dried under high vacuum overnight to cleanly afford the title compound (180 mg, 93% yield). MS (apci) m/z=503.2 (M+H).

Example 523

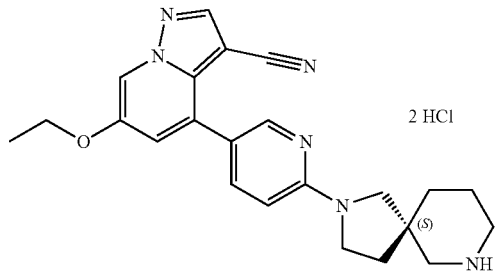

(S)-4-(6-(2,7-diazaspiro[4.5]decan-2-yl)pyridin-3-yl)-6-ethoxypyrazolo[1,5-a]pyridine-3-carbonitrile dihydrochloride Method A A solution of tert-butyl (R)-2-(5-(3-cyano-6-ethoxypyrazolo[1,5-a]pyridin-4-yl)pyridin-2-yl)-2,7-diazaspiro[4.5]decane-7-carboxylate (Example 522; 160 mg, 0.318 mmol) in 5-6 N HCl in iPrOH (1.27 mL, 6.37 mmol) was stirred at for 2 h at ambient temperature before diluting with EtOH (1 mL). The resulting suspension was stirred for 15 min and then vacuum filtered. The isolated solids were rinsed sequentially with EtOH (3×200 μL) and Et₂O (3×1 mL) and set aside. The filtrate was diluted with MeOH, and concentrated in vacuo. The solid residue was combined with the solids from the filtration, and dried under high vacuum over night to cleanly afford the title compound (141 mg, 93% yield). MS (apci) m/z=403.2 (M+H).

Method B

Racemic 4-(6-(2,7-diazaspiro[4.5]decan-2-yl)pyridin-3-yl)-6-ethoxypyrazolo[1,5-a]pyridine-3-carbonitrile dihydrochloride (Example 518; 10 mg, 0.021 mmol) was partitioned between saturated Na₂CO₃₍aq₎ and CHCl₃. Following phase separation, the organic extracts were dissolved in a mix solvent of MeOH:IPA:DIEA (80:20:0.1) then subjected to SFC chiral HPLC (ChiralTech IA; 5 to 70% Solvent A in Solvent B; Solvent A=MeOH:IPA:DIEA/80:20:0.1; Solvent B=CO₂). Fractions containing Peak 2 of this chiral separation were independently isolated, combined, and concentrated in vacuo to afford (S)-4-(6-(2,7-diazaspiro[4.5]decan-2-yl)pyridin-3-yl)-6-ethoxypyrazolo[1,5-a]pyridine-3-carbonitrile (4 mg, 94% yield). MS (apci) m/z=403.2 (M+H). The chirality was assigned by chiral HPLC comparison of the material prepared according to Method A for the preparation of (S)-4-(6-(2,7-diazaspiro[4.5]decan-2-yl)pyridin-3-yl)-6-ethoxypyrazolo[1,5-a]pyridine-3-carbonitrile.

Example 524

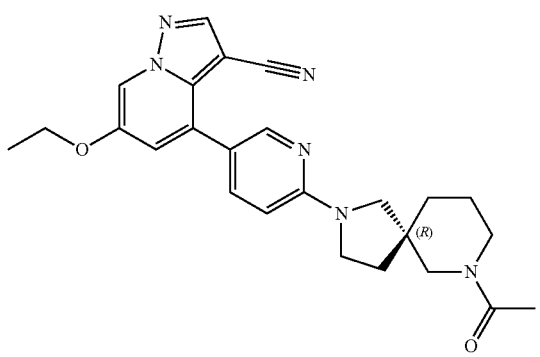

(R)-4-(6-(7-acetyl-2,7-diazaspiro[4.5]decan-2-yl)pyridin-3-yl)-6-ethoxypyrazolo[1,5-a]pyridine-3-carbonitrile A mixture of (S)-4-(6-(2,7-diazaspiro[4.5]decan-2-yl)pyridin-3-yl)-6-ethoxypyrazolo[1,5-a]pyridine-3-carbonitrile dihydrochloride (Example 523; 5.7 mg, 0.012 mmol) and acetyl chloride (1.3 µL, 0.018 mmol) in DCM (60 µL) was treated with DIEA (6.3 µL, 0.036 mmol), and stirred for 30 min at ambient temperature. The mixture was diluted with DCM (1 mL), then sequentially washed with saturated NaHCO$_{3(aq)}$ (1 mL) and water (1 mL), filtered through a PS frit and concentrated in vacuo to afford the title compound (2.5 mg, 47% yield). MS (apci) m/z=445.2 (M+H).

Example 525

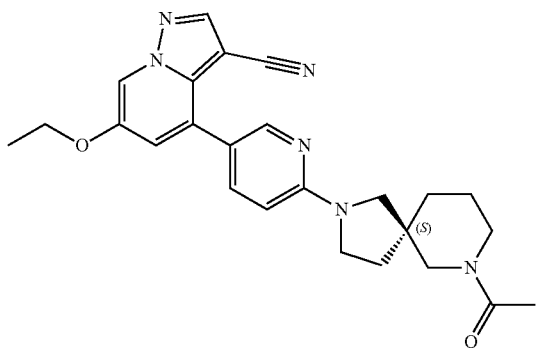

(S)-4-(6-(7-acetyl-2,7-diazaspiro[4.5]decan-2-yl)pyridin-3-yl)-6-ethoxypyrazolo[1,5-a]pyridine-3-carbonitrile A mixture of (R)-4-(6-(2,7-diazaspiro[4.5]decan-2-yl)pyridin-3-yl)-6-ethoxypyrazolo[1,5-a]pyridine-3-carbonitrile dihydrochloride (Example 521; 5.3 mg, 0.011 mmol) and acetyl chloride (1.2 µL, 0.017 mmol) in DCM (56 µL) was treated with DIEA (5.8 µL, 0.033 mmol), and stirred for 30 min at ambient temperature. The mixture was diluted with DCM (1 mL), then sequentially washed with saturated NaHCO$_{3(aq)}$ (1 mL) and water (1 mL), filtered through a PS frit and concentrated in vacuo to afford the title compound (1.6 mg, 32% yield). MS (apci) m/z=445.2 (M+H).

Example 526

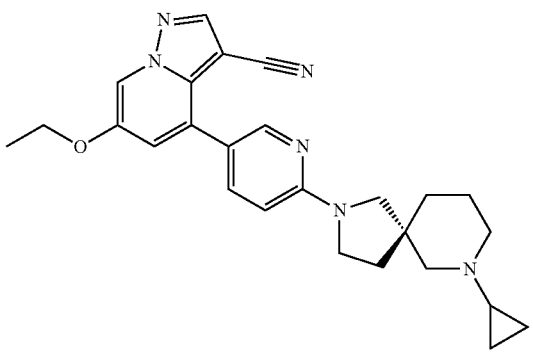 [SMILES: CCOc1cc(-c2ccc(N3CC[C@]4(CCCN(C5CC5)C4)C3)nc2)c2c(C#N)cnn2c1]

(S)-4-(6-(7-cyclopropyl-2,7-diazaspiro[4.5]decan-2-yl)pyridin-3-yl)-6-ethoxypyrazolo[1,5-a]pyridine-3-carbonitrile A mixture of (S)-4-(6-(2,7-diazaspiro[4.5]decan-2-yl)pyridin-3-yl)-6-ethoxypyrazolo[1,5-a]pyridine-3-carbonitrile dihydrochloride (Example 523; 25 mg, 0.0526 mmol), (1-ethoxycyclopropoxy)trimethylsilane (52.9 µL, 0.263 mmol), dry 4A molecular sieves, and acetic acid (63.2 µL, 1.05 mmol) in MeOH (526 µL) was stirred for 5 min at ambient temperature before introducing NaBH$_3$CN (19.8 mg, 0.316 mmol). The resulting mixture was stirred for 27 h at 50° C., then cooled to ambient temperature, and filtered. The filtrate was directly purified by C18 reverse phase chromatography (5 to 50% ACN in water) to afford the title compound (9.7 mg, 42% yield). MS (apci) m/z=443.2 (M+H).

Example 527

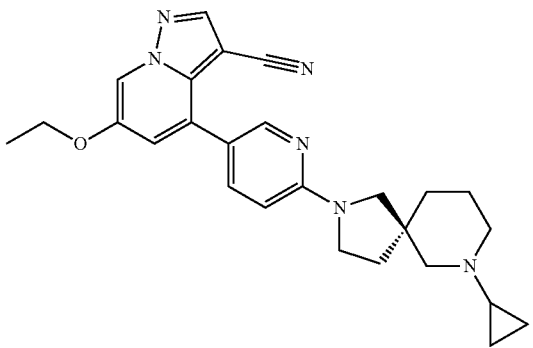 [SMILES: CCOc1cc(-c2ccc(N3CC[C@@]4(CCCN(C5CC5)C4)C3)nc2)c2c(C#N)cnn2c1]

(R)-4-(6-(7-cyclopropyl-2,7-diazaspiro[4.5]decan-2-yl)pyridin-3-yl)-6-ethoxypyrazolo[1,5-a]pyridine-3-carbonitrile A solution of (R)-4-(6-(2,7-diazaspiro[4.5]decan-2-yl)pyridin-3-yl)-6-ethoxypyrazolo[1,5-a]pyridine-3-carbonitrile dihydrochloride (Example 521; 10 mg, 0.025 mmol) in DCM (1 mL) was treated sequentially with (1-ethoxycyclopropoxy)trimethylsilane (20 μL, 0.099 mmol), and NaBH$_3$CN (3.1 mg, 0.050 mmol). After stirring overnight at ambient temperature, the reaction mixture was treated sequentially with acetic acid (14 μL, 0.25 mmol) and Me$_4$N(AcO)$_3$BH (13 mg, 0.050 mmol). The reaction mixture was stirred for 3 d before sequentially introducing additional (1-ethoxycyclopropoxy)trimethylsilane (20 μL, 0.099 mmol) and NaBH$_3$CN (3.1 mg, 0.050 mmol). The mixture was stirred for an additional 2 d period, before dry molecular sieves (20 mg) were added. The mixture was stirred for a final 24 h period at ambient temperature. The resulting suspension was filtered, and the solids were washed with DCM (2×2 mL). The DCM filtrate was washed with 1 N NaOH$_{(aq)}$ (1 mL) in a PS frit, then concentrated in vacuo. The crude residue was purified by C18 reverse phase chromatography (using 0-60% ACN/water as the gradient eluent) to afford the title compound (1.3 mg, 12% yield). MS (apci) m/z=443.2 (M+H).

Example 528

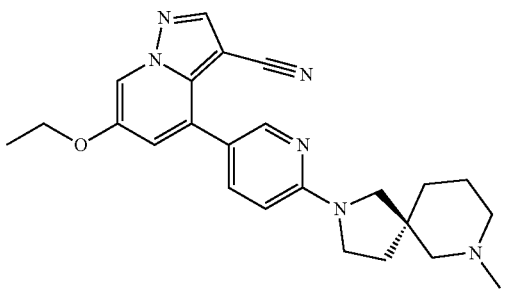 [SMILES: CCOc1cc(-c2ccc(N3CC[C@@]4(CCCN(C)C4)C3)nc2)c2c(C#N)cnn2c1]

(R)-6-ethoxy-4-(6-(7-methyl-2,7-diazaspiro[4.5]decan-2-yl)pyridin-3-yl)pyrazolo[1,5-a]pyridine-3-carbonitrile A mixture of (R)-4-(6-(2,7-diazaspiro[4.5]decan-2-yl)pyridin-3-yl)-6-ethoxypyrazolo[1,5-a]pyridine-3-carbonitrile dihydrochloride (Example 521; 20 mg, 0.042 mmol) and formaldehyde (37 wt. % in water; 31.52 μL, 0.4207 mmol) in DCM (210.3 μL) was treated with NaBH(AcO)$_3$ (178.3 mg, 0.8414 mmol), then stirred for 10 min at ambient temperature. The reaction mixture was partitioned between EtOAc (1 mL) and 2 M NaOH$_{(aq)}$ (1 mL). Following phase separation, the organic extracts were concentrated in vacuo. The crude residue was purified by C18 reverse phase chromatography (using 5-40% ACN in water as the gradient eluent) to cleanly afford the title compound (9.6 mg, 55% yield). MS (apci) m/z=417.2 (M+H).

Example 529

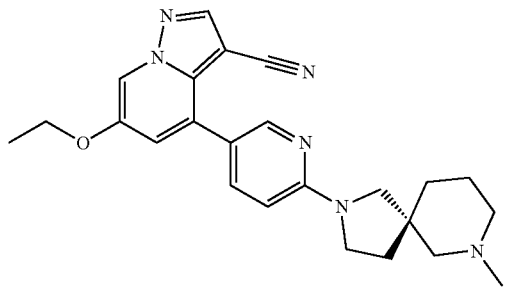 [SMILES: CCOc1cc(-c2ccc(N3CC[C@]4(CCCN(C)C4)C3)nc2)c2c(C#N)cnn2c1]

(S)-6-ethoxy-4-(6-(7-methyl-2,7-diazaspiro[4.5]decan-2-yl)pyridin-3-yl)pyrazolo[1,5-a]pyridine-3-carbonitrile A mixture of ((S)-4-(6-(2,7-diazaspiro[4.5]decan-2-yl)pyridin-3-yl)-6-ethoxypyrazolo[1,5-a]pyridine-3-carbonitrile dihydrochloride (Example 523; 15 mg, 0.032 mmol) and formaldehyde (37 wt. % in water; 23.7 μL, 0.316 mmol) in DCM (158 μL) was treated with NaBH(AcO)$_3$ (134 mg, 0.631 mmol), then stirred for 10 min at ambient temperature. The reaction mixture was partitioned between EtOAc (1 mL) and 2 M NaOH$_{(aq)}$ (1 mL). Following phase separation, aqueous phase was back extracted with additional EtOAc (1 mL). The organic extracts were combined, and concentrated in vacuo. The crude residue was purified by C18 reverse phase chromatography (using 5-95% ACN in water as the gradient eluent) to cleanly afford the title compound (13 mg, 99% yield). MS (apci) m/z=417.25 (M+H).

Example 530

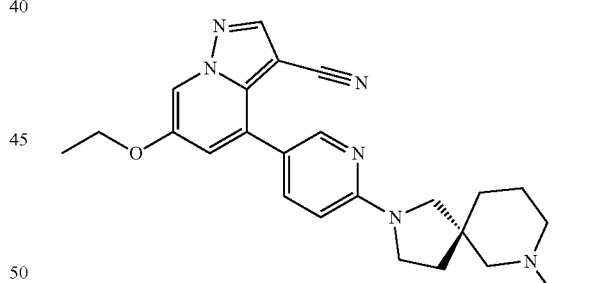

(S)-6-ethoxy-4-(6-(7-ethyl-2,7-diazaspiro[4.5]decan-2-yl)pyridin-3-yl)pyrazolo[1,5-a]pyridine-3-carbonitrile A mixture of ((S)-4-(6-(2,7-diazaspiro[4.5]decan-2-yl)pyridin-3-yl)-6-ethoxypyrazolo[1,5-a]pyridine-3-carbonitrile dihydrochloride (Example 523; 15 mg, 0.032 mmol) and acetaldehyde (7.5 mg, 0.063 mmol) in DCM (158 μL) was treated with NaBH(AcO)$_3$ (40 mg, 0.19 mmol), then stirred overnight at ambient temperature. The reaction mixture was partitioned between EtOAc (1 mL) and 2 M NaOH$_{(aq)}$ (1 mL). Following phase separation, aqueous phase was back extracted with additional EtOAc (1 mL). The organic extracts were combined, and concentrated in vacuo. The crude residue was purified by C18 reverse phase chromatography (using 5-60% ACN in water as the gradient eluent) to cleanly afford the title compound (8.5 mg, 63% yield). MS (apci) m/z=431.2 (M+H).

Example 531

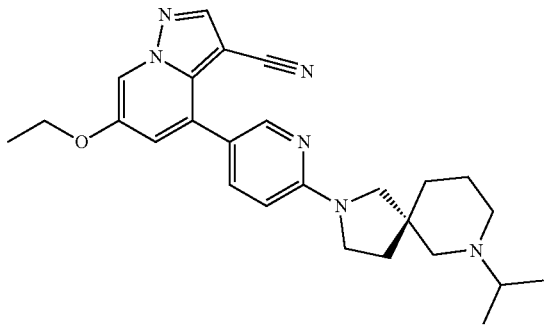 [SMILES: CCOc1cc(-c2ccc(N3CC[C@]4(CCCN(C(C)C)C4)C3)nc2)c2c(C#N)cnn2c1]

(S)-6-ethoxy-4-(6-(7-isopropyl-2,7-diazaspiro[4.5] decan-2-yl)pyridin-3-yl)pyrazolo[1,5-a]pyridine-3-carbonitrile A mixture of (S)-4-(6-(2,7-diazaspiro[4.5]decan-2-yl) pyridin-3-yl)-6-ethoxypyrazolo[1,5-a]pyridine-3-carbonitrile dihydrochloride (Example 523; 15 mg, 0.032 mmol) and 2-iodopropane (5.90 mg, 0.0347 mmol) in DCM (158 µL) was treated with DIEA (5.50 µL, 0.0316 mmol), then the reaction vessel was sealed. The reaction mixture was stirred for 18 h at 50° C. Additional 2-iodopropane (one drop) and DIEA (one drop) were introduced, the vessel was re-sealed, and the mixture was stirred for stirred for an additional 2 h at 50° C. After cooling to ambient temperature, the mixture was directly purified by C18 reverse phase chromatography (using 5-95% ACN in water as the gradient eluent) to afford the title compound (10.3 mg, 73% yield). MS (apci) m/z=445.3 (M+H).

Example 532

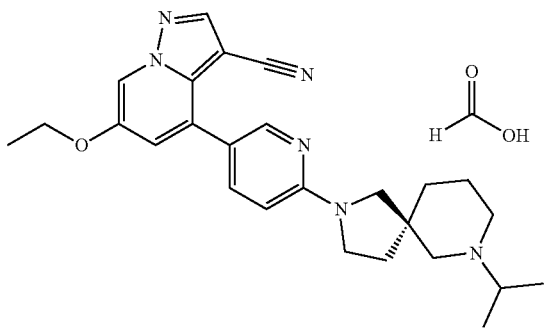

(R)-6-ethoxy-4-(6-(7-isopropyl-2,7-diazaspiro[4.5] decan-2-yl)pyridin-3-yl)pyrazolo[1,5-a]pyridine-3-carbonitrile formate A mixture of (R)-4-(6-(2,7-diazaspiro[4.5]decan-2-yl) pyridin-3-yl)-6-ethoxypyrazolo[1,5-a]pyridine-3-carbonitrile dihydrochloride (Example 521; 15 mg, 0.032 mmol) and 2-iodopropane (5.9 mg, 0.035 mmol) in DCM (158 µL) was treated with DIEA (16 µL, 0.035 mmol), then the reaction vessel was sealed. The reaction mixture was stirred for 18 h at ambient temperature. Additional 2-iodopropane (one drop) and DIEA (one drop) were introduced, the vessel was re-sealed, and the mixture was stirred for stirred for 2 h at 50° C. After cooling to ambient temperature, the mixture was directly purified by C18 reverse phase chromatography (using 5-40% ACN in water with 0.1% formic acid as the gradient eluent) to afford the title compound (6.7 mg, 48% yield). MS (apci) m/z=445.3 (M+H).

Example 533

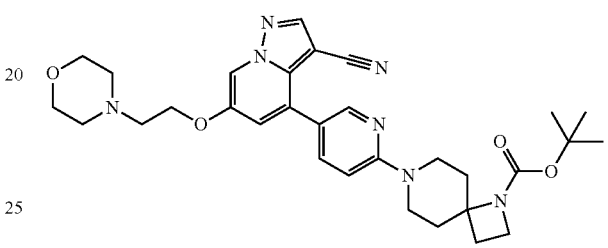

tert-butyl 7-(5-(3-cyano-6-(2-morpholinoethoxy) pyrazolo[1,5-a]pyridin-4-yl)pyridin-2-yl)-1,7-diazaspiro[3.5]nonane-1-carboxylate A suspension of 4-(6-fluoropyridin-3-yl)-6-(2-morpholinoethoxy)pyrazolo[1,5-a]pyridine-3-carbonitrile (Intermediate P95; 400 mg, 1.09 mmol) in DMSO (2.5 mL) was treated with DIEA (570.5 µL, 3.266 mmol) and tert-butyl 1,7-diazaspiro[3.5]nonane-1-carboxylate (345.0 mg, 1.524 mmol), and then stirred for 17 h at 90° C. After cooling to ambient temperature, the resulting suspension was diluted with water (10 mL), stirred for 1 h at ambient temperature, and then filtered. The isolated solids were rinsed with water, and dried under high vacuum overnight to cleanly provide the title compound (650.6 mg, quantitative yield). MS (apci) m/z=574.3 (M+H).

Example 534

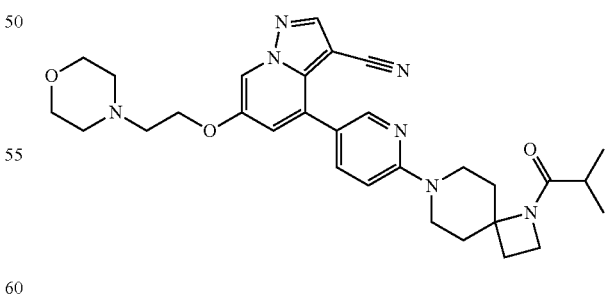

4-(6-(1-isobutyryl-1,7-diazaspiro[3.5]nonan-7-yl) pyridin-3-yl)-6-(2-morpholinoethoxy)pyrazolo[1,5-a]pyridine-3-carbonitrile A solution of 4-(6-(1,7-diazaspiro[3.5]nonan-7-yl)pyridin-3-yl)-6-(2-morpholinoethoxy)pyrazolo[1,5-a]pyridine- 3-carbonitrile dihydrochloride (Intermediate P96; 25 mg, 0.046 mmol) in DMA (500 µL) was treated sequentially with DIEA (23.9 µL, 0.137 mmol), isobutyric acid (6.36 µL, 0.0686 mmol) and HATU (26.1 mg, 0.0686 mmol). The reaction mixture was stirred for 1 h at ambient temperature. The resulting suspension was diluted with water to dissolve the precipitate, and the solution was directly purified by C18 reverse phase chromatography (using 5-95% ACN/water as the gradient eluent) to afford the title compound (10.4 mg, 42% yield). MS (apci) m/z=544.3 (M+H).

Example 535

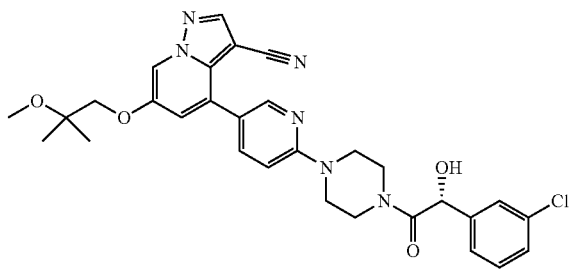 [SMILES: COC(C)(C)COc1cc(-c2ccc(N3CCN(C(=O)[C@H](O)c4cccc(Cl)c4)CC3)nc2)c2c(C#N)cnn2c1]

(R)-4-(6-(4-(2-(3-chlorophenyl)-2-hydroxyacetyl)piperazin-1-yl)pyridin-3-yl)-6-(2-methoxy-2-methyl-propoxy)pyrazolo[1,5-a]pyridine-3-carbonitrile A solution of 6-(2-methoxy-2-methylpropoxy)-4-(6-(piperazin-1-yl)pyridin-3-yl)pyrazolo[1,5-a]pyridine-3-carbonitrile dihydrochloride (Example 246; 25 mg, 0.052 mmol) and (R)-2-(3-chlorophenyl)-2-hydroxyacetic acid (10 mg, 0.052 mmol) in DCM (520 µL) was treated sequentially with DIEA (55 µL, 0.313 mmol) and HATU (22 mg, 0.057 mmol), then stirred for 16 h at ambient temperature. The resulting mixture was diluted with water (20 mL) and extracted with DCM (3×20 mL). The organic extracts were combined and concentrated in vacuo. The crude residue was purified by silica chromatography (using 0-100% Acetone/Hexanes as the gradient eluent) to cleanly afford the title compound (27 mg, 42% yield). MS (apci) m/z=575.2 (M+H).

Example 536

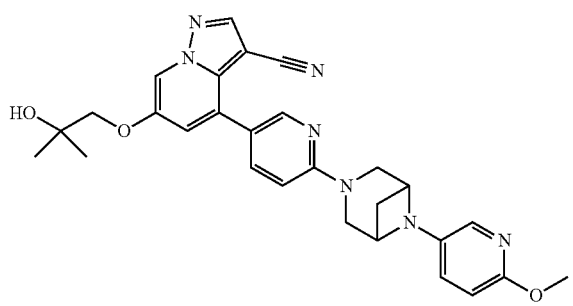 [SMILES: COc1ccc(N2C3CC2CN(c2ccc(-c4cc(OCC(C)(C)O)cn5ncc(C#N)c45)cn2)C3)cn1]

6-(2-hydroxy-2-methylpropoxy)-4-(6-(6-(6-methoxypyridin-3-yl)-3,6-diazabicyclo[3.1.1]heptan-3-yl)pyridin-3-yl)pyrazolo[1,5-a]pyridine-3-carbonitrile A mixture of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (Intermediate P43; 100 mg, 0.210 mmol), 5-bromo-2-methoxypyridine (40.66 µL, 0.3142 mmol), KOtBu (117.5 mg, 1.047 mmol), $Pd_2(dba)_3 \cdot CHCl_3$ (10.84 mg, 0.01047 mmol) and X-phos (19.97 mg, 0.04189 mmol) in toluene (1047 µL) was sparged with $N_{2(g)}$ for 30 seconds. After sealing the vessel under $N_{2(g)}$, the reaction mixture was stirred for 90 min at 100° C. After cooling to ambient temperature, the reaction mixture was partitioned between DCM (10 mL) and water (10 mL). After phase separation, the aqueous extracts were washed with additional DCM (3×5 mL). The organic extracts were combined, dried over anhydrous $Na_2SO_{4(s)}$, filtered and concentrated in vacuo. The resulting crude residue was purified by C18 reverse phase chromatography (using 5-55% ACN in water, and again using 5-45% ACN in water as the gradient eluents) to cleanly afford the title compound (4 mg, 4% yield). MS (apci) m/z=512.2 (M+H).

Example 537

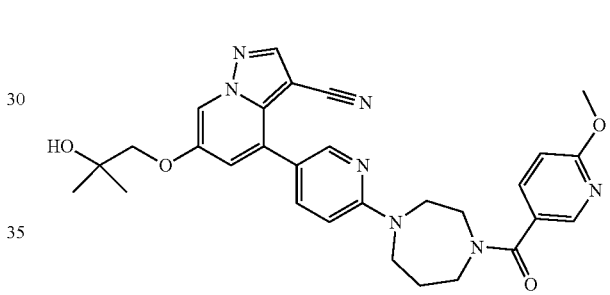

6-(2-hydroxy-2-methylpropoxy)-4-(6-(4-(6-methoxynicotinoyl)-1,4-diazepan-1-yl)pyridin-3-yl)pyrazolo[1,5-a]pyridine-3-carbonitrile A mixture of 4-(6-(1,4-diazepan-1-yl)pyridin-3-yl)-6-(2-hydroxy-2-methylpropoxy)pyrazolo[1,5-a]pyridine-3-carbonitrile bis(2,2,2-trifluoroacetate) (Intermediate P98; 50 mg, 0.0788 mmol), DIEA (68.6 µL, 0.394 mmol), HATU (89.9 mg, 0.236 mmol) and 6-methoxynicotinic acid (36.2 mg, 0.236 mmol) in DMF (500 µL) was stirred overnight at ambient temperature. The reaction mixture was treated with additional DIEA (50 µL, 0.287 mmol), 6-methoxynicotinic acid (30 mg, 0.196 mmol), and HATU (50 mg, 0.131 mmol), and stirred for an additional 5 h at ambient temperature. The reaction mixture was diluted with DCM, and quenched with saturated $NH_4Cl_{(aq)}$. After phase separation, the aqueous extracts were washed with additional DCM (3×). The combined organic extracts then were dried over anhydrous $Na_2SO_{4(s)}$, filtered and concentrated in vacuo. The crude residue was purified by silica chromatography (using 0-20% MeOH [1% $NH_4OH$]/EtOAc as the gradient eluent) to cleanly afford the title compound (42.7 mg, quantitative yield). MS (apci) m/z=542.3 (M+H).

Example 538

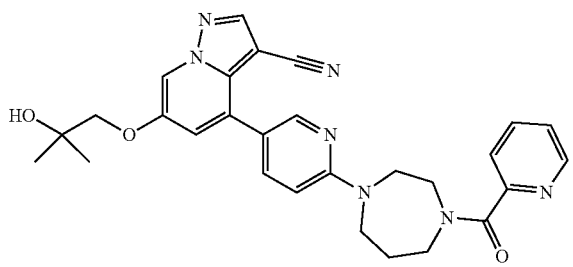 [SMILES: CC(C)(O)COc1cc(-c2ccc(N3CCCN(C(=O)c4ccccn4)CC3)nc2)c2c(C#N)cnn2c1]

6-(2-hydroxy-2-methylpropoxy)-4-(6-(4-picolinoyl-1,4-diazepan-1-yl)pyridin-3-yl)pyrazolo[1,5-a]pyridine-3-carbonitrile The title compound (37.5 mg, 93% yield) was prepared using a similar procedure to that described for (6-(2-hydroxy-2-methylpropoxy)-4-(6-(4-(6-methoxynicotinoyl)-1,4-diazepan-1-yl)pyridin-3-yl)pyrazolo[1,5-a]pyridine-3-carbonitrile (Example 537), replacing 6-methoxynicotinic acid with picolinic acid. MS (apci) m/z=512.25 (M+H).

Example 539

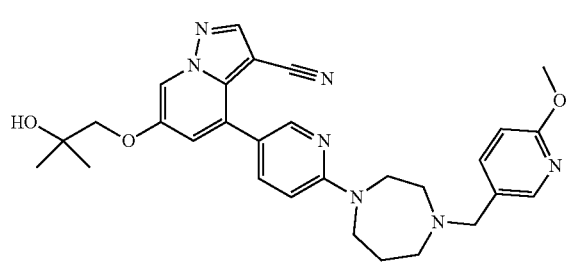 [SMILES: COc1ccc(CN2CCCN(c3ccc(-c4cc(OCC(C)(C)O)cn5ncc(C#N)c45)cn3)CC2)cn1]

6-(2-hydroxy-2-methylpropoxy)-4-(6-(4-((6-methoxypyridin-3-yl)methyl)-1,4-diazepan-1-yl)pyridin-3-yl)pyrazolo[1,5-a]pyridine-3-carbonitrile A mixture of 4-(6-(1,4-diazepan-1-yl)pyridin-3-yl)-6-(2-hydroxy-2-methylpropoxy)pyrazolo[1,5-a]pyridine-3-carbonitrile bis(2,2,2-trifluoroacetate) (Intermediate P98; 50 mg, 0.0788 mmol), TEA (54.9 µL, 0.394 mmol), NaBH(AcO)$_3$ (50.1 mg, 0.236 mmol) and 6-methoxynicotinaldehyde (32.4 mg, 0.236 mmol) in DMF (500 µL) was stirred overnight at ambient temperature. The reaction mixture was diluted with DCM, and quenched with saturated NH$_4$Cl$_{(aq)}$. After phase separation, the aqueous extracts were washed with additional DCM (3×). The combined organic extracts then were dried over anhydrous Na$_2$SO$_{4(s)}$, filtered and concentrated in vacuo. The crude residue was purified by silica chromatography (using 0-20% MeOH/EtOAc as the gradient eluent) to cleanly afford the title compound (33.8 mg, 81% yield). MS (apci) m/z=528.3 (M+H).

Example 540

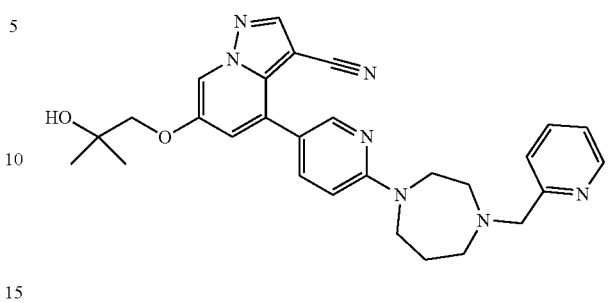

6-(2-hydroxy-2-methylpropoxy)-4-(6-(4-(pyridin-2-ylmethyl)-1,4-diazepan-1-yl)pyridin-3-yl)pyrazolo[1,5-a]pyridine-3-carbonitrile The title compound (39 mg, 99% yield) was prepared using a similar procedure to that described for 6-(2-hydroxy-2-methylpropoxy)-4-(6-(4-((6-methoxypyridin-3-yl)methyl)-1,4-diazepan-1-yl)pyridin-3-yl)pyrazolo[1,5-a]pyridine-3-carbonitrile (Example 539), replacing 6-methoxynicotinaldehyde with picolinaldehyde. MS (apci) m/z=498.3 (M+H).

Example 541

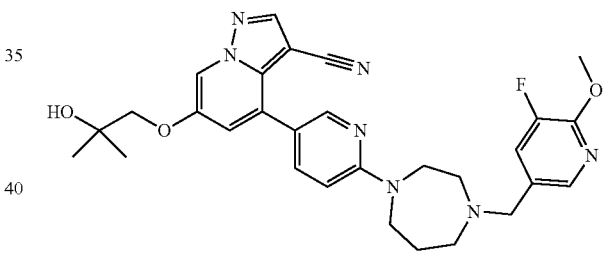

4-(6-(4-((5-fluoro-6-methoxypyridin-3-yl)methyl)-1,4-diazepan-1-yl)pyridin-3-yl)-6-(2-hydroxy-2-methylpropoxy)pyrazolo[1,5-a]pyridine-3-carbonitrile A solution of 4-(6-(1,4-diazepan-1-yl)pyridin-3-yl)-6-(2-hydroxy-2-methylpropoxy)pyrazolo[1,5-a]pyridine-3-carbonitrile bis(2,2,2-trifluoroacetate) (Intermediate P98; 50 mg, 0.0788 mmol) in DMA (500 µL) was treated with 5-fluoro-6-methoxynicotininaldehyde (36.7 mg, 0.237 mmol), TEA (77 µL, 0.55 mmol) and (NaBH(AcO)$_3$ (50 mg, 0.237 mmol), then stirred overnight at ambient temperature. The reaction mixture was treated with additional TEA (77 µL, 0.55 mmol), NaBH(AcO)$_3$ (50 mg, 0.237 mmol) and 5-fluoro-6-methoxynicotininaldehyde (36.7 mg, 0.237 mmol), and then stirred at ambient temperature until LCMS indicated complete consumption of starting material. The reaction mixture was purified directly by silica chromatography (using 0-25% EtOAc/MeOH as the gradient eluent) and again by C18 reverse phase chromatography (using 5-95% ACN in water with 0.1% TFA as the gradient eluent) to afford impure title compound as the TFA salt. The TFA salt was neutralized with 1 M NaOH and brine, and then extracted with EtOAc. The organic extracts then were dried over anhydrous Na$_2$SO$_{4(s)}$, filtered and concentrated in vacuo to cleanly afford the title compound (30 mg, 70% yield). MS (apci) m/z=546.2 (M+H).

Example 542

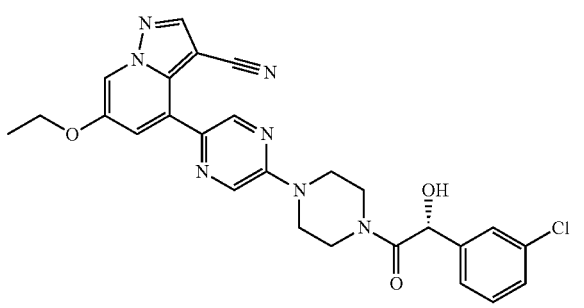 [SMILES: CCOc1cc(-c2cnc(N3CCN(C(=O)[C@H](O)c4cccc(Cl)c4)CC3)cn2)c2c(C#N)cnn2c1]

(R)-4-(5-(4-(2-(3-chlorophenyl)-2-hydroxyacetyl)piperazin-1-yl)pyrazin-2-yl)-6-ethoxypyrazolo[1,5-a]pyridine-3-carbonitrile A mixture of 6-ethoxy-4-(5-(piperazin-1-yl)pyrazin-2-yl)pyrazolo[1,5-a]pyridine-3-carbonitrile bis(2,2,2-trifluoroacetate) (Intermediate P101; 35 mg, 0.061 mmol), (R)-(−)-3-Chloromandelic acid (14 mg, 0.073 mmol), HATU (25 mg, 0.067 mmol) in DCM (606 µL) was treated with DIEA (32 µL, 0.18 mmol), then stirred overnight at ambient temperature. The reaction mixture was concentrated in vacuo. The crude residue was purified by silica chromatography (using 0-100% EtOAc in Hexanes then 0-10% MeOH in EtOAc as the gradient eluents), and the fractions containing desired product were combined, and concentrated in vacuo. The residue was triturated with MeOH. The resulting precipitate was collected by filtration to cleanly afford the title compound (6 mg, 19% yield). MS (apci) m/z=518.1 (M+H).

Example 543

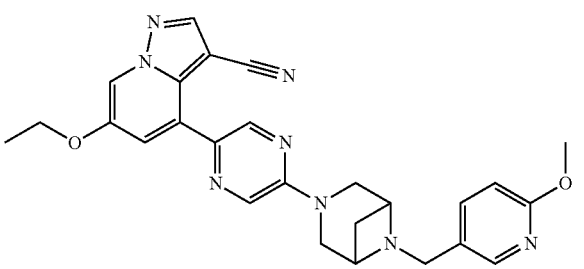 [SMILES: CCOc1cc(-c2cnc(N3CC4CC(C3)N4Cc3ccc(OC)nc3)cn2)c2c(C#N)cnn2c1]

6-ethoxy-4-(5-(6-(((6-methoxypyridin-3-yl)methyl)-3,6-diazabicyclo[3.1.1]heptan-3-yl)pyrazin-2-yl)pyrazolo[1,5-a]pyridine-3-carbonitrile A mixture of 4-(5-(3,6-diazabicyclo[3.1.1]heptan-3-yl)pyrazin-2-yl)-6-ethoxypyrazolo[1,5-a]pyridine-3-carbonitrile bis(2,2,2-trifluoroacetate) (Intermediate P103; 20 mg, 0.034 mmol) in DCM (679 µL) was treated with 6-methoxynicotinaldehyde (14 mg, 0.10 mmol) and NaBH(AcO)$_3$ (36 mg, 0.17 mmol), then stirred overnight at ambient temperature. The reaction mixture was purified directly by silica chromatography (0-10% MeOH in DCM with 0.1% NH$_4$OH) to cleanly afford the title compound (15 mg, 92% yield). MS (apci) m/z=483.2 (M+H).

Example 544

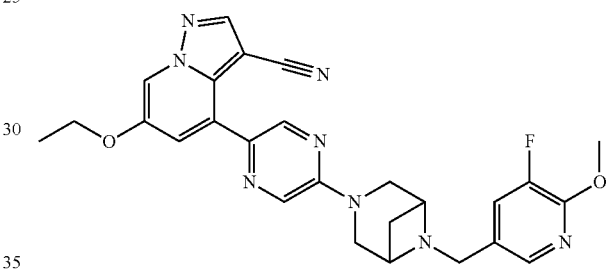

6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile A mixture of 4-(5-(3,6-diazabicyclo[3.1.1]heptan-3-yl)pyrazin-2-yl)-6-ethoxypyrazolo[1,5-a]pyridine-3-carbonitrile bis(2,2,2-trifluoroacetate) (Intermediate P103; 20 mg, 0.034 mmol) in DCM (679 µL) was treated with 5-fluoro-6-methoxynicotininaldehyde (16 mg, 0.10 mmol) and NaBH(AcO)$_3$ (36 mg, 0.17 mmol), then stirred overnight at ambient temperature. The reaction mixture was purified directly by silica chromatography (using 0-10% MeOH in DCM with 0.1% NH$_4$OH as the gradient eluent) to cleanly afford the title compound (14 mg, 82% yield). MS (apci) m/z=501.2 (M+H).

The compounds in Table GG were prepared using a similar method to that described in the synthesis of 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile (Example 544), replacing 5-fluoro-6-methoxynicotininaldehyde with the appropriate aldehyde. Reactions were monitored for completion by LCMS, as such reaction durations were adjusted accordingly. Title compounds were isolated following chromatographic purification using an appropriate gradient eluent.

TABLE GG

| Ex # | Structure | Chemical Name | MS apci (m/z) |
|---|---|---|---|
| 545 | 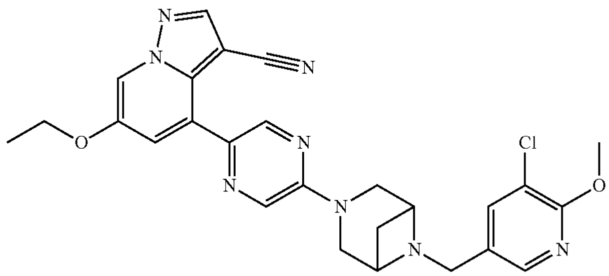 [SMILES: CCOc1cc(-c2cnc(N3CC4CC(C3)N4Cc3cnc(OC)c(Cl)c3)cn2)c2c(C#N)cnn2c1] | 4-(5-(6-((5-chloro-6-methoxypyridin-3-yl)methyl)-3,6-diazabicyclo[3.1.1]heptan-3-yl)pyrazin-2-yl)-6-ethoxypyrazolo[1,5-a]pyridine-3-carbonitrile | 517.1 (M + H) |
| 546 | 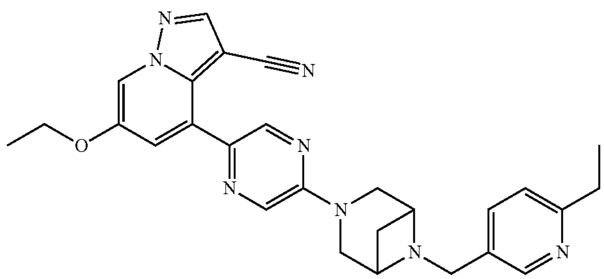 [SMILES: CCOc1cc(-c2cnc(N3CC4CC(C3)N4Cc3ccc(CC)nc3)cn2)c2c(C#N)cnn2c1] | 6-ethoxy-4-(5-(6-((6-ethylpyridin-3-yl)methyl)-3,6-diazabicyclo[3.1.1]heptan-3-yl)pyrazin-2-yl)pyrazolo[1,5-a]pyridine-3-carbonitrile | 481.2 (M + H) |
| 547 | 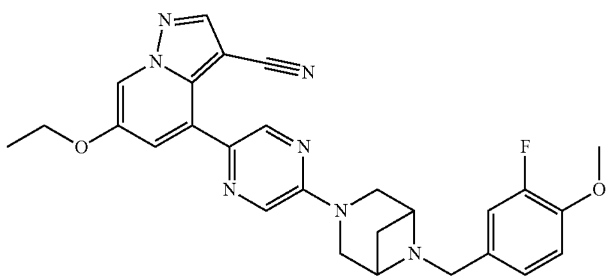 [SMILES: CCOc1cc(-c2cnc(N3CC4CC(C3)N4Cc3ccc(OC)c(F)c3)cn2)c2c(C#N)cnn2c1] | 6-ethoxy-4-(5-(6-(3-fluoro-4-methoxybenzyl)-3,6-diazabicyclo[3.1.1]heptan-3-yl)pyrazin-2-yl)pyrazolo[1,5-a]pyridine-3-carbonitrile | 500.2 (M + H) |
| 548 | 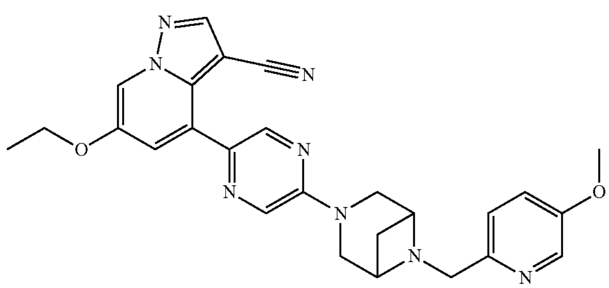 [SMILES: CCOc1cc(-c2cnc(N3CC4CC(C3)N4Cc3ccc(OC)cn3)cn2)c2c(C#N)cnn2c1] | 6-ethoxy-4-(5-(6-((5-methoxypyridin-2-yl)methyl)-3,6-diazabicyclo[3.1.1]heptan-3-yl)pyrazin-2-yl)pyrazolo[1,5-a]pyridine-3-carbonitrile | 483.2 (M + H) |

Example 549

4-(5-(6-((5-chloro-6-methoxypyridin-3-yl)methyl)-3,6-diazabicyclo[3.1.1]heptan-3-yl)pyrazin-2-yl)-6-(2-morpholinoethoxy)pyrazolo[1,5-a]pyridine-3-carbonitrile

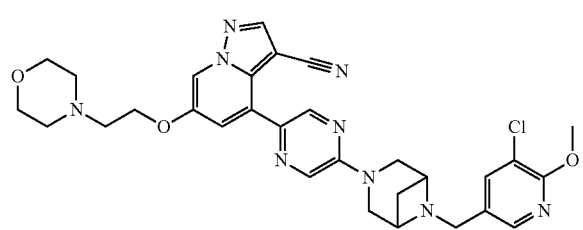 [SMILES: COc1ncc(CN2C3CC2CN(c2cnc(-c4cc(OCCN5CCOCC5)cn5ncc(C#N)c45)cn2)C3)cc1Cl]

A solution of 4-(5-(3,6-diazabicyclo[3.1.1]heptan-3-yl)pyrazin-2-yl)-6-(2-morpholinoethoxy)pyrazolo[1,5-a]pyridine-3-carbonitrile bis(2,2,2-trifluoroacetate) (Intermediate P106; 22.2 mg, 0.0329 mmol) in DCM (658.2 µL) was treated sequentially with 5-chloro-6-methoxynicotinaldehyde (28.23 mg, 0.1646 mmol) and NaBH(AcO)₃ (69.75 mg, 0.3291 mmol), then stirred overnight at ambient temperature. The reaction mixture was filtered through a PVDF (0.45 µm) disc syringe filter. The filtrate was purified directly by silica chromatography (using 0-100% DCM in Hexanes then 0-10% MeOH in DCM with 0.1% NH₄OH as the gradient eluents). Fractions containing the desired product were concentrated in vacuo azeotroping with Et₂O to cleanly afford the title compound (13.08 mg, 66% yield). MS (apci) m/z=602.2 (M+H).

Example 550

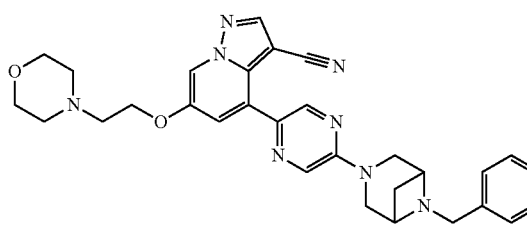

4-(5-(6-((6-methoxypyridin-3-yl)methyl)-3,6-diaz-abicyclo[3.1.1]heptan-3-yl)pyrazin-2-yl)-6-(2-morpholinoethoxy)pyrazolo[1,5-a]pyridine-3-carbonitrile The title compound (2.07 mg, 7% yield) was prepared using a similar procedure to that described for the synthesis of 4-(5-(6-((5-chloro-6-methoxypyridin-3-yl)methyl)-3,6-diazabicyclo[3.1.1]heptan-3-yl)pyrazin-2-yl)-6-(2-morpholinoethoxy)pyrazolo[1,5-a]pyridine-3-carbonitrile (Example 549), replacing (5-chloro-6-methoxynicotinaldehyde with 6-methoxynicotinaldehyde, and adding an additional chromatographic purification (using a silica column and 0-10% MeOH in EtOAc as the gradient eluent). MS (apci) m/z=568.3 (M+H).

Example 551

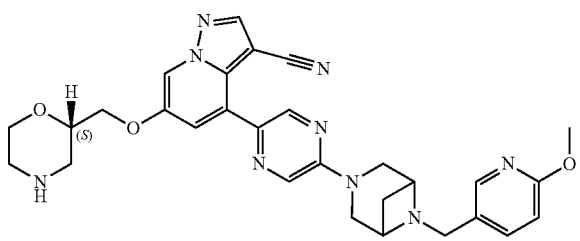

4-(5-(6-((6-methoxypyridin-3-yl)methyl)-3,6-diaz-abicyclo[3.1.1]heptan-3-yl)pyrazin-2-yl)-6-(((S)-morpholin-2-yl)methoxy)pyrazolo[1,5-a]pyridine-3-carbonitrile A solution of tert-butyl (2S)-2-(((3-cyano-4-(5-(6-((6-methoxypyridin-3-yl)methyl)-3,6-diazabicyclo[3.1.1]heptan-3-yl)pyrazin-2-yl)pyrazolo[1,5-a]pyridin-6-yl)oxy)methyl)morpholine-4-carboxylate (Intermediate P112; 55.9 mg, 0.0855 mmol) in DCM (2.0 mL) was treated with TFA (1 mL, 13.1 mmol), and stirred for 2 h at ambient temperature. The resulting mixture was concentrated in vacuo to afford the TFA salt. The TFA salt residue was purified and converted to the free base by silica chromatography (using 0-20% DCM/MeOH/2% NH₄OH as the gradient eluent) to cleanly afford the title compound (19 mg, 40% yield). MS (apci) m/z=554.3 (M+H).

Example 552

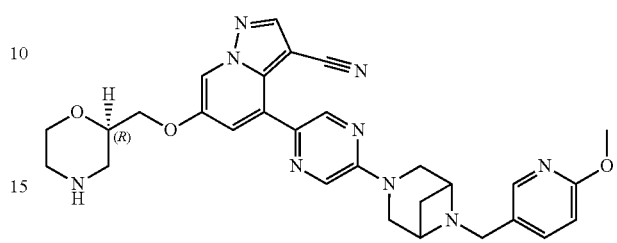

4-(5-(6-((6-methoxypyridin-3-yl)methyl)-3,6-diaz-abicyclo[3.1.1]heptan-3-yl)pyrazin-2-yl)-6-(((R)-morpholin-2-yl)methoxy)pyrazolo[1,5-a]pyridine-3-carbonitrile The title compound (1.6 mg, 3% yield) was prepared using a similar procedure to that described for the synthesis of 4-(5-(6-((6-methoxypyridin-3-yl)methyl)-3,6-diazabicyclo[3.1.1]heptan-3-yl)pyrazin-2-yl)-6-(((S)-morpholin-2-yl)methoxy)pyrazolo[1,5-a]pyridine-3-carbonitrile (Example 551), replacing tert-butyl (2S)-2-(((3-cyano-4-(5-(6-((6-methoxypyridin-3-yl)methyl)-3,6-diazabicyclo[3.1.1]heptan-3-yl)pyrazin-2-yl)pyrazolo[1,5-a]pyridin-6-yl)oxy)methyl)morpholine-4-carboxylate (Intermediate P112) with tert-butyl (2R)-2-(((3-cyano-4-(5-(6-((6-methoxypyridin-3-yl)methyl)-3,6-diazabicyclo[3.1.1]heptan-3-yl)pyrazin-2-yl)pyrazolo[1,5-a]pyridin-6-yl)oxy)methyl)morpholine-4-carboxylate (Intermediate P111). MS (apci) m/z=554.3 (M+H).

Example 553

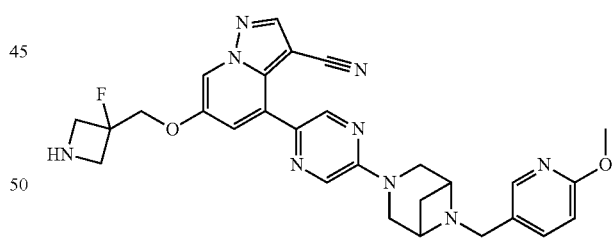

6-((3-fluoroazetidin-3-yl)methoxy)-4-(5-(6-((6-methoxypyridin-3-yl)methyl)-3,6-diazabicyclo [3.1.1]heptan-3-yl)pyrazin-2-yl)pyrazolo[1,5-a]pyridine-3-carbonitrile A solution of tert-butyl 3-(((3-cyano-4-(5-(6-((6-methoxypyridin-3-yl)methyl)-3,6-diazabicyclo[3.1.1]heptan-3-yl)pyrazin-2-yl)pyrazolo[1,5-a]pyridin-6-yl)oxy)methyl)-3-fluoroazetidine-1-carboxylate (Intermediate P115; 48 mg, 0.075 mmol) in DCM (1.0 mL) was treated with TFA (1 mL, 13.1 mmol), and stirred for 1 h at ambient temperature. The resulting mixture was diluted with DCM (10 mL) and neutralized by extracting with saturated NaHCO$_{3(aq)}$ (10 mL). The biphasic mixture was extracted with additional DCM (3×), and the combined DCM extracts were concentrated in vacuo. The residue was triturated with DCM (1 mL) and Pentane (5 mL). The precipitate that formed was collected by vacuum filtration, and dried under high vacuum to cleanly afford the title compound (20 mg, 49% yield). MS (apci) m/z=542.2 (M+H).

Example 554

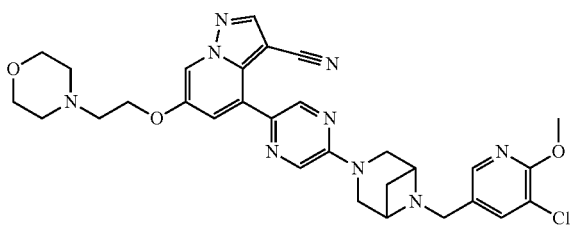 [SMILES: COc1ncc(CN2C3CC2CN(c2cnc(-c4cc(OCCN5CCOCC5)cn5ncc(C#N)c45)cn2)C3)cc1Cl]

4-(2-(6-((5-chloro-6-methoxypyridin-3-yl)methyl)-3,6-diazabicyclo[3.1.1]heptan-3-yl)pyrimidin-5-yl)-6-(2-morpholinoethoxy)pyrazolo[1,5-a]pyridine-3-carbonitrile A mixture of 5-chloro-6-methoxynicotinaldehyde (59.56 mg, 0.3471 mmol), 4-(2-(3,6-diazabicyclo[3.1.1]heptan-3-yl)pyrimidin-5-yl)-6-(2-morpholinoethoxy)pyrazolo[1,5-a]pyridine-3-carbonitrile (Intermediate P117; 31 mg, 0.069 mmol) and NaBH(AcO)$_3$ (147.1 mg, 0.6943 mmol) in DCM (694.3 µL) was stirred overnight at ambient temperature. The reaction mixture was purified directly by silica chromatography (using 0-10% MeOH in EtOAc with 0.1% NH$_4$OH as the gradient eluent) to cleanly afford the title compound (15.19 mg, 35% yield). MS (apci) m/z=602.3 (M+H).

Example 555

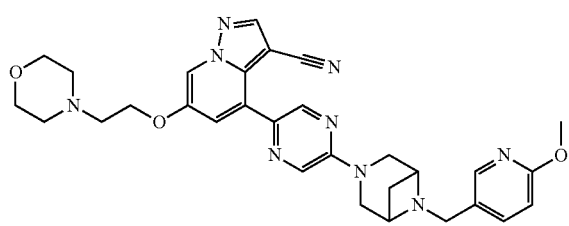 [SMILES: COc1ccc(CN2C3CC2CN(c2cnc(-c4cc(OCCN5CCOCC5)cn5ncc(C#N)c45)cn2)C3)cn1]

4-(2-(6-((6-methoxypyridin-3-yl)methyl)-3,6-diazabicyclo[3.1.1]heptan-3-yl)pyrimidin-5-yl)-6-(2-morpholinoethoxy)pyrazolo[1,5-a]pyridine-3-carbonitrile A mixture of 6-methoxynicotinaldehyde (47.6 mg, 0.347 mmol), 4-(2-(3,6-diazabicyclo[3.1.1]heptan-3-yl)pyrimidin-5-yl)-6-(2-morpholinoethoxy)pyrazolo[1,5-a]pyridine-3-carbonitrile (Intermediate P117; 31 mg, 0.069 mmol) and NaBH(AcO)$_3$ (147 mg, 0.694 mmol) in DCM (694 µL) was stirred overnight at ambient temperature. The reaction mixture was purified directly by silica chromatography (using 0-10% MeOH in DCM with 0.1% NH$_4$OH as the gradient eluent) to cleanly afford the title compound (7.37 mg, 19% yield). MS (apci) m/z=568.3 (M+H).

Example 556

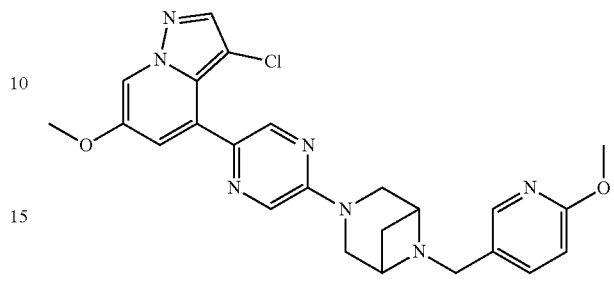

3-(5-(3-chloro-6-methoxypyrazolo[1,5-a]pyridin-4-yl)pyrazin-2-yl)-6-((6-methoxypyridin-3-yl)methyl)-3,6-diazabicyclo[3.1.1]heptane A mixture of 3-chloro-6-methoxy-4-(4,4,5,5-tetramethyl-1,3,2-dioxaborolan-2-yl)pyrazolo[1,5-a]pyridine (Intermediate P98; 75 mg, 0.24 mmol), 3-(5-chloropyrazin-2-yl)-6-((6-methoxypyridin-3-yl)methyl)-3,6-diazabicyclo[3.1.1]heptane (Intermediate R25; 108 mg, 0.16 mmol), X-phos (15 mg, 0.032 mmol) and Pd$_2$(dba)$_3$ (7.4 mg, 0.0081 mmol) in dioxane (810 µL) was treated with 2 M K$_3$PO$_{4(aq)}$ (243 µL, 0.49 mmol). The mixture was sparged with Ar$_{(g)}$, and then the reaction vessel was sealed. The reaction mixture was stirred overnight at 80° C. After cooling to ambient temperature, the reaction mixture was diluted with DCM and extracted sequentially with water and brine. The organic extracts were dried over anhydrous Na$_2$SO$_{4(s)}$, filtered and concentrated in vacuo. The crude residue was purified by silica chromatography (using 10% MeOH in DCM with 0.1% NH$_4$OH as the gradient eluent). Fractions containing the desired product were concentrated in vacuo, and the residue was triturated with DCM (0.5 mL) and pentane (1 mL). The precipitate was collected by filtration, and dried in vacuo to cleanly afford the title compound (10 mg, 13% yield). MS (apci) m/z=478.1 (M+H).

Example 557

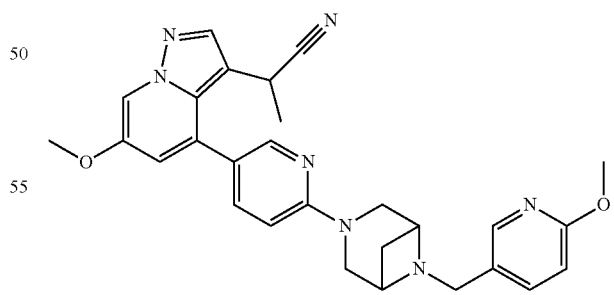

2-(6-methoxy-4-(6-(6-((6-methoxypyridin-3-yl)methyl)-3,6-diazabicyclo[3.1.1]heptan-3-yl)pyridin-3-yl)pyrazolo[1,5-a]pyridin-3-yl)propanenitrile A mixture of 2-(4-bromo-6-methoxypyrazolo[1,5-a]pyridin-3-yl)propanenitrile (Intermediate P120; 33 mg, 0.12 mmol), 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane (Intermediate R28; 42 mg, 0.099 mmol), Pd(PPh₃)₄ (11 mg, 0.0099 mmol) and 2 M Na₂CO₃(aq) (250 L, 0.50 mmol) in dioxane (1 mL) was stirred for 15 h at 80° C. The reaction mixture was concentrated in vacuo. The crude residue was purified by C18 reverse phase chromatography (using 0-30% ACN in water with 0.1% TFA as the gradient eluent), converted to the free base with saturated NaHCO₃ (aq), extracted with DCM and concentrated to cleanly provide the title compound (33 mg, 67% yield). MS (apci) m/z=496.2 (M+H).

Example 558

2-(6-methoxy-4-(6-(6-((6-methoxypyridin-3-yl)methyl)-3,6-diazabicyclo[3.1.1]heptan-3-yl)pyridin-3-yl)pyrazolo[1,5-a]pyridin-3-yl)acetonitrile A mixture of 2-(4-bromo-6-methoxypyrazolo[1,5-a]pyridin-3-yl)acetonitrile (Intermediate P122; 32 mg, 0.12 mmol), 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane (Intermediate R28; 42 mg, 0.099 mmol), Pd(PPh₃)₄ (11 mg, 0.0099 mmol) and 2 M Na₂CO₃(aq) (250 μL, 0.50 mmol) in dioxane (1 mL) was stirred for 15 h at 80° C. The reaction mixture was concentrated in vacuo. The crude residue was purified by C18 reverse phase chromatography (using 0-30% ACN in water with 0.1% TFA as the gradient eluent), converted to the free base with saturated NaHCO₃ (aq), extracted with DCM and concentrated to cleanly provide the title compound (36 mg, 75% yield). MS (apci) m/z=482.2 (M+H).

The compounds in Table HH were prepared using a similar method to that described in the synthesis of 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile (Example 544), replacing 5-fluoro-6-methoxynicotininaldehyde with the appropriate aldehyde.

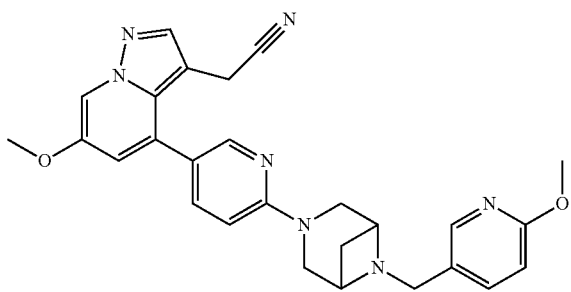

TABLE HH

| Ex # | Structure | Chemical Name | MS apci (m/z) |
|---|---|---|---|
| 559 | 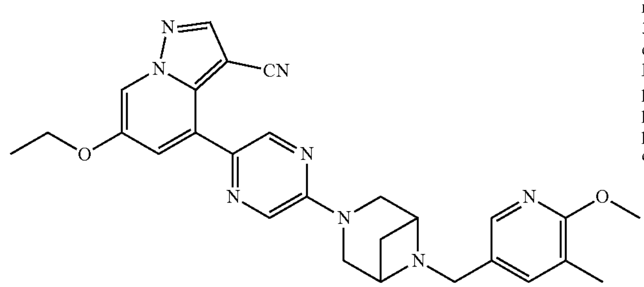 | 6-ethoxy-4-(5-(6-((6-methoxy-5-methylpyridin-3-yl)methyl)-3,6-diazabicyclo[3.1.1]heptan-3-yl)pyrazin-2-yl)pyrazolo[1,5-a]pyridine-3-carbonitrile | 497.2 (M + H) |
| 560 | 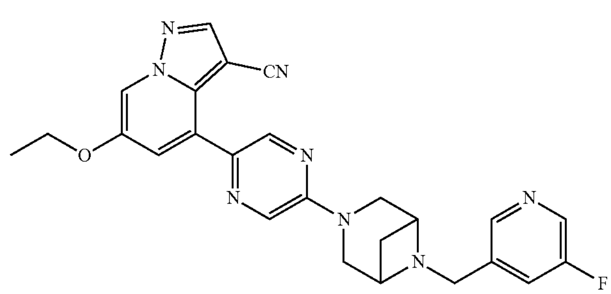 [SMILES: CCOc1cc(-c2cnc(N3CC4CC(C3)N4Cc3cncc(F)c3)cn2)c2c(C#N)cnn2c1] | 6-ethoxy-4-(5-(6-((5-fluoropyridin-3-yl)methyl)-3,6-diazabicyclo[3.1.1]heptan-3-yl)pyrazin-2-yl)pyrazolo[1,5-a]pyridine-3-carbonitrile | 471.2 (M + H) |

Example 561

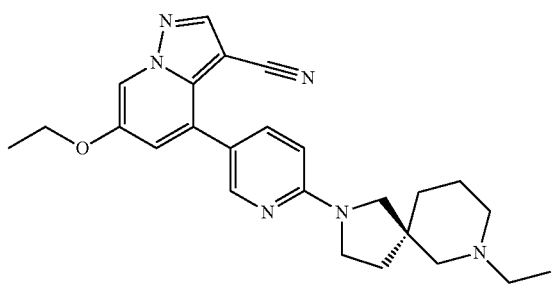 [SMILES: CCOc1cc(-c2ccc(N3CC[C@@]4(CCCN(CC)C4)C3)nc2)c2c(C#N)cnn2c1]

(R)-6-ethoxy-4-(6-(7-ethyl-2,7-diazaspiro[4.5]decan-2-yl)pyridin-3-yl)pyrazolo[1,5-a]pyridine-3-carbonitrile The compound was prepared using a similar method to that described in the synthesis of (R)-6-ethoxy-4-(6-(7-methyl-2,7-diazaspiro[4.5]decan-2-yl)pyridin-3-yl)pyrazolo[1,5-a]pyridine-3-carbonitrile (Example 528), replacing formaldehyde with acetaldehyde. The crude was purified by reverse phase chromatography (5 to 45% ACN in water with 0.1% TFA) followed by free-basing with NaHCO$_3$ (sat.) to yield the title product as solid (3.9 mg, 29% yield). MS (apci) m/z=431.3 (M+H).

Abbreviations

| | |
|---|---|
| 18-Crown-6 | 1,4,7,10,13,16-hexaoxacyclooctadecane |
| ACN | Acetonitrile |
| AcOH | Acetic Acid |
| (±)-BINAP | 2,2'-Bis(diphenylphosphino)-1,1'-binaphthalene |
| Bis(pinacolato)diboron | 4,4,4',4',5,5,5',5'-octamethyl-2,2'-bi(1,3,2-dioxaborolane) |
| BF$_3$•Et$_2$O | Boron trifluoride diethyl etherate |
| Boc | tert-butyl carboxylate group |
| Boc-anhydride | di-tert-butyl dicarbonate |
| n-BuLi | n-butyllithium or 1-butyllithium |
| s-BuOH | Sec-Butanol or 2-Butanol |
| t-BuOH | tert-Butanol or 2-Methylpropan-2-ol |
| CuI | Copper (I) iodide |
| Cu(OAc)$_2$ | Copper (II) diacetate |
| d | day, days |
| DBU | 1,8-Diazabicyclo[5.4.0]undec-7-ene |
| DCE | 1,2-Dichloroethane |
| DCM | Dichloromethane |
| DIAD | Diisopropyl azodi carboxylate |
| DIEA | N,N-Diisopropylethylamine |
| DI water | Deionized water |
| dioxane | 1,4-dioxane |
| DMA | N,N-Dimethylacetamide |
| DMAP | 4-Dimethylaminopyridine |
| DME | 1,2-Dimethoxyethane |
| DMF | N,N-Dimethylformamide |
| DMP | Dess-MartinPeriodinane; 1,1,1-Tris(acetyloxy)-1,1-dihydro-1,2-benziodoxol-3-(1H)-one |
| DMSO | Dimethylsulfoxide |
| dioxane | 1,4-dioxane |
| EDC-HCl | 1-Ethyl-3-(3-dimethylaminopropyl)carbodiimide hydrochloride |
| Et$_2$O | Diethyl Ether |
| EtOAc | Ethyl Acetate |
| EtOH | Ethanol |
| eq | equivalent |
| GF/F paper | GF/F glass microfiber filter paper |
| h | hour, hours |
| HATU | 1-[Bis(dimethylamino)methylene]-1H-1,2,3-triazolo[4,5-b]pyridinium 3-oxide hexafluorophosphate or 2-(7-Aza-1H-benzotriazole-1-yl)-1,1,3,3-tetramethyluronium hexafluorophosphate |
| HBTU | 3-[Bis(dimethylamino)methyliumyl]-3H-benzotriazol-1-oxide hexafluorophosphate or 2-(1H-benzotriazole-1-yl)-1,1,3,3-tetramethyluronium hexafluorophosphate |
| HOAc | Acetic Acid |
| iPrOH | Isopropanol |
| i-PrMgCl | Isopropyl magnesium chloride |
| KOAc | Potassium Acetate |
| LCMS | Liquid chromatography-mass spectrometry |
| LiHMDS | Lithium Hexamethyldisilazide |
| MeOH | Methanol |
| Me$_4$N(AcO)$_3$BH | Tetramethylammonium Triacetoxyborohydride |
| min | minute, minutes |
| MsCl | methanesulfonyl chloride |
| MSH | o-(mesitylsulfonyl)hydroxylamine |
| MTBE | Methyl tert-Butyl Ether |
| NCS | N-Chlorosuccinimide |
| NBS | N-Bromosuccinimide |
| NIS | N-Iodosuccinimide |
| NaBH(AcO)$_3$ | Sodium Triacetoxyborohydride |
| NH$_4$OAc | Ammonium Acetate |

-continued

| | |
|---|---|
| 10% Pd/C | Palladium 10 wt. % (dry basis), active carbon, wet, Degussa |
| Pd(PPh$_3$)$_4$ | Tetrakis(triphenylphosphine)palladium (0) |
| Pd$_2$(dba)$_3$ | tris(dibenzylideneacetone)dipalladium (0) |
| PdCl$_2$(dppf)·CH$_2$Cl$_2$ | 1,1'-Bis(diphenylphosphino)ferrocene-palladium(II)dichloride dichloromethane complex |
| Pd$_2$(dba)$_3$·CHCl$_3$ | tris(dibenzylideneacetone)dipalladium (0) chloroform complex |
| PdCl$_2$(PPh$_3$)$_2$ | Palladium(II)bis(triphenylphosphine) dichloride, |
| PPh$_3$ | Triphenylphosphine |
| P1-HCO$_3$ resin | Stratospheres MP-HCO3 |
| PPTS | Pyridinium p-toluenesulfonate |
| PS frit | Biotage ® "Isolute ® Phase Separators" |
| PS paper | Whatman ® silicone treated Phase Separators filter paper |
| PVDF (0.45 μm) disc | polyvinylidene difluoride membrane with a 0.45-micron pore size |
| rt | Room temperature |
| TBAF | Tetra-n-butylammonium fluoride |
| TEA | Triethylamine |
| Tf-O-Tf | trifluoromethanesulfonic anhydride |
| TFA | Trifluoroacetic acid |
| THF | tetrahydrofuran |
| TMSCN | Trimethylsilyl cyanide |
| Triphosgene | (bis(trichloromethyl) carbonate |
| TsCl | 4-Toluenesulfonyl chloride |
| X-Phos | dicyclohexyl(2',4',6'-triisopropyl-[1,1'-biphenyl]-2-yl)phosphine |

What is claimed is:

1. A compound of the Formula I:

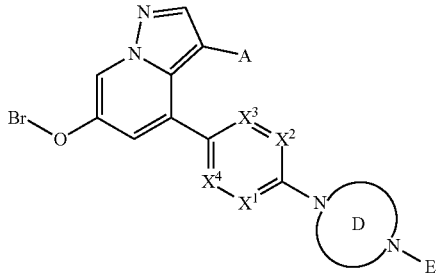

I and pharmaceutically acceptable salts thereof, wherein:

$X^1$, $X^2$, $X^3$ and $X^4$ are independently CH, CF or N, wherein zero, one or two of $X^1$, $X^2$, $X^3$ and $X^4$ is N;

A is H, CN, Cl, $CH_3$—, $CH_3CH_2$—, cyclopropyl, —$CH_2CN$ or —$CH(CN)CH_3$;

B is
(a) hydrogen,
(b) C1-C6 alkyl optionally substituted with 1-3 fluoros,
(c) hydroxyC2-C6 alkyl- wherein the alkyl portion is optionally substituted with a C3-C6 cycloalkylidene ring,
(d) dihydroxyC3-C6 alkyl-, wherein the alkyl portion is optionally substituted with a C3-C6 cycloalkylidene ring,
(e) (C1-C6 alkoxy)C1-C6 alkyl- optionally substituted with 1-3 fluoros,
(f) ($R^1R^2N$)C1-C6 alkyl- wherein $R^1$ and $R^2$ are independently H or C1-C6 alkyl (optionally substituted with 1-3 fluoros);
(g) hetAr$^1$C1-C3 alkyl-, wherein hetAr$^1$ is a 5-6 membered heteroaryl ring having 1-3 ring heteroatoms independently selected from N, O and S and is optionally substituted with one or more independently selected C1-C6 alkyl substituents;
(h) (C3-C6 cycloalkyl)C1-C3 alkyl-,
(i) (hetCyc$^a$)C1-C3 alkyl-, or
(j) hetCyc$^a$;

hetCyc$^a$ is a 4-6 membered heterocyclic ring having 1-2 ring heteroatoms independently selected from N and O and is optionally substituted with OH, C1-C6 alkyl (optionally substituted with 1-3 fluoros) or hydroxyC1-C6 alkyl-;

Ring D is

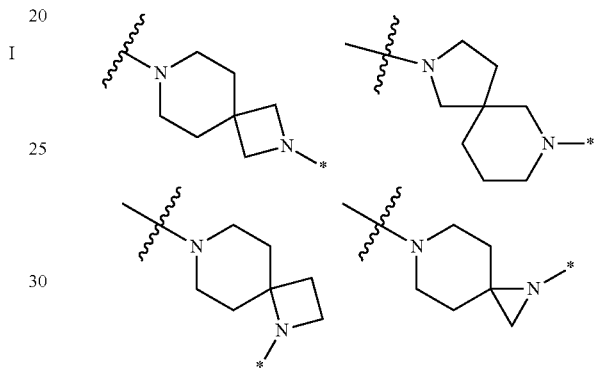

wherein the wavy line indicates the point of attachment of Ring D to the ring comprising $X^1$, $X^2$, $X^3$ and $X^4$, and the asterisk indicates the point of attachment to E;

E is
(a) hydrogen,
(b) C1-C6 alkyl optionally substituted with 1-3 fluoros,
(d) (C1-C6 alkyl)C(=O)— wherein said alkyl portion is optionally substituted with 1-3 fluoros or with a $R^gR^hN$— substituent wherein $R^g$ and $R^h$ are independently H or C1-C6 alkyl,
(f) (C1-C6 alkoxy)C(=O),
(l) hetAr$^2$C(=O)—,
(o) $R^3R^4NC$(=O)—,
(s) Ar$^1$SO$_2$—,
(t) hetAr$^2$SO$_2$—,
(v) Ar$^1$C(=O)—,
(cc) hetAr$^2$, or
(dd) C3-C6 cycloalkyl;

$R^3$ is H or C1-C6 alkyl; and
$R^4$ is C1-C6 alkyl.

2. A compound according to claim 1, wherein $X^1$ is N; $X^2$, $X^3$, and $X^4$ are each CH.

3. A compound according to claim 1, wherein A is CN.

4. A compound according to claim 1, wherein B is (C1-C6 alkoxy)C1-C6 alkyl- optionally substituted with 1-3 fluoros, or hydroxyC2-C6 alkyl- wherein the alkyl portion is optionally substituted with a C3-C6 cycloalkylidene ring.

5. A compound according to 1, wherein Ring D is unsubstituted.

6. A pharmaceutical composition, comprising a compound according to claim 1, or a pharmaceutically acceptable salt thereof, in admixture with a pharmaceutically acceptable diluent or carrier.

7. A method for treating cancer in a patient in need thereof, the method comprising administering to the patient an effective amount of a compound of claim 1, or a pharmaceutically acceptable salt thereof.

8. A method of treating a RET-associated cancer in a patient, the method comprising administering to a patient identified or diagnosed as having a RET-associated cancer a therapeutically effective amount of a compound of claim 1, or a pharmaceutically acceptable salt thereof.

9. A method of treating a RET-associated cancer in a patient, the method comprising:
  determining that the cancer in the patient is a RET-associated cancer; and
  administering to a patient determined to have a RET-associated cancer a therapeutically effective amount of a compound of claim 1, or a pharmaceutically acceptable salt thereof.

10. A method for inhibiting RET kinase activity in a mammalian cell, the method comprising contacting the mammalian cell with a compound of claim 1, or a pharmaceutically acceptable salt thereof.

11. The method of claim 10, wherein the mammalian cancer cell is a mammalian RET-associated cancer cell.

12. A method for inhibiting metastasis of a cancer in a patient in need thereof, the method comprising administering to the patient a therapeutically effective amount of a compound of claim 1, or a pharmaceutically acceptable salt thereof.

\* \* \* \* \*

UNITED STATES PATENT AND TRADEMARK OFFICE
CERTIFICATE OF CORRECTION

PATENT NO. : 10,555,944 B2
APPLICATION NO. : 16/173100
DATED : February 11, 2020
INVENTOR(S) : Steven W. Andrews et al.

Page 1 of 1

It is certified that error appears in the above-identified patent and that said Letters Patent is hereby corrected as shown below:

In the Claims

Column 609, Line 20-33 (Approx.):

In Claim 1, delete " 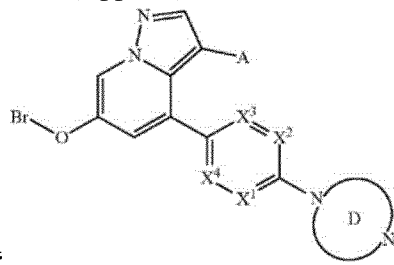 " and insert

-- 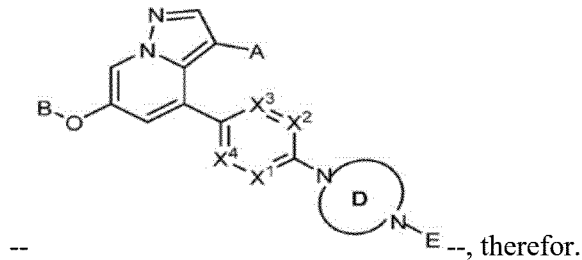 --, therefor.

Column 609, Line 65:
In Claim 1, delete "0" and insert -- O --, therefor.

Column 610, Line 62:
In Claim 5, after "to" insert -- claim --.

Signed and Sealed this
Second Day of June, 2020

Andrei Iancu
*Director of the United States Patent and Trademark Office*

SEQUENCE LISTING

<160> NUMBER OF SEQ ID NOS: 1

<210> SEQ ID NO 1
<211> LENGTH: 1114
<212> TYPE: PRT
<213> ORGANISM: Homo sapiens

<400> SEQUENCE: 1

```
Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205
```

```
Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Met Val
                245                 250                 255

Pro Phe Pro Val Thr Val Tyr Asp Glu Asp Ser Ala Pro Thr Phe
            260                 265                 270

Pro Ala Gly Val Asp Thr Ala Ser Ala Val Val Glu Phe Lys Arg Lys
                275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
                355                 360                 365

Thr Met Gln Leu Ala Val Leu Val Asn Asp Ser Asp Phe Gln Gly Pro
370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
                420                 425                 430

Phe Ser Gly Ile Asn Val Gln Tyr Lys Leu His Ser Ser Gly Ala Asn
            435                 440                 445

Cys Ser Thr Leu Gly Val Val Thr Ser Ala Glu Asp Thr Ser Gly Ile
450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
            515                 520                 525

Glu Glu Cys Gly Gly Leu Gly Ser Pro Thr Gly Arg Cys Glu Trp Arg
530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
                595                 600                 605

Cys Asn Cys Phe Pro Glu Glu Lys Cys Phe Cys Glu Pro Glu Asp
610                 615                 620
```

```
Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
            645                 650                 655

Ile His Cys Tyr His Lys Phe Ala His Lys Pro Pro Ile Ser Ser Ala
        660                 665                 670

Glu Met Thr Phe Arg Arg Pro Ala Gln Ala Phe Pro Val Ser Tyr Ser
    675                 680                 685

Ser Ser Gly Ala Arg Arg Pro Ser Leu Asp Ser Met Glu Asn Gln Val
690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp Ile Ser Lys Asp Leu Glu Lys Met
        995                 1000                1005

Met Val Lys Arg Arg Asp Tyr Leu Asp Leu Ala Ala Ser Thr Pro
    1010                1015                1020

Ser Asp Ser Leu Ile Tyr Asp Asp Gly Leu Ser Glu Glu Thr
    1025                1030                1035

Pro Leu Val Asp Cys Asn Asn Ala Pro Leu Pro Arg Ala Leu Pro
```

-continued

```
           1040              1045              1050
Ser Thr Trp Ile Glu Asn Lys Leu Tyr Gly Met Ser Asp Pro Asn
   1055              1060              1065

Trp Pro Gly Glu Ser Pro Val Pro Leu Thr Arg Ala Asp Gly Thr
   1070              1075              1080

Asn Thr Gly Phe Pro Arg Tyr Pro Asn Asp Ser Val Tyr Ala Asn
   1085              1090              1095

Trp Met Leu Ser Pro Ser Ala Ala Lys Leu Met Asp Thr Phe Asp
   1100              1105              1110

Ser
```